(12) United States Patent
Shackney

(10) Patent No.: US 8,877,445 B2
(45) Date of Patent: Nov. 4, 2014

(54) METHODS FOR IDENTIFICATION OF TUMOR PHENOTYPE AND TREATMENT

(75) Inventor: Stanley E. Shackney, Pittsburgh, PA (US)

(73) Assignee: Intelligent Oncotherapeutics, Inc., Pittsburgh, PA (US)

( * ) Notice: Subject to any disclaimer, the term of this patent is extended or adjusted under 35 U.S.C. 154(b) by 394 days.

(21) Appl. No.: 13/126,023

(22) PCT Filed: Nov. 13, 2009

(86) PCT No.: PCT/US2009/064294
§ 371 (c)(1),
(2), (4) Date: Apr. 26, 2011

(87) PCT Pub. No.: WO2010/056931
PCT Pub. Date: May 20, 2010

(65) Prior Publication Data
US 2012/0028907 A1    Feb. 2, 2012

Related U.S. Application Data

(60) Provisional application No. 61/199,295, filed on Nov. 14, 2008.

(51) Int. Cl.
*C12Q 1/68* (2006.01)
*G01N 33/50* (2006.01)

(52) U.S. Cl.
USPC .............................. 435/6.14; 702/19; 702/20

(58) Field of Classification Search
None
See application file for complete search history.

(56) References Cited

PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Robert, F. et al., "Phase 1 Trial of SNS-314, a Novel Selective Inhibitor of Aurora Kinases A, B and C, in Advanced Solid Tumor Patients," *Journal of Clinical Oncology*, 2008, vol. 26, Abstract #14642, 6 pages.
Grabowski, P. et al., "Aurora Kinases as Novel Drug Targets in Gastroenteropancreatic Neuroendocrine Tumor Diseases Antiproliferative and Pro-Apoptotic Effects of ZM 447439, a New Aurora Kinase Inhibitor, in BON and QGP-1 Cells," *Journal of Clinical Oncology*, 2008, vol. 26, Abstract #22023, 5 pages.
Jones, S. F. et al., "Phase 1 Accelerated Dose-Escalation, Pharmacokinetic (PK) and Pharmacodynarnic Study of PF-03814735, an Oral Aurora Kinase Inhibitor, in patients with Advanced Solid Tumors; Preliminary Results," *Journal of Clinical Oncology*, 2008, vol. 26, Abstract #2517, 6 pages.
Gartel, A. at al., "Thiazole Antibiotics that Inhibit FoxM1 Are Potential Anticancer Drugs," *99th AACR Annual Meeting*, Apr. 12-16, 2008, Abstract #2663, 2 pages.
Hodi, F.S. et al., "Novel Efficacy Criteria for Antitumor Activity to Immunotherapy Using the Example of Ipilimumab, an Anti-CTLA-4 Monoclonal Antibody," *Journal of Clinical Oncology*, 2008, vol. 26, Abstract #3008, 6 pages.
Rubin, E H. et al., "A Phase 1 Clinical and Pharmacokinetic (PK) Trial of the Aurora Kinase (AK) Inhibitor MK-0457 in Cancer Patients," *Journal of Clinical Onoclogy*, 2006 ASCO Annual Meeting Proceedings Part I, vol. 24, No. 18S, Abstract #3009, 5 pages.
Annereau, J.-P. et al., "Establishment and Characterization of a Human A549 Non Small Cell Lung Cancer Cell Line Resistant to the Novel Vectorized Cytotoxic Drug F14521," *99th AACR Annual Meeting*, Apr. 12-16, 2008, Abstract #3237, 2 pages.
Kwok, J. et al., "A Novel Thiazole Antibiotic Compound Selectively Kills Breast Cancer Cells through the Inhibition of Forkhead Box M1 Expression," *99th AACR Annual Meeting*, Apr. 12-16, 2008, Abstract #3280, two pages.
De Jonge, M. et al., "Phase 1 Study of the Aurora Kinases (AKs) Inhibitor PHA-739358 Administered as a 6 and 3HIV Infusion on Days 1, 8, 15 every 4 Weeks in Patients with Advanced Solid Tumors," *Journal of Clincal Oncology*, 2008, vol. 26, Abstract #3507, 6 pages.
Kopetz, S., "First in Human Phase I Study of BSI-201, a Small Molecule Inhibitor of Poly ADP-Ribose Polymerase (PARP) in Subjects with Advanced Solid Tumors," *2008 ASCO Annual Meeting*, Abstract #3577, 1 page.
Tsimberidou, A.M. et al., "Phase I First-in-Human Study of S-trans, Trans-farnesylthiosalicylic Acid (saliraship) in Patients with Solid Tumors," *Journal of Clinical Oncology*, 2008, vol. 26, Abstract #3536, 6 pages.
Suzuki, H. et al., "Alternative Non-Steroidal Antiandrogen Therapy for Advanced Prostate Cancer that Has Relapsed after Initial Maximum Androgen Blockade," *Journal of Clinical Oncology*, 2008, vol. 26, Abstract #5135, 5 pages.
Gonzalez, R. et al., "A Phase II Sutdy of YM155, a Novel Survivin Suppressant, Administered by 168 Hour Continuous Infusion in Patients with Unresectable Stage II or Stage IV Melanoma," *Journal of Clinical Oncology*, 2007 ASCO Annual Meeting Proceedings Part I, vol. 25, No. 18S, Abstract #8538, 5 pages.
Renshaw, J.S. et al., "A Phase I Two Arm Trial of AS703569 (R763), an Orally Available Aurora Kinase Inhibitor, in Subjects with Solid Tumors: Preliminary Results," *Journal of Clinical Oncoloqy*, 2007 ASCO Annual Meeting Part I, vol. 25, No. 18S, Abstract #14130, 5 pages.
Abdel-Fatah, T. M. A. et al., "Morphologic and Molecular Evolutionary Pathways of Low Nuclear Grade Invasive Breast Cancers and their Putative Precursor Lesions: Further Evidence to Support the Concept of the Low Nuclear Grade Breast Neopiasia Family," *Am J Surg Pathol*, Apr. 2008, vol. 32, No. 4, pp. 513-523.

(Continued)

*Primary Examiner* — James Martinell
(74) *Attorney, Agent, or Firm* — DLA Piper LLP (US)

(57) ABSTRACT

The disclosure relates to methods for identifying a tumor as an E2F-responsive gene over-expressing (ERGO) tumor, methods of determining the likelihood that an ERGO tumor patient will survive to a future date, methods of treating an ERGO tumor in a patient, and methods of selecting patients diagnosed as ERGO tumor prostate cancer patients for aggressive clinical treatment. The methods of the disclosure are applicable to ERGO tumors present in different human organs and tissues such as breast, lung, thyroid, ovary, and prostate.

19 Claims, 546 Drawing Sheets

(56) References Cited

PUBLICATIONS

Agnese, V et al., "The Role of Aurora-A Inhibitors in Cancer Therapy" *Annals of Oncology*, 2007, vol. 18, pp. vi47-vi52.

Arlot-Bonnemains, Y. et al., "Effects of the Aurora Kinase Inhibitor VX-680 on Anaplastic Thyroid Cancer-Derived Cell Lines," *Endocrine-Related Cancer*, 2008, vol. 15, pp. 559-568.

Arnes, J. B. et al., "Placental Cadherin and the Basal Epithelial Phenotype of BRCA1—Related Breast Cancer," *Clinical Cancer Research*, Jun. 1, 2005, vol. 11, pp. 4003-4011.

Bachmann, I. M. et al., "EZH2 Expression is Associated with High Proliferaton Rate and Aggressive Tumor Subgroups in Cutaneous Melanoma and Cancers of the Endometrium, Prostate, and Breast," *Journal of Clinical Oncology*, Jan. 10, 2006, vol. 24, No. 2, pp. 268-273.

Beardmore, V. A. et al., "Survivin Dynamics Increases at Centromeres during G2/M Phase Transition and is Regulated by Microtubule-Attachment and Aurora B Kinase Activity," *Journal of Cell Science*, 2004. vol. 117, Pt 18, pp. 4033-4042.

Beger C. et al., "identification of *Id4* as a Regulator of BRCA1 Expression by Using a Ribozyme-Library-Based Inverse Genomics Approach," *PNAS*, Jan. 2, 2001, vol. 98, No. 1, pp. 130-135.

Bettoun, D. J. et al., "Retinoid X Receptor is a Nonsilent Major Contributor to Vitamin D Receptor-Mediated Transcriptional Activation," *Molecular Endocrinology*, 2003, vol. 17, No. 11, pp. 2320-2328.

Black, E. P. et al, "Distinct Gene Expression Phenotypes of Cells Lacking Rb and Rb Family Members," *Cancer Research*, 2003, vol. 63, pp. 3716-3723.

Buck M. B. at al, "Prognostic Significance of Transforming Growth Factor Beta Receptor II in Estrogen Receptor-Negative Breast Cancer Patients," *Clinical Cancer Research*, 2004, vol. 10, pp. 491-498.

Buck, M. B. et al., "TGF-Beta Signaling in Breast Cancer," *Ann. N. Y. Acad. Sci.*, 2006, vol. 1089, pp. 119-126.

Callagy, G. M. et al., "Bcl-2 is a Prognostic Marker in Breast Cancer Independently of The Nottingham Prognostic Index," *Clinical Cancer Research*, 2006, vol. 12, pp. 2468-2475.

Carter. S. L. et al., "A Signature of Chromosomal instability Inferred from Gene Expression Profiles Predicts Clinical Outcome in Multiple Human Cancers," *Nature Genetics*, 2006, vol. 38, No. 9, pp. 1043-1048.

Chandran, U. R. et al., "Gene Expression Profiles of Prostate Cancer Reveal Involvement of Multiple Molecular Pathways in the Metastatic Process," *BMC Cancer*, 2007, vol. 7, No. 64, pp. 1-21.

Charafe-Jauffret, E. et al., "Gene Expression Profiling of Breast Cell Lines Identifies Potential New Basal Markers," *Oncogene*, 2006, vol. 25, pp. 2273-2284.

Charafe-Jauffret, E. et al., "Moesin Expression is a Marker of Basal Breast Carcinomas," *Int. J Cancer*, 2007, vol. 121, pp. 1779-1785.

Collett, K. at al, "Expression of Enhancer of Zeste Homologue 2 is Significantly Associated with Increased Tumor Cell Proliferation and is a Marker of Aggressive Breast Cancer," *Clinical Cancer Research*, 2006, vol. 12; pp. 1168-1174.

Dai, H. et al., "A Cell Proliferation Signature is a Marker of Extremely Poor Outcome in a Subpopulation of Breast Cancer Patients," *Cancer Research*, 2005, vol. 65, pp. 4059-4066.

Dankof, A. et al., "KPNA2 Protein Expression in Invasive Breast Carcinoma and Matched Peritumoral Ductal Carcinoma in situ," *Virchows Arch*, 2007, vol. 451, pp. 877-881.

Dolled-Filhart, M. at al. "Classification of Breast Cancer Using Genetic Algorithms and Tissue Microarrays," *Clinical Cancer Research*, 2006, vol. 12, pp. 6459-6468.

Dyrskjøt L. et al., "Gene Expression in the Urinary Bladder: A Common Carcinoma in situ Gene Expression Signature Exists Disregarding Histopathological Classification," *Cancer Res*, 2004, pp. 4040-4048.

Ekholm-Reed, S. at al., Deregulation of Cyclin E in Human Cells interferes with Prereplication Complex Assembly, *The Journal of Cell Biology*, 2004, vol. 165, No. 6, pp. 789-800.

Esseghir, S. et al, "Identification of *NTN4, TRA1*, and *STC2* as Prognostic Markers in Breast Cancer in a Screen for Signal Sequence Encoding Proteins," *Clinical Cancer Research*, 2007, vol. 13, No. 11, pp. 3164-3173.

Foulkes, W. D. et al., "The Prognostic Implication of the Basal-Like (Cyclin $E^{high}/p27^{low}/p53+$/Glomeruloid-Microvascular-Proliferation$^+$) Phenotype of BRCA1-Related Breast Cancer," *Cancer Research*, 2004, vol. 64, pp. 830-835.

Frasor, J. et al., "Estrogen Down-Regulation of the Corepressor N-CoR: Mechanism and Implications for Estrogen Derepression of N-CoR-Regulated Genes," *PNAS*, 2005, vol. 102, No. 37, pp. 13153-13157.

Frasor, J. et al., "Profiling of Estrogen Up- and Down-Regulated Gene Expression in Human Breast Cancer Cells: Insights into Gene Networks and Pathways Underlying Estrogenic Control of Proliferation and Cell Phenotype," *Endocrinology*, 2003, vol. 144, No. 10, pp. 4562-4574.

Fritzsche, F. R. et al. "Prognostic Relevance of AGR2 Expression in Breast Cancer," *Clinical Cancer Research*, 2006, vol. 12, No. 6, pp. 1728-1734.

Fulford, L. G. et al., "Basal-Like Grade III Invasive Ductal Carcinoma of the Breast: Patterns of Metastasis and Long-Term Survival," *Breast Cancer Res*, 2007, vol. 9, No. 1, pp. 1-11.

Garcia, S. et al., "Poor Prognosis in Breast Carcinomas Correlates with Increased Expression of Targetable CD146 and c-Met and with Proteomic Basal-Like Phenotype," *Human Pathology*, 2007, vol. 38, issue 6, pp. 830-841.

Gartel, A. et al., "The Growth-Regulatory Role of p21 (WAF1/CIP1)," *Progress in Molecular and Subcellular Biology*, 1998, vol. 20, pp. 43-71.

Georlette, B. et al., "Genomic Profiling and Expression Studies Reveal both Positive and Negative Activities for the Drosophila Myb MuvB/dREAM Complex in Proliferating Cells," *Genes Dev*, 2007, vol. 21, No. 22, pp. 2880-2896.

Ghosh, R. et al, "Eugenol Causes Melanoma Growth Suppression through Inhibition lot E2F1 Transcriptional Activity," *The Journal of Biological Chemistry*, 2005, vol. 280, No. 7, pp. 5812-5819.

Gonçalves, A. et al., "Protein Profiling of Human Breast Tumor Cells Identifies Novel Biomarkers Associated with Molecular Subtypes," *Molecular & Cellular Proteomics*, 2008, pp. 1-23.

Gonzalez, M. A. et al, "Minichromosome Maintenance Protein 2 is Strong Independent Prognostic Marker in Breast Cancer," *Journal of Clinical Oncology*, 2003, vol. 21, No. 23, pp. 4306-4313.

Gray-Bablin, J. et al., "Cyclin E, a Redundant Cyclin in Breast Cancer," *Proc. Natl. Acad. Sci. USA*, 1996, vol. 93, pp. 15215-15220.

Gusarova, G.A. et al., A Cell-Penetrating ARF Peptide inhibitor of FoxM1 in Mouse Hepatocelluar Carcinoma Treatment, *The Journal of Clinical investigation*, 2007, vol. 117, No. 1, pp. 99-111.

"Some *C. Elegans* Class B Synthetic Multivulva Proteins Encode a Conserved LIN-35 Rb-Containing Complex Distinct from a NuRD-Like Complex," *PNAS*, 2006, vol. 103, No. 45, pp. 16782-16787, Harrison at al.

"VX-680, a Potent and Selective Small-Molecule Inhibitor of the Aurora Kineses, Suppresses Tumor Growth In Vivo," *Nature Medicine*, Mar. 2004, vol. 10, No. 3, pp. 262-267, Harrington et al.

Huang, H. et al., "Aberrant Expression of Novel and Previously Described Cell Membrane Markers in Human Breast Cancer Cell Lines and Tumors," *Clinical Cancer Research*, 2005, vol. 11, No. 12, pp. 4357-4364.

Ignatiadis, M. et al, "Different Prognostic Value of Cytokeratin-19 mRNA-Positive Circulating Tumor Cells accordings to Estrogen Receptor and HER2 Status in Early-Stage Breast Cancer," *Journal of Clinical Oncology*, 2007, vol. 25, No. 33, pp. 5194-5202.

Inamura, K. et al., "Two Subclasses of Lung Squamous Cell Carcinmoa with Different Gene Expression Profiles and Prognosis Identified by Hierachical Clustering and Non-Negative Matrix Factorization," *Oncogene*, 2005, vol. 24, pp. 7105-7113.

Ishida, S. et al, "Role for E2F in Control of both DNA Replication and Mitotic Functions as Revealed from DNA Microarray Analysis," *Molecular and Cellular Biology*, 2001, vol. 21, No. 14, pp. 4684-4699.

(56) References Cited

OTHER PUBLICATIONS

Jones, C. et al., "Expression Profiling of Purified Normal Human Luminal and Myoepithelial Breast Cells: Identification of Novel Prognostic Markers for Breast Cancer," *Cancer Research*, 2004, vol. 64, pp. 3037-3045.

Jones, M. H. at al., "Two Prognostically Significant Subtypes of High-Grade Lung Neuroendocrine Tumors Independent of Small-Cello and Large-Cell Neuroendocrine Carcinomas Identified by Gene Expression Profiles," *Lancet*, 2004, vol. 363, issue 9411, pp. 775-781.

Jones, S.F. at al., "Phase 1 Clinical Trial of MLN8054, a Selective Inhibitor of Aurora A Kinase," *Journal of Clinical Oncology*, 2007 ASCO Annual Meeting Proceedings Part 1, vol. 25, No. 18S, Abstract #3577 (6 pages).

Kalin, T. V. et al., "Increased Levels of the FoxM1 Transcription Factor Accelerate Development and Progression of Prostate Carcinomas in both TRAMP and LADY Transgenic Mice," *Cancer Research*, 2006, vol. 66, No. 3, pp. 1712-1720.

Kalinichenko et al. "Foxm1b Transcription Factor is Essential for Development of Hepatocellular Carcinomas and is Negatively Regulated by the $p19^{ARF}$ Tumor Suppressor," *Genes Development*, 2004, vol. 18, pp. 830-850.

Katzenellenbogen, B. S. et at, "Therapeutic Targeting in the Estrogen Receptor Hormonal Pathway," *Semin Oncol*, 2004, vol. 31, No. 1, Suppl 3, pp. 28-38 (1 page Abstract only).

Kittler, R. et al., "Genome-Scale RNAi Profiling of Cell Division in Human Tissue Culture Cells," *Nature Cell Biology*, 2007, vol. 9, No. 12, pp. 1401-1412 (and supplementary Information).

Klopocki, E. et al., "Loss of SFRP1 is Associated with Breast Cancer Progression and Poor Prognosis in Early Stage Tumors," *Int J Oncol*, 2004, vol. 25, No. 3, pp. 641-649 (1 page Abstract only).

Knauer, S. K. et al., "Survivin's Dual Role: An Export's View," *Cell Cycle*, 2007, vol. 6, issue 5, pp. 518-521.

Knowlden, J. M. et al., "Elevated Levels of Epidermal Growth Factor Receptor/c-erbB2 Heterodimers Mediate an Autocrine Growth Regulatory Pathway in Tamoxifen-Resistant MCF-7 Cells," *Endocrinology*, 2003, vol. 144, No. 3, pp. 1032-1044.

Kotake, Y. et al, "pRB Family Proteins Are Required for H3K27 Trimethylation and Polycornb Repression Complexes Binding to and Silencing $p16^{INK4a}$ Tumor Suppressor Gene," *Genes Development*, 2007, vol. 21, pp. 49-54.

Lee, R. J. et at, "Cyclin D1 is Required for Transformation by Activated Neu and is Induced through an E2F-Dependent Signaling Pathway," *Molecular Cell Biology*, 2000, vol. 20, No. 2, pp. 672-683.

Li, X. et al., "Expression Level of Insulin-Like Growth Factor Binding Protein 5 mRNA is a Prognostic Factor for Breast Cancer," *Cancer Sci.* 2007, vol. 98, No, 10, pp. 1592-1596.

Livasy, C. A. et al., "Phenotypic Evaluation of the Basal-Like Subtype of Invasive Breast Carcinoma," *Modern Pathology*, 2006, vol. 19, pp. 264-271.

Lu, S. et al.; "Analysis of Integrin β4 Expression in Human Breast Cancer: Association with Basal-Like Tumors and Prognostic Significance," *Clinical Cancer Research*, 2008, vol. 14, No. 4, pp. 1050-1058.

Lukas, J, et al., "Cyclin D1 is Dispensable for $G_1$ Control in Retinoblastoma Gene-Deficient Cells Independently of cdk4 Activity," *Molecular Cell Biology*, 1995, vol. 15, No. 5, pp. 2600-2611.

Major, M. L. et al., "Forkhead Box M1B Transcriptional Activity Requires Binding of Cdk-cyclin Complexes for Phosphorylation-Dependent Recruitment of p300/CBP Coactivators," *Molecular Cell Biology*, 2004, vol. 24, No. 7, pp. 2649-2661.

Manfredi, M.G. et al , "Antitumor Activity of MLN0854, an Orally Active Small-Molecule Inhibitor of Aurora A Kinase," *PNAS*, 2007, vol. 104, No. 10, pp. 4106-4111.

Matos, I. et al., "p63, cytokeratin 5, and P-cadherin: Three Molecular Markers to Distinguish Basal Phenotype in Breast Carcinomas," *Virchows Arch*, 2005, vol. 447, pp. 688-694.

McBryan, J. et al., "ERα-CITED1 Co-Regulated Genes Expressed during Pubertal Mammary Gland Development: Implications for Breast Cancer Prognosis," *Oncogene*, 2007, vol. 26, pp. 6406-6419.

McCarthy, M. M. et al. "Evaluating the Expression and Prognostic Value of TRAIL-R1 and TRAIL-R2 in Breast Cancer," *Clinical Cancer Research*, 2005, vol. 11, No. 14, pp. 5188-5194.

Mehra, R. et al., "Identification of GATA3 as a Breast Cancer Prognostic Marker by Global Gene Expression Meta-Analysis," *Cancer Research*, 2005, vol. 65, No. 24, pp. 11259-11264.

Moyano, J. V. et al., "αB-Crystallin is a Novel Oncoprotein that Predicts Poor Clinical Outcome in Breast Cancer," *The Journal of Clinical Investigation*, 2006, vol. 116, No. 1, pp. 261-270.

Myatt, S. S. at al., "The Emerging Roles of Forkhead Box (Fox) Proteins in Cancer," *Nature Reviews Cancer*, 2007, vol. 7, pp. 847-859.

Nadler, V, at al., "Expression Patterns and Prognostic Value of Bag-1 and Bcl-2 in Breast Cancer," *Breast Cancer Research*, 2008, vol. 10, R35, pp. 1-12.

Nakahara, T. et al., "YM155, a Novel Small-Molecule Survivin Suppressant, Induces Regression of Established Human Hormone-Refractory Prostate Tumor Xenografts," *Cancer Research*, 2007, vol. 67, No. 17, pp. 8014-8021.

Nielsen, N. H. at al,, "Deregulation of Cyclin E and D1 in Breast Cancer is Associated with Inactivation of the Retinoblastoma Protein," *Oncogene*, 1997, vol. 14, pp. 295-304.

Nielsen, T. O. et al., "Immunohistochemical and Clinical Characterization of the Basal-Like Subtype of Invasive Breast Carcinoma," *Clinical Cancer Research*, 2004, vol. 10, pp. 5367-5374.

O'Brien, S. L. et al., "CENP-F Expression is Associated with Poor Prognosis and Chromosomal Instability in Patients with Primary Breast Cancer," *Int J Cancer*, 2007, vol. 120, pp. 1434-1443.

O'Connor, J. K. et al., "Topoisomerase IIα Expression Correlates with Diminished Disease-Free Survival in Invasive Breast Cancer," *Int. J. Radiation Oncology Biol. Phys.*, 2006, vol. 65, No. 5, pp. 1411-1415.

Olsson, A. Y. et al., "Role of E2F3 Expression in Modulating Cellular Proliferation Rate in Human Bladder and Prostate Cancer Cells," *Oncogene*, 2007, vol. 26, pp. 1028-1037.

Pan, C. et al, "Aurora Kinase Small Molecule inhibitor Destroys Mitotic Spindle, Suppresses Cell Growth, and induces Apoptosis in Oral Squamous Cancer Cells," *Oral Oncology*, Jul. 2008, vol. 44, issue 7, pp. 639-645 (printout 1-11 pages).

Paredes, J. et al., "P-Cadherin and Cytokeratin 5: Useful Adjunct Markers to Distinguish Basal-Like Ductal Carcinomas In Situ," *Virchows Arch*, 2007, vol. 450, pp. 73-80.

Potemski, P. et al., "Prognostic Relevance of Basal Cytokeratin Expression in Operable Breast Cancer," *Oncology*, 2005, vol. 69, pp. 478-485.

Rai, D. et al., "Distinctive Actions of Membrane-Targeted versus Nuclear Localized Estrogen Receptors in Breast Cancer Cells," *Molecular Endocrinology*, 2005, vol. 19, No. 6, pp. 1606-1617.

Rakha, E. A. et al., "Prognostic Markers in Triple-Negative Breast Cancer," *Cancer*, 2007, vol. 109, No. 1, pp. 25-32.

Rakha, E. A. et al., "Basal-Like Breast Cancer: A Critical Review," *Journal Clinical Oncology*, 2008, vol. 26, No. 15, pp. 2568-2581.

Rodriguez-Pinilla, S. M. et al., "Prognostic Significance of Basal-Like Phenotype and Fascin Expression in Node-Negative Invasive Breast Carcinomas," *Clinical Cancer Research*, 2006, vol. 12, pp. 1533-1539.

Rodriguez-Pinilla, S. M. et al., "Vimentin and Laminin Expression is Associated with Basal-Like Phenotype in Both Sporadic and BRCA1-Associated Breast Carcinomas," *J Clin Pathol*, 2007, vol. 60, pp. 1006-1012.

Rodriguez-Pinilla, S. M. et al., "Sox2: a Possible Driver of the Basal-Like Phenotype in Sporadic Breast Cancer," *Modern Pathology*, 2007, vol. 20, pp. 474-481.

Saeed, A. I. et al., "TM4: Microarray Software Suite," *Methods in Enzymology*, DNA Microarrays, Part B, 2006, vol. 411, pp. 134-193.

Saeed, A. I. et al., "TM4: a Free Open-Source System for Microarray Data Management and Analysis," *Biotechniques*, 2003, vol. 34, No. 2, pp. 374-378.

Salvatore, G. et al., "A Cell Proliferation and Chromosomal Instability Signature in Anaplastic Thyroid Carcinoma," *Cancer Research*, 2007, vol. 67, No. 21, 10148-10158.

Savage, K. et al., "Caveolin 1 is Overexpressed and Amplified in a Subset of Basal-Like and Metaplastic Breast Carcinomas: A

(56) References Cited

OTHER PUBLICATIONS

Morphologic, Ultrastructural, Immunohistochemical, and In Situ Hybridization Analysis," *Clinical Cancer Research*, 2007, vol. 13, No. 1, pp. 90-101.

Savage, K. et al., "Distribution and Significance of Caveolin 2 Expression in Normal Breast and invasive Breast Cancer: An Immunofluorescence and Immunohistochemical Analysis," *Breast Cancer Res Treat*, 2008, vol. 110, pp. 245-256.

Schmit, F. et al., "LINC, a Human Complex that is Related to pRB-Containing Complexes in Invertebrates Regulates the Expression of G2/M Genes," *Cell Cycle*, 2007, vol. 6, No. 15, pp. 1903-1913.

Shackney, S. E. at al., "Molecular Evolutionary Patterns in Breast Cancer," *Adv Anat Pathol*, 2003, vol. 10, No. 5, pp. 278-290.

Sherr, C. J., "The Pezcoller Lecture: Cancer Cell Cycles Revistited," *Cancer Research*, 2000, vol. 60, pp. 3689-3695.

Sitterding, S. M. et al., "αB-Crystallin: A Novel Marker of Invasive Basal-Like and Metaplastic Breast Carcinomas," *Annals of Diagnostic Pathology*, 2008, vol. 12, issue 1, pp. 33-40 (Printout pp. 1-9).

Sørlie, T. et al., "Gene Expression Patterns of Breast Carcinomas Distinguish Tumor Subclasses with Clinical Implications," *PNAS*, 2001, vol. 98, No. 19, pp. 10869-10874.

Sotiriou, C. at al., "Breast Cancer Classification and Prognosis Based on Gene Expression Profiles from a Population-Based Study," *PNAS*, 2003, vol. 100, No. 18, pp. 10393-10398.

Stauber, R. H. at at., "Nuclear and Cytoplasmic Survivin: Molecular Mechanism, Prognostic, and Therapeutic Potential," *Cancer Research*, 2007, vol. 67, No. 13, pp. 5999-6002.

Stein, T. et al. "Annexin A8 is Up-Regulated During Mouse Mammary Gland Involution and Predicts Poor Survival in Breast Cancer," *Clinical Cancer Research*, 2005, vol. 11, No. 19, pp. 6872-6879.

Stender, J. D. et al., "Estrogen-Regulated Gene Networks in Human Breast Cancer Cells: Involvement of E2F1 in the Regulation of Cell Proliferation," *Molecular Endocrinology*, 2007, vol. 27, No. 9, pp. 2112-2123.

Stossi, F. et al., "Transcriptional Profiling of Estrogen-Regulated Gene Expression via Estrogen Receptor (ER) α or ERβ in Human Osteosarcoma Cells: Distinct and Common Target Genes for these Receptors," *Endocrinology*, 2004, vol. 145, No. 7, pp. 3473-3486.

Stuelten, C. H. et al,, "Smad4-Expression is Decreased in Breast Cancer Tissues: A Retrospective Study," *BMC Cancer*, 2006, vol. 6, No. 25, pp. 1-10.

Sun, L. at al, "Small-Molecule Inhibition of Aurora Kinases Triggers Spindle Checkpoint-independent Apoptosis in Cancer Cells" *Biochemical Pharmacology*, 2008, vol. 75, issue 5, pp. 1027-1034 (Prinout 1-10 pages).

Suzuki, T. et al., "Nuclear Cyclin B1 in Human Breast Carcinoma as a Potent Prognostic Factor," *Cancer Sci*, 2007, vol. 98, No. 5, pp. 644-651.

Tabach, Y. et al., "The Promoters of Human Cell Cycle Genes integrate Signals from Two Tumor Suppressive Pathways during Cellular Transformation," *Molecular System Biology*, 2005, pp. 1-15.

Tan, D. S. at al., "Triple Negative Breast Cancer: Molecular Profiling and Prognostic Impact in Adjuvant Anthracycline-Treated Patients," *Breast Cancer Res Treat*, 2008, vol. 111, pp. 27-44.

Thorat, M. A. et al., "Forkhead Box A1 Expression in Breast Cancer is Associated with Luminal Subtype and Good Prognosis," *J Clin Pathol*, 2008, vol. 61, pp. 327-332.

Tone, A. A. et al., "Gene Expression Profiles of Luteal Phase Fallopian Tube Epithelium from BRCA Mutation Carriers Resemble High-Grade Serous Carcinoma," *Clinical Cancer Research*, 2008, vol. 14, No. 13, pp. 4067-4078.

Turner, N. C. et al., "BRCA1 Dysfunction in Sporadic Basal-Like Breast Cancer," *Oncogene*, 2007, vol. 26, pp. 2126-2132.

van de Rijn, M. et al., "Expression of Cytokeratins 17 and Identifies a Group of Breast Carcinomas with Poor Clinical Outcome," *American Journal of Pathology*, 2002, vol. 161, No. 6, pp. 1991-1996.

van der Vegt, B. et al., "The Expression Pattern of MUC1 (EMA) is Related to Tumor Characteristics and Clinical Outcome of Invasive Ductal Breast Carcinoma," *Histopathology*, 2007, vol. 51, pp. 322-335.

van't Veer, L. J, et al., "Gene Expression Profiling Predicts Clinical Outcome of Breast Cancer," *Nature*, 2002, vol. 415, No. 31, pp. 530-536.

Veeck, J. et al., "Epigenetic Inactivation of the Secreted Frizzled-Related Protein-5 (SFRP5) Gene in Human Breast Cancer is Associated with Unfavorable Prognosis," *Carcinogenesis*, 2008, vol. 29, No. 5, pp. 991-998.

Veeck, J. et al., "Aberrant Methylation of the Wnt Antagonist SFRP1 in Breast Cancer is Associated with Unfavourable Prognosis," *Oncogene*, 2006, vol. 25, pp. 3479-3488.

Vogel, C. L. at al., "Efficacy and Safety of Trastuzumab as a Single Agent in First-Line Treatment of *HER2*-Overexpressing Metastic Breast Cancer," *Journal Clinical Oncology*, 2002, vol. 20, No. 3, pp. 719-726.

Wang, I-C. et al., "Forkhead Box M1 Regulates the Transcriptional Network of Genes Essential for Mitotic Progression and Genes Encoding the SCF (Skp2-Cks1) Ubiquitin Ligase," *Molecular and Cellular Biology*, 2005, vol. 25, No. 24, pp. 10875-10894.

Wang, L. et al., "Cyclin e Expression and Prognosis in Breast Cancer Patients: A Meta-Analysis of Published Studies," *Cancer Invest*, 2006, vol. 24, No. 6, pp. 581-587 (Abstract—1 page).

Wang, W. et al., "Transcriptional Activation of E2F1 Gene Expression by 17β-Estradiol in MCF-7 Cells is Regulated by NF-Y-Sp1/estrogen Receptor Interactions," *Molecular Endocrinology*, 1999, vol. 13, No. 8, pp. 1373-1387.

Watkins, G. et al., "Increased Levels of SPARC (Osteonectin) in Human Breast Cancer Tissues and its Association with Clinical Outcomes," *Prostaglandins Leukotienes and Essential Fatty Acids*, 2005, vol. 72, No. 4, pp. 267-272.

Wykoff, C. C. et al., "Expression of the Hypoxia-Inducible and Tumor-Associated Carbonic Anhydrases in Ductal Carcinoma in Situ of the Breast," *American Journal of Pathology*, 2001, vol. 158, No. 3, pp. 1011-1019.

Yamashita, S. et al., "Survivin Expression Predicts Early Recurrence in Early-Stage Breast Cancer," *Anticancer Research*, 2007, vol. 27, pp. 2803-2808.

Yao, E. S. et al., "Increased β1 Integrin is Associated with Decreased Survival in Invasive Breast Cancer," *Cancer Research*, 2007, vol. 67, No. 2, pp. 659-664.

Yu, Q., et al., "Specific Protection against Breast Cancers by Cyclin D1 Ablation," *Nature*, 2001, pp. 1017-1021.

Zerkowski, M. P. et al., "Quantitative Analysis of Breast Cancer Tissue Microarrays Shows High Cox-2 Expression is Associated with Poor Outcome." *Cancer Invest*, 2007, vol. 25, No. 1, pp. 19-26 (Abstract only—1 page).

* cited by examiner

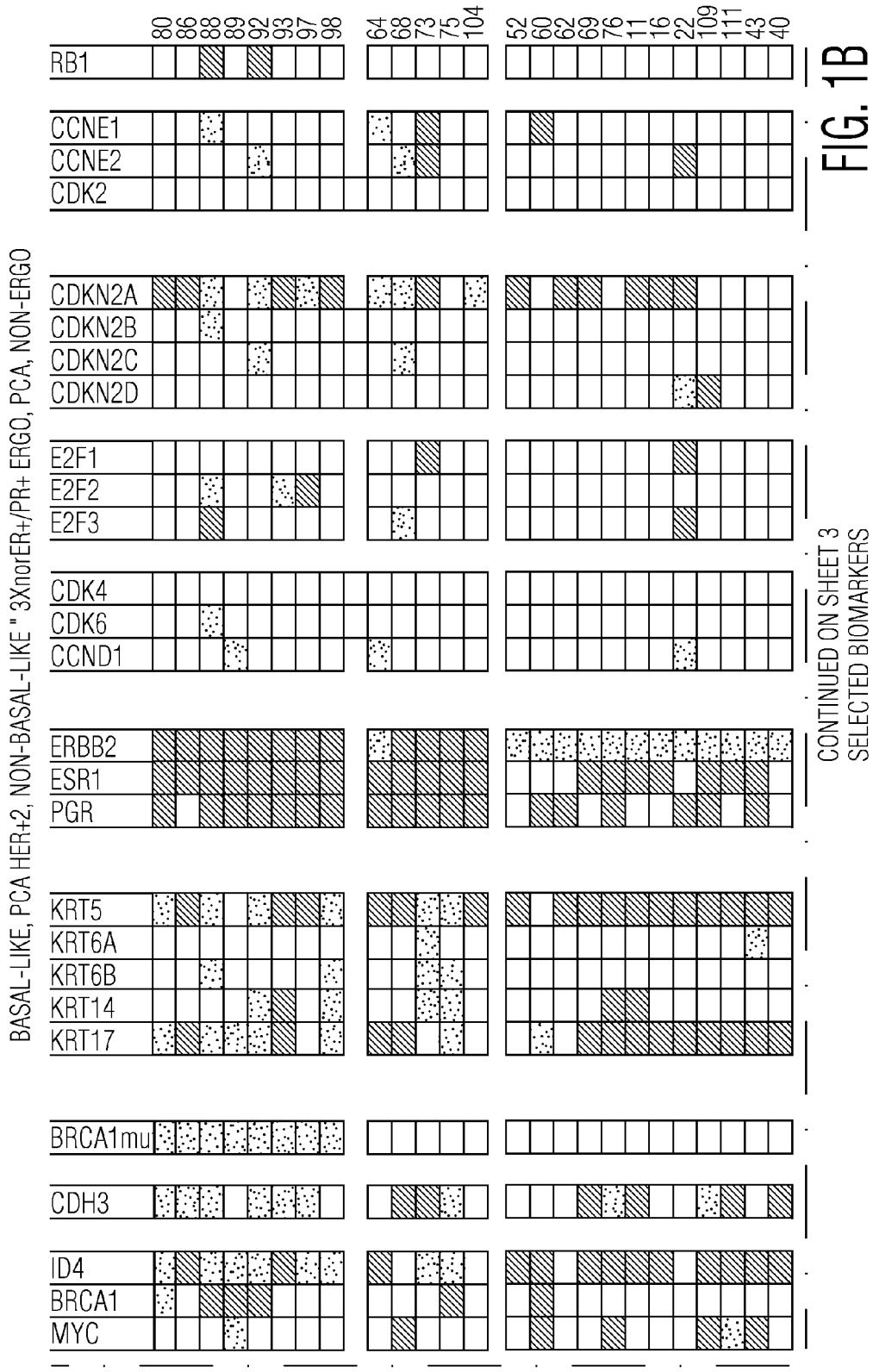

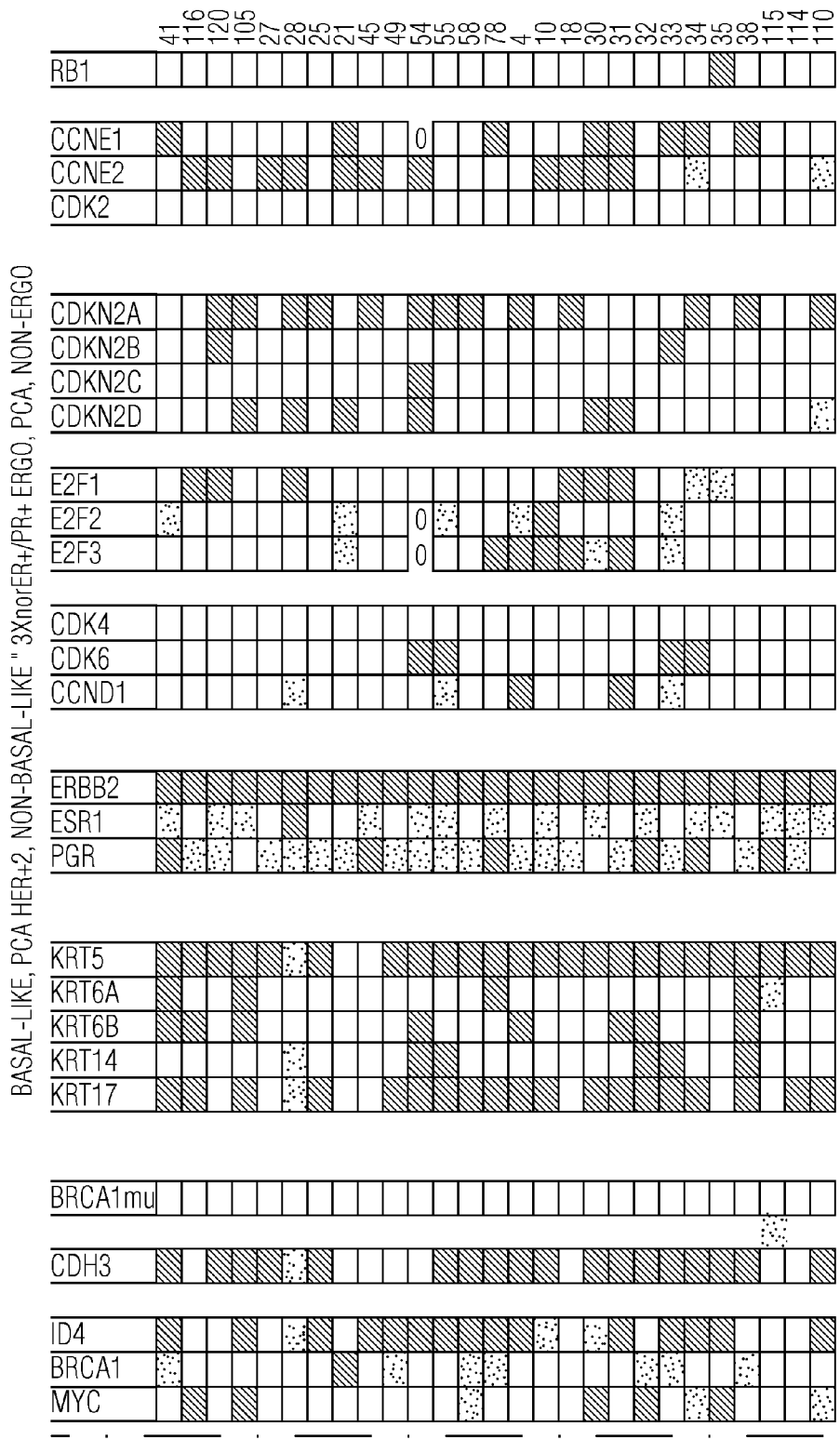

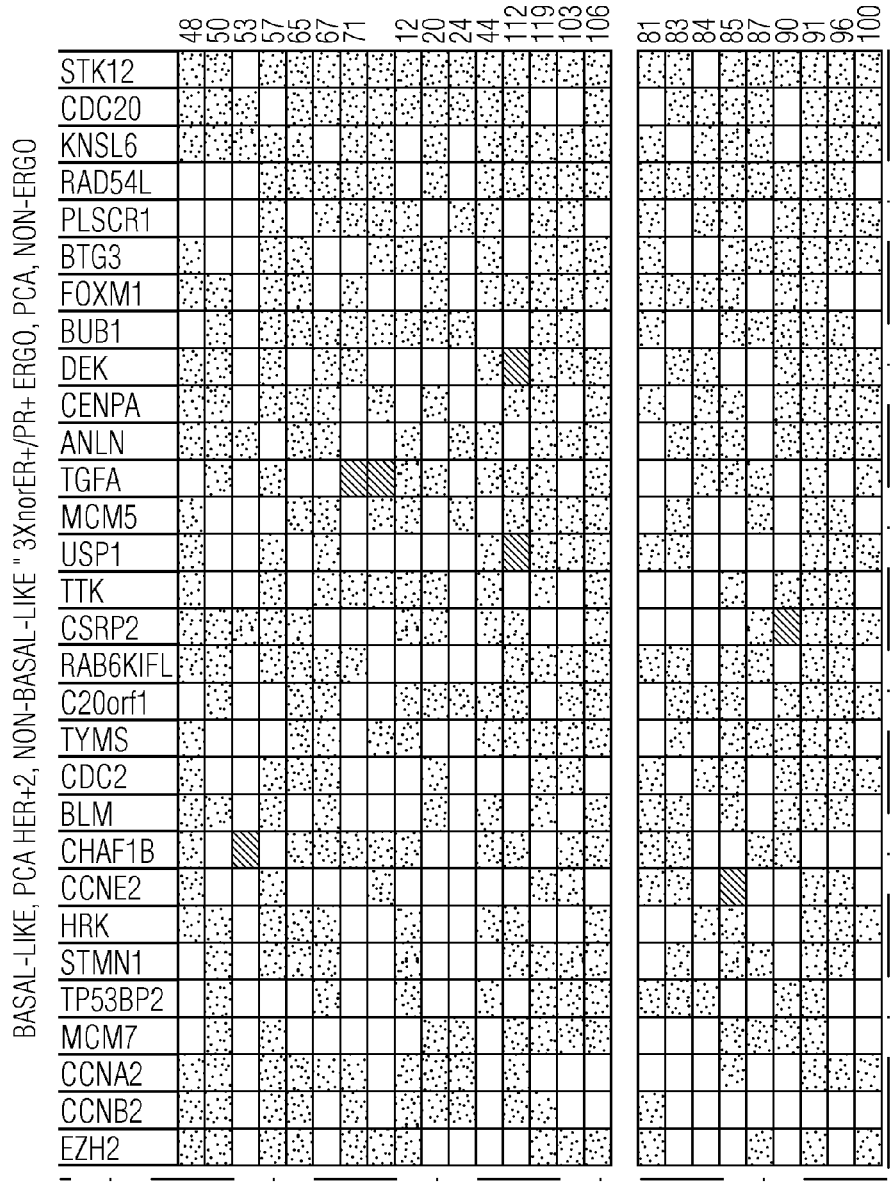

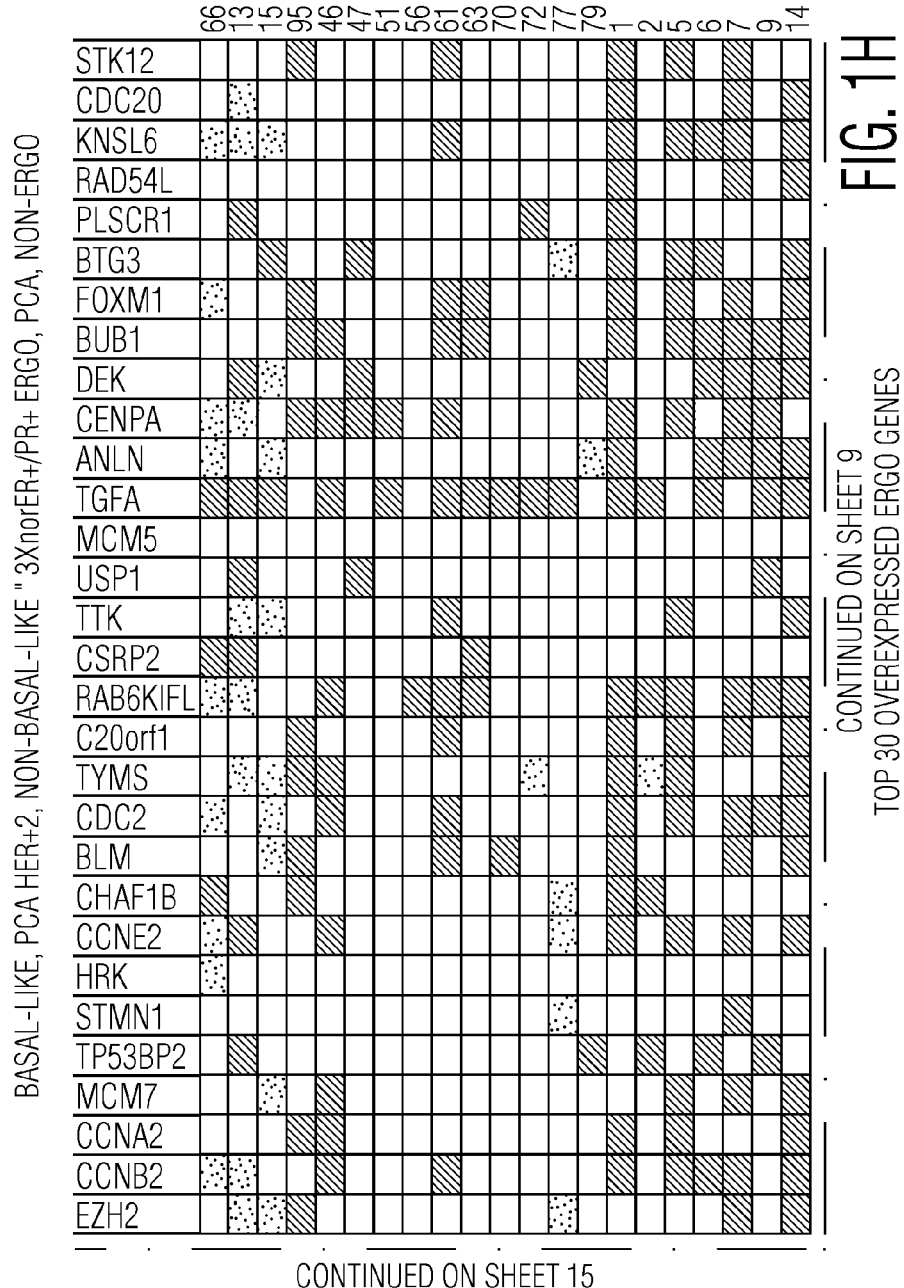

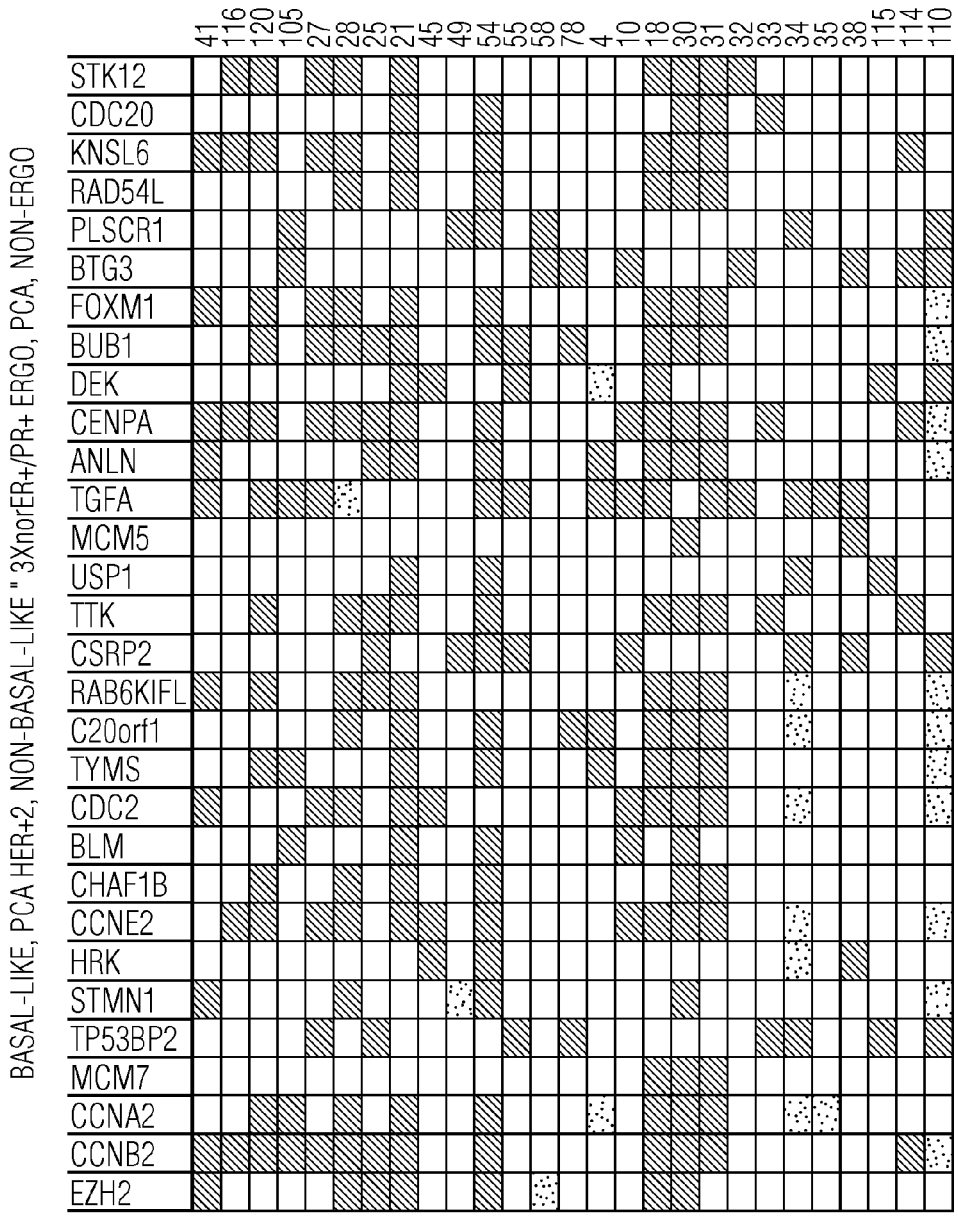

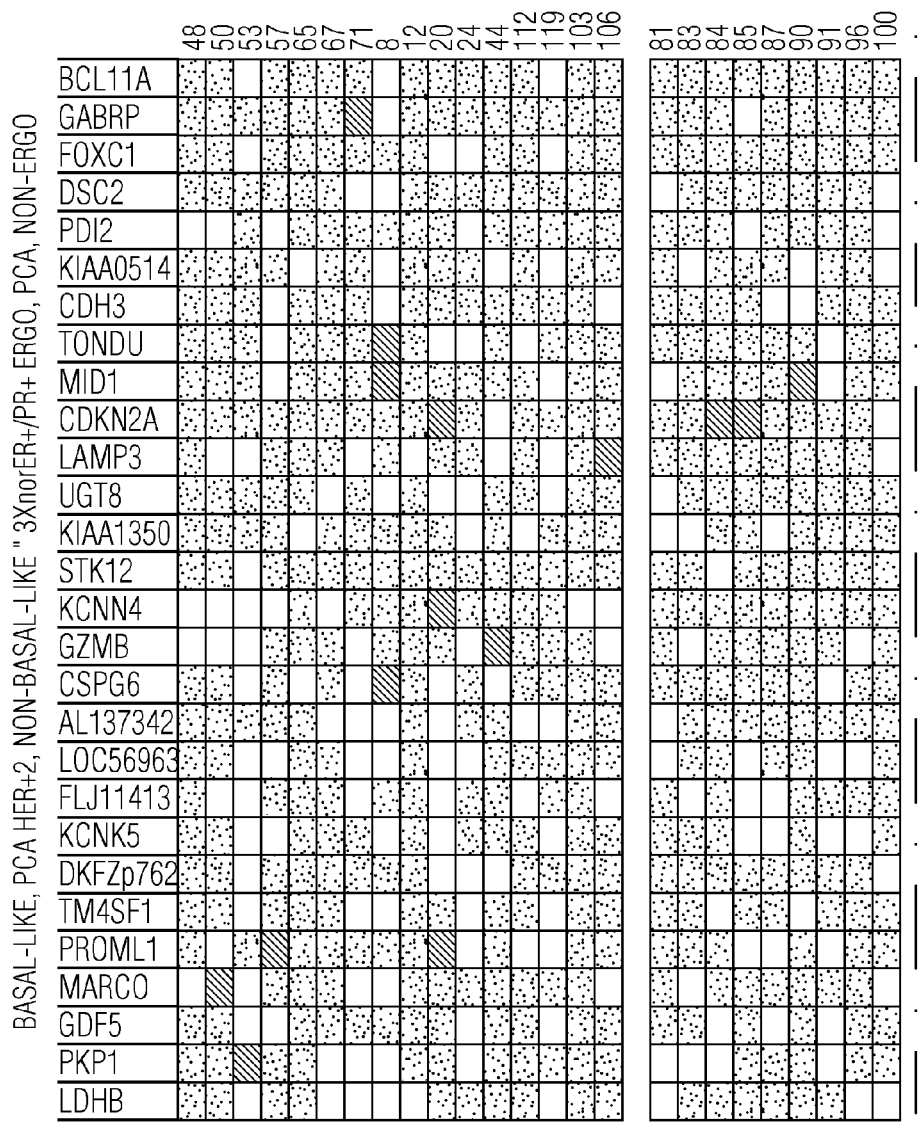

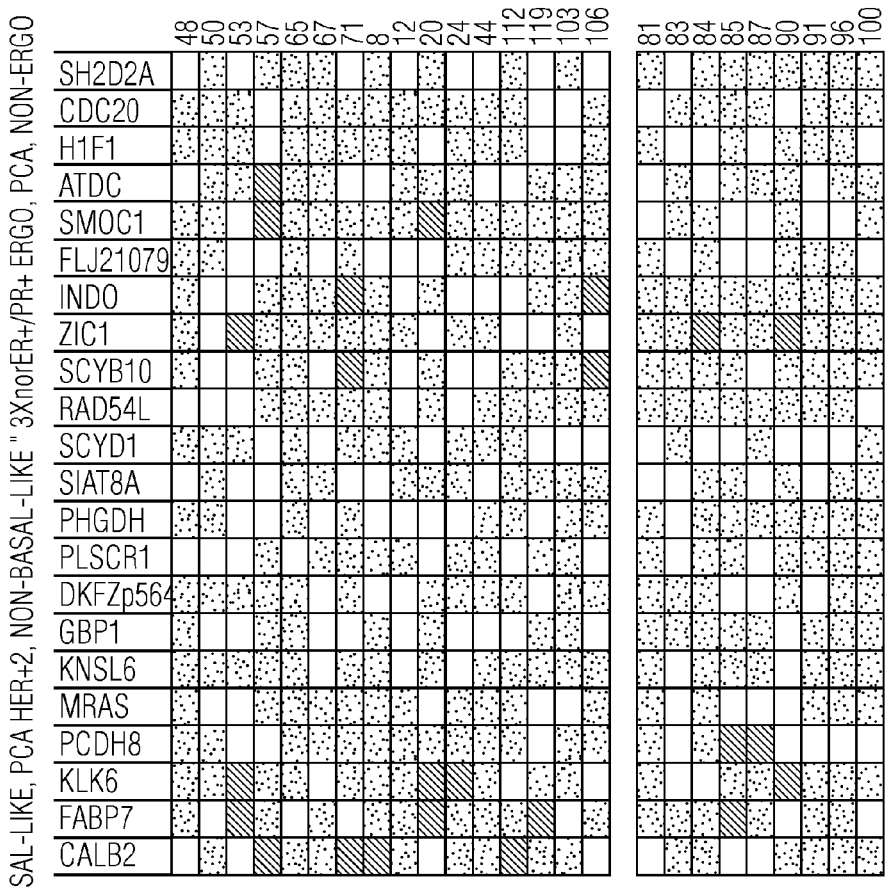

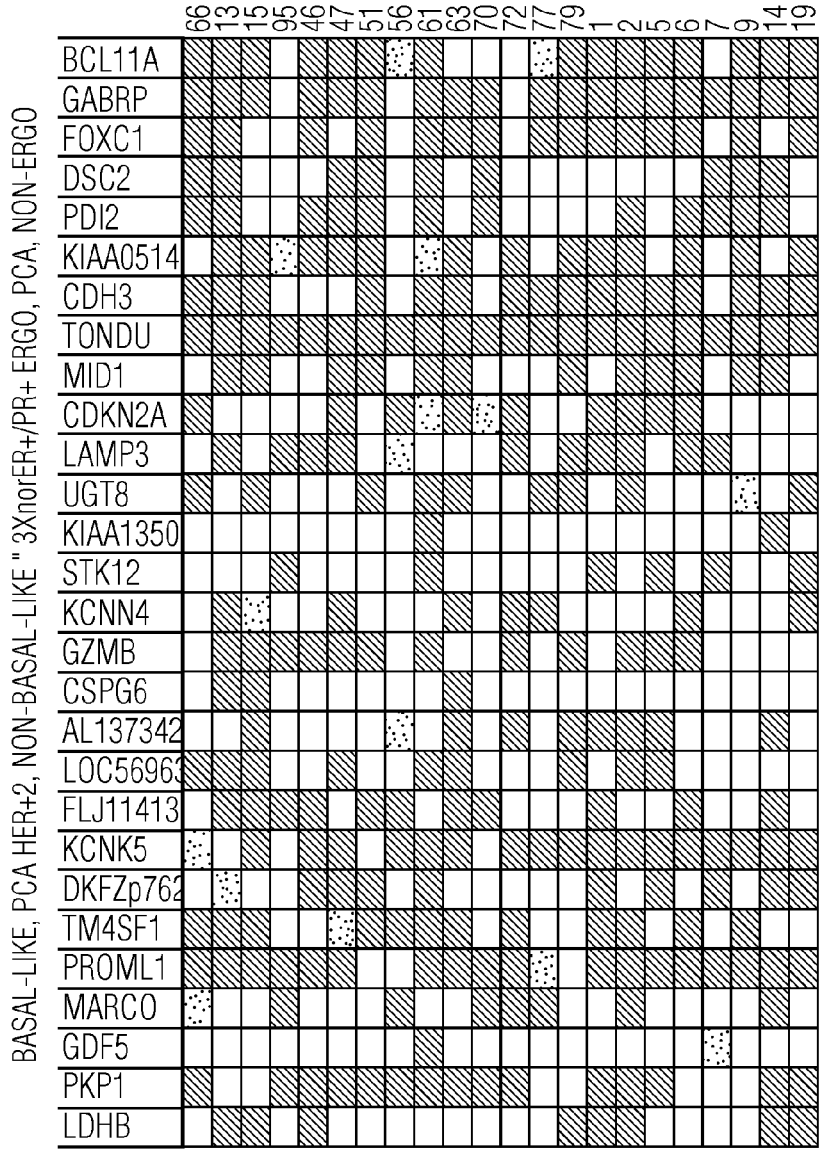

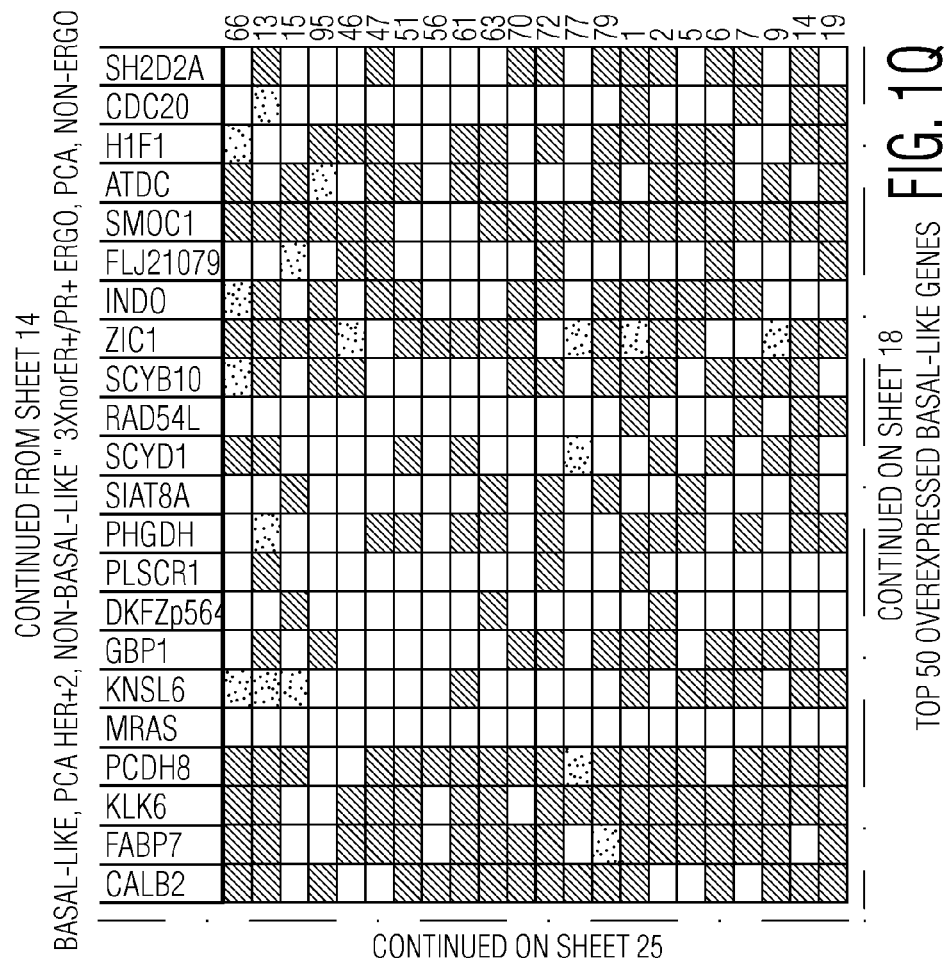

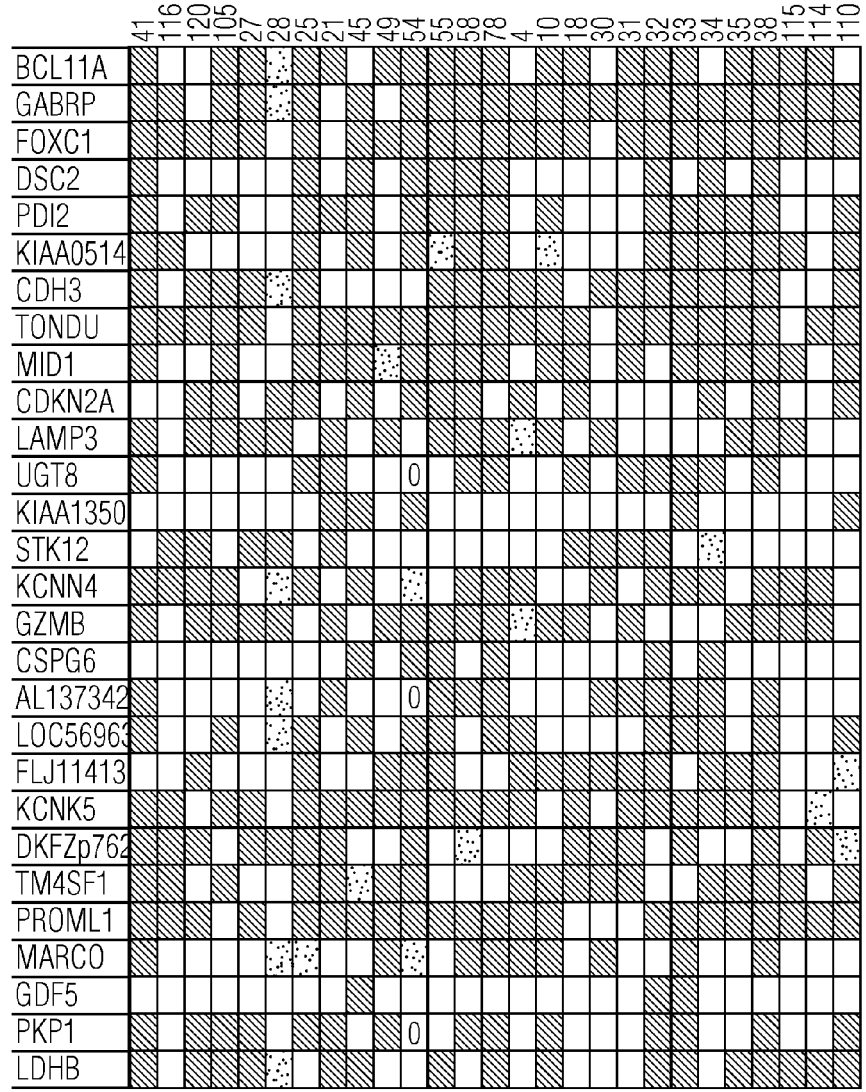

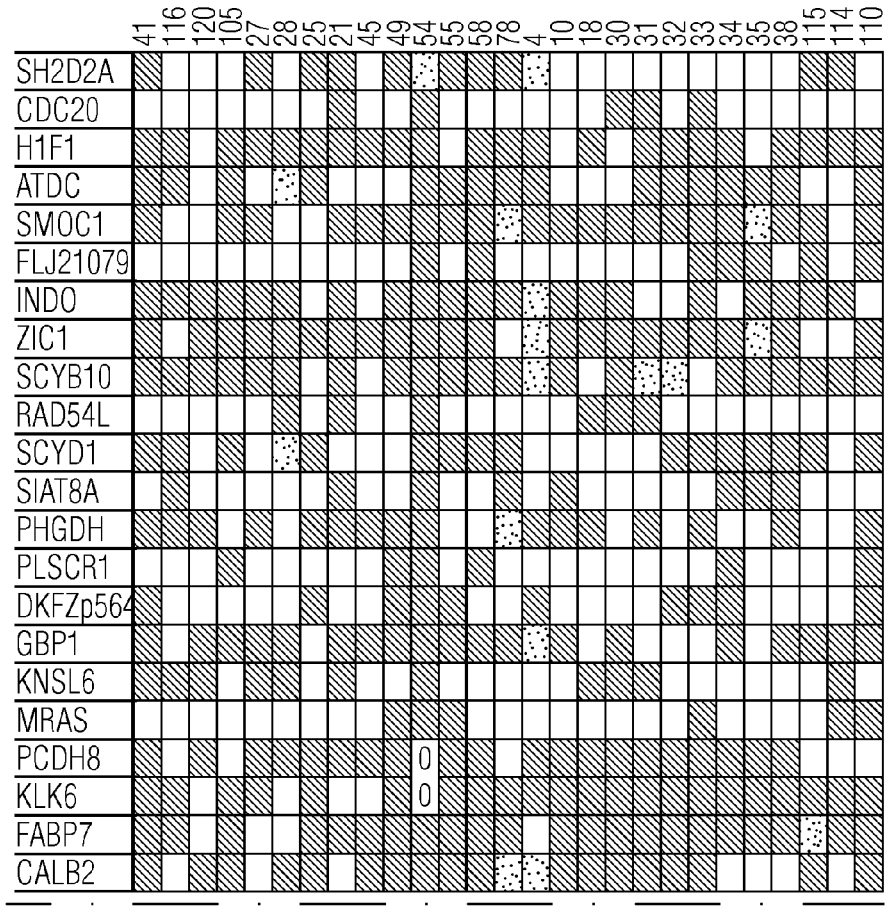

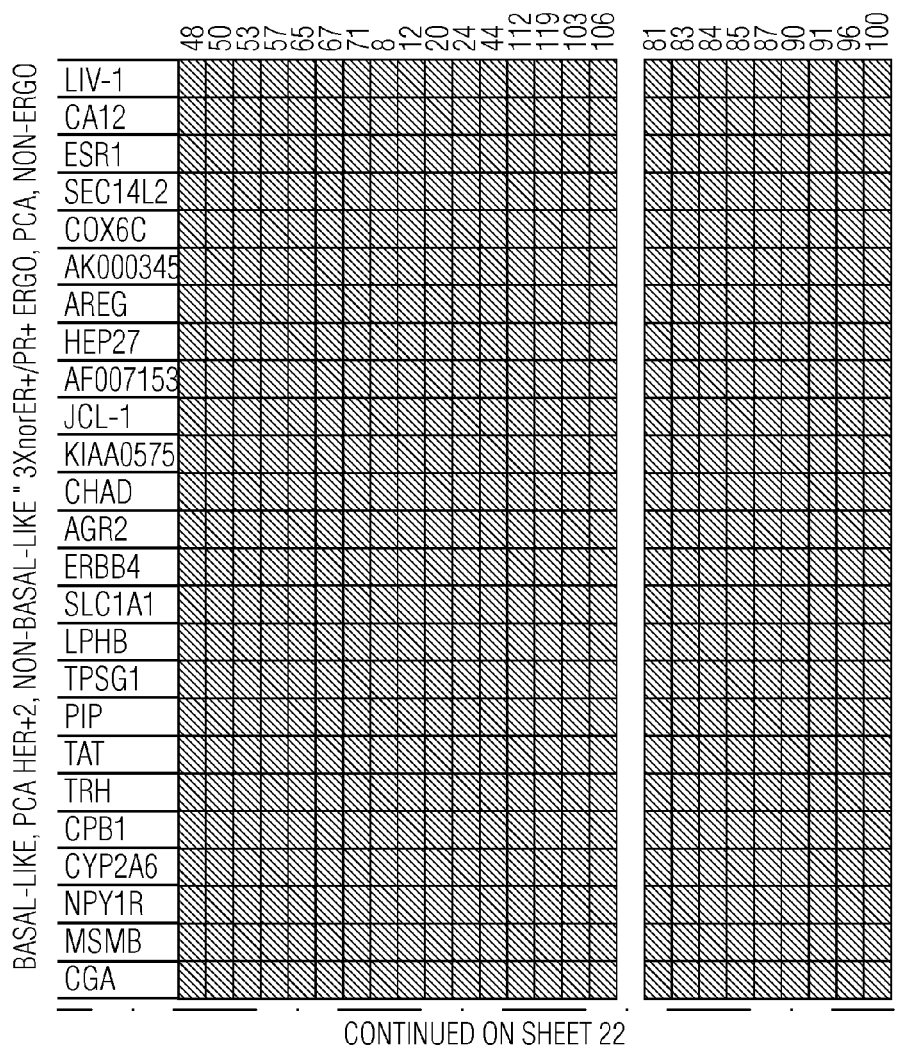

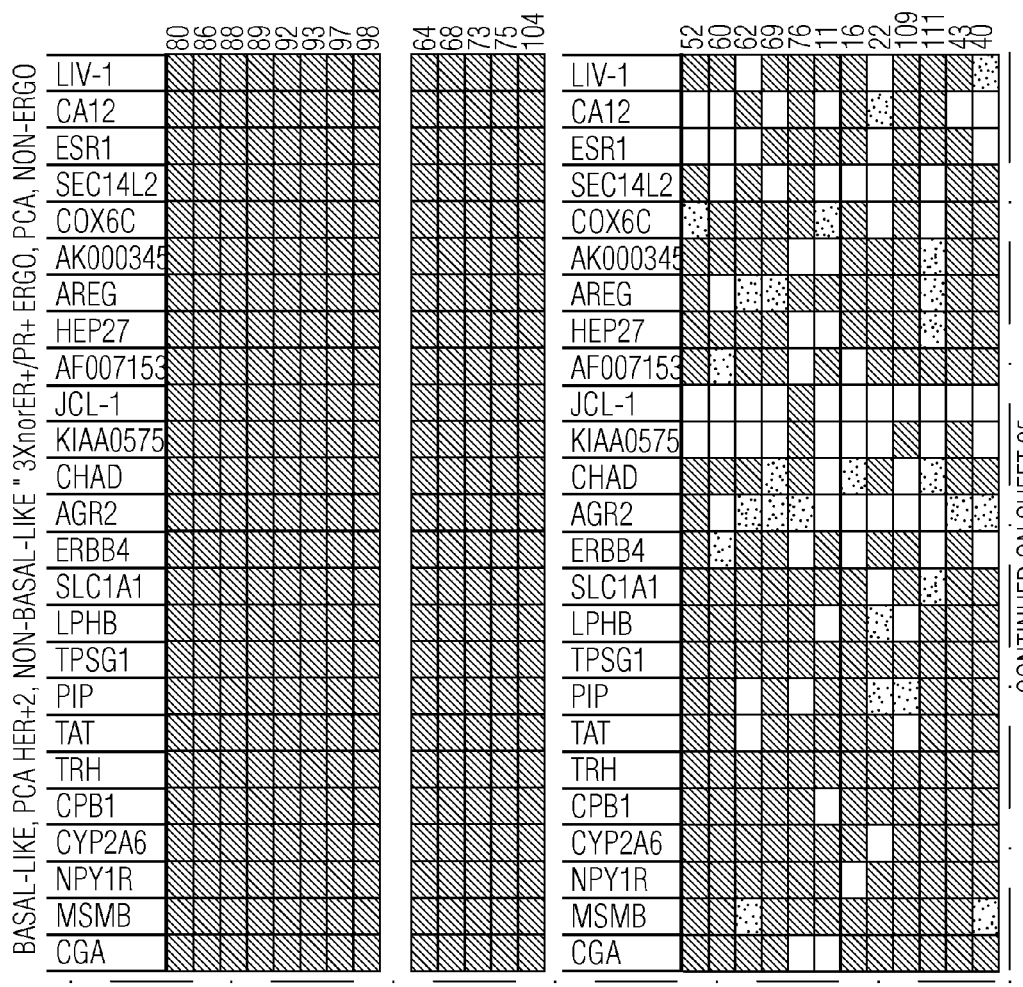

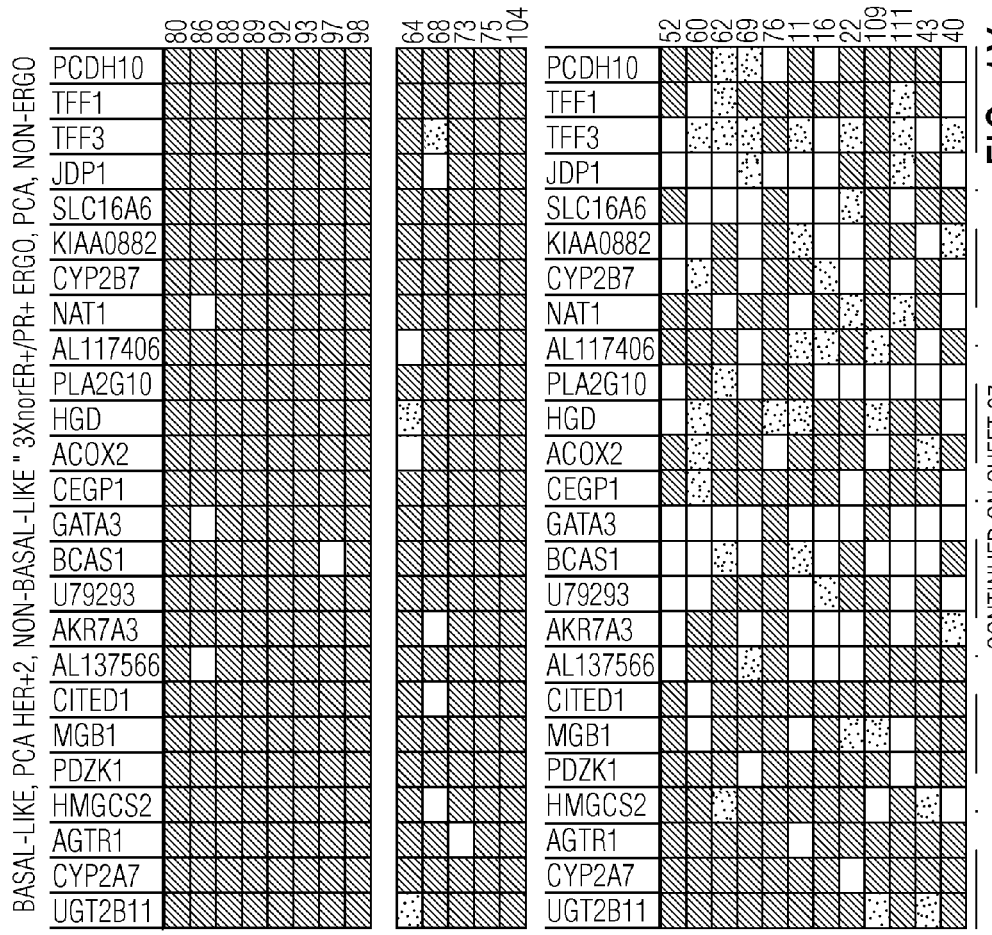

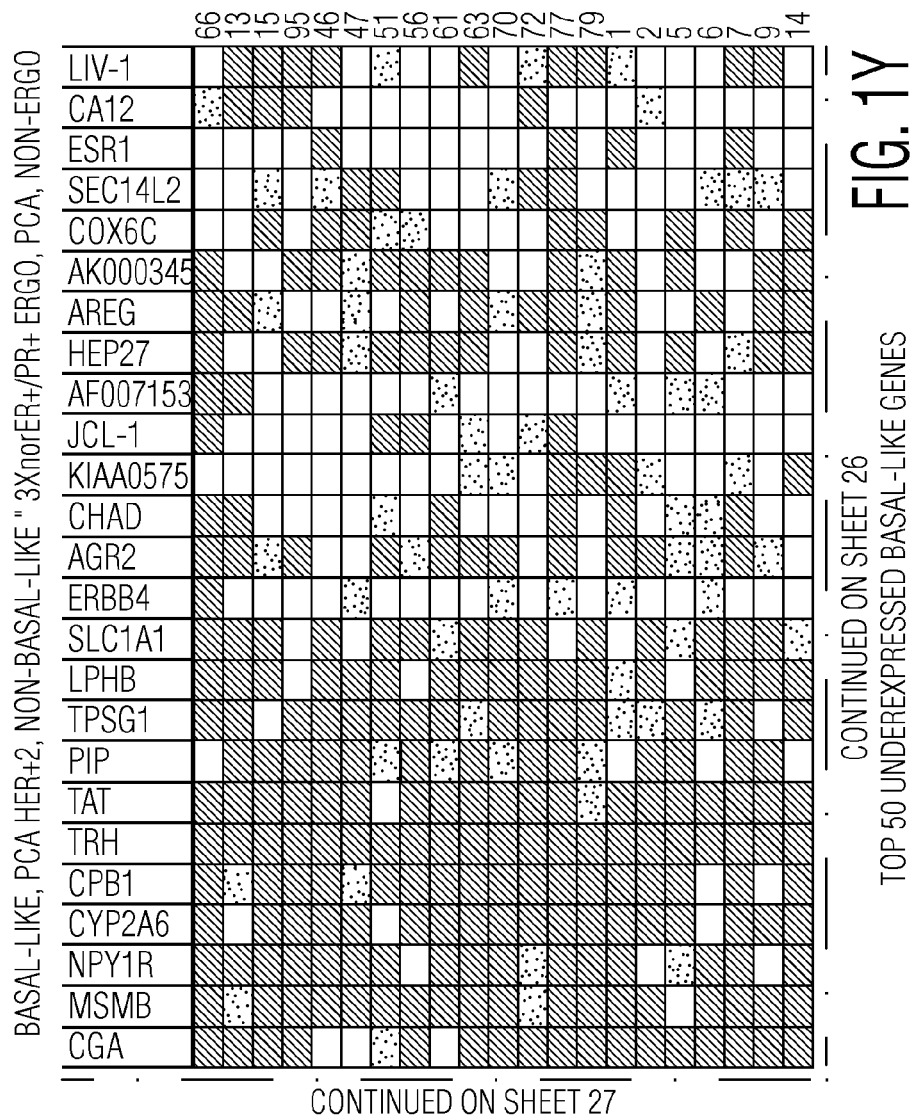

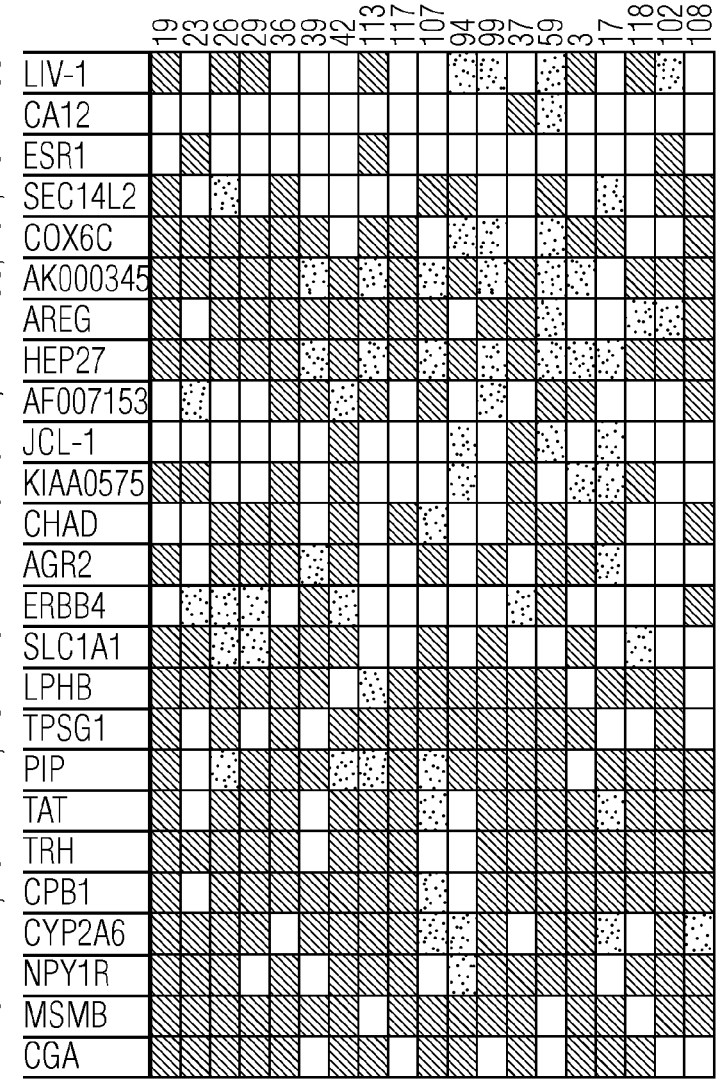

FIG. 1AA

TOP 50 UNDEREXPRESSED BASAL-LIKE GENES

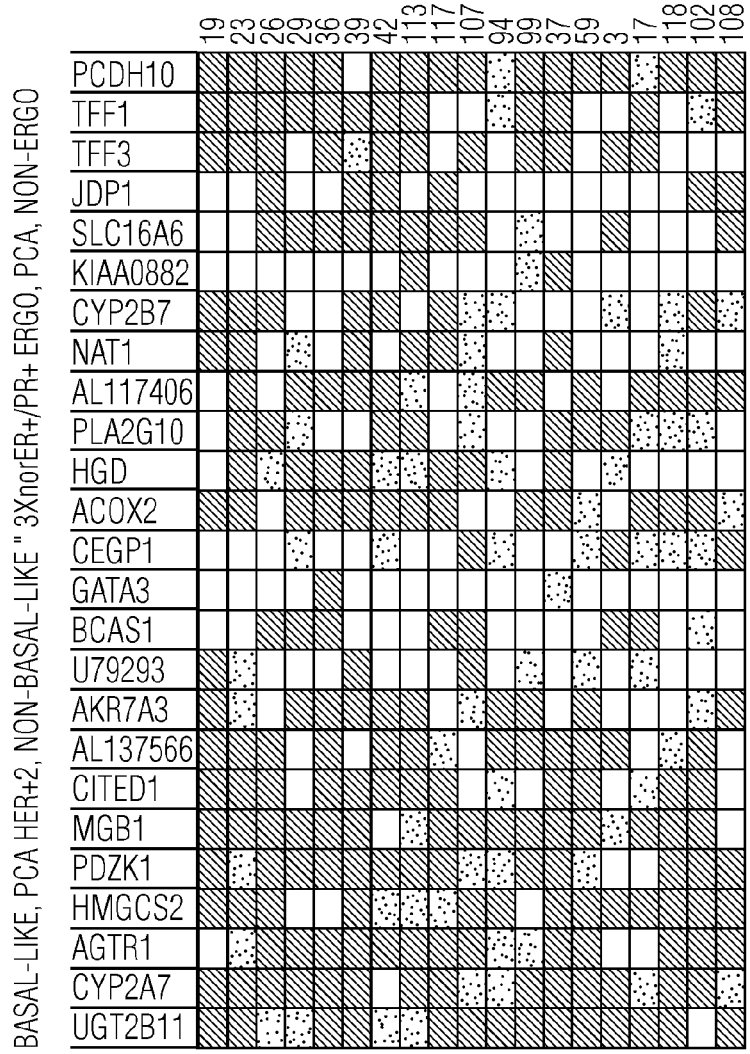

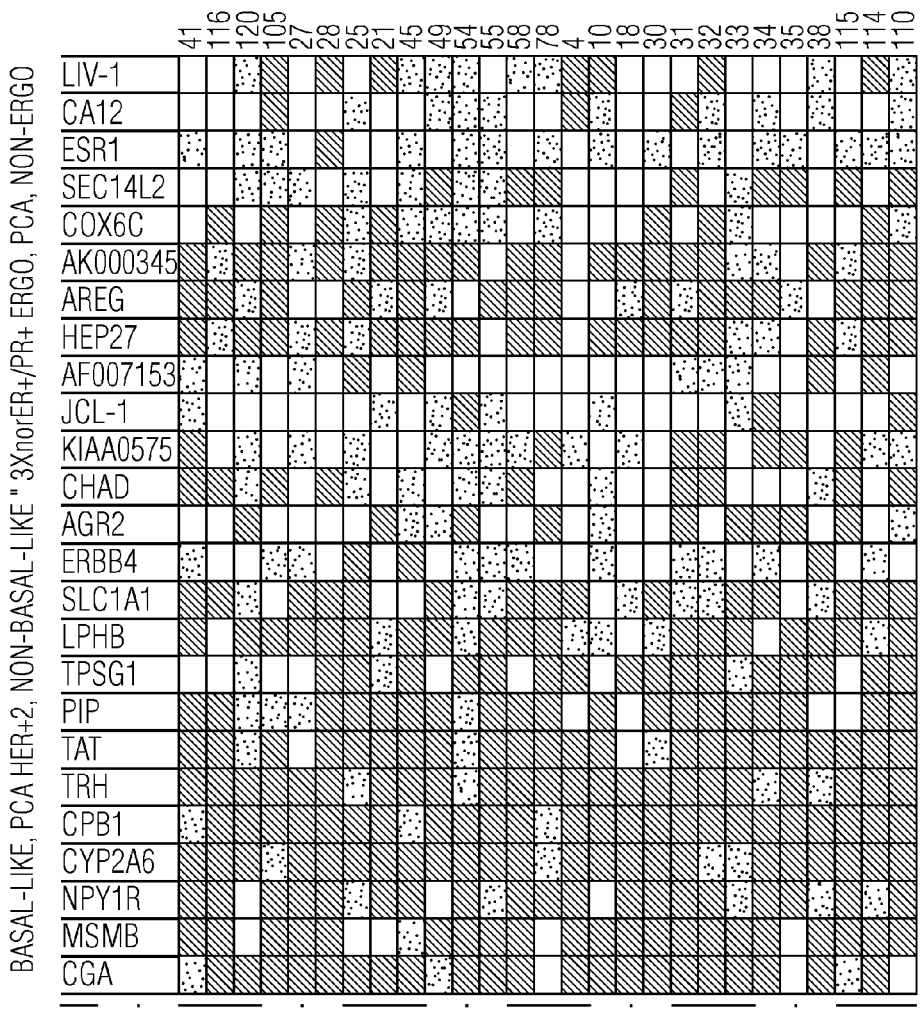

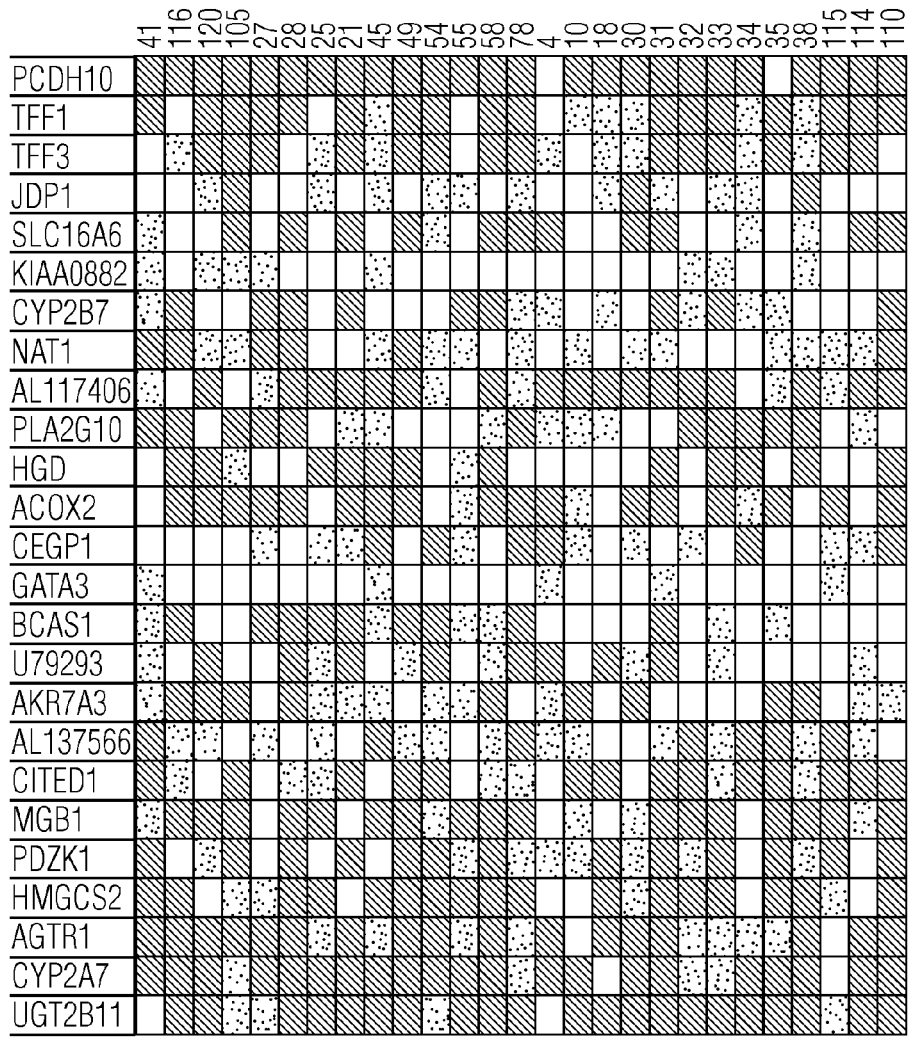

| | | | | |
|---|---|---|---|---|
| 16 | TP533BP2 | | KNSL1 | 13 |
| 15 | MCM7 | | LMNB1 | 13 |
| 15 | CCNA2 | | ORC6L | 12 |
| 15 | CCNB2 | | TP53BP2 | 12 |
| 15 | EZH2 | | NEK2 | 12 |
| 15 | TEAD4 | | CCNE2 | 12 |
| 14 | KNSL2 | | RFC4 | 11 |
| 14 | PTTG1 | | MCM2 | 11 |
| 14 | CDC25A | | STK15 | 11 |
| 14 | FDJ22009 | | DNA2L | 11 |
| 14 | SMC4L1 | | SOX9 | 11 |
| 14 | MAP3K14 | | MYC | 11 |
| 13 | TK1 | | PRIM2A | 10 |
| 13 | KIAA0175 | | CKS1 | 10 |
| 13 | CDC45L | | NUP155 | 10 |
| 13 | MCM2 | | NASP | 10 |
| 13 | SOX9 | | CSDA | 10 |
| 13 | VEGF | | KPNA2 | 10 |
| 13 | UBCH10 | | CDC25B | 10 |
| 13 | KNSL1 | | MAP3K14 | 10 |
| 12 | HEC | | NOLC1 | 9 |
| 12 | RFC4 | | CKS2 | 9 |
| 12 | RFC4 | | FLJ22009 | 9 |
| 12 | MCM6 | | CCNB1 | 9 |
| 12 | ORC6L | | RRM2 | 9 |
| 12 | PRIM2A | | ANXA8 | 9 |
| 12 | BIRC5 | | KIF4A | 8 |
| 12 | CSDA | | | |
| 11 | MYC | | | |
| 11 | KPNA2 | | | |
| 11 | MAD2L1 | | | |
| 11 | DNA2L | | | |
| 11 | CKS1 | | | |
| 11 | CDC7L1 | | | |
| 11 | RTRSN1 | | | |
| 11 | ECT2 | | | |
| 10 | NUP155 | | | |
| 10 | PRC1 | | | |
| 10 | NASP | | | |
| 10 | NEK2 | | | |
| 9 | PIR51 | | | |

13/38 = 34%
11/38 = 28.9%
11/31 = 35.4%
9/31 = 29%

CONTINUED ON SHEET 3

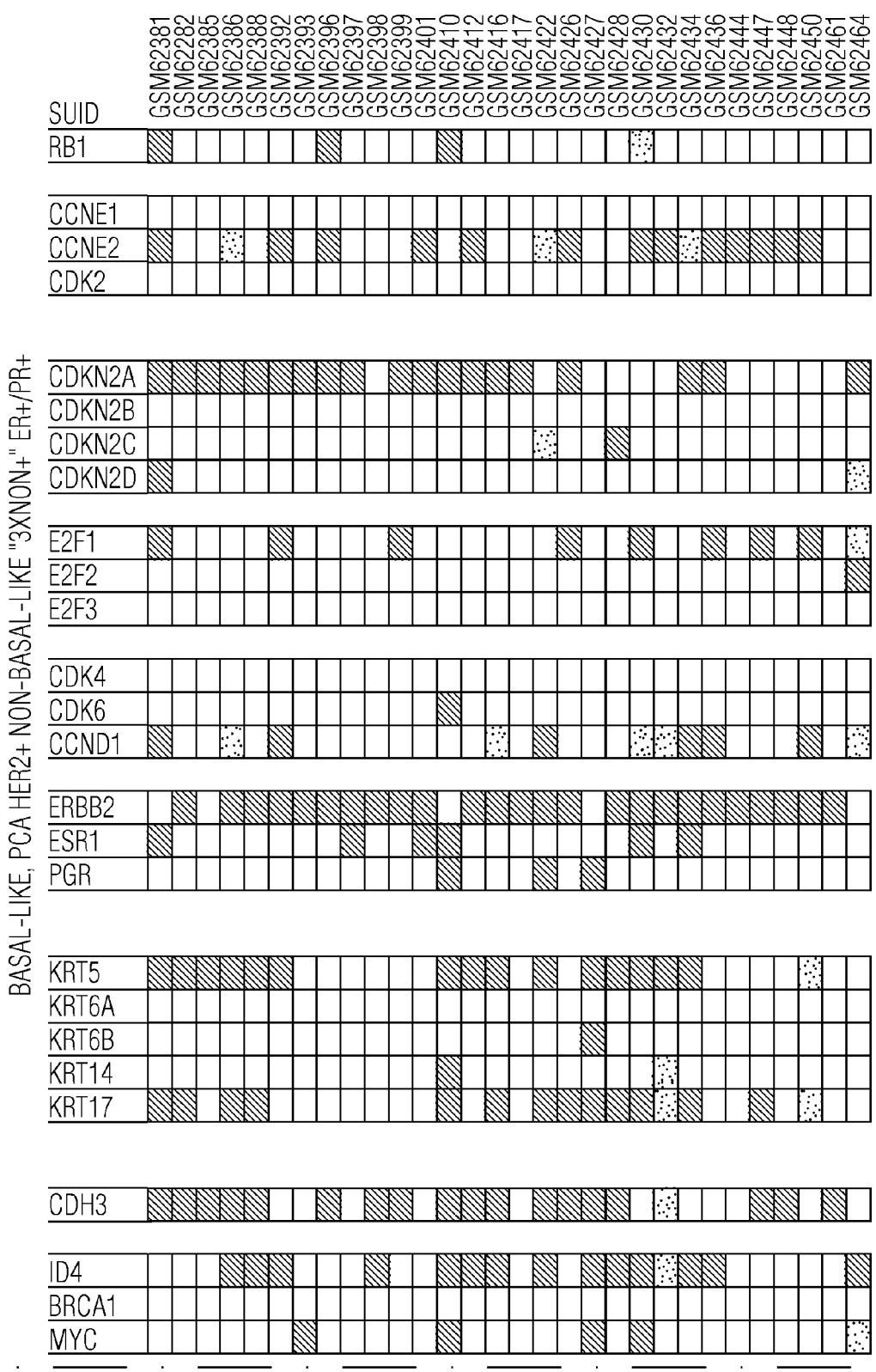

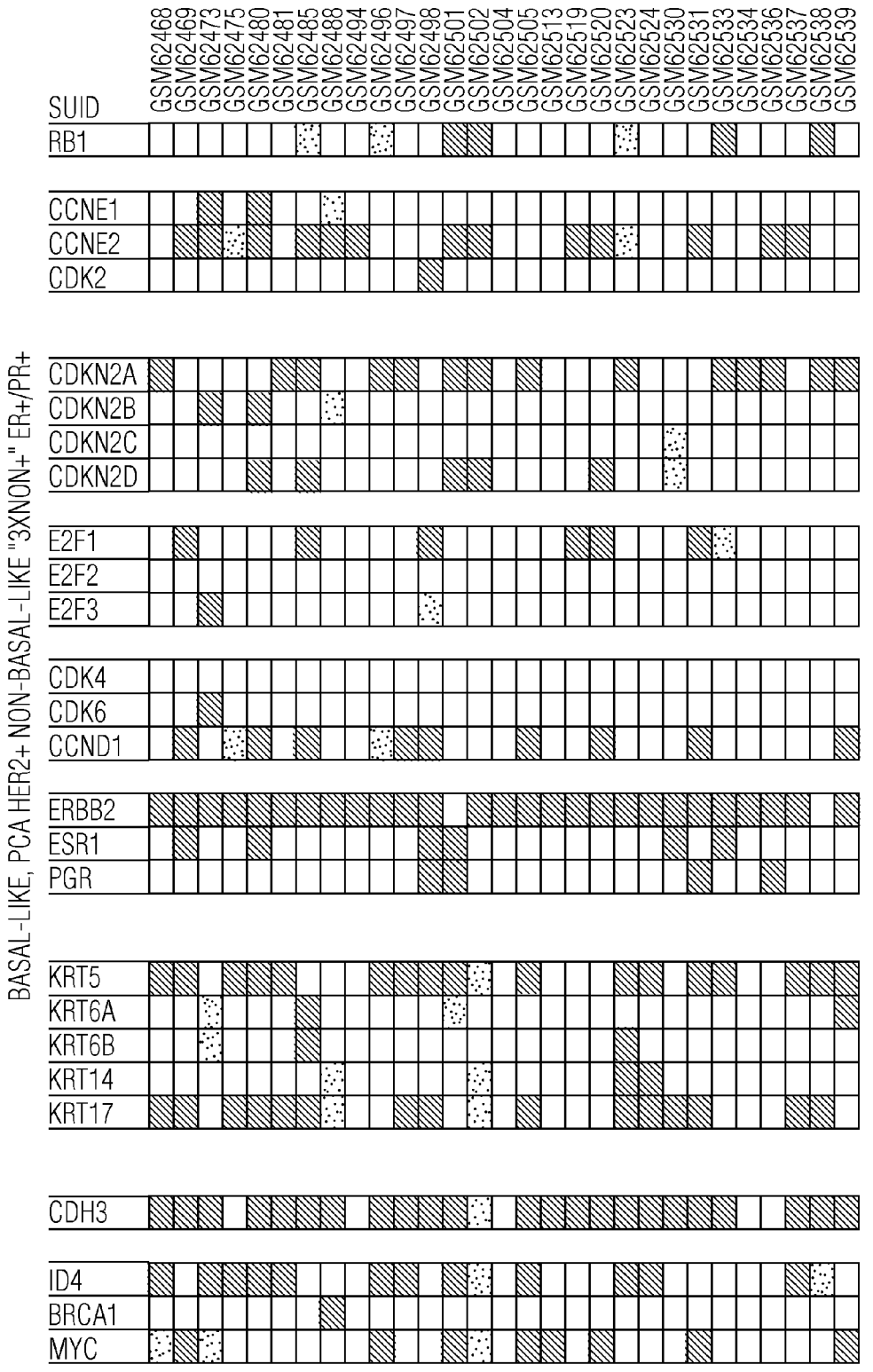

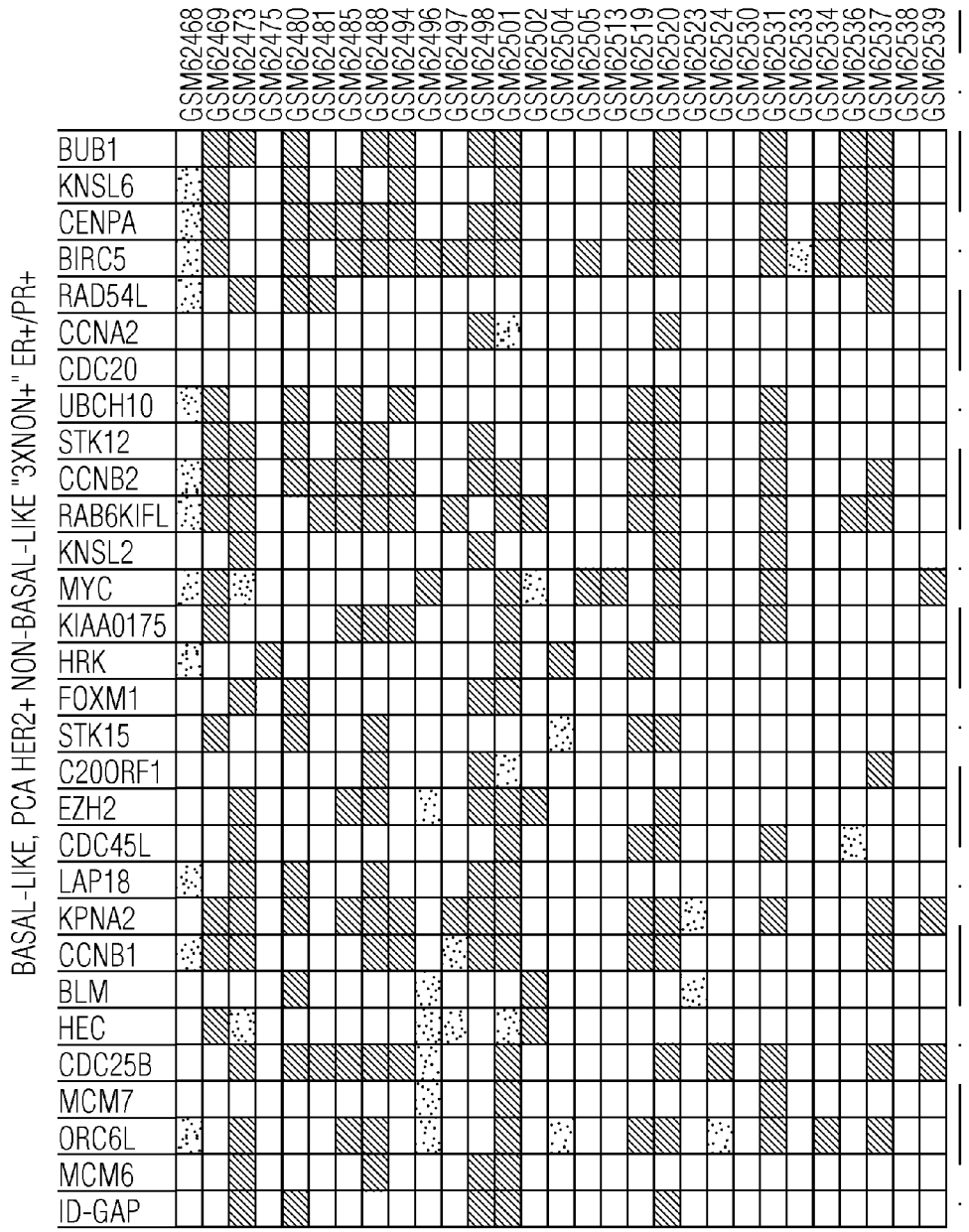

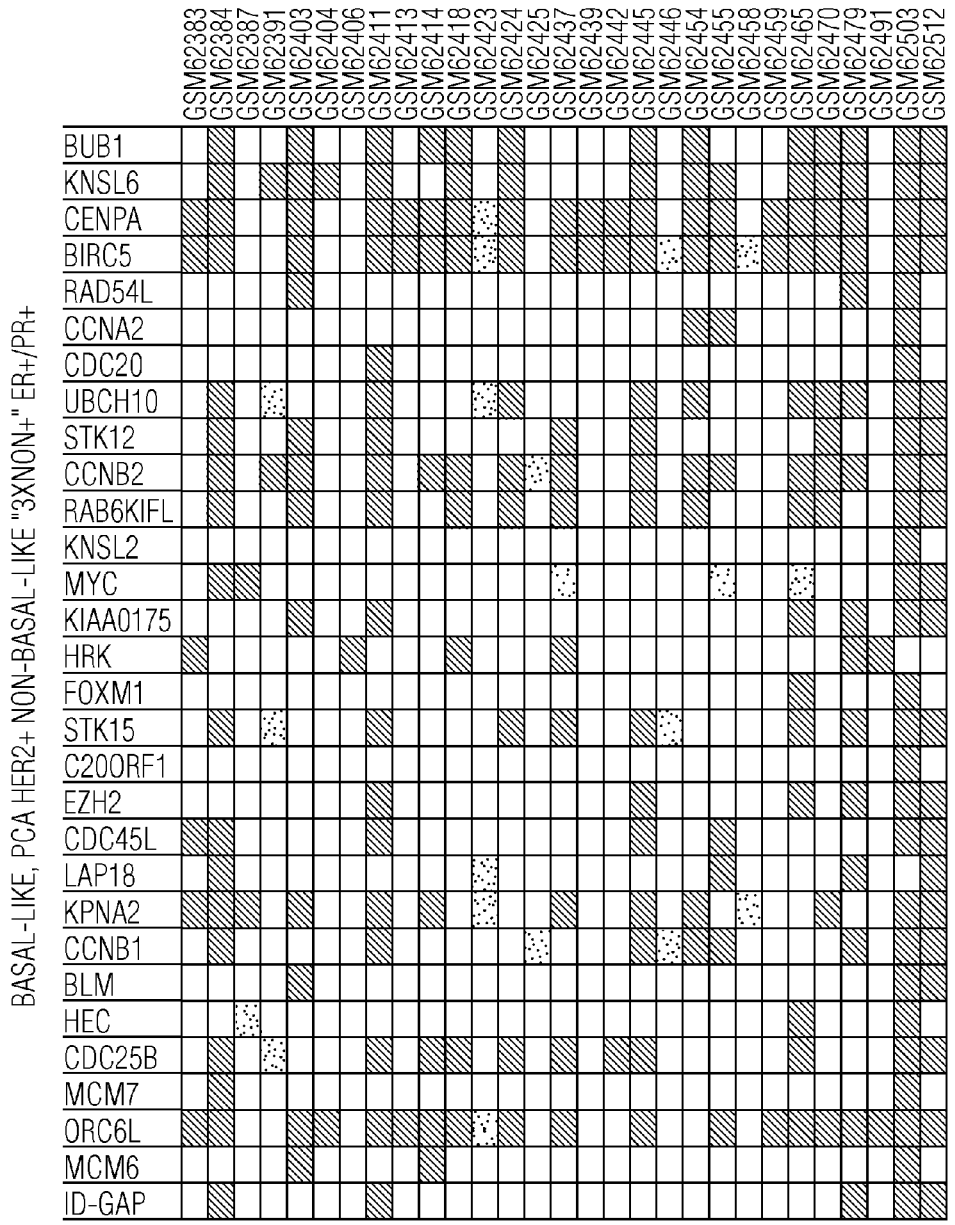

BASAL-LIKE, PCA HER2+ NON-BASAL-LIKE "3XNON+" ER+/PR+
TOP 50 OVEREXPRESSED BASAL-LIKE GENES

BASAL-LIKE, PCA HER2+ NON-BASAL-LIKE "3XNON+" ER+/PR+
TOP 50 OVEREXPRESSED BASAL-LIKE GENES

FIG. 4Z

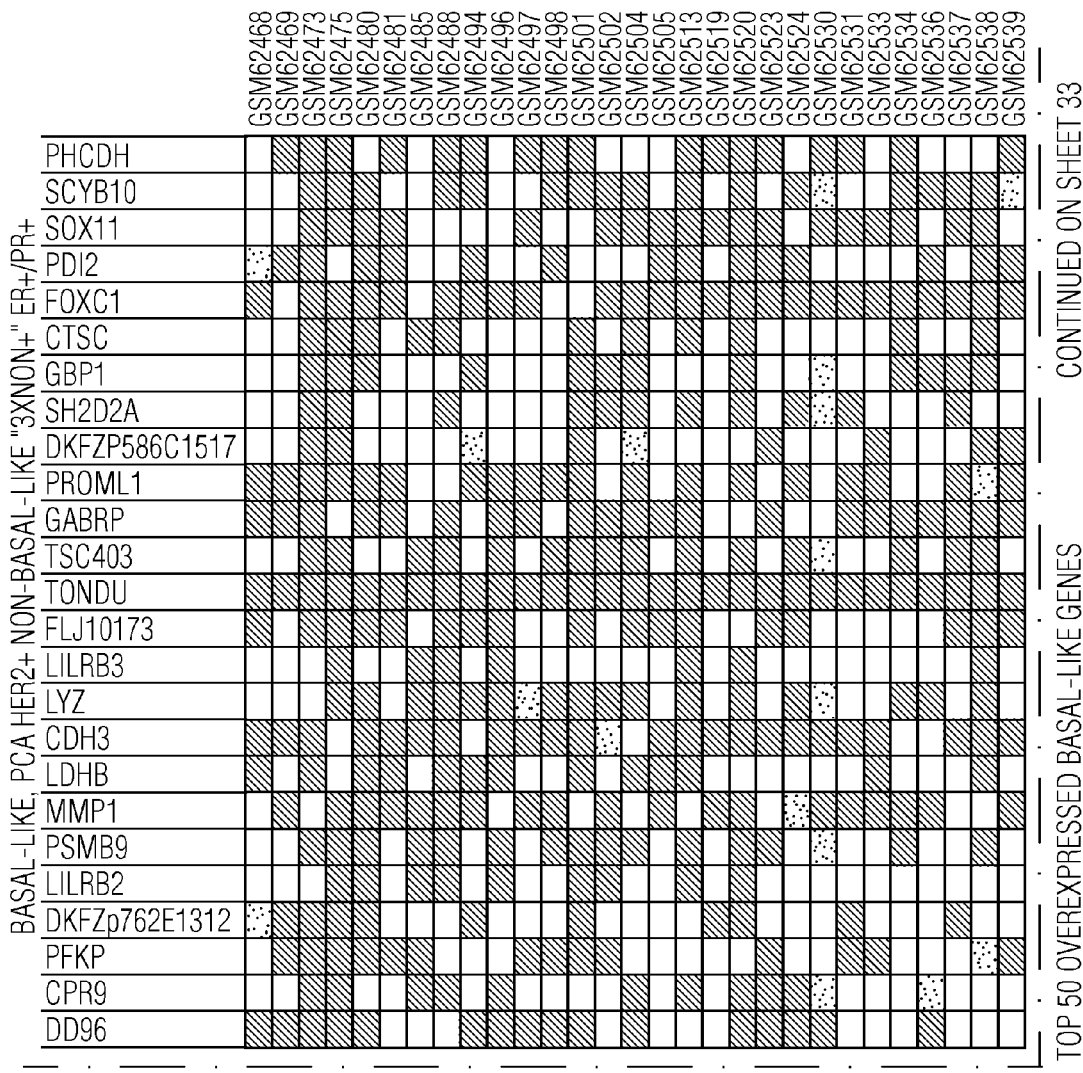

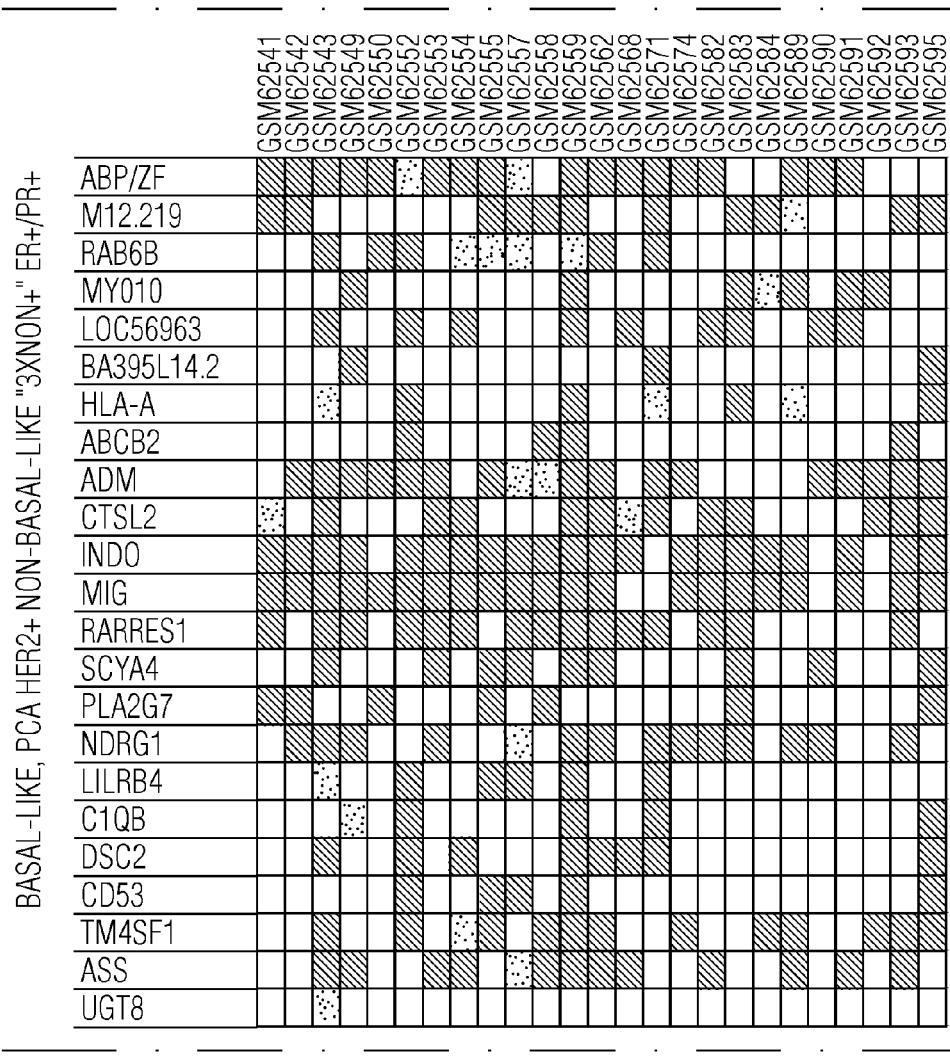

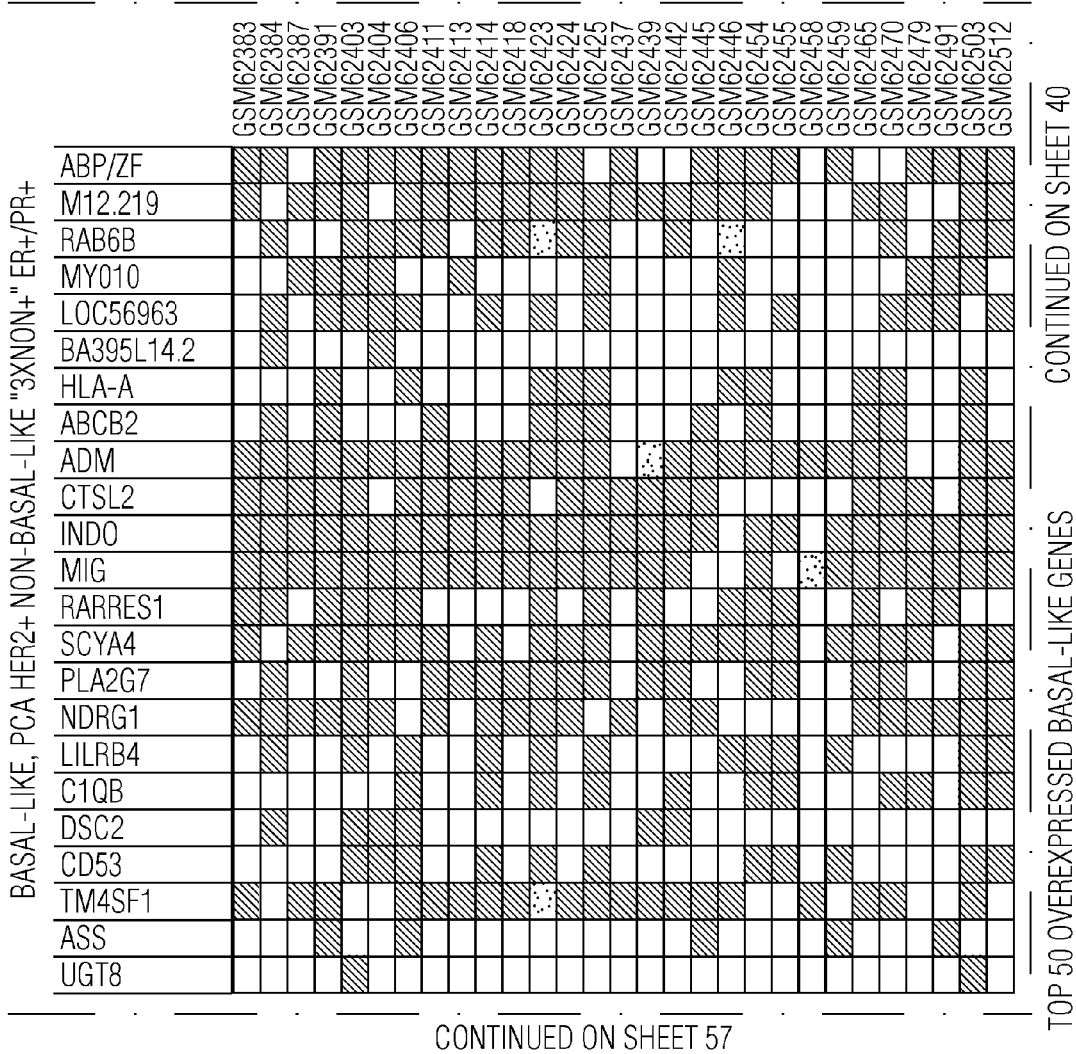

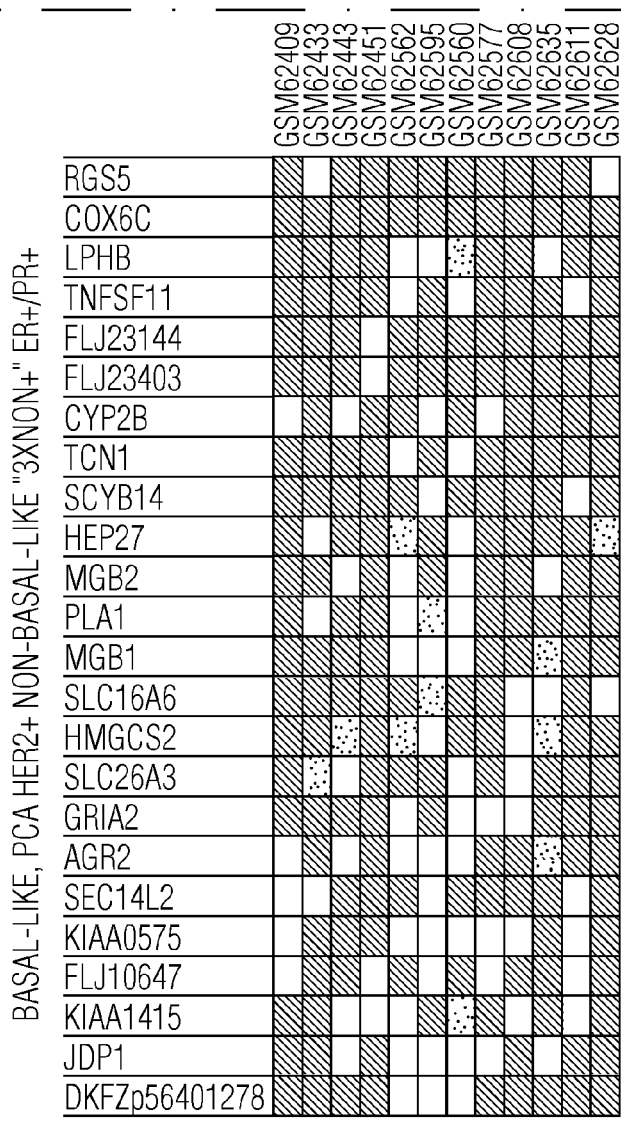

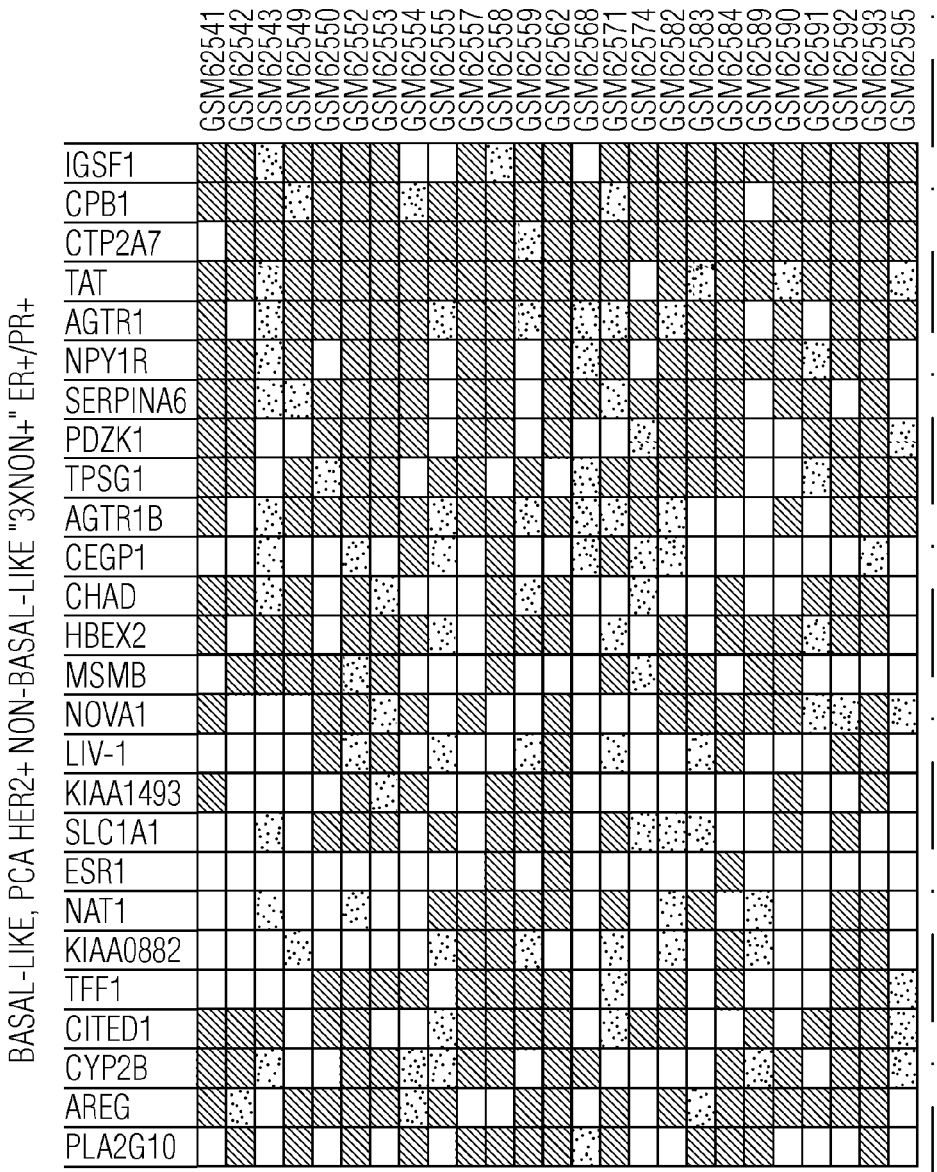
FIG. 4AAAA

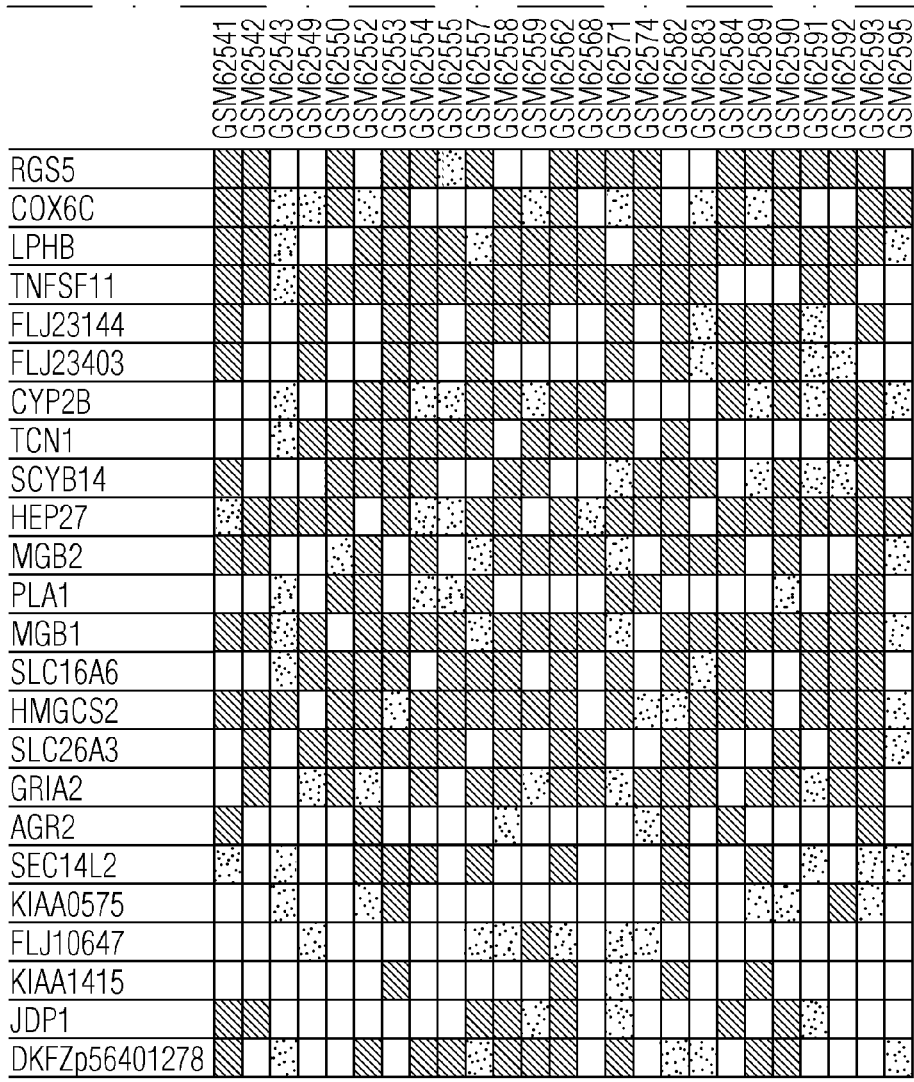
FIG. 4BBB

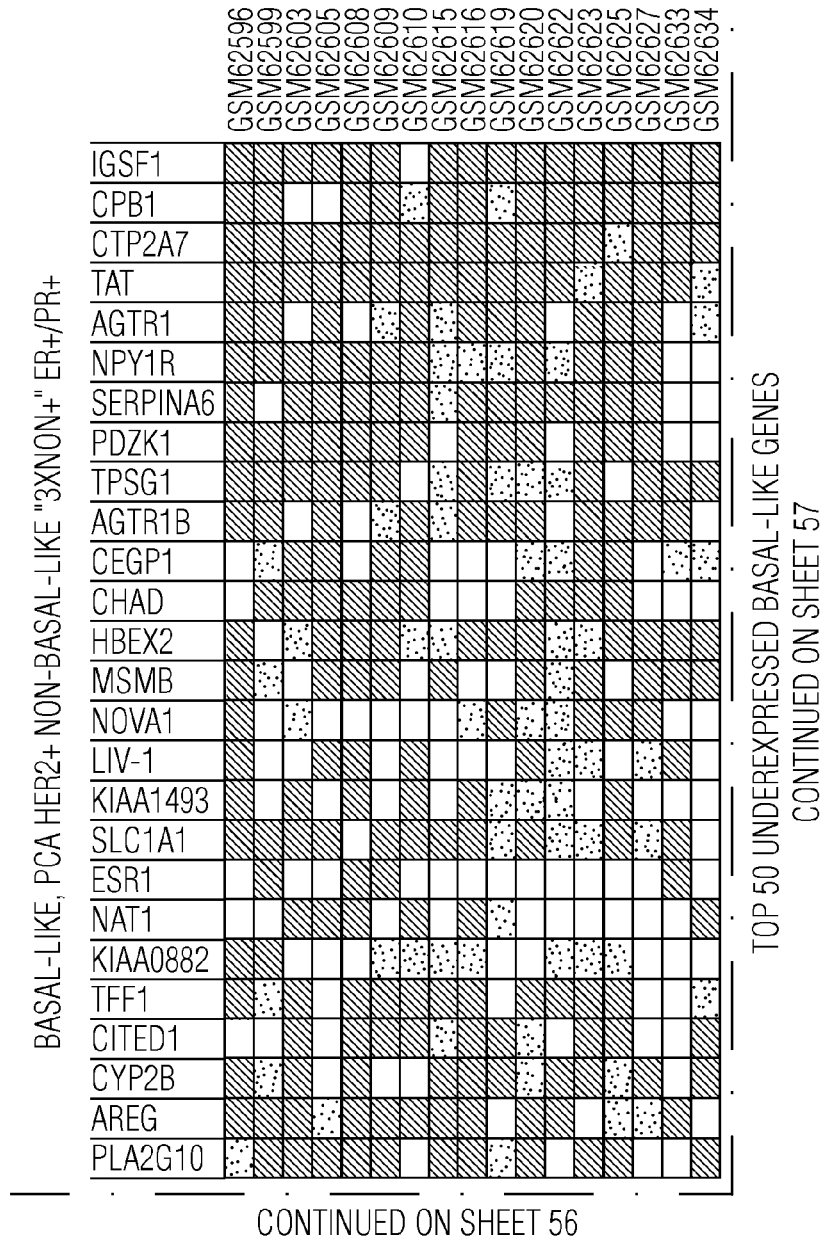

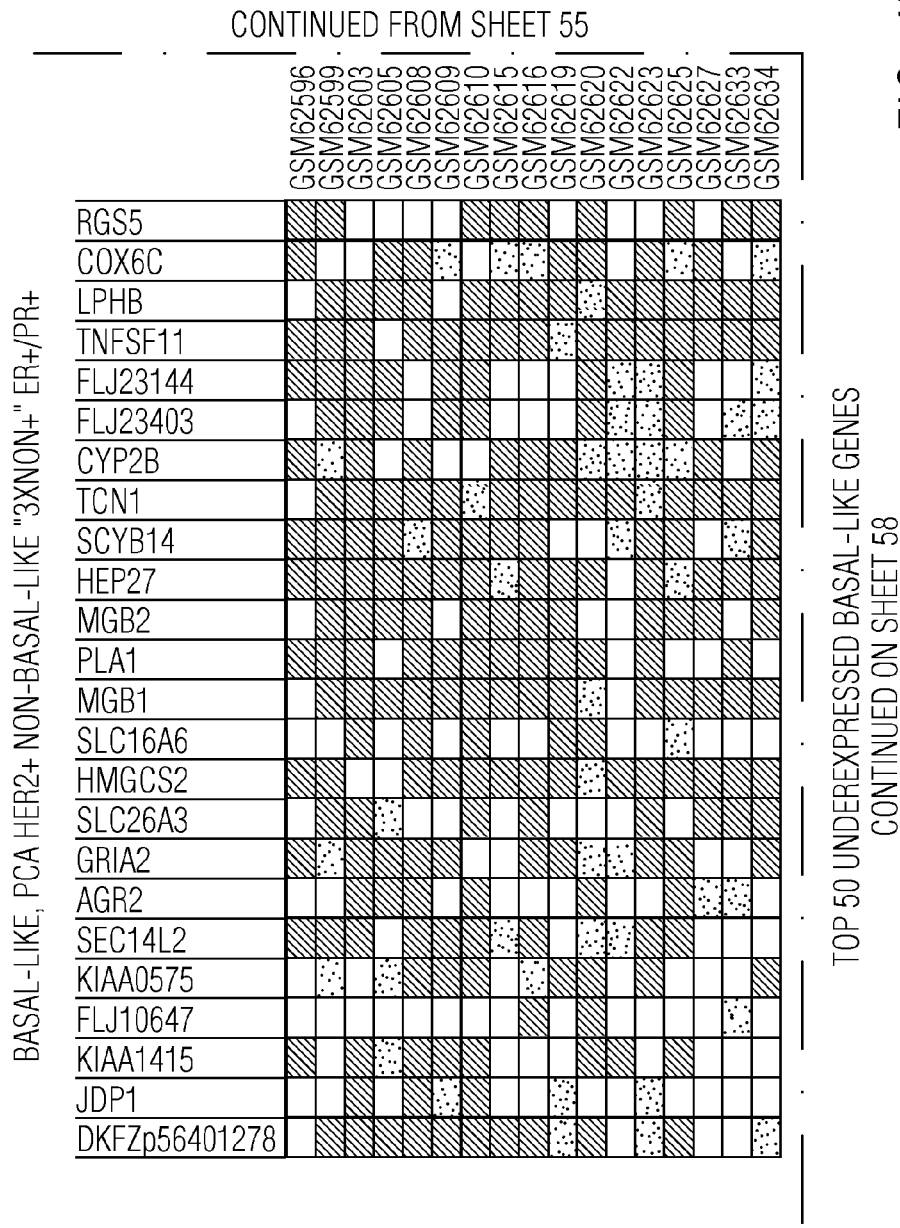
FIG. 4DDD

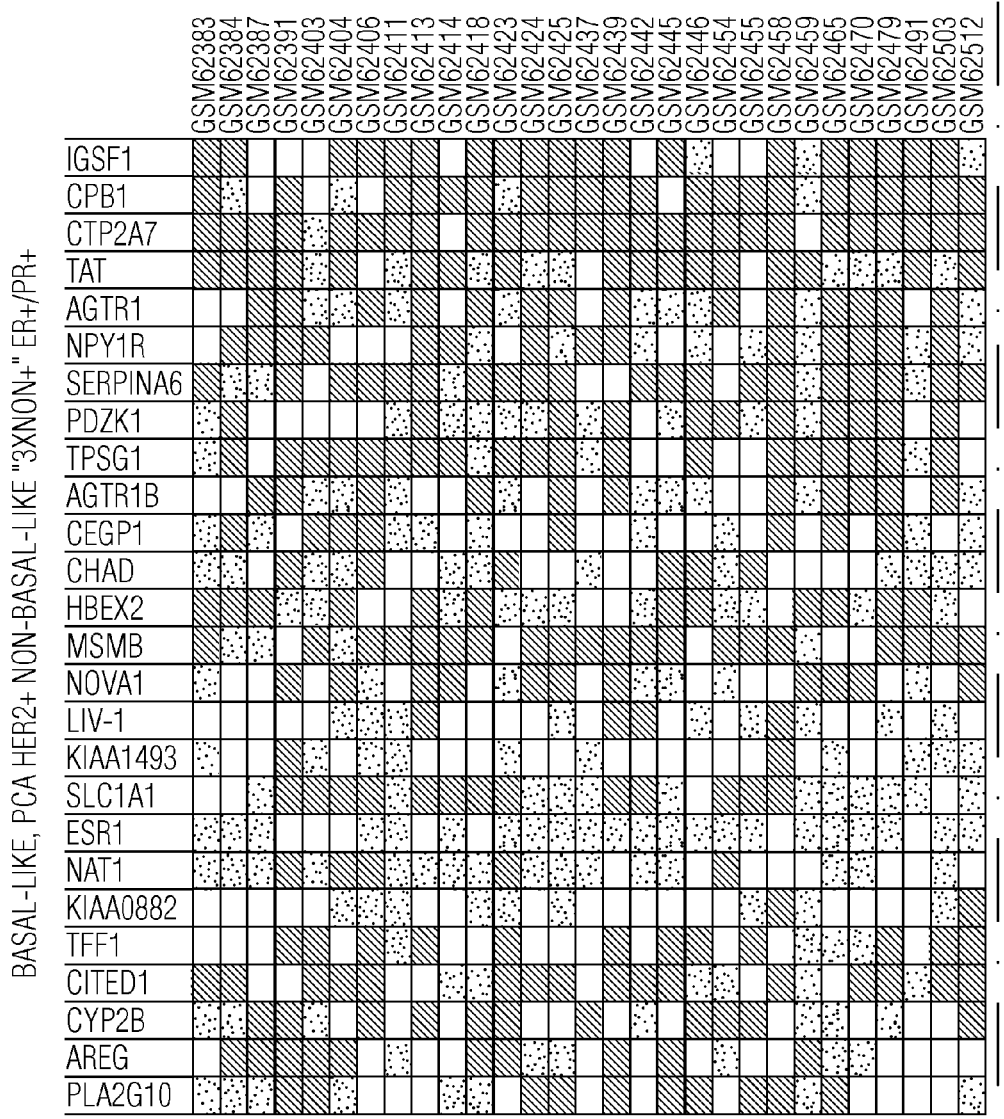
FIG. 4EEE

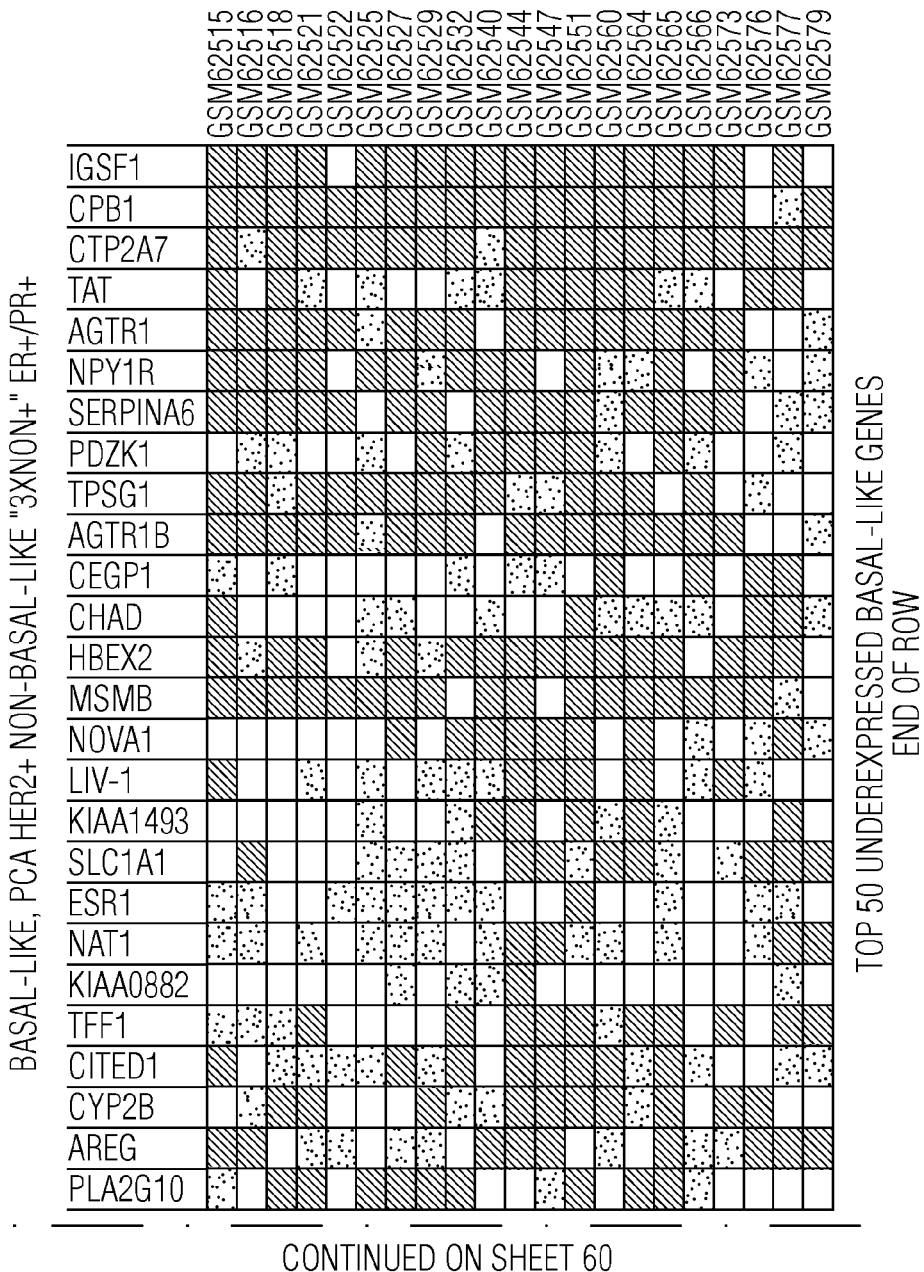
FIG. 4FFF

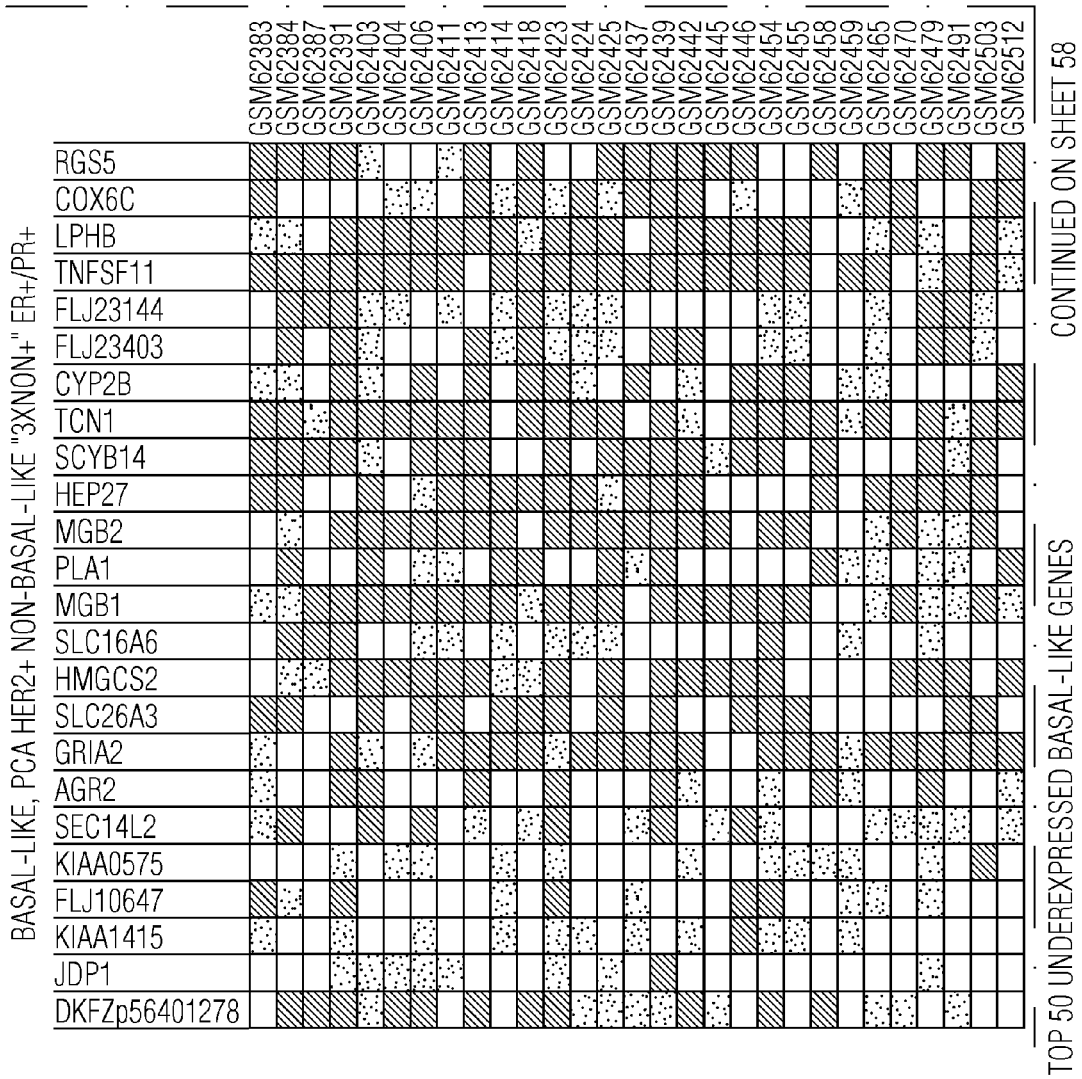
FIG. 4GGG

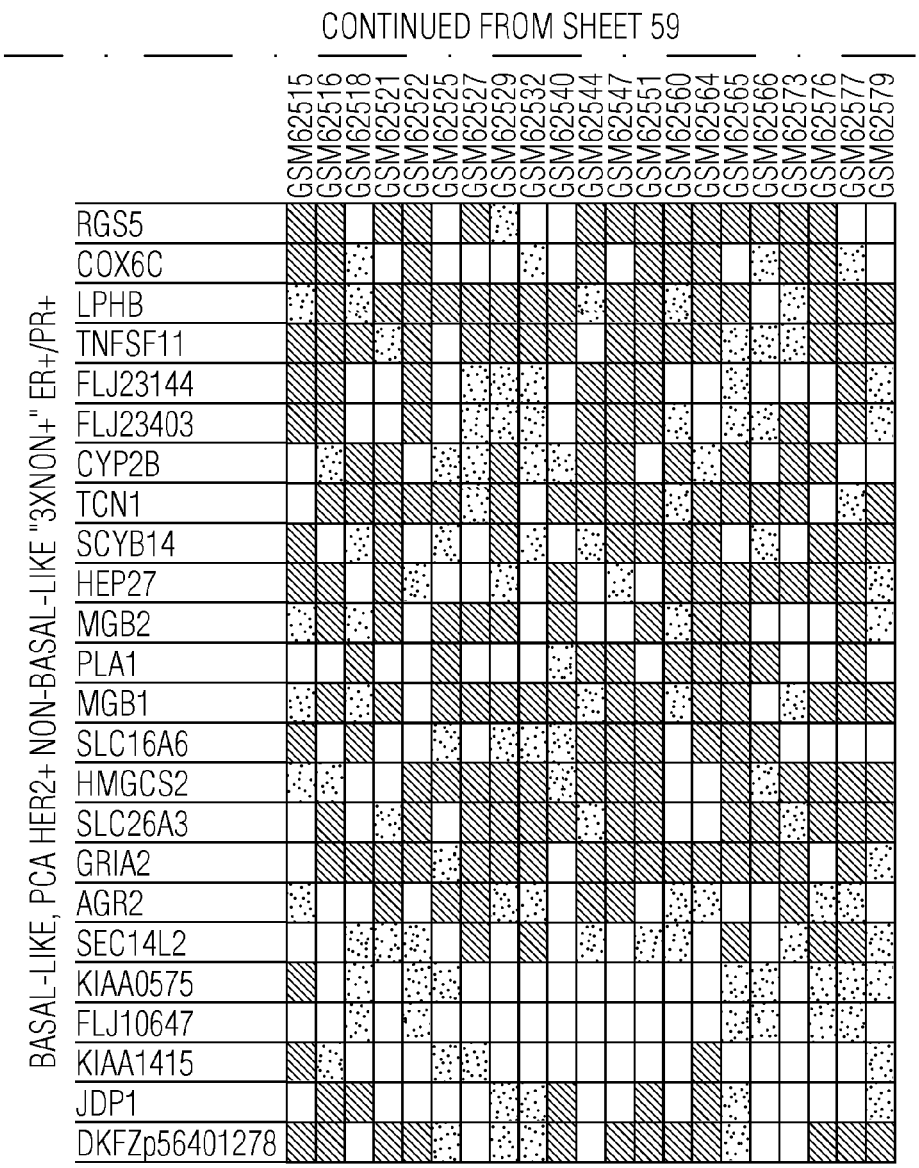
FIG. 4HHH

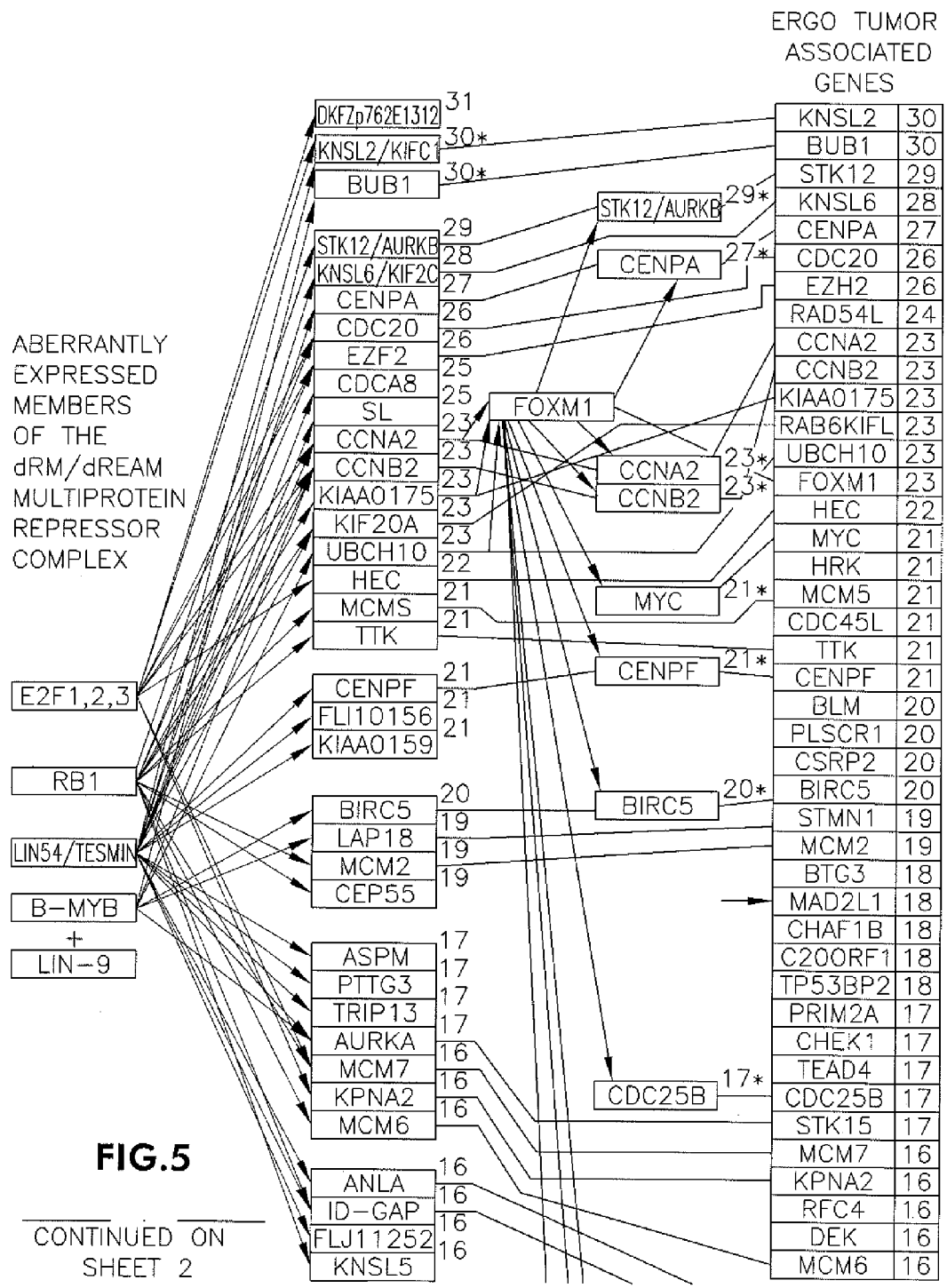
FIG.5
CONTINUED ON SHEET 2

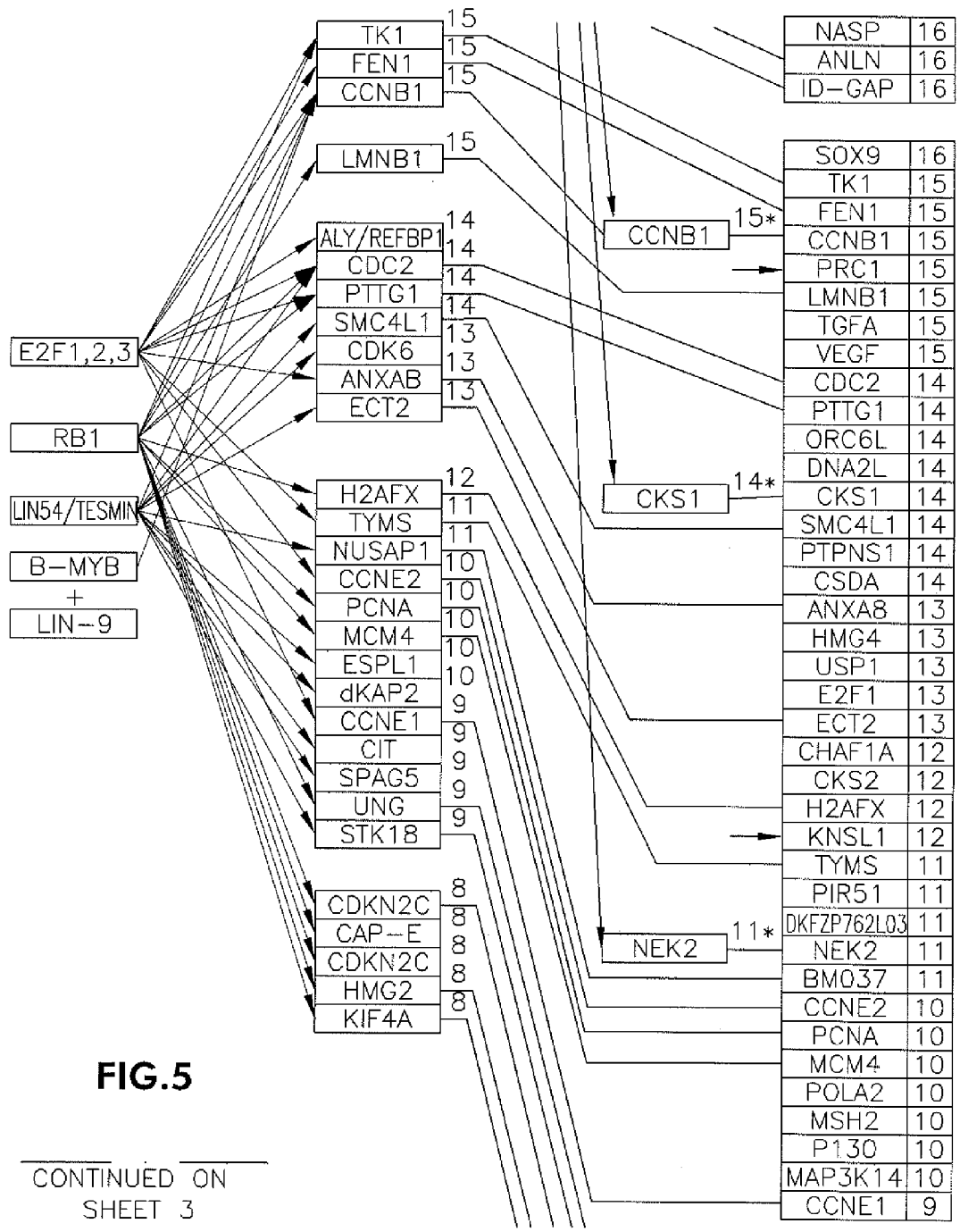
FIG.5
CONTINUED ON SHEET 3

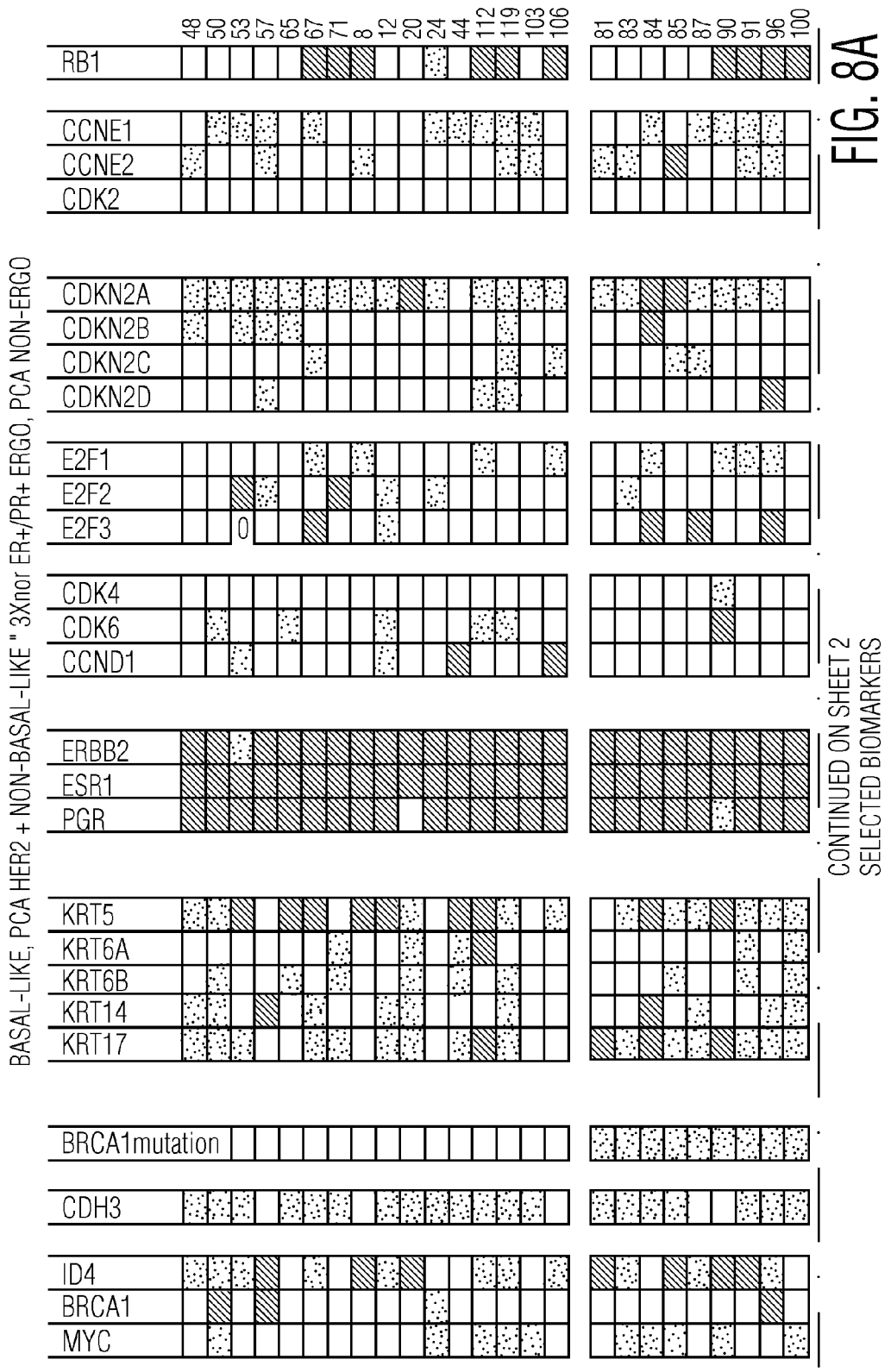

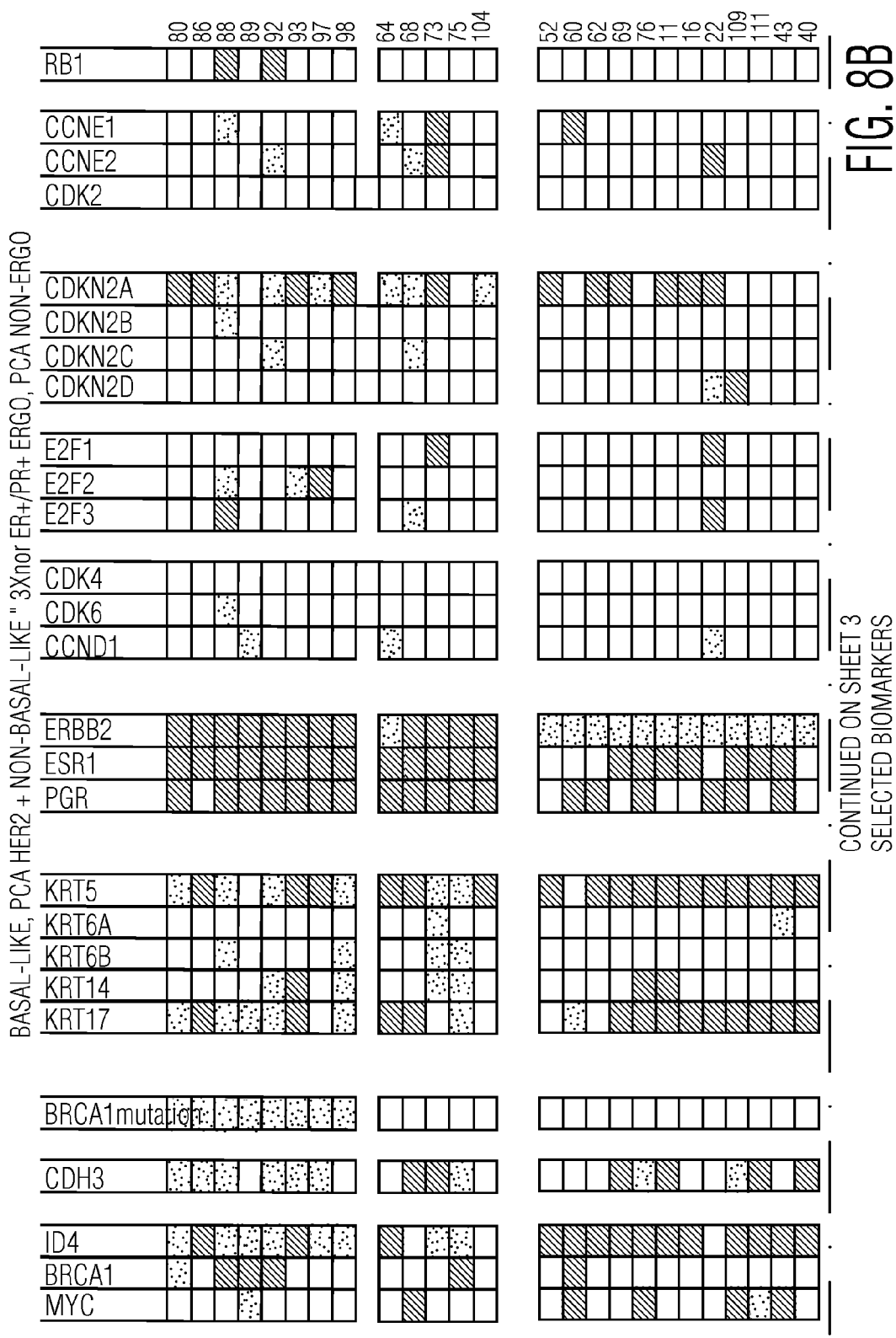

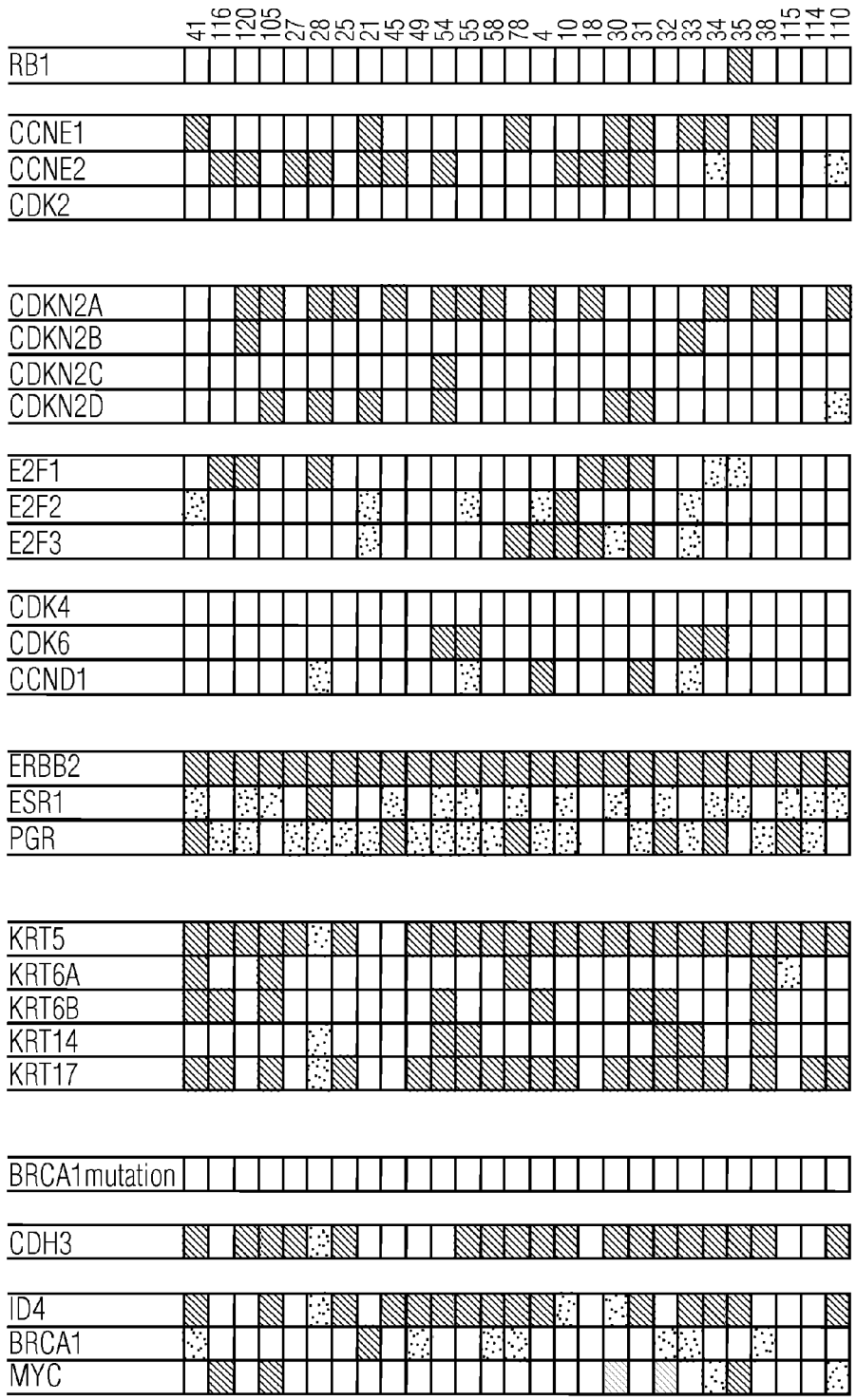

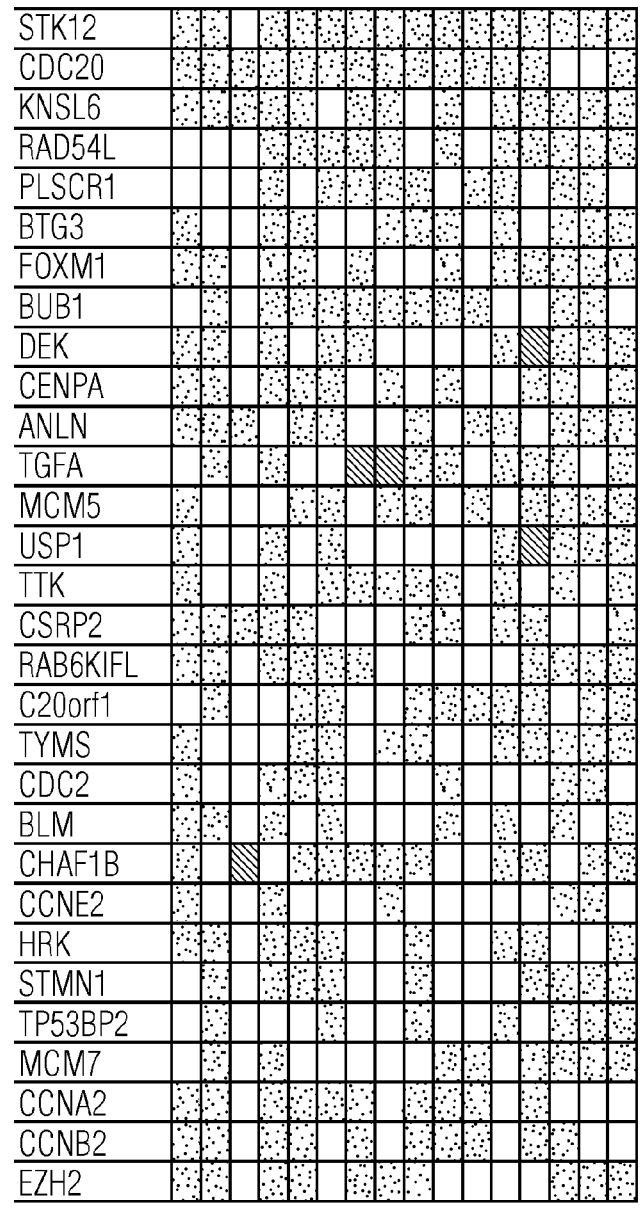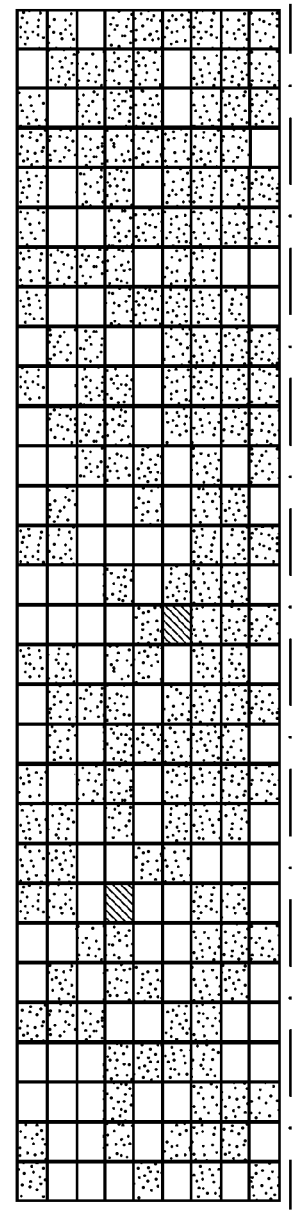
FIG. 8F

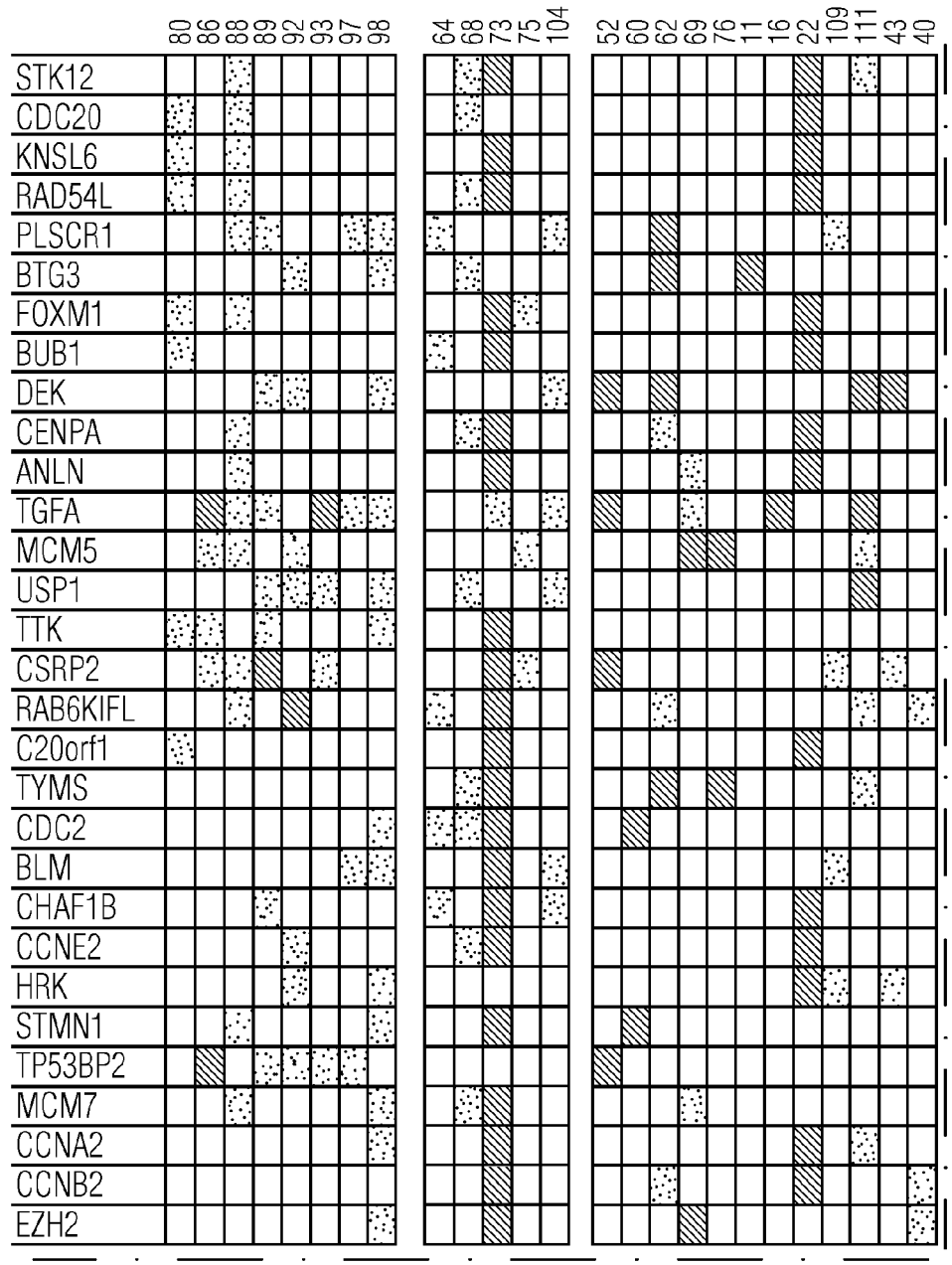

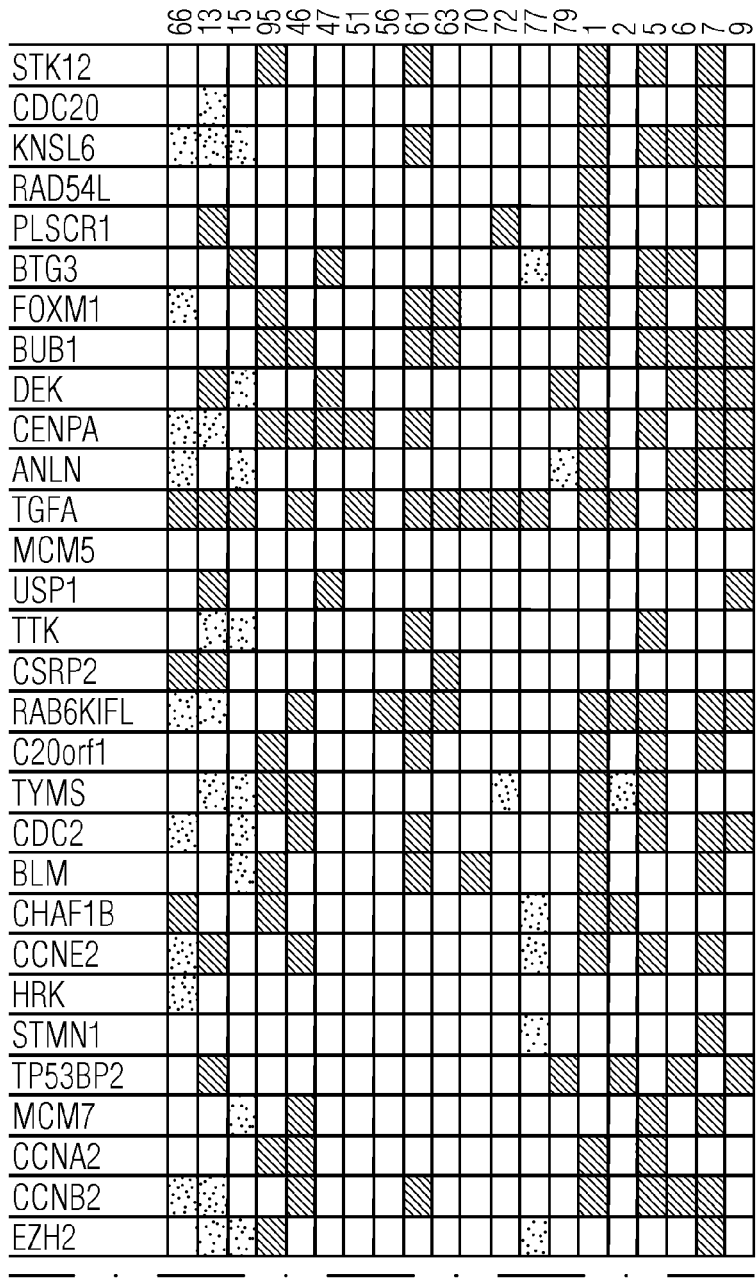

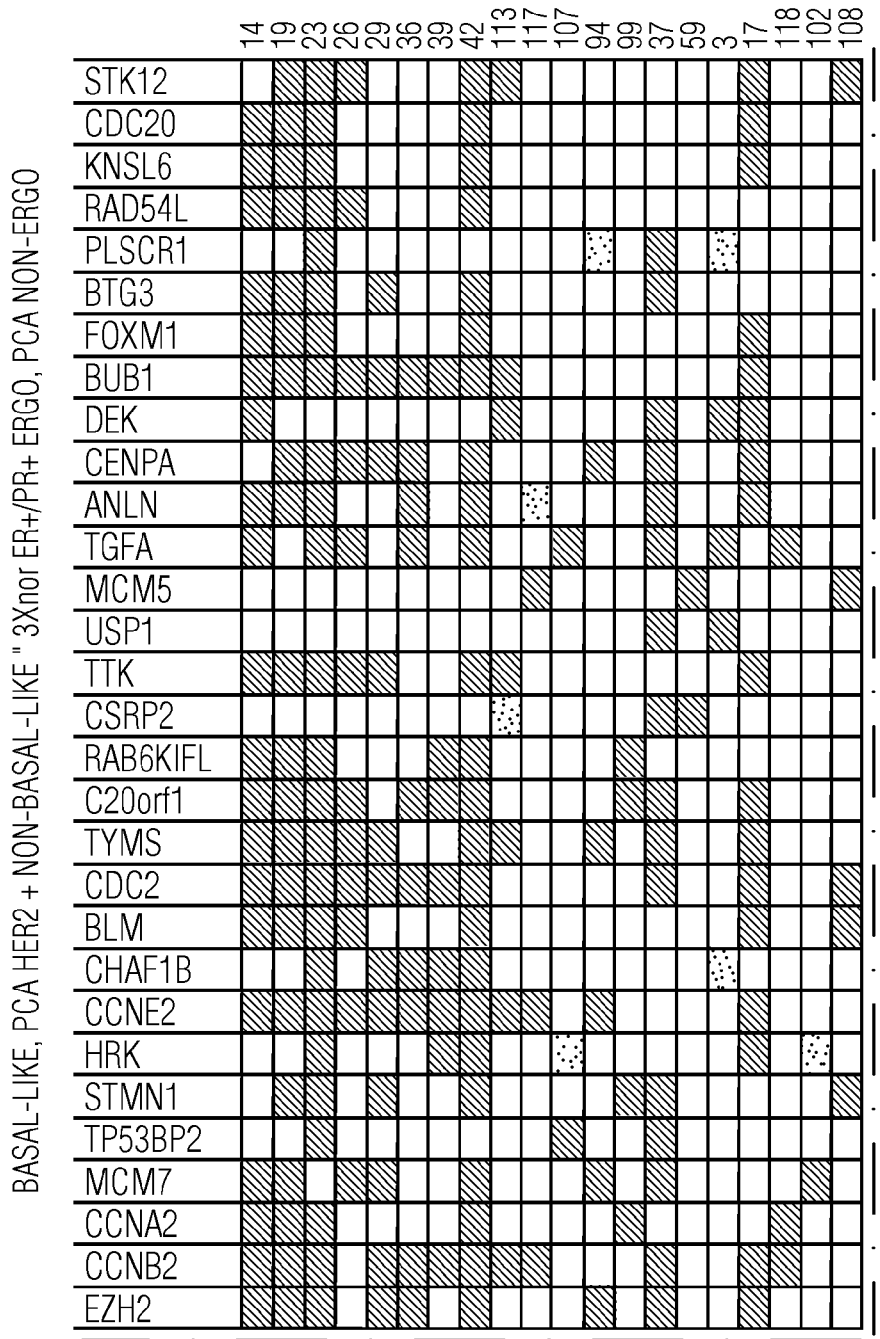

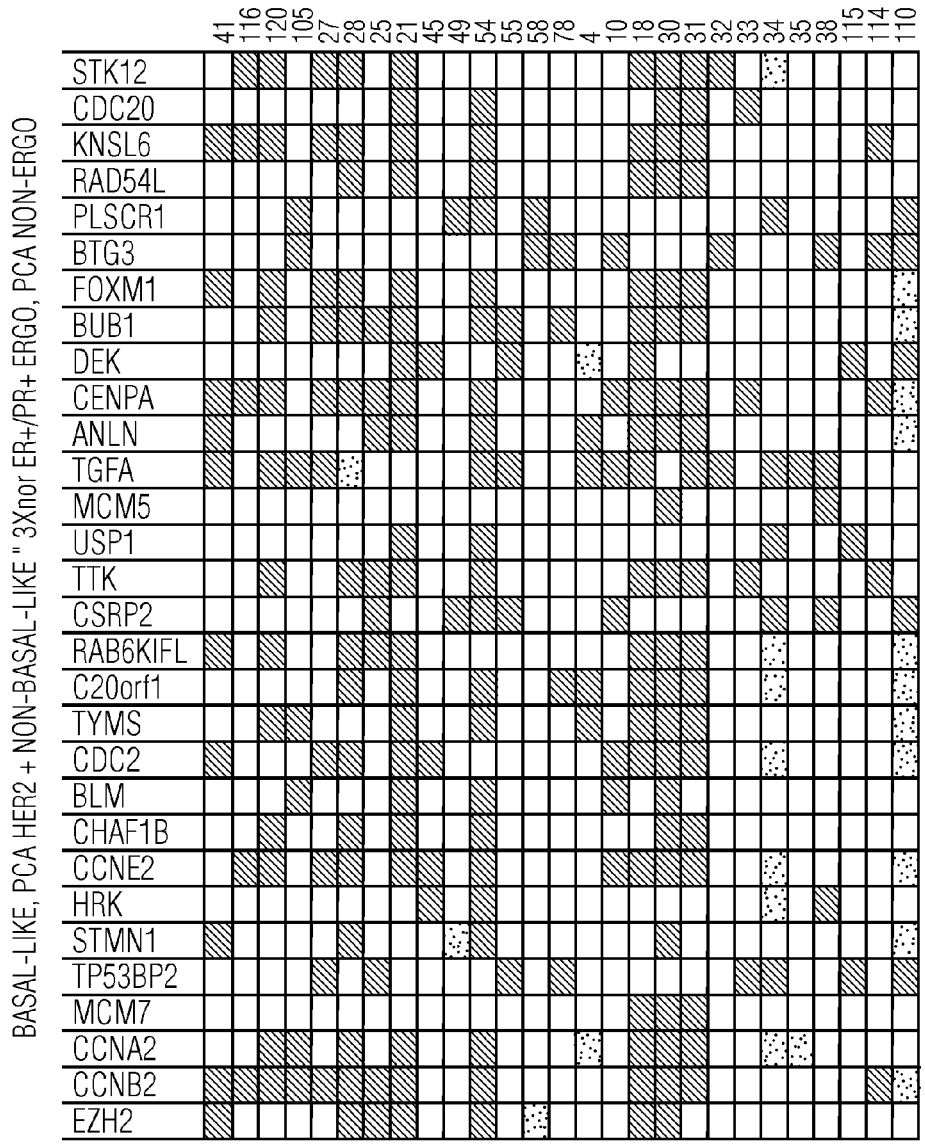

TOP 50 OVEREXPRESSED BASAL-LIKE GENES

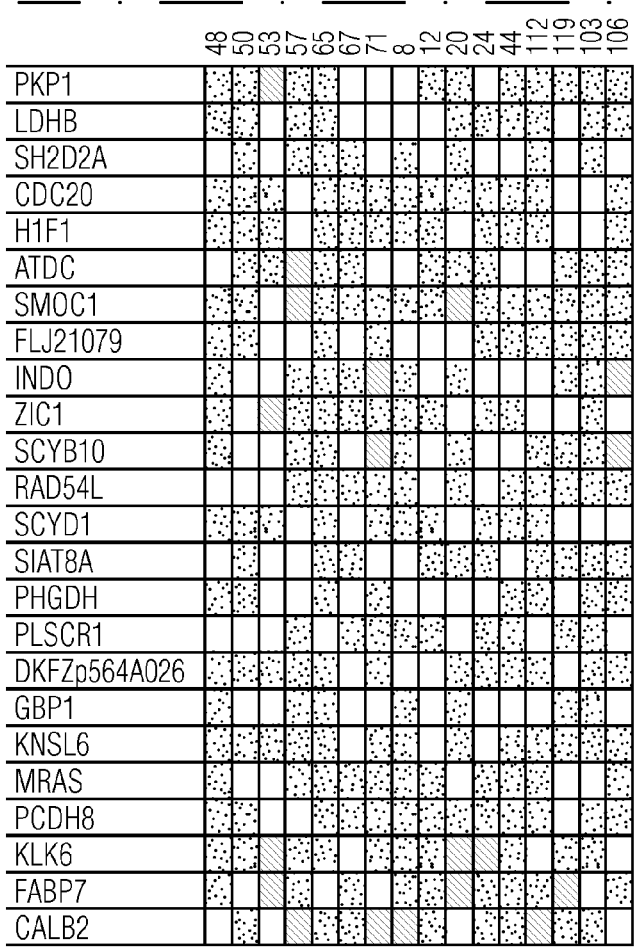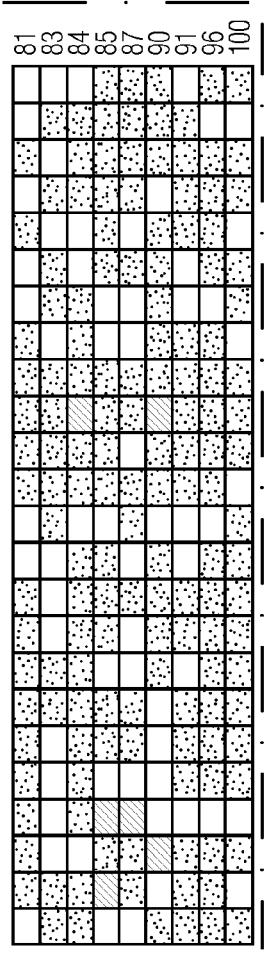
FIG. 8L
TOP 50 OVEREXPRESSED BASAL-LIKE GENES

FIG. 8M

|  | 80 | 86 | 88 | 89 | 92 | 93 | 97 | 98 | 64 | 68 | 73 | 75 | 104 |
|---|---|---|---|---|---|---|---|---|---|---|---|---|---|
| BCL11A | | | | | | | | | | | | | |
| GABRP | | | | | | | | | | | | | |
| FOXC1 | | | | | | | | | | | | | |
| DSC2 | | | | | | | | | | | | | |
| PDI2 | | | | | | | | | | | | | |
| KIAA0514 | | | | | | | | | | | | | |
| CDH3 | | | | | | | | | | | | | |
| TONDU | | | | | | | | | | | | | |
| MID1 | | | | | | | | | | | | | |
| CDKN2A | | | | | | | | | | | | | |
| LAMP3 | | | | | | | | | | | | | |
| UGT8 | | | | | | | | | | | | | |
| KIAA1350 | | | | | | | | | | | | | |
| STK12 | | | | | | | | | | | | | |
| KCNN4 | | | | | | | | | | | | | |
| GZMB | | | | | | | | | | | | | |
| CSPG6 | | | | | | | | | | | | | |
| AL137342 | | | | | | | | | | | | | |
| LOC56963 | | | | | | | | | | | | | |
| FLJ11413 | | | | | | | | | | | | | |
| KCNK5 | | | | | | | | | | | | | |
| DKFZp762E1312 | | | | | | | | | | | | | |
| TM4SF1 | | | | | | | | | | | | | |
| PROML1 | | | | | | | | | | | | | |
| MARCO | | | | | | | | | | | | | |
| GDF5 | | | | | | | | | | | | | |

BASAL-LIKE, PCA HER2 + NON-BASAL-LIKE " 3Xnor ER+/PR+ ERGO, PCA NON-ERGO

CONTINUED ON SHEET 15
TOP 50 OVEREXPRESSED BASAL-LIKE GENES

CONTINUED ON SHEET 14

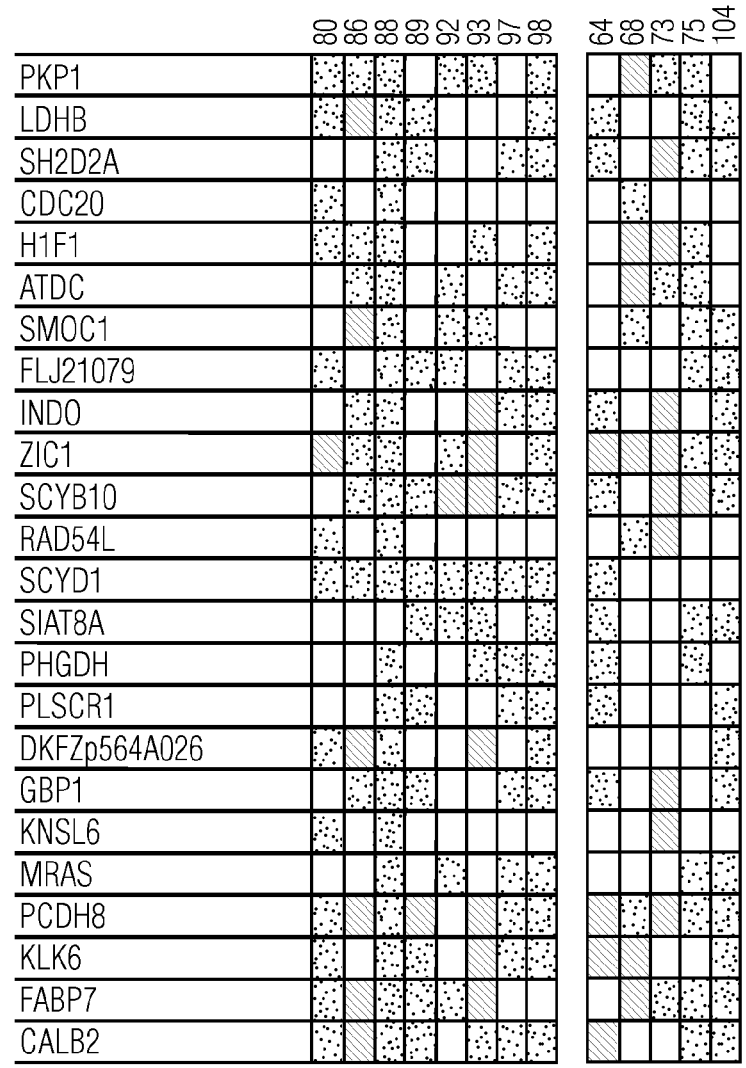

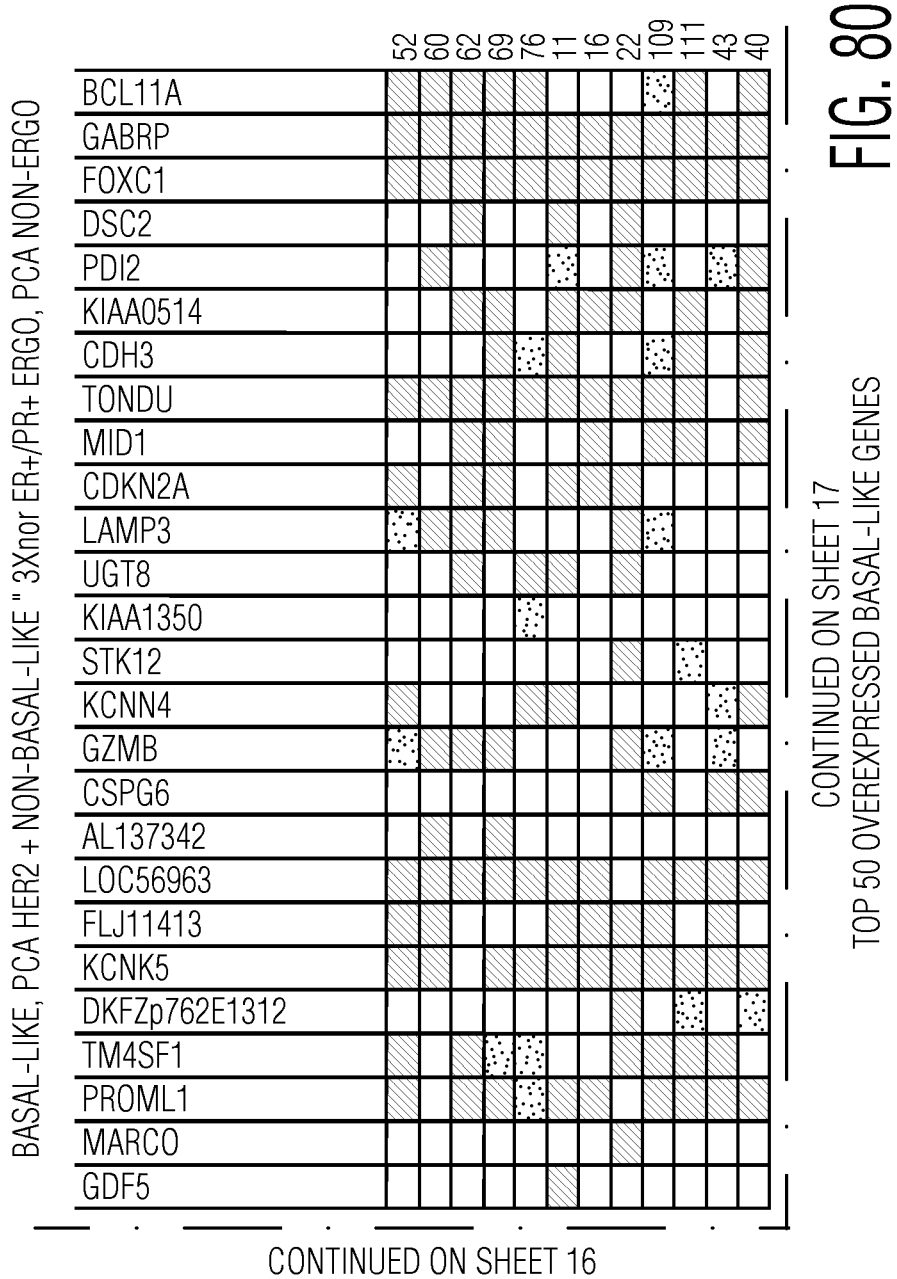

FIG. 8P

CONTINUED FROM SHEET 15

TOP 50 OVEREXPRESSED BASAL-LIKE GENES / CONTINUED ON SHEET 18

BASAL-LIKE, PCA HER2 + NON-BASAL-LIKE "3Xnor ER+/PR+ ERGO, PCA NON-ERGO

Columns: 52, 60, 62, 69, 76, 11, 16, 22, 109, 111, 43, 40

Genes (rows):
- PKP1
- LDHB
- SH2D2A
- CDC20
- H1F1
- ATDC
- SMOC1
- FLJ21079
- INDO
- ZIC1
- SCYB10
- RAD54L
- SCYD1
- SIAT8A
- PHGDH
- PLSCR1
- DKFZp564A026
- GBP1
- KNSL6
- MRAS
- PCDH8
- KLK6
- FABP7
- CALB2

CONTINUED ON SHEET 26

FIG. 8R

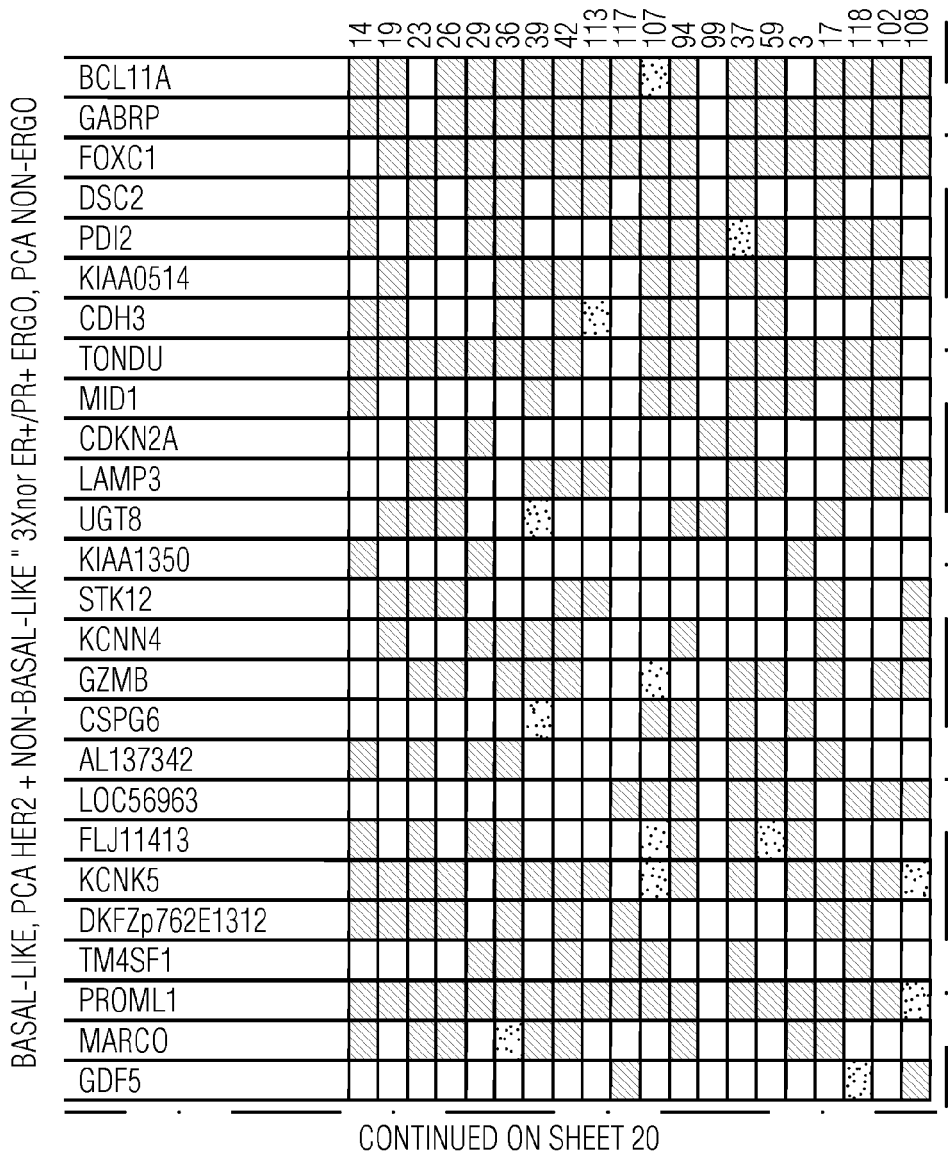

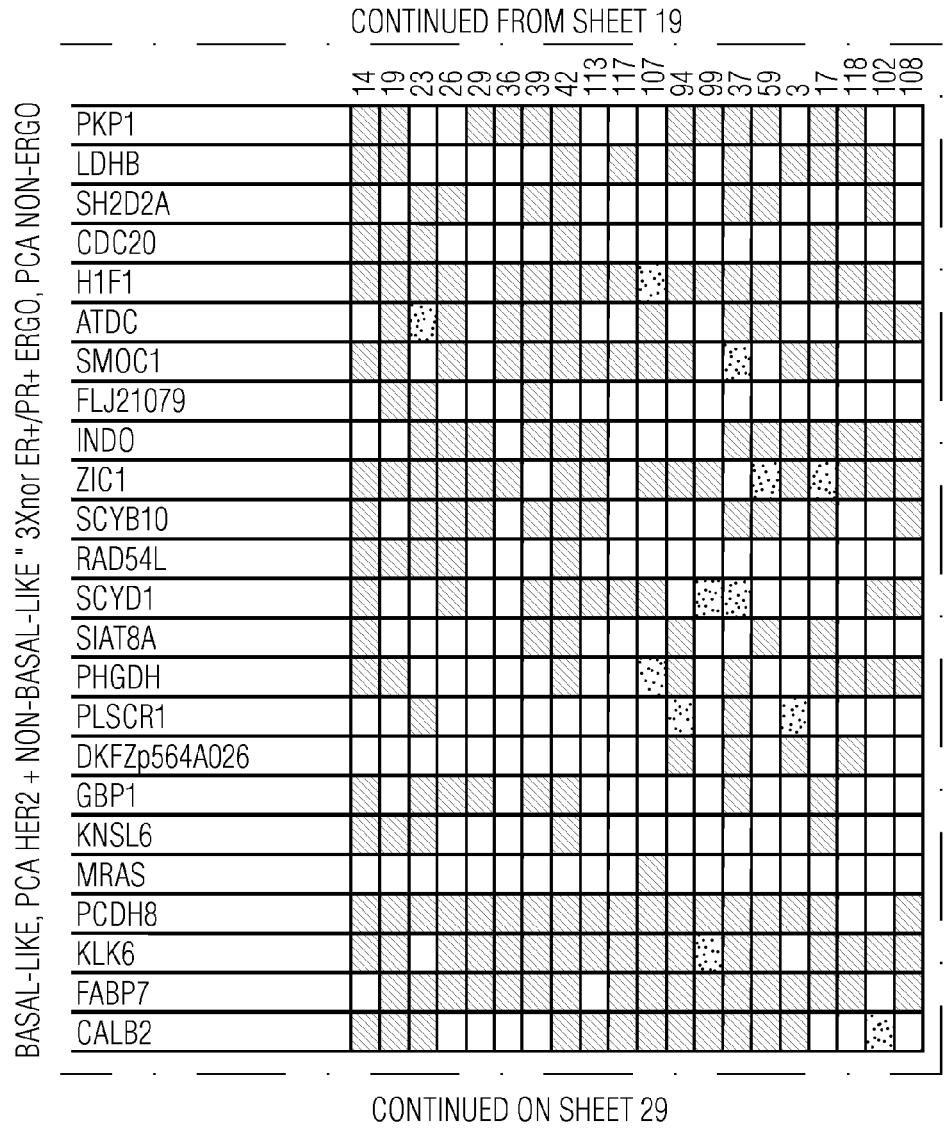

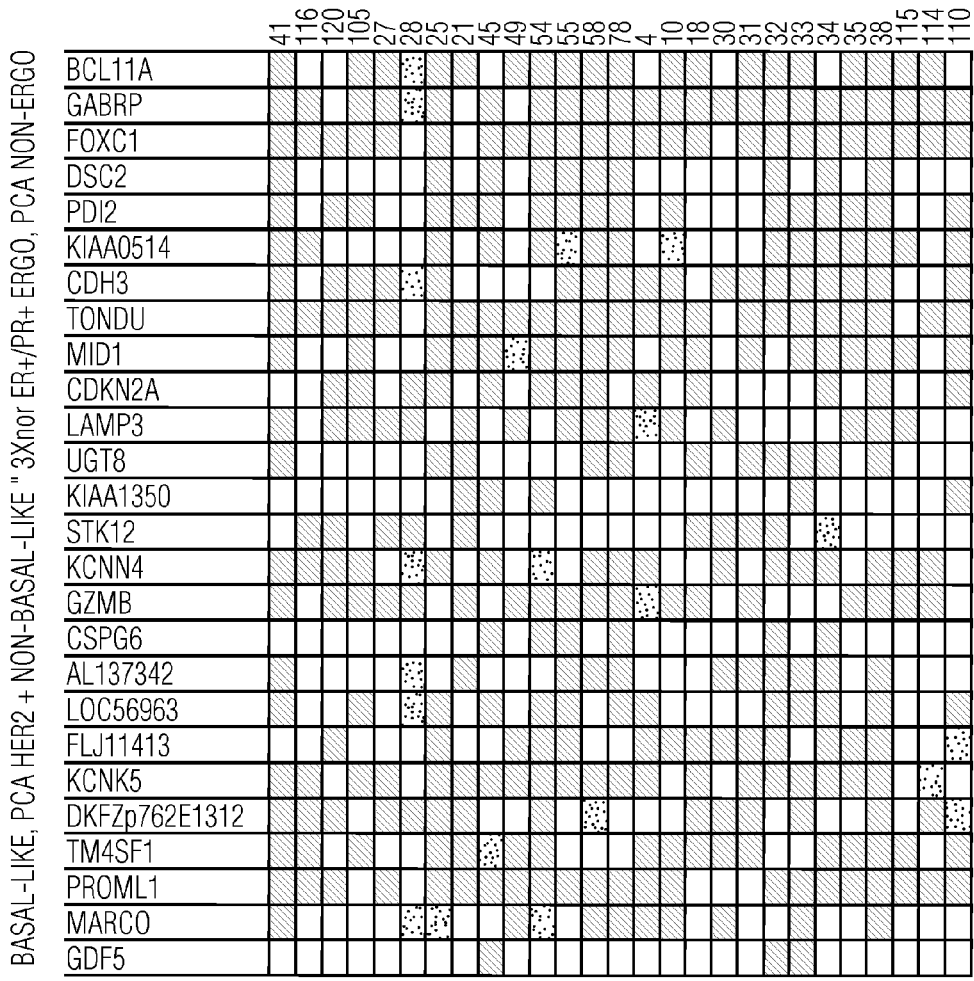

FIG. 8W

Gene labels (rows): LIV-1, CA12, ESR1, SEC14L2, COX6C, AK0003451, AREG, HEP27, AF007153, JCL-1, KIAA0575, CHAD, AGR2, ERBB4, SLC1A1, LPHB, TPSG1, PIP, TAT, TRH, CPB1, CYP2A6, NPY1R, MSMB, CGA Column labels (left block): 48, 50, 53, 57, 65, 67, 71, 8, 12, 20, 24, 44, 112, 119, 103, 106

Column labels (right block): 81, 83, 84, 85, 87, 90, 91, 96, 100

Left axis label: BASAL-LIKE, PCA HER2 + NON-BASAL-LIKE "3Xnor ER+/PR+ ERGO, PCA NON-ERGO Right annotation: TOP 50 UNDEREXPRESSED BASAL-LIKE GENES
CONTINUED ON SHEET 25

CONTINUED ON SHEET 24

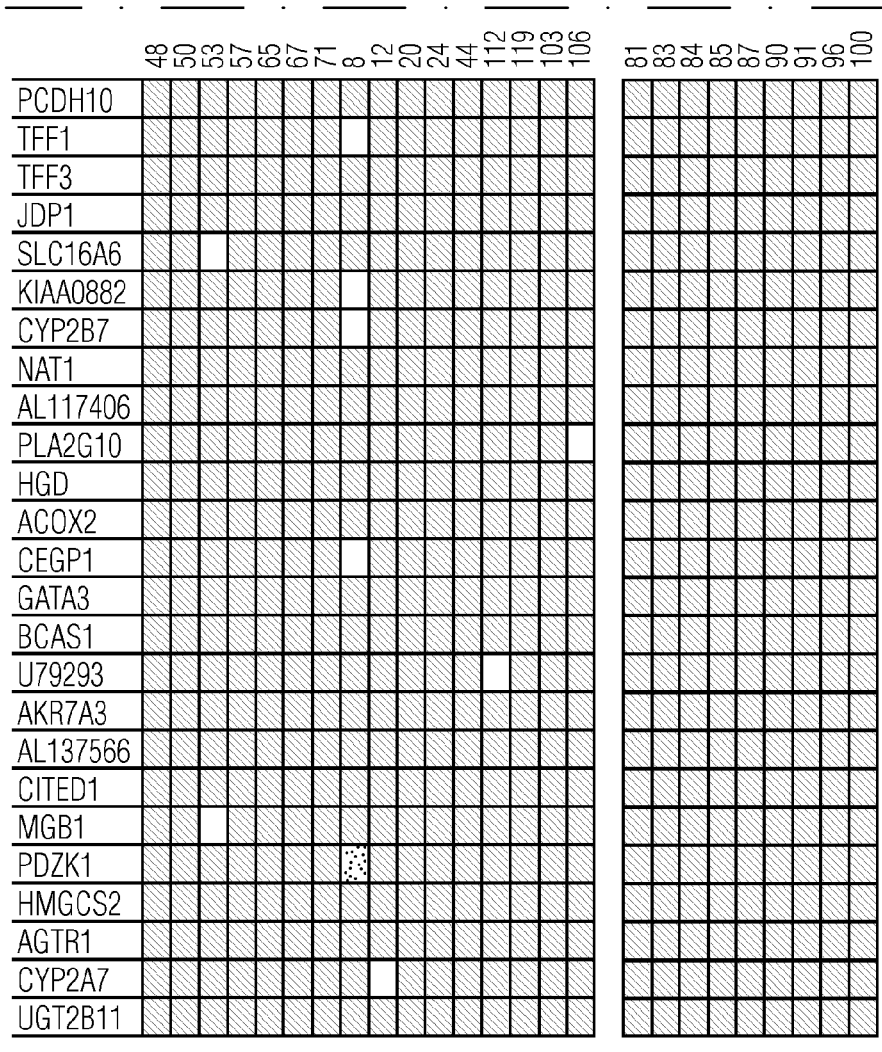

BASAL-LIKE, PCA HER2 + NON-BASAL-LIKE " 3Xnor ER+/PR+ ERGO, PCA NON-ERGO

FIG. 8Y

TOP 50 UNDEREXPRESSED BASAL-LIKE GENES

| Gene | 80 | 86 | 88 | 86 | 92 | 93 | 97 | 98 | | 64 | 68 | 73 | 75 | 104 |
|---|---|---|---|---|---|---|---|---|---|---|---|---|---|---|
| LIV-1 | | | | | | | | | | | | | | |
| CA12 | | | | | | | | | | | | | | |
| ESR1 | | | | | | | | | | | | | | |
| SEC14L2 | | | | | | | | | | | | | | |
| COX6C | | | | | | | | | | | | | | |
| AK000345 | | | | | | | | | | | | | | |
| AREG | | | | | | | | | | | | | | |
| HEP27 | | | | | | | | | | | | | | |
| AF007153 | | | | | | | | | | | | | | |
| JCL-1 | | | | | | | | | | | | | | |
| KIAA0575 | | | | | | | | | | | | | | |
| CHAD | | | | | | | | | | | | | | |
| AGR2 | | | | | | | | | | | | | | |
| ERBB4 | | | | | | | | | | | | | | |
| SLC1A1 | | | | | | | | | | | | | | |
| LPHB | | | | | | | | | | | | | | |
| TPSG1 | | | | | | | | | | | | | | |
| PIP | | | | | | | | | | | | | | |
| TAT | | | | | | | | | | | | | | |
| TRH | | | | | | | | | | | | | | |
| CPB1 | | | | | | | | | | | | | | |
| CYP2A6 | | | | | | | | | | | | | | |
| NPY1R | | | | | | | | | | | | | | |
| MSMB | | | | | | | | | | | | | | |
| CGA | | | | | | | | | | | | | | |

CONTINUED THIS SHEET

| Gene | 80 | 86 | 88 | 86 | 92 | 93 | 97 | 98 | | 64 | 68 | 73 | 75 | 104 |
|---|---|---|---|---|---|---|---|---|---|---|---|---|---|---|
| PCDH10 | | | | | | | | | | | | | | |
| TFF1 | | | | | | | | | | | | | | |
| TFF3 | | | | | | | | | | | | | | |
| JDP1 | | | | | | | | | | | | | | |
| SLC16A6 | | | | | | | | | | | | | | |
| KIAA0882 | | | | | | | | | | | | | | |
| CYP2B7 | | | | | | | | | | | | | | |
| NAT1 | | | | | | | | | | | | | | |
| AL117406 | | | | | | | | | | | | | | |
| PLA2G10 | | | | | | | | | | | | | | |
| HGD | | | | | | | | | | | | | | |
| ACOX2 | | | | | | | | | | | | | | |
| CEGP1 | | | | | | | | | | | | | | |
| GATA3 | | | | | | | | | | | | | | |
| BCAS1 | | | | | | | | | | | | | | |
| U79293 | | | | | | | | | | | | | | |
| AKR7A3 | | | | | | | | | | | | | | |
| AL137566 | | | | | | | | | | | | | | |
| CITED1 | | | | | | | | | | | | | | |
| MGB1 | | | | | | | | | | | | | | |
| PDZK1 | | | | | | | | | | | | | | |
| HMGCS2 | | | | | | | | | | | | | | |
| AGTR1 | | | | | | | | | | | | | | |
| CYP2A7 | | | | | | | | | | | | | | |
| UGT2B11 | | | | | | | | | | | | | | |

CONTINUED ON SHEET 26

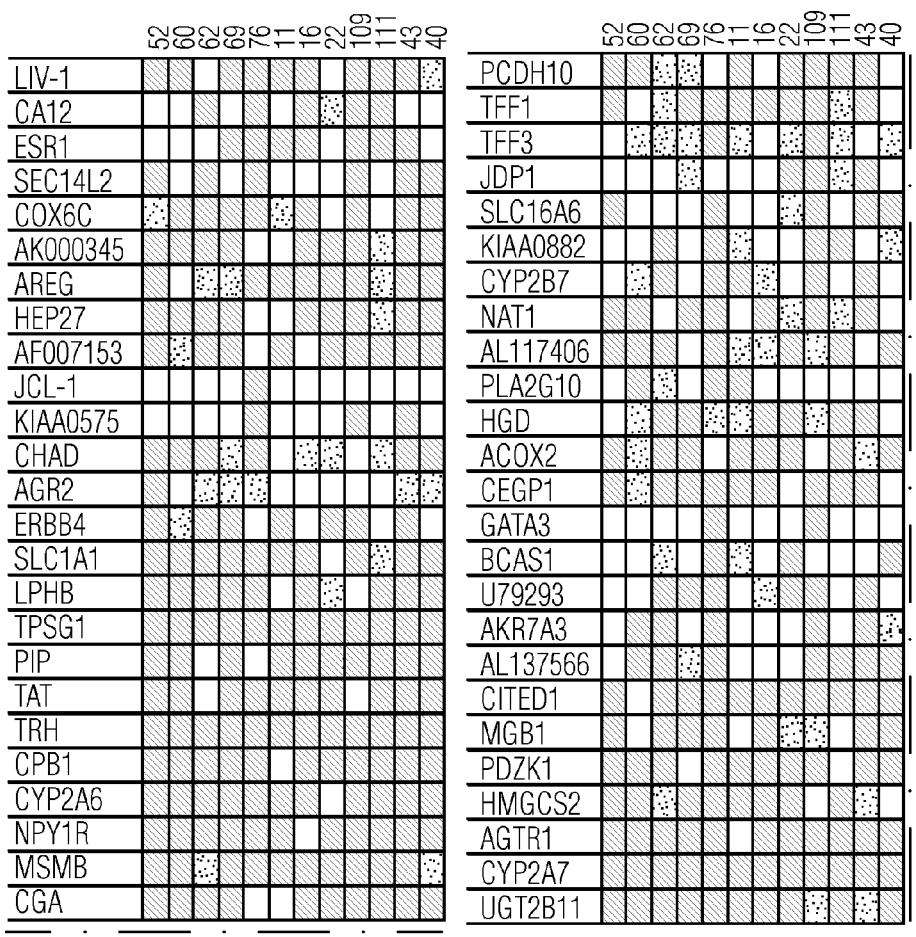

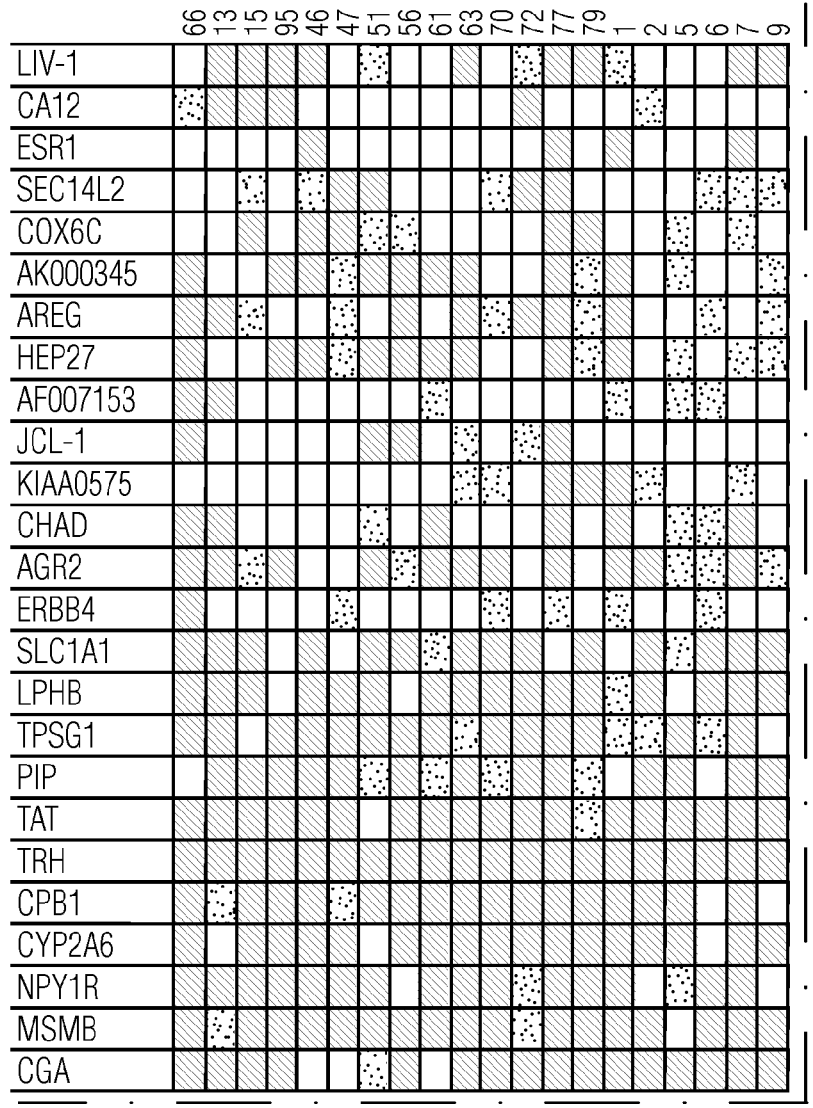

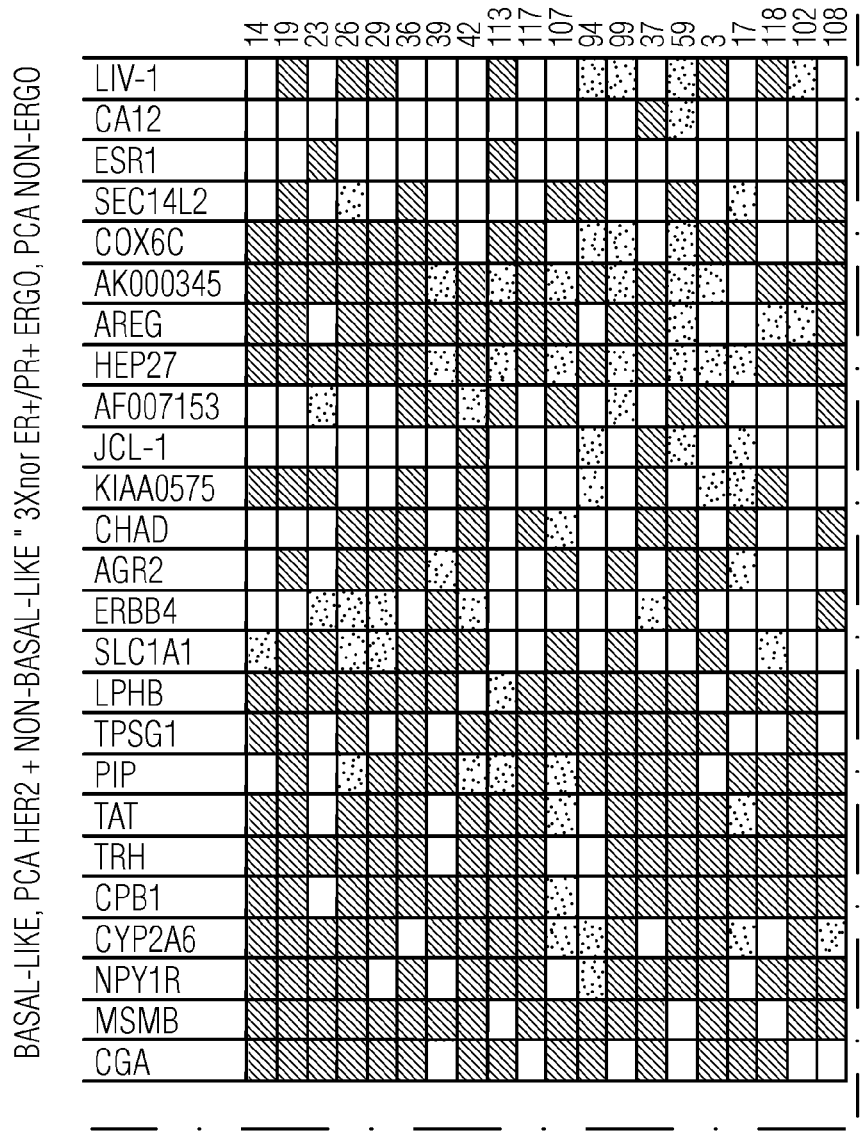

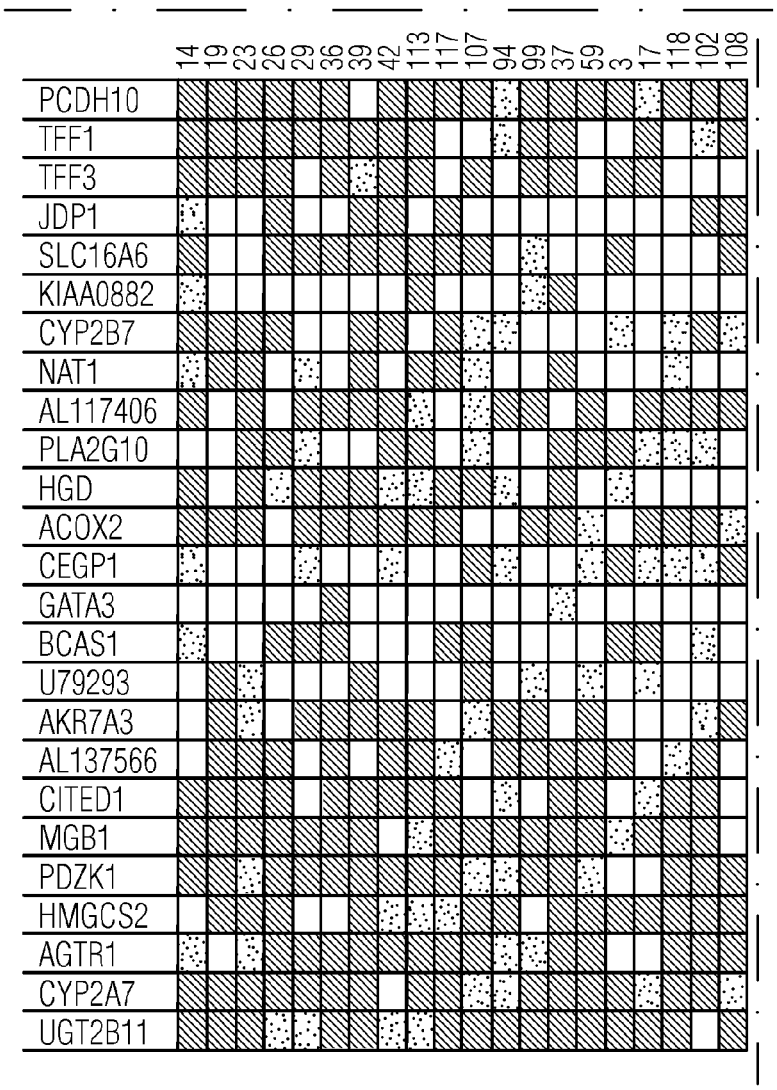

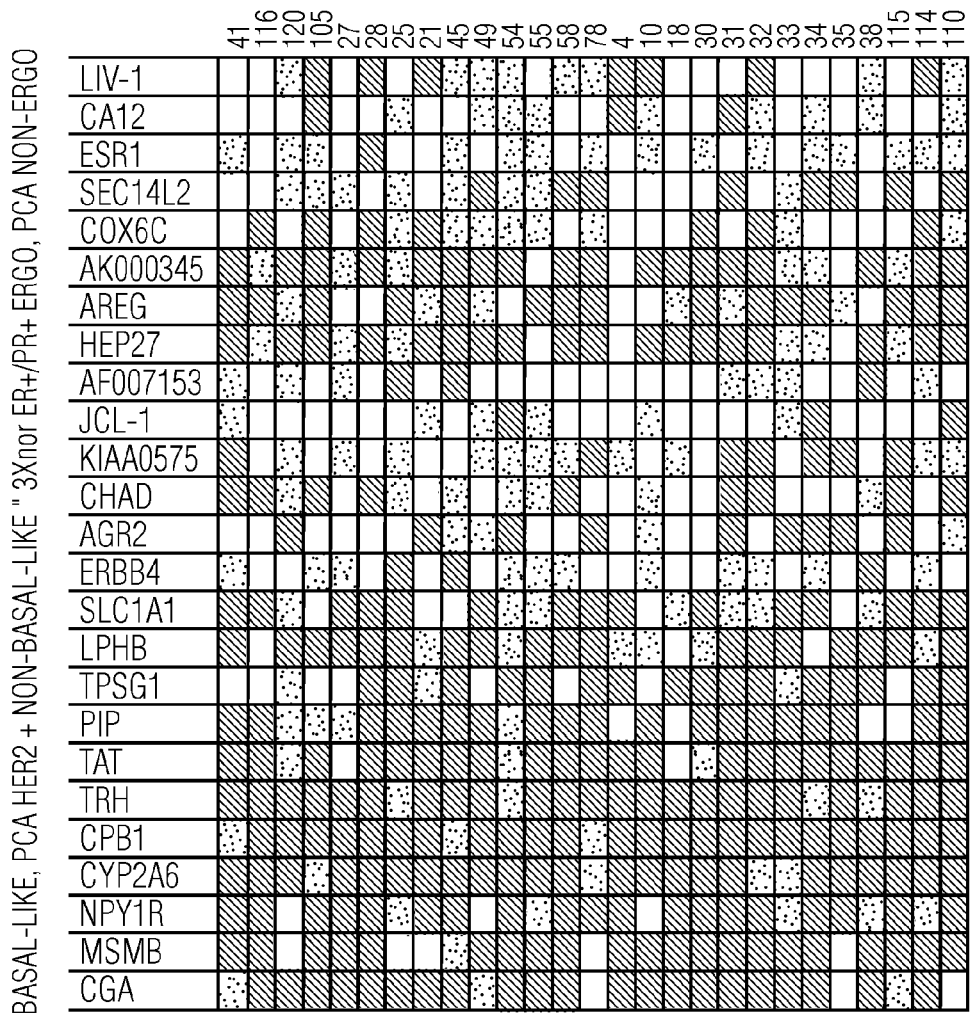

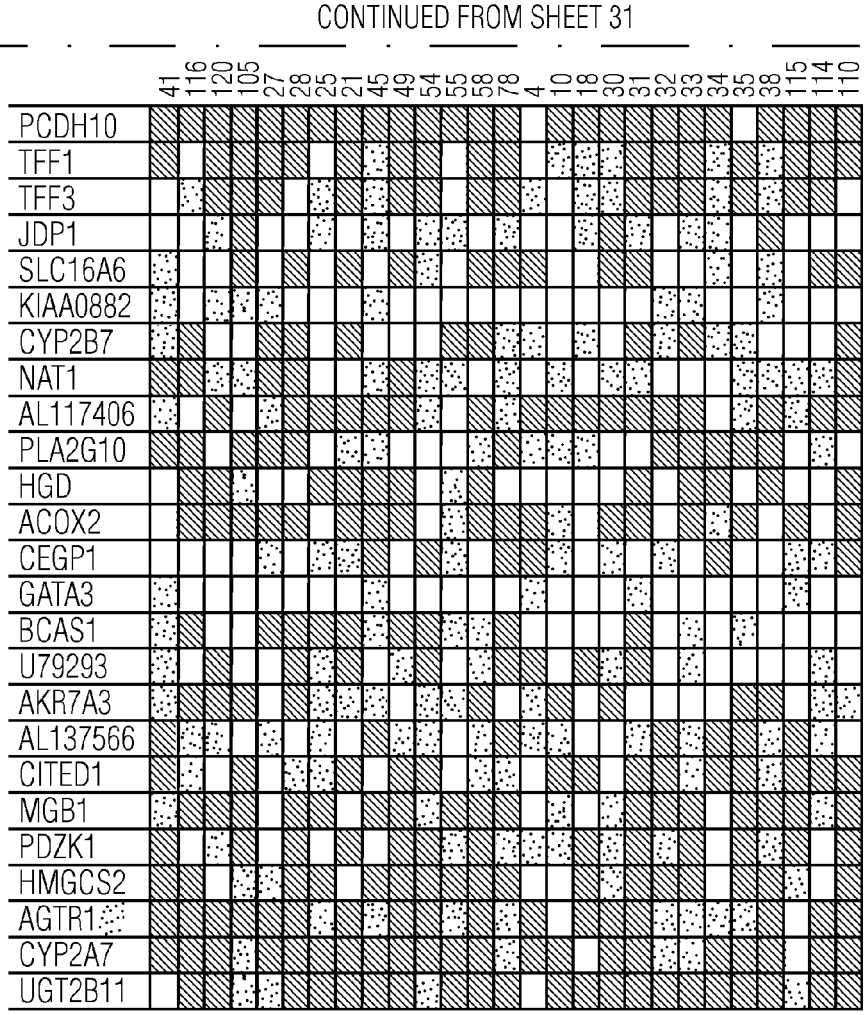

FIG. 10

OVEREXPRESSED E2F RESPONSIVE GENES IN ERGO TUMORS THAT ARE COMMON TO DATASETS S1 AND S2

Non-shared genes are indicated with hatching.

S1

| Count | Gene |
|---|---|
| 25 | STK12 |
| 23 | KNSL6 |
| 22 | CENPA |
| 22 | CDC20 |
| 21 | RAD54L |
| 21 | ANLN |
| 20 | FOXM1 |
| 20 | RAB6KIFL |
| 20 | TYMS |
| 19 | BTG3 |
| 19 | CDC2 |
| 18 | BUB1 |
| 18 | CCNB2 |
| 18 | C20orf1 |
| 18 | PLSCR1 |
| 17 | STMN1 |
| 17 | BLM |
| 17 | EZH2 |
| 17 | PTTG1 |
| 16 | TTK |
| 16 | HRK |
| 16 | CDC25A (non-shared) |
| 16 | MCM7 |
| 16 | DEK |
| 16 | CDC45L |
| 15 | CCNA2 |
| 15 | MCM5 |
| 15 | UBCH10 |
| 15 | TGFA (non-shared) |
| 14 | BIRC5 |
| 14 | KNSL2 |
| 14 | TEAD4 |
| 14 | CCNE1 (non-shared) |
| 14 | TK1 |
| 14 | SMC4L1 |
| 14 | MCM6 |
| 14 | KNSL1 |
| 14 | TP53BP2 |
| 13 | HEC |
| 13 | KIAA0175 |

S1 CONTINUED

| Count | Gene |
|---|---|
| 13 | PRC1 |
| 13 | CHAF1B |
| 13 | CSRP2 |
| 13 | USP1 (non-shared) |
| 13 | LMNB1 |
| 12 | PRIM2A |
| 12 | MAD2L1 |
| 12 | NFK2 |
| 12 | CCNE2 (non-shared) |
| 11 | RFC4 |
| 11 | MCM2 |
| 11 | STK15 |
| 11 | DNA2L |
| 11 | SOX9 |
| 11 | MYC |
| 10 | ORC6L |
| 10 | CKS1 |
| 10 | NUP155 |
| 10 | NASP |
| 10 | CSDA |
| 10 | KPNA2 |
| 10 | CDC7L1 |
| 10 | MAP3K14 |
| 9 | NOLC1 |
| 9 | CKS2 |
| 9 | FLJ22009 |
| 9 | CCNB1 |
| 9 | RRM2 (non-shared) |
| 9 | ANXA8 |
| 8 | KIF4A |
| 8 | CDC25B |
| 8 | HMC4 |
| 8 | HMMR |
| 8 | VEGF (non-shared) |

61/70 = 87%

S2

| Count | Gene |
|---|---|
| 27 | KNSL2 |
| 25 | CENPA |
| 24 | BUB1 |
| 23 | STK12 |
| 23 | KNSL6 |
| 22 | UBCH10 |
| 20 | CDC20 |
| 20 | RAD54L |
| 20 | CCNA2 |
| 20 | CCNB2 |
| 19 | FOXM1 |
| 19 | MCM2 |
| 18 | RAB6KIFL |
| 18 | MYC |
| 18 | EZH2 |
| 18 | BIRC5 |
| 18 | HRK |
| 17 | KIAA0175 |
| 17 | C20ORF1 |
| 17 | STK15 |
| 17 | BLM |
| 17 | CENPF (non-shared) |
| 16 | KPNA2 |
| 16 | HEC |
| 16 | ID-GAP |
| 15 | MCM5 |
| 15 | CDC25B |
| 15 | TP53BP2 |
| 15 | MAD2L1 |
| 15 | NASP |
| 15 | CHAF1B |
| 15 | MCM7 |
| 15 | TYMS |
| 15 | TTK |
| 15 | TK1 |
| 14 | CDC45L |
| 14 | CCNB1 |
| 14 | CSRP2 |
| 14 | CHEK1 (non-shared) |
| 14 | FEN1 (non-shared) |
| 14 | E2F1 (non-shared) |
| 14 | PLSCR1 |
| 14 | PRC1 |
| 13 | MCM6 |

S2 CONTINUED

| Count | Gene |
|---|---|
| 13 | PTTG1 |
| 13 | CKS1 |
| 13 | LMNB1 |
| 13 | CSDA |
| 12 | RFC4 |
| 12 | PTPNS1 (non-shared) |
| 12 | TEAD4 |
| 12 | NEK2 |
| 12 | SOX9 |
| 12 | ANLN |
| 12 | CDC2 |
| 11 | BTG3 |
| 11 | PRIM2A |
| 11 | ORC6L |
| 11 | POLA2 (non-shared) |
| 11 | HMG4 |
| 10 | DEK |
| 10 | HSPC150 |
| 10 | MTHFD1 (non-shared) |
| 10 | DKFZP762L0311 |
| 9 | TMPO (non-shared) |
| 9 | UNG (non-shared) |
| 9 | STK18 (non-shared) |
| 9 | PCNA (non-shared) |
| 9 | CHAF1A (non-shared) |
| 9 | DNA2L |
| 8 | CDC7L1 |
| 8 | KNSL1 |
| 8 | NUP155 |
| 8 | DNMT1 (non-shared) |
| 8 | CDC25C (non-shared) |
| 8 | ECT2 (non-shared) |
| 8 | CKS2 |
| 8 | H2AFZ (non-shared) |
| 7 | KIF4A |
| 7 | PIR51 (non-shared) |
| 7 | FLJ10335 (non-shared) |
| 7 | HMMR (non-shared) |

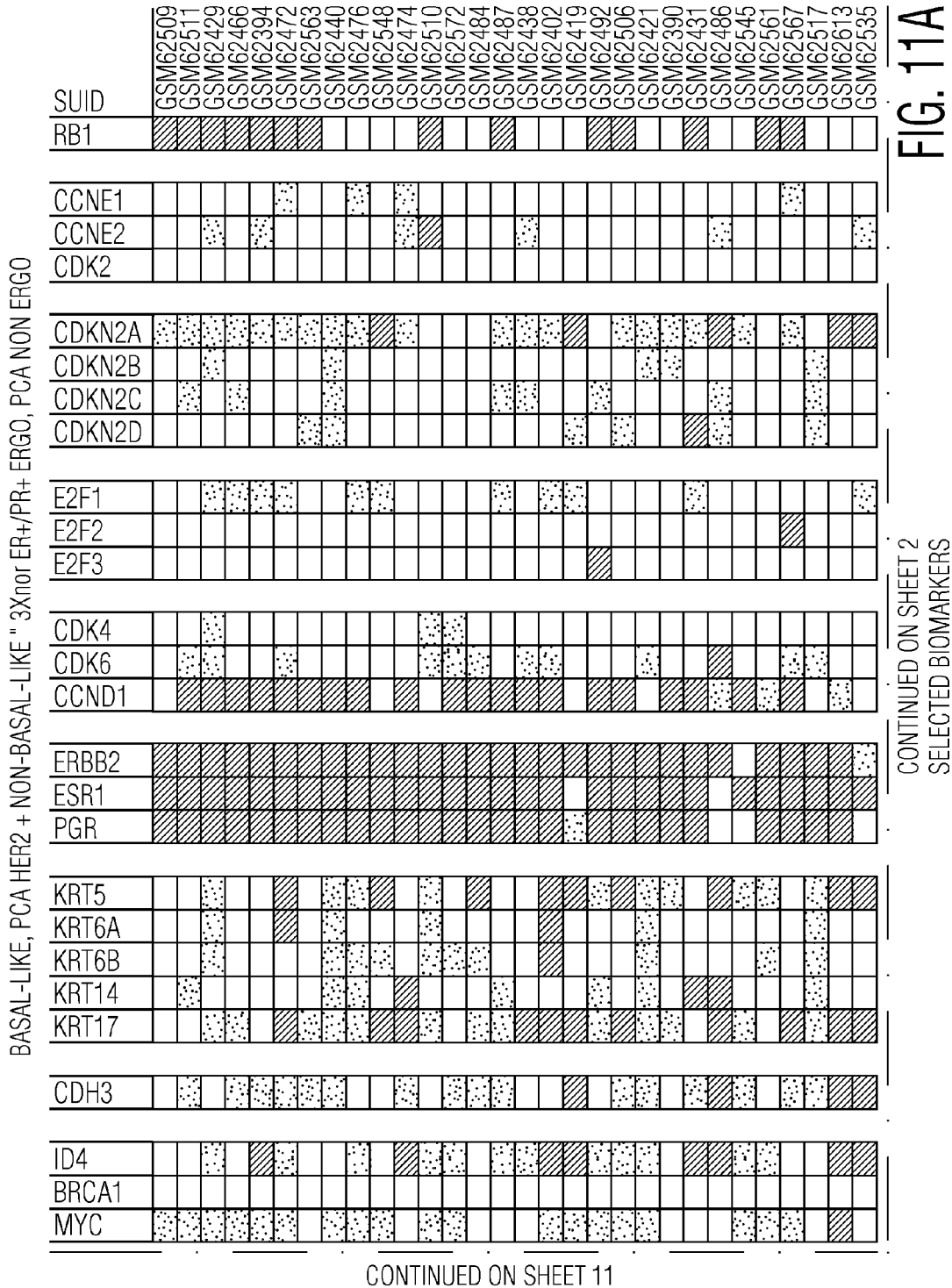

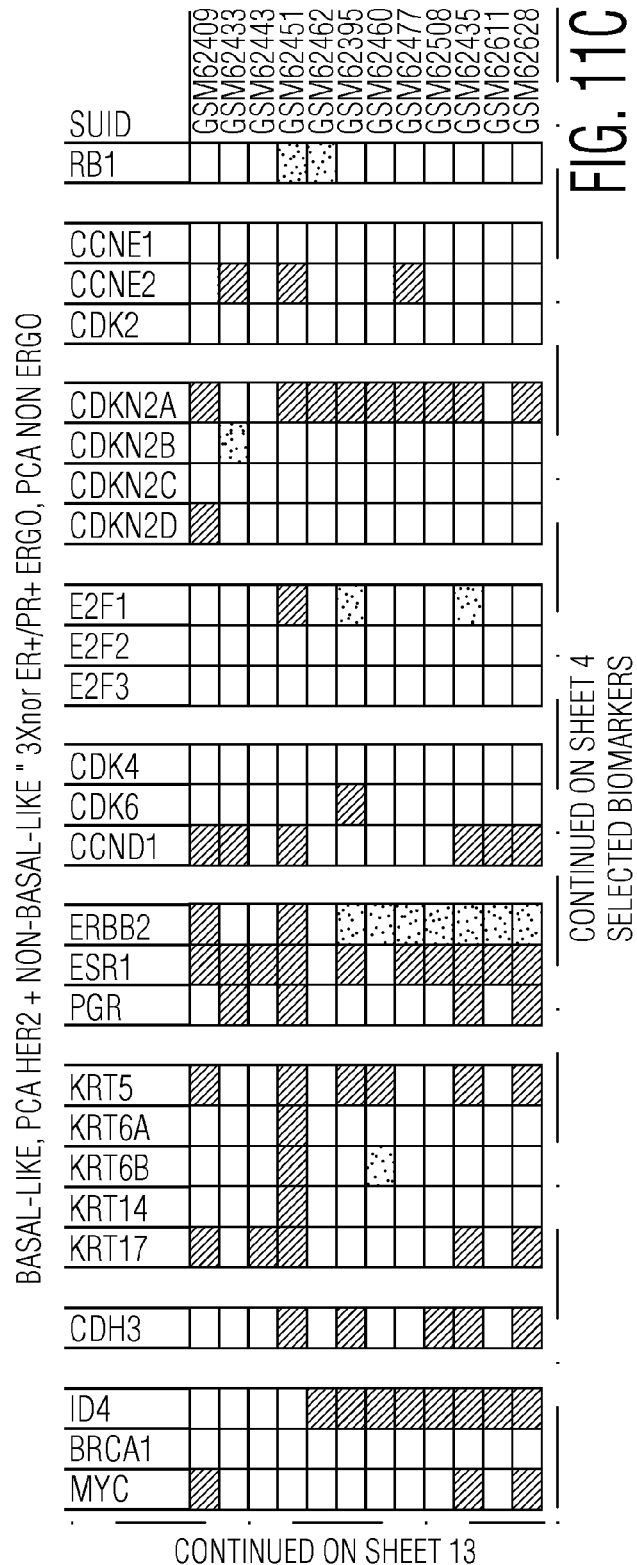

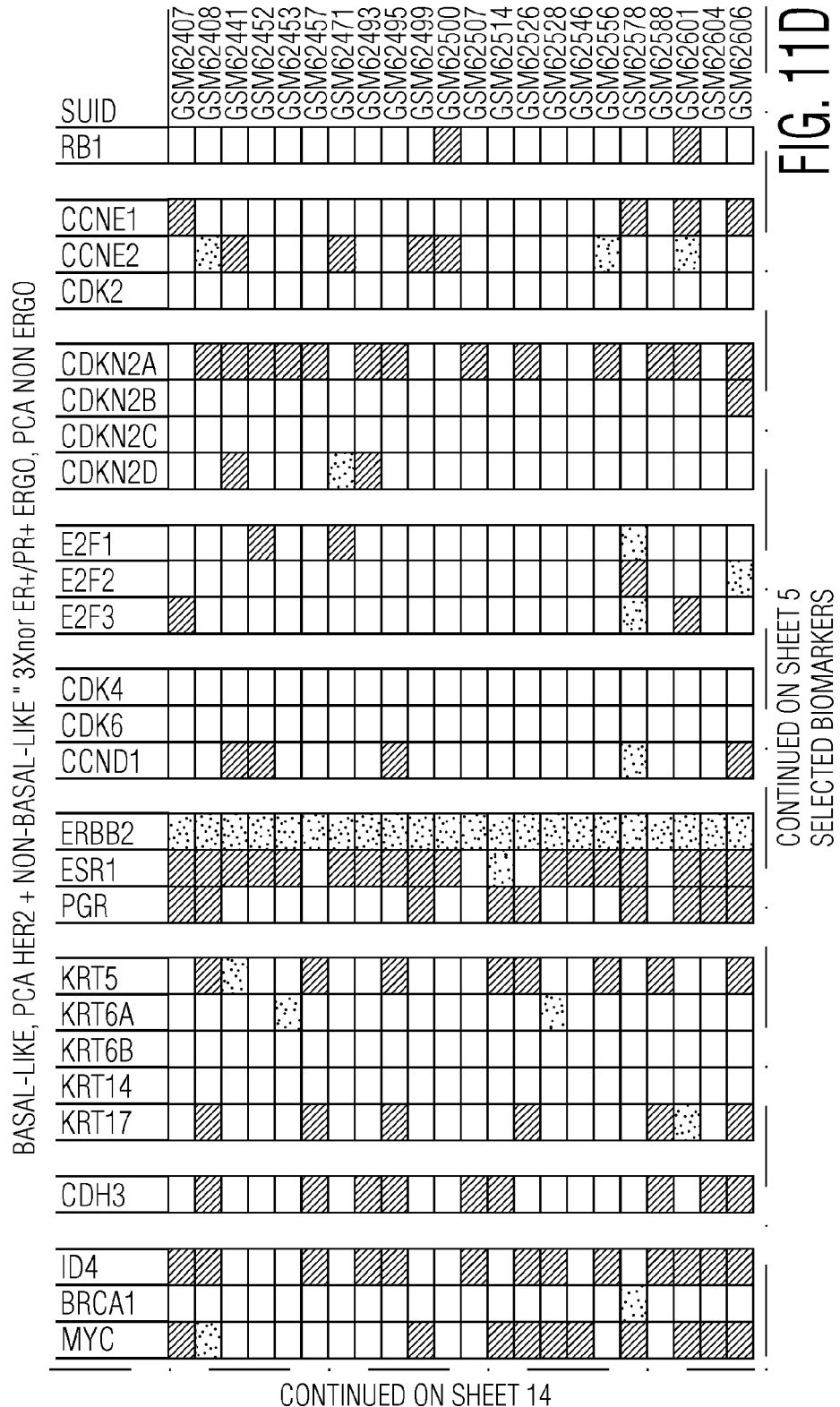

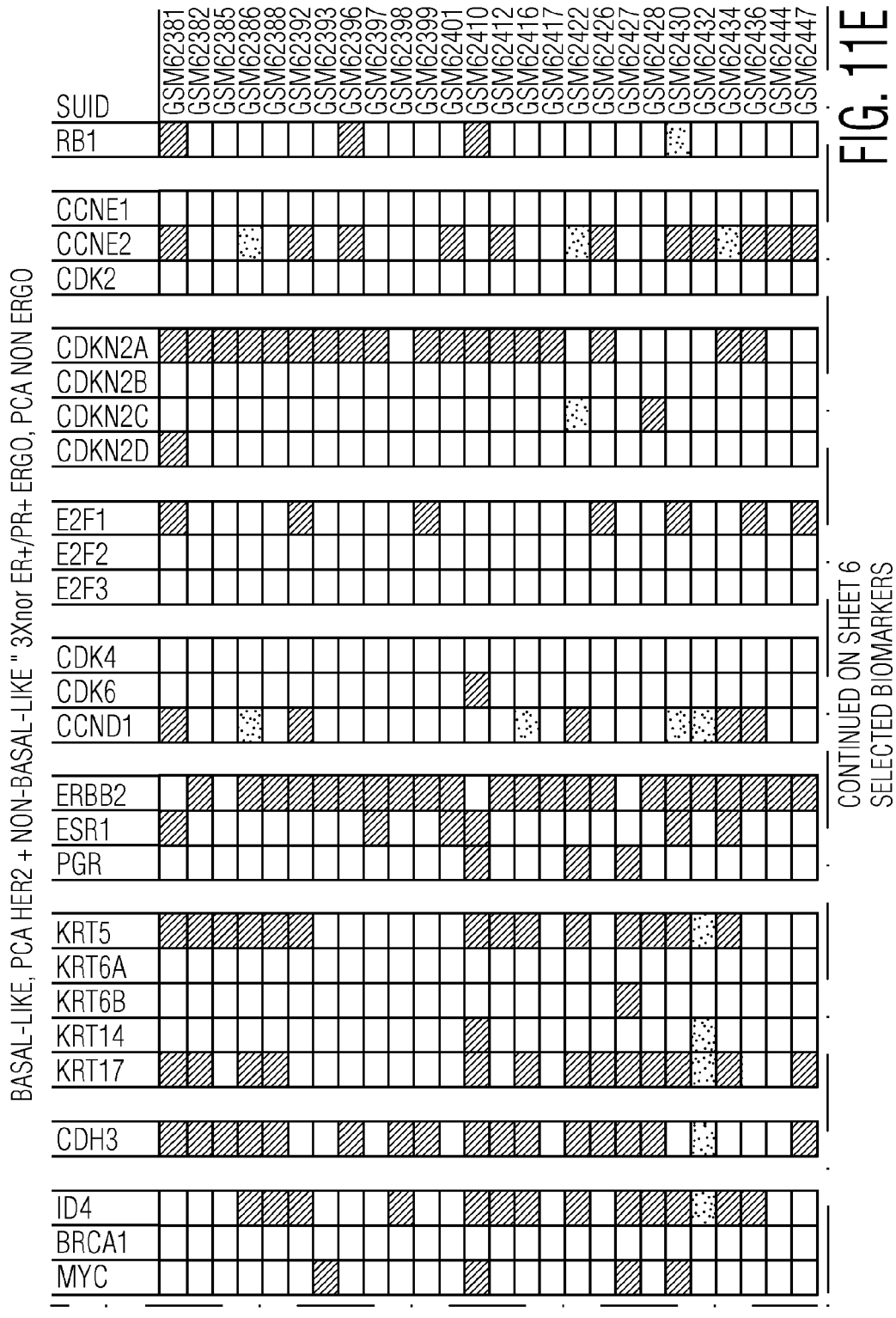

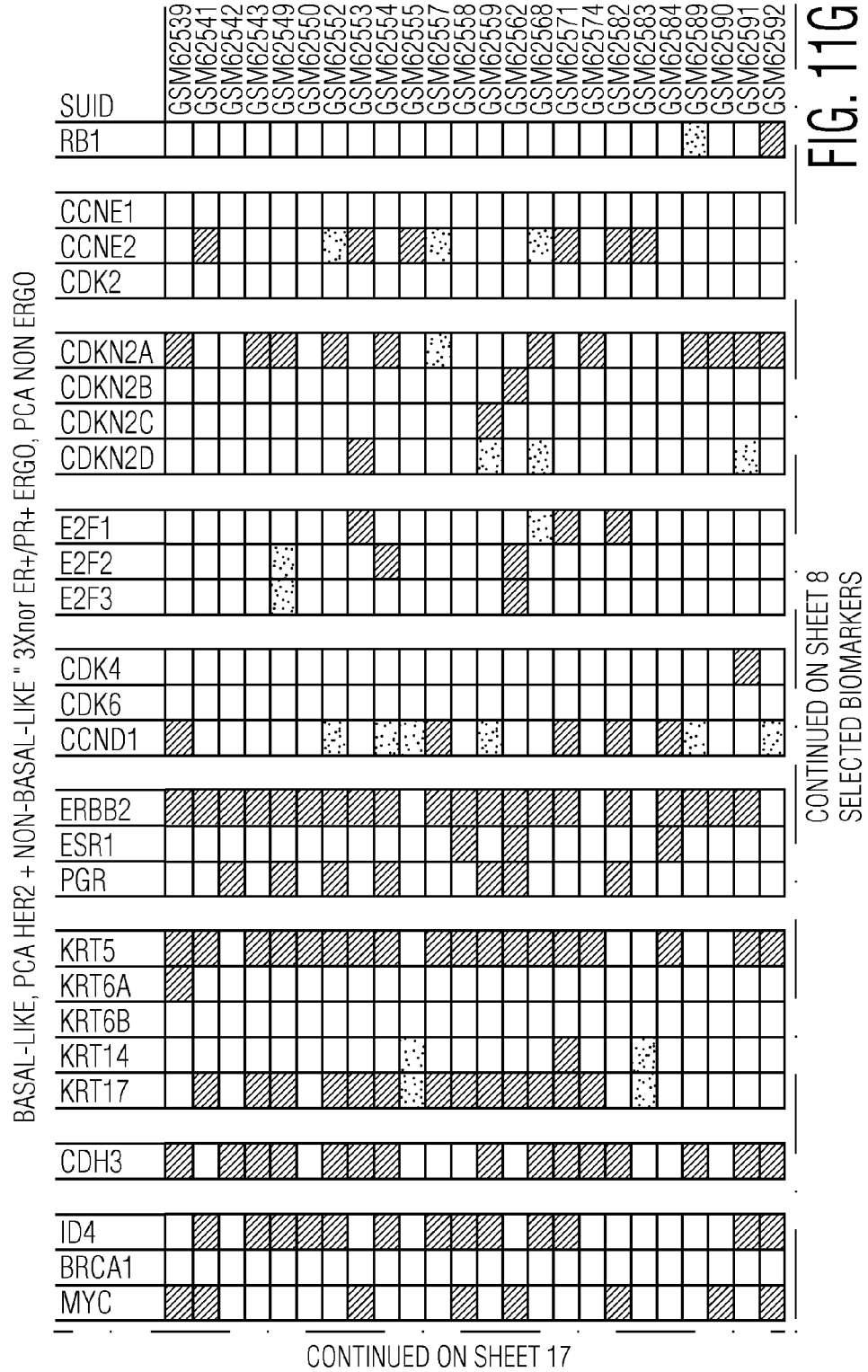

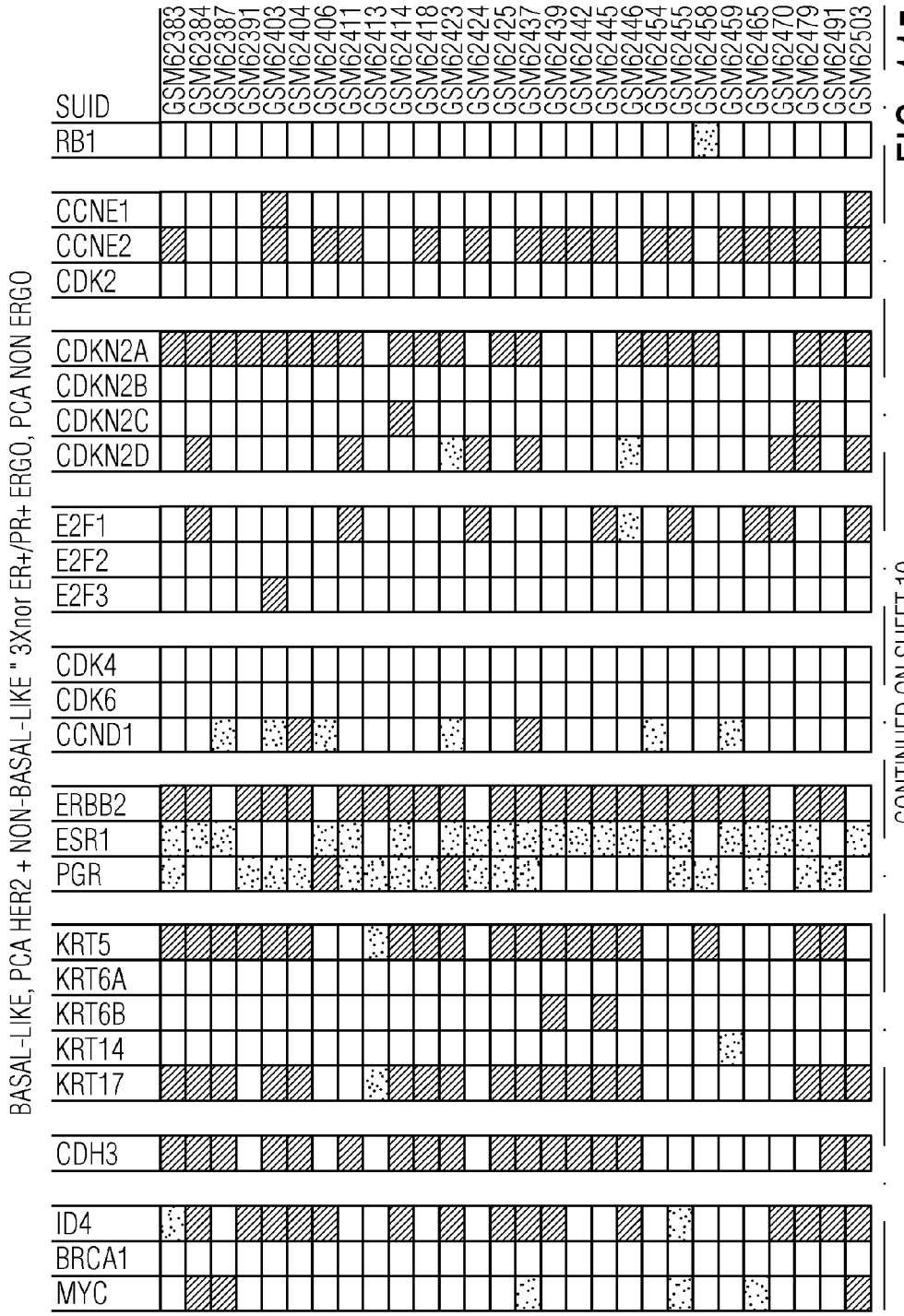

FIG. 11K

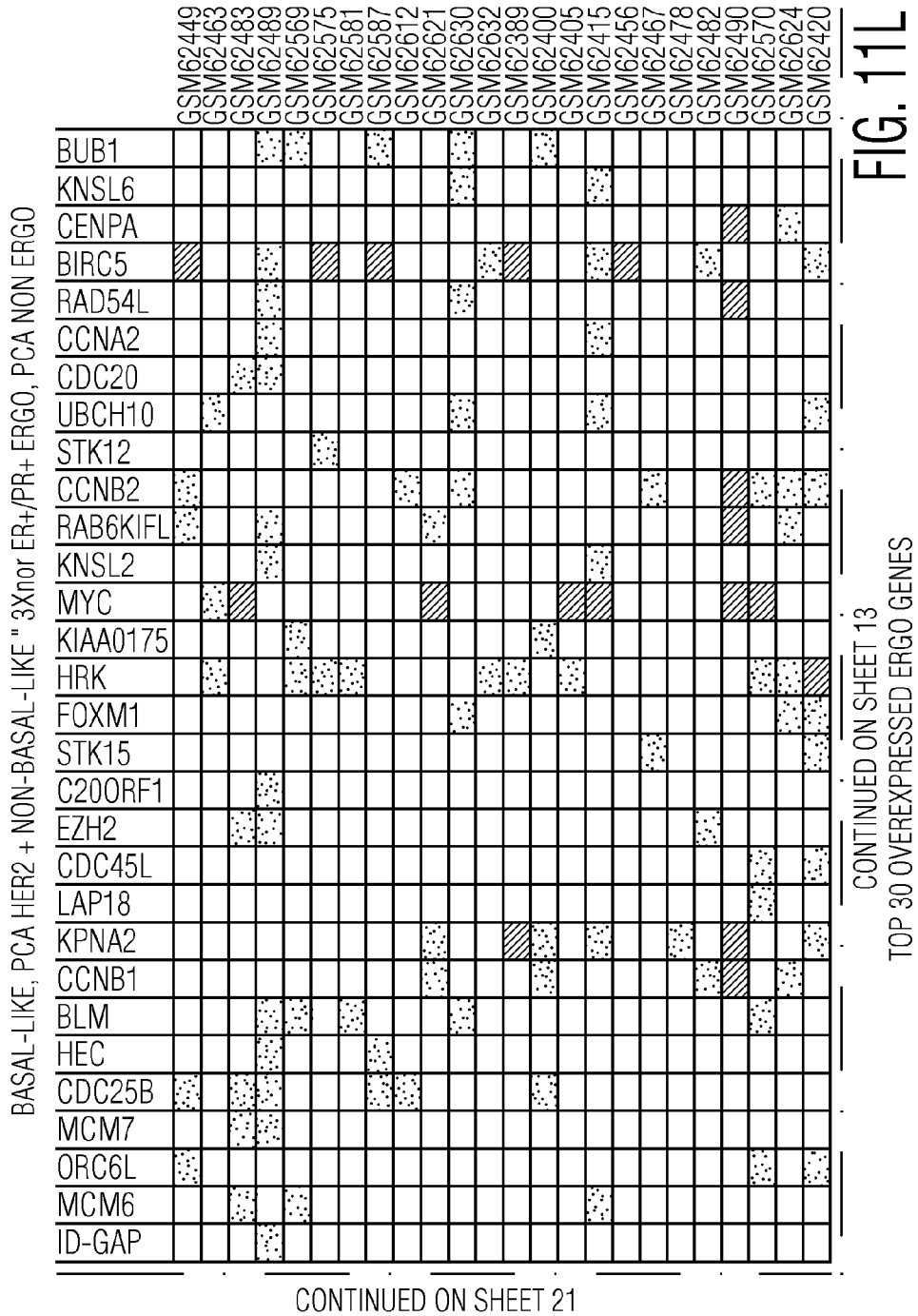

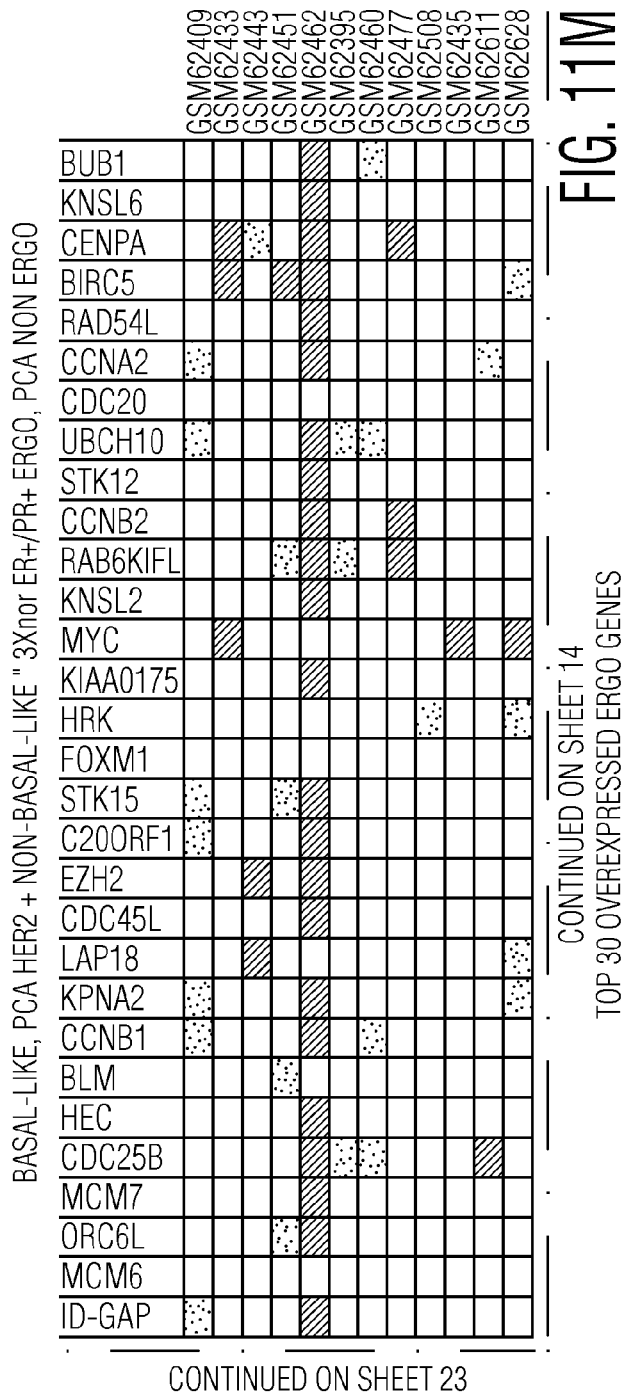

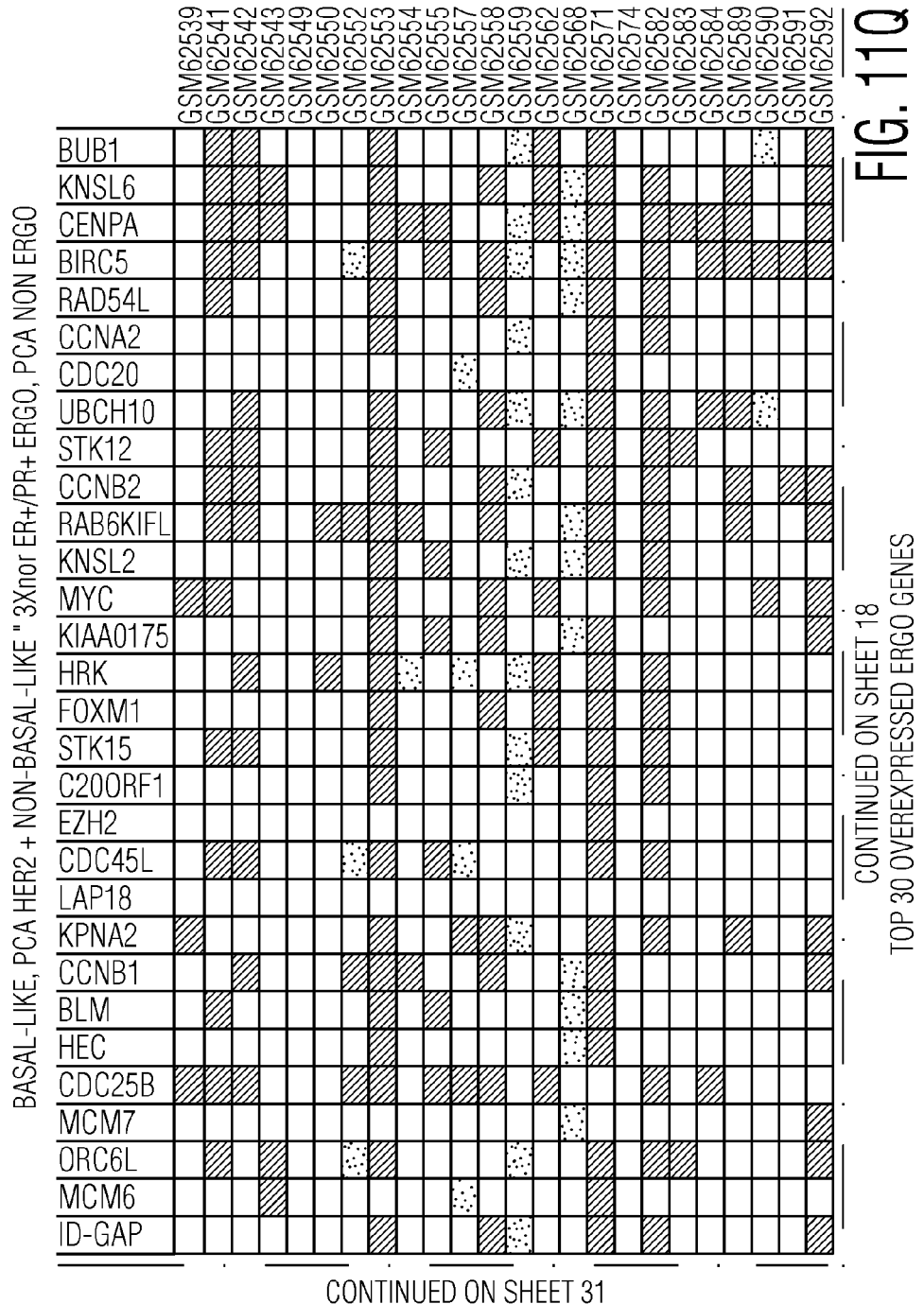

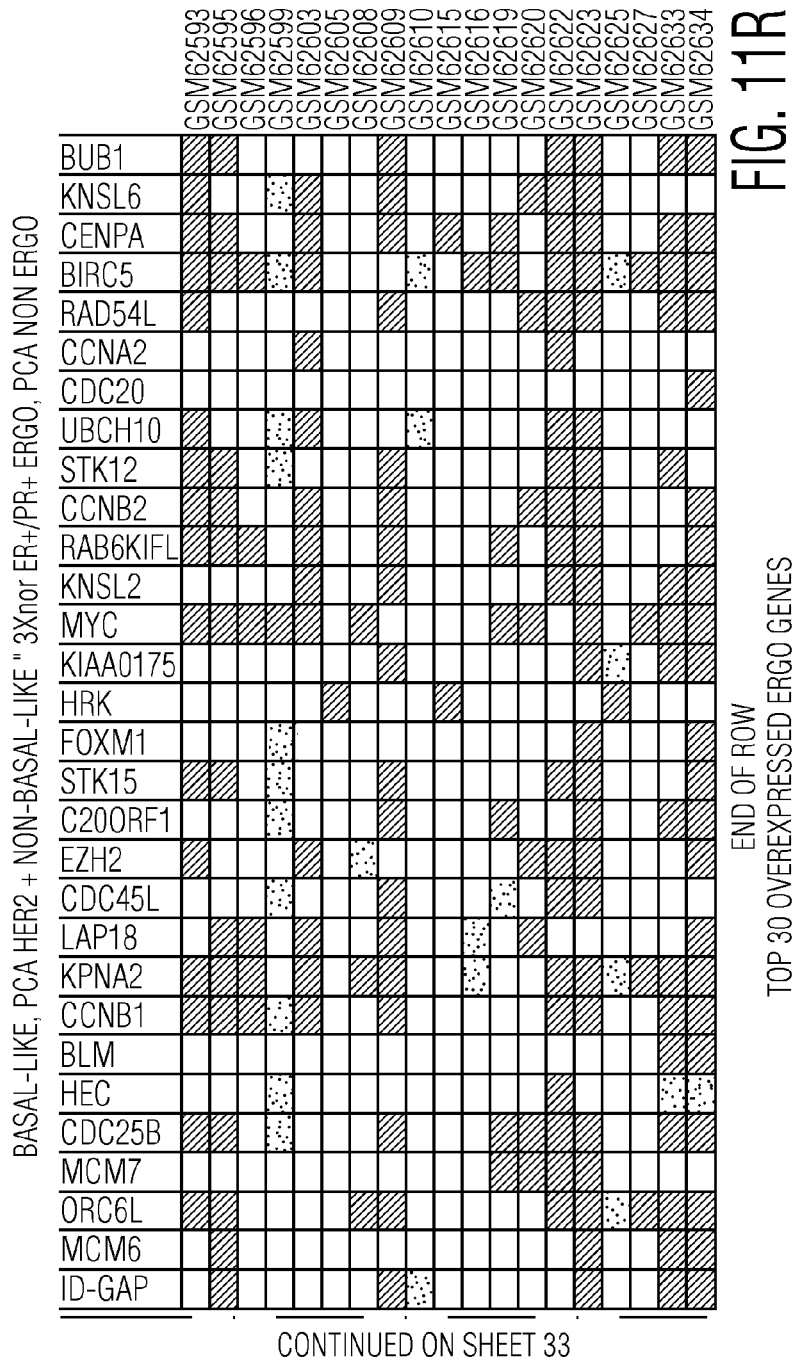

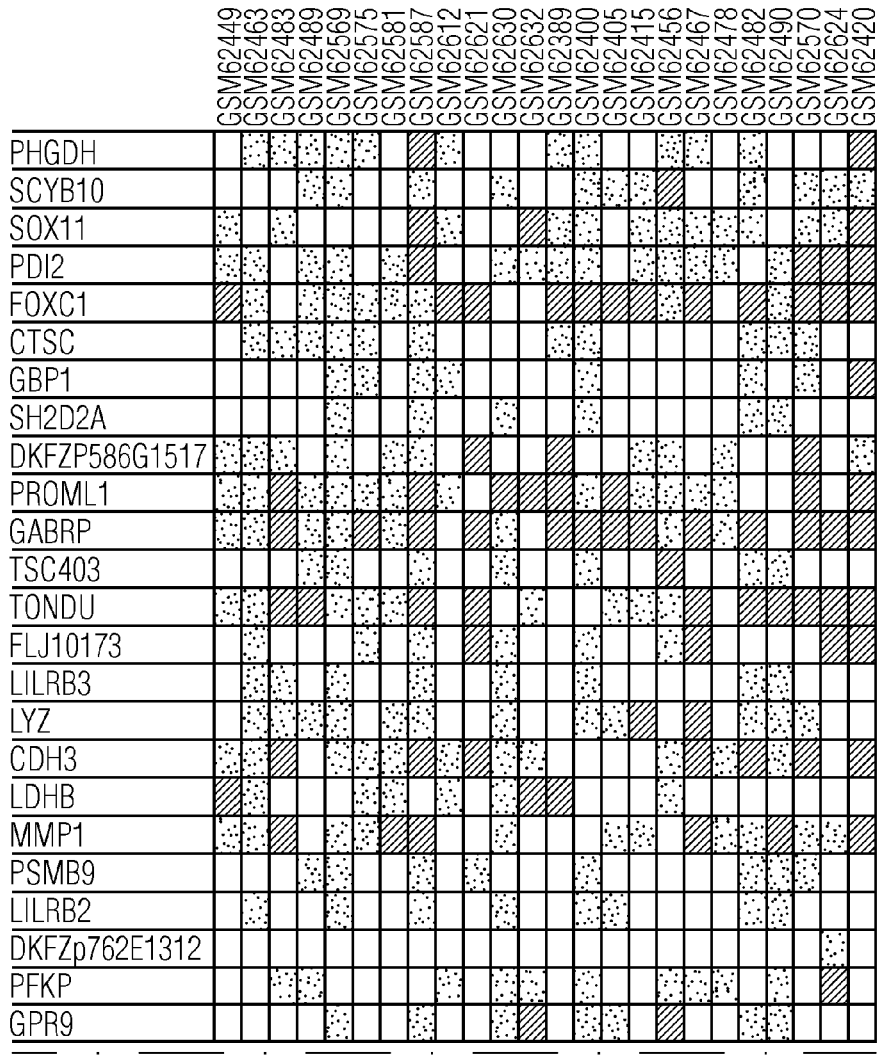

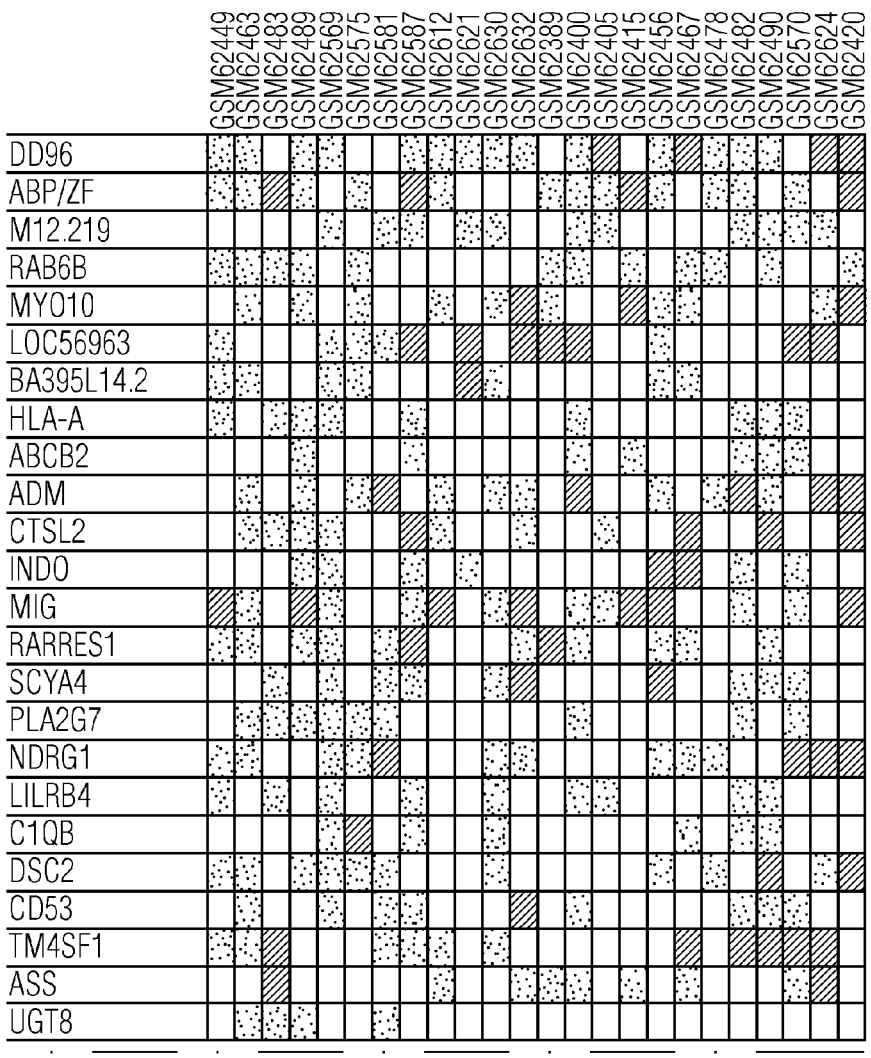

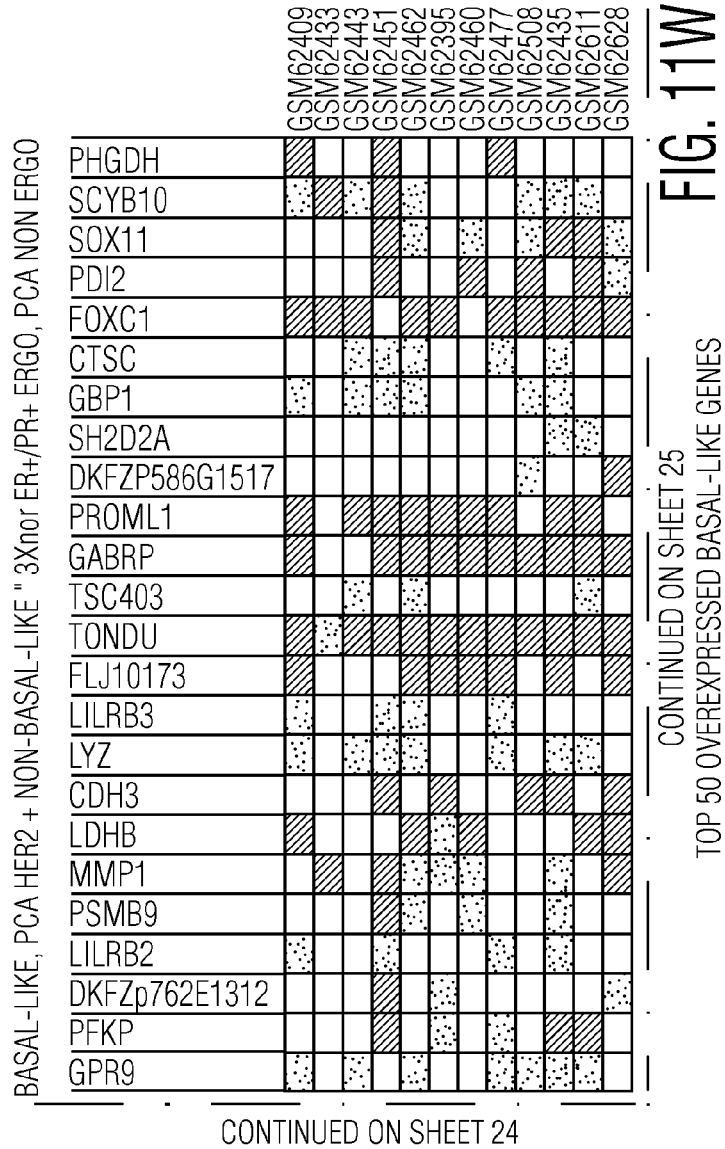

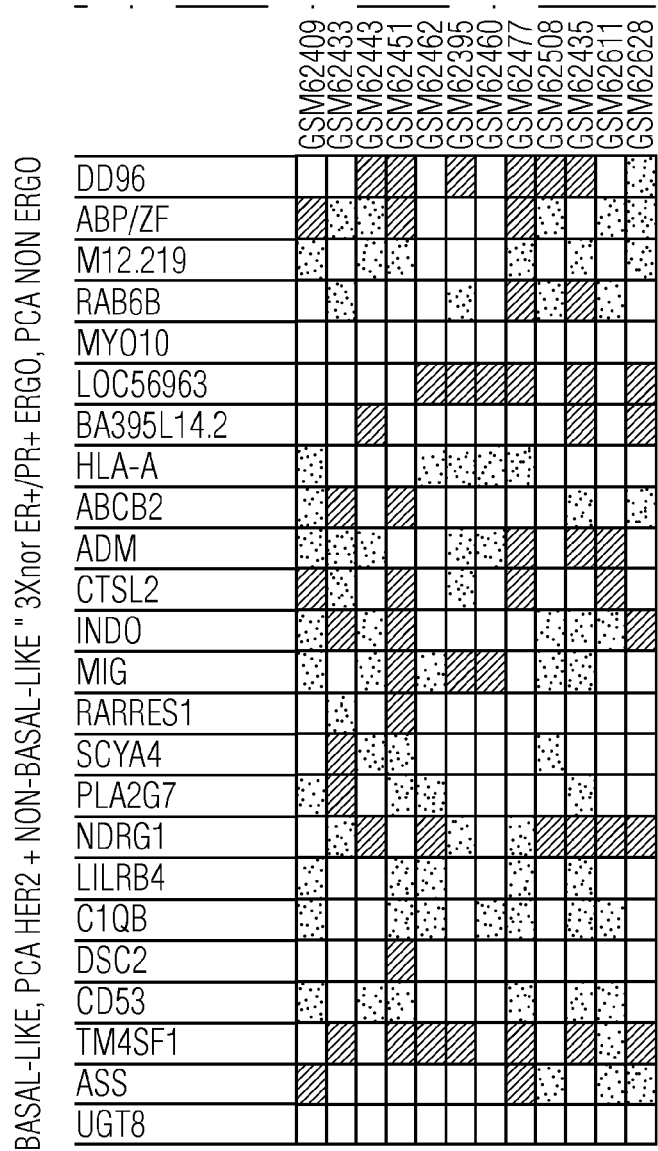

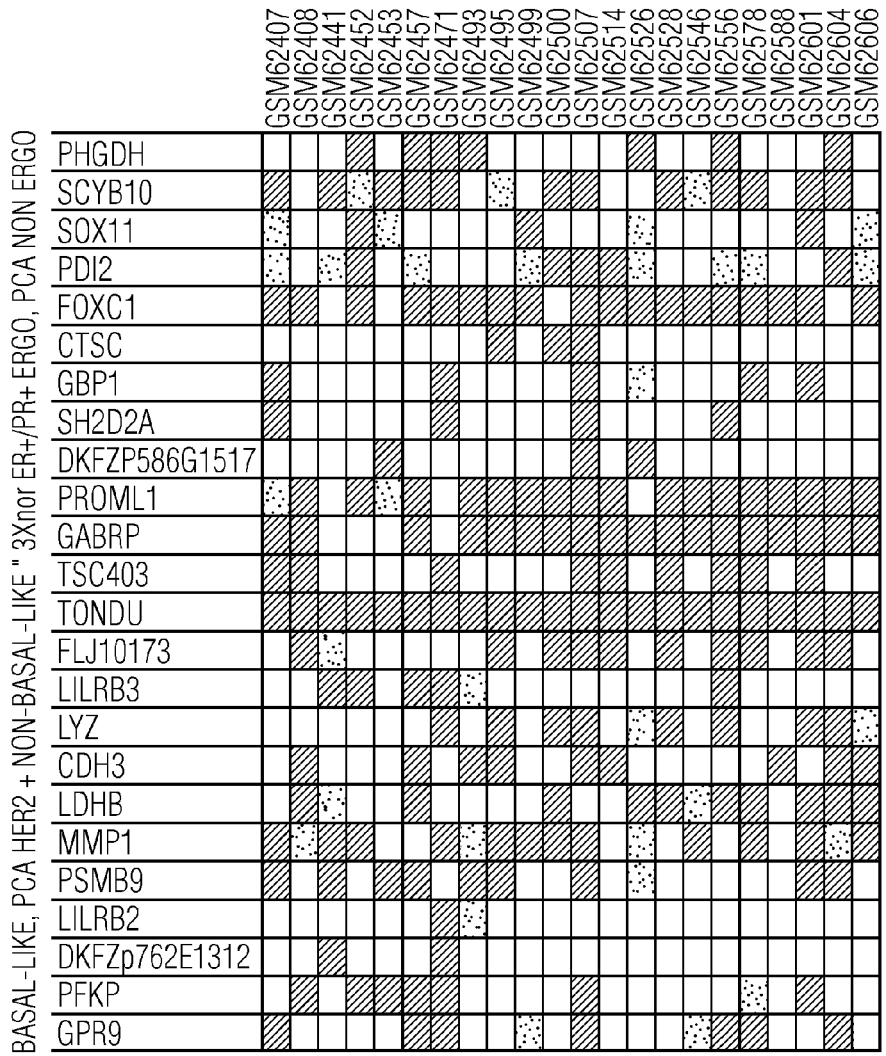

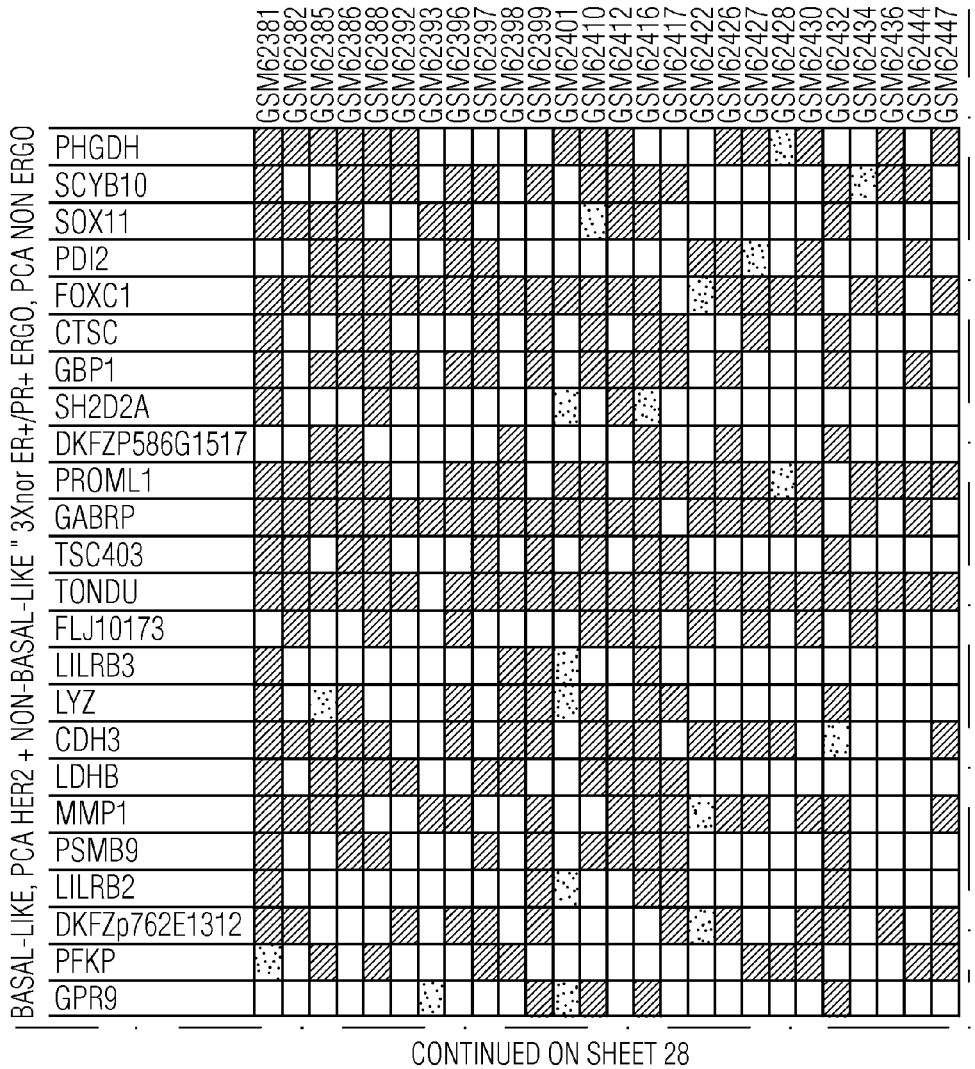

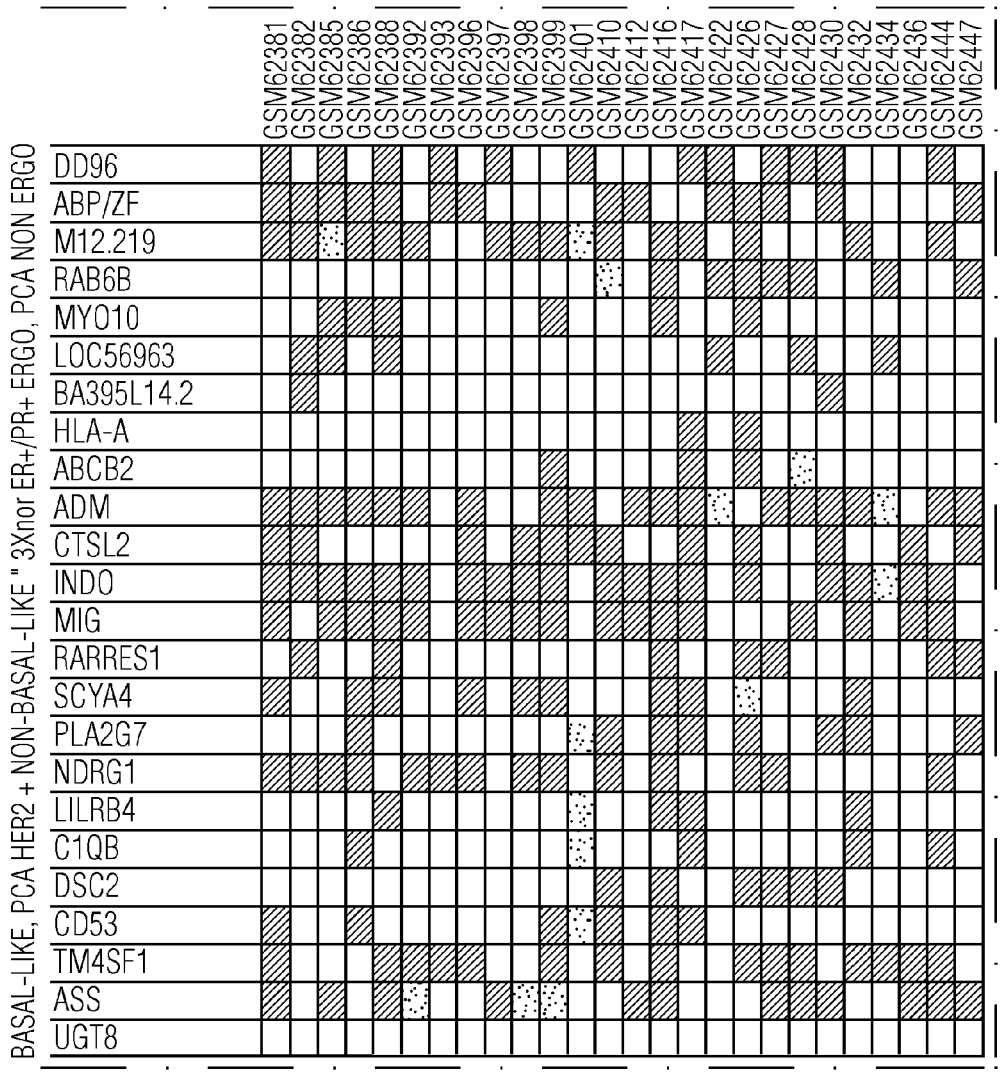

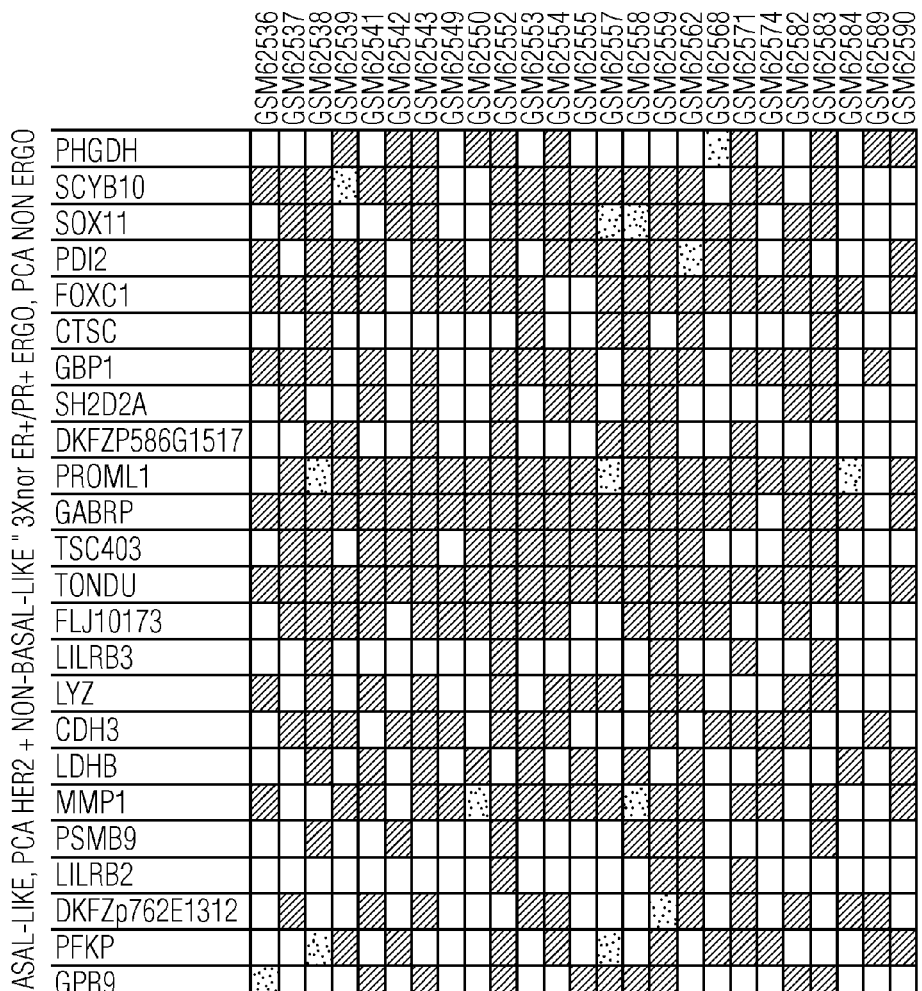

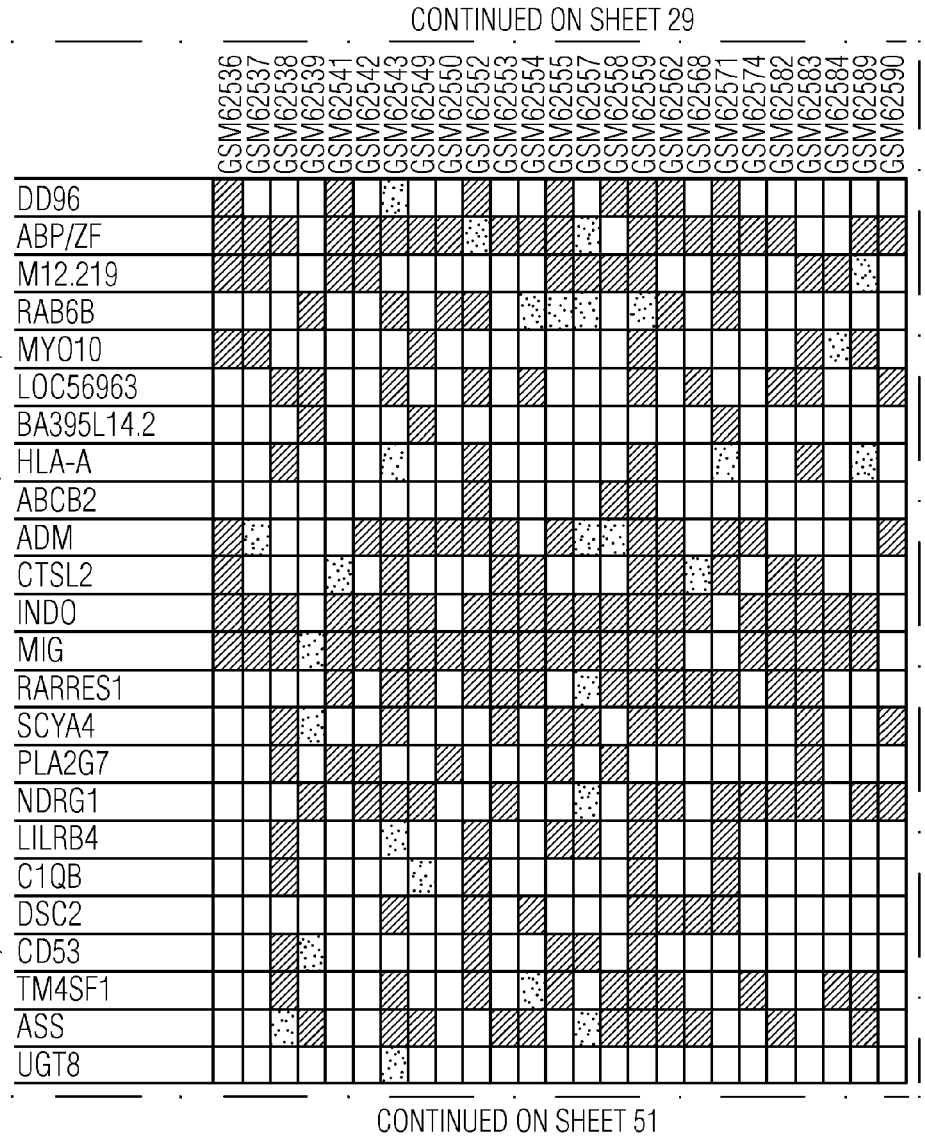

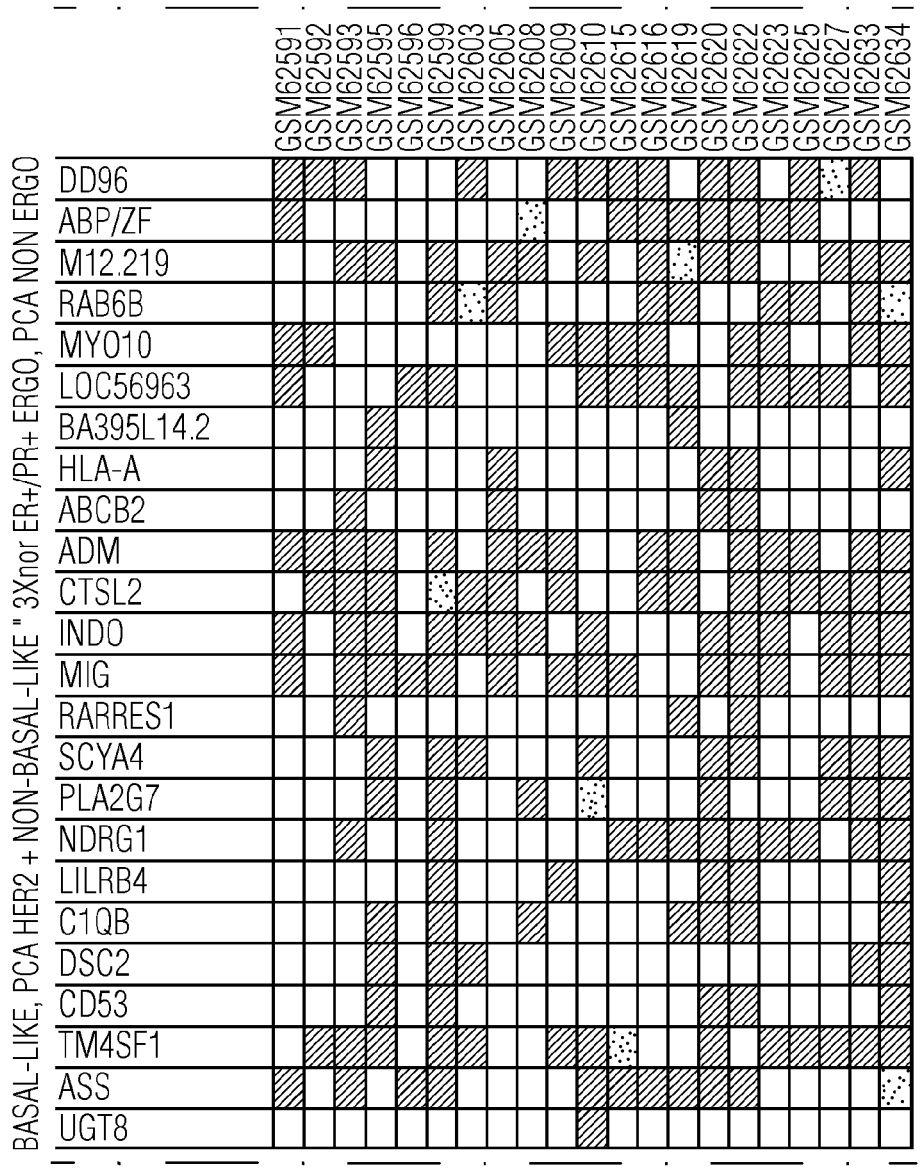

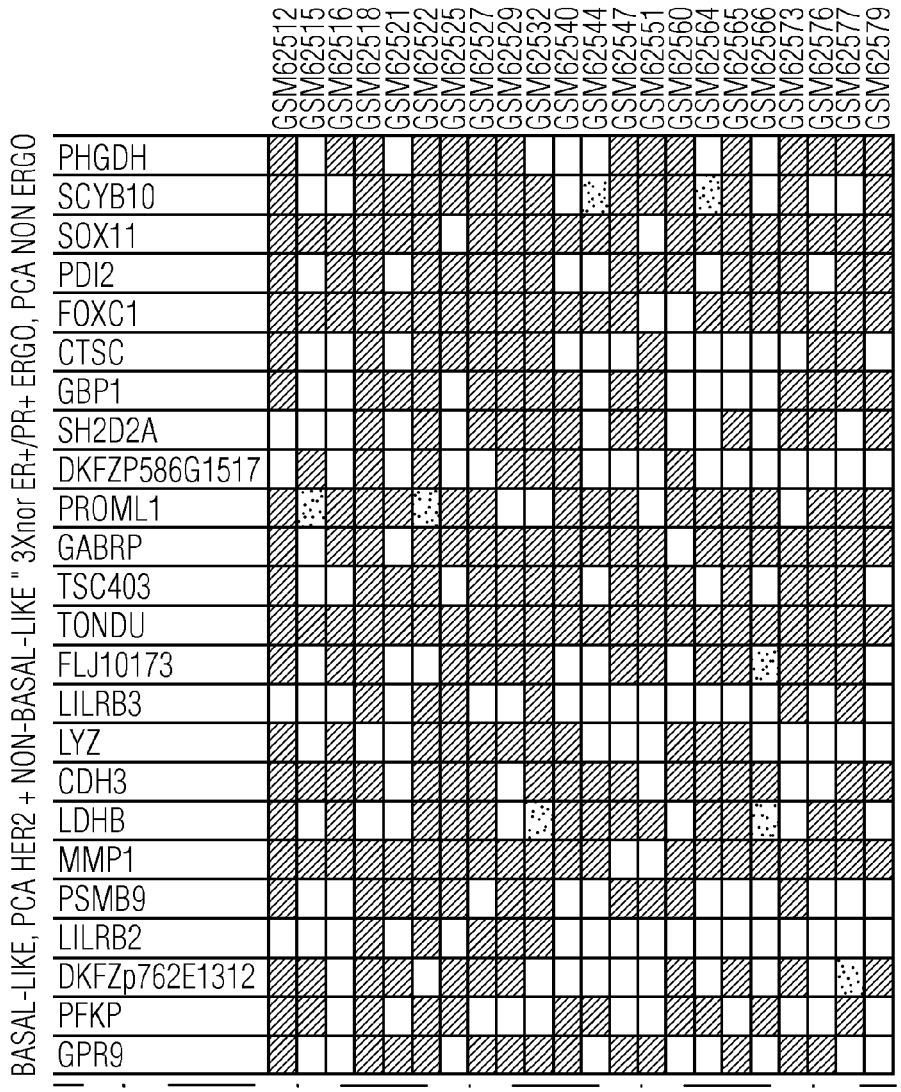

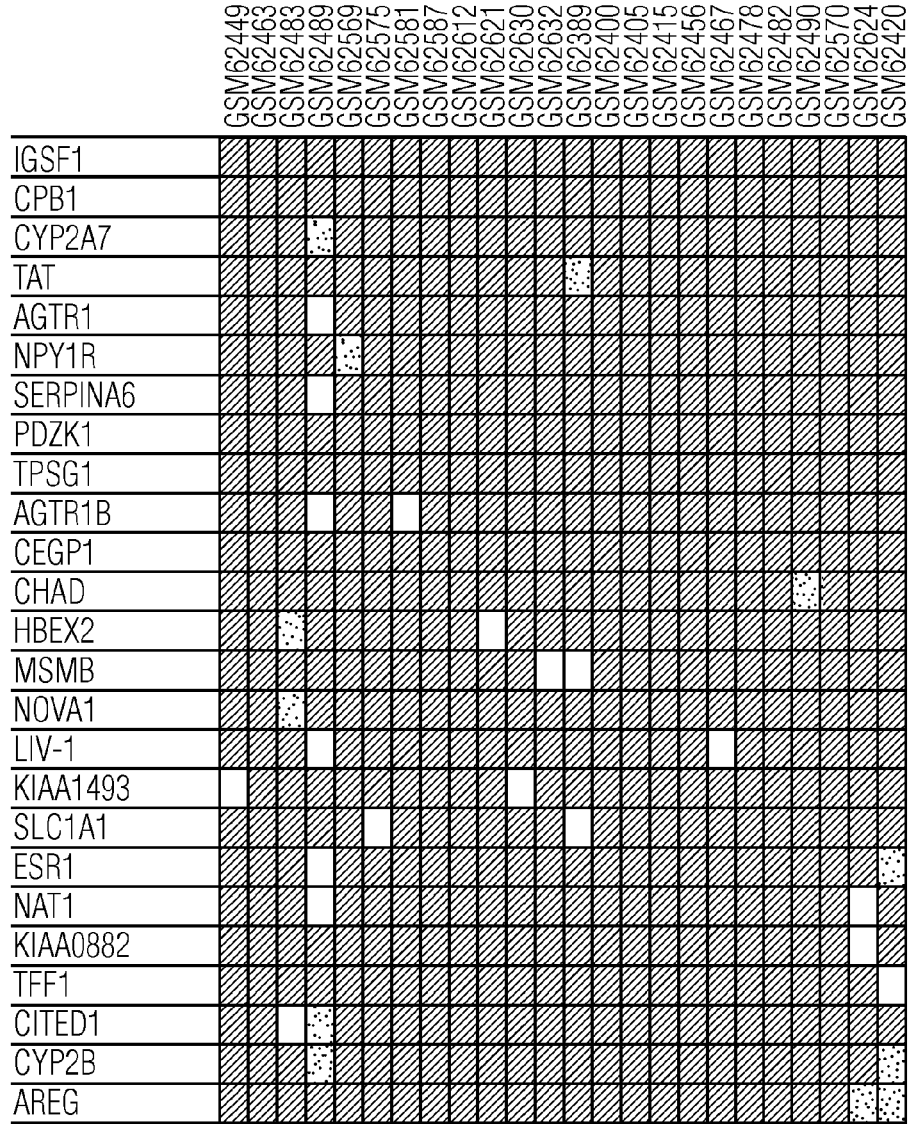

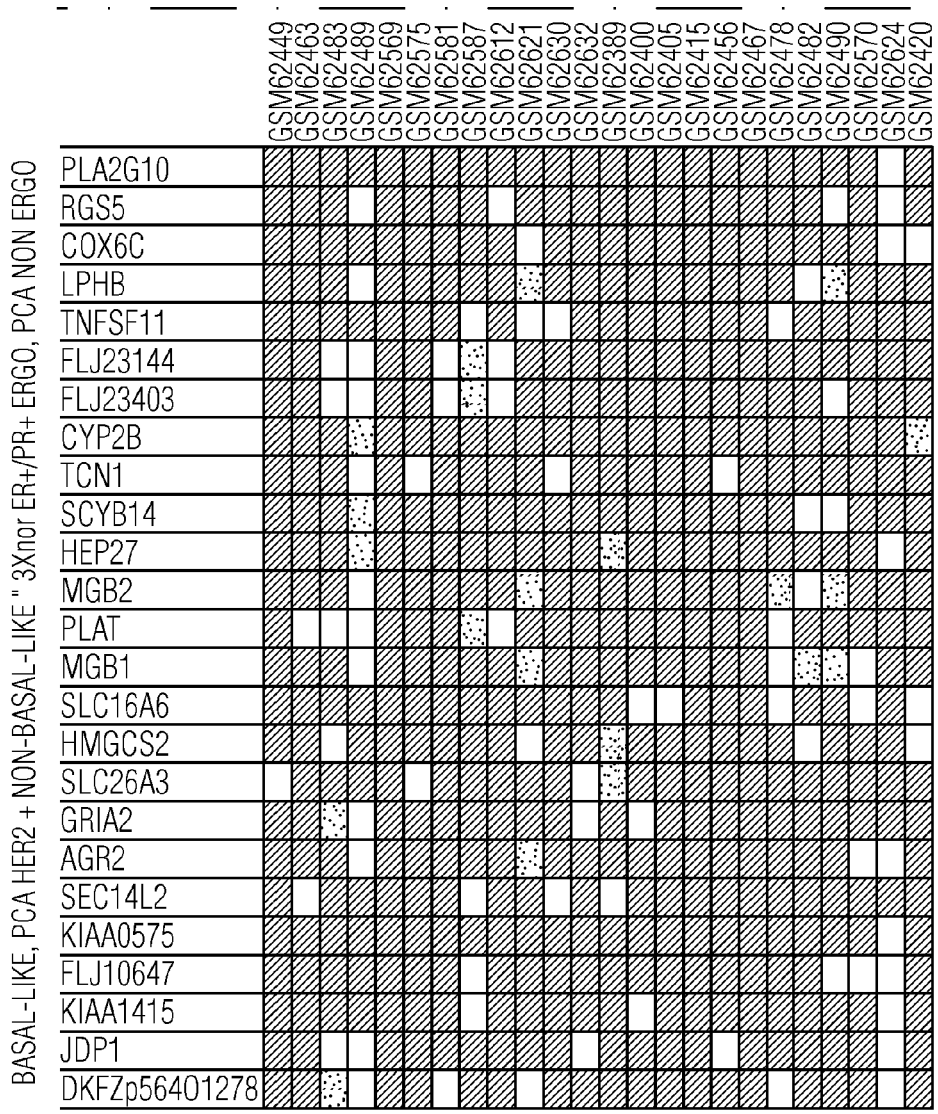

FIG. 11QQ

Columns: GSM62409, GSM62433, GSM62443, GSM62451, GSM62462, GSM62395, GSM62460, GSM62477, GSM62508, GSM62435, GSM62611, GSM62628

Rows (genes):
IGSF1, CPB1, CYP2A7, TAT, AGTR1, NPY1R, SERPINA6, PDZK1, TPSG1, AGTR1B, CEGP1, CHAD, HBEX2, MSMB, NOVA1, LIV-1, KIAA1493, SLC1A1, ESR1, NAT1, KIAA0882, TFF1, CITED1, CYP2B, AREG Left axis label: BASAL-LIKE, PCA HER2 + NON-BASAL-LIKE "3Xnor ER+/PR+ ERGO, PCA NON ERGO Right label: CONTINUED ON SHEET 45 — TOP 50 OVEREXPRESSED BASAL-LIKE GENES

CONTINUED ON SHEET 44

FIG. 11RR

CONTINUED FROM SHEET 43

CONTINUED ON SHEET 46

TOP 50 UNDEREXPRESSED BASAL-LIKE GENES

BASAL-LIKE, PCA HER2 + NON-BASAL-LIKE "3Xnor ER+/PR+ ERGO, PCA NON ERGO

| Gene | GSM62409 | GSM62433 | GSM62443 | GSM62451 | GSM62462 | GSM62395 | GSM62460 | GSM62477 | GSM62508 | GSM62435 | GSM62611 | GSM62628 |
|---|---|---|---|---|---|---|---|---|---|---|---|---|
| PLA2G10 | | | | | | | | | | | | |
| RGS5 | | | | | | | | | | | | |
| COX6C | | | | | | | | | | | | |
| LPHB | | | | | | | | | | | | |
| TNFSF11 | | | | | | | | | | | | |
| FLJ23144 | | | | | | | | | | | | |
| FLJ23403 | | | | | | | | | | | | |
| CYP2B | | | | | | | | | | | | |
| TCN1 | | | | | | | | | | | | |
| SCYB14 | | | | | | | | | | | | |
| HEP27 | | | | | | | | | | | | |
| MGB2 | | | | | | | | | | | | |
| PLAT | | | | | | | | | | | | |
| MGB1 | | | | | | | | | | | | |
| SLC16A6 | | | | | | | | | | | | |
| HMGCS2 | | | | | | | | | | | | |
| SLC26A3 | | | | | | | | | | | | |
| GRIA2 | | | | | | | | | | | | |
| AGR2 | | | | | | | | | | | | |
| SEC14L2 | | | | | | | | | | | | |
| KIAA0575 | | | | | | | | | | | | |
| FLJ10647 | | | | | | | | | | | | |
| KIAA1415 | | | | | | | | | | | | |
| JDP1 | | | | | | | | | | | | |
| DKFZp564O1278 | | | | | | | | | | | | |

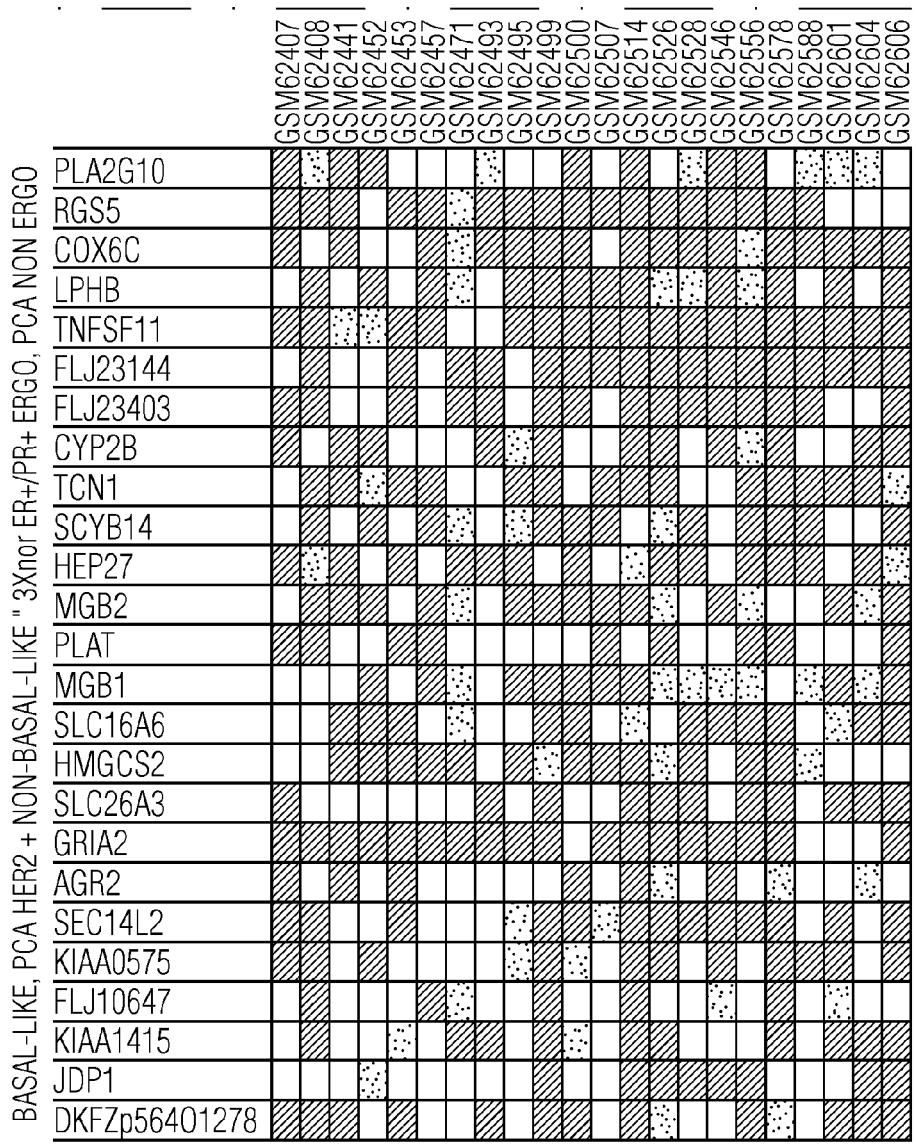

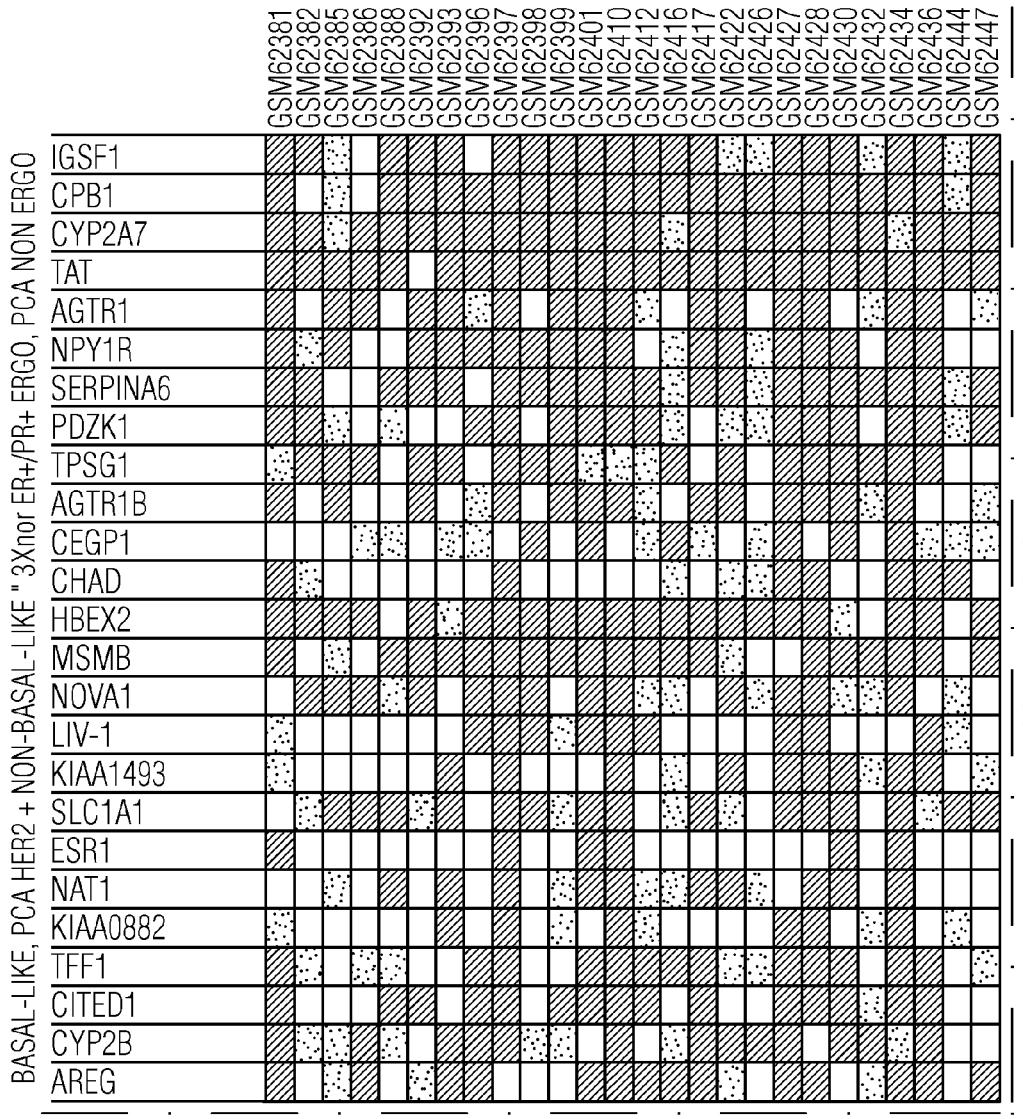

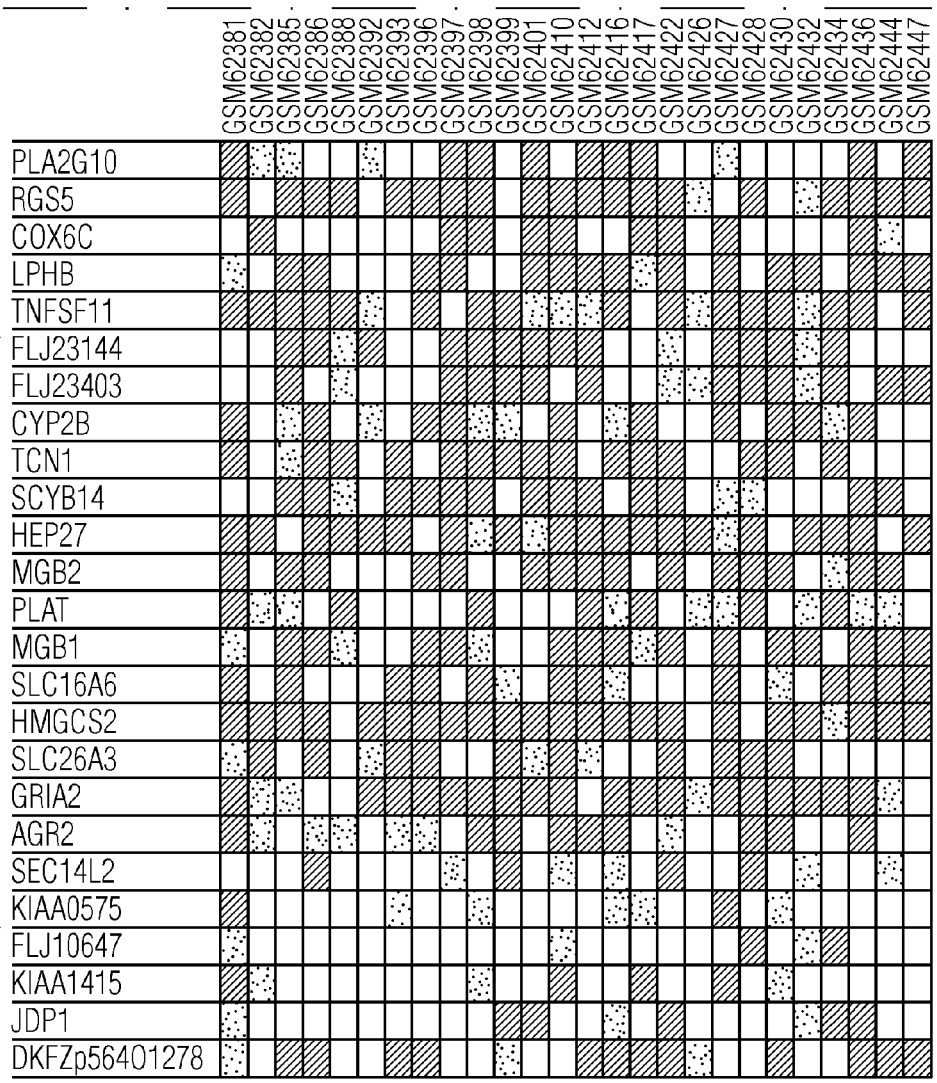

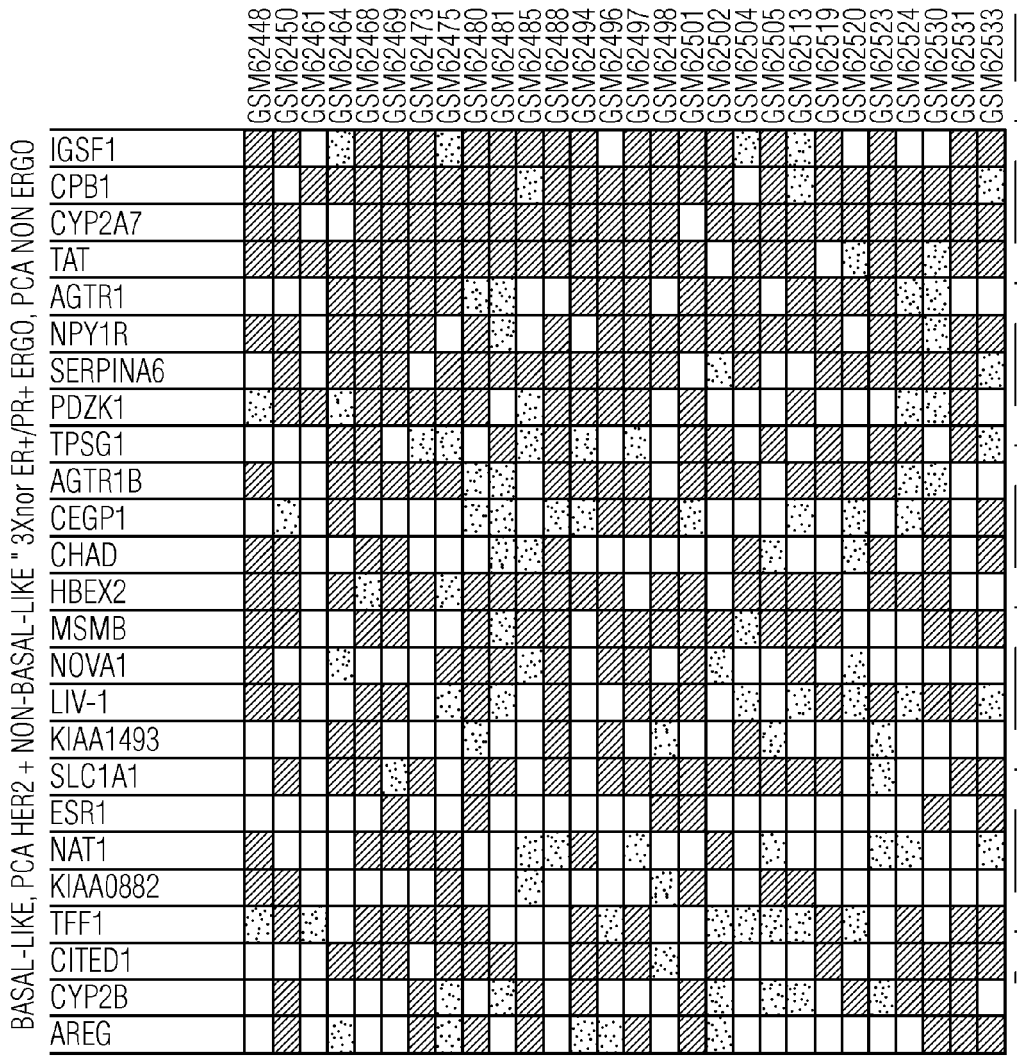

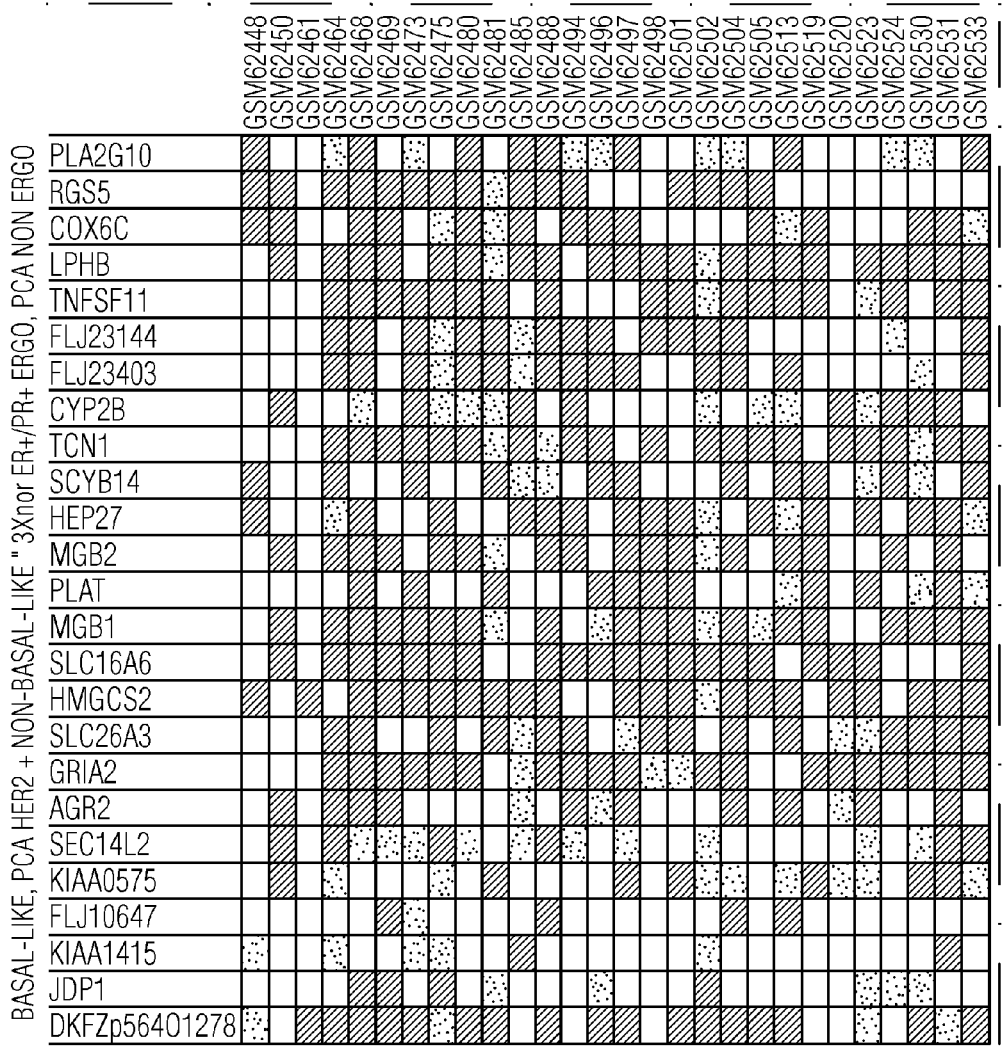

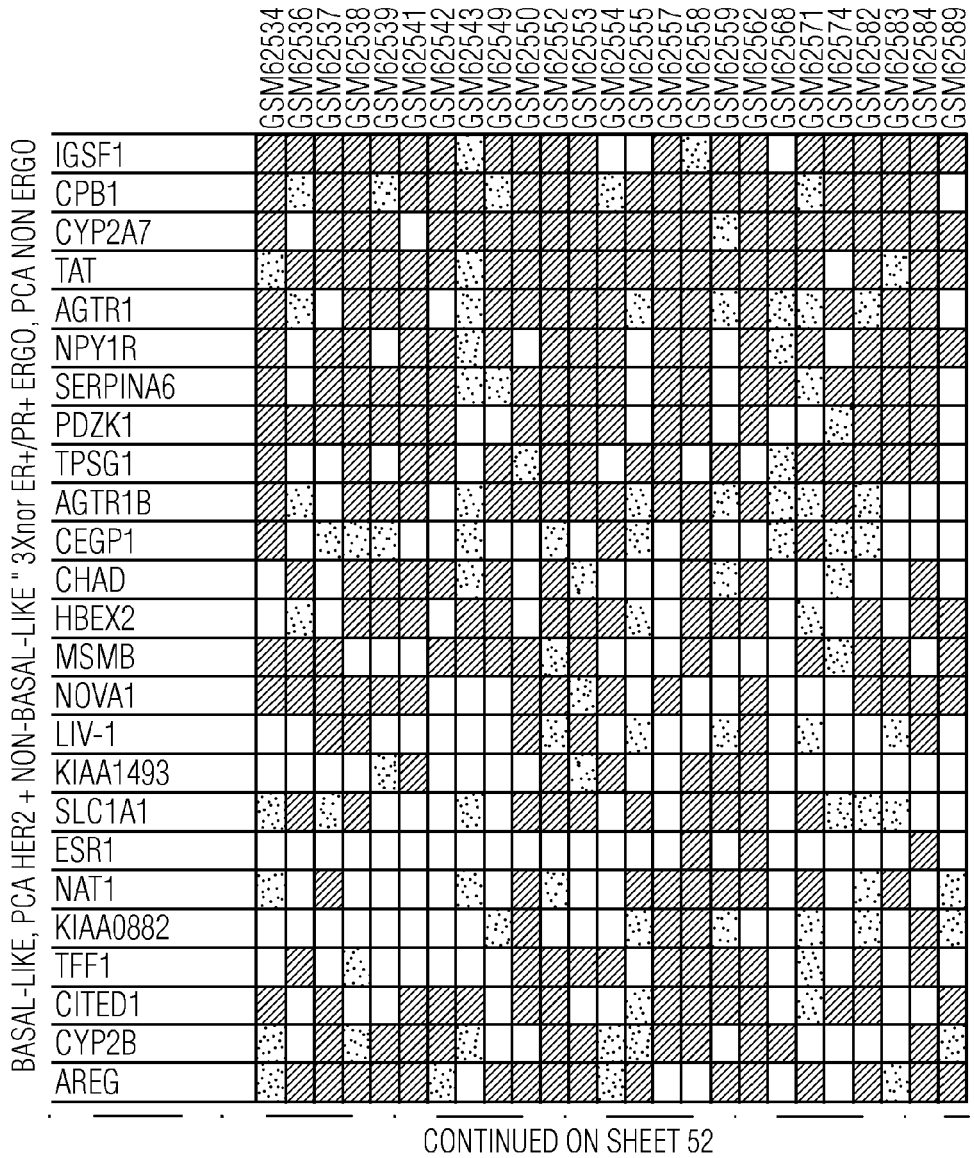

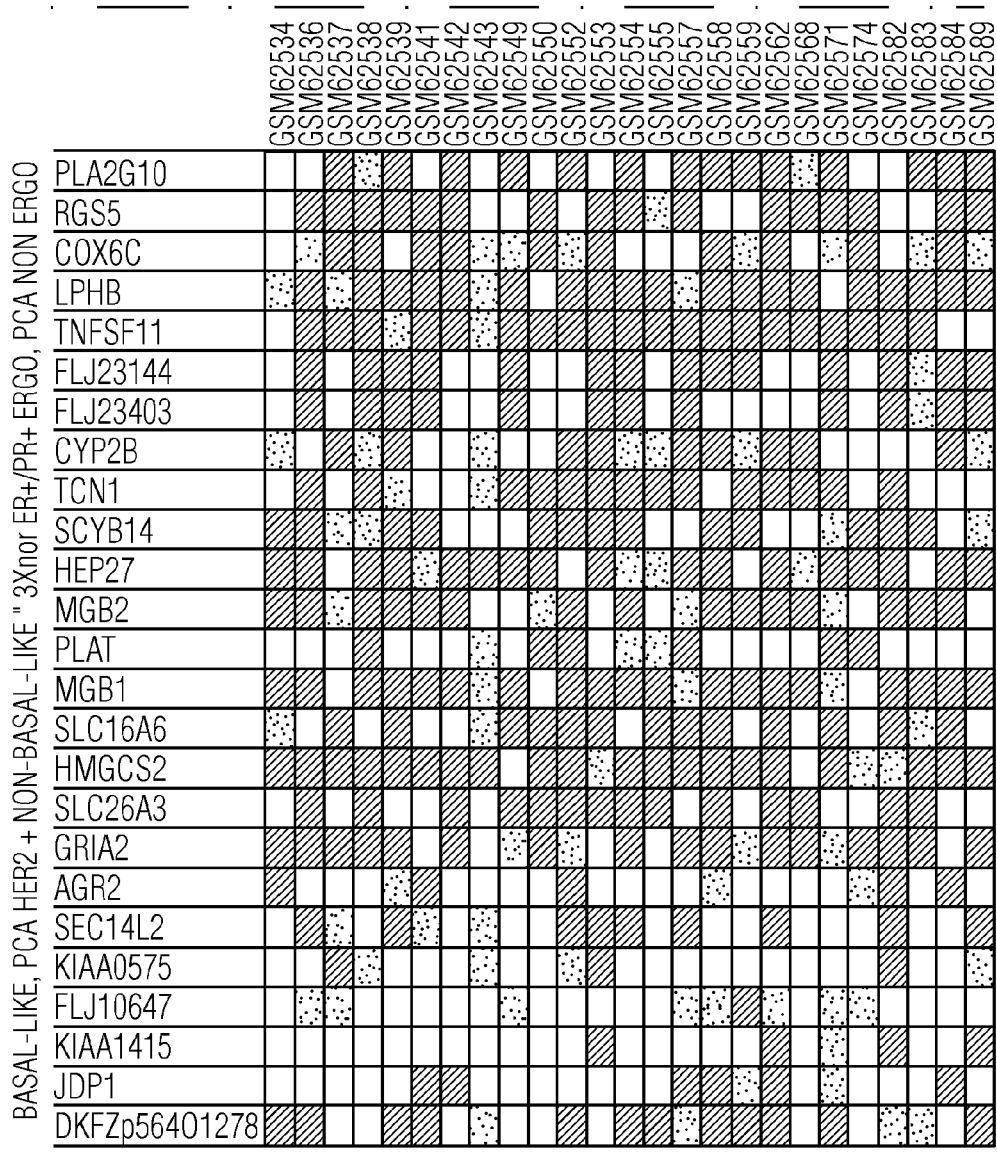

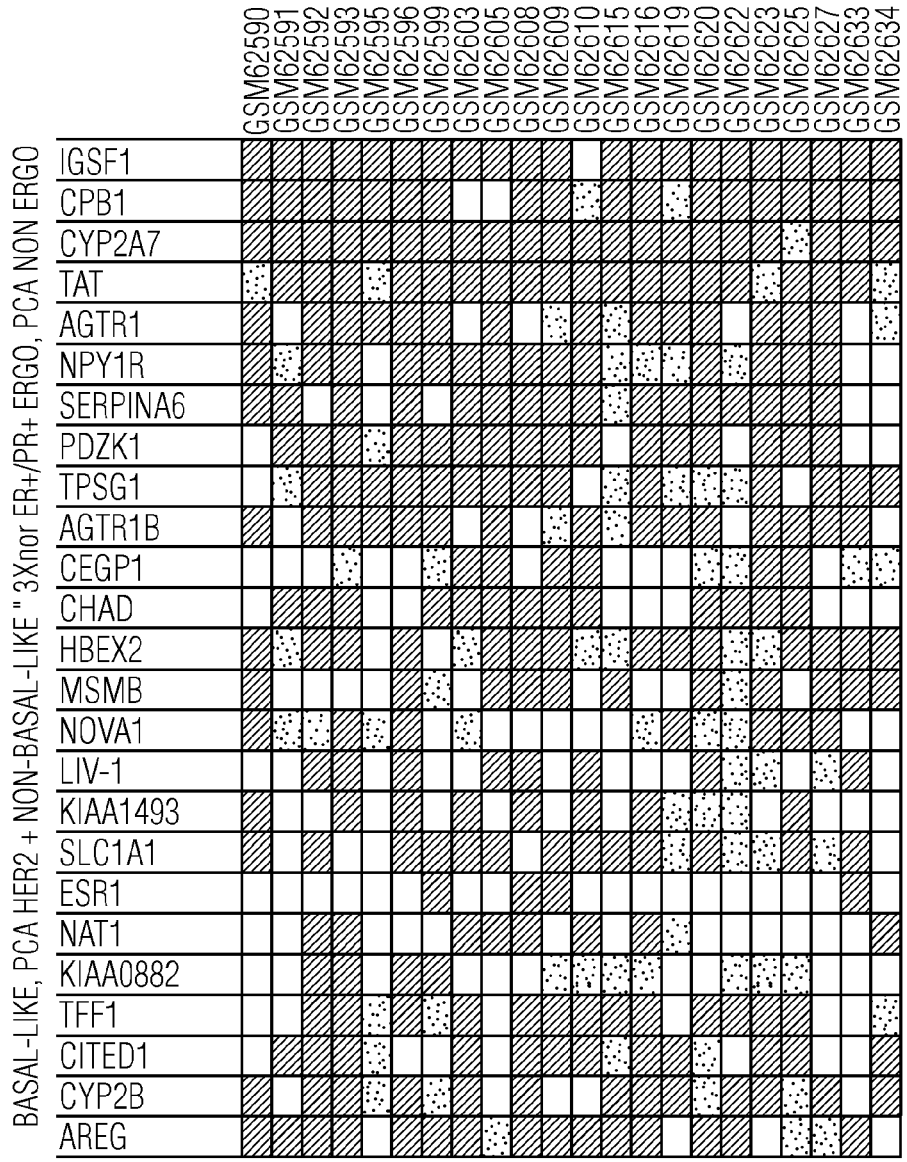

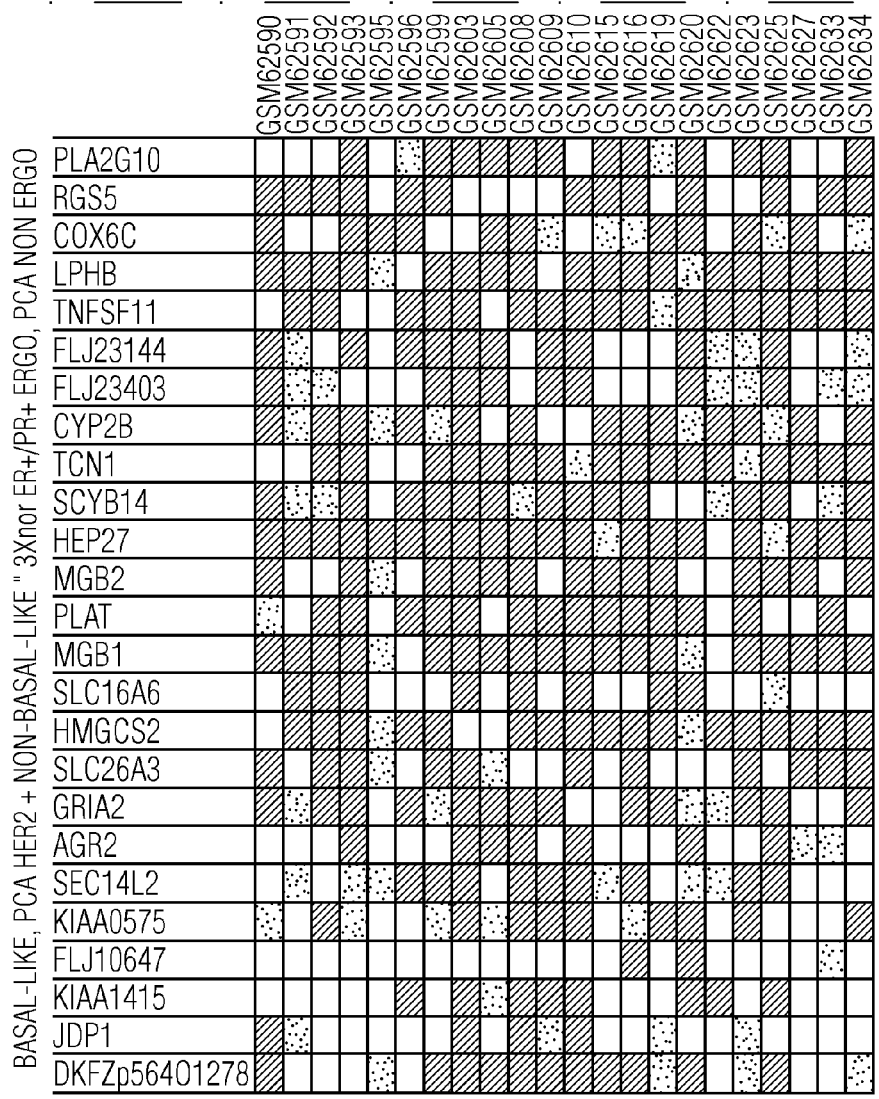

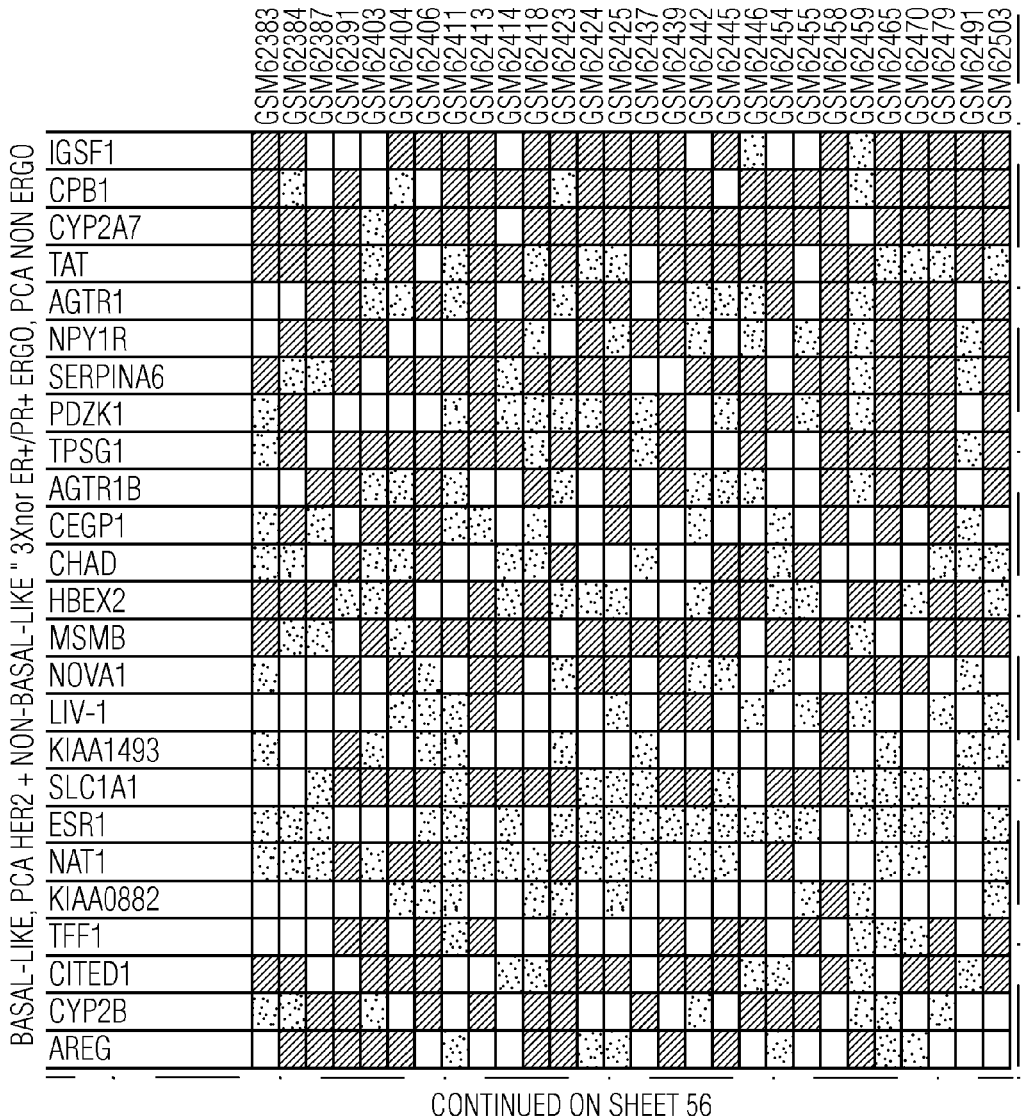

FIG. 11DDD

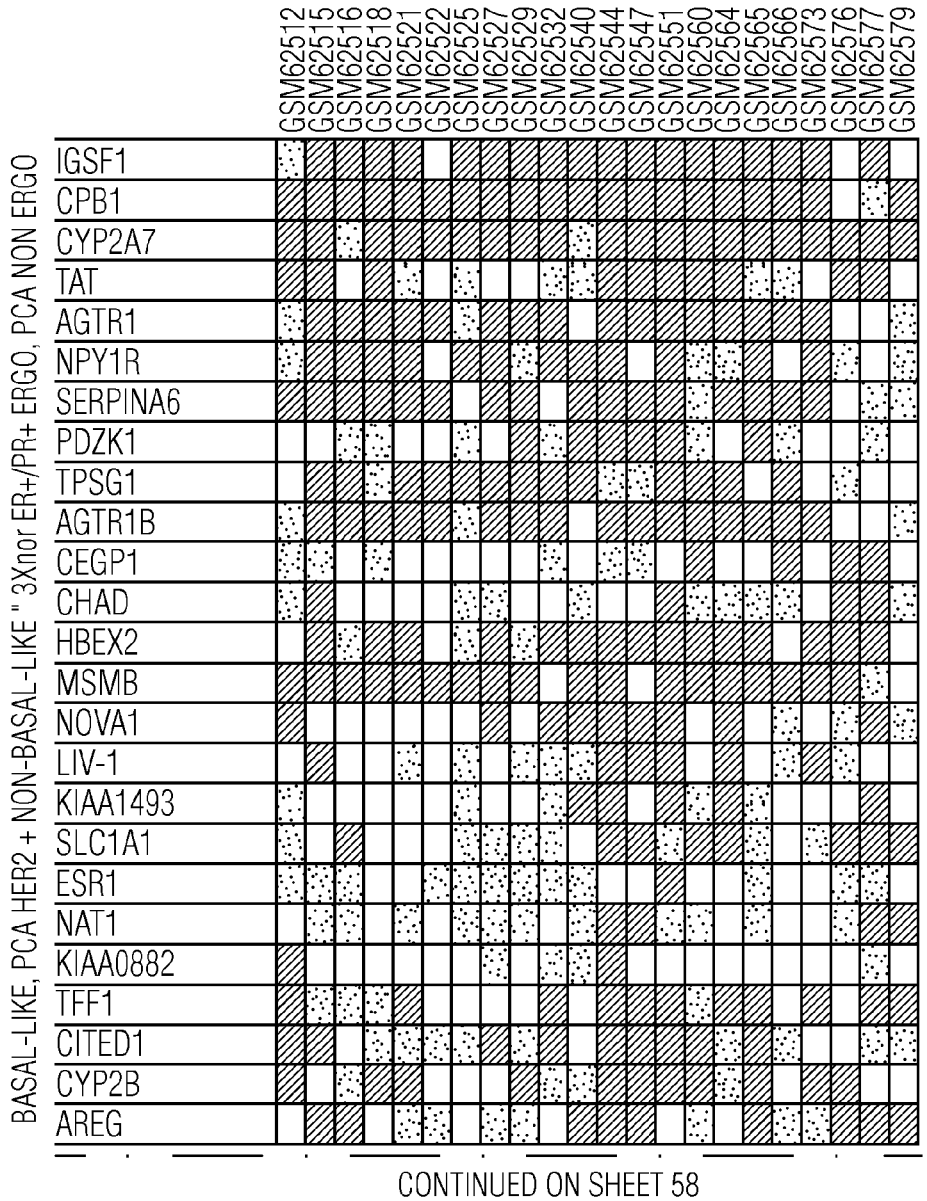
FIG. 11EEE

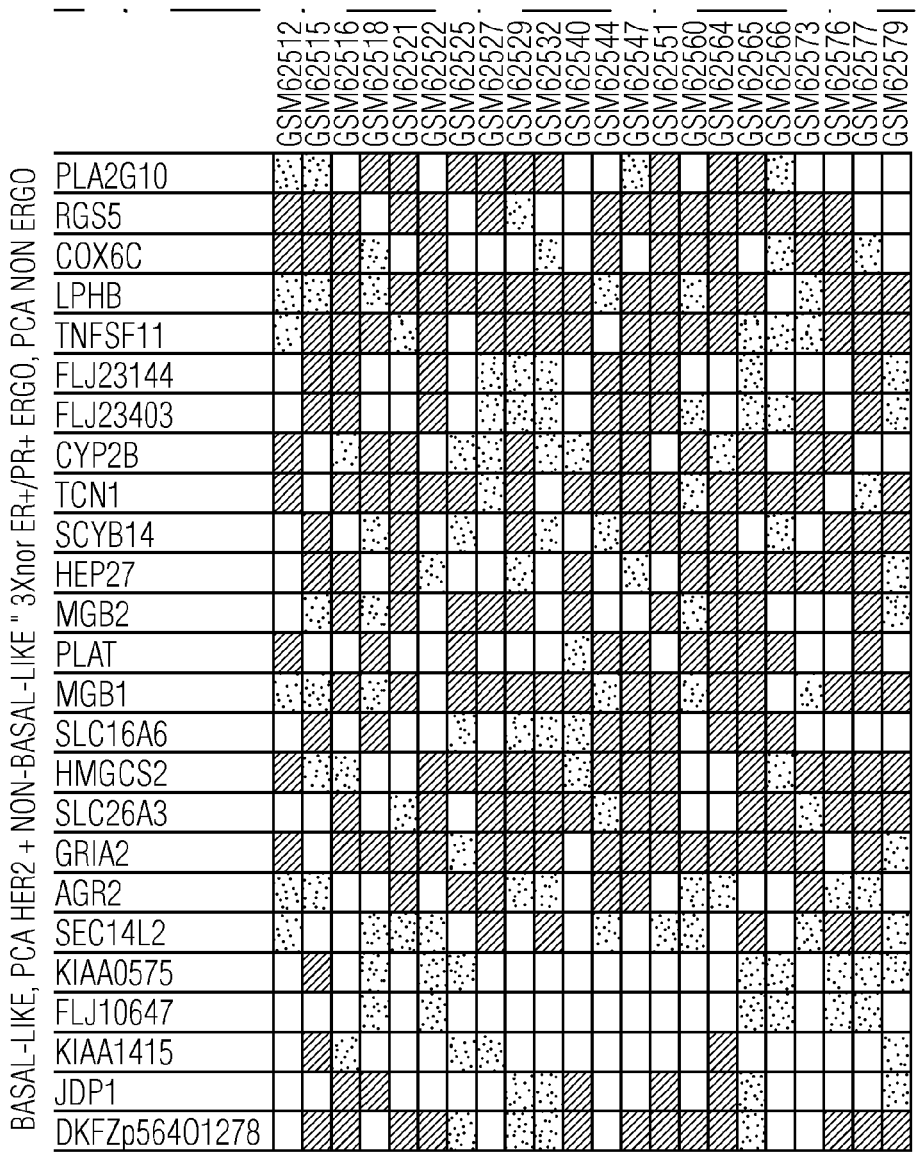
FIG. 11FFF

| 24 | STK12 |
|---|---|
| 23 | CDC20 |
| 22 | KNSL6 |
| 21 | RAD54L |
| 21 | ANLN |
| 20 | BUB1 |
| 20 | BTG3 |
| 19 | CENPA |
| 19 | C20orf1 |
| 18 | FOXM1 |
| 18 | TYMS |
| 18 | PLSCR1 |
| 18 | RAB6KIFL |
| 18 | CCNB2 |
| 17 | DEK |
| 17 | CCNE1 |
| 17 | HRK |
| 16 | CDC2 |
| 16 | CCNA2 |
| 16 | STMN1 |
| 16 | EZH2 |
| 16 | BLM |
| 16 | MCM5 |
| 15 | TTK |
| 15 | TEAD4 |
| 15 | CSRP2 |
| 15 | CHAF1B |
| 15 | KNSL2 |
| 15 | PTTG1 |
| 14 | CDC25A |
| 14 | TGFA |
| 14 | TK1 |
| 14 | MCM7 |
| 14 | HEC |
| 13 | KIAA0175 |
| 13 | CDC45L |
| 13 | USP1 |
| 12 | BIRC5 |
| 12 | UBCH10 |
| 12 | TP53BP2 |
| 12 | KNSL1 |

S1.BREAST.ERGO.G.COMPS.25

| 12 | RFC4 |
|---|---|
| 12 | MCM6 |
| 12 | ORC6L |
| 12 | MCM2 |
| 12 | SMC4L1 |
| 12 | SOX9 |
| 12 | MYC |
| 11 | KPNA2 |
| 11 | PRIM2A |
| 11 | NUP155 |
| 11 | MAD2L1 |
| 11 | PRC1 |
| 11 | DNA2L |
| 11 | FLJ22009 |
| 10 | CKS1 |
| 10 | NEK2 |
| 10 | CCNE2 |
| 10 | PIR51 |
| 10 | NASP |
| 10 | LMNB1 |
| 10 | STK15 |
| 9 | NOLC1 |
| 9 | CSDA |
| 9 | MAP3K14 |
| 9 | ECT2 |
| 9 | RAD51 |
| 9 | ANXA8 |
| 9 | CKS2 |
| 9 | POLD1 |
| 9 | PTPNS1 |
| 8 | TOPBP1 |
| 8 | E2F1 |
| 8 | VEGF |
| 8 | RRM2 |

| 8 | FEN1 |
|---|---|
| 8 | HMG2 |
| 8 | CHAF1A |
| 8 | CTGF |
| 8 | CHEK1 |
| 8 | CENPE |
| 8 | KIF4A |
| 8 | CDKN3 |
| 7 | CDC7L1 |
| 7 | OSMR |
| 7 | ORC3L |

| | |
|---|---|
| CENPA | 24 |
| BUB1 | 23 |
| KNSL2 | 22 |
| KNSL6 | 21 |
| STK12 | 21 |
| CDC20 | 20 |
| CCNB2 | 20 |
| FOXM1 | 19 |
| MYC | 19 |
| UBCH10 | 18 |
| KIAA0175 | 18 |
| EZH2 | 18 |
| CCNA2 | 18 |
| HRK | 18 |
| CDC45L | 17 |
| RAD54L | 17 |
| RAB6KIFL | 17 |
| HEC | 16 |
| BLM | 16 |
| BIRC5 | 16 |
| MAD2L1 | 16 |
| MCM5 | 16 |
| CSRP2 | 16 |
| STK15 | 15 |
| ID-GAP | 15 |
| CDC25B | 15 |
| KPNA2 | 15 |
| MCM2 | 15 |
| LAP18/STMN1 | 15 |
| TTK | 14 |
| C20ORF1 | 14 |
| CCNB1 | 14 |
| CHEK1 | 14 |
| TP53BP2 | 14 |
| MCM6 | 13 |
| TEAD4 | 13 |
| SOX9 | 13 |
| PRC1 | 12 |
| MCM7 | 12 |
| CKS1 | 12 |
| HMG4 | 12 |

S2.ERGO.COMPS.25

| | |
|---|---|
| LMNB1 | 12 |
| NASP | 12 |
| PRIM2A | 12 |
| CHAF1B | 12 |
| PLSCR1 | 12 |
| VEGF | 12 |
| CSDA | 12 |
| PTTG1 | 11 |
| E2F1 | 11 |
| FEN1 | 11 |
| TK1 | 11 |
| RFC4 | 11 |
| BTG3 | 11 |
| PTPNS1 | 11 |
| ORC6L | 10 |
| CHAF1A | 10 |
| CDC2 | 10 |
| POLA2 | 10 |
| ANLN | 10 |
| ANXA8 | 10 |
| TGFA | 10 |
| HSPC150 | 9 |
| NEK2 | 9 |
| ECT2 | 9 |
| KNSL1 | 9 |
| CAP-C/SMC4L1 | 9 |
| UNG | 9 |
| H2AFX | 9 |
| P130/NOLC1 | 9 |
| DEK | 9 |
| PCNA | 8 |
| CKS2 | 8 |
| CDC7L1 | 8 |
| DNA2L | 8 |

| | |
|---|---|
| CDKN2C | 8 |
| DNMT1 | 8 |
| GCH1 | 8 |
| MCM4 | 8 |
| DKFZp762L0311 | 8 |
| MTHFD1 | 8 |
| USP1 | 8 |
| MAP3K14 | 8 |
| STK18 | 7 |
| BM037 | 7 |
| TYMS | 7 |
| PIR51 | 7 |
| LHX2 | 7 |
| FLJ10335 | 7 |
| TMPO | 7 |
| EED | 7 |
| CCNE2 | 6 |
| KIF4A | 6 |
| CDC25C | 6 |
| MSH2 | 6 |
| NUP155 | 6 |
| BARD1 | 6 |
| BID | 6 |
| DMRT1 | 6 |
| OSMR | 6 |
| GAB2 | 6 |

FIG. 12B

PCA ERGO TUMOR LARGE CELL
NEUROENDOCRINE TUMOR CARCINOIDS

FIG. 14C

PCA ERGO TUMOR LARGE CELL
NEUROENDOCRINE TUMOR CARCINOIDS
CONTINUED FROM SHEET 4

FIG. 14E

PCA ERGO TUMOR LARGE CELL
NEUROENDOCRINE TUMOR CARCINOIDS
CONTINUED FROM SHEET 5

| | | GSM17195 | GSM17196 | GSM17306 | GSM17307 | GSM17308 | GSM17309 | GSM17310 | GSM17311 | GSM17312 | GSM17313 | GSM17332 | GSM17335 | GSM17337 | GSM17342 |
|---|---|---|---|---|---|---|---|---|---|---|---|---|---|---|---|
| KNSL1 | KNSL1 | | | ░ | | ░ | ░ | ░ | | | | | ░ | ░ | |
| PMAIP1 | PMAIP1 | ▨ | | | ░ | | | ▨ | | | | | | | |
| KPNA2 | KPNA2 | | | ░ | | ░ | ░ | | | | | | | | |
| DNMT1 | DNMT1 | | ░ | ░ | | ░ | | ░ | ░ | | | | | | |
| USP1 | USP1 | ░ | | | | | | | | | | | ░ | ░ | |
| E2F3 | E2F3 | | | | | | | | | | ░ | | | | |
| KNSL6 | KNSL6 | | | ░ | | ░ | ░ | ░ | ░ | | | | ░ | | |
| RFC2 | RFC2 | | ░ | | ░ | | ░ | ░ | ░ | | | | ░ | | |
| BUB3 | BUB3 | | ░ | | ░ | | ░ | ░ | ░ | | | | ░ | | |
| UBE2C | UBch10 | | | ░ | | ░ | ░ | ░ | | | | | ░ | | |
| HMGB3 | HMG4 | | | ░ | ░ | | | | | | | | | | |
| MCM6 | MCM6 | | ░ | | | | ░ | ░ | | | | | | | |
| CDC45L | CDC45L | | | | ░ | | ░ | ░ | | | | ░ | | | |
| CKS2 | CKS2 | | | ░ | | ░ | ░ | | | | | | | | |
| NUP155 | NUP155 | | | ░ | | ░ | ░ | | | | | | | | |
| POLE2 | POLE2 | | ░ | | | ░ | | ░ | | | | ░ | ░ | | |
| DCK | DCK | ░ | ░ | | | | | | | | | | | ░ | |
| VRK1 | VRK1 | | ░ | ░ | | | | ░ | | | | | ░ | | |
| SFRS2 | SFRS2 | | | ░ | | | | ░ | | | | ░ | | | |
| RAD51 | RAD51 | ░ | | ░ | | ░ | | | | | | | | | |
| BUB1 | BUB1 | | | ░ | | ░ | ░ | | | | | | | | |
| MELK | KIAA0175 | | | | | ░ | | | ░ | | | | | | |
| PRIM2A | PRIM2A | | | | | | | | | | | | ░ | | |
| BRCA1 | BRCA1 | | ░ | | | | | | | | | | ░ | ░ | |
| FEN1 | FEN1 | | ░ | ░ | | | | | | | | | | ░ | |
| CSTF1 | CSTF1 | | | | | ░ | | | ░ | | | | | | |
| TP53BP2 | TP53BP2 | | ░ | | | | ░ | | | | | | | | |

OVEREXPRESSED E2F-RESPONSIVE GENES

CONTINUED ON SHEET 9

END OF COLUMN

FIG. 14F

PCA ERGO TUMOR LARGE CELL
NEUROENDOCRINE TUMOR CARCINOIDS
CONTINUED FROM SHEET 7

FIG. 14H

CONTINUED ON SHEET 9 / CONTINUED ON SHEET 11

OVEREXPRESSED E2F-RESPONSIVE GENES:

| Gene | Alt |
|---|---|
| BARD1 | BARD1 |
| CHAF1A | CHAF1A |
| NPAT | NPAT |
| H2AFZ | H2AFZ |
| SMARCA5 | SMARCA5 |
| SSX2IP** | KIAA0923 |
| RPA2 | RPA2 |
| RAD54L | RAD54L |
| CENPA | CENPA |
| NEK2 | NEK2 |
| CHAF1B | CHAF1B |
| HOXA7 | HOXA7 |
| ORC3L | ORC3L |
| MCM3 | MCM3 |
| CCNB2 | CCNB2 |
| TCF19 | TCF19 |
| PRC1 | PRC1 |
| BUB1B | BUB1B |
| HMMR | HMMR |
| MTHFD1 | MTHFD1 |
| STK6 | STK15 |
| CDKN3 | CDKN3 |
| SRGAP2 | KIAA0456 |
| CASP8 | CASP8 |
| CDK2 | CDK2 |
| FLJ10604 | FLJ10604 |
| MSH2 | MSH2 |
| SMC4L1 | SMC4L1 |
| HMGB1 | HMGB1 |
| CDC7L1 | CDC7L1 |
| BIRC5 | BIRC5 |

Columns: GSM16557, GSM16560, GSM17327, GSM17328, GSM17333, GSM17340, GSM17341, GSM17343, GSM17344, GSM17345, GSM17346, GSM17348, GSM17349, GSM17355, GSM18306, GSM18307, GSM18311

PCA ERGO TUMOR LARGE CELL
NEUROENDOCRINE TUMOR CARCINOIDS

CONTINUED FROM SHEET 8

| OVEREXPRESSED E2F-RESPONSIVE GENES | | GSM16557 | GSM16560 | GSM17327 | GSM17328 | GSM17333 | GSM17340 | GSM17341 | GSM17343 | GSM17344 | GSM17345 | GSM17346 | GSM17348 | GSM17349 | GSM17355 | GSM18306 | GSM18307 | GSM18311 |
|---|---|---|---|---|---|---|---|---|---|---|---|---|---|---|---|---|---|---|
| KNSL1 | KNSL1 | ▨ | | | | | | | | | | | | | | | | |
| PMAIP1 | PMAIP1 | | | | ▨ | | | | ▨ | | | ▨ | | | | | | |
| KPNA2 | KPNA2 | ▨ | | | | | | | | | | | ▨ | ▨ | | | | |
| DNMT1 | DNMT1 | | | | | | | | | | | | | | | | | |
| USP1 | USP1 | | | | | ▨ | | | | | | | ▨ | | ▨ | | | |
| E2F3 | E2F3 | | | ▨ | | ▨ | ▨ | ▨ | ▨ | ▨ | ▨ | ▨ | | | | | | |
| KNSL6 | KNSL6 | | | | | | | | | | | | | | | | | |
| RFC2 | RFC2 | ▨ | | | | | | | | | | | | | | | | |
| BUB3 | BUB3 | ▨ | | | | | | | | | | | | | | | | |
| UBE2C | UBch10 | ▨ | | | | | | | | | | | ▨ | | ▨ | | | |
| HMGB3 | HMG4 | | | | ▨ | ▨ | | | | | | | | | ▨ | | | |
| MCM6 | MCM6 | | | | | | | | | | ▨ | | | | | | | |
| CDC45L | CDC45L | | | | | ▨ | ▨ | | | | | | ▨ | | | | | |
| CKS2 | CKS2 | ▨ | | | | | | | | | | | | | ▨ | | | |
| NUP155 | NUP155 | | | | | | ▨ | | | | | ▨ | ▨ | | ▨ | | | |
| POLE2 | POLE2 | ▨ | | | | | | | | | | | | | | | | |
| DCK | DCK | | | | | | ▨ | | | | | | | | ▨ | | ▨ | |
| VRK1 | VRK1 | | | | | | | | | | | | | | | | | ▨ |
| SFRS2 | SFRS2 | | | ▨ | | ▨ | | | | | | | | | | | | |
| RAD51 | RAD51 | ▨ | | | | ▨ | | | ▨ | | | | | | ▨ | | | |
| BUB1 | BUB1 | ▨ | | | | | | | | | | | | | | | | |
| MELK | KIAA0175 | ▨ | | | | | | | | | | | ▨ | | ▨ | | | |
| PRIM2A | PRIM2A | | | ▨ | ▨ | | ▨ | | | | | ▨ | | | | | | |
| BRCA1 | BRCA1 | | | | | | | | | | | | | | | | | ▨ |
| FEN1 | FEN1 | | | | | | | | | | | | | | | | | |
| CSTF1 | CSTF1 | ▨ | | | | | | | | | | | | | | | | |
| TP53BP2 | TP53BP2 | | | | | | | | | | | | | ▨ | | | | |

END OF COLUMN

CONTINUED ON SHEET 12

FIG. 14I

PCA ERGO TUMOR LARGE CELL
NEUROENDOCRINE TUMOR CARCINOIDS

| | | GSM17315 | GSM17316 | GSM17317 | GSM17318 | GSM17319 | GSM17320 | GSM17321 | GSM17322 | GSM17324 | GSM17325 | GSM17326 | |
|---|---|---|---|---|---|---|---|---|---|---|---|---|---|
| STMN1 | STMN1 | | | | | | | | | | | | 24 |
| TOP2A | TOP2A | | | | | | | | | | | | 22 |
| BCL2 | BCL2 | | | | | | | | | | | | 19 |
| UNG | UNG | | | | | | | | | | | | 19 |
| PCNA | PCNA | | | | | | | | | | | | 17 |
| SMC2L1 | SMC2L1 | | | | | | | | | | | | 17 |
| CENPF | CENPF | | | | | | | | | | | | 17 |
| CDKN2C | CDKN2C | | | | | | | | | | | | 16 |
| LHX2 | LHX2 | | | | | | | | | | | | 16 |
| TMPO | TMPO | | | | | | | | | | | | 16 |
| RFC4 | RFC4 | | | | | | | | | | | | 16 |
| DEK | DEK | | | | | | | | | | | | 16 |
| TIMELESS | TIMELESS | | | | | | | | | | | | 16 |
| MAD2L1 | MAD2L1 | | | | | | | | | | | | 15 |
| HSPC150 | HSPC150 | | | | | | | | | | | | 15 |
| ADPRT | ADPRT | | | | | | | | | | | | 14 |
| C20orf1 | C20orf1 | | | | | | | | | | | | 14 |
| ECT2 | ECT2 | | | | | | | | | | | | 14 |
| PTTG1 | PTTG1 | | | | | | | | | | | | 13 |
| PLK4** | STK18 | | | | | | | | | | | | 13 |
| TTK | TTK | | | | | | | | | | | | 13 |
| SFPQ | SFPQ | | | | | | | | | | | | 13 |
| CDC25B | CDC25B | | | | | | | | | | | | 13 |
| CBX3 | CBX3 | | | | | | | | | | | | 13 |
| RAD51C | RAD51C | | | | | | | | | | | | 13 |
| TYMS | TYMS | | | | | | | | | | | | 12 |
| CDC2 | CDC2 | | | | | | | | | | | | 12 |
| AURKB* | STK12 | | | | | | | | | | | | 12 |
| TOPBP1 | TOPBP1 | | | | | | | | | | | | 12 |
| MYB | MYB | | | | | | | | | | | | 11 |
| MCM7 | MCM7 | | | | | | | | | | | | 11 |

OVEREXPRESSED E2F-RESPONSIVE GENES

END OF ROW

CONTINUED ON SHEET 11

FIG. 14J

PCA ERGO TUMOR LARGE CELL
NEUROENDOCRINE TUMOR CARCINOIDS
CONTINUED FROM SHEET 10

| OVEREXPRESSED E2F-RESPONSIVE GENES | | GSM17315 | GSM17316 | GSM17317 | GSM17318 | GSM17319 | GSM17320 | GSM17321 | GSM17322 | GSM17324 | GSM17325 | GSM17326 | END OF ROW |
|---|---|---|---|---|---|---|---|---|---|---|---|---|---|
| BARD1 | BARD1 | | | | ▨ | | ▨ | ▨ | ▨ | ▨ | ▨ | | 11 |
| CHAF1A | CHAF1A | | | | | | | ▨ | | | | | 11 |
| NPAT | NPAT | | | | | ░ | | ▨ | | | | | 11 |
| H2AFZ | H2AFZ | | | | ▨ | | ▨ | ▨ | ▨ | | | | 11 |
| SMARCA5 | SMARCA5 | | | ░ | ░ | | ▨ | ░ | ▨ | | | | 11 |
| SSX2IP** | KIAA0923 | | | ░ | ▨ | | | ░ | | | | | 11 |
| RPA2 | RPA2 | | | | | ░ | | ▨ | | | | | 11 |
| RAD54L | RAD54L | | | | ▨ | | ▨ | ▨ | ▨ | ▨ | | | 11 |
| CENPA | CENPA | | ▨ | | ▨ | ▨ | ▨ | ▨ | ▨ | | | | 11 |
| NEK2 | NEK2 | | ▨ | | ▨ | | ▨ | ▨ | | | | | 11 |
| CHAF1B | CHAF1B | | | | ▨ | | ▨ | ▨ | | ▨ | | | 11 |
| HOXA7 | HOXA7 | | | ░ | | ░ | | | | | | | 11 |
| ORC3L | ORC3L | | | | ░ | ▨ | ░ | ░ | ▨ | | | | 11 |
| MCM3 | MCM3 | ▨ | | | ▨ | | ▨ | ▨ | ▨ | ▨ | | | 10 |
| CCNB2 | CCNB2 | | | | | | ▨ | ▨ | ▨ | | | | 10 |
| TCF19 | TCF19 | | | | ▨ | ▨ | | ▨ | | | | | 10 |
| PRC1 | PRC1 | | | | ▨ | | ▨ | ▨ | | | | | 10 |
| BUB1B | BUB1B | | | | | ▨ | ▨ | | ▨ | | | | 10 |
| HMMR | HMMR | ▨ | | | ▨ | | ▨ | | | | | | 10 |
| MTHFD1 | MTHFD1 | | ░ | ░ | | | | ░ | | | | | 10 |
| STK6 | STK15 | ▨ | ▨ | ▨ | ▨ | ▨ | ▨ | ▨ | ▨ | ▨ | | | 10 |
| CDKN3 | CDKN3 | | | | | ▨ | ▨ | ▨ | | | | | 10 |
| SRGAP2 | KIAA0456 | | | ░ | ▨ | | | ▨ | | ▨ | | | 10 |
| CASP8 | CASP8 | | | ░ | ░ | | ▨ | | ▨ | | | | 9 |
| CDK2 | CDK2 | | | | | ▨ | ▨ | | | | | | 9 |
| FLJ10604 | FLJ10604 | | | | ▨ | ▨ | | ▨ | | ▨ | | | 9 |
| MSH2 | MSH2 | | | ░ | ░ | | | | | | | | 9 |
| SMC4L1 | SMC4L1 | ▨ | | | ▨ | | | ▨ | | | | | 9 |
| HMGB1 | HMGB1 | | | | | ░ | | | | | | | 9 |
| CDC7L1 | CDC7L1 | | | | | ▨ | | | | | | | 9 |
| BIRC5 | BIRC5 | ▨ | | ▨ | ▨ | ▨ | ▨ | ▨ | ▨ | ▨ | | | 9 |

CONTINUED ON SHEET 12

FIG. 14K

PCA ERGO TUMOR LARGE CELL
NEUROENDOCRINE TUMOR CARCINOIDS
CONTINUED FROM SHEET 11

| | | GSM17315 | GSM17316 | GSM17317 | GSM17318 | GSM17319 | GSM17320 | GSM17321 | GSM17322 | GSM17324 | GSM17325 | GSM17326 | |
|---|---|---|---|---|---|---|---|---|---|---|---|---|---|
| KNSL1 | KNSL1 | | | | ▨ | | ▨ | ▨ | ▨ | ▨ | ▨ | ▨ | 9 |
| PMAIP1 | PMAIP1 | ▨ | ▦ | ▨ | ▨ | ▨ | ▨ | ▨ | ▨ | | ▨ | | 9 |
| KPNA2 | KPNA2 | ▨ | | ▨ | ▨ | ▨ | | ▨ | ▨ | ▨ | | ▨ | 8 |
| DNMT1 | DNMT1 | | | ▨ | ▨ | ▨ | ▨ | ▨ | | ▨ | ▨ | ▨ | 8 |
| USP1 | USP1 | | | ▨ | ▨ | ▨ | | ▨ | ▨ | ▨ | ▨ | ▨ | 8 |
| E2F3 | E2F3 | ▨ | ▨ | ▨ | ▨ | ▨ | ▨ | ▨ | | | | ▨ | 8 |
| KNSL6 | KNSL6 | | | ▨ | ▨ | ▨ | | ▨ | ▨ | ▨ | ▨ | ▨ | 8 |
| RFC2 | RFC2 | | | ▨ | ▨ | ▨ | ▨ | ▨ | ▨ | ▨ | | ▨ | 8 |
| BUB3 | BUB3 | | | | ▦ | ▨ | ▦ | ▨ | ▦ | ▨ | ▨ | ▨ | 8 |
| UBE2C | UBch10 | ▨ | ▨ | ▨ | ▨ | ▨ | ▨ | ▨ | | | ▨ | | 8 |
| HMGB3 | HMG4 | ▨ | | ▨ | ▨ | ▨ | | ▨ | ▨ | | ▨ | | 7 |
| MCM6 | MCM6 | | | ▨ | ▨ | ▨ | | ▨ | | ▨ | ▨ | ▨ | 7 |
| CDC45L | CDC45L | ▨ | | ▨ | ▨ | ▨ | | ▨ | | ▨ | | ▨ | 7 |
| CKS2 | CKS2 | ▨ | | ▨ | ▨ | | ▨ | ▨ | | ▨ | | ▨ | 7 |
| NUP155 | NUP155 | ▨ | | ▨ | | ▨ | ▨ | ▨ | | ▨ | ▨ | | 7 |
| POLE2 | POLE2 | ▨ | | | ▨ | ▨ | | ▨ | ▨ | | ▨ | ▨ | 7 |
| DCK | DCK | | | ▨ | | ▨ | | ▨ | | ▨ | ▨ | ▨ | 6 |
| VRK1 | VRK1 | | | ▨ | ▨ | ▨ | | ▨ | | ▨ | | ▨ | 6 |
| SFRS2 | SFRS2 | ▨ | ▦ | ▨ | | ▨ | ▨ | | | ▨ | | ▨ | 6 |
| RAD51 | RAD51 | ▨ | | ▨ | ▨ | ▨ | | | | ▨ | | | 5 |
| BUB1 | BUB1 | ▨ | | ▨ | ▨ | | | ▨ | | | | ▨ | 5 |
| MELK | KIAA0175 | ▨ | ▨ | ▨ | | ▨ | | | | ▨ | | ▨ | 5 |
| PRIM2A | PRIM2A | ▨ | | ▨ | | | | ▨ | | ▨ | | ▨ | 5 |
| BRCA1 | BRCA1 | ▨ | | | ▨ | | ▨ | | | ▨ | | ▨ | 5 |
| FEN1 | FEN1 | | | ▨ | | | ▨ | | | | ▨ | | 3 |
| CSTF1 | CSTF1 | | | ▨ | | | | ▨ | | ▨ | | | 3 |
| TP53BP2 | TP53BP2 | ▨ | | ▨ | | ▨ | ▨ | | | ▨ | | | 3 |

OVEREXPRESSED E2F-RESPONSIVE GENES

END OF ROW

END OF COLUMN

FIG. 14L

THYROID 25

| Gene | Value |
|---|---|
| PBK | 7 |
| CKS2 | 7 |
| CDC6 | 7 |
| BUB1 | 7 |
| TK1 | 7 |
| ASF1B/FLJ10604 | 7 |
| BRCA1 | 7 |
| CCNB2 | 6 |
| SERPINE1 | 6 |
| LMNB1 | 6 |
| ANLN | 6 |
| CENPF | 6 |
| CCNF | 6 |
| CDC45L | 6 |
| AURKB | 6 |
| PLAU | 6 |
| CCNA2 | 5 |
| MAD2L1 | 5 |
| PLK1 | 5 |
| MCM2 | 5 |
| KIF2C/KNSL6 | 5 |
| TTK | 5 |
| CENPE | 5 |
| CENPA | 5 |
| AURKA/STK15 | 5 |
| INHBA | 5 |
| TPX2/C20ORF1 | 5 |
| NUSAP1/BM037 | 5 |
| STMN1 | 5 |
| BUB1B | 5 |
| MKI67 | 5 |
| HMMR | 5 |
| CCND1 | 5 |
| MYC | 4 |
| KIFC1/KNSL2 | 4 |
| UHRF1/ICBP90 | 4 |
| CDC25C | 4 |
| E2F1 | 4 |
| MTHFD1L | 4 |
| HIST1H2BF | 4 |

| Gene | Value |
|---|---|
| SPHK1 | 4 |
| UNG | 4 |
| NDC80/HEC | 3 |
| GCH1 | 3 |
| TYMS | 3 |
| CDCA4/FLJ20764 | 3 |
| MCM6 | 3 |
| CDKN3 | 3 |
| KIF11/KNSL1 | 3 |
| CDC25B | 3 |
| HIST1H2BN | 3 |
| FST | 3 |
| RPA1 | 3 |
| BACH1 | 3 |
| RRM1 | 2 |
| PLK2/SNK | 2 |
| BLM | 2 |
| TIMELESS | 2 |
| CHEK1 | 2 |
| SMC4 | 2 |
| GEM | 2 |
| RECQL | 2 |
| UBE2C/UBCH10 | 2 |
| ARHGAP4 | 2 |
| SRGAP2 | 2 |
| H2AFX | 2 |
| MMP16 | 2 |
| RRM2 | 2 |
| ADAMTS1 | 2 |
| HRK | 2 |
| EGR1 | 2 |
| TGFB3 | 2 |
| SERPINF2 | 2 |

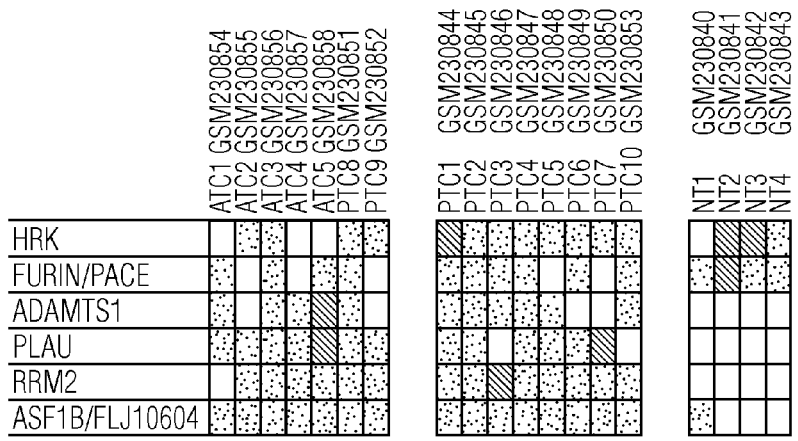
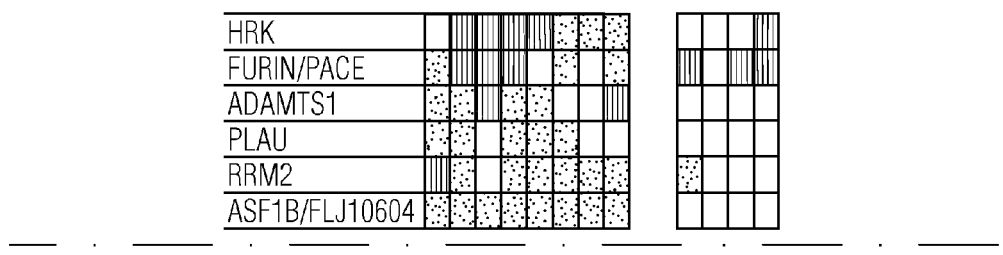
FIG. 16F

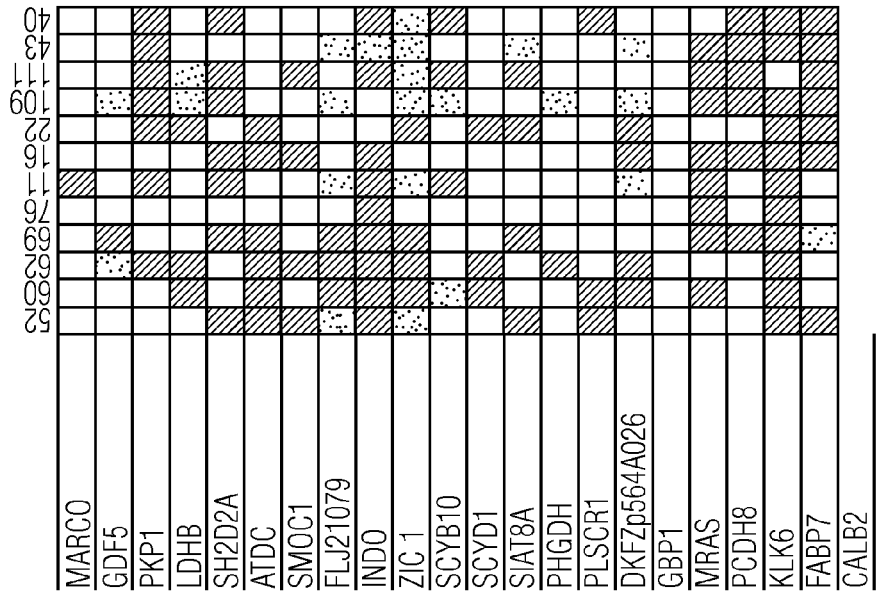
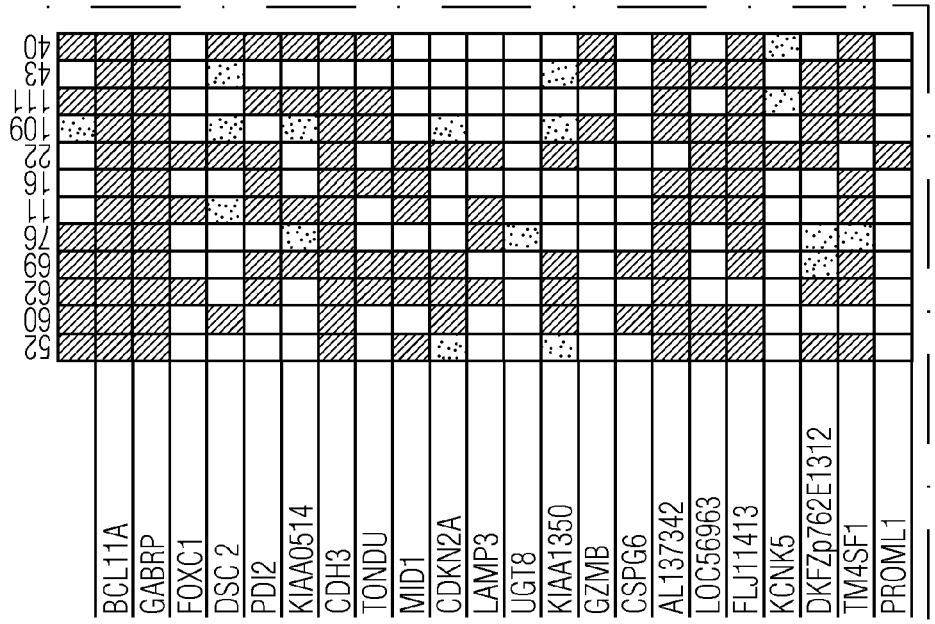
FIG. 18H

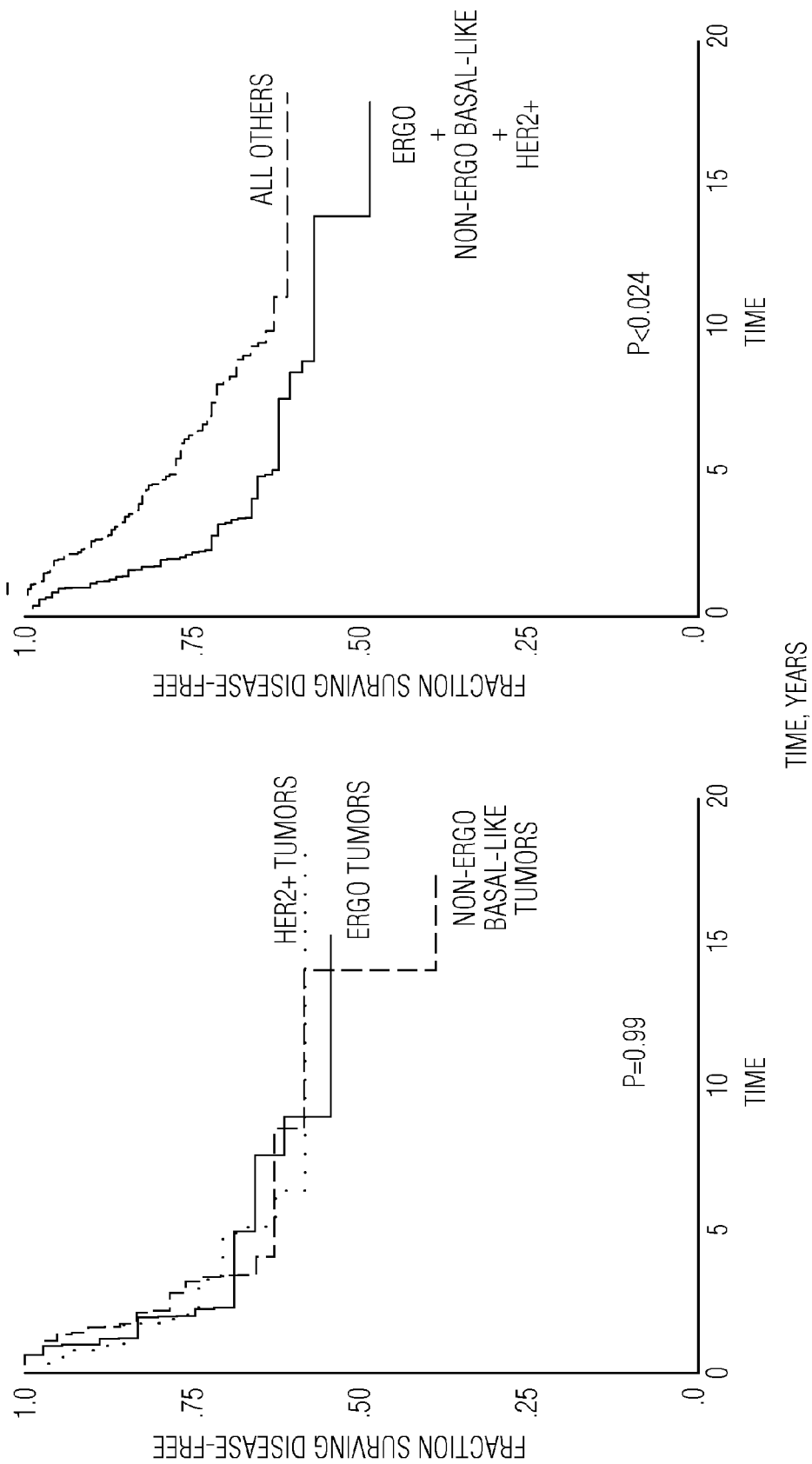

Primary Prostate Cancer (GG:=Gleason Grade) — Transitional PCA Pattern (white)

| Sample | GG | NDC80 | RAD52 | SNAPC1 | TOPBP1 | CHAF1A | PAWR | MELK | PBX3 | BMP2 | KPNA2 | MCM7 | POLA2 | HSP90B1 | RECQL5 | CFLAR | LHX2 | DBF4 | UMPS | STMN1 | HMGB1 | ACOX1 | EGR1 | NEK2 | CASP3 | PRG4 | RPA3 | CENPE | HIST1H2AC | CBX5 | E2F2 | RAD51 | BBC3 | GCH1 | CASP8 | MCL1 | SLPI | PPP1R13B | PRIM1 |
|---|---|---|---|---|---|---|---|---|---|---|---|---|---|---|---|---|---|---|---|---|---|---|---|---|---|---|---|---|---|---|---|---|---|---|---|---|---|---|---|
| GSM152943 | GG:7 | | | | | | | | | | | | | | | | | | | | | | | | | | | | | | | | | | | | | | |
| GSM152977 | GG:7 | | | | | | | | | | | | | | | | | | | | | | | | | | | | | | | | | | | | | | |
| GSM152957 | GG:9 | | | | | | | | | | | | | | | | | | | | | | | | | | | | | | | | | | | | | | |
| GSM152959 | GG:9 | | | | | | | | | | | | | | | | | | | | | | | | | | | | | | | | | | | | | | |
| GSM152982 | GG:9 | | | | | | | | | | | | | | | | | | | | | | | | | | | | | | | | | | | | | | |
| GSM152968 | GG:8 | | | | | | | | | | | | | | | | | | | | | | | | | | | | | | | | | | | | | | |
| GSM152962 | GG:8 | | | | | | | | | | | | | | | | | | | | | | | | | | | | | | | | | | | | | | |
| GSM187536 | GG:7 | | | | | | | | | | | | | | | | | | | | | | | | | | | | | | | | | | | | | | |
| GSM152937 | GG:7 | | | | | | | | | | | | | | | | | | | | | | | | | | | | | | | | | | | | | | |
| GSM152954 | GG:7 | | | | | | | | | | | | | | | | | | | | | | | | | | | | | | | | | | | | | | |
| GSM152972 | GG:7 | | | | | | | | | | | | | | | | | | | | | | | | | | | | | | | | | | | | | | |
| GSM152983 | GG:7 | | | | | | | | | | | | | | | | | | | | | | | | | | | | | | | | | | | | | | |
| GSM152986 | GG:7 | | | | | | | | | | | | | | | | | | | | | | | | | | | | | | | | | | | | | | |
| GSM152934 | GG:6 | | | | | | | | | | | | | | | | | | | | | | | | | | | | | | | | | | | | | | |
| GSM152945 | GG:6 | | | | | | | | | | | | | | | | | | | | | | | | | | | | | | | | | | | | | | |
| GSM152981 | GG:6 | | | | | | | | | | | | | | | | | | | | | | | | | | | | | | | | | | | | | | |

FROM SHEET 21 RIGHT COLUMN — CONTINUED ON THIS SHEET RIGHT COLUMN — CONTINUED ON SHEET 23

FIG. 20W

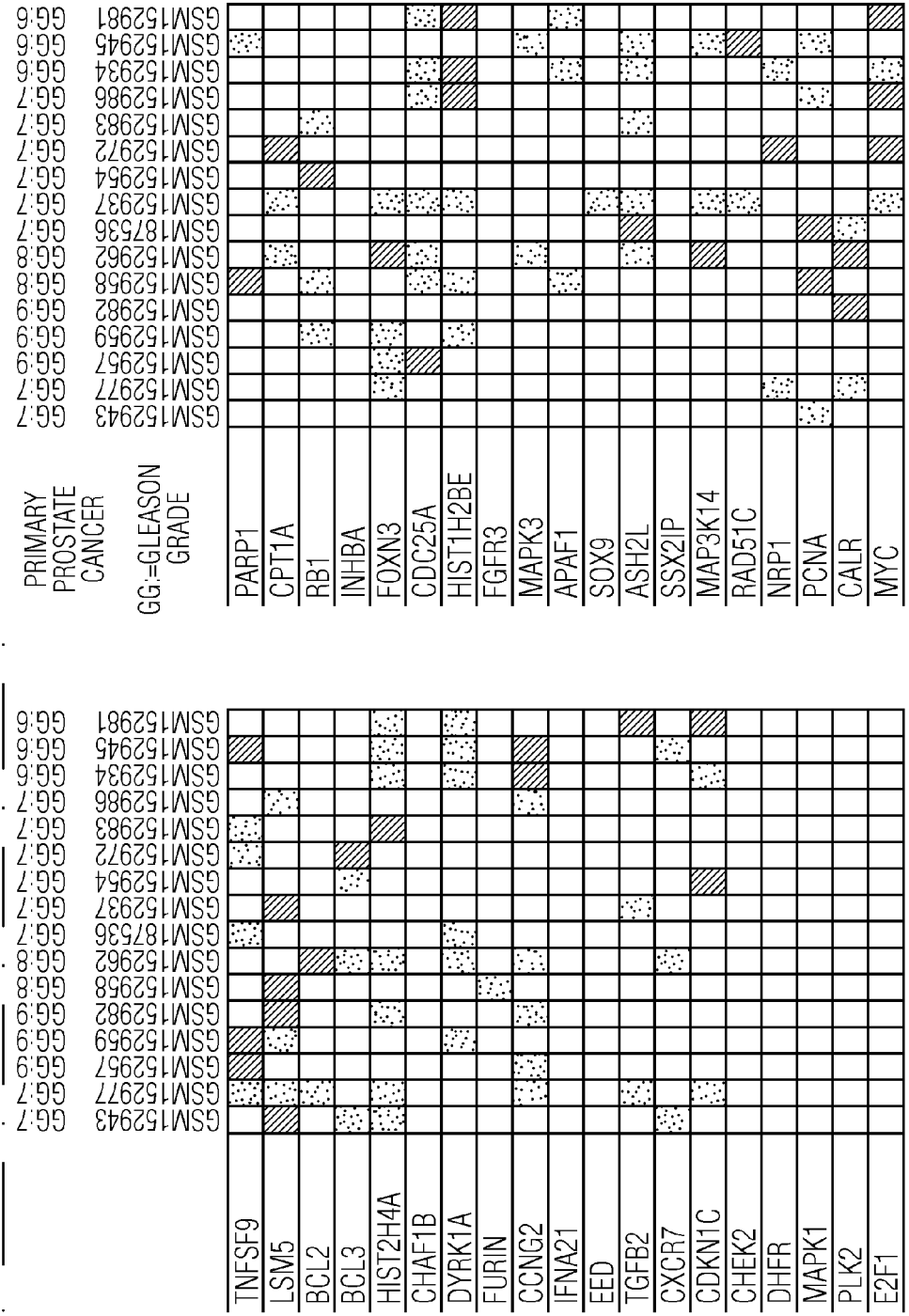

PRIMARY PROSTATE CANCER — NON-AGGRESIVE PCA PATTERN (GREEN)

| Sample | GG | BAD | CDK2 | PLSCR1 | GADD45B | MCM5 | MCM2 | MAPK4 | CBFB | PRPS1 | MAPK9 | HRK | MCM6 | CCNF | CKS1B | BACH1 | ORC3L | MAP2K1 | MAP2K2 | DEK |
|---|---|---|---|---|---|---|---|---|---|---|---|---|---|---|---|---|---|---|---|---|
| GSM1529970 | GG:9 | ▨ | ▨ | | | | | | | | | | | | | | | | | ▒ |
| GSM1529975 | GG:9 | | | | | | | | | | | ▒ | | | | | | | | |
| GSM1529988 | GG:9 | | | | | | | | | | ▨ | ▒ | | | ▒ | | | | | |
| GSM1529990 | GG:9 | | | | | | | | | | ▨ | ▒ | | | ▒ | | | | | |
| GSM1529966 | GG:8 | | | | | | | | | | | | | | | | | | | ▒ |
| GSM1529942 | GG:8 | | | | | | | | | | | | | ▒ | | | | | | |
| GSM1529935 | GG:7 | | | | | | | | | | | | | | ▒ | | | | | |
| GSM1529938 | GG:7 | | | | | | | | | | | | | ▒ | | | | | | |
| GSM1529949 | GG:7 | | | | | | | | | | | | | | | | | | | |
| GSM1529950 | GG:7 | | | | | | | | | | | | | | | | | | | |
| GSM1529951 | GG:7 | | | | | | | | | ▒ | | | ▒ | | | | | | | |
| GSM1529952 | GG:7 | ▨ | | | | | | | | | | | | | | | | | | |
| GSM1529953 | GG:7 | | | | | | | | | | | | | ▨ | | | | | | |
| GSM1529955 | GG:7 | | | | | | | | | | | | | | ▒ | | | | | |
| GSM1529963 | GG:7 | | | | | | | | | | | | | | ▒ | | | | | |
| GSM1529965 | GG:7 | | | | | | | | | | | | | | | | | | | |
| GSM1529971 | GG:7 | | | | | | | | | | | | | | | | | | | |
| GSM1529974 | GG:7 | | | | | | | | | | | ▒ | | | | | | | | |
| GSM1529979 | GG:7 | | | | | | | ▨ | | | | | | | | | | | | |
| GSM1529980 | GG:7 | | | | | | | | | | | | | | | | | ▨ | | |
| GSM1529991 | GG:7 | | | ▨ | | | | | | | | | | | ▒ | | | | | |
| GSM1529967 | GG:6 | | | | | | | | | | | | | | | | | | | |
| GSM1529968 | GG:6 | | | | | | | | | | ▒ | | | | | | | | | |
| GSM1529939 | GG:6 | | | | | | | | | | ▒ | | | | | | | | | |
| GSM1529933 | GG:6 | | | | | | | | | | | | | | | | | | | |
| GSM1529944 | GG:6 | | | | | | | | | | | | | | | | | | | |
| GSM1529946 | GG:6 | | | ▨ | | | | | | | ▨ | | | | | | | | | |
| GSM1529948 | GG:6 | | | | | ▨ | | | | | ▒ | | | | | | | | | |
| GSM1529969 | GG:6 | | | | | | | | | | | ▨ | | | | | | | | |
| GSM1529978 | GG:6 | | | ▨ | | | ▒ | ▨ | | | ▒ | | | | | | ▨ | | | |
| GSM1529932 | GG:5 | | | | | | ▒ | | | | ▒ | | | | | | | | | |
| GSM1529956 | GG:5 | | | | | | | ▨ | | | ▒ | | | | | | | | | |

FROM SHEET 35 — END OF ROW — CONTINUED ON SHEET 37

FIG. 20KK

| | GEM | MTHFD1 | YY1 | HIST1H3E | CSRP2 | MAF |
|---|---|---|---|---|---|---|
| GSM152970 GG:9 | | | | | | |
| GSM152975 GG:9 | | | | | | |
| GSM152988 GG:9 | | | | | | |
| GSM152990 GG:9 | | | | | | |
| GSM152966 GG:8 | | | | | | |
| GSM152942 GG:8 | | | | | | |
| GSM152935 GG:7 | | | | | | |
| GSM152938 GG:7 | | | | | | |
| GSM152949 GG:7 | | | | | | |
| GSM152950 GG:7 | | | | | | |
| GSM152951 GG:7 | | | | | | |
| GSM152952 GG:7 | | | | | | |
| GSM152953 GG:7 | | | | | | |
| GSM152955 GG:7 | | | | | | |
| GSM152963 GG:7 | | | | | ▨ | |
| GSM152965 GG:7 | | | | | | |
| GSM152971 GG:7 | | | | | | |
| GSM152974 GG:7 | | | | | | |
| GSM152979 GG:7 | | | | | | |
| GSM152980 GG:7 | | | | | | |
| GSM152991 GG:7 | | | | | | |
| GSM152967 GG:6 | | | | | | |
| GSM152968 GG:6 | | | | | | |
| GSM152939 GG:6 | | | | | | |
| GSM152933 GG:6 | | | | | ▨ | |
| GSM152944 GG:6 | | | ░ | | | |
| GSM152946 GG:6 | | | | | | |
| GSM152948 GG:6 | | | | | | |
| GSM152969 GG:6 | | | | | | |
| GSM152978 GG:6 | | | | | | |
| GSM152932 GG:5 | | | | | | |
| GSM152956 GG:5 | | | | | ░ | ░ |

PRIMARY PROSTATE CANCER — NON-AGGRESIVE PCA PATTERN (GREEN)

FROM SHEET 36

END OF ROW
END OF COLUMN

| | NFP:1 | NFP:2 | NFP:3 | NFP:4 | NFP:5 | NFP:6 | NFP:7 | NFP:8 | NFP:11 | NFP:12 | NFP:10 | NFP:9 | NFP:1 | NFP:2 | NFP:3 | NFP:4 | NFP:5 | NFP:6 | NFP:7 | NFP:8 | NFP:11 | NFP:10 | |
|---|---|---|---|---|---|---|---|---|---|---|---|---|---|---|---|---|---|---|---|---|---|---|---|
| | GSM277788 | GSM277789 | GSM277790 | GSM277791 | GSM277792 | GSM277793 | GSM277794 | GSM277795 | GSM277798 | GSM277799 | GSM277797 | GSM277796 | GSM277788 | GSM277789 | GSM277790 | GSM277791 | GSM277792 | GSM277793 | GSM277794 | GSM277795 | GSM277798 | GSM277799 | GSM277797 | |
| | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | BM:538INSC | |
| CDC7 | | | | | | | | | | | | | | | | | | | | | | | | 9 |
| PARP1 | | | | | | | | | | | | | | | | | | | | | | | | 9 |
| ORC6L | | | | | | | | | | | | | | | | | | | | | | | | 8 |
| CDK2 | | | | | | | | | | | | | | | | | | | | | | | | 8 |
| RFC3 | | | | | | | | | | | | | | | | | | | | | | | | 8 |
| PRIM1 | | | | | | | | | | | | | | | | | | | | | | | | 8 |
| RAD51 | | | | | | | | | | | | | | | | | | | | | | | | 8 |
| TMPO | | | | | | | | | | | | | | | | | | | | | | | | 8 |
| CHAF1A | | | | | | | | | | | | | | | | | | | | | | | | 8 |
| CDCA7L | | | | | | | | | | | | | | | | | | | | | | | | 8 |
| MCM6 | | | | | | | | | | | | | | | | | | | | | | | | 8 |
| DNMT1 | | | | | | | | | | | | | | | | | | | | | | | | 8 |
| DNA2L | | | | | | | | | | | | | | | | | | | | | | | | 8 |
| PLK4 | | | | | | | | | | | | | | | | | | | | | | | | 8 |
| NUP107 | | | | | | | | | | | | | | | | | | | | | | | | 8 |
| RFC2 | | | | | | | | | | | | | | | | | | | | | | | | 8 |
| RAD54L | | | | | | | | | | | | | | | | | | | | | | | | 8 |
| KIF4A | | | | | | | | | | | | | | | | | | | | | | | | 8 |
| MRE11A | | | | | | | | | | | | | | | | | | | | | | | | 8 |
| CENPH | | | | | | | | | | | | | | | | | | | | | | | | 8 |
| MPHOSPH1 | | | | | | | | | | | | | | | | | | | | | | | | 8 |
| CXCR7 | | | | | | | | | | | | | | | | | | | | | | | | 7 |
| SLBP | | | | | | | | | | | | | | | | | | | | | | | | 7 |
| VRK1 | | | | | | | | | | | | | | | | | | | | | | | | 7 |
| CDC6 | | | | | | | | | | | | | | | | | | | | | | | | 7 |
| CENPK | | | | | | | | | | | | | | | | | | | | | | | | 7 |

CONTINUED ON SHEET 6

| | GSM277788 BM:538INSC NFP:1 | GSM277789 BM:538INSC NFP:2 | GSM277790 BM:538INSC NFP:3 | GSM277791 BM:538INSC NFP:4 | GSM277792 BM:538INSC NFP:5 | GSM277793 BM:538INSC NFP:6 | GSM277794 BM:538INSC NFP:7 | GSM277795 BM:538INSC NFP:8 | GSM277798 BM:538INSC NFP:11 | GSM277799 BM:538INSC NFP:12 | GSM277797 BM:538INSC NFP:10 | GSM277796 BM:538INSC NFP:9 | GSM277788 BM:538INSC NFP:1 | GSM277789 BM:538INSC NFP:2 | GSM277790 BM:538INSC NFP:3 | GSM277791 BM:538INSC NFP:4 | GSM277792 BM:538INSC NFP:5 | GSM277793 BM:538INSC NFP:6 | GSM277794 BM:538INSC NFP:7 | GSM277795 BM:538INSC NFP:8 | GSM277798 BM:538INSC NFP:11 | GSM277799 BM:538INSC NFP:12 | GSM277797 BM:538INSC NFP:10 | |
|---|---|---|---|---|---|---|---|---|---|---|---|---|---|---|---|---|---|---|---|---|---|---|---|---|
| GADD45A | | | | | | | | | | | | | | | | | | | | | | | | 1 |
| TNFSF9 | | | | | | | | | | | | | | | | | | | | | | | | 1 |
| FGF2 | | | | | | | | | | | | | | | | | | | | | | | | 1 |
| SRGAP2 | | | | | | | | | | | | | | | | | | | | | | | | 1 |
| DIP | | | | | | | | | | | | | | | | | | | | | | | | 1 |
| SIVA1 | | | | | | | | | | | | | | | | | | | | | | | | 1 |
| DIABLO | | | | | | | | | | | | | | | | | | | | | | | | 1 |
| FOXO1A | | | | | | | | | | | | | | | | | | | | | | | | 1 |
| RB1 | | | | | | | | | | | | | | | | | | | | | | | | 0 |
| SKP2 | | | | | | | | | | | | | | | | | | | | | | | | 0 |
| PLSCR1 | | | | | | | | | | | | | | | | | | | | | | | | 0 |
| FGFR2 | | | | | | | | | | | | | | | | | | | | | | | | 0 |
| TGFB2 | | | | | | | | | | | | | | | | | | | | | | | | 0 |
| INMT | | | | | | | | | | | | | | | | | | | | | | | | 0 |
| BCL2L11 | | | | | | | | | | | | | | | | | | | | | | | | 0 |
| CDKN2C | | | | | | | | | | | | | | | | | | | | | | | | 0 |
| MYC | | | | | | | | | | | | | | | | | | | | | | | | 0 |
| MAP3K5 | | | | | | | | | | | | | | | | | | | | | | | | 0 |
| BMP2 | | | | | | | | | | | | | | | | | | | | | | | | 0 |
| MAPK3 | | | | | | | | | | | | | | | | | | | | | | | | 0 |
| MAPK4 | | | | | | | | | | | | | | | | | | | | | | | | 0 |
| MAP2K2 | | | | | | | | | | | | | | | | | | | | | | | | 0 |
| FOXO3A | | | | | | | | | | | | | | | | | | | | | | | | 0 |
| BCL2 | | | | | | | | | | | | | | | | | | | | | | | | 0 |
| CCND3 | | | | | | | | | | | | | | | | | | | | | | | | 0 |
| CHES1 | | | | | | | | | | | | | | | | | | | | | | | | 0 |

CONTINUED ON SHEET 12

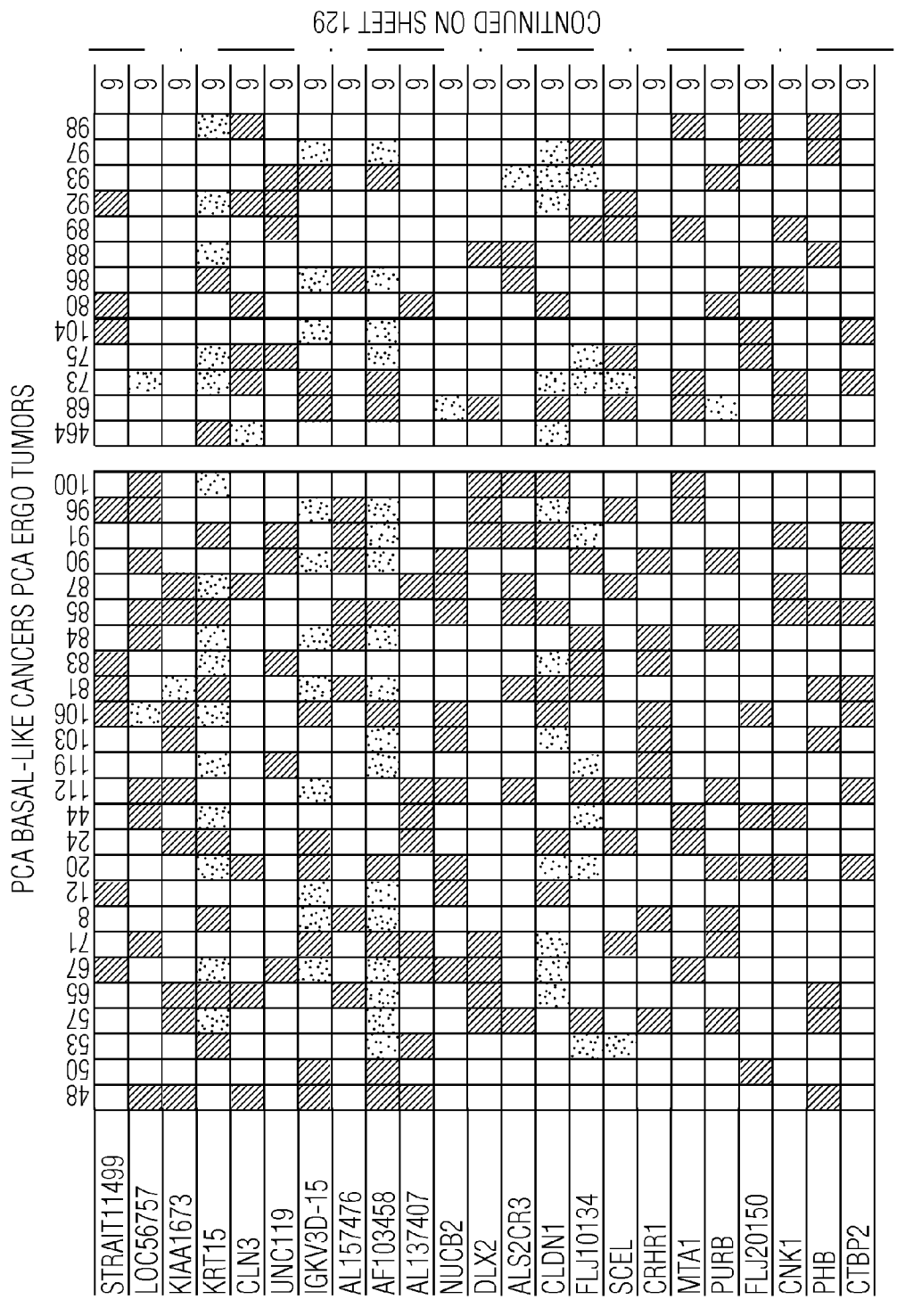
FIG. 2400

FIG. 24XX

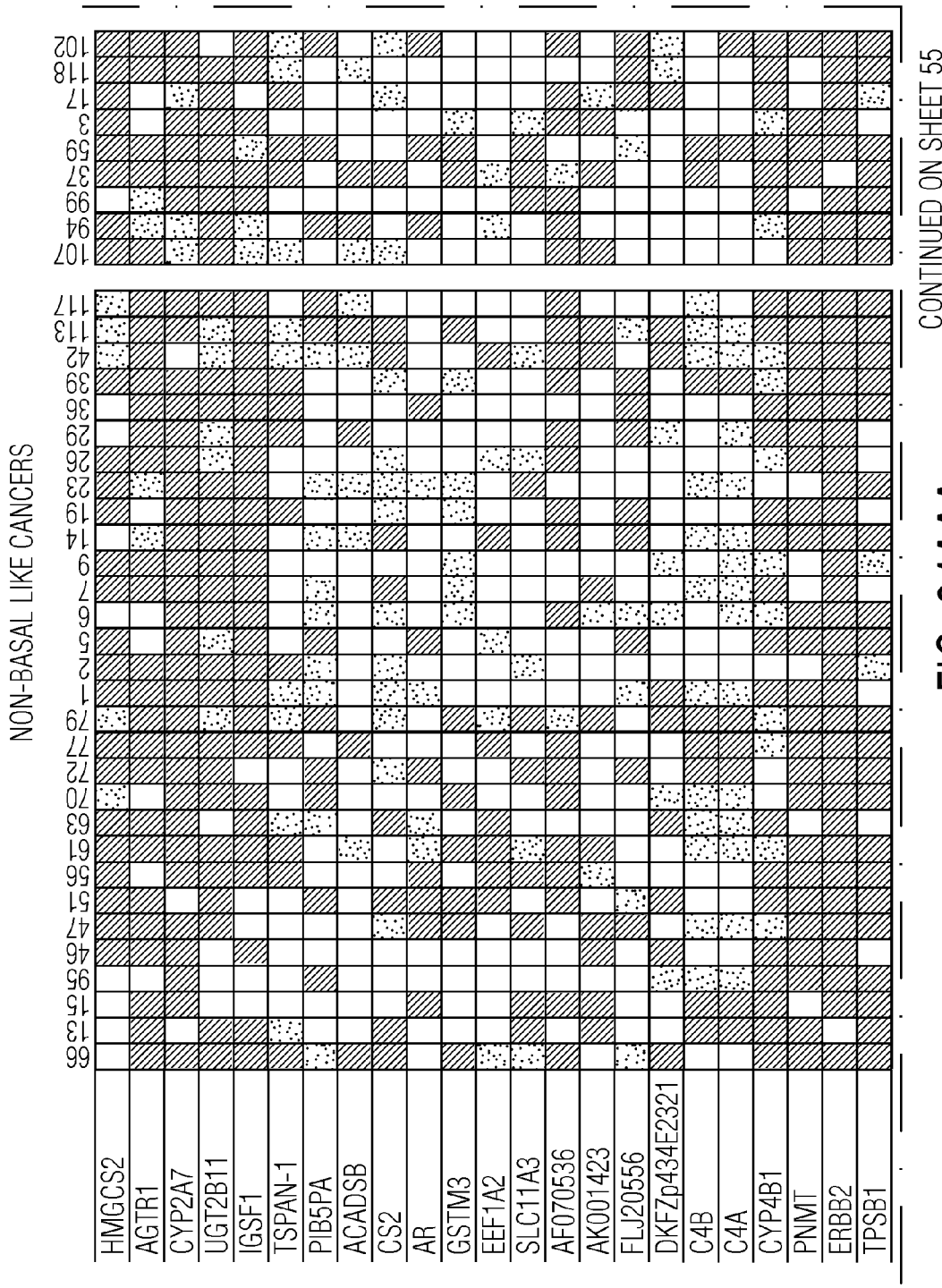
FIG. 24AAAA

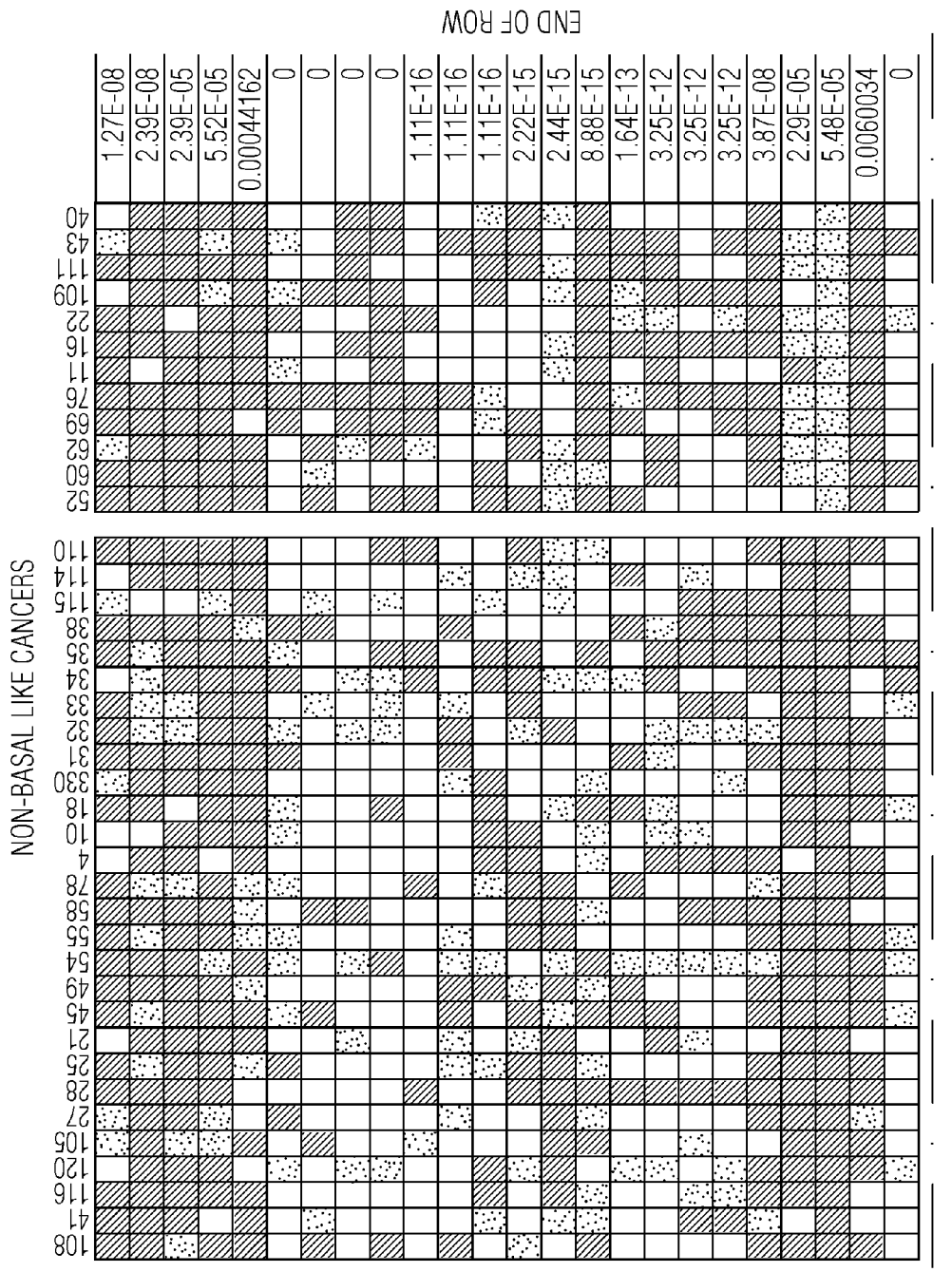
FIG. 24BBB

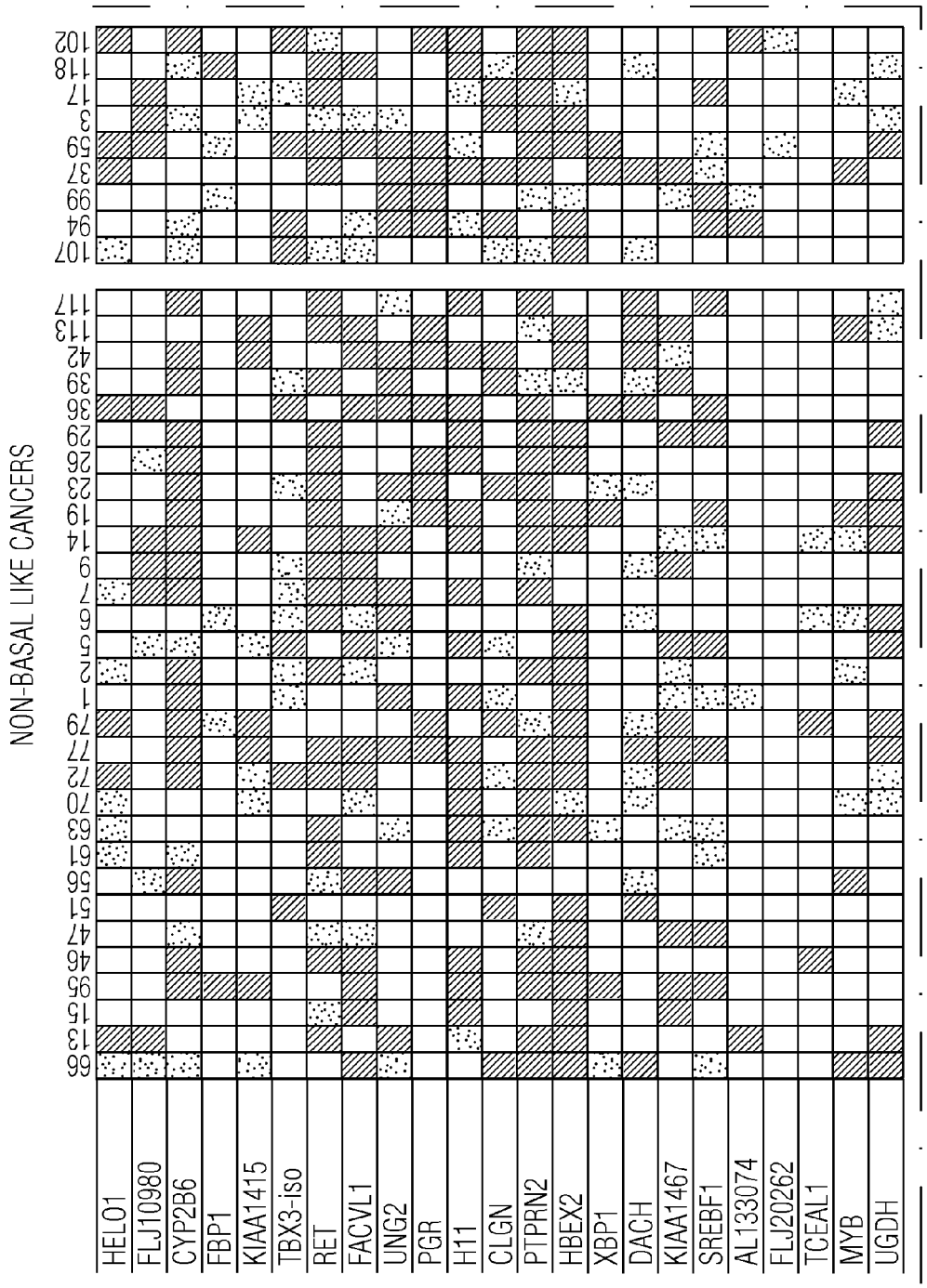
FIG. 24CCC

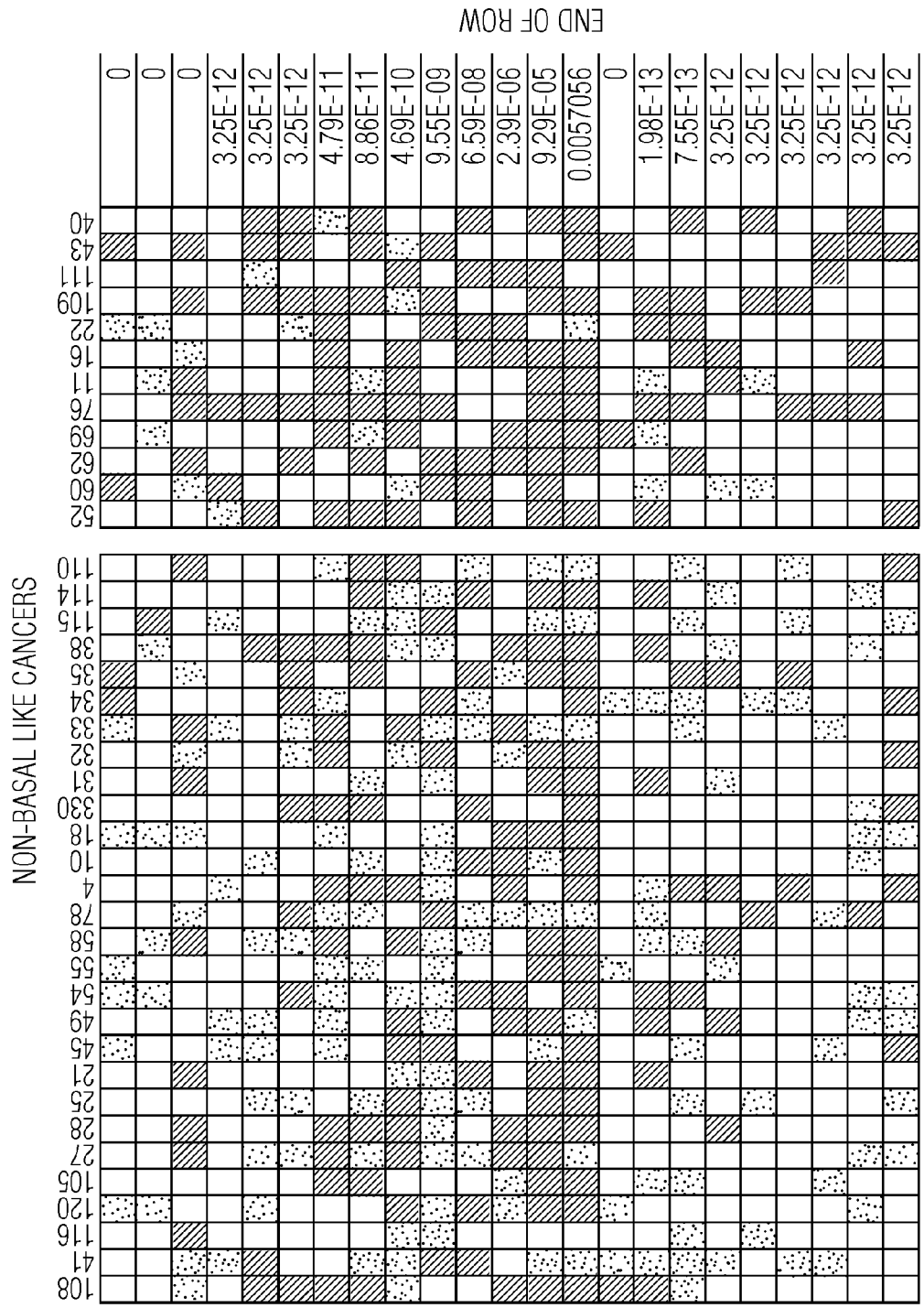
FIG. 24DDD

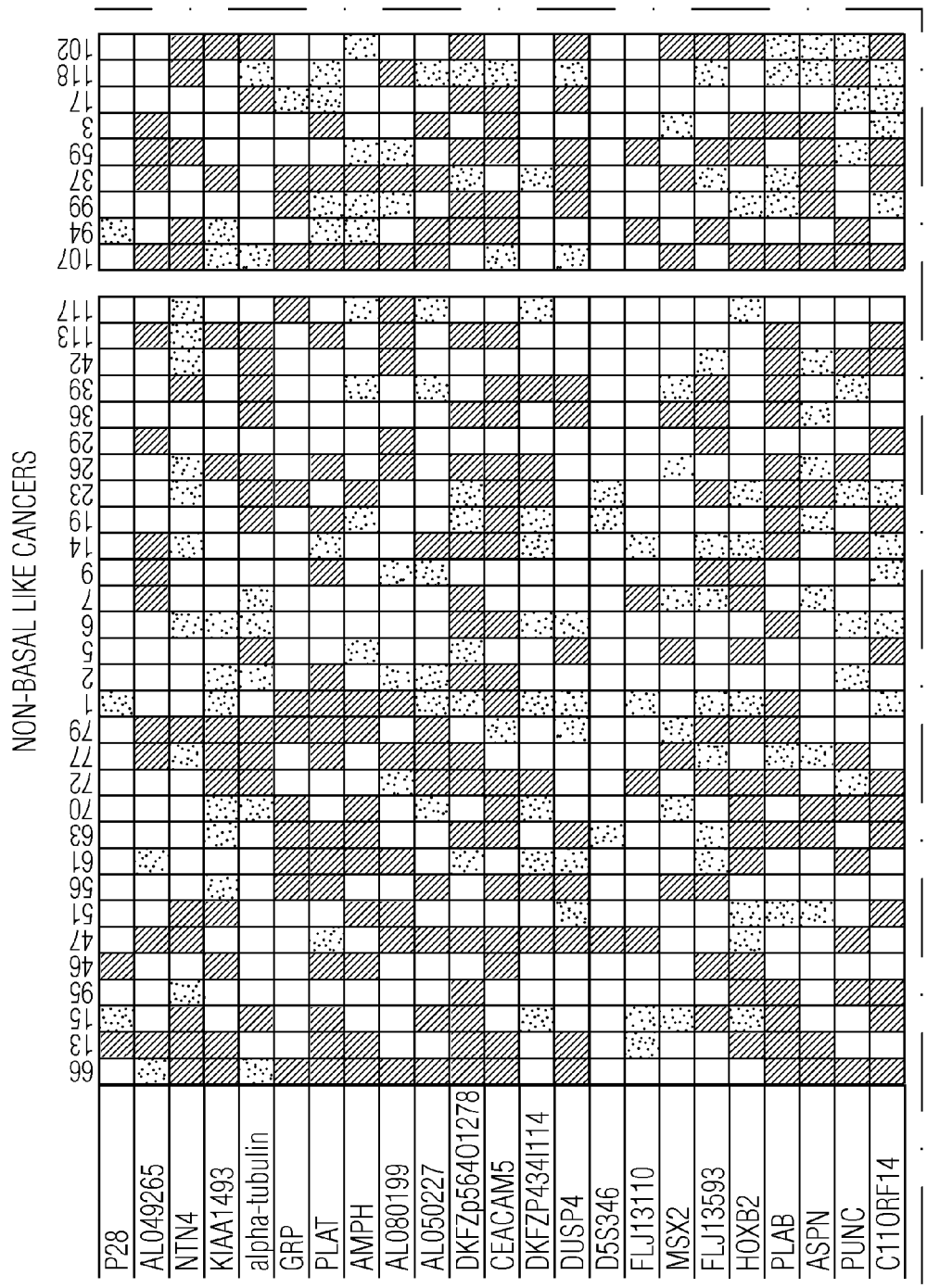
FIG. 24EEE

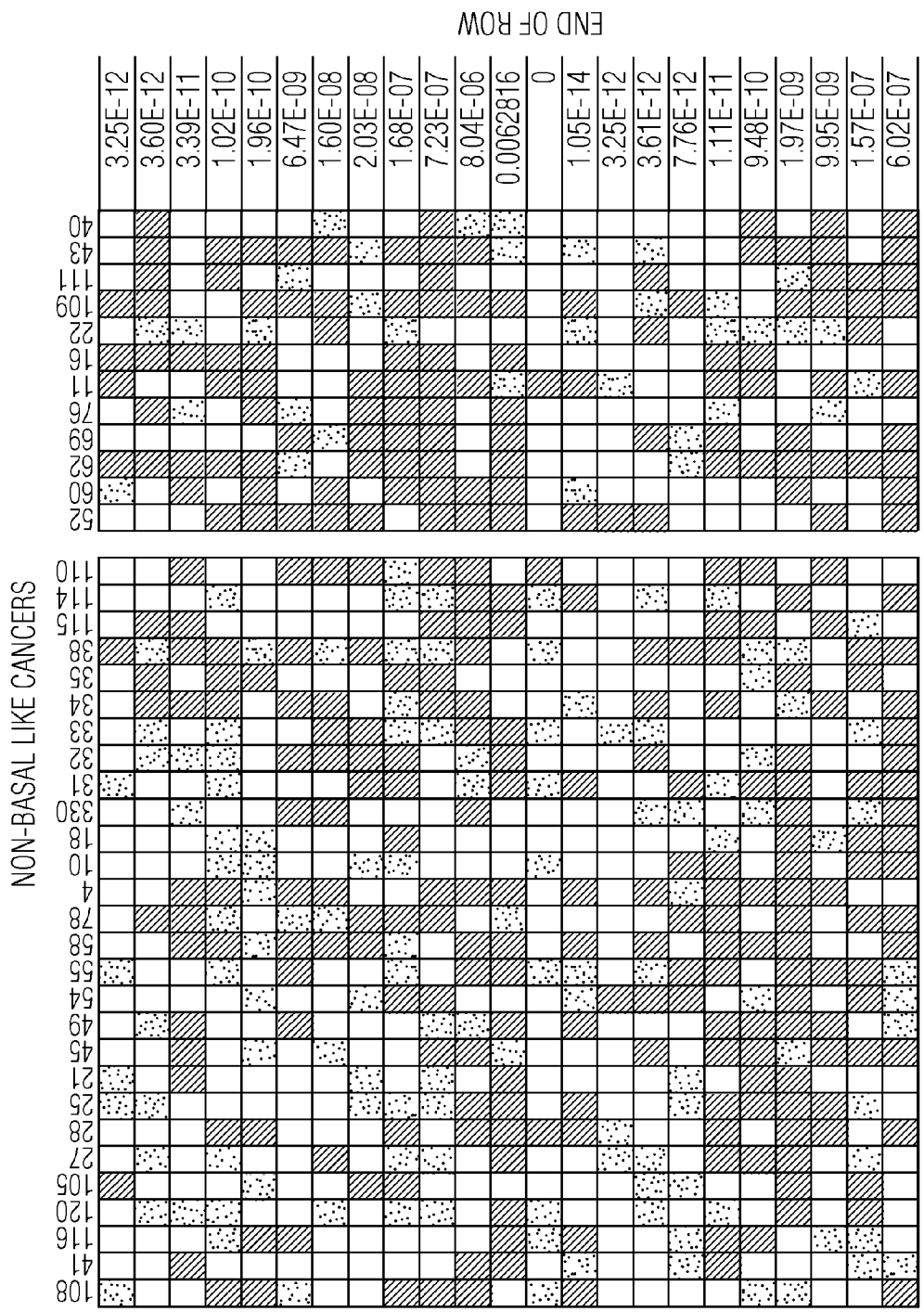
FIG. 24FFF

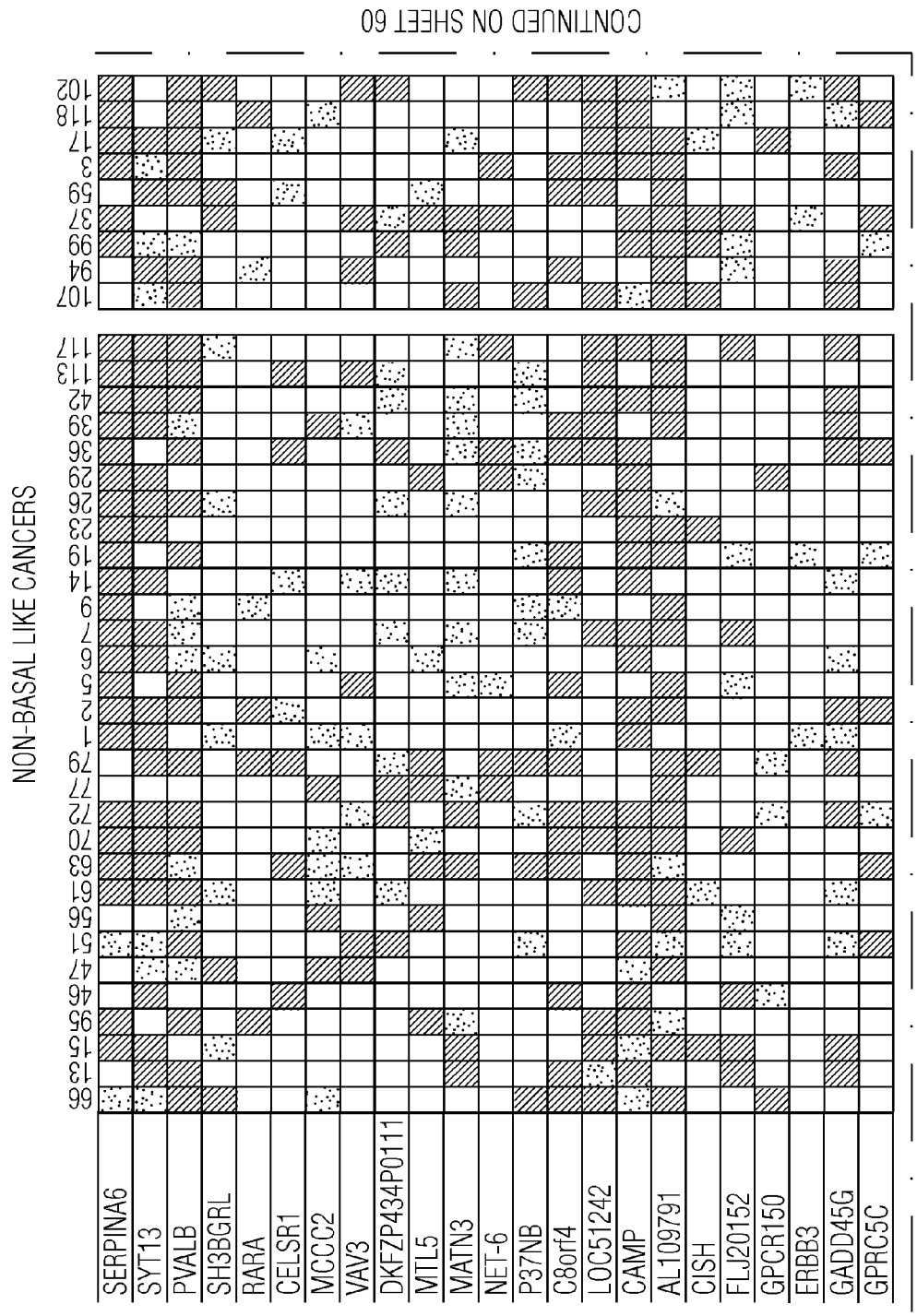
FIG. 24GGG

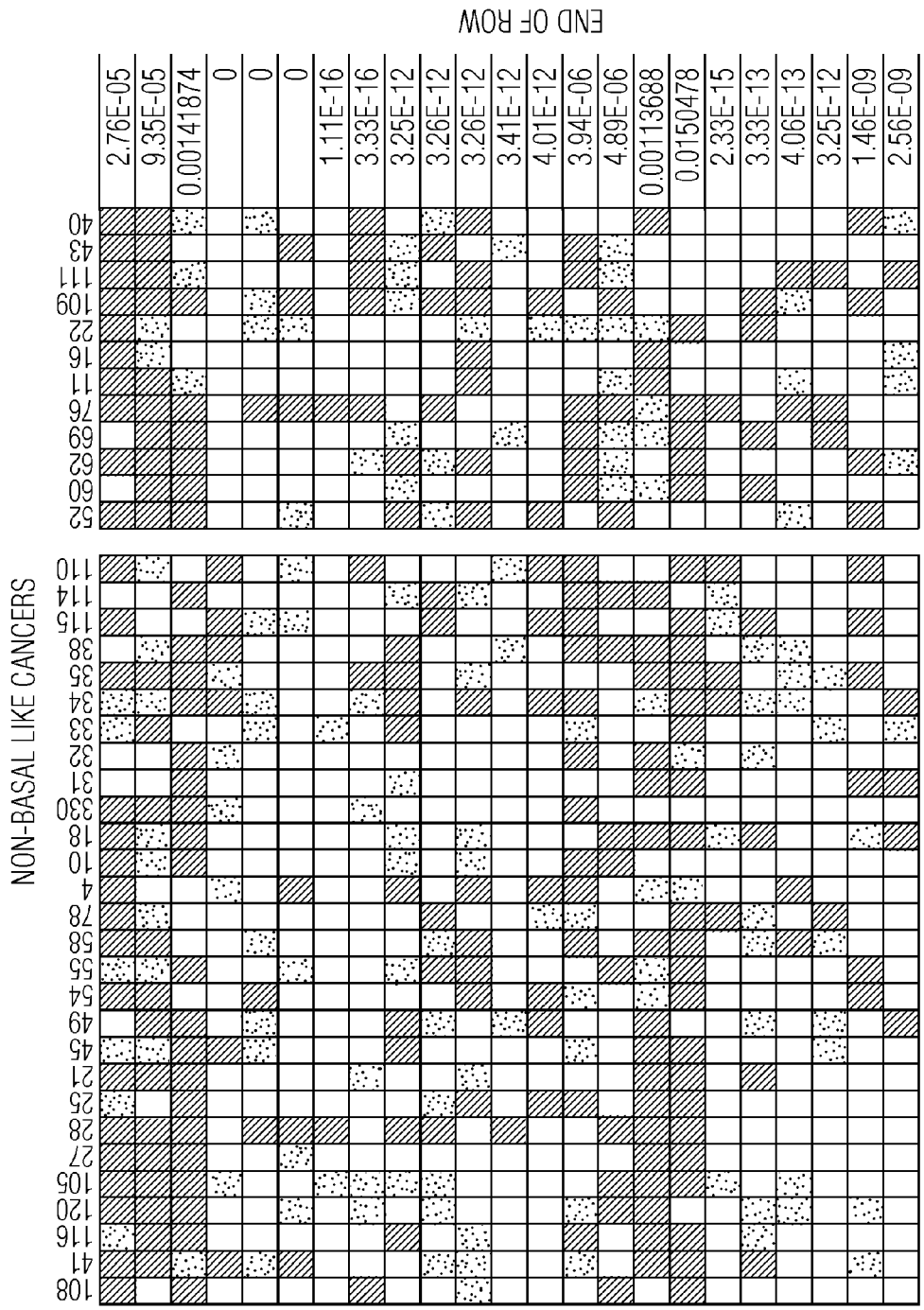
FIG. 24HHH

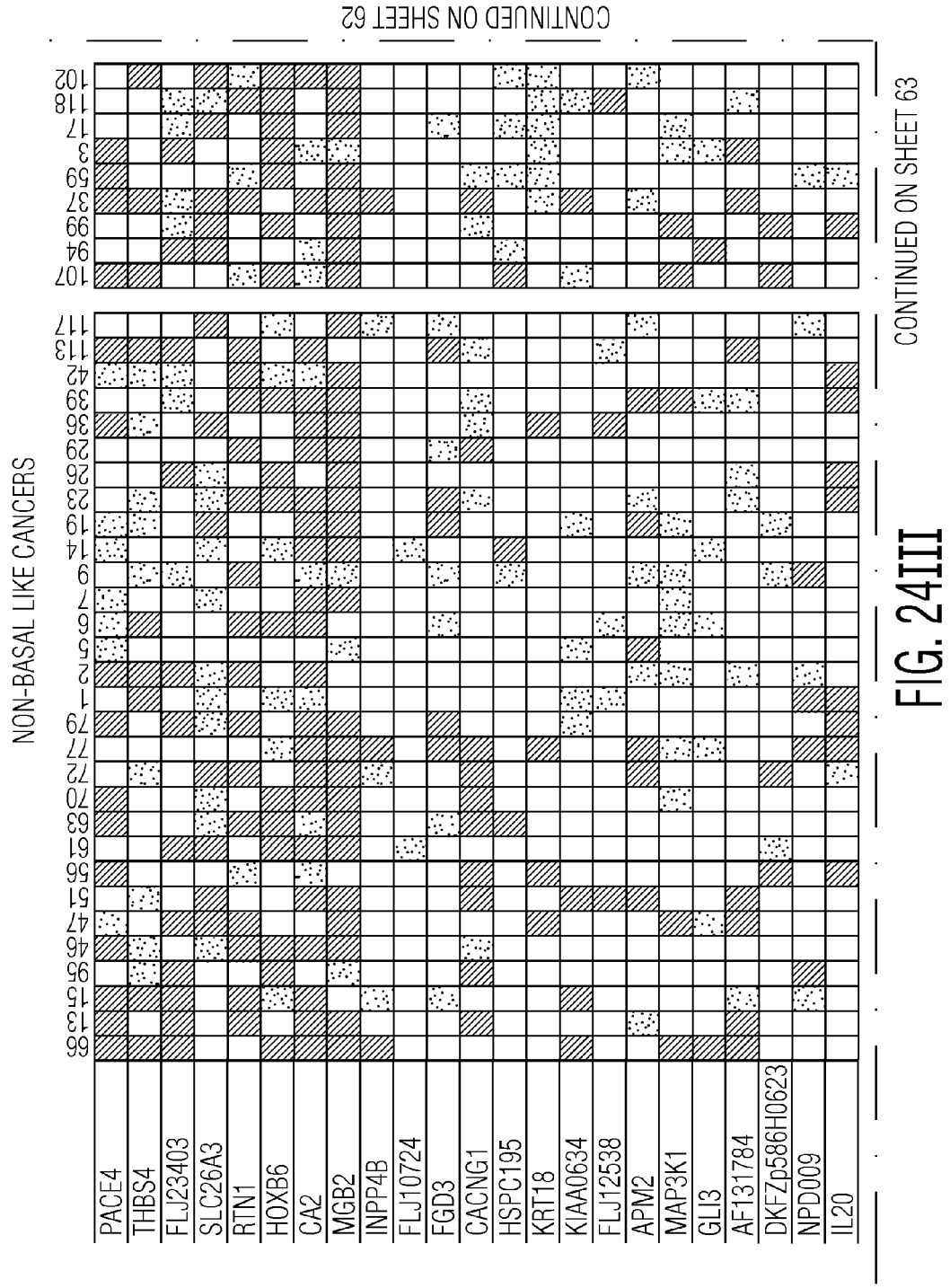
FIG. 24III

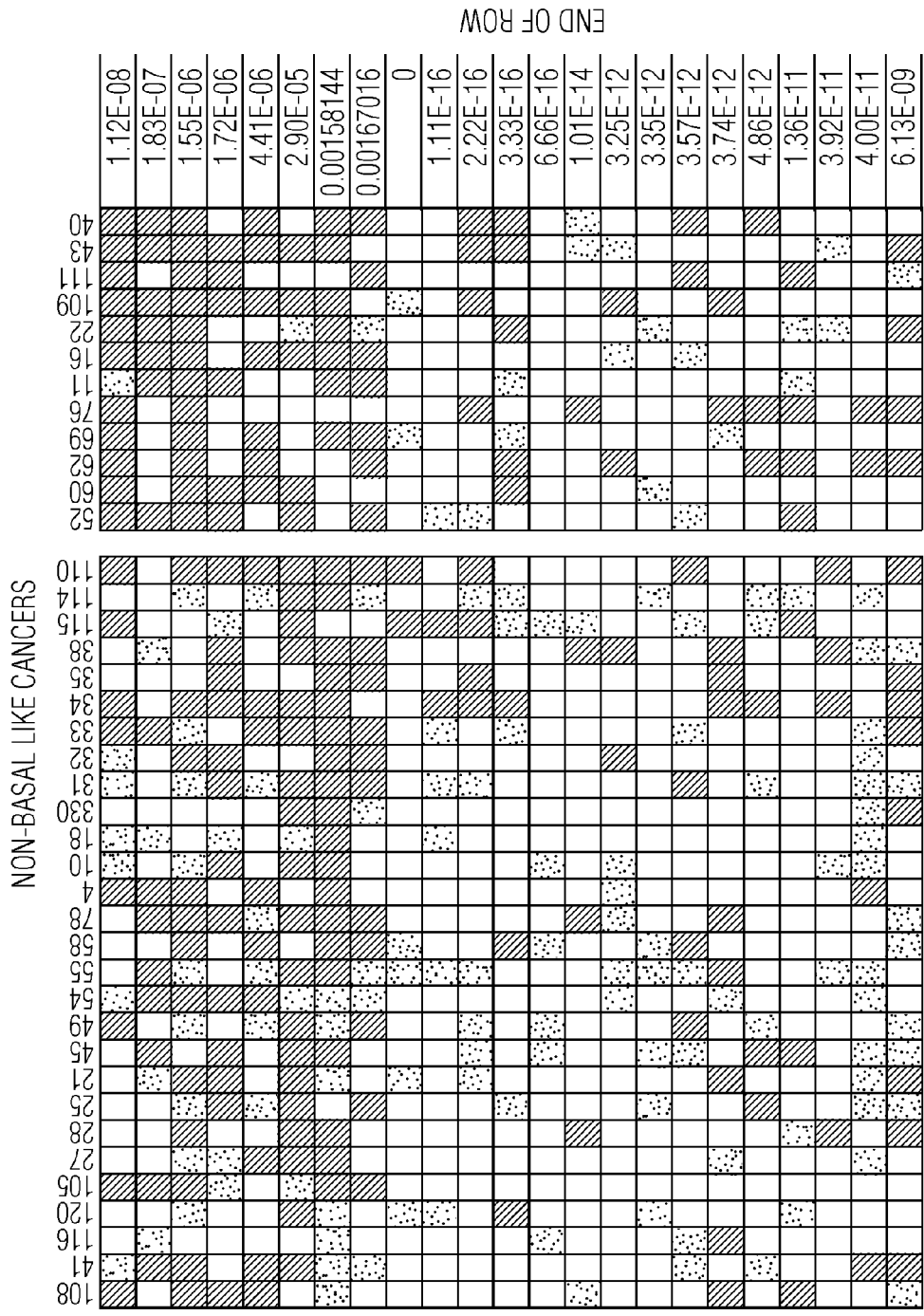
FIG. 24JJJ

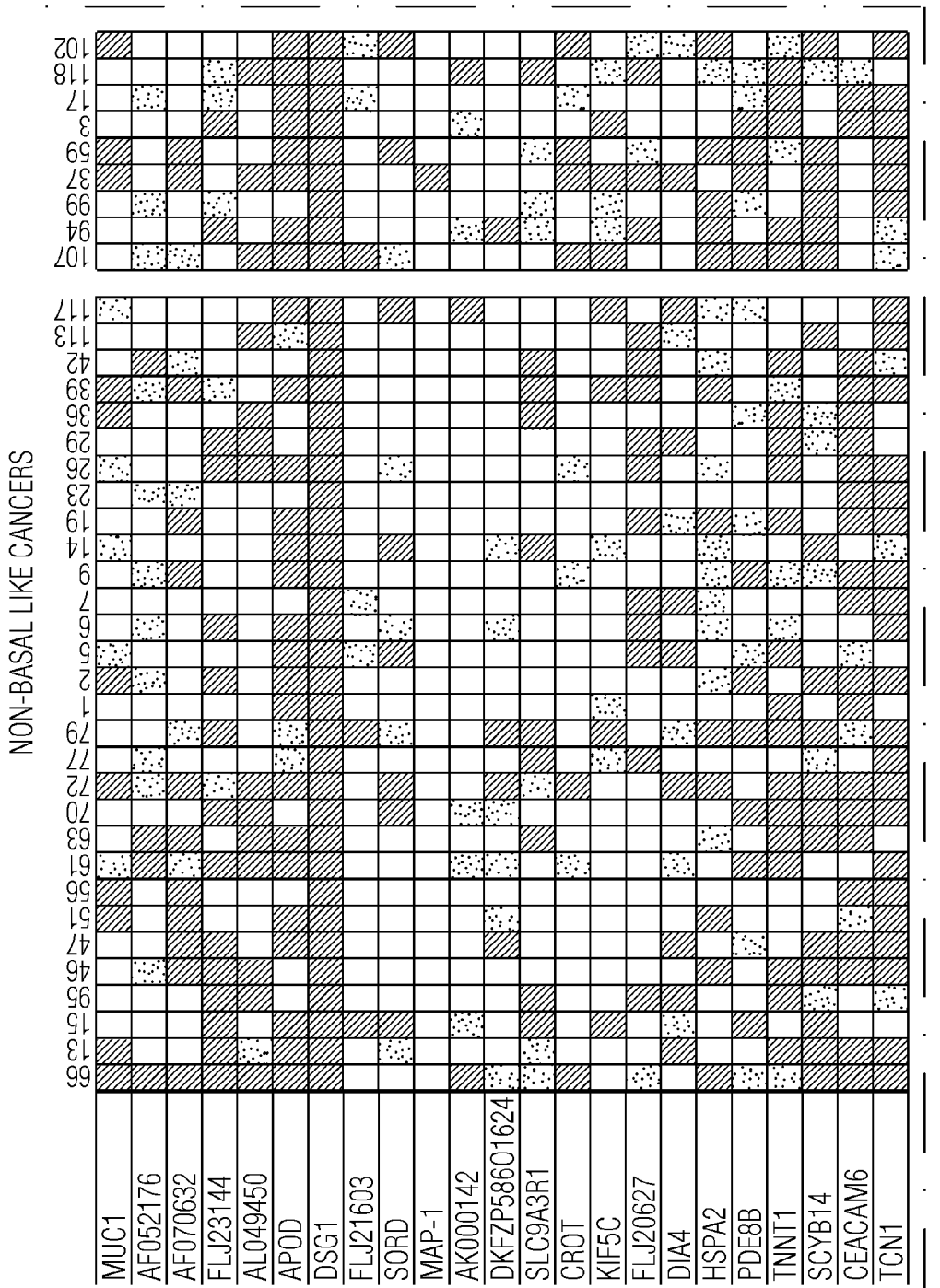
FIG. 24KKK

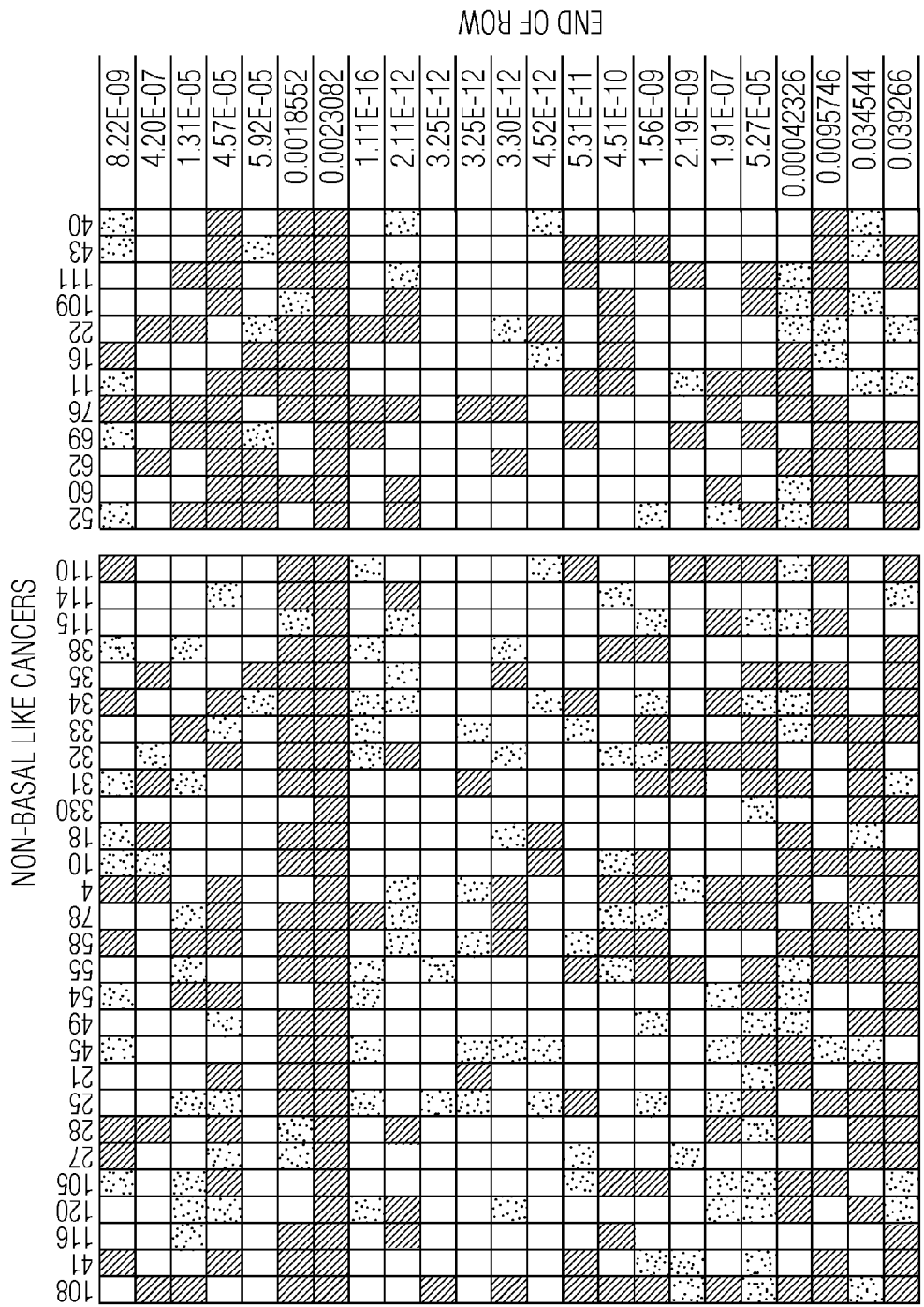
FIG. 24LLL

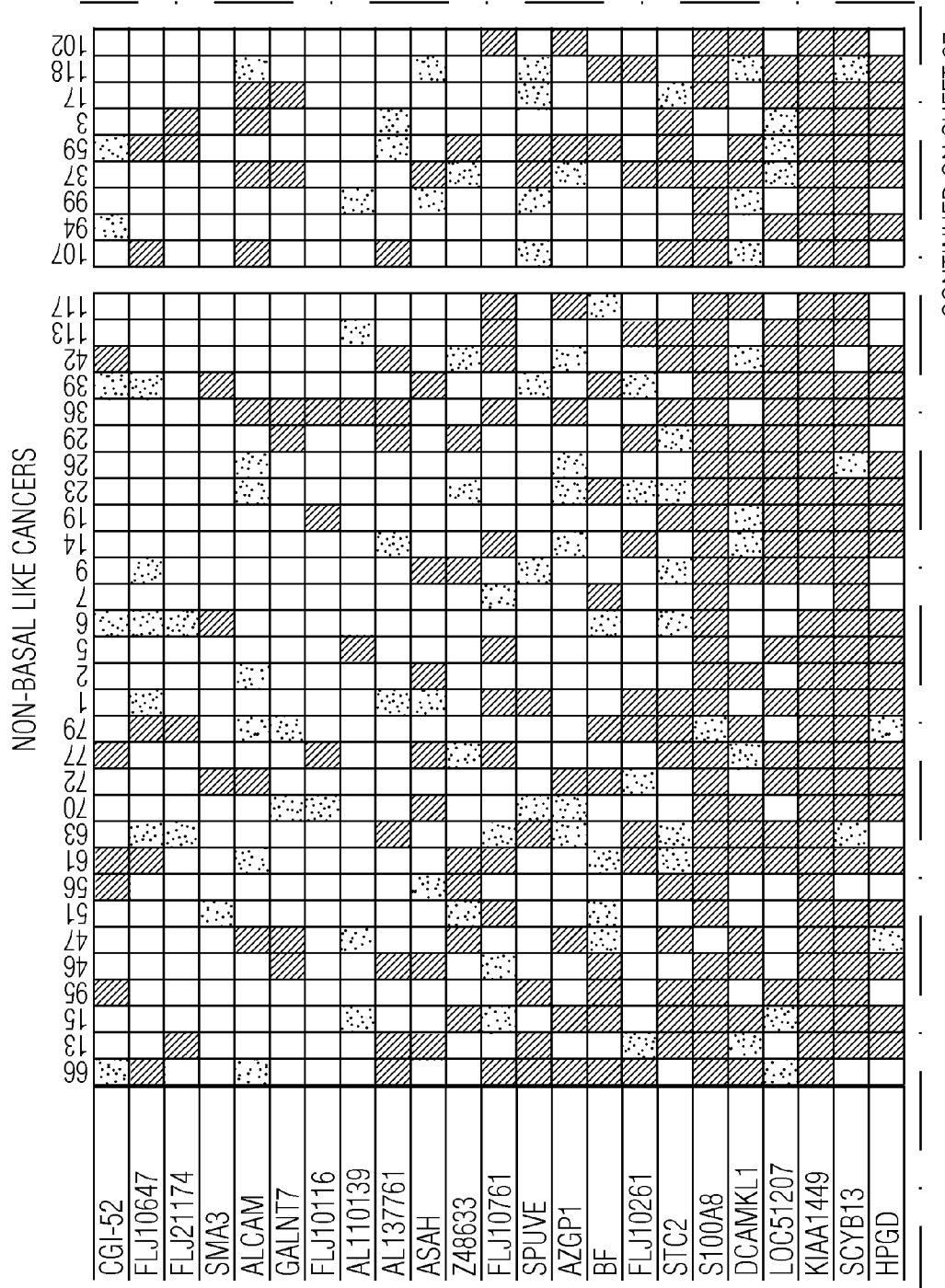
FIG. 24MMM

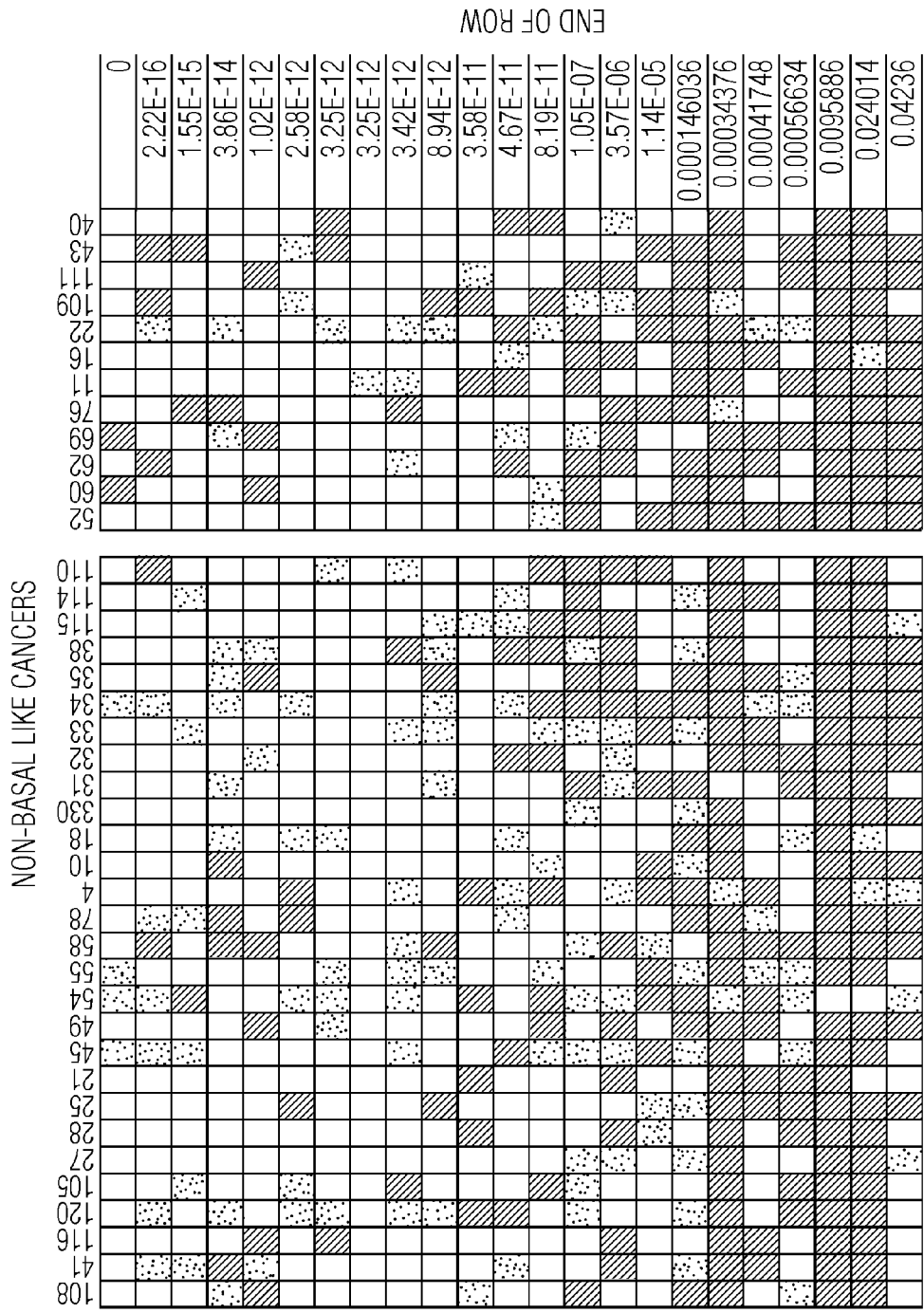
FIG. 24NNN

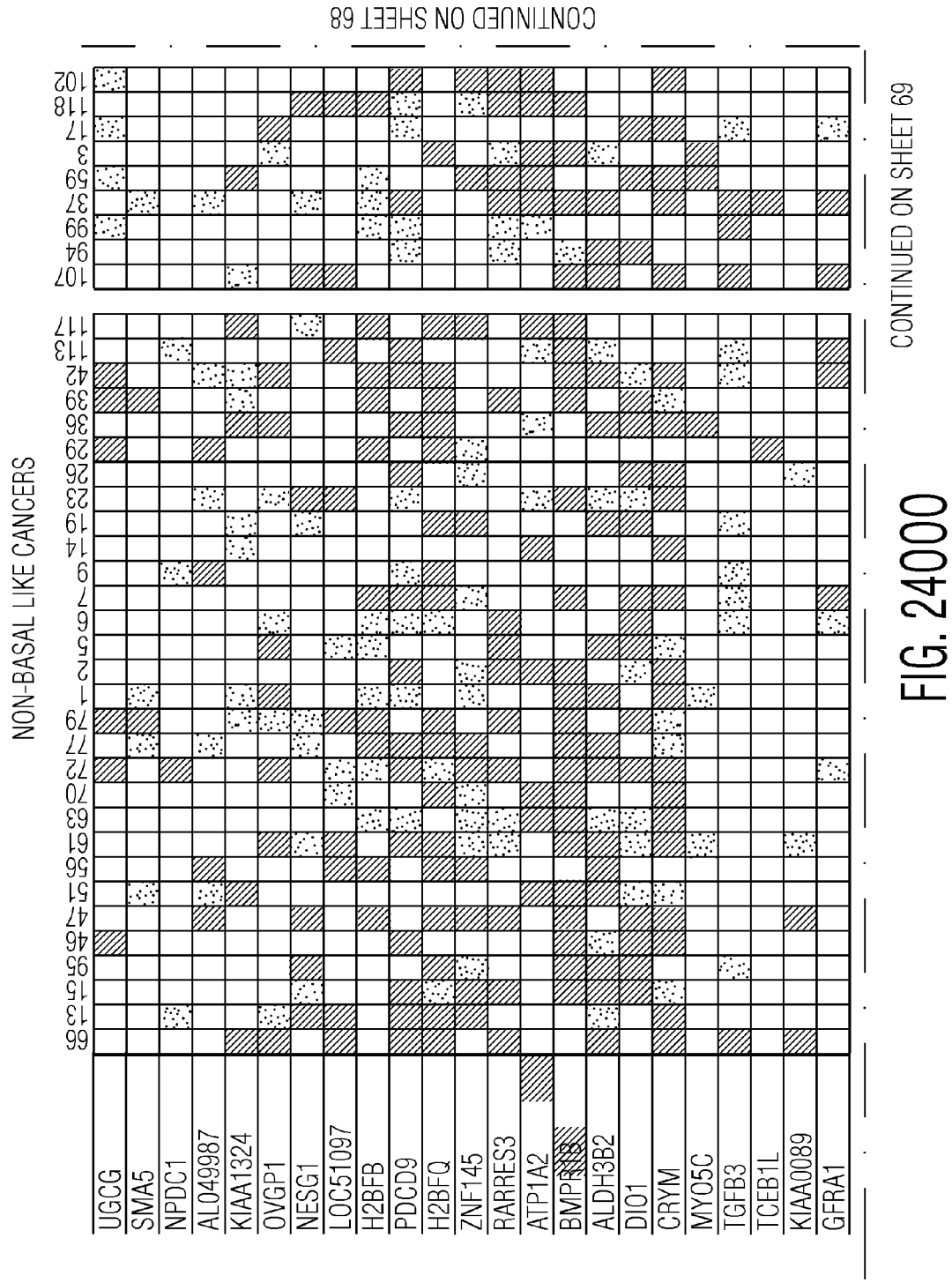
FIG. 24000

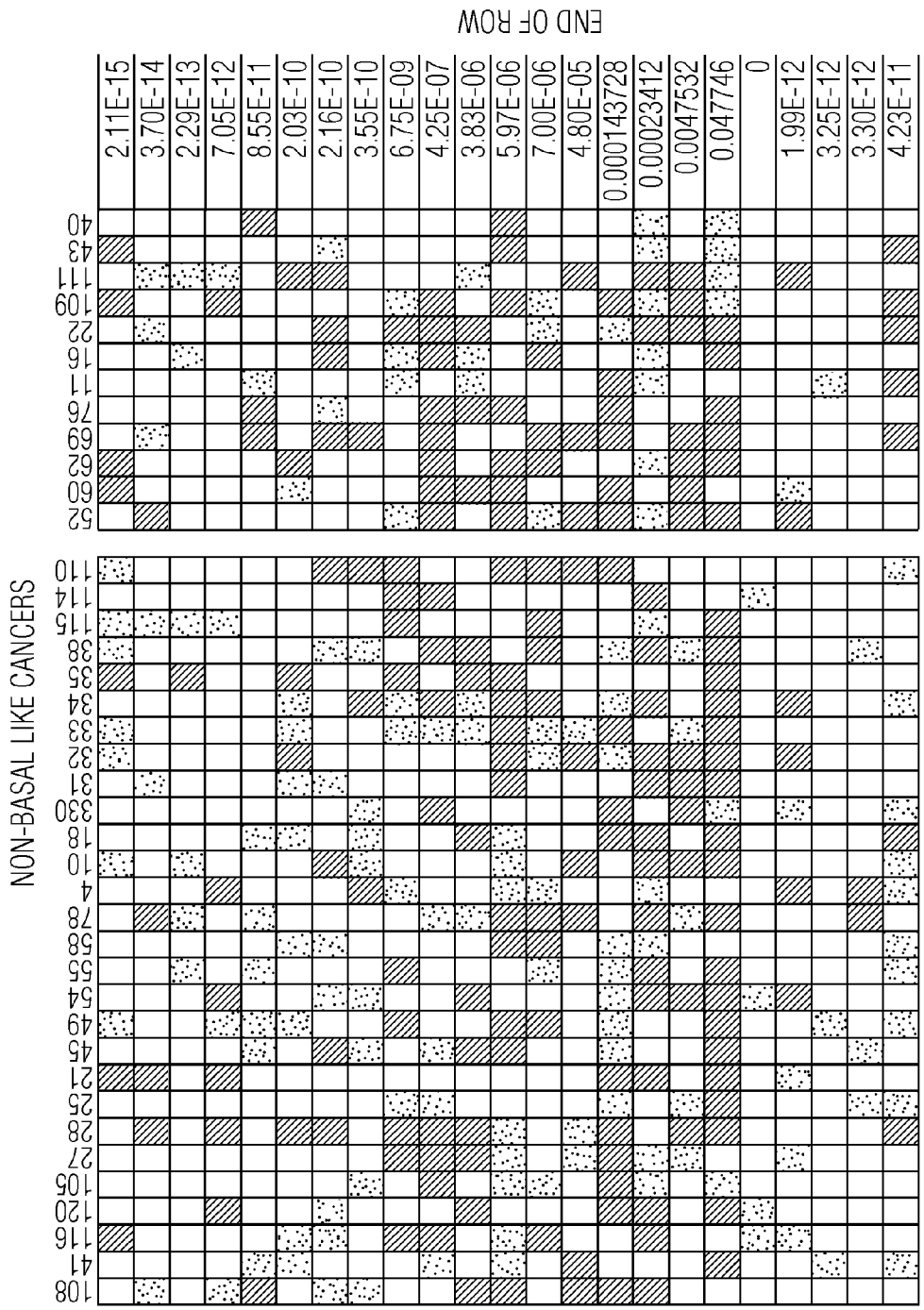
FIG. 24PPP

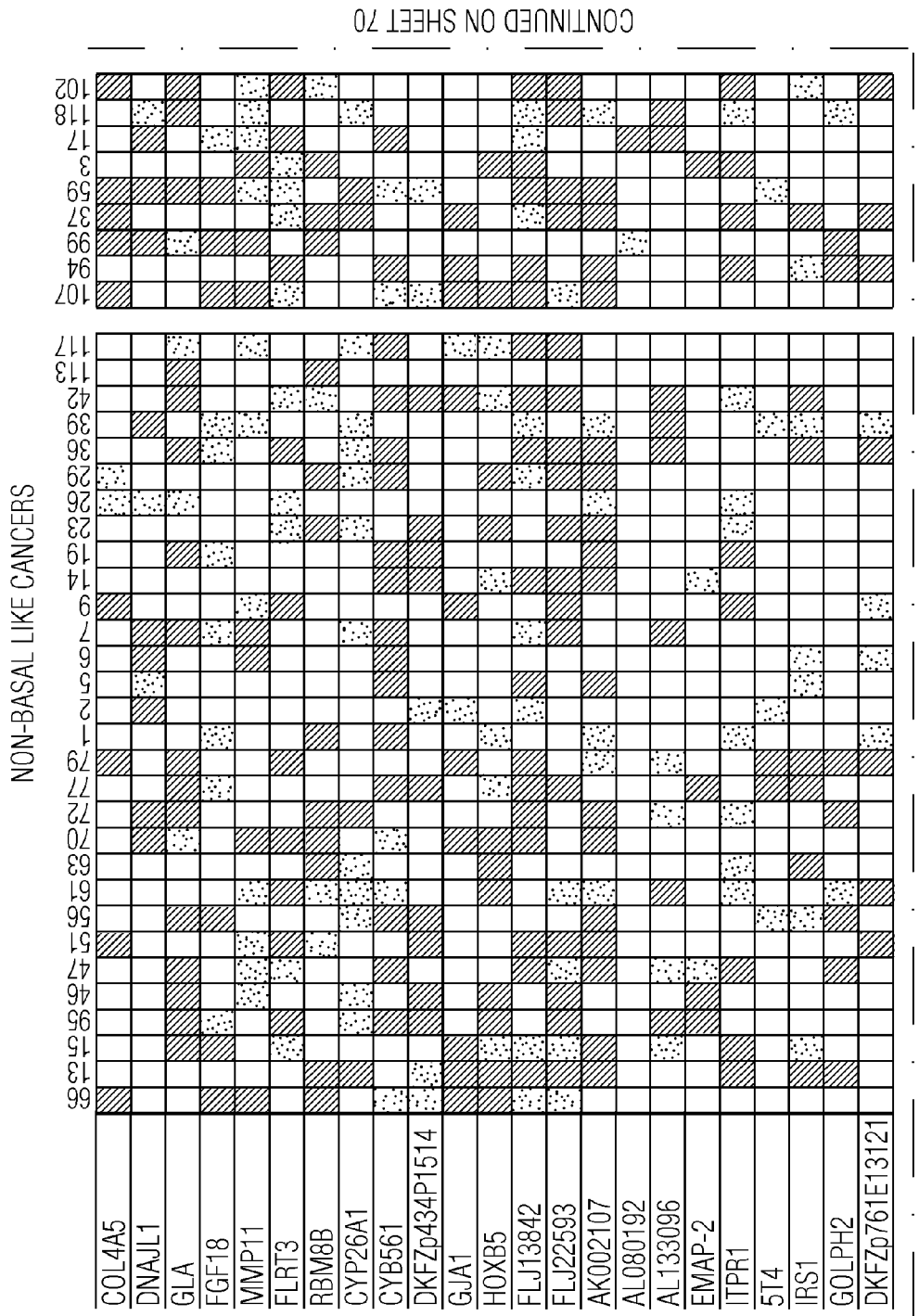
FIG. 24QQQ

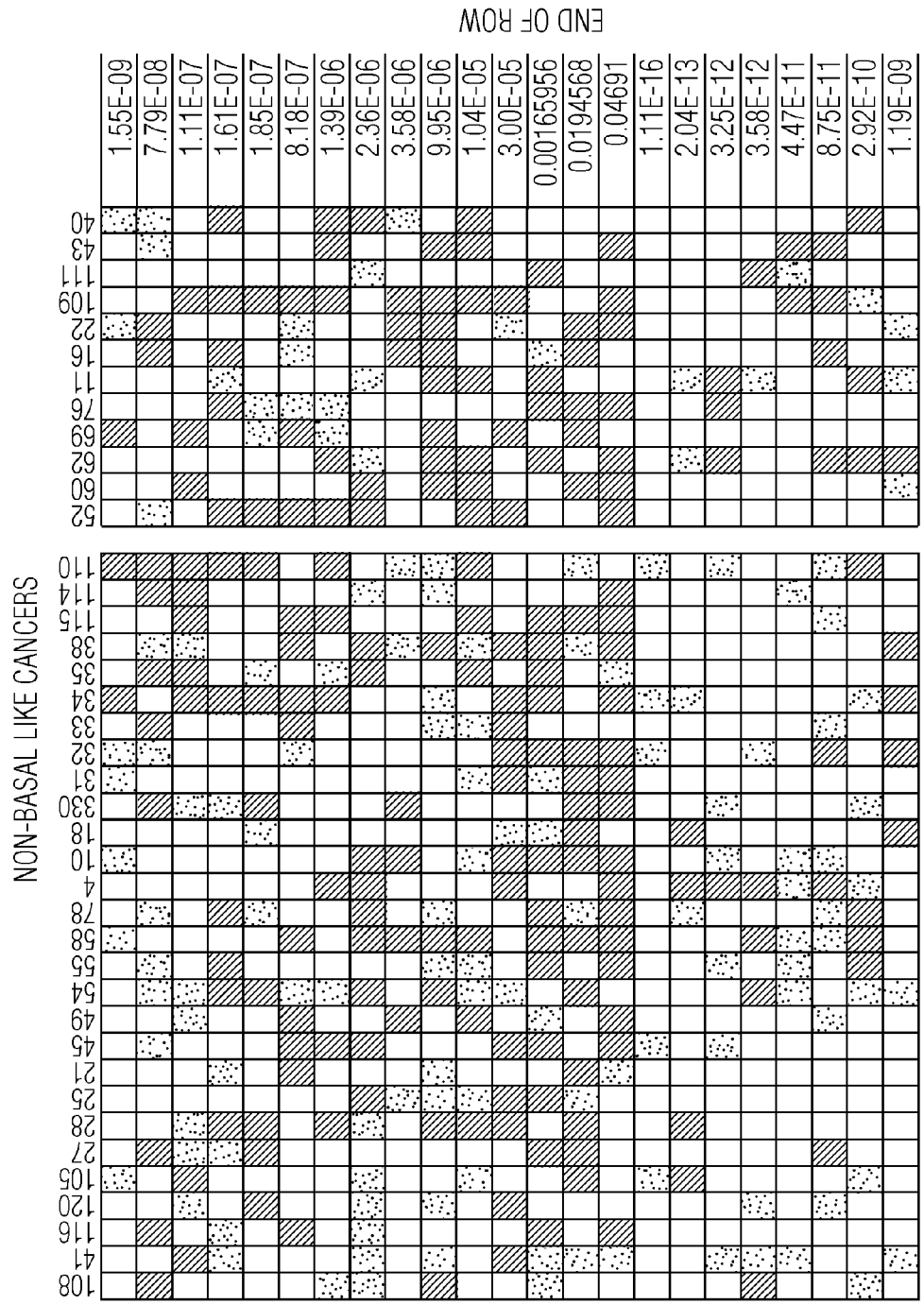
FIG. 24RRR

FIG. 24SSS

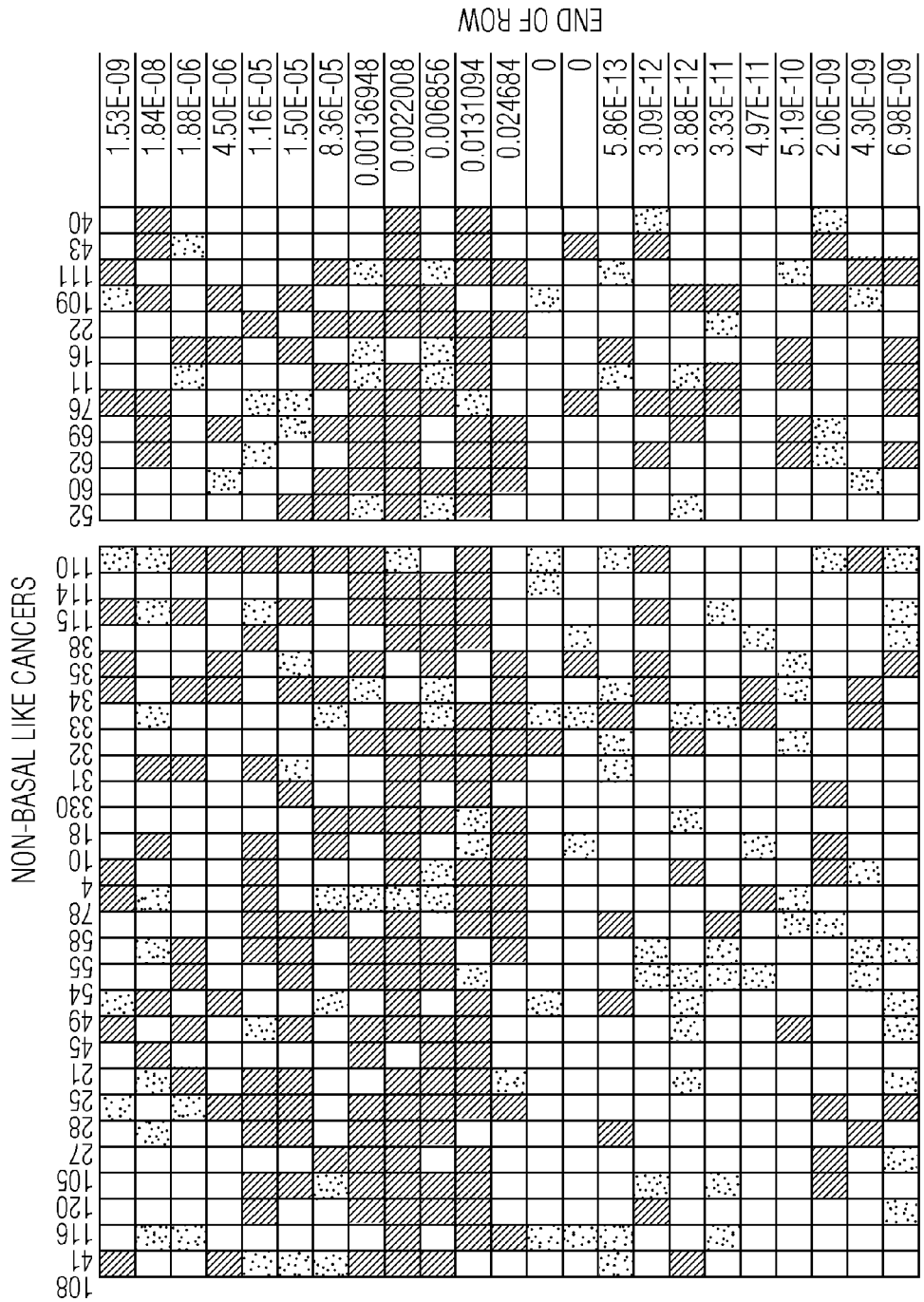
FIG. 24TTT

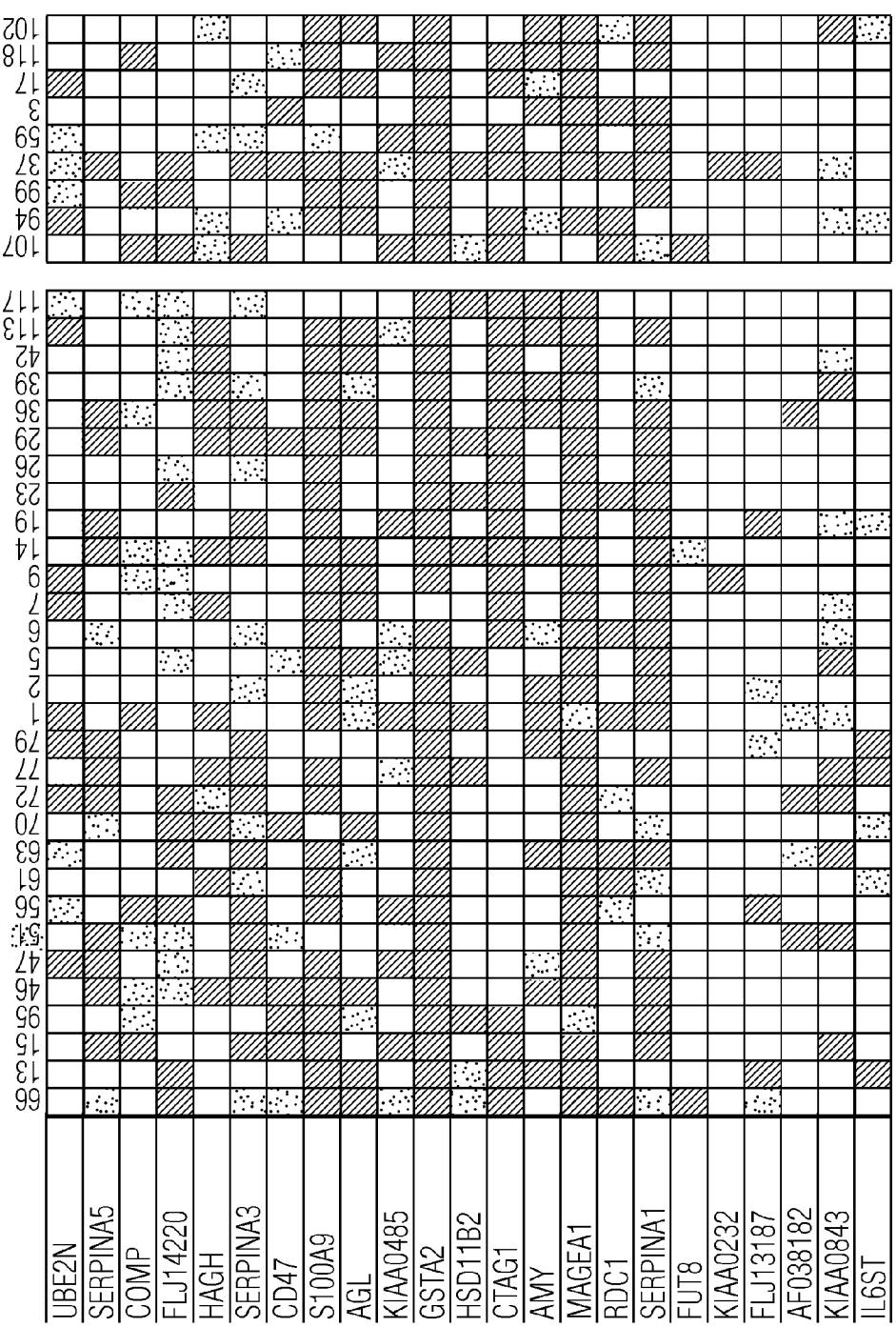
FIG. 24UUU

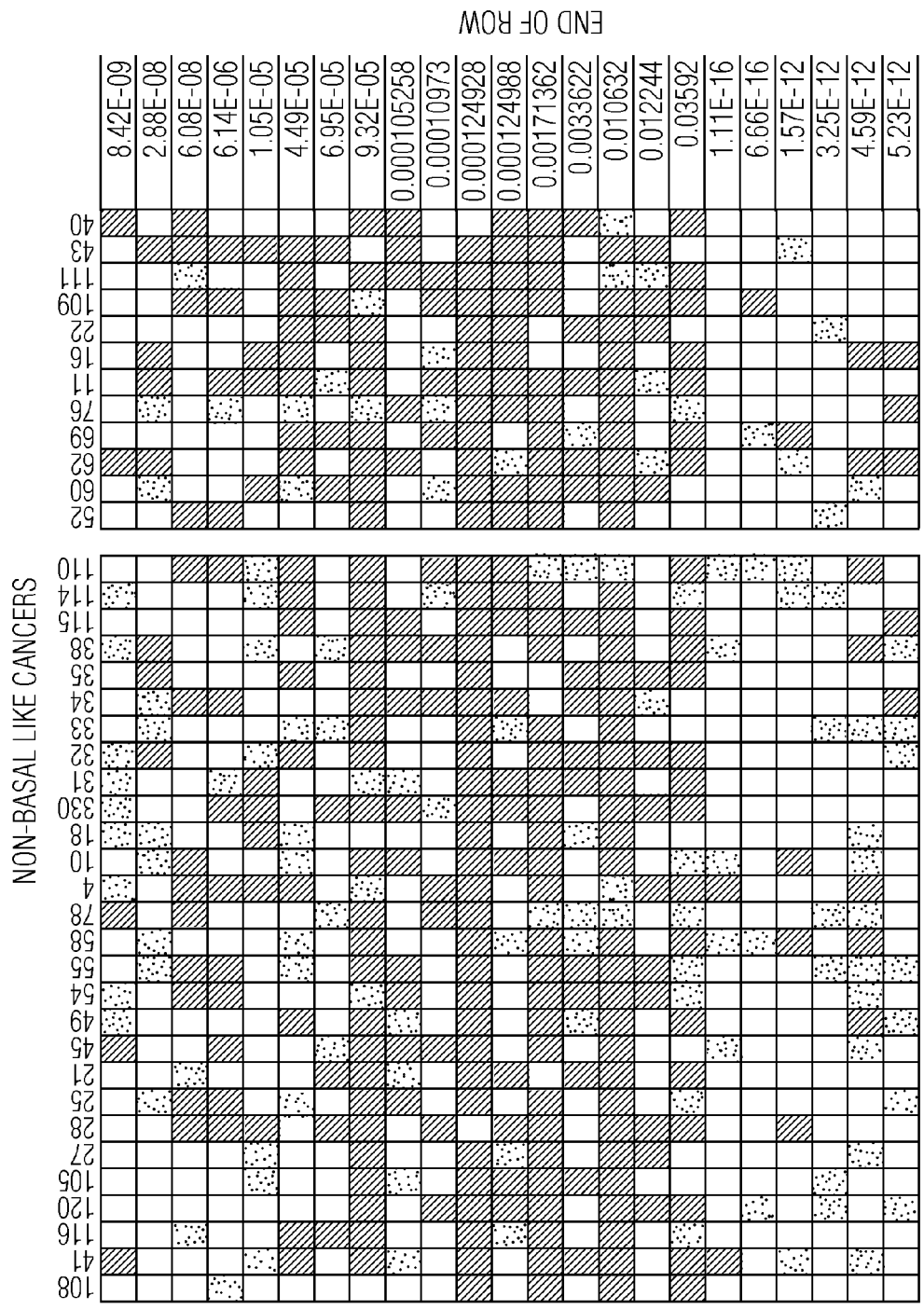
FIG. 24VVV

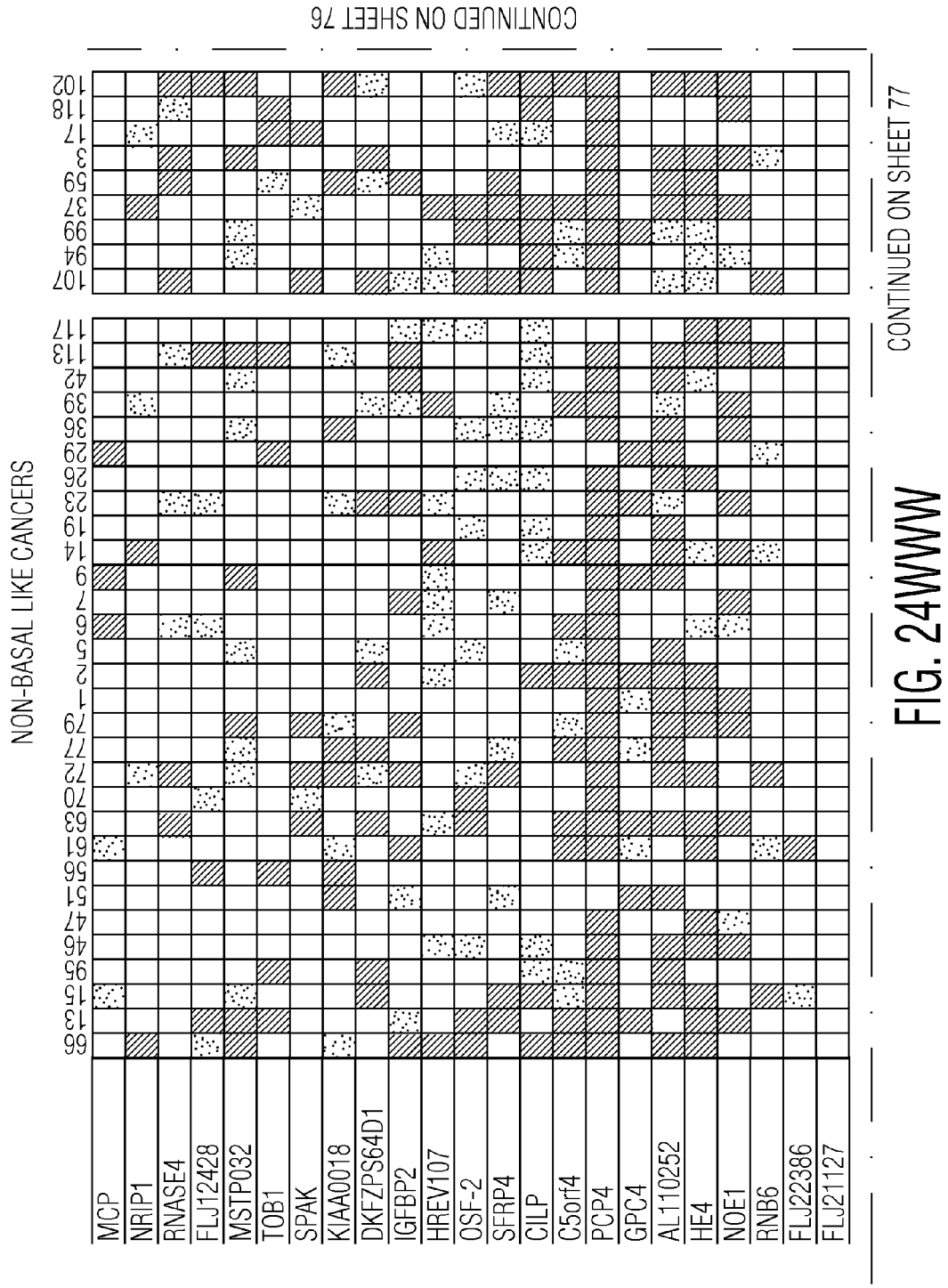
FIG. 24WWWW

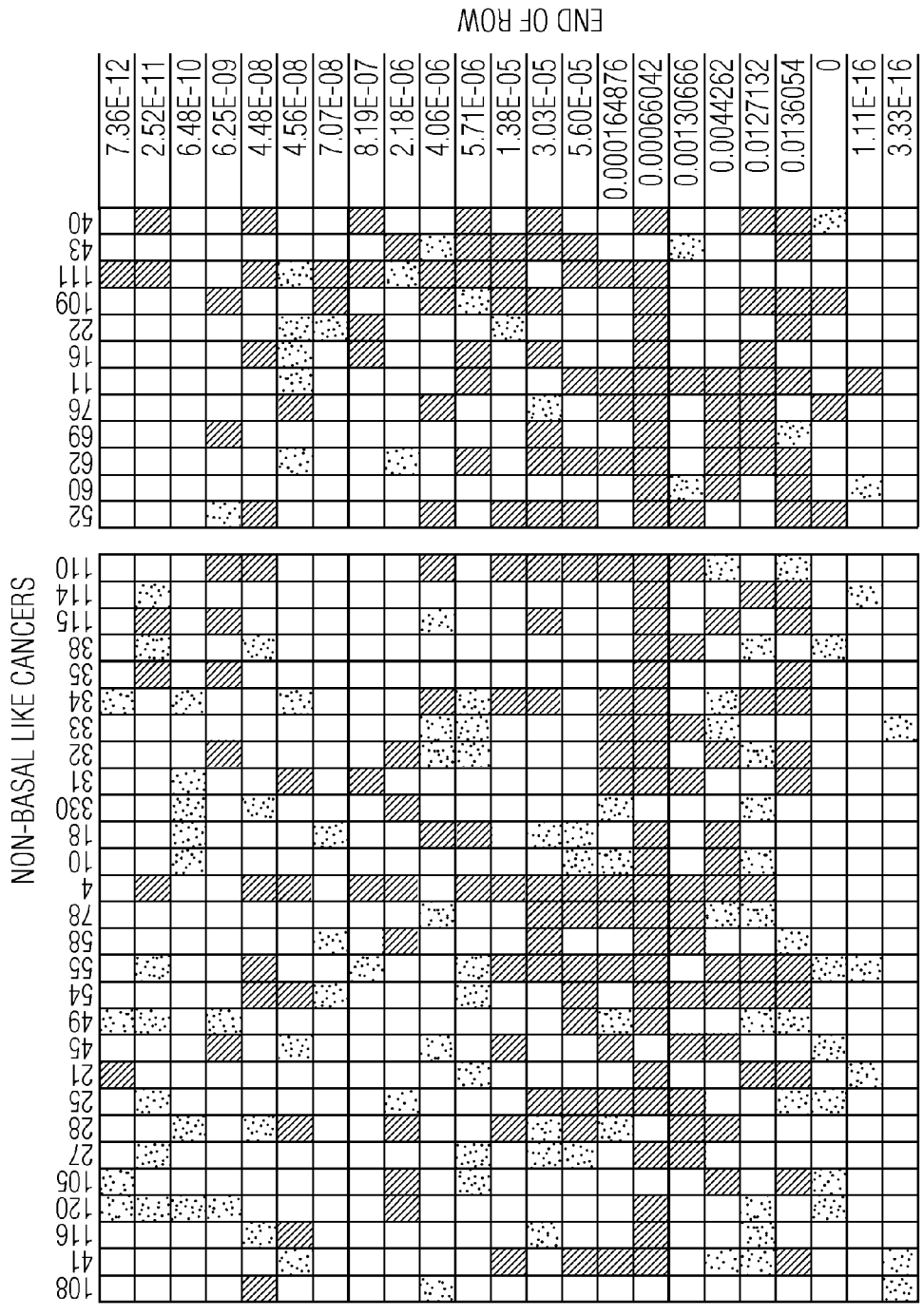
FIG. 24XXX

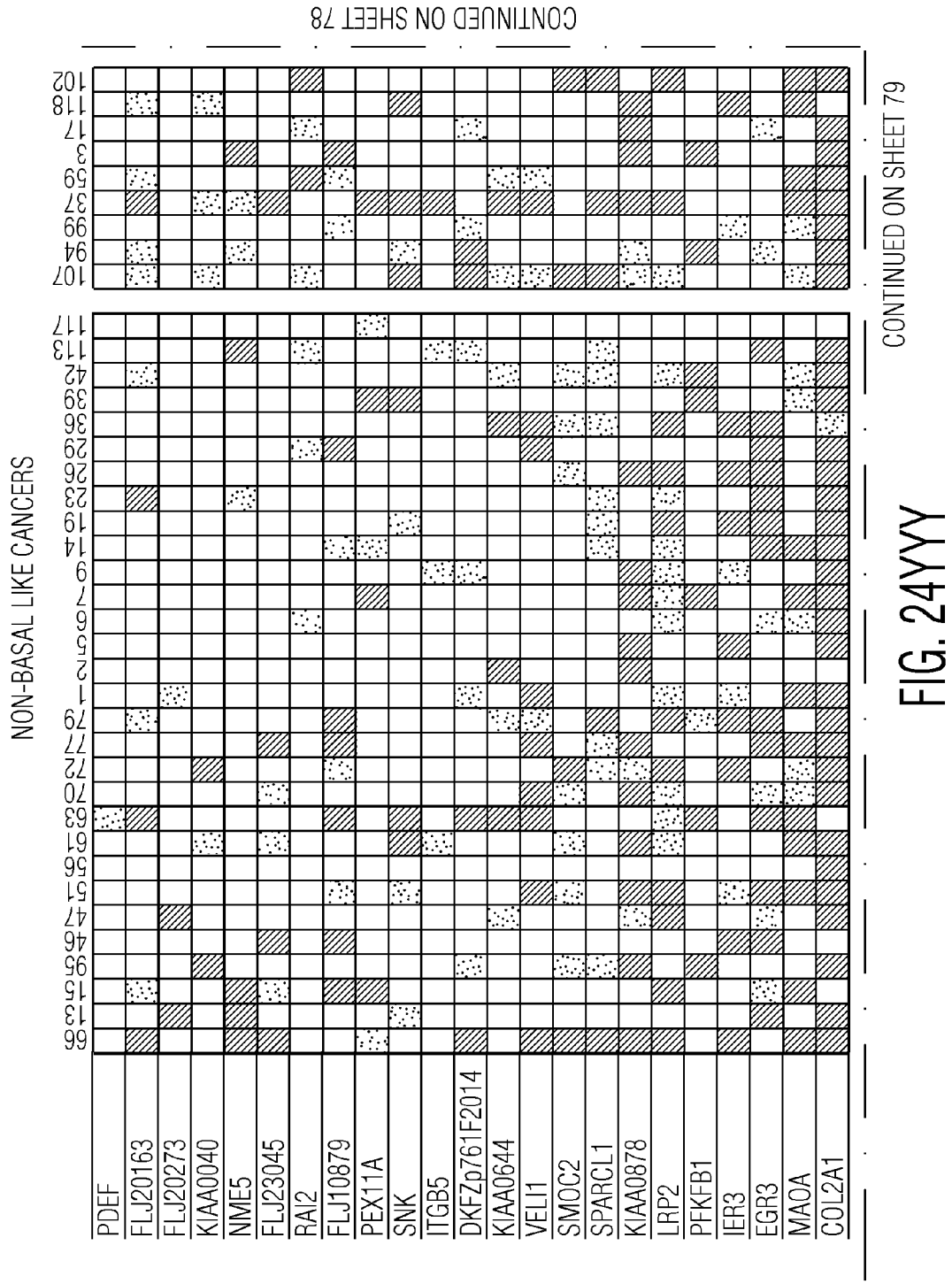
FIG. 24YYYY

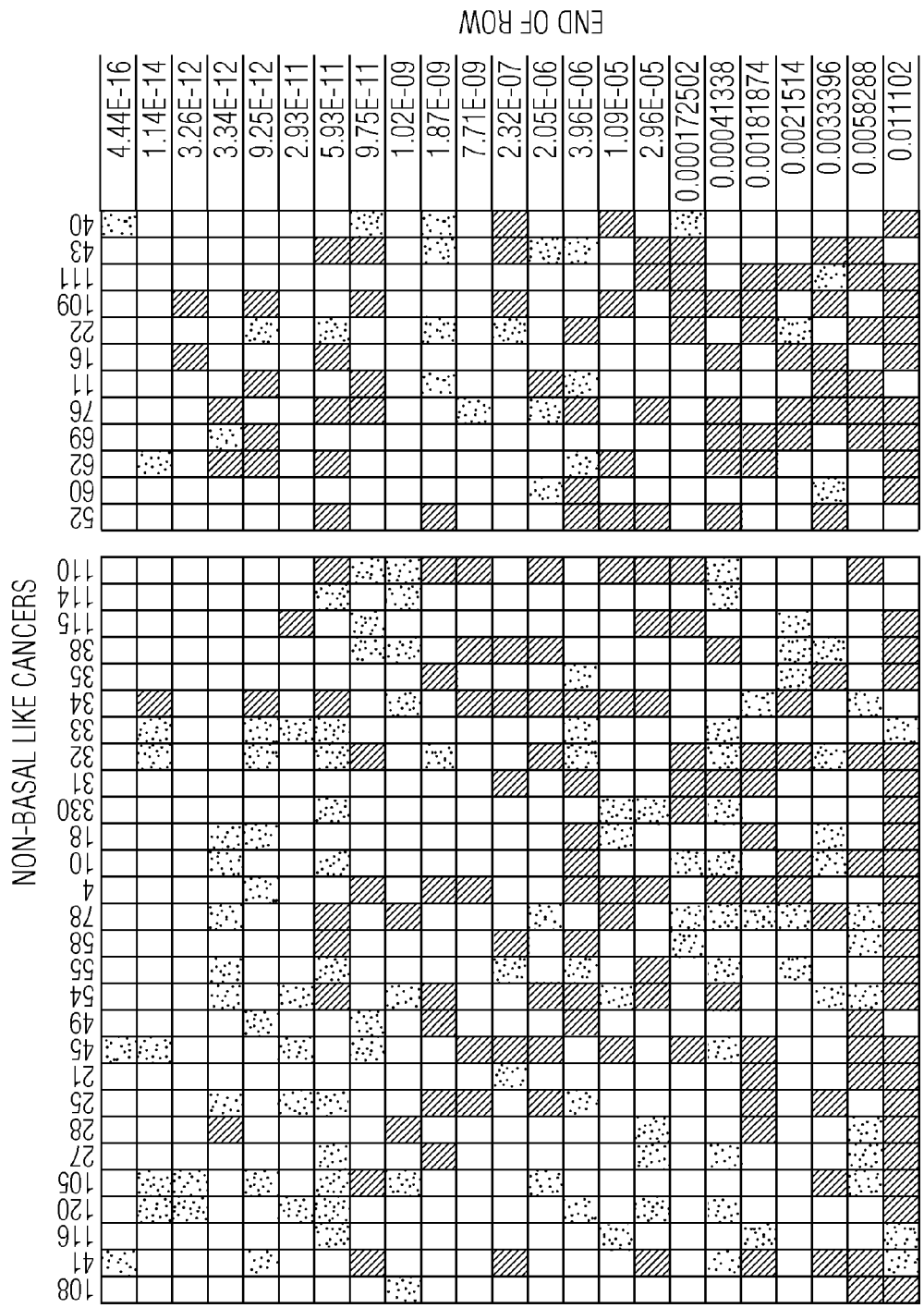
FIG. 24ZZZ

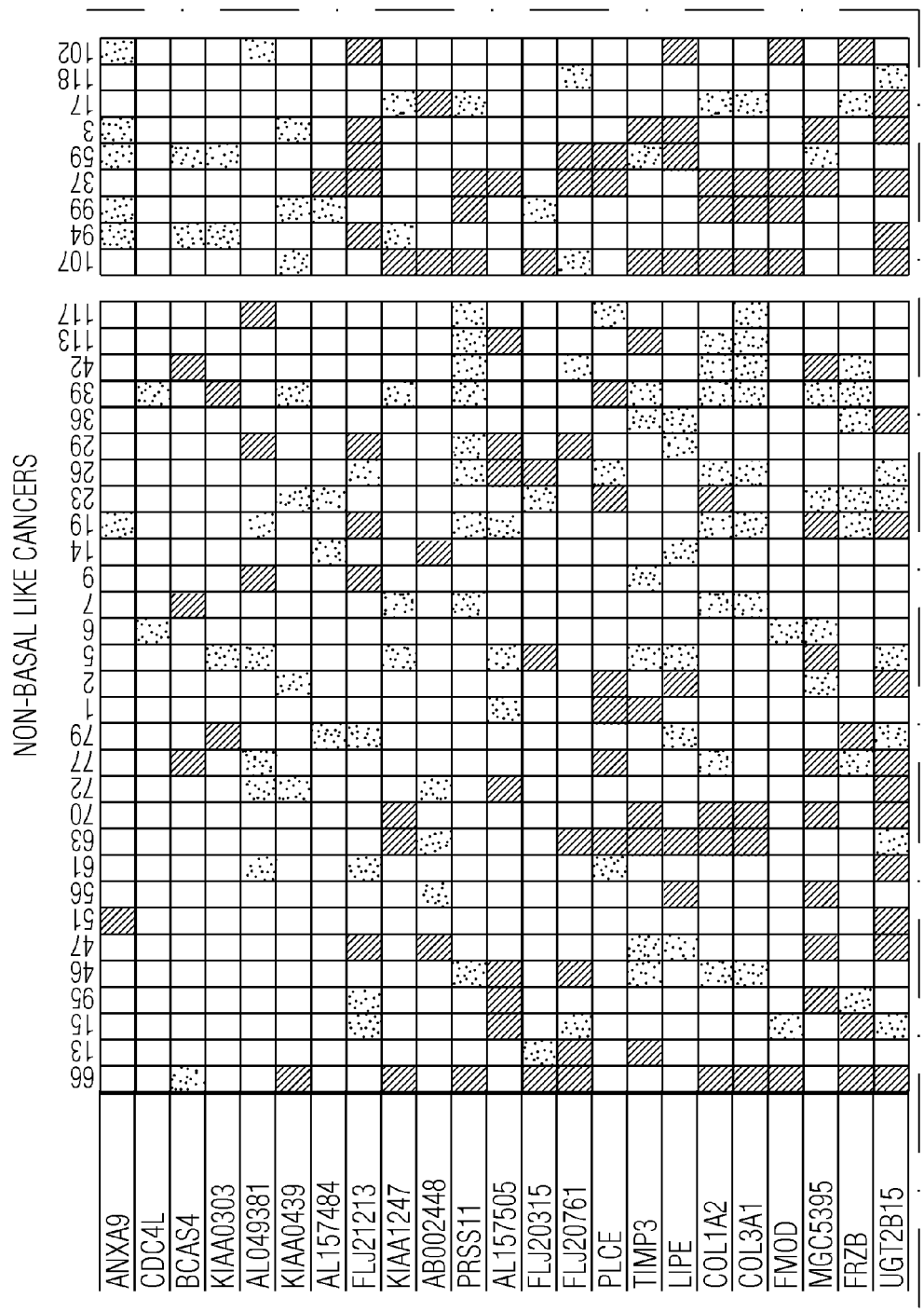
FIG. 24AAAA

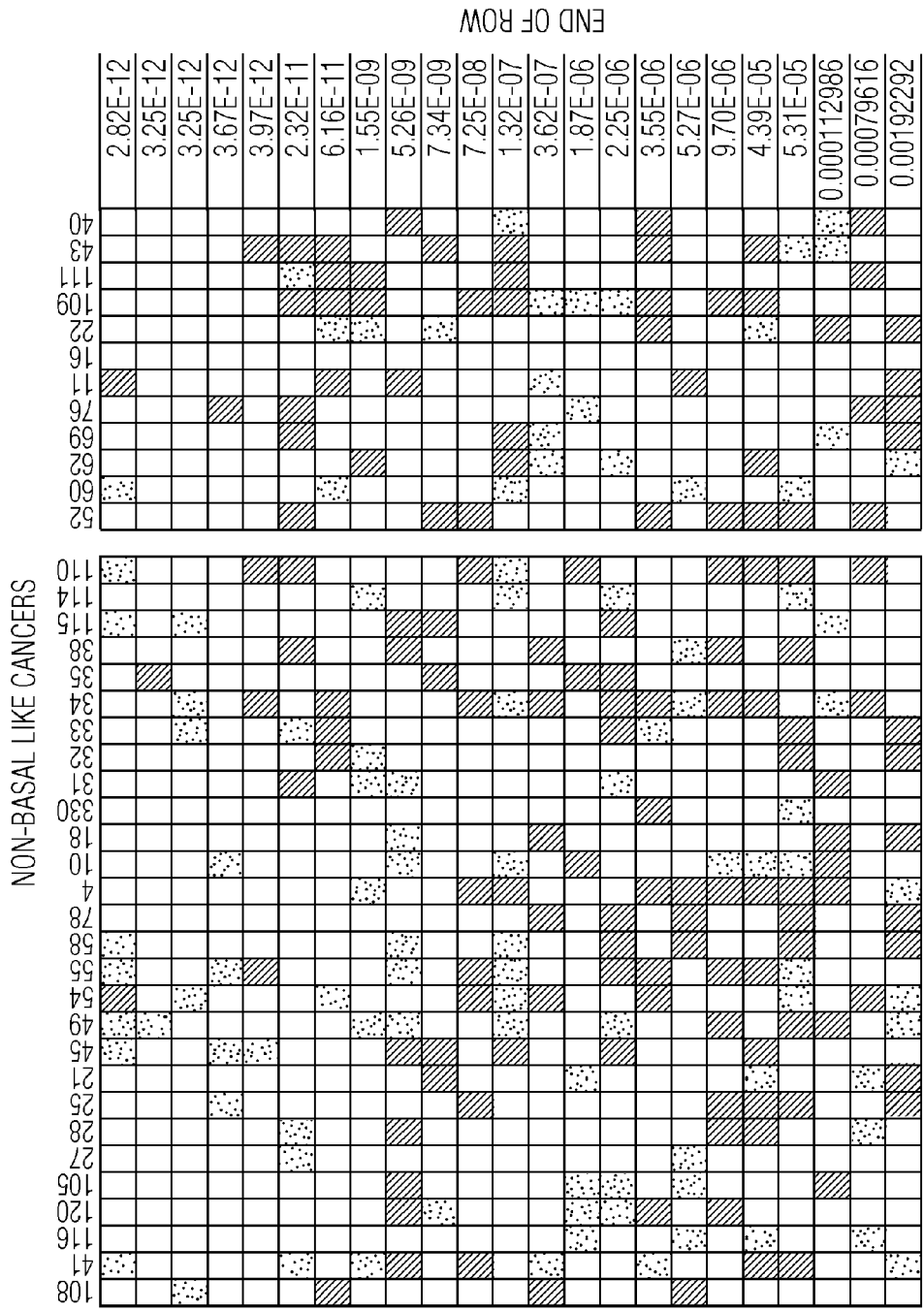
FIG. 24BBBB

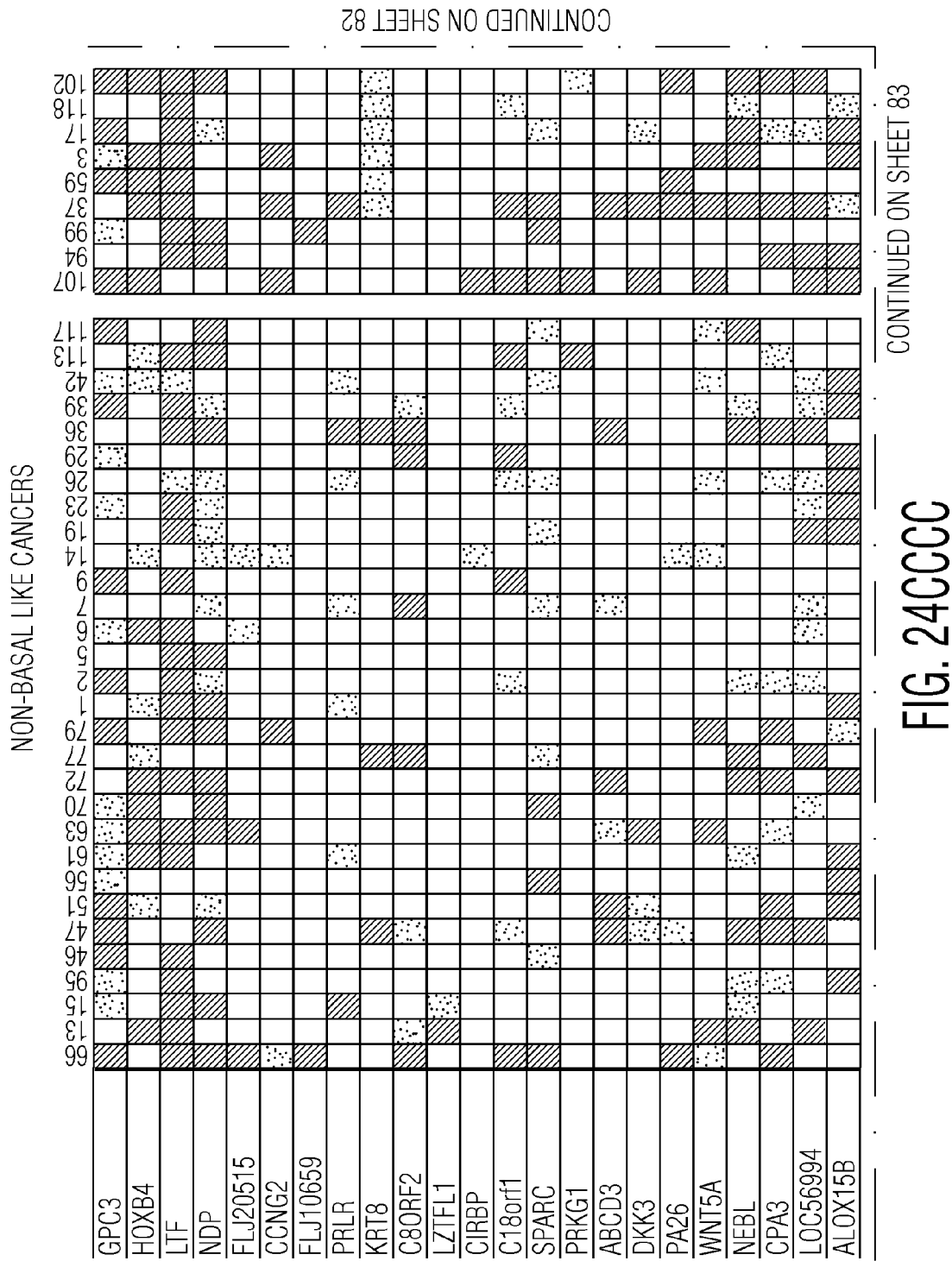
FIG. 24CCCC

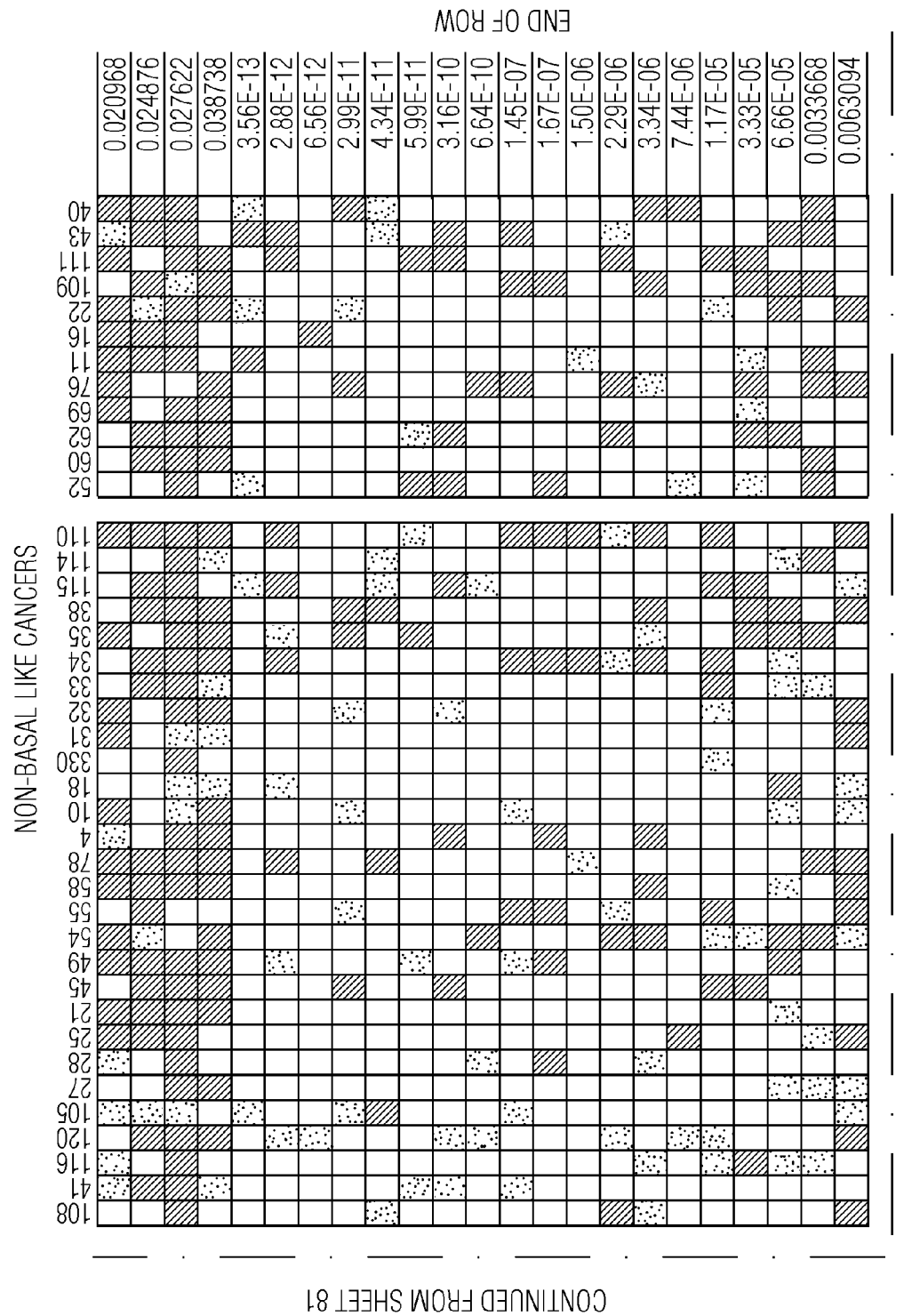
FIG. 24DDDD

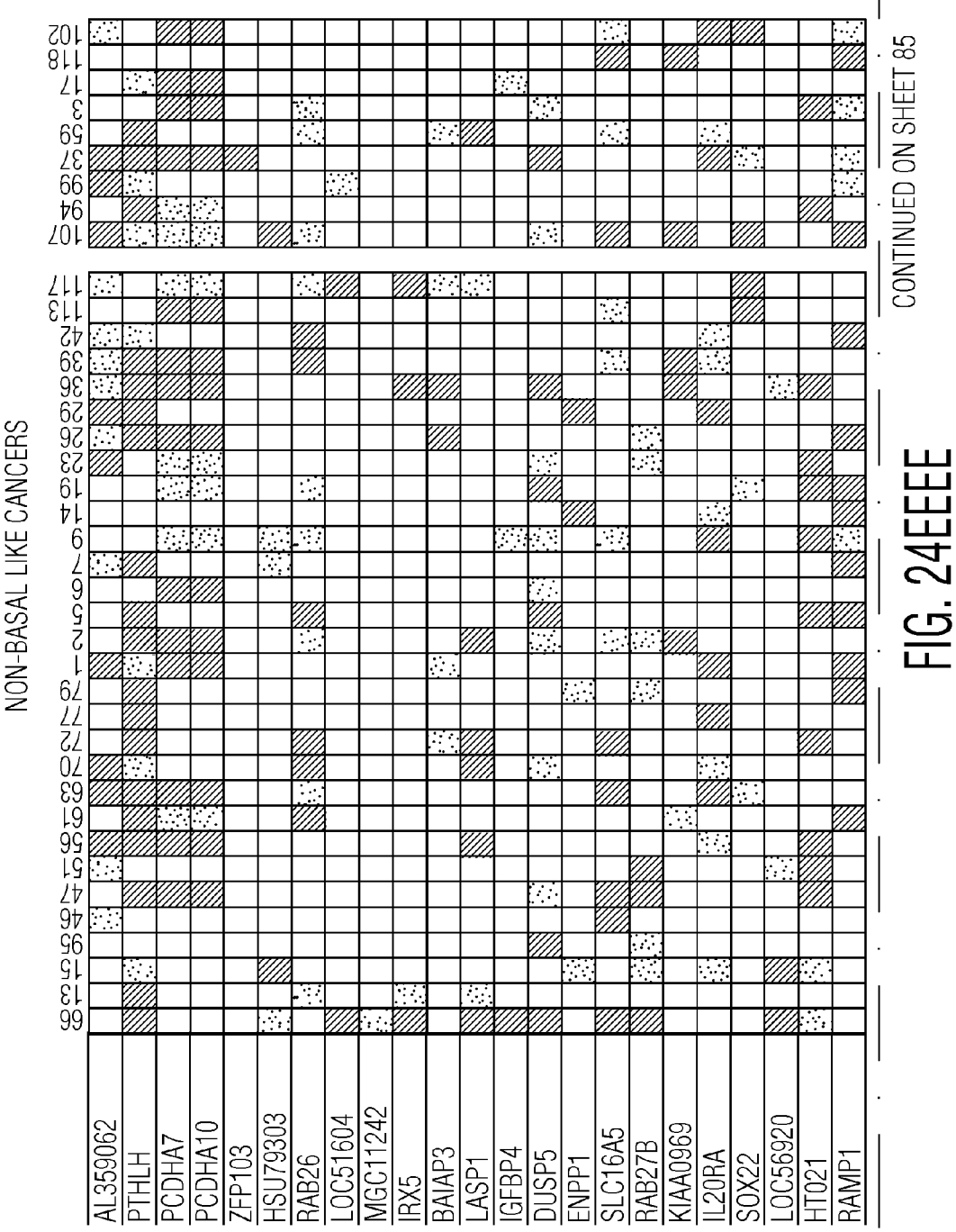
FIG. 24EEEE

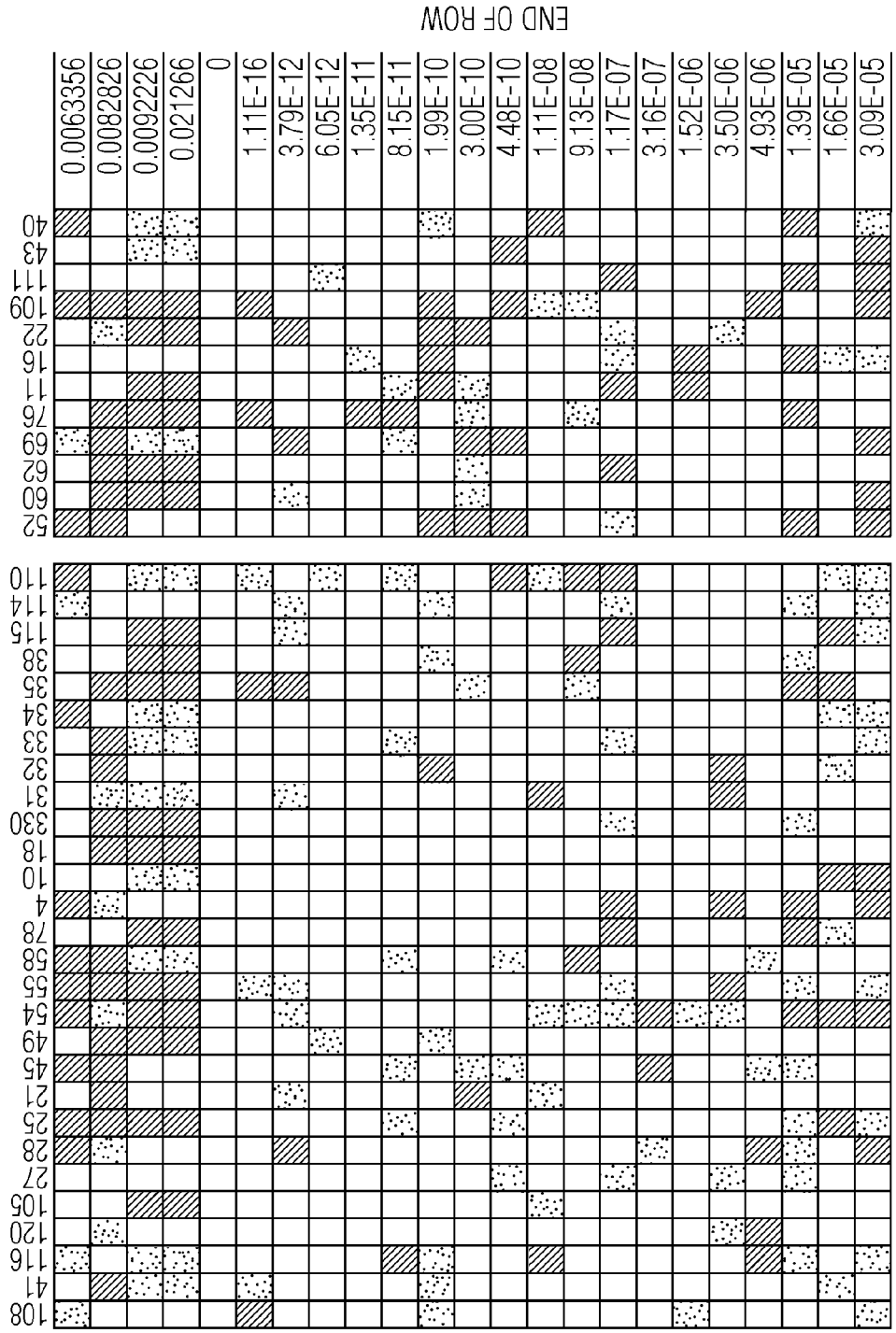
FIG. 24FFFF

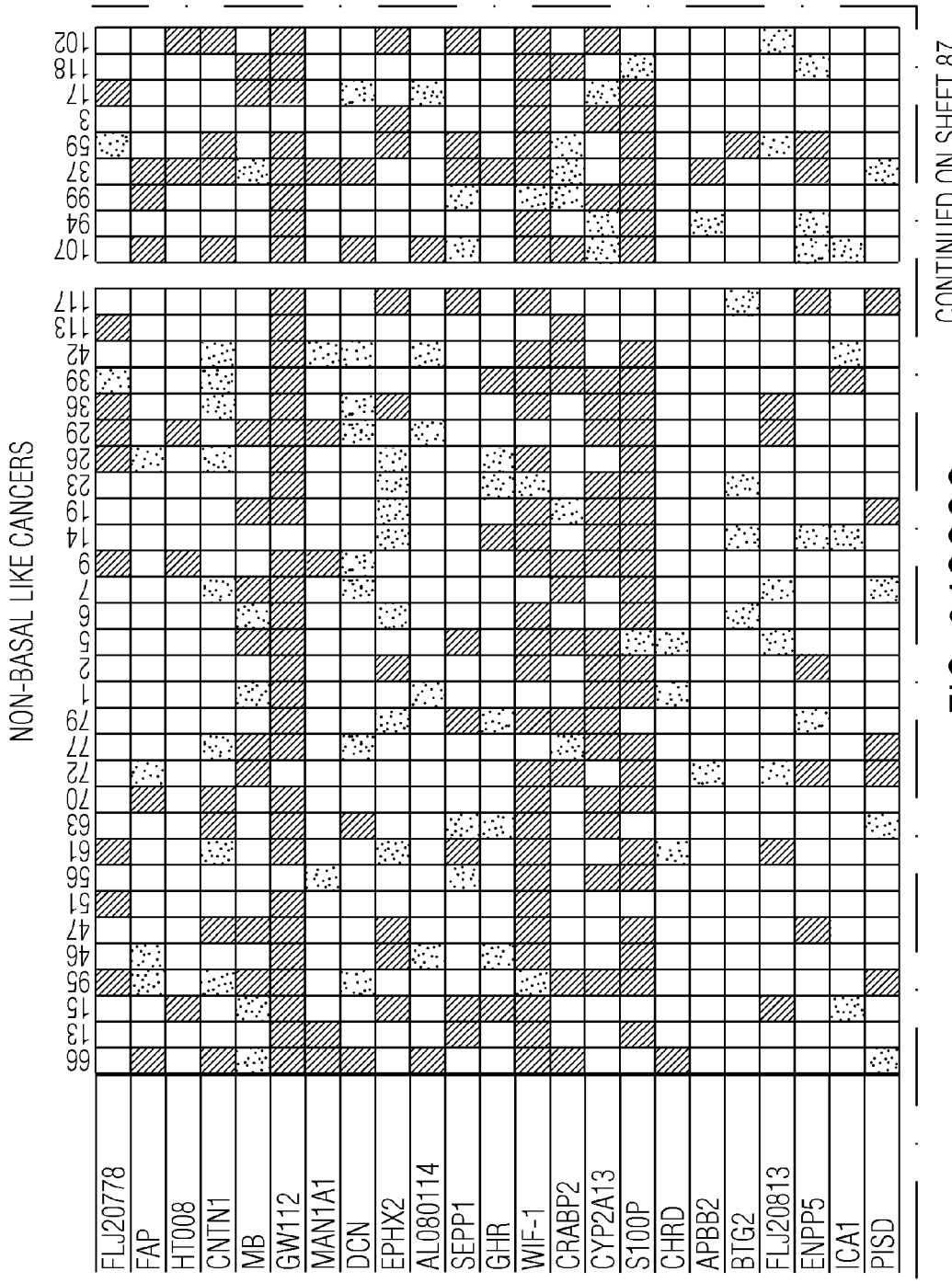
FIG. 24GGGG

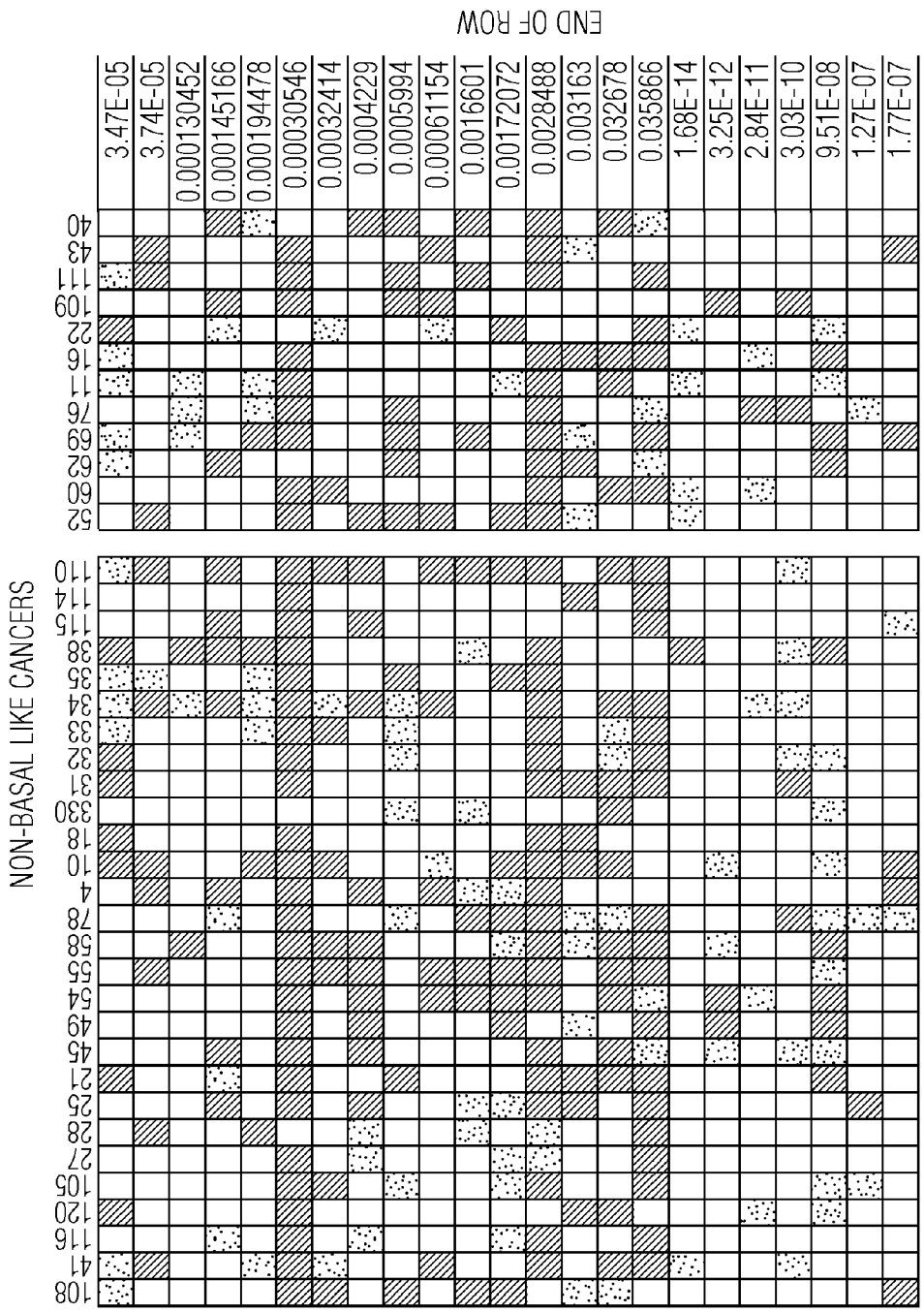
FIG. 24HHHH

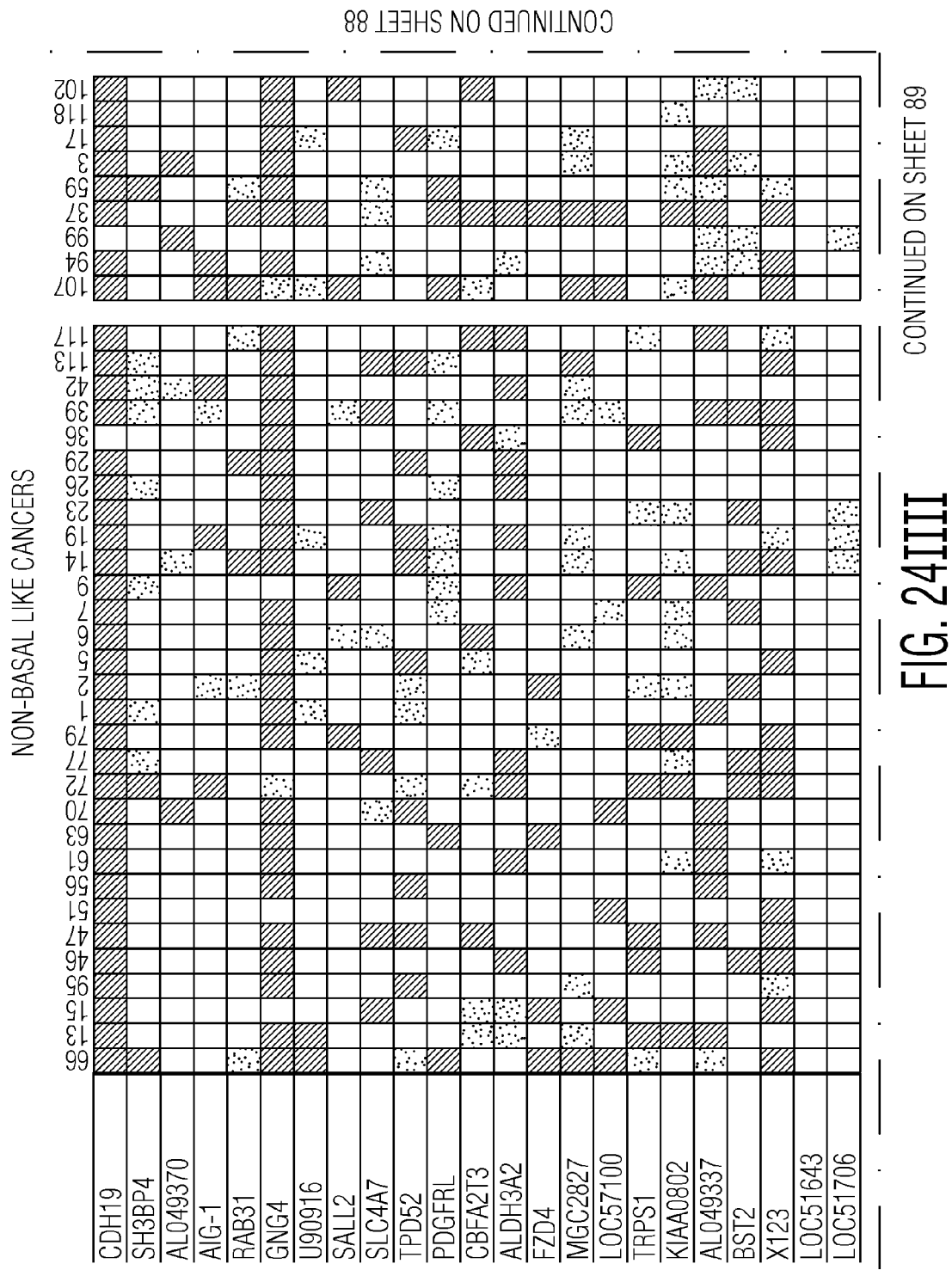
FIG. 24III

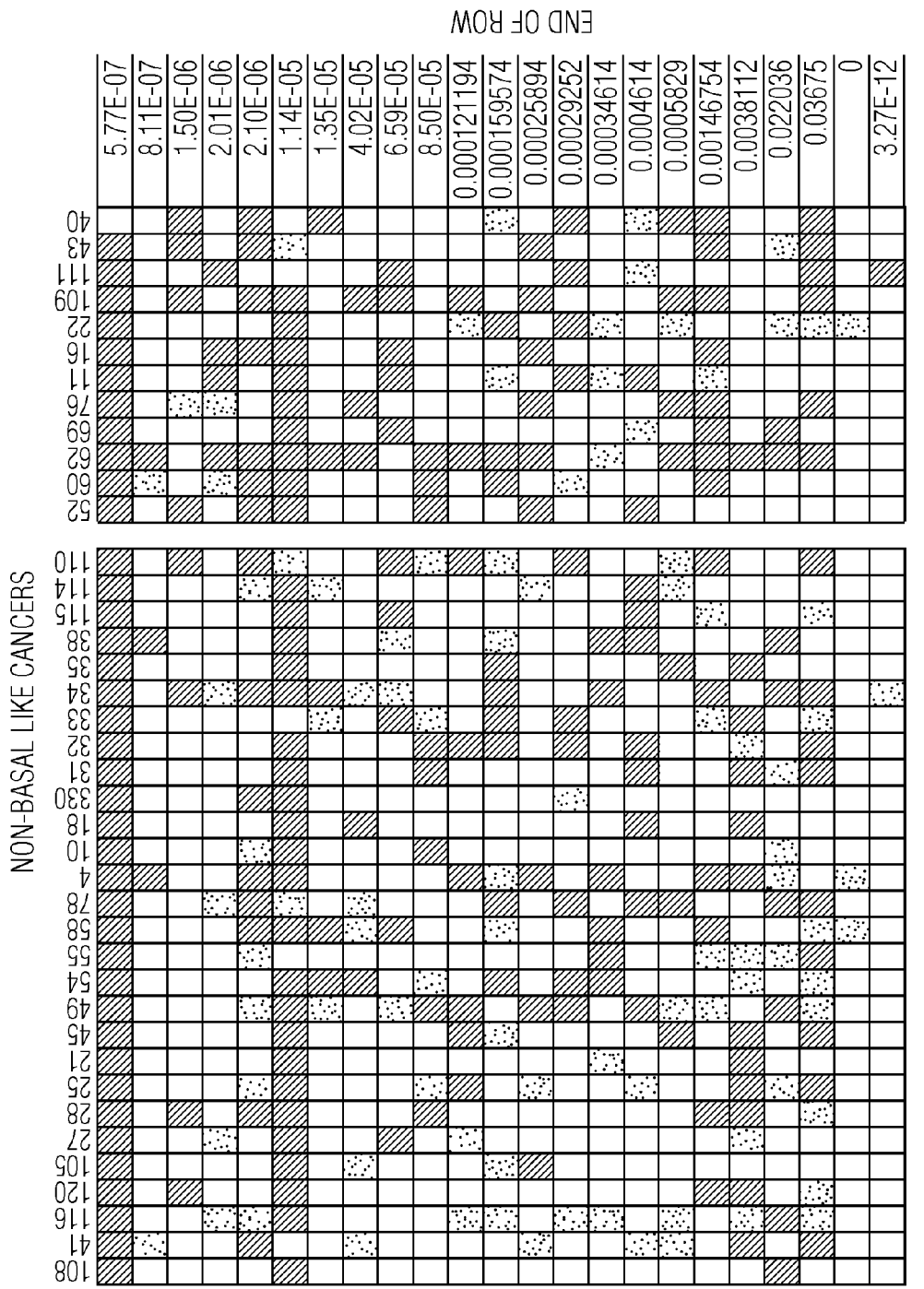
FIG. 24JJJJ

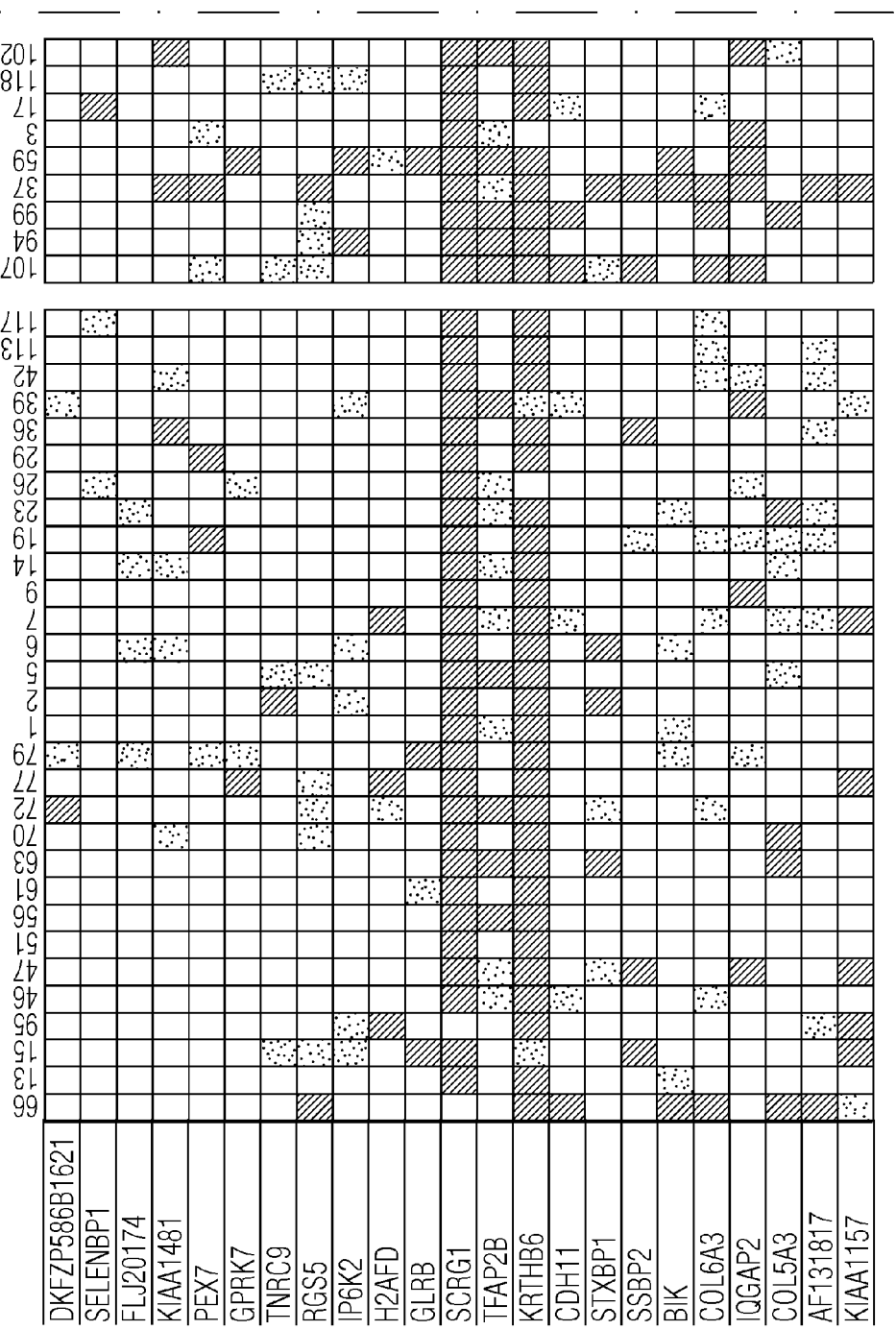
FIG. 24KKKK

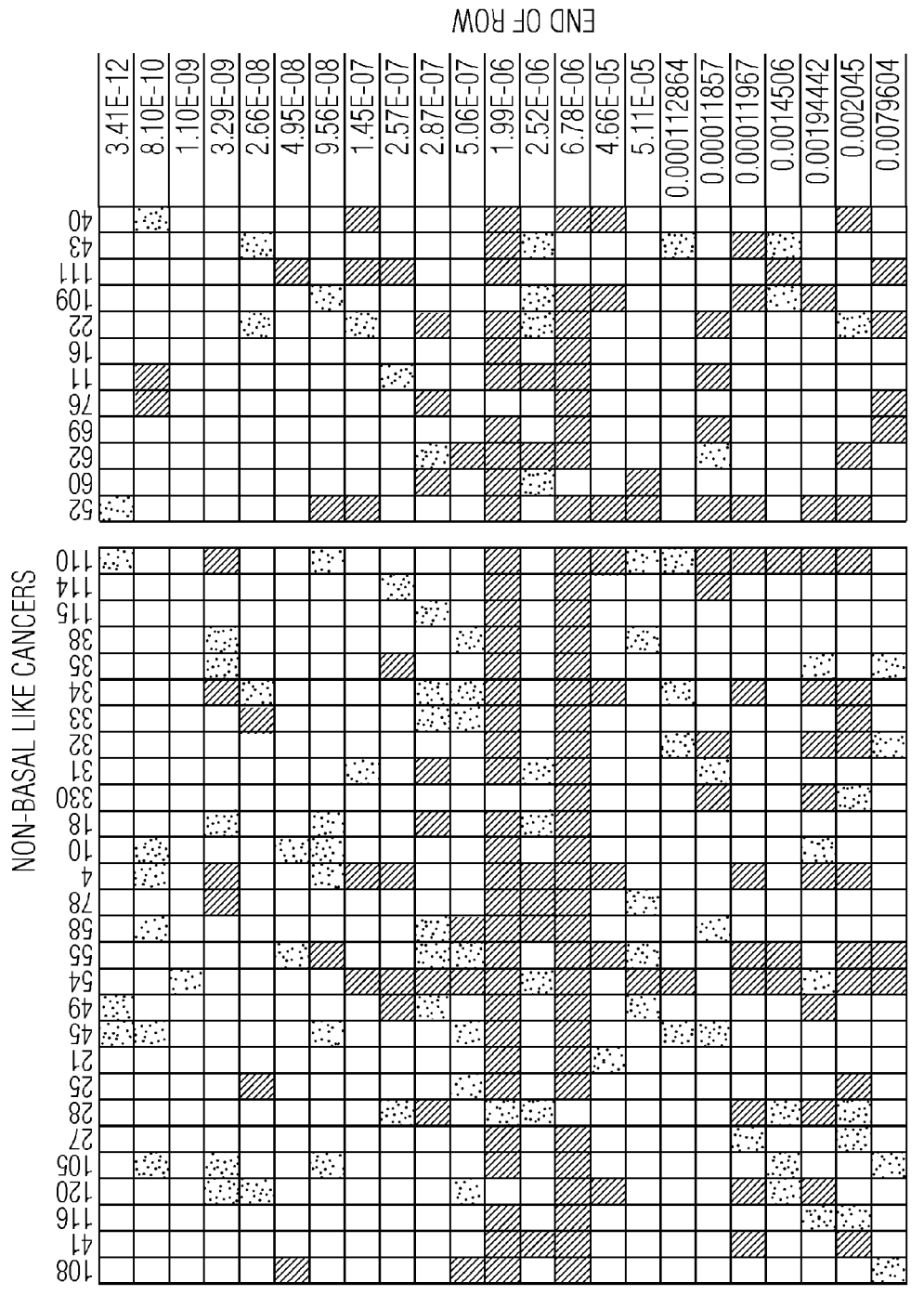
FIG. 24LLLL

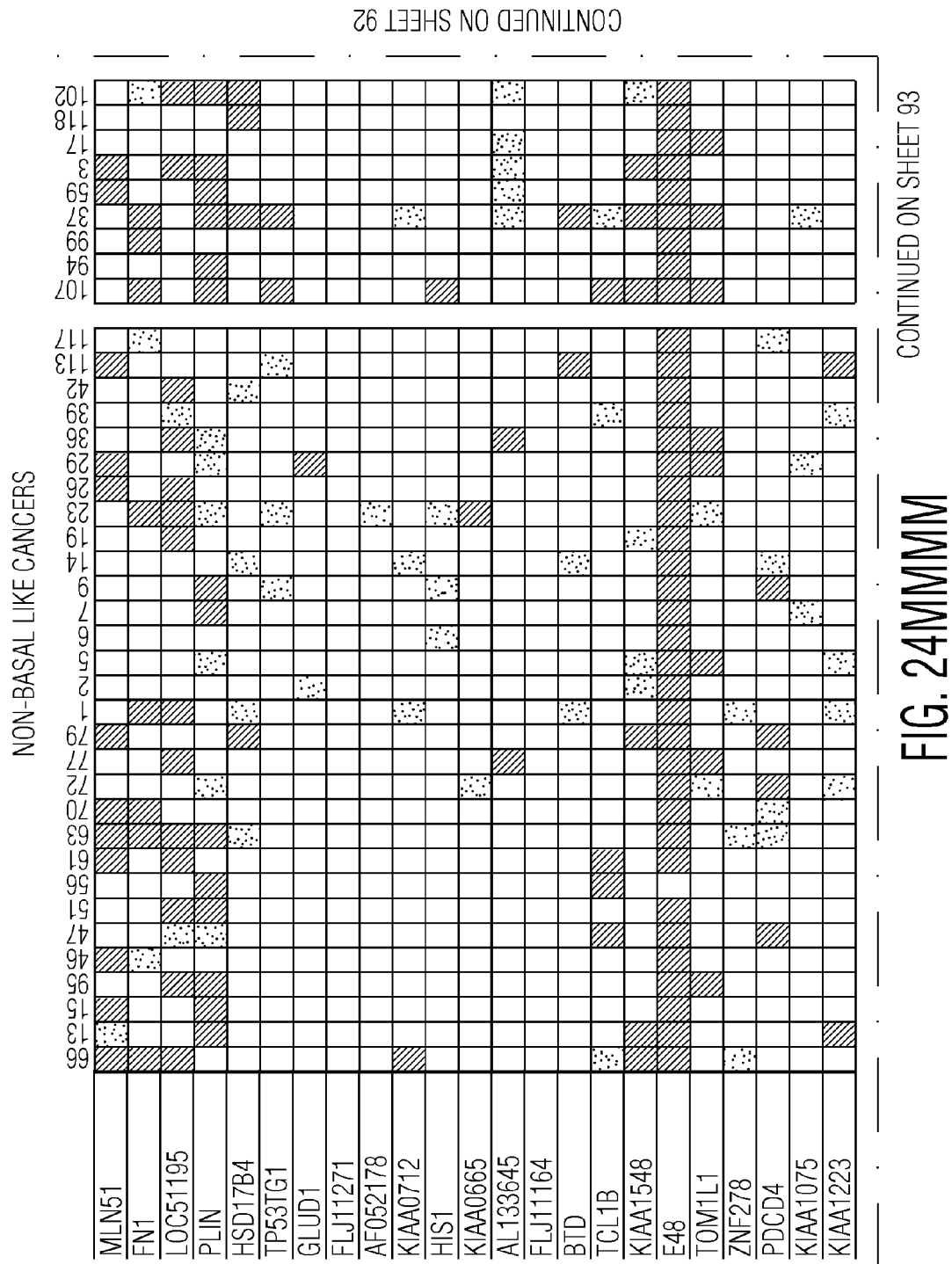
FIG. 24MMMM

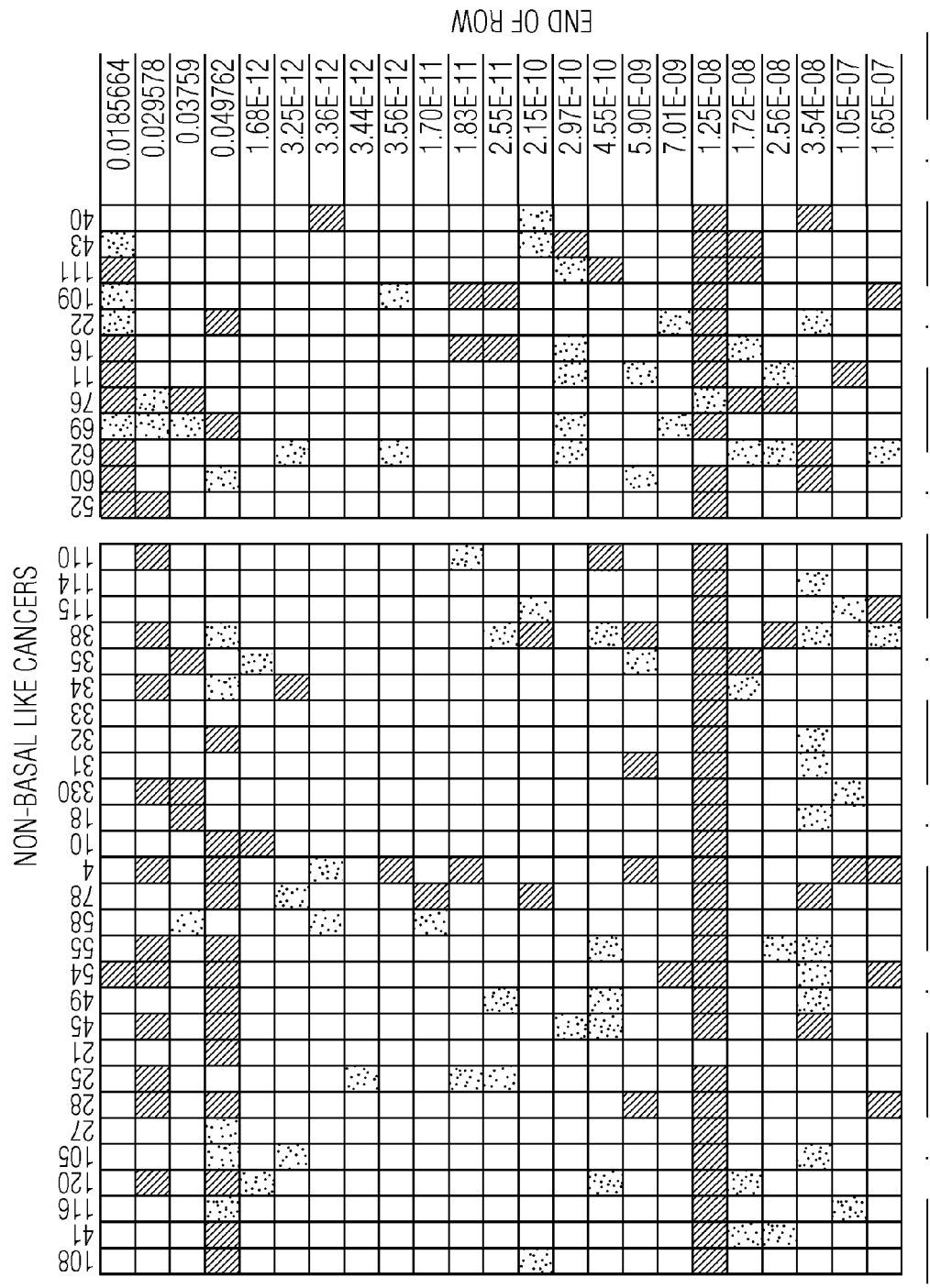
FIG. 24NNNN

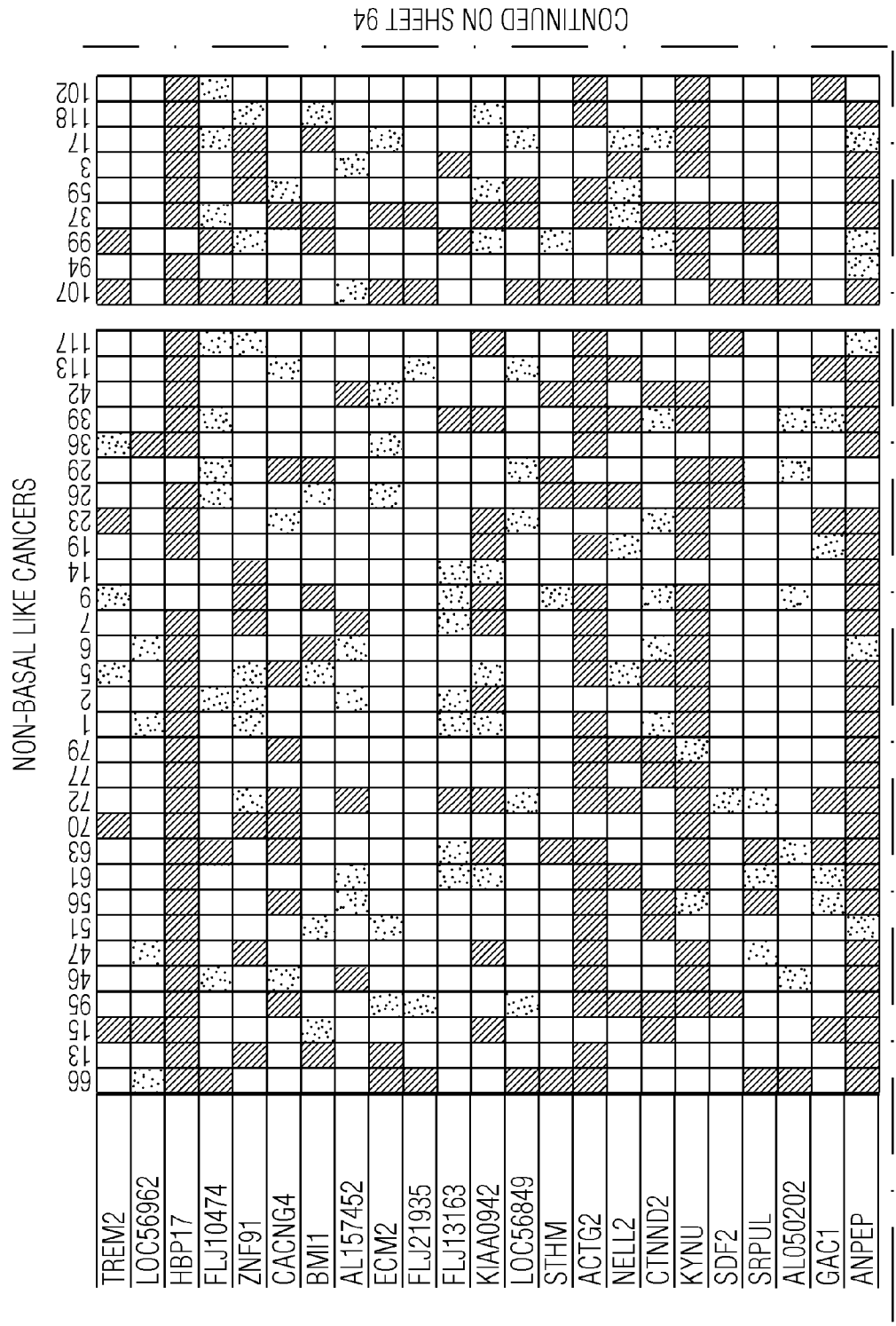
FIG. 240000

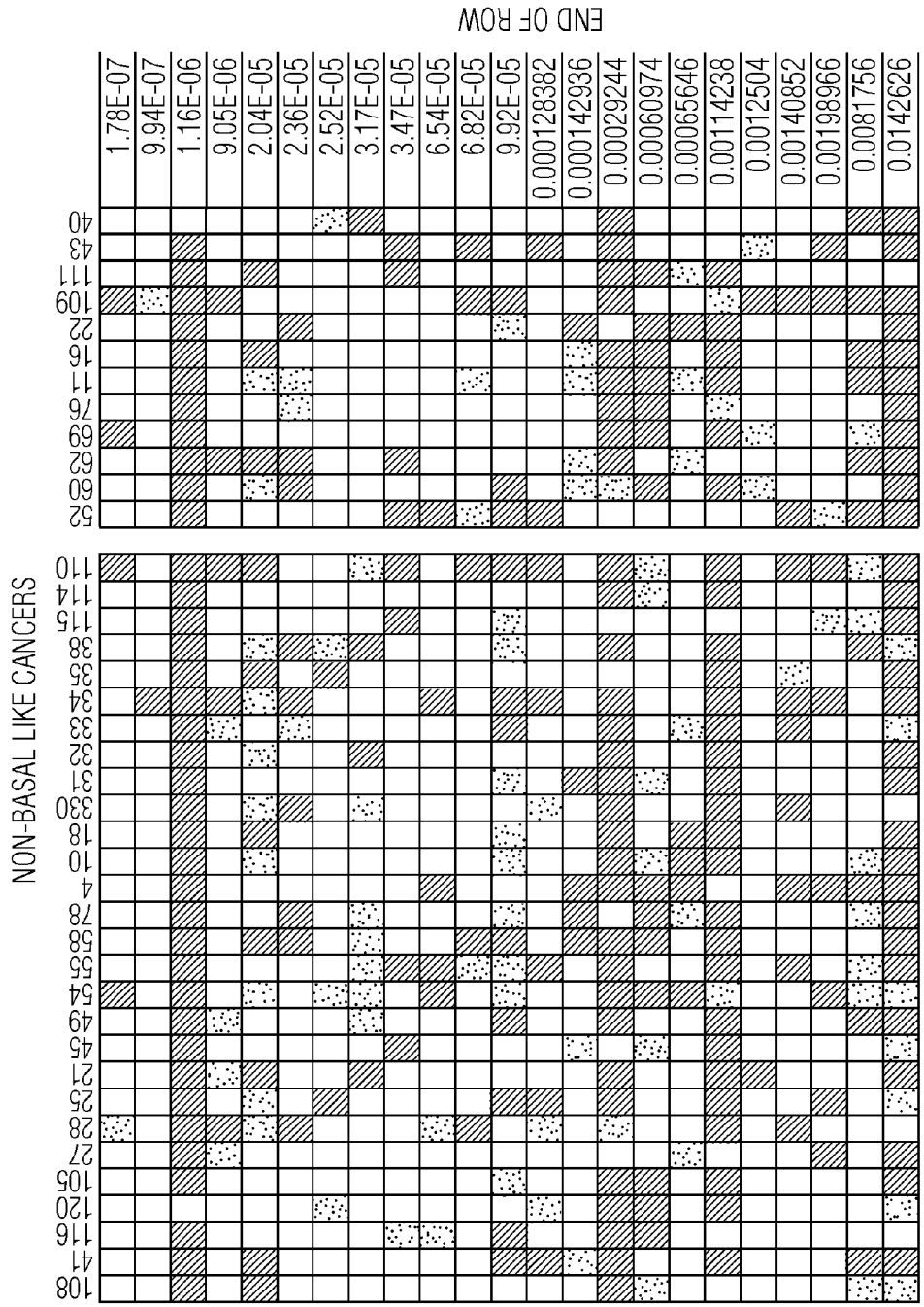
FIG. 24PPPP

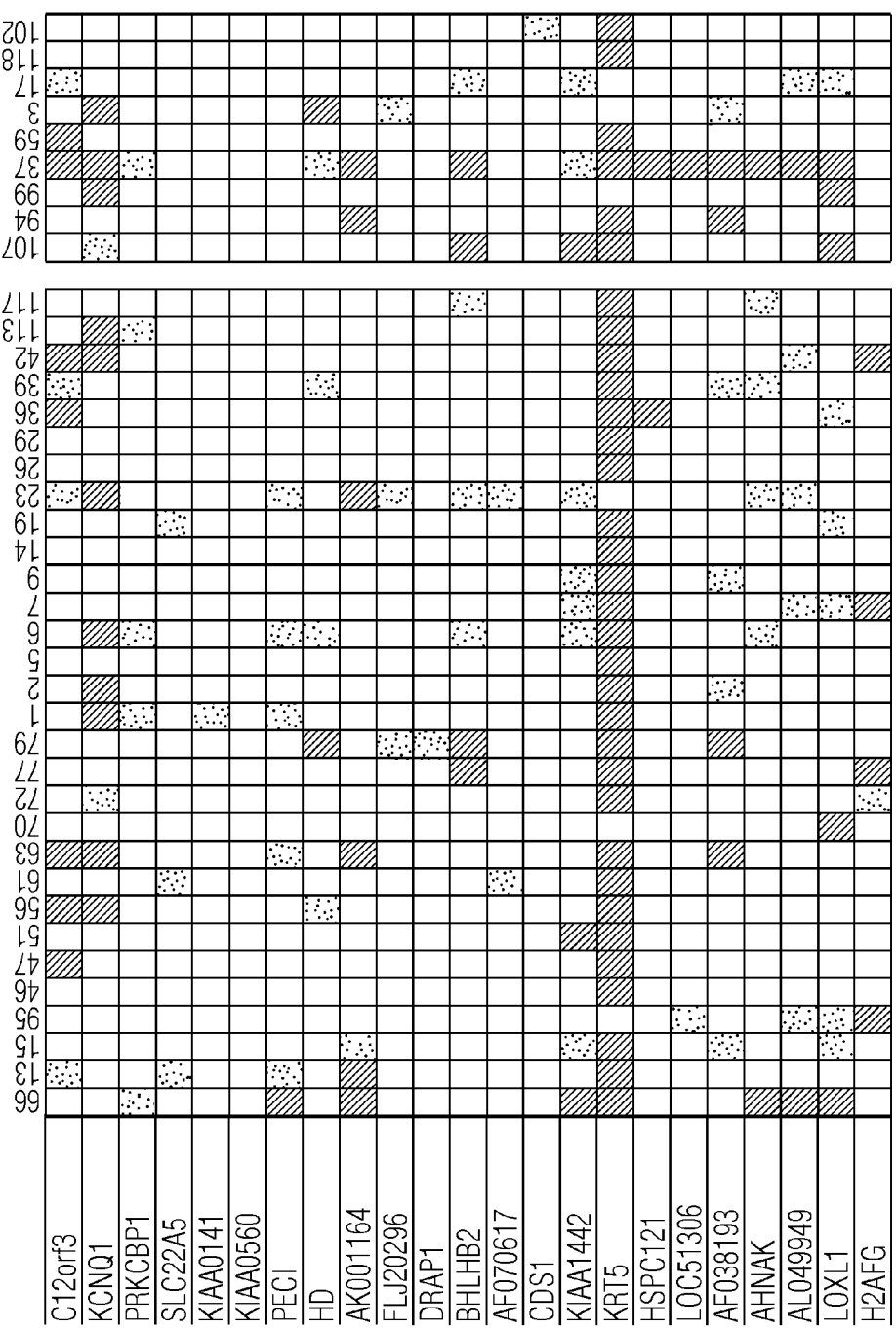
FIG. 24QQQQ

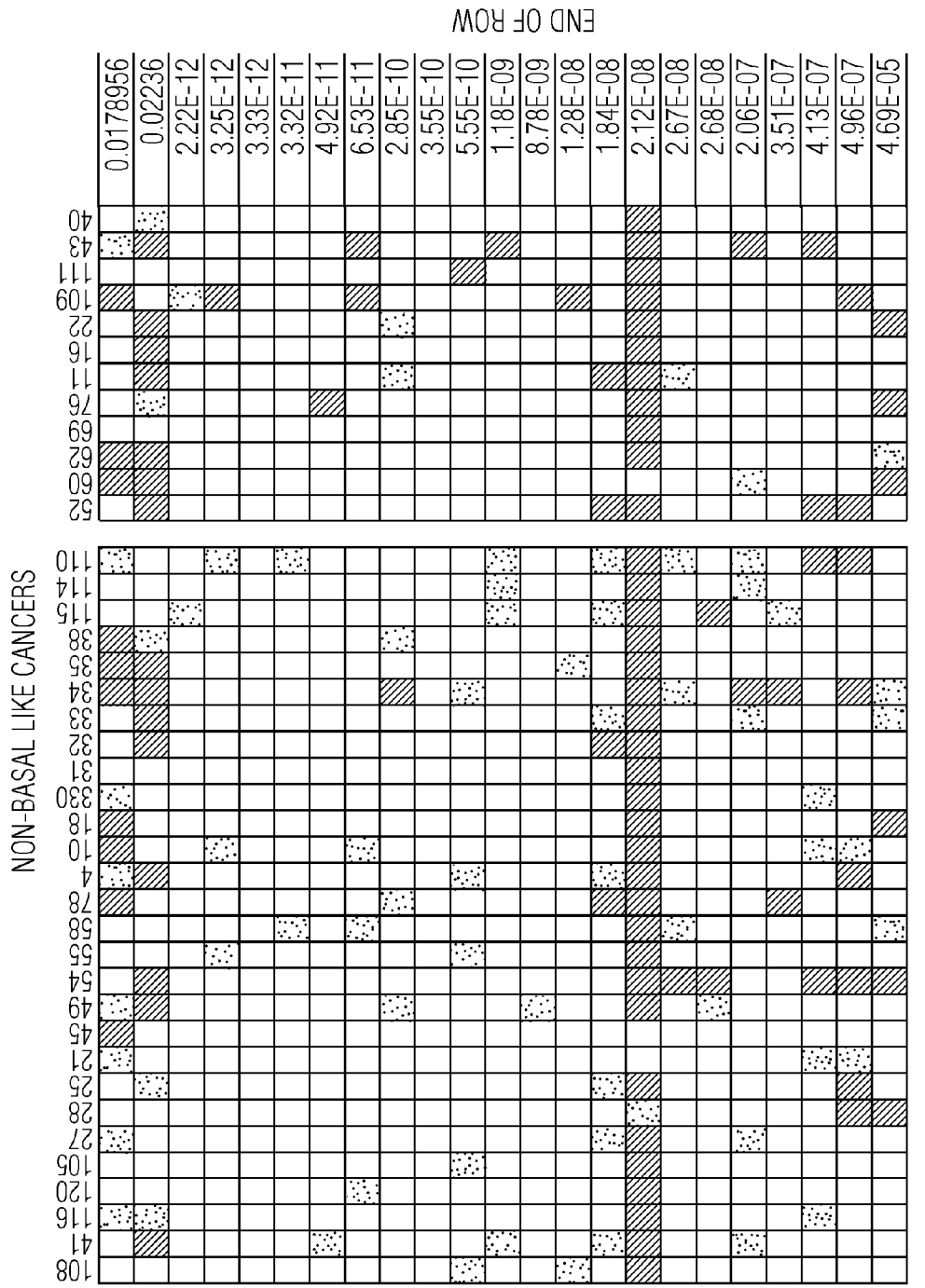
FIG. 24RRRR

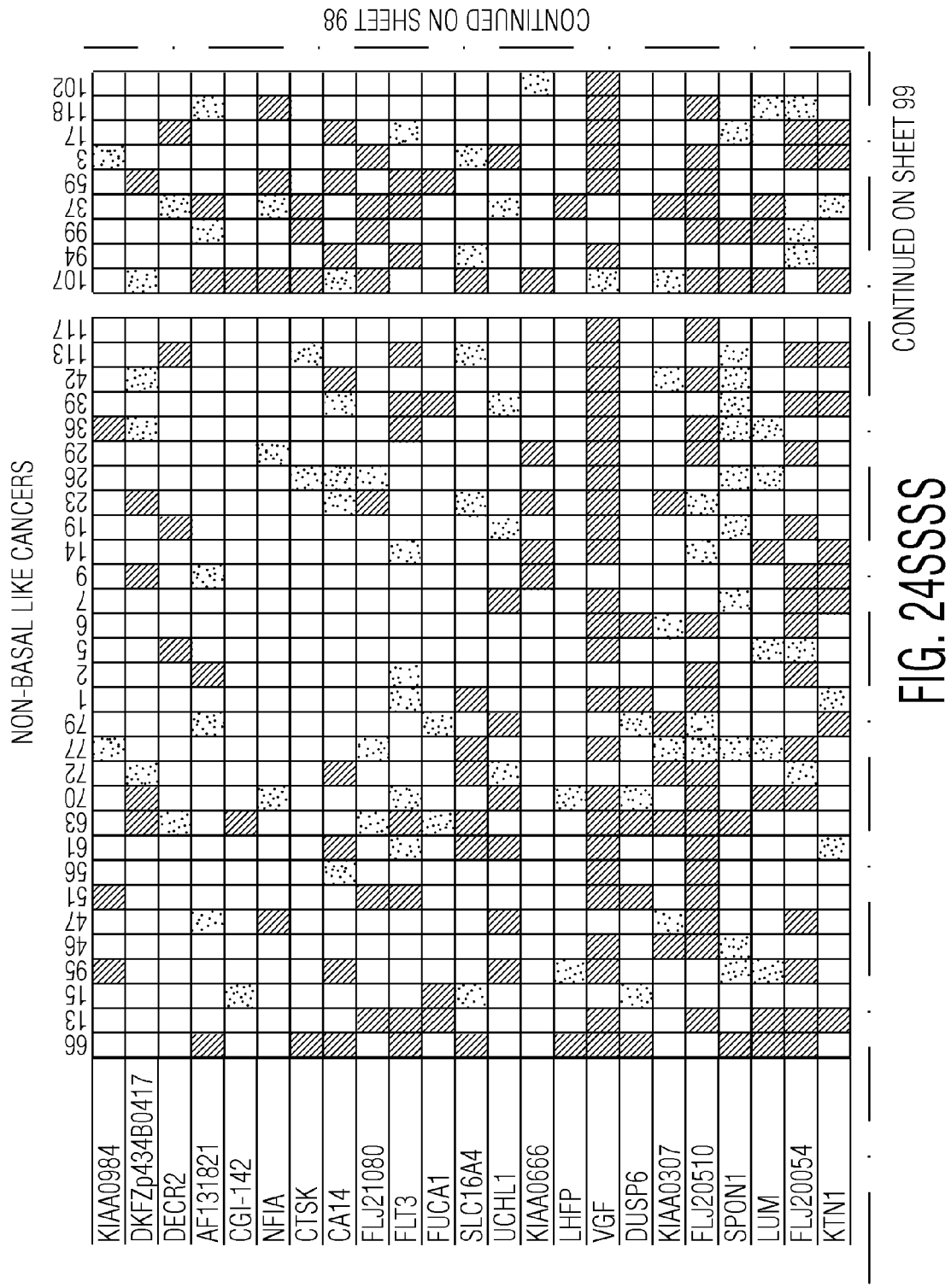
FIG. 24SSSS

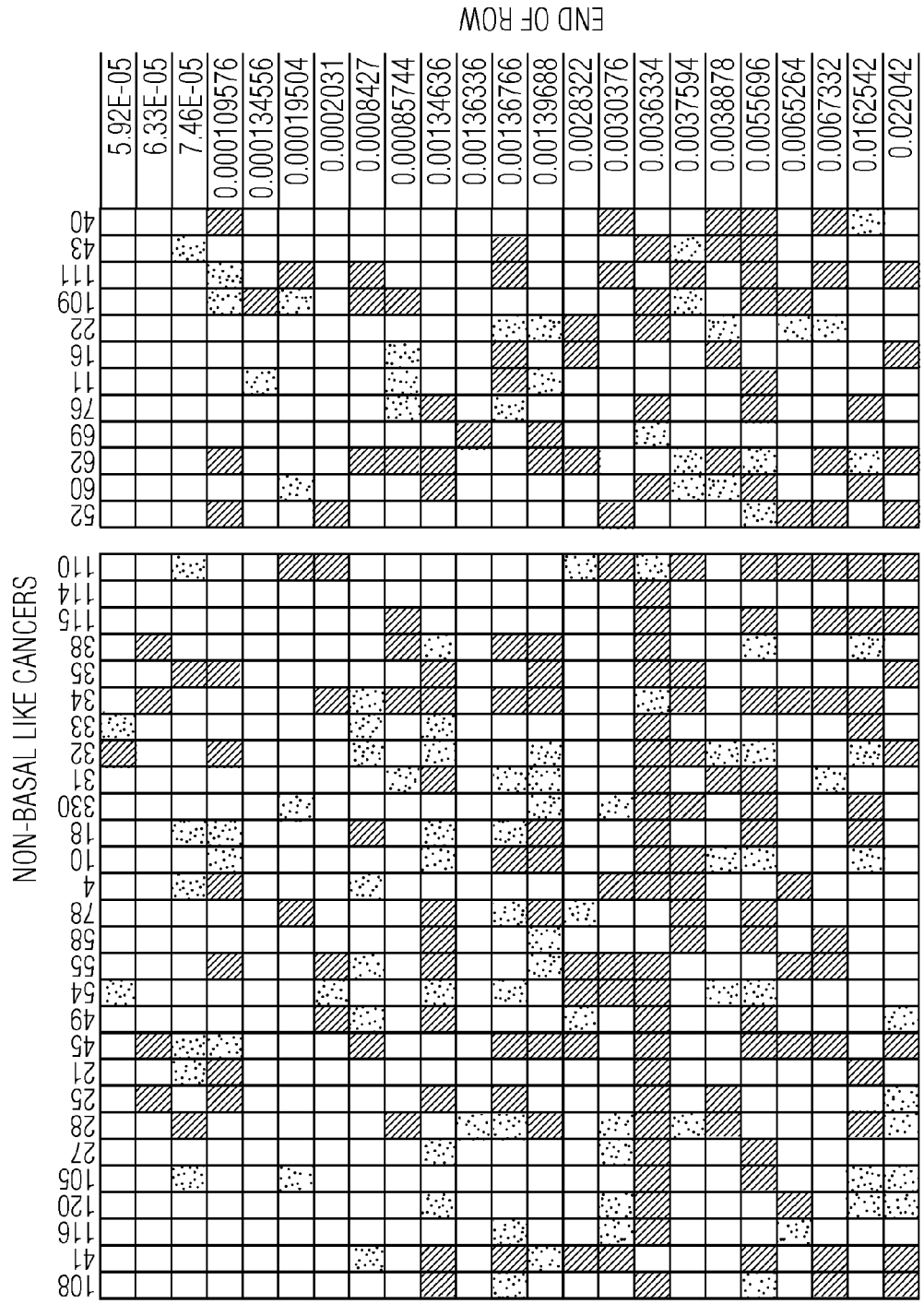
FIG. 24TTTT

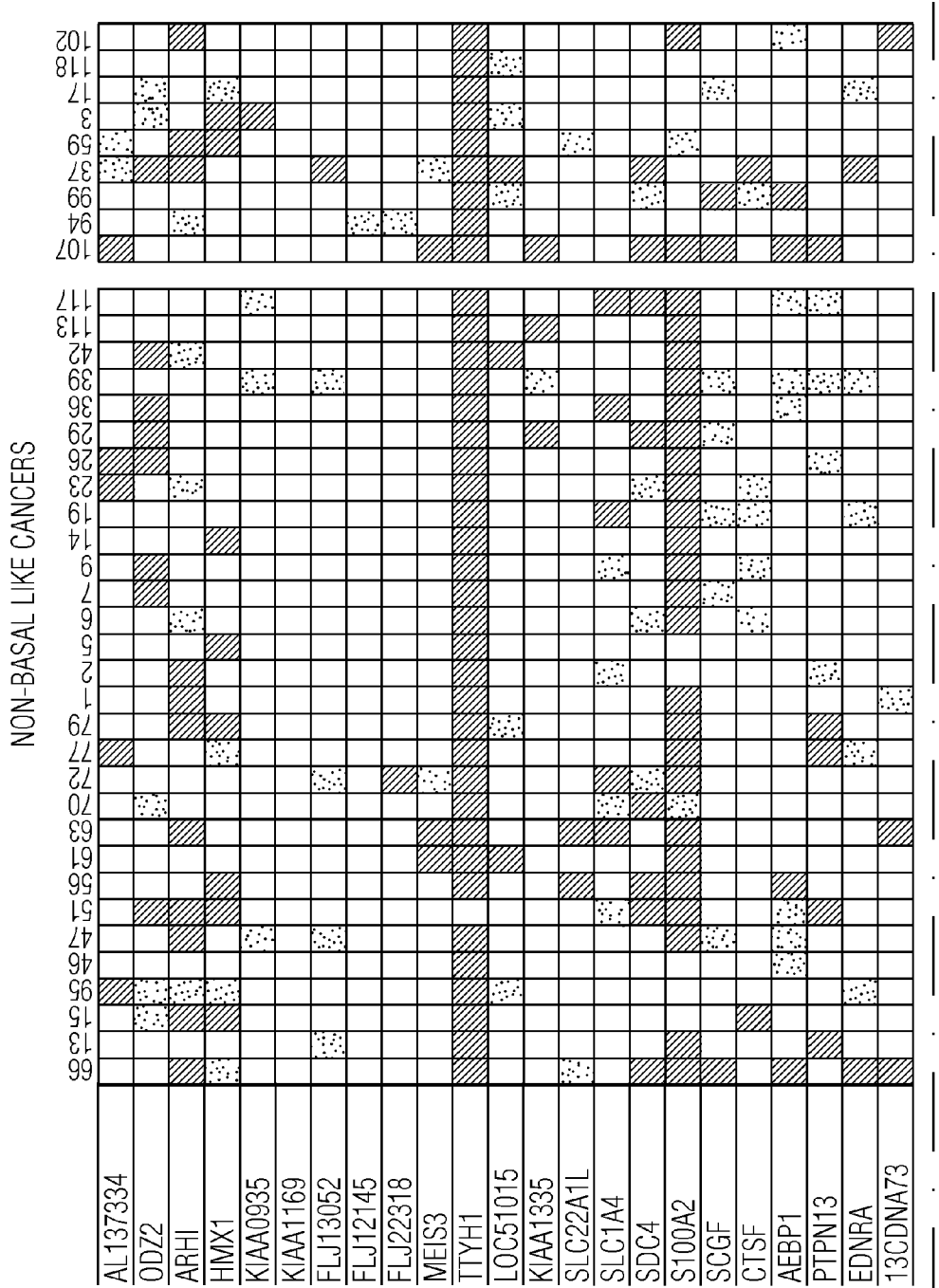
FIG. 24UUUU

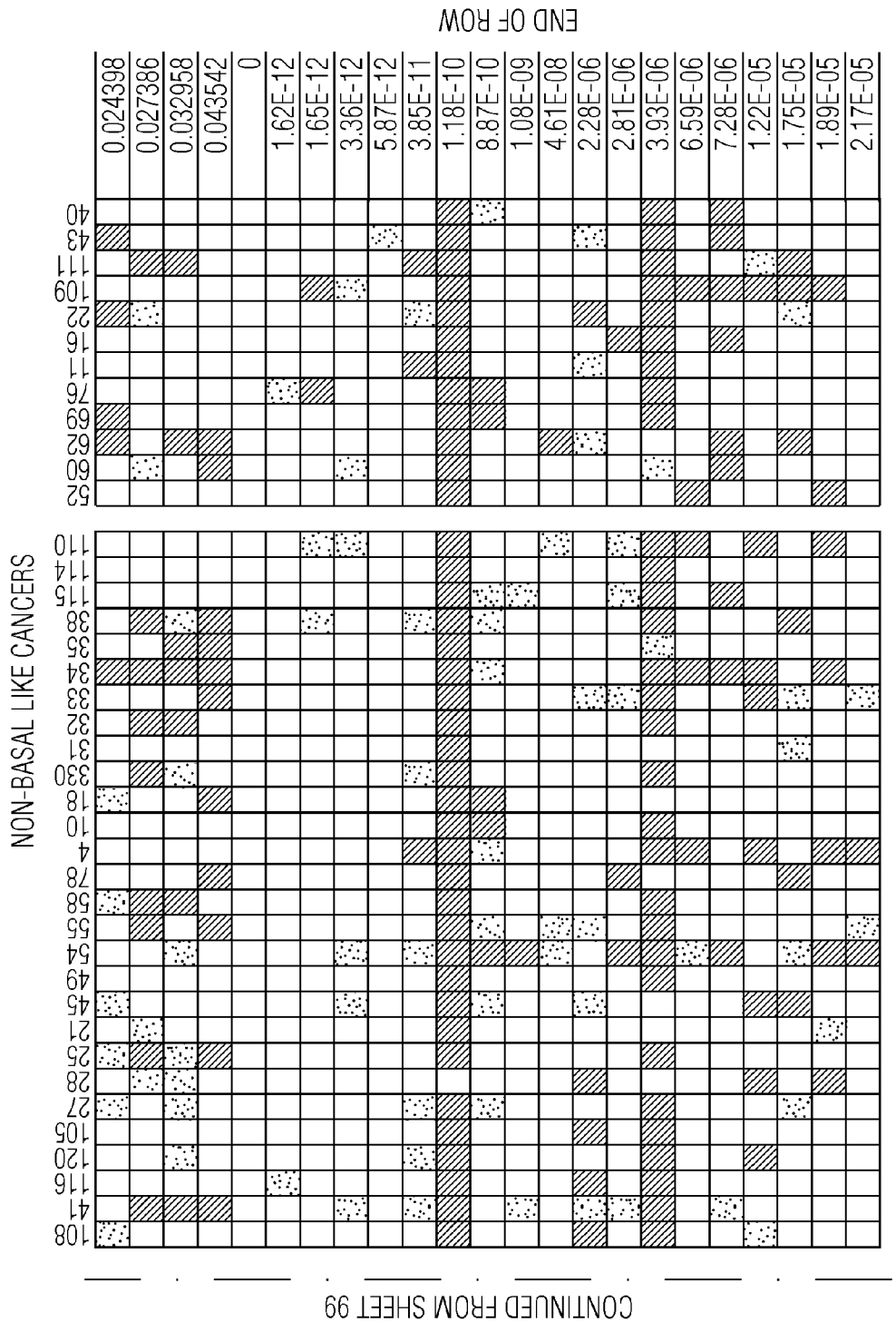
FIG. 24VVV

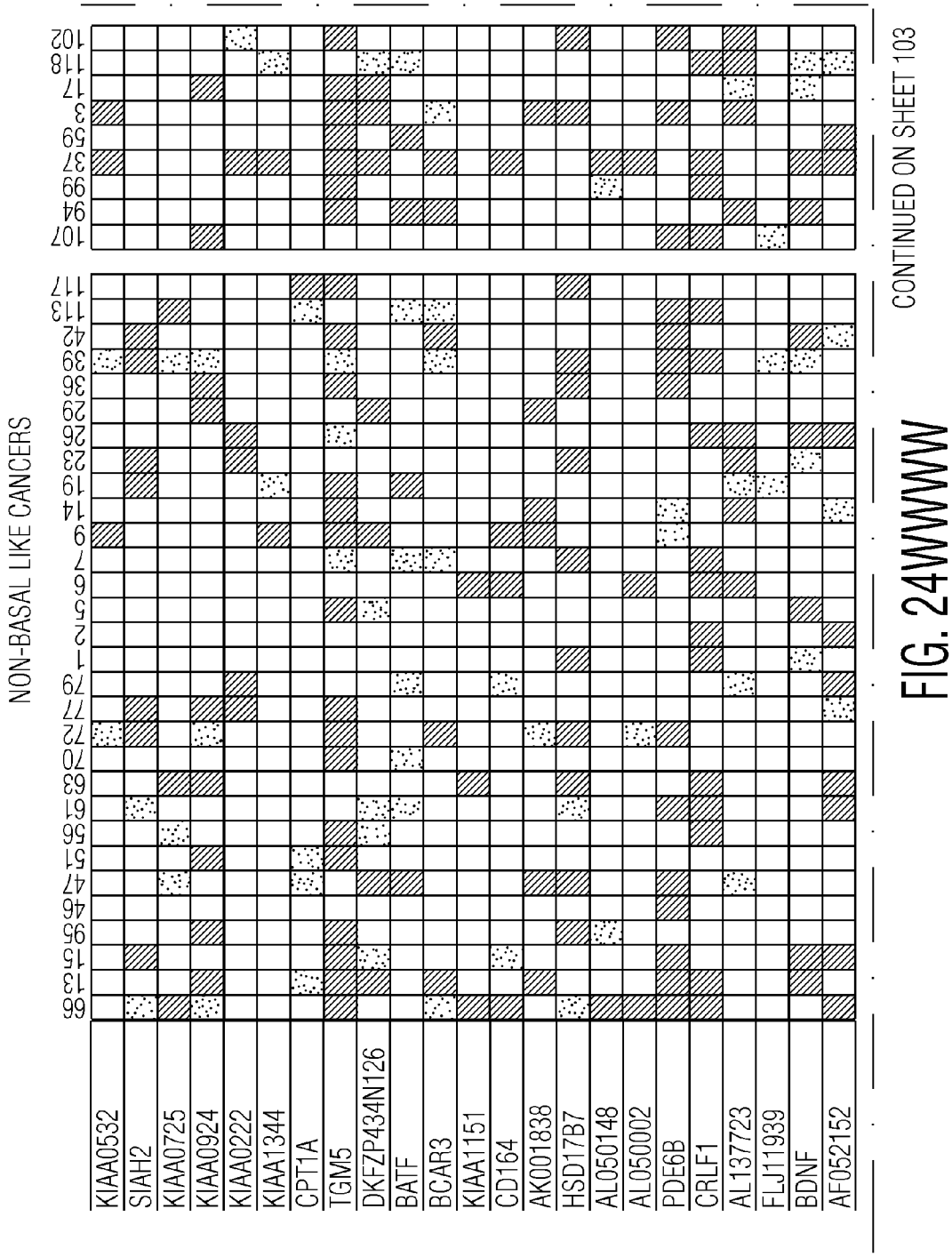
FIG. 24WWWWW

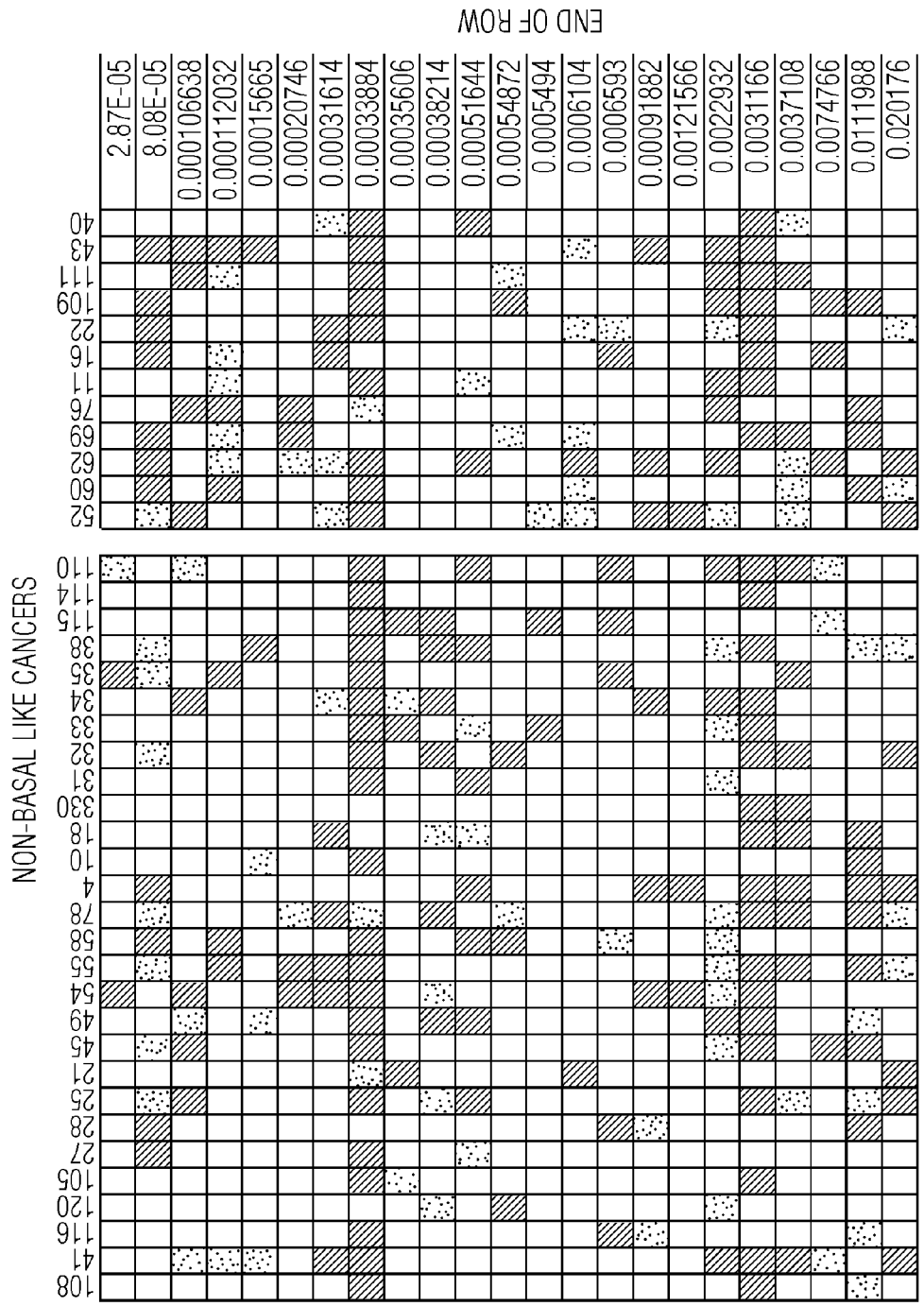
FIG. 24XXXX

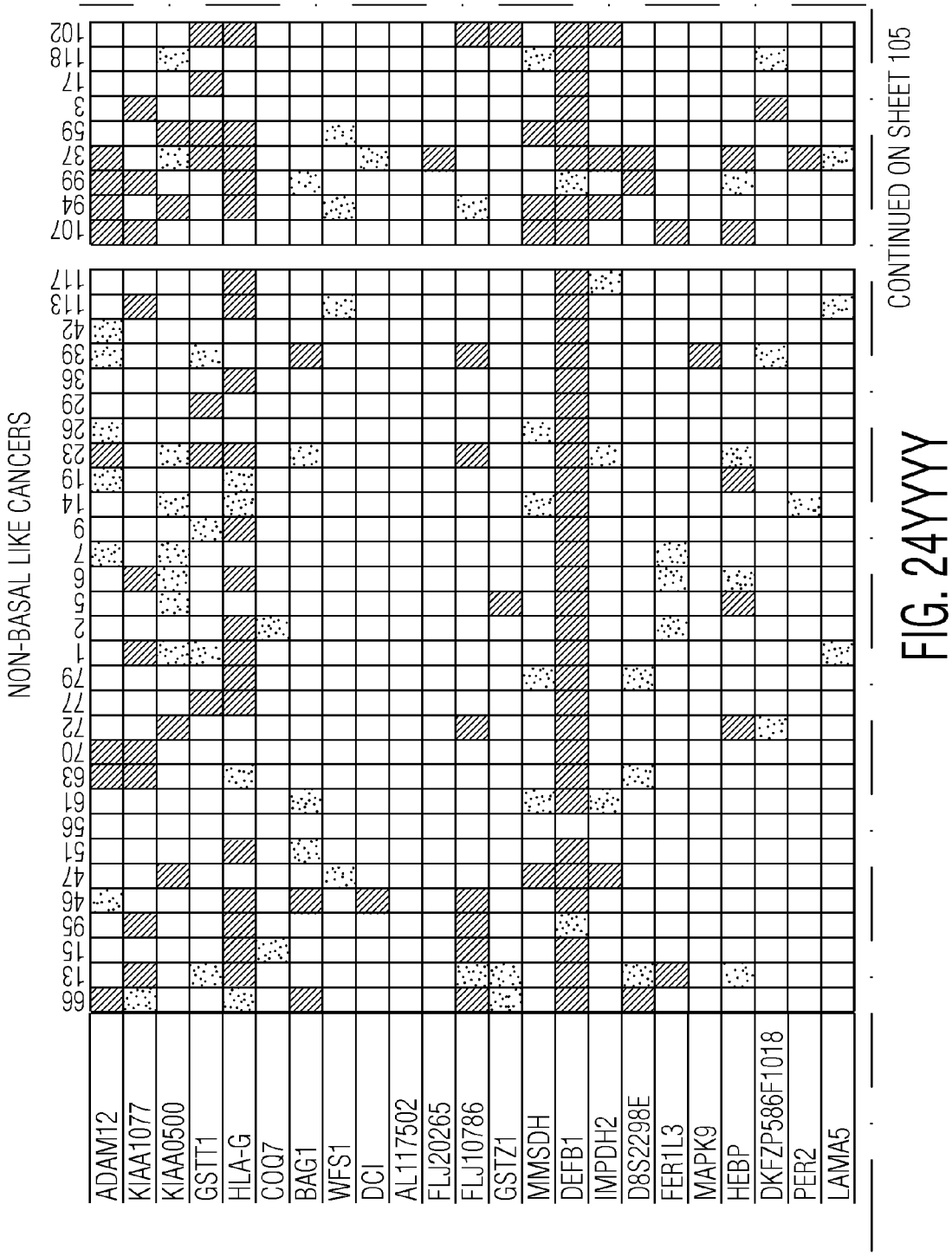
FIG. 24YYYY

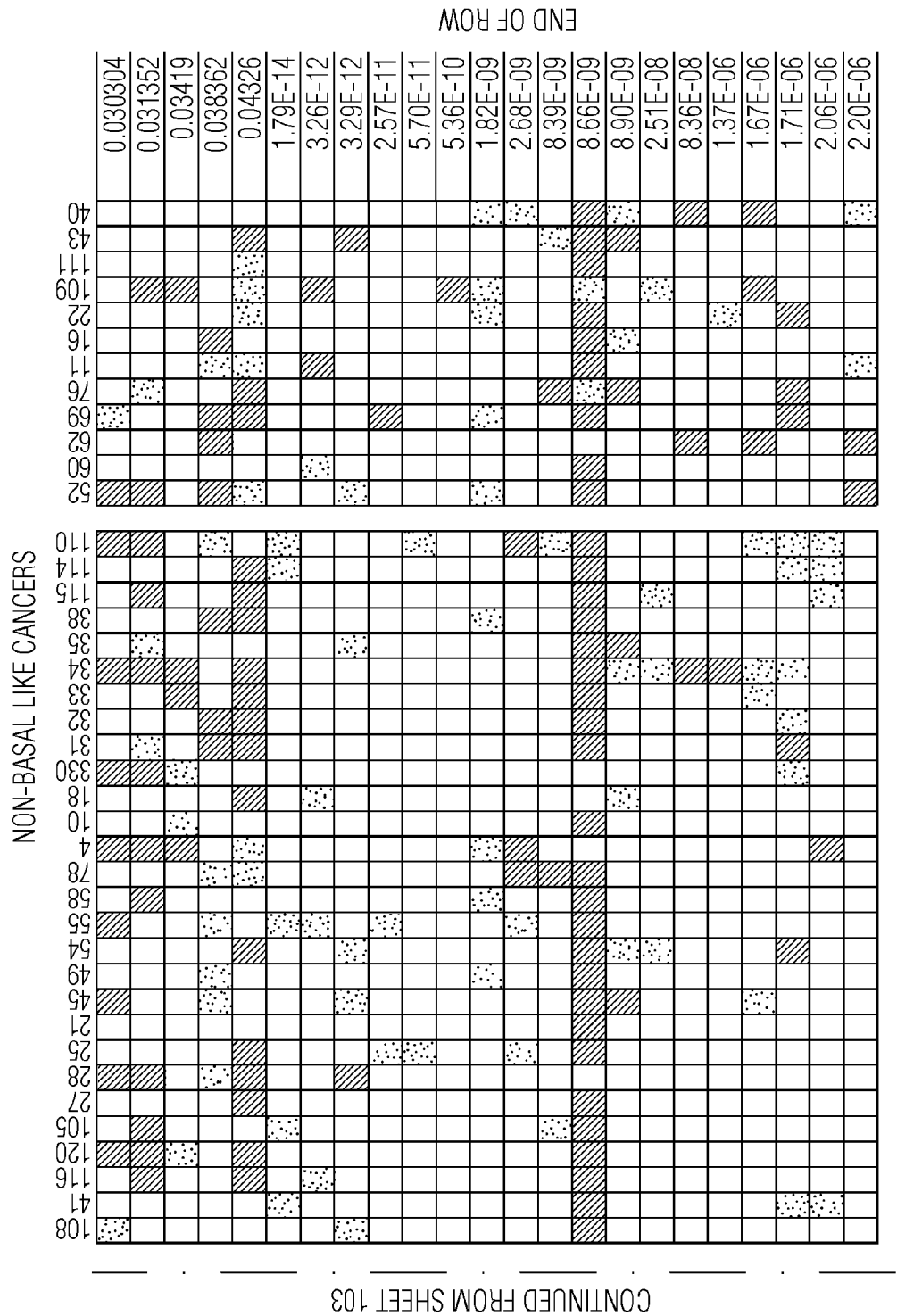
FIG. 24ZZZZ

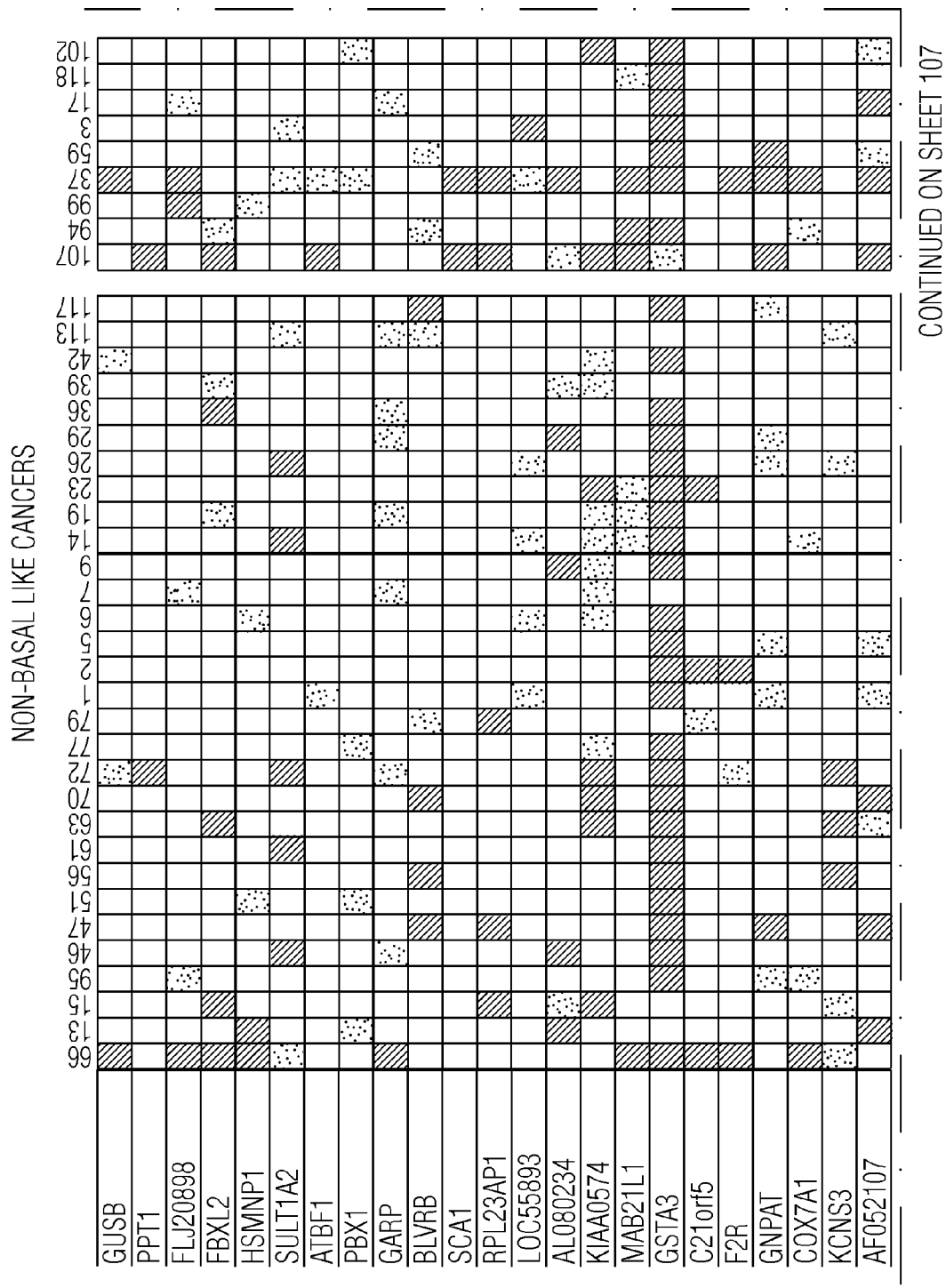
FIG. 24AAAAAA

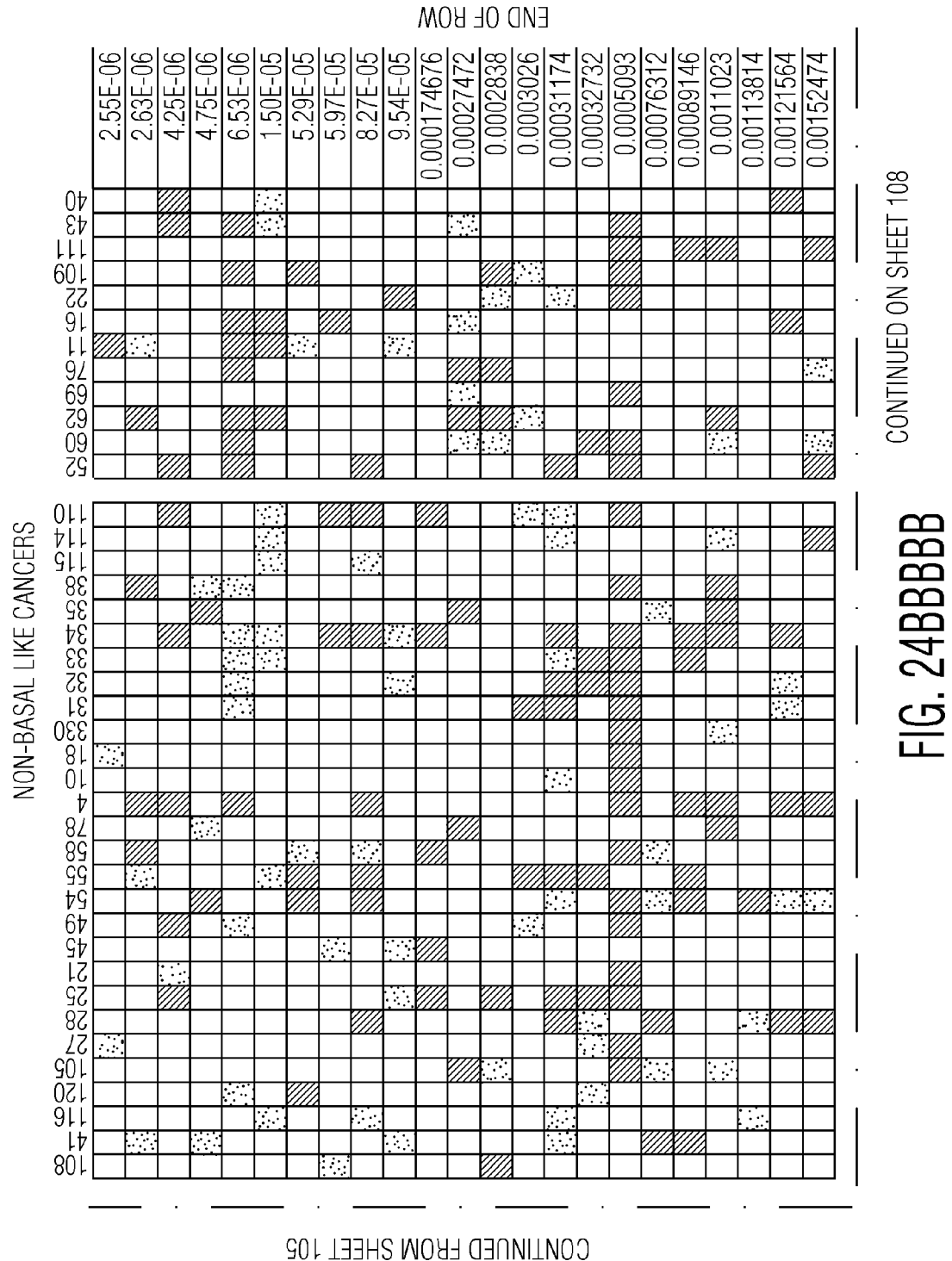
FIG. 24BBBBB

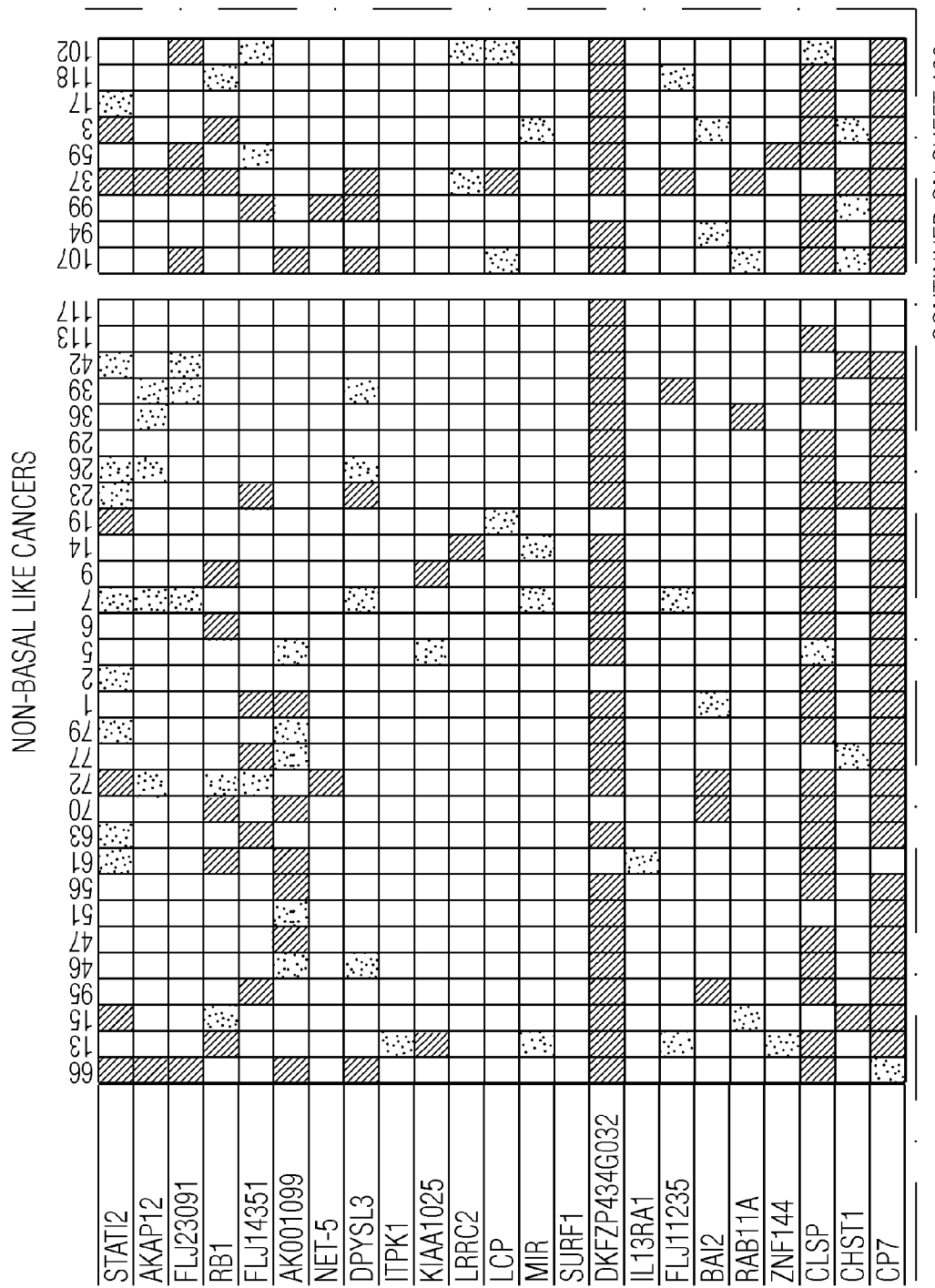
FIG. 24CCCCC

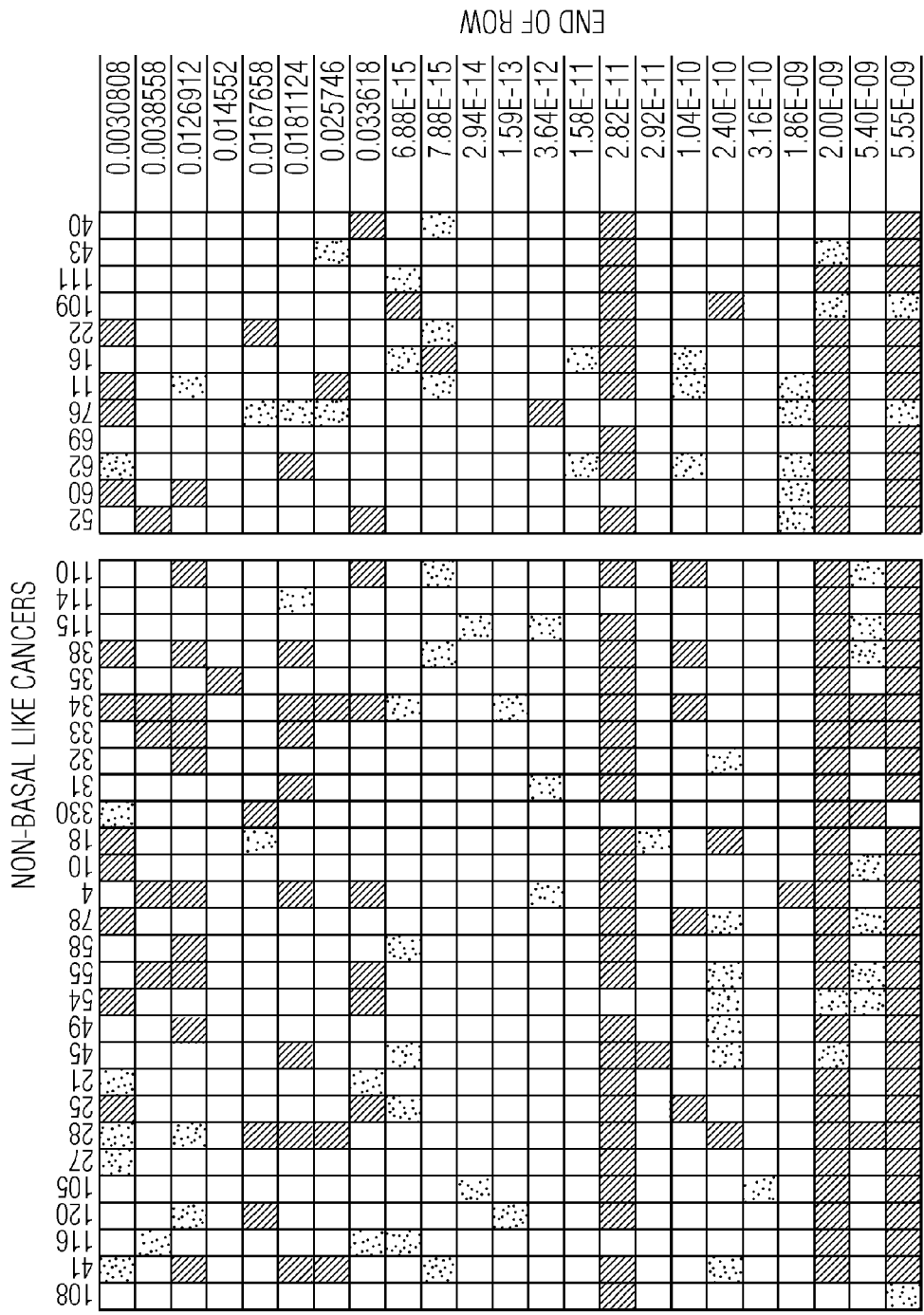
FIG. 24DDDDDD

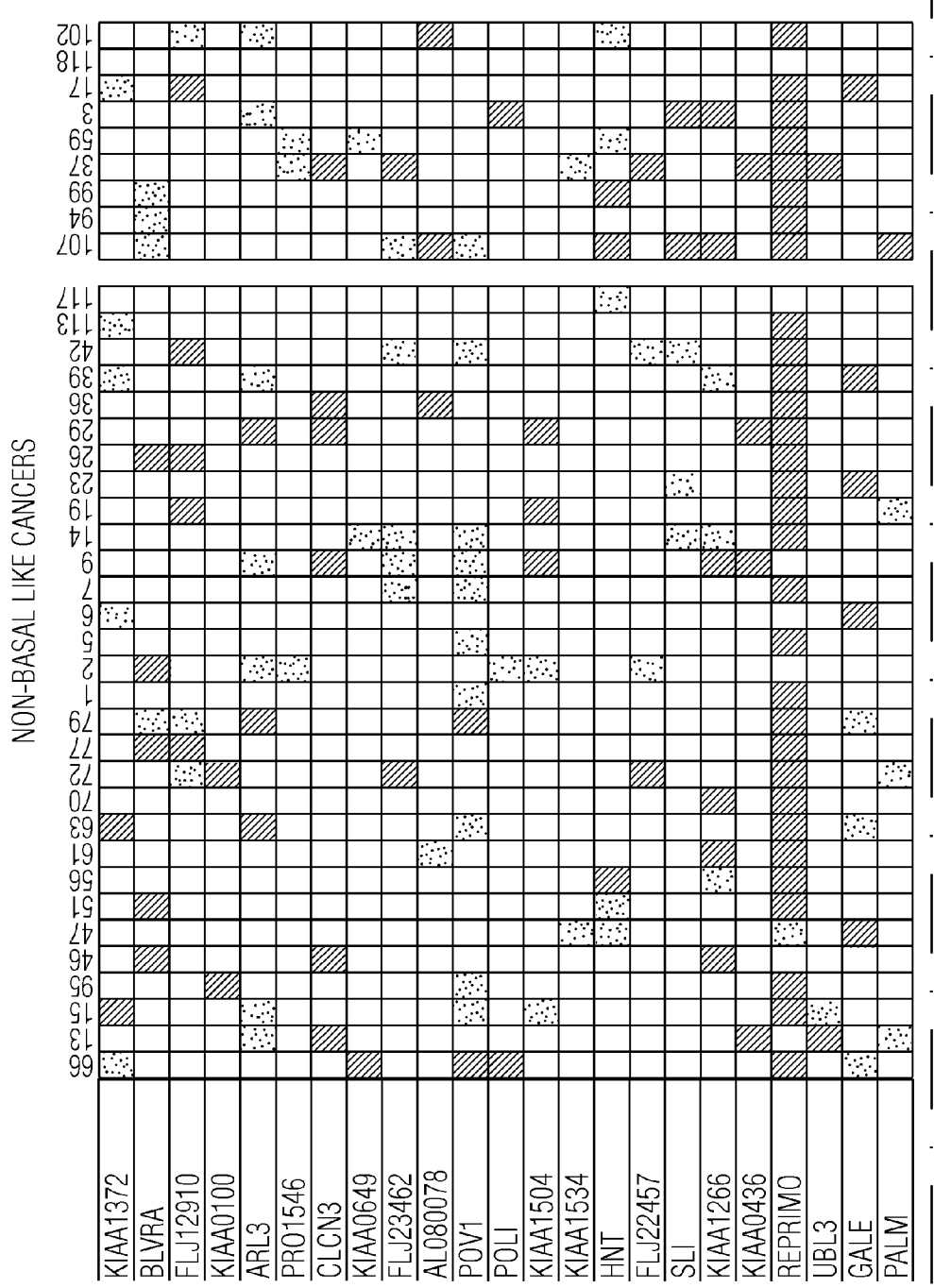
FIG. 24EEEEE

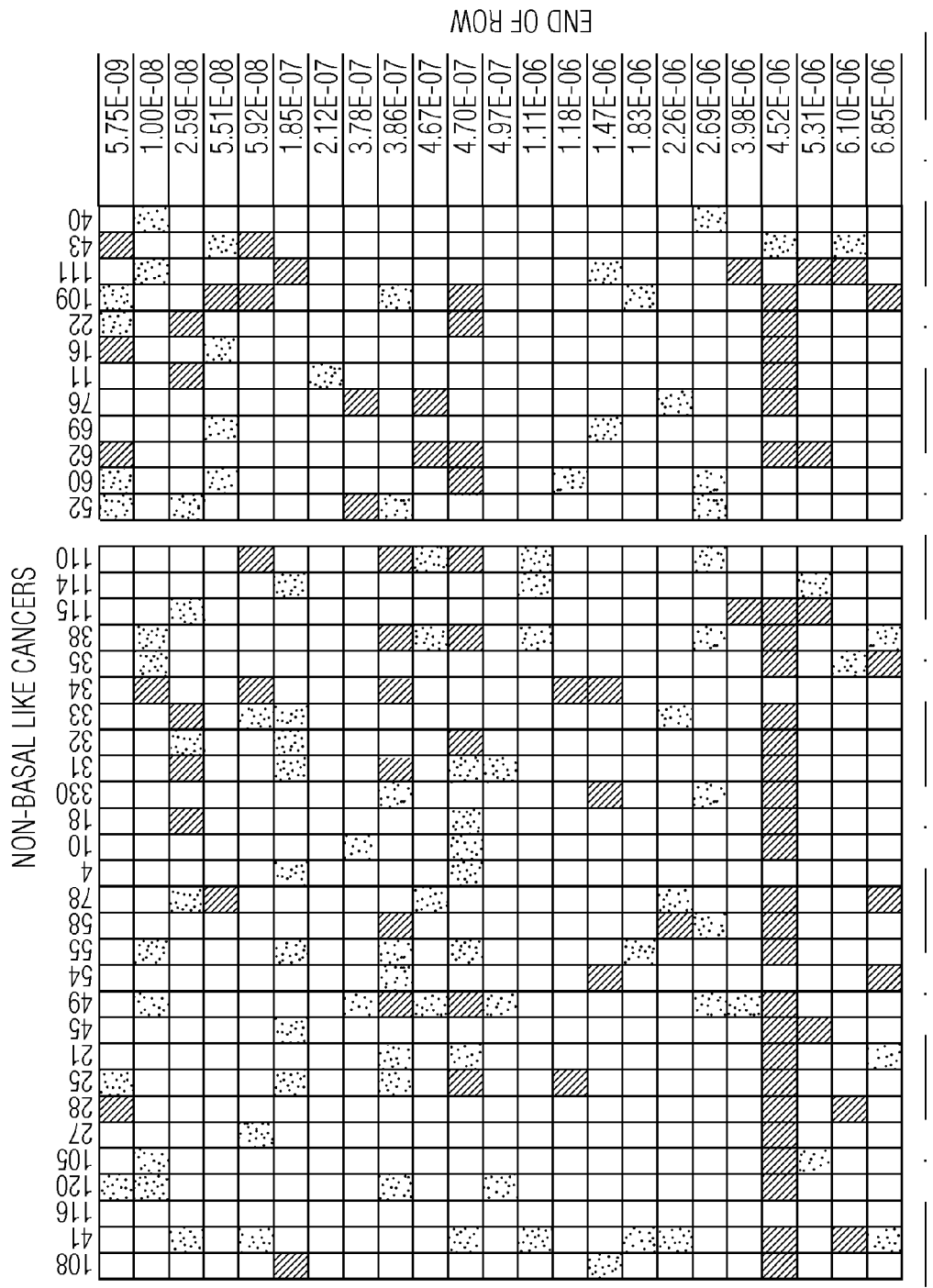
FIG. 24FFFFF

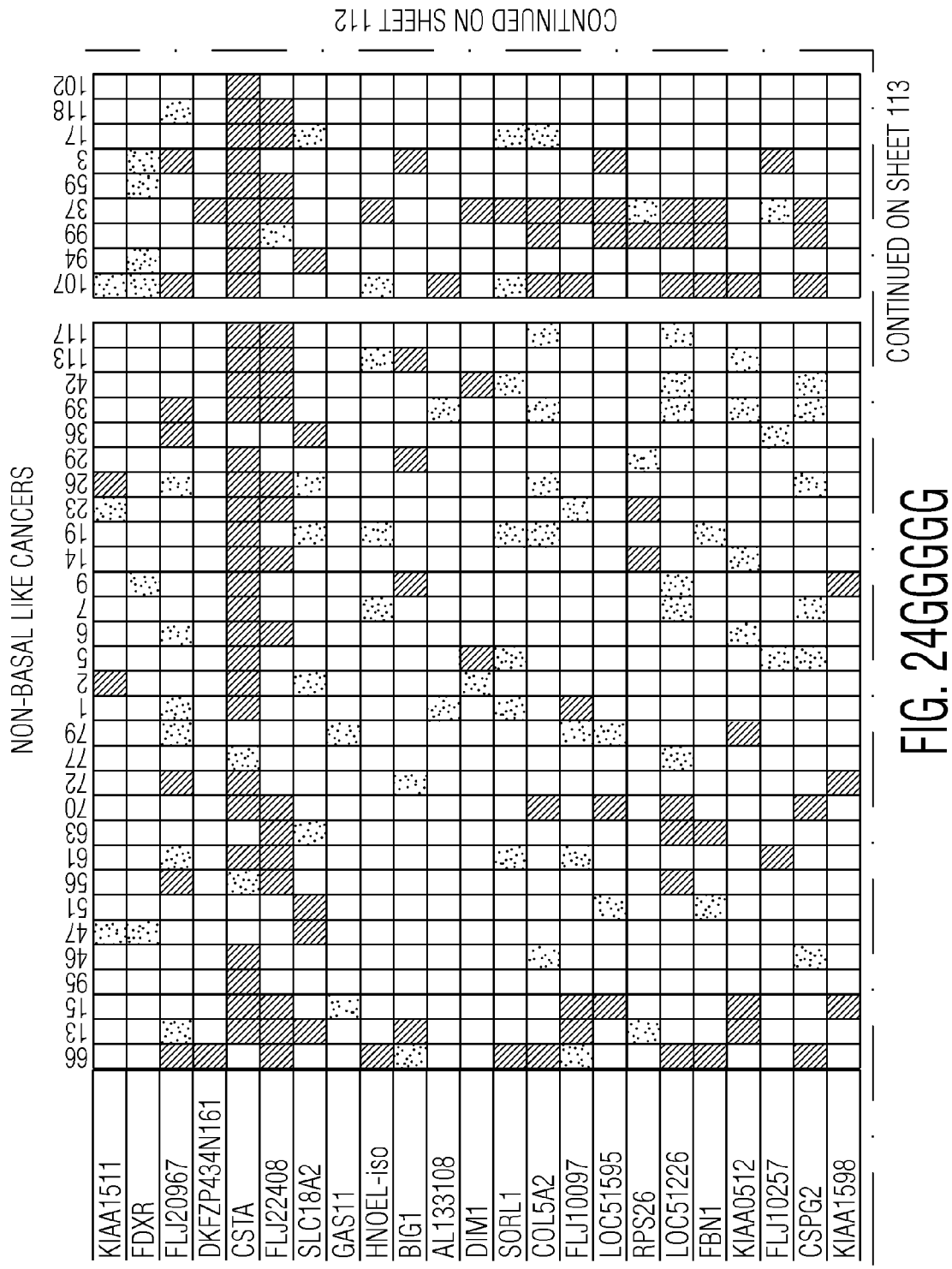
FIG. 24GGGGG

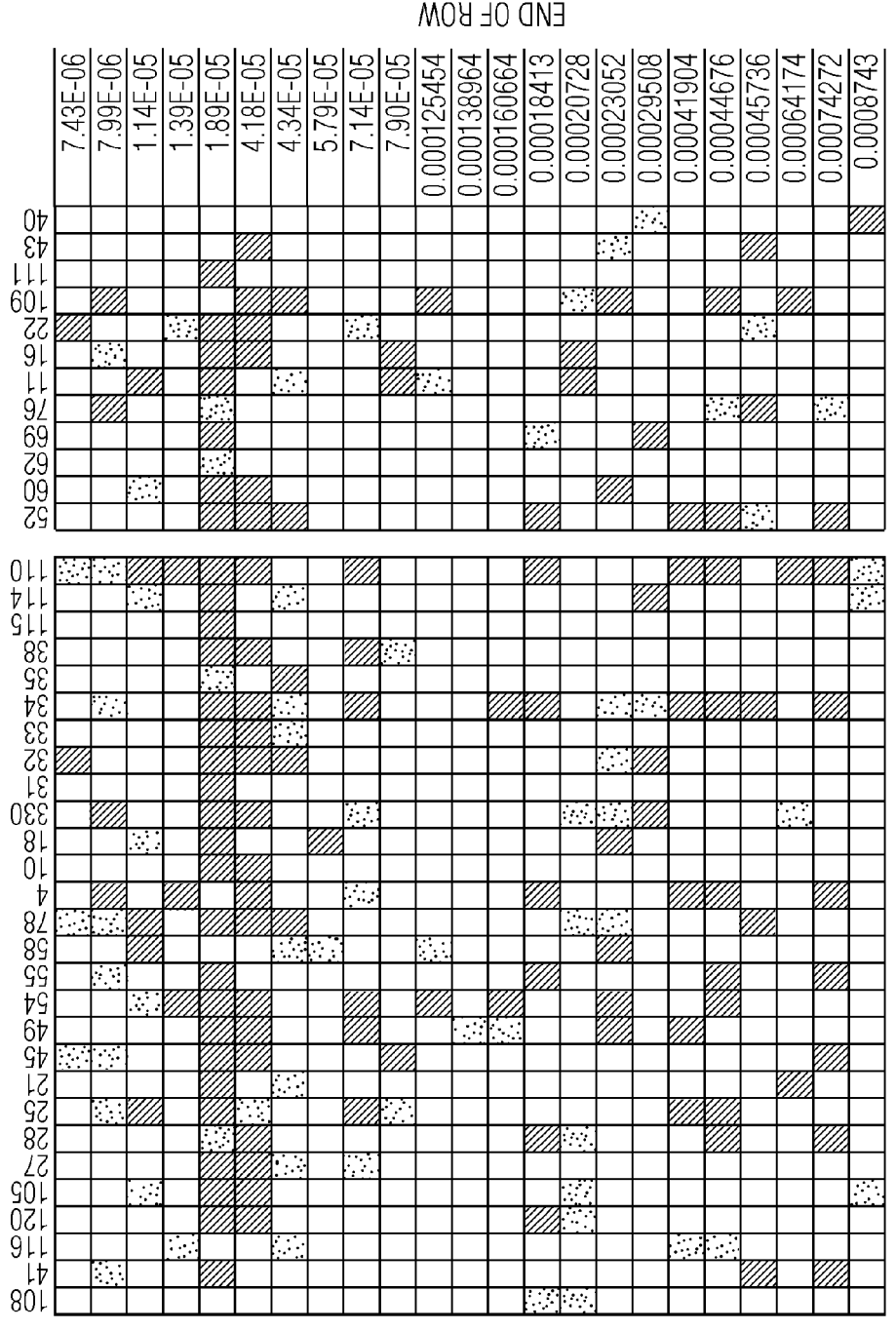
FIG. 24HHHHH

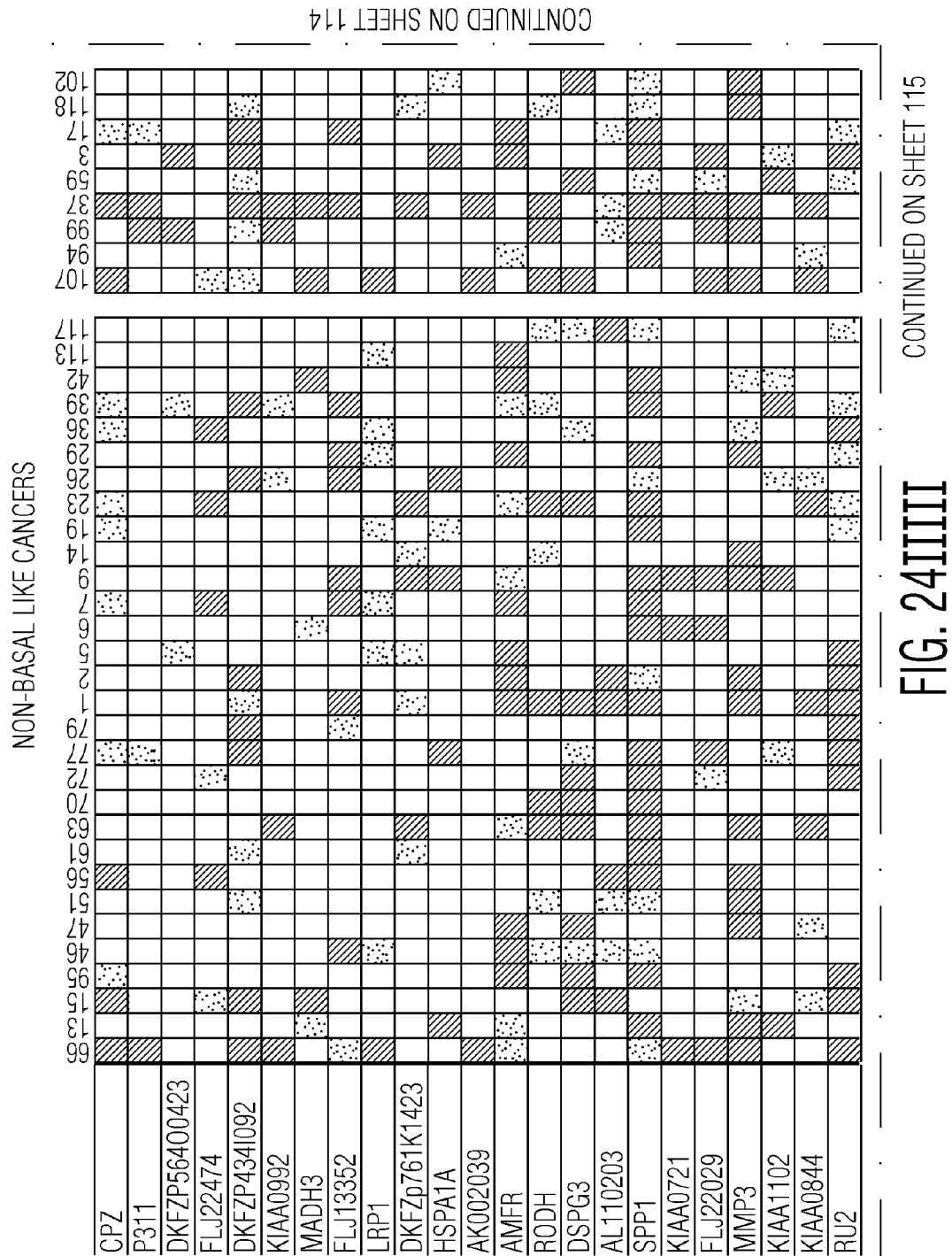
FIG. 24IIII

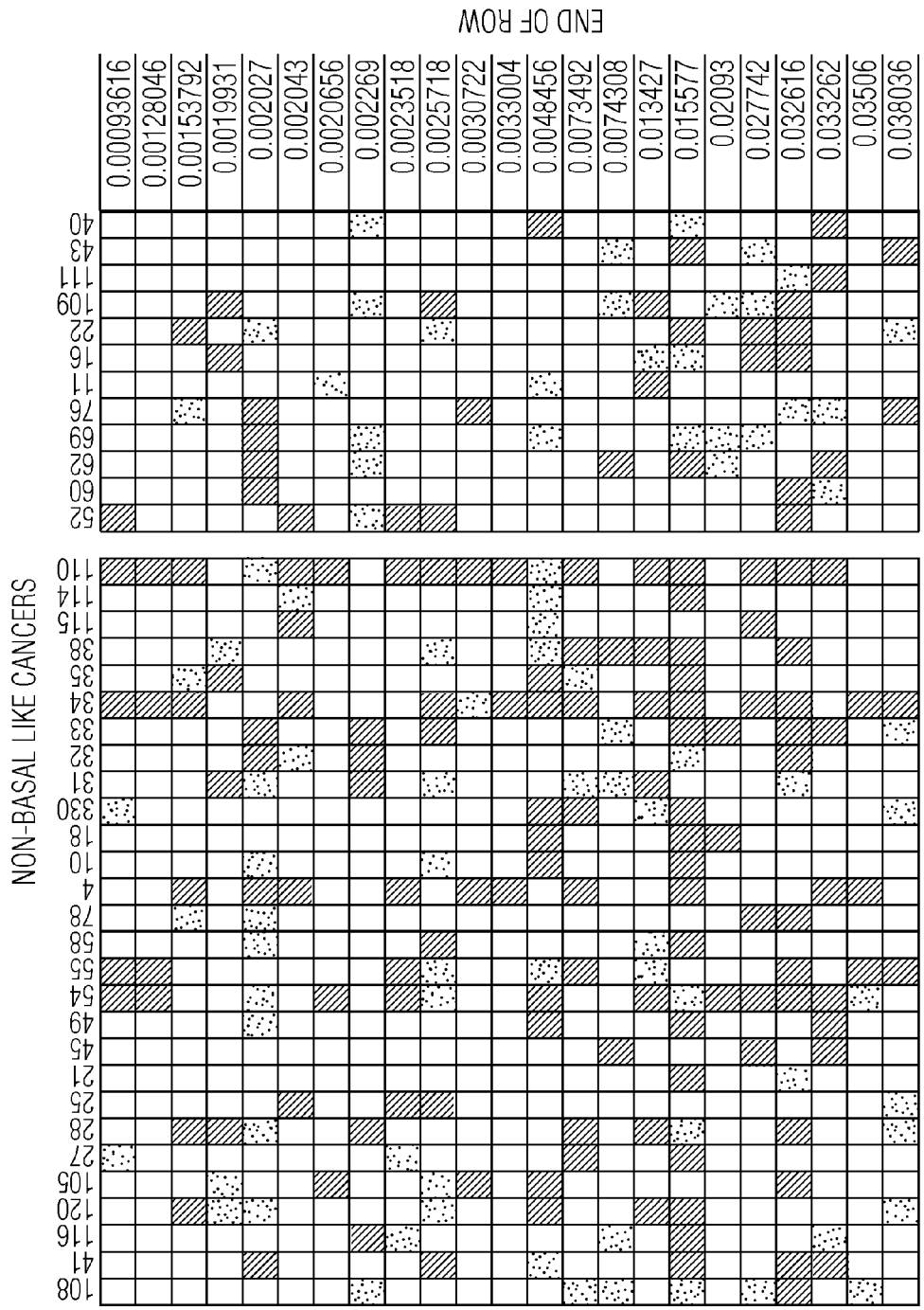
FIG. 24JJJJ

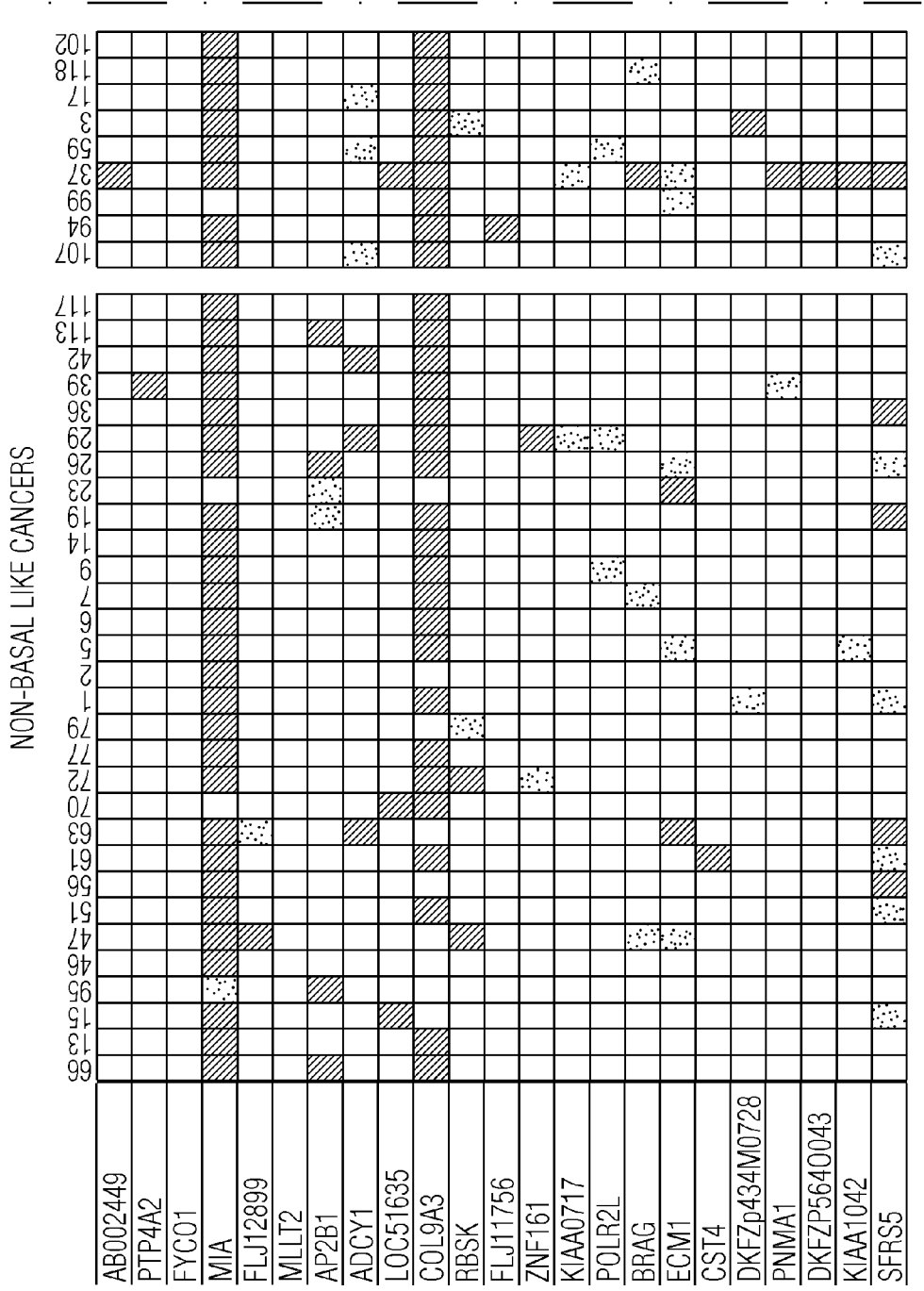
FIG. 24KKKKK

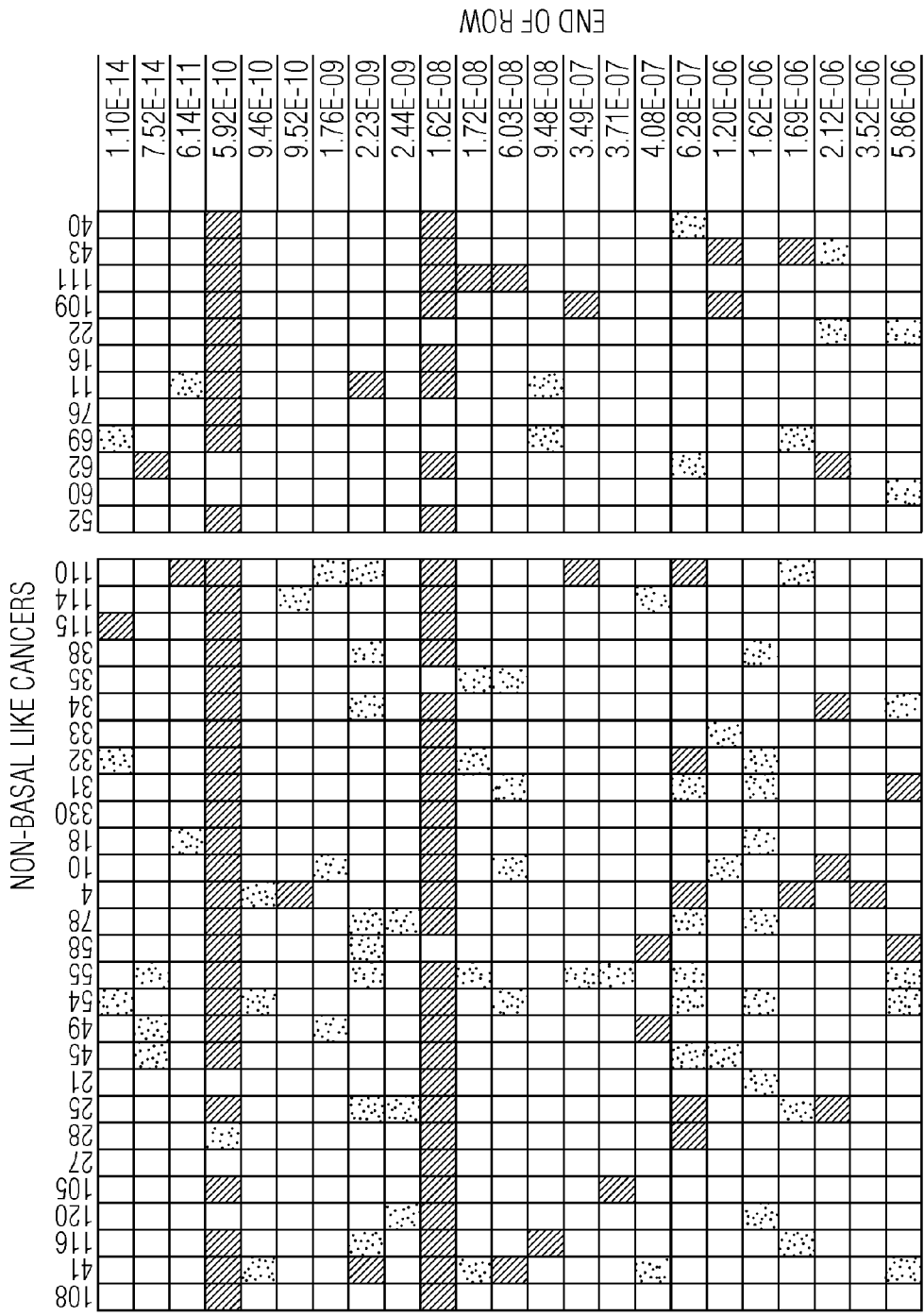
FIG. 24LLLLL

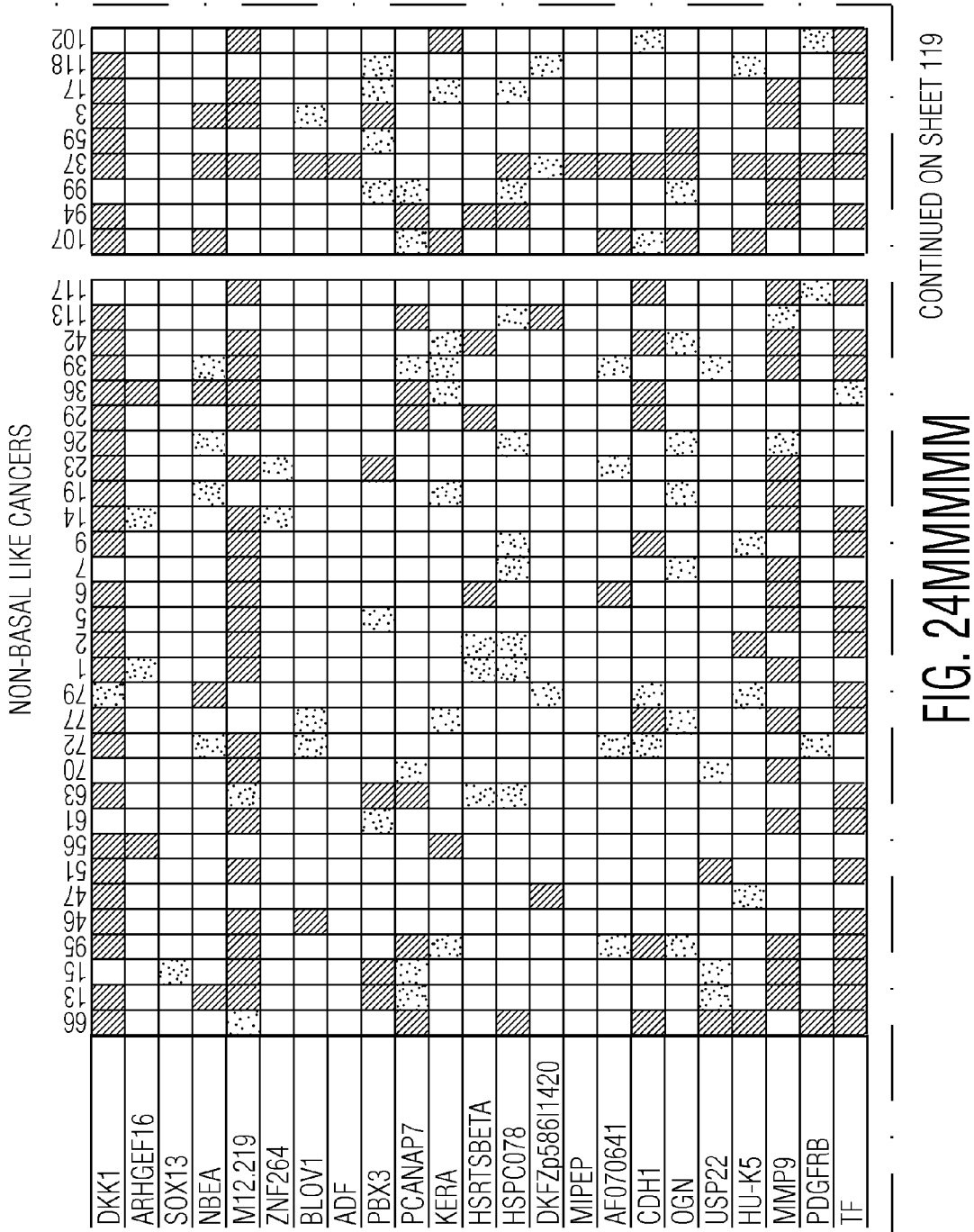
FIG. 24MMMMM

FIG. 24NNNNN

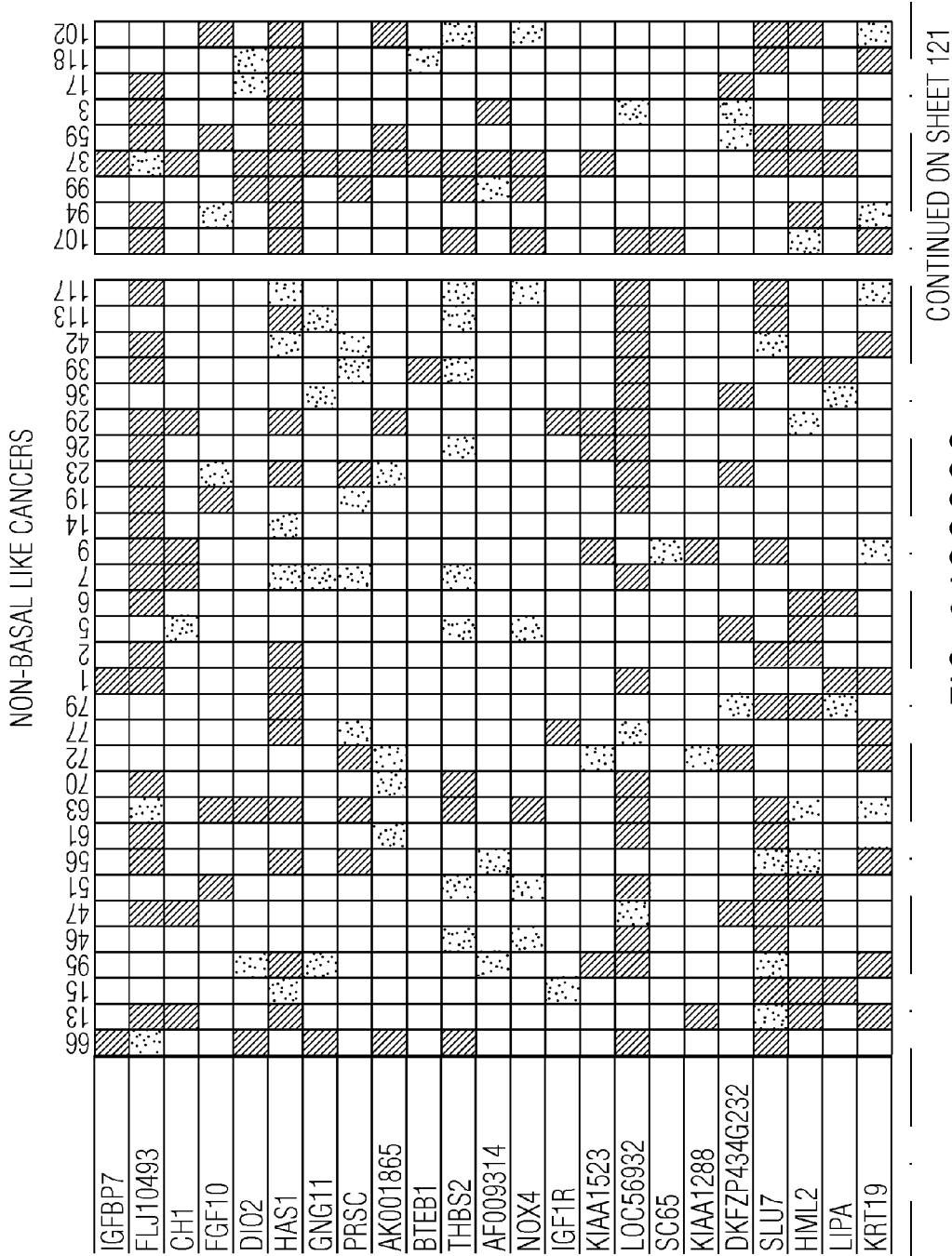
FIG. 2400000

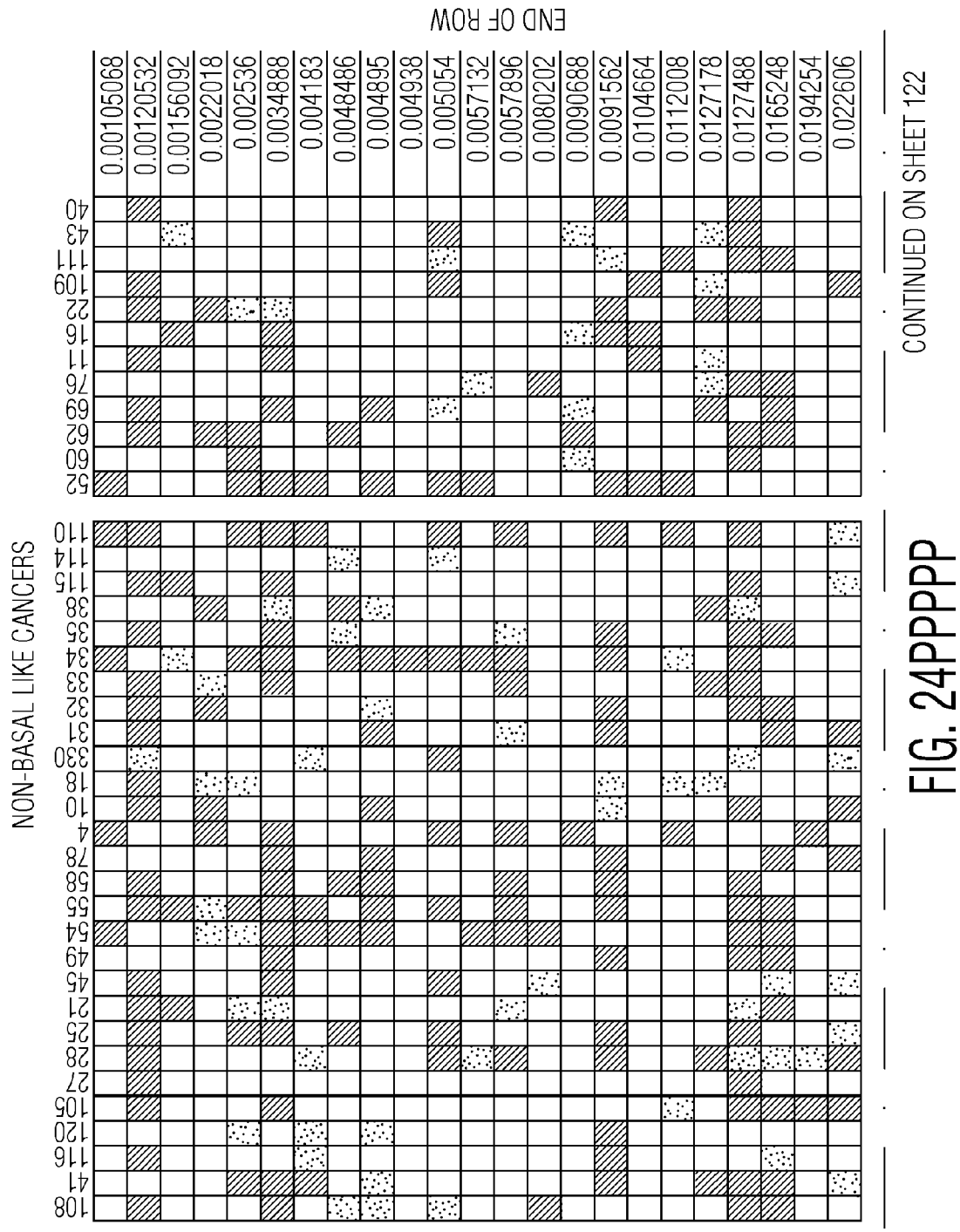
FIG. 24PPPPP

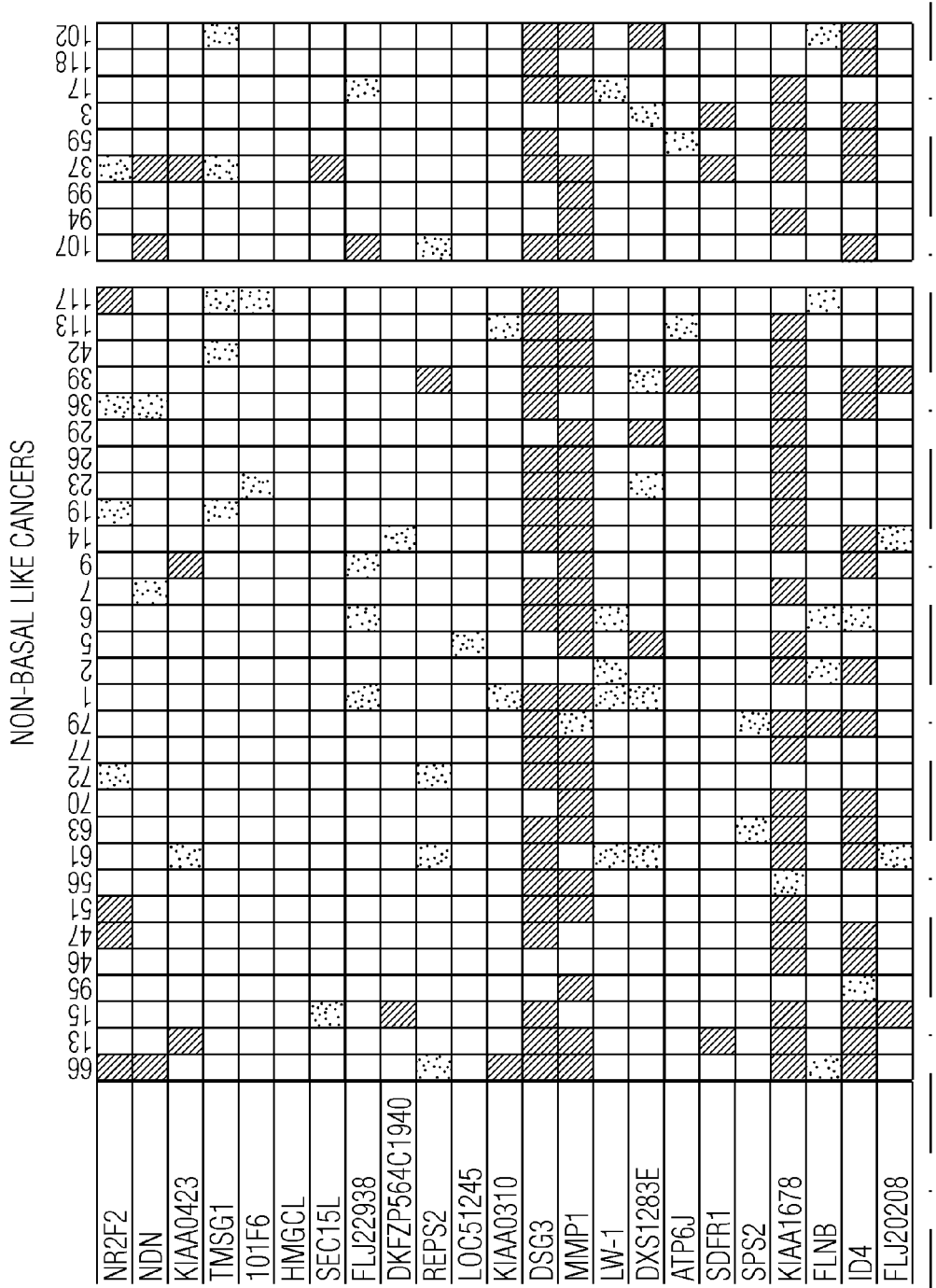
FIG. 24QQQQQ

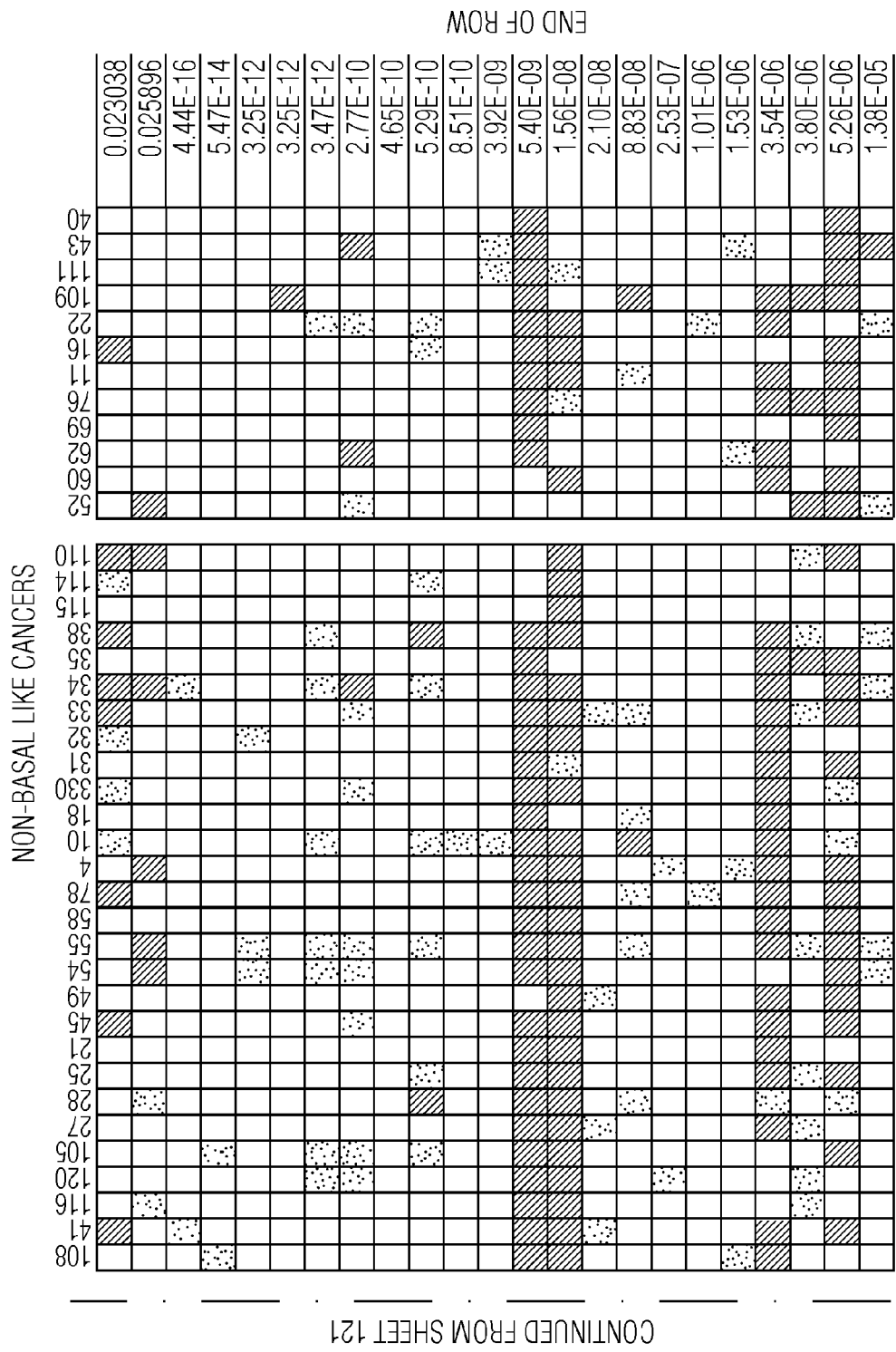
FIG. 24RRRRR

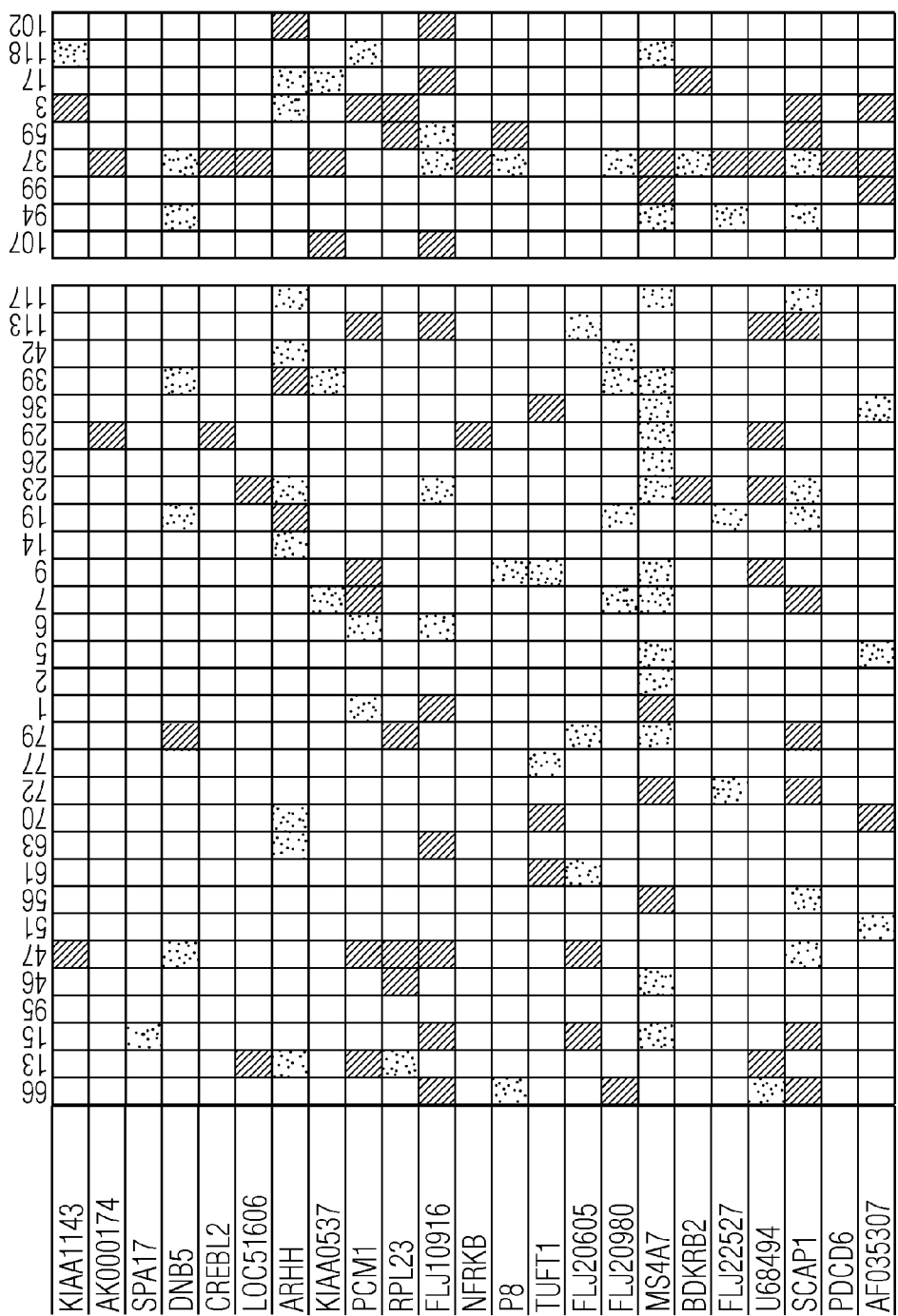
FIG. 24SSSSS

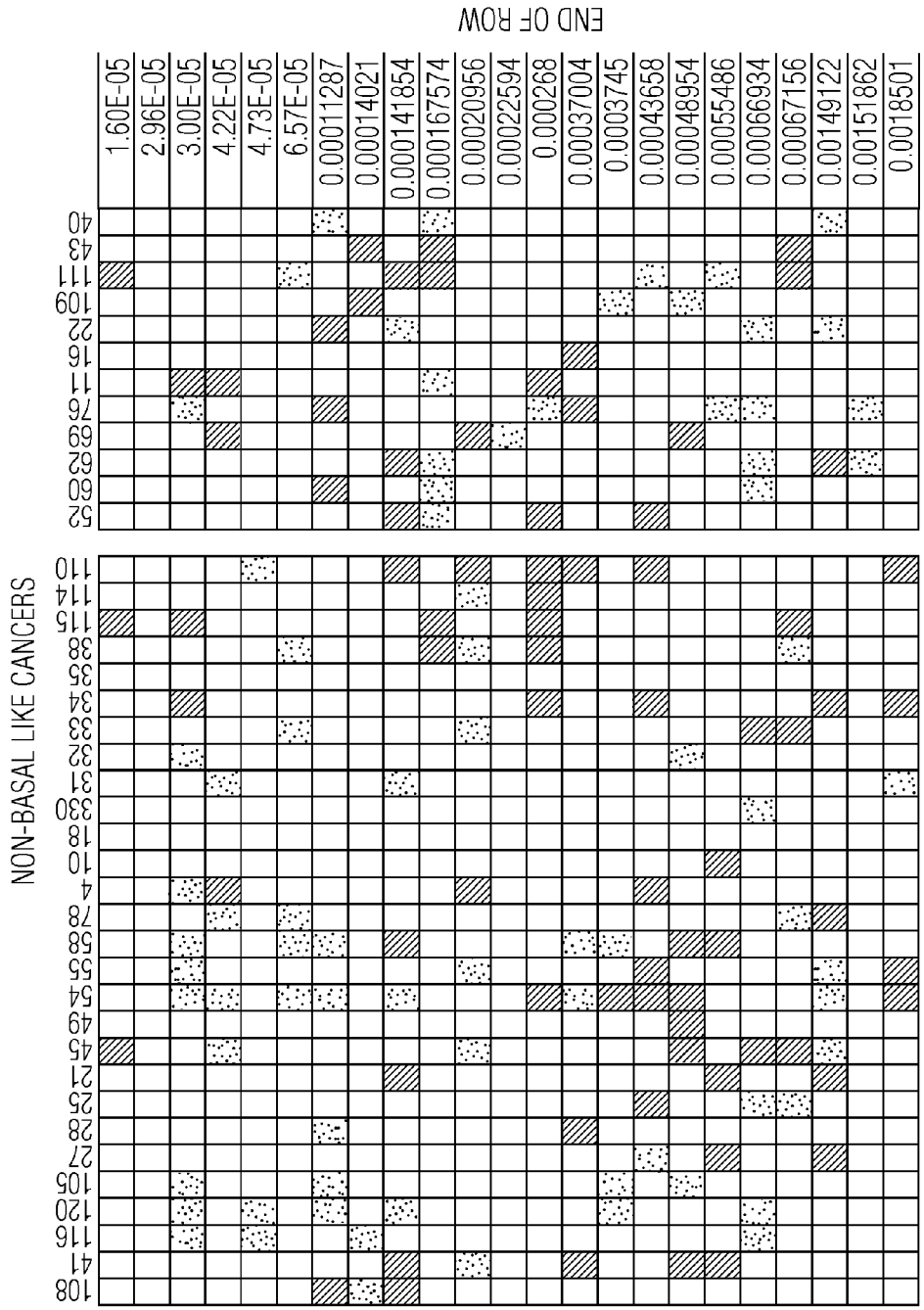
FIG. 24TTTTT

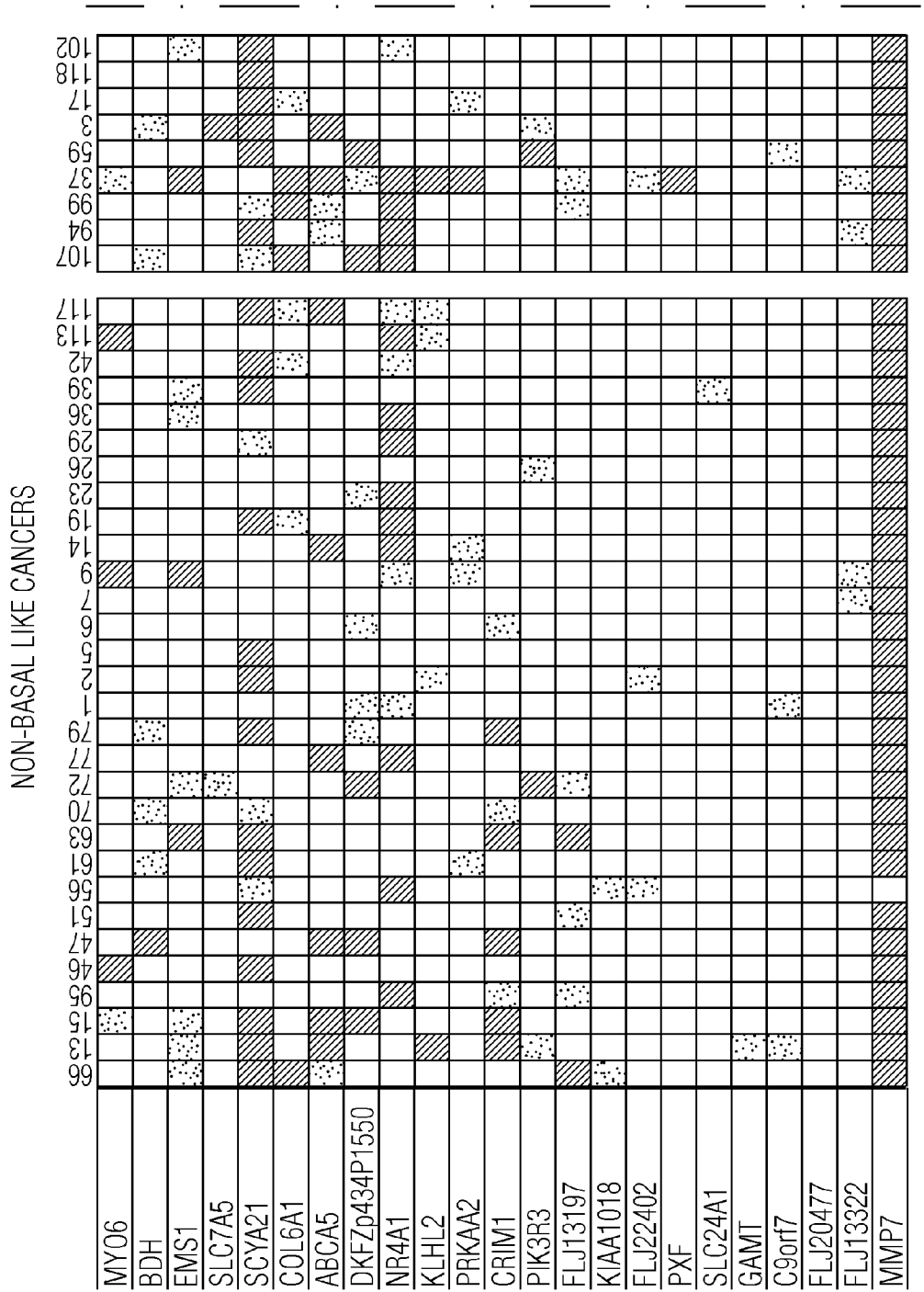
FIG. 24UUUUU

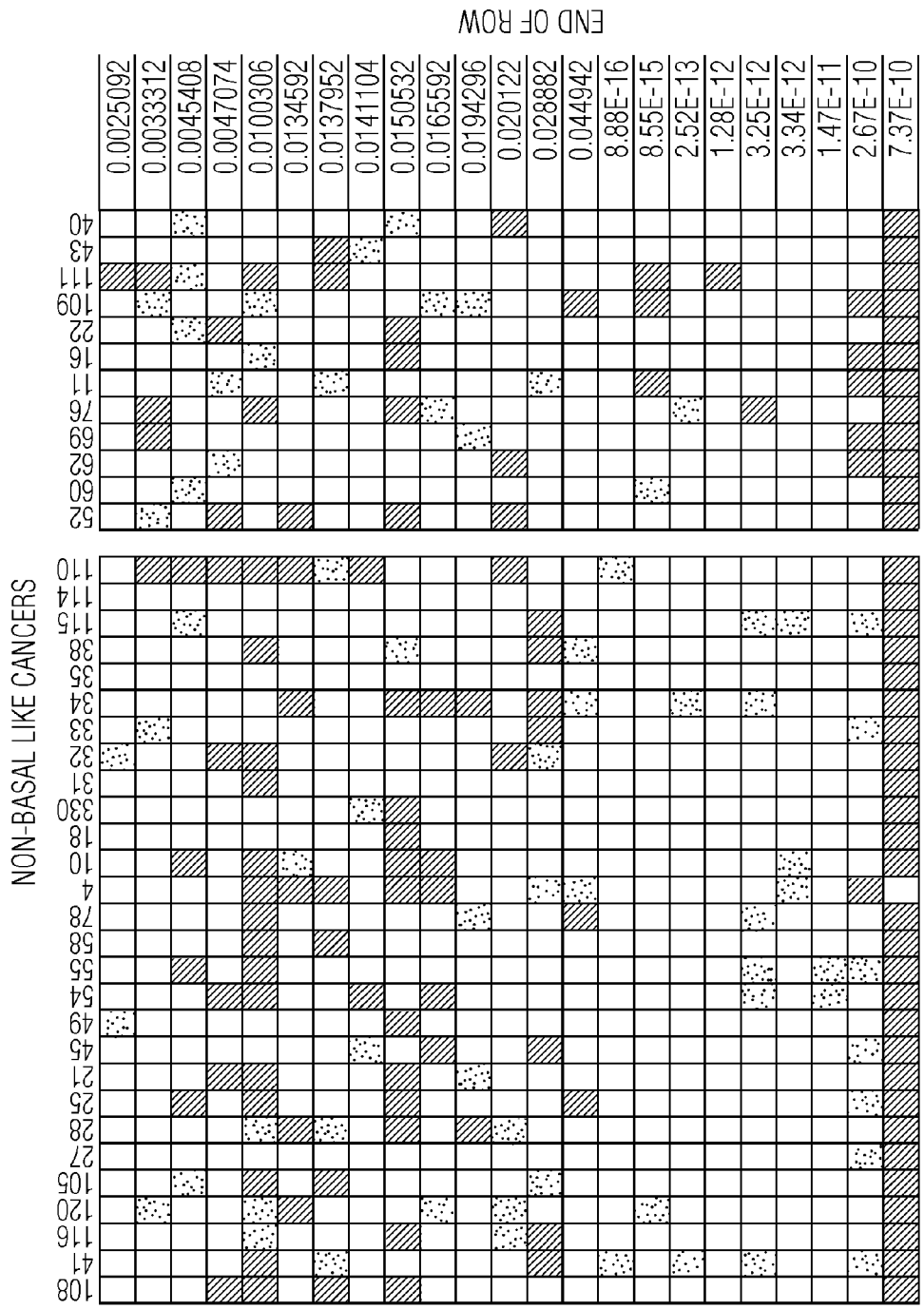
FIG. 24VVVV

FIG. 24WWWWW

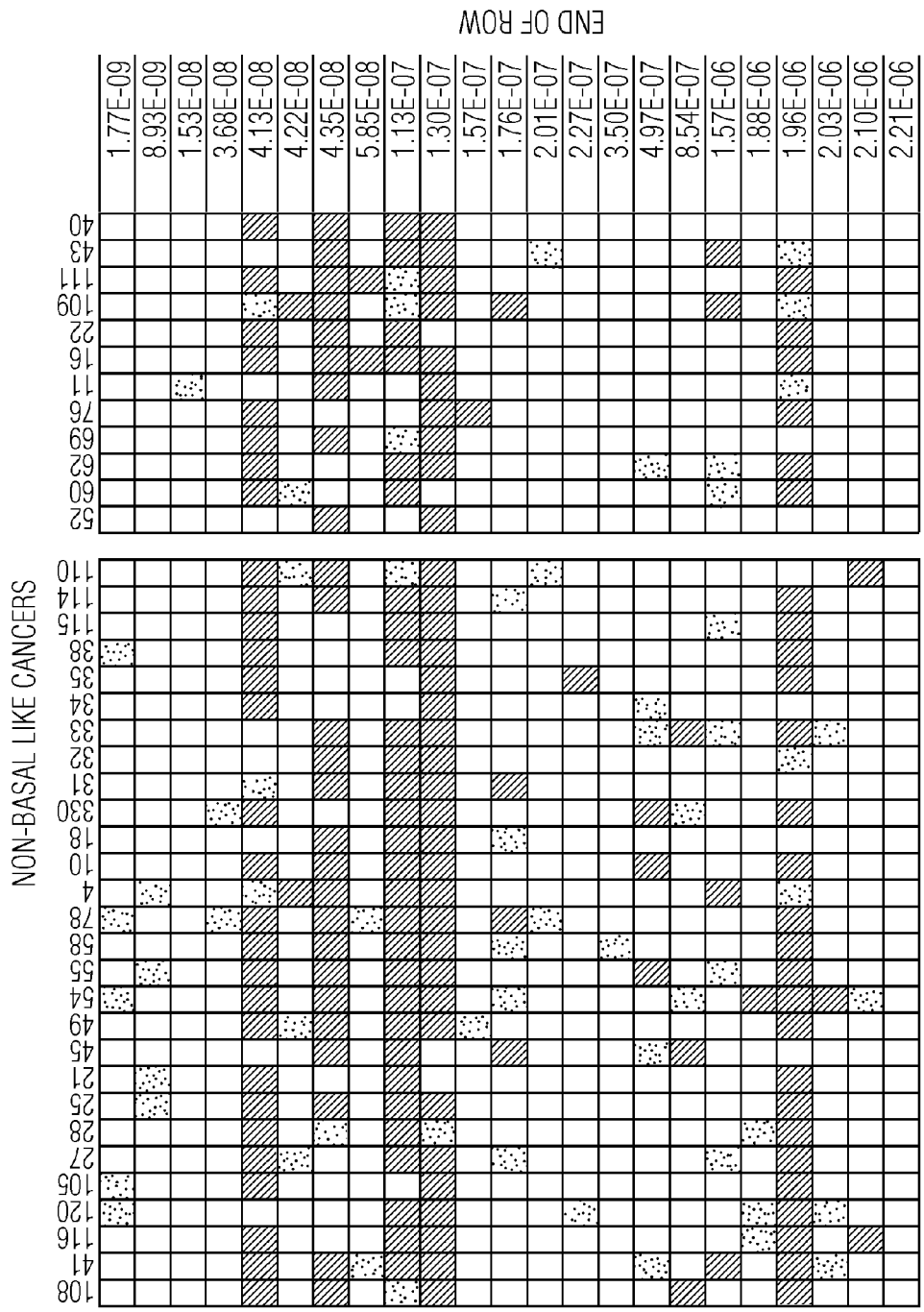
FIG. 24XXXXX

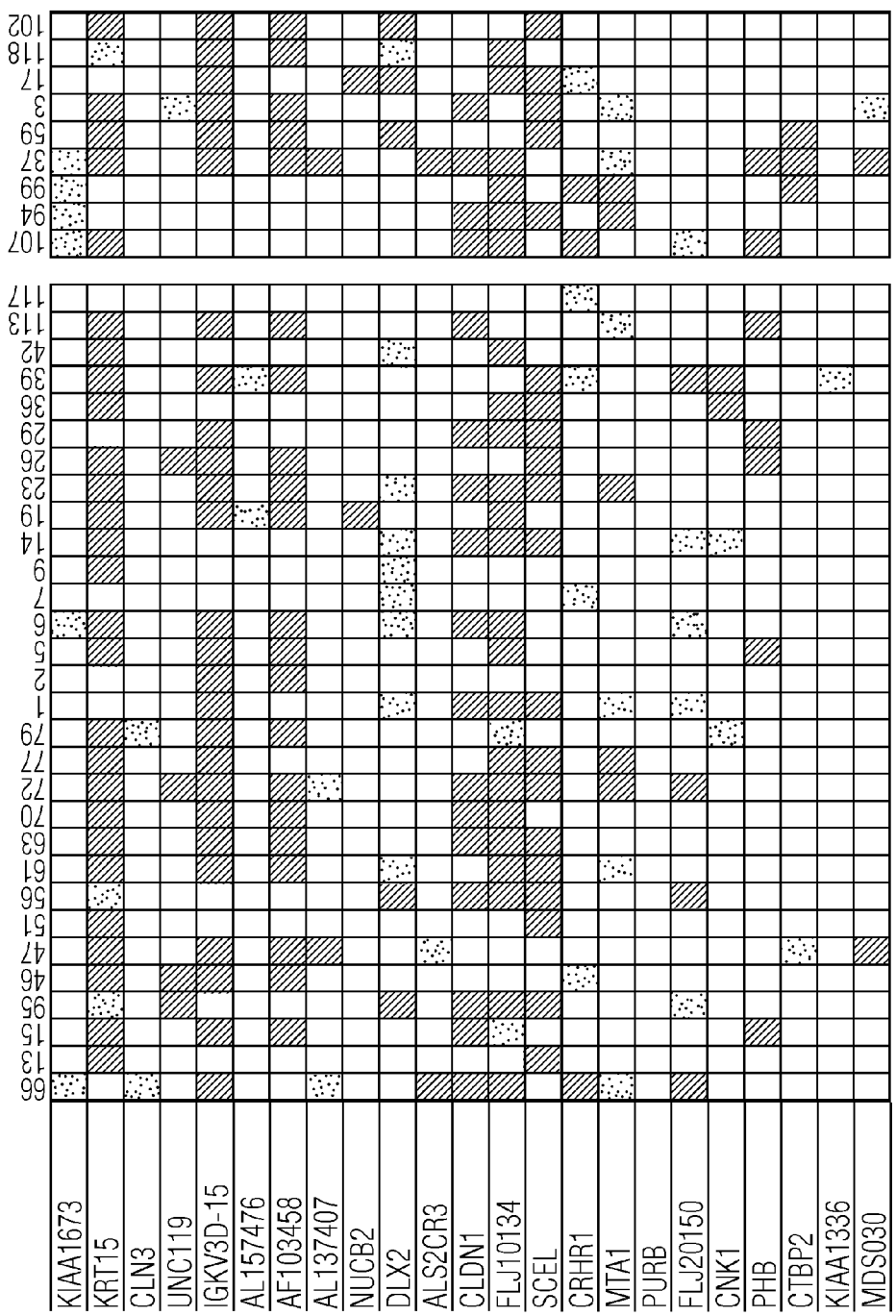
FIG. 24YYYYY

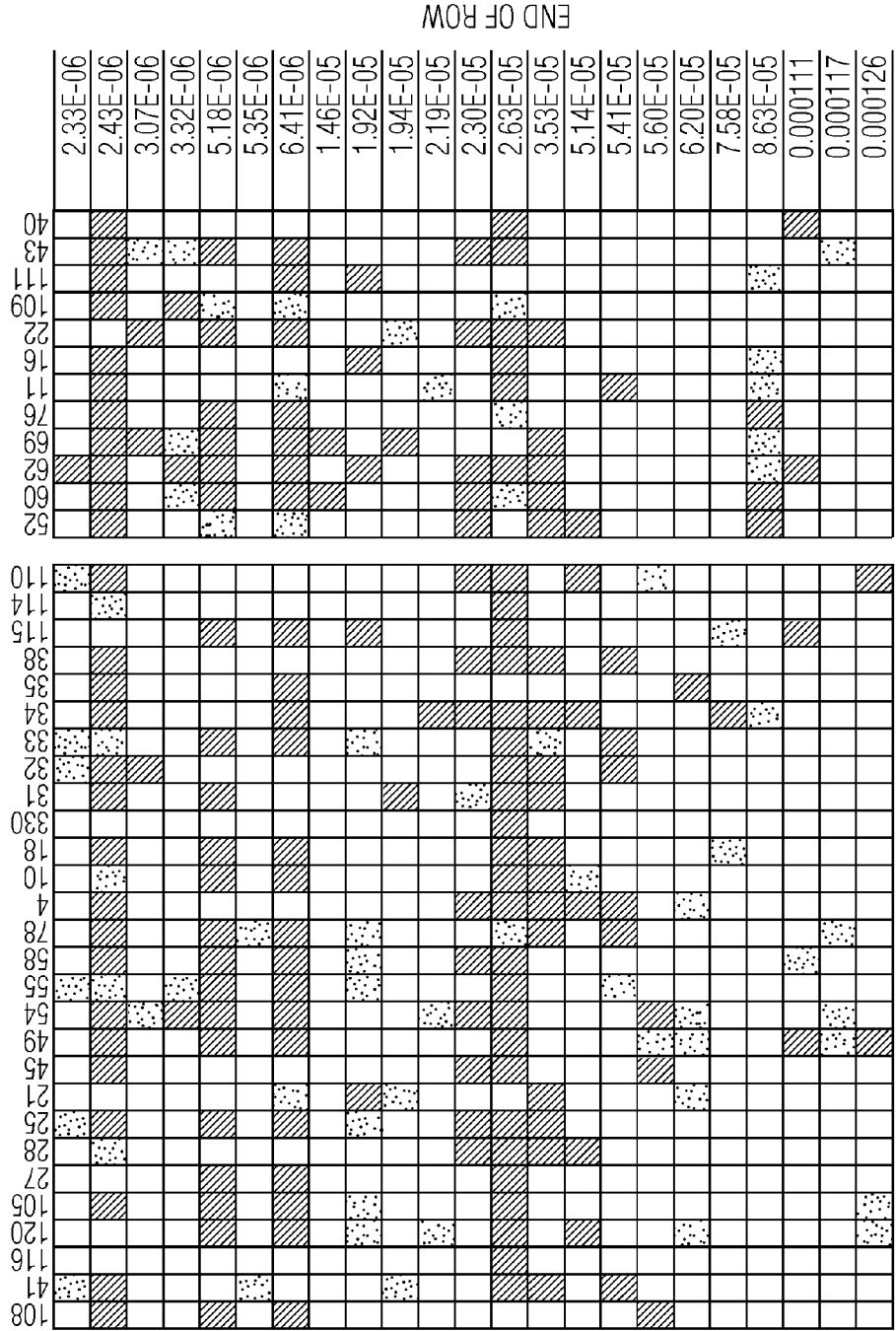
FIG. 24ZZZZZZ

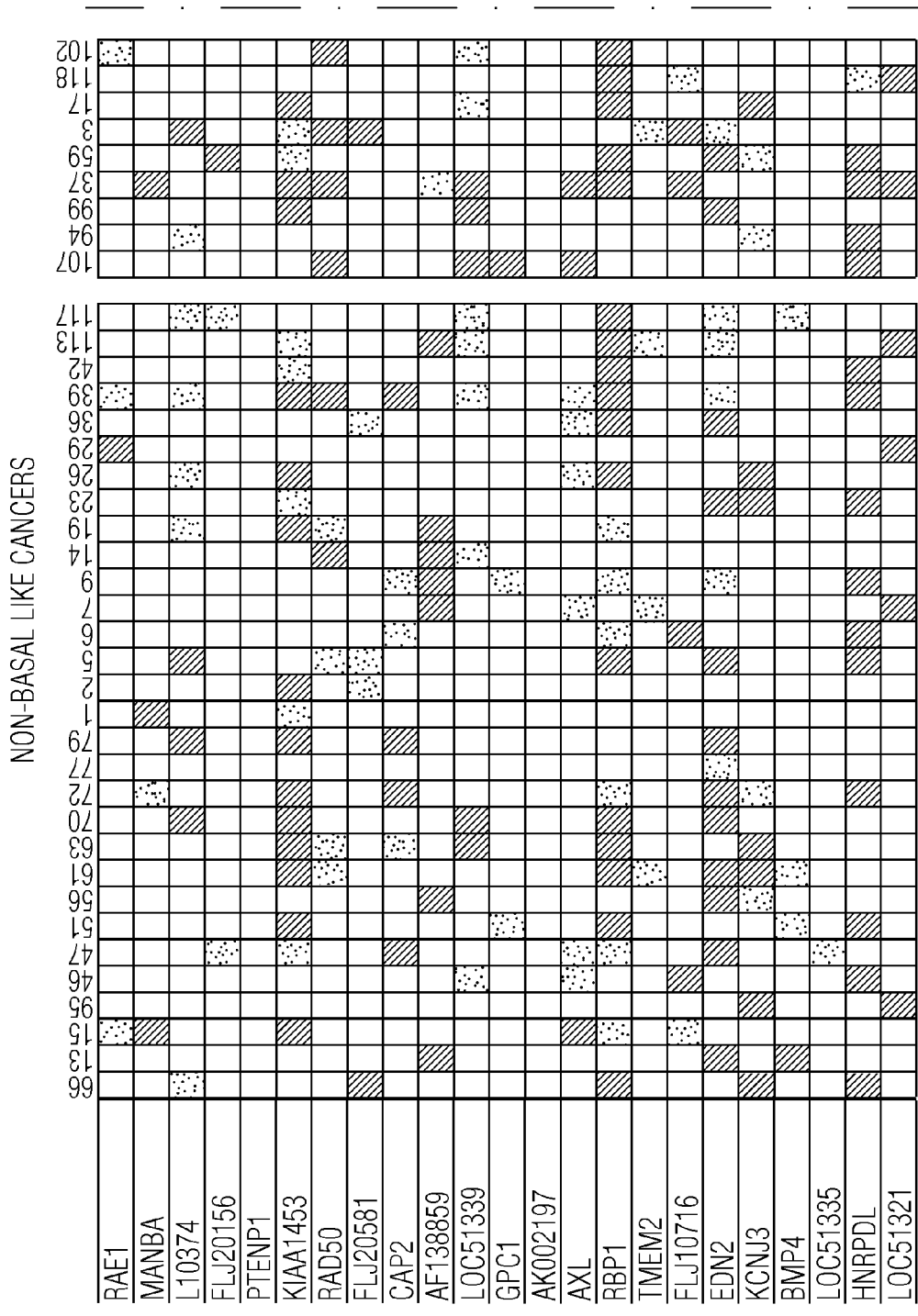
FIG. 24AAAAAAA

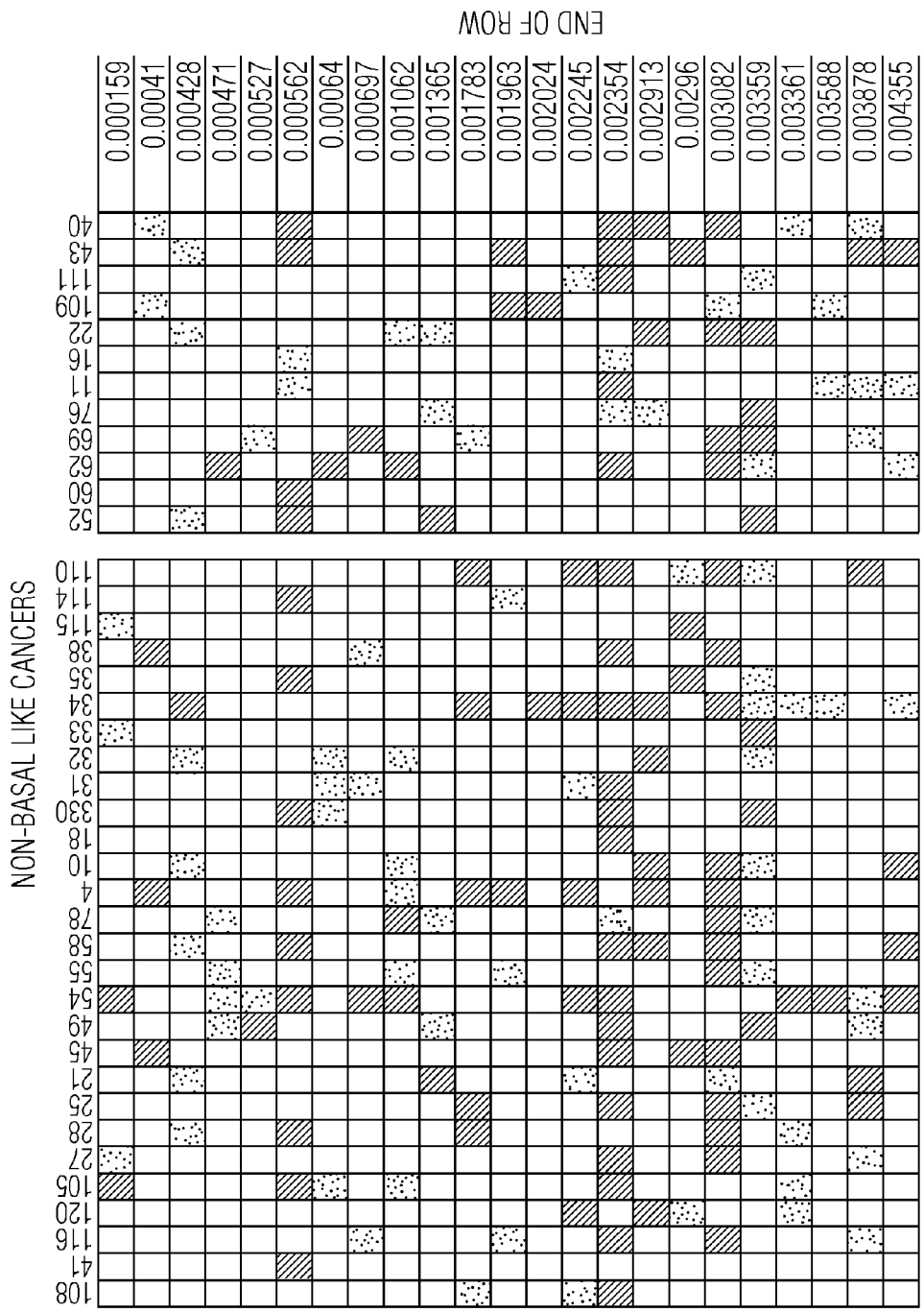
FIG. 24BBBBBB

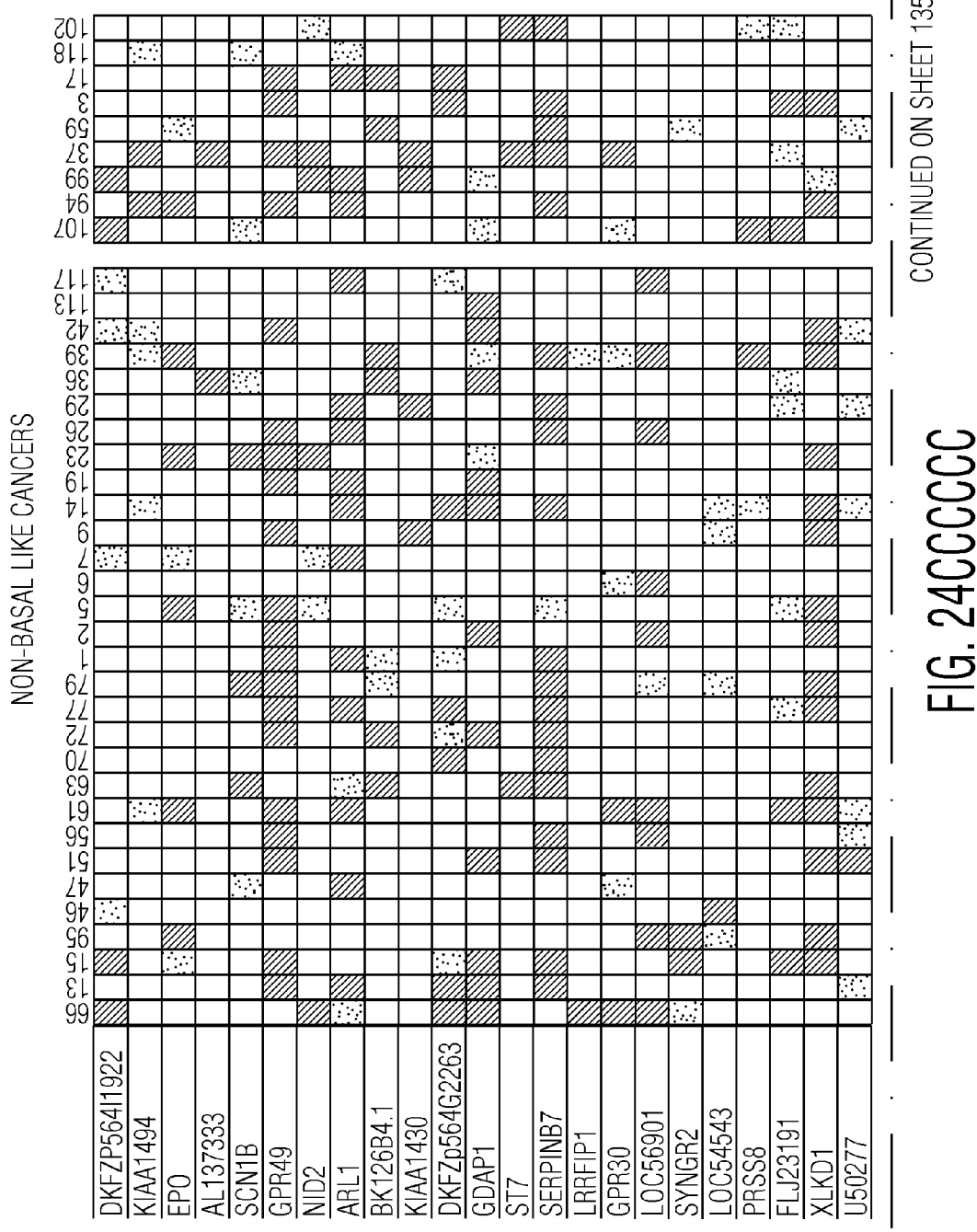
FIG. 24CCCCCC

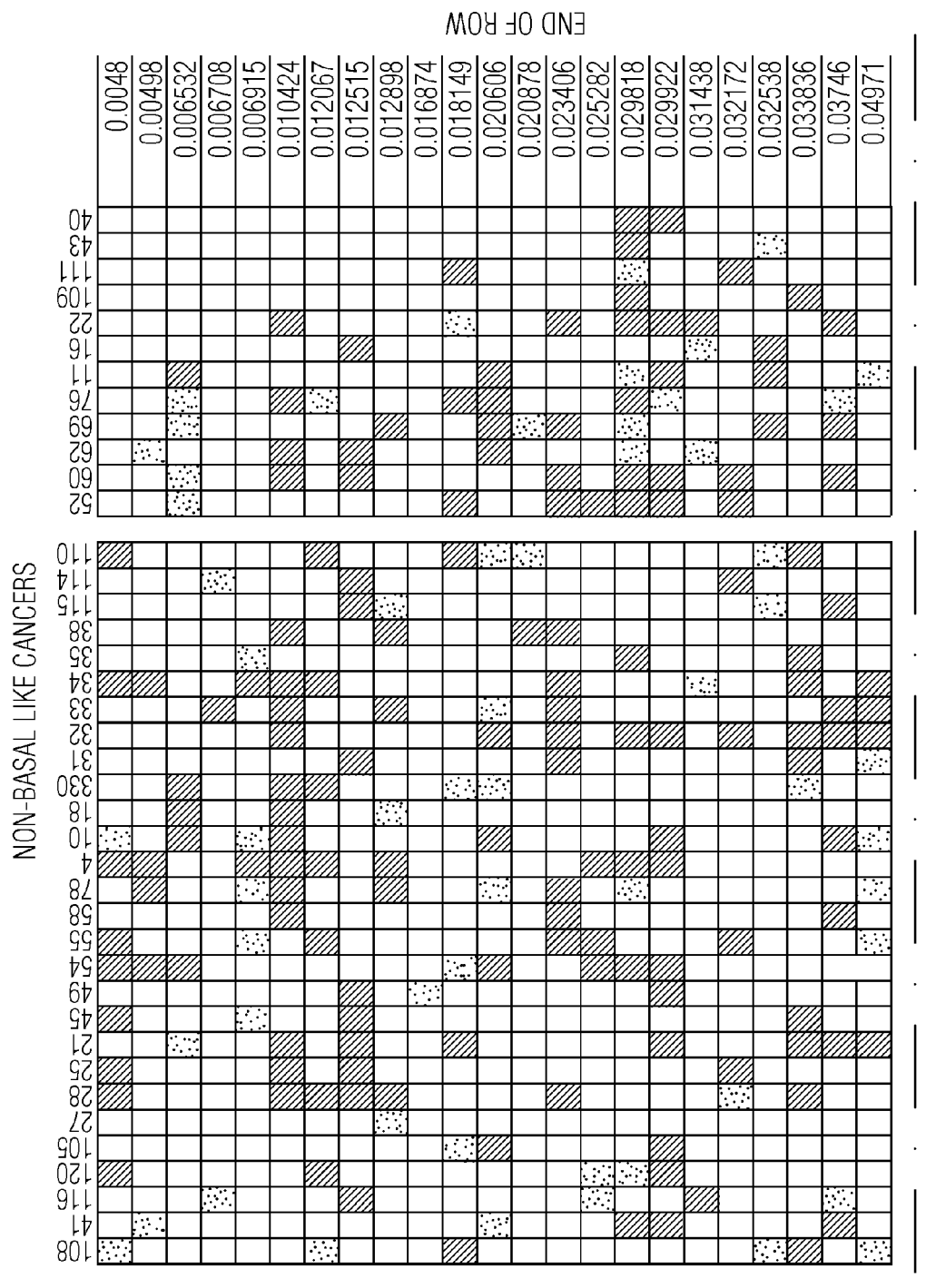
FIG. 24DDDDDD

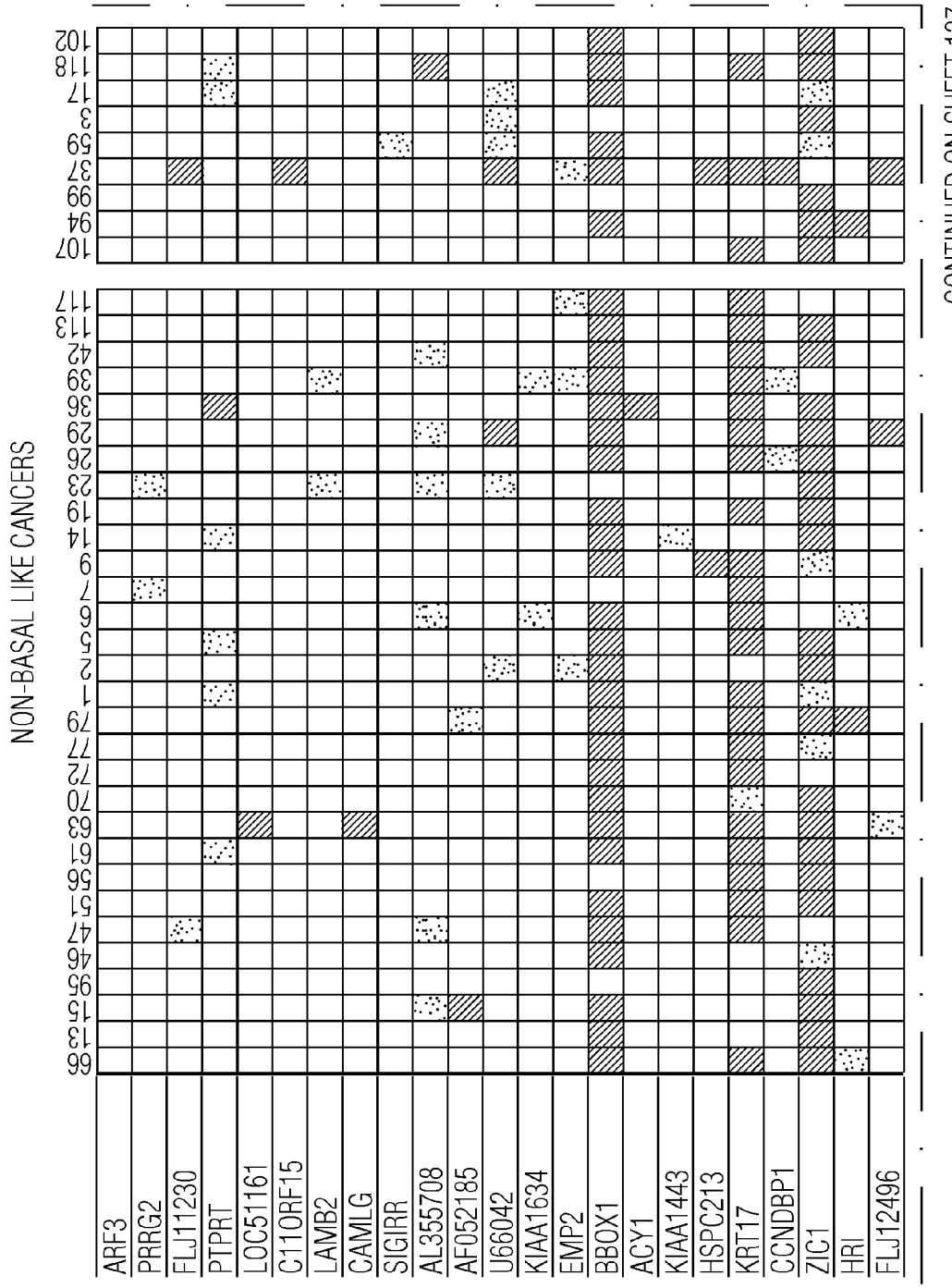
FIG. 24EEEEEE

FIG. 24FFFFFF

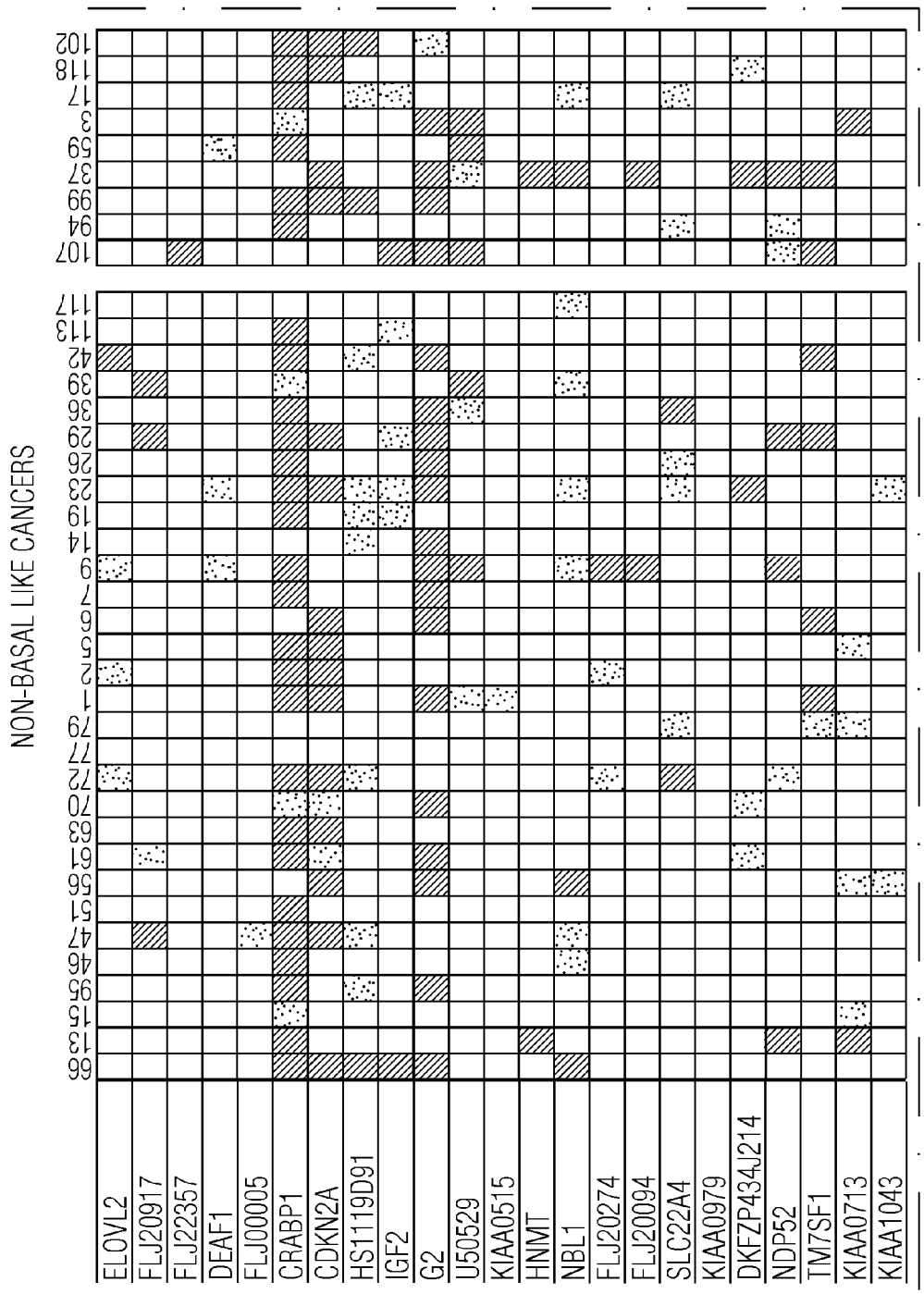
FIG. 24GGGGGG

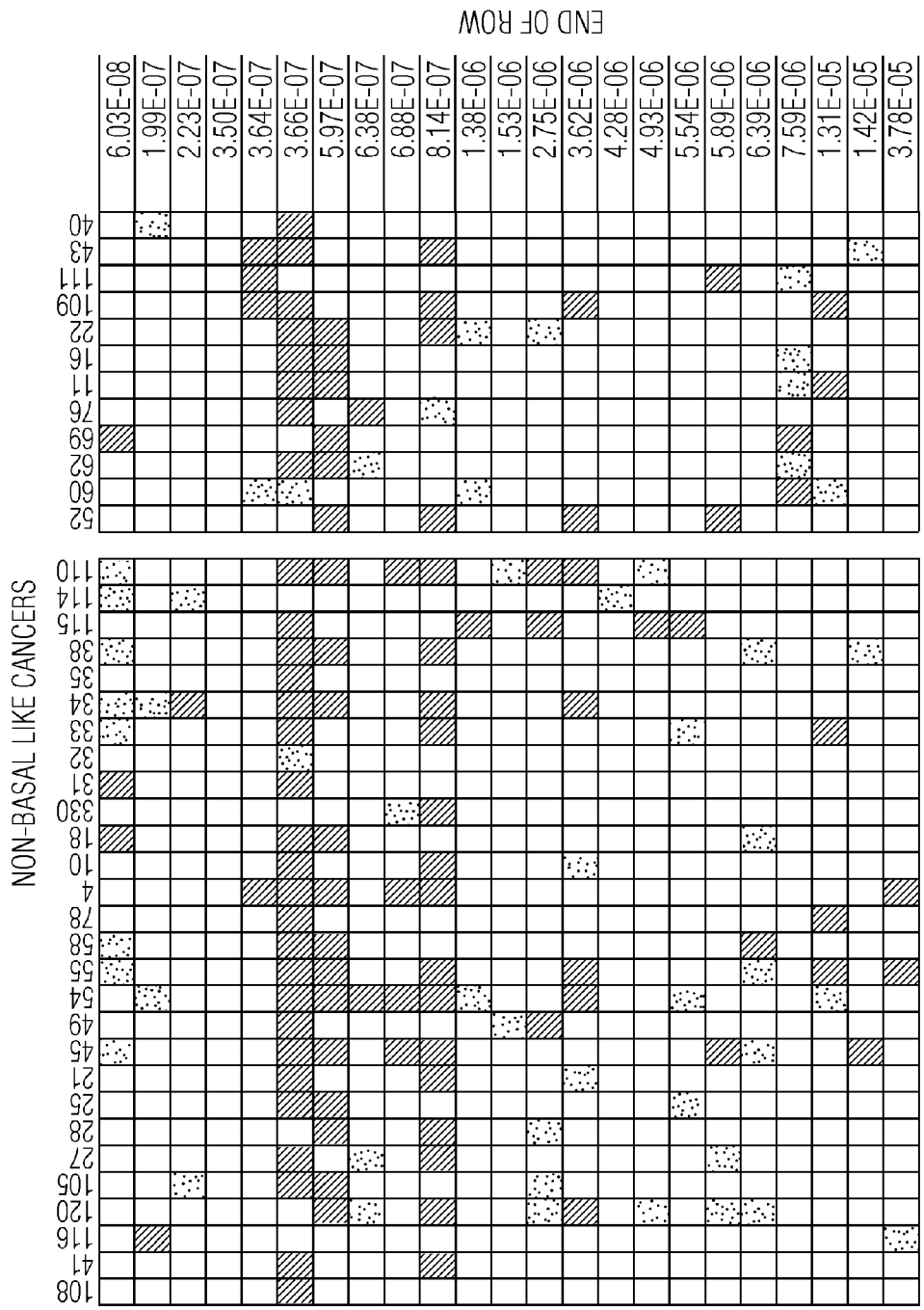
FIG. 24HHHHHH

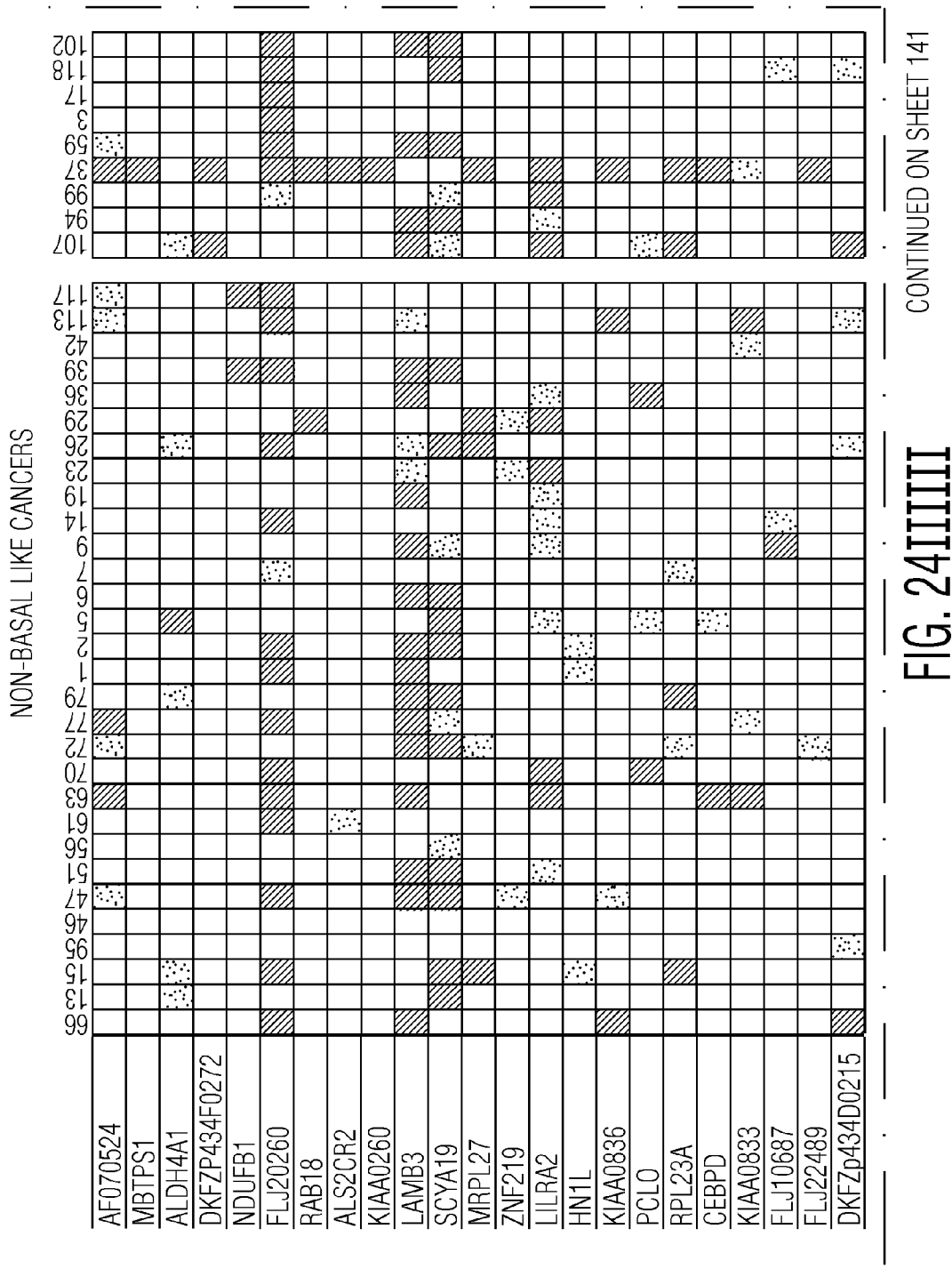

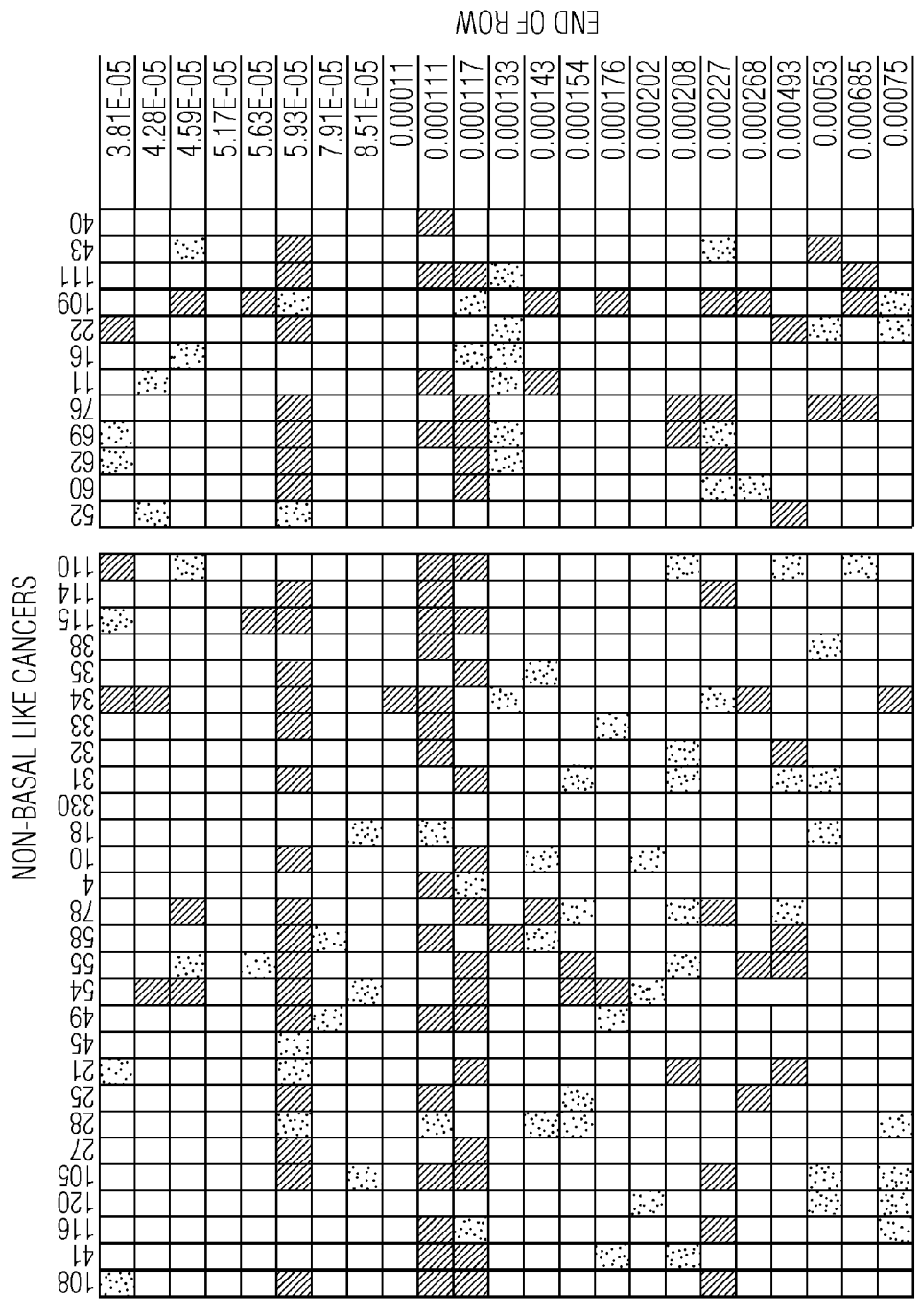
FIG. 24JJJJJ

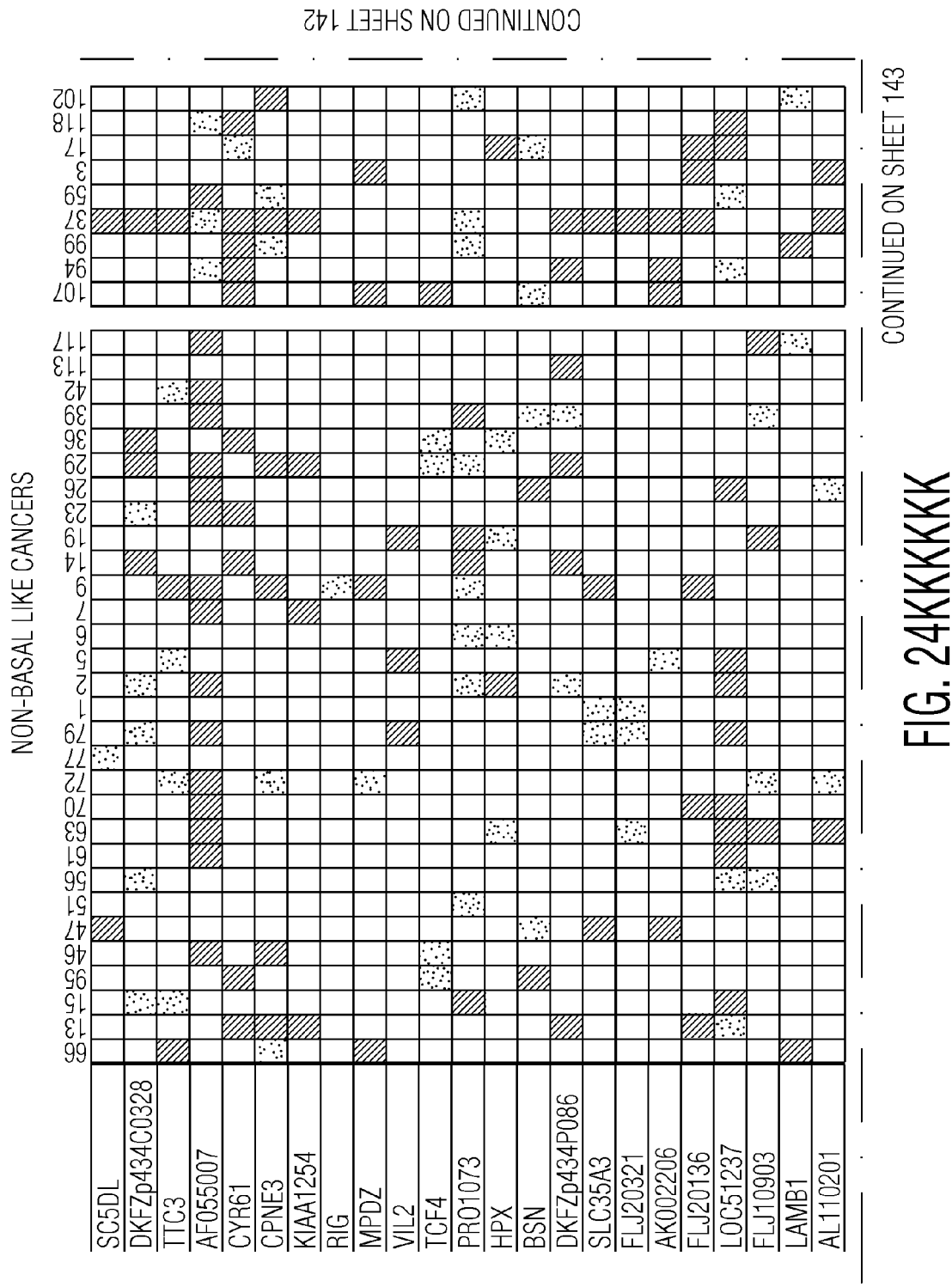
FIG. 24KKKKKK

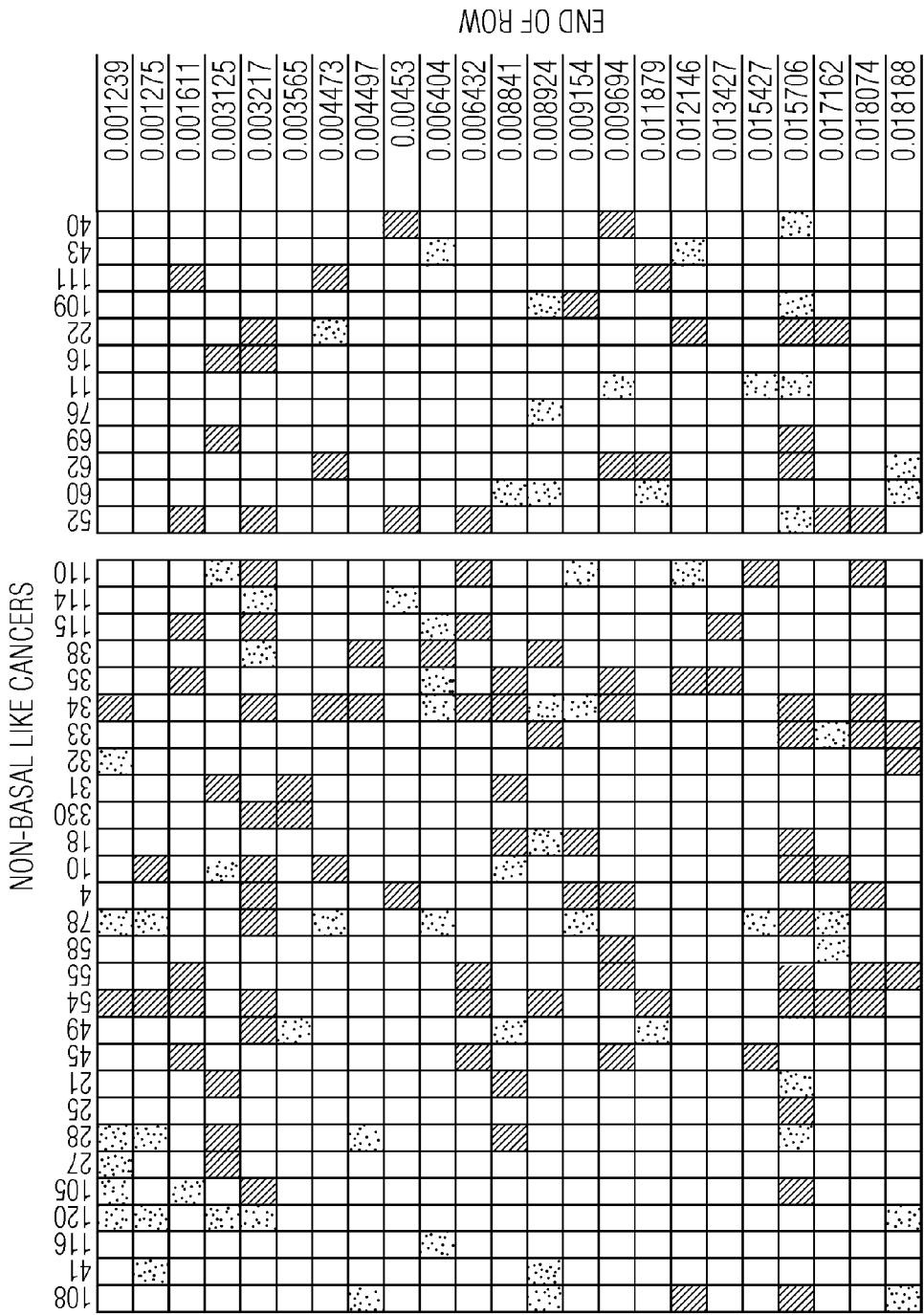
FIG. 24LLLLLL

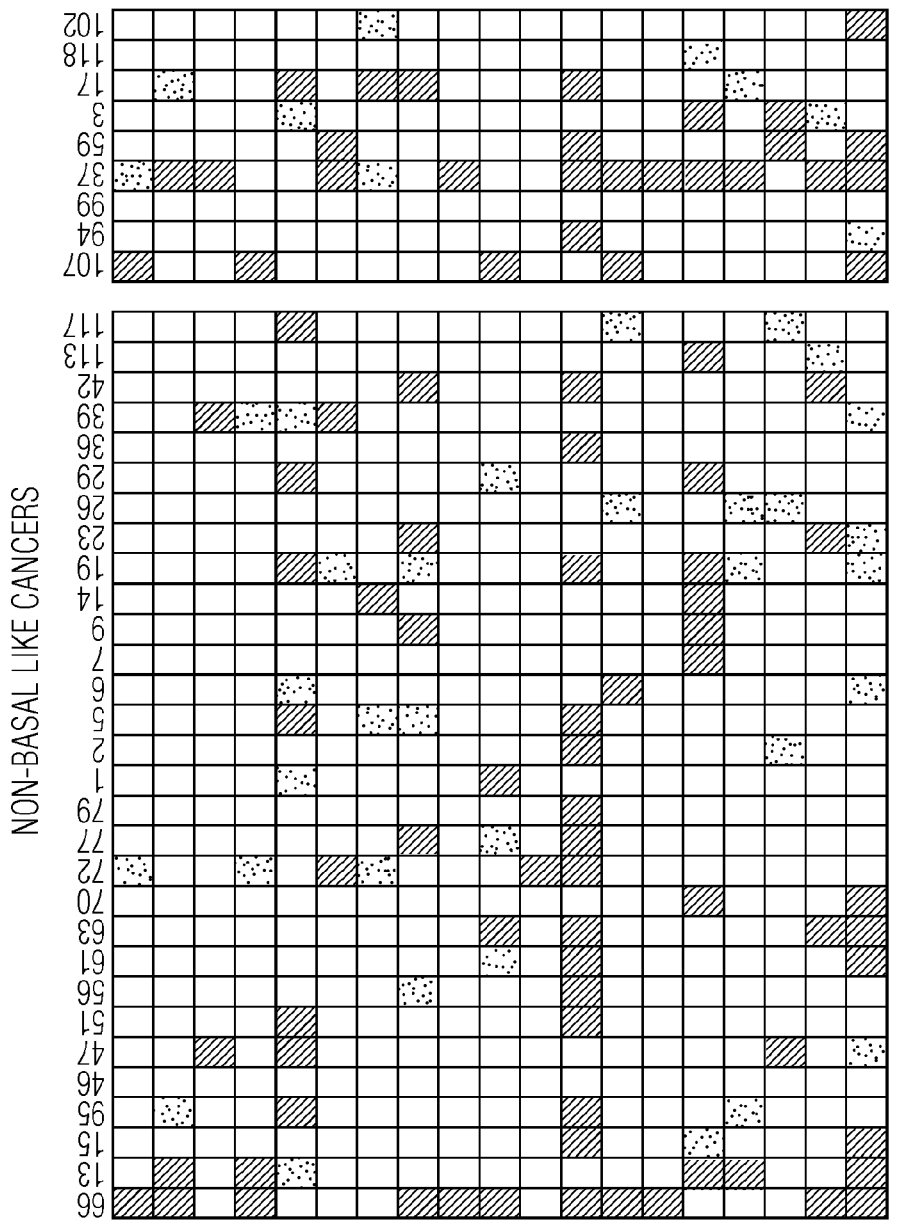
FIG. 24MMMMM

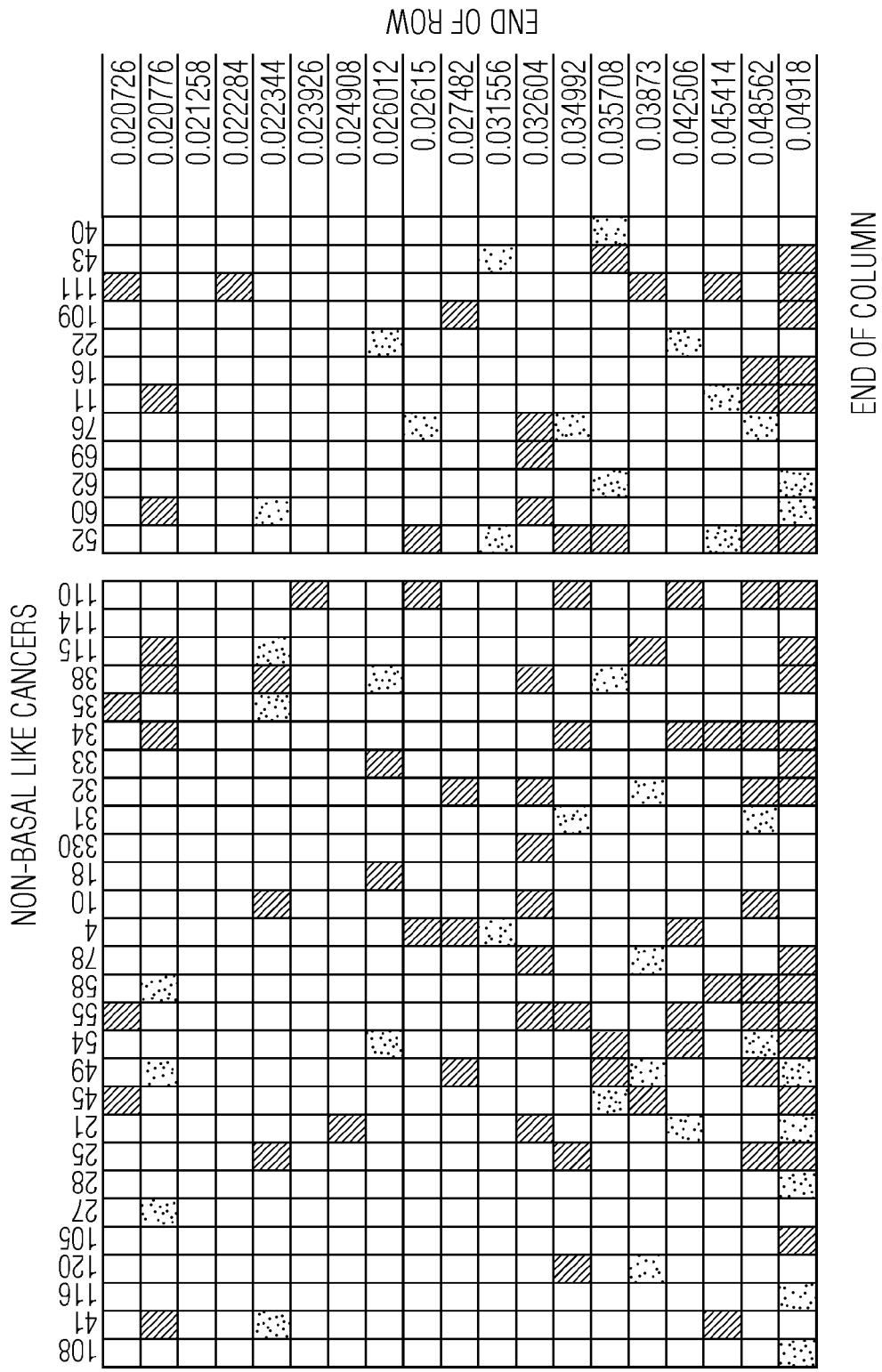
FIG. 24NNNNNN

FIG. 25S

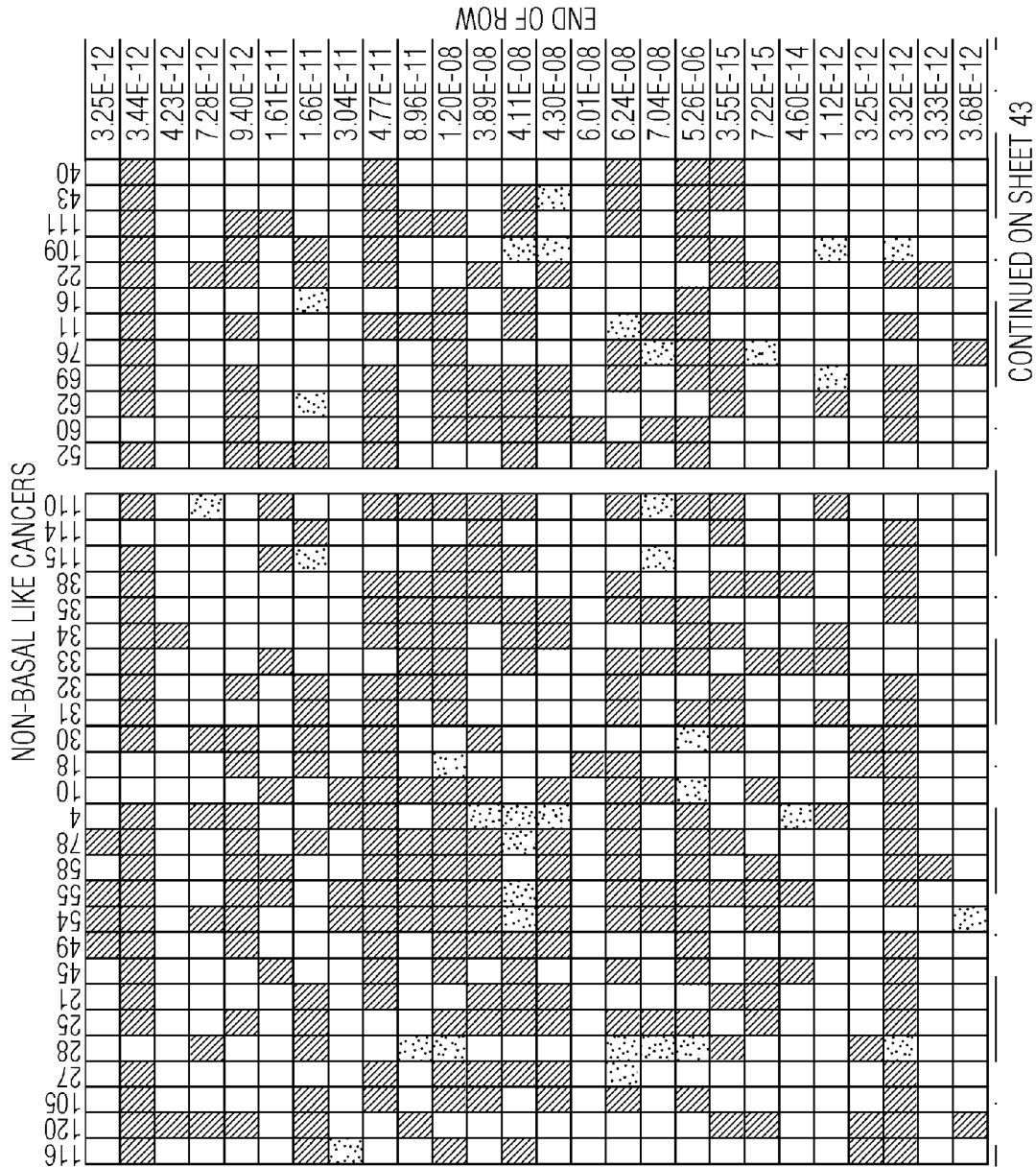
FIG. 2500

FIG. 25RR

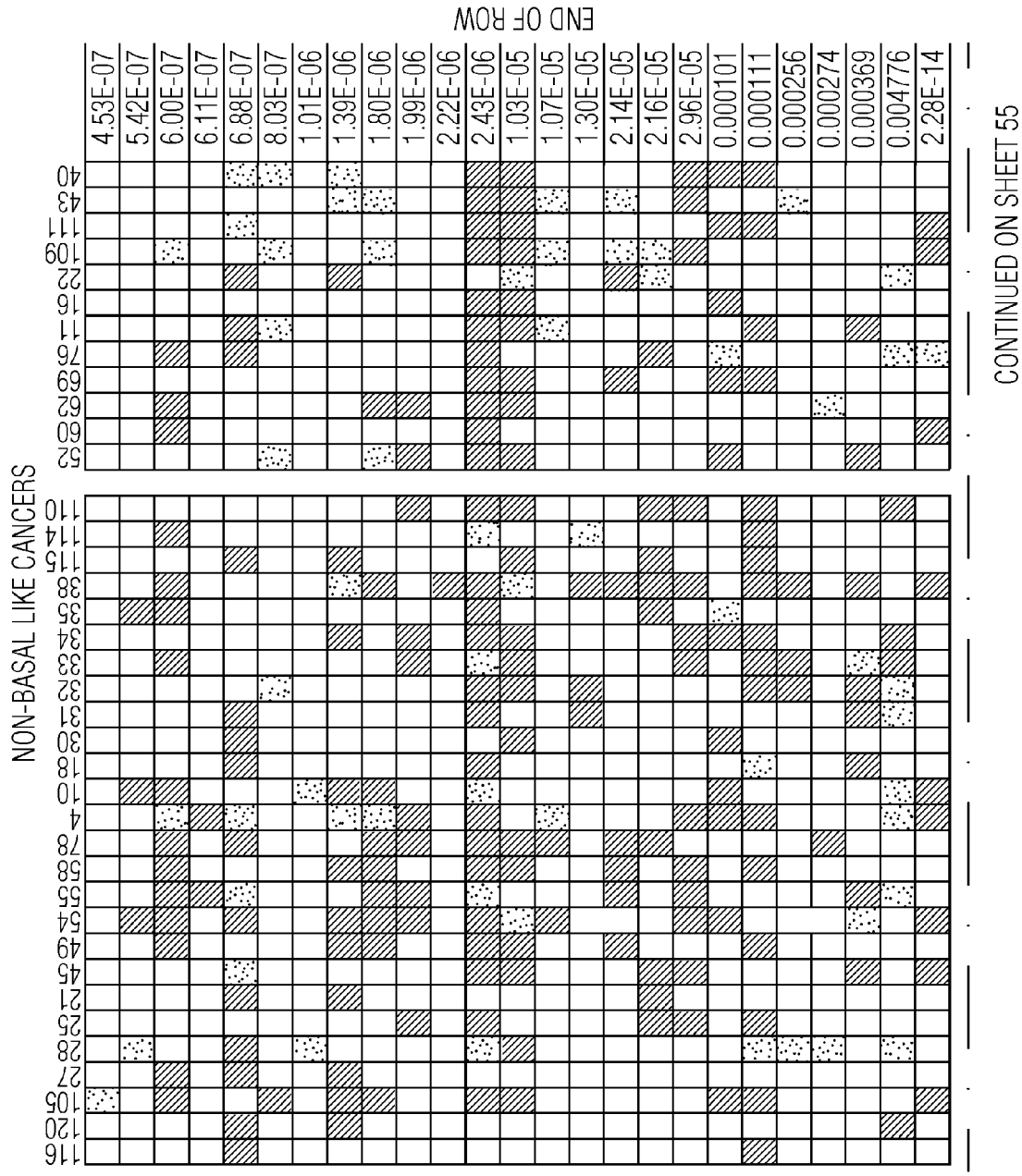
FIG. 25AAA

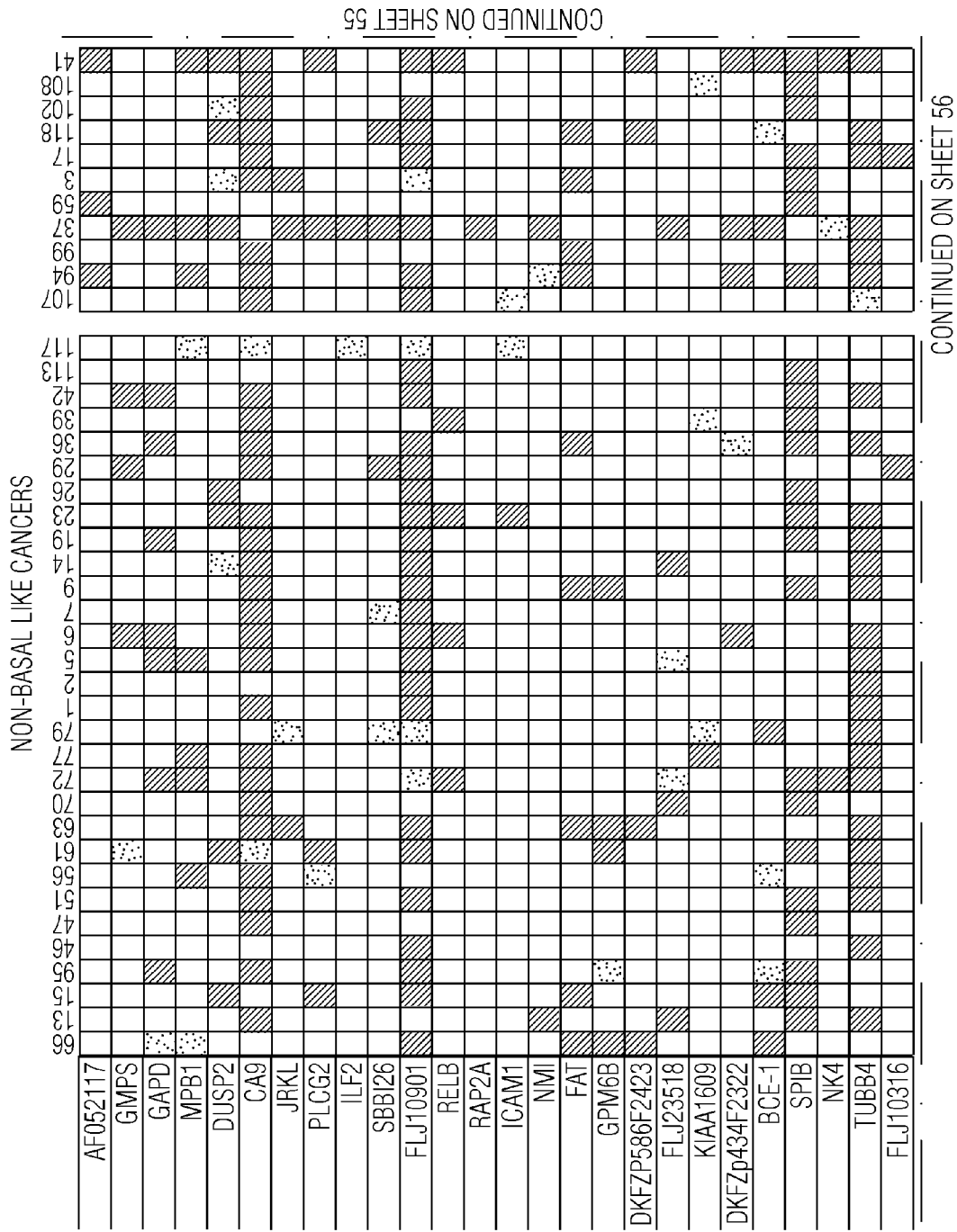
FIG. 25BBB

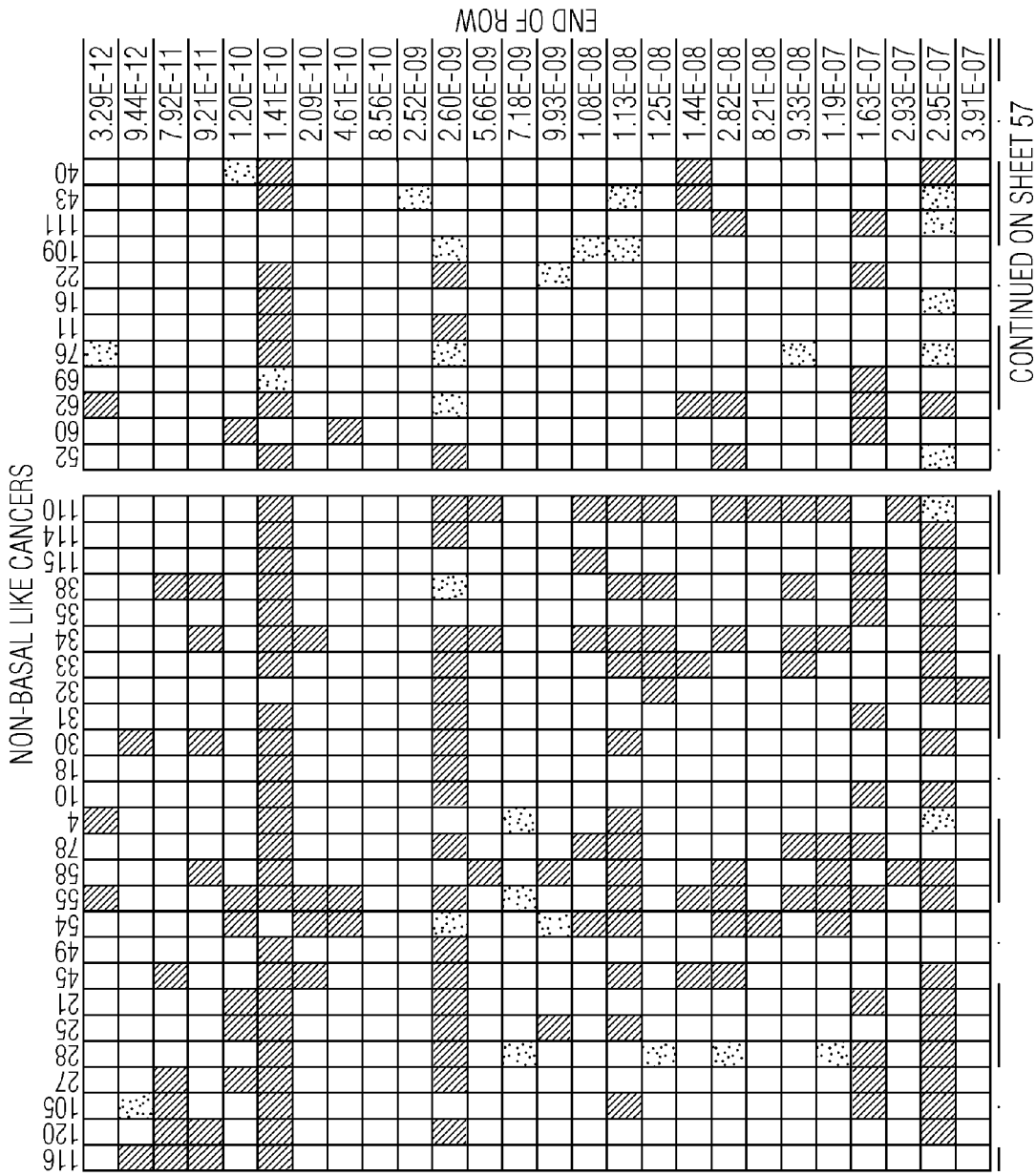
FIG. 25CCC

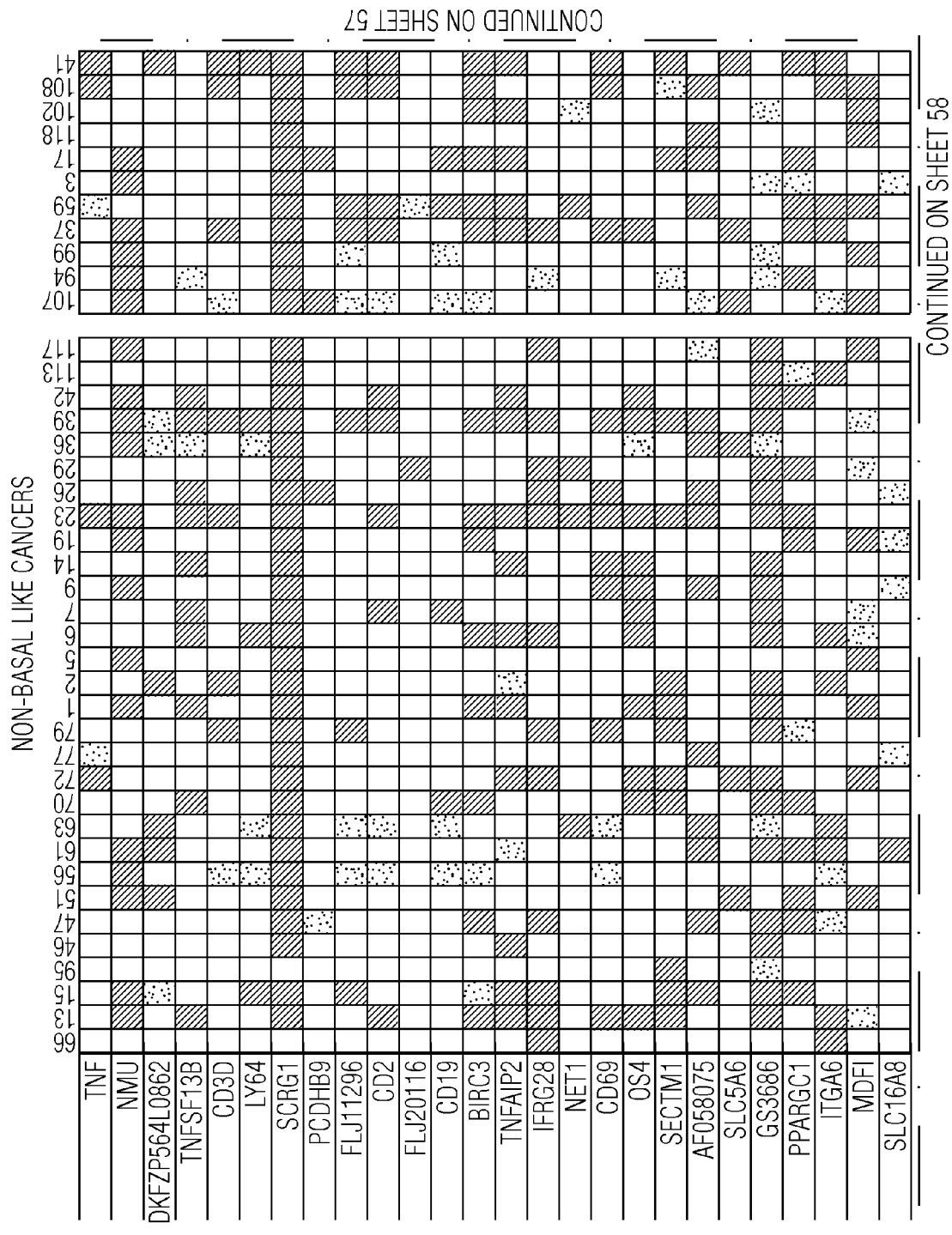
FIG. 25DDD

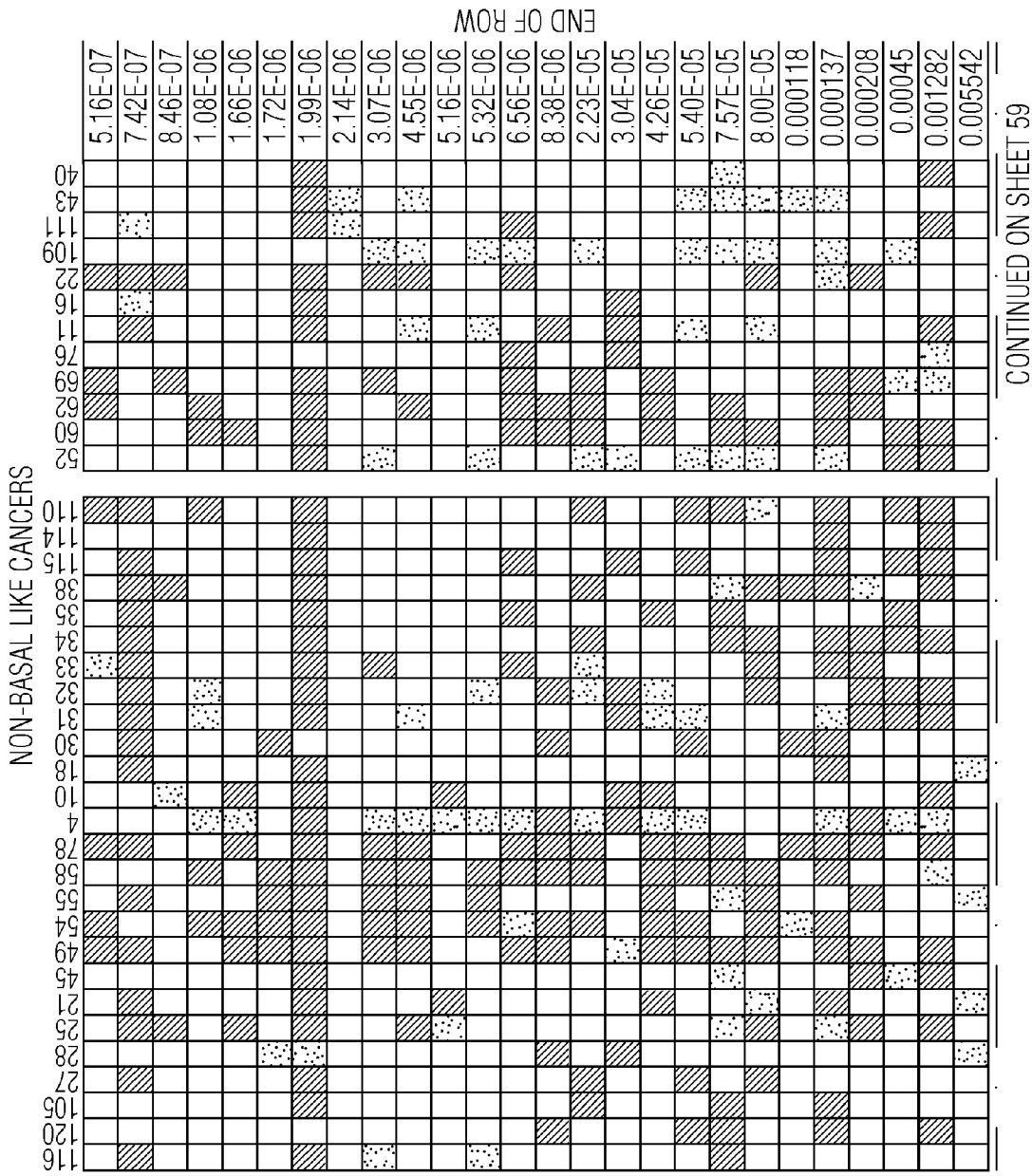
FIG. 25EEE

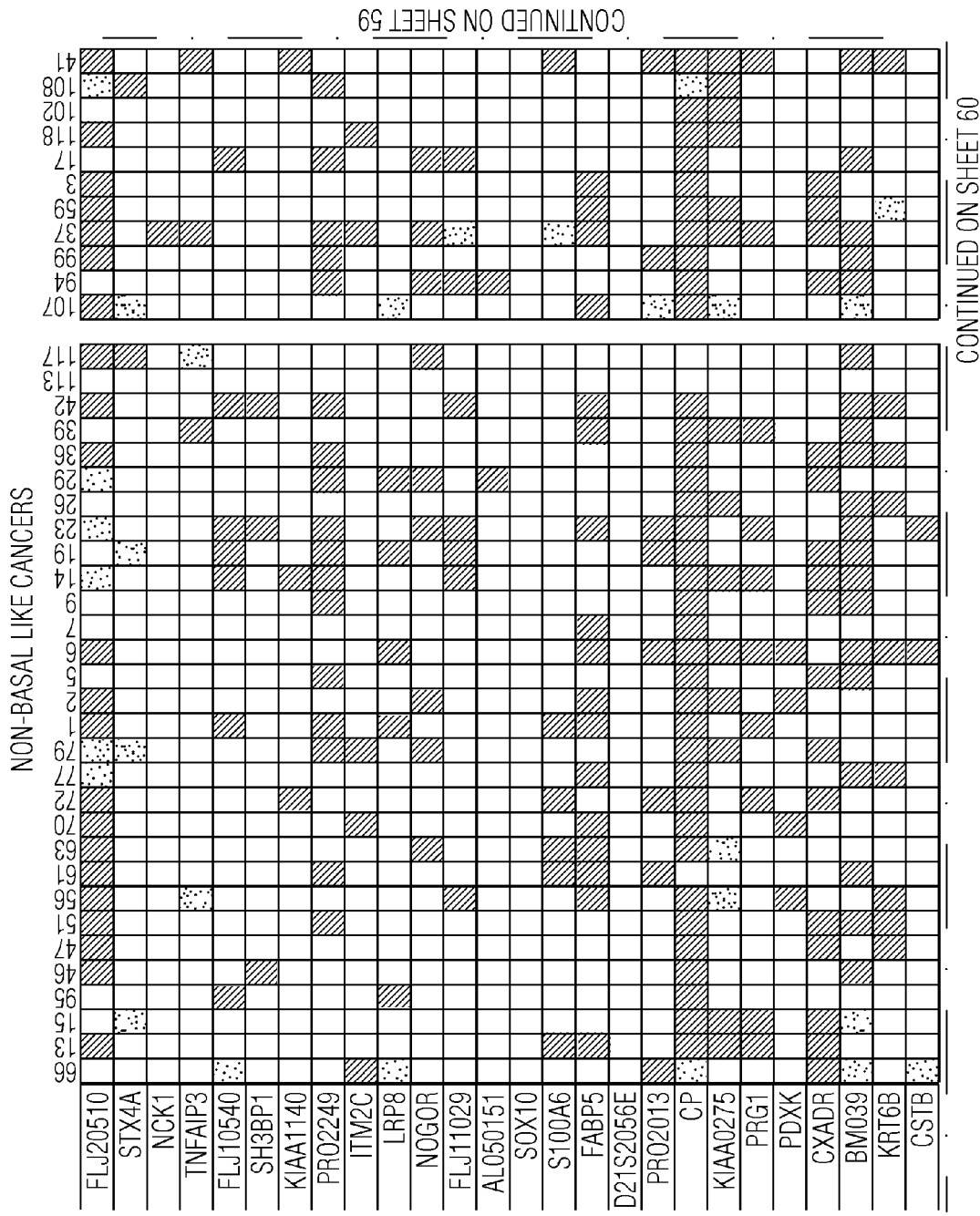
FIG. 25FFF

FIG. 25GGG

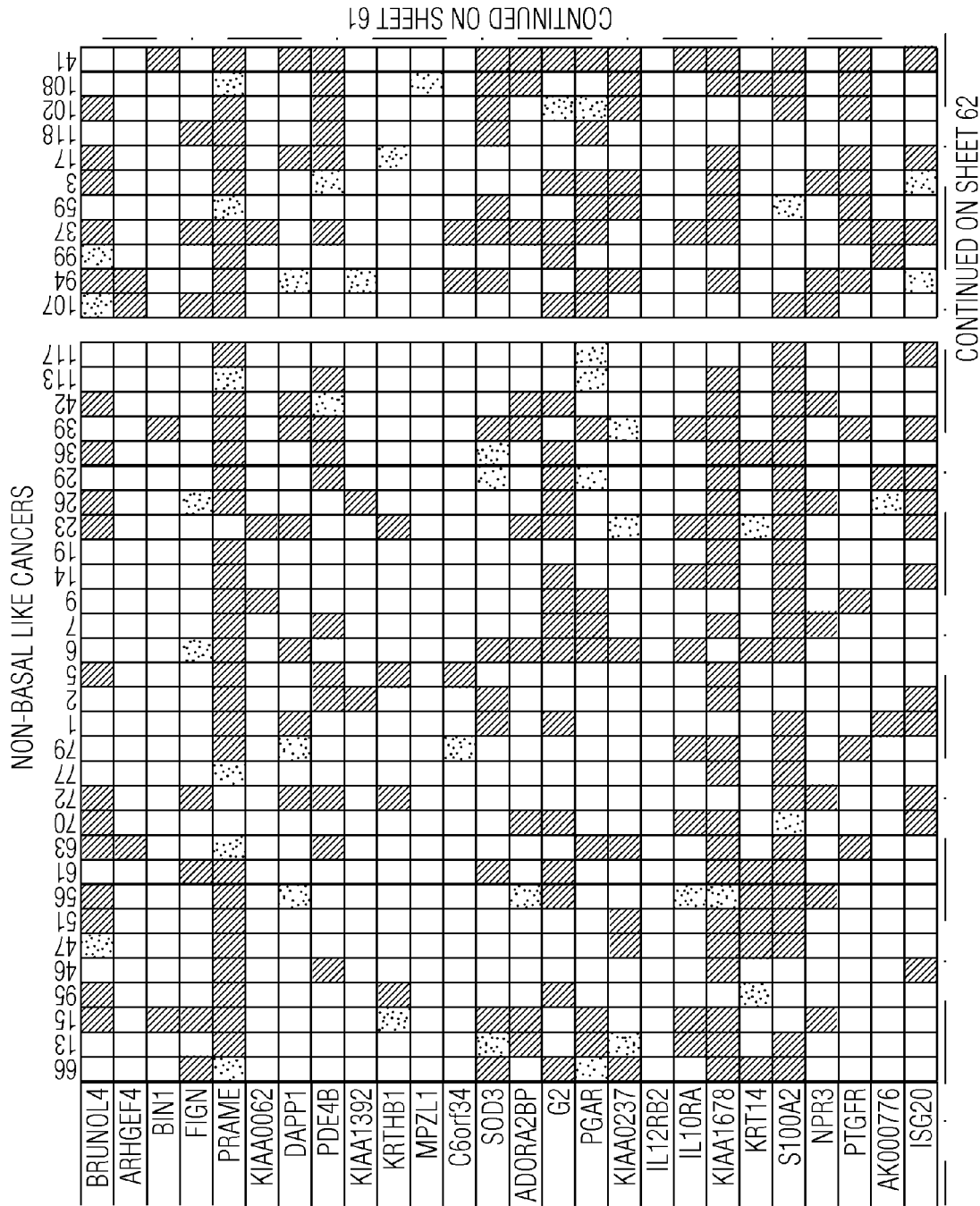
FIG. 25HHH

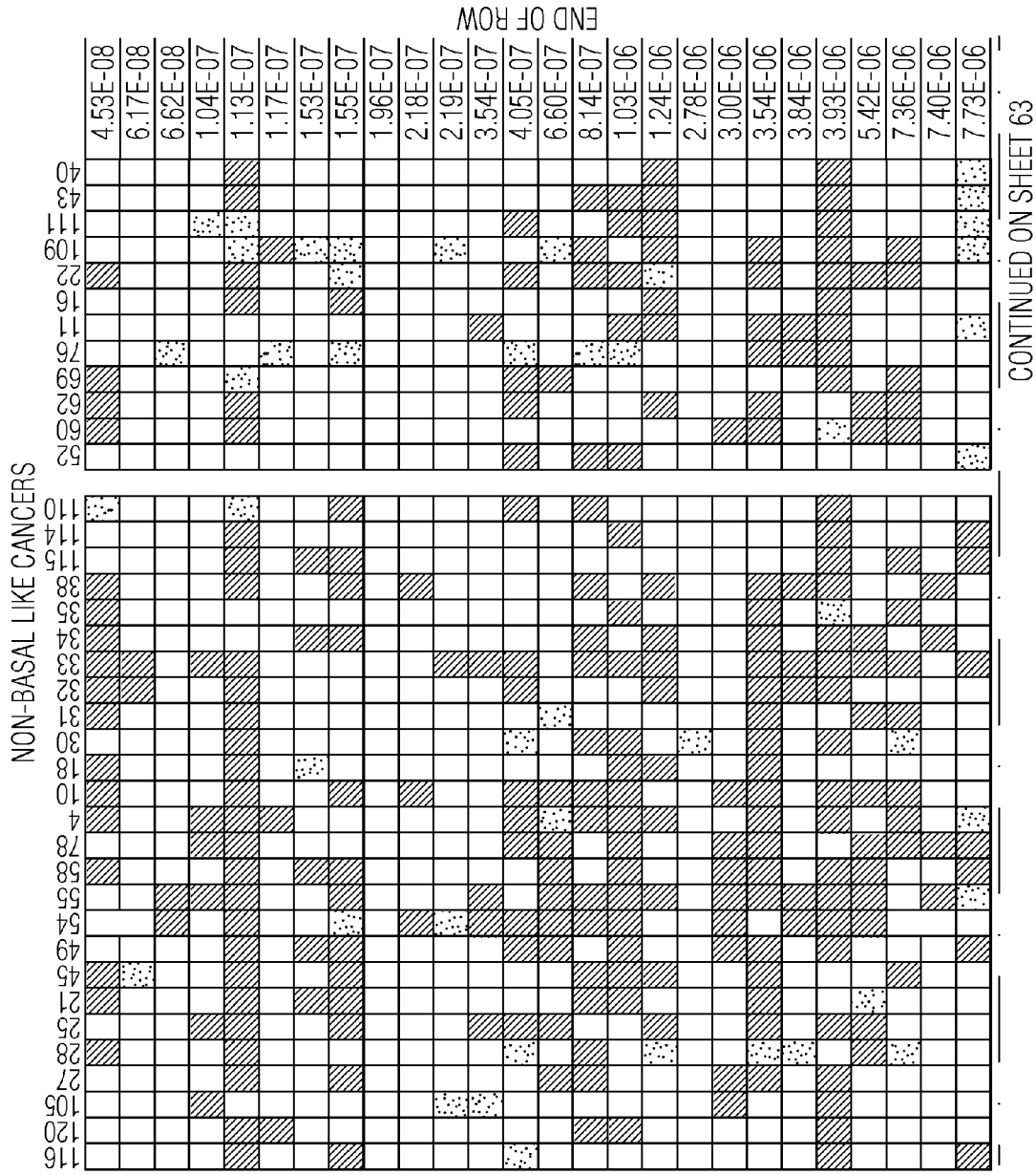
FIG. 25III

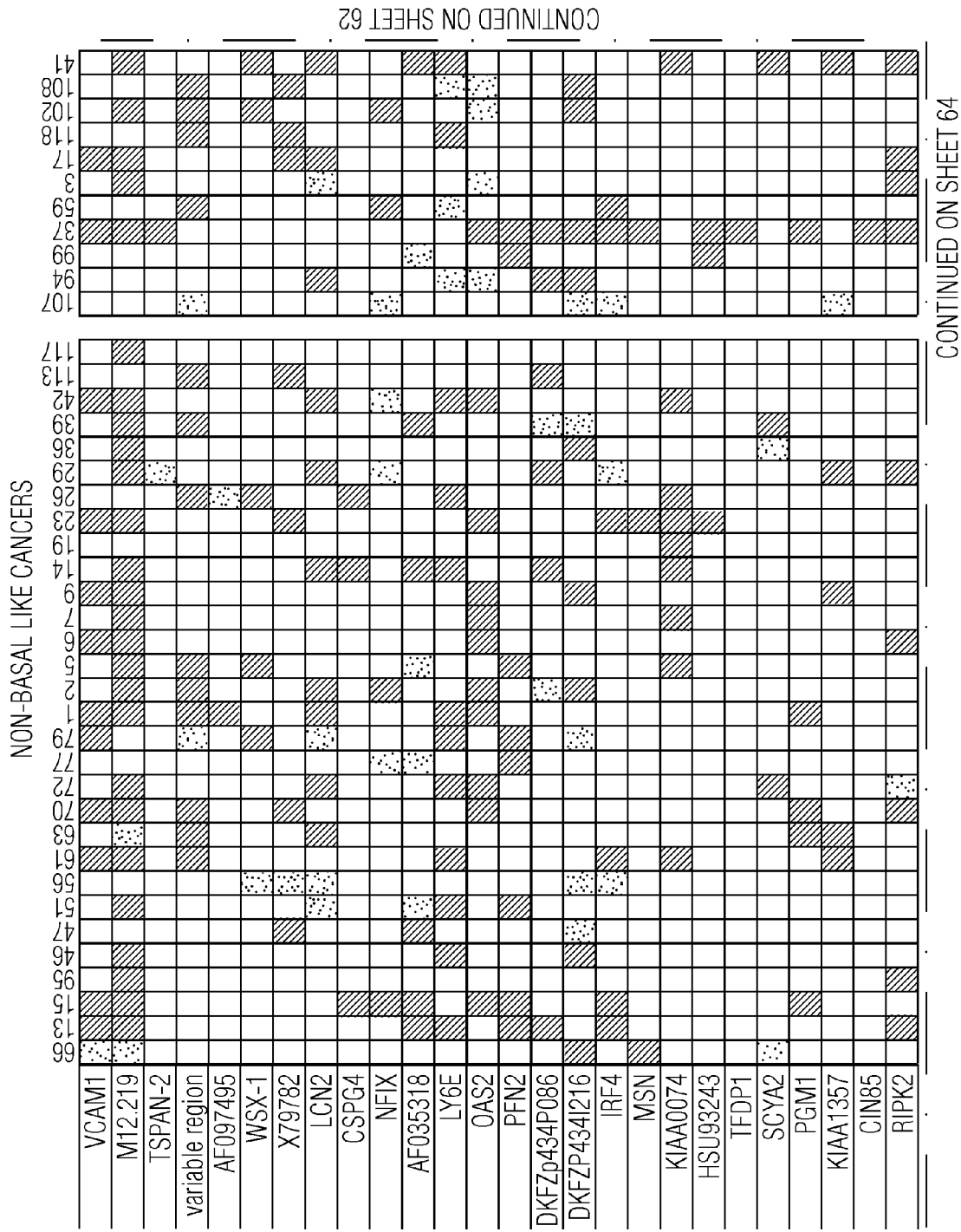
FIG. 25JJJ

FIG. 25KKK

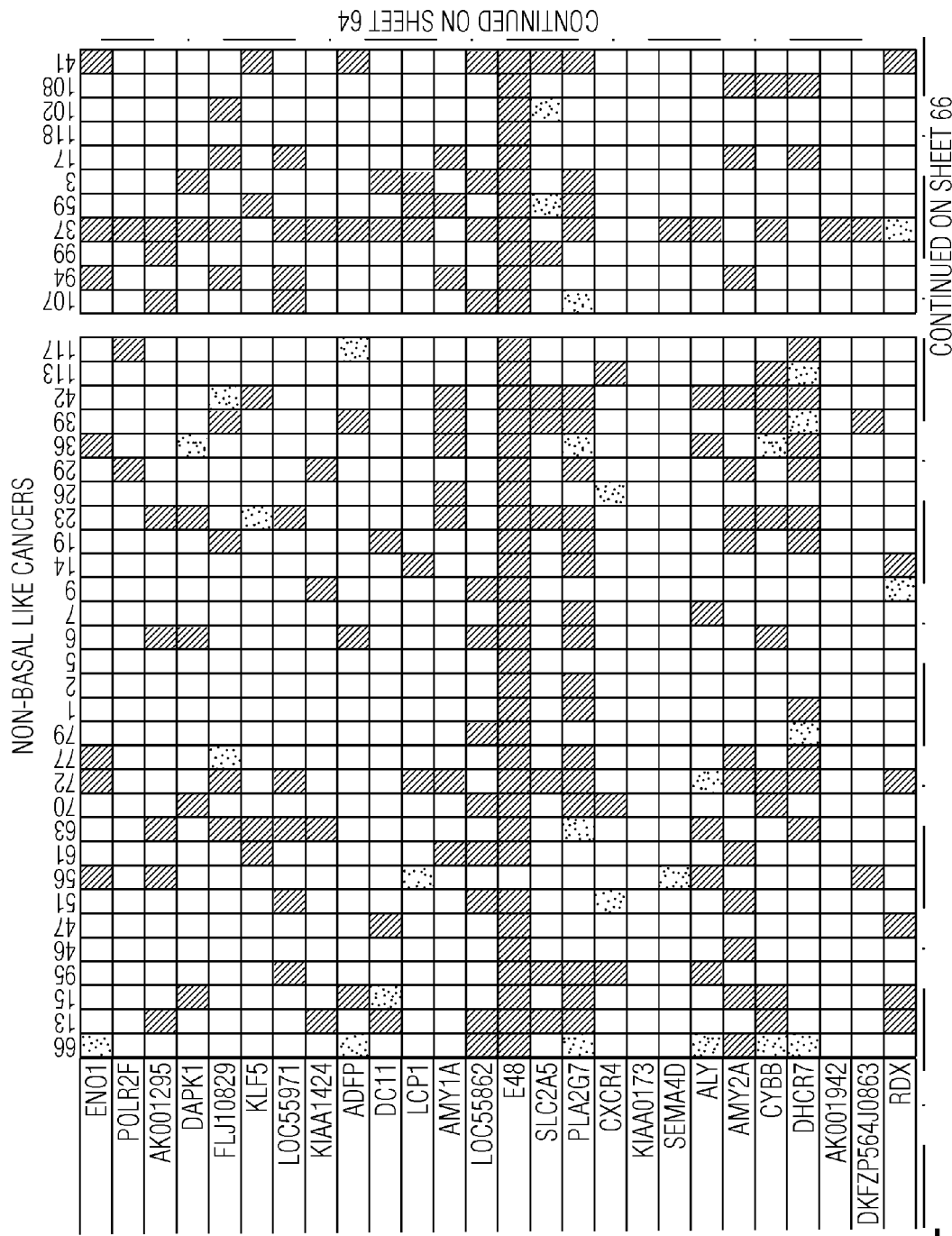
FIG. 25LLL

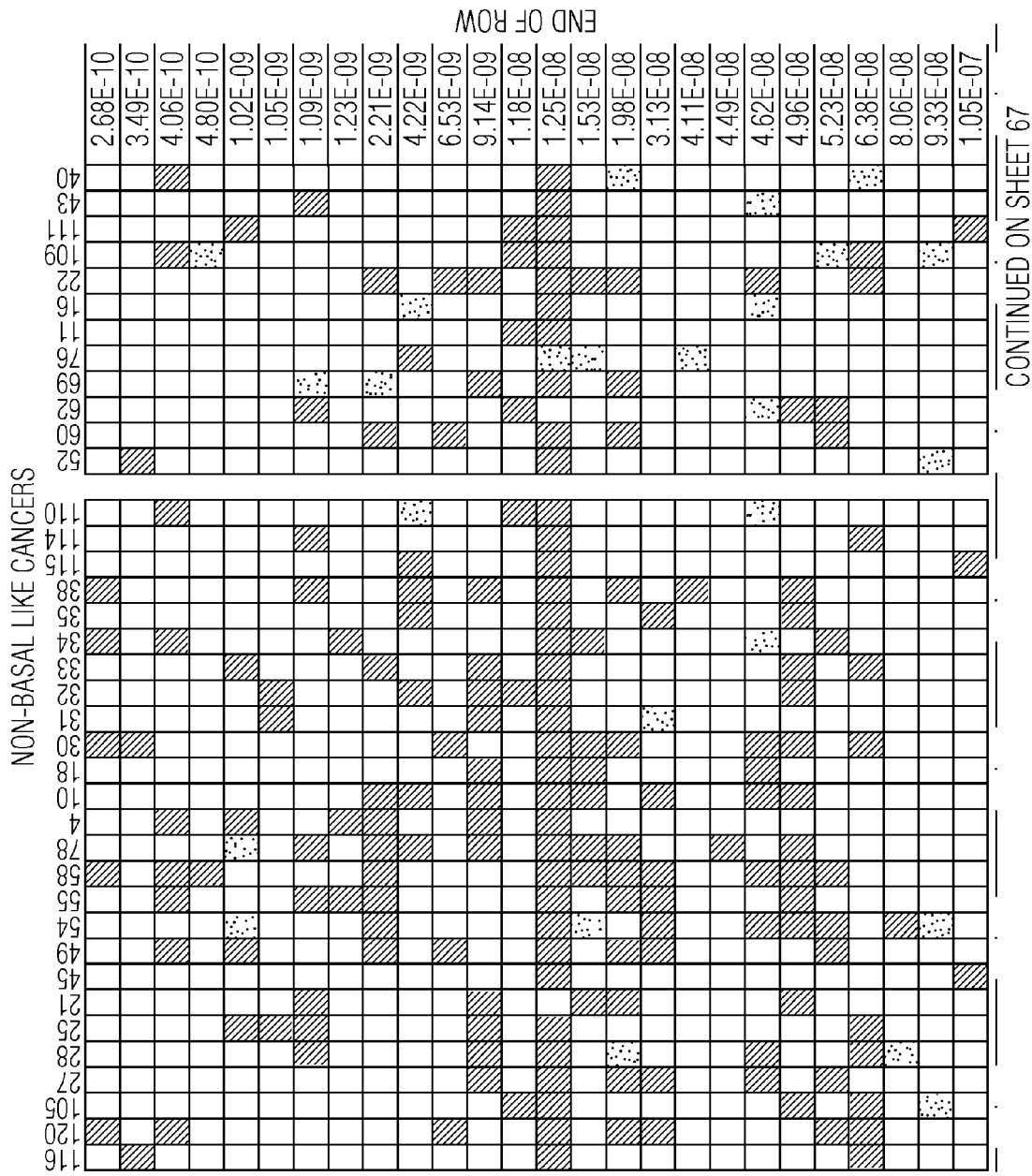
FIG. 25MMM

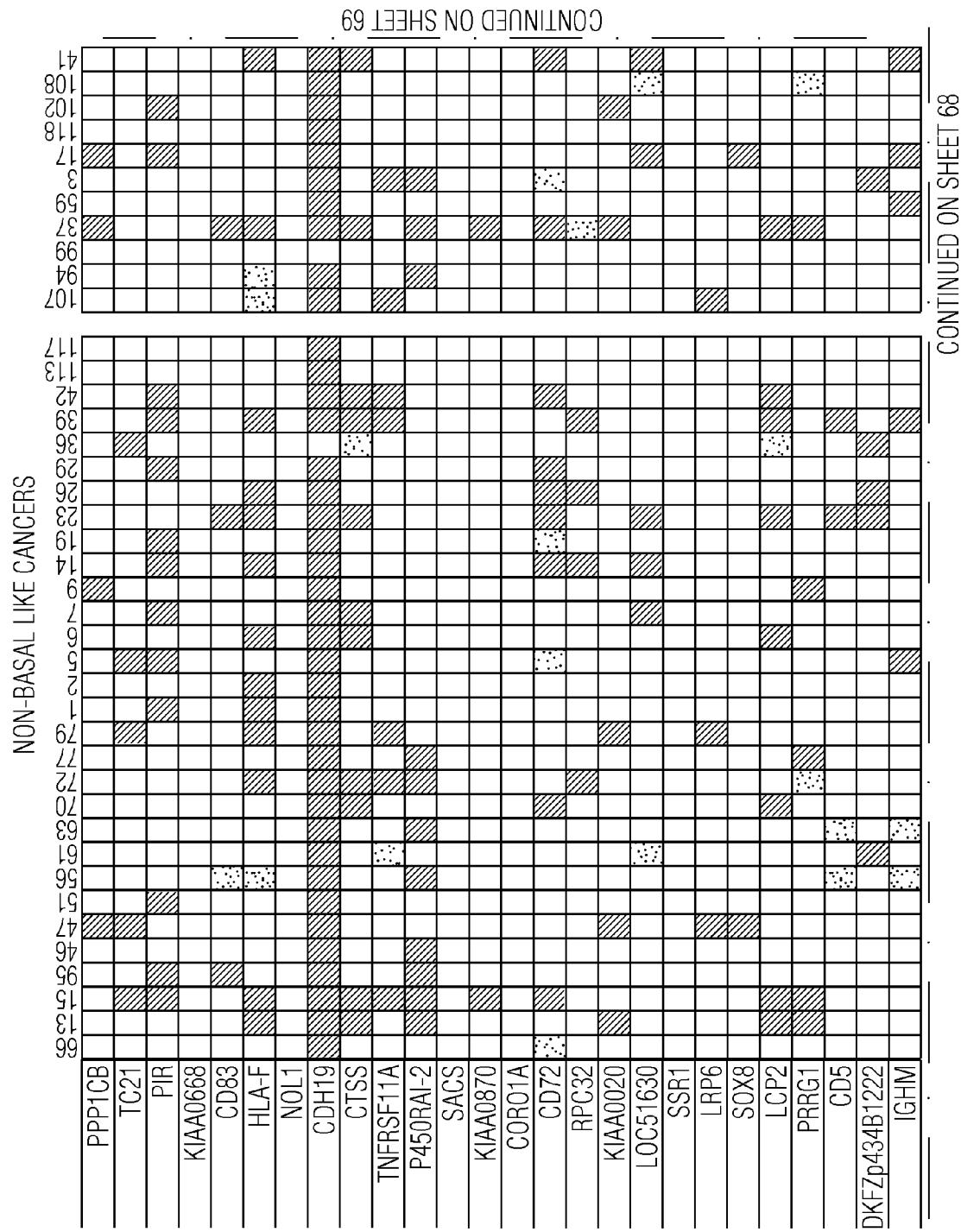
FIG. 25NNN

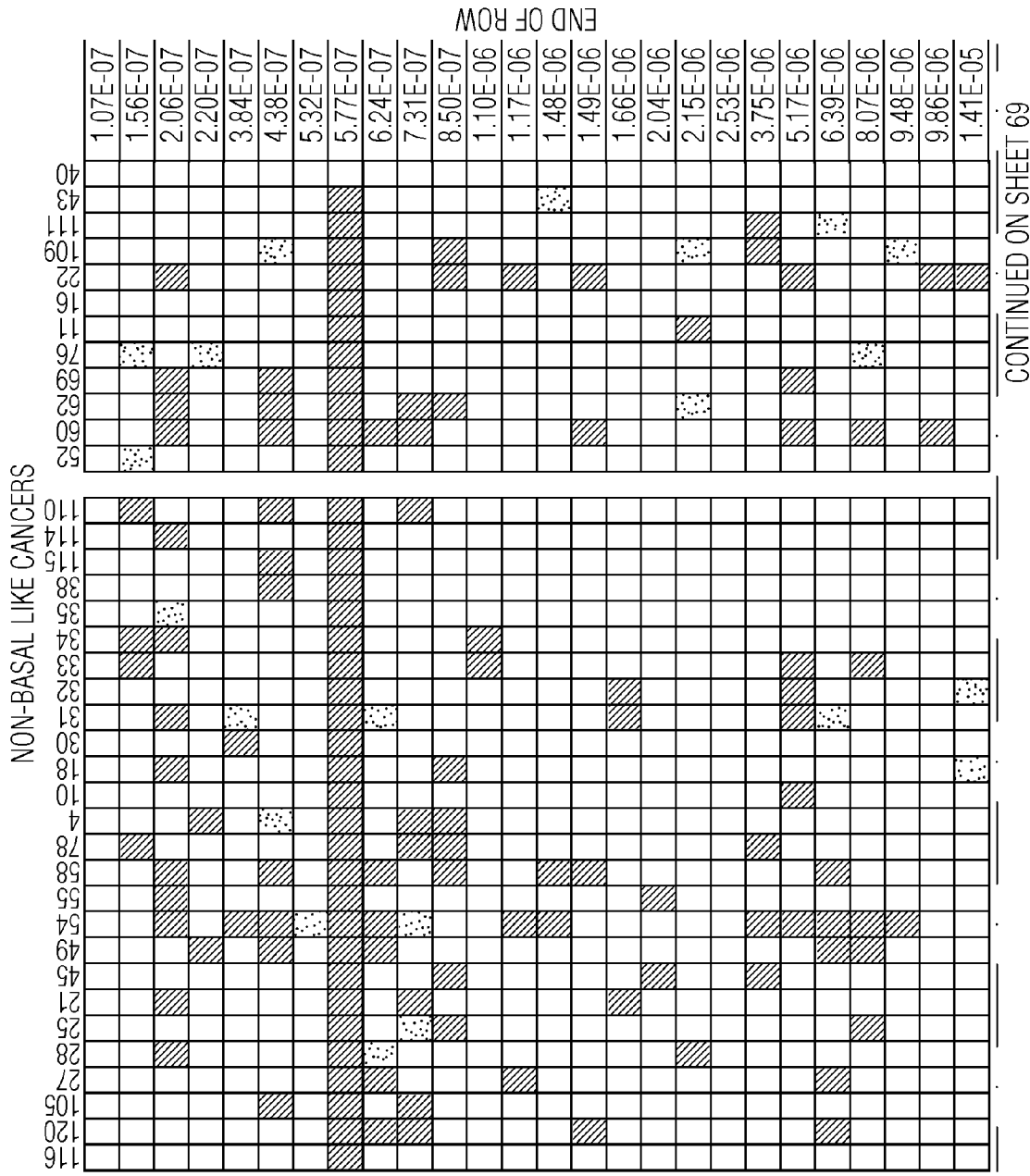
FIG. 25000

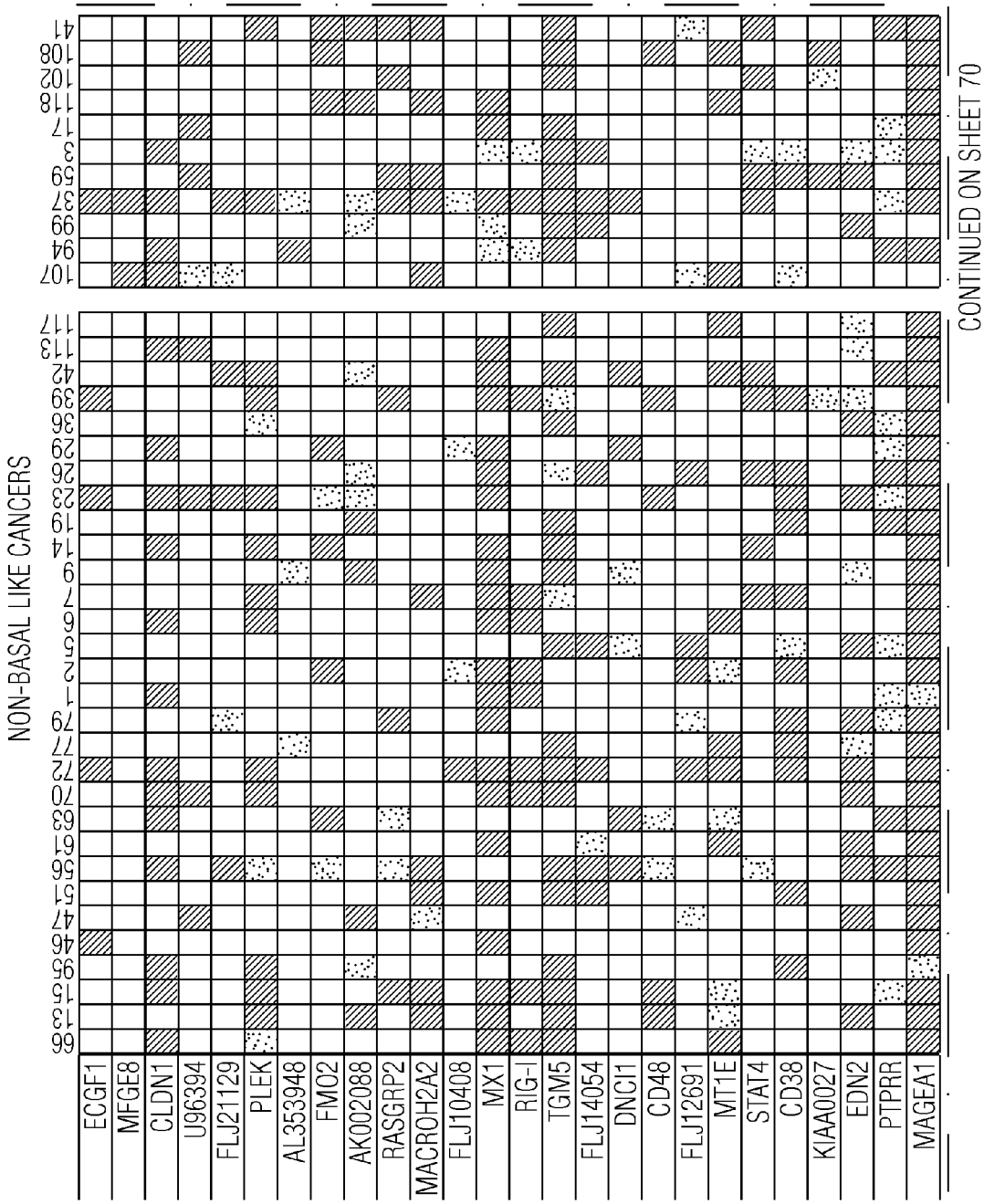
FIG. 25PPP

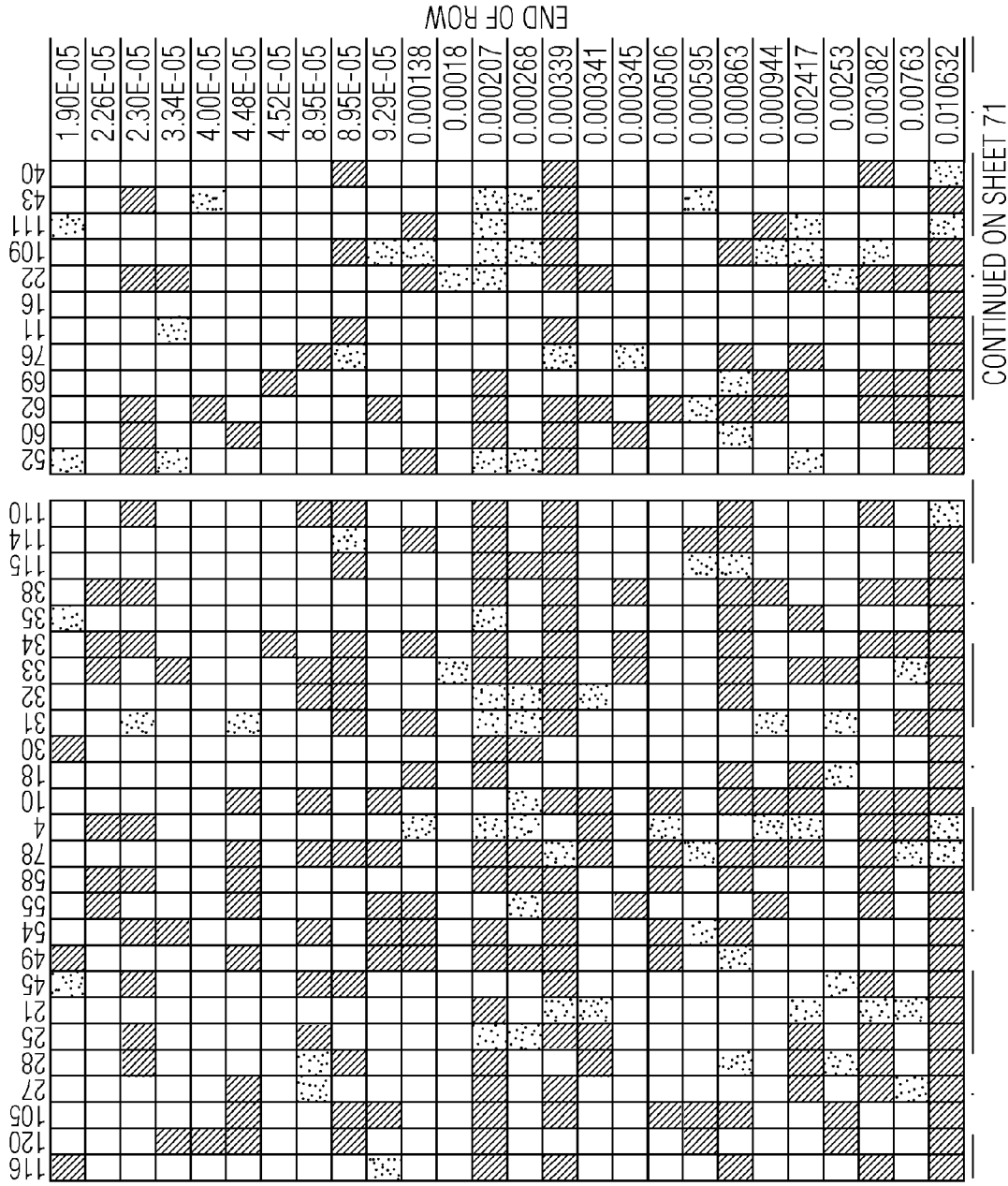
FIG. 25QQQ

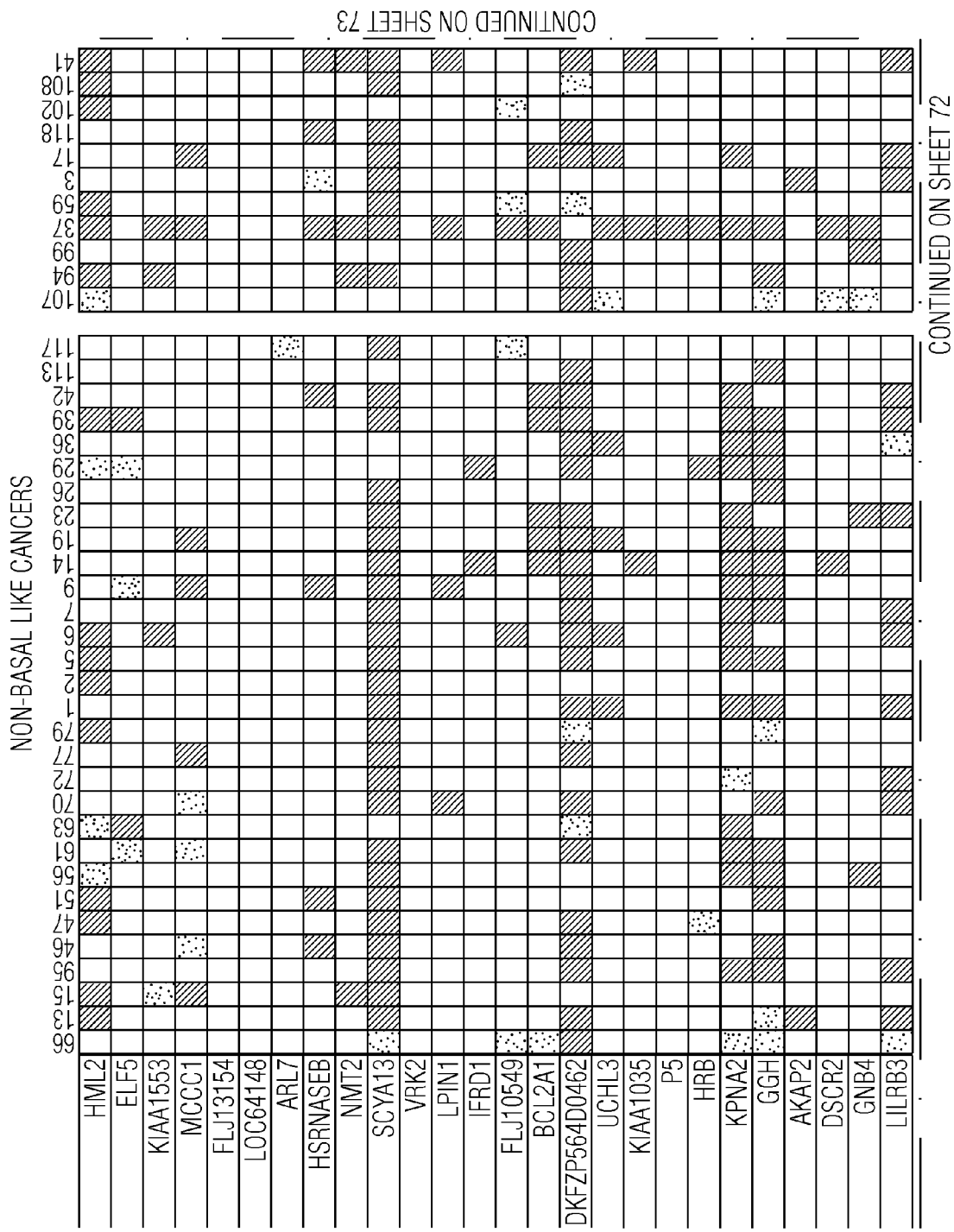
FIG. 25RRR

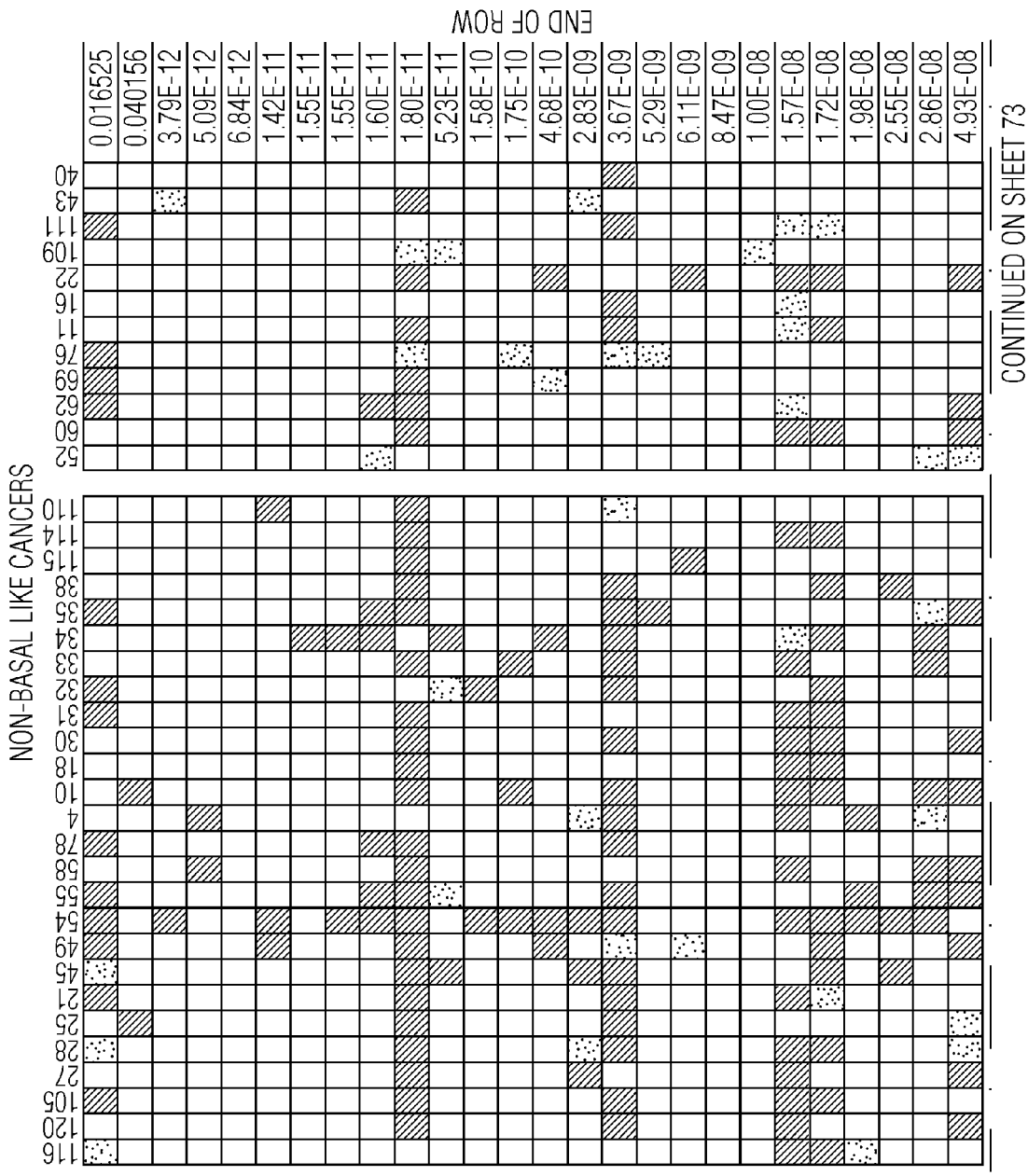
FIG. 25SSS

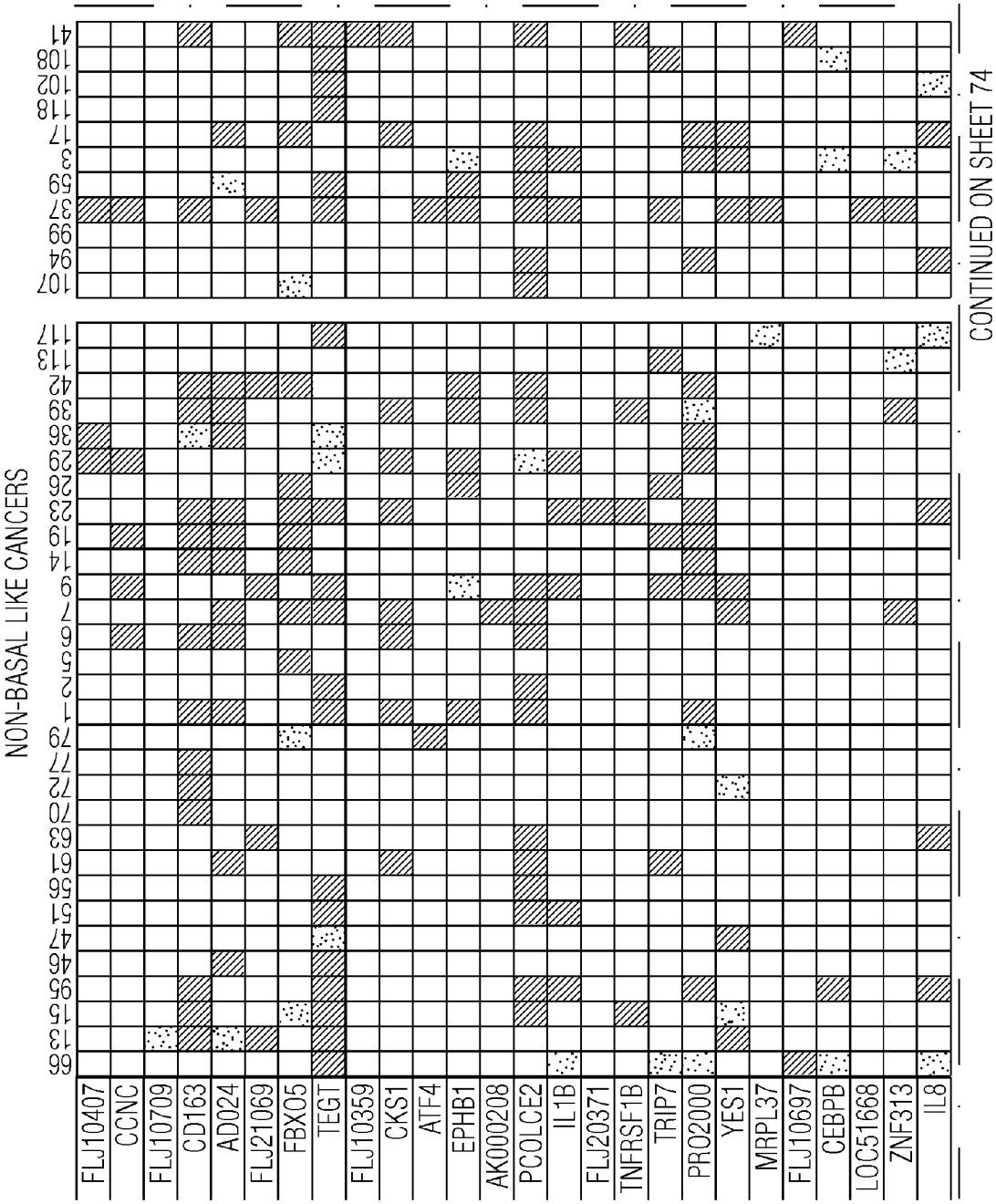
FIG. 25TTT

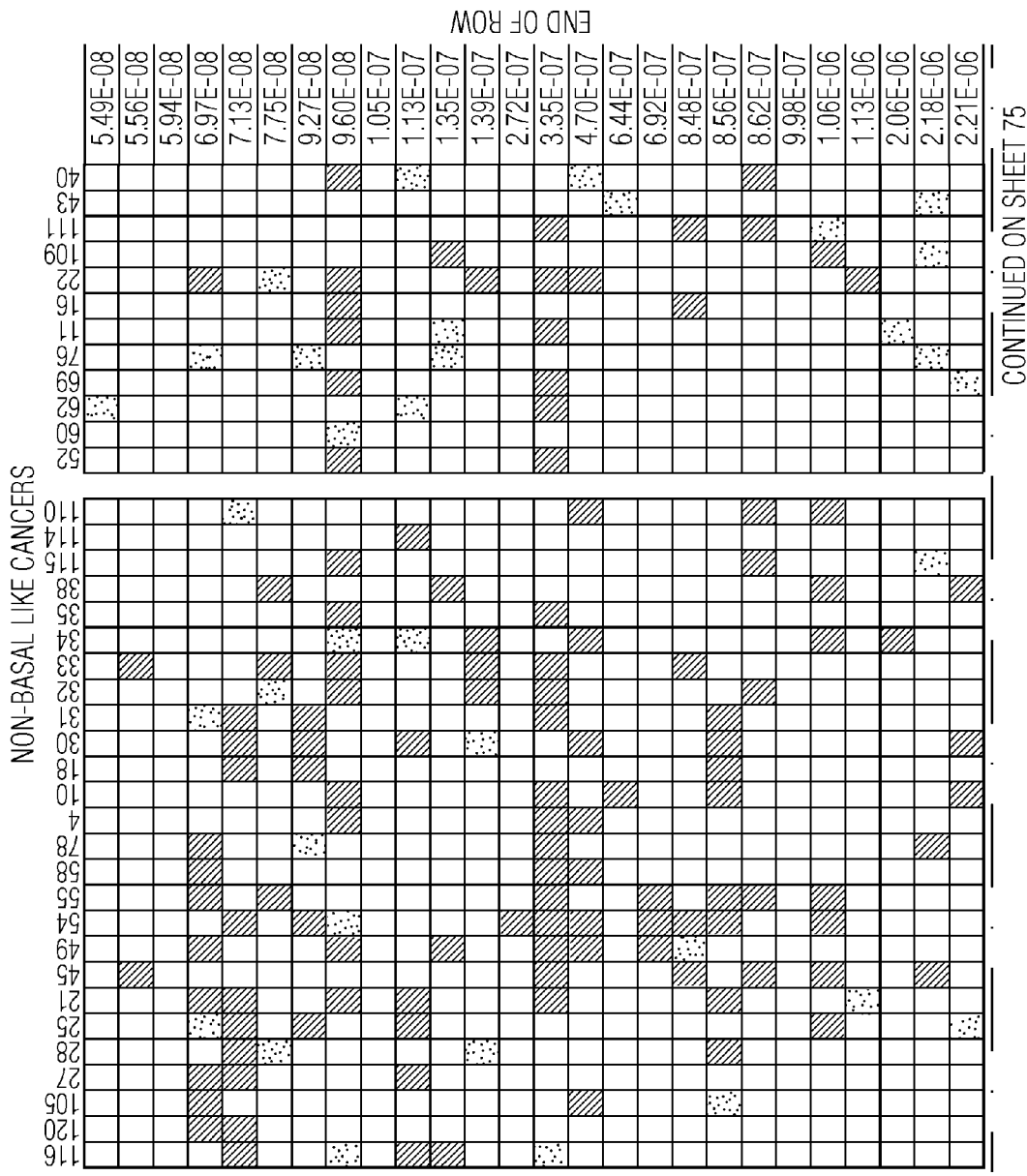
FIG. 25UUU

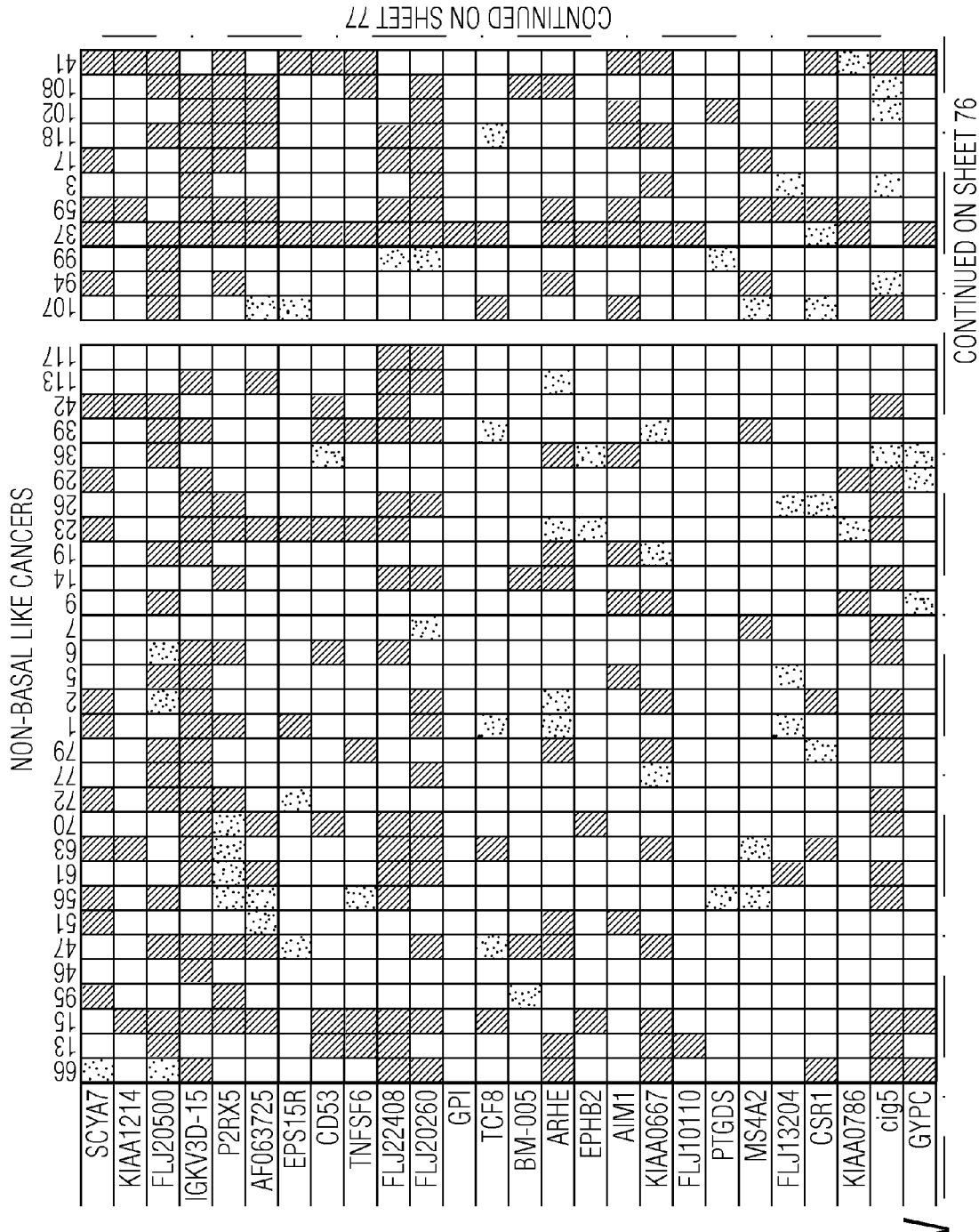
FIG. 25VVV

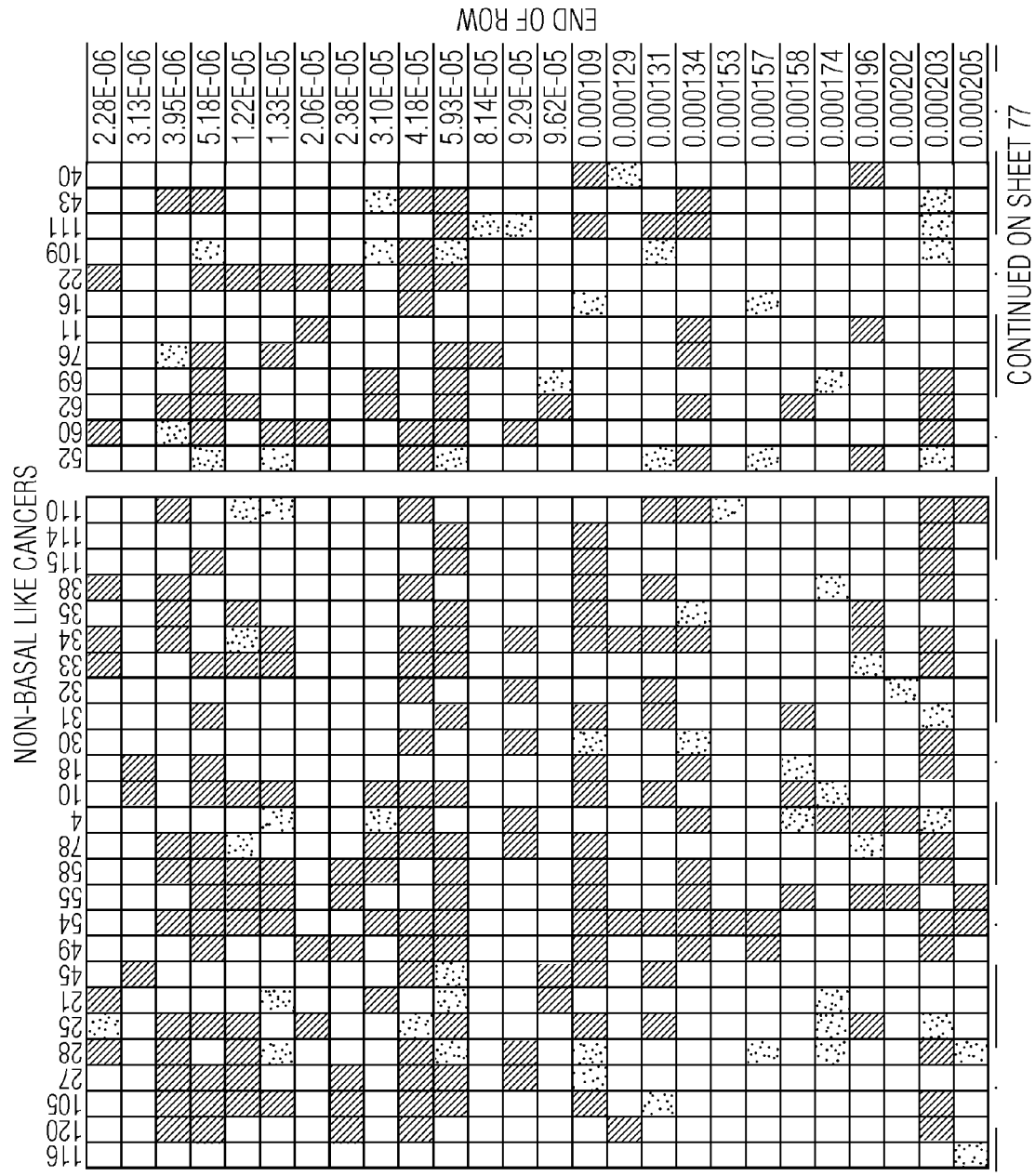
FIG. 25WWW

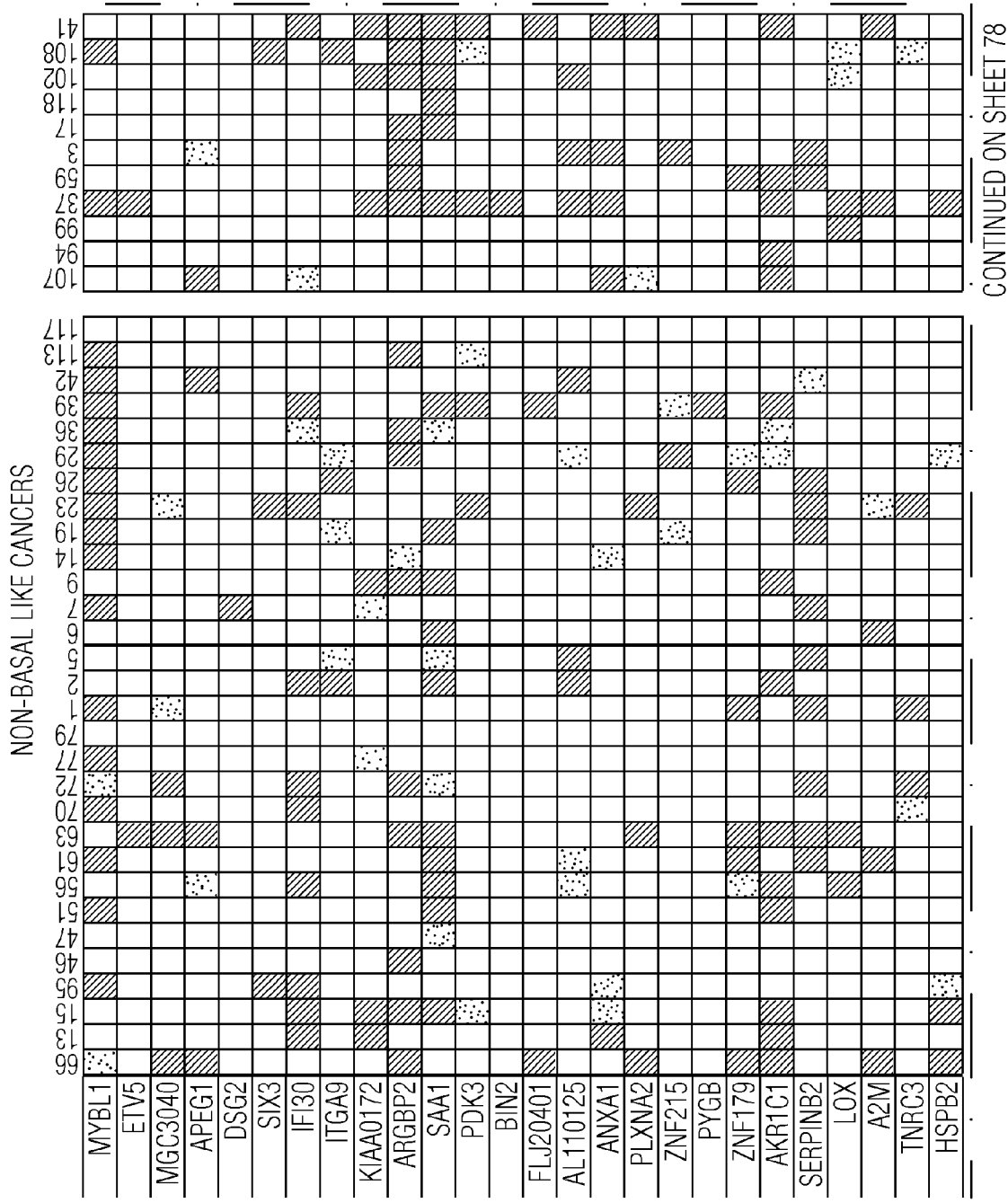
FIG. 25XXX

FIG. 25YYY

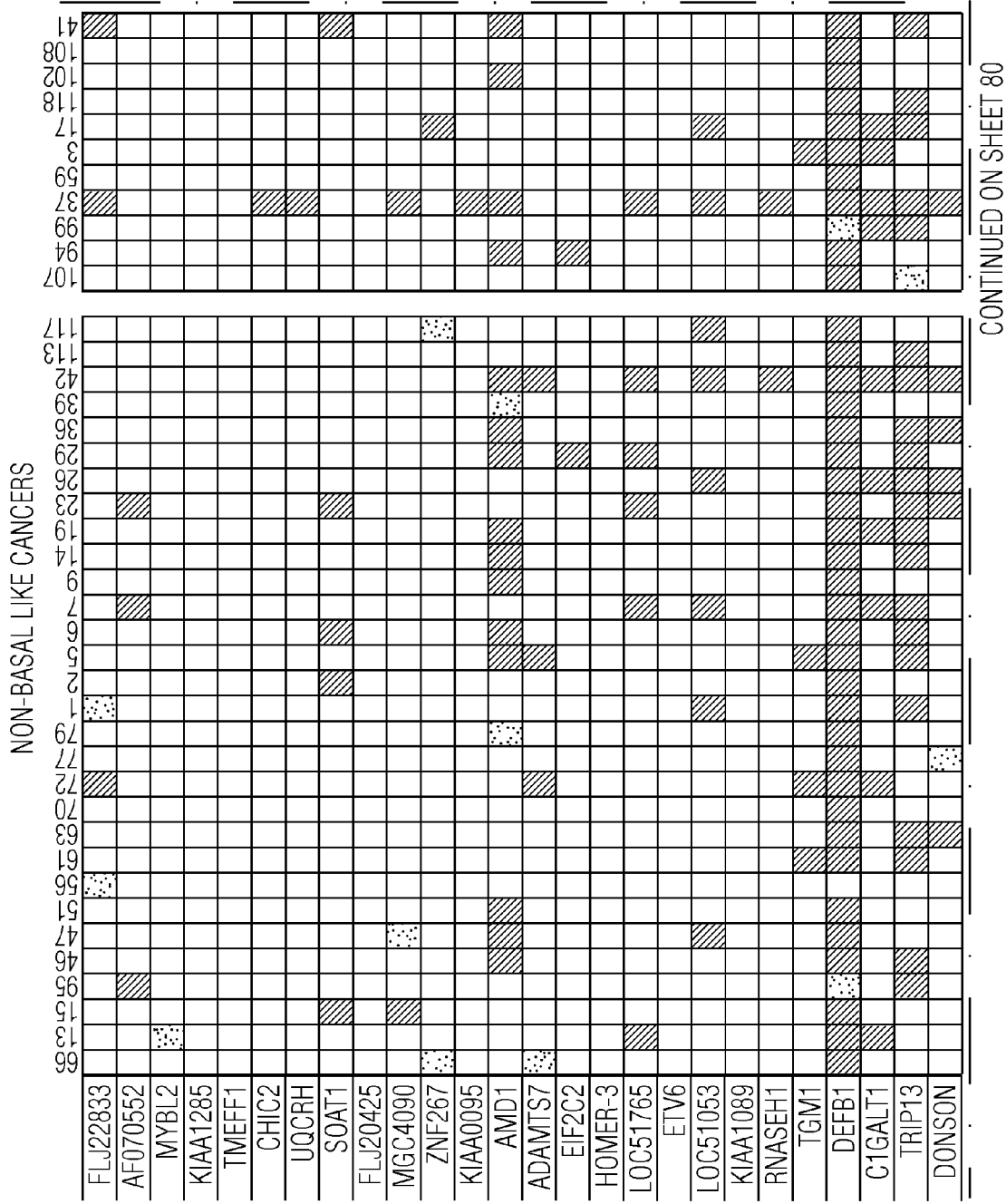
FIG. 25ZZZ

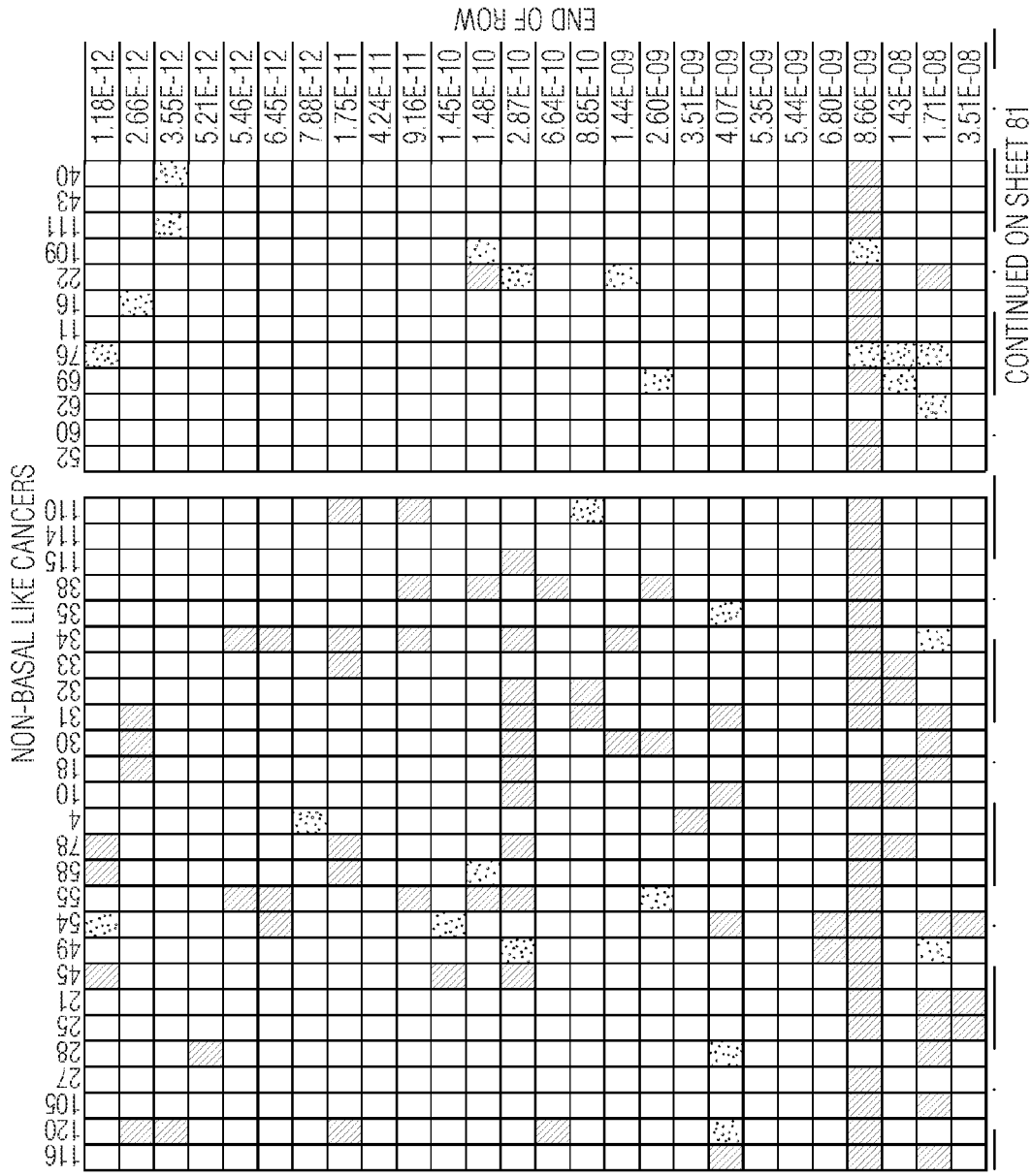
FIG. 25AAAA

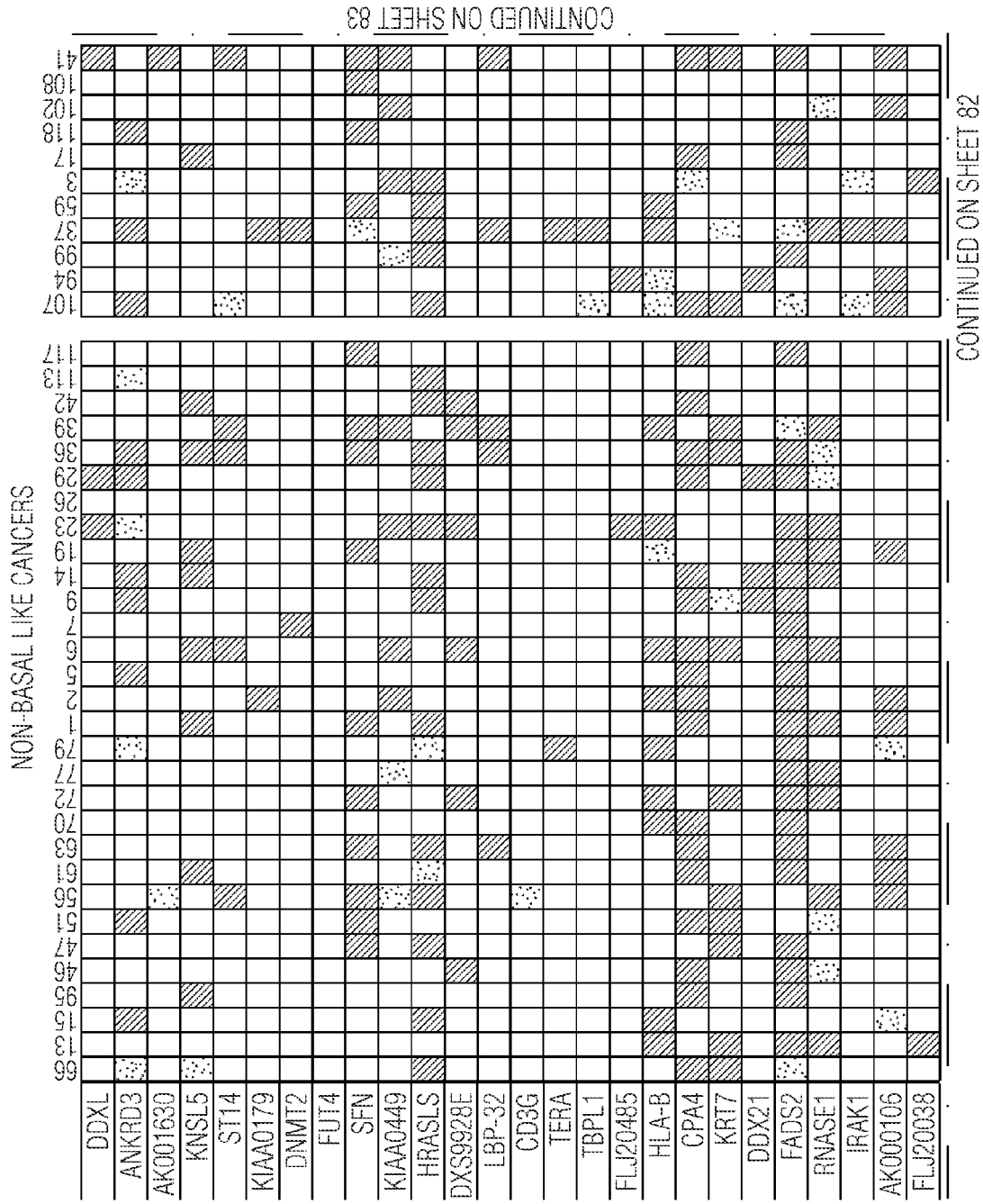
FIG. 25BBBB

FIG. 25CCC

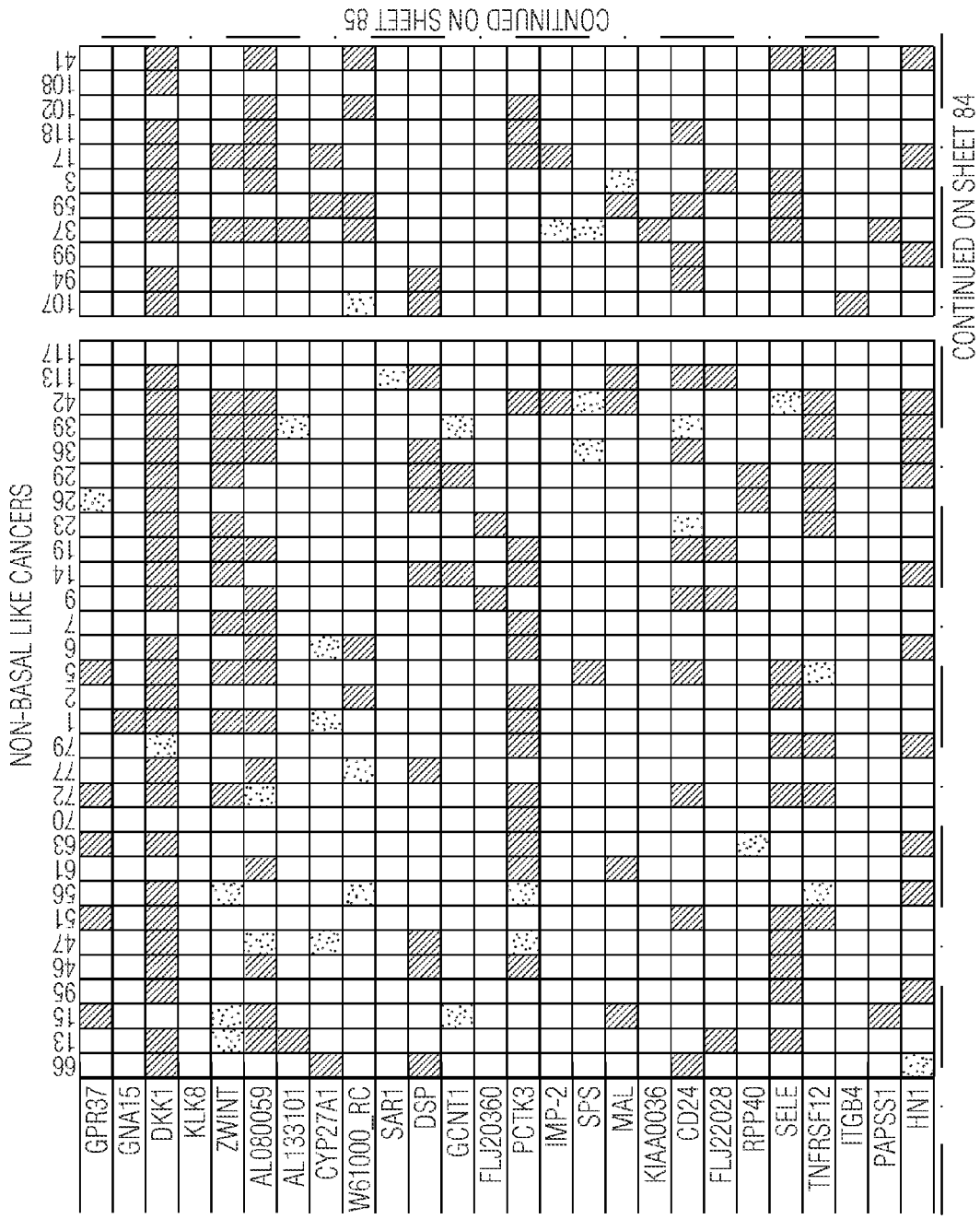
FIG. 25DDDD

FIG. 25EEEE

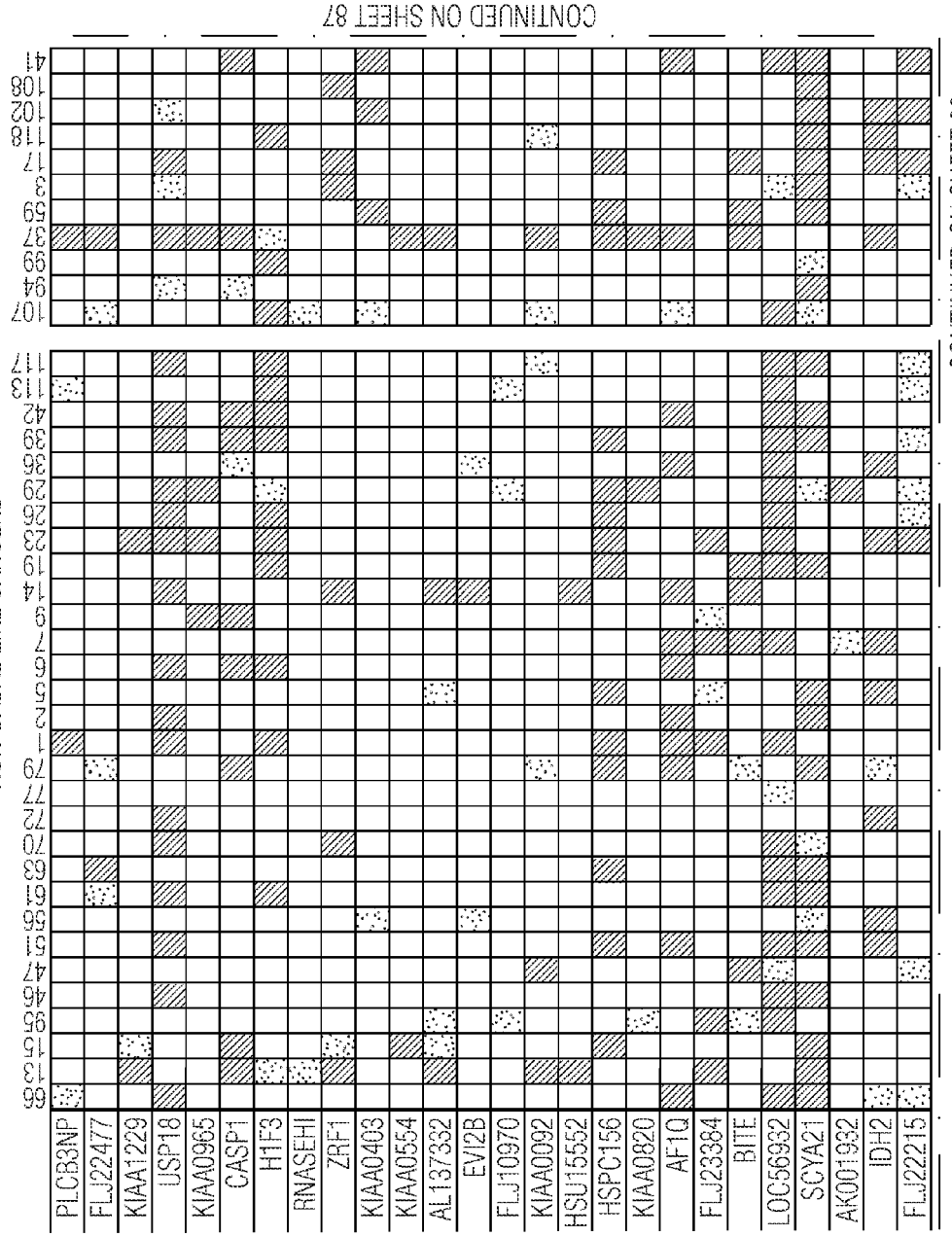
FIG. 25FFFF

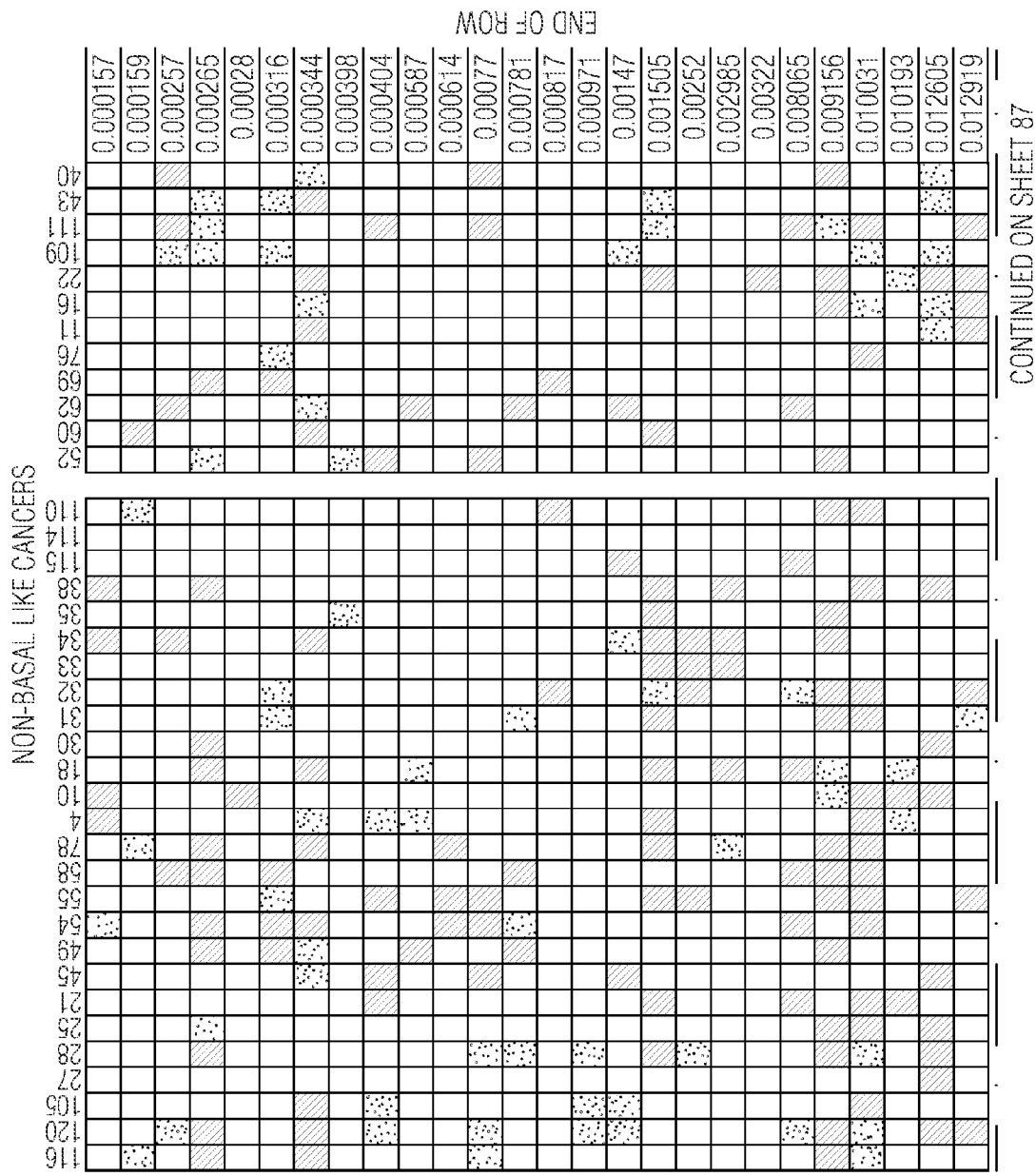
FIG. 25GGGG

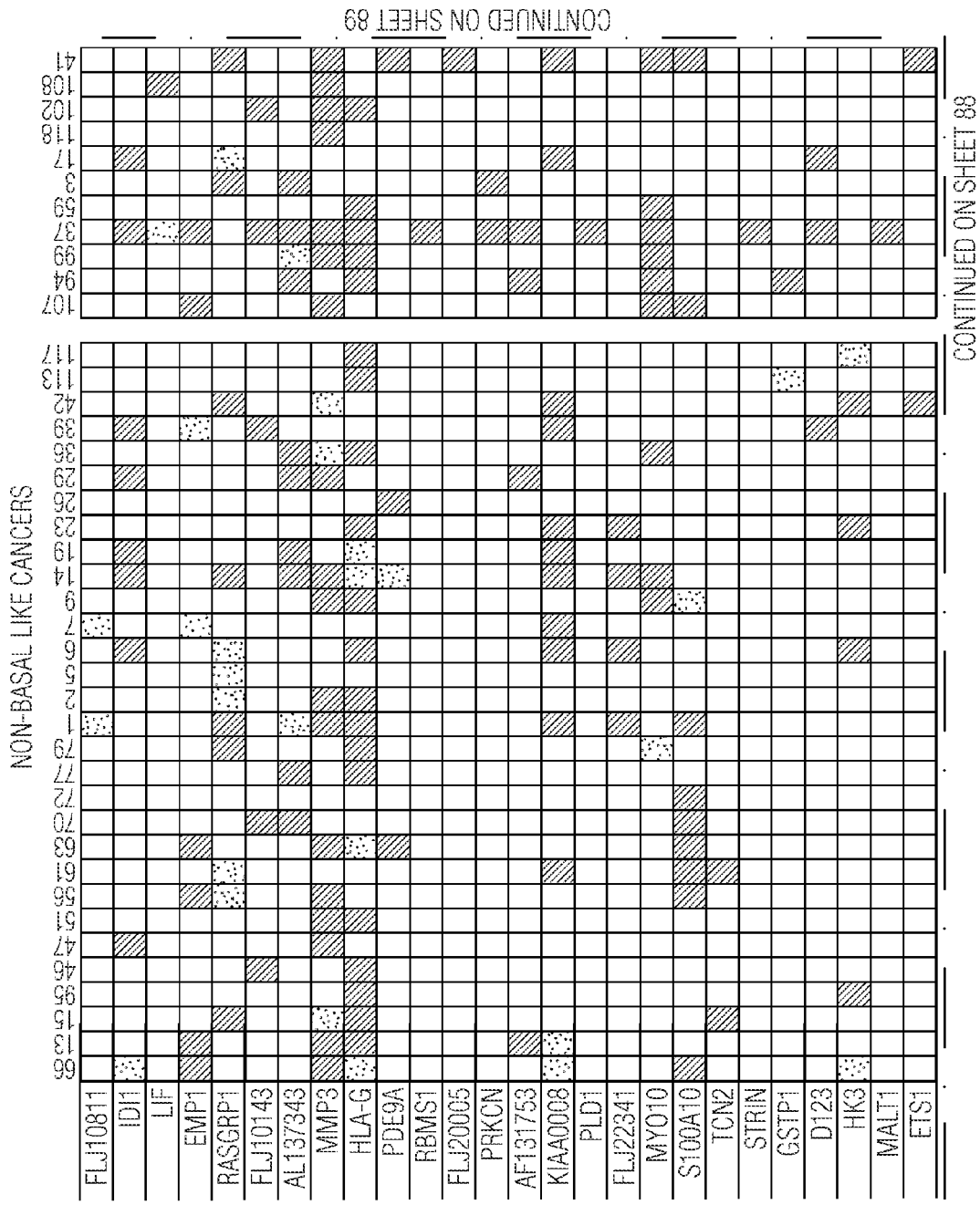
FIG. 25HHHH

FIG. 25IIIII

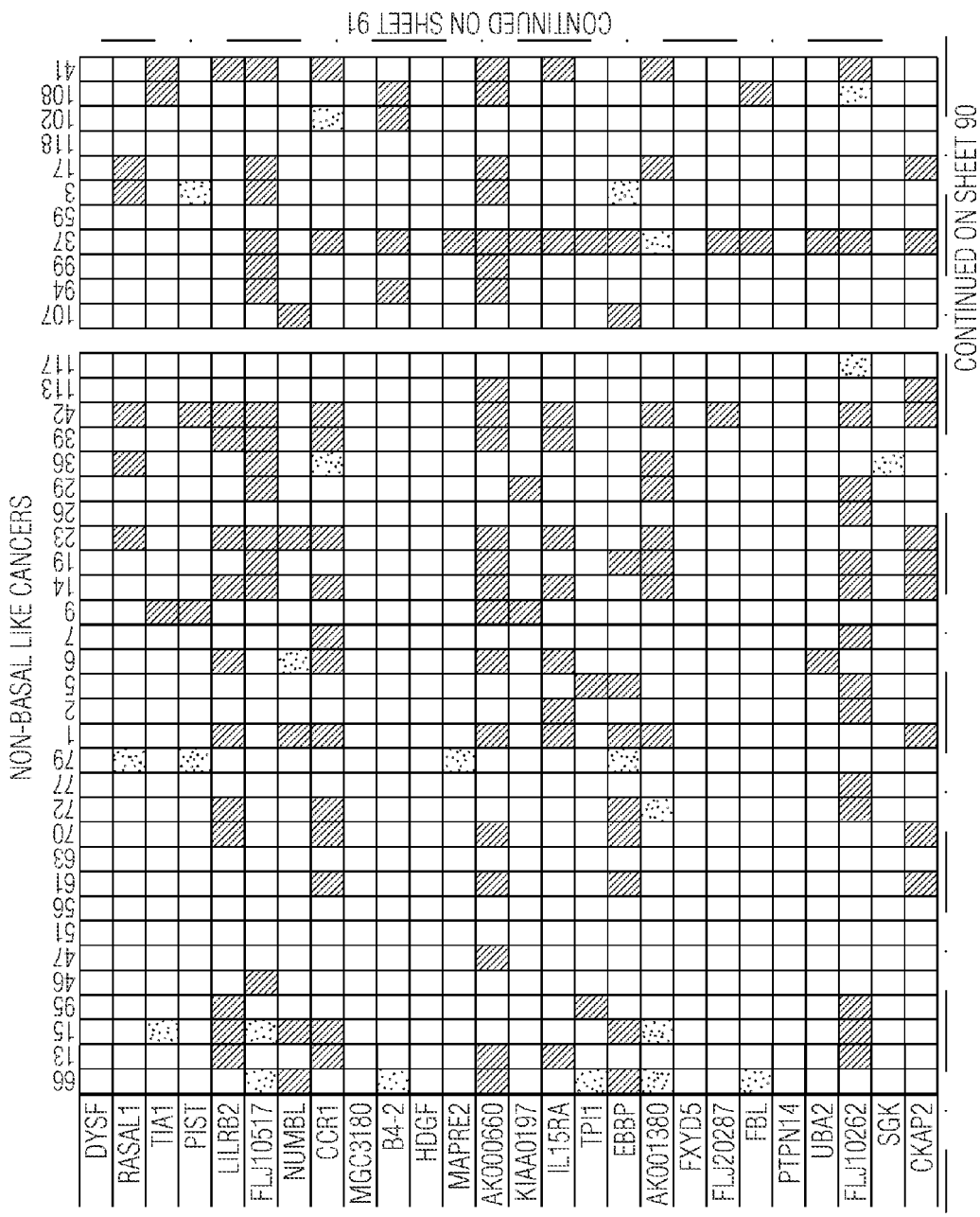
FIG. 25JJJJ

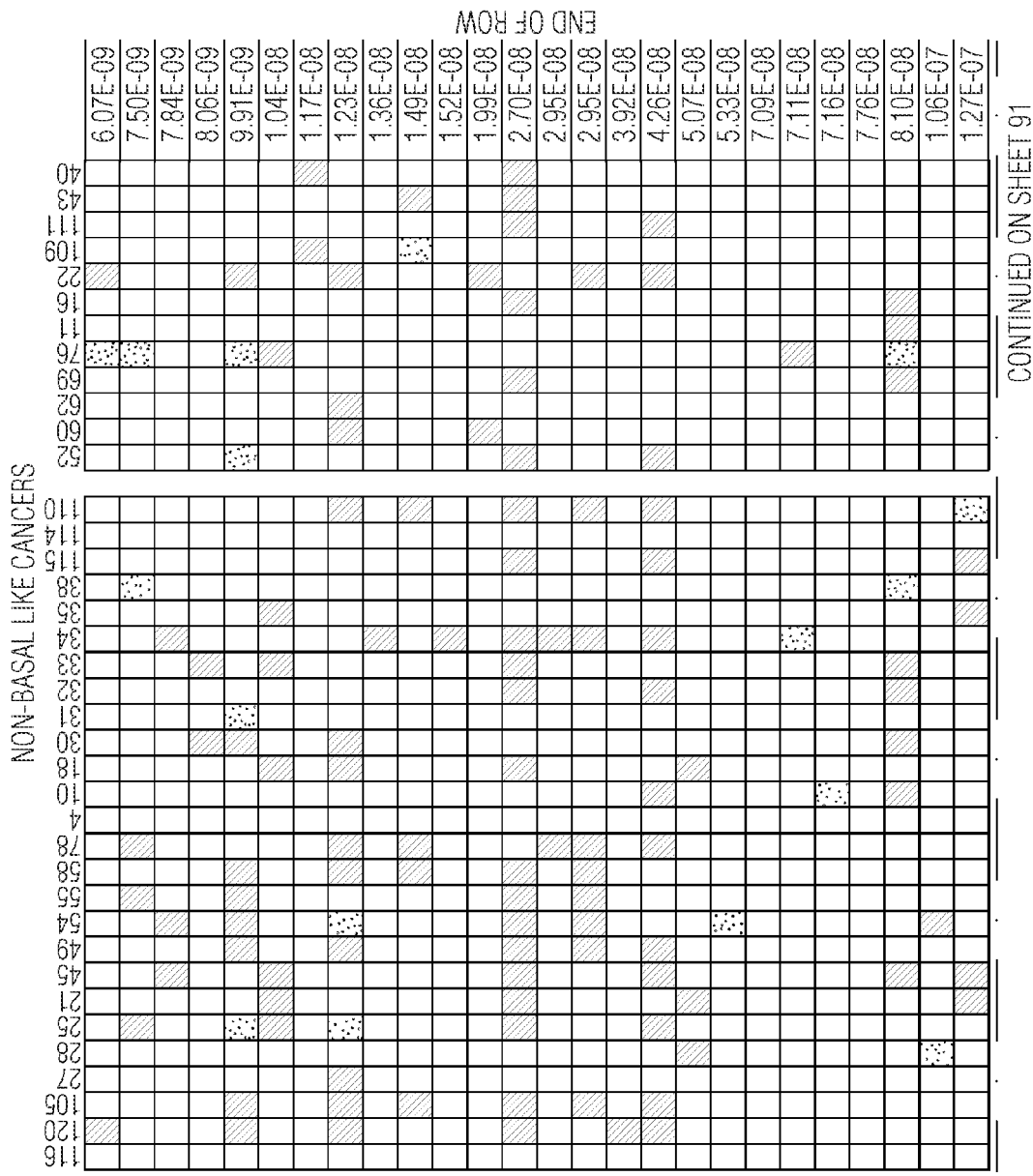
FIG. 25KKKK

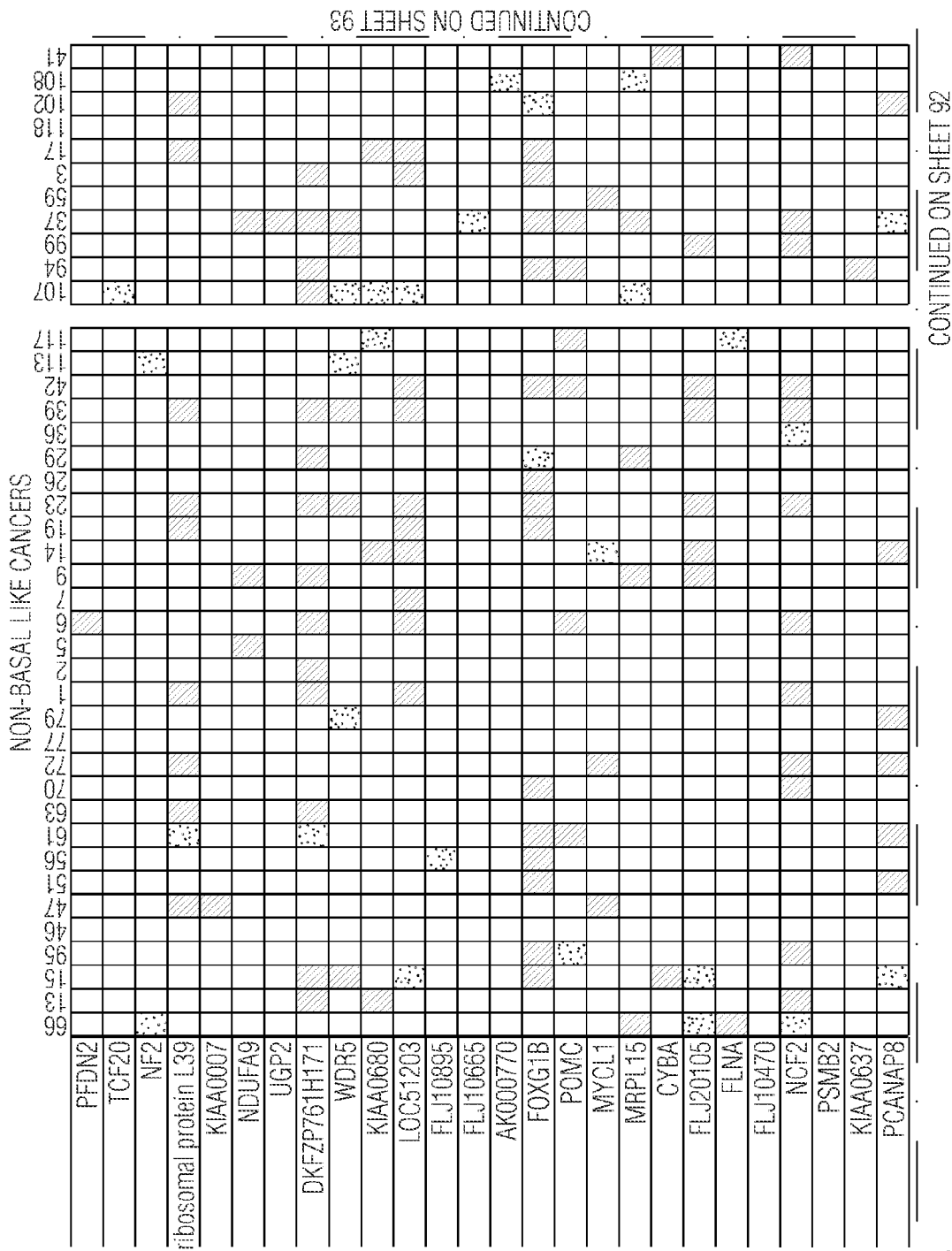
FIG. 25LLLL

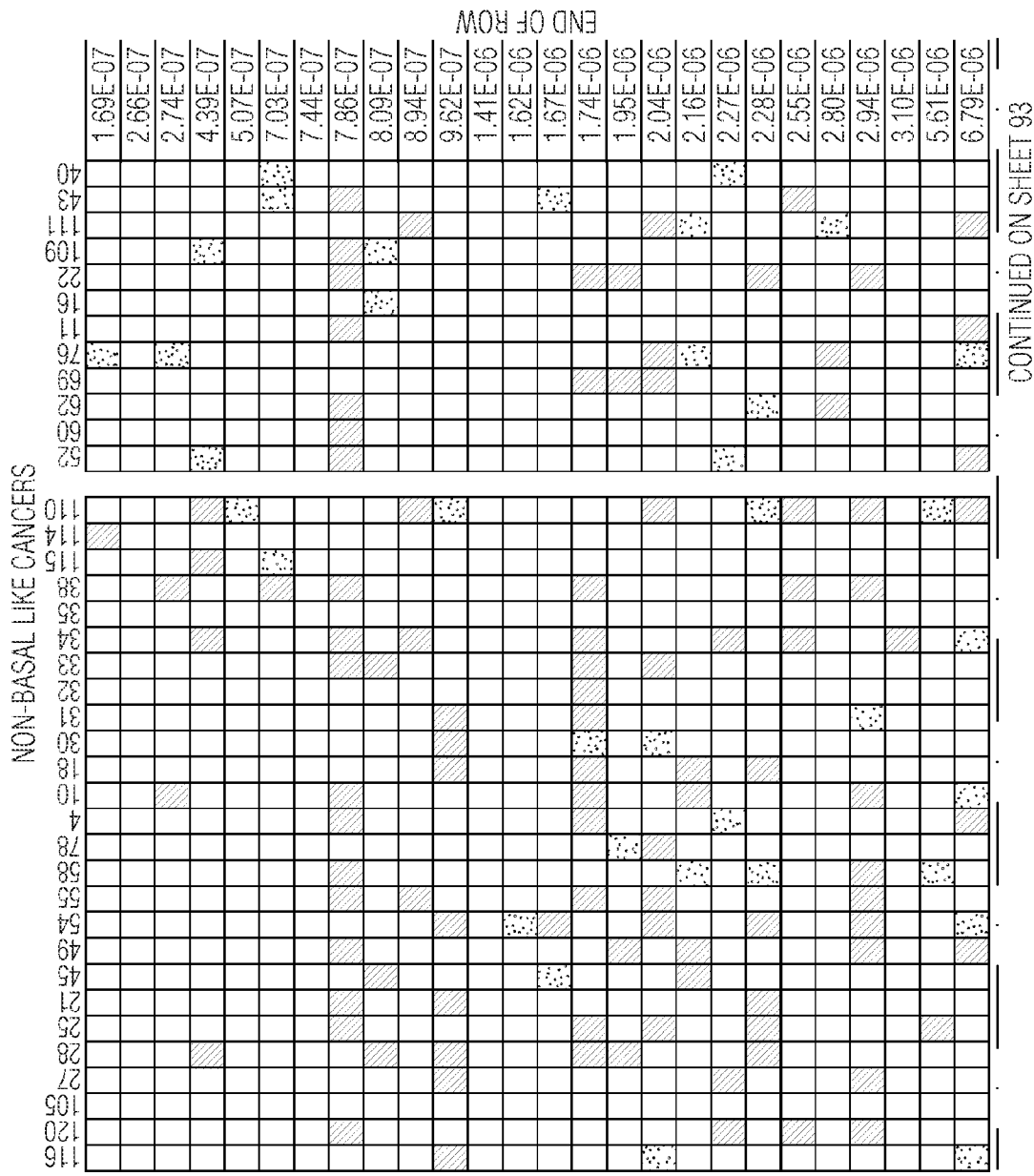
FIG. 25MMMM

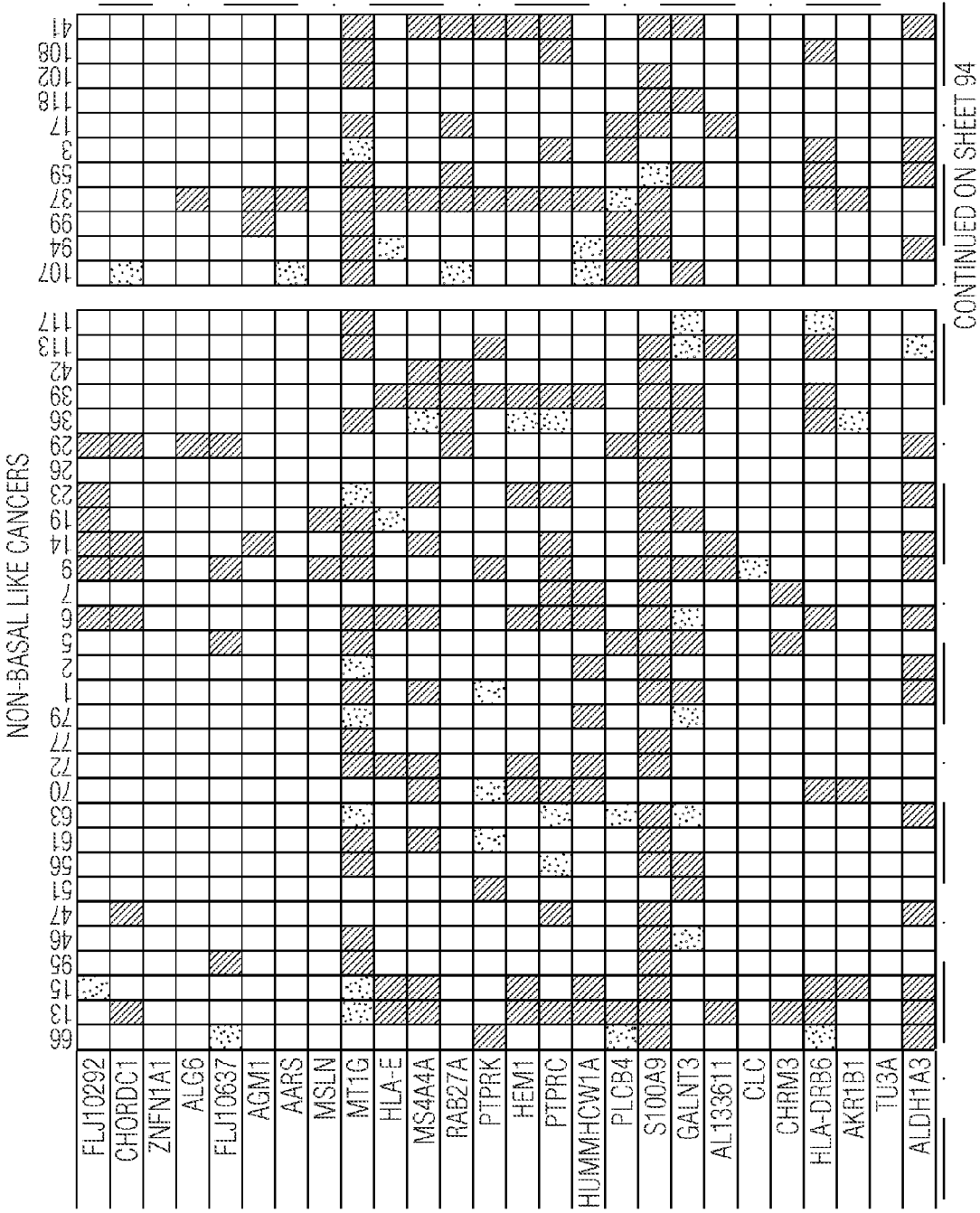
FIG. 25NNNN

FIG. 250000

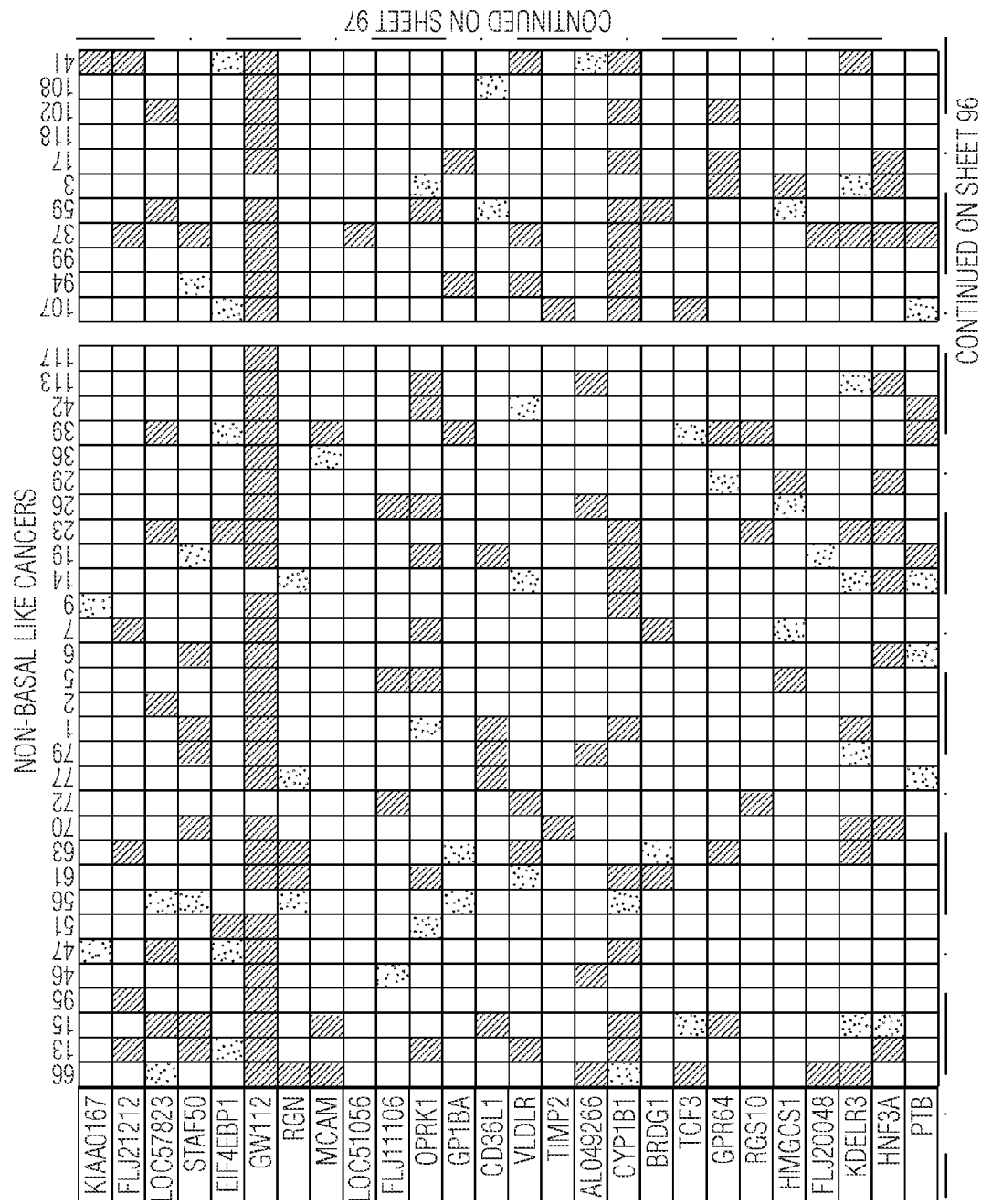
FIG. 25PPPP

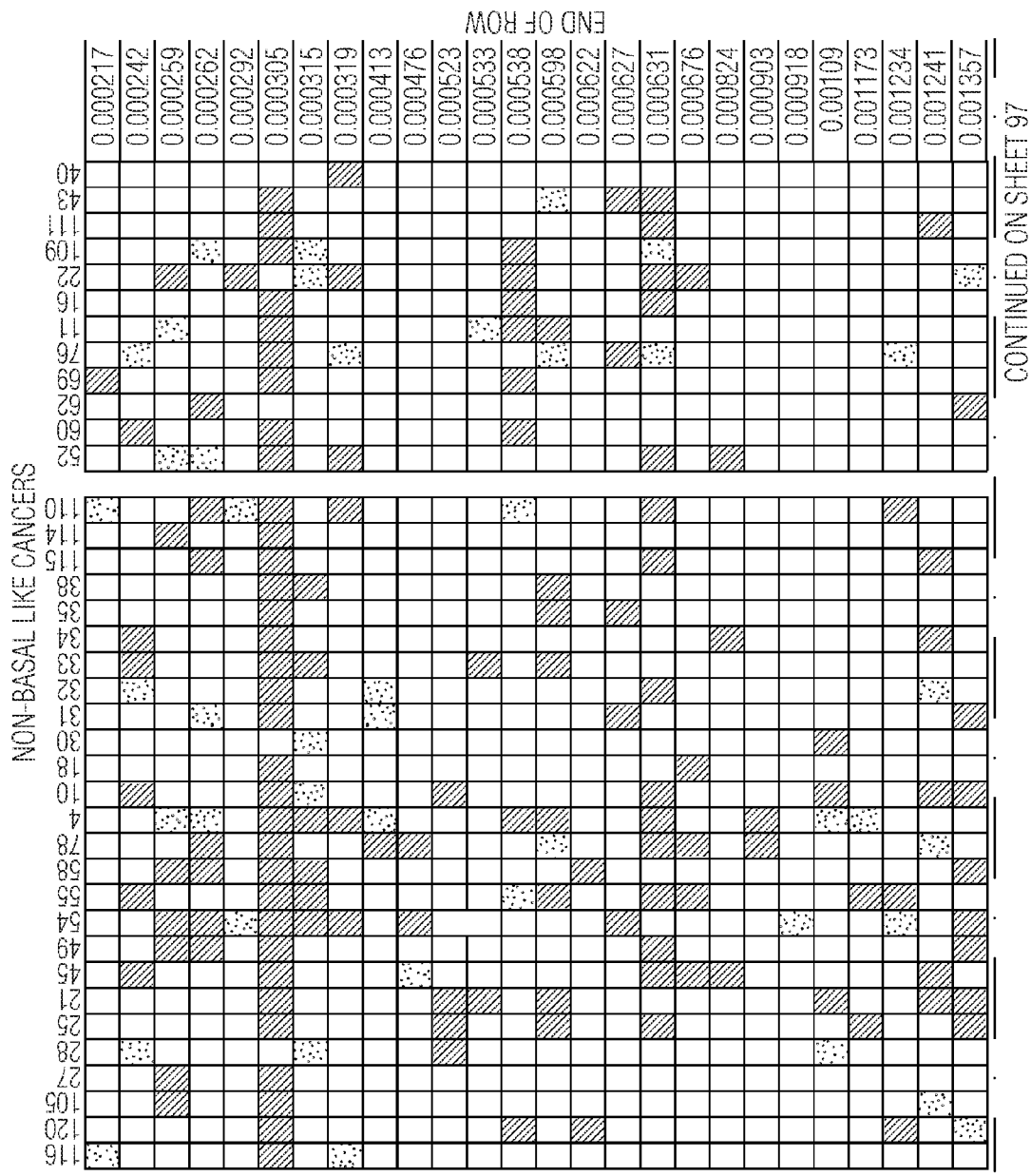
FIG. 25QQQQ

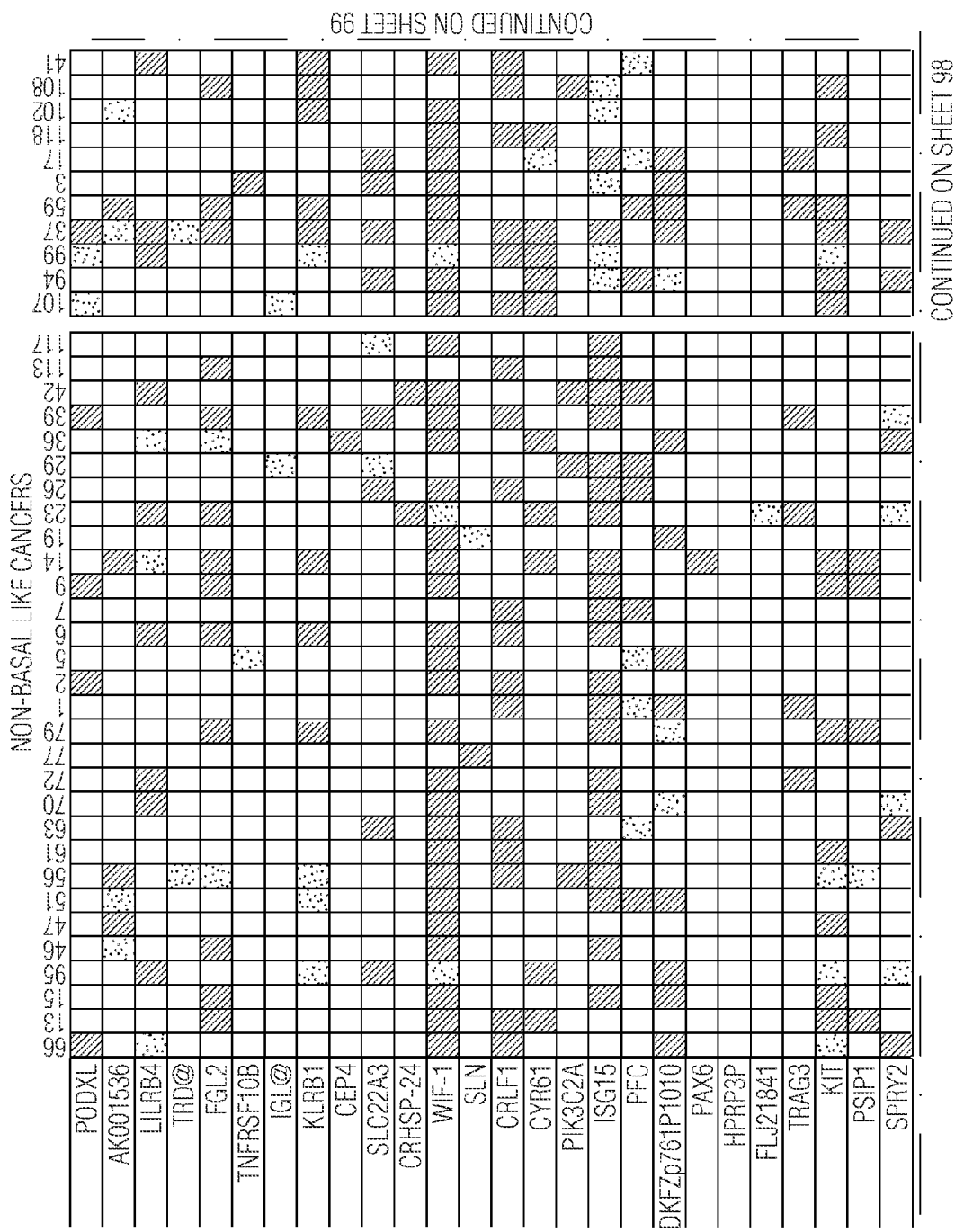
FIG. 25RRRR

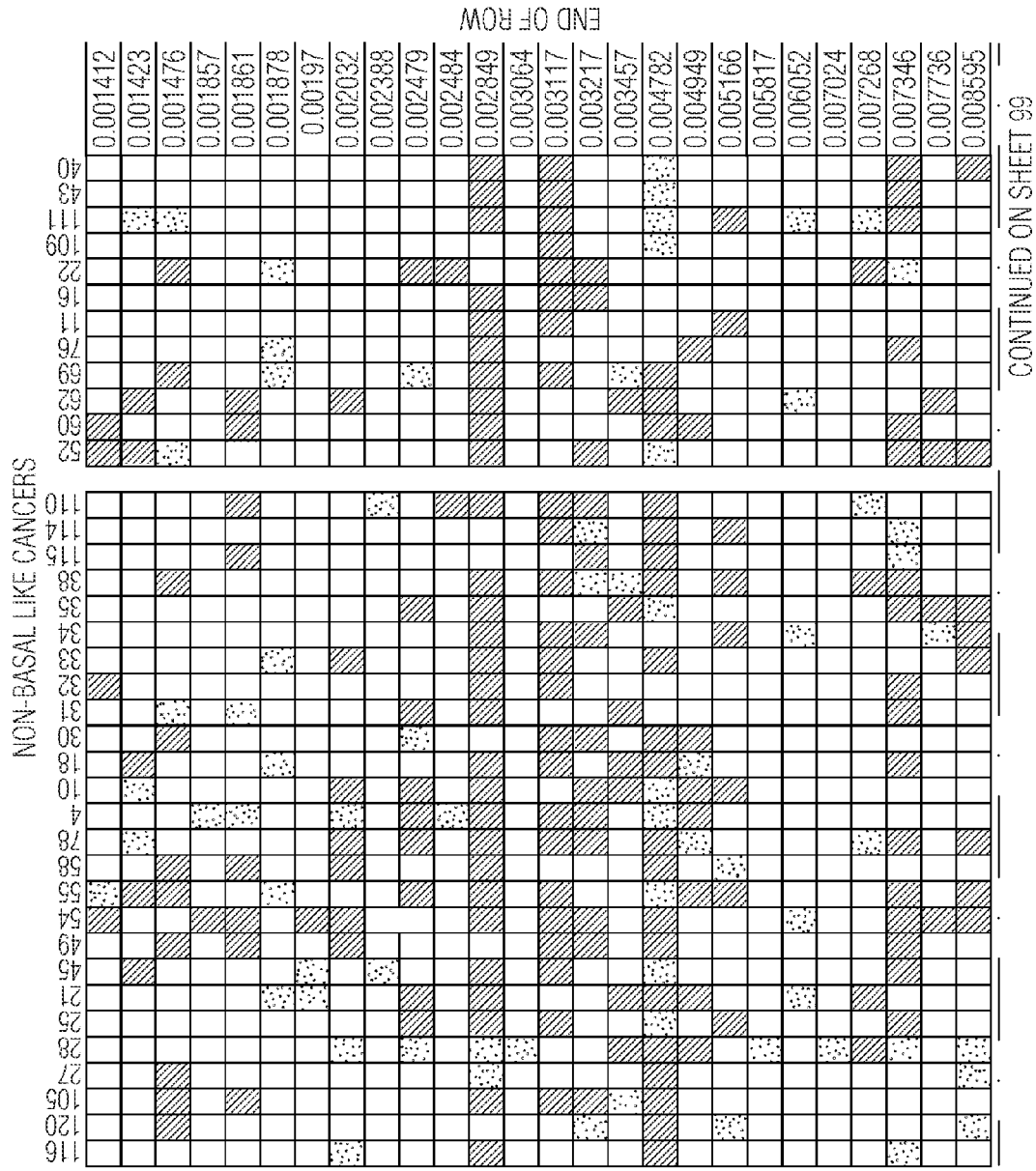
FIG. 25SSSS

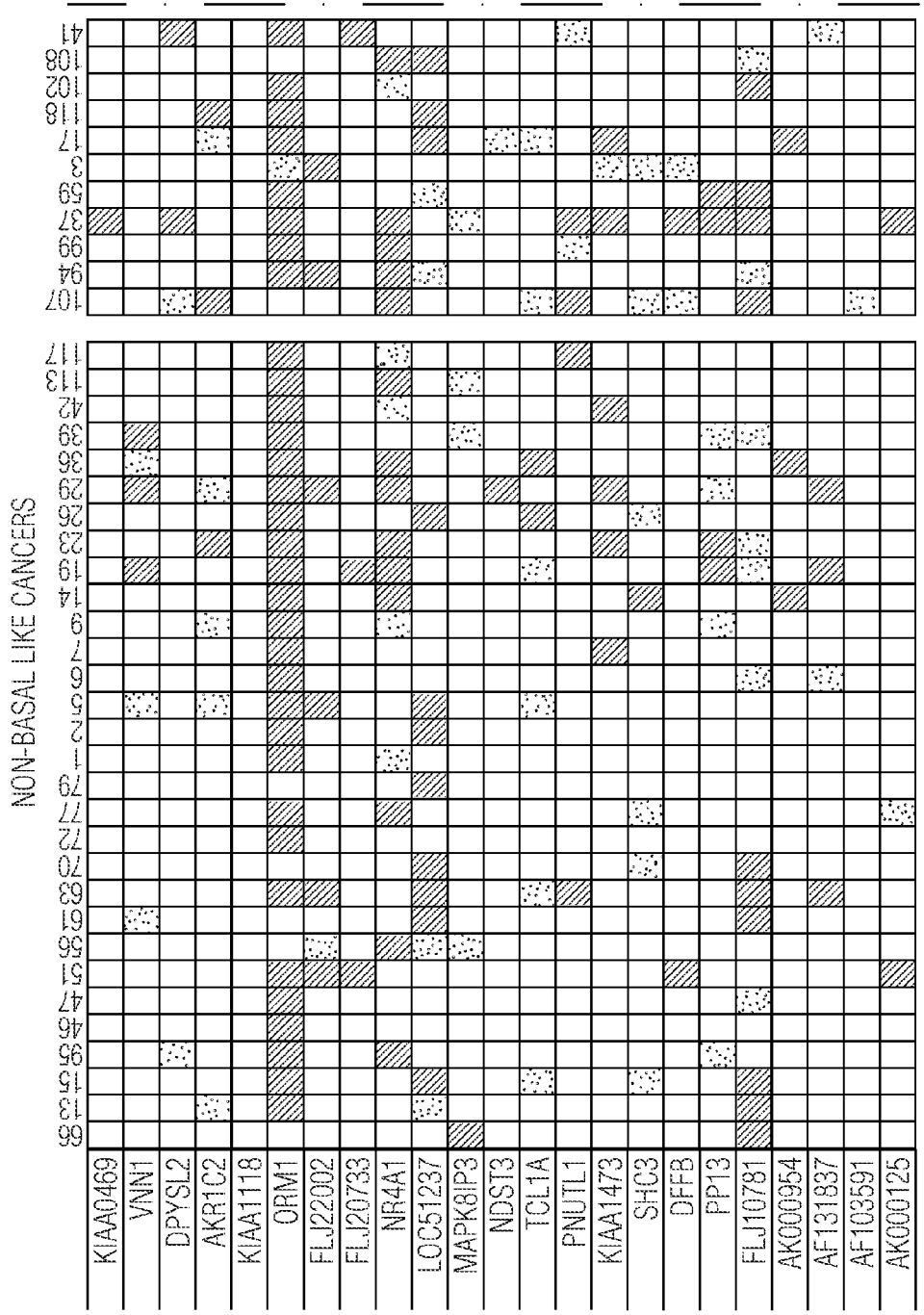
FIG. 25TTTT

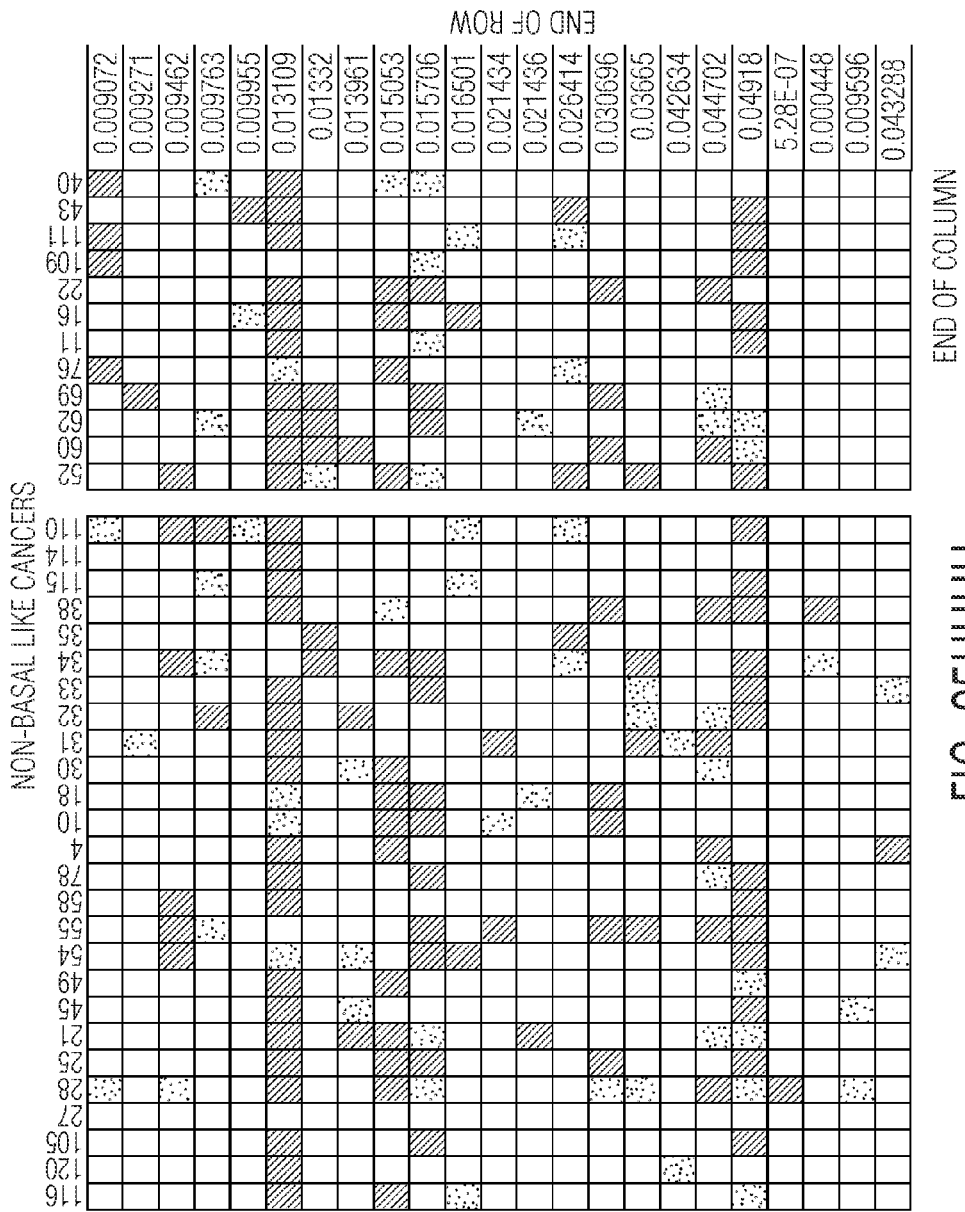
FIG. 25UUUU

FIG. 26A

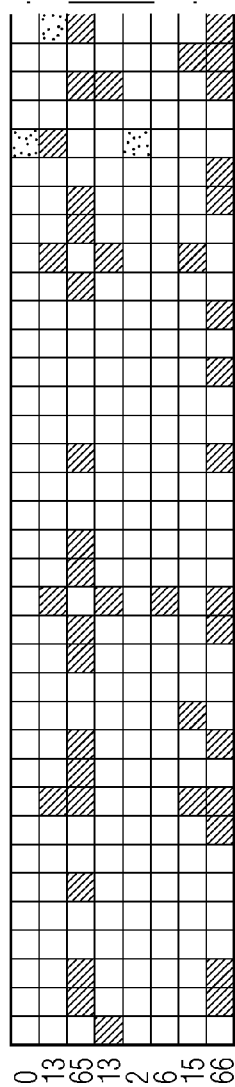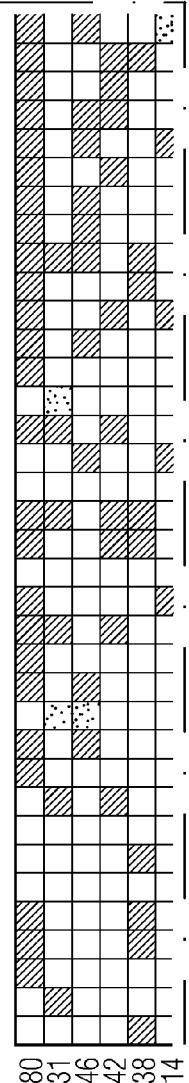
FIG. 26E

FIG. 27A

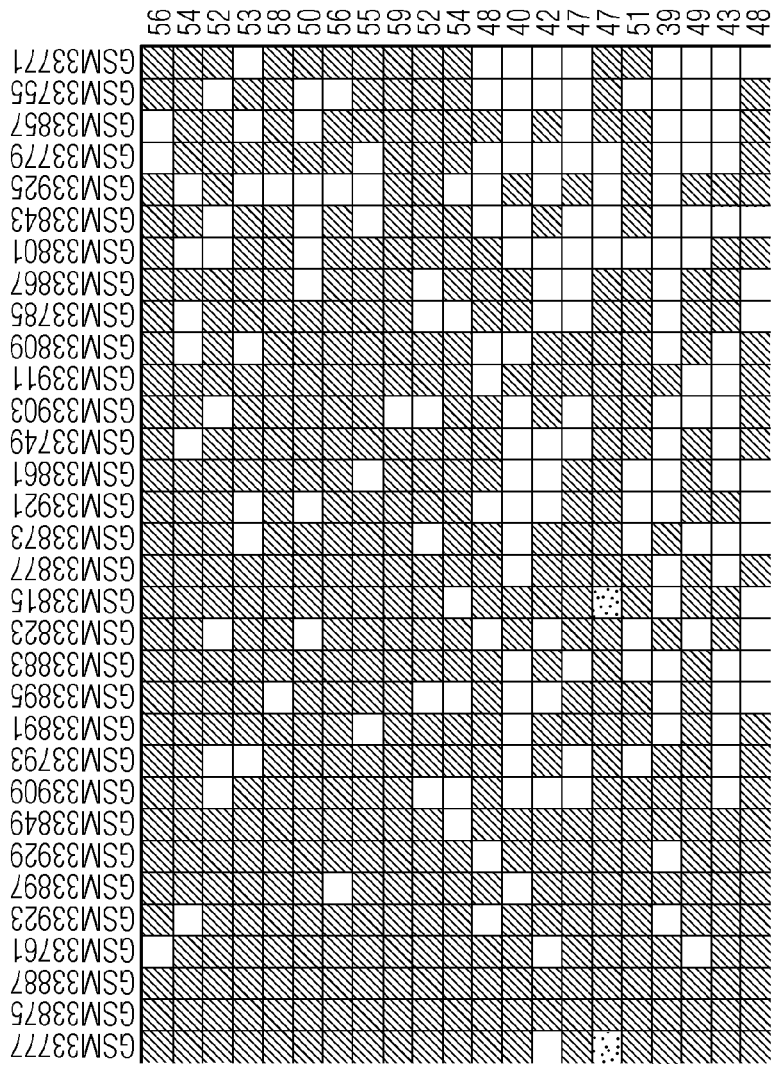

FIG. 27C

METHODS FOR IDENTIFICATION OF TUMOR PHENOTYPE AND TREATMENT

RELATED APPLICATIONS

This is a 371 of International Application No. PCT/US2009/064294, with an international filing date of Nov. 13, 2009 (WO 2010/056931 A1, published May 20, 2010) which is based on U.S. Patent Application No. 61/199,295 filed Nov. 14, 2008, the subject matter of which is incorporated by reference.

SEQUENCE LISTING

The instant application contains a Sequence Listing which has been submitted in ASCII format via EFS-Web and is hereby incorporated by reference in its entirety. Said ASCII copy, created on Jul. 13, 2011, is named SES081US.txt and is 1,433,258 bytes in size.

FIELD OF THE DISCLOSURE

The disclosure relates to methods for identifying a tumor as an E2F-responsive gene over-expressing (ERGO) tumor, methods of determining the likelihood that an ERGO tumor patient will survive to a future date, methods of treating an ERGO tumor in a patient, and methods of selecting patients diagnosed as ERGO tumor prostate cancer patients for aggressive clinical treatment. The methods of the disclosure are applicable to ERGO tumors present in different human organs and tissues such as breast, lung, thyroid, ovary, and prostate.

BACKGROUND OF THE DISCLOSURE

A major challenge in cancer treatment is to target specific therapies to distinct tumor types in order to maximize efficacy and minimize toxicity. Meeting this challenge requires that physicians and others involved in the treatment of cancer patients be able to identify distinct tumor types, determine the likelihood of patient survival given the patient's distinct tumor type, and be able to select appropriate treatments.

In the oncology field it is currently standard practice to identify tumor types using the microscopic histopathologic appearance of fixed and stained tumor samples, and to utilize the tumor-node-metastasis (TNM) system to determine the clinical extent of tumor spread. The TNM system uses the size of the tumor, the presence or absence of tumors in regional lymph nodes, and the presence or absence of distant metastases to assign a stage to the tumor. The tumor type and the stage assigned to a tumor are used as a basis for the selection of appropriate therapy and for prognostic purposes. However, this approach has serious limitations. This is because tumors with similar histopathologic appearance can exhibit significant variability in terms of clinical course and response to therapy. For example, some tumors spread early to distant sites and are rapidly progressive while others are not, and some tumors respond readily to hormonal therapy or chemotherapy while others are resistant.

Basal-like breast cancer tumors are one example of a tumor type that grows rapidly and which typically are not treated effectively with conventional adjuvant therapies such as hormonal therapy or chemotherapy. Clinically, basal-like breast cancers behave aggressively, and while they may respond to chemotherapy initially, these responses are generally of brief duration, and survival times for most patients with these tumors are relatively short. Histologically, most basal-like breast cancers are poorly differentiated ductal carcinomas. Breast cancer tumors are normally classified as basal-like in the clinical setting based on whether the tumors have a so-called "triple-negative" phenotype characterized by a lack of over-expression of human epidermal growth factor receptor 2 (HER2), the estrogen receptor (ER), and the progesterone receptor (PR) and if the tumor over-expresses basal-like cytokeratins or other basal-like markers. Unfortunately, therapeutic options for patients with basal-like breast cancers are limited, because patients with such tumors are not candidates for hormonal therapy or targeted therapy against HER2 and there currently is no clear understanding of the underlying pathobiology of basal-like breast cancers. Importantly, basal-like tumors and distinct subsets of such tumors may also arise in other tissues and organs such as lung, thyroid, ovarian, and prostate tissues, but this has been poorly studied.

Furthermore, many tumors have aberrations in the expression or biological activity of proteins encoded by tumor suppressor genes. Aberrations in the biological activity of proteins encoded by tumor suppressor genes due to mutations in these genes or decreased gene transcription at the level of mRNA or protein expression can lead to unrestrained cell division. The Rb protein is an example of a protein encoded by a tumor suppressor gene. Normally, the Rb tumor suppressor protein binds to the E2F transcription factor and regulates E2F mediated gene transcription to negatively modulate and control cell proliferation. Importantly, the role of Rb and E2F in basal-like tumors in breast tissues and other tissues such as lung, thyroid, ovarian, and prostate tissues is also poorly understood.

Thus, there is a need for methods to identify tumors that over-express E2F responsive genes, methods for determining the likelihood that a patient diagnosed with a particular distinct tumor type will survive to a future date, methods for identifying and treating distinct tumor types, and methods for identifying target proteins expressed by a distinct tumor type in different tissues such as breast, lung, thyroid, ovarian prostate and other tissues.

SUMMARY OF THE DISCLOSURE

One aspect of the disclosure is a method of identifying a tumor as an ERGO tumor comprising the steps of providing a tumor sample; providing a reference; measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123; 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340; measuring the reference to produce a reference value; and comparing the indicator value to the reference value to determine which of the gene transcripts is over-expressed; whereby tumor is identified as an ERGO tumor if at least 21 of these gene transcripts are over-expressed.

Another aspect of the disclosure is a method of determining the odds that an individual ERGO tumor patient will survive to a future date comprising the steps of providing a tumor sample from an individual patient; providing a reference; measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340; measuring the reference to produce a reference value; and comparing the indicator value to the reference value to determine which of the gene transcripts is over-expressed, whereby the tumor is identified as an ERGO tumor and the individual patient is diagnosed as an ERGO tumor patient if at least 21 of these gene transcripts are over-expressed; plotting the fraction of surviving patients in a population of patients diagnosed as ERGO tumor patients as a function of the time since diagnosis of the ERGO tumor to generate a survival plot; and selecting a future date after the individual patient is diagnosed as an ERGO tumor patient and determining the fraction of surviving patients in the population from the survival plot; whereby the fraction of surviving patients on the survival plot at the future date predicts the odds that an individual tumor patient will survive to the future date.

Another aspect of the disclosure is a method of treating an ERGO tumor in a patient comprising the steps of providing a tumor sample from a patient; providing a reference; measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 204, 217, 246-247, 249, 254, 259, 267, 269, 274-275, 292-295, 298, 307, 311, 316, 321-323, 331, 333, and 335-340; measuring the reference to produce a reference value; comparing the indicator value to the reference value to determine which of the gene transcripts is over-expressed, whereby the tumor is identified as an ERGO tumor if at least 21 of these gene transcripts are over-expressed; selecting a drug capable of killing or inhibiting division of an ERGO tumor cell expressing at least one protein encoded by at least one gene transcript selected from the group consisting of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340; and administering a pharmaceutically acceptable amount of the drug to the patient; whereby the ERGO tumor in the patient is treated.

Another aspect of the disclosure is a method of identifying an individual tumor in a population of tumors as an ERGO tumor comprising the steps of providing a population of tumor samples; providing a reference; measuring gene transcript levels in the tumor samples to produce a transcript value for each of the following gene transcripts having the nucleic acid sequences shown in SEQ ID NO:s 10-340; comparing the transcript value to the reference value for each tumor to identify the gene transcripts over-expressed by each tumor; ranking the tumors in the population with a rank ordering algorithm to order the tumors according to the number of the gene transcripts over-expressed by each tumor; and removing individual tumors from the population that over-express the smallest number of each gene transcript per cell and that have the lowest levels of over-expression of each gene transcript per cell until at least 20% of the individual tumors remaining in the population over-express at least 20% of the gene transcripts; whereby an individual tumor remaining in the population of tumors is identified as an ERGO tumor.

Another aspect of the disclosure is a method of identifying an individual tumor in a population of tumors as an ERGO tumor comprising the steps of providing a population of tumor samples; providing a reference; measuring gene transcript levels in the tumor samples to produce a transcript value for each of the following gene transcripts having the nucleic acid sequence shown in SEQ ID NO:s 10-340; comparing the transcript value to the reference value for each tumor to identify the gene transcripts over-expressed by each tumor; and applying a principle component analysis algorithm in which the analyzed gene set is restricted to each gene transcript having the nucleic acid sequence shown in SEQ ID NO:s 10-340 to identify a tumor cluster over-expressing these E2F-responsive genes; whereby an individual tumor in the population of tumors in the cluster is identified as an ERGO tumor.

Another aspect of the disclosure is a method of selecting treatment for a prostate cancer patient comprising the steps of providing a tumor sample from a prostate cancer patient; providing a reference; measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201; 203, 205, 209, 217, 246-247, 249, 254, 259, 267, 269, 274-275, 292-295, 298, 307, 311, 316, 321-323, 331, 333, and 335-340; measuring the reference to produce a reference value; and comparing the indicator value to the reference value to determine which of the gene transcripts is over-expressed, whereby the tumor is identified as an ERGO tumor and the prostate cancer patient is diagnosed as an ERGO tumor prostate cancer patient if at least 21 of these gene transcripts are over-expressed; and choosing at least one treatment selected from the group consisting of removal of at least one tumor and adjuvant therapy, if the patient is diagnosed as an ERGO tumor prostate cancer patient; whereby a treatment is selected for the prostate cancer patient.

BRIEF DESCRIPTION OF THE DRAWINGS

FIGS. 1A to 1DD span thirty sheets.

FIG. 3 spans three sheets.

FIGS. 4A to 4HHH span sixty sheets.

FIG. 5 spans three sheets.

FIGS. 8A to 8FF span thirty-two sheets.

FIG. 10 shows the most frequently over-expressed E2F-responsive genes in ERGO tumors identified by weighted rank ordering of tumors in the Van't Veer set (s1) and purged Dai microarray set (s2).

Figure 11K:
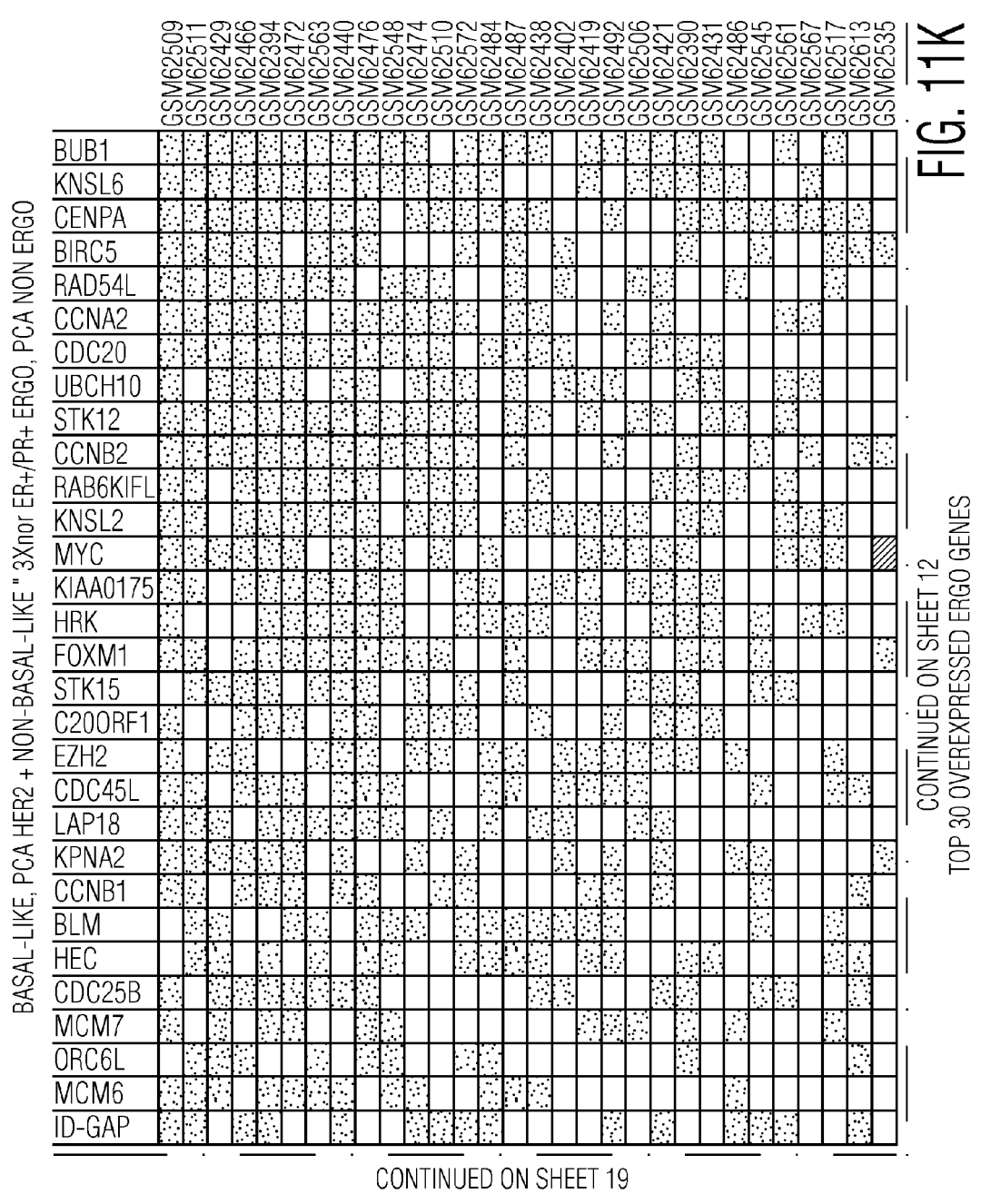
Figure 11:
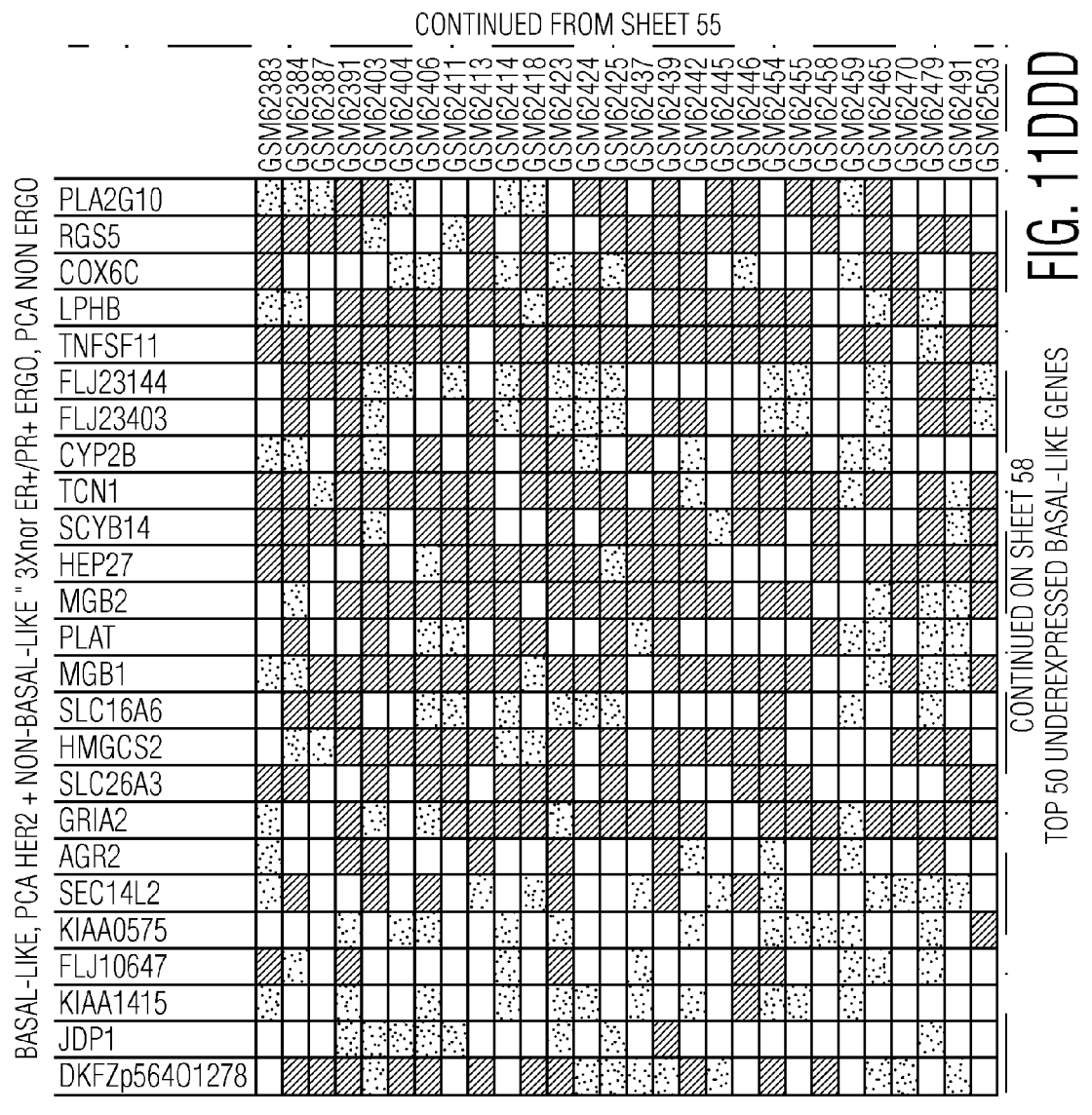

FIGS. 11A to 11FFF span fifty-eight sheets.

FIGS. 12A and 12B show partial views intended to form one complete view of a comparison of the most highly over-expressed E2F-responsive genes in ERGO tumors identified by PCA of the Van't Veer human breast cancer microarray set (s1) and ERGO tumors identified by refined PCA of the purged Dai human breast cancer microarray set (s2). FIGS. 12A and 12B span two sheets.

FIGS. 14A to 14L show partial views intended to form one complete view of microarray data for ERGO tumors identified by refined PCA, as well as large cell neuroendocrine tumors and carcinoid tumors identified by PCA of the Jones human lung cancer microarray set. FIGS. 14A to 14L span twelve sheets.

FIGS. 15A to 15C show partial views intended to form one complete view of a comparison of the most highly over-expressed E2F-responsive genes of ERGO tumors identified by refined PCA in the Van't Veer human breast cancer microarray set (s1) and ERGO) tumors identified by refined PCA in the purged Dai human breast cancer microarray set (s2) with small cell lung cancer tumors identified by PCA in the Salvatore human thyroid cancer microarray set. FIGS. 15A to 15C span three sheets.

FIGS. 16A to 16L show partial views intended to form one complete view of microarray data for ERGO tumors identified by refined PCA, as well as large cell papillary cancer tumors identified by PCA of the Salvatore human thyroid cancer microarray set. FIGS. 16A to 16L span twelve sheets.

FIGS. 17A to 17C show span four sheets.

FIGS. 18A to 18L show partial views intended to form one complete view of microarray data from basal-like and non-basal like tumors identified by PCA for the top 25 most highly over-expressed published basal-like marker genes and the top 50 most highly over-expressed basal-like marker genes. FIGS. 18A to 18L span twelve sheets.

FIG. 19A shows the clinical survival data for ERGO tumors, non-ERGO basal-like tumors, and HER2 over-expressing tumors subsets. "Survival" on the Y-axis indicates the fraction of all patients diagnosed with PCA basal-like breast cancers that survive at a given time.

FIG. 19B shows the clinical survival data for non-ERGO "triple non-positive" and all other tumor subsets. "Survival" on the Y-axis indicates the fraction of all patients diagnosed with PCA basal-like breast cancers that survive at a given time.

Figure 20B:
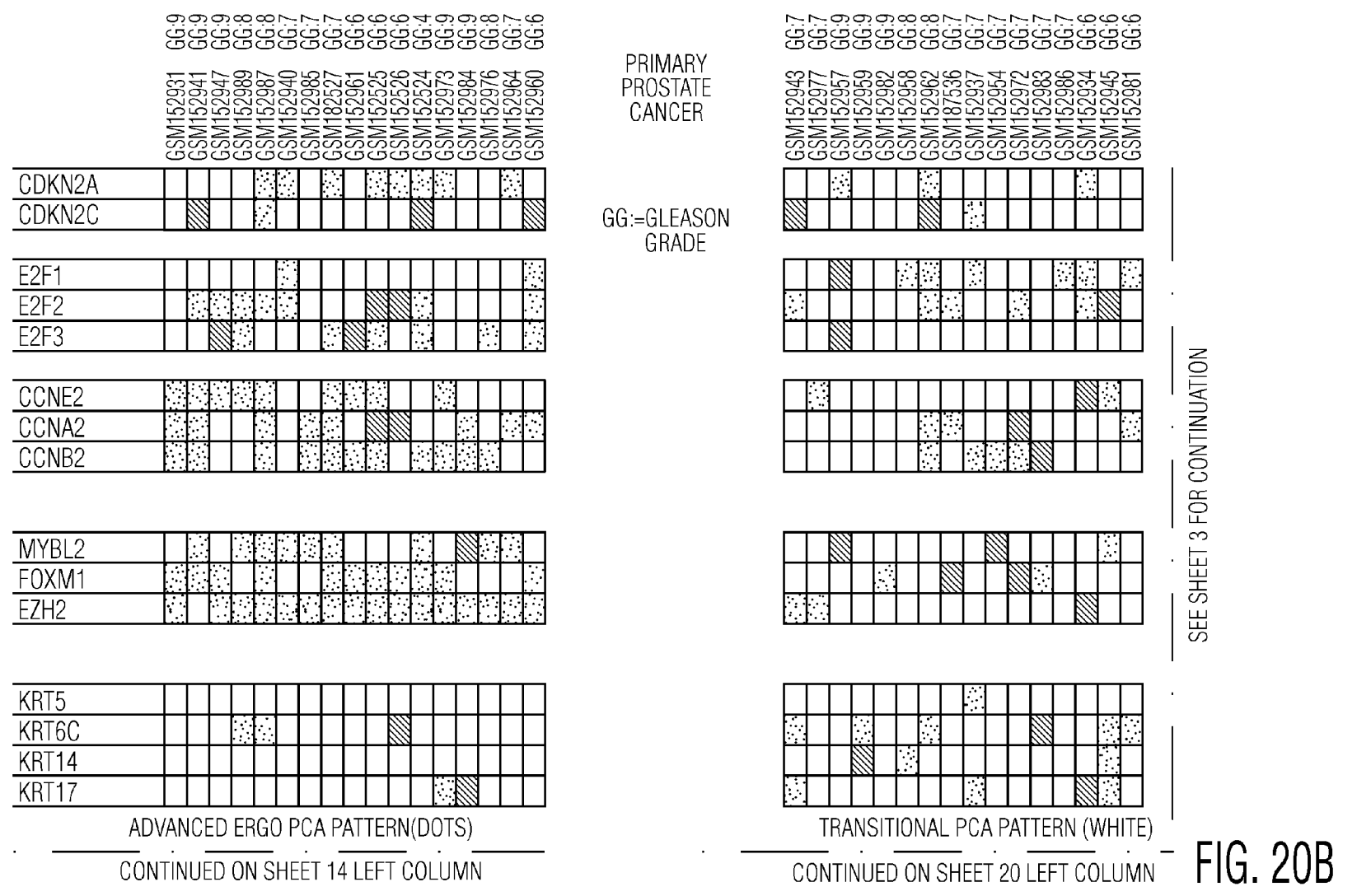
Figure 20P:
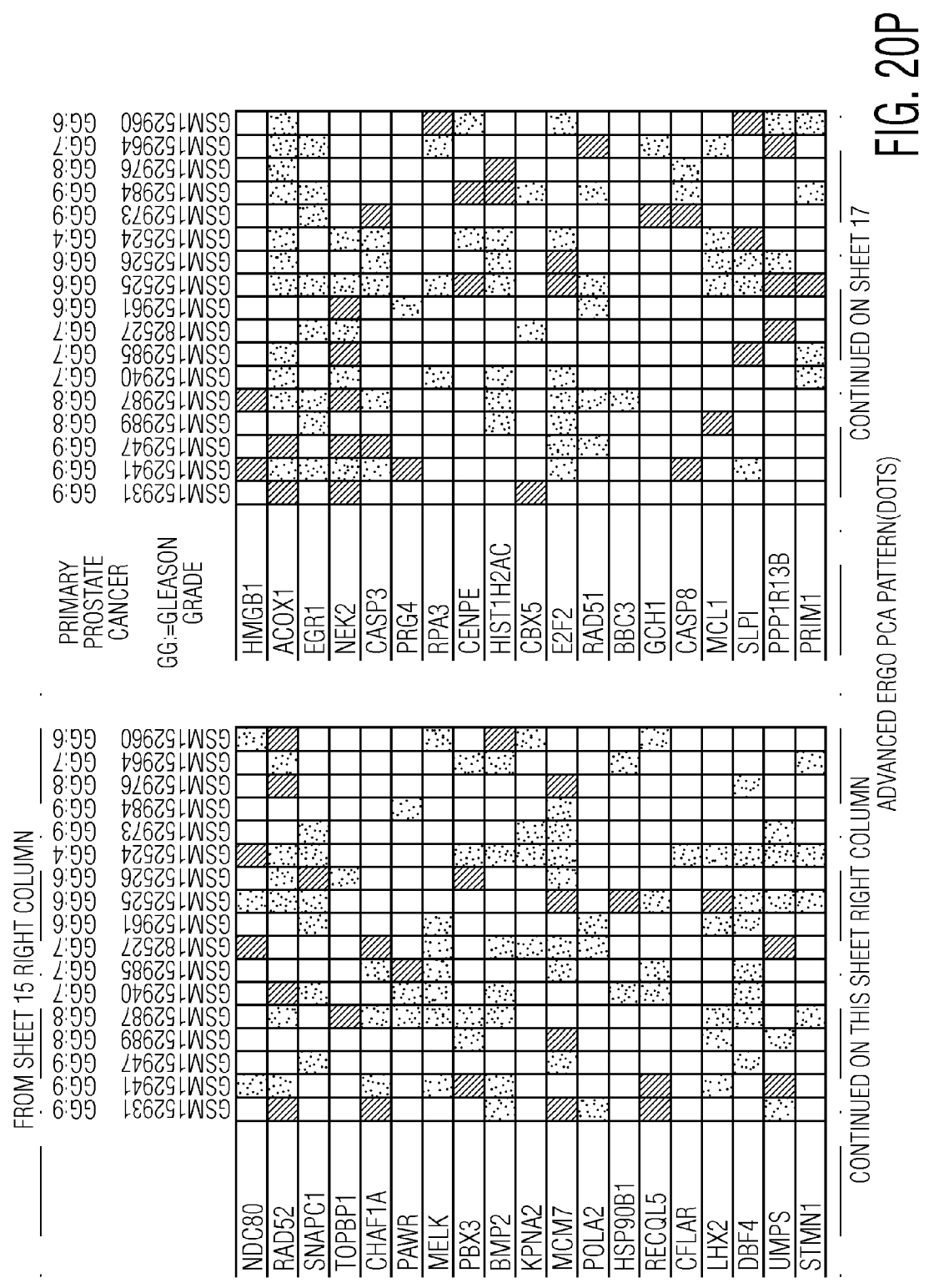
Figure 20Q:
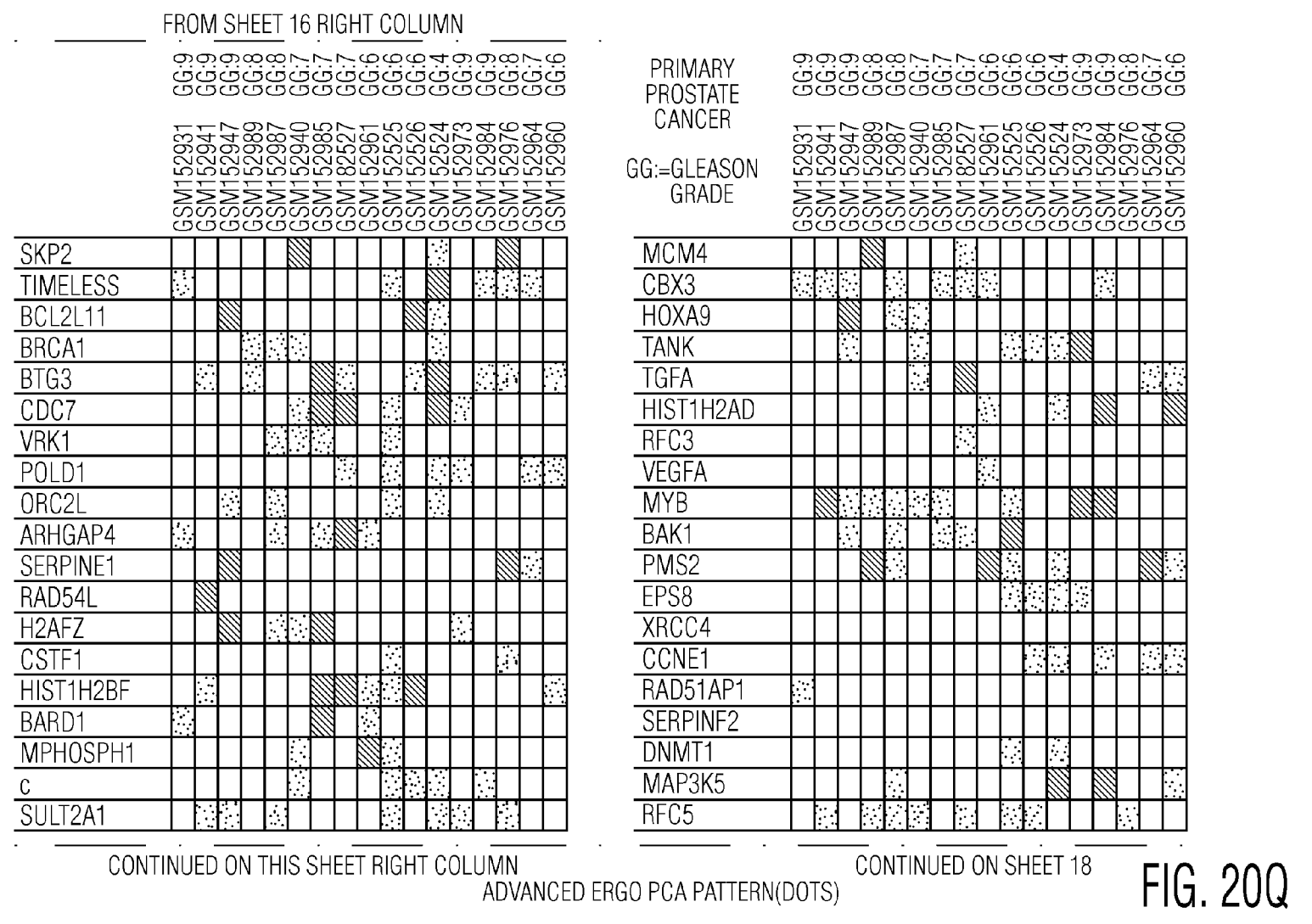
Figure 20R:
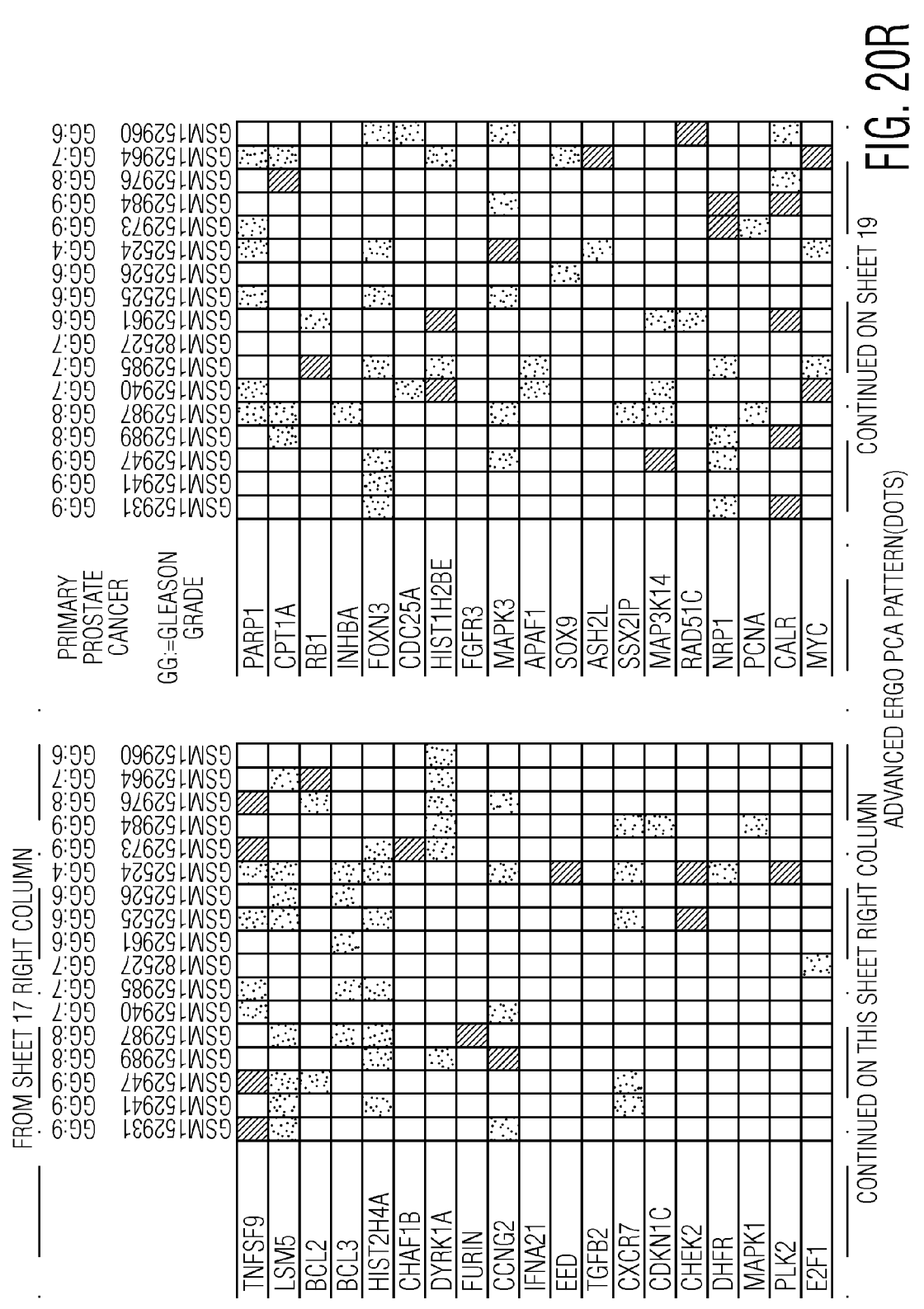
Figure 20W:
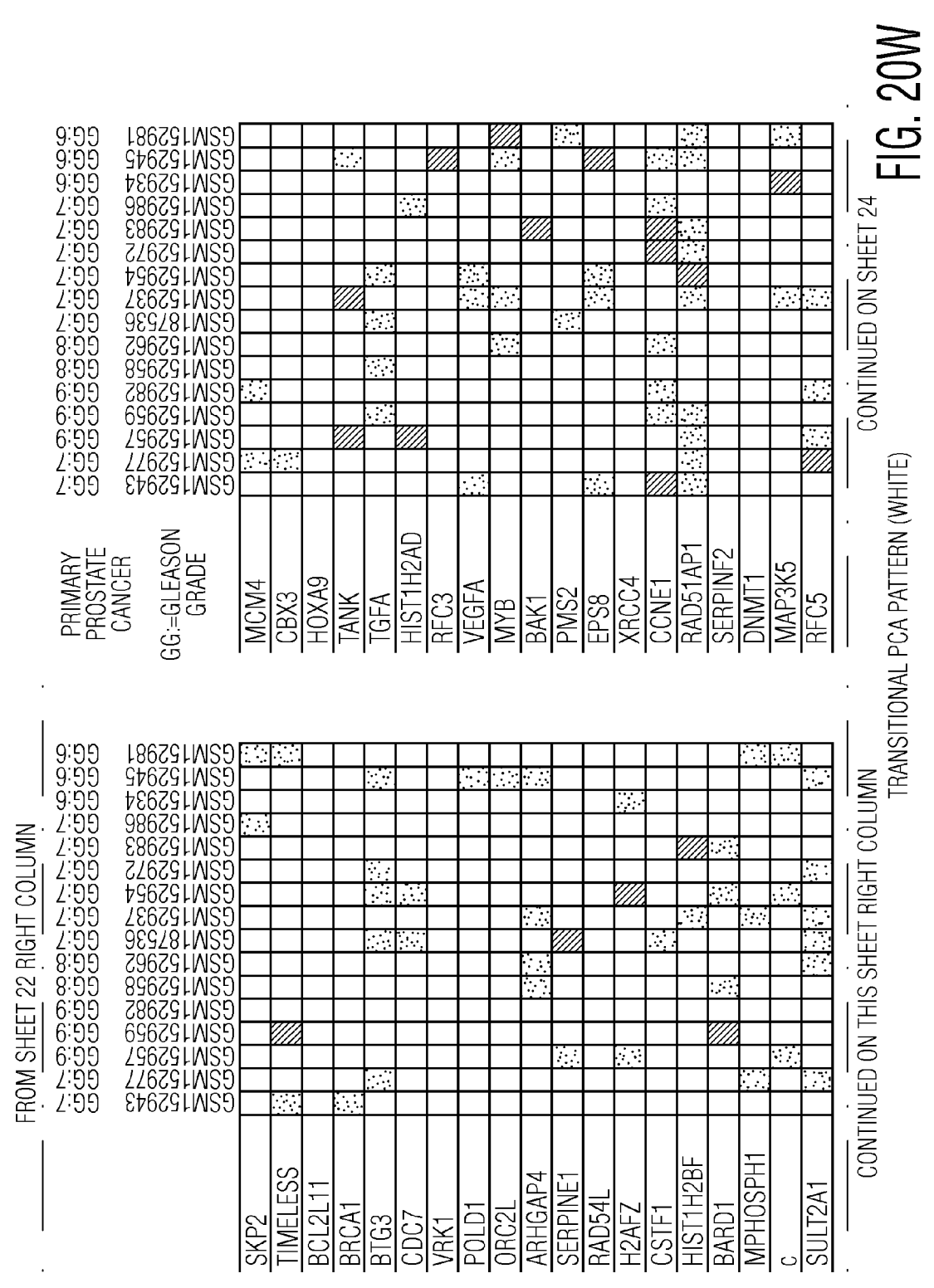
Figure 20Z:
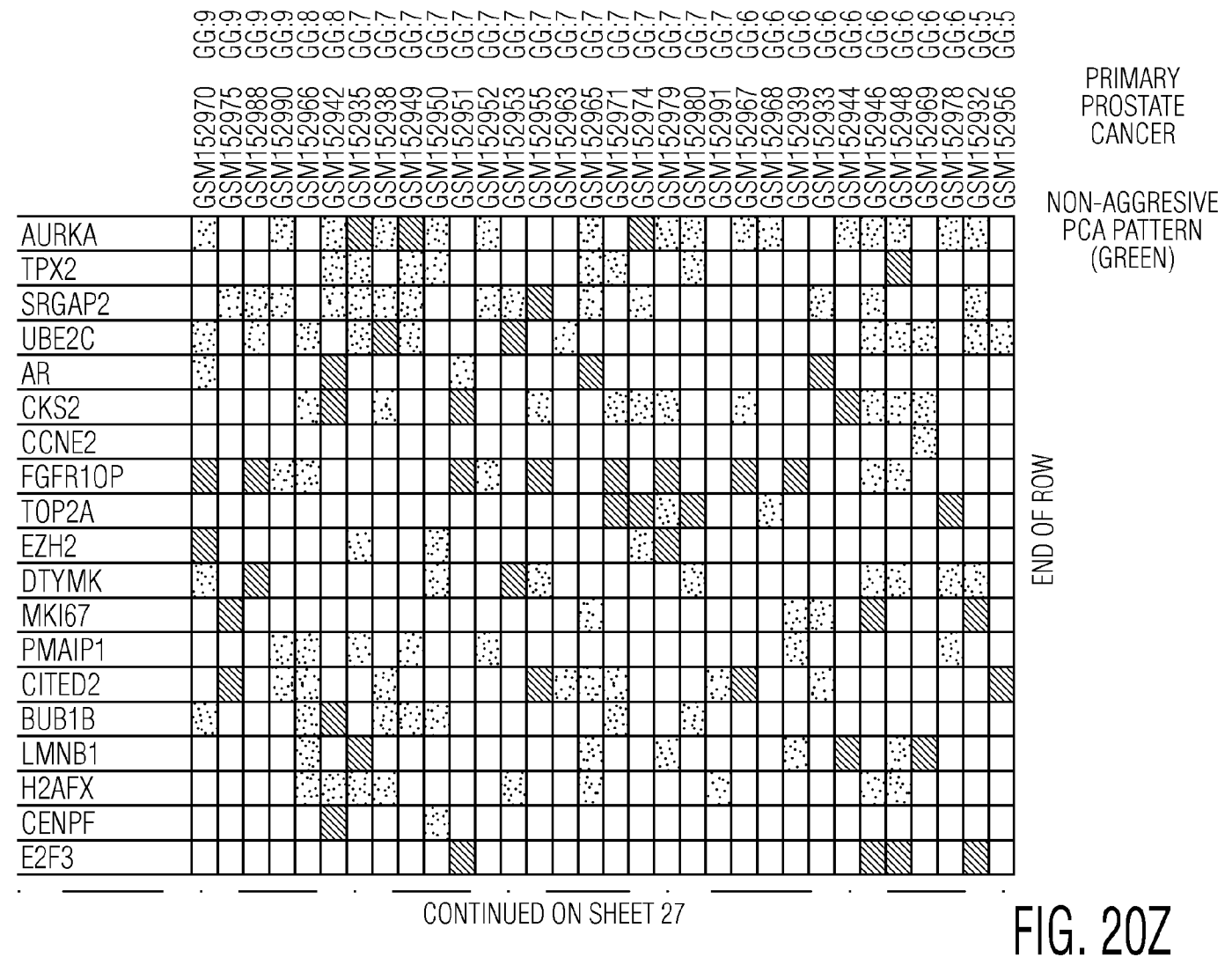

FIGS. 20A to 20KK span thirty-seven sheets.

FIGS. 23A to 23N span fourteen sheets.

Figure 24:
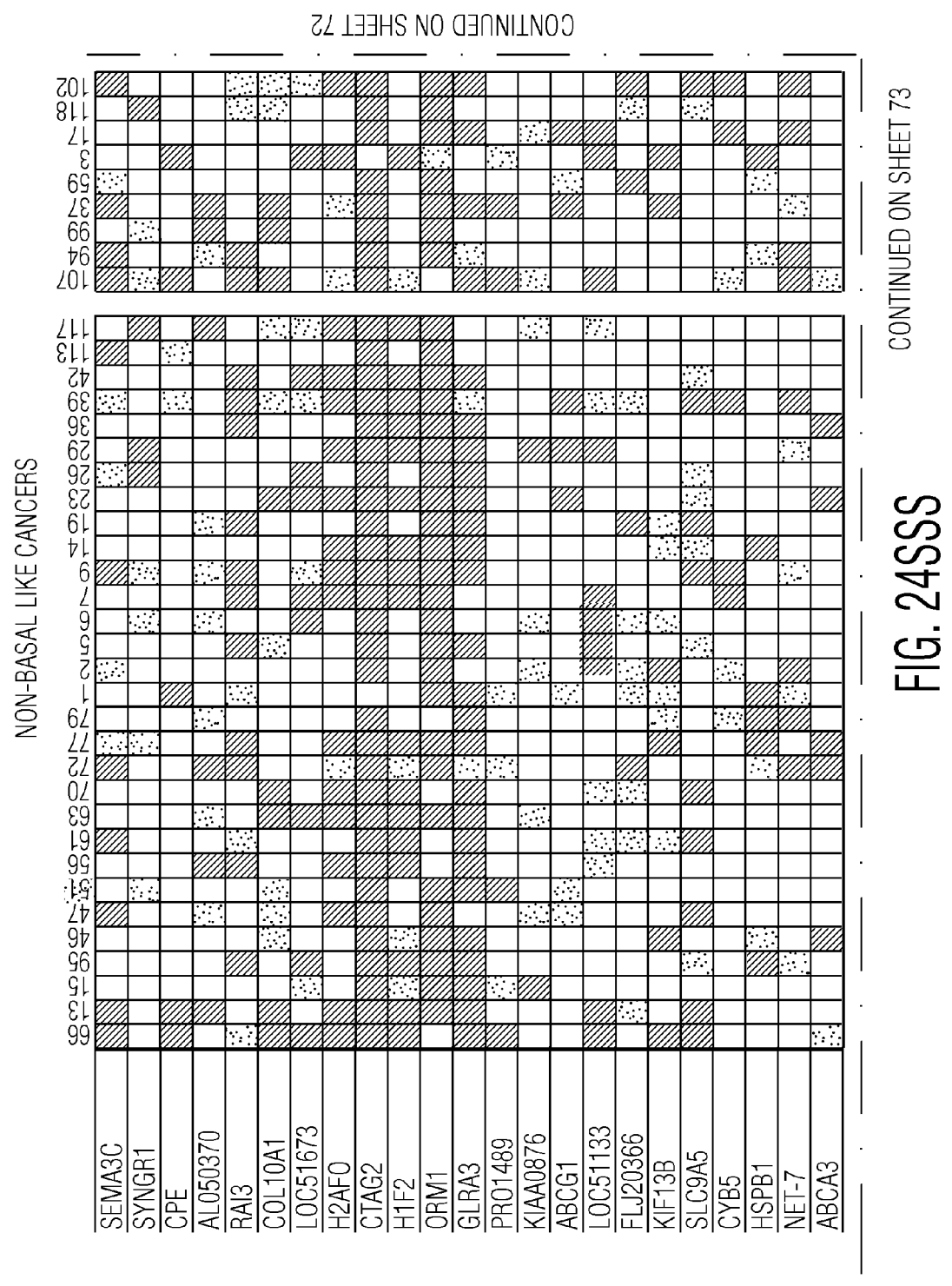
Figure 24:
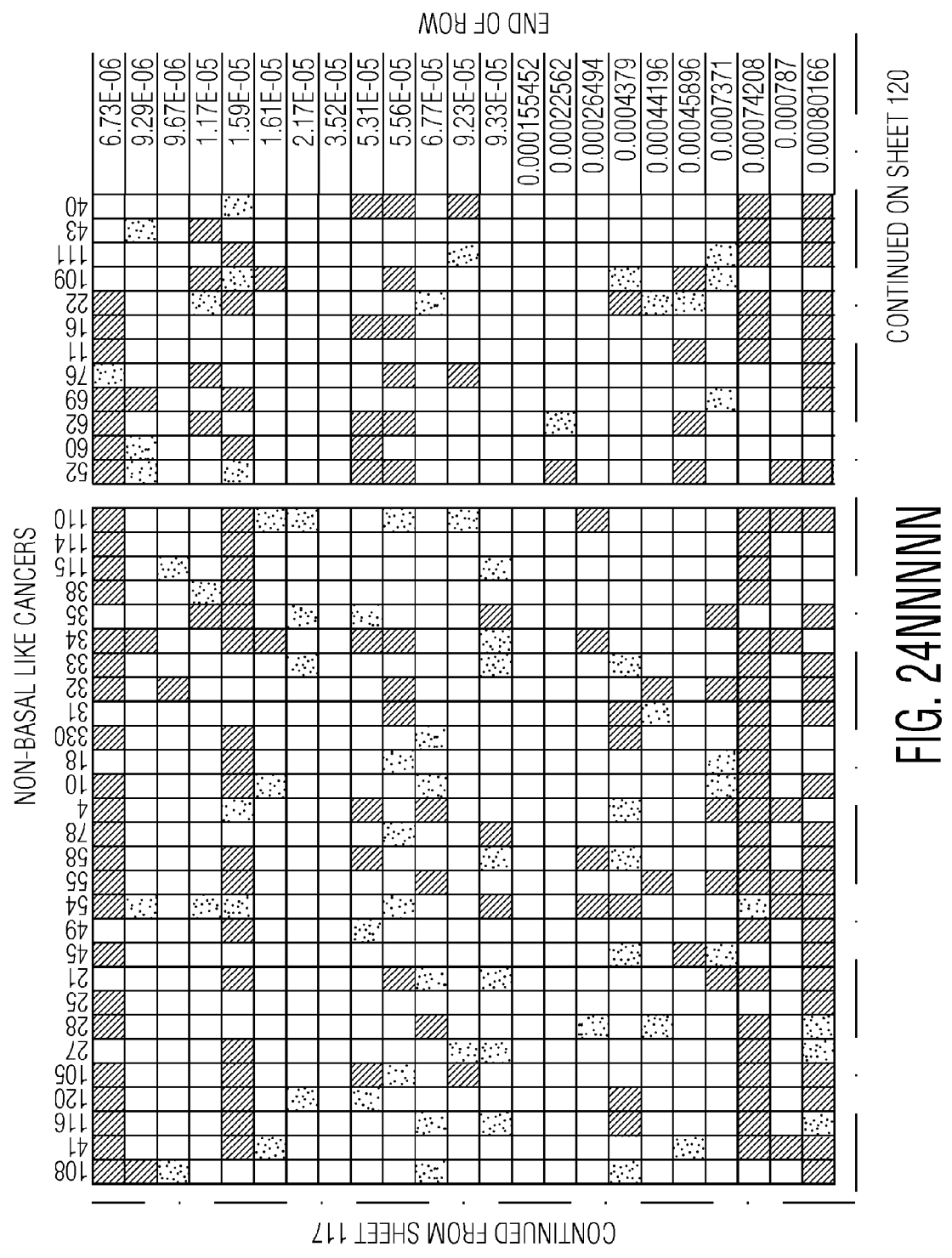
Figure 24:
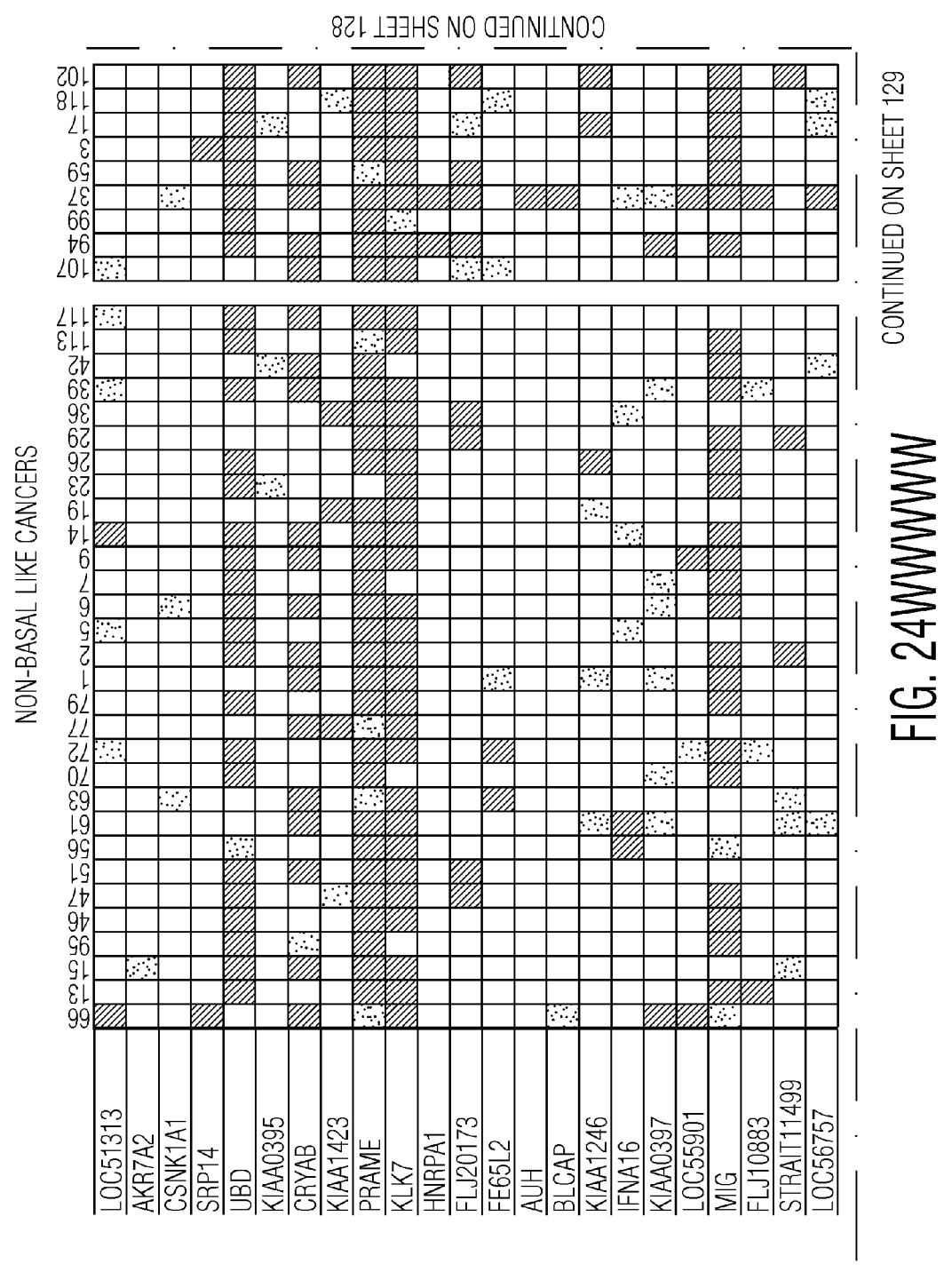
Figure 24:
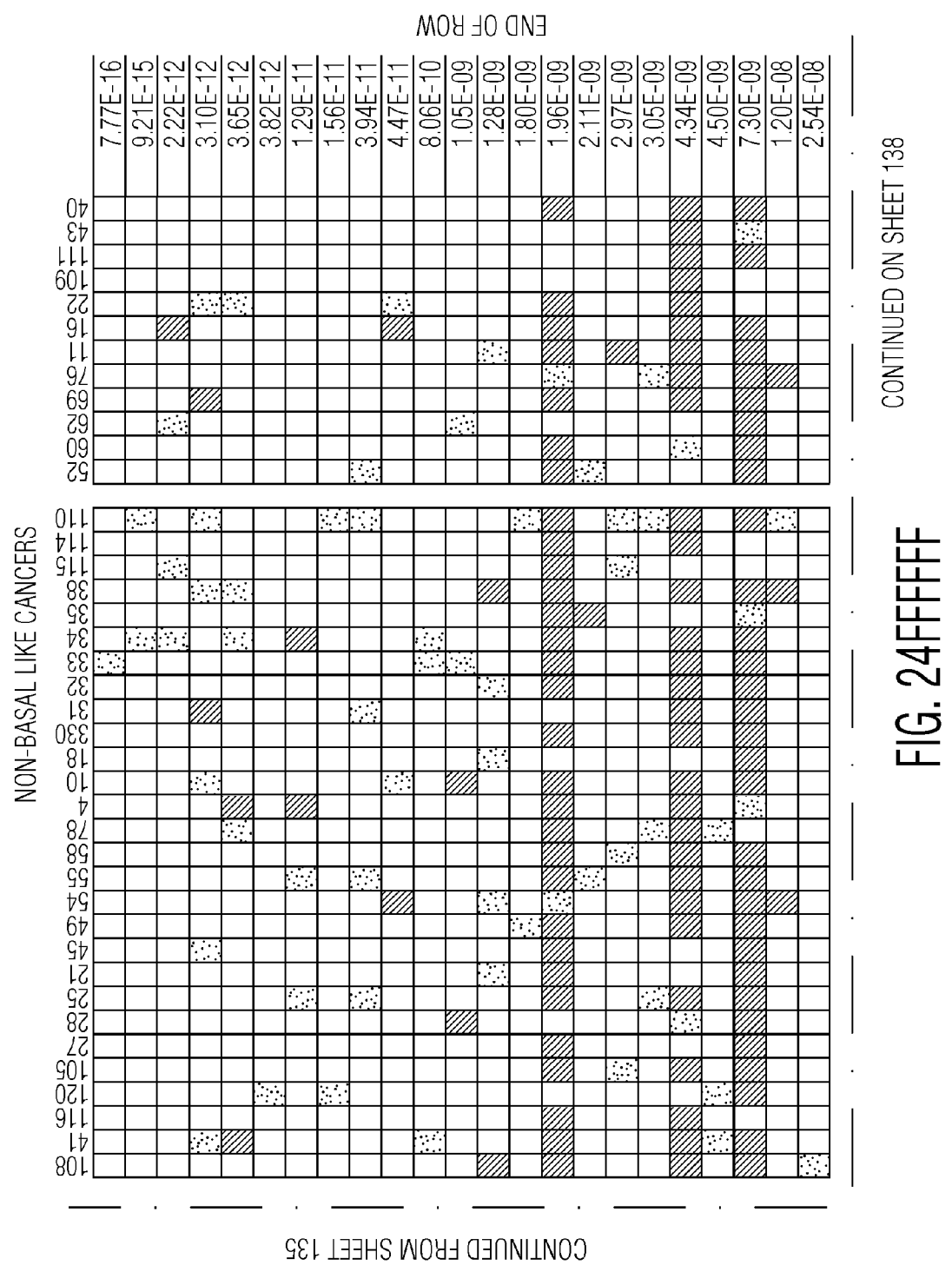

FIGS. 24A to 24NNNNNN span one hundred forty-four sheets.

Figure 25:
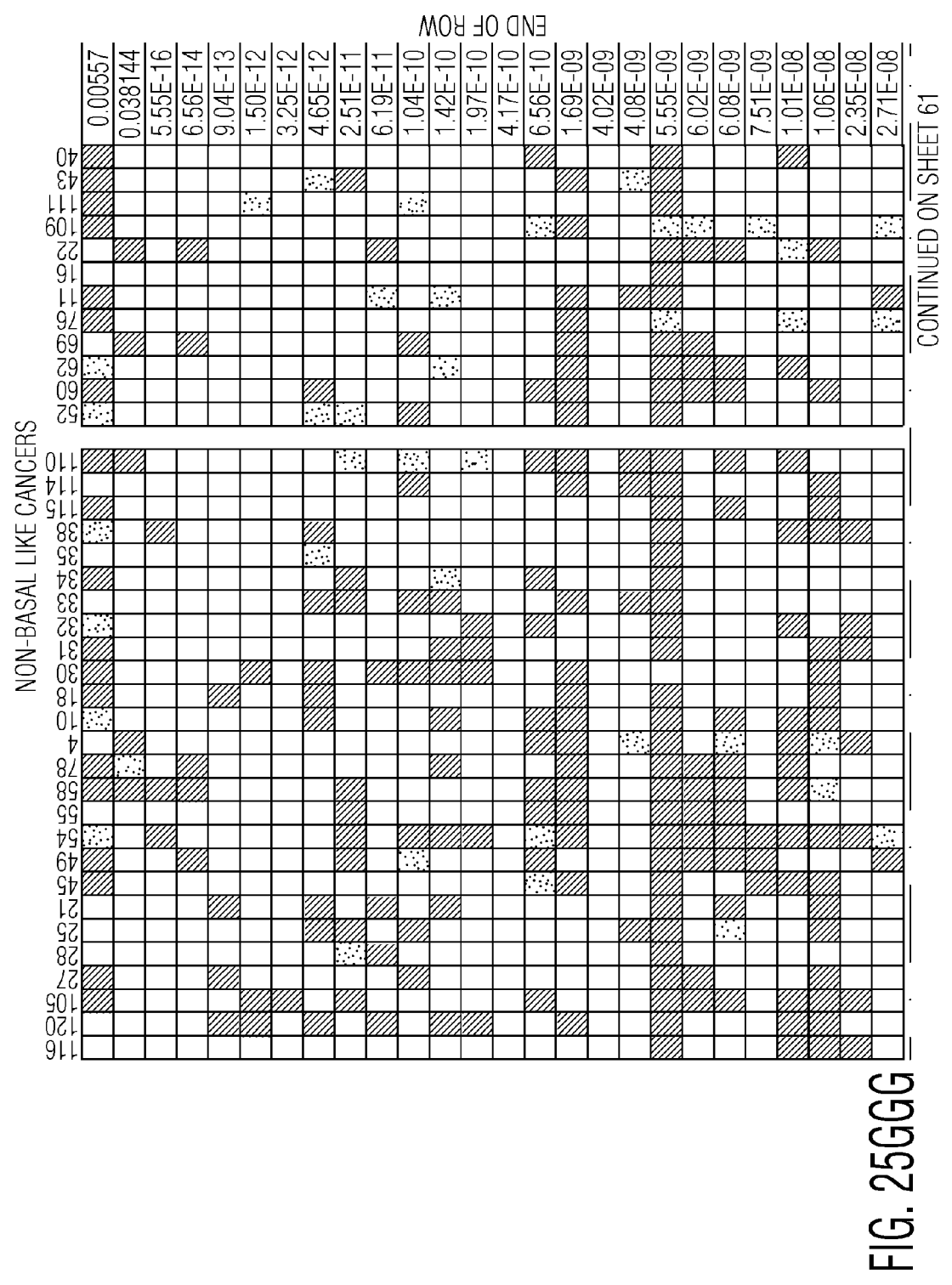
Figure 25:
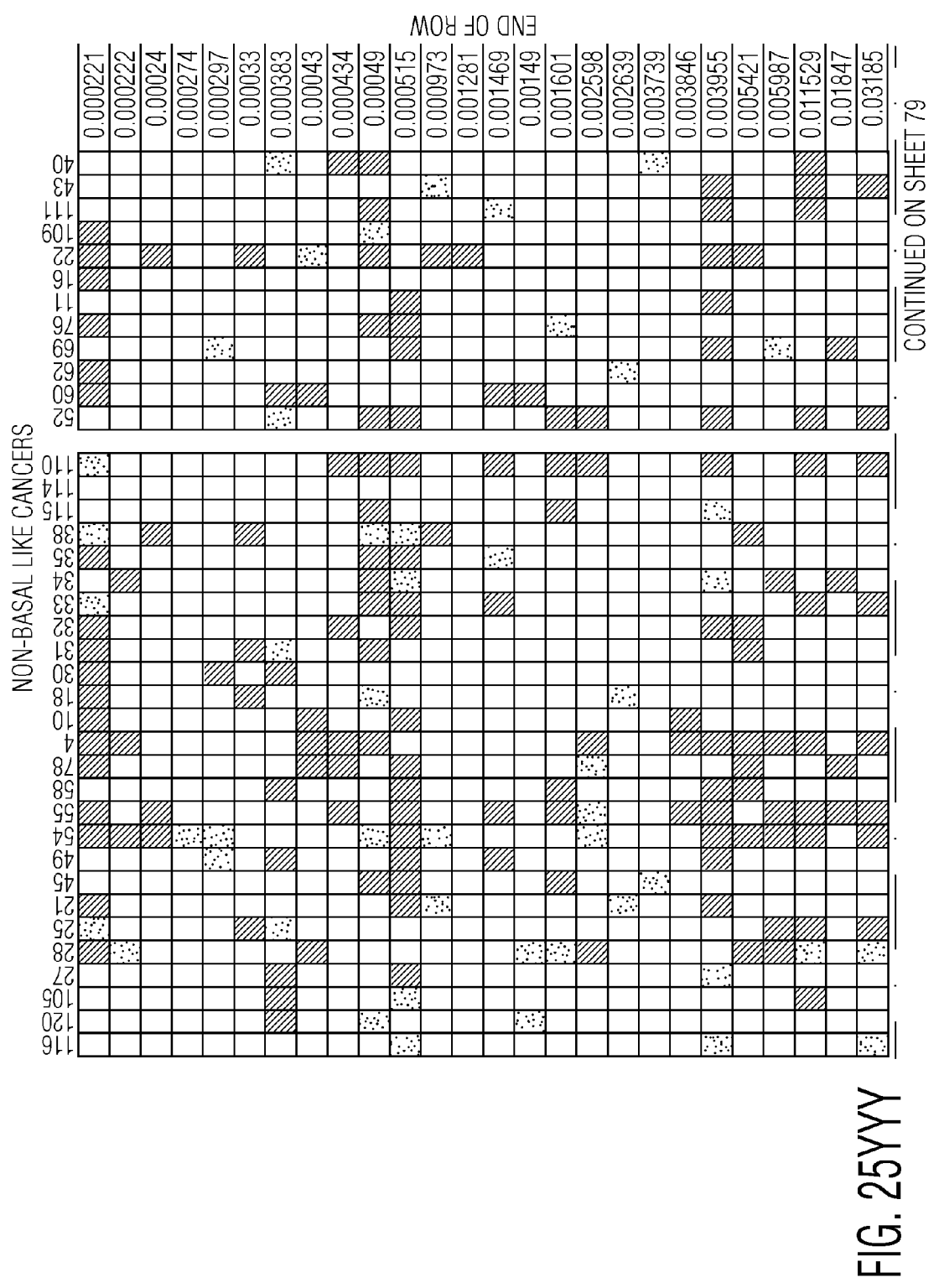
Figure 25:
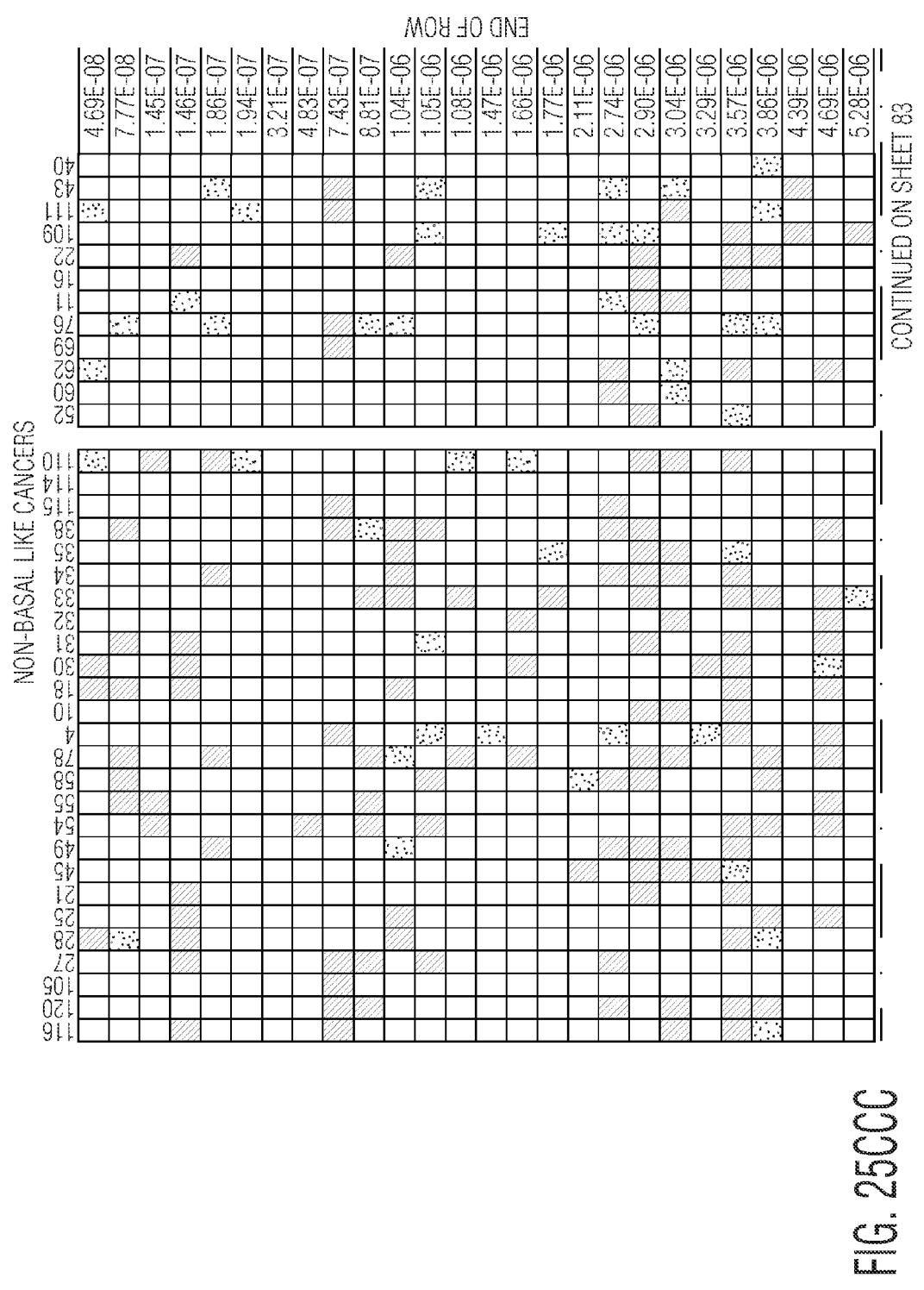
Figure 25:
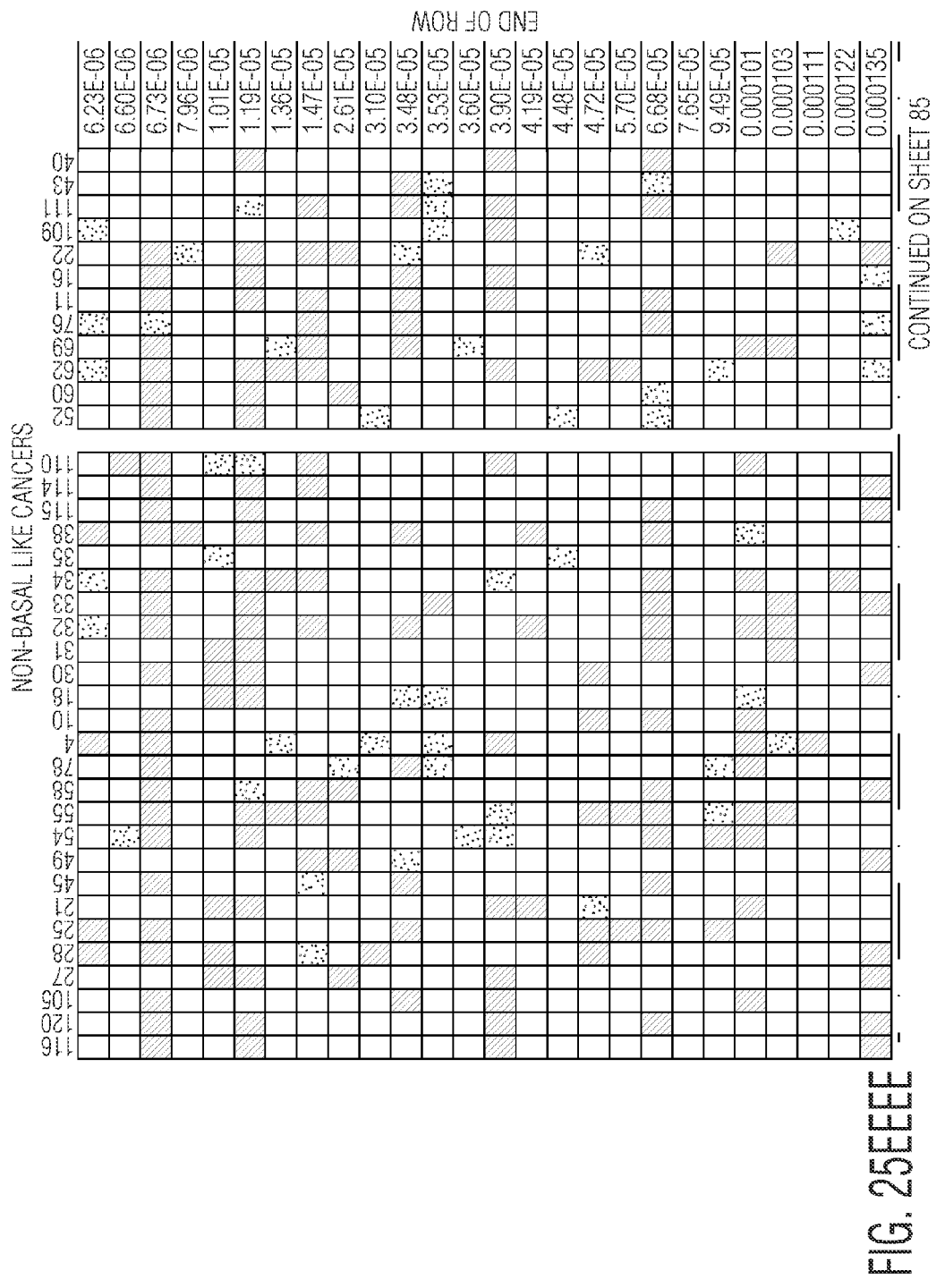
Figure 25:
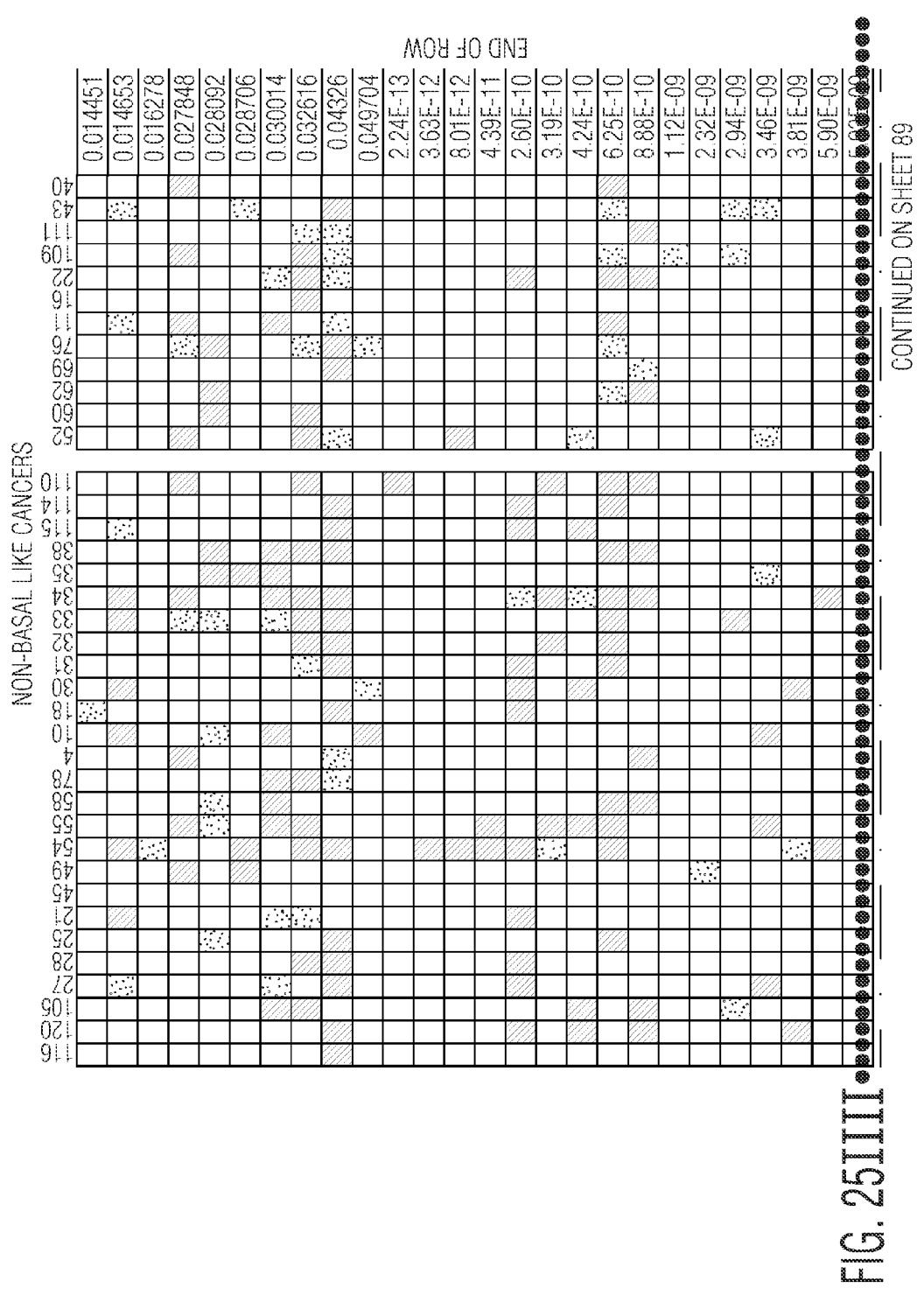

FIGS. 25A to 25UUUU span ninety-nine sheets.

Figure 26A:
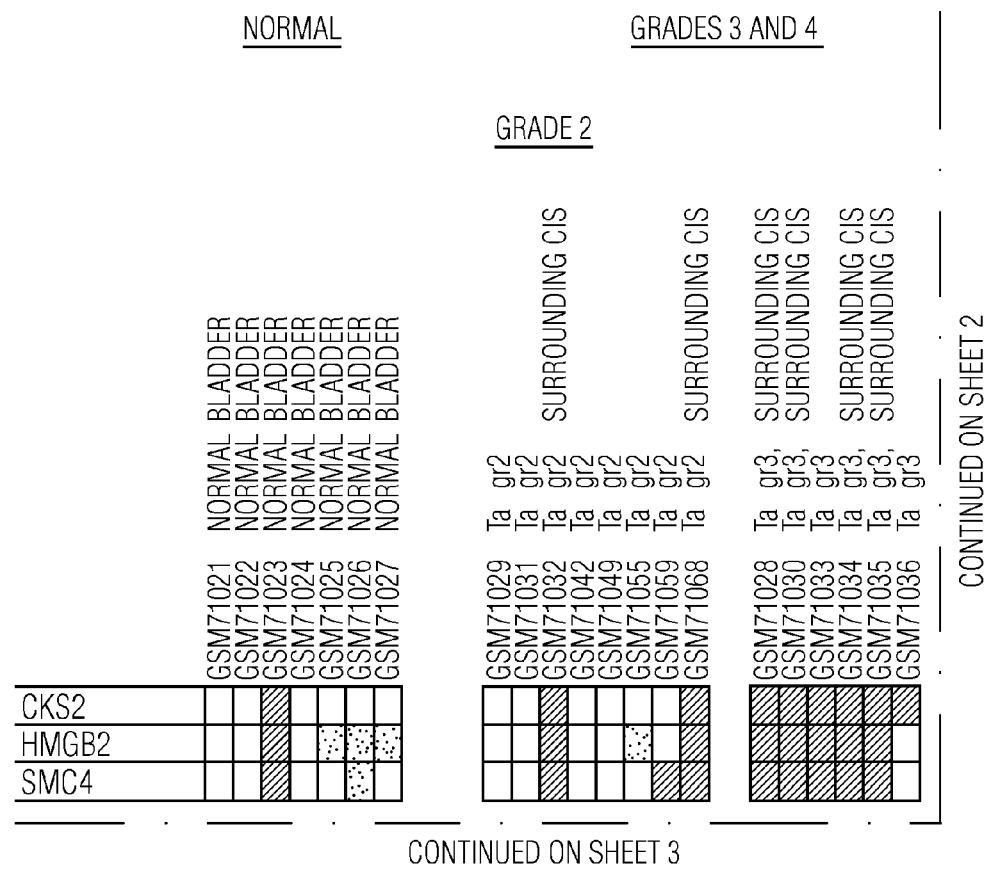

FIGS. 26A to 26F show partial views intended to form one complete view of microarray data from bladder cancer patients and the identification of ERGO genes and ERGO tumors in cancers from such patients. FIGS. 26A to 26F span six sheets.

FIGS. 27A to 27F show partial views intended to form one complete view of microarray data from hepatoma patients and the identification of ERGO genes and ERGO tumors in such patients. FIGS. 27A to 27F span six sheets.

DETAILED DESCRIPTION OF THE DISCLOSURE

Figure 1A:
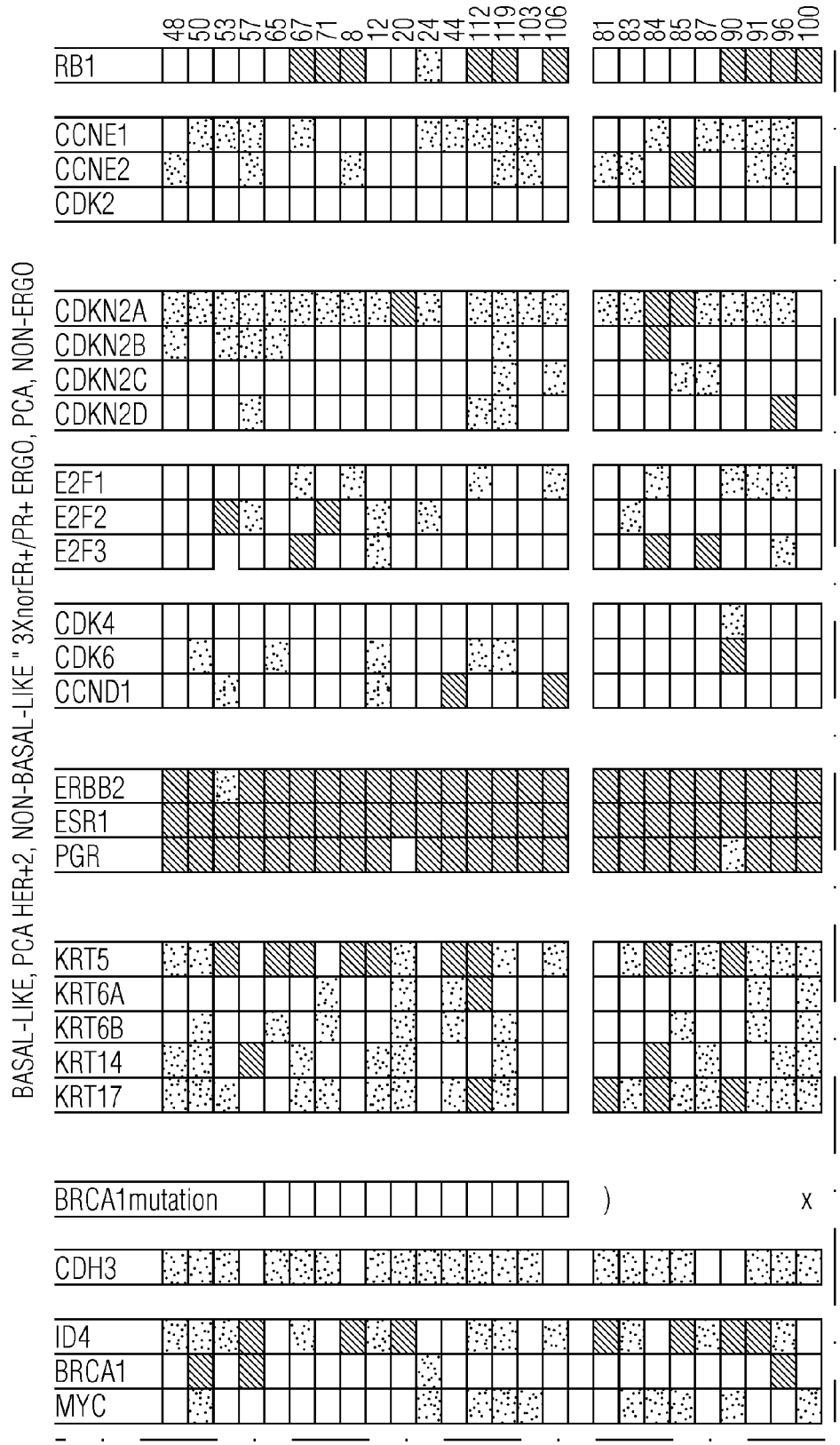
FIGS. 1A to 1DD show partial views intended to form one complete view of microarray data of a selected gene expression profile for the ERGO, non-ERGO HER2-over-expressing, ER/PR over-expressing non-ERGO, and triple-non-positive non-ERGO tumor subsets identified in the Van't Veer human breast cancer microarray set (s1).
Figure 1C:
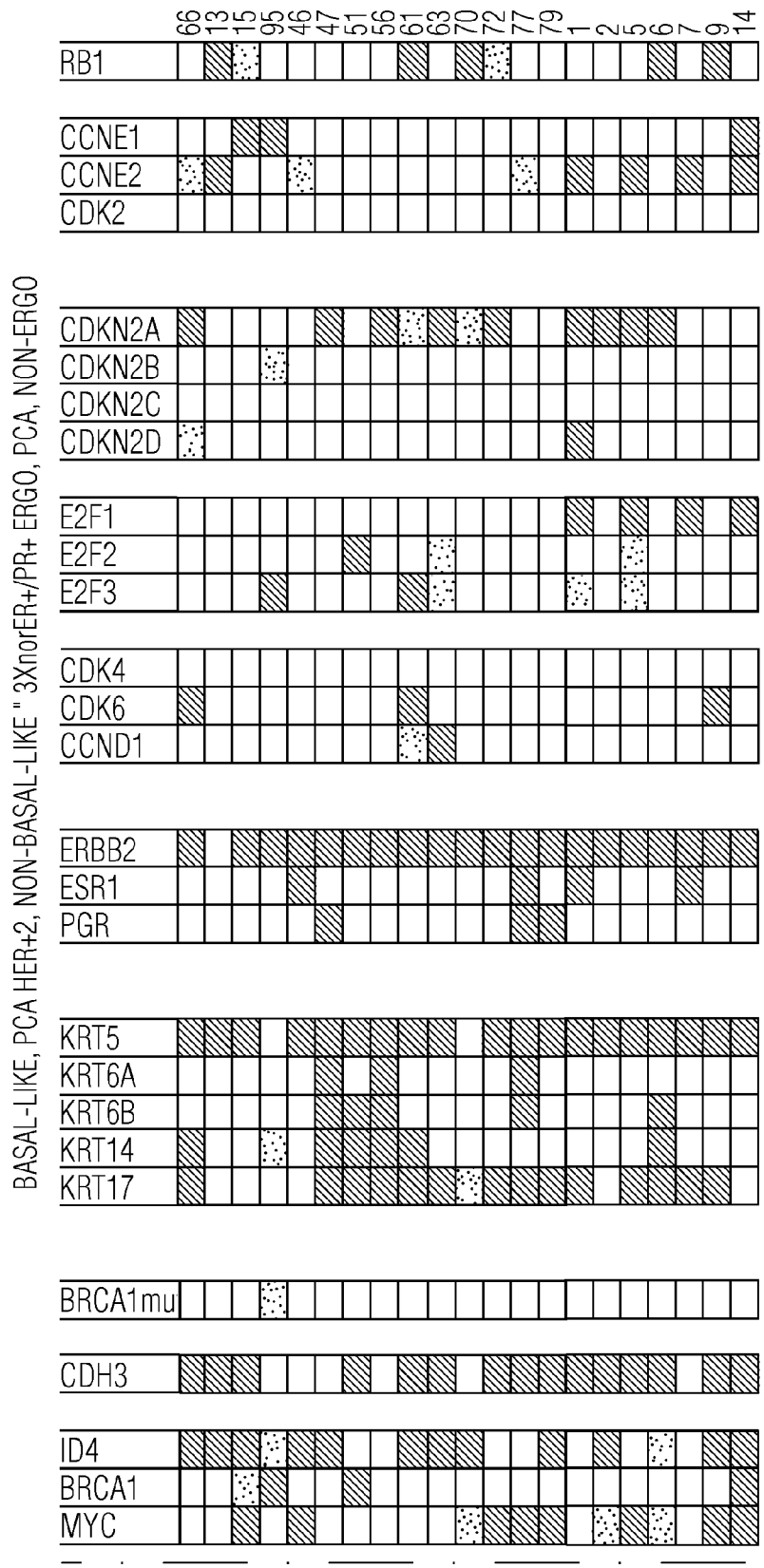
Figure 1D:
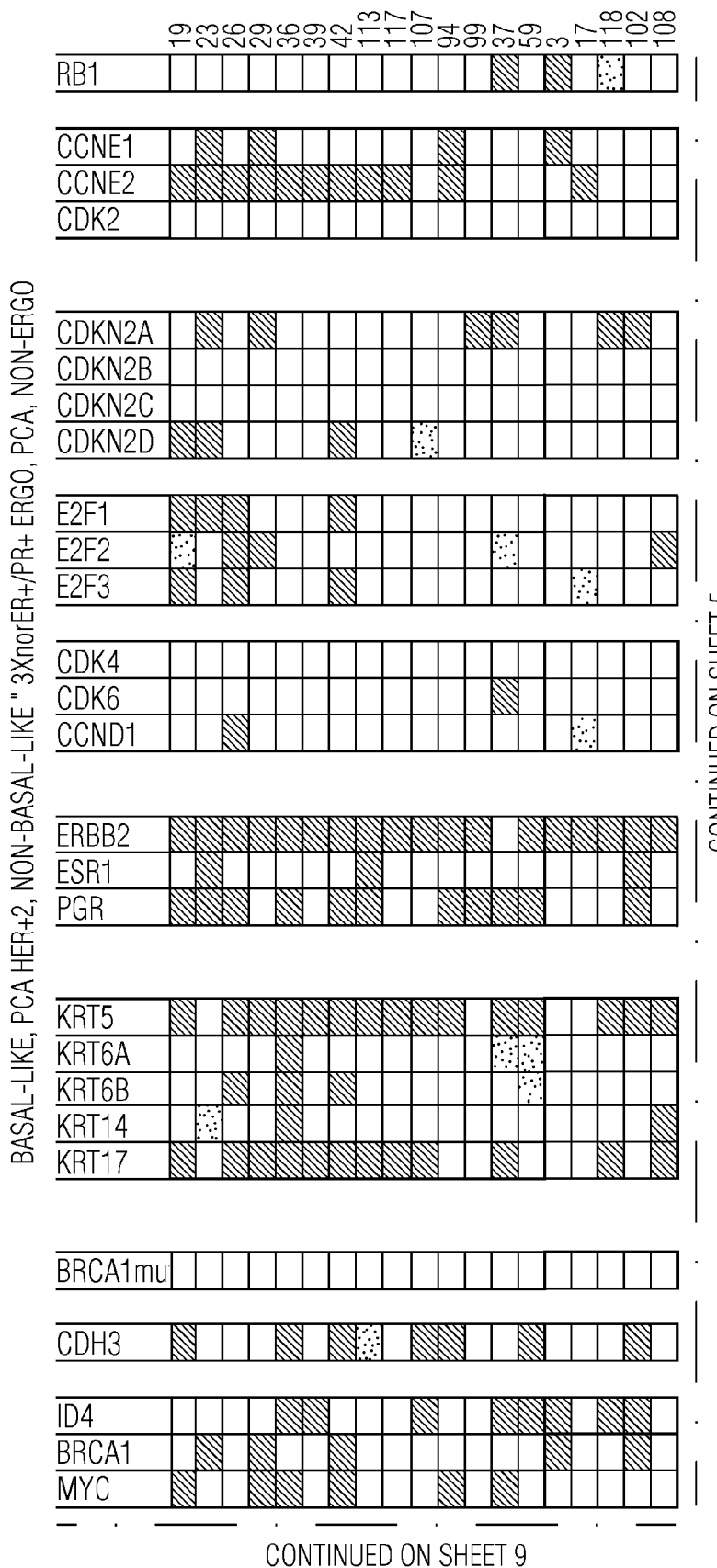
Figure 1G:
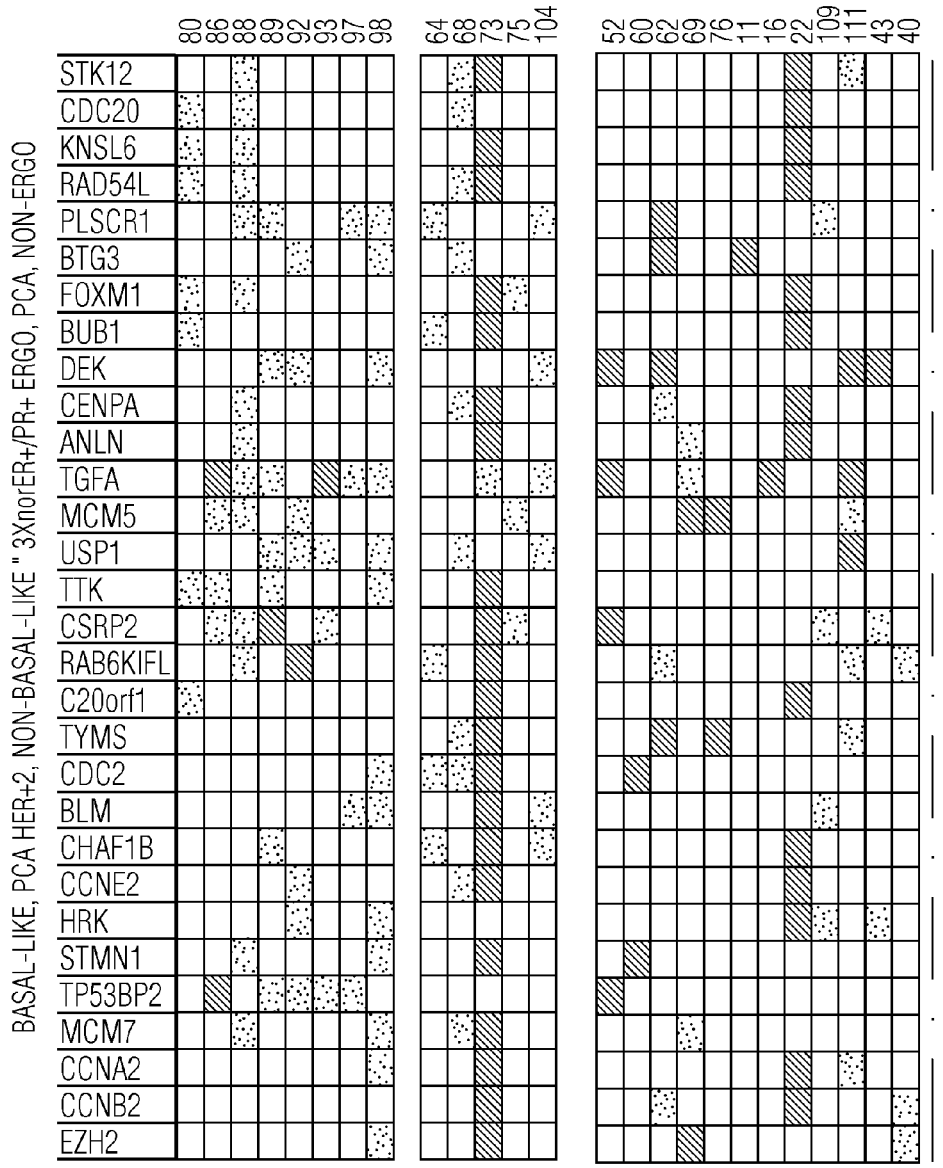
Figure 1I:
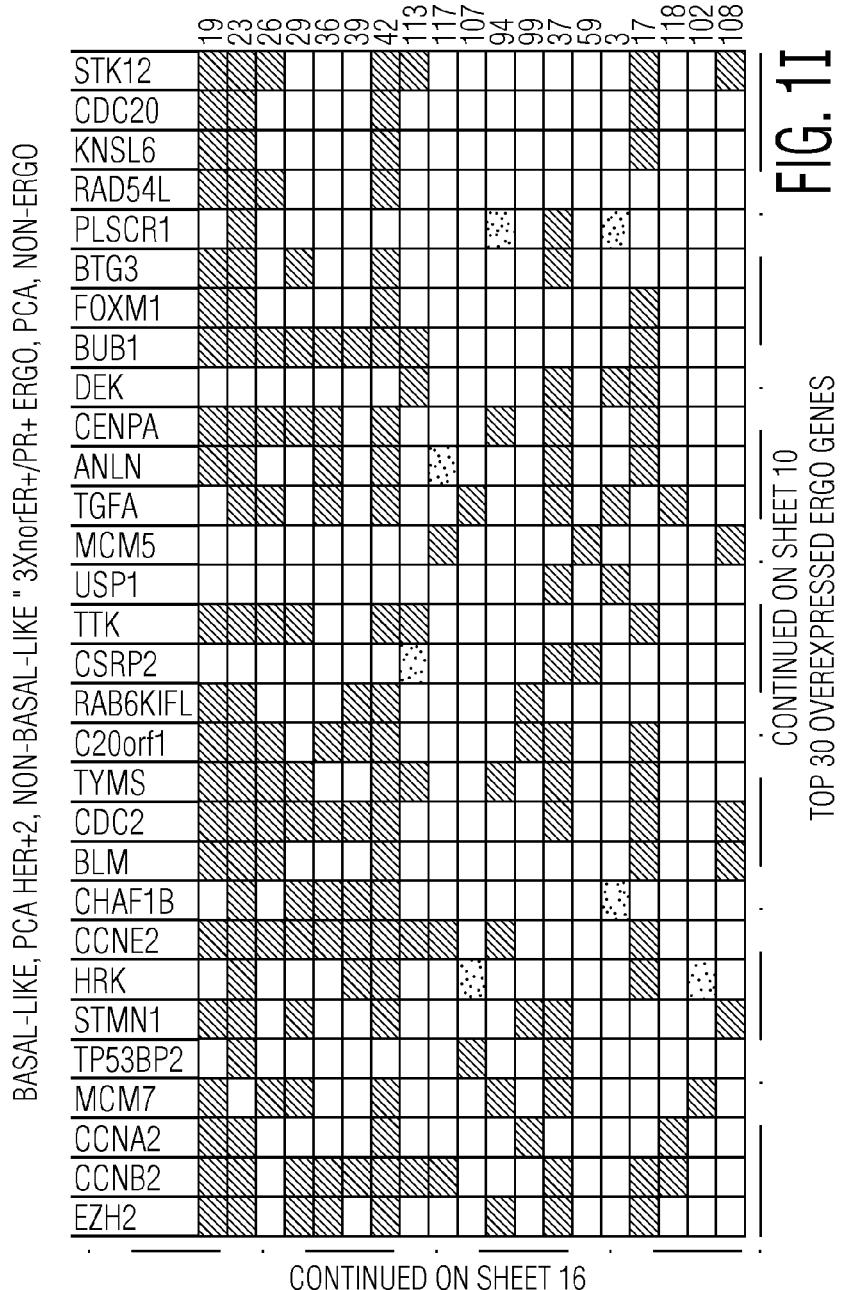
Figure 1M:
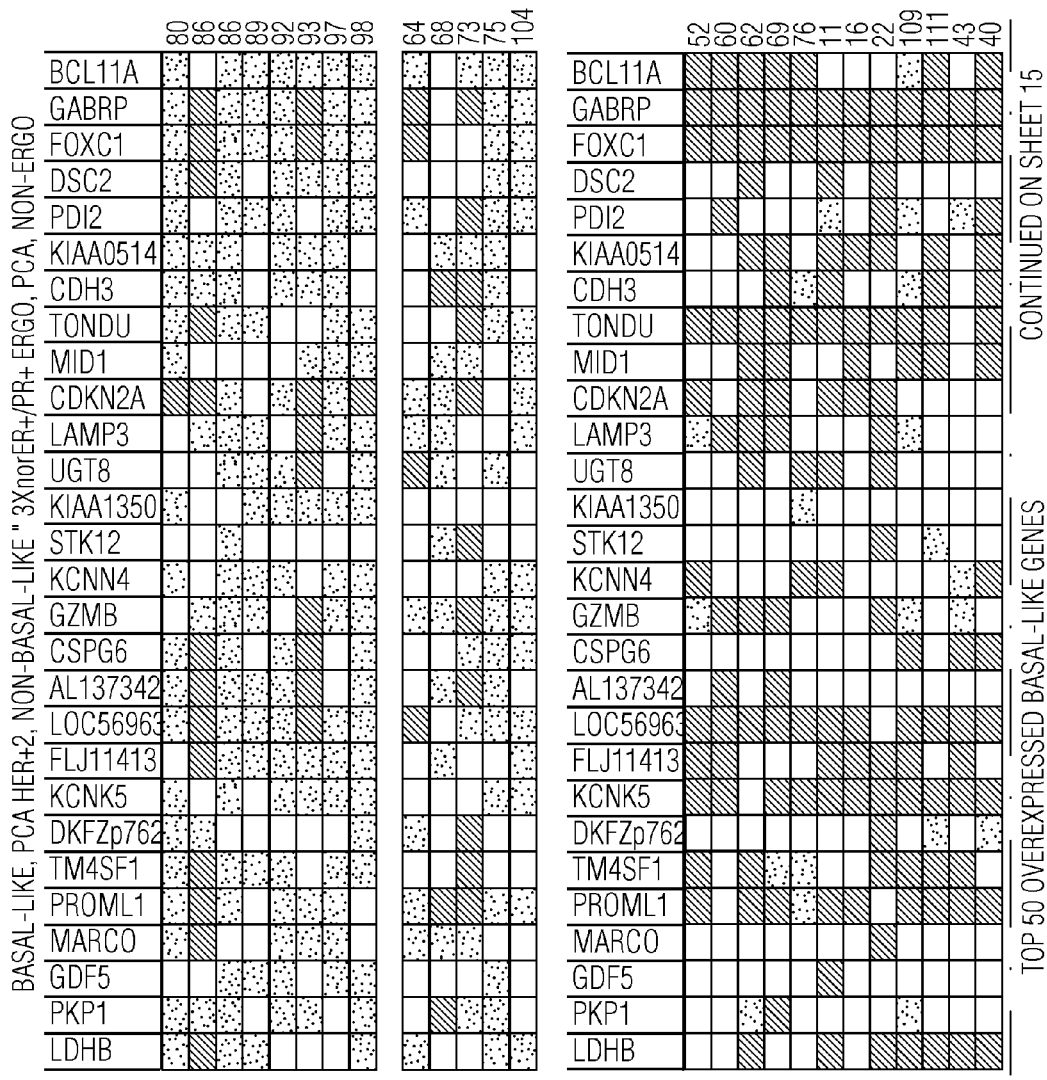
Figure 1N:
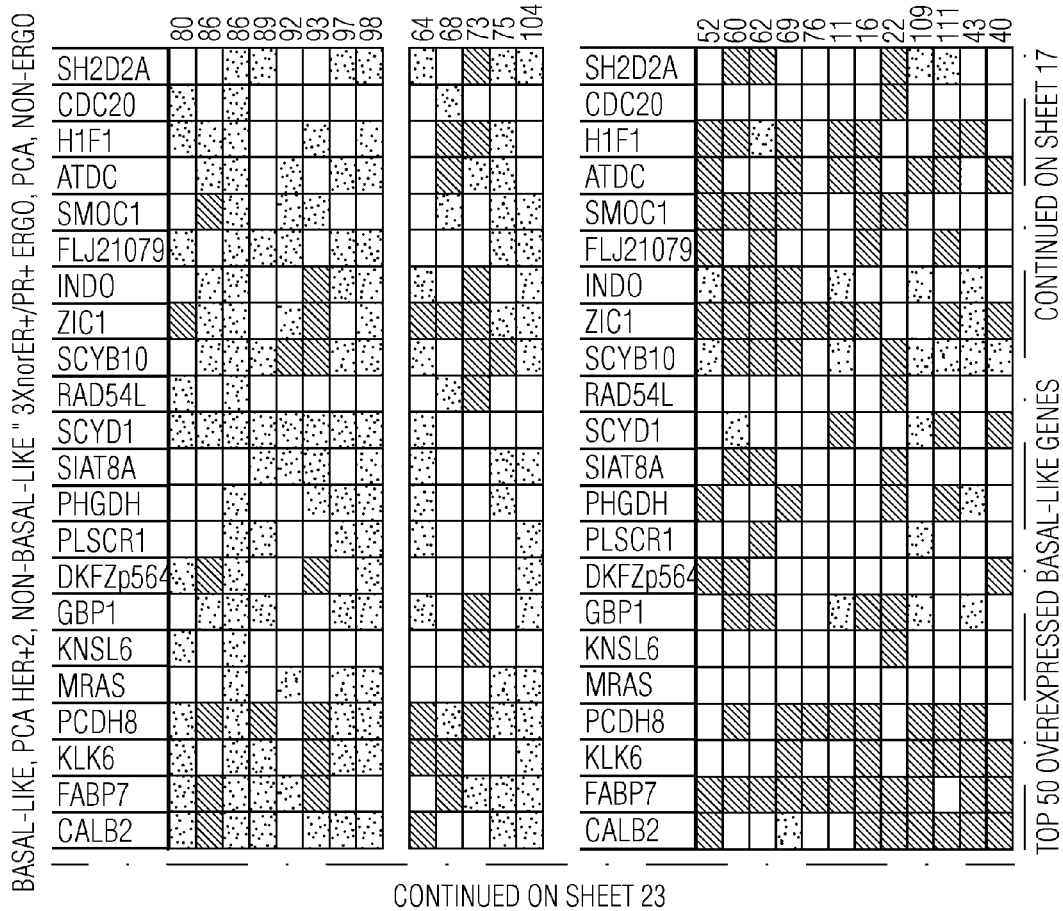
Figure 1P:
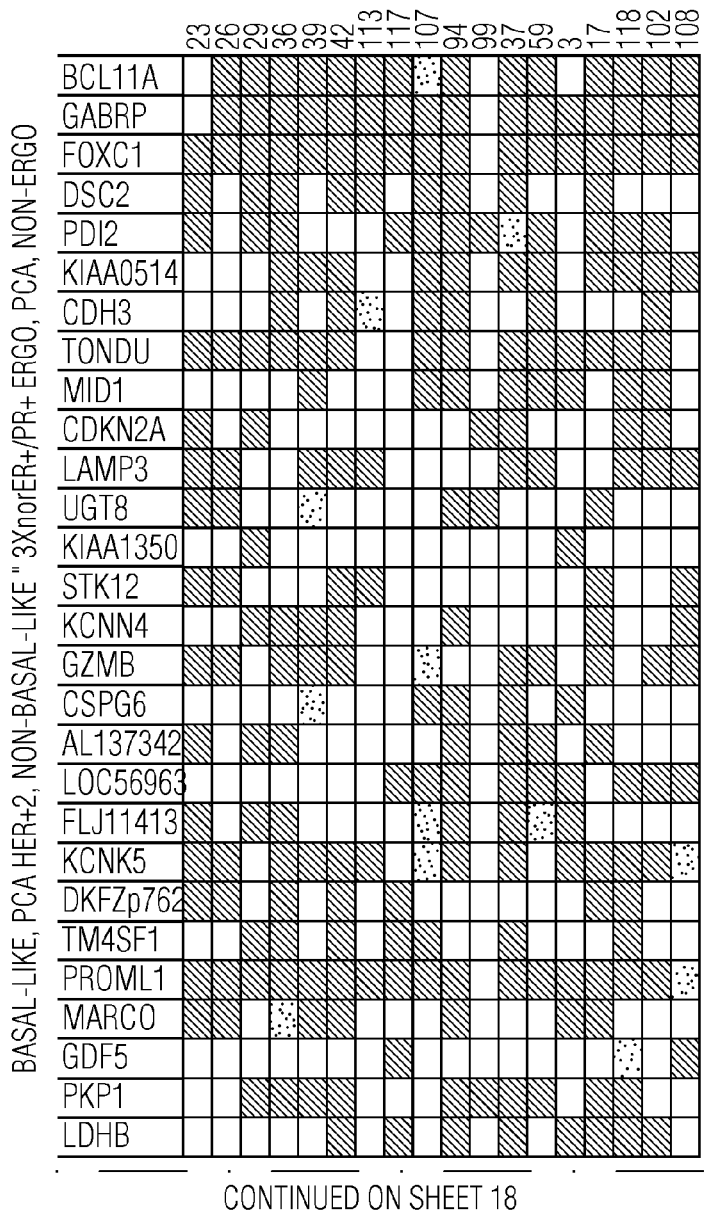
Figure 1R:
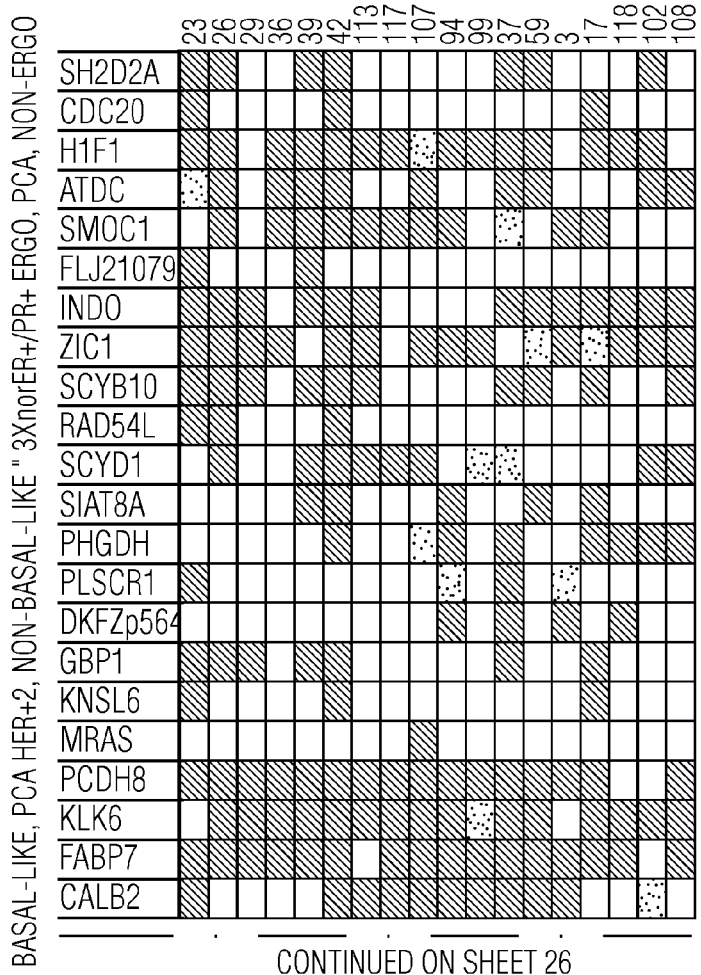
Figure 1V:
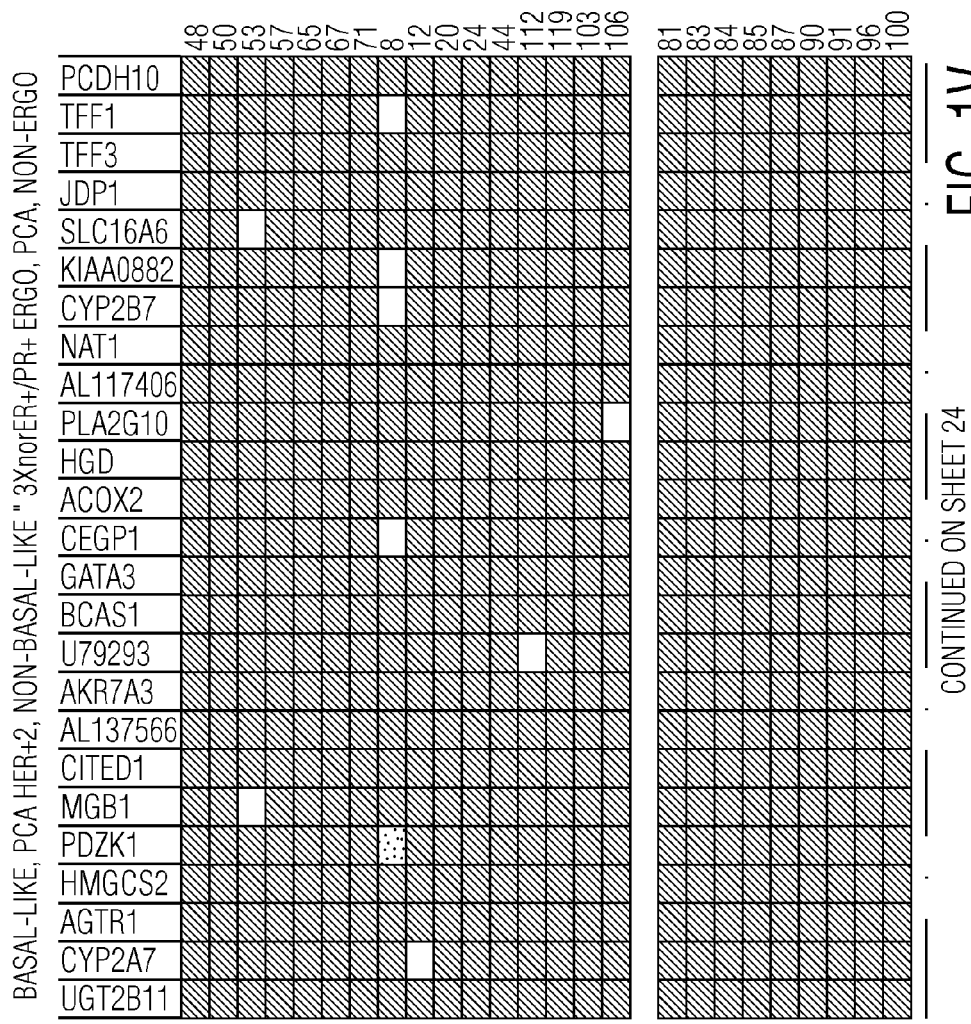

The term "agonist" as used herein means a molecule that partially or completely activates, by any mechanism, a biological activity or effect of another molecule or complex of molecules. As used herein, an "agonist" is a molecule that is capable of, directly or indirectly, substantially activating, stimulating, or increasing the biological activity or effects of another molecule or complex of molecules. Such agonists may be, for example, small organic molecules, peptides, antibodies, antibody fragments, or polynucleotides. Increasing the expression of a molecule or complex of molecules can be used to agonize the biological activities or effects of the molecule or complex of molecules. For example, an over-expressed molecule or a complex of molecules can be considered to be an "agonist."

The term "antagonist" as used herein means a molecule that partially or completely inhibits, by any mechanism, a biological activity or effect of another molecule or complex of molecules. As used herein, an "antagonist" is a molecule that is capable of, directly or indirectly, substantially counteracting, reducing or inhibiting the biological activity or effects of another molecule or complex of molecules. Such antagonists may be, for example, small organic molecules, peptides, antibodies, antibody fragments, or polynucleotides.

The term "aurora kinase" as used herein means a peptide chain which is at least 90% identical to the mature form of the Homo sapiens Aurora A kinase amino acid sequence shown in SEQ ID NO: 1 (described by Accession Number NP_003591), the mature form of the Homo sapiens Aurora B kinase amino acid sequence shown in SEQ ID NO: 2 (described by Accession Number NP_004208); or the Homo sapiens Aurora C kinase amino acid sequence shown in SEQ ID NO: 3 (described by Accession Number NP_001015878) as determined using the default settings of the CLUSTALW algorithm.

As used herein the term "date" as used herein means a specified time. For example, a date may be a specific time or day in the future.

The term "drug" as used herein means a substance which produces physiological effects in an organism, or effects on cells, that result in the cure, mitigation, treatment, or prevention of a pathological condition.

The term "E2F" as used herein means a peptide chain which is at least 90% identical to the mature form of the Homo sapiens E2F-1 amino acid sequence shown in SEQ ID NO: 6 (described by Accession Number NP_005216), the mature form of the Homo sapiens E2F-2 amino acid sequence shown in SEQ ID NO: 7 (described by Accession Number NP_004082); or the Homo sapiens E2F-3a amino acid sequence shown in SEQ ID NO: 8 (described by Accession Number NP_005215) as determined using the default settings of the CLUSTALW algorithm.

The term "FOXM1" as used herein means a peptide chain which is at least 90% identical to the mature form of the Homo sapiens FOXM1 amino acid sequence shown in SEQ ID NO: 5 (described by Accession Number NP_068772) as determined using the default settings of the CLUSTALW algorithm.

The term "indicator of gene transcript levels" as used herein means a measurable endpoint that correlates to the level of a gene transcript. Such indicators may be nucleic acids corresponding to mRNA gene transcripts (e.g. cDNAs) or peptide chains, such as proteins and other polypeptides, that correlate to a gene transcript from which they are translated. Indicators that correlate to a given gene transcript may also comprise other nucleic acids such as splice variants, nucleic acids encoding different peptide chain isoforms, or other nucleic acid sequence variants capable of hybridizing to any portion of a gene transcript including both non-coding sequences such as 5' and 3' untranslated regions or coding sequences.

The term "LINC protein complex" as used herein means a complex of proteins comprising a peptide chain which is at least 90% identical to the mature form of the Homo sapiens LIN-9 amino acid sequence shown in SEQ ID NO: 9 (described by Accession Number NP_775106) as determined using the default settings of the CLUSTALW algorithm and which has the biological activity of repressing gene transcription. The LINC multiprotein complex is also known to contain human LIN-37, RbAP48, which is a human homolog of LIN-53, B-MYB, and DKFZp686L1814, a human homolog of C. elegans LIN-54, and LIN-52. Tesmin is another human homolog of LIN-54 and Rb, p107, p130, and E2F isoforms also associate with the core complex in different phases of the cell cycle. See Schmit et al., 6 Cell Cycle 1903 (2007).

The term "normalizing" as used herein means means placing a measured value in a first data set, and a measured value in a second data set, on a common scale to facilitate the comparison of the measured values in the first data set and the measured values in the second data set. Typically, normalization of measured values in different data sets (e.g. tumor sample data set and reference data) is performed by identifying a parameter common to both the first data set and second data sets, measuring the value of common parameter in both the first data set and second data set, dividing measured values in the first data set by the value of the common parameter in the first data set and dividing measured values in the second data set by the value of the common parameter in the second data set to place the data in the first data set and second data set on a common scale so they can be easily compared. For example, in the methods of the disclosure an indicator value can be measured for a first gene transcript (e.g. SEQ ID NO: 12) in a tumor sample, an indicator value can be measured for the first gene transcript (e.g. SEQ ID NO: 12) in a reference such as a normal tissue sample, an indicator value can be measured for a second gene transcript (e.g. a housekeeping gene such as SEQ ID NO: 162) in the tumor sample to produce a housekeeping value, an indicator value can be measured for the second gene transcript (e.g. a housekeeping gene such as SEQ ID NO: 162) in the normal tissue sample to produce a housekeeping value, the indicator value of the first gene transcript in the tumor sample can be divided by the housekeeping value for the tumor sample, the indicator value of the first gene transcript in the normal tissue sample can be divided by the housekeeping value for the normal tissue sample and the resulting normalized values, which are now on a common scale, can be compared. Importantly, as those of ordinary skill in the art will readily recognize a variety of approaches may be taken to normalize data such as, for example, normalizing to an aggregate of common parameter values (e.g. for multiple housekeeping genes). Normalization may also be performed across an entire data set (e.g. all indicator values for every gene transcript on an array) or for only a portion a data set (e.g. an individual indicator value for a single gene transcript on an array).

The term "nucleic acid" as used herein means a molecule comprising at least two nucleic acid residues linked to form a chain. Such nucleic acid residues may be those found in DNA or RNA. Small nucleic acids of less than 50 residues may be referred to as "oligonucleotides."

The term "over-expressed" as used herein means that a measured indicator of gene transcript levels is greater than a reference value. Over-expression occurs when an indicator value is, for example, at least 1.5 times greater than a reference value or at least 1.8 times greater than a reference value.

The term "peptide chain" as used herein means a molecule comprising at least two amino acid residues linked by a peptide bond to form a chain. Large peptide chains of more than 50 amino acids may be referred to as "polypeptides" or "proteins." Small peptide chains of less than 50 amino acids may be referred to as "peptides."

The term "principal component analysis algorithm" as used herein mean an algorithm that performs a mathematical procedure that transforms a number of potentially correlated variables into a smaller number of uncorrelated variables called principal components. Principle component analysis (PCA) is mathematically defined as an orthogonal linear transformation that transforms data to a new coordinate system such that the greatest variance by any projection of the data comes to lie on the first coordinate which is called the first principal component, the second greatest variance on the second coordinate, and so on. PCA is theoretically the optimum transform for a given data in least square terms. Depending on the field of application, PCA is also named the discrete Karhunen-Loève transform (KLT), the Hotelling transform or proper orthogonal decomposition (POD). PCA and methods steps utilizing can be performed on a computer.

The term "rank ordering algorithm" as used herein mean an algorithm that performs a mathematical procedure that orders data based on use selected data. Data can be rank ordered in any coordinate system such as a graph or table using user defined criteria. In one application of such an algorithm varying degrees of stringency and criteria may be used such as the following:

a) Each tumor in a tumor subset to be ordered must over-express at least X percent of 325 E2F responsive genes having the nucleic acid sequence shown in SEQ ID NO:s 10-334; and b) Each of the 325 E2F responsive genes having the nucleic acid sequence shown in SEQ ID NO:s 10-334 in the tumor subset must be over-expressed in at least X percent of the tumors in the tumor subset;

where X might be 14%, 17%, 20%, 25%, or 33% and the value of X reflects increasing degrees of stringency. Rank ordering algorithms and method steps using rank orderin algorithms can be performed on a computer.

The term "reference" as used herein means a standard of comparison. A reference may be normal cells or tissues. Alternatively, a reference may be the average of the signal intensity values from all sample-probed gene spots on a microarray set. A reference may also be a signal corresponding to one or more gene transcripts, such as a housekeeping genes like GAPDH or others, which are assumed not to vary significantly in living cells.

The term "survival plot" as used herein means a plot in a coordinate system such as a graph or table in which an indicator of the number of surviving patients in a population is described as a function of the time after the patients in the population were diagnosed as having a particular condition.

The term "survivin" as used herein means a peptide chain which is at least 90% identical to the mature form of the Homo sapiens survivin amino acid sequence shown in SEQ ID NO: 4 (described by Accession Number NP_001012270) as determined using the default settings of the CLUSTALW algorithm.

The term "therapeutically effective amount" as used herein means those doses of a drug that, in a given individual patient, produce a response that results in the killing of an ERGO tumor cell or that inhibits the division of an ERGO tumor cell. Therapeutically effective amounts, or doses, appropriate for an individual patient can be readily determined using routine clinical techniques well known by those of skill in the art (e.g. dose response plots).

The term "tissue" as used herein means an aggregate of cells that form a structure in an organ or other part of an animal.

The term "tumor sample" as used herein means a portion of a tumor from a patient. Tumor samples can comprise individual cells isolated from a tumor, cell lines isolated from a tumor, or larger portions of a tumor comprising multiple different cells in the tumor. A tumor sample can also comprise a portion of molecules from a tumor such as a collection of peptide chain molecules expressed by a tumor or a collection of nucleic acids such as reverse transcribed mRNAs (i.e. cDNAs) from a tumor.

One aspect of the disclosure is a method of identifying a tumor as an ERGO tumor comprising the steps of providing a tumor sample; providing a reference; measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249; 254, 259, 267, 269, 274-275, 292-295, 298, 307, 311, 316, 321-323, 331, 333, and 335-340; measuring the reference to produce a reference value; and comparing the indicator value to the reference value to determine which of the gene transcripts is over-expressed; whereby the tumor is identified as an ERGO tumor if at least 21 of these gene transcripts are over-expressed.

Importantly, the methods of the disclosure and the steps of the disclosed methods can be performed on a specifically programmed computer including, for example, a personal computer or programmable logic controller. In particular, the comparison steps of the methods or the application of PCA or rank ordering algorithms can be performed using such a computer. The methods of the disclosure and steps of the disclosed methods may also be tied to a nucleic acid array analyzer, capable of detecting signals correlated to the amount of a particular probe nucleic acid on an nucleic acid array which has hybridized to a nucleic acid present in a sample such as a tumor sample. The GeneChip® Array Station manufactured by Affymetrix, Inc. (Santa Clara, Calif.) is one example of such a nucleic acid array analyzer. Typically, such nucleic acid array analyzers comprise a nuclei acid array, a fluid handler, an oven or other means such as a heat block for maintaining a specific temperature (e.g. a specific hybridization temperature), a hybridization signal detection means (e.g. photomultiplier, scintillation counter, phosphor imager etc.), and a data collection means such as a computer or other means for collecting data (e.g. conventional photographic film or digital photographic film). Optionally, such nucleic acid array analyzers can comprise one or more automated nucleic acid array autoloaders for providing nucleic acid arrays to be analyzed. The output representing the physical transformation associated with a nucleic acid hybridization or other result produced by the methods of the disclosure can also be displayed on an output display such as a video monitor or printer. The methods of the disclosure and the steps of these methods can also produce a physical transformation because nucleic acid hybridization can be a result of performing the steps of the methods. Last, any combination of the above machines and apparatuses or physical transformations may be used in performing the methods of the disclosure or a method step of the disclosure.

In the methods of the disclosure a tumor is identified as an ERGO tumor if at least 21 of gene transcripts of SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201; 203, 205, 209, 217, 246-247, 249, 254, 259, 267, 269, 274-275, 292-295, 298, 307, 311, 316, 321-323, 331, 333, and 335-340; are expressed. Alternatively, a tumor is may be as an ERGO tumor if from 20% to 100% of these gene transcripts are overexpressed. Importantly, the recitation of this range is intended to support the recitation of any value in the range (e.g. 20%, 100% or all values between 20% and 100%).

In a method of the disclosure it is preferred that cDNA microarrays be used for the measurement of indicators of gene transcript levels and reference values. Importantly, gene transcript levels, as measured in microarray experiments, are generally regarded by those of ordinary skill in the art as a proxy for gene (protein) expression levels. Consequently, the measurement of gene transcripts is referred to in the art and in some instances herein as the measurement of gene expression, overexpression, or under-expression depending on the type of analysis being performed.

DNA microarrays consist of multiple of different DNAs, such as oligonucleotide DNA nucleic acid chains or cDNAs, spotted onto known locations on a solid support, such as a glass microscope slide. The cDNAs are typically obtained by PCR amplification of plasmid library inserts using primers complementary to the vector backbone portion of the plasmid or to the gene itself for genes where sequence is known. PCR products suitable for production of microarrays are typically between 0.5 and 2.5 kb in length. Full length cDNAs, expressed sequence tags (ESTs), or randomly chosen cDNAs from any library of interest can be chosen. ESTs are partially sequenced cDNAs as described. In general, the cDNAs are of sufficient length to hybridize to cDNAs obtained from mRNAs representing splice variants or nucleic acids encoding different peptide chain isoforms derived from a single gene or the polymorphs of a single gene under the hybridization conditions of a microarray experiment. The DNAs immobilized on an array may also be nucleic acid chains comprising less than 100 nucleic acid residues (e.g. oligonucleotides). Nucleic acids immobilized on an array may also comprise alternative backbone chemistries such as phosphothiorate bond based chemistries, and alternative nucleoside residues such as modified residues capable of pairing with multiple nucleoside base residues. Those skilled in the art will recognize a variety of chemical modifications that can be made to the basic nucleic acid structure to create non-naturally occurring molecules with improved properties which are still capable of hybridizing to other nucleic acid molecules. In general, such modifications are those that improve the stability of such molecules, the hybridization properties of such molecules, or the ability of such molecules to couple to a substrate such as an immobilized substrate.

In a typical microarray experiment, a microarray is hybridized with differentially labeled RNA or DNA populations derived from two different samples. Most commonly RNA is isolated from cells or tissues of interest and is reverse transcribed to yield cDNA. Such RNA may be either total RNA or polyadenylated RNA. Labeling is usually performed during reverse transcription by incorporating a labeled nucleotide in the reaction mixture, but RNAs can also be labeled. Although various different labels can be used, most commonly the nucleotide is conjugated with fluorophores such as the fluorescent dyes Cy3 or Cy5 (e.g., Cy5-dUTP and Cy3-dUTP). cDNA or RNA derived from one sample representing, for example, a particular cell type, tissue type or growth condition is labeled with one fluorophore while cDNA or RNA derived from a second sample representing, for example, a different cell type, tissue type, or growth condition is labeled with the second fluorophore. Similar amounts of labeled material from the two samples are hybridized to the microarray. In the case of a microarray experiment in which the samples are labeled with Cy5 which fluoresces red light and Cy3 which fluoresces green light, the primary data obtained by scanning the microarray using a detector capable of quantitatively detecting fluorescence intensity are ratios of red/green fluorescence intensity. These ratios represent the relative concentrations of labeled cDNA or RNA molecules that hybridized to the DNA on the microarray and thus reflect the relative expression levels of the mRNA corresponding to each cDNA or gene represented on the microarray.

Alternatively, different labeled probe samples can be hybridized to an array at different times by hybridizing a first sample, collecting fluorescence intensity data for the first sample, stripping the array, collecting background fluorescence intensity data, hybridizing the second sample, and then collecting fluorescence intensity data. This type of approach can be used to probe an array with a tumor sample and then a reference such as a sample from normal tissue to measure an indicator of gene transcript levels in a tumor sample or to measure a reference to produce a reference value. Those of ordinary skill in the art will recognize other strategies for measuring an indicator of gene transcript levels in a tumor sample and measuring a reference to produce a reference value. Additionally, those of ordinary skill in the art will recognize hybridization based analyses can be performed in other non-array based formats, and that when array based formats are used the array need not be on the micro-scale and can instead be provided in other formats.

Hybridizations to arrays can be performed under a variety of stringent conditions by varying temperature or salt; detergent, and crowding agent concentrations. Additionally, microarray hybridization reagents are commercially available such as, for example, the Agilent Gene Expression Hybridization Kit (part number 5188-5242; Agilent Technologies Inc. Santa Clara, Calif.) or Agilent Oligo aCGH Hybridization Kit (part number 5188-5220; Agilent Technologies Inc. Santa Clara, Calif.). The term "stringent hybridization conditions" as used herein means those conditions which promote the hybridization of a given nucleic acid sequence to its sequence complement, without that sequence hybridizing significantly with sequences having a lesser degree of complementarity (e.g. having one or more mismatches or less than 85% or less than 90% sequence identity as measured by CLUSTALW alignment using the default settings of the CLUSTALW algorithm). More generally, "stringent hybridization conditions" means conditions which allow hybridization of a given sequence with its intended targets, without significant hybridization of the sequence with other, nucleic acid sequences having different nucleic acid sequences that may be present.

Tumor samples for use in the methods of the disclosure can be prepared by collecting a fresh portion of the tumor by core needle biopsy or surgery. Tumor samples to be used for microarray or other nucleic acid hybridization based analyses can then be placed in cold RNALATER™ (Applied Biosystems/Ambion Inc., Austin, Tex.) on ice for 30 minutes followed by freezing at −80° C. until RNA extraction. RNA can be extracted from tumor samples using the RNEASY™ system (Qiagen Inc., Valencia, Calif.) and contaminating DNAs can be removed with TURBO™ DNAse (Applied Biosystems/Ambion Inc., Austin, Tex.). Each tumor sample RNA preparation can then be assayed for purity by PCR/reverse transcription-PCR differential amplification analysis to confirm satisfactory removal of contaminating DNAs from the preparation. Each tumor sample RNA preparation can also be assessed for RNA quality using capillary electrophoresis RNA 6000 Ladder LABCHIP™ kits and an Agilent 2100 Bioanalyzer system (Agilent Technologies Inc. Santa Clara, Calif.) to produce electropherograms for assessment of RNA quality. RNA quality can be evaluated by examining electropherograms to confirm the 18 S and 28 S rRNA subunit peaks are present and in the appropriate 1:2 ratio. Assessment of 18 S and 28 S rRNA by this and other techniques is accepted in the art as an indicator of the relative intactness or; quality of other isolated RNAs in a sample such as mRNAs and as an indicator of RNAse degradation of such isolated RNAs.

The Agilent 2100 Bioanalyzer system can also assess RNA quality using software that produces a RNA integrity number (RIN) for estimating the integrity of total RNA samples. This software automatically assigns an integrity number to RNA sample. Such that sample integrity is no longer determined by the ratio of the ribosomal bands, but instead by the entire electrophoretic trace in an electropherogram prepared using the RNA sample. This includes the presence or absence of degradation products. RIN based analyses facilitates interpretation of an electropherogram comparison of samples and helps ensure the reproducibility of experiments or analysis. Importantly, the assigned RIN is independent of sample concentration, instrument and analyst.

Only tumor sample RNA preparations satisfying the differential amplification assay and electropherogram assay or other RNA integrity analyses are used to generate probes for the microarray analysis or other hybridization based analyses. Tumor sample RNA preparations can be labeled for use as probes as described above, or by using a commercially available labeling kits according to the manufacturer's instructions. The Invitrogen SUPERSCRIPT™ Indirect cDNA Labeling System (Invitrogen Inc., Carlsbad, Calif.) is one example of such a commercially available kit. Those of ordinary skill in the art will readily recognize others. Alternatively, RNA preparations can be converted to DNA preparations by reverse transcription and RNAse treatment, labeled and used as probes as discussed above in more detail.

In the methods of the disclosure indicators of gene transcript levels and reference values can be determined using techniques such as multi-dimensional gel electrophoresis, chromatography based techniques for measuring expressed peptide chains encoded by a gene, and other techniques such as fluorescence activated cell sorting or protein array analyses. In chromatography based techniques the presence of a given protein in a sample can be determined by techniques such as mass spectroscopy or antibody based detection techniques (e.g. ELISA), which are well known in the art.

A protein microarray, sometimes referred to as a protein binding microarray, comprises a substrate such as glass on which different molecules of protein have been affixed at specific locations in an ordered manner to form an array. The most common protein microarray is the antibody microarray, where antibodies Specific to different individual expressed peptide chains are spotted onto the substrate and are used as capture molecules to detect the level of the different individual expressed peptide chains (e.g., specific proteins) cell lysate solutions. This is typically done by blocking the array to minimize non-specific signals, incubating a lysate sample with the array, washing the array, blocking again, and probing the array. Additional wash and blocking steps may be necessary depending on the strategy selected for probing the array and the method used to detect peptide chains bound to the probed array. Expressed peptide chains binding to antibody arrays may be detected directly or via a secondary antibodies in a sandwich type immuno-assay (e.g., ELISA). Expressed peptide chains present in a lysate can be directly labeled with an appropriate chromophore or fluorophore using well known techniques. Where pairs of antibodies specific to the same expressed peptide chain are available, sandwich immunoassays provide high specificity and sensitivity. Additionally, label-free methods for detecting expressed peptide chains binding to an antibody array are available and include mass spectrometry, surface plasmon resonance and atomic force microscopy. Multichannel fluorescence activated cell sorting can also be used in conjunction with a selected panel of peptide chain specific antibodies to identify cells expressing a given set of peptide chains. Those of ordinary skill in the art will recognize other techniques, as well as variations on the techniques described above, for measuring an indicator of gene transcript levels and reference values which are suitable for use in the methods of the invention.

In one embodiment of the methods of the disclosure, the tumor sample is from lung tissue.

In another embodiment of the methods of the disclosure, the tumor sample is from thyroid tissue.

In another embodiment of the methods of the disclosure, the tumor sample is from ovarian tissue.

In another embodiment of the methods of the disclosure, the tumor sample is from prostate tissue.

In another embodiment of the methods of the disclosure, the indicator value is at least 1.8 times greater than the reference value for each of the gene transcripts.

Another aspect of the disclosure is a method of determining the odds that an individual ERGO tumor patient will survive to a future date comprising the steps of providing a tumor sample from an individual patient; providing a reference; measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72; 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267; 269, 274-275, 292-295, 298, 307, 311, 316, 321-323, 331, 333, and 335-340; measuring the reference to produce a reference value; and comparing the indicator value to the reference value to determine which of the gene transcripts is over-expressed, whereby the tumor is identified as an ERGO tumor and the individual patient is diagnosed as an ERGO tumor patient if at least 21 of these gene transcripts are over-expressed; plotting the fraction of surviving patients in a population of patients diagnosed as ERGO tumor patients as a function of the time since diagnosis of the ERGO tumor to generate a survival plot; and selecting a future date after the individual patient is diagnosed as an ERGO tumor patient and determining the fraction of surviving patients in the population from the survival plot; whereby the fraction of surviving patients on the survival plot at the future date predicts the odds that an individual tumor patient will survive to the future date.

In one embodiment of the methods of the disclosure the tumor sample is from lung tissue and the population of patients is diagnosed as ERGO lung tumor patients.

In another embodiment of the methods of the disclosure the tumor sample is from thyroid tissue and the population of patients is diagnosed as ERGO thyroid tumor patients.

In another embodiment of the methods of the disclosure the tumor sample is from ovarian tissue and the population of patients is diagnosed as ERGO ovarian tumor patients.

In another embodiment of the methods of the disclosure, the tumor sample is from prostate tissue and the population of patients is diagnosed as ERGO prostate tumor patients.

Another aspect of the disclosure is a method of treating an ERGO tumor in a patient comprising the steps of providing a tumor sample from a patient; providing a reference; measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340; measuring the reference to produce a reference value; and comparing the indicator value to the reference value to determine which of the gene transcripts is over-expressed, whereby the tumor is identified as an ERGO tumor if at least 21 of these gene transcripts are over-expressed; selecting a drug capable of killing or inhibiting division of an ERGO tumor cell expressing at least one protein encoded by at least one gene transcript selected from the group consisting of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193; 196, 198, 200-201, 203, 205, 209, 217, 246-247, 249, 254, 259, 267, 269, 274-275, 292-295, 298, 307, 311, 316, 321-323; 331, 333, and 335-340; and administering a pharmaceutically acceptable amount of the drug to the patient; whereby the ERGO tumor in the patient is treated.

Drugs useful in the methods of the disclosure may be, for example, small organic molecules, peptides, antibodies, antibody fragments or polynucleotides. Such drugs may kill ERGO tumors or inhibit the division of an ERGO tumor cell. Division of an ERGO tumor cell is inhibited when the division of an ERGO tumor cell treated with a drug is decreased relative to an ERGO tumor cell which has not been treated with the compound.

In the methods of the disclosure, drugs may be administered by a variety of routes including, for example, orally, intravenously, intramuscularly, intra-arterially, subcutaneously, intraventricularly, transdermally, rectally, intravaginally, intraperitoneally, topically, or bucally, as a spray, aerosol, power, liquid or ointment. In general, the most appropriate route of administration will depend upon a variety of factors including the nature of the compound (e.g. its stability in the environment of the gastrointestinal tract), the condition of the patient (e.g. whether the patient is able to tolerate oral administration) etc. At present, the intravenous route is most commonly used to deliver therapeutic antibodies and nucleic acids. However, the disclosure encompasses the delivery of the pharmaceutical composition by any appropriate route. Those of ordinary skill in the art will recognize additional routes and techniques for the administration of drugs to a patient.

In the methods of the disclosure, drugs can be provided in a pharmaceutical composition. Such pharmaceutical compositions may comprise a number of different dosage forms such as solids or liquids or combinations of these. Such drugs can also be provided in pharmaceutically effective amounts sufficient to kill ERGO tumors or inhibit the division of an ERGO tumor cell. Pharmaceutically effective amounts of drugs can be readily identified using dose-response curves and other techniques well known the art.

In one embodiment of the methods of the disclosure the drug is an aurora kinase antagonist. A number of aurora kinase inhibitors have been in clinical phase I trial and results were reported in abstract form in 2008 for the SNS-314 aurora kinase inhibitor compound, Abstract #1462; the aurora kinase inhibitor compounds ZM 447439 (American Society of Clinical Oncology 2008 Meeting Abstract #2203), PF-03814735 (American Society of Clinical Oncology 2008 Meeting Abstract #2517), PHA-739358 (American Society of Clinical Oncology 2008 Meeting Abstract #3507), AS703569 (American Society of Clinical Oncology 2008 Meeting Abstract #14130), and MLN8054 (American Society of Clinical Oncology 2008 Meeting Abstract #3577). These drugs produced disease stabilization in some 20-40% of patients with tolerable toxicities and are suitable for use in the methods of the disclosure.

In another embodiment of the methods of the disclosure the aurora kinase antagonist is at least one molecule selected from the group consisting of VX-680, MLN8237, MLN8054, AZD1152, hesperadin, and ZM-447439. VX-680 has the structure shown below and includes the pharmaceutically acceptable derivatives of this compound.

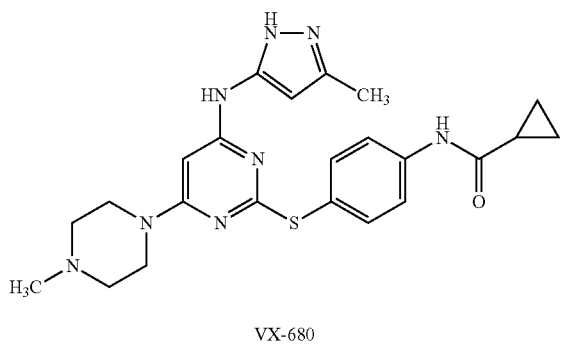

VX-680

VX-680 is an aurora kinase inhibitor manufactured by Merck and Company Inc. (Whitehouse Station, N.J.) which has been shown to block cell proliferation, disrupt bipolar spindle formation, and lead to accumulation of cells with 4N or greater numbers of chromosomal DNA copies and eventual cell death (reviewed in Agnese, V et al., Annals of Oncology 18: vi47-vi52, 2007). In vivo, VX-680 blocks cell-cycle progression and induces apoptosis in a wide range of human tumor types (Pan et al, Oral Oncol. 2008 July; 44(7):639-45). VX-680 causes substantial inhibition of tumor growth in xenograft models, leading to regression of leukemia, colon and pancreatic tumors at well-tolerated doses (Harrington E, et al., Nat. Med. 2004 March; 10(3):262-7). The results of a phase I clinical trial with VX-680 were reported at the ASCO 2008 Annual Meeting, in abstract #3009. In the trial three of 16 patients achieved stable disease at dose levels that were well below those which cause dose-limiting toxicity.

The compound AZD-1152 has the structure shown below and includes the pharmaceutically acceptable derivatives of this compound.

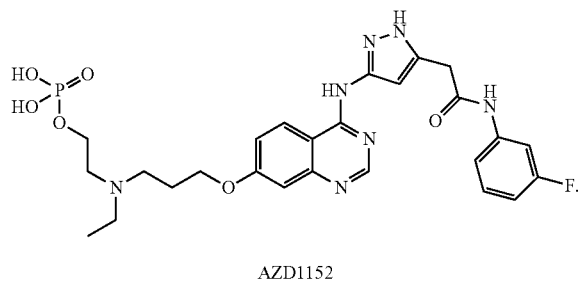 [SMILES: CCN(CCCOc1ccc2c(Nc3cc(CC(=O)Nc4cccc(F)c4)[nH]n3)ncnc2c1)CCOP(=O)(O)O]

AZD1152

AD1152 is an aurora kinase inhibitor manufactured by AstraZeneca PLC (London, GB) that has been in phase I clinical trials. In the trial 5 of 12 patients had significant disease stabilization, with neutropenia as the only significant toxicity (Abstract #3008, American Society of Clinical Oncology (ASCO) 2008 Annual meeting).

The compound hesperadin has the structure shown below and includes pharmaceutically acceptable derivatives of this compound.

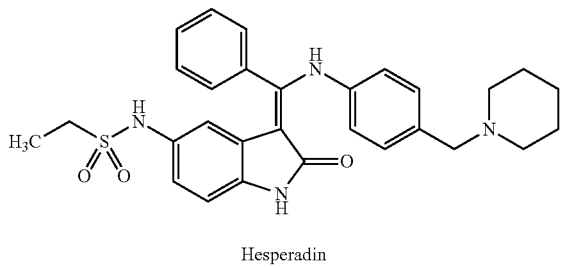 [SMILES: CCS(=O)(=O)Nc1ccc2c(c1)/C(=C(/Nc1ccc(CN3CCCCC3)cc1)c1ccccc1)C(=O)N2]

Hesperadin

The compound ZM-447439 has the structure shown below and includes pharmaceutically acceptable derivatives of this compound.

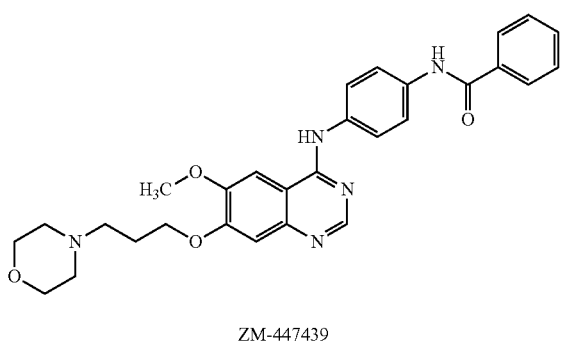 [SMILES: COc1cc2c(Nc3ccc(NC(=O)c4ccccc4)cc3)ncnc2cc1OCCCN1CCOCC1]

ZM-447439

MLN8237 is an aurora A kinase inhibitor manufactured by Millenium Pharmaceuticals, Inc. (Cambridge, Mass.). The results of in vivo studies with MLN8237 were reported at the American Association for Cancer Research (AACR) 2008 Annual Meeting, in abstract #3237. The treatment of cultured human tumor cells with MLN8237 resulted in mitotic spindle abnormalities, mitotic accumulation, inhibition of cell proliferation and apoptosis. MLN8237 is orally bioavailable and has a favorable pharmacokinetic profile. A single oral administration of MLN8237 to nude mice bearing subcutaneous human tumor xenografts resulted in a time dependent accumulation of mitotic cells, consistent with the pharmacological effect being mediated through aurora A inhibition. Repeated oral administration of MLN8237 at well tolerated doses to nude mice bearing subcutaneous human tumor xenografts resulted in, dramatic tumor growth inhibition in all tumor models evaluated. In these models MLN8237 induced mitotic accumulation and apoptosis. MLN8237 did not appreciably inhibit aurora B at efficacious concentrations, as indicated by measuring phosphorylated histone H3 Ser10 staining. MLN8237 is currently in Phase I clinical trials in patients with advanced malignancies.

MLN8054 is a selective small-molecule Aurora A kinase inhibitor that has entered Phase I clinical trials for advanced solid tumors. MLN8054 inhibits recombinant Aurora A kinase activity in vitro and is selective for Aurora A over the family member Aurora B in cultured cells. MLN8054 treatment results in $G_2/M$ accumulation and spindle defects and inhibits proliferation in multiple cultured human tumor cells lines. Growth of human tumor xenografts in nude mice was dramatically inhibited after oral administration of MLN8054 at well tolerated doses. Moreover, the tumor growth inhibition was sustained after discontinuing MLN8054 treatment. In human tumor xenografts, MLN8054 induced mitotic accumulation and apoptosis, phenotypes consistent with inhibition of Aurora A. MLN8054 is a selective inhibitor of Aurora A kinase that robustly inhibits growth of human tumor xenografts and can be used in the treatment of cancers. The compound MLN8054 has the structure shown below and includes pharmaceutically acceptable derivatives of this compound. See Manfredz et al., 104 Proc. Nat. Acad. See USA 4106 (2007).

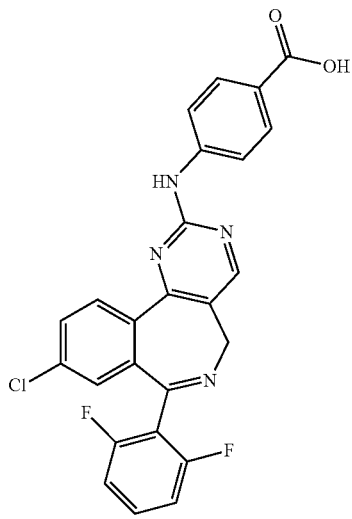 [SMILES: O=C(O)c1ccc(Nc2ncc3c(n2)-c2ccc(Cl)cc2C(c2c(F)cccc2F)=NC3)cc1]

In another embodiment of the methods of the disclosure the drug is a survivin antagonist.

In another embodiment of the methods of the disclosure the survivin antagonist is YM155. The compound YM155 has the structure shown below and includes pharmaceutically acceptable derivatives of this compound. YM155 is targeted therapy against survivin an E2F-responsive genes that is over-expressed in ERGO tumors. YM155 has also been in phase I clinical trials, and has shown clinical activity in solid tumors (American Society of Oncologist 2008 Meeting Abstracts #3536, 5135, and 8538) with tolerable toxicity.

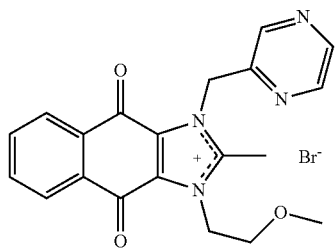

In another embodiment of the methods of the disclosure the drug is a FOXM1 antagonist. FOXM1 itself is a transcription factor that controls at least a dozen other E2F-responsive genes that are over-expressed ERGO tumors, including Aurora B kinase, survivin, and PLK1. A small peptide named (D-Arg)$_9$-p19ARF 26-44 has been developed that blocks FOXM1, and is active both in vitro and in vivo, producing growth inhibition, reduction in levels of survivin, aurora B kinase, and PLK1 as well as inducing apoptosis (Gusarova, et al., J Clin Invest, 117: 99-111, 2007). Other small molecule inhibitors of FOXM1 have been found to be active in vitro and to down-regulate downstream targets of FOXM1 (American Association of Cancer Researchers 2008 Meeting Abstract #2663). These small molecule FOXM1 inhibitors can inducing apoptosis in breast cancer cell lines including the MDA-MB-231 basal-like breast cancer derived cell line (American Association of Cancer Researchers 2008 Meeting Abstract #3280).

In another embodiment of the methods of the disclosure the FOXM1 antagonist is the (D-Arg)$_9$-p19ARF 26-44 peptide. The compound (D-Arg)$_9$-p19ARF 26-44 has the structure of rrrrrrrrrKFVRSRRPRTAS-CALAFVN containing nine D-Arg residues at the amino terminus and pharmaceutically acceptable derivatives of this compound.

In another embodiment of the methods of the disclosure the drug is an E2F antagonist.

In another embodiment of the methods of the disclosure the E2F antagonist is eugenol. Eugenol has the structure below and includes pharmaceutically acceptable derivatives of this compound.

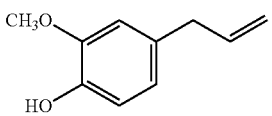

Eugenol is the active agent in Clove oil and has been reported to target E2F1 and kill melanoma cells in vitro (Ghosh, R., et al., J Biol Chem. 2005 Feb. 18; 280(7):5812-9).

In another embodiment of the methods of the disclosure, the drug is a LINC protein complex agonist. Such an agonist can be over-expressed LINC protein complexes.

Another aspect of the disclosure is a method of identifying an individual tumor in a population of tumors as an ERGO tumor comprising the steps of providing a population of tumor samples; providing a reference; measuring gene transcript levels in the tumor samples to produce a transcript value for each of the following gene transcripts having the nucleic acid sequences shown in SEQ ID NO:s 10-340; comparing the transcript value to the reference value for each tumor to identify the gene transcripts over-expressed by each tumor; ranking the tumors in the population with a rank ordering algorithm to order the tumors according to the number of the gene transcripts over-expressed by each tumor; and removing individual tumors from the population that over-express the smallest number of each gene transcript per cell and that have the lowest levels of over-expression of each gene transcript per cell until at least 20% of the individual tumors remaining in the population over-express at least 20% of the gene transcripts; whereby an individual tumor remaining in the population of tumors is identified as an ERGO tumor.

Another aspect of the disclosure is a method of identifying an individual tumor in a population of tumors as an ERGO tumor comprising the steps of providing a population of tumor samples; providing a reference; measuring gene transcript levels in the tumor samples to produce a transcript value for each of the following gene transcripts having the nucleic acid sequence shown in SEQ ID NO:s 10-340; comparing the transcript value to the reference value for each tumor to identify the gene transcripts over-expressed by each tumor; and applying a principle component analysis algorithm in which the analyzed gene set is restricted to each gene transcript having the nucleic acid sequence shown in SEQ ID NO:s 10-340 to identify a tumor cluster over-expressing these E2F-responsive genes; whereby an individual tumor in the population of tumors in the cluster is identified as an ERGO tumor.

Another aspect of the disclosure is a method of selecting treatment for a prostate cancer patient comprising the steps of providing a tumor sample from a prostate cancer patient; providing a reference; measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340; measuring the reference to produce a reference value; and comparing the indicator value to the reference value to determine which of the gene transcripts is over-expressed, whereby the tumor is identified as an ERGO tumor and the prostate cancer patient is diagnosed as an ERGO tumor prostate cancer patient if at least 21 of these gene transcripts are over-expressed; and choosing at least one treatment selected from the group consisting of removal of at least one tumor and adjuvant therapy, if the patient is diagnosed as an ERGO tumor prostate cancer patient; whereby a treatment is selected for the prostate cancer patient.

An important clinical problem for patients diagnosed with prostate cancer is that only about 15% of all such patients will ever die of their disease, but it is difficult to know whether an individual patient is in this unfortunate population of 15% of all patients. Furthermore, many prostate tumors, including those in older patients, grow slowly and without metastasis. Consequently, patients diagnosed with prostate cancer and physicians have to select either of two approaches after a prostate cancer diagnosis. The first approach is known as the "watchful waiting" approach in which tumor growth and related indicators are monitored over time. In this approach no treatment is necessary until a change in disease severity or symptoms occurs. The second approach is to undergo a primary treatment such as conventional and other surgeries, cryosurgery, or radiation therapy to remove or kill the prostate cancer tumor and any metastasis. Additionally, as part of this approach adjuvant therapies such as chemotherapy or hormonal therapy may be necessary to help ensure effective treatment to prevent or postpone the prostate cancer from coming back after the primary treatment. Unfortunately, a number of side effects are potentially associated with the primary treatment and the adjuvant therapies of this second approach including impotence, urinary incontinence, nausea, fatigue, diarrhea, and infertility. Consequently, there is a need for methods of selecting treatment for patients diagnosed with prostate cancer to help insure a given treatment approach is appropriate for an individual patient and the patient's type of prostate tumor.

Importantly, the Applicant has discovered that about 20% of primary prostate cancers from individual patients are ERGO tumors irrespective of the Gleason score conventionally used to functionally classify prostate cancers assigned to these cancers. Furthermore, greater than 80% of all metastases associated with prostate cancer tumors are ERGO tumors. Consequently, the identification of prostate cancer ERGO tumors in patients diagnosed with prostate cancer provides a means for identifying those prostate cancer tumors that are most likely to metastasize or grow profusely and to select appropriate patient treatment.

In one aspect of the method of the disclosure the removal of at least one tumor is performed using at least one therapy selected from the group consisting of using focused energy, cryoablation, and radiation therapy. Examples of focused energy include light such as high intensity laser beams of appropriate wavelengths, and other forms of electromagnetic radiation such as microwaves, as well as X-rays or other types of ionizing radiation. In the methods of the disclosure, tumors are considered to be removed by these or other techniques such as cryoablation (freezing) and radiation therapy if the tumor or cells forming some portion of the tumor are killed, burned, or otherwise destroyed (e.g. by electromagnetic radiation).

In another aspect of the method of the disclosure the adjuvant therapy is at least one therapy selected from the group consisting of chemotherapy, hormone therapy, and immunotherapy. Chemotherapy treatment with drugs such as small molecules that kill cancer cells. Examples of drugs useful in chemo-therapy include, for example, anthracyclines such as doxorubicin, epirubicin and liposomal doxorubicin; taxanes such as docetaxel, paclitaxel, and protein-bound paclitaxel; cyclophosphamide; capecitabine; 5-fluorouracil (5 FU); vinorelbine; emcitabine; mitoxantrone; estramustine; etoposide (VP-16); vinblastine; and carboplatin. These drugs, and others disclosed herein, may be used in the manufacture of medicaments for the treatment of ERGO tumors identified according to the disclosed methods. Hormone therapy is also called androgen deprivation therapy (ADT) or androgen suppression therapy. The goal of hormone therapy in prostate cancer patients is to reduce levels of the male hormones, called androgens, in the body. The main androgens are testosterone and dihydrotestosterone (DHT). Androgens, produced mainly in the testicles, stimulate prostate cancer cells to grow. Lowering androgen levels often makes prostate cancers shrink or grow more slowly. Drugs useful in such hormone therapy include, for example, luteinizing hormone-releasing hormone (LHRH) analogs including leuprolide, goserelin and triptorelin; luteinizing hormone-releasing hormone (LHRH) antagonists such as abarefix; anti-androgens such as flutamide, bicalutamide, nilutamide; and ketoconazole. Hormone therapy may also require orchiectomy (surgical castration) to control androgen production. Immunotherapy treatments include treatments that stimulate a patient's own immune system to kill prostate tumors cells. The sipuleucel-T (PROVENGE™) treatment system (Dendreon Corp., Seattle, Wash.) is one example of an immunotherapy. In this system immune system white blood cells are removed from a prostate cancer patient, antigen presenting cells (APCs) are then isolated from these white blood cells by apheresis, and the patient's isolated APCs are co-cultured with a recombinant fusion protein antigen comprising prostatic acid phosphatase (PAP). The activated, antigen-loaded APCs at this point are designated as "sipuleucel-T" and injected into the prostate cancer patient. Once administered to the patient these APCs present the recombinant PAP antigen to T-cells and help stimulate the patient's own immune system to produce a killer T-cell response against his prostate cancer tumor cells. Those of ordinary skill in the art will recognize other chemotherapies, hormone therapies, and immunotherapies.

In another embodiment the methods of the disclosure further comprise measuring an indicator of gene transcript levels in at least one selected from the group consisting of the tumor sample and the reference to produce a housekeeping value for at least one gene transcript selected from the group consisting of the nucleic acid sequences shown in SEQ ID NO:s 162, 341-365 and 366; and normalizing at least one selected from the group consisting of the indicator value and the reference value to the housekeeping value. This embodiment is particularly useful in relation to methods for the identification of ERGO tumors in prostate tissue and methods for the selection of treatment for a prostate cancer patient.

Another embodiment of the disclosure is the use of an aurora kinase antagonist in the manufacture of a medicament for the treatment of an ERGO tumor identified according to the methods of the disclosure.

Another embodiment of the disclosure is the use of VX-680 in the manufacture of a medicament for the treatment of an ERGO tumor identified according to the methods of the disclosure.

Another embodiment of the disclosure is the use of MLN8237 in the manufacture of a medicament for the treatment of an ERGO tumor identified according to the methods of the disclosure.

Another embodiment of the disclosure is the use of MLN8054 in the manufacture of a medicament for the treatment of an ERGO tumor identified according to the methods of the disclosure.

Another embodiment of the disclosure is the use of AZD1152 in the manufacture of a medicament for the treatment of an ERGO tumor identified according to the methods of the disclosure.

Another embodiment of the disclosure is the use of hesperadin in the manufacture of a medicament for the treatment of an ERGO tumor identified according to the methods of the disclosure.

Another embodiment of the disclosure is the use of ZM-447439 in the manufacture of a medicament for the treatment of an ERGO tumor identified according to the methods of the disclosure.

Another embodiment of the disclosure is the use of a survivin antagonist in the manufacture of a medicament for the treatment of an ERGO tumor identified according to the methods of the disclosure.

Another embodiment of the disclosure is the use of YM155 in the manufacture of a medicament for the treatment of an ERGO tumor identified according to the methods of the disclosure.

Another embodiment of the disclosure is the use of a FOXM1 antagonist in the manufacture of a medicament for the treatment of an ERGO tumor identified according to the methods of the disclosure.

Another embodiment of the disclosure is the use of the (D-Arg)$_9$-p19ARF 26-44 peptide in the manufacture of a medicament for the treatment of an ERGO tumor identified according to the methods of the disclosure.

Another embodiment of the disclosure is the use of an E2F antagonist in the manufacture of a medicament for the treatment of an ERGO tumor identified according to the methods of the disclosure.

Another embodiment of the disclosure is the use of eugenol in the manufacture of a medicament for the treatment of an ERGO tumor identified according to the methods of the disclosure.

Another embodiment of the disclosure is the use of a LINC protein complex agonist in the manufacture of a medicament for the treatment of an ERGO tumor identified according to the methods of the disclosure.

Another embodiment of the disclosure is an apparatus comprising a specifically programmed computer in communication with a nucleic acid array analyzer and an output display, wherein the specifically programmed computer is adapted to compare indicator values to reference values and to determine Which gene transcripts are over-expressed in a tumor sample; a nucleic acid array comprising at least 21 of the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340 adapted for hybridization to nucleic acids in a tumor sample; a memory containing an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340 produced by hybridization of the nucleic acid array to the nucleic acids in the tumor sample, and containing reference values for the gene transcripts; and an output display which shows the tumor sample is an ERGO tumor when the specifically programmed computer determines at least 21 of the gene transcripts are over-expressed in a tumor sample.

In another embodiment of the methods of the disclosure, the tumor sample is from liver tissue.

In another embodiment of the methods of the disclosure, the tumor sample is from bladder tissue.

In another embodiment of the methods of the disclosure, the tumor sample is from liver tissue and the population of patients is diagnosed as ERGO hepatoma tumor patients.

In another embodiment of the methods of the disclosure, the tumor sample is from bladder tissue and the population of patients is diagnosed as ERGO bladder tumor patients.

In another embodiment of the methods of the disclosure, the ERGO tumor is from a tissue selected from the group consisting of lung tissue, thyroid tissue, ovarian tissue, prostate tissue, liver tissue and bladder tissue.

In another embodiment of the methods of the disclosure, the tumor sample is from a tissue selected from the group consisting of lung tissue, thyroid tissue, ovarian tissue, prostate tissue, liver tissue and bladder tissue.

It is understood that modifications which do not substantially affect the activity of the various embodiments of this disclosure are also included within the definition of the disclosure provided herein. Accordingly, the following examples are intended to illustrate but not limit the present disclosure.

EXAMPLES

Example 1

Identification of Human Breast Cancer E2F Responsive Gene Over-Expressing (ERGO) Tumors Breast Cancer Microarray Sets A gene expression microarray set from 117 different patient breast cancer samples described by Van't Veer et al. was analyzed. This microarray set was selected for analysis because it included 18 tumors obtained from patients with known BRCA1 mutations. The breast cancer microarray set described by Dai et al. was used to confirm the analytical results obtained using the Van't Veer microarray set. The gene expression microarray sets of Van't Veer and Dai both contained 57 samples that were identical and were excluded from the analyses of the Dai microarray set (also referred to herein as the "purged Dai microarray set") in the present study.

Weighted Rank Ordering Methods and Criteria for Identification of ERGO Tumors

First, a reference signal intensity value was obtained by averaging the signal intensity values from all sample probed gene spots on the Van't Veer microarray set to be analyzed. The reference signal intensity value was obtained by averaging the signal intensity values from all sample probed gene spots on the Van't Veer microarray set to be analyzed.

Then "over-expressed," "under-expressed," and non-over-expressed genes were identified. Gene "over-expression" was determined to occur when the signal intensity corresponding to a given gene transcript in the microarray set was 1.8 fold greater than the reference signal intensity value discussed above. Gene "under-expression" was determined to occur when the signal intensity corresponding to a given gene transcript in the microarray was 1.8 fold less than a reference signal intensity value. Gene "non-over-expression" was determined to occur when a gene was neither "over-expressed" nor "under-expressed."

Next, weighted rank ordering methods were performed using EXCEL™ software (Microsoft Corp., Redmond, Wash.) to rank the over-expressed genes by their frequency of expression among the tumors. In these rank ordering analyses the most highly over-expressed genes were placed closest to the origin and the contribution of each tumor to the ranking was weighted by its proximity to the origin of the tumor axis.

These weighted rank ordering methods were then used to rank the tumors by the number of the 325 specific E2F-responsive genes, shown in Table 1 (shown below), over-expressed per tumor ("1" or other value indicates gene functions).

TABLE 1

| gene-name | microaray name | transcription, regulation | DNA replication | DNA repair | check-point | mitosis | apoptosis | other |
|---|---|---|---|---|---|---|---|---|
| BCL2L11* | BCL2L11 | | | | | | | |
| FOXO1A* | FOXO1A | | | | | | | |
| CCNE2* | CCNE2 | | 1 | | | | | |
| CDKN2C* | CDKN2C | | 1 | | 1 | | | |
| CCNE1* | CCNE1 | | 1 | | | | | |
| MYC* | MYC | | | | | | | |
| FGFR3* | FGFR3 | | | | | | | 1 |
| MAP3K5* | MAP3K5 | | | | | | 1 | |
| BMP2* | BMP2 | 1 | | | | | | 2 |
| MYB* | MYB | 1 | | | | | | |
| LHX2** | LHX2 | | | | | | | |
| GCH1* | GCH1 | | | | | | | 1 |
| MAPK9* | MAPK9 | | | | | | | 1 |
| MAPK8* | MAPK8 | | | | | | | 1 |
| MAPK3* | MAPK3 | | | | 1 | | | 1 |
| MAPK1* | MAPK1 | | | | 1 | | 1 | 1 |
| MAPK4* | MAPK4 | | | | | | | 1 |
| MAP2K1* | MAP2K1 | | | | | | | 1 |
| MAP2K2* | MAP2K2 | | | | | | | 1 |
| FOXO3A* | FOXO3A | 1 | | | 1 | 1 | | |
| GADD45B* | GADD45B | | | | | 1 | | |
| MCL1* | MCL1 | | | | | 1 | | |
| BCL2** | BCL2 | | | | | 1 | | |
| CCND3* | CCND3 | | | | 1 | | | |
| CHES1** | CHES1 | 1 | | | 1 | 1 | | |
| MKI67** | MKI67 | | | | | | | 1 |
| CDKN1C** | CDKN1C | | | | 1 | | | |
| KIFC1** | KNSL2 | | | | | | | |
| PRG4** | PRG4 | | | | | | | 1 |
| PMS2** | PMS2 | | | | | | | |
| PLK2** | SNK | | | | | 1 | | |
| HRK* | HRK | | | | | 1 | | |
| CASP8** | CASP8 | | | | | | | |
| TYMS* | TYMS | | 1 | 1 | | | | |
| TK1* | TK1 | | 1 | | | | | |
| DUT** | DUT | | 1 | | | | | |
| RRM1* | RRM1 | | 1 | | | | | |
| RRM2* | RRM2 | | 1 | | | | | |
| CDK2* | CDK2 | | 1 | | | 1 | | |
| MCM3* | MCM3 | | 1 | | | | | |
| MCM7* | MCM7 | 1 | 1 | | | | | |
| PCNA* | PCNA | | 1 | 1 | | | | |
| RFC3* | RFC3 | | 1 | | | | | |
| PRIM1** | PRIM1 | | 1 | | | | | |
| TOP2A* | TOP2A | | 1 | 1 | | 1 | | |
| LIG1** | LIG1 | | 1 | 1 | | | | |
| FEN1** | FEN1 | | 1 | | | | | |
| RAD51** | RAD51 | | | 1 | | | | |
| CDC20** | CDC20 | | | | | 1 | | |
| CDC2* | CDC2 | | | | 1 | 1 | 1 | |
| CCNA2* | CCNA2 | 1 | | | | 1 | | |
| CCNB1* | CCNB1 | | | | | 1 | | |
| CCNB2** | CCNB2 | | | | | 1 | | |
| SMC2** | SMC2L1 | | | | | 1 | | |
| STMN1* | STMN1 | | | | | 1 | | 1 |
| NDC80** | HEC | | | | | 1 | | |
| BUB1** | BUB1 | | | | | 1 | | |
| KPNA2* | KPNA2 | | | | | | | |

TABLE 1-continued

| gene-name | microaray name | transcription, regulation | DNA replication | DNA repair | check-point | mitosis | apoptosis | other |
|---|---|---|---|---|---|---|---|---|
| HMGB2** | HMG2 | 1 | 1 | 1 | | | | |
| EZH2* | EZH2 | 1 | | | | | | |
| AURKB* | STK12 | | | | | 1 | | |
| PTTG1** | PTTG1 | 1 | | 1 | | 1 | | |
| SLBP* | SLBP | | 1 | | | | | |
| RB1* | RB1 | 1 | | | 1 | 1 | | |
| ANXA8* | ANXA8 | | | | | | | 1 |
| DCK** | DCK | | | | | | | 1 |
| CDC25A* | CDC25A | | | | 1 | 1 | | |
| EPS8** | EPS8 | | | | | | | 1 |
| FST* | FST | 1 | | | | | | 3 |
| TMPO* | TMPO | 1 | | | | | | |
| RAD51AP1** | PIR51 | | | 1 | | | | |
| ASF1B** | FLJ10604 | | | | | | | 3 |
| CDCA4* | FLJ20764 | | | | | | | |
| RFC4** | RFC4 | | 1 | 1 | | | | |
| BLM** | BLM | | 1 | 1 | | | | |
| VRK1** | VRK1 | | | | | | | 1 |
| BARD1** | BARD1 | | 1 | 1 | | | | |
| BTG3** | BTG3 | | | | | | | 1 |
| CHAF1A** | CHAF1A | 1 | 1 | 1 | | | | 3 |
| NPAT* | NPAT | | | | | | | 3 |
| HUNK* | HUNK | | | | | | | 1 |
| DEK** | DEK | 1 | | | | | | 1 |
| EED** | EED | | | | | | | 3 |
| MCM4** | MCM4 | 1 | 1 | | | | | |
| MELK** | KIAA0175 | | | | | | | 1 |
| TCF19** | TCF19 | 1 | | | | | | |
| FANCL** | FLJ10335 | | | 1 | | | | |
| PBX3** | PBX3 | 1 | | | | | | 1 |
| EGR1* | EGR1 | 1 | | | | | | |
| CDCA7L** | DKFZp762L0311 | 1 | | | | | | |
| SKP2* | SKP2 | | | | | | | 1 |
| CTGF* | CTGF | | | | | | | 2 |
| CITED2** | CITED2 | | | | | | | |
| SERPINE1* | SERPINE1 | | | | | | | 2 |
| CCND1* | CCND1 | | | | 1 | | | |
| UHRF1* | ICBP90 | | | 1 | | | | |
| MCM5* | MCM5 | 1 | 1 | | | | | |
| HMGB3** | HMG4 | 1 | | | | | | |
| MCM6* | MCM6 | 1 | 1 | | | | | |
| CDC45L** | CDC45L | | 1 | | 1 | | | |
| CDC6* | CDC6 | | 1 | | 1 | 1 | | |
| ORC6L* | ORC6L | | 1 | | | 1 | | |
| CKS2** | CKS2 | | | | | 1 | | |
| GMNN* | GEM | | 1 | | 1 | | | |
| PRIM2** | PRIM2A | | 1 | | | | | |
| CENPK** | FKSG14 | | | | | 1 | | |
| NUP155** | NUP155 | | | | | | | 1 |
| FIGNL1** | FIGNL1 | | | | | | | 1 |
| MAD2L1* | MAD2L1 | | | | 1 | 1 | | |
| CCNF** | CCNF | | | | | 1 | | |
| DNMT1* | DNMT1 | 1 | | | | | | |
| RPA1** | RPA1 | | 1 | 1 | | | | |
| PRC1** | PRC1 | | | | | 1 | | |
| RBL1** | RBL1 | 1 | | | | | | |
| BRCA1* | BRCA1 | 1 | 1 | 1 | 1 | | | |
| H2AFZ** | H2AFZ | | | | | | | 3 |
| DTYMK** | DTYMK | | | | | | | 1 |
| PLK1** | PLK | | | | | 1 | | |
| POLA2* | POLA2 | | 1 | | | | | |
| PBK** | SPK | | | | | 1 | | |
| CASP7* | CASP7 | | | | | | 1 | |
| MCM2* | MCM2 | 1 | 1 | | | | | |
| RPA3** | RPA3 | | 1 | 1 | | | | |
| GJA7** | GJA7 | | | | | | | 1 |
| USP1** | USP1 | | | 1 | | | | |
| DNA2L** | DNA2L | | 1 | | | | | |
| CITED1** | CITED1 | 1 | | | | | | |
| NASP** | NASP | | 1 | | | | | 1 |
| RFC5** | RFC5 | | 1 | 1 | | | | |
| SMARCA5** | SMARCA5 | 1 | | | | | | 1 |
| SHCBP1** | FLJ22009 | | | | | | | 1 |
| SSX2IP** | KIAA0923 | | | | | | | |
| MFAP1** | MFAP1 | | | | | | | 1 |
| ROD1** | ROD1 | | | | | | | 1 |
| BMPR1A* | BMPR1A | | | | | | | 2 |

TABLE 1-continued

| gene-name | microarray name | transcription, regulation | DNA replication | DNA repair | check-point | mitosis | apoptosis | other |
|---|---|---|---|---|---|---|---|---|
| E2F3** | E2F3 | 1 | | | | | | |
| UNG* | UNG | | | 1 | | | | |
| ENO3** | ENO3 | | | | | | | 1 |
| MSH2** | MSH2 | | | 1 | | | 1 | |
| PLK4** | STK18 | | | | | | | 1 |
| ACTA2** | ACTA2 | | | | | | | 1 |
| TIMELESS** | TIMELESS | 1 | | | | | | |
| BOK* | BOK | | | | | | 1 | |
| KBTBD10** | SARCOSIN | | | | | | | 1 |
| BUB1B** | BUB1B | | | | 1 | 1 | | |
| NUP107** | NUP107 | | | | | | | 1 |
| KIF2C** | KNSL6 | | | | | 1 | | |
| LMNB1* | LMNB1 | | | | | | | 1 |
| RPA2** | RPA2 | | 1 | | | | | |
| CHEK2** | CDS1 | | | | | | | 1 |
| COL11A1** | COL11A1 | | | | | | | 2 |
| TGFB3** | TGFB3 | | | | | | | 2 |
| CALR** | CALR | 1 | | | | | 1 | 1 |
| TTK* | TTK | | | | 1 | 1 | | |
| E2F2* | E2F2 | 1 | | | | | | |
| CKS1B** | CKS1 | | | | | | | 1 |
| RFC2** | RFC2 | | 1 | | | | | |
| UMPS** | UMPS | | | | | | | 1 |
| DBF4* | ASK | | 1 | | | | | |
| CHEK1** | CHEK1 | | | 1 | 1 | 1 | | |
| BUB3** | BUB3 | | | | | 1 | | |
| CENPE** | CENPE | | | | | 1 | | |
| CSTF1** | CSTF1 | | | | | | | 1 |
| RAD54L* | RAD54L | | | 1 | | | | |
| POLD1** | POLD1 | | | 1 | | | | |
| MLH1** | MLH1 | | | 1 | | | | |
| CENPA** | CENPA | | | | | 1 | | |
| SMC4** | SMC4L1 | | | | | 1 | | |
| HMGB1** | HMG1 | 1 | | 1 | | | 1 | |
| HIST1H3D** | H3FB | | | | | | | 4 |
| H2AFX** | H2AFX | | | 1 | | | | 1 |
| CBX5** | CBX5 | | | | | | | 3 |
| HIST1H2AC** | H2AFL | | | | | | | 4 |
| KIF22** | KNSL4 | | | | | 1 | | |
| NEK2* | NEK2 | | | | | 1 | | |
| KIF4A** | KIF4A | | | | | 1 | | |
| HMMR** | HMMR | | | | | | | 1 |
| MTHFD1** | MTHFD1 | | | | | | | 1 |
| GINS1* | KIAA0186 | | 1 | | | | | |
| SFPQ** | SFPQ | 1 | | 1 | | | | |
| HSP90B1* | TRA1 | 1 | | 1 | | | | |
| MAP3K7** | MAP3K7 | | | | | | | 2 |
| PLSCR1** | PLSCR1 | | | | | | | 1 |
| ANLN** | ANLN | | | | | 1 | | |
| SFRS2** | SFRS2 | 1 | | | | | | |
| ID3** | ID3 | 1 | | | | | | |
| TEAD4* | TEAD4 | 1 | | | | | | |
| SRPR** | SRPR | | | | | | | 1 |
| UBE2T** | HSPC150 | | | | | | | 1 |
| INCENP** | INCENP | | | | | 1 | | |
| CDC25B** | CDC25B | | | | | 1 | | |
| AURKA* | STK15 | | | | | 1 | | |
| DHFR* | DHFR | | | | | | | 1 |
| CDKN3** | CDKN3 | | 1 | | | | | |
| CDC7** | CDC7L1 | | 1 | | | | | |
| RACGAP1** | ID-GAP | | | | | 1 | | |
| CSRP2** | CSRP2 | | | | | | | 1 |
| MAF** | MAF | 1 | | | | | | |
| CBX3** | CBX3 | 1 | | | | | | 3 |
| CHAF1B* | CHAF1B | 1 | 1 | 1 | | | | 3 |
| ADAMTS1** | ADAMTS1 | | | | | | | 1 |
| TCOF1** | TCOF1 | | | | | | | 1 |
| LSM5** | LSM5 | | | | | | | 1 |
| HNRPC** | HNRPC | | | | | | | 1 |
| APAF1* | APAF1 | | | | | | 1 | |
| ASH2L* | ASH2L | 1 | | | | | | |
| BCL3* | BCL3 | 1 | | | | | | 1 |
| CASP3* | CASP3 | | | | | | 1 | |
| CAV1* | CAV1 | | | | | | | 1 |
| CD58* | CD58 | | | | | | | 1 |
| DMRT1* | DMRT1 | 1 | | | | | | |
| DYRK1A* | DYRK1A | | | | | | | 1 |

TABLE 1-continued

| gene-name | microaray name | transcription, regulation | DNA replication | DNA repair | check-point | mitosis | apoptosis | other |
|---|---|---|---|---|---|---|---|---|
| LIMA1* | EPLIN | | | | | | | 1 |
| FGFR2* | FGFR2 | | | | | | | 1 |
| HEY1* | HEY1 | 1 | | | | | | |
| INHBA* | INHBA | 1 | | | | | 1 | 2 |
| TBC1D2B* | KIAA1055 | | | | | | | 1 |
| OSMR* | OSMR | | | | | | | 1 |
| FURIN* | PACE | | | | | | | 1 |
| PRKAR2B* | PRKAR2B | | | | | | | 1 |
| PTPNS1* | PTPNS1 | | | | | | | 1 |
| RANBP9* | RANBP9 | | | | | | | 1 |
| SOX9* | SOX9 | | | | | | | 1 |
| SPHK1* | SPHK1 | | | | | | | 1 |
| TACC1* | TACC1 | | | | | | | 1 |
| TGFA* | TGFA | | | | | | | 1 |
| TGFB2* | TGFB2 | | | | | | | 2 |
| YY1* | YY1 | 1 | | | | | | |
| SNAPC1** | SNAPC1 | 1 | | | | | | |
| CCNG2** | CCNG2 | | | | 1 | 1 | | |
| HOXA7** | HOXA7 | 1 | | | | | | |
| HOXA9** | HOXA9 | 1 | | | | | 1 | |
| PITX1** | PITX1 | 1 | | | | | | 1 |
| SMARCA2** | SMARCA2 | 1 | | | | | | |
| BACH1** | BACH1 | 1 | | | | | | |
| CBFB** | CBFB | 1 | | | | | | |
| BIRC5* | BIRC5 | | | | 1 | 1 | 1 | |
| CDC25C** | CDC25C | | | | | 1 | | |
| ORC3L** | ORC3L | | 1 | | | | | |
| TOPBP1** | TOPBP1 | | | 1 | | | | |
| MRE11A** | MRE11A | | | 1 | | 1 | | |
| ATM* | ATM | | | 1 | 1 | 1 | | |
| XRCC4** | XRCC4 | | | 1 | | | | |
| RECQL** | RECQL | | | 1 | | | | |
| CENPF** | CENPF | | | | | 1 | | |
| CENPH** | PMF1 | | | | | 1 | | |
| NOLC1** | NOLC1 | | | | | 1 | | |
| MPHOSPH1** | MPHOSPH1 | | | | | 1 | | |
| BMI1* | BMI1 | | | | | | | 3 |
| HIST1H2AE** | H2AFA | | | | | | | 3 |
| HIST1H2AD** | H2AFG | | | | | | | 4 |
| HIST1H2BN** | H2BFD | | | | | | | 4 |
| HIST1H2BE** | H2BFH | | | | | | | 4 |
| HIST1H2BO** | H2BFN | | | | | | | 4 |
| HIST1H2BJ** | H2BFR | | | | | | | 4 |
| HIST1H3B** | H3FL | | | | | | | 4 |
| HIST2H4** | H4F2 | | | | | | | 4 |
| HIST1H2BF** | H2BFG | | | | | | | 4 |
| HIST1H3E** | H3FD | | | | | | | 4 |
| KIF20A** | RAB6KIFL | | | | | 1 | | 3 |
| FGFR1OP** | FOP | | | | | | | 1 |
| DHPS** | DHPS | | | | | | | 1 |
| PEX19** | PXF | | | | | | | 1 |
| PPM1D* | PPM1D | | | | | 1 | | |
| E2F1* | E2F1 | 1 | | | | | 1 | |
| PARP1** | ADPRT | 1 | | | | | | |
| ORC2L** | ORC2L | 1 | 1 | | | | | |
| VEGFA** | VEGF | | | | | | 1 | 1 |
| APOE** | APOE | | | | | | | 3 |
| PRPS1** | PRPS1 | | | | | | | 1 |
| TGFB1I1* | TGFB1I1 | 1 | | | | | | |
| CXCR7* | RDC1 | | | | | | | 1 |
| PDGFRA** | PDGFRA | | | | | | | 1 |
| SLPI* | SLPI | | | | | | | 1 |
| FAS** | TNFRSF6 | | | | | | 1 | |
| CPT1A* | CPT1A | | | | | | | 1 |
| PDCD4* | PDCD4 | 1 | | | | | 1 | |
| TANK** | TANK | | | | | | | 1 |
| APBB2* | APBB2 | 1 | | | | | 1 | 1 |
| GADD45A** | GADD45A | | | 1 | | | 1 | 1 |
| ACOX1** | ACOX1 | | | | | | | 1 |
| CSDA* | CSDA | 1 | | | | 1 | | |
| UBE2C** | UBCH10 | | | | | 1 | | |
| TPX2** | C20orf1 | | | | | 1 | | |
| NUSAP1** | BM037 | | | | | 1 | | |
| SULT2A1* | SULT2A1 | | | | | | | 1 |
| INMT* | INMT | | | | | | | 1 |
| ARHGAP4* | ARHGAP4 | | | | | | | 1 |
| RAD52* | RAD52 | | | 1 | | | | |

TABLE 1-continued

| gene-name | microarray name | transcription, regulation | DNA replication | DNA repair | check-point | mitosis | apoptosis | other |
|---|---|---|---|---|---|---|---|---|
| TNFSF9* | TNFSF9 | | | | | | 1 | |
| BAD* | BAD | | | | | | 1 | |
| BAK1* | BAK1 | | | | | | 1 | |
| BID* | BID | | | | | | 1 | |
| CFLAR* | CFLAR | | | | | | 1 | |
| MAP3K14* | MAP3K14 | | | | | | | 1 |
| PAWR* | PAWR | 1 | | | | | 1 | |
| FGF2• | FGF2 | | | | | | 1 | 1 |
| MMP16* | MMP16 | | | | | | | 1 |
| TP53BP2* | TP53BP2 | | | | | | 1 | 1 |
| VEGFB* | VEGFB | | | | | | | 1 |
| IFNA2* | IFNA2 | | | | | | 1 | |
| SRGAP2* | KIAA0456 | | | | | | | 1 |
| DIP* | KIAA0767 | | | | | | 1 | |
| SERPINF2* | SERPINF2 | | | | | | | 1 |
| CCNU* | UNG2 | | | | | | | 1 |
| TP73* | TP73 | 1 | | 1 | 1 | | 1 | |
| POLE2* | POLE2 | | 1 | | | | | |
| RAD51C** | RAD51C | | | 1 | | | | |
| PMS2L1** | PMS2L1 | | | 1 | | | | |
| DDB2* | DDB2 | | | 1 | | | | |
| NFKB2** | NFKB2 | 1 | | | | | | 1 |
| KIF11** | KNSL1 | | | | | 1 | | |
| FOXM1* | FOXM1 | 1 | | | | | | |
| PLAU* | PLAU | | | | | | | 2 |
| BBC3* | BBC3 | | | | | | 1 | |
| PMAIP1* | PMAIP1 | | | | | | 1 | |
| GAB2* | GAB2 | | | | | | 1 | 1 |
| SIVA1* | SIVA | | | | | | 1 | |
| PPP1R13B* | PPP1R13B | | | | | | 1 | |
| AXIN2* | AXIN2 | | | | | | | 1 |
| DIABLO* | SMAC | | | | | | 1 | |
| AR* | AR | 1 | | | | | | 1 |
| NRP1* | NRP1 | | | | | | | 1 |
| ECT2* | ECT2 | | | | | | | 1 |
| ISYNA1* | ISYNA1 | | | | | | | 1 |

Tumors with the highest number of over-expressed genes per tumor were placed closest to the origin. The contribution of each gene to the ranking was positively weighted by its proximity to the origin of the gene axis.

Individual tumors with the lowest number of over-expressed genes per tumor, and individual genes with the lowest over-expression frequency among the tumors were then iteratively stripped out of the dataset, with recalculation of rankings, until predetermined stopping conditions were met. The stopping conditions were that at least 20% of the tumors remaining in the dataset over-express at least 20% of the remaining E2F-responsive genes. Tumors that remained in the data set after satisfaction of the stopping conditions were identified as ERGO tumors.

Identification of the ERGO Tumor Subset of Human Breast Cancers by Weighted Rank Ordering The Van't Veer breast cancer microarray set was weighted rank ordered by the number of over-expressed E2F-responsive genes per tumor and by the number of tumors over-expressing E2F-responsive genes using the stopping criteria described above. These analyses resulted in identification of a group containing only 31 of the 117 tumors in the set analyzed and the identification of a set of 74 different E2F-responsive genes that met the stopping condition criteria that at least 20% of the tumors remaining in the set over-express at least 20% of the remaining E2F-responsive genes. These 31 tumors were identified as ERGO tumors because they remained in the data set after the criteria of the stopping conditions described above were satisfied.

The set of 74 different E2F-responsive genes identified are listed in Table 2 shown below.

TABLE 2

| gene/protein name | P value, ERGO vs. non-ERGO | number of over-expressing tumors among total of 31 tumors |
|---|---|---|
| STK12 | 5.00E−16 | 23 |
| KNSL6 | 5.00E−16 | 21 |
| CENPA | 5.00E−16 | 19 |
| RAD54L | 3.25E−12 | 18 |
| FOXM1 | 3.25E−12 | 17 |
| RAB6KIFL | 0.00E+00 | 19 |
| ANLN | 5.21E−13 | 19 |
| CDC20 | 0.00E+00 | 21 |
| BTG3 | 1.10E−08 | 17 |
| BUB1 | 1.11E−16 | 16 |
| TYMS | 3.25E−12 | 19 |
| CCNB2 | 0.00E+00 | 16 |
| STMN1 | 1.06E−13 | 17 |
| C20orf1 | 0.00E+00 | 16 |
| CDC2 | 3.25E−12 | 16 |
| TTK | 1.41E−12 | 16 |
| BLM | 3.31E−12 | 14 |
| HRK | 1.49E−06 | 15 |
| PLSCR1 | 5.89E−07 | 15 |
| EZH2 | 1.68E−12 | 16 |
| HEC | 3.26E−12 | 12 |
| BIRC5 | 2.98E−13 | 13 |
| CCNA2 | 3.04E−09 | 15 |
| CDC25A | 1.11E−16 | 14 |
| MCM5 | 4.69E−11 | 15 |
| MCM7 | 3.04E−11 | 15 |
| PTTG1 | 2.10E−13 | 14 |
| DEK | 5.94E−06 | 15 |
| KNSL2 | 1.22E−15 | 13 |
| CDC45L | 0.00E+00 | 15 |

TABLE 2-continued

| gene/protein name | P value, ERGO vs. non-ERGO | number of over-expressing tumors among total of 31 tumors |
|---|---|---|
| UBCH10 | 1.44E−15 | 14 |
| KIAA0175 | 3.68E−12 | 12 |
| TEAD4 | 2.83E−07 | 13 |
| CCNE1 | 2.59E−07 | 12 |
| PRC1 | 3.25E−12 | 12 |
| CHAF1B | 2.03E−06 | 12 |
| TK1 | 6.93E−08 | 12 |
| SMC4L1 | 3.15E−08 | 13 |
| RFC4 | 8.28E−11 | 10 |
| MCM6 | 1.32E−11 | 12 |
| CSRP2 | 3.07E−04 | 14 |
| TGFA | 2.10E−05 | 14 |
| ORC6L | 3.27E−12 | 11 |
| PRIM2A | 1.30E−09 | 10 |
| KNSL1 | 6.25E−09 | 10 |
| USP1 | 3.14E−06 | 13 |
| MCM2 | 7.86E−09 | 11 |
| MAD2L1 | 3.69E−12 | 14 |
| TP53BP2 | 3.84E−07 | 9 |
| CKS1 | 1.44E−09 | 9 |
| NUP155 | 4.73E−09 | 8 |
| NEK2 | 4.03E−13 | 10 |
| STK15 | 2.34E−11 | 9 |
| NASP | 2.83E−08 | 10 |
| DNA2L | 2.22E−08 | 10 |
| LMNB1 | 4.43E−09 | 13 |
| NOLC1 | 1.03E−05 | 8 |
| CKS2 | 3.29E−08 | 8 |
| CSDA | 3.35E−05 | 8 |
| SOX9 | 6.86E−04 | 11 |
| MYC | 3.29E−05 | 9 |
| KPNA2 | 4.49E−11 | 8 |
| CCNE2 | 5.50E−08 | 11 |
| FLJ22009 | 2.14E−09 | 8 |
| KIF4A | 8.99E−12 | 7 |
| CCNB1 | 6.79E−12 | 9 |
| RRM2 | 2.33E−11 | 8 |
| CDC7L1 | 4.32E−08 | 6 |
| CDC25B | 2.86E−08 | 10 |
| HMG4 | 6.95E−10 | 8 |
| MAP3K14 | 8.30E−03 | 8 |
| HMMR | 5.27E−07 | 7 |
| VEGF | 3.75E−05 | 8 |
| ANXA8 | 3.51E−05 | 9 |

This group of 74 different E2F-responsive genes was enriched for genes that are involved in the $G_1/S$ cell cycle transition stage and DNA replication (e.g. TYMS, TTK, ORC6L, MCM2, CCNE2MCM5, MCM6, MCM7, RFC4) and that are involved in the $G_2/M$ cell cycle transition and mitosis (e.g. AURKB, KNSL6, CENPA, KIF20A, BUB1, CCNB2, STMN1, TPX2, BIRC5, KNSL2). Differences between the frequencies of gene over-expression in ERGO and non-ERGO tumors were highly statistically significant for all genes in the ERGO subset and the P-values ranged from $1\times10^{-5}$ to $<1\times10^{-16}$. However, these statistical comparisons are purely confirmatory in nature since the ERGO tumor subset was established by rank ordering.

In order to compare the ERGO tumors identified with other non-ERGO breast cancer tumor subsets, the non-ERGO tumors were subdivided into:
a) non-ERGO tumors over-expressing the HER2 receptor;
b) non-ERGO tumors over-expressing the estrogen receptor (ER) and/or the progesterone receptor (PR), and
c) non-ERGO tumors that do not over-express HER2, ER and/or PR.

Importantly, this last set of non-ERGO tumors which did not over-express HER2, ER and/or PR represents a residual "triple non-positive" tumor subset of non-HER2 over-expressing, non-ER over-expressing and/or non-PR over-expressing tumors. This tumor subset was designated the non-ERGO "triple non-positive" tumor subset. A selected gene expression profile for each of these subsets is shown in FIG. 1 and with more detail at FIG. 8.

The ERGO tumor subset is truly "triple-negative" or "triple non-positive," in that essentially all tumors in this set under-express the HER2 receptor, estrogen receptor (ER) and progesterone receptor (PR). This is significant because tumors over-expressing the HER2 receptor can be treated with trastuzumab, while tumors over-expressing the ER or PR receptors can be targeted with hormone therapy based treatment regimens using drugs that prevent estrogen and progesterone from stimulating these receptors. In contrast, "triple non-positive" tumors are unlikely to be responsive to treatments targeting over-expressed HER2, ER, or PR receptors.

Among the 31 ERGO tumors identified, 25 out of 31 (81%) of these tumors over-expressed cyclin E1, cyclin E2, and/or p16. However, over-expression of cyclin E1, cyclin E2, and/or p16 was observed in just 6 out of 46 (13%) of the non-ERGO "triple non-positive" tumors identified, 1 out of 26 (4%) of non-ERGO ER/PR over-expressing tumors, and 2 out of 14 (14%) of the non-ERGO HER2 over-expressing tumors. Importantly, this elevated expression of the cyclin E1, cyclin E2, and/or p16 genes in the ERGO tumor group indicates that E2F expression and E2F mediated regulation of the expression of these proteins is impaired in ERGO tumors, but not in most other tumors.

This is confirmed by the observation that among the 31 ERGO tumors identified 14 out 31 (45%) of these tumors over-expressed E2F1, E2F2, and/or E2F3. In contrast, over-expression of E2F1, E2F2, and/or E2F3 was observed in just 7 out 46 (15%) non-ERGO "triple non-positive" tumors identified, 8 out of 26 (31%) of the ER/PR over-expressing non-ERGO tumors identified (ER is known to induce E2F), and in none of the 14 HER2 over-expressing non-ERGO tumors identified. These findings are consistent with the conclusion that aberrant expression (e.g. under-expression) of E2Fs (such as E2F1) is occurring in the ERGO breast cancer tumors identified.

Additionally, 16 out of the 31 (52%) ERGO tumors identified over-expressed at least two basal-like tumor cytokeratin markers selected from the group consisting of the cytokeratin 5, cytokeratin 6A, cytokeratin 6B, cytokeratin 14, and cytokeratin 17 basal-like tumor markers. In contrast, over-expression of at least two of these basal-like tumor cytokeratin markers was observed in just 5 out of 46 (11%) non-ERGO "triple non-positive" tumors identified, 2 out of 26 (8%) of the ER/PR over-expressing non-ERGO tumors identified, and in none of the HER2 over-expressing non-ERGO tumors identified.

Importantly, over-expression of these cytokeratin markers is an important criterion for the identification of basal-like tumors. Consequently, the observation here that over-expression of at least two basal like cytokeratins occurred in both the ERGO tumors identified and non-ERGO "triple non-positive" tumor subset identified indicates that the basal-like tumors may represent a genus of tumors with a phenotype that includes both the "triple non-positive" ERGO tumor subset identified and the non-ERGO "triple non-positive" tumor subset identified.

The Van't Veer microarray set analyzed also included tumor samples from 18 patients with known hereditary BRCA1 mutations. Such BRCA1 mutations are believed to pre-dispose patients carrying such mutant genes to cancer. This is because the BRCA1 protein product is involved in DNA damage repair, ubiquitination, transcriptional regulation and other cellular functions. The BRCA1 protein and expression of the gene encoding BRCA1 is important because BRCA1 helps maintain genomic integrity by promoting high fidelity DNA repair when genomic DNA mutations occur. Mutations in the BRCA1 gene or defects in the expression of the gene encoding BRCA1 are believed to result in the accumulation of genomic DNA mutations that can lead to uncontrolled cell division and cancer.

Importantly, 11 of the 18 tumors (61%) from patients with BRCA1 mutations were ERGO tumors, and 8 of these 11 tumors (73%) over-expressed at least two basal-like tumor cytokeratin markers selected from the group consisting of cytokeratin 5, cytokeratin 6A, cytokeratin 6B, cytokeratin 14, and cytokeratin 17 basal-like tumor markers. The 7 other tumors (out of 18) from patients with BRCA1 mutations were non-ERGO "triple non-positive" tumors, and only 2 of these 7 tumors (29%) over-expressed at least two of the basal-like tumor cytokeratin markers. These findings further confirm that the basal-like tumor genus includes both the ERGO tumor subset and the non-ERGO "triple non-positive" tumor subset. Additionally, these data also indicate that over-expression of basal-like cytokeratins alone is inadequate as a marker for identifying all members of the basal-like tumor genus. This is significant, because it indicates that the ability to identify ERGO tumors by using the gene expression profile of a tumor to determine if it is an ERGO tumor will permit the identification of appropriate tumor treatment regimens and survival predictions for an individual patient.

Last, ID4 which is a basal-like tumor marker was over-expressed in 10 out of 16 of the ERGO tumors (63%) identified, and 4 put of 4 of the non-ERGO "triple non-positive" tumors which over-expressed at least two of the basal-like tumor cytokeratins markers described above. However, ID4 was also over-expressed in 2 ERGO tumors and 3 non-ERGO BRCA1 tumors that did not over-express at least two basal-like cytokeratins. CDH3 which is another basal-like tumor marker was over-expressed in 14 out of 16 (88%) of the ERGO tumors over-expressing at least two basal-like cytokeratins, and in 3 out of 4 (75%) of the non-ERGO "triple, non-positive" tumors identified that over-expressed at least two basal like cytokeratins. However, CDH3 was also over-expressed in 4 ERGO tumors and 4 non-ERGO tumors, including 3 non-ERGO tumors from patients with BRCA1 mutations that did not over-express at least two basal-like cytokeratins. Furthermore, ID4 and CDH3 over-expression was also observed in 3 non-ERGO tumors over-expressing the HER2 receptor. Together, these observations indicated that the basal-like tumor genus is not limited solely to ERGO tumors and non-ERGO "triple non-positive" tumors.

Principal Component Analysis and the Basal-Like Subset.

Principal component analysis (PCA) was then performed on the Van't Veer microarray set using TM4 software version 4.1.01 (www.TM4.org; Dana-Farber Cancer Institute, Boston, Mass., USA). This alternative methodology was used to confirm and validate the analytical results obtained with the weighted rank ordering method. PCA was performed using the default settings of the TM4 software unless otherwise indicated.

Principal component analysis of the Van't Veer microarray set revealed a tumor cluster consisting of 38 tumors (FIG. 2A) which all under-expressed the ER based on the criteria described above for "under-expression." 35 of these 38 tumors (92%) were "triple negative. Twenty (20) of these 38 tumors (53%) over-expressed at least two of the basal-like cytokeratins described above. Moreover, only 2 of the 79 tumors (3%) not included in this cluster over-expressed at least two of these basal-like cytokeratins. Importantly, 91% of all tumors that over-expressed at least two basal-like cytokeratins were found in this cluster of 38 tumors.

Thirty-three (33) of the 38 tumors (87%) in the cluster over-expressed the basal-tumor markers ID4 and/or CDH3, but only 8 of the 79 (10%) tumors that were not in the cluster over-expressed these basal-tumor markers. Among 25 published markers for basal-like tumors (see Table 3 below) that are over-expressed in basal-like tumors, all members of the PCA cluster over-expressed at least 2 of these markers, and 35 out of 38 of the tumors in this cluster over-expressed at least 3 such markers (92%). Thus all members of this tumor cluster identified by PCA can be identified as basal-like tumors based on the over-expression of these markers.

TABLE 3

| gene name | type | ref |
| --- | --- | --- |
| CDH3 | dx/prog | Ames, 2005; Matos, 2005 |
| KRT17 | dx/prog | van de Rijn, 2002 |
| CRYAB | dx/prog | Moyano, 2006, 2008 |
| SNL/fascin | dx | Rodriguez-Pinilla, 2006 |
| ID4 | dx | turner, 2007 |
| KRT5 | dx/prog | van de Rijn, 2002 |
| VIM | dx/prog | Rodriguez-Pinilla, 2007 |
| ACTG2 | dx | livasy, 2006 |
| CCNE1 | dx/prog | Foulkes, 2004 |
| EZH2 | dx/prog | Collett, 2006 |
| LAMB3 | dx | Rodriguez-Pinilla 2007 |
| KRT6B | dx/prog | van de Rijn, 2002 |
| KRT14 | dx/prog | Fulford, 2007 |
| MSN | dx/prog | Charafe-Jauffret 2007 |
| ANXA8 | dx/prog | Stein, 2005 |
| CCNE2 | dx/prog | Foulkes, 2004 |
| CD44 | dx | Charafe-Jauffret, 2006 |
| ITGB4 | dx/prog | Lu, 2008 |
| S100A9 | dx/prog | Goncalves, 2008 |
| MCAM/cd146 | dx/prog | Garcia, 2007 |
| KIT | dx | Nielsen, 2004 |
| KRT6A | dx/prog | van de Rijn, 2002 |
| P63 | dx | Matos, 2005 |
| EGFR | dx | Nielsen, 2004 |
| TGFBR2 | prog | uck, 2004 |

This basal-like tumor cluster identified by PCA contained 27 of the 31 (87%) ERGO tumors identified by the rank ordering method and also included all 11 ERGO tumors from patients with BRCA1 mutations. Of the four ERGO tumors that were excluded from the basal-like tumor cluster identified by PCA, three were borderline by the ranking method, and would have not been identified as ERGO tumors if the stopping criteria for the ranking method been more stringent (e.g., requiring that ERGO tumors over-express at least 25% of over-expressed E2F-responsive genes instead of 20%). The basal-like tumor cluster identified by PCA also contained 6 out of 7 of the non-ERGO tumors identified from patients with BRCA1 mutations. Together, these results identify ERGO tumors as members of the basal-like breast cancer tumor subset identified by PCA, and confirms that both the ERGO tumors and non-ERGO tumors from patients with BRCA1 mutations identified by the rank ordering method are members of the basal-like tumor subset identified by the PCA method.

Refined Principal Component Analysis and the Identification of the ERGO Tumor Subset within the Basal-Like Tumor Subset Identified by PCA.

The basal-like tumor cluster identified by PCA as described above was further analyzed. This was done by using further refined PCA in which the analyzed gene set was restricted to the E2F-responsive genes listed in Table 1 shown above. In these analyses only those tumors in the basal-like tumor cluster identified by PCA as described above were used as input data. The result of this refined PCA analysis was that the non-ERGO tumors clustered separately from the ERGO tumors (FIG. 2B), although 2 of 27 ERGO tumors identified by the ranking method did not separate cleanly from the non-ERGO tumors.

Figure 3A:
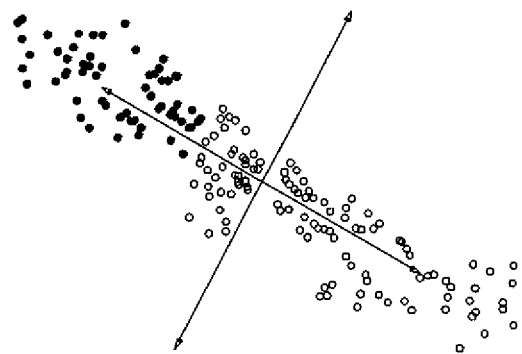
FIG. 3A shows a continuous strand of genes strung along the axis of the first principal component, rather than discrete gene clusters, identified by refined PCA gene clustering with the basal-like tumors from the Van't Veer microarray set as input.
Figure 3C:
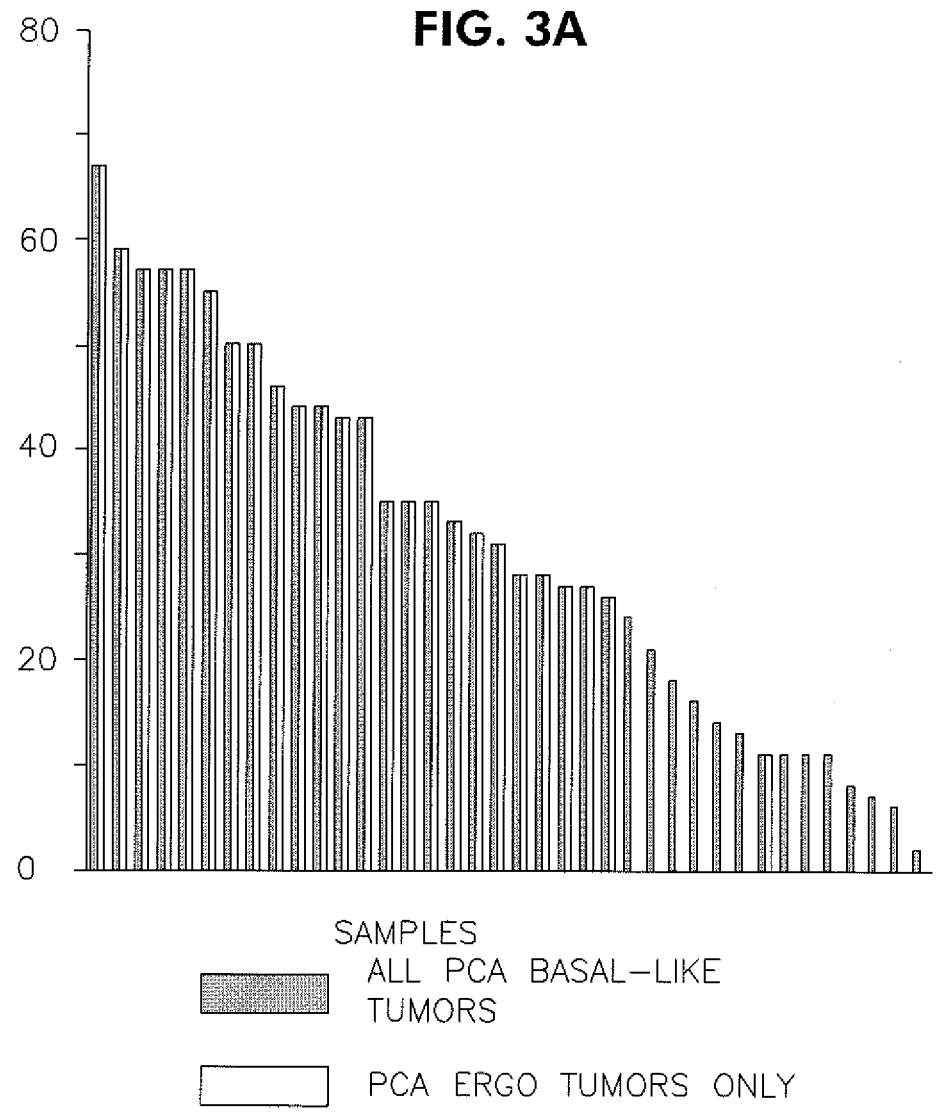
FIG. 3C shows a comparison of the frequency of over-expressed E2F-responsive genes per basal-like tumor sample identified by PCA gene clustering in FIG. 3A with the most frequently over-expressed E2F-responsive genes in ERGO tumors.
Figure 3B:
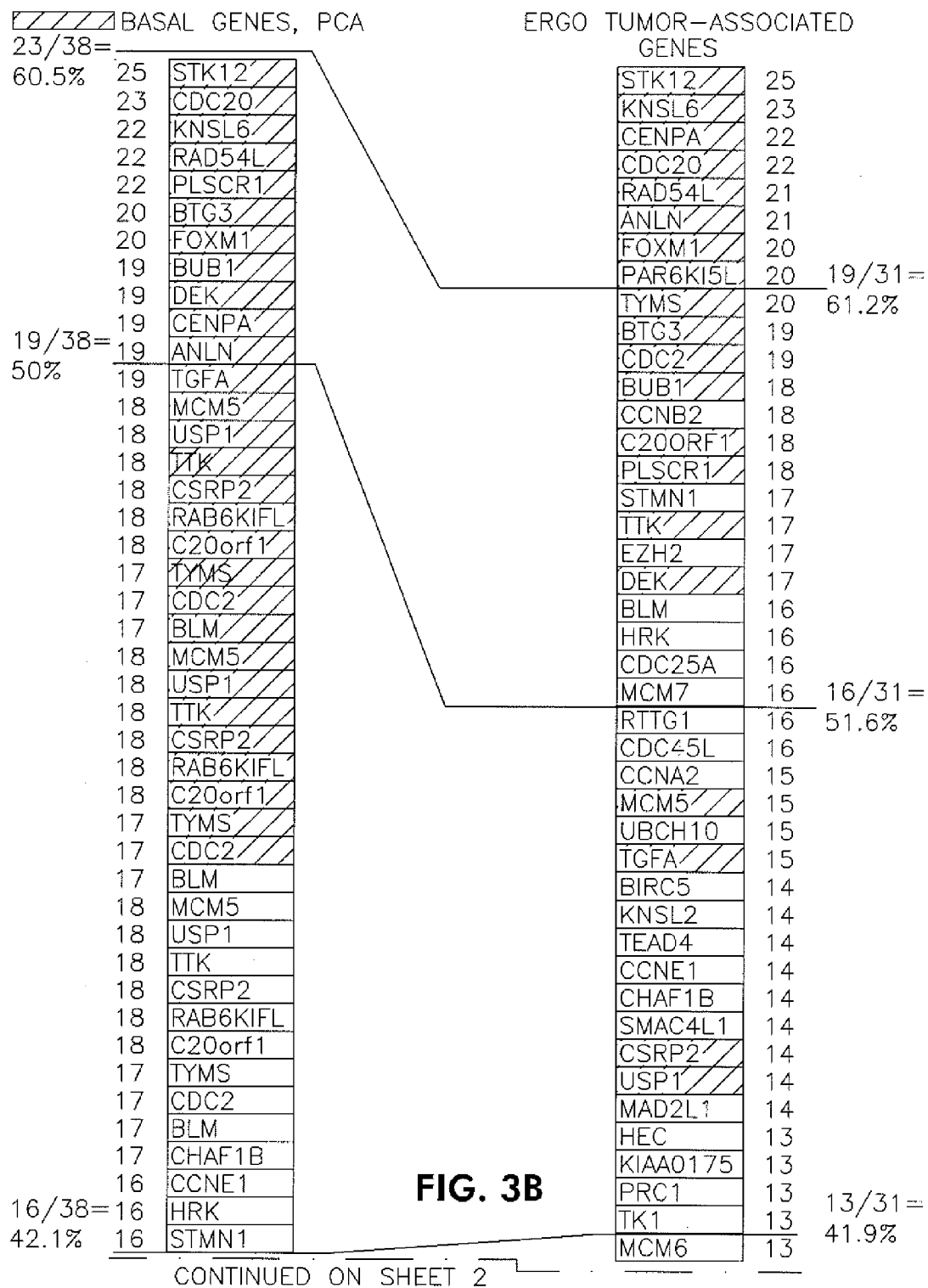
FIG. 3B is a graph comparing the genes identified by refined PCA clustering of the basal-like tumors from the Van't Veer human breast cancer microarray set in FIG. 3A with the most frequently over-expressed E2F-responsive genes in the ERGO tumors identified by the weighted rank ordering of all tumors from the Van't Veer microarray set.
Figure 3B:
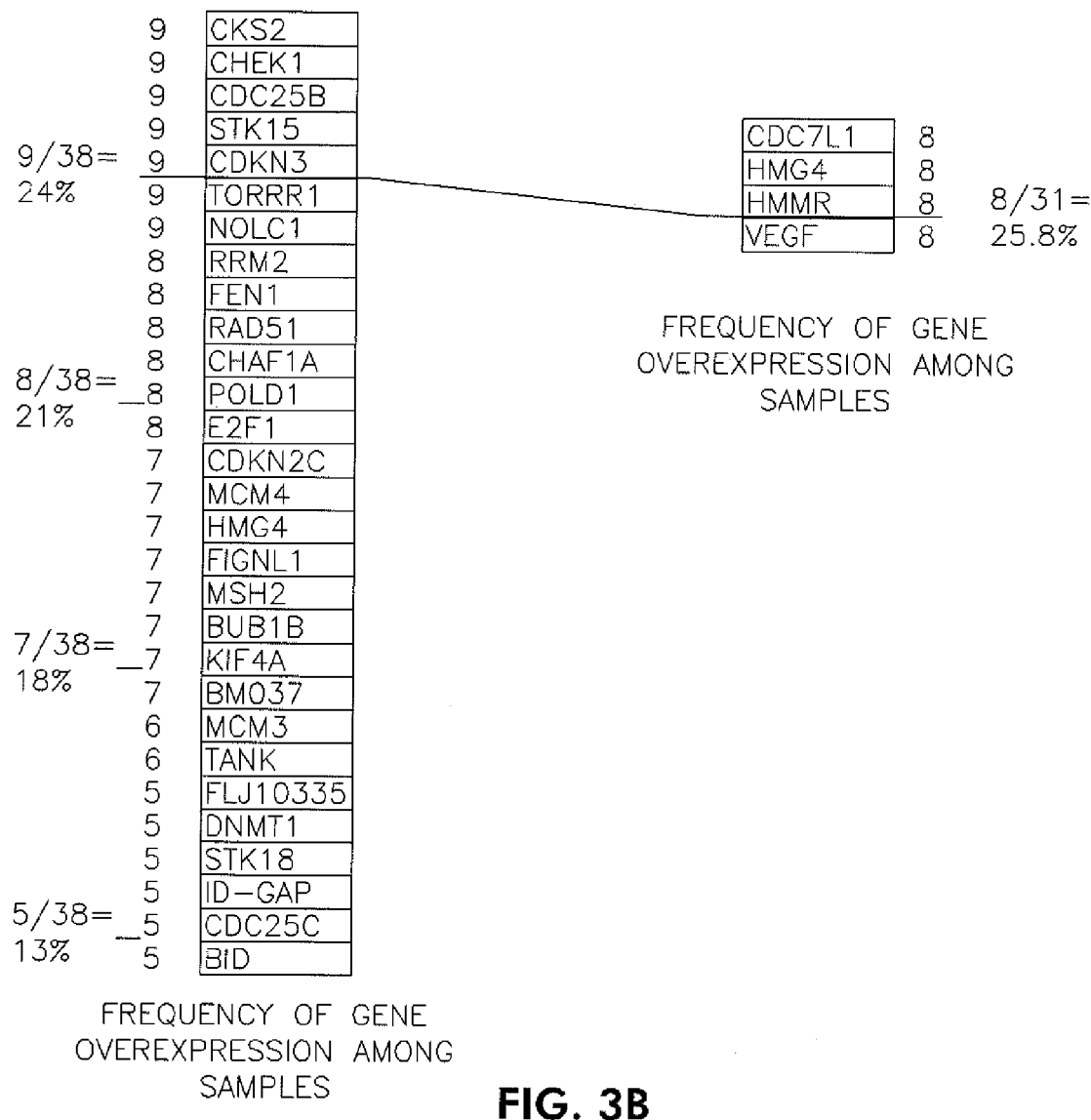
Figure 4B:
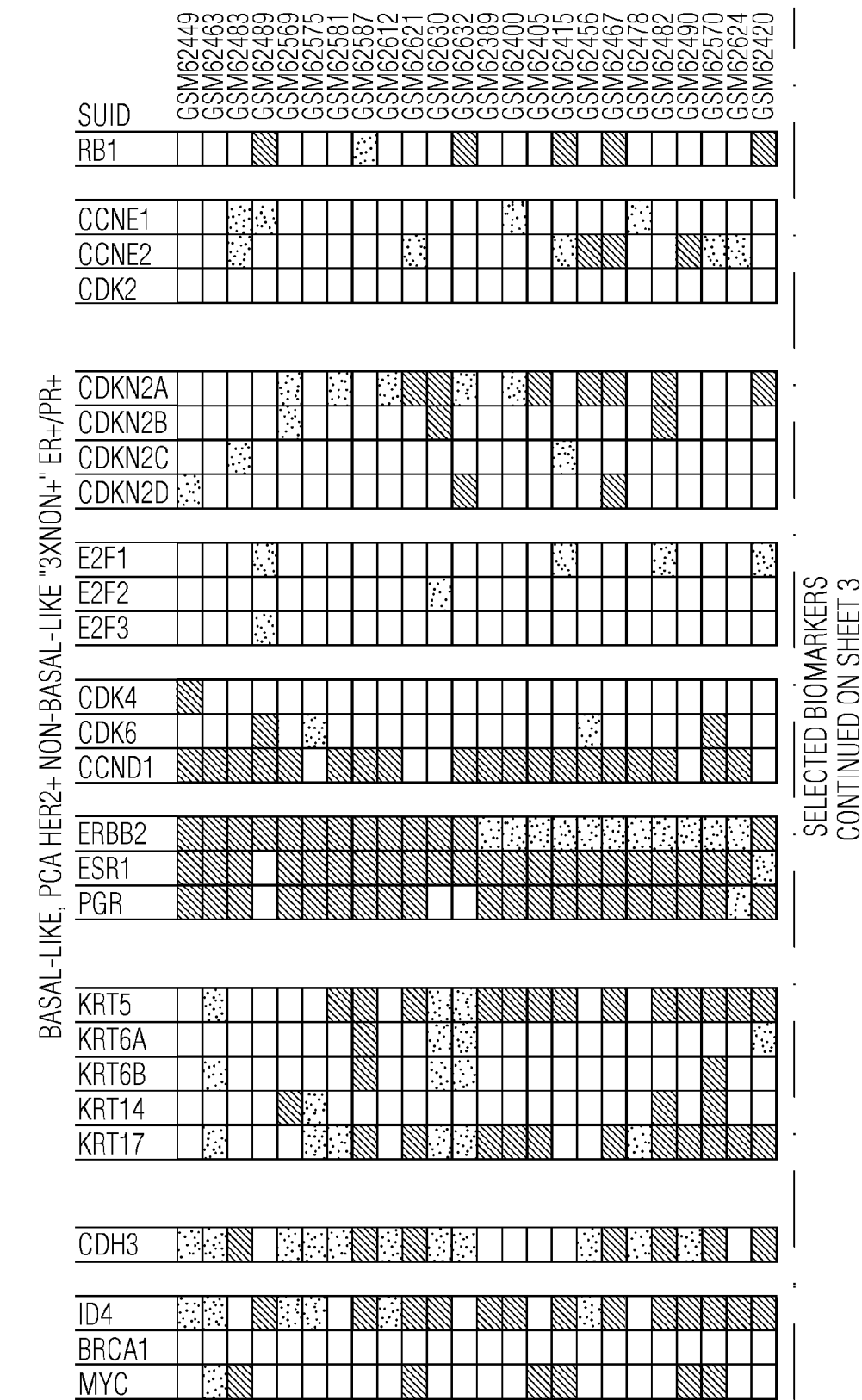
FIGS. 4A to 4HHH show partial views intended to form one complete view of microarray data for HER2 positive tumors identified by PCA of the purged Dai human breast cancer microarray set (s2) and per ERGO tumor sample identified by refined PCA of the basal-like tumors in this microarray set.
Figure 4C:
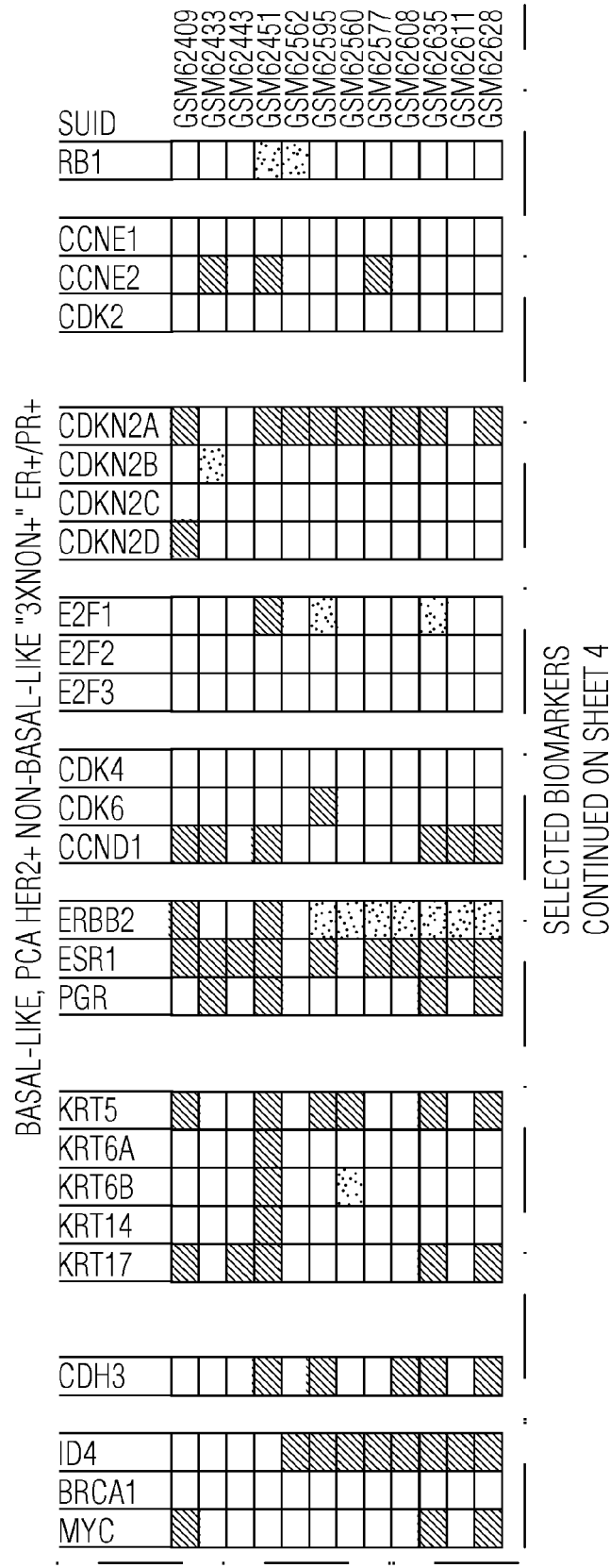
Figure 4D:
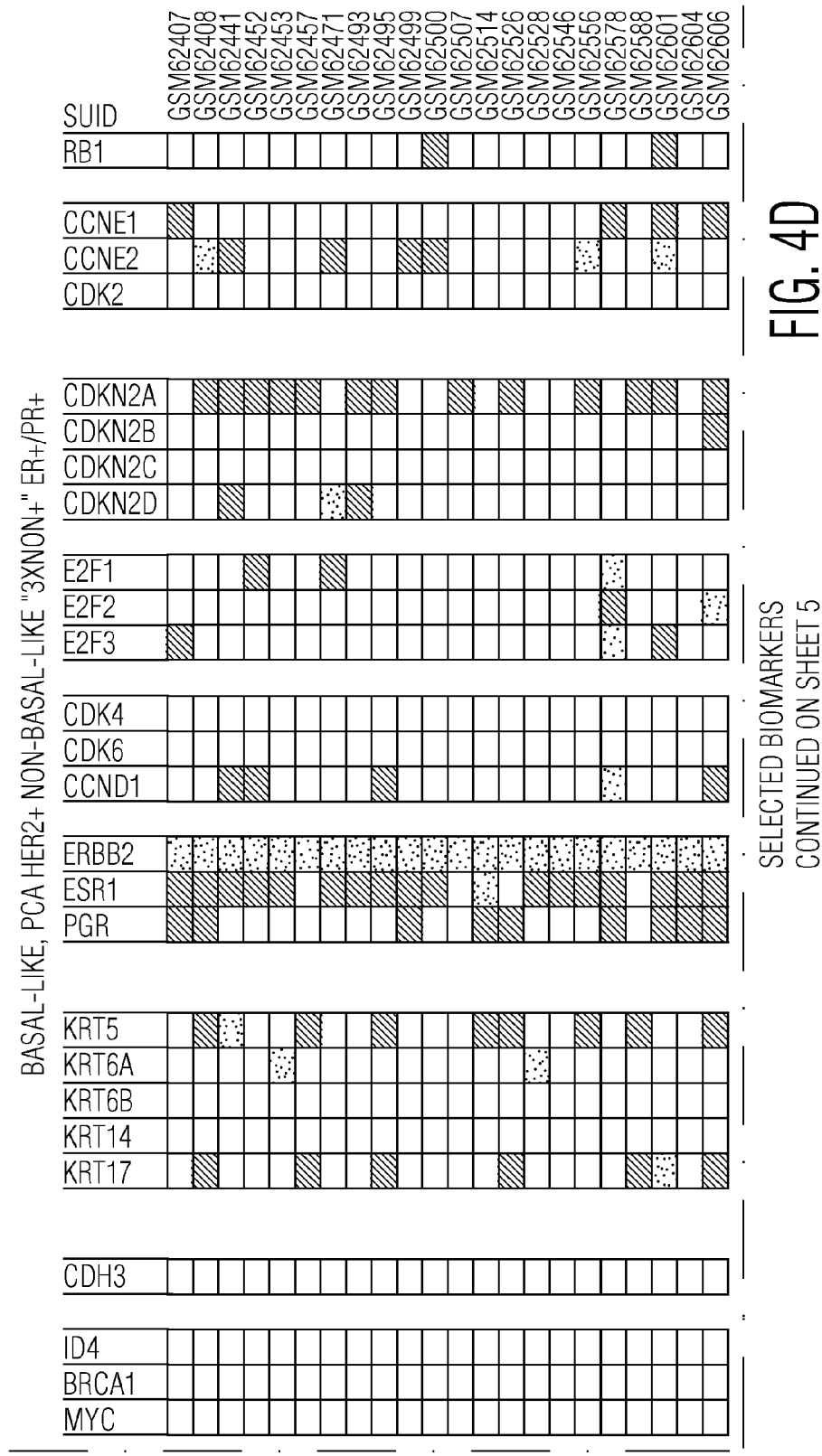
Figure 4G:
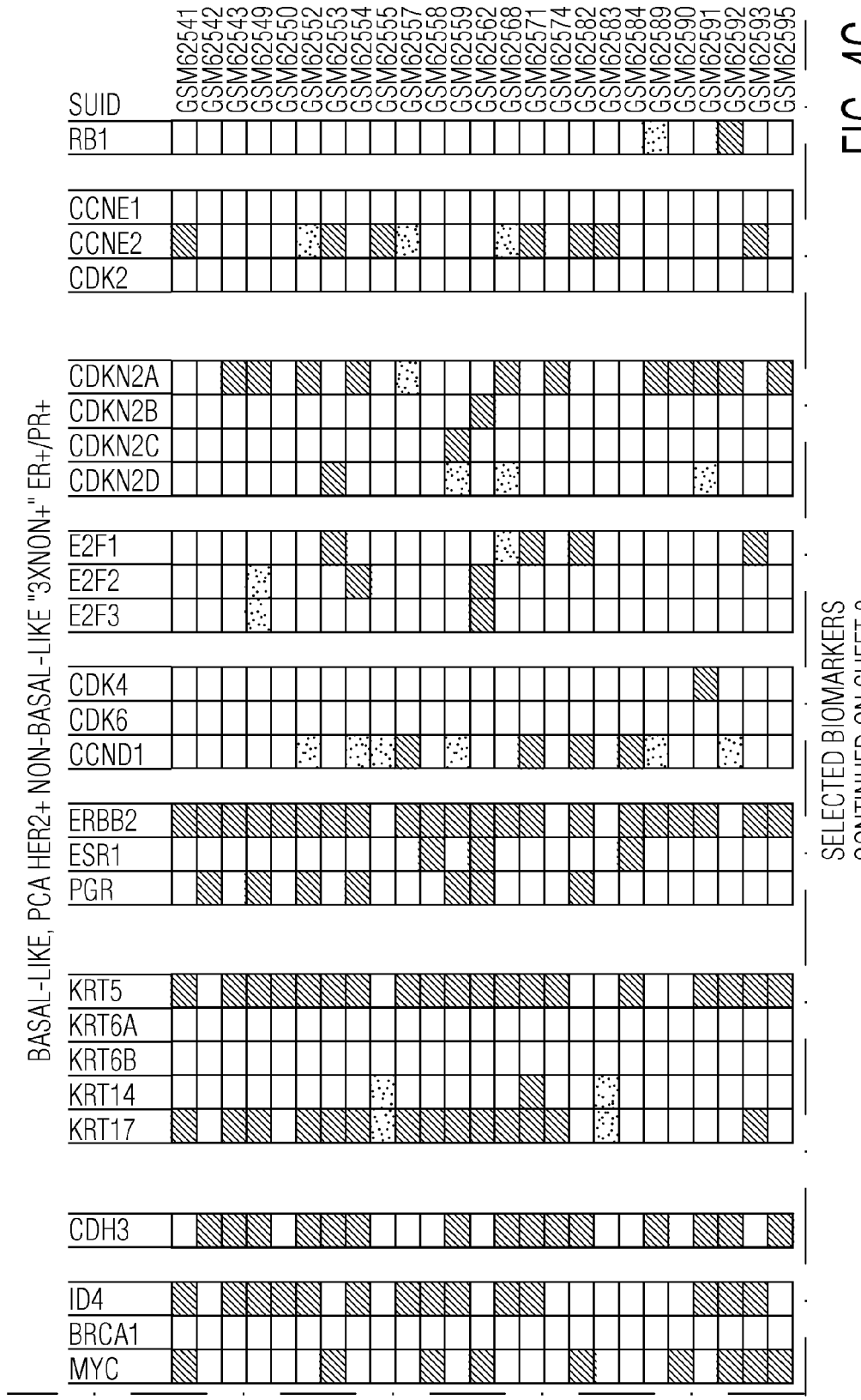
Figure 4H:
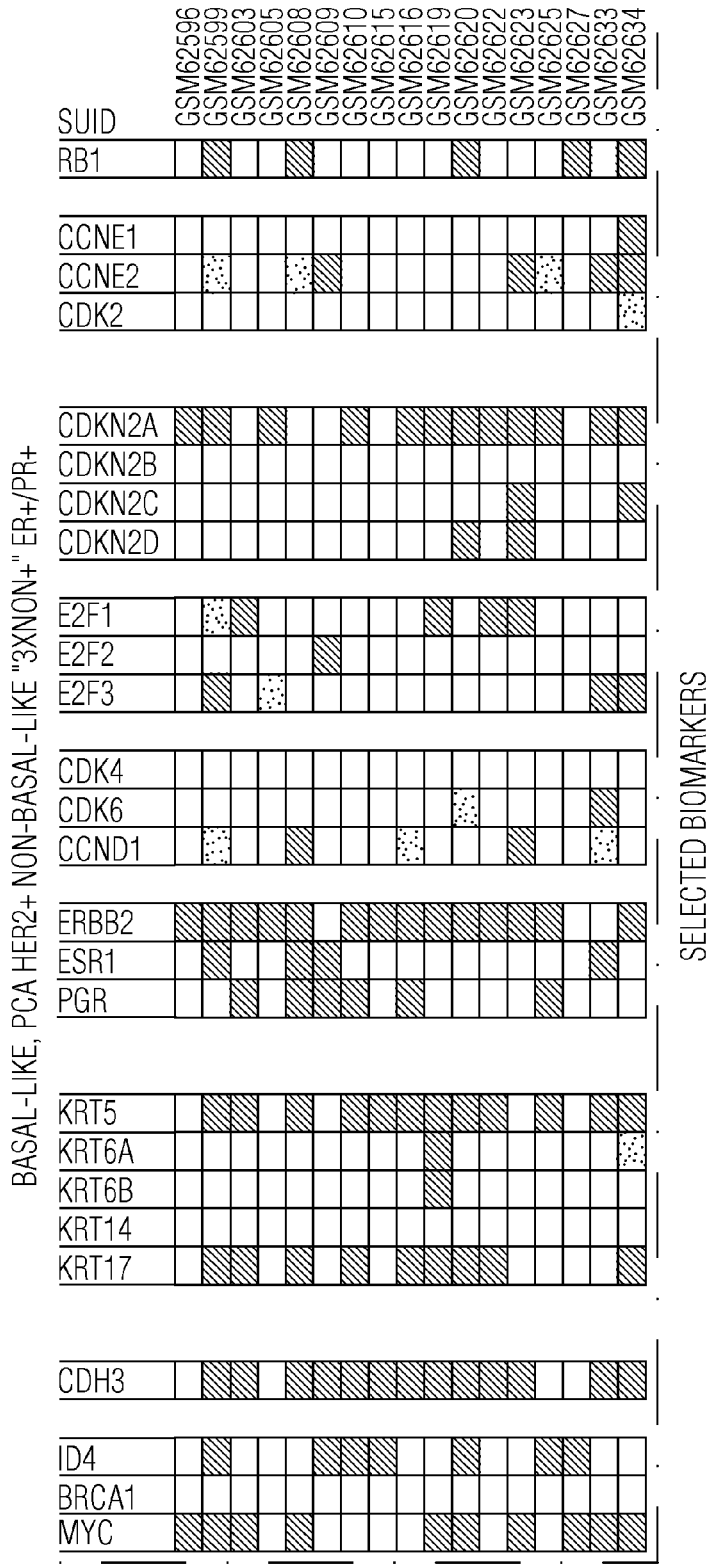
Figure 4I:
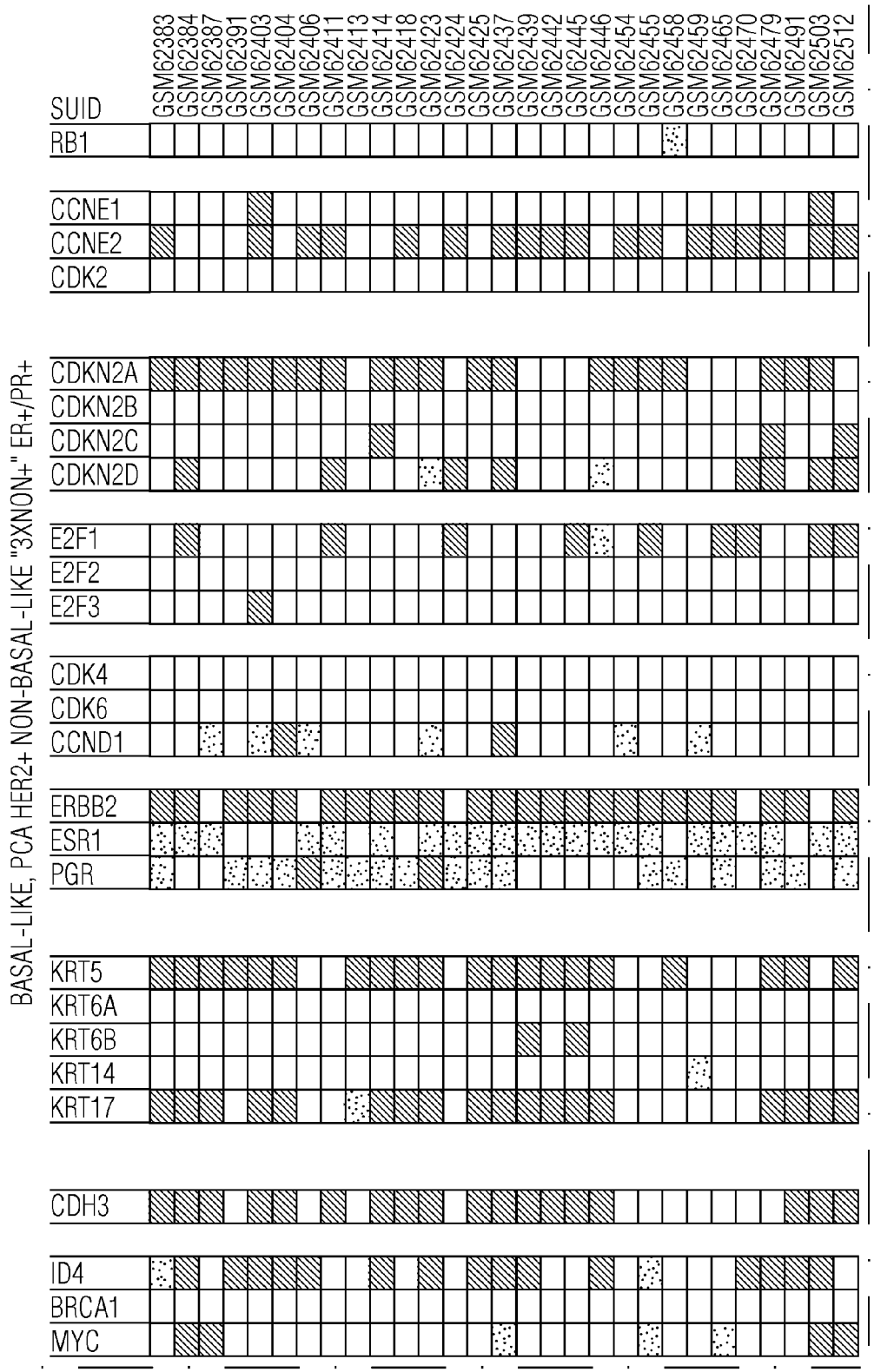
Figure 4J:
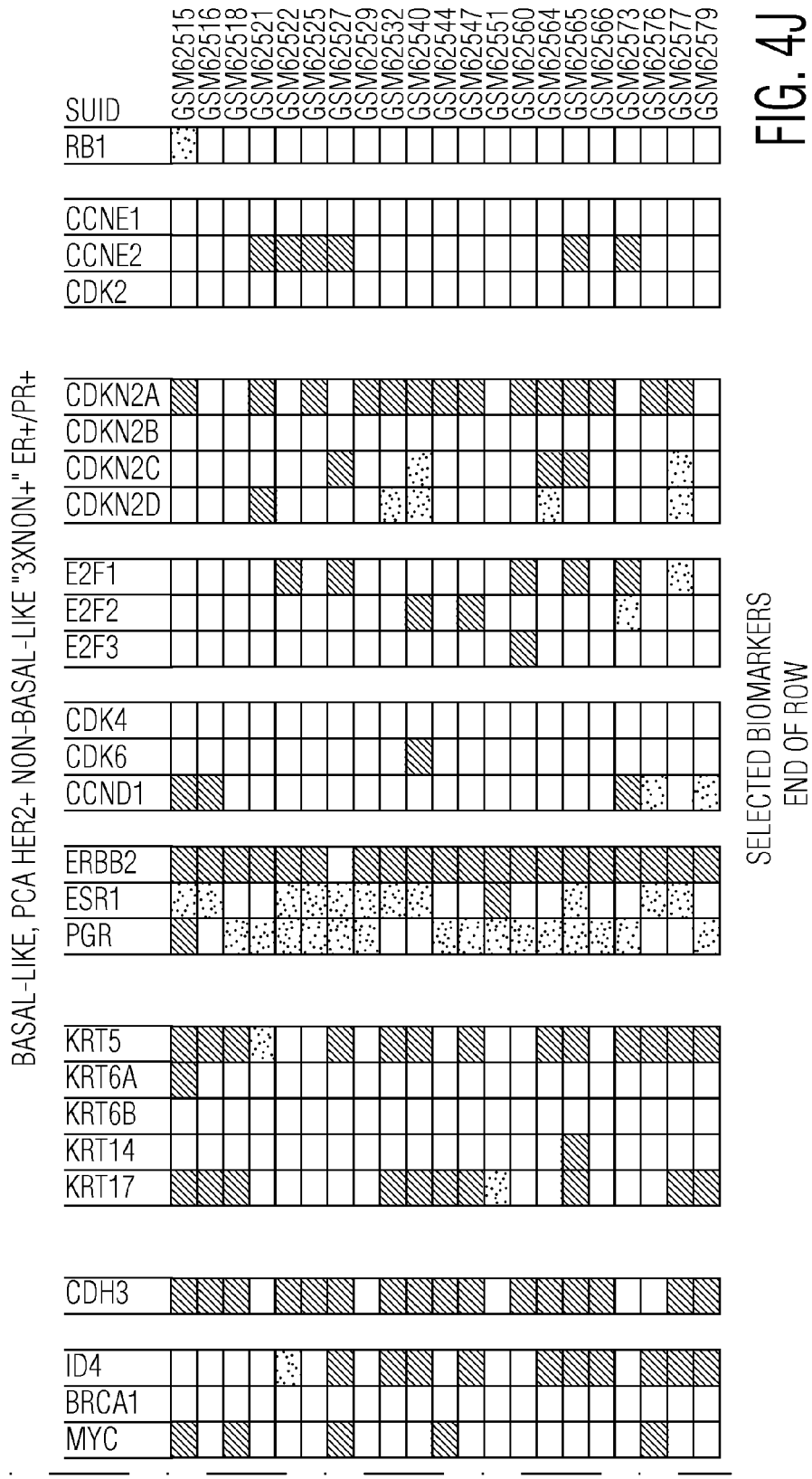
Figure 4K:
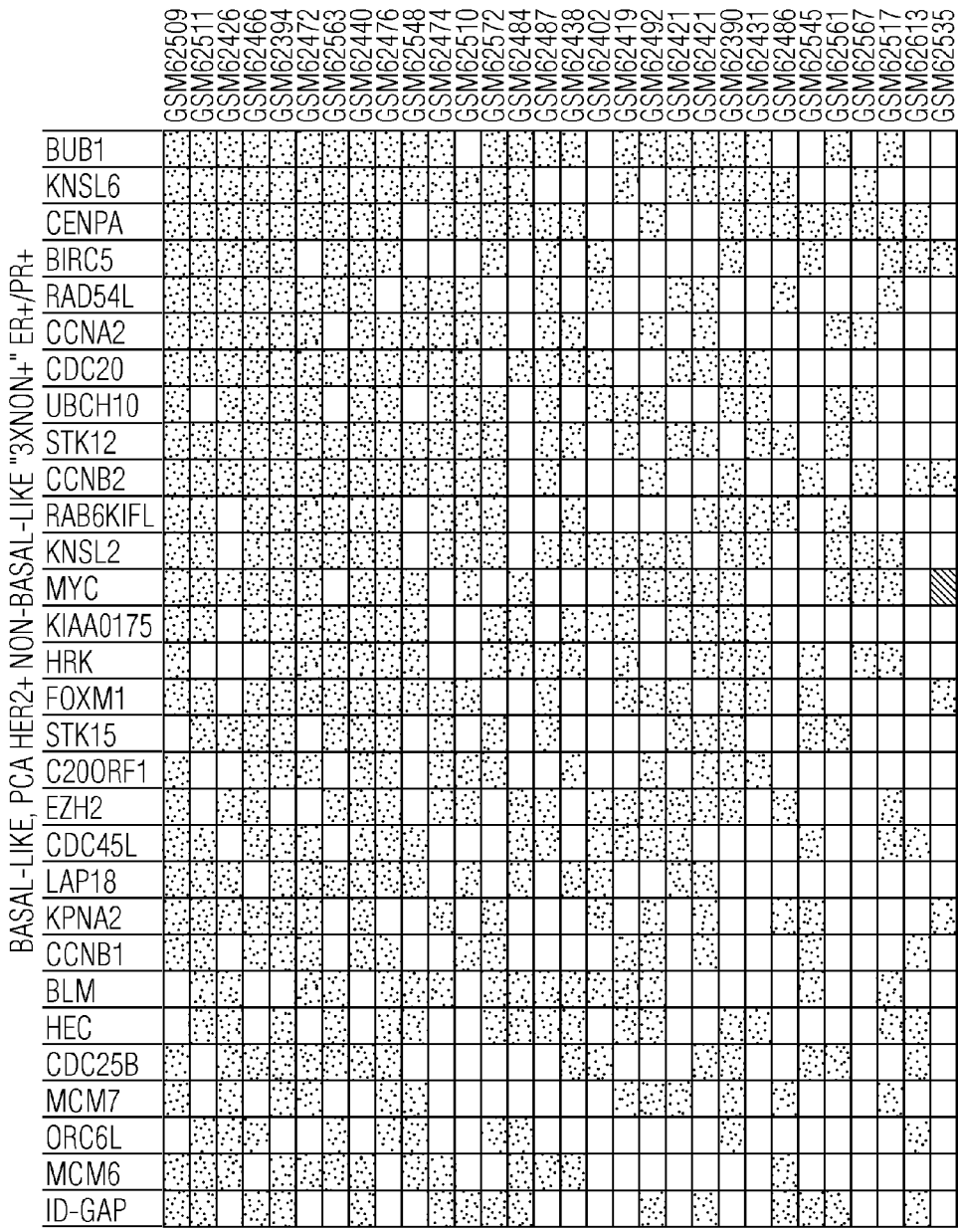
Figure 4L:
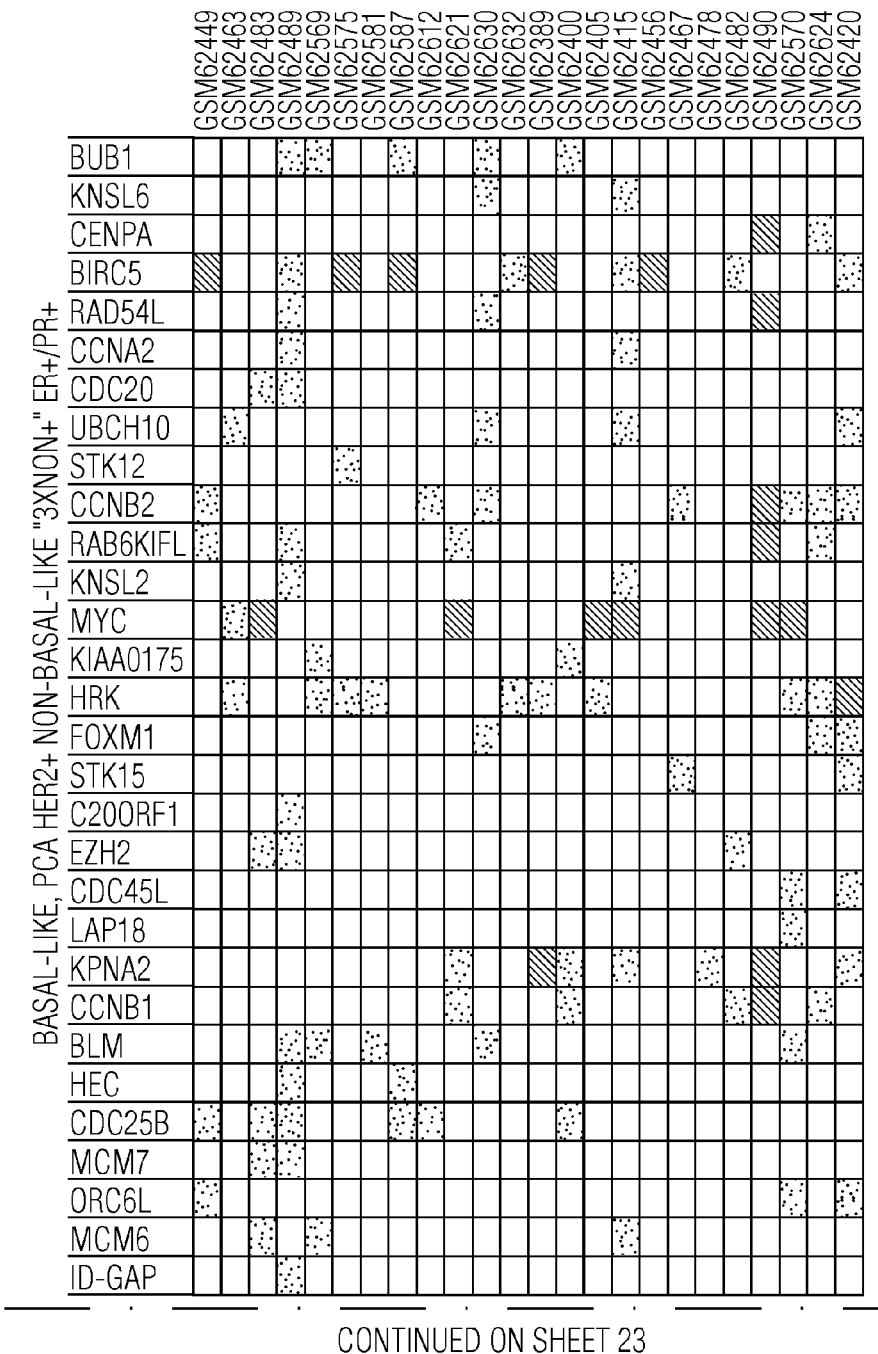
Figure 4M:
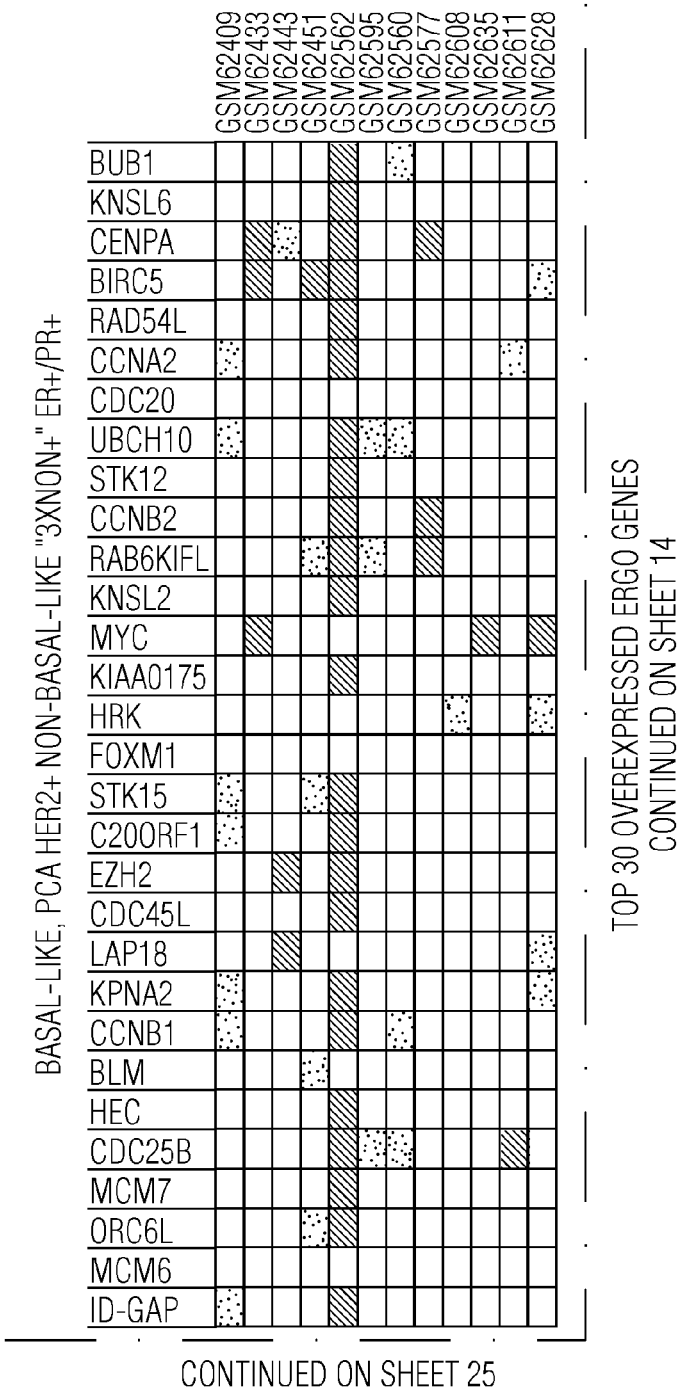
Figure 4N:
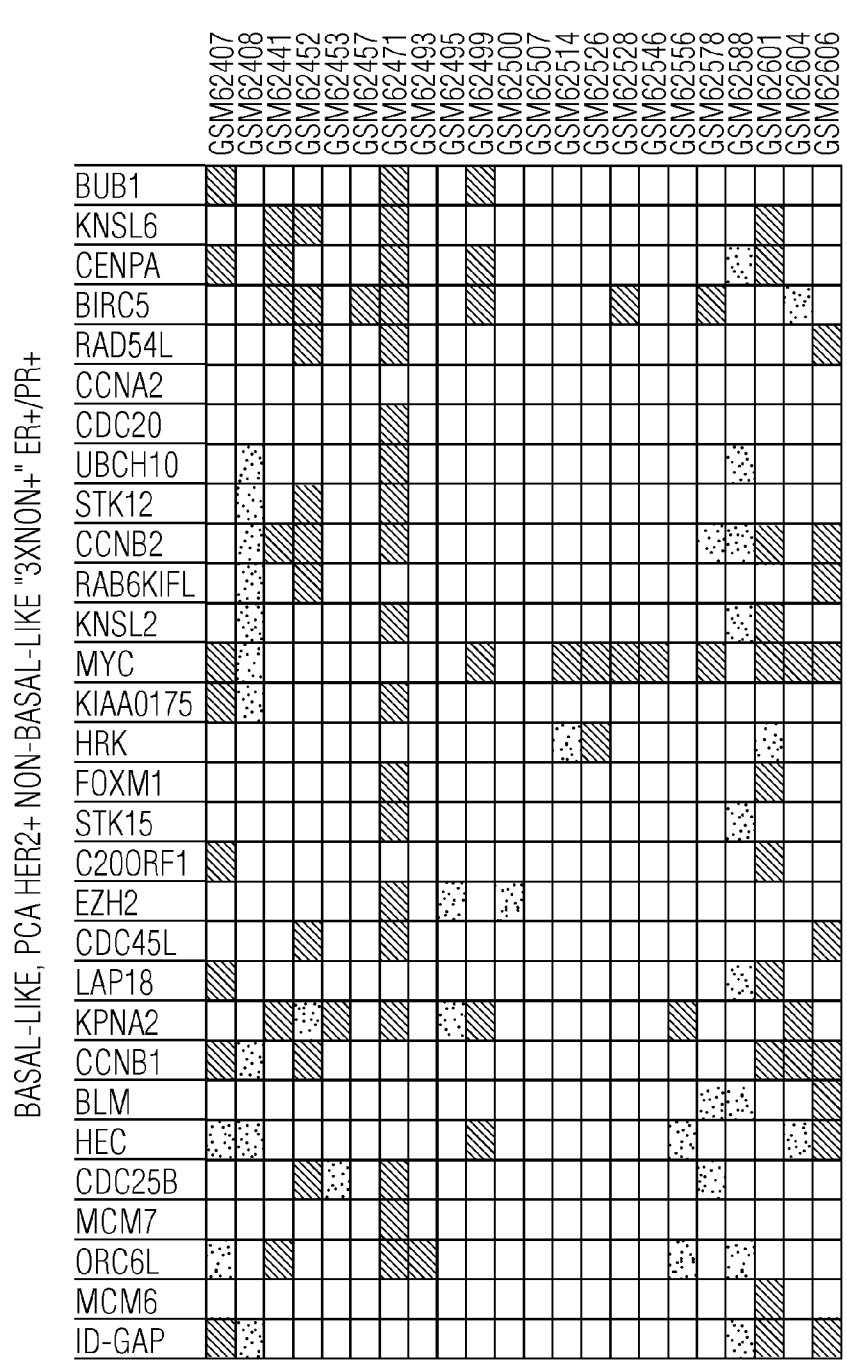
Figure 40:
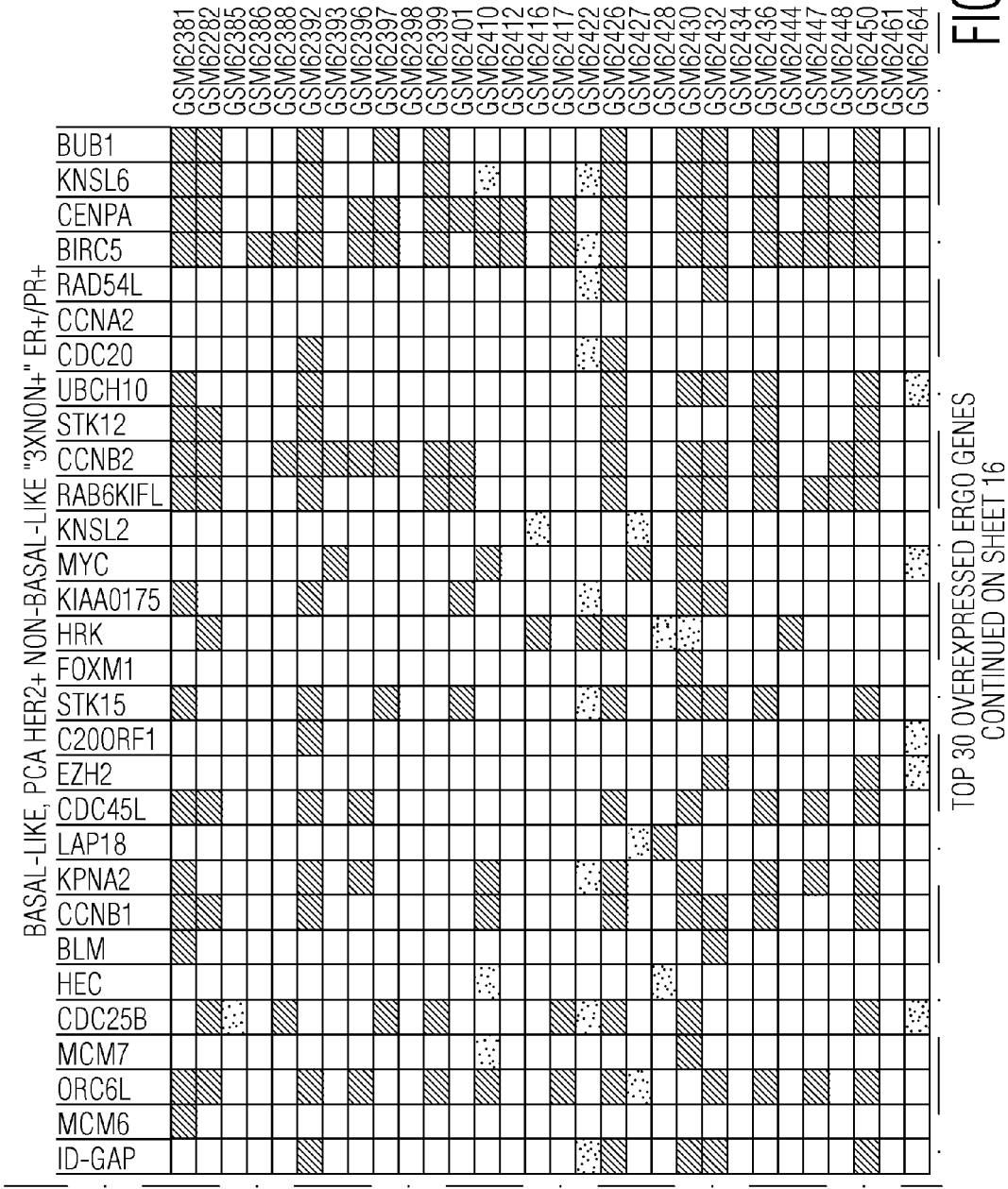
Figure 4Q:
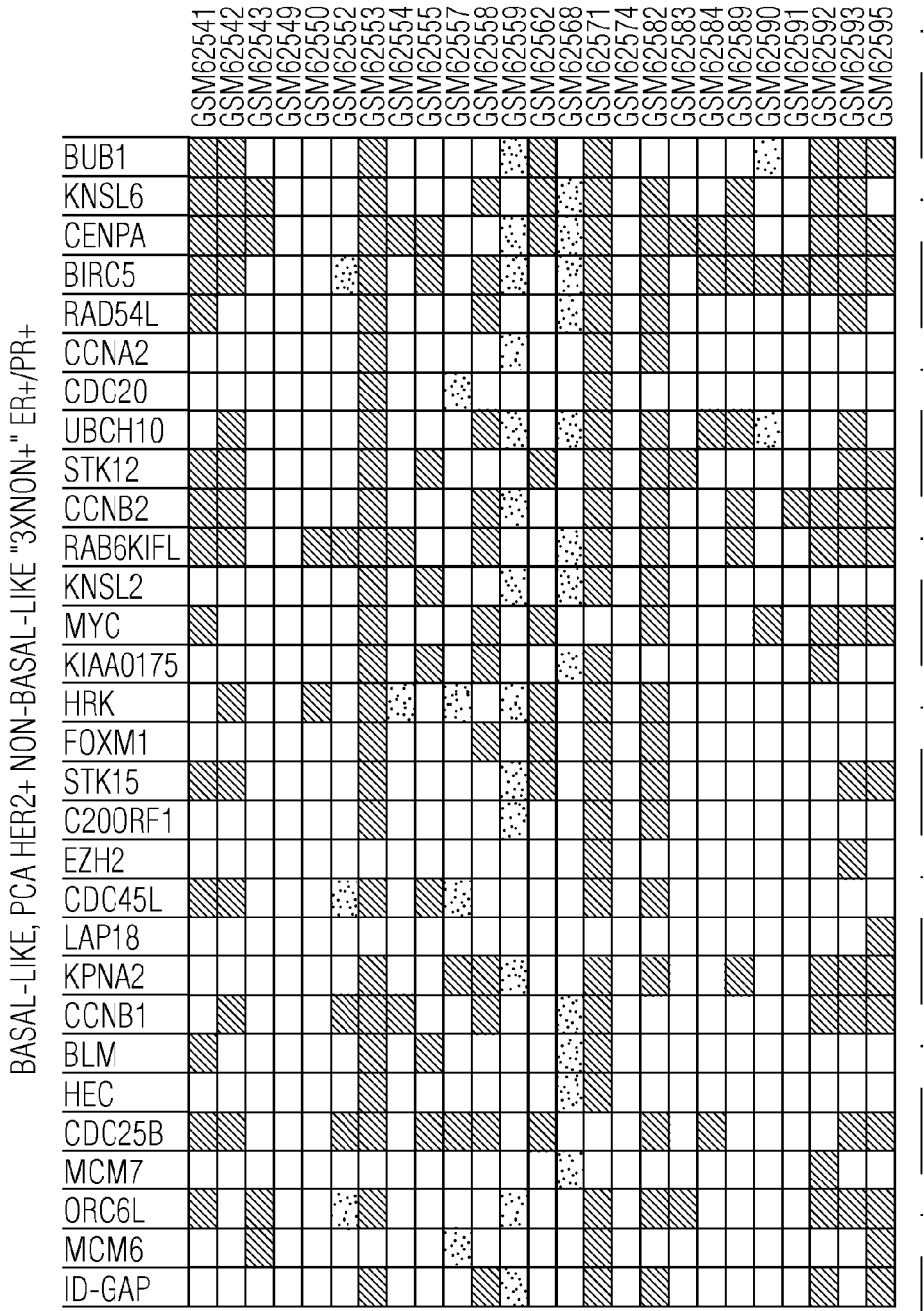
Figure 4R:
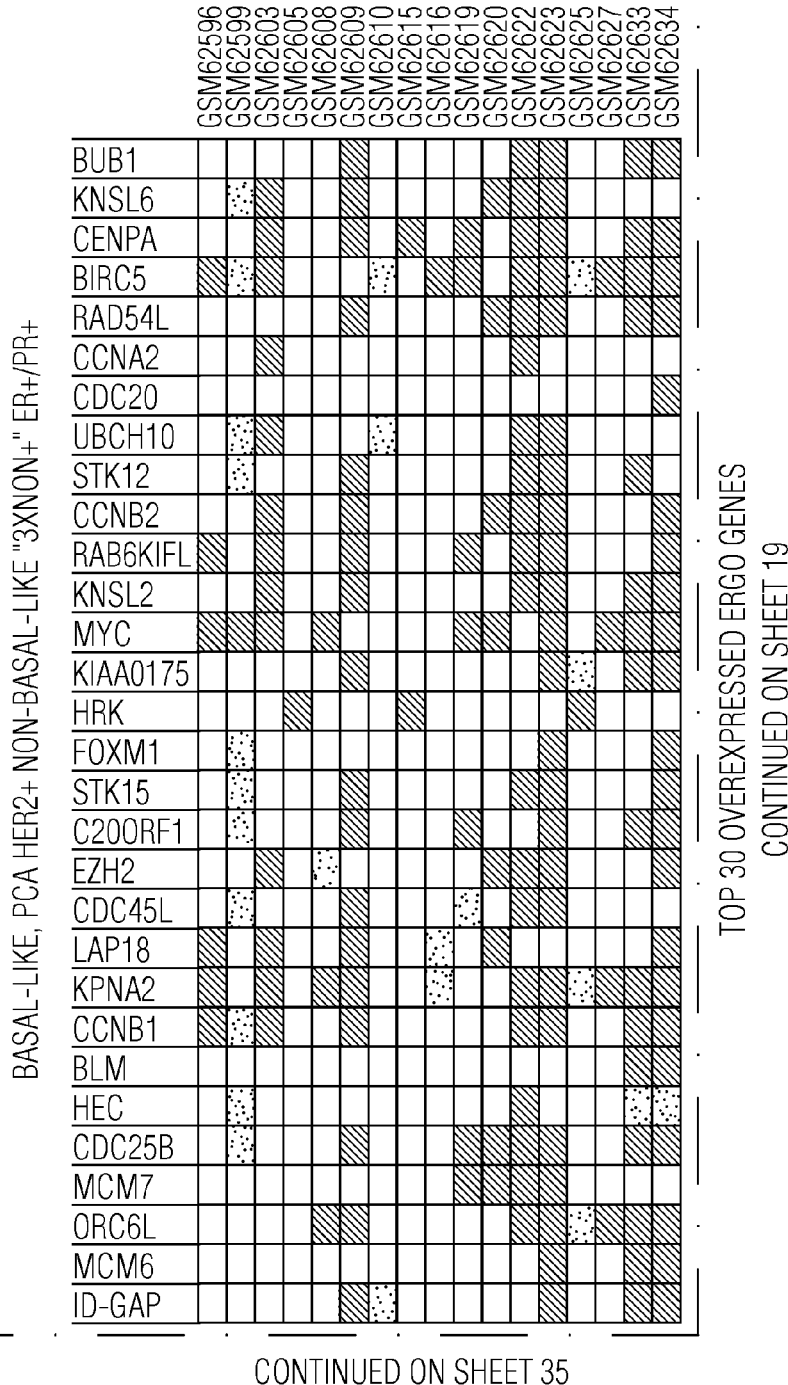
Figure 4T:
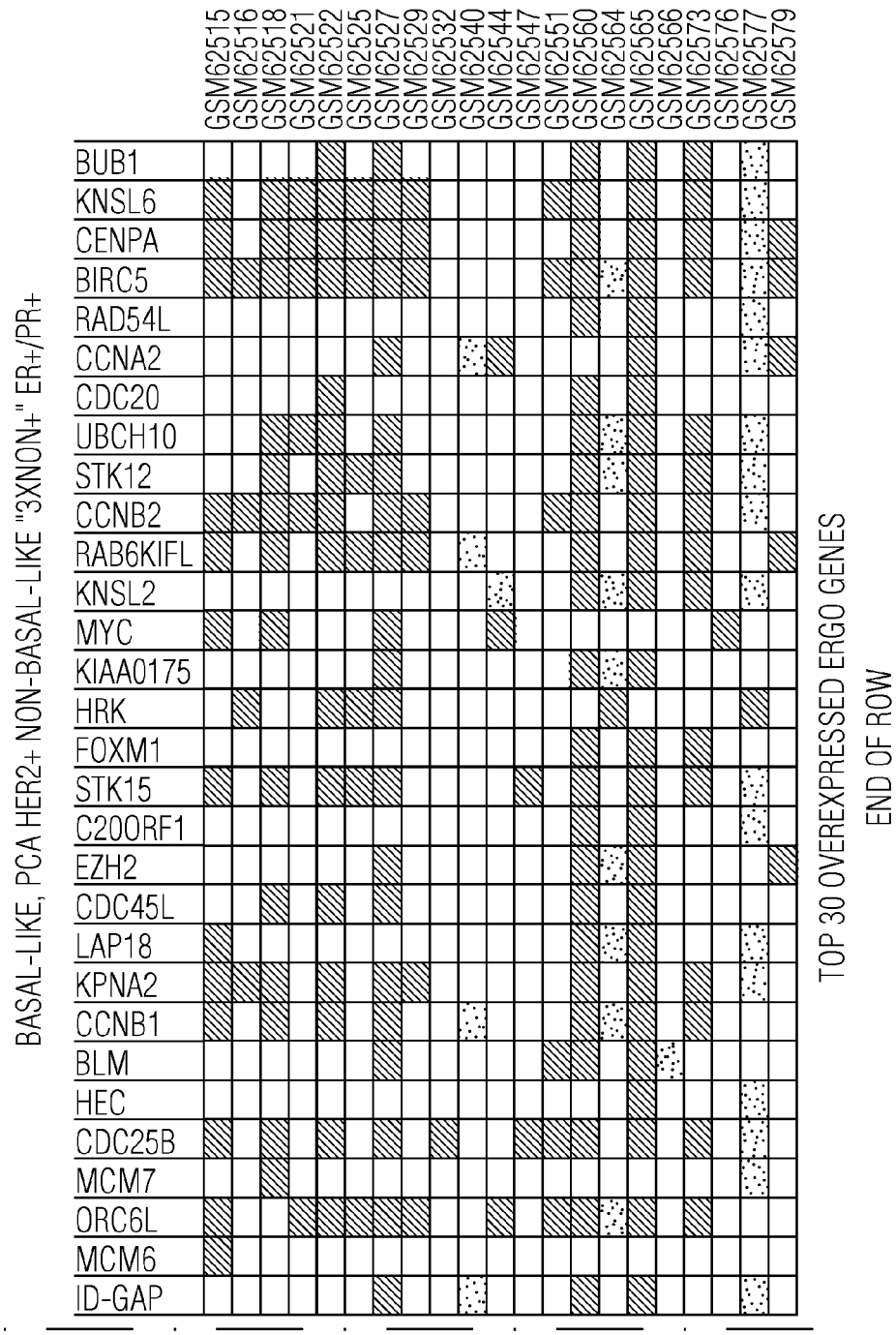
Figure 4U:
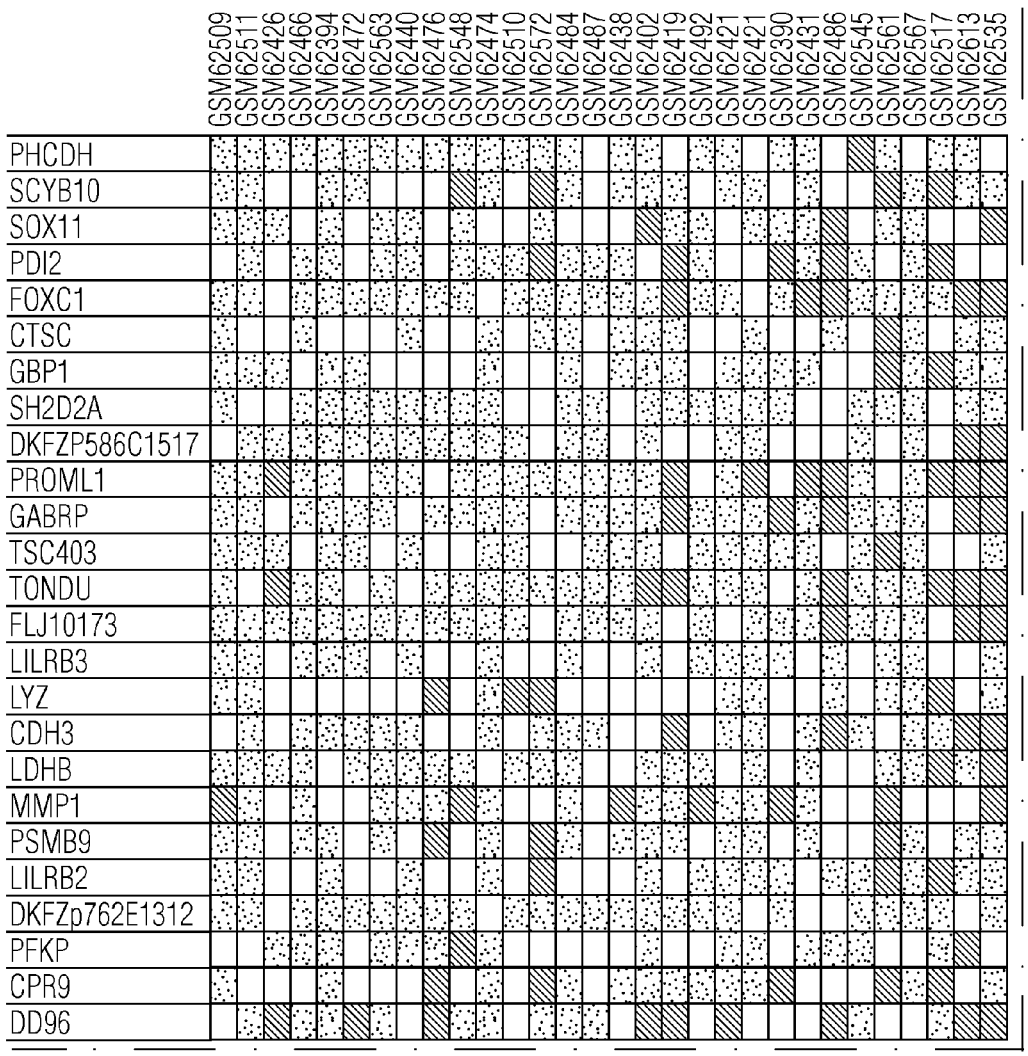
Figure 4V:
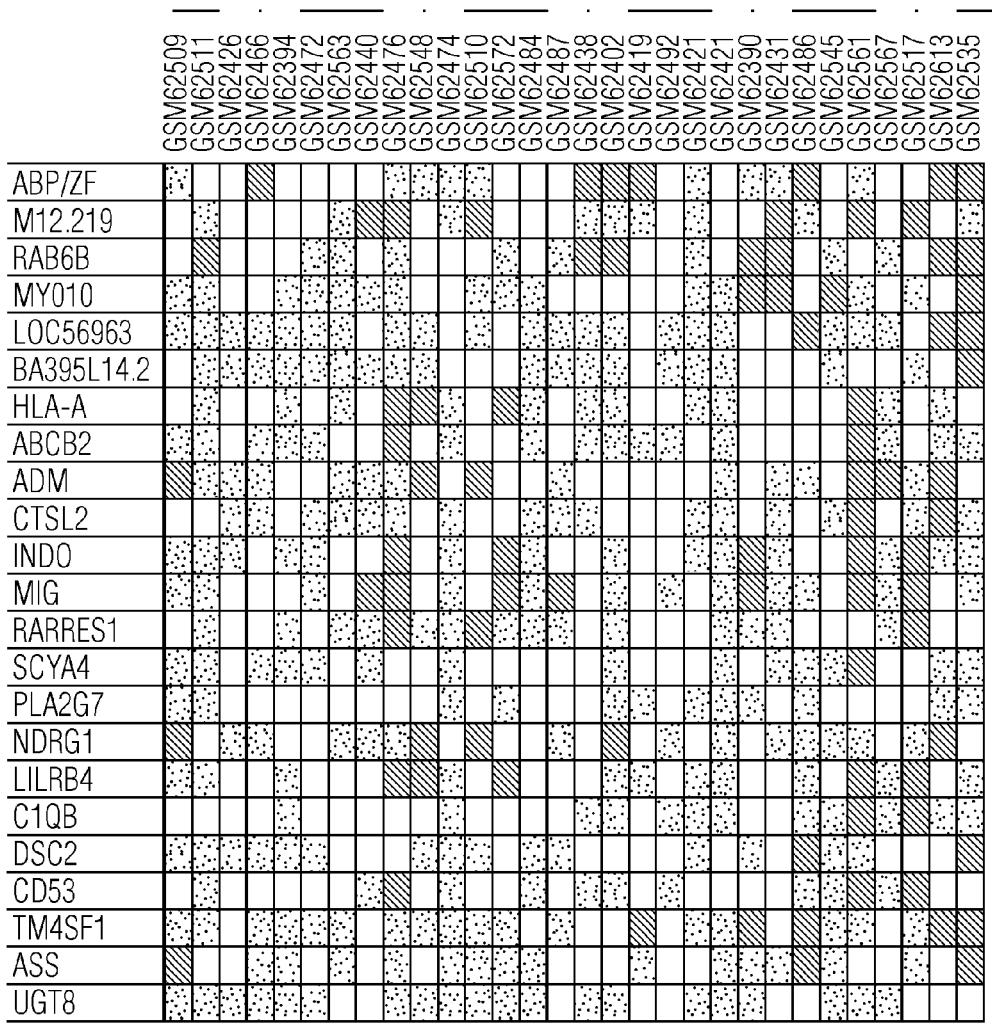
Figure 4W:
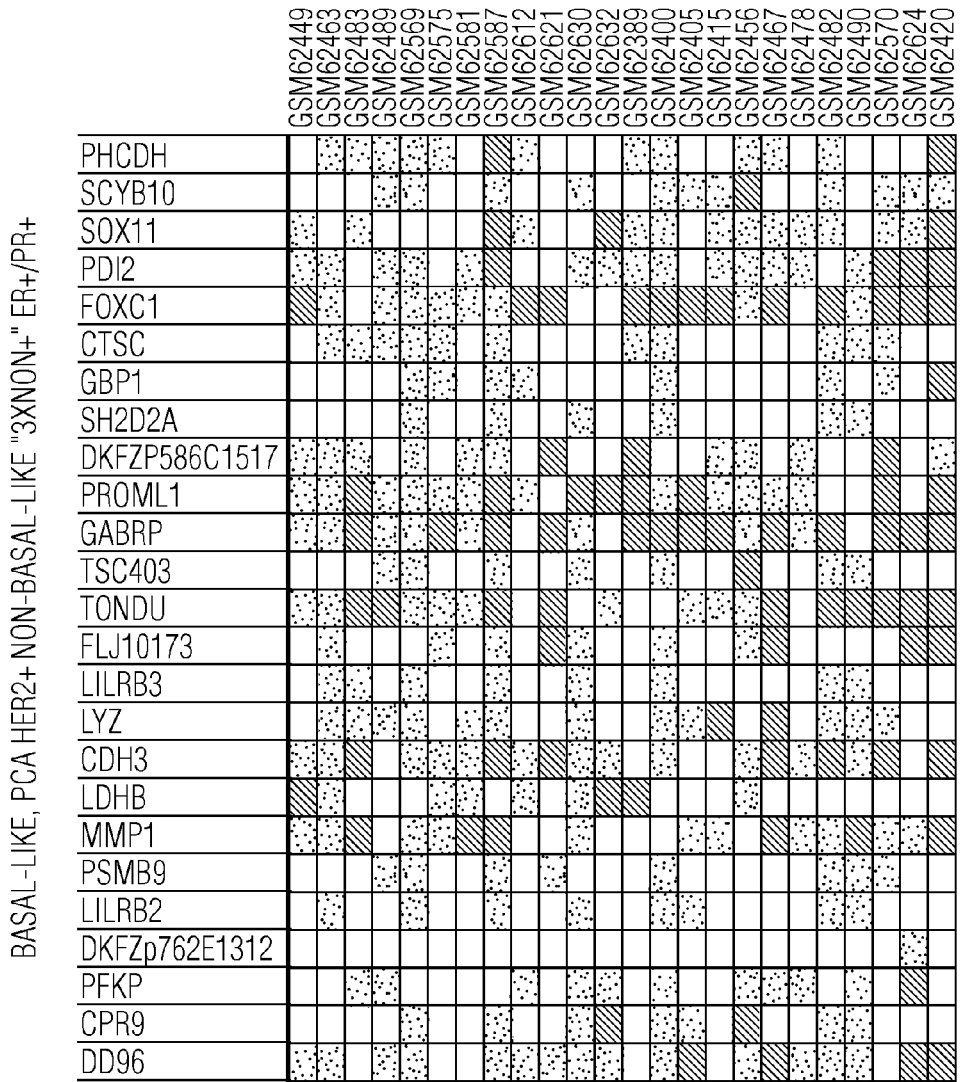
Figure 4X:
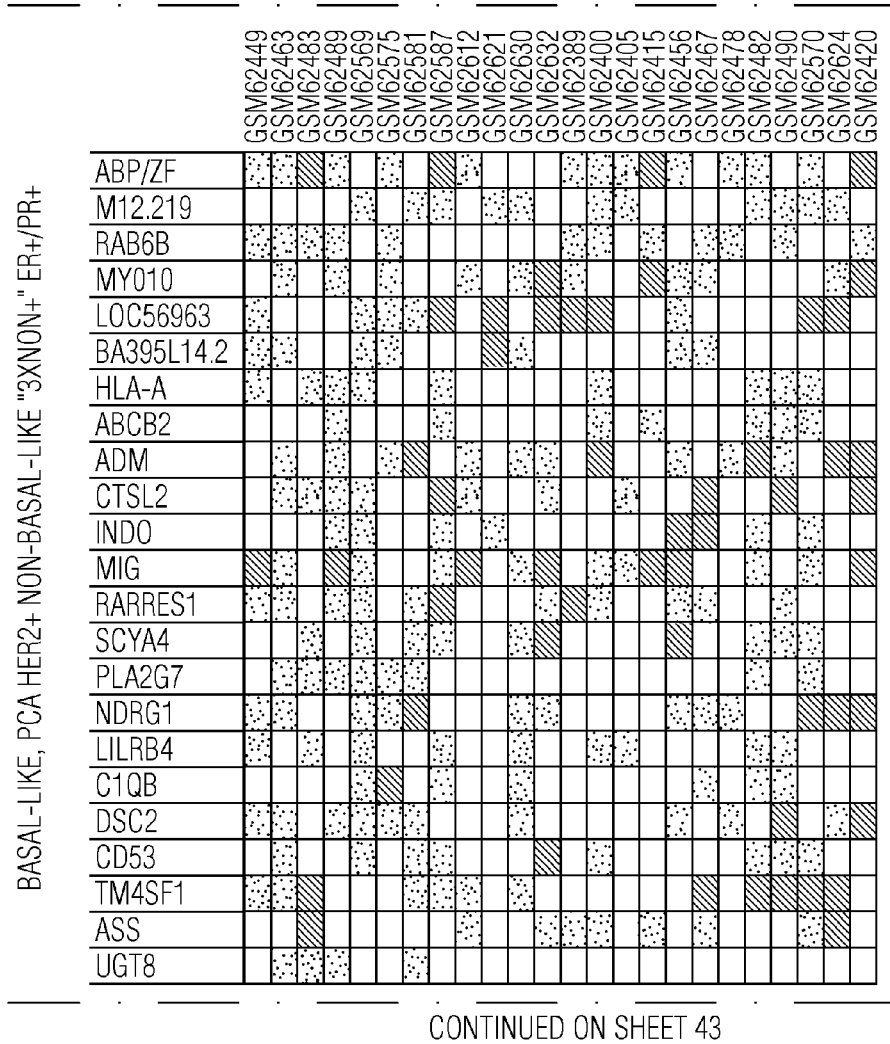
Figure 4Y:
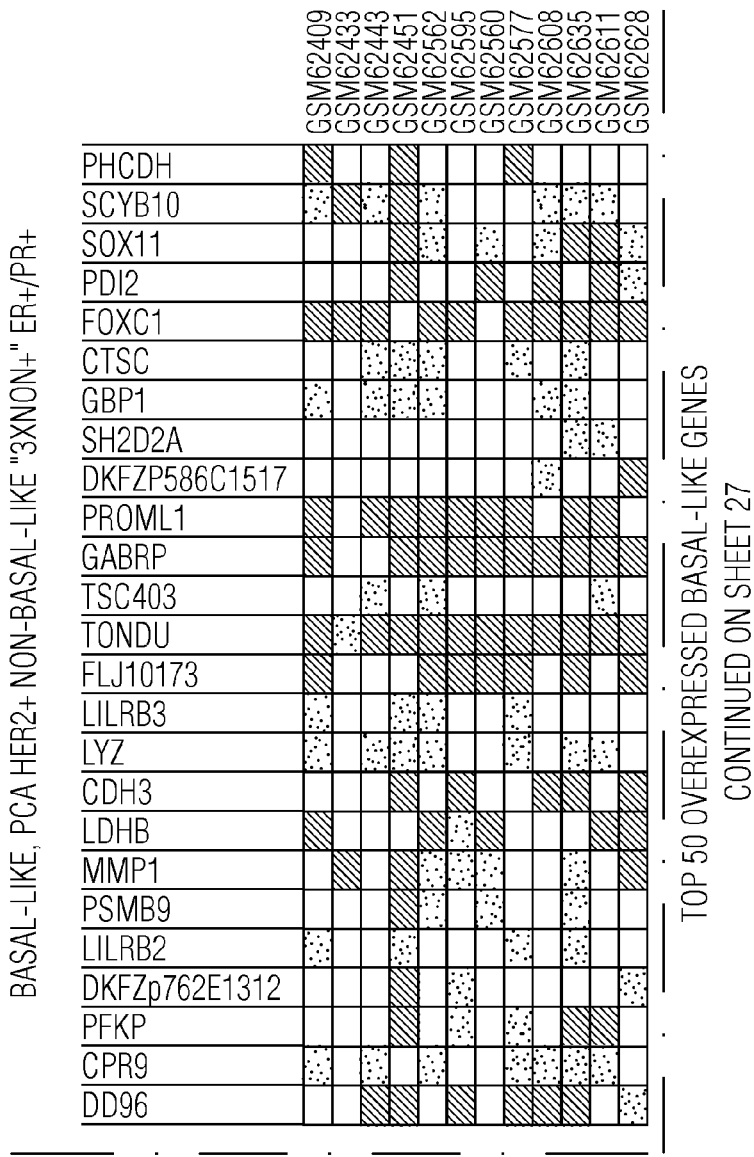
Figure 4A:
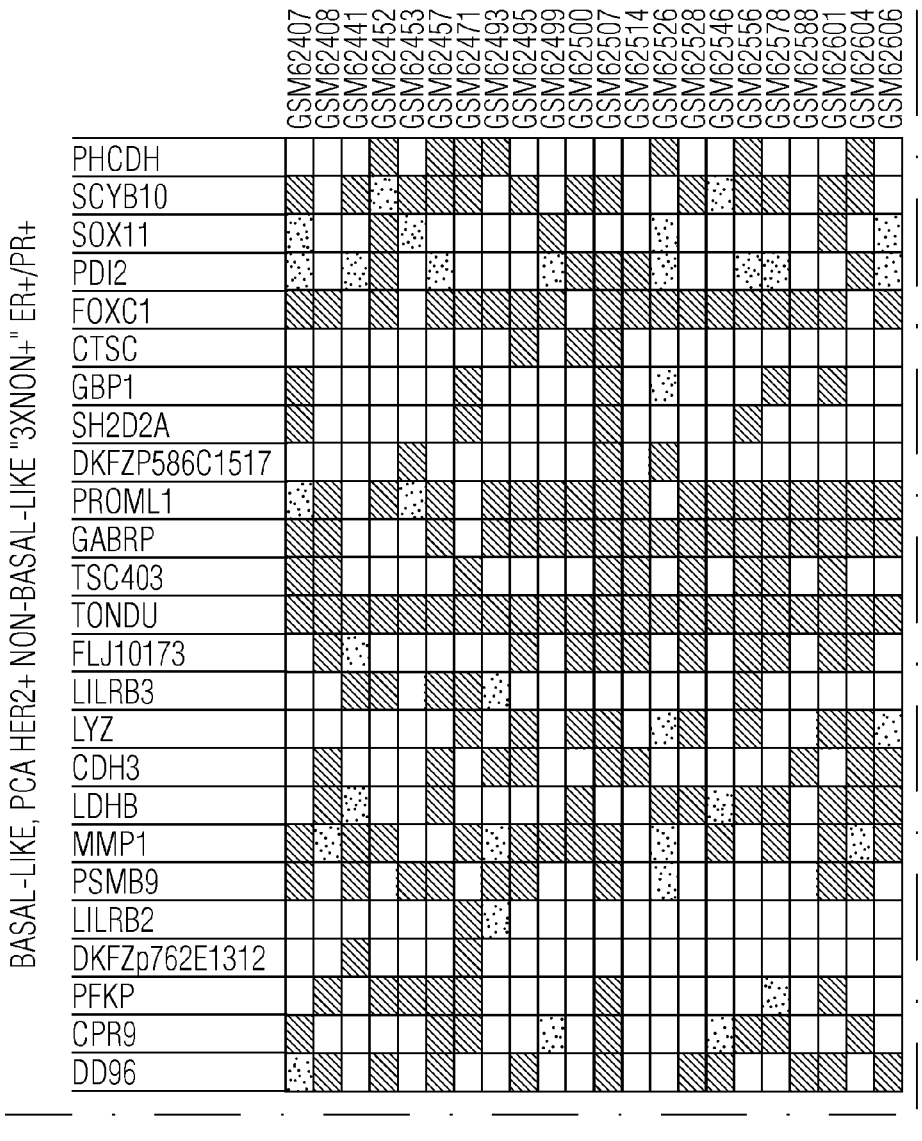
Figure 4B:
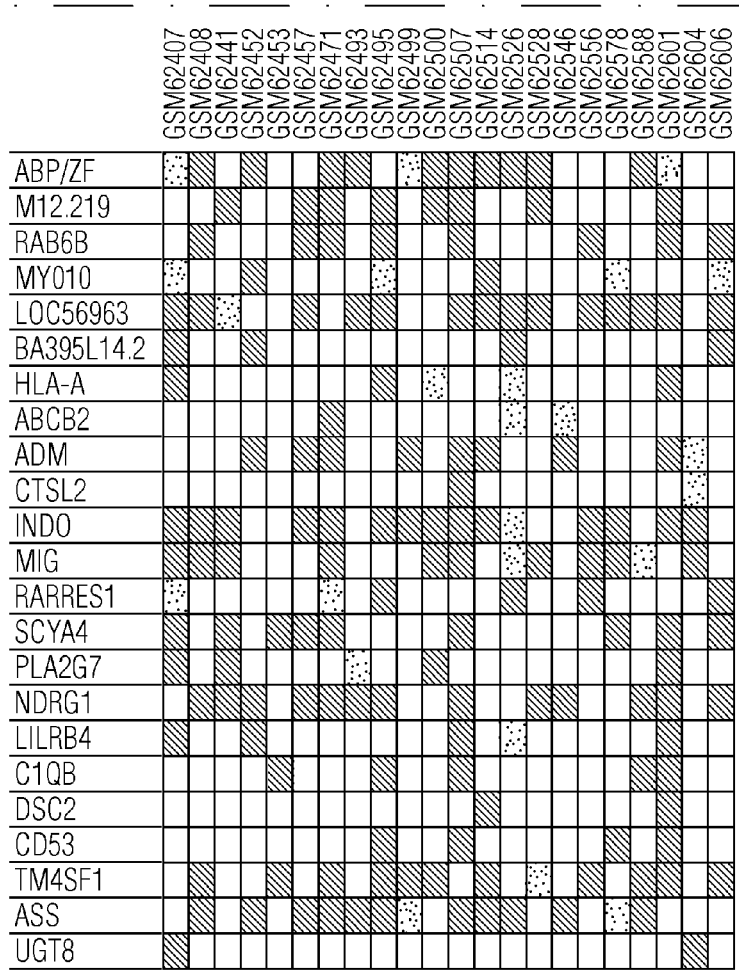
Figure 4C:
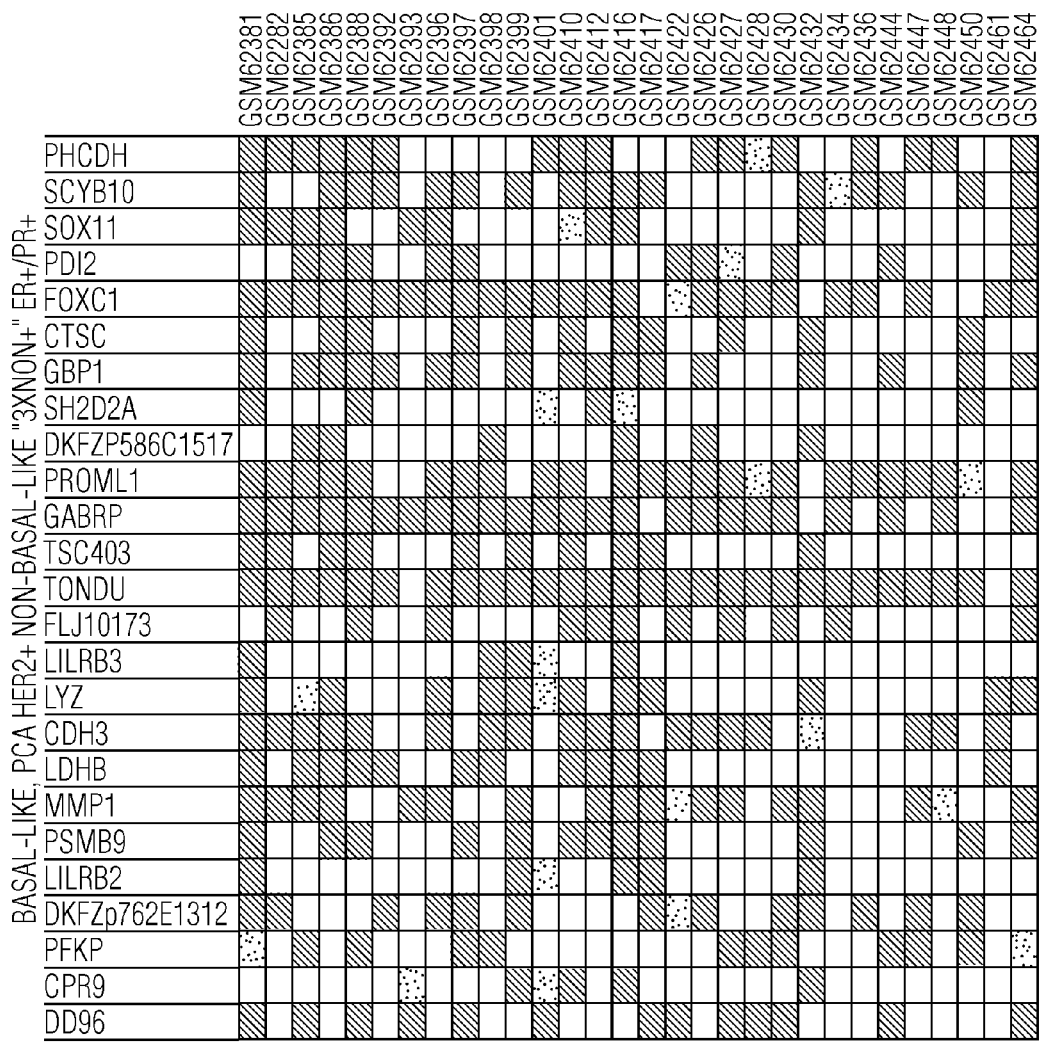
Figure 4D:
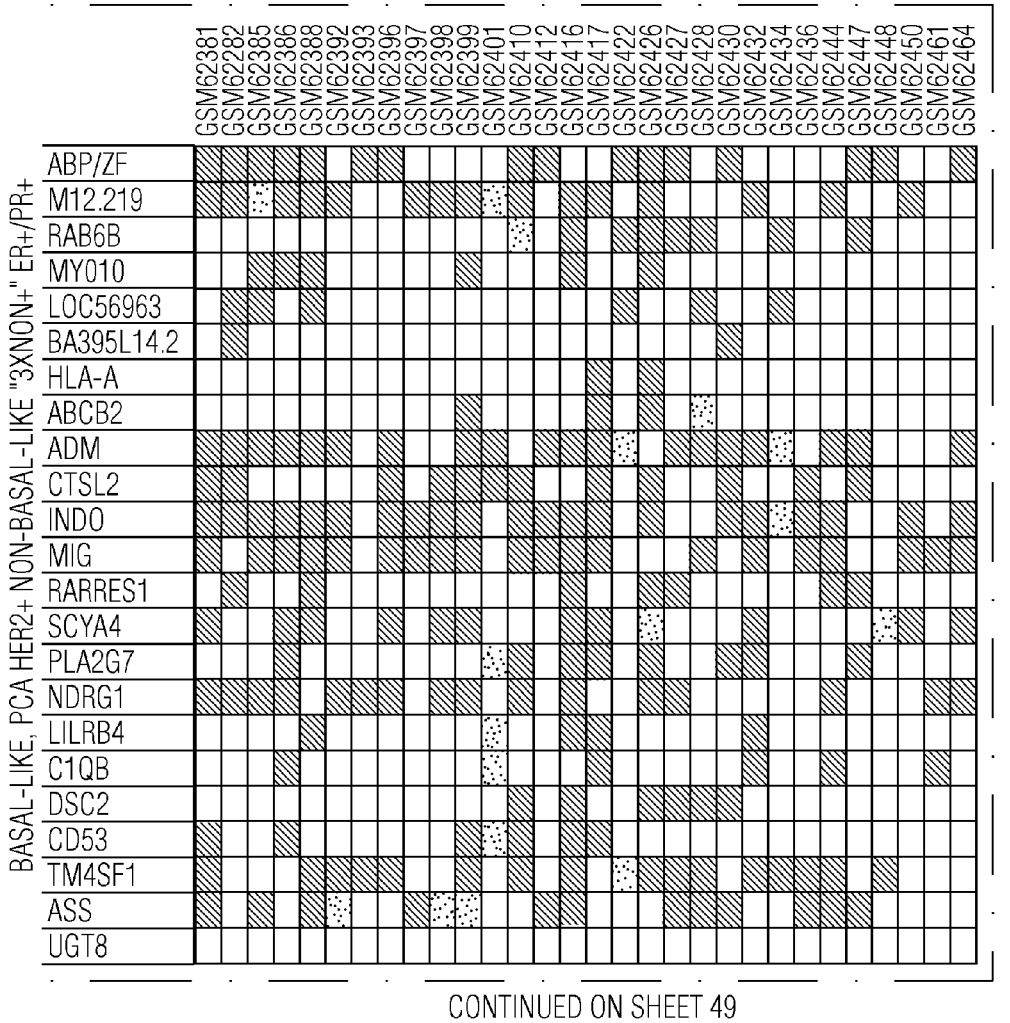
Figure 4F:
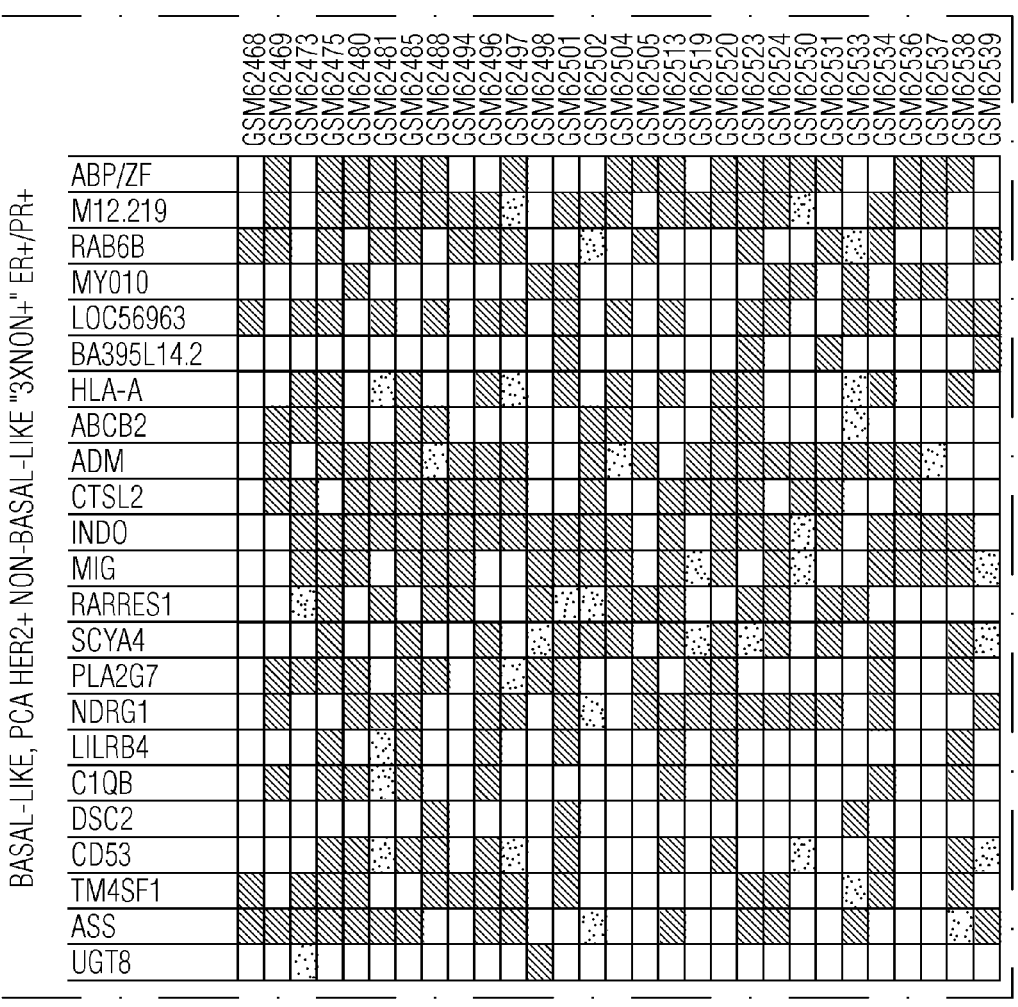
Figure 4G:
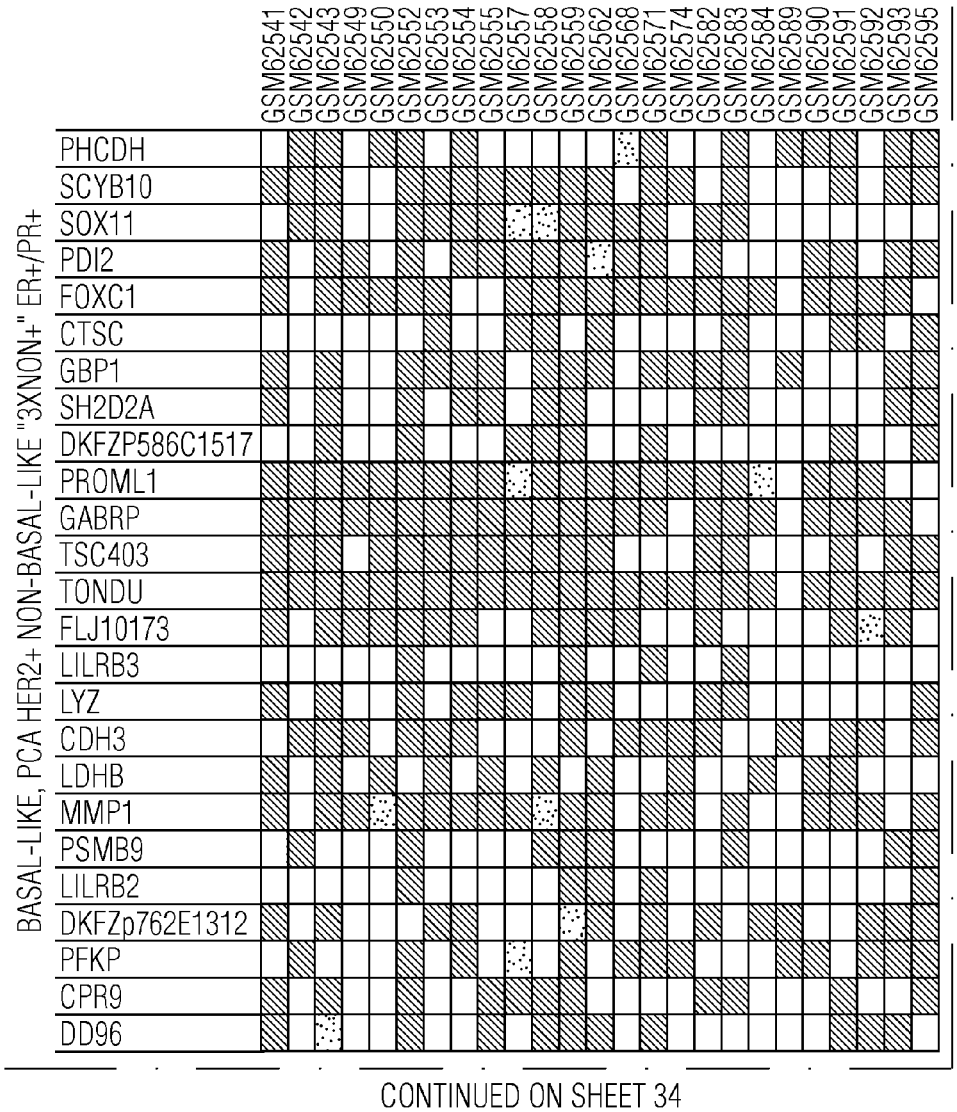
Figure 4I:
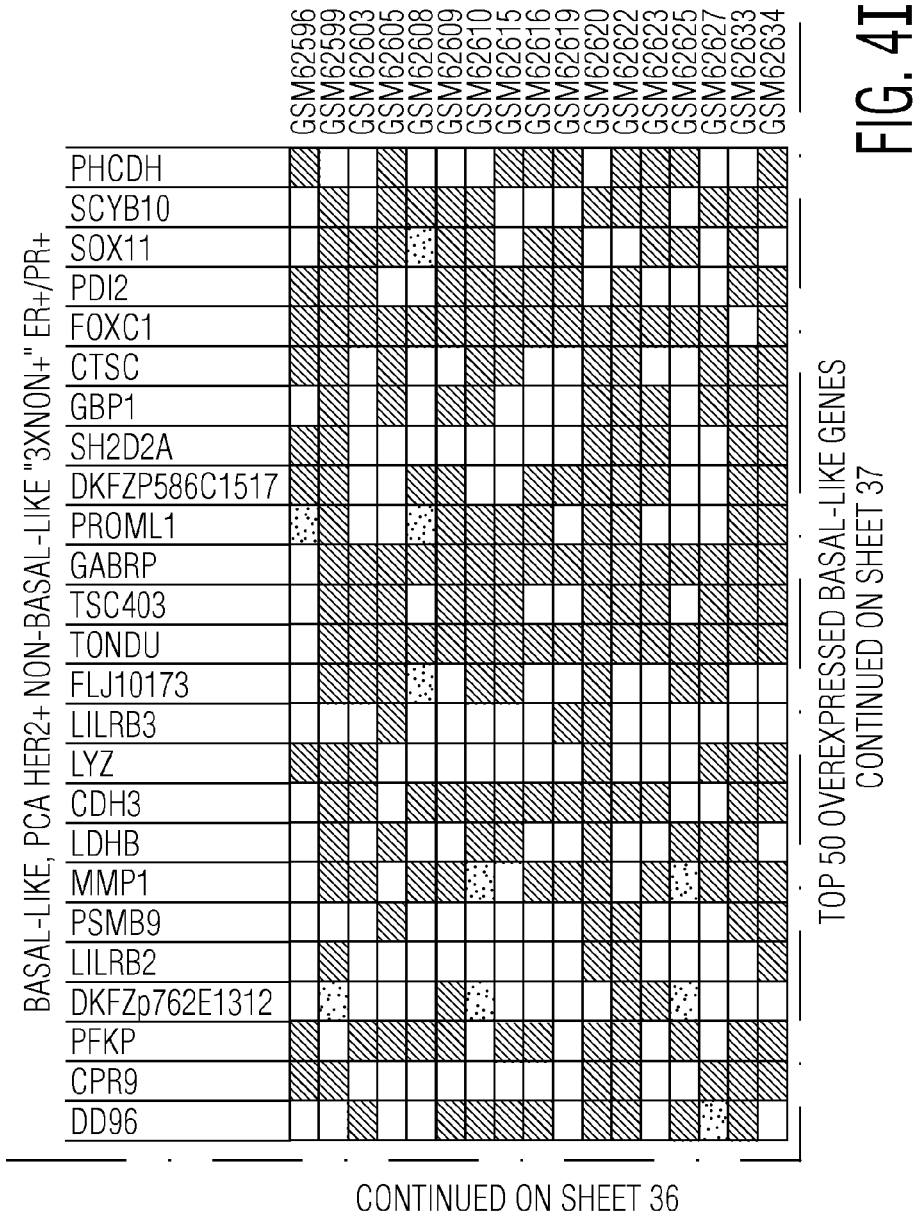
Figure 4J:
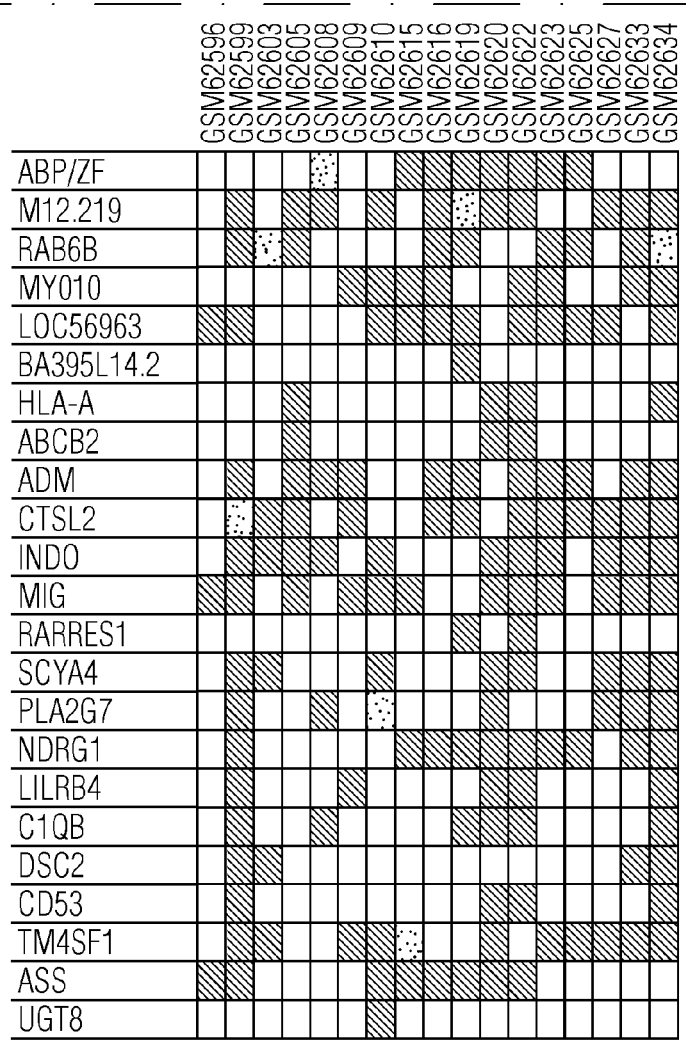
Figure 4K:
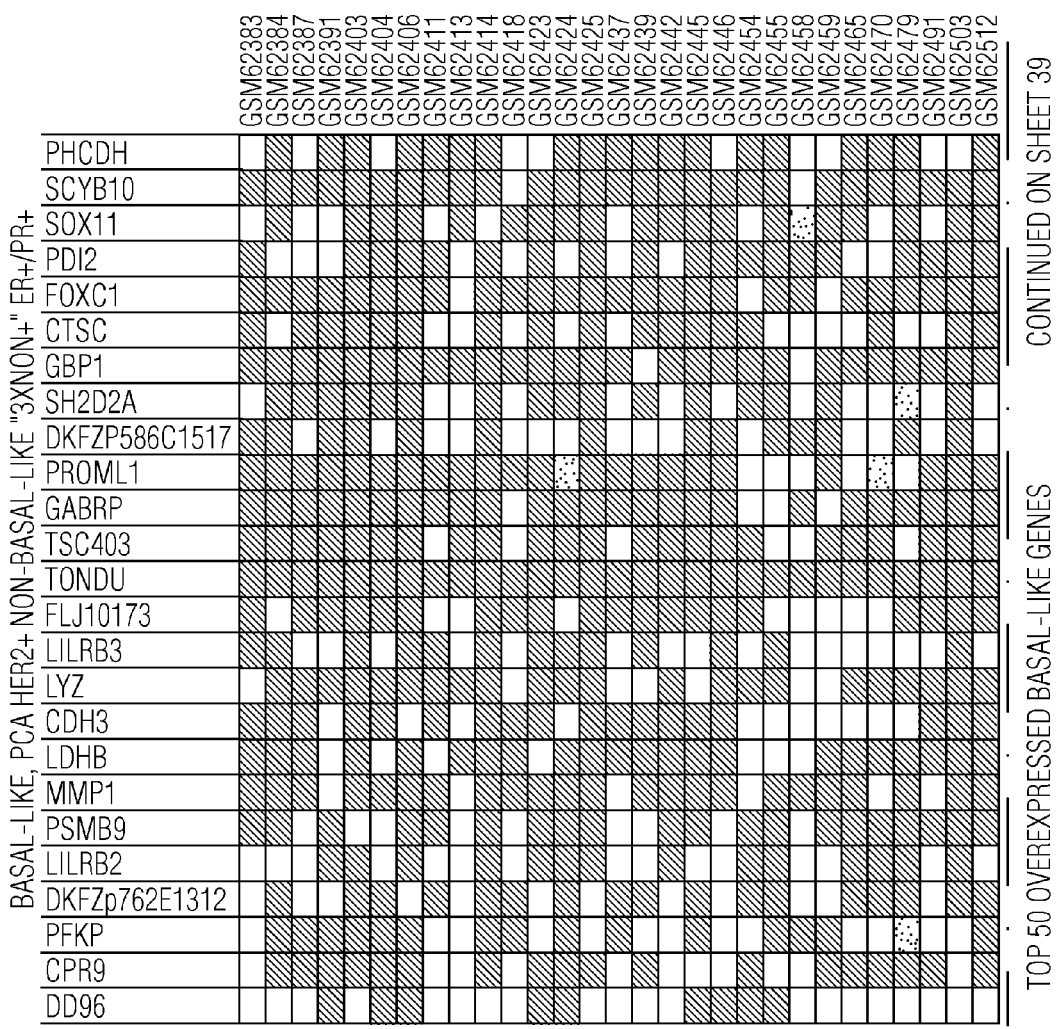
Figure 4M:
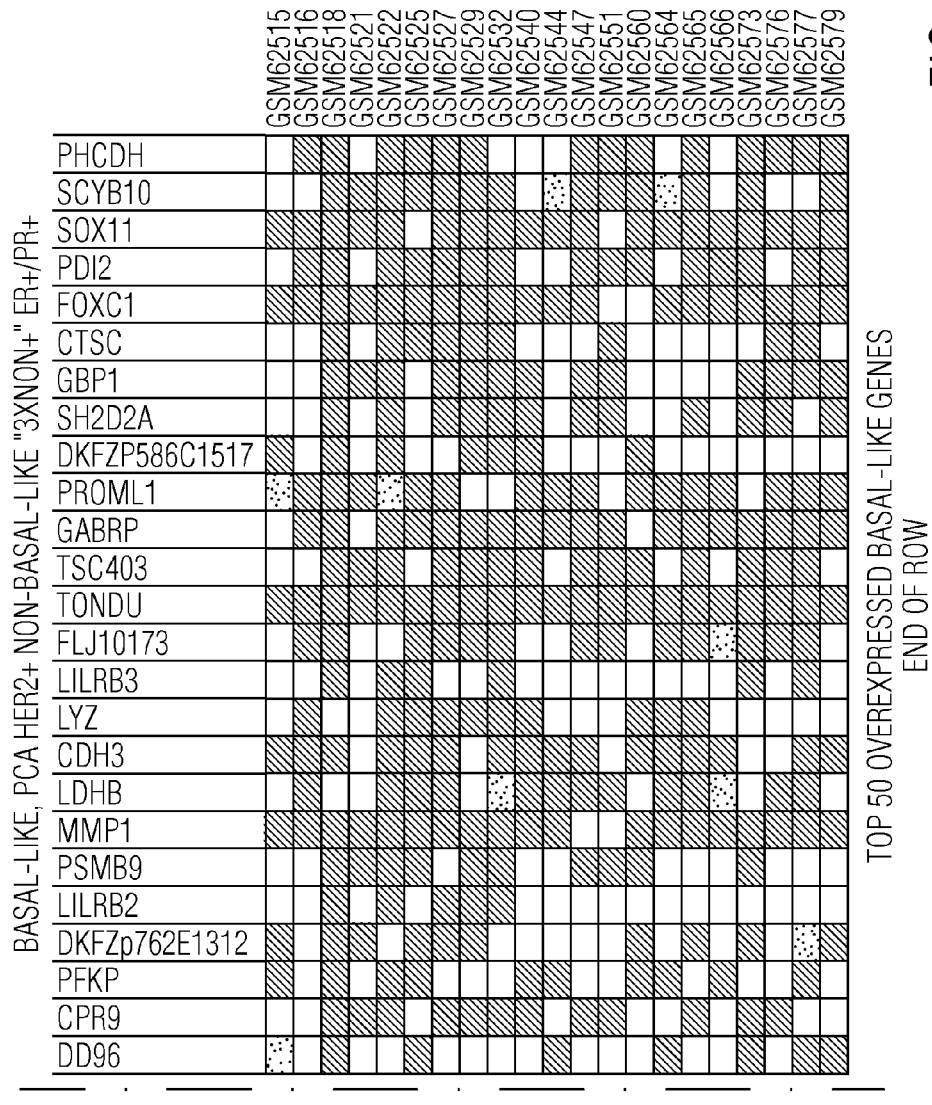
Figure 4N:
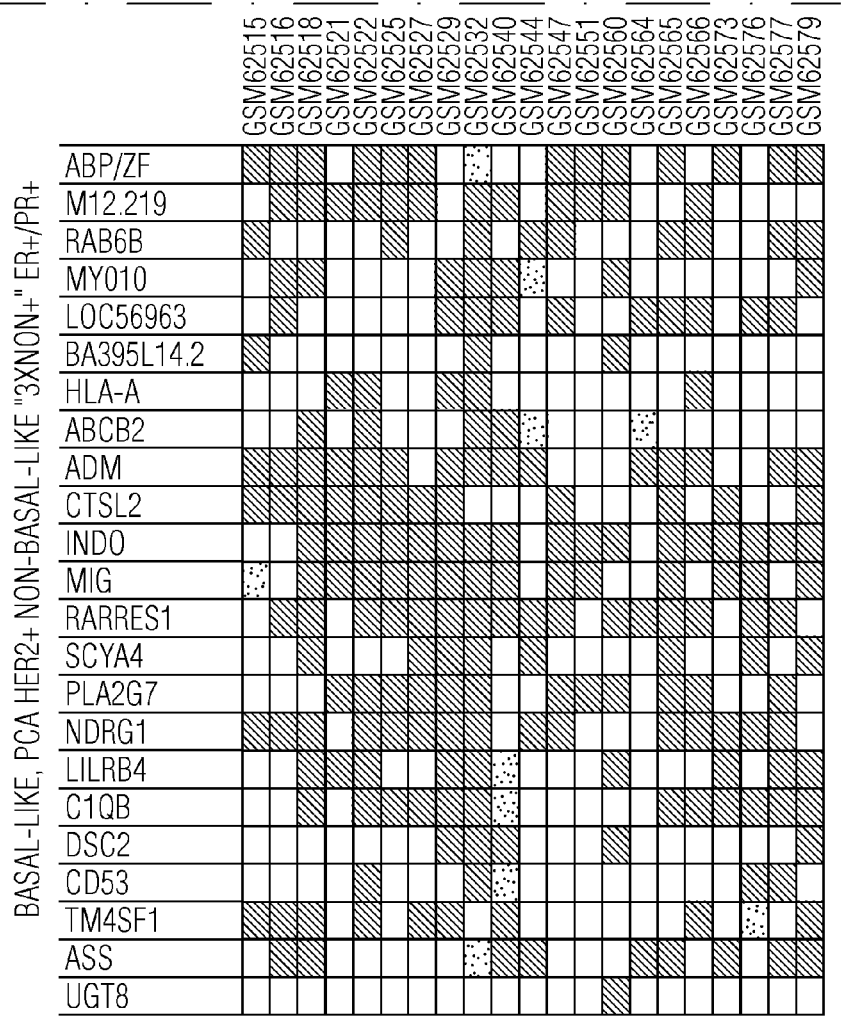
Figure 40O:
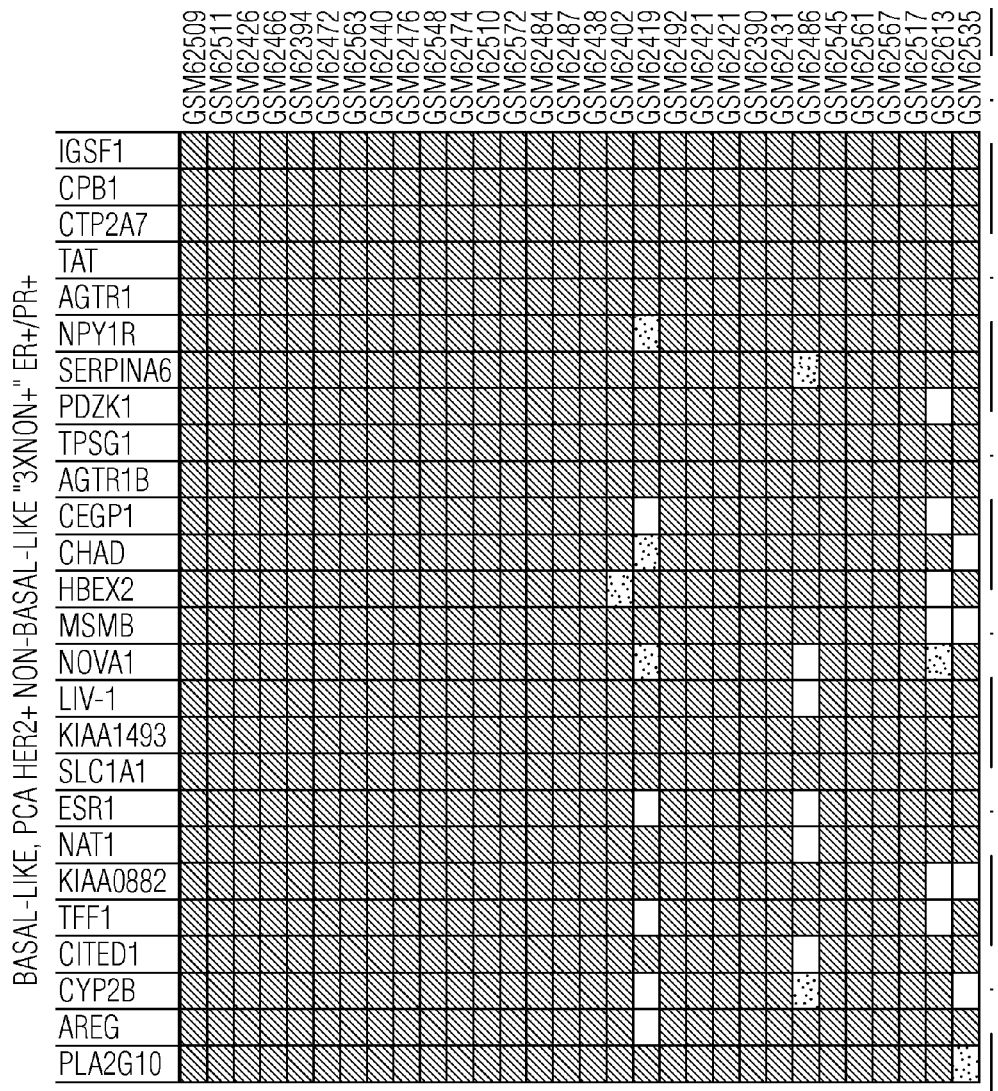
Figure 4P:
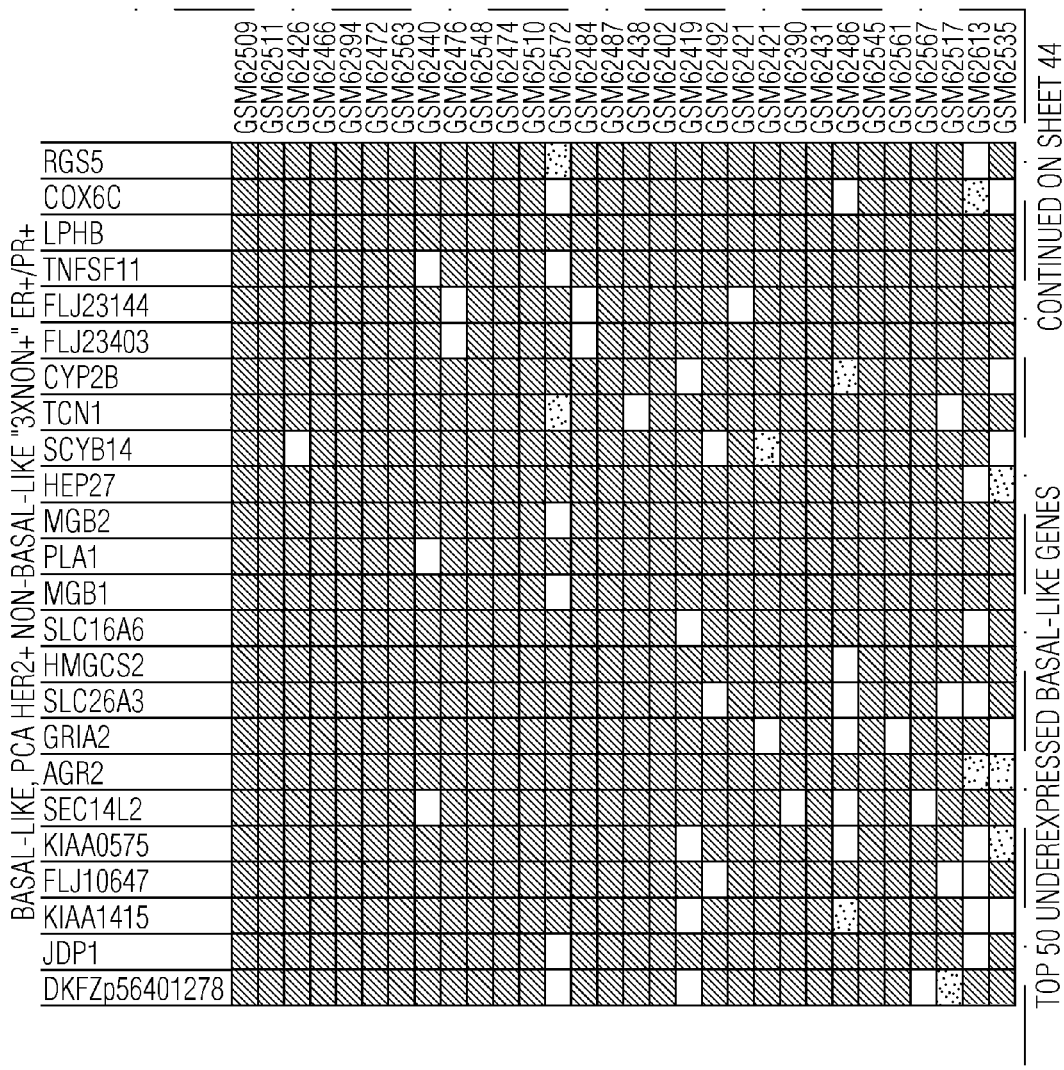
Figure 4Q:
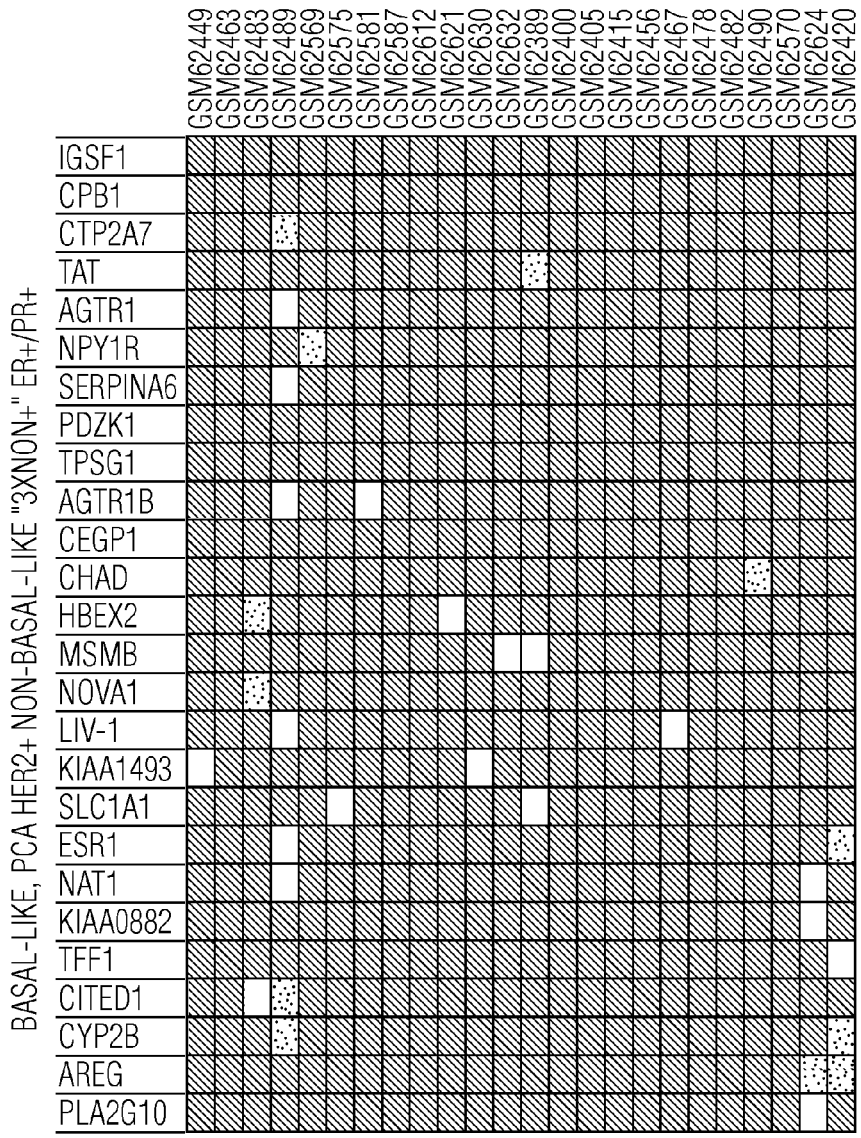
Figure 4R:
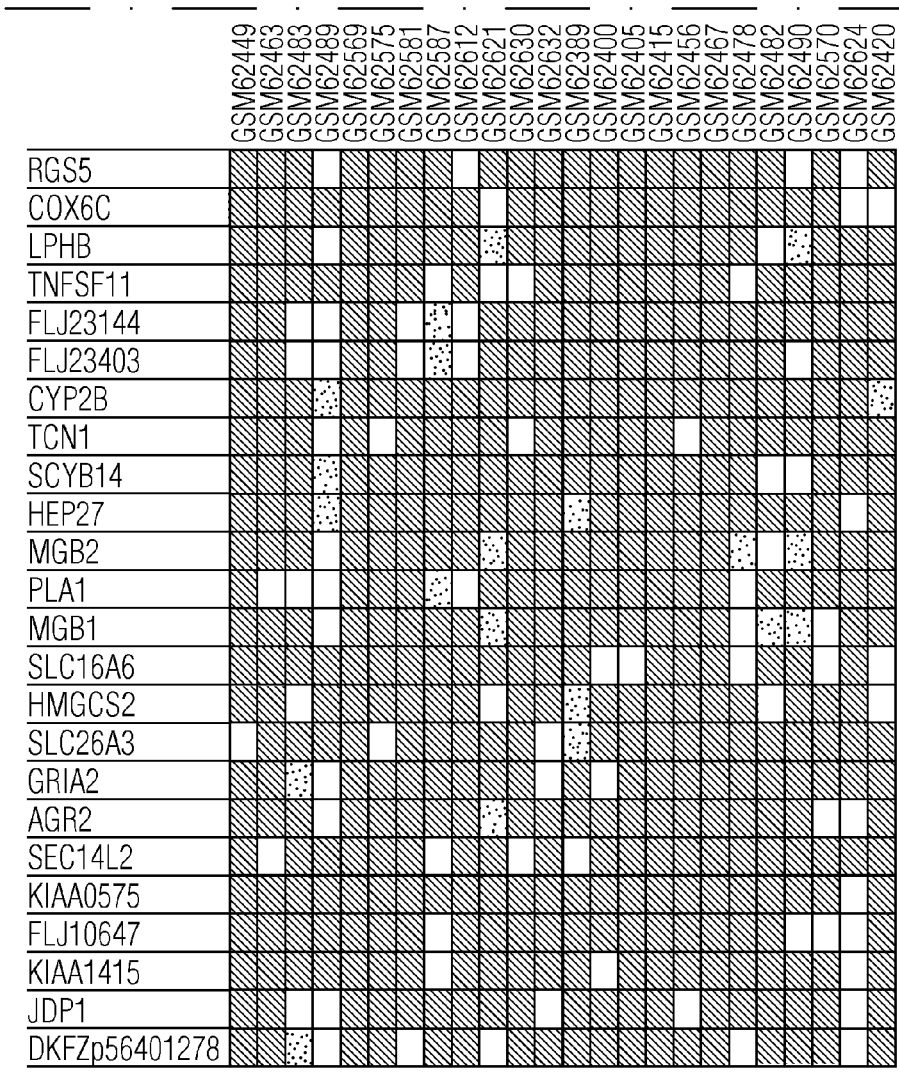
Figure 4S:
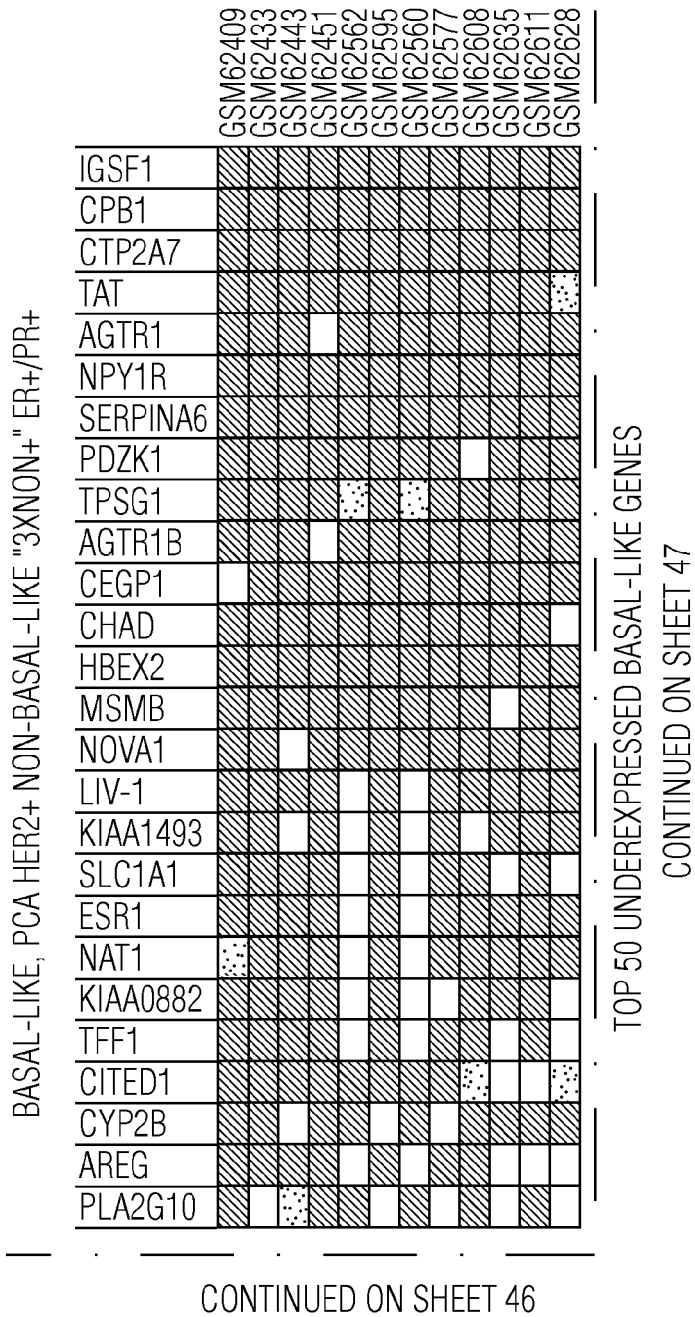
Figure 4U:
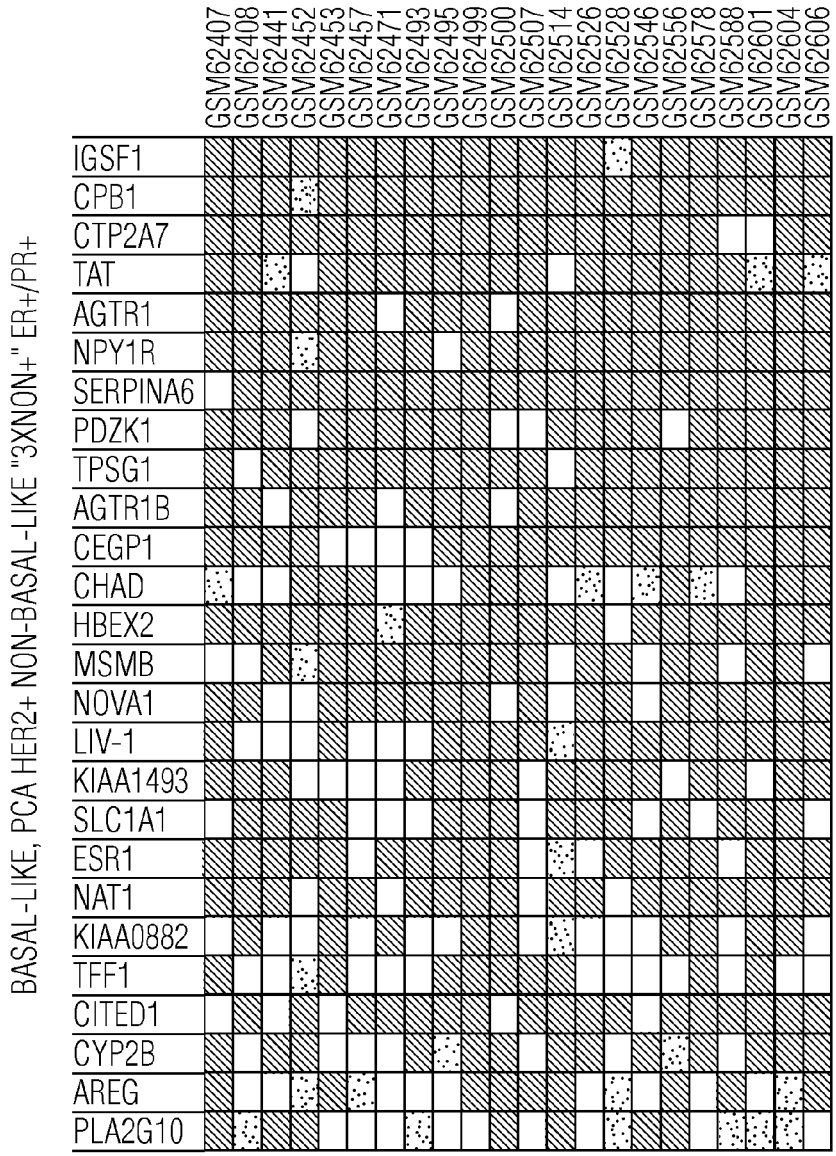
Figure 4V:
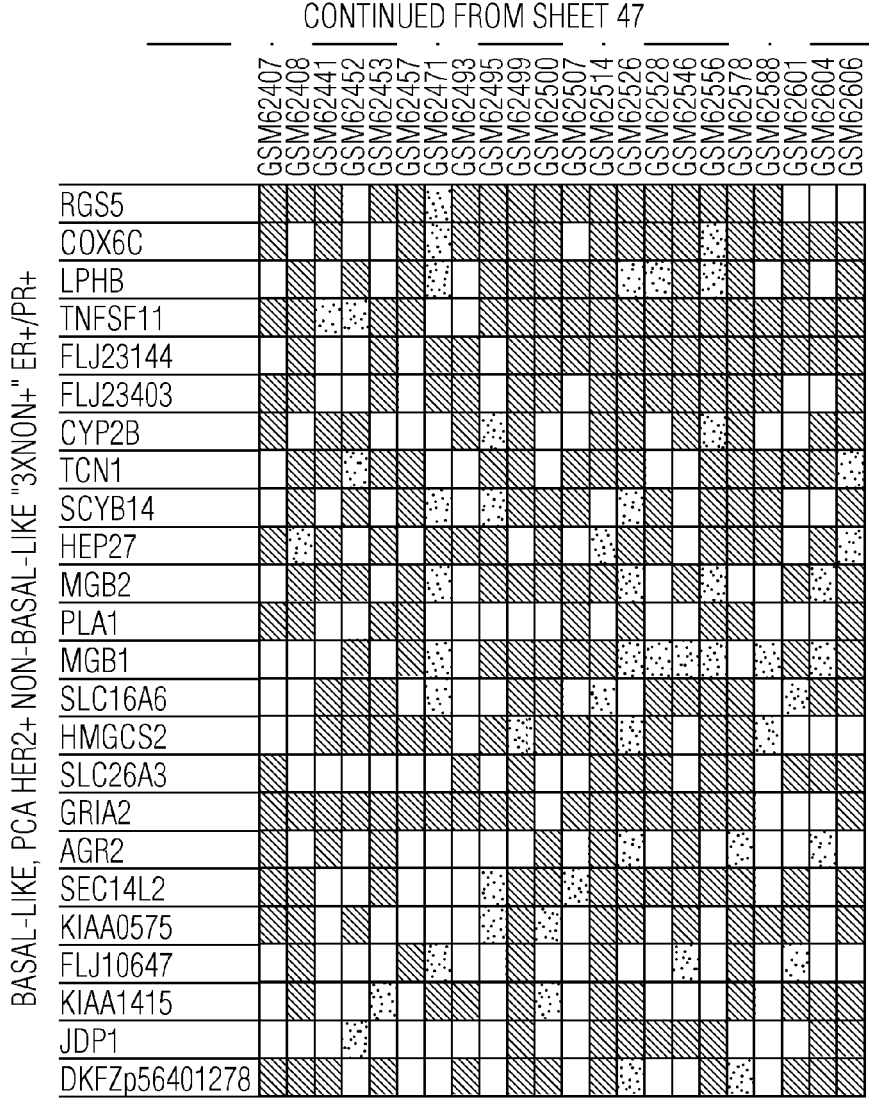
Figure 4W:
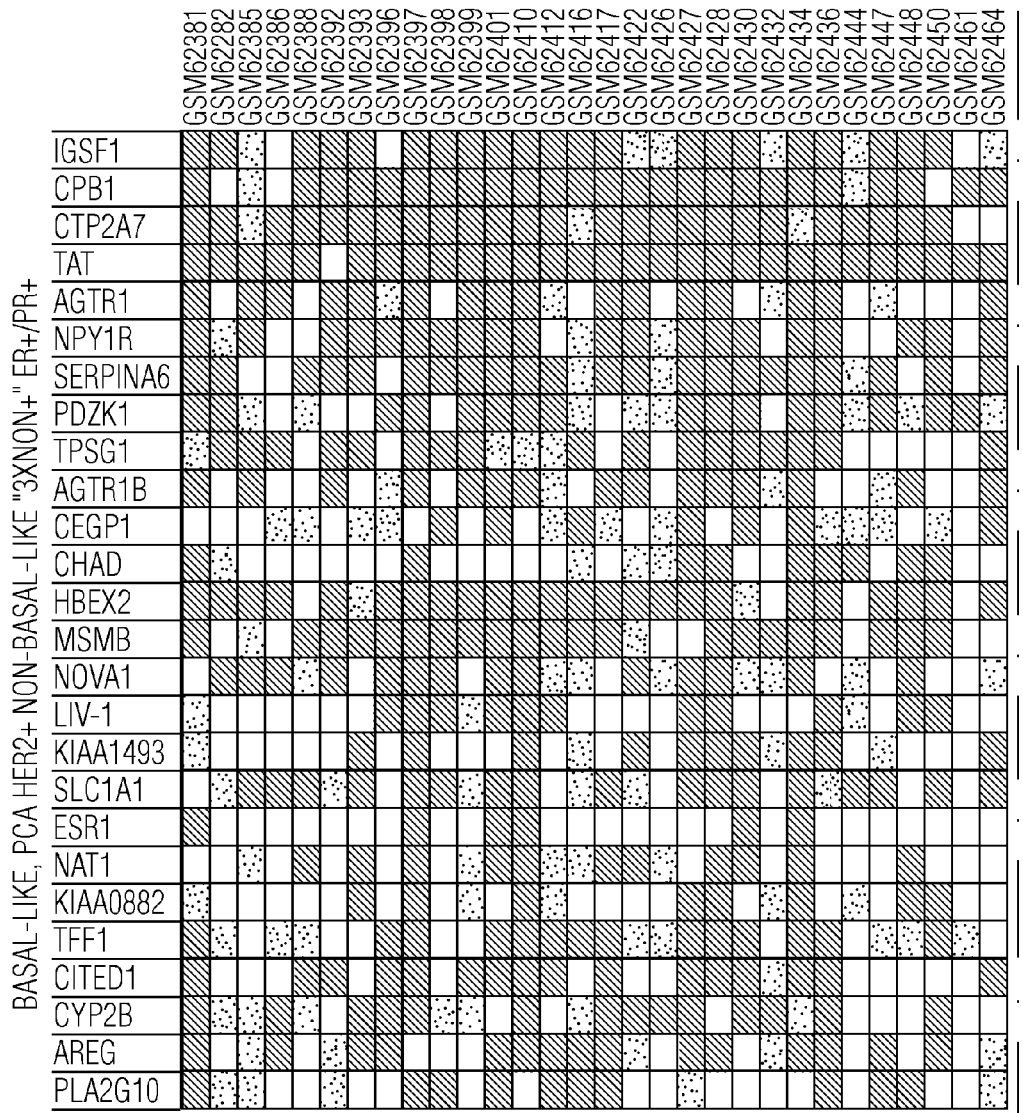
Figure 4X:
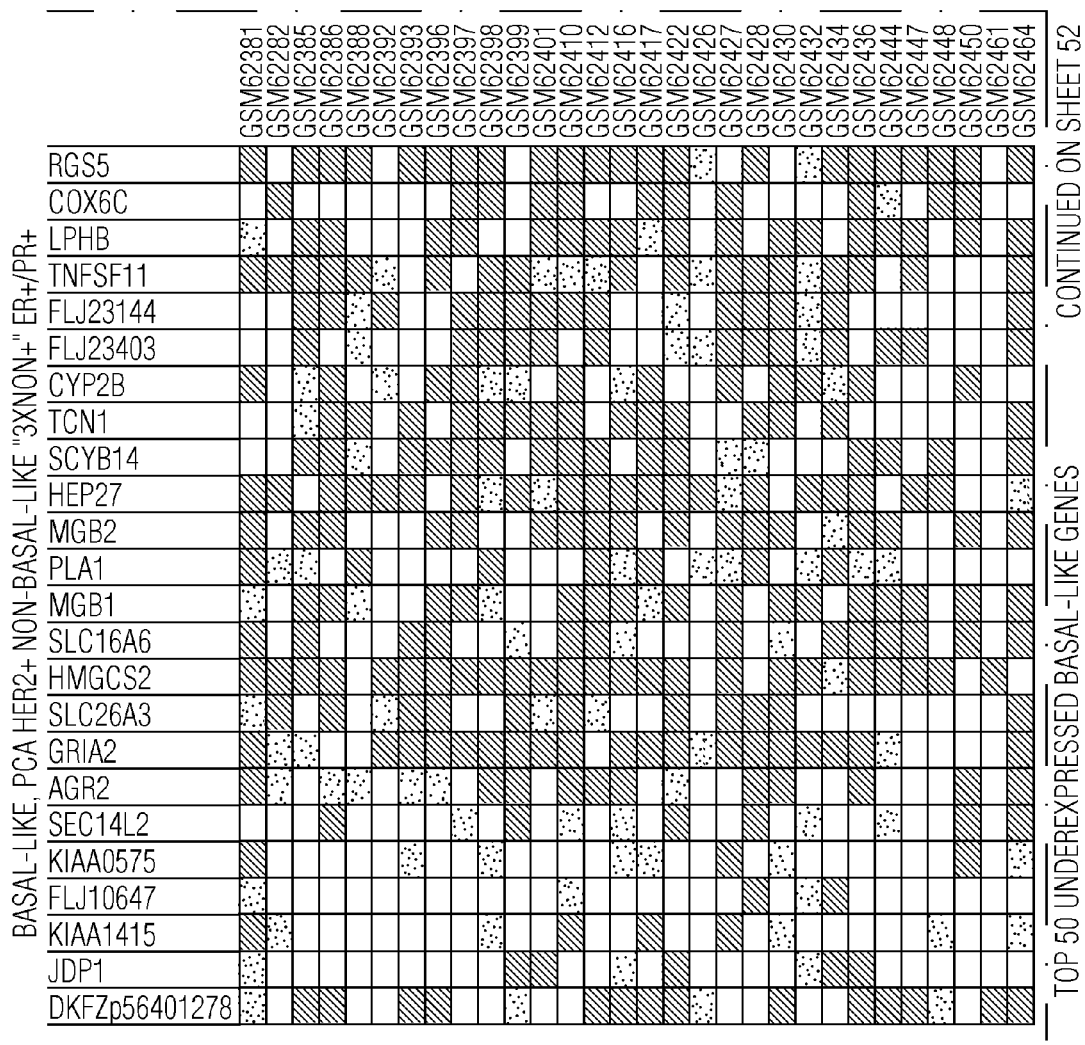
Figure 4Y:
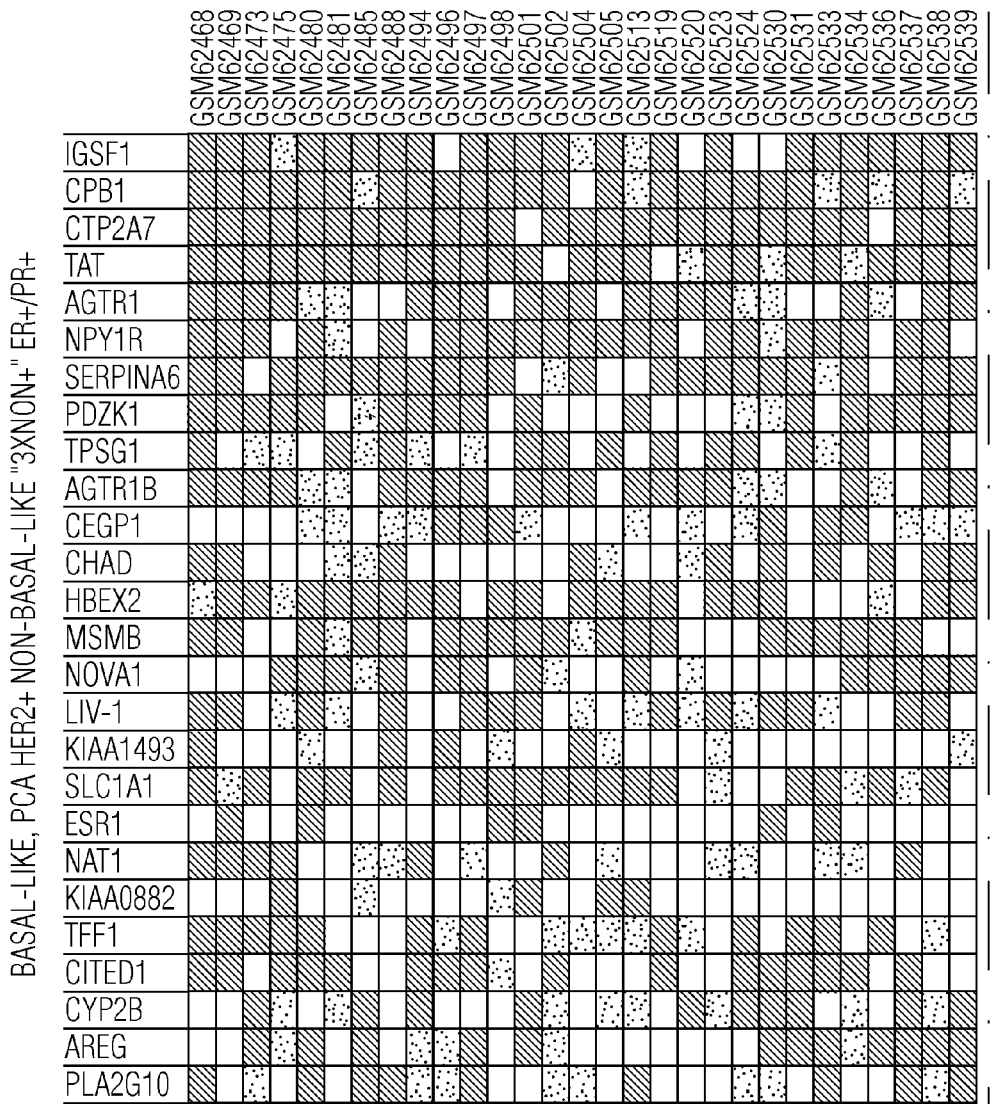
Figure 4Z:
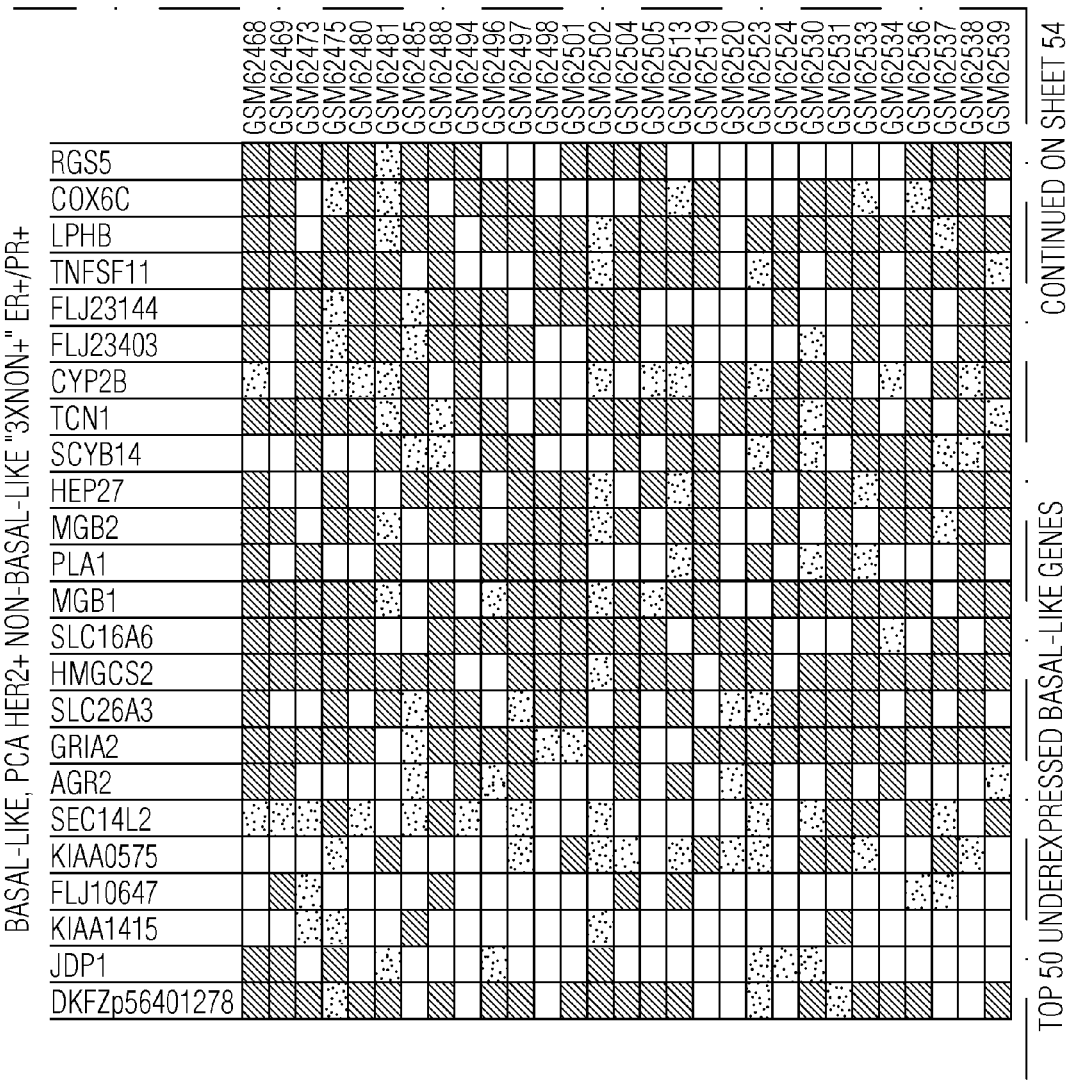

This refined PCA gene clustering analysis revealed a continuous strand of genes strung along the axis of the first principal component, rather than discrete gene clusters (FIG. 3A). The group of genes shown in black in the upper left in FIG. 3A are the E2F-responsive genes over-expressed most frequently among the basal-like tumor cluster identified by PCA as described above. A list of the most frequently over-expressed genes in the basal-like tumors identified by PCA was then compared to a list of most frequently over-expressed E2F-responsive genes in the ERGO tumors identified by the weighted rank ordering method. As shown in FIG. 3B these two lists are essentially identical for genes that are over-expressed in greater than 35% of the basal-like tumors identified by PCA or the ERGO tumors identified by the weighted rank-ordering method. Very few of the genes that were over-expressed in less than 25% of the basal-like tumors identified by PCA were also over-expressed by the ERGO tumors identified by the rank ordering method. Importantly, it was the ERGO tumors identified by the refined PCA analysis of the basal-like tumor cluster identified by PCA that over-expressed the highest number of E2F-responsive genes per individual tumor (FIG. 3C).

Patterns of Over-Expression and Under-Expression of Non-E2F-Responsive Genes in the Basal-Like Tumors Identified by PCA and the ERGO Tumors Identified by Refined PCA.

Over 850 non-E2F-responsive genes were over-expressed in at least 20% of PCA basal-like tumors identified by PCA, such that the differences in frequency of over-expression between the basal-like tumors identified by PCA and the non-basal-like tumors identified by PCA was statistically significant at the $P<0.05$ level. See FIG. 25 and Table 4 below.

TABLE 4

PCA Basal-Like Cancers

| gene name | mean(1) > mean(2) |
|---|---|
| KIAA0514 | 0 |
| BCL11A | 1.11E−16 |
| LDHB | 1.11E−16 |
| TONDU | 2.22E−16 |
| SH2D2A | 2.22E−16 |
| NCK1 | 5.55E−16 |
| CLCN4 | 6.66E−16 |
| C2orf2 | 6.66E−16 |
| FOXC1 | 1.22E−15 |
| CDH3 | 1.44E−15 |
| MSN | 1.67E−15 |
| LAMP3 | 2.78E−15 |
| PDI2 | 2.89E−15 |
| IMPA2 | 3.55E−15 |
| PFKP | 6.99E−15 |
| LOC51323 | 7.22E−15 |
| DKFZP564M2423 | 8.10E−15 |
| CTSL2 | 1.30E−14 |
| ODC1 | 2.28E−14 |
| NSEP1 | 4.60E−14 |
| LOC56963 | 5.01E−14 |
| TNFAIP3 | 6.56E−14 |
| CEBPG | 7.44E−14 |
| UGT8 | 2.06E−13 |
| RBMS1 | 2.24E−13 |
| ST5 | 2.75E−13 |
| H1F1 | 4.00E−13 |
| BA395L14.2 | 4.70E−13 |
| KIAA1209 | 5.83E−13 |

TABLE 4-continued

PCA Basal-Like Cancers

| gene name | mean(1) > mean(2) |
|---|---|
| ASNS | 7.26E−13 |
| FLJ10540 | 9.04E−13 |
| DKFZP586C1619 | 9.71E−13 |
| SCYD1 | 1.09E−12 |
| FLJ23399 | 1.12E−12 |
| FLJ11413 | 1.13E−12 |
| FLJ22833 | 1.18E−12 |
| DKFZp762A227 | 1.21E−12 |
| SH3BP1 | 1.50E−12 |
| KIAA0042 | 1.71E−12 |
| AF070552 | 2.66E−12 |
| KCNK5 | 3.25E−12 |
| LMO4 | 3.25E−12 |
| KIAA1350 | 3.25E−12 |
| SIAT8A | 3.25E−12 |
| PSA | 3.25E−12 |
| CTPS | 3.25E−12 |
| DSC2 | 3.25E−12 |
| KIAA1140 | 3.25E−12 |
| GABRP | 3.25E−12 |
| PHGDH | 3.25E−12 |
| DKFZp762E1312 | 3.25E−12 |
| PIM1 | 3.25E−12 |
| SIL | 3.25E−12 |
| TM4SF1 | 3.25E−12 |
| ATDC | 3.26E−12 |
| DKFZp564A026 | 3.27E−12 |
| NFIL3 | 3.27E−12 |
| PROML1 | 3.29E−12 |
| AF052117 | 3.29E−12 |
| PRO1659 | 3.29E−12 |
| DIAPH3 | 3.30E−12 |
| SCYA18 | 3.32E−12 |
| ICB-1 | 3.33E−12 |
| IL6 | 3.34E−12 |
| GBP1 | 3.35E−12 |
| SERPINB5 | 3.44E−12 |
| KCNN4 | 3.49E−12 |
| MID1 | 3.49E−12 |
| KIP2 | 3.54E−12 |
| MYBL2 | 3.55E−12 |
| FLJ20005 | 3.63E−12 |
| KIAA0074 | 3.64E−12 |
| HMGIY | 3.68E−12 |
| NDRG1 | 3.75E−12 |
| KIAA1553 | 3.79E−12 |
| EXO1 | 4.20E−12 |
| SNL | 4.23E−12 |
| HSU54999 | 4.36E−12 |
| GZMB | 4.53E−12 |
| PRO2249 | 4.65E−12 |
| MCCC1 | 5.09E−12 |
| KIAA1285 | 5.21E−12 |
| SMOC1 | 5.43E−12 |
| KIAA0481 | 5.45E−12 |
| TMEFF1 | 5.46E−12 |
| NSAP1 | 5.53E−12 |
| VIM | 5.58E−12 |
| FLJ20354 | 6.05E−12 |
| RUNX3 | 6.14E−12 |
| CHIC2 | 6.45E−12 |
| FLJ13154 | 6.84E−12 |
| FLJ10468 | 7.28E−12 |
| UQCRH | 7.88E−12 |
| PRKCN | 8.01E−12 |
| ME1 | 8.11E−12 |
| MARCO | 8.25E−12 |
| PRKX | 8.73E−12 |
| FLJ20186 | 8.79E−12 |
| FZD9 | 9.40E−12 |
| GMPS | 9.44E−12 |
| DKFZP762N2316 | 9.90E−12 |
| KIAA0159 | 1.07E−11 |
| LOC51700 | 1.07E−11 |
| NMB | 1.13E−11 |

TABLE 4-continued

PCA Basal-Like Cancers

| gene name | mean(1) > mean(2) |
|---|---|
| LOC64148 | 1.42E−11 |
| HSPC159 | 1.42E−11 |
| GAPDS | 1.43E−11 |
| TRIM2 | 1.49E−11 |
| LAD1 | 1.54E−11 |
| ARL7 | 1.55E−11 |
| HSRNASEB | 1.55E−11 |
| NMT2 | 1.60E−11 |
| AL110202 | 1.61E−11 |
| FLJ10156 | 1.66E−11 |
| KRT16 | 1.73E−11 |
| SOAT1 | 1.75E−11 |
| SCYA13 | 1.80E−11 |
| KIAA0746 | 1.85E−11 |
| FLJ21079 | 2.01E−11 |
| ITM2C | 2.51E−11 |
| DKFZP434G032 | 2.82E−11 |
| DKFZP586G1517 | 2.82E−11 |
| FLJ12649 | 3.04E−11 |
| MRAS | 3.17E−11 |
| NFE2L3 | 3.79E−11 |
| FLJ20425 | 4.24E−11 |
| AF131753 | 4.39E−11 |
| PTX3 | 4.77E−11 |
| KIAA1448 | 4.81E−11 |
| HSU93243 | 5.16E−11 |
| VRK2 | 5.23E−11 |
| DUSP9 | 5.30E−11 |
| FLJ23293 | 5.74E−11 |
| LRP8 | 6.19E−11 |
| TFDP1 | 6.74E−11 |
| SCHIP1 | 6.88E−11 |
| FLJ10549 | 7.01E−11 |
| EGFL6 | 7.63E−11 |
| PCDH8 | 7.84E−11 |
| GAPD | 7.92E−11 |
| FLJ23414 | 8.75E−11 |
| KIAA1069 | 8.88E−11 |
| CHI3L1 | 8.96E−11 |
| SCYA2 | 9.14E−11 |
| MGC4090 | 9.16E−11 |
| MPB1 | 9.21E−11 |
| CSPG6 | 9.66E−11 |
| NOGOR | 1.04E−10 |
| FLJ11252 | 1.08E−10 |
| KIAA0077 | 1.10E−10 |
| TTYH1 | 1.18E−10 |
| DUSP2 | 1.20E−10 |
| HHGP | 1.26E−10 |
| SRPK1 | 1.30E−10 |
| CA9 | 1.41E−10 |
| FLJ11029 | 1.42E−10 |
| ZNF267 | 1.45E−10 |
| KIAA0095 | 1.48E−10 |
| LPIN1 | 1.58E−10 |
| PGM1 | 1.62E−10 |
| KIAA1357 | 1.65E−10 |
| KLK6 | 1.72E−10 |
| CHST2 | 1.75E−10 |
| IFRD1 | 1.75E−10 |
| CIN85 | 1.93E−10 |
| AL050151 | 1.97E−10 |
| JRKL | 2.09E−10 |
| ADM | 2.10E−10 |
| RIPK2 | 2.12E−10 |
| DJ742C19.2 | 2.47E−10 |
| KIAA0008 | 2.60E−10 |
| ENO1 | 2.68E−10 |
| LOC56938 | 2.72E−10 |
| AMD1 | 2.87E−10 |
| SNN | 3.00E−10 |
| UMPK | 3.11E−10 |
| PLD1 | 3.19E−10 |
| FABP7 | 3.21E−10 |
| POLR2F | 3.49E−10 |
| SOX11 | 3.57E−10 |
| AK001295 | 4.06E−10 |
| SOX10 | 4.17E−10 |
| FLJ22341 | 4.24E−10 |
| SOD2 | 4.40E−10 |
| PLCG2 | 4.61E−10 |
| FLJ10549 | 4.68E−10 |
| MMP12 | 4.70E−10 |
| CALB2 | 4.77E−10 |
| DAPK1 | 4.80E−10 |
| EBI2 | 5.53E−10 |
| RAB6B | 5.84E−10 |
| MIA | 5.92E−10 |
| PTTG2 | 6.06E−10 |
| MYO10 | 6.25E−10 |
| LIPG | 6.43E−10 |
| S100A6 | 6.56E−10 |
| ADAMTS7 | 6.64E−10 |
| MMP7 | 7.37E−10 |
| GDF5 | 7.90E−10 |
| RARRES1 | 8.20E−10 |
| ILF2 | 8.56E−10 |
| EIF2C2 | 8.85E−10 |
| S100A10 | 8.88E−10 |
| FLJ10829 | 1.02E−09 |
| KLF5 | 1.05E−09 |
| PLA2G4A | 1.08E−09 |
| LOC55971 | 1.09E−09 |
| TCN2 | 1.12E−09 |
| BENE | 1.19E−09 |
| KIAA1424 | 1.23E−09 |
| HOMER-3 | 1.44E−09 |
| ADORA2B | 1.59E−09 |
| FABP5 | 1.69E−09 |
| CLSP | 2.00E−09 |
| LCK | 2.20E−09 |
| ADFP | 2.21E−09 |
| STRIN | 2.32E−09 |
| INDO | 2.33E−09 |
| CDK2AP1 | 2.51E−09 |
| ASS | 2.51E−09 |
| SBBI26 | 2.52E−09 |
| LOC51765 | 2.60E−09 |
| FLJ10901 | 2.60E−09 |
| BCL2A1 | 2.83E−09 |
| GSTP1 | 2.94E−09 |
| BPI | 3.21E−09 |
| CYP39A1 | 3.41E−09 |
| D123 | 3.46E−09 |
| ETV6 | 3.51E−09 |
| DKFZP564D0462 | 3.67E−09 |
| SLC2A1 | 3.72E−09 |
| HK3 | 3.81E−09 |
| D21S2056E | 4.02E−09 |
| LOC51053 | 4.07E−09 |
| PRO2013 | 4.08E−09 |
| DC11 | 4.22E−09 |
| KRT17 | 4.34E−09 |
| EDN1 | 5.04E−09 |
| UCHL3 | 5.29E−09 |
| KIAA1089 | 5.35E−09 |
| DSG3 | 5.40E−09 |
| RNASEH1 | 5.44E−09 |
| CP | 5.55E−09 |
| RELB | 5.66E−09 |
| MALT1 | 5.90E−09 |
| ETS1 | 5.93E−09 |
| KIAA0275 | 6.02E−09 |
| DYSF | 6.07E−09 |
| PRG1 | 6.08E−09 |
| KIAA1035 | 6.11E−09 |
| AMY2B | 6.11E−09 |
| LBP-9 | 6.44E−09 |
| LCP1 | 6.53E−09 |
| PKP1 | 6.67E−09 |

TABLE 4-continued

PCA Basal-Like Cancers

| gene name | mean(1) > mean(2) |
|---|---|
| TGM1 | 6.80E−09 |
| RAP2A | 7.18E−09 |
| ZIC1 | 7.30E−09 |
| RASAL1 | 7.50E−09 |
| PDXK | 7.51E−09 |
| FLJ21324 | 7.80E−09 |
| TIA1 | 7.84E−09 |
| PIST | 8.06E−09 |
| ABP/ZF | 8.18E−09 |
| P5 | 8.47E−09 |
| DEFB1 | 8.66E−09 |
| DSCR1 | 8.90E−09 |
| AMY1A | 9.14E−09 |
| LILRB2 | 9.91E−09 |
| ICAM1 | 9.93E−09 |
| HRB | 1.00E−08 |
| CXADR | 1.01E−08 |
| MT1L | 1.02E−08 |
| BCL11B | 1.04E−08 |
| FLJ10517 | 1.04E−08 |
| BM039 | 1.06E−08 |
| NMI | 1.08E−08 |
| FAT | 1.13E−08 |
| NUMBL | 1.17E−08 |
| LOC55862 | 1.18E−08 |
| SLC6A14 | 1.20E−08 |
| CCR1 | 1.23E−08 |
| GPM6B | 1.25E−08 |
| E48 | 1.25E−08 |
| IGHG3 | 1.31E−08 |
| MGC3180 | 1.36E−08 |
| C1GALT1 | 1.43E−08 |
| DKFZP586F2423 | 1.44E−08 |
| ART3 | 1.47E−08 |
| B4-2 | 1.49E−08 |
| DKFZP586E1621 | 1.51E−08 |
| HDGF | 1.52E−08 |
| SLC2A5 | 1.53E−08 |
| MMP1 | 1.56E−08 |
| KPNA2 | 1.57E−08 |
| COL9A3 | 1.62E−08 |
| TRIP13 | 1.71E−08 |
| GGH | 1.72E−08 |
| FLJ10706 | 1.79E−08 |
| TEL2 | 1.87E−08 |
| PLA2G7 | 1.98E−08 |
| AKAP2 | 1.98E−08 |
| MAPRE2 | 1.99E−08 |
| TAP1 | 2.02E−08 |
| KRT5 | 2.12E−08 |
| ARP3BETA | 2.32E−08 |
| KRT6B | 2.35E−08 |
| DSCR2 | 2.55E−08 |
| AK000660 | 2.70E−08 |
| CSTB | 2.71E−08 |
| FLJ23518 | 2.82E−08 |
| GNB4 | 2.86E−08 |
| KIAA0197 | 2.95E−08 |
| IL15RA | 2.95E−08 |
| DMD | 2.98E−08 |
| CXCR4 | 3.13E−08 |
| DONSON | 3.51E−08 |
| S100A1 | 3.54E−08 |
| SLC16A1 | 3.78E−08 |
| WARS | 3.87E−08 |
| LTB | 3.89E−08 |
| TPI1 | 3.92E−08 |
| EPHA2 | 3.93E−08 |
| DD96 | 4.11E−08 |
| KIAA0173 | 4.11E−08 |
| UBD | 4.13E−08 |
| EBBP | 4.26E−08 |
| SCYA5 | 4.30E−08 |
| CRYAB | 4.35E−08 |
| SEMA4D | 4.49E−08 |
| BRUNOL4 | 4.53E−08 |
| ALY | 4.62E−08 |
| DDXL | 4.69E−08 |
| STAC | 4.89E−08 |
| LILRB3 | 4.93E−08 |
| AMY2A | 4.96E−08 |
| AK001380 | 5.07E−08 |
| CYBB | 5.23E−08 |
| FXYD5 | 5.33E−08 |
| GRO1 | 5.34E−08 |
| FLJ10407 | 5.49E−08 |
| CCNC | 5.56E−08 |
| FLJ10709 | 5.94E−08 |
| PHRET1 | 6.01E−08 |
| PDL2 | 6.10E−08 |
| ARHGEF4 | 6.17E−08 |
| KIAA0353 | 6.24E−08 |
| DHCR7 | 6.38E−08 |
| AL137342 | 6.47E−08 |
| PTGS2 | 6.59E−08 |
| BIN1 | 6.62E−08 |
| SCYB11 | 6.86E−08 |
| KIAA0552 | 6.92E−08 |
| CD163 | 6.97E−08 |
| GPRC5B | 7.04E−08 |
| FLJ20287 | 7.09E−08 |
| FBL | 7.11E−08 |
| AD024 | 7.13E−08 |
| PTPN14 | 7.16E−08 |
| SFRP1 | 7.25E−08 |
| FOXD1 | 7.28E−08 |
| PSMB9 | 7.54E−08 |
| FLJ21069 | 7.75E−08 |
| UBA2 | 7.76E−08 |
| ANKRD3 | 7.77E−08 |
| DSC3 | 7.95E−08 |
| AK001942 | 8.06E−08 |
| FLJ10262 | 8.10E−08 |
| KIAA1609 | 8.21E−08 |
| MX2 | 8.47E−08 |
| FBXO5 | 9.27E−08 |
| DKFZP564J0863 | 9.33E−08 |
| DKFZp434F2322 | 9.33E−08 |
| TEGT | 9.60E−08 |
| FIGN | 1.04E−07 |
| RDX | 1.05E−07 |
| FLJ10359 | 1.05E−07 |
| SGK | 1.06E−07 |
| PPP1CB | 1.07E−07 |
| PRAME | 1.13E−07 |
| CKS1 | 1.13E−07 |
| TMSNB | 1.13E−07 |
| KIAA0062 | 1.17E−07 |
| BCE-1 | 1.19E−07 |
| CKAP2 | 1.27E−07 |
| KLK7 | 1.30E−07 |
| ATF4 | 1.35E−07 |
| SCYB10 | 1.38E−07 |
| EPHB1 | 1.39E−07 |
| AK001630 | 1.45E−07 |
| KNSL5 | 1.46E−07 |
| DAPP1 | 1.53E−07 |
| PDE4B | 1.55E−07 |
| TC21 | 1.56E−07 |
| SPIB | 1.63E−07 |
| PFDN2 | 1.69E−07 |
| GATA6 | 1.77E−07 |
| CD3Z | 1.82E−07 |
| ST14 | 1.86E−07 |
| KIAA0179 | 1.94E−07 |
| KIAA1392 | 1.96E−07 |
| PIR | 2.06E−07 |
| KRTHB1 | 2.18E−07 |
| MPZL1 | 2.19E−07 |
| KIAA0668 | 2.20E−07 |

TABLE 4-continued

PCA Basal-Like Cancers

| gene name | mean(1) > mean(2) |
|---|---|
| TRAF1 | 2.41E−07 |
| LYZ | 2.56E−07 |
| APS | 2.60E−07 |
| TRB@ | 2.64E−07 |
| TCF20 | 2.66E−07 |
| AK000208 | 2.72E−07 |
| NF2 | 2.74E−07 |
| NK4 | 2.93E−07 |
| TUBB4 | 2.95E−07 |
| DNMT2 | 3.21E−07 |
| PCOLCE2 | 3.35E−07 |
| C6orf34 | 3.54E−07 |
| CRABP1 | 3.66E−07 |
| OTRPC4 | 3.76E−07 |
| CD83 | 3.84E−07 |
| FLJ10316 | 3.91E−07 |
| SOD3 | 4.05E−07 |
| FLJ12505 | 4.17E−07 |
| CCR7 | 4.26E−07 |
| HLA-F | 4.38E−07 |
| ribosomal protein L39 | 4.39E−07 |
| PTPLA | 4.45E−07 |
| EPHB3 | 4.53E−07 |
| IL1B | 4.70E−07 |
| FUT4 | 4.83E−07 |
| PTPRCAP | 5.06E−07 |
| KIAA0007 | 5.07E−07 |
| TNF | 5.16E−07 |
| MTAP44 | 5.20E−07 |
| AK000954 | 5.28E−07 |
| NOL1 | 5.32E−07 |
| TCF7 | 5.42E−07 |
| CDH19 | 5.77E−07 |
| CDKN2A | 5.97E−07 |
| LOC51316 | 6.00E−07 |
| AK001394 | 6.11E−07 |
| CTSS | 6.24E−07 |
| FLJ20371 | 6.44E−07 |
| ADORA2BP | 6.60E−07 |
| H1F5 | 6.88E−07 |
| TNFRSF1B | 6.92E−07 |
| NDUFA9 | 7.03E−07 |
| TNFRSF11A | 7.31E−07 |
| AIM2 | 7.41E−07 |
| NMU | 7.42E−07 |
| SFN | 7.43E−07 |
| UGP2 | 7.44E−07 |
| DKFZP761H171 | 7.86E−07 |
| MTR1 | 8.03E−07 |
| WDR5 | 8.09E−07 |
| G2 | 8.14E−07 |
| DKFZP564L0862 | 8.46E−07 |
| TRIP7 | 8.48E−07 |
| P450RAI-2 | 8.50E−07 |
| PRO2000 | 8.56E−07 |
| YES1 | 8.62E−07 |
| KLK5 | 8.66E−07 |
| KIAA0449 | 8.81E−07 |
| KIAA0680 | 8.94E−07 |
| LOC51203 | 9.62E−07 |
| MRPL37 | 9.98E−07 |
| CAPN6 | 1.01E−06 |
| PGAR | 1.03E−06 |
| HRASLS | 1.04E−06 |
| DXS9928E | 1.05E−06 |
| FLJ10697 | 1.06E−06 |
| FLJ20330 | 1.06E−06 |
| TNFSF13B | 1.08E−06 |
| LBP-32 | 1.08E−06 |
| SACS | 1.10E−06 |
| CEBPB | 1.13E−06 |
| KIAA0870 | 1.17E−06 |
| KIAA0237 | 1.24E−06 |
| SCYA4 | 1.39E−06 |
| FLJ10895 | 1.41E−06 |
| CD3G | 1.47E−06 |
| CORO1A | 1.48E−06 |
| CD72 | 1.49E−06 |
| FZD7 | 1.52E−06 |
| FLJ10665 | 1.62E−06 |
| RPC32 | 1.66E−06 |
| CD3D | 1.66E−06 |
| TERA | 1.66E−06 |
| AK000770 | 1.67E−06 |
| LY64 | 1.72E−06 |
| FOXG1B | 1.74E−06 |
| TBPL1 | 1.77E−06 |
| SIRP-b2 | 1.80E−06 |
| RGS2 | 1.92E−06 |
| POMC | 1.95E−06 |
| MIG | 1.96E−06 |
| ROR1 | 1.99E−06 |
| SCRG1 | 1.99E−06 |
| MYCL1 | 2.04E−06 |
| KIAA0020 | 2.04E−06 |
| LOC51668 | 2.06E−06 |
| FLJ20485 | 2.11E−06 |
| PCDHB9 | 2.14E−06 |
| LOC51630 | 2.15E−06 |
| MRPL15 | 2.16E−06 |
| ZNF313 | 2.18E−06 |
| IL8 | 2.21E−06 |
| NFIB | 2.22E−06 |
| FLJ20435 | 2.25E−06 |
| CYBA | 2.27E−06 |
| SCYA7 | 2.28E−06 |
| FLJ20105 | 2.28E−06 |
| POU2AF1 | 2.33E−06 |
| KRT15 | 2.43E−06 |
| SSR1 | 2.53E−06 |
| FLNA | 2.55E−06 |
| HLA-B | 2.74E−06 |
| IL12RB2 | 2.78E−06 |
| FLJ10470 | 2.80E−06 |
| CPA4 | 2.90E−06 |
| NCF2 | 2.94E−06 |
| IL10RA | 3.00E−06 |
| CHI3L2 | 3.03E−06 |
| KRT7 | 3.04E−06 |
| FLJ11296 | 3.07E−06 |
| PSMB2 | 3.10E−06 |
| KIAA1214 | 3.13E−06 |
| NDRG2 | 3.13E−06 |
| DDX21 | 3.29E−06 |
| KIAA1678 | 3.54E−06 |
| FADS2 | 3.57E−06 |
| LRP6 | 3.75E−06 |
| CNGA1 | 3.84E−06 |
| KRT14 | 3.84E−06 |
| RNASE1 | 3.86E−06 |
| S100A2 | 3.93E−06 |
| FLJ20500 | 3.95E−06 |
| IRAK1 | 4.39E−06 |
| CD2 | 4.55E−06 |
| AK000106 | 4.69E−06 |
| Immunoglobulin | 4.78E−06 |
| FLJ20116 | 5.16E−06 |
| SOX8 | 5.17E−06 |
| IGKV3D-15 | 5.18E−06 |
| ID4 | 5.26E−06 |
| FLJ20038 | 5.28E−06 |
| CD19 | 5.32E−06 |
| NPR3 | 5.42E−06 |
| KIAA0637 | 5.61E−06 |
| GPR37 | 6.23E−06 |
| LCP2 | 6.39E−06 |
| AF103458 | 6.41E−06 |
| FOLR1 | 6.55E−06 |
| BIRC3 | 6.56E−06 |
| GNA15 | 6.60E−06 |

TABLE 4-continued

PCA Basal-Like Cancers

| gene name | mean(1) > mean(2) |
|---|---|
| GPR9 | 6.61E−06 |
| DKK1 | 6.73E−06 |
| PCANAP8 | 6.79E−06 |
| PTGFR | 7.36E−06 |
| AK000776 | 7.40E−06 |
| ISG20 | 7.73E−06 |
| FLJ10292 | 7.84E−06 |
| KLK8 | 7.96E−06 |
| PRRG1 | 8.07E−06 |
| TNFAIP2 | 8.38E−06 |
| CHORDC1 | 8.59E−06 |
| VCAM1 | 9.46E−06 |
| CD5 | 9.48E−06 |
| DKFZp434B1222 | 9.86E−06 |
| ZWINT | 1.01E−05 |
| DKFZP586N2124 | 1.03E−05 |
| IL2RB | 1.07E−05 |
| GNG4 | 1.14E−05 |
| AL080059 | 1.19E−05 |
| P2RX5 | 1.22E−05 |
| ZNFN1A1 | 1.24E−05 |
| SLC15A1 | 1.29E−05 |
| KLK10 | 1.30E−05 |
| AF063725 | 1.33E−05 |
| AL133101 | 1.36E−05 |
| PIM2 | 1.36E−05 |
| IGHM | 1.41E−05 |
| CYP27A1 | 1.47E−05 |
| ALG6 | 1.54E−05 |
| M12.219 | 1.59E−05 |
| FLJ10637 | 1.62E−05 |
| AGM1 | 1.62E−05 |
| AARS | 1.67E−05 |
| SELL | 1.78E−05 |
| ECGF1 | 1.90E−05 |
| MSLN | 1.99E−05 |
| EPS15R | 2.06E−05 |
| TYMSTR | 2.14E−05 |
| MT1G | 2.15E−05 |
| AK000933 | 2.16E−05 |
| IFRG28 | 2.23E−05 |
| MFGE8 | 2.26E−05 |
| CLDN1 | 2.30E−05 |
| CD53 | 2.38E−05 |
| HLA-E | 2.38E−05 |
| TSPAN-2 | 2.39E−05 |
| W61000_RC | 2.61E−05 |
| PLS3 | 2.96E−05 |
| NET1 | 3.04E−05 |
| SAR1 | 3.10E−05 |
| TNFSF6 | 3.10E−05 |
| U96394 | 3.34E−05 |
| DSP | 3.48E−05 |
| GCNT1 | 3.53E−05 |
| MS4A4A | 3.54E−05 |
| FLJ20360 | 3.60E−05 |
| PCTK3 | 3.90E−05 |
| RAB27A | 3.91E−05 |
| FLJ21129 | 4.00E−05 |
| IGLL1 | 4.01E−05 |
| PTPRK | 4.11E−05 |
| FLJ22408 | 4.18E−05 |
| IMP-2 | 4.19E−05 |
| HEM1 | 4.24E−05 |
| CD69 | 4.26E−05 |
| SPS | 4.48E−05 |
| PLEK | 4.48E−05 |
| AL353948 | 4.52E−05 |
| MAL | 4.72E−05 |
| variable region | 4.83E−05 |
| AF097495 | 5.06E−05 |
| OS4 | 5.40E−05 |
| KIAA0036 | 5.70E−05 |
| PTPRC | 5.86E−05 |
| HUMMHCW1A | 5.92E−05 |
| FLJ20260 | 5.93E−05 |
| ANXA3 | 6.00E−05 |
| AL137346 | 6.02E−05 |
| CD24 | 6.68E−05 |
| SECTM1 | 7.57E−05 |
| FLJ22028 | 7.65E−05 |
| AF058075 | 8.00E−05 |
| GPI | 8.14E−05 |
| FMO2 | 8.95E−05 |
| AK002088 | 8.95E−05 |
| PLCB4 | 9.26E−05 |
| TCF8 | 9.29E−05 |
| RASGRP2 | 9.29E−05 |
| S100A9 | 9.32E−05 |
| RPP40 | 9.49E−05 |
| BM-005 | 9.62E−05 |
| SELE | 0.00010074 |
| AL137736 | 0.00010102 |
| GALNT3 | 0.00010121 |
| AL133611 | 0.00010218 |
| TNFRSF12 | 0.00010285 |
| WSX-1 | 0.00010743 |
| ARHE | 0.00010941 |
| ITGB4 | 0.00011071 |
| LAMB3 | 0.00011149 |
| X79782 | 0.00011171 |
| SCYA19 | 0.00011704 |
| SLC5A6 | 0.00011832 |
| PAPSS1 | 0.00012229 |
| CLC | 0.00012443 |
| CHRM3 | 0.00012635 |
| EPHB2 | 0.00012862 |
| AIM1 | 0.00013146 |
| KIAA0667 | 0.00013373 |
| HN1 | 0.00013498 |
| GS3686 | 0.00013717 |
| MACROH2A2 | 0.00013758 |
| LCN2 | 0.00014652 |
| FLJ10110 | 0.00015325 |
| PLCB3NP | 0.00015669 |
| PTGDS | 0.0001567 |
| MS4A2 | 0.00015756 |
| FLJ22477 | 0.00015882 |
| HLA-DRB6 | 0.00016152 |
| FLJ13204 | 0.00017364 |
| FLJ10408 | 0.00018014 |
| AKR1B1 | 0.00018344 |
| CSR1 | 0.00019574 |
| KIAA0786 | 0.00020194 |
| cig5 | 0.00020328 |
| GYPC | 0.00020494 |
| MX1 | 0.0002066 |
| PPARGC1 | 0.00020788 |
| TU3A | 0.00020804 |
| ALDH1A3 | 0.00021256 |
| KIAA0167 | 0.0002174 |
| CSPG4 | 0.00021782 |
| MYBL1 | 0.00022132 |
| ETV5 | 0.00022218 |
| NFIX | 0.00022432 |
| MGC3040 | 0.00023986 |
| FLJ21212 | 0.00024208 |
| DKFZP564D206 | 0.00025636 |
| KIAA1229 | 0.00025668 |
| LOC57823 | 0.00025934 |
| STAF50 | 0.00026248 |
| USP18 | 0.00026452 |
| AF035318 | 0.00026674 |
| RIG-I | 0.00026756 |
| APEG1 | 0.00027352 |
| LOC51678 | 0.00027438 |
| KIAA0965 | 0.00027974 |
| ACTG2 | 0.00029244 |
| EIF4EBP1 | 0.00029248 |
| DSG2 | 0.0002974 |

TABLE 4-continued

PCA Basal-Like Cancers

| gene name | mean(1) > mean(2) |
|---|---|
| GW112 | 0.00030546 |
| RGN | 0.00031526 |
| CASP1 | 0.00031578 |
| MCAM | 0.00031884 |
| SIX3 | 0.00032956 |
| LY6E | 0.0003374 |
| TGM5 | 0.00033884 |
| FLJ14054 | 0.00034114 |
| H1F3 | 0.00034446 |
| DNCI1 | 0.00034532 |
| KIAA1566 | 0.00036884 |
| IFI30 | 0.00038314 |
| RNASEHI | 0.00039798 |
| ZRF1 | 0.00040436 |
| LOC51056 | 0.00041266 |
| ITGA9 | 0.00043048 |
| KIAA0172 | 0.0004343 |
| AF131837 | 0.00044782 |
| ITGA6 | 0.00044988 |
| FLJ11106 | 0.0004756 |
| ARGBP2 | 0.0004899 |
| CD48 | 0.00050636 |
| SAA1 | 0.0005154 |
| OPRK1 | 0.0005226 |
| GP1BA | 0.0005325 |
| CD36L1 | 0.00053766 |
| KIAA1453 | 0.00056168 |
| CBS | 0.00056362 |
| KIAA0403 | 0.0005869 |
| FLJ12691 | 0.00059502 |
| VLDLR | 0.00059822 |
| KIAA0554 | 0.00061354 |
| TIMP2 | 0.0006222 |
| AL049266 | 0.00062746 |
| CYP1B1 | 0.00063132 |
| OAS2 | 0.0006379 |
| BRDG1 | 0.00067598 |
| PFN2 | 0.00068956 |
| AL137332 | 0.00077032 |
| EVI2B | 0.00078094 |
| FLJ10970 | 0.00081688 |
| TCF3 | 0.00082408 |
| MT1E | 0.00086288 |
| GPR64 | 0.0009027 |
| RGS10 | 0.00091806 |
| STAT4 | 0.00094354 |
| KIAA0092 | 0.00097058 |
| PDK3 | 0.00097262 |
| HMGCS1 | 0.0010899 |
| FLJ20048 | 0.00117324 |
| KDELR3 | 0.0012341 |
| HNF3A | 0.00124078 |
| BIN2 | 0.00128052 |
| MDFI | 0.0012817 |
| PTB | 0.00135722 |
| PODXL | 0.00141214 |
| AK001536 | 0.00142296 |
| FLJ20401 | 0.00146878 |
| HSU15552 | 0.00147042 |
| LILRB4 | 0.00147626 |
| AL110125 | 0.00148956 |
| HSPC156 | 0.00150478 |
| ANXA1 | 0.00160068 |
| TRD@ | 0.00185688 |
| FGL2 | 0.00186104 |
| TNFRSF10B | 0.00187774 |
| IGL@ | 0.00197044 |
| KLRB1 | 0.0020324 |
| CEP4 | 0.0023878 |
| CD38 | 0.002417 |
| SLC22A3 | 0.0024792 |
| CRHSP-24 | 0.0024844 |
| KIAA0820 | 0.00252 |
| KIAA0027 | 0.00253 |
| PLXNA2 | 0.0025982 |

TABLE 4-continued

PCA Basal-Like Cancers

| gene name | mean(1) > mean(2) |
|---|---|
| ZNF215 | 0.0026394 |
| WIF-1 | 0.0028488 |
| AF1Q | 0.0029846 |
| SLN | 0.0030636 |
| EDN2 | 0.0030818 |
| CRLF1 | 0.0031166 |
| AF055007 | 0.003125 |
| CYR61 | 0.0032168 |
| FLJ23384 | 0.0032198 |
| PIK3C2A | 0.0034572 |
| PYGB | 0.0037392 |
| ZNF179 | 0.0038464 |
| AKR1C1 | 0.0039554 |
| ITGB8 | 0.004776 |
| ISG15 | 0.004782 |
| PFC | 0.004949 |
| DKFZp761P1010 | 0.0051658 |
| SERPINB2 | 0.0054208 |
| SLC16A8 | 0.005542 |
| FLJ20510 | 0.0055696 |
| PAX6 | 0.0058166 |
| LOX | 0.0059874 |
| HPRP3P | 0.0060524 |
| FLJ21841 | 0.0070238 |
| TRAG3 | 0.007268 |
| KIT | 0.0073464 |
| PTPRR | 0.0076296 |
| PSIP1 | 0.007736 |
| BITE | 0.0080652 |
| SPRY2 | 0.0085948 |
| KIAA0469 | 0.0090724 |
| LOC56932 | 0.0091562 |
| VNN1 | 0.0092706 |
| DPYSL2 | 0.0094624 |
| AF103591 | 0.0095962 |
| DKFZp434P086 | 0.009694 |
| AKR1C2 | 0.0097626 |
| KIAA1118 | 0.009955 |
| SCYA21 | 0.0100306 |
| AK001932 | 0.0101928 |
| DKFZP434I216 | 0.0106252 |
| MAGEA1 | 0.010632 |
| A2M | 0.0115294 |
| IDH2 | 0.0126046 |
| FLJ22215 | 0.0129192 |
| ORM1 | 0.0131094 |
| FLJ22002 | 0.0133204 |
| FLJ20733 | 0.0139614 |
| FLJ10811 | 0.0144508 |
| IDI1 | 0.0146528 |
| NR4A1 | 0.0150532 |
| LOC51237 | 0.0157056 |
| IRF4 | 0.0159874 |
| LIF | 0.0162782 |
| MAPK8IP3 | 0.0165006 |
| HML2 | 0.0165248 |
| TNRC3 | 0.0184704 |
| NDST3 | 0.021434 |
| TCL1A | 0.021436 |
| PNUTL1 | 0.026414 |
| EMP1 | 0.027848 |
| RASGRP1 | 0.028092 |
| FLJ10143 | 0.028706 |
| AL137343 | 0.030014 |
| KIAA1473 | 0.030696 |
| HSPB2 | 0.03185 |
| MMP3 | 0.032616 |
| SHC3 | 0.03665 |
| STX4A | 0.038144 |
| ELF5 | 0.040156 |
| DFFB | 0.042634 |
| HLA-G | 0.04326 |
| AK000125 | 0.043288 |

TABLE 4-continued

PCA Basal-Like Cancers

| gene name | mean(1) > mean(2) |
|---|---|
| PP13 | 0.044702 |
| FLJ10781 | 0.04918 |
| PDE9A | 0.049704 |

For the top 100 over-expressed genes, P values ranged from $1\times10^{-11}$ to $<1\times10^{-16}$ (See first 100 genes listed in Table 4). The basal-like tumors identified by PCA also under-expressed over 1000 non-E2F-responsive genes in at least 20% of PCA basal-like tumor, such that the differences in frequency of under-expression between the basal-like tumors identified by PCA and the non-basal-like tumors identified by PCA was statistically significant at the P<0.05 level. See FIG. 24. This further establishes that the basal-like tumors identified by PCA are members of a separate and distinct subset of human breast cancers. Additionally, these patterns of gene over-expression and under-expression were shared by both the ERGO tumors identified by refined PCA and non-ERGO tumors identified by refined PCA. Altogether, the analyses here indicate that ERGO tumors developed in, and evolved from, basal-like tumor precursors.

Reproducibility of Findings Across Microarray Sets.

The Dai microarray set was purged of patient tumors that overlapped with those included the Van't Veer microarray set (i.e. indentical tumor samples from identical patients), and was used to evaluate the reproducibility of the analytical results in the Van't Veer microarray set. The Figures and Tables herein may refer to the Van't Veer microarray set as "s1" and the purged Dai microarray set as "s2." Application of the weighted rank ordering method identified 33 tumors out of 236 total tumors (14%) in the purged Dai microarray set that over-expressed at least 20% of the top over-expressed. E2F-responsive genes, and 82 E2F-responsive genes that were over-expressed in at least 20% of the ERGO tumors identified by the weighted rank ordering method in the purged Dai microarray set. Importantly, the lower 26% frequency of ERGO tumors identified in the purged Dai microarray set relative to the Van't Veer microarray set may be more representative of the overall frequency of ERGO tumors in the general population, since the purged Dai microarray set was not enriched with tumors from patients having known BRCA1 mutations.

As described above, 74 E2F-responsive genes were over-expressed in the ERGO tumors identified by the weighted rank ordering method using the Van't Veer microarray set. Importantly, 70 of these same E2F-responsive genes were also over-expressed in the ERGO tumors identified in the purged Dai microarray set by the weighted rank ordering method. Sixty-one (61) of these 70 genes (87%) were over-expressed in the ERGO tumors identified by the weighted rank ordering method in both the purged Dai and Van't Veer microarray sets. The frequencies of over-expression of these individual E2F-responsive genes in the ERGO tumors identified by weighted rank ordering methods and the level of statistical significance were comparable in the purged Dai microarray set (s2) and the Van't Veer microarray set (s1) and were preserved in the most highly over-expressed genes (FIG. 10).

Figure 2:
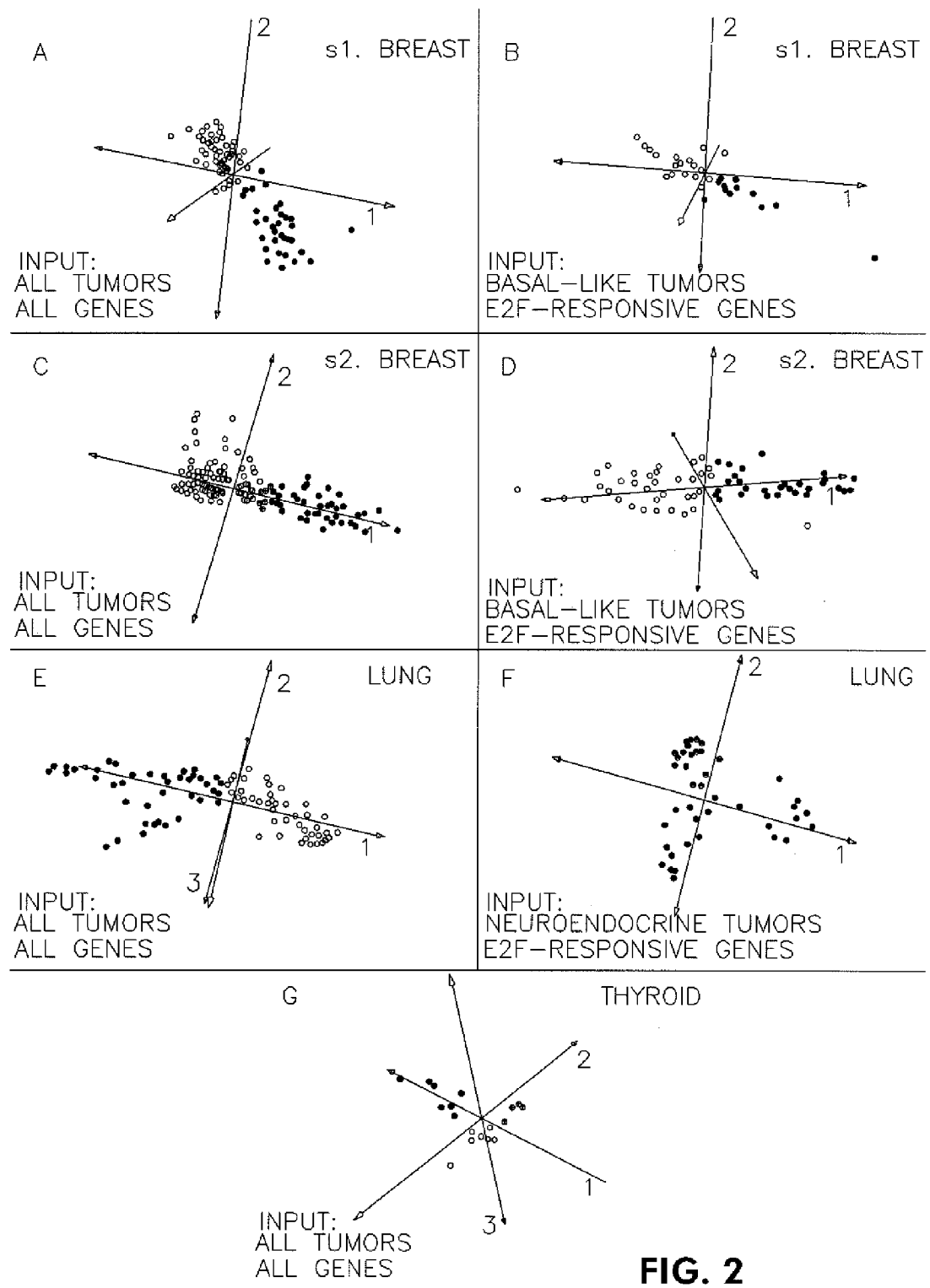
FIG. 2A shows a tumor cluster consisting of 38 samples identified by PCA of all tumors in the Van't Veer human breast cancer microarray set (s1).
FIG. 2B shows non-ERGO tumors clustered separately from the ERGO tumors identified by refined PCA analysis of basal-like tumors identified in the Van't Veer human breast cancer microarray set (s1).
FIG. 2C shows the transitional basal-like HER2 over-expressing tumors identified by refined PCA of all tumors in the purged Dai human breast cancer microarray set (s2).
FIG. 2D shows clusters comprising 30 ERGO and 36 non-ERGO tumor subsets identified by refined PCA of basal-like tumors in the purged Dai human breast cancer microarray set (s2).
FIG. 2E shows a cluster of tumors that contained carcinoids, large cell neuroendocrine tumors, and small cell lung cancers identified by PCA of all tumors in the Jones human lung cancer microarray set.
FIG. 2F shows carcinoids, large cell neuroendocrine tumors, and small cell lung cancer clusters identified by refined PCA of the neuroendocrine tumors in the Jones human lung cancer microarray set.
FIG. 2G shows anaplastic thyroid cancer clusters identified by PCA of all tumors in the Salvatore human thyroid cancer microarray set.

PCA identified a cluster of 66 tumors in the purged Dai microarray set (s2) that exhibited the basal-like phenotype (FIG. 2C). These 66 tumors were then further analyzed. This was done by using refined PCA in which the analyzed gene set was restricted to the E2F-responsive genes listed in Table 1 shown above. In these analyses only those tumors in the) basal-like tumor cluster identified by PCA were used as input data. Two clusters comprising 30 ERGO and 36 non-ERGO tumor subsets were identified by refined PCA analysis of these 66 tumors (FIG. 2D). In the purged Dai microarray set, HER2 positive tumors were among the basal-like tumors identified by refined PCA which clearly exhibited a basal-like phenotype (FIG. 4). These data can be viewed in greater detail in Supplementary FIG. 4. There was also a group of HER2 over-expressing basal-like tumors identified by refined PCA in the purged Dai set that exhibited a "transitional" phenotype intermediate to that of the basal-like tumors and that of non-basal-like HER2 over-expressing tumors identified by PCA. In FIG. 2C the transitional HER2-over-expressing basal-like tumors identified are marked with crosses and are found within the basal-like cluster. The presence of HER2 over-expressing basal-like tumors and the transitional sub-group were not apparent from the analyses of the Van't Veer microarray set (s1).

In general, the gene expression profiles of ERGO tumors and the other breast cancer subtypes identified and analyzed in the purged Dai microarray set (s2) was quite similar to those observed after analysis of the Van't Veer microarray set (s1) (see FIG. 1 and Tables 6, 7 and 8). In both datasets, the ERGO tumors identified were almost entirely "triple-non-positive" for HER2, ER, and PR over-expression, and virtually all of the basal-like tumors identified order-expressed ER and PR. The under-expression of Rb, the over-expression of cyclin E1 and E2, the over-expression of $p16^{Ink4a}$, the over-expression of E2F1, and the under-expression of cyclin D1 were prominent in ERGO tumors. However, this was less pronounced in non-ERGO basal-like tumors, and rare in the other tumor subtypes. Together, these observations further indicated that aberrations in E2F1 mediated control of transcription and the cell cycle is a feature of ERGO tumors. Last, the over-expression of multiple basal cytokeratins and of other published basal-like tumor markers was restricted largely to ERGO tumors and non-HER2-over-expressing, non-ERGO basal-like tumors. Over-expression of the MYC proto-oncogene was more readily apparent as an ERGO tumor feature by inspection of the results from analysis of the purged Dai microarray set than by inspection of the results from the analysis of the Van't Veer microarray set.

One hundred and one (101) E2F-responsive genes were over-expressed in at least 25% of the ERGO tumors identified by refined PCA analysis of the purged Dai microarray set. In contrast, 86 E2F-responsive genes were over-expressed in at least 25% of the ERGO tumors identified by refined PCA analysis of the Van't Veer microarray set (FIG. 12). The 101 E2F-responsive genes identified by refined PCA analysis of the purged Dai microarray set and the 86 E2F-responsive genes identified by refined PCA analysis of the purged Van't Veer microarray set were then compared. This comparison showed that 74 of the 86 genes (86%) over-expressed in ERGO tumors identified by refined PCA in the purged Dai microarray set were also over-expressed in the ERGO, tumors identified by refined PCA in the Van't Veer microarray set. Importantly, the relative frequencies of over-expression of individual genes among tumor were generally preserved in the two datasets especially among the most frequently over-expressed genes. In both the purged Dai microarray set and the Van't Veer microarray set the group of multiple E2F-responsive genes that were most frequently over-expressed in the ERGO tumor identified in these data sets by refined PCA were over-expressed only sporadically in PCA non-ERGO basal-like tumors identified in these microarray sets by refined PCA (FIG. 4).

In the Van't Veer microarray set both ERGO tumors identified by refined PCA and non-ERGO basal-like tumors identified by refined PCA differentially over-expressed and under-expressed hundreds of non-E2F-responsive genes. The top 50 most frequently over-expressed, and most frequently under-expressed, of these genes each are shown in FIG. 4. Surprisingly, these genes were reproducibly observed across both the purged Dai microarray set and the Van't Veer microarray sets. This observation was particularly apparent among the most frequently over-expressed genes. For example, among the top 200 genes most frequently over-expressed genes in the basal-like tumor subset identified by PCA of the Van't Veer microarray set some 70% of these genes were also over-expressed in the purged Dai microarray set.

Patients with Basal-Like Tumors as Identified by PCA Have an Adverse Clinical Prognosis.

Figure 9:
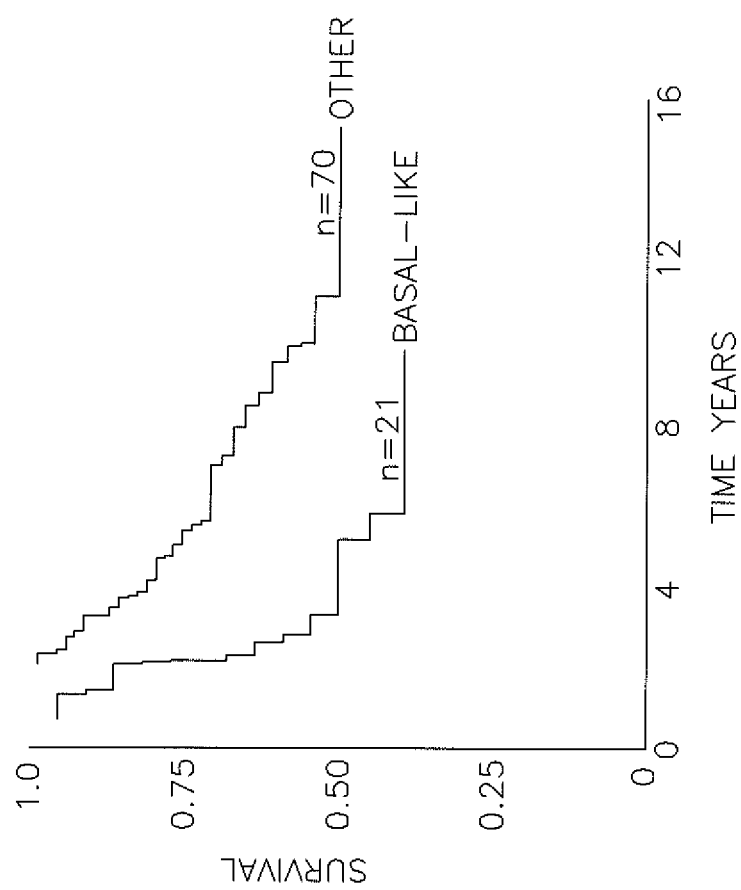
FIG. 9 shows the clinical survival data for PCA basal-like breast cancers and non-basal-like tumors identified by PCA analysis. "Survival" on the Y-axis indicates the fraction of all patients diagnosed with PCA basal-like breast cancers that survive at a given time.
Figure 11B:
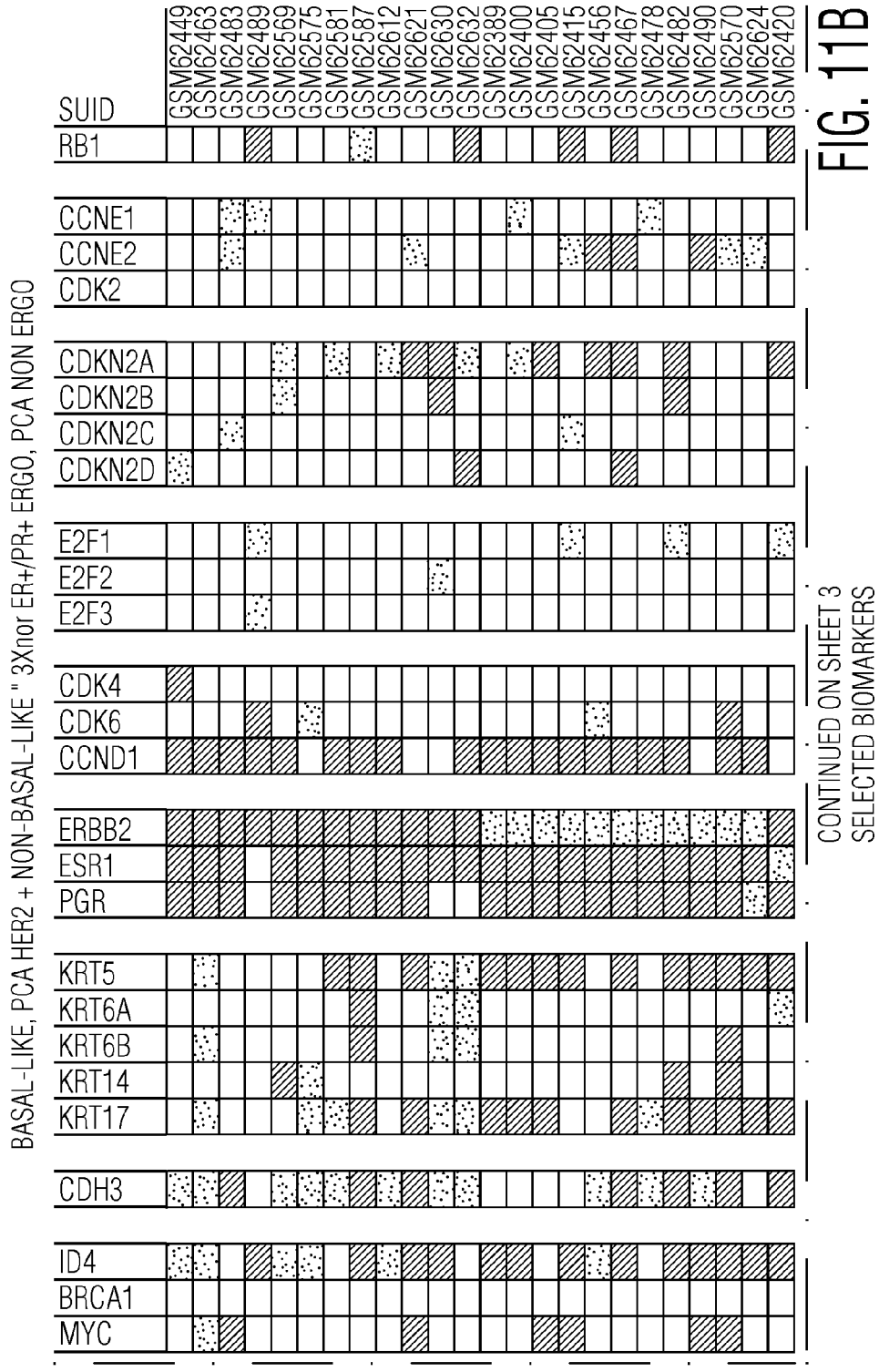
FIGS. 11A to 11FFF show partial views intended to form one complete view of microarray data for HER2 positive basal-like tumors identified by PCA of the purged Dai human breast cancer microarray set (s2).
Figure 11F:
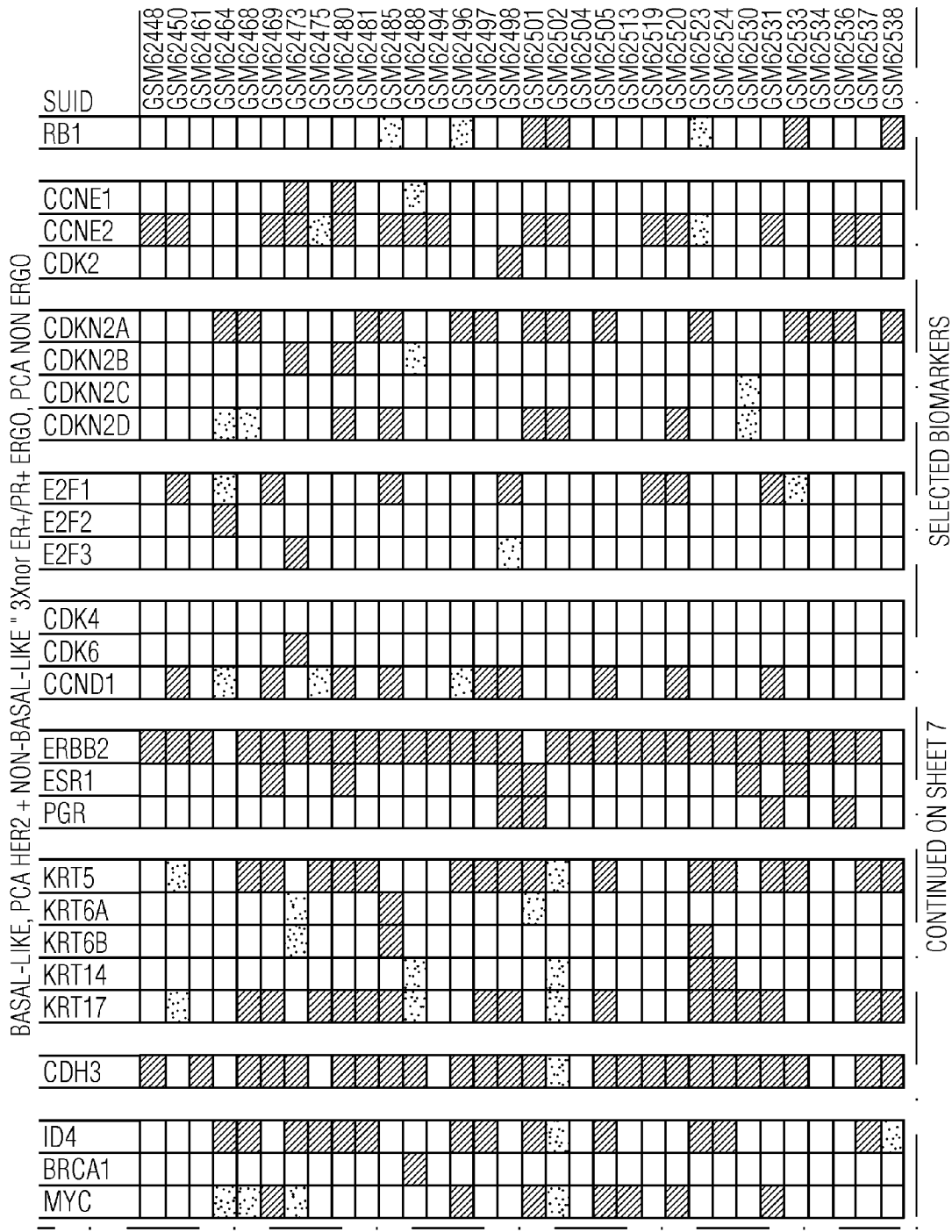
Figure 11H:
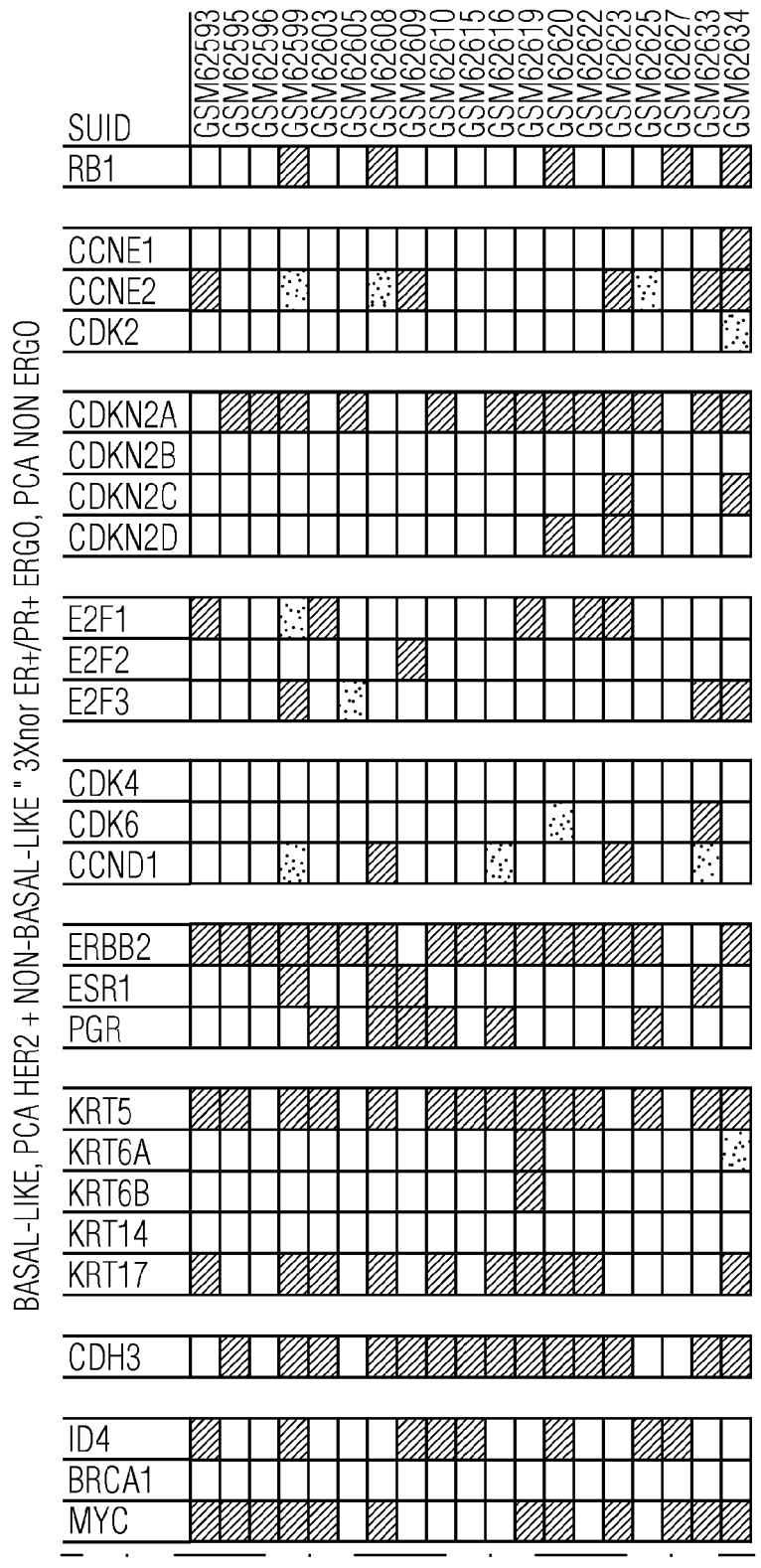
Figure 11J:
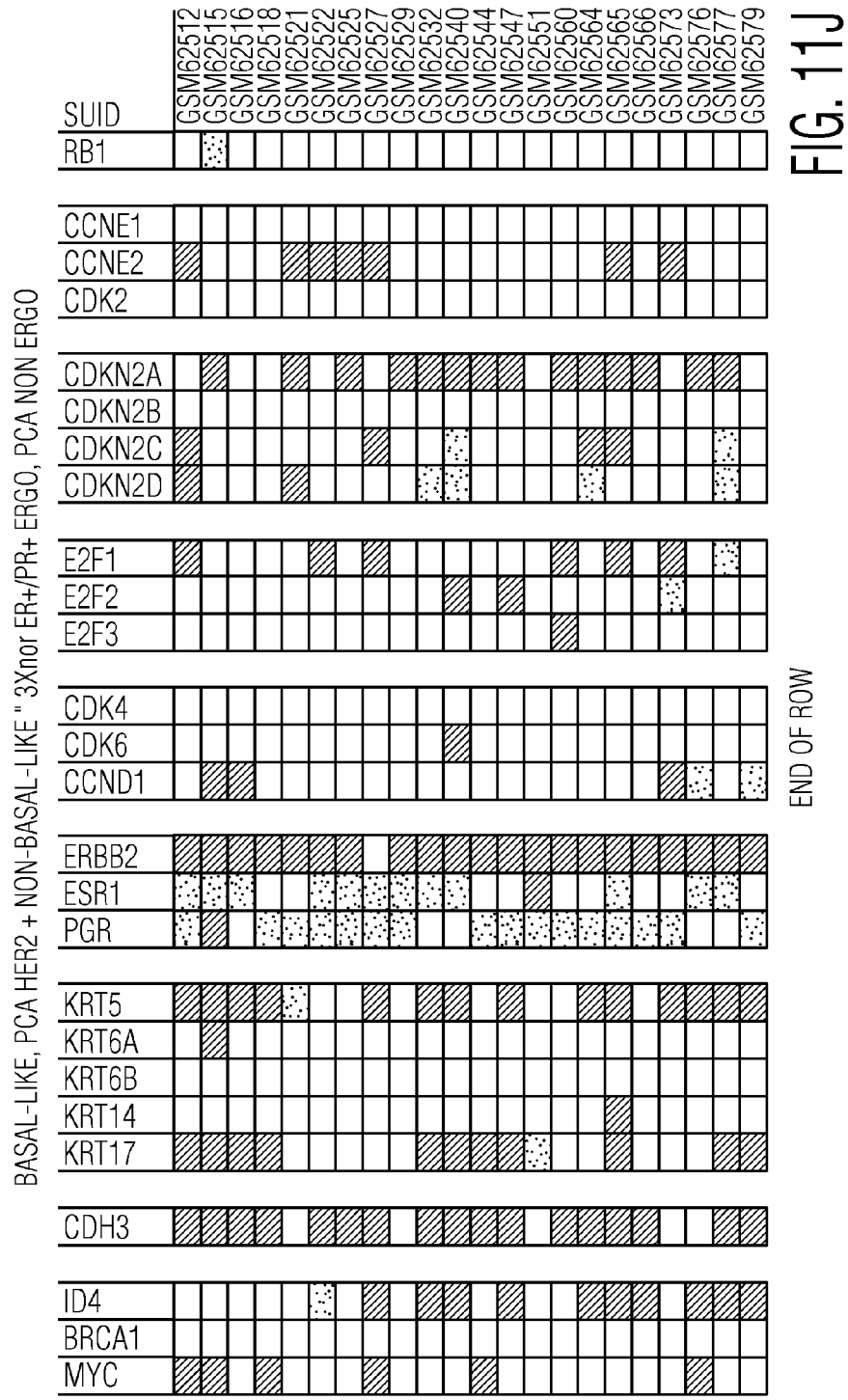
Figure 11N:
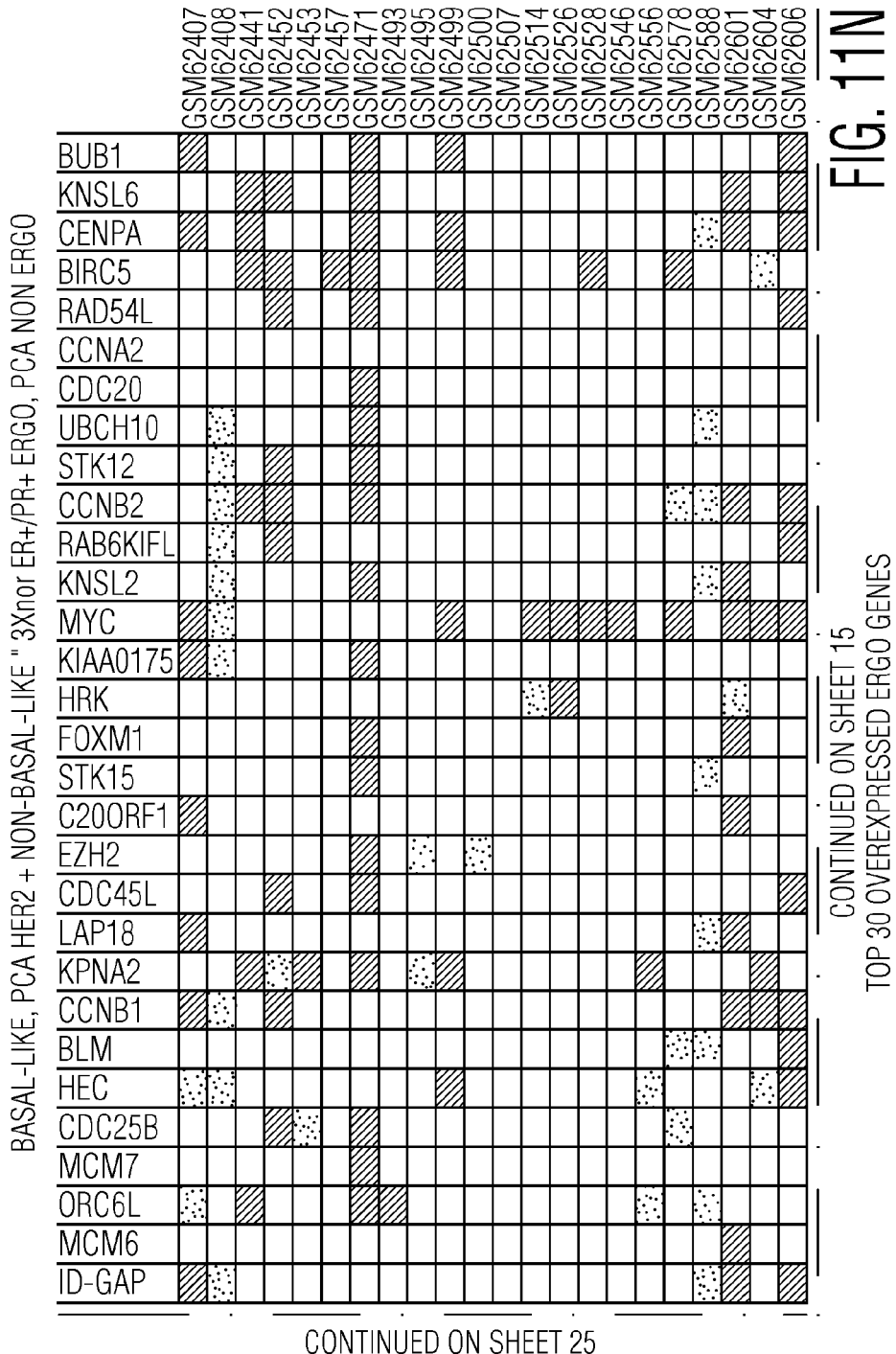
Figure 110:
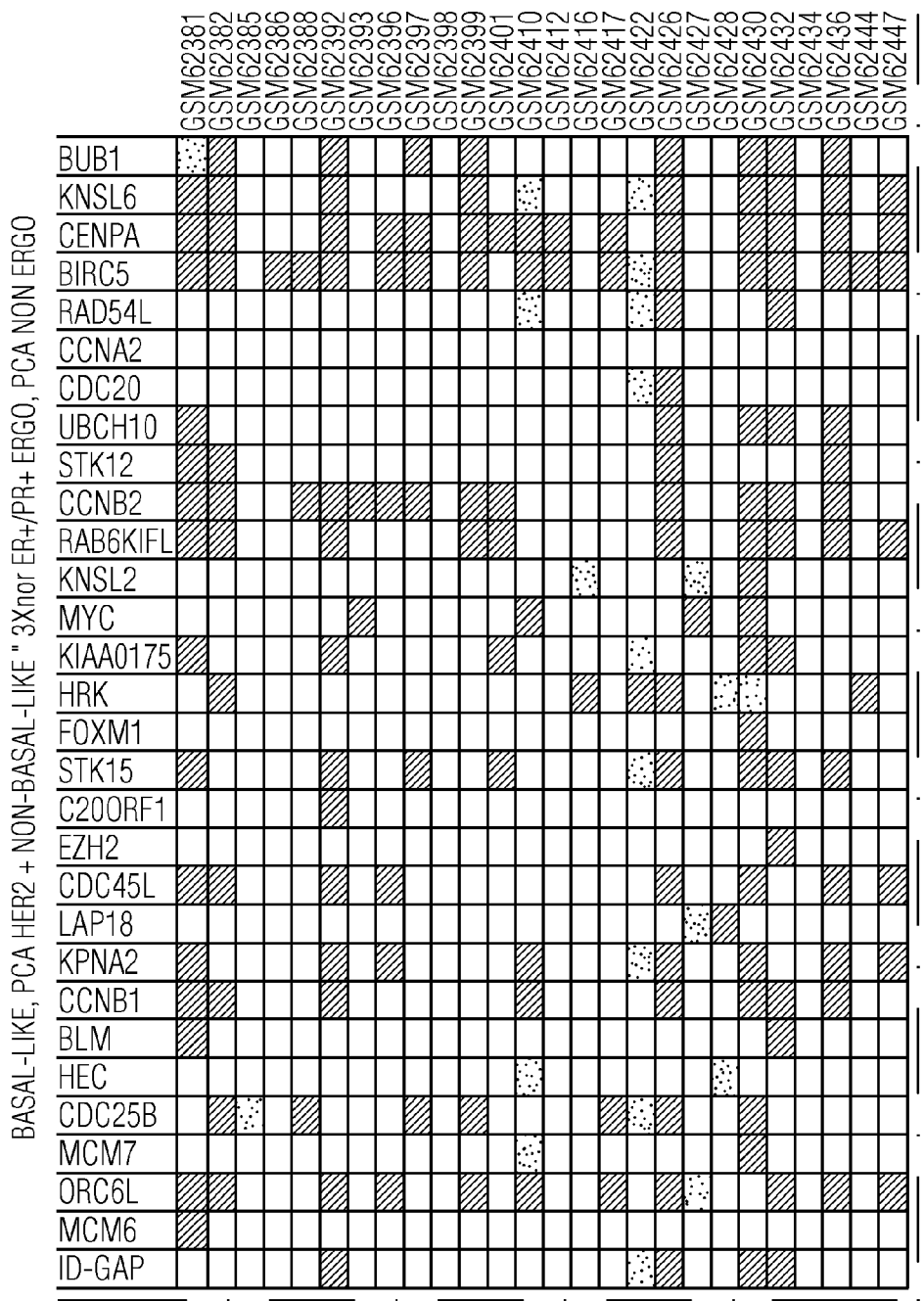
Figure 11P:
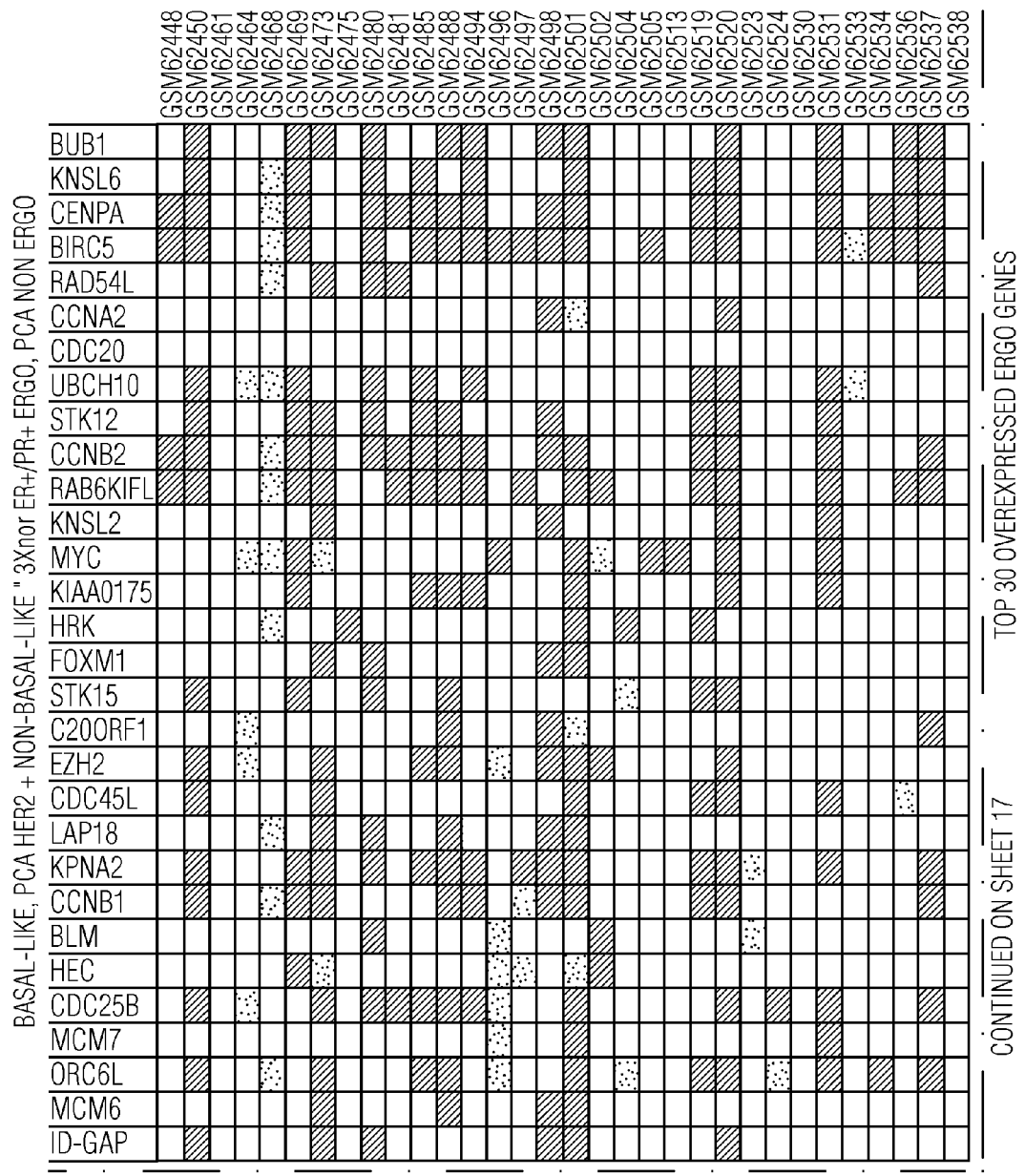
Figure 11S:
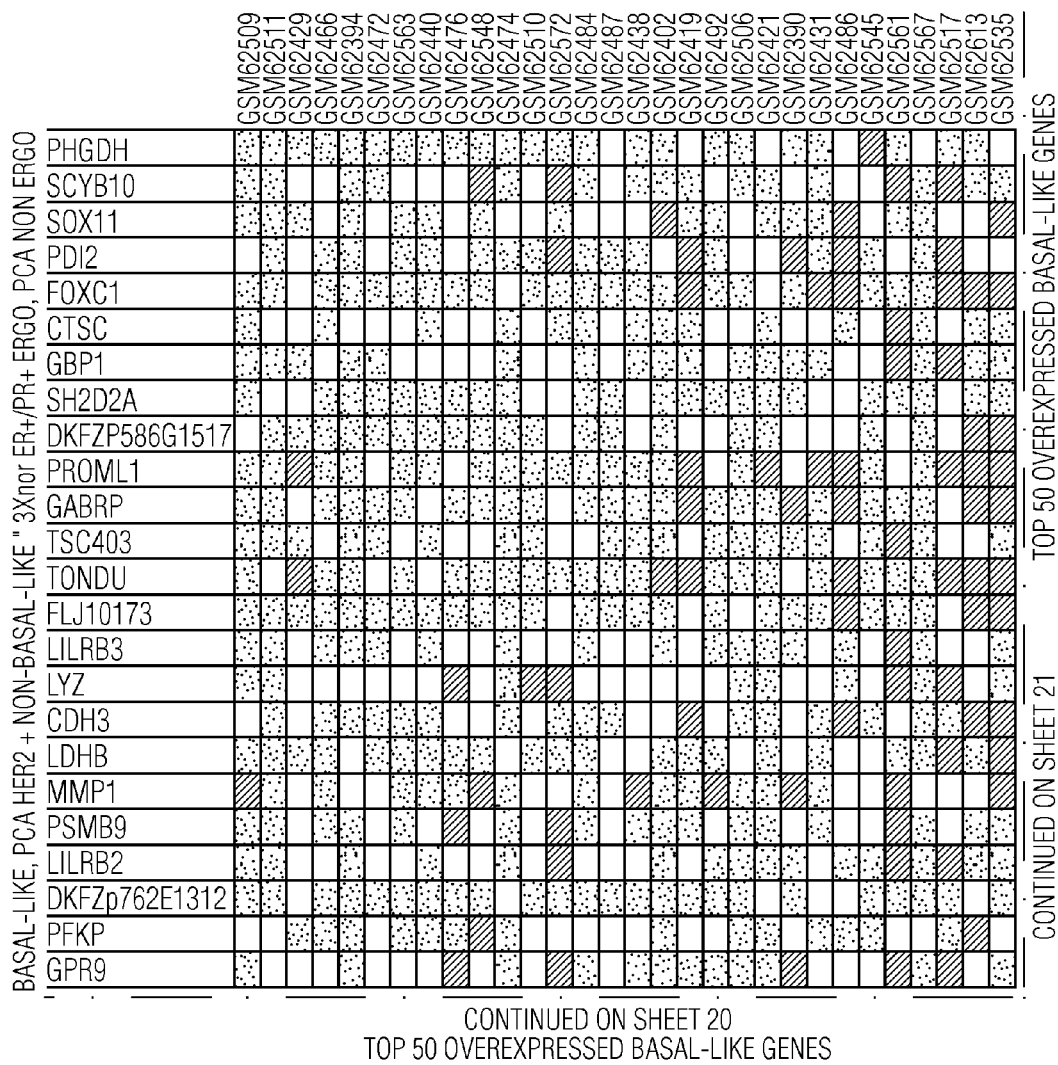
Figure 11T:
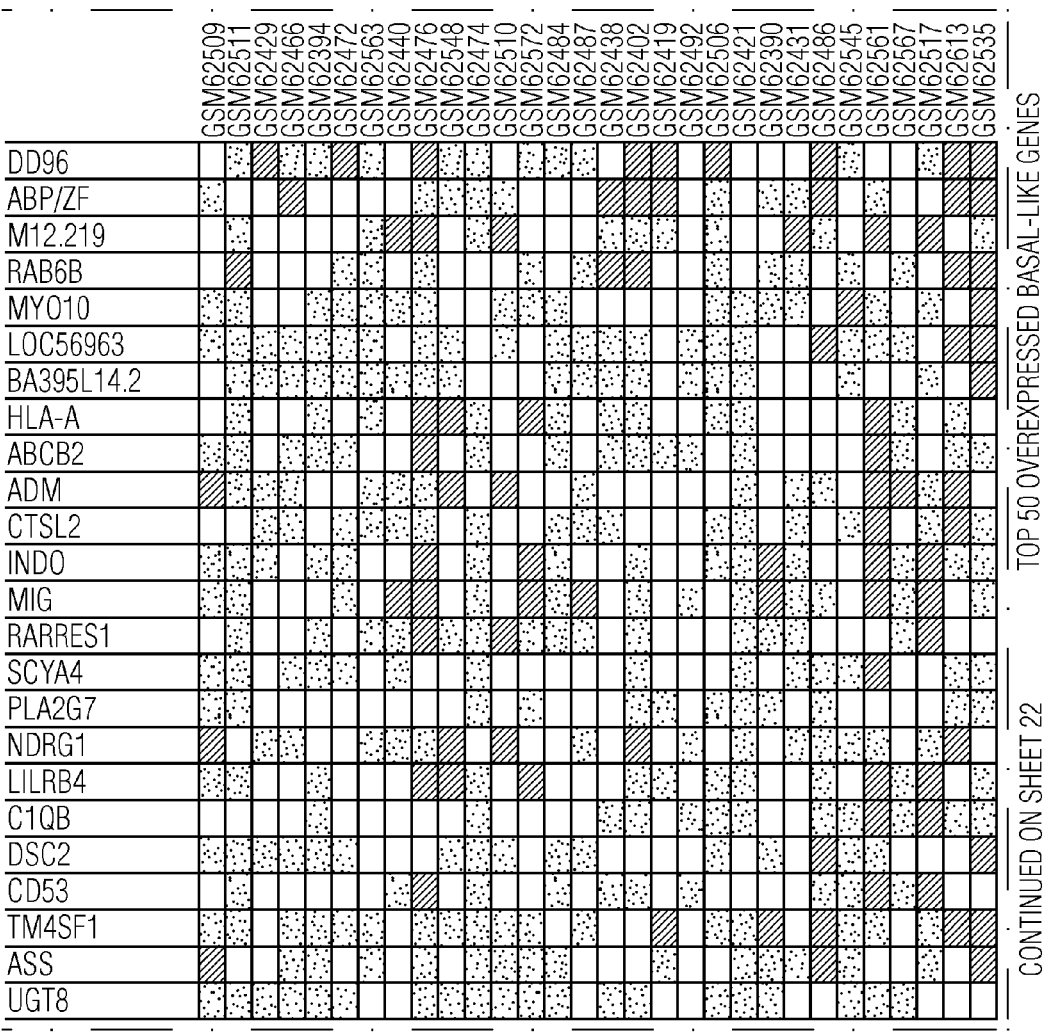
Figure 11Z:
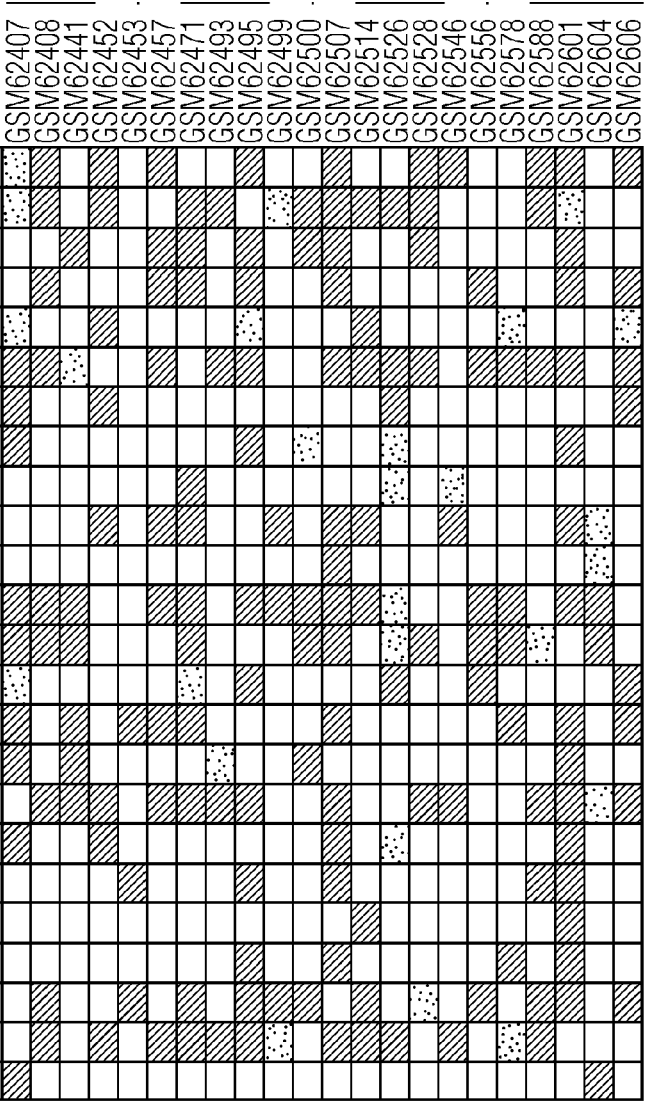
Figure 11C:
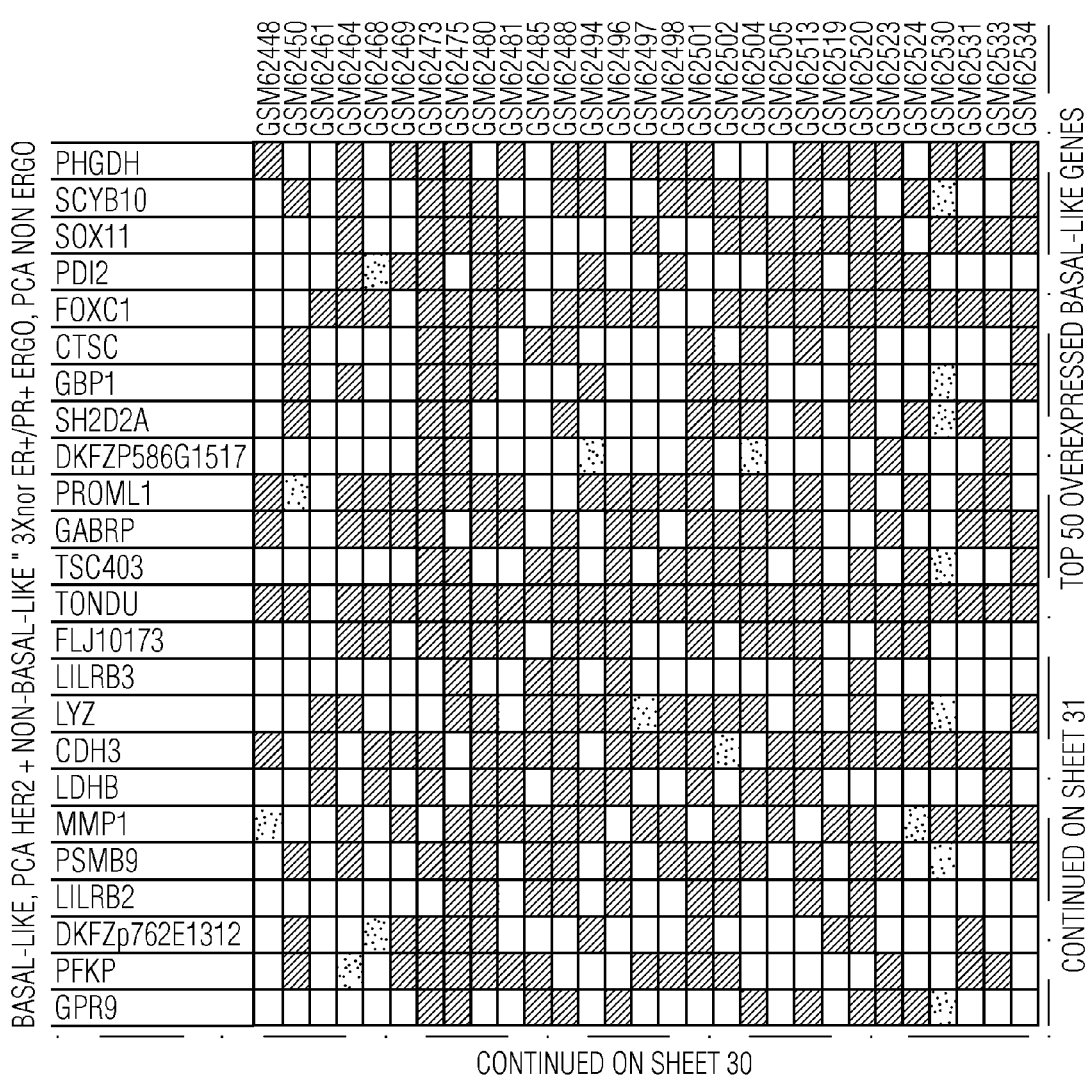
Figure 11D:
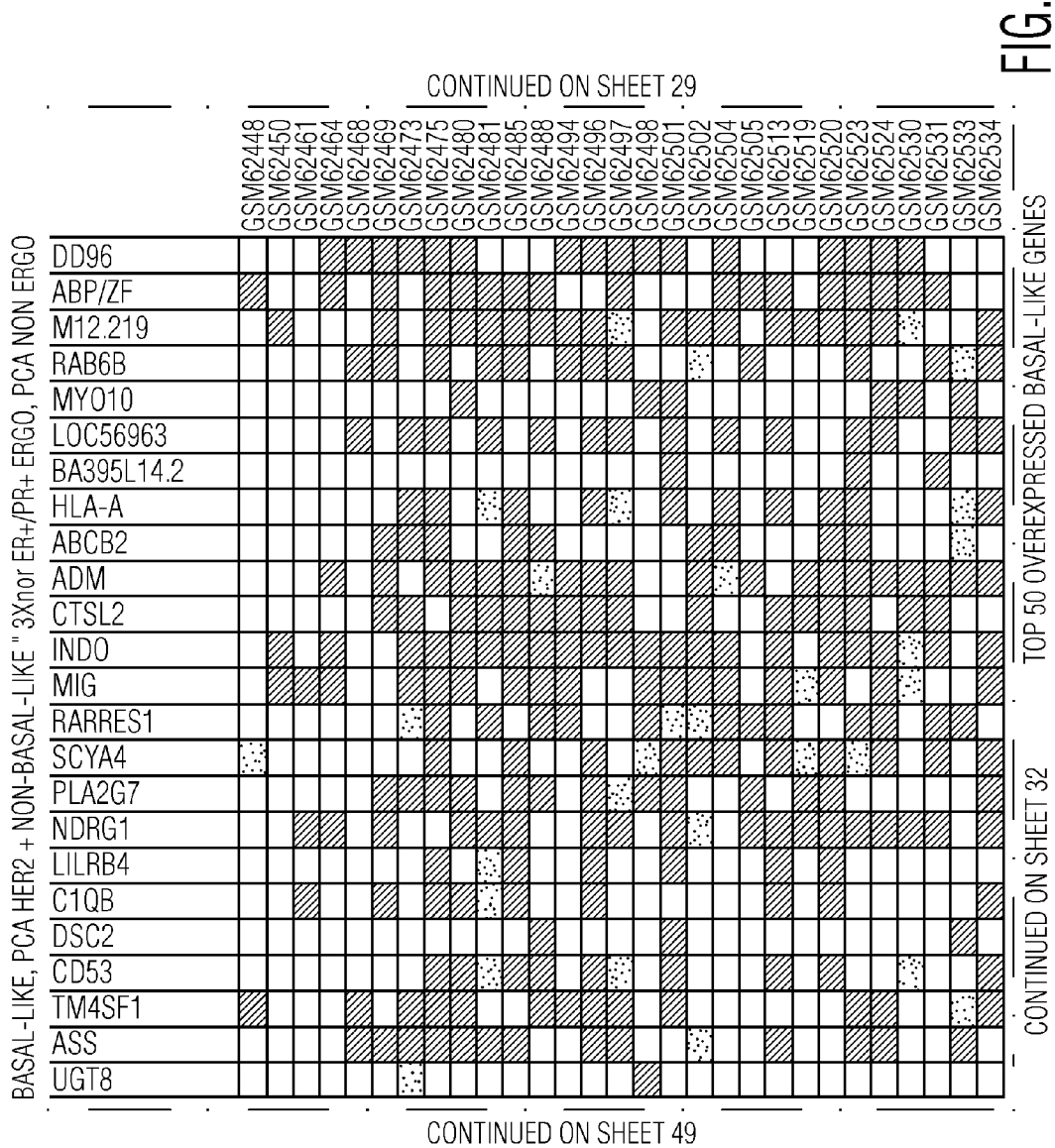
Figure 11G:
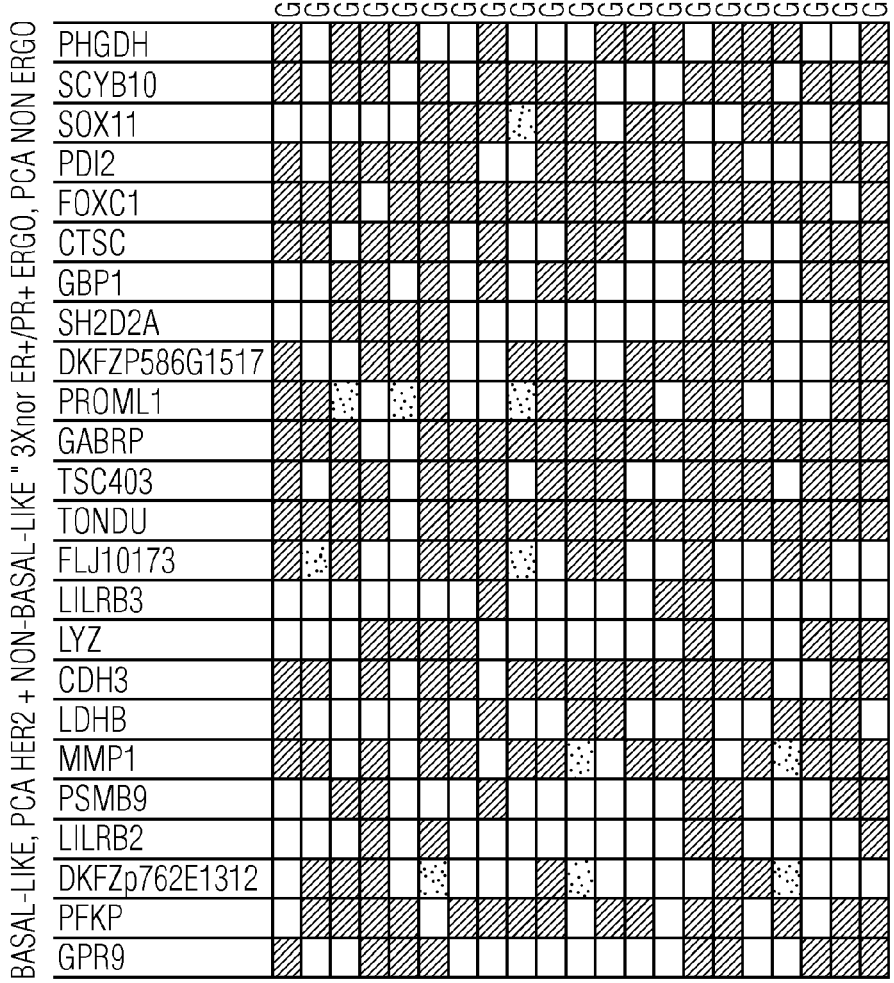
Figure 11I:
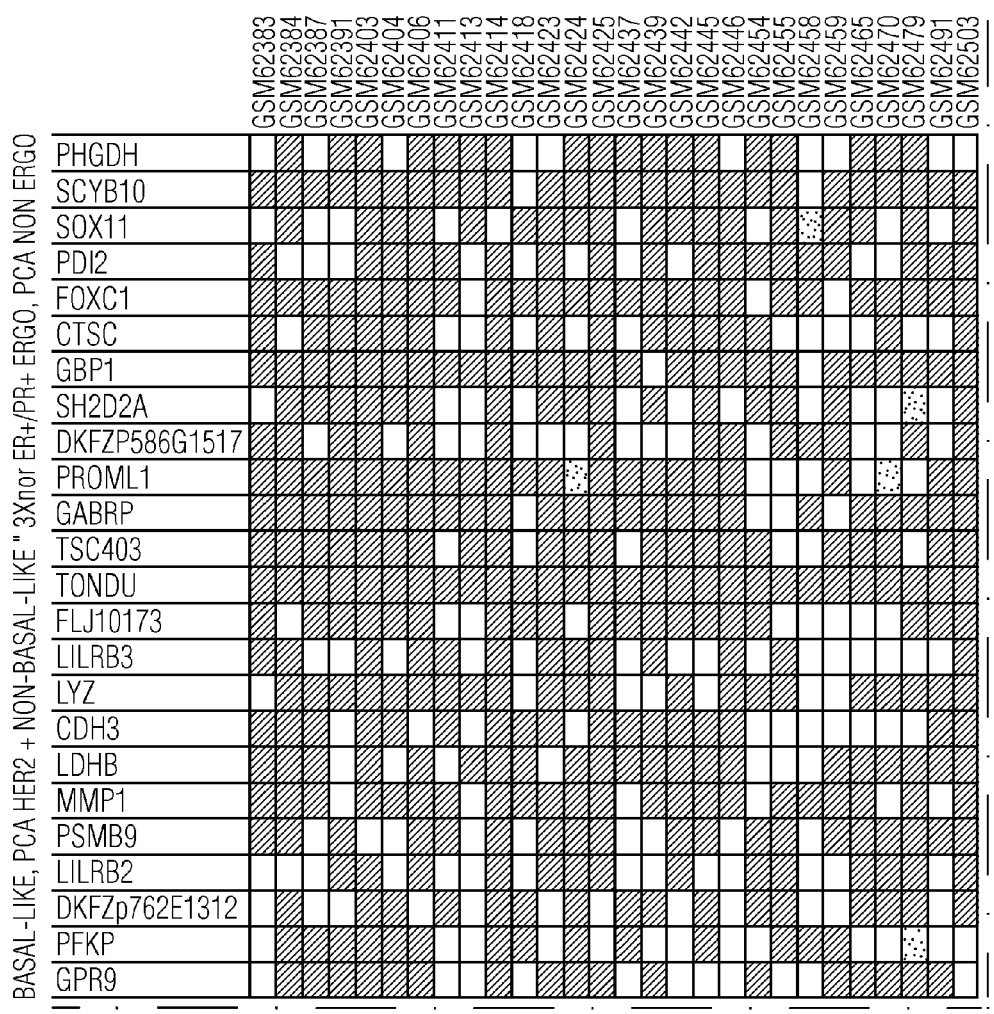
Figure 11J:
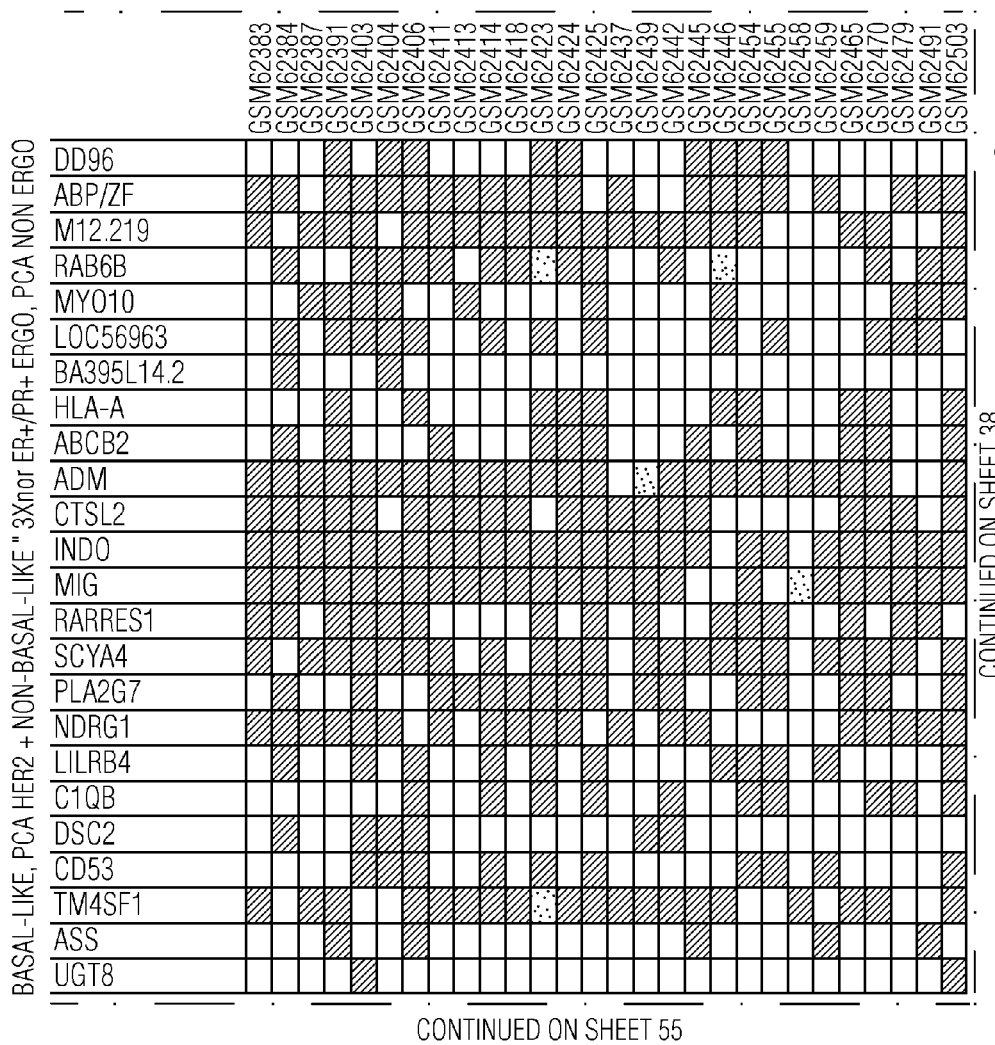
Figure 11L:
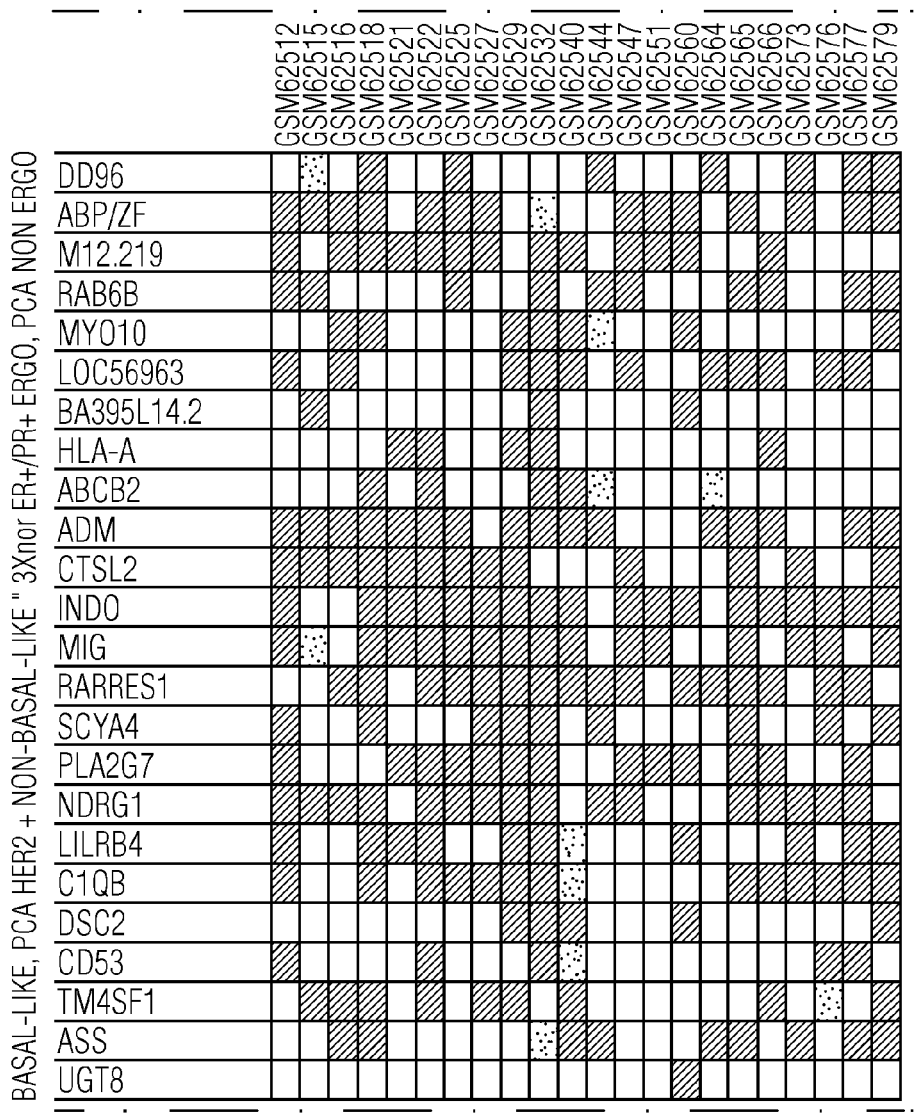
Figure 11M:
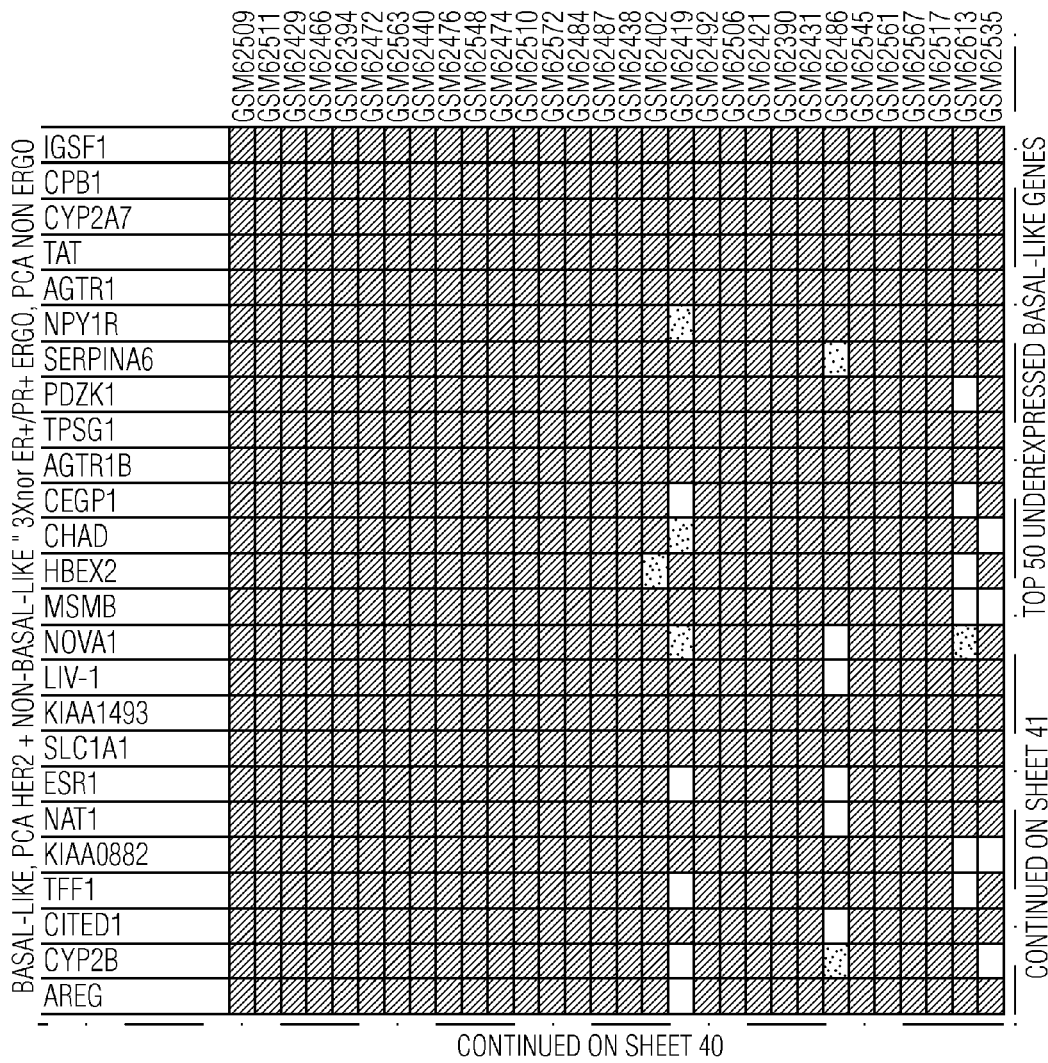
Figure 11N:
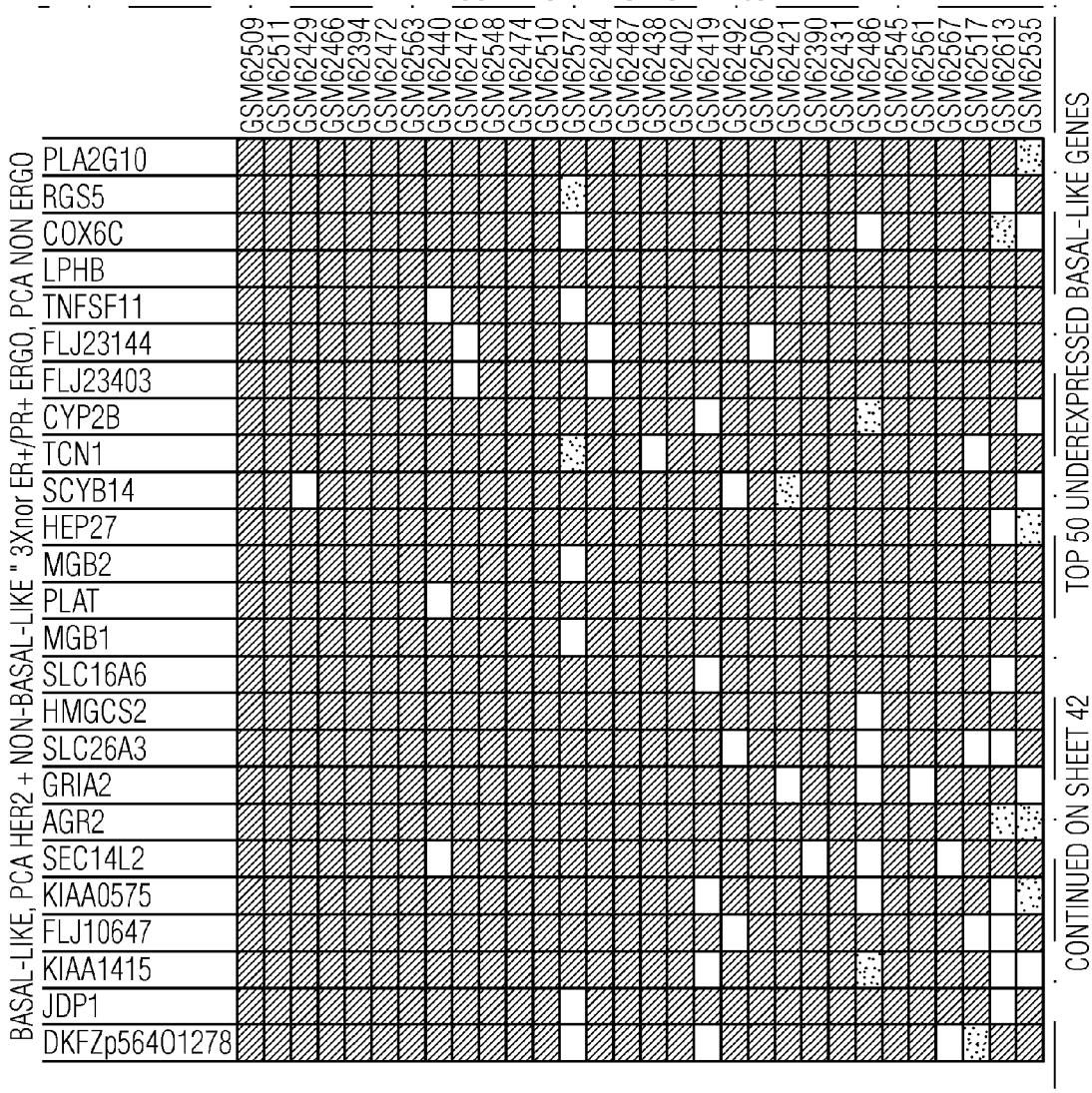
Figure 11S:
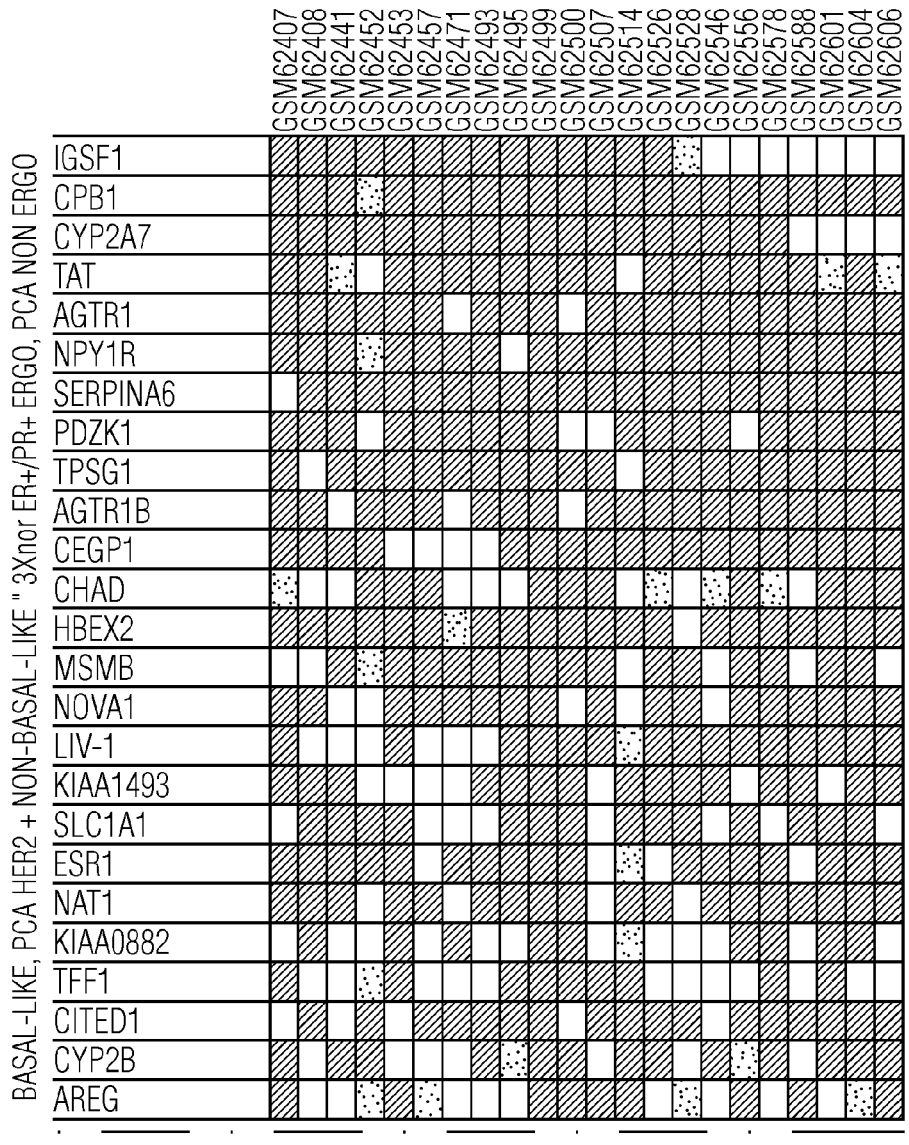

Detailed clinical survival data are available for 91 patients who provided tumor samples included in the Van't Veer microarray set. Clinical survival data are also available for the patients who provided tumor samples included in the Dai microarray set. The survival of patients with PCA basal-like breast cancer tumors, as identified by PCA, was shorter than for breast cancer patients identified by PCA as having other types of tumors (P<0.002). Seventy five percent of patients with non-basal like tumors as identified by PCA survived five years, whereas only fifty percent of patients with basal-like tumors as identified by PCA survived five years (FIG. 9). Patient survival data were plotted by the Kaplan-Meyer method and survival curves were compared using the Haentzel-Mantel statistic.

Detailed clinical survival data are also available for the 311 patients who provided tumor samples included in the Dai microarray set. FIG. 19 shows the clinical survival data for ERGO tumors, non-ERGO basal-like tumors, and the HER2 over-expressing tumors (FIG. 19A) subsets as well as the non-ERGO "triple non-positive" and all the remaining tumor subsets (FIG. 19B) identified by PCA analysis of the Dai microarray set. Patient survival data were plotted by the Kaplan-Meyer method and survival curves were compared using the Haentzel-Mantel statistic. Comparison of FIGS. 19A and 19B shows that patients with ERGO tumors, non-ERGO basal-like tumors, and the HER2 over-expressing tumors had a statistically significantly worse prognosis and odds of survival than all the remaining tumor subsets identified in the Dai microarray set by PCA analysis. These findings illustrate the point that different patient subsets with the same prognosis must be distinguished phenotypically for therapeutic purposes, even though the odds of survival are similar. This is because only HER2 over-expressing tumors can be treated with anti-HER2 therapeutics (e.g. trastuzumab) and only ERGO tumors can be considered for targeted therapy against ERGO tumor-associated genes. Stated differently, this data shows that individual HER2 over-expressing tumors and ERGO tumors must be classified and assigned to their appropriate treatment class followed by selection of an appropriate therapy for each individual patient having tumors in these clusters despite the similar survival prognosis for patients with tumors of either distinct type.

Example 2

Identification of E2F Responsive Gene Over-Expressing (ERGO) Tumors in Lung and Thyroid Organ Sites Lung Cancer Microarray Set.

The lung cancer microarray set published by Jones et al. was used to investigate E2F-responsive gene expression in human lung cancers and human lung cancer derived cell lines. Gene expression data from tumor sample probed gene spots this microarray set was normalized to data from normal human lung tissue sample probed gene spots that were included in the microarray set. Preliminary analysis by rank ordering methods confirmed that results obtained from microarray samples identified as human small cell lung cancer clinical samples and from samples identified as human derived small cell lung cancer cell lines were sufficiently similar to justify including data from both sample types in the analyses here.

Thyroid Cancer Microarray Set.

The gene expression microarray set published by Salvatore et al. was used to study E2F-responsive gene expression in human thyroid cancer. Microarray data from human thyroid cancer tumors were normalized to normal human thyroid tissue samples that were included in the microarray set. Gene expression data from tumor sample probed gene spots this microarray set was normalized to data from normal human thyroid tissue sample probed gene spots that were included in the microarray set.

Weighted Rank Ordering Methods and Criteria for Identification of ERGO Tumors in Lung and Thyroid Organ Sites.

First, a reference signal intensity value was obtained by determining the signal intensity values for the gene transcripts from normal lung or thyroid tissues samples as appropriate for a given array set to be analyzed. Then "over-expressed," "under-expressed," and non-over-expressed genes were identified. Gene "over-expression" was determined to occur when the signal intensity corresponding to a given gene transcript in the microarray set was 1.8 fold greater than the reference signal intensity value for the gene in normal lung or thyroid tissue as appropriate. Gene "under-expression" was determined to occur when the signal intensity corresponding to a given gene transcript in the microarray was 1.8 fold less than the reference signal intensity value for the gene in normal lung or thyroid tissue as appropriate. Gene "non-over-expression" was determined to occur when a gene was neither "over-expressed" nor "under-expressed."

Weighted rank ordering methods were performed using EXCEL™ software (Microsoft Corp., Redmond, Wash.) to rank the over-expressed genes by their frequency of expression among tumors. In these rank ordering analyses the most highly over-expressed genes were placed closest to the origin and the contribution of each tumor to the ranking was weighted by its proximity to the origin of the tumor axis.

These weighted rank ordering methods were then used to rank the tumors by the number of the 325 specific E2F-responsive genes, shown above in Table 1, over-expressed per tumor. Tumors with the highest number of over-expressed genes per tumor were placed closest to the origin. The contribution of each gene to the ranking was positively weighted by its proximity to the origin of the gene axis.

Individual tumors with the lowest number of over-expressed genes per tumor, and individual genes with the lowest over-expression frequency among the tumors were then iteratively stripped out of the dataset, with recalculation of rankings, until predetermined stopping conditions were met. The stopping conditions were that at least 20% of the tumors remaining in the dataset over-express at least 20% of the remaining E2F-responsive genes. Tumors that remained in the data set after satisfaction of the stopping conditions were identified as ERGO tumors.

Identification of ERGO Tumors in Lung.

Microarray based studies of human lung cancer have been able to resolve adenocarcinomas, carcinoids, large cell cancers, and normal lung tissue, but have been unable to distinguish large cell neuroendocrine tumors from small cell lung cancers. The analyses here were undertaken because many small cell lung cancers are known to have Rb gene abnormalities. This is significant because normally the Rb tumor suppressor protein binds to E2F and regulates E2F mediated gene transcription. Thus, the analyses here sought to determine if some of these small cell lung cancers could be ERGO tumors and whether these ERGO tumors could be distinguished from non-ERGO neuroendocrine precursors by PCA based methods.

PCA Analysis of the Jones Lung Cancer Microarray Set Identified a Cluster of Tumors that Contained Carcinoids, Large Cell Neuroendocrine Tumors, and Small Cell Lung Cancers (FIG. 2E).

This lung cancer tumor cluster, identified by PCA was then further analyzed. This was done by using further refined PCA in which the analyzed gene set was restricted to the E2F-responsive genes listed in Table 1 shown above. In these refined PCA analyses only those tumors in the lung cancer tumor cluster initially identified by PCA were used as input data.

Figure 13:
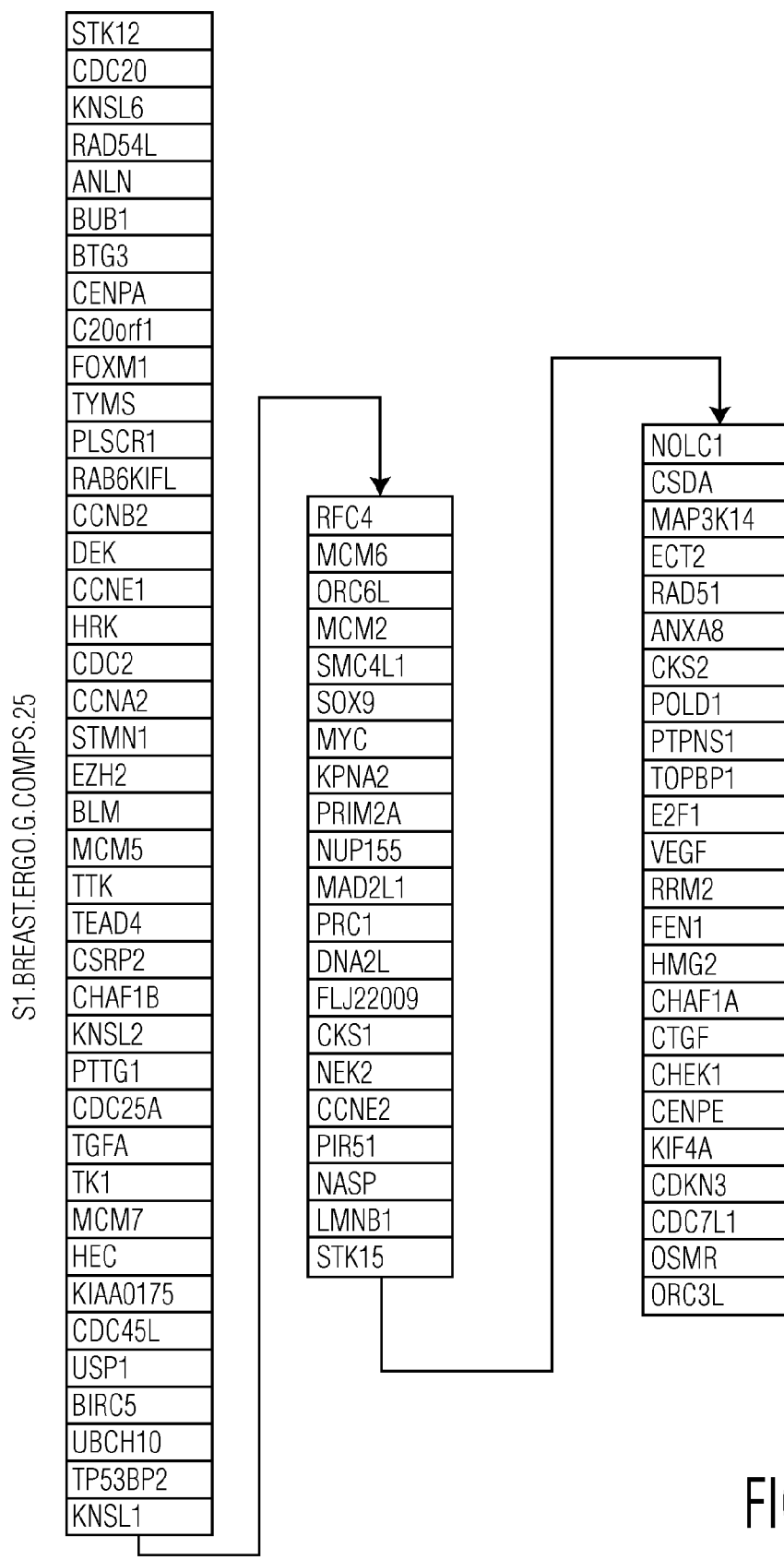
FIG. 13 shows a comparison of the most highly over-expressed E2F-responsive genes of ERGO tumors identified by refined PCA in the Van't Veer human breast cancer microarray set (s1), and ERGO tumors identified by refined PCA in the purged Dai human breast cancer microarray set (s2) with small cell lung cancer tumors identified by PCA in the Jones human lung cancer microarray set.
Figure 14A:
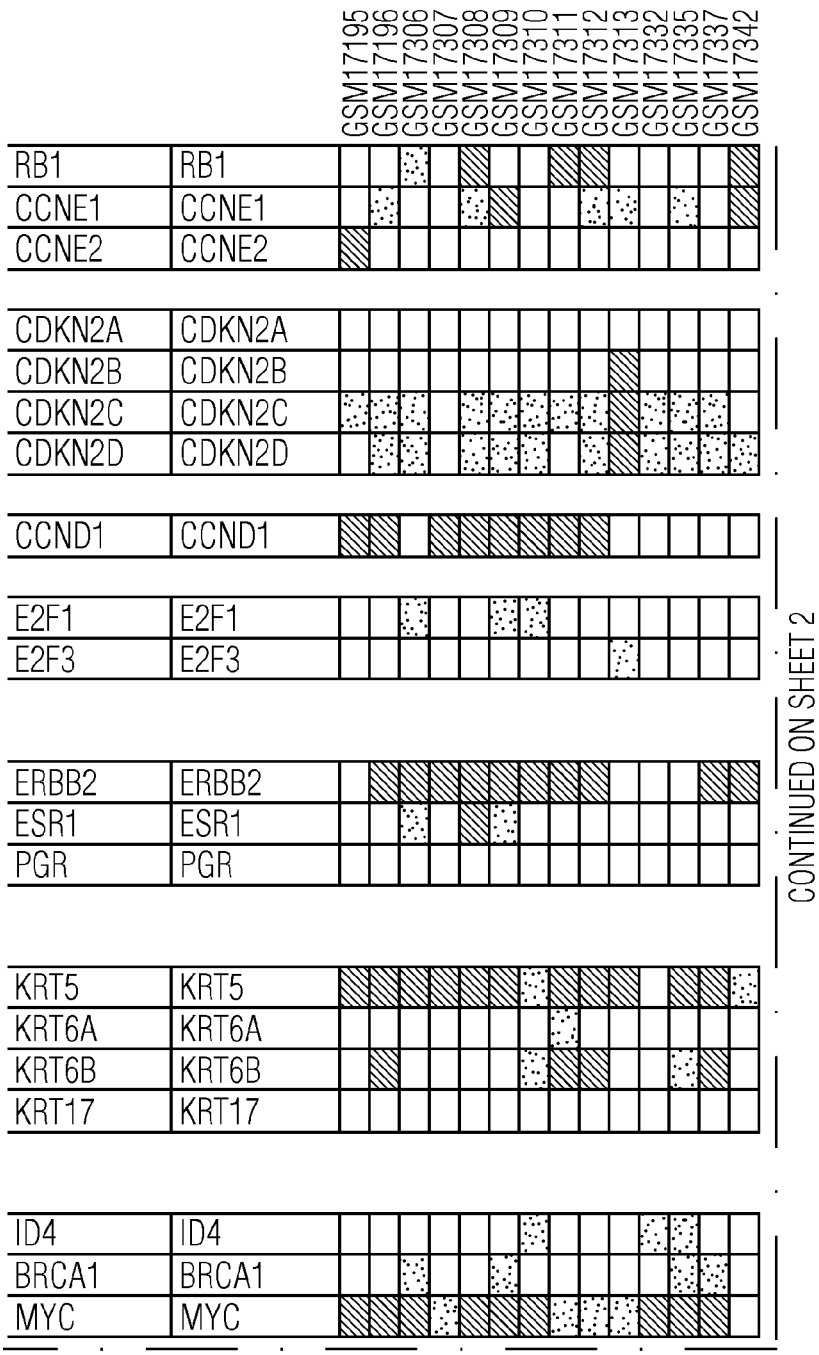
Figure 14B:
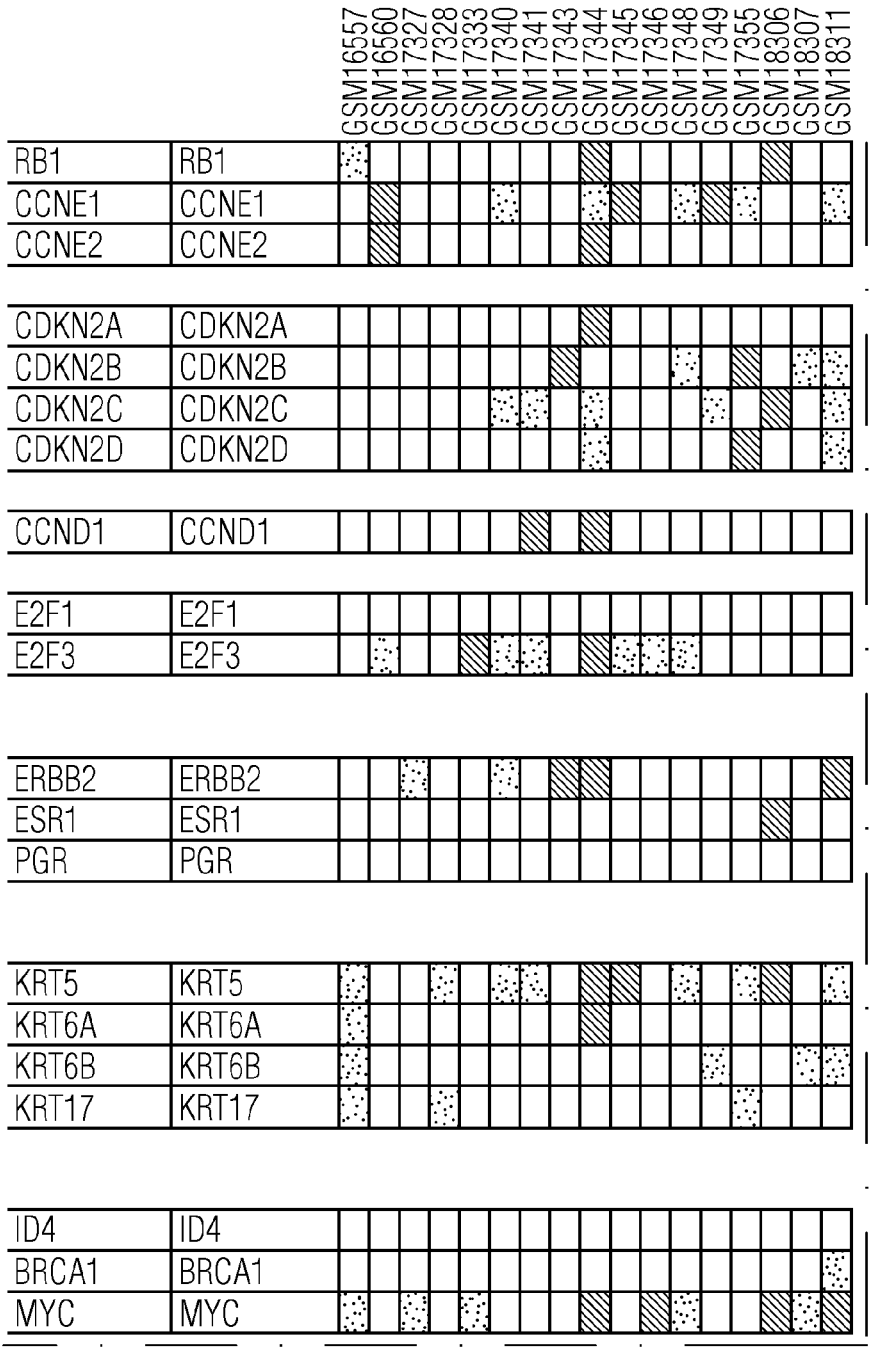
Figure 14D:
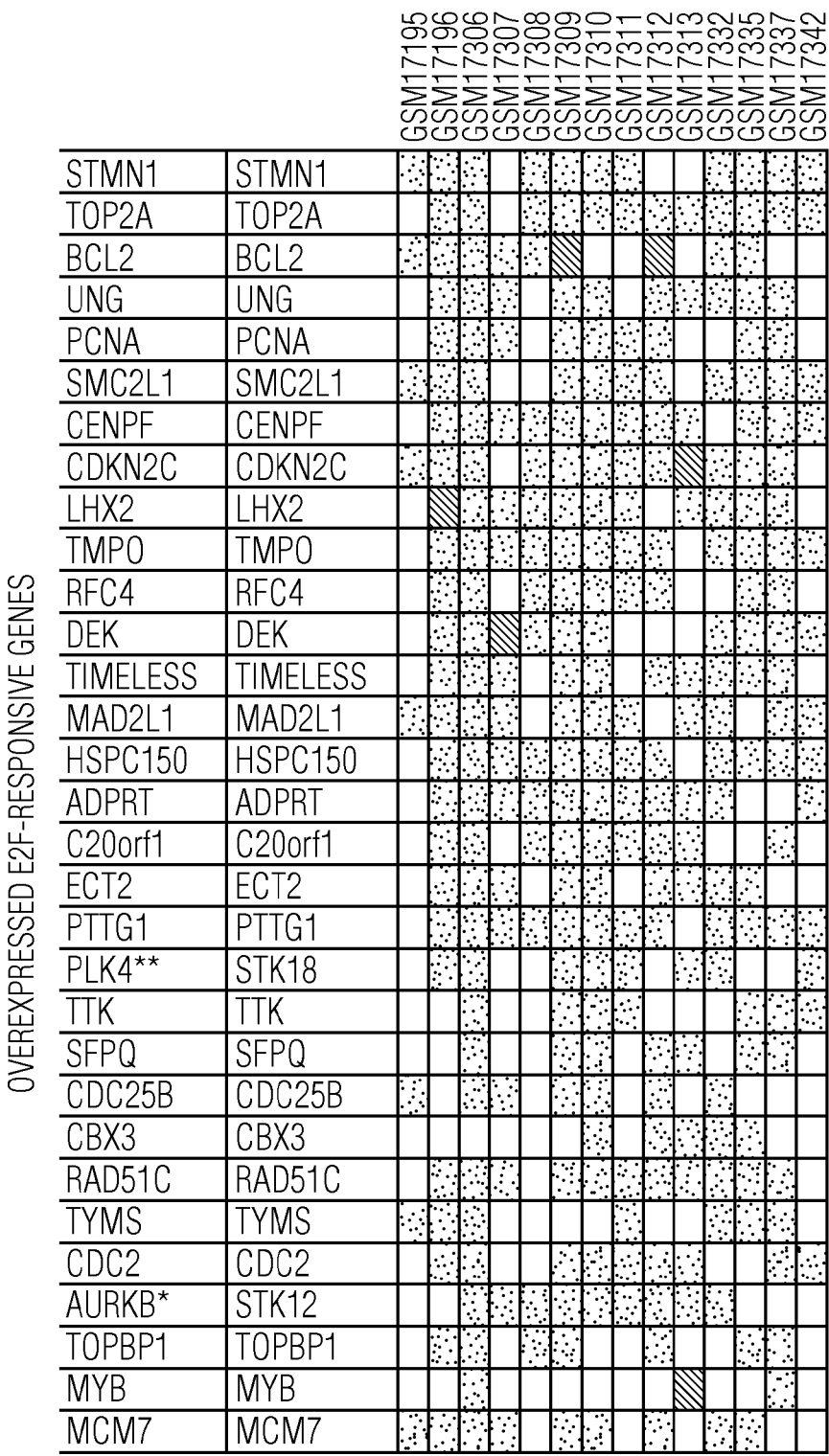
Figure 14G:
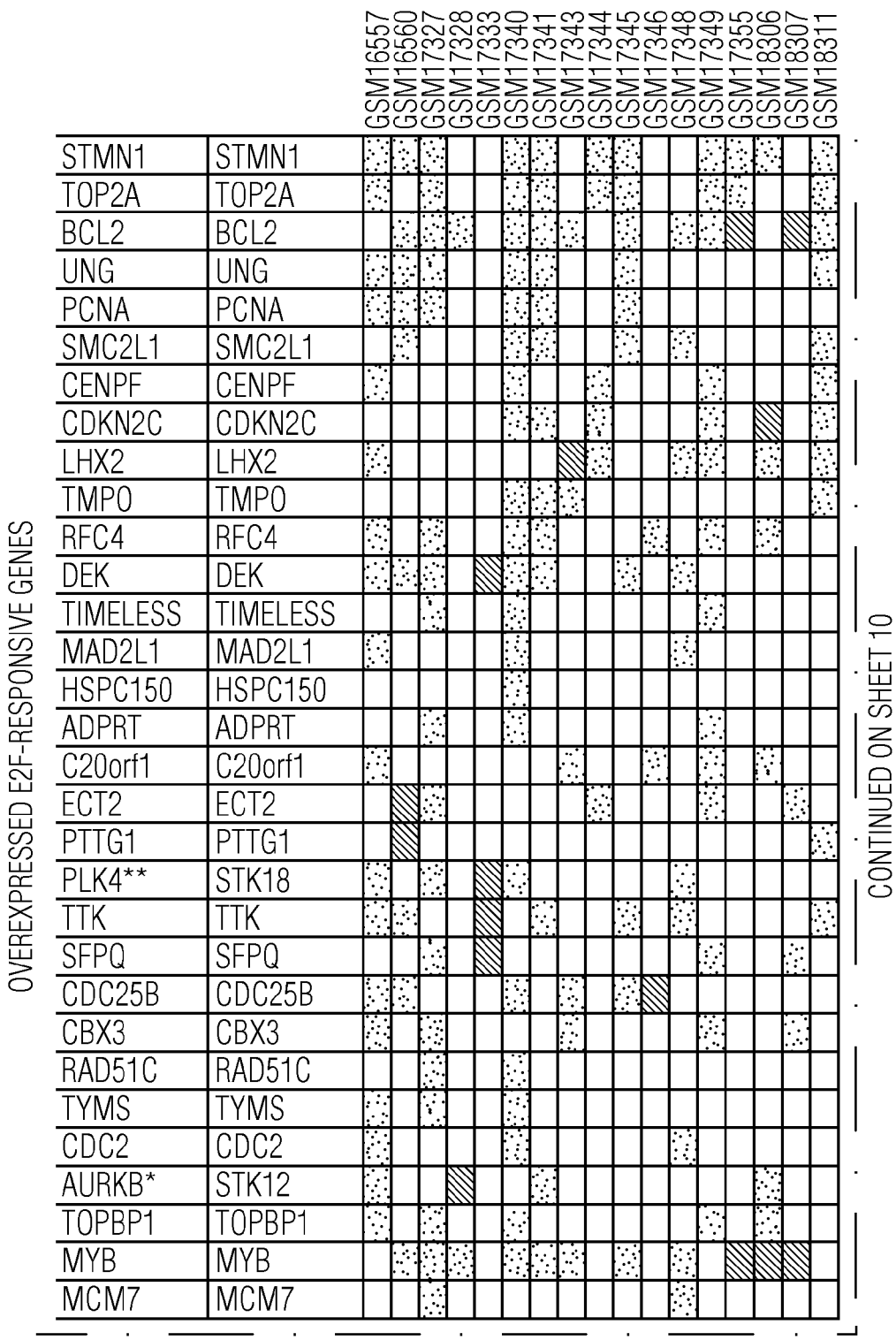

The result of this refined PCA analysis was that three clusters corresponding to carcinoids, large cell neuroendocrine tumors, and small cell lung cancers were identified (FIG. 2F). The cluster consisting largely of small cell lung cancers over-expressed a number of E2F-responsive genes identical to those found in ERGO breast cancers such that over 50% of the E2F-responsive genes expressed in the ERGO breast cancer tumors identified by refined PCA and the E2F-responsive genes expressed in the small cell lung cancer cluster identified by refined PCA were identical (FIG. 13). This indicates that this sub-group of small cell lung cancers are ERGO tumors. The E2F-responsive genes that are over-expressed in ERGO lung cancers are over-expressed infrequently in most large cell neuroendocrine tumors and carcinoid tumors.

Small cell lung cancer ERGO tumors appear to have E2F regulatory defects (FIG. 14 and Table 8). Twenty-nine percent of small cell lung cancer ERGO tumors under-express Rb, and 36% over-express cyclin E1 or cyclin E2. This observation and the under-expression of cyclin D1 in 57% of small cell lung cancer ERGO tumors further indicates E2F dysregulation in ERGO tumors. There is no p16$^{ink4a}$ over-expression in small cell lung cancer ERGO tumors. However, p18 and p19, which like p16$^{ink4a}$ are cdk4 and cdk6 inhibitors that block phosphorylation of Rb by cyclin D1, are over-expressed in abundance and over-expression of p18 is found in 86% of the small cell lung cancer ERGO tumors 86% while over-expression of p19 is found in 71% of these small cell lung cancer ERGO tumors. p18 and p19 are believed to function analogously to p16$^{ink4a}$ and therefore their over-expression can be a marker for E2F dysregulation.

Additionally, the over-expression patterns of non-E2F-responsive genes in these small cell lung cancer ERGO tumors are shared with large cell neuroendocrine tumors, but not carcinoid tumors, indicating that these small cell lung cancers are derived from large-cell neuroendocrine tumors. In addition, there are non-E2F-responsive genes that are over-expressed in small cell tumors and large cell neuroendocrine tumors that are also over-expressed in carinoid tumors, indicating that both small cell tumors and large cell neuroendocrine tumors share a common heritage with carcinoids (FIG. 14).

Importantly, the E2F-responsive genes that are over-expressed in small cell lung cancer ERGO tumors identified by refined PCA and in breast cancer ERGO tumors identified by refined PCA strongly overlap, but the non-E2F responsive genes that are over-expressed in their respective precursor cells are mostly different, with several notable exceptions.

Like breast cancer ERGO tumors, large cell neuroendocrine tumors over-express basal cytokeratins and other basal-like markers.

Microarray based studies have shown the phenotype of anaplastic thyroid cancers differs from that of papillary thyroid cancers and normal thyroid tissue with regard to the over-expression of genes involved in cell cycle control and chromosome segregation. The analyses here were undertaken because the transcriptional promoters of many of these cell cycle control and chromosome segregation genes are known to contain E2F binding sites.

Identification of ERGO Tumors in Thyroid.

Figure 15A:
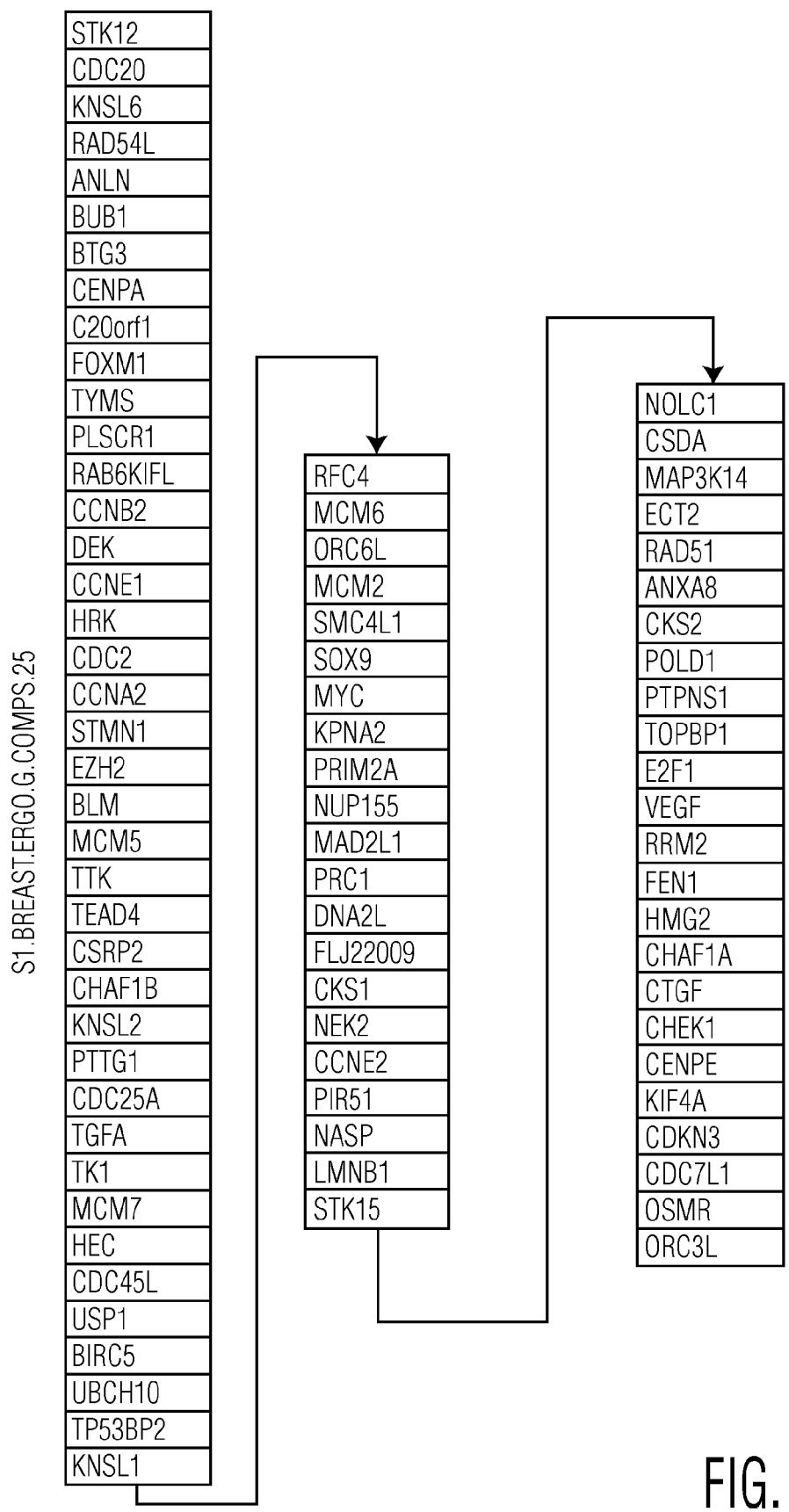
Figure 15C:
Figure 16A:
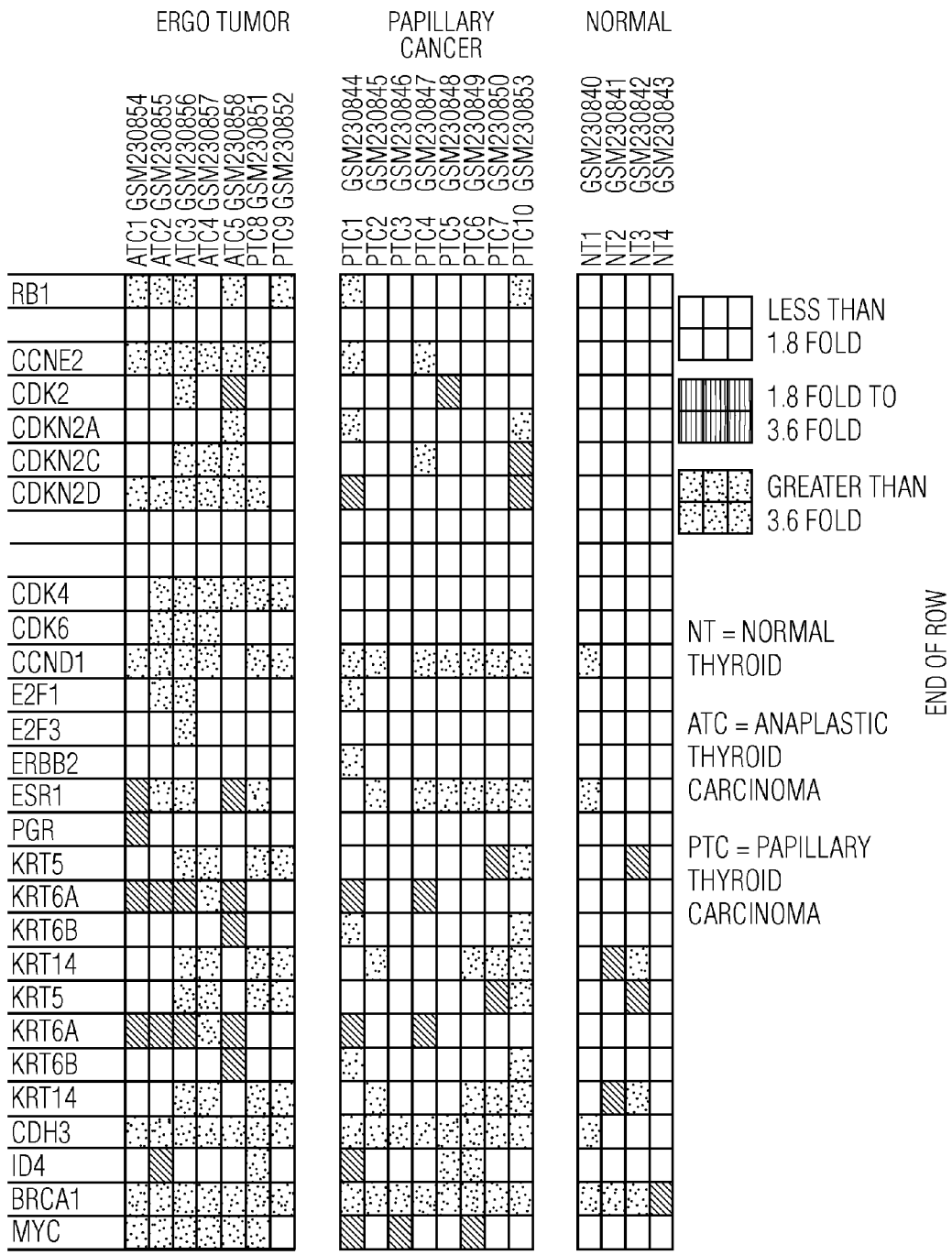
Figure 16C:
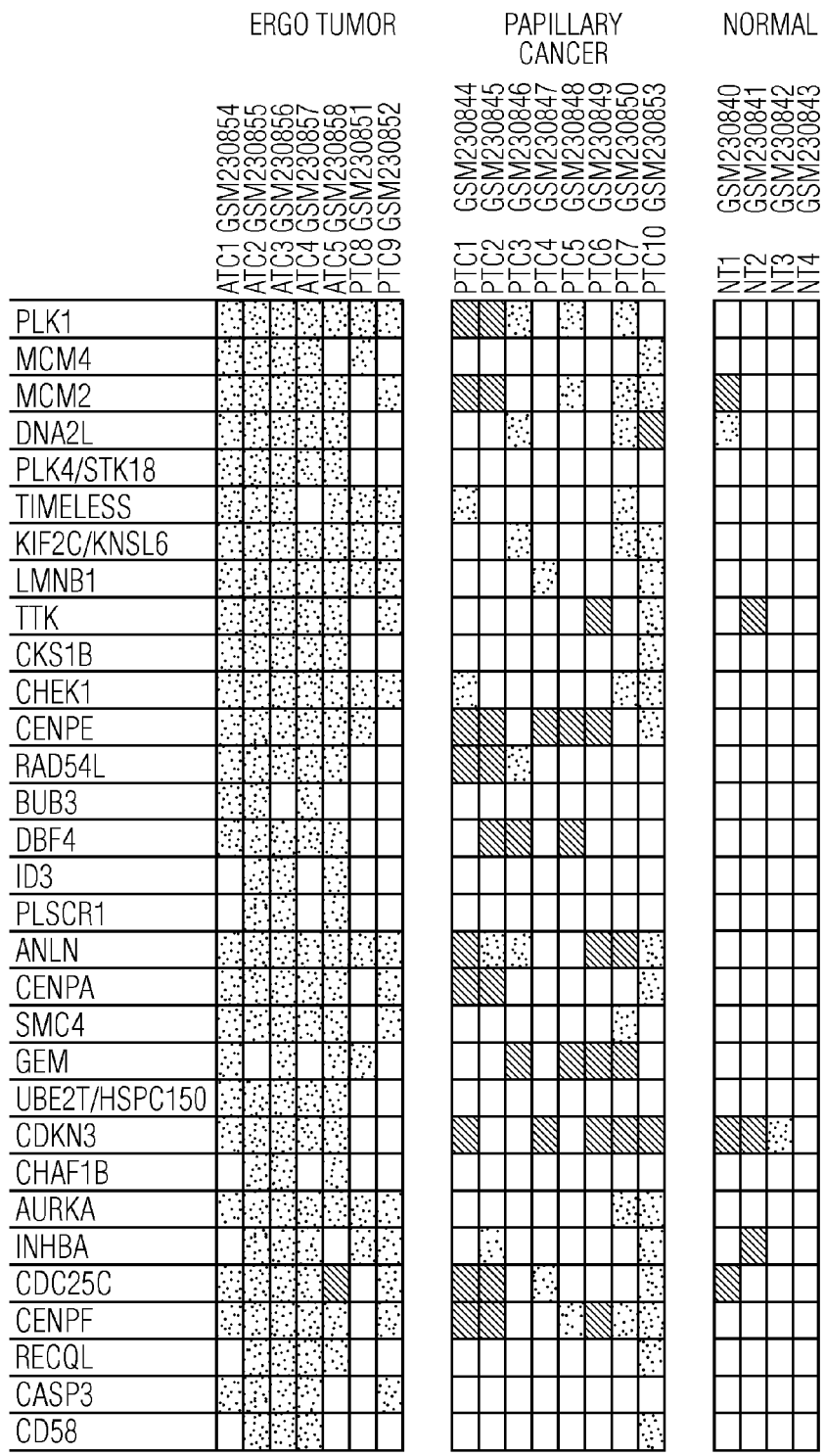
Figure 16E:
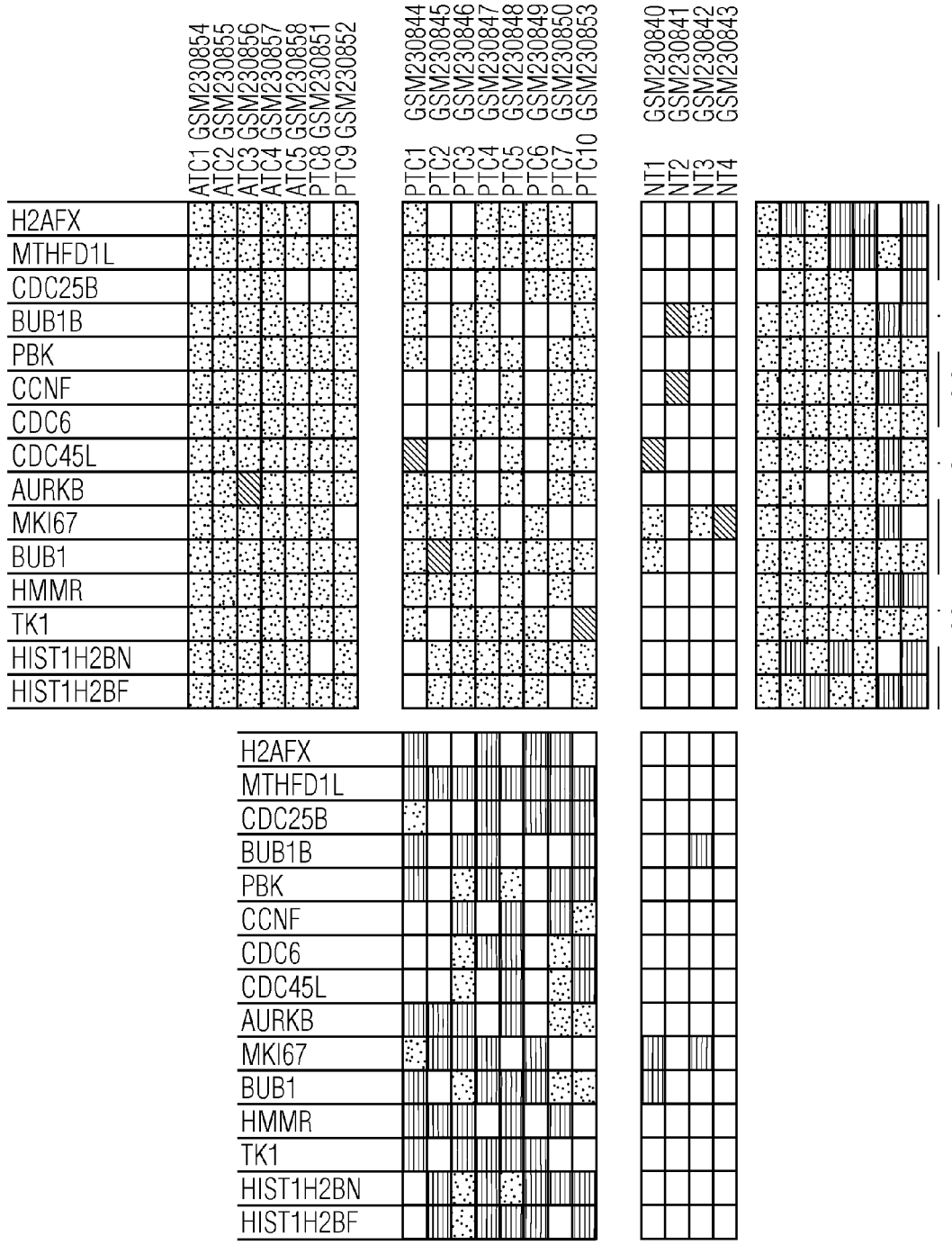
Figure 16G:
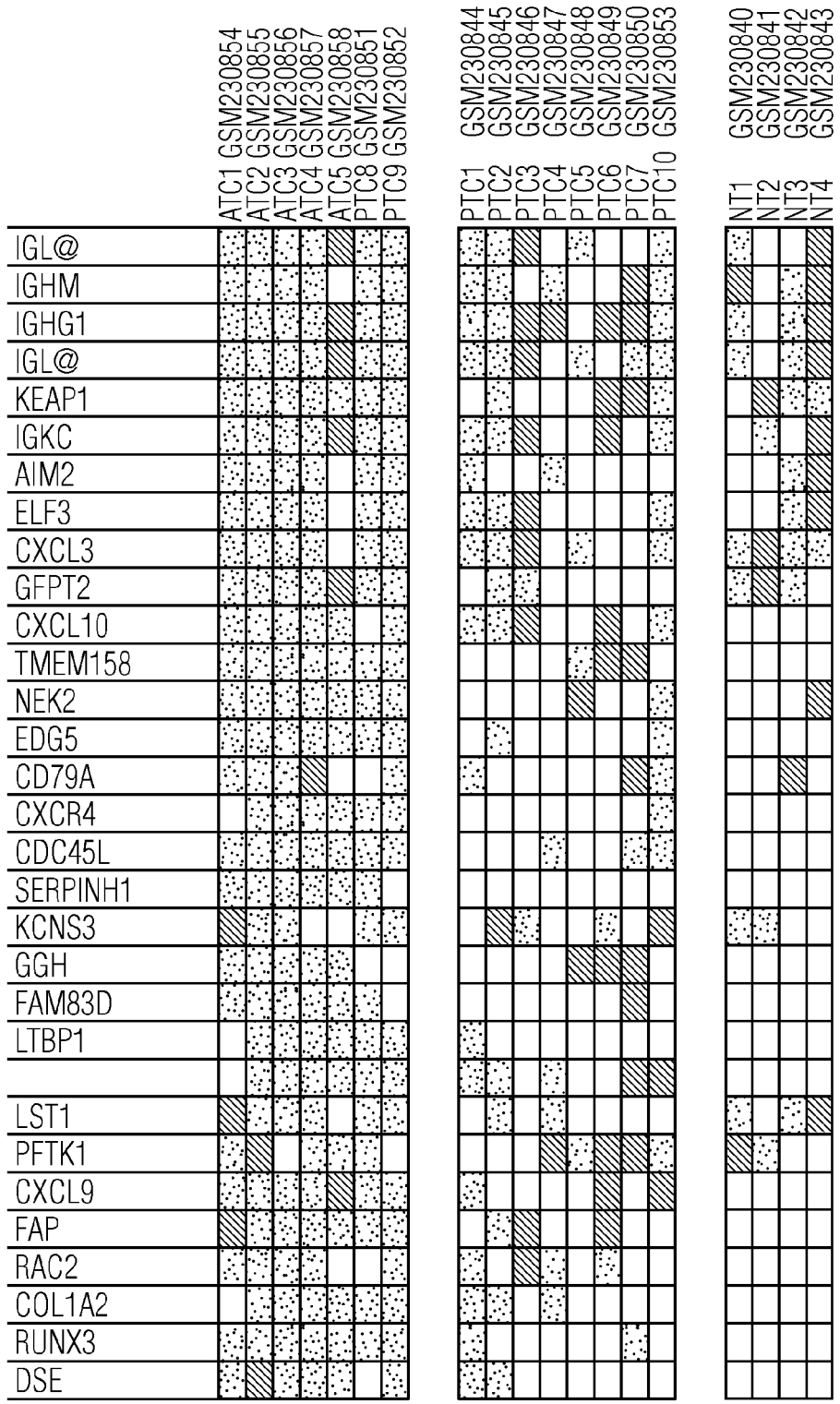
Figure 16H:
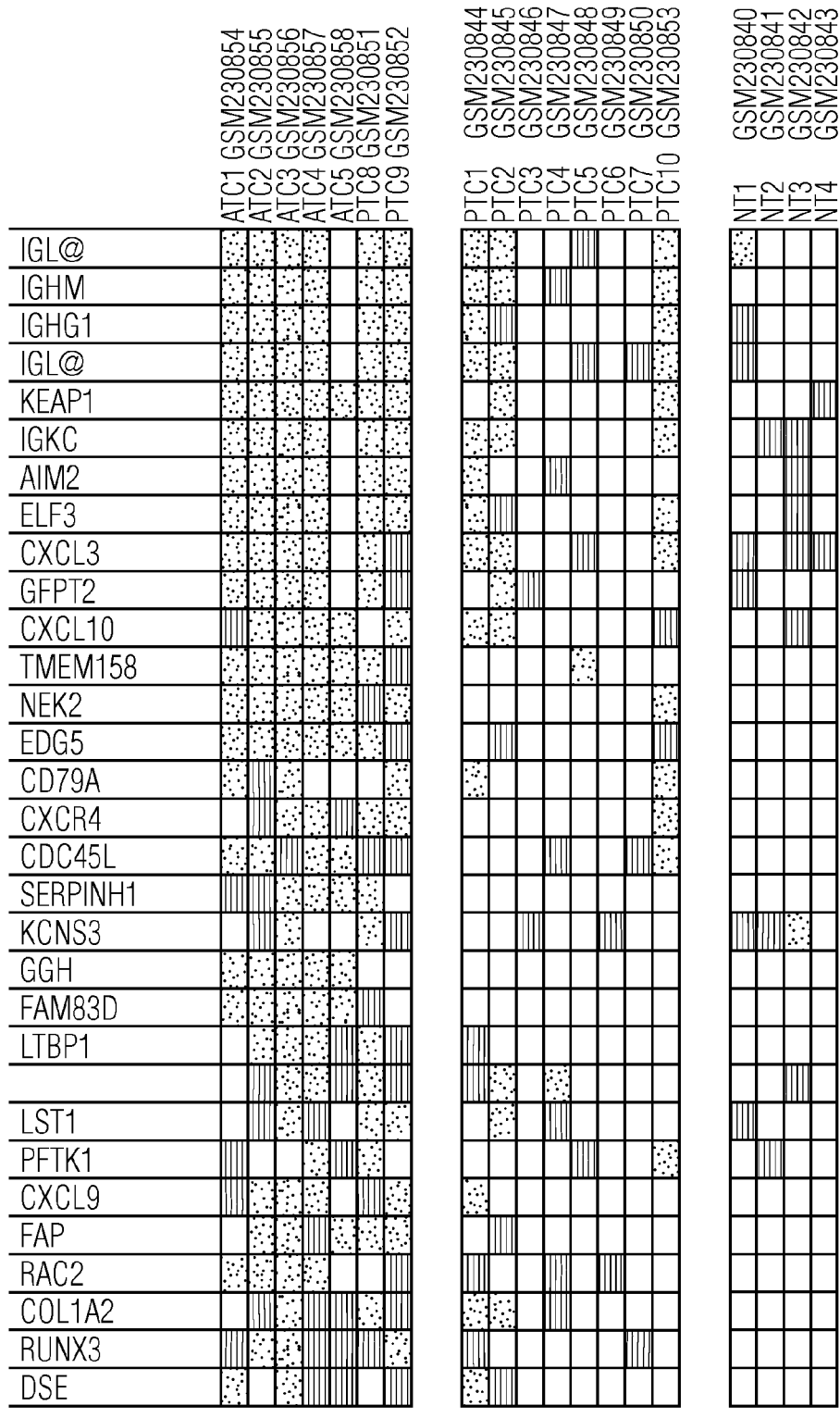
Figure 16I:
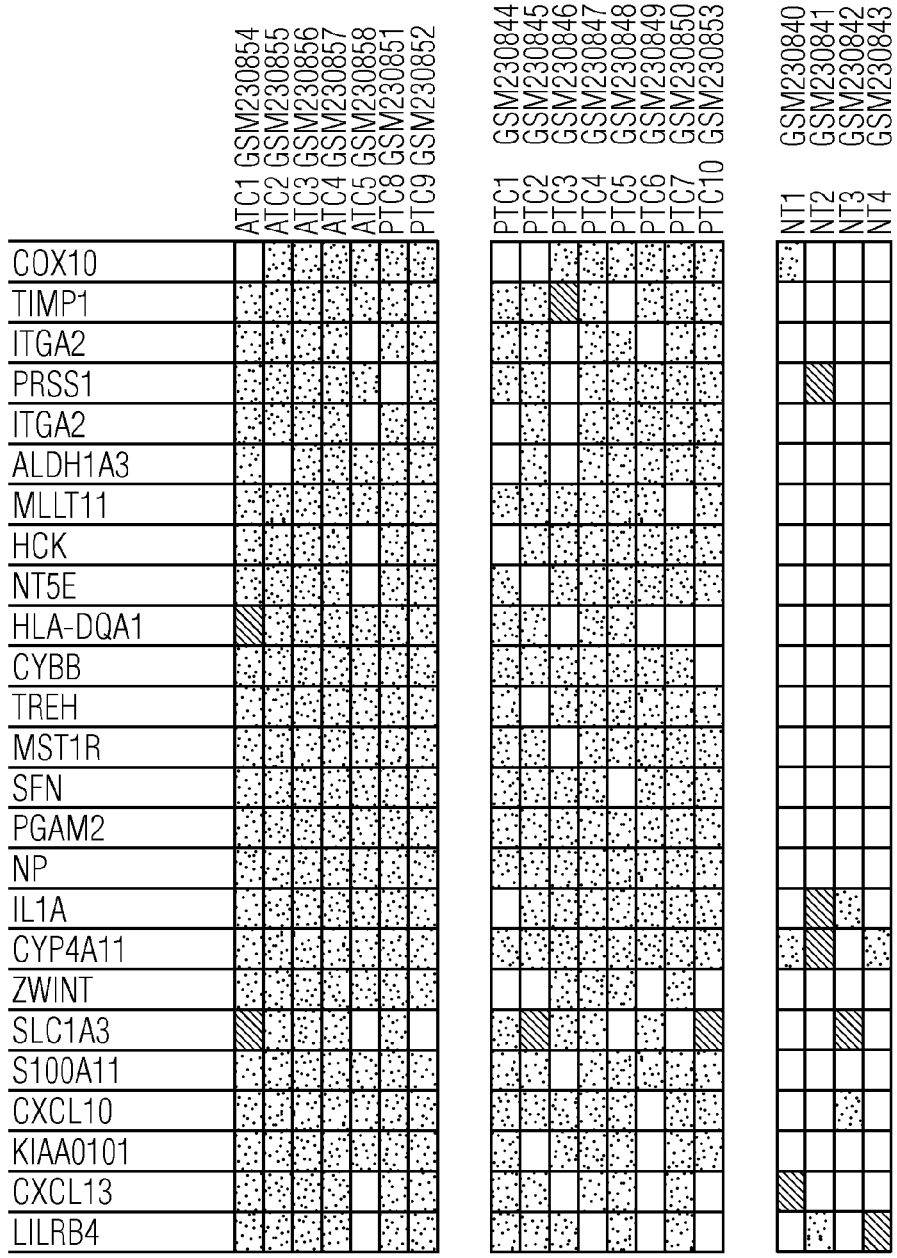
Figure 16B:
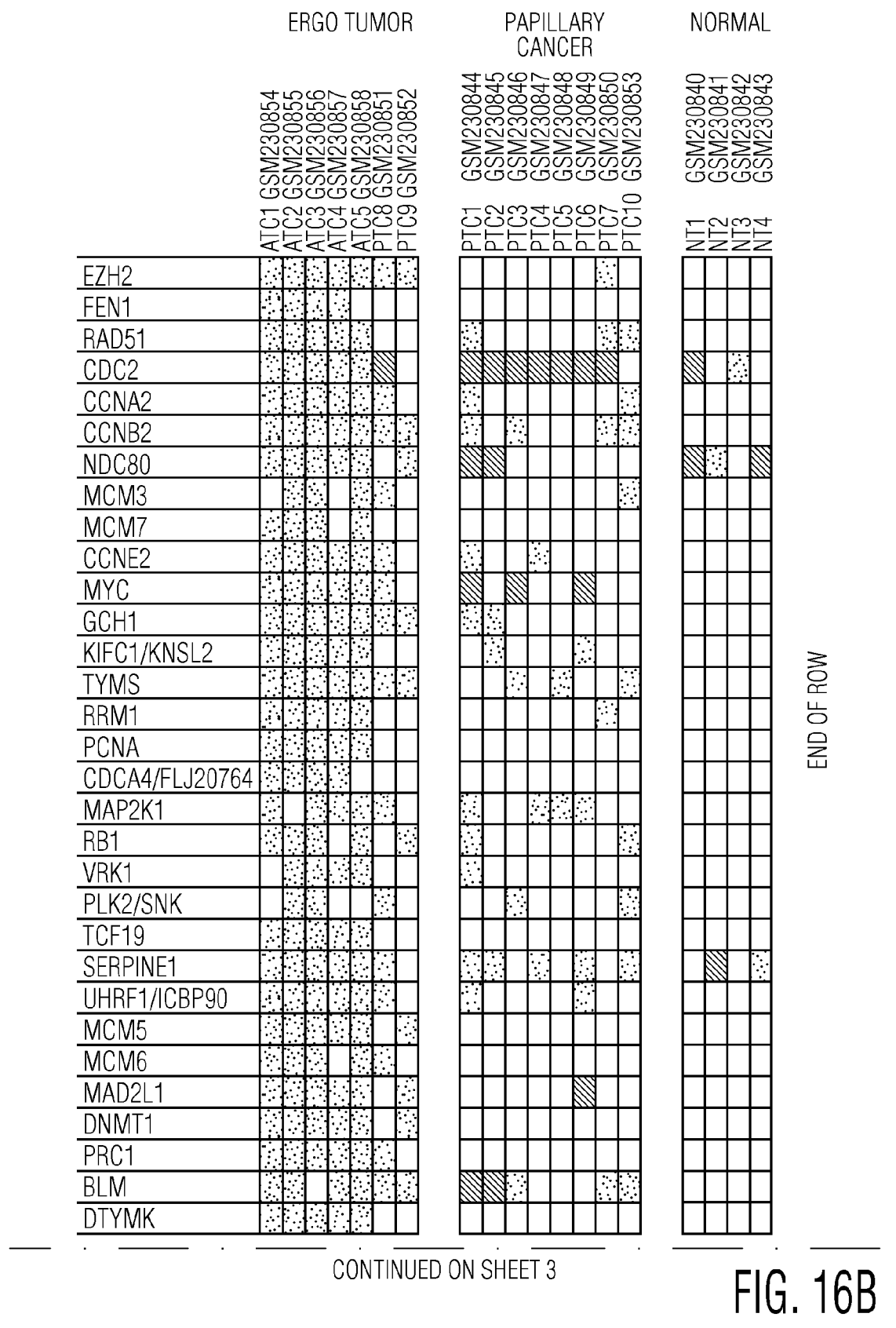
Figure 16D:
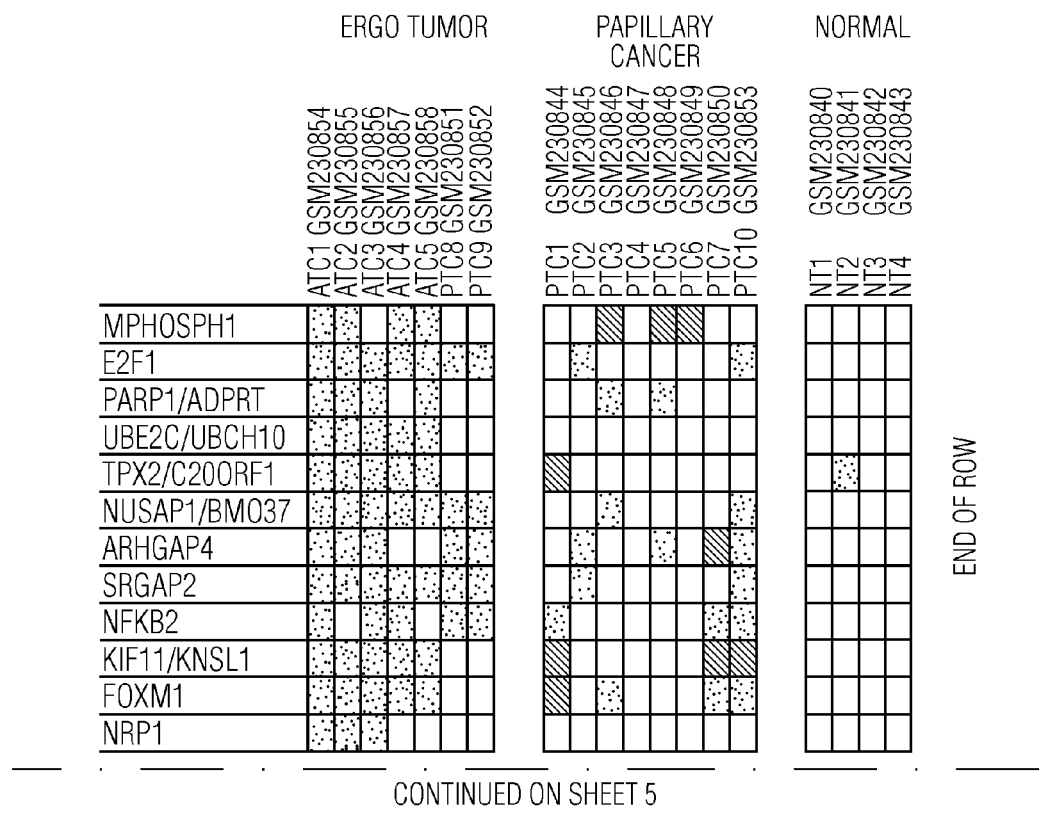
Figure 16J:
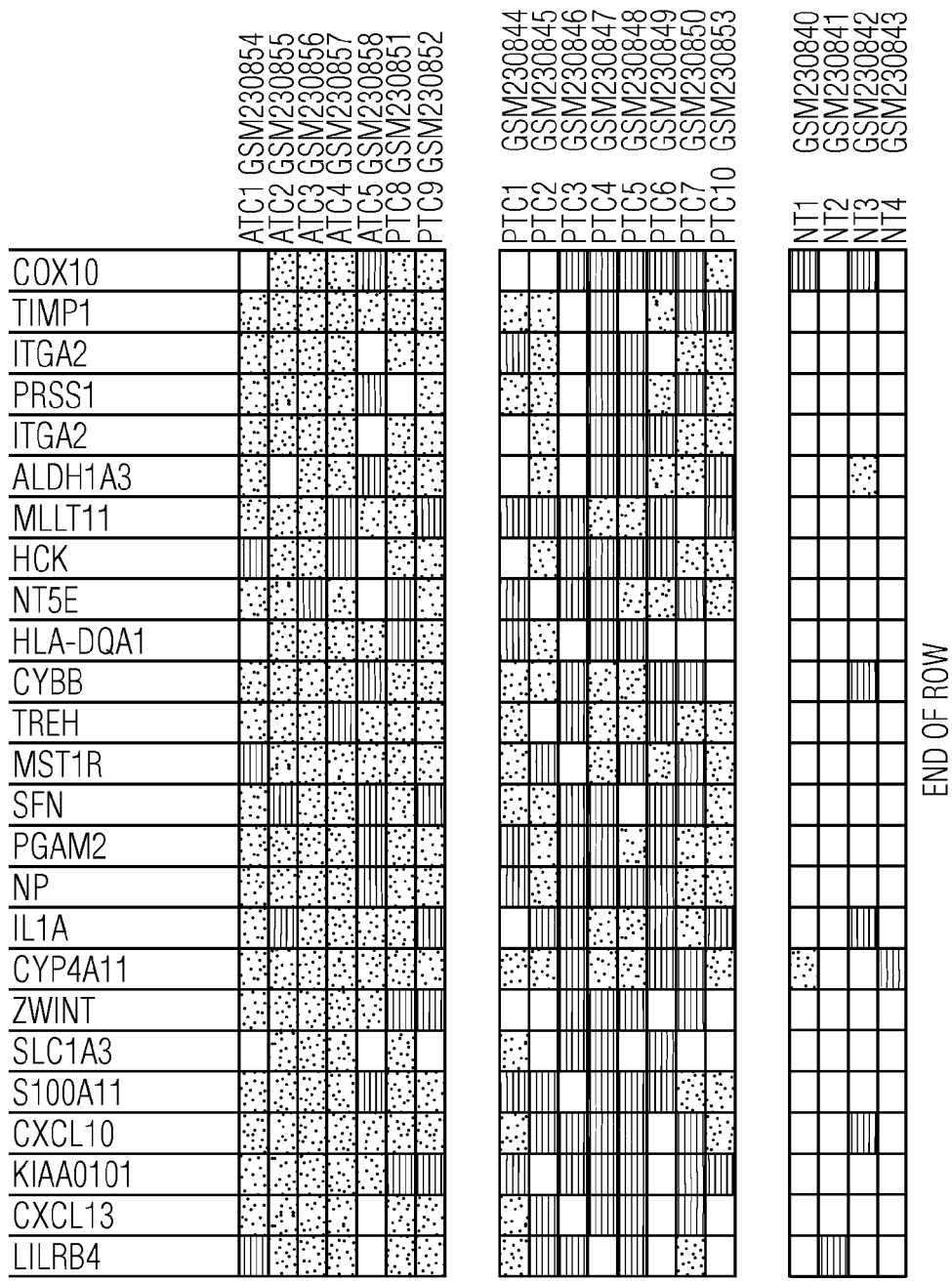
Figure 16K:
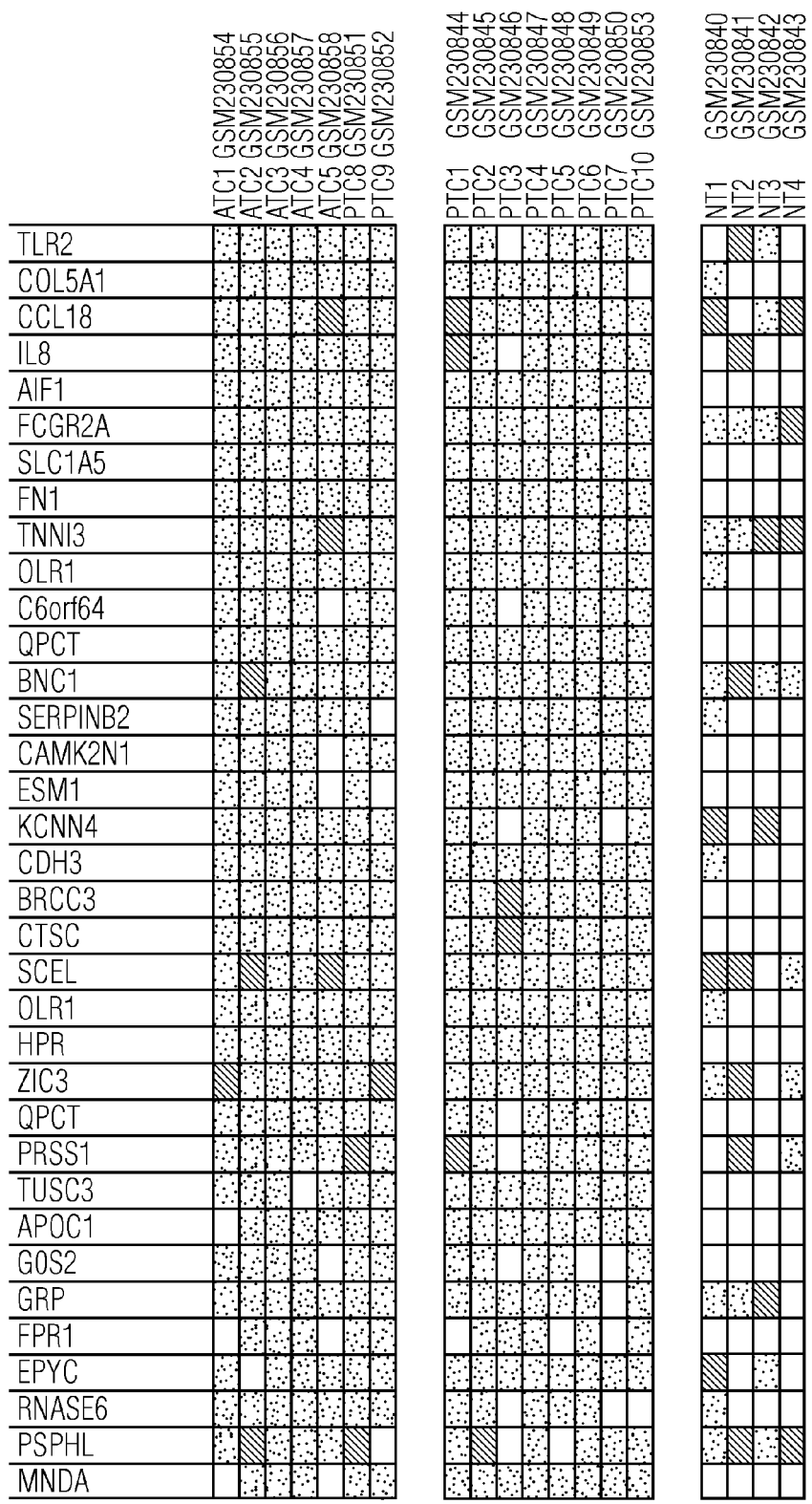
Figure 16L:
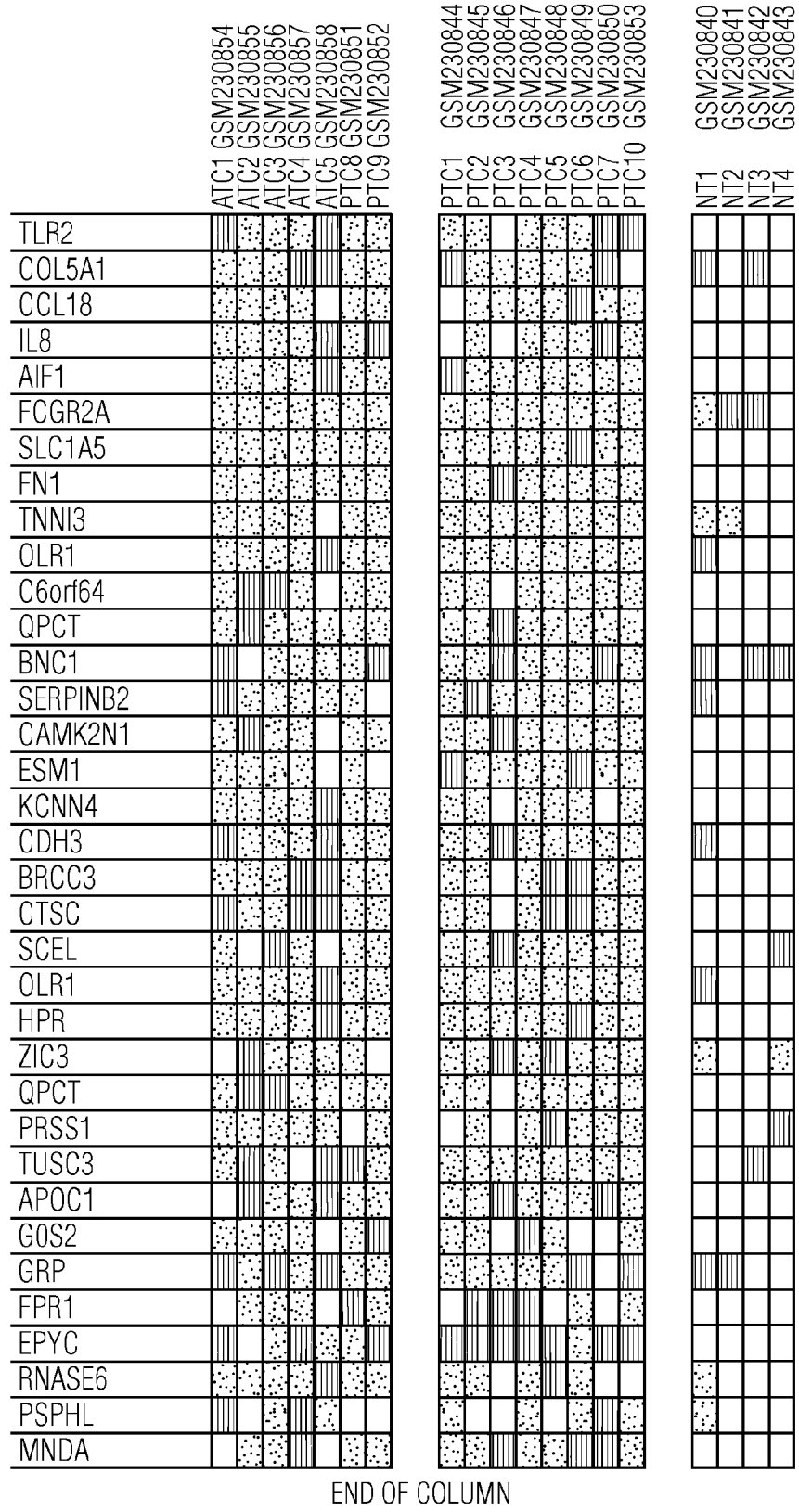

The human thyroid cancer microarray set of Salvatore was also analyzed by PCA. Anaplastic thyroid cancers clustered separately by PCA (FIG. 2G), but this anaplastic thyroid cancer cluster also included two papillary thyroid cancers with transitional phenotypic patterns. There were 73 E2F-responsive genes that were over-expressed in at least 25% of the thyroid cancer samples in this anaplastic thyroid cancer cluster. Importantly, these 73 E2F-responsive genes were not over-expressed in those thyroid cancer samples that were not part of the anaplastic thyroid cancer cluster identified by PCA. Furthermore, fifty-one percent (51%) of these 73 E2F-responsive genes were identical to the over-expressed E2F-responsive genes that are characteristic of the ERGO breast cancer tumors identified by refined PCA (FIG. 15). A profile of selected over-expressed genes in thyroid cancer is provided in FIG. 16. There is also a group of E2F-responsive genes that was over-expressed in both anaplastic and papillary thyroid cancers, although the over-expression occurred at higher levels in the anaplastic thyroid cancer tumors which clearly identifies the papillary thyroid cancers as precursors of the ERGO anaplastic thyroid cancers. This conclusion is further supported by the observation that large numbers of both E2F-responsive and non-E2F-responsive genes were over-expressed in both tumor types, but without clear differences in levels of gene over-expression between the ERGO anaplastic thyroid cancers and papillary thyroid cancers (FIG. 16).

Figure 17A:
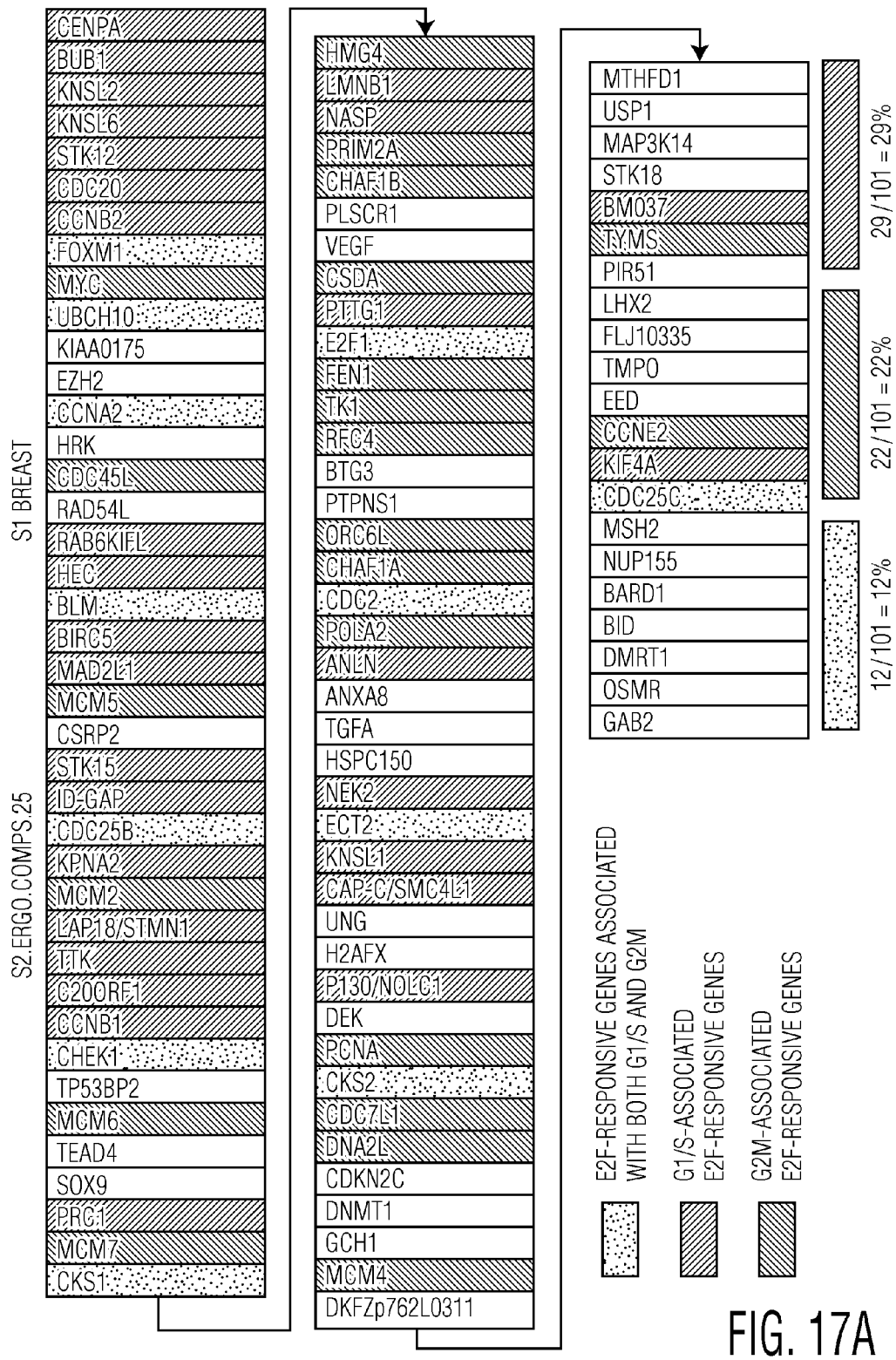
FIGS. 17A to 17C show partial views intended to form one complete view of the over-expressed genes in ERGO tumors identified by refined PCA analysis in the Van't Veer human breast cancer microarray set (s1), the purged Dai human breast cancer microarray set (s2), the Jones human lung cancer microarray set, and the Salvatore human two prominent subclasses of E2F-responsive genes, a group that affects the G1/S cell cycle phase transition, and group that affects the G2M portion of the cell cycle.
Figure 17B:
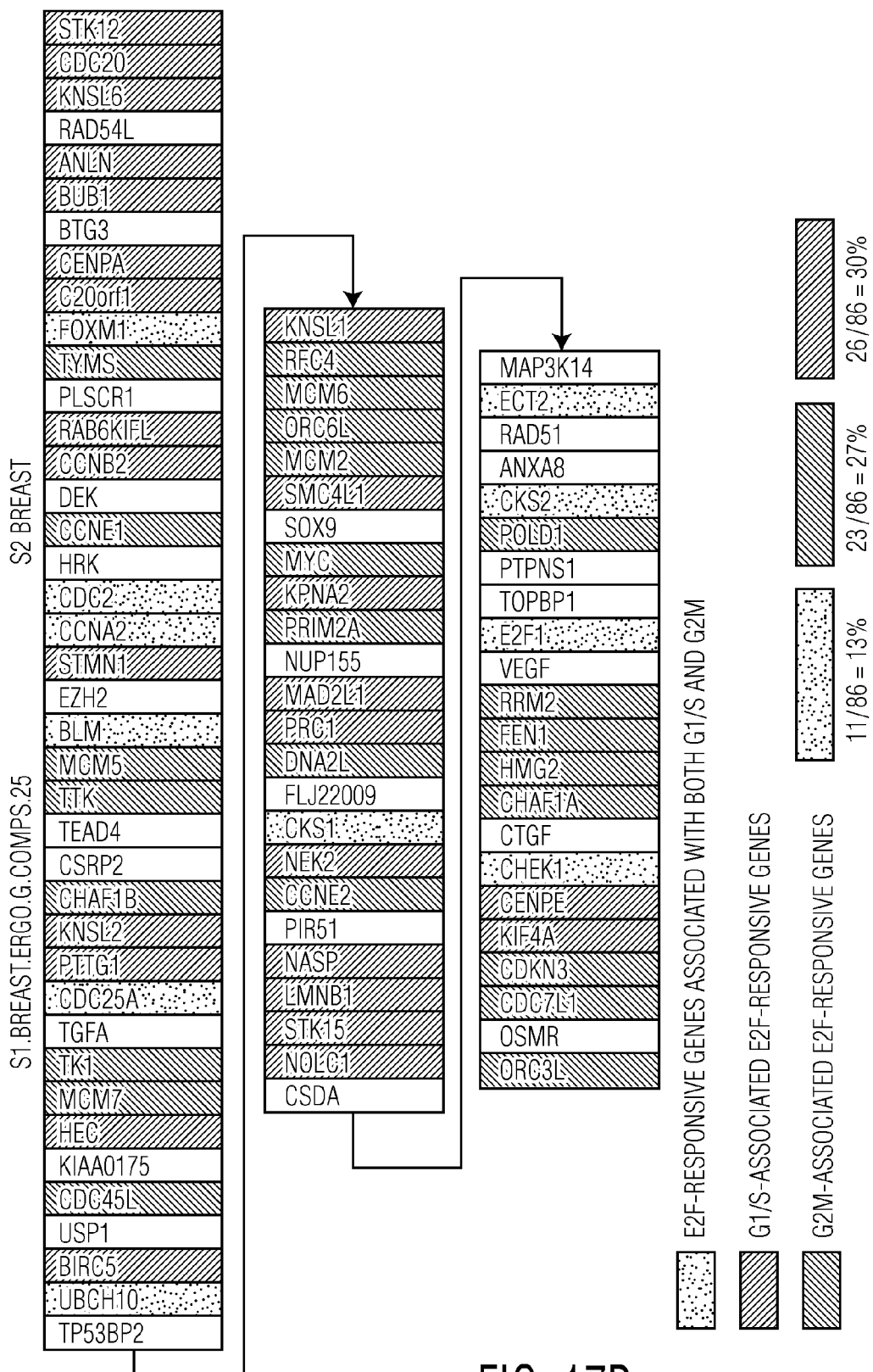
Figure 17C:
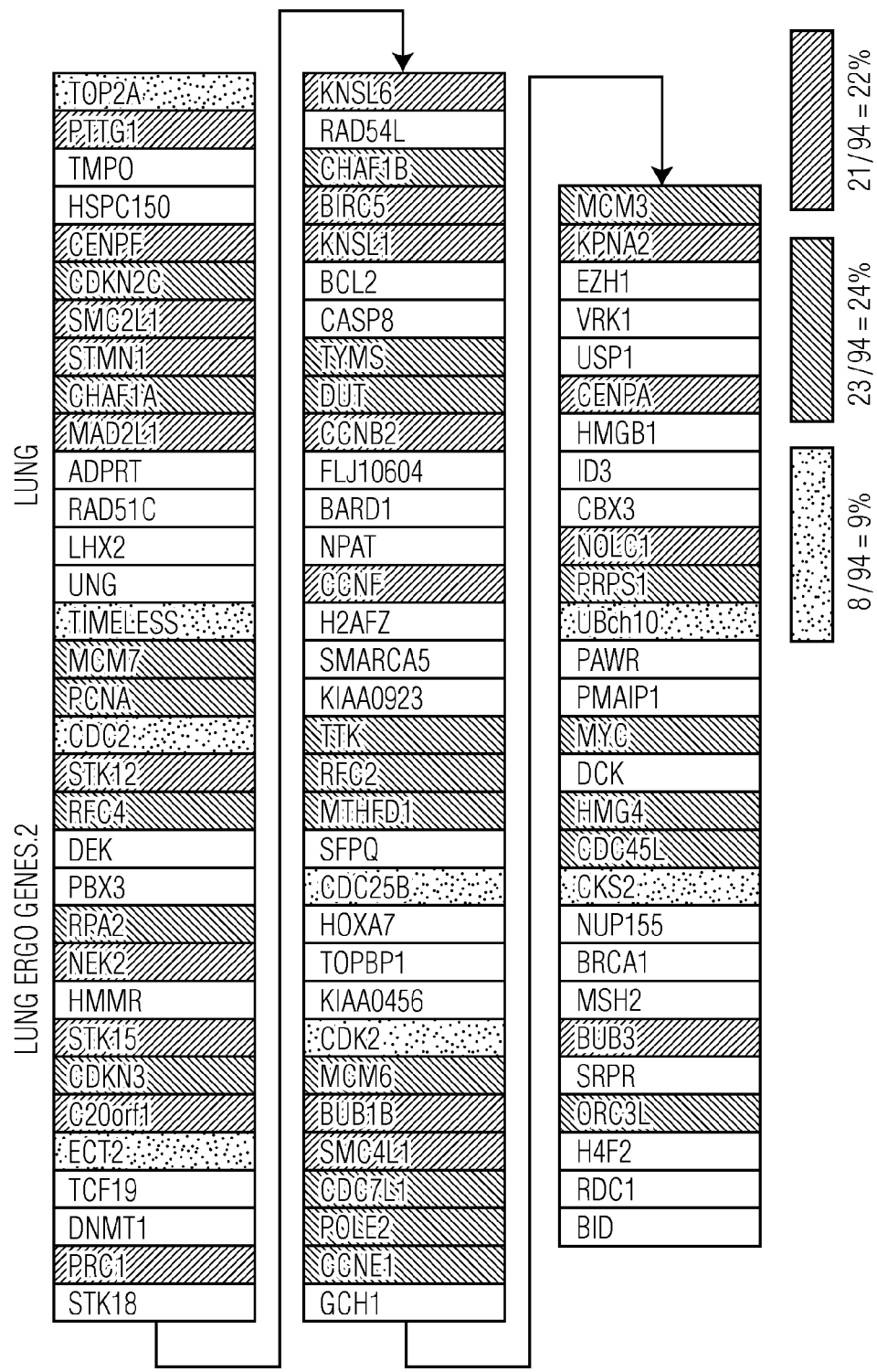
Figure 18A:
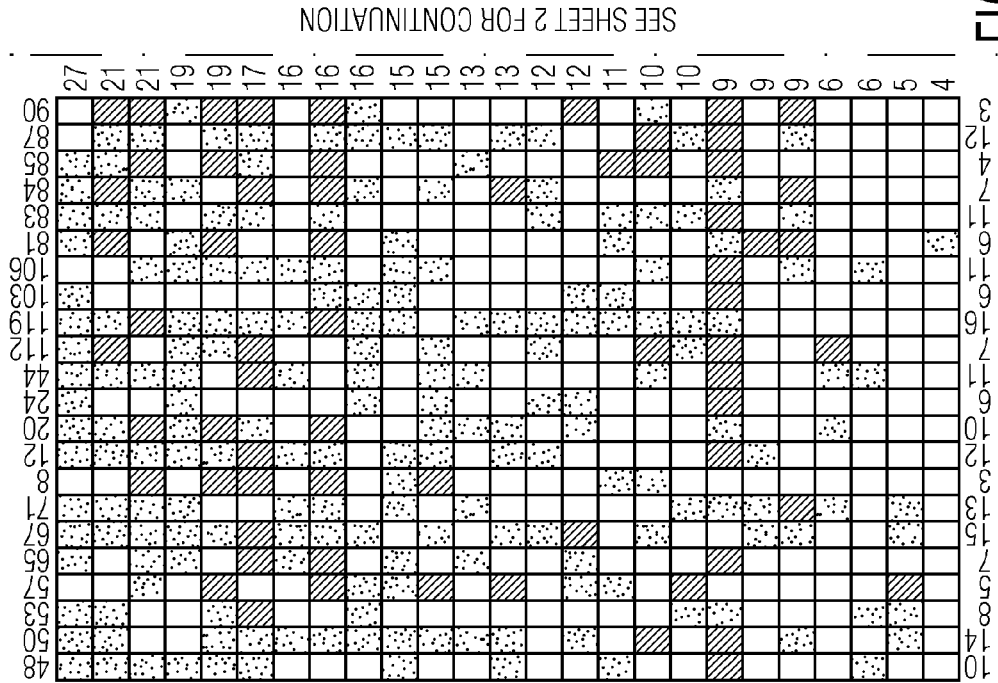
Figure 18B:
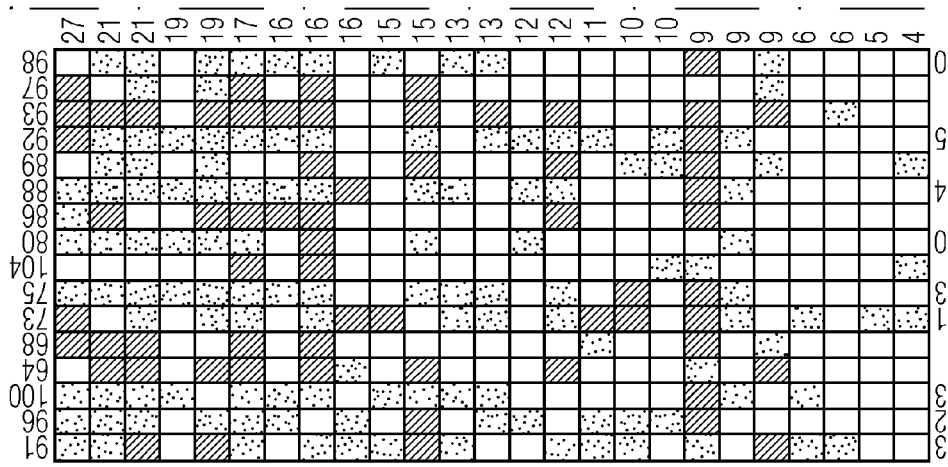
Figure 18C:
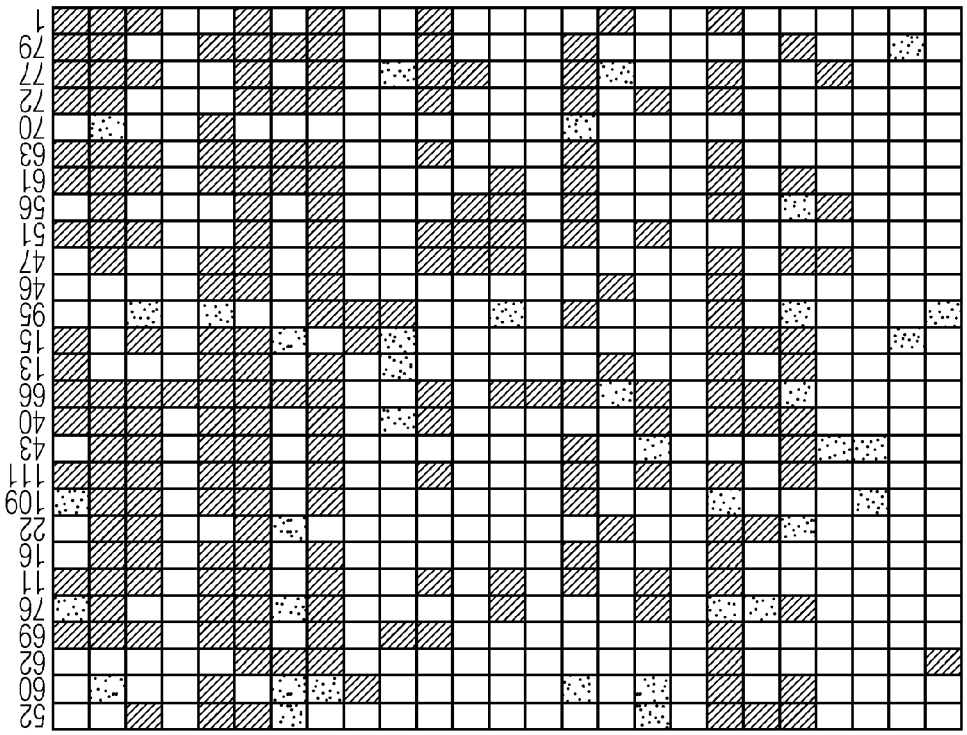
Figure 18D:
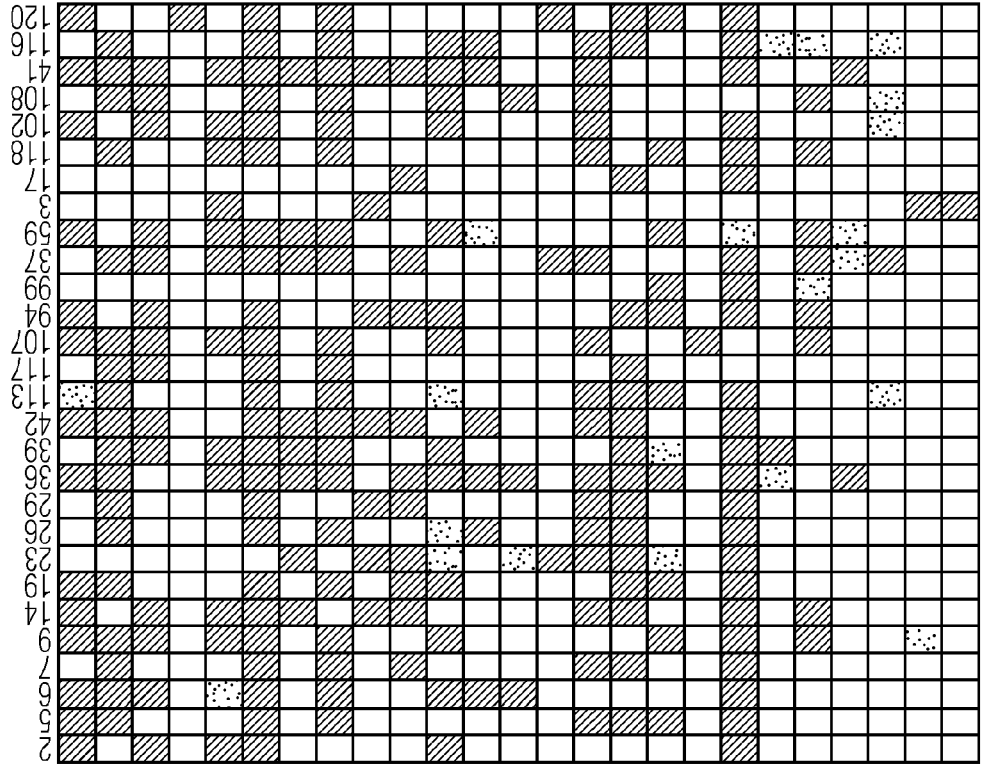
Figure 18E:
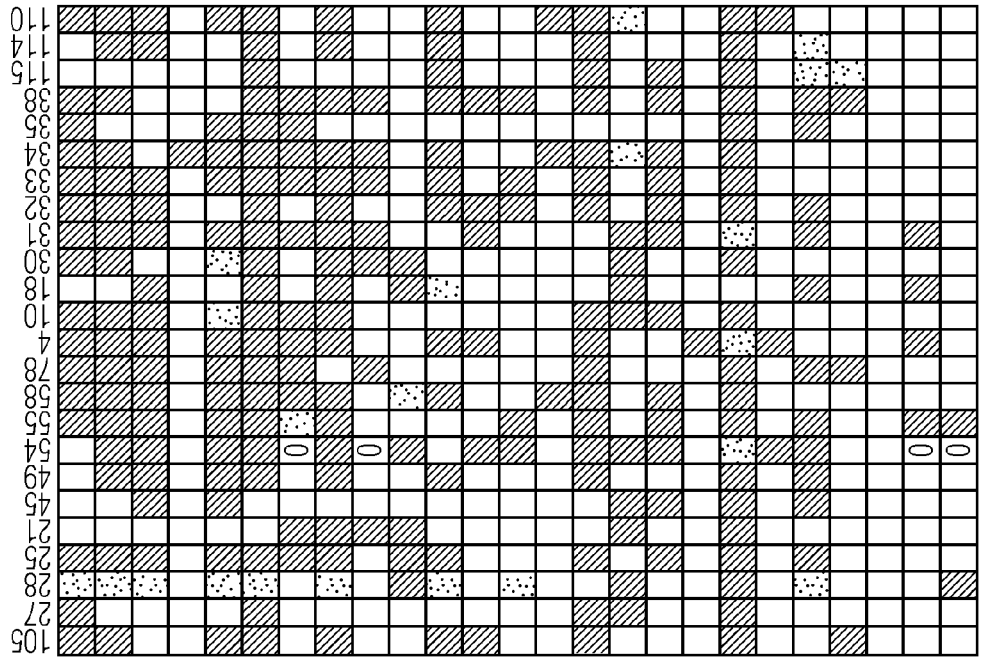
Figure 18F:
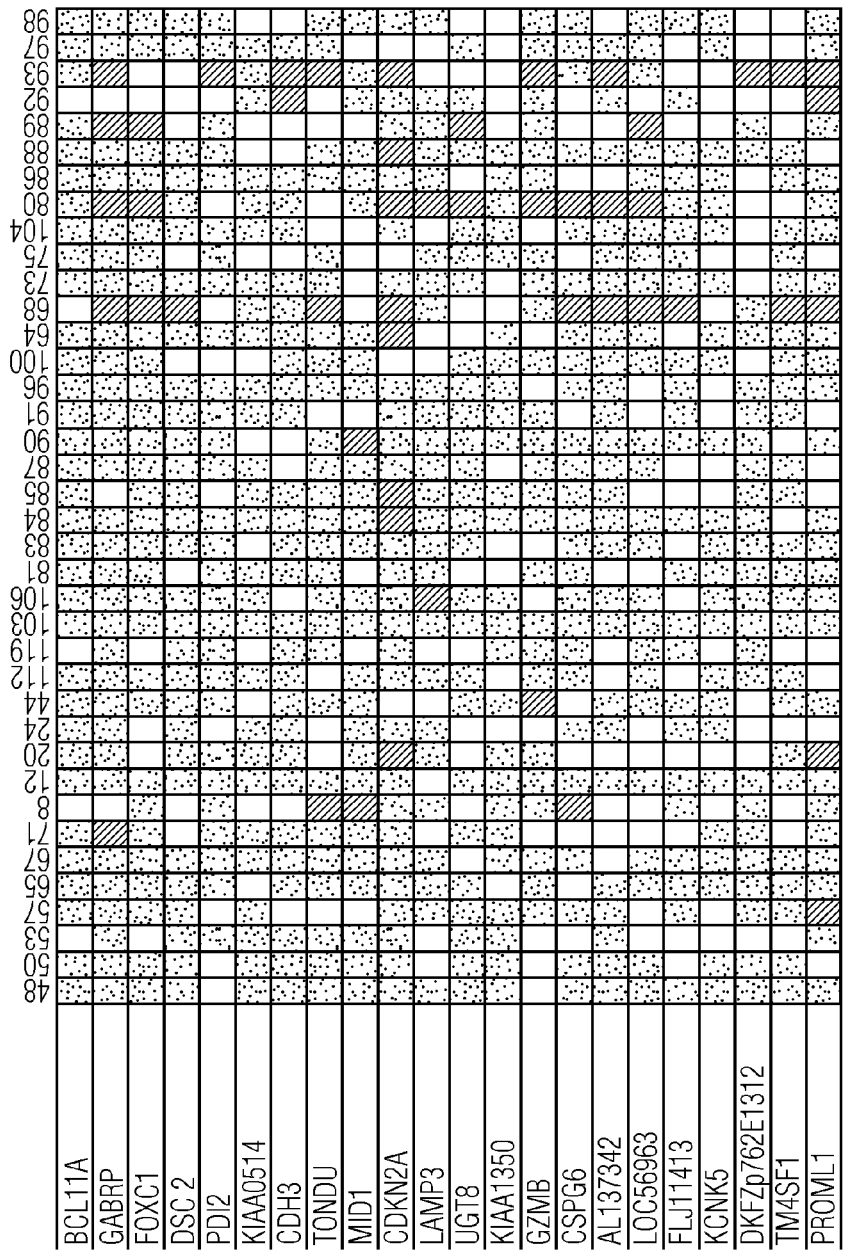
Figure 18G:
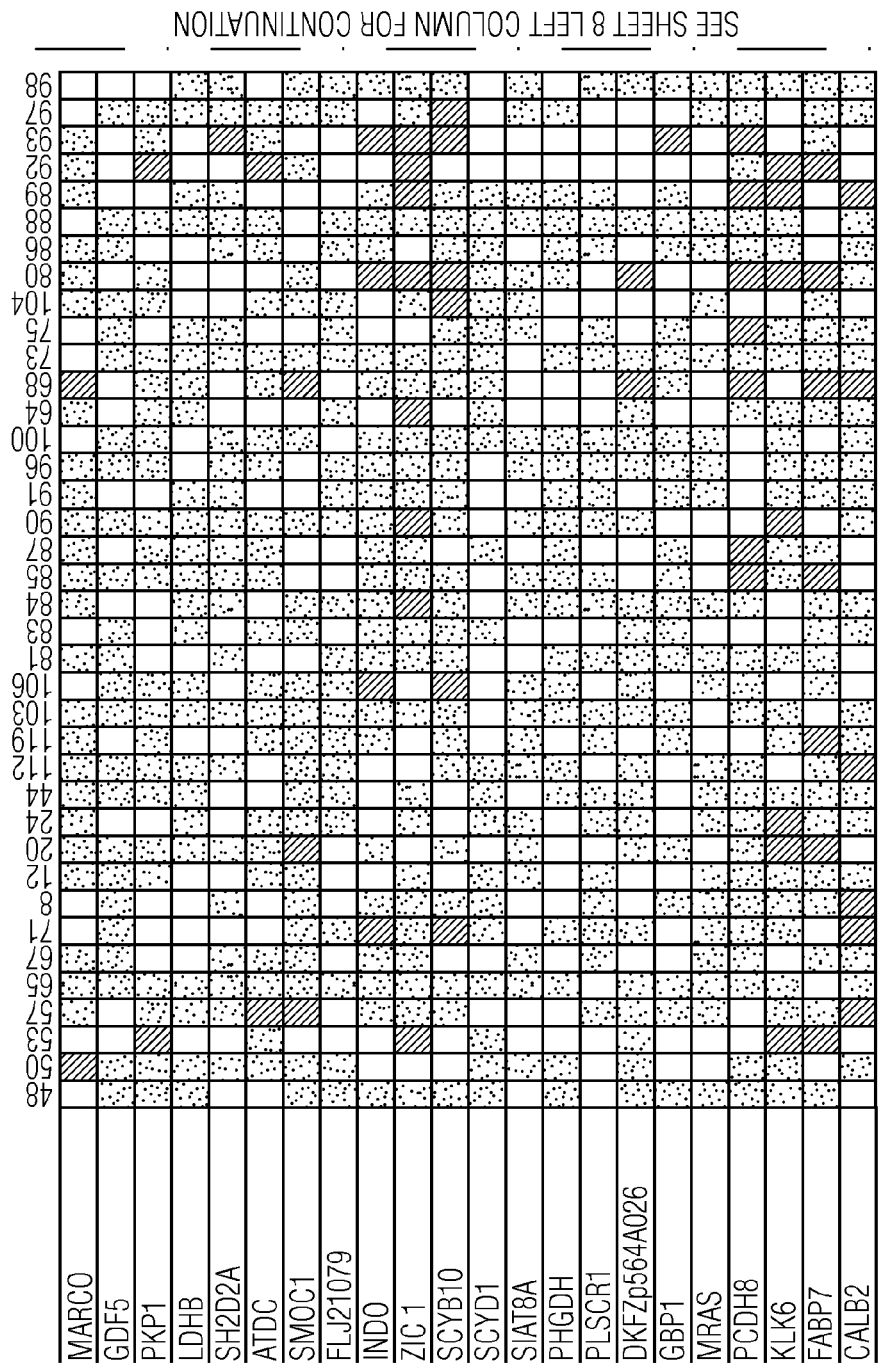
Figure 18I:
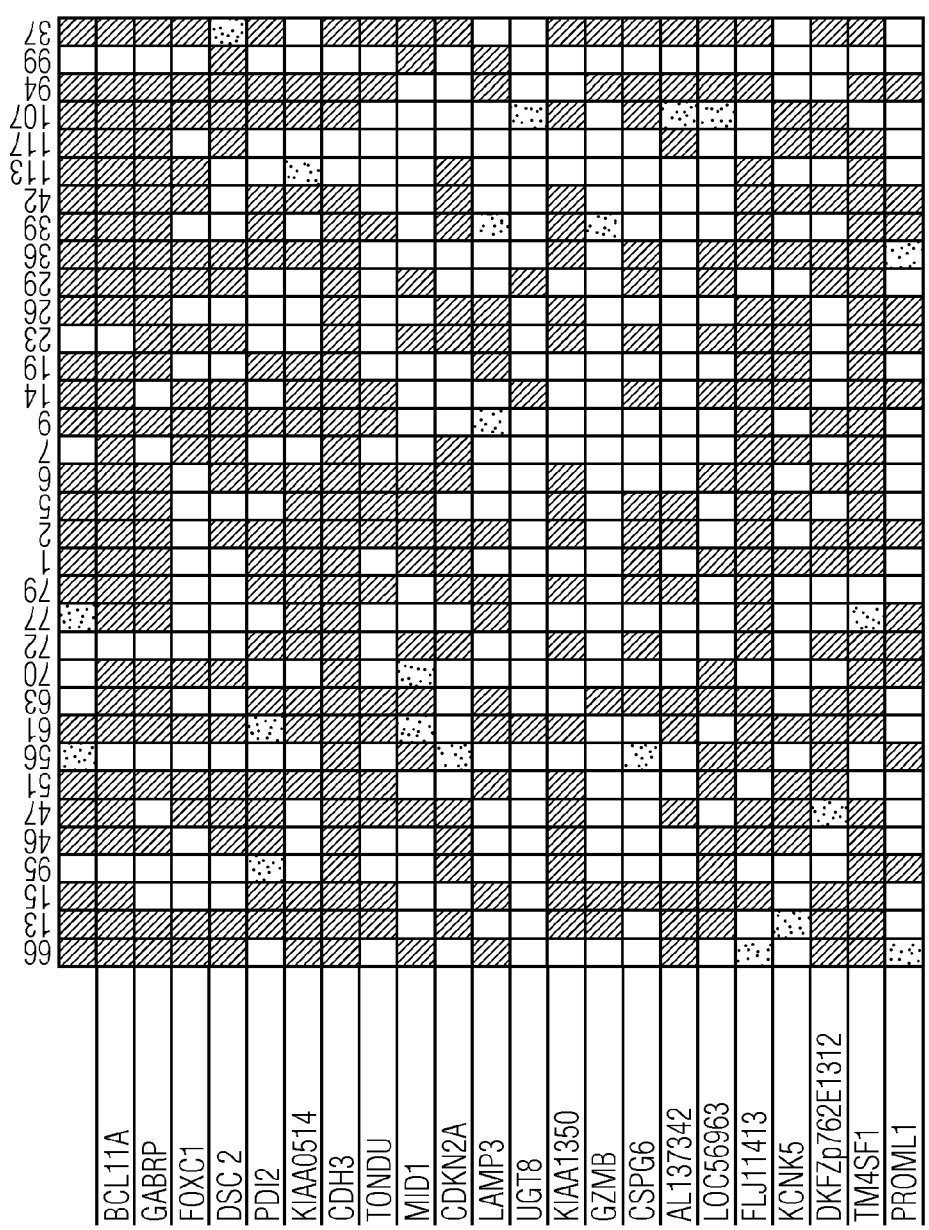
Figure 18J:
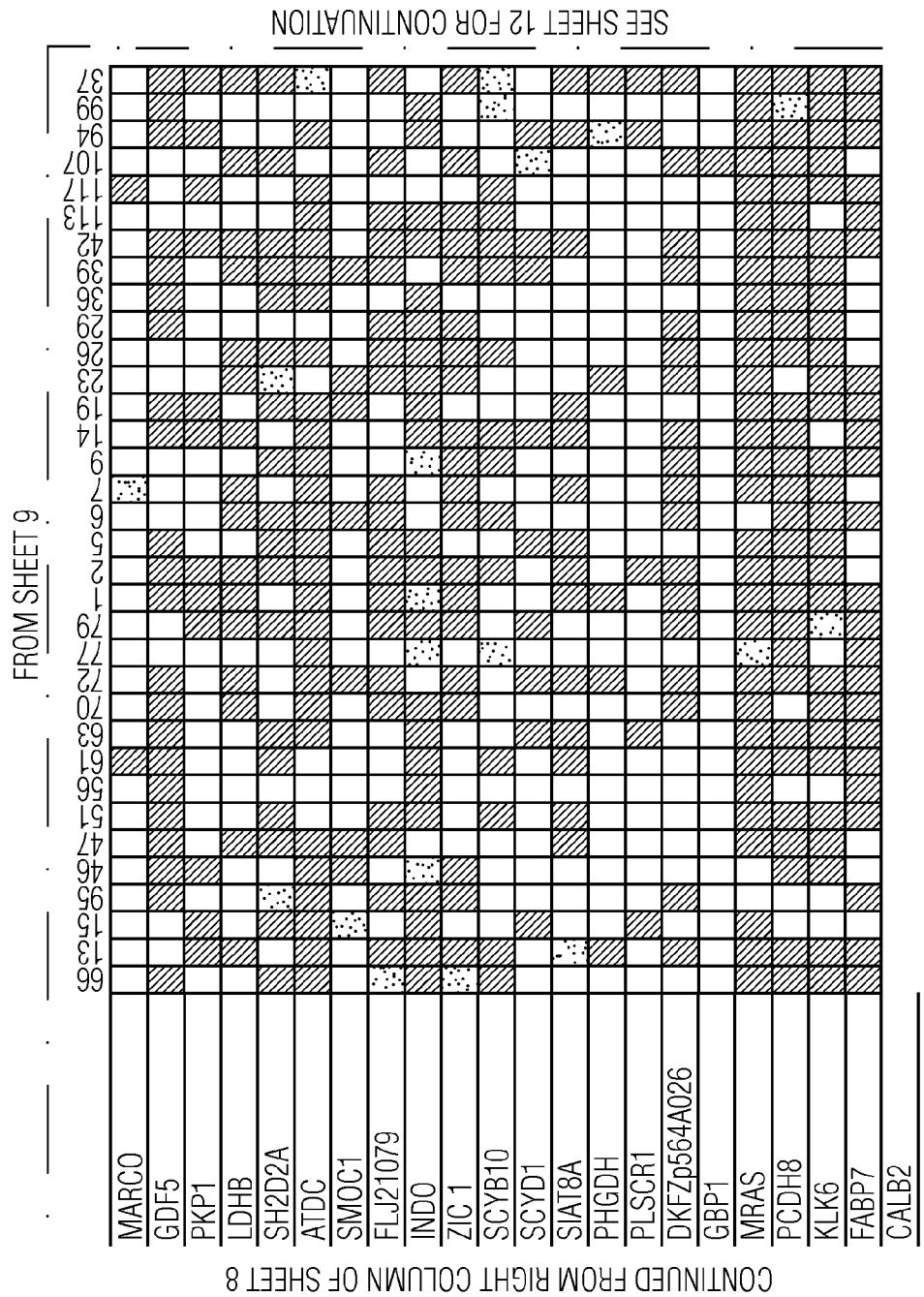
Figure 18K:
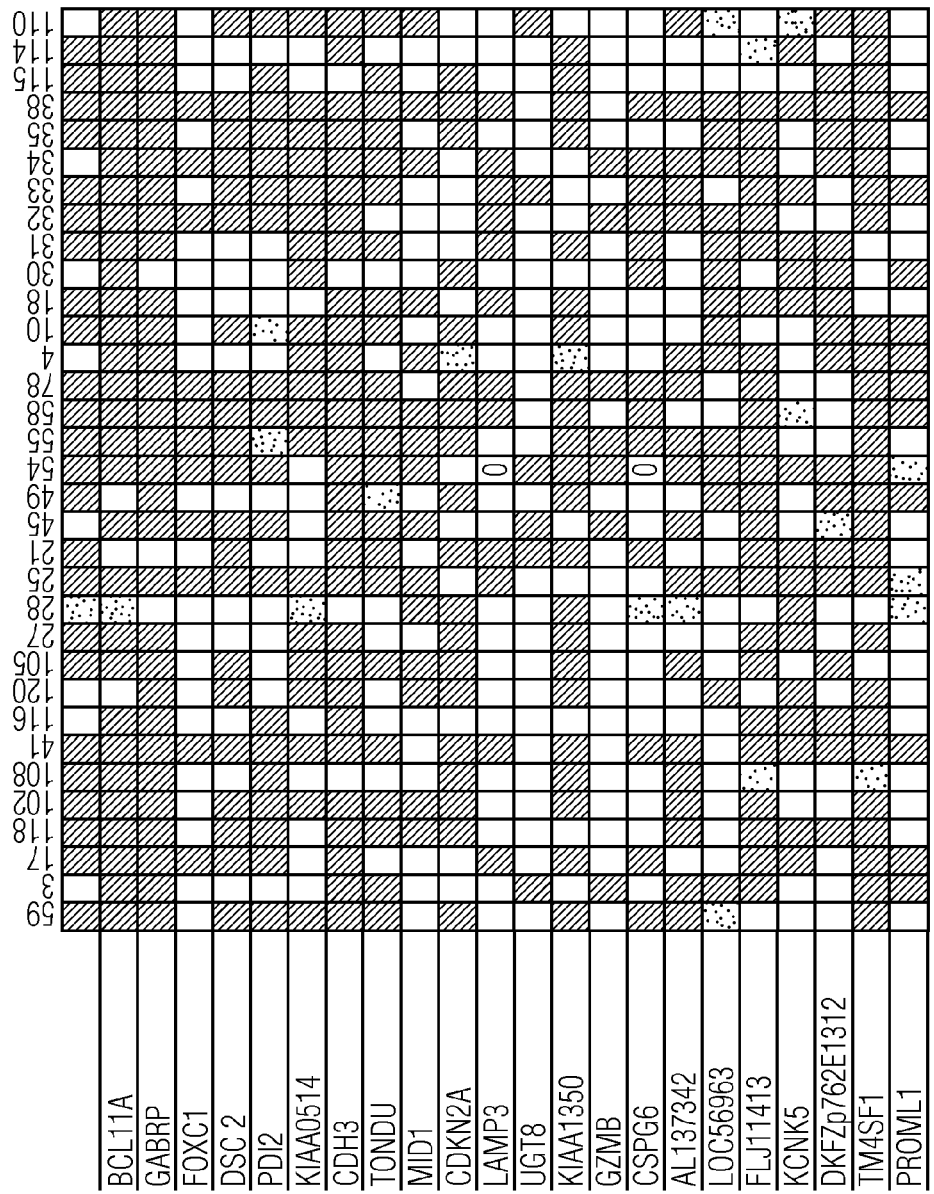
Figure 18L:
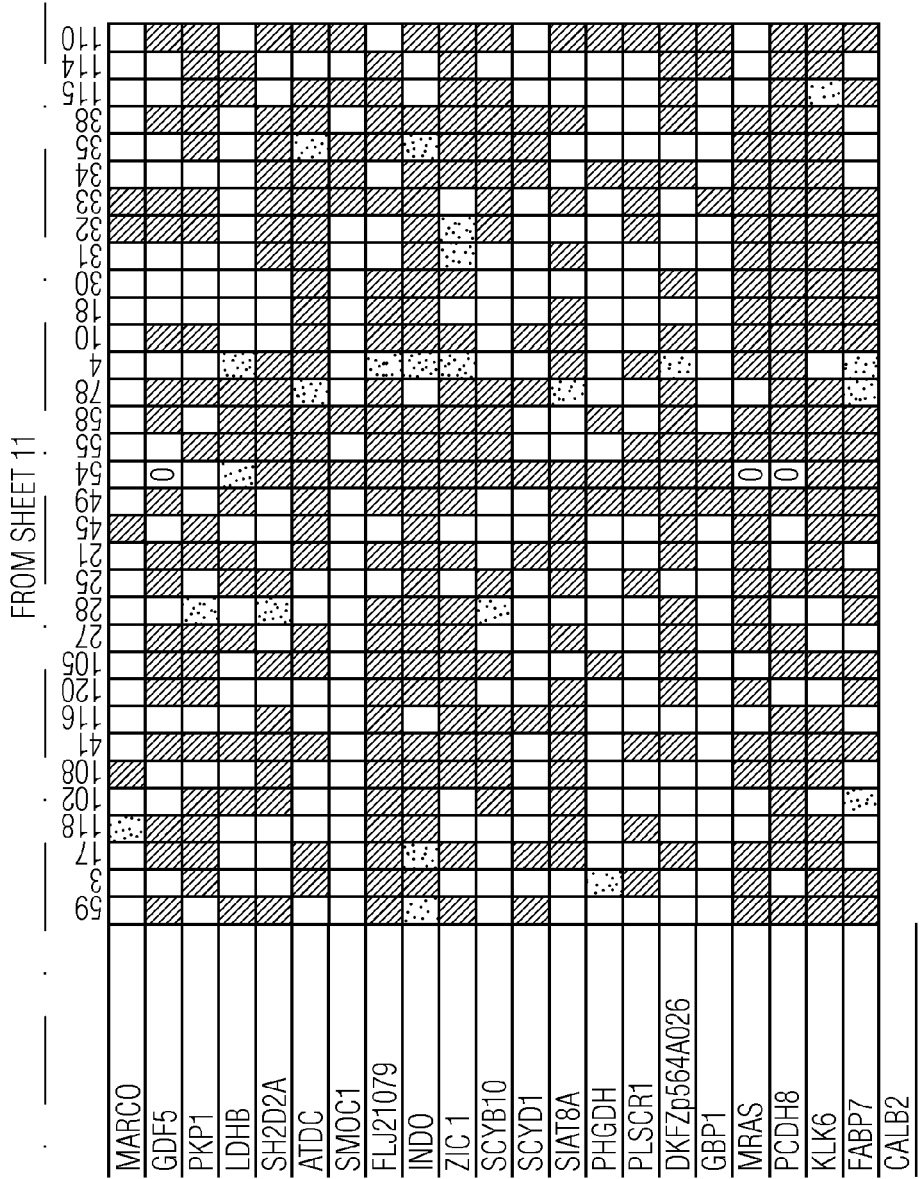
Figure 20A:
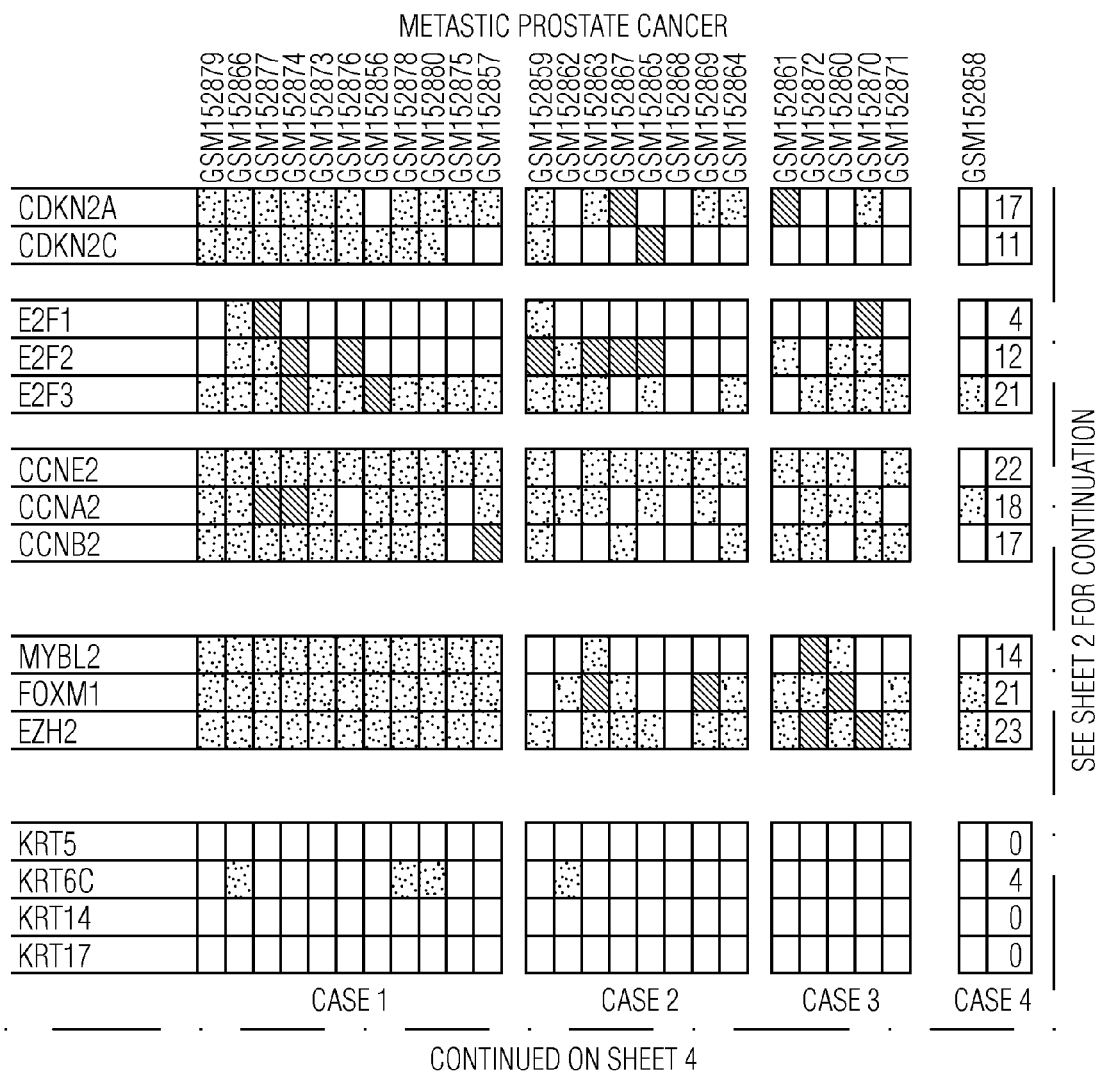
FIGS. 20A to 20KK show partial views intended to form one complete view of microarray data from prostate cancer patients and the identification of ERGO) genes and ERGO tumors in cancers from such patients.
Figure 20C:
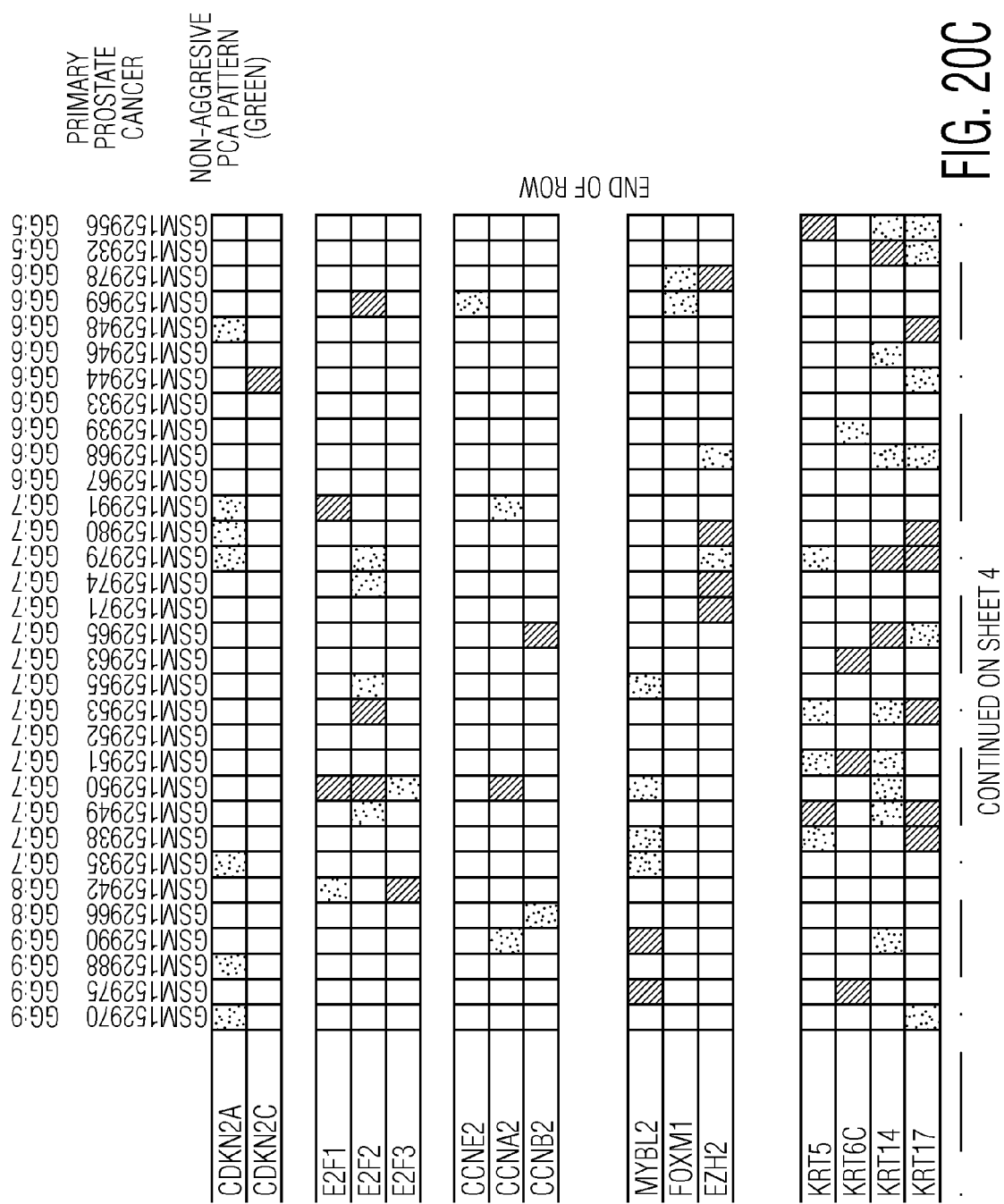
Figure 20D:
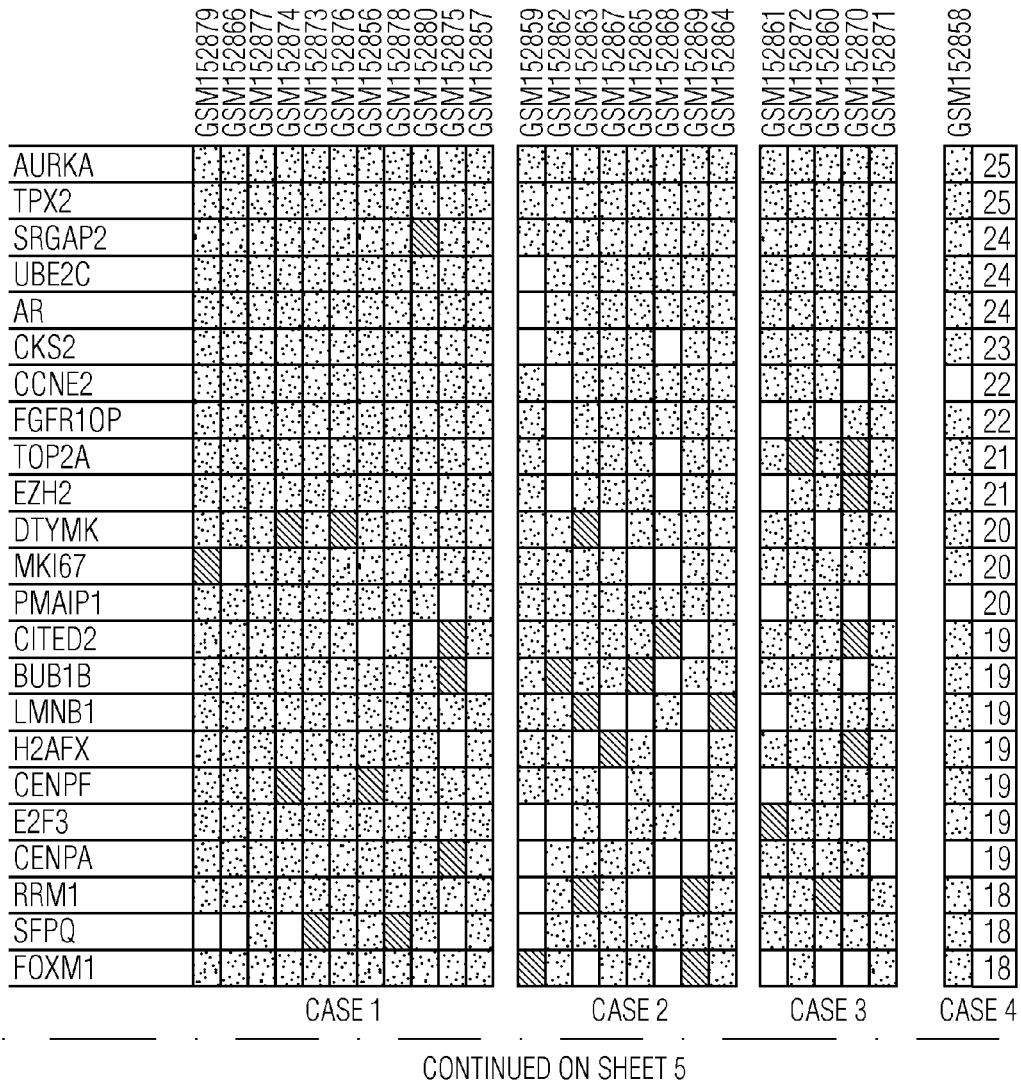
Figure 20E:
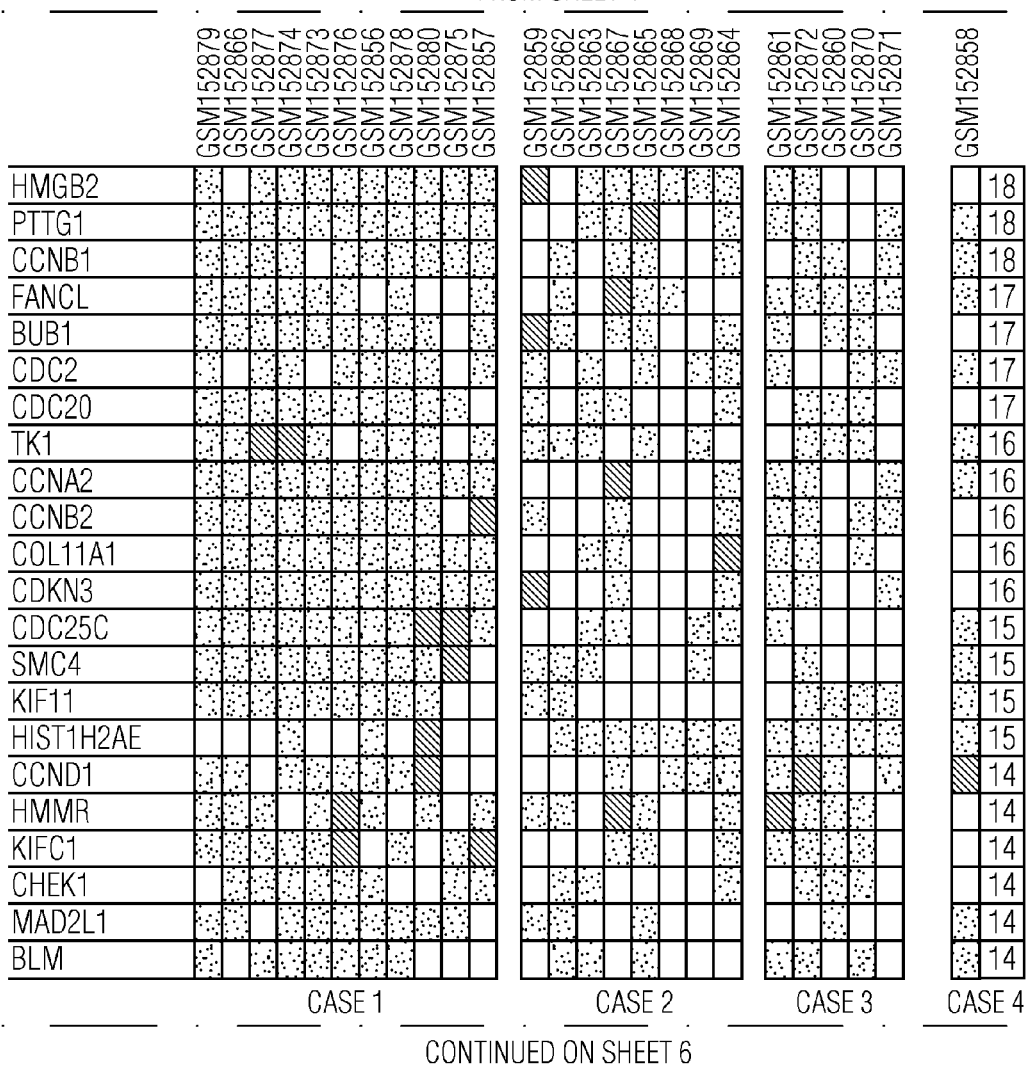
Figure 20F:
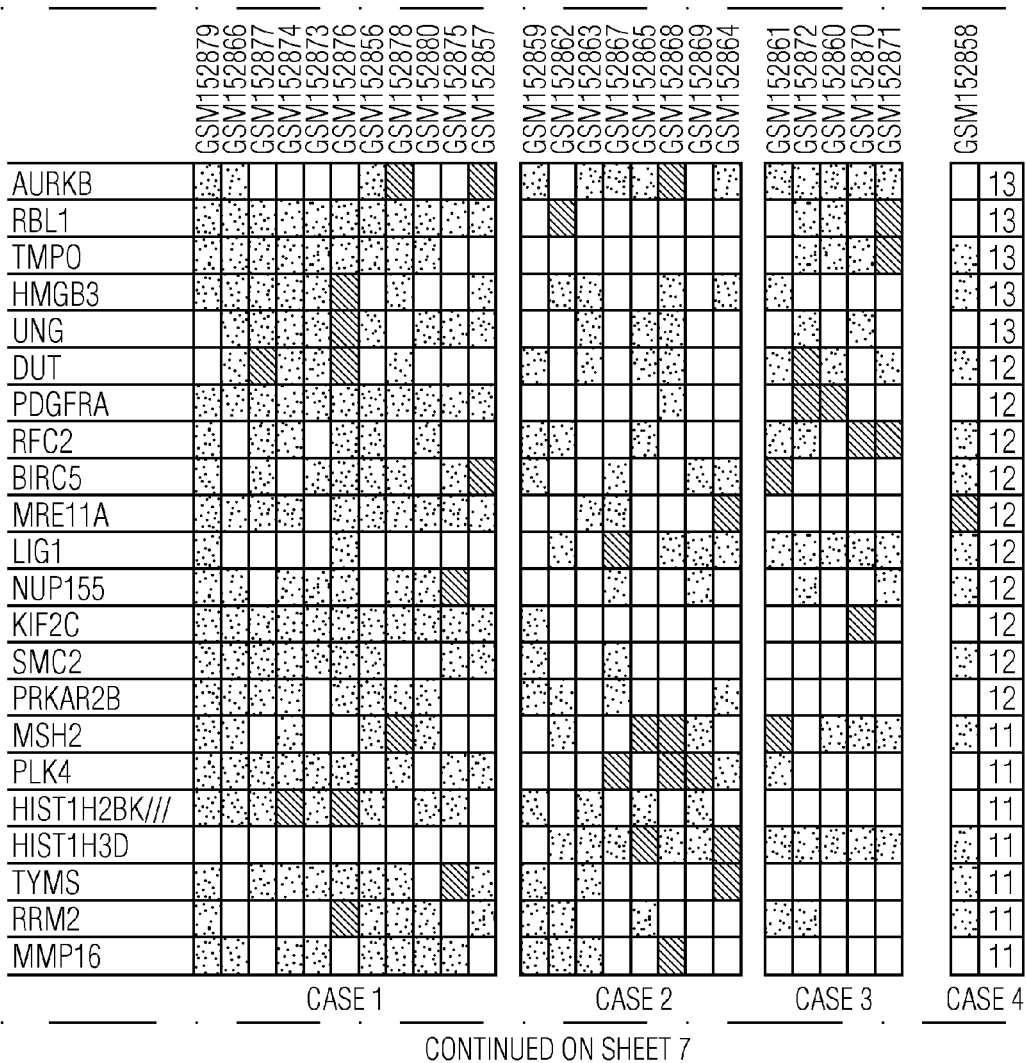
Figure 20G:
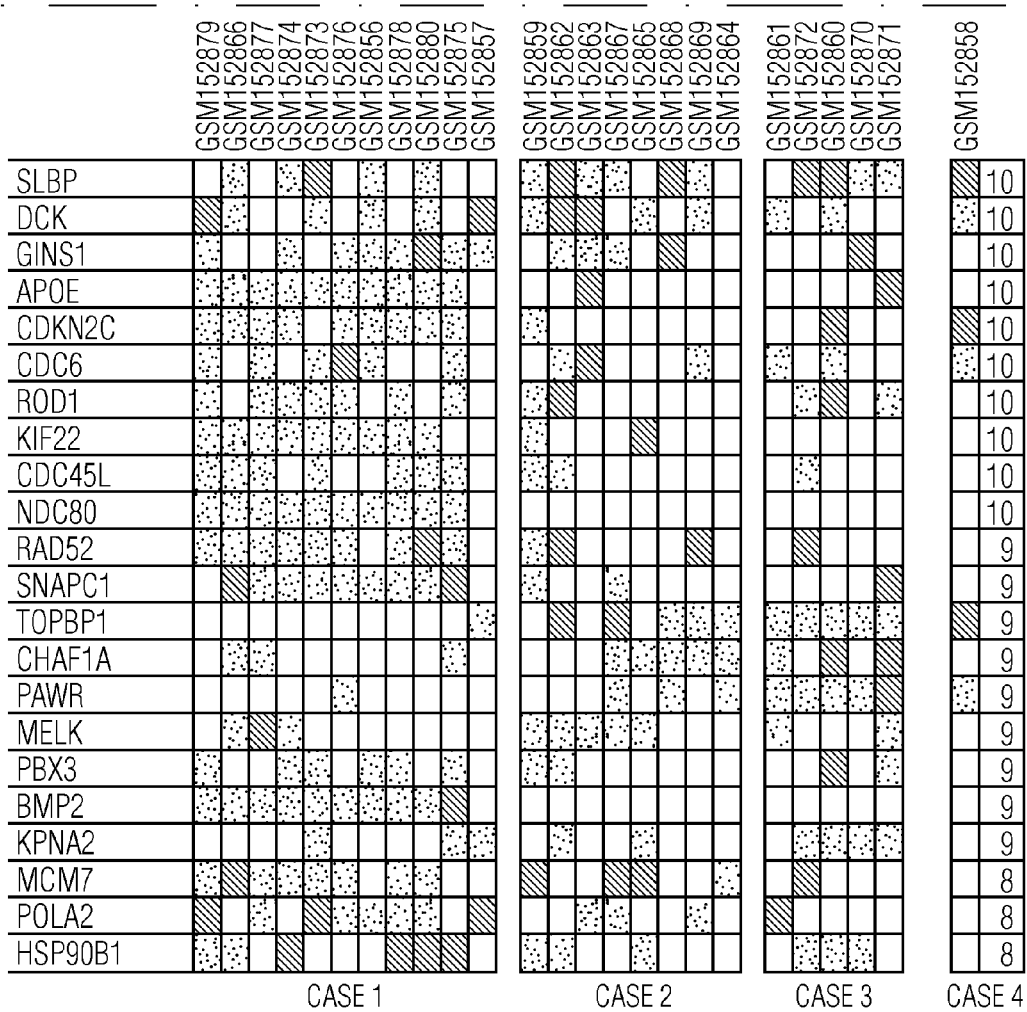
Figure 20H:
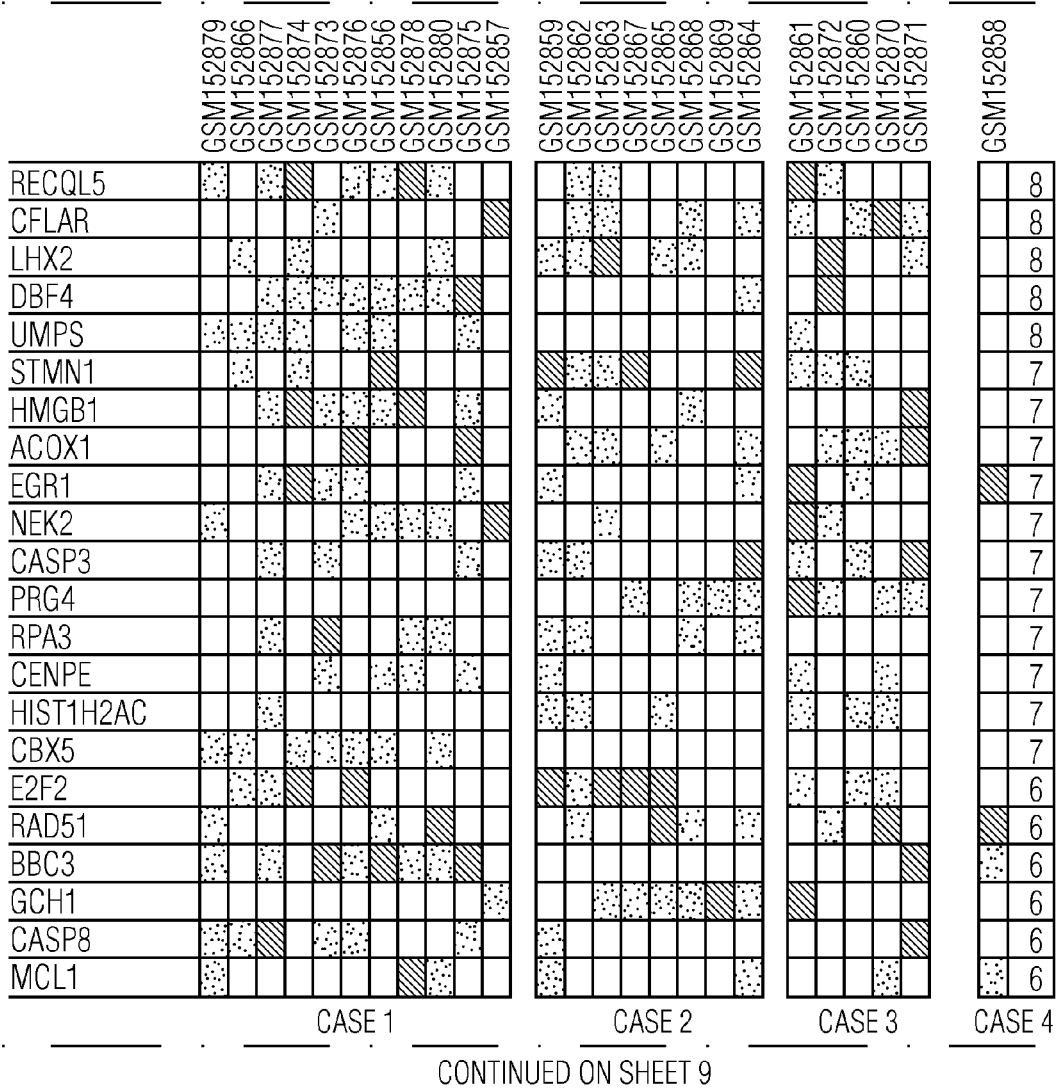
Figure 20I:
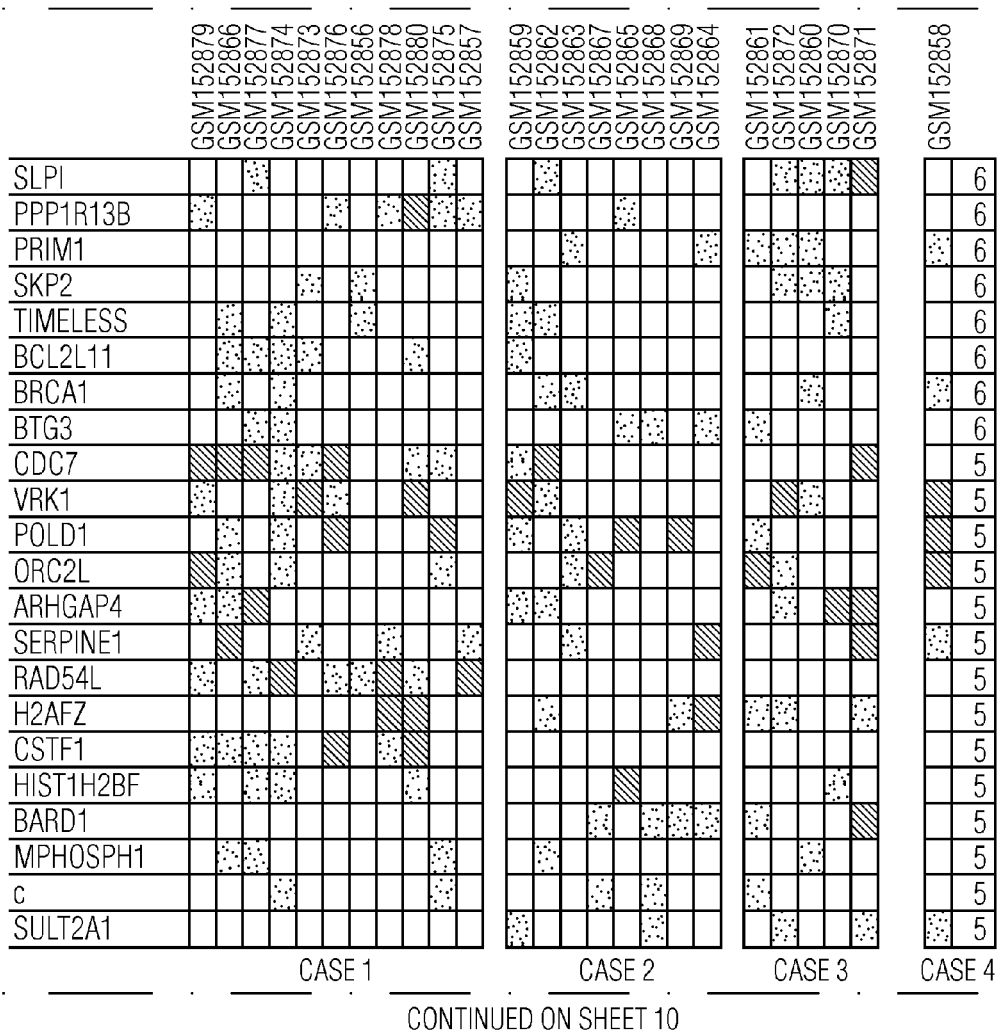
Figure 20J:
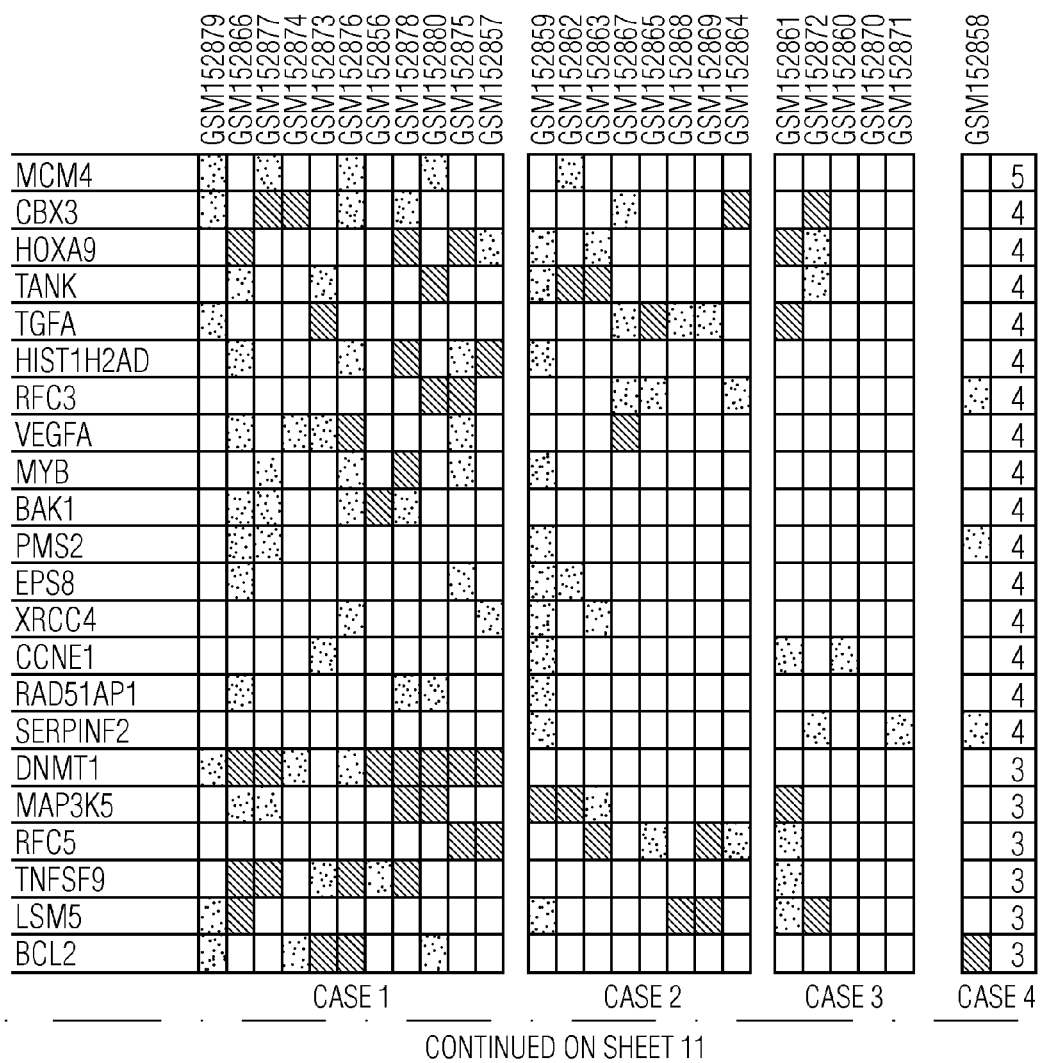
Figure 20K:
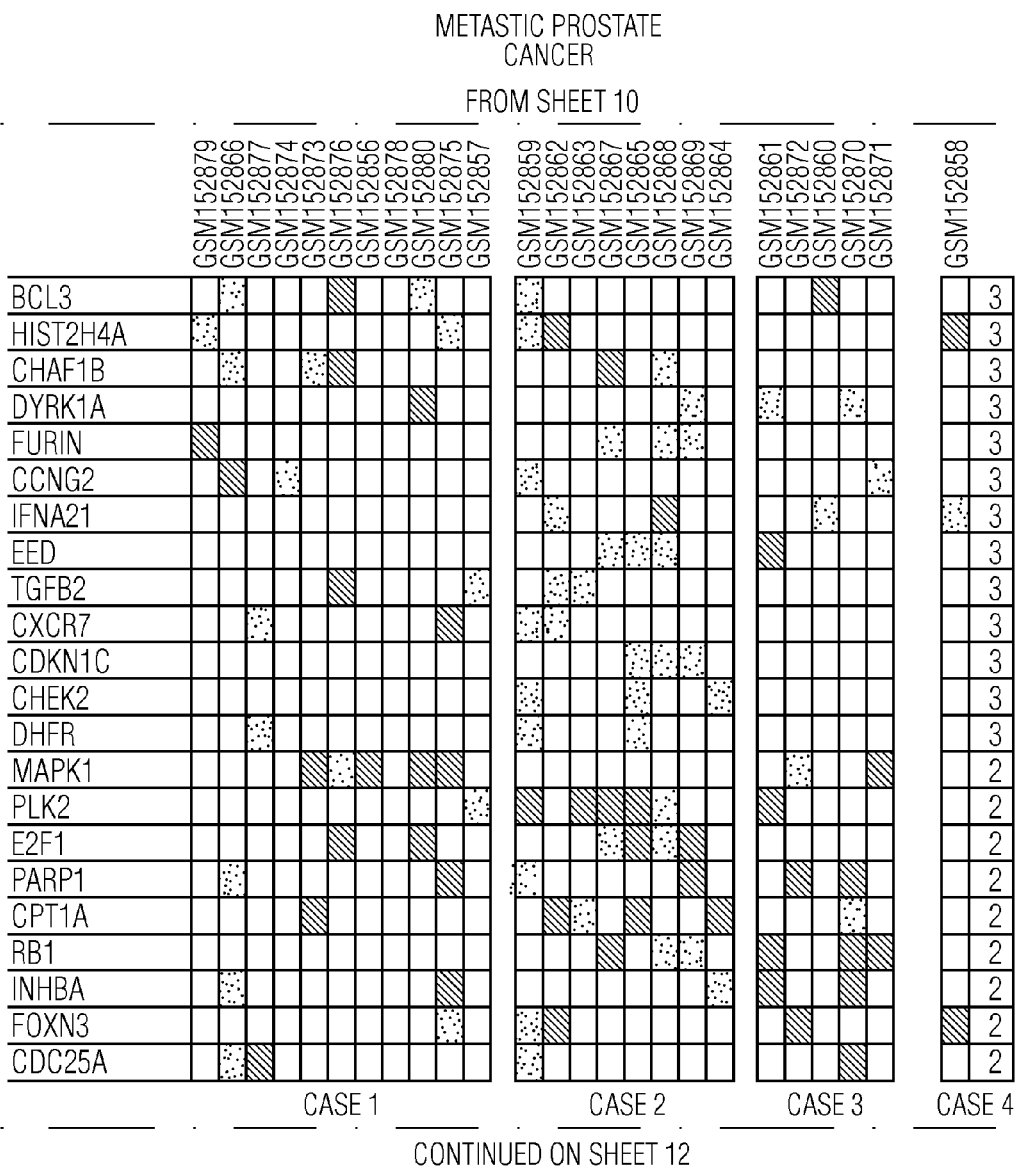
Figure 20L:
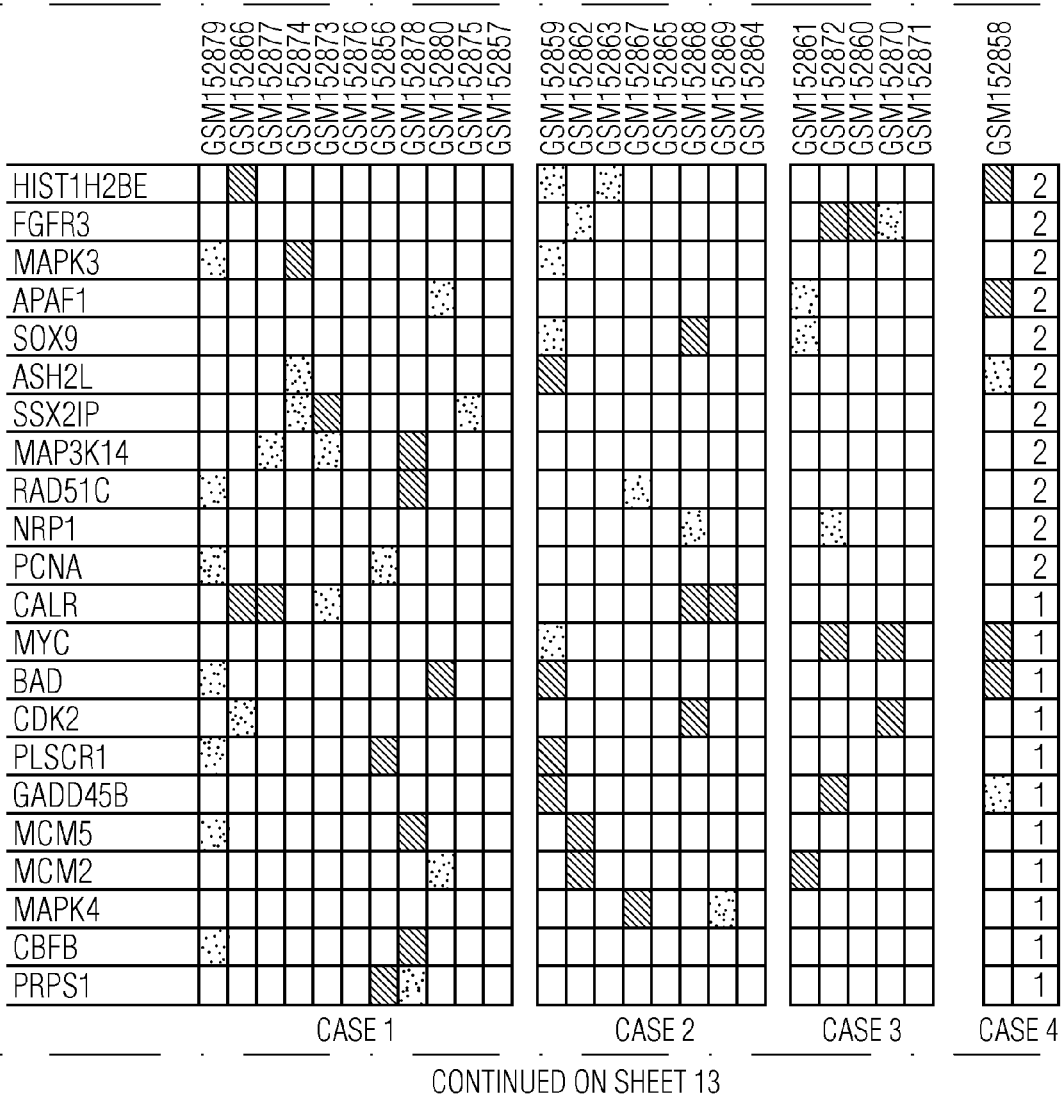
Figure 20M:
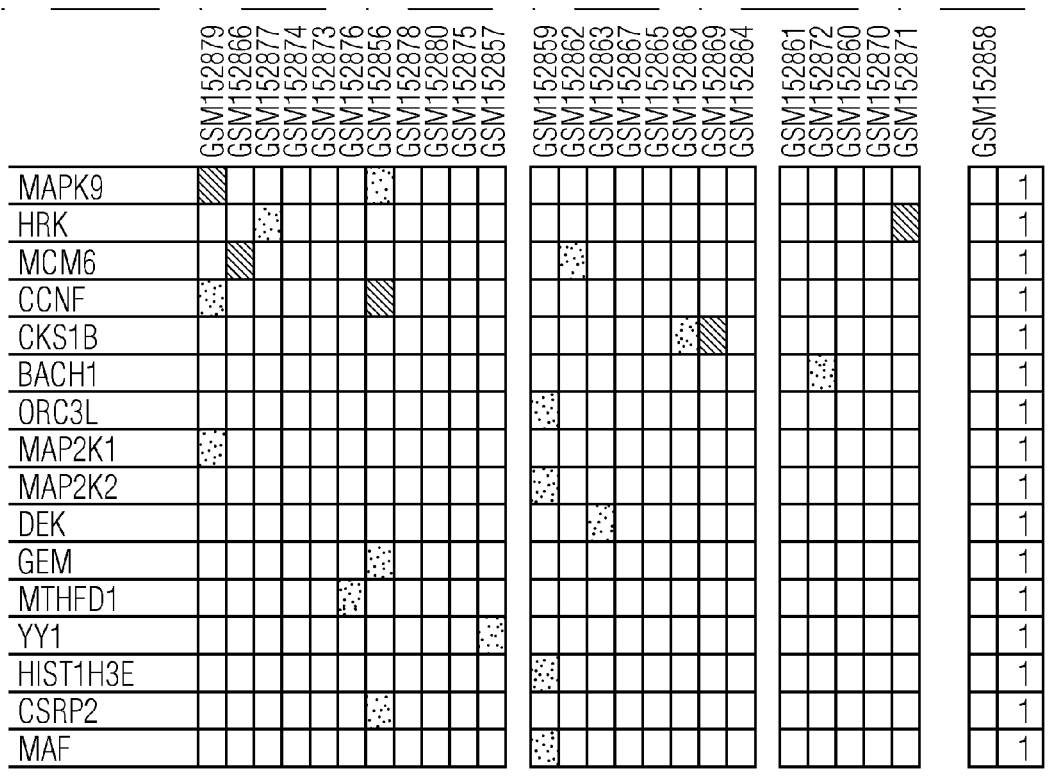
Figure 20N:
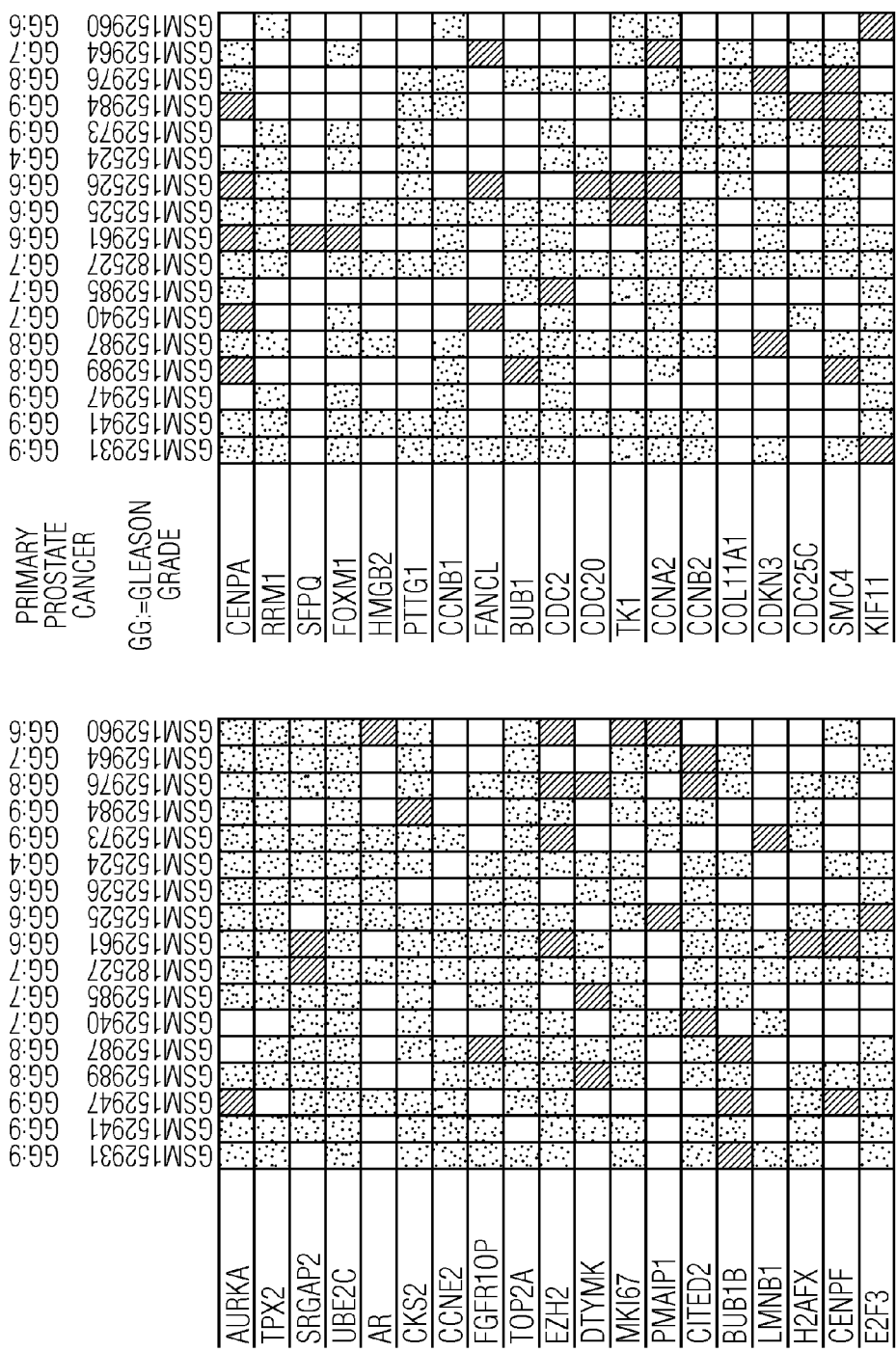
Figure 20S:
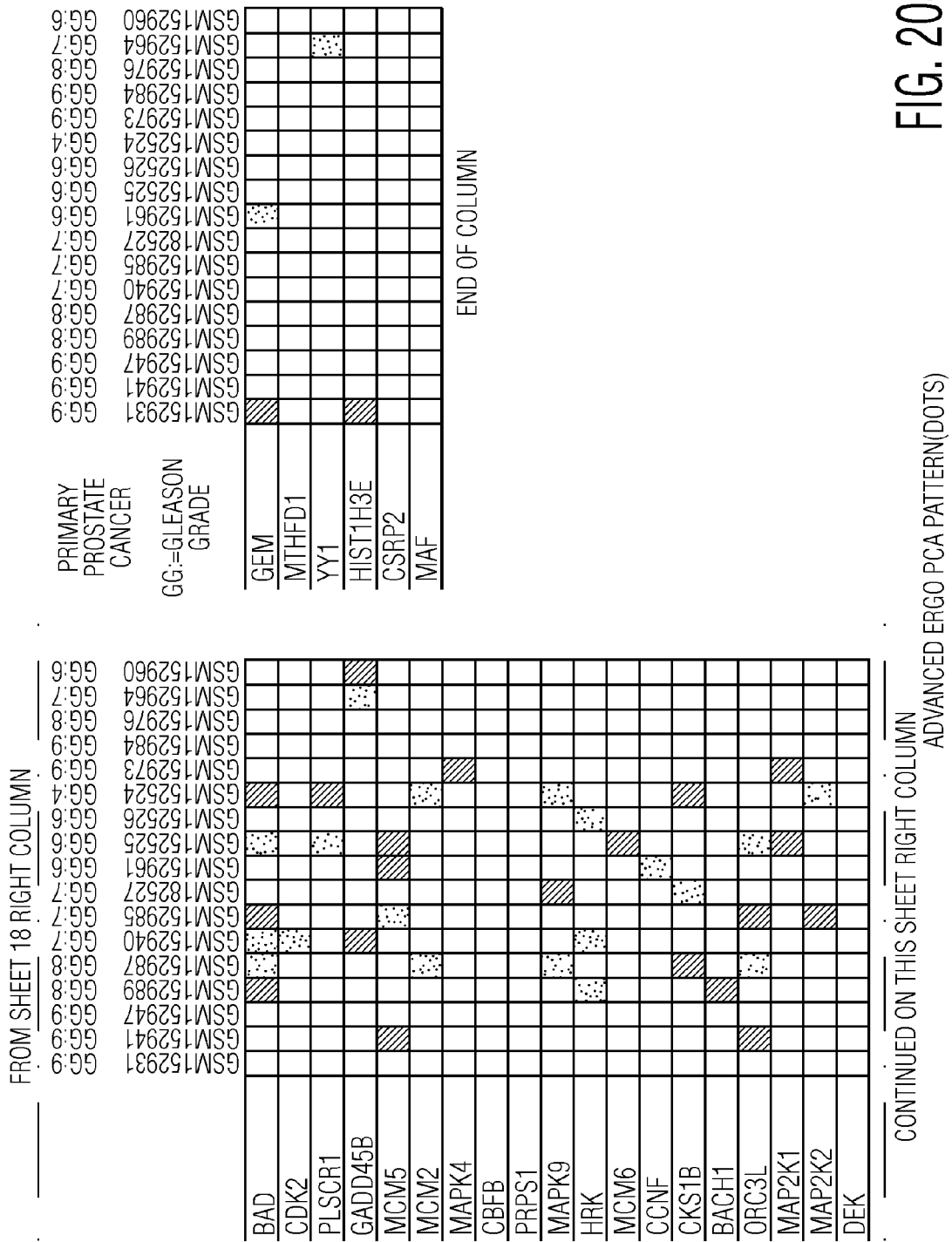
Figure 20T:
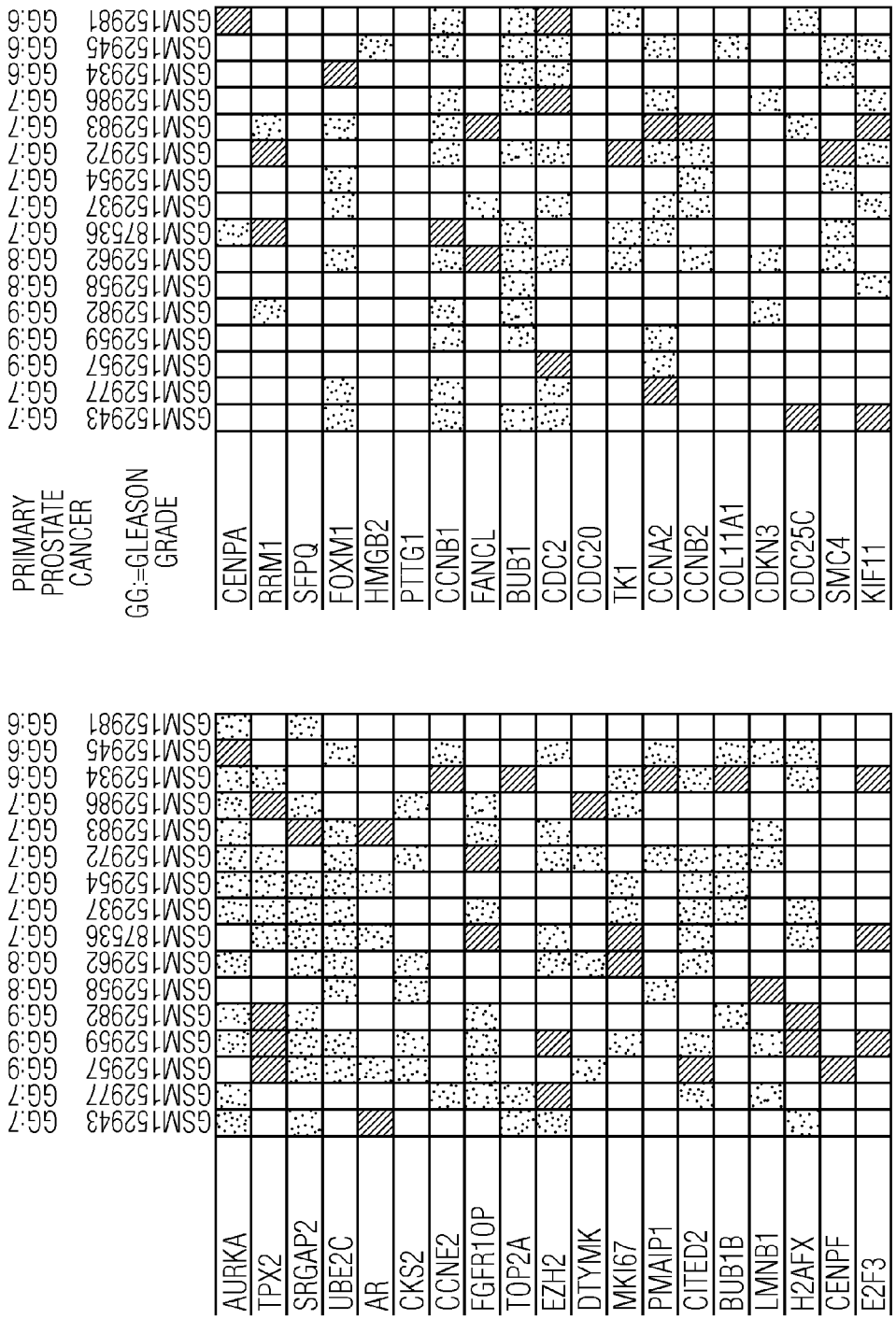
Figure 20U:
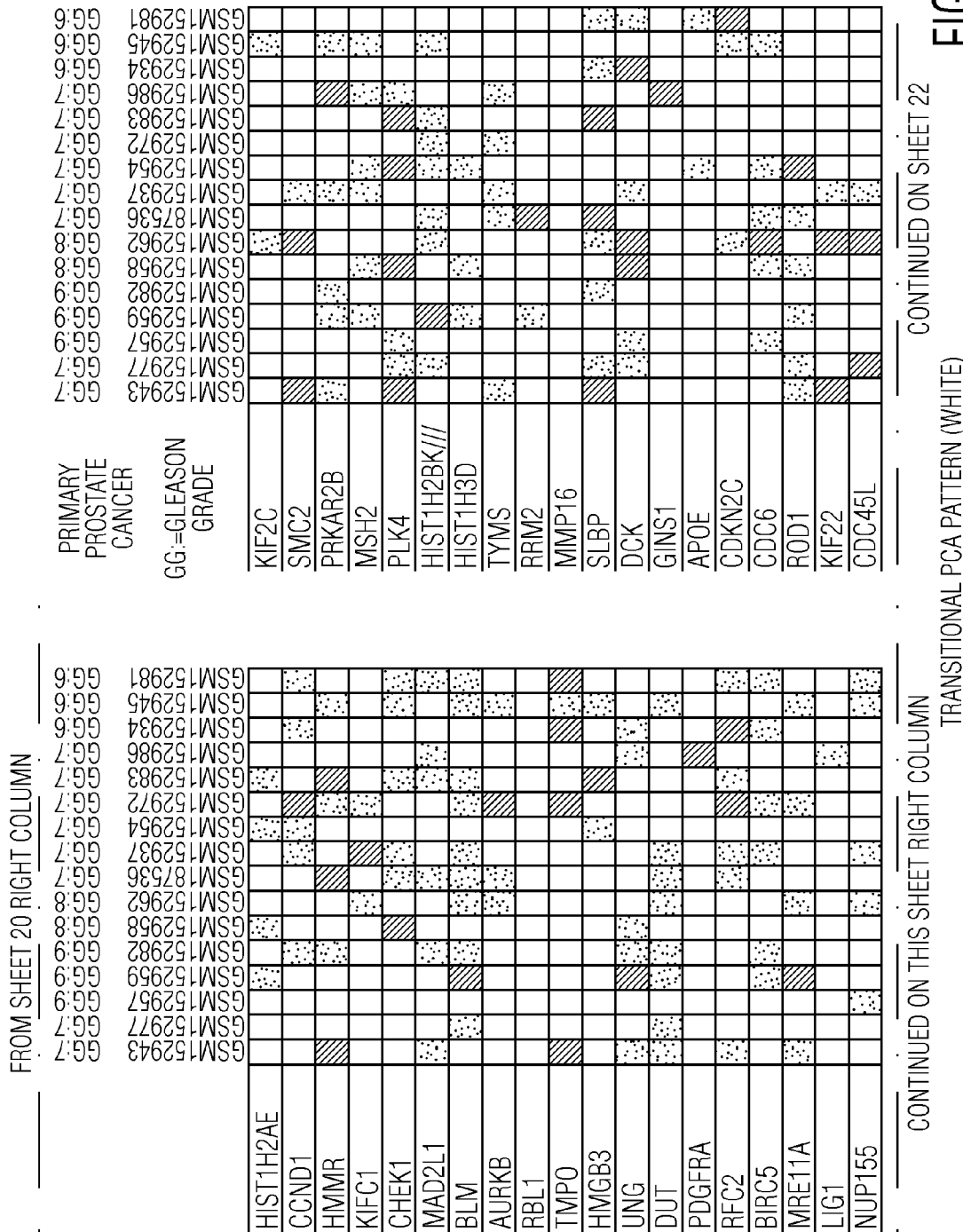
Figure 20Y:
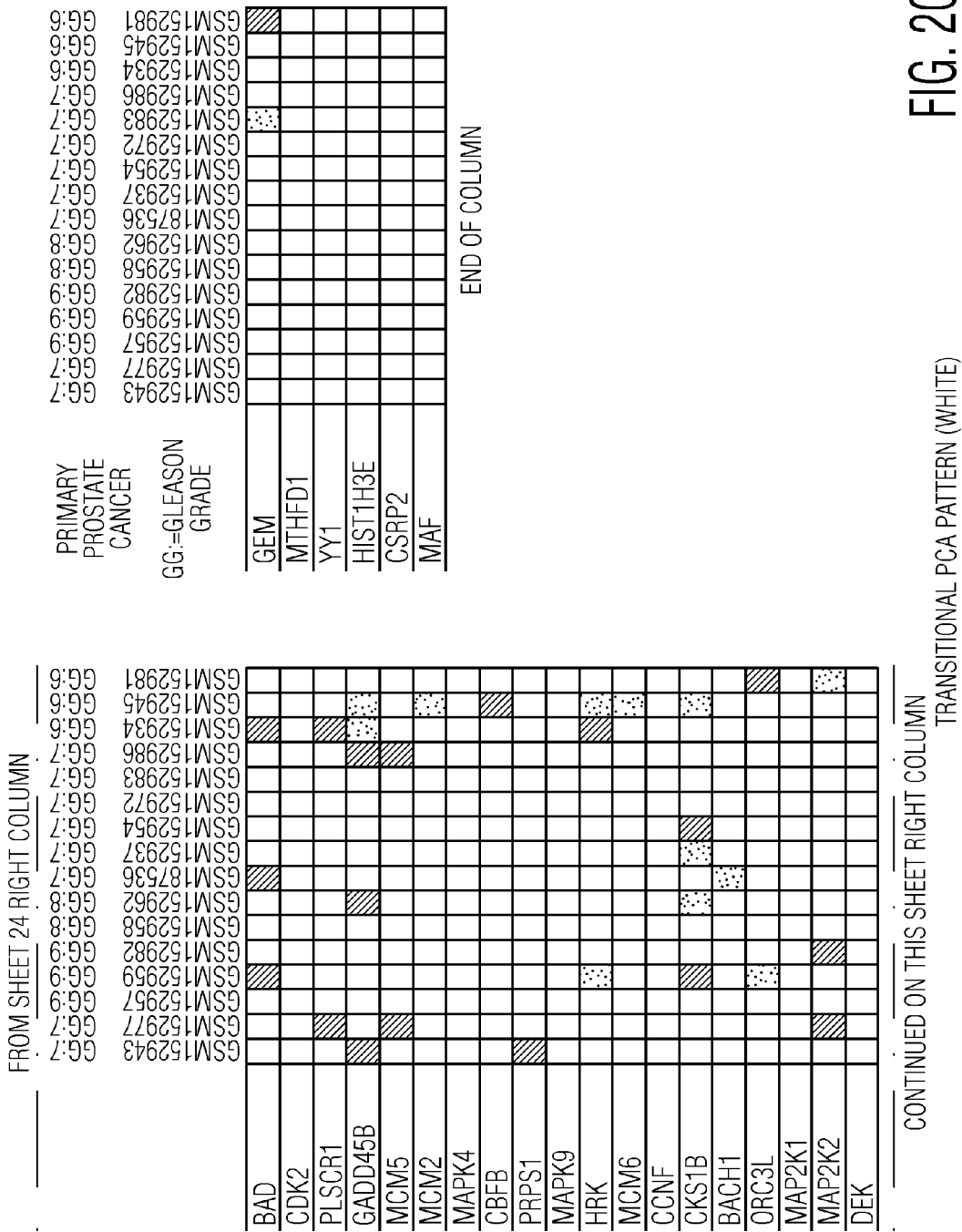
Figure 20A:
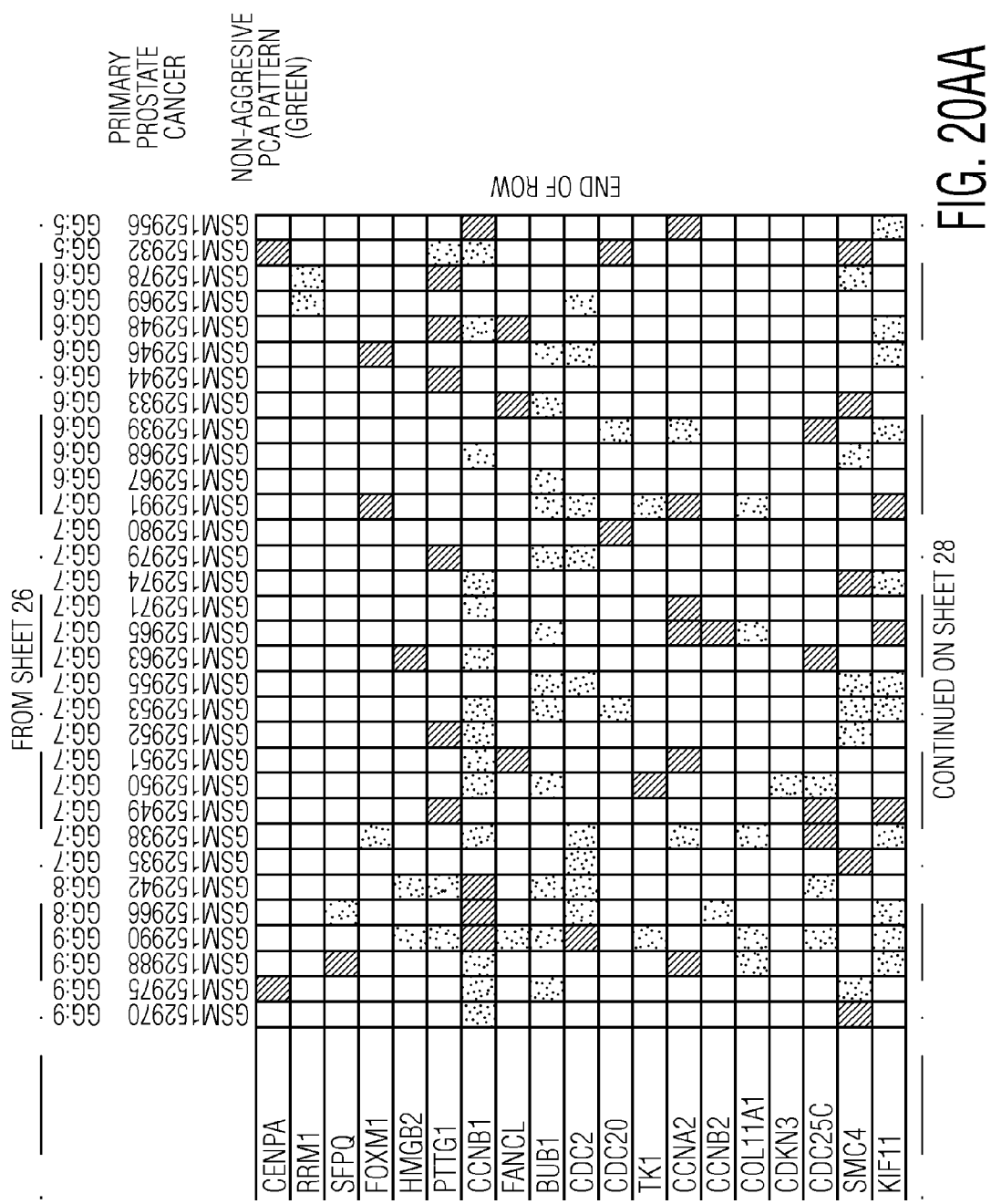
Figure 20C:
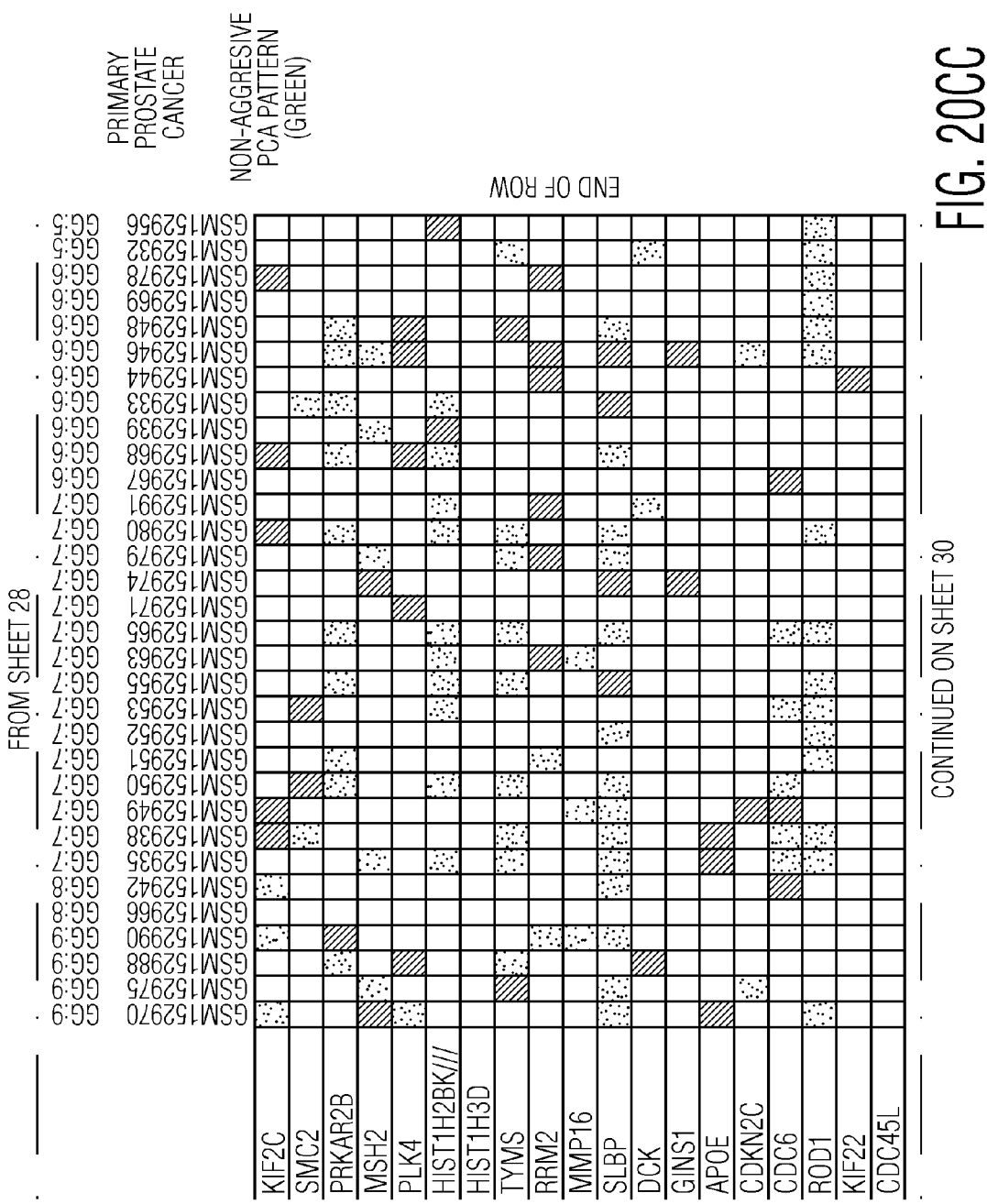
Figure 20E:
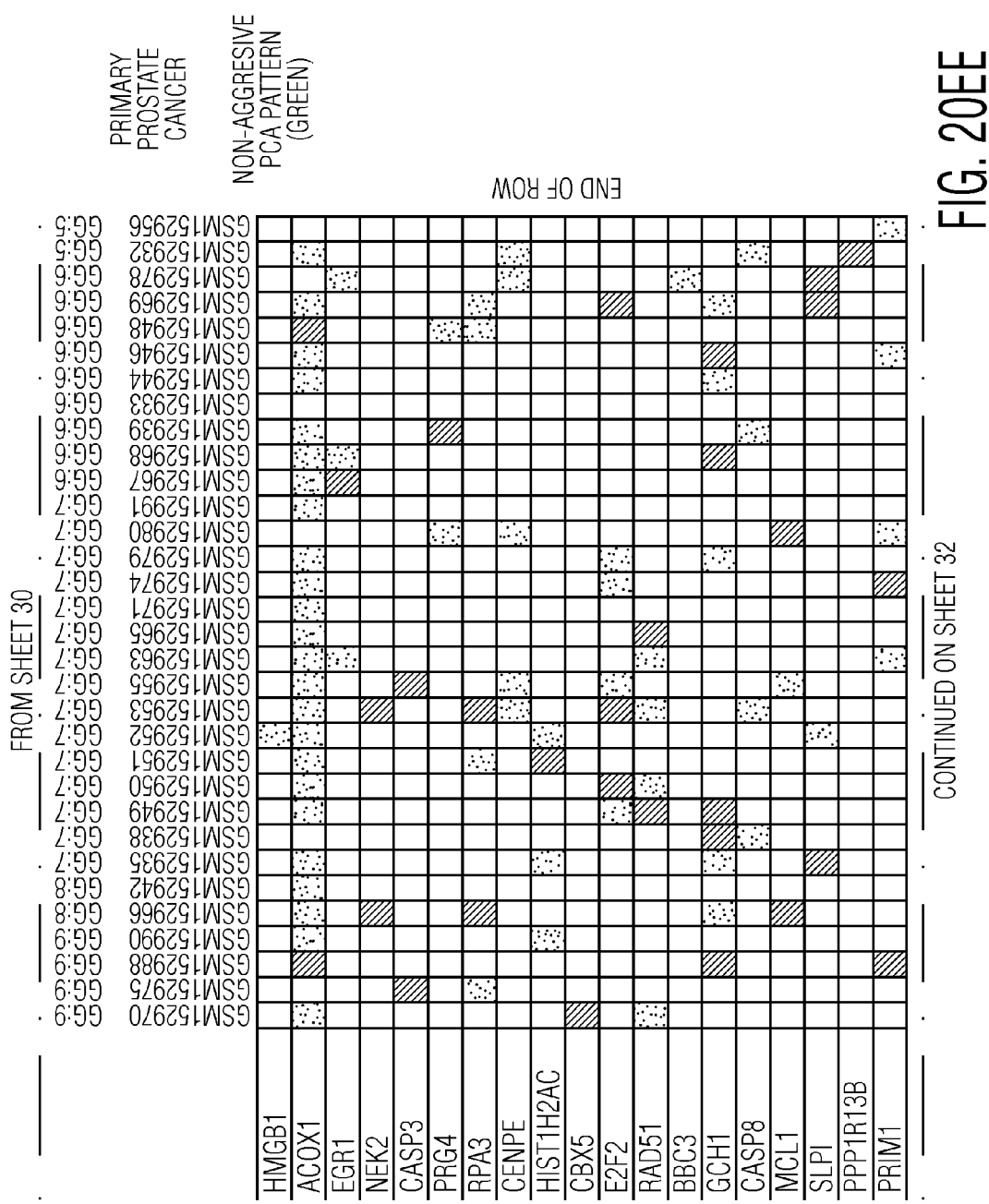
Figure 20I:
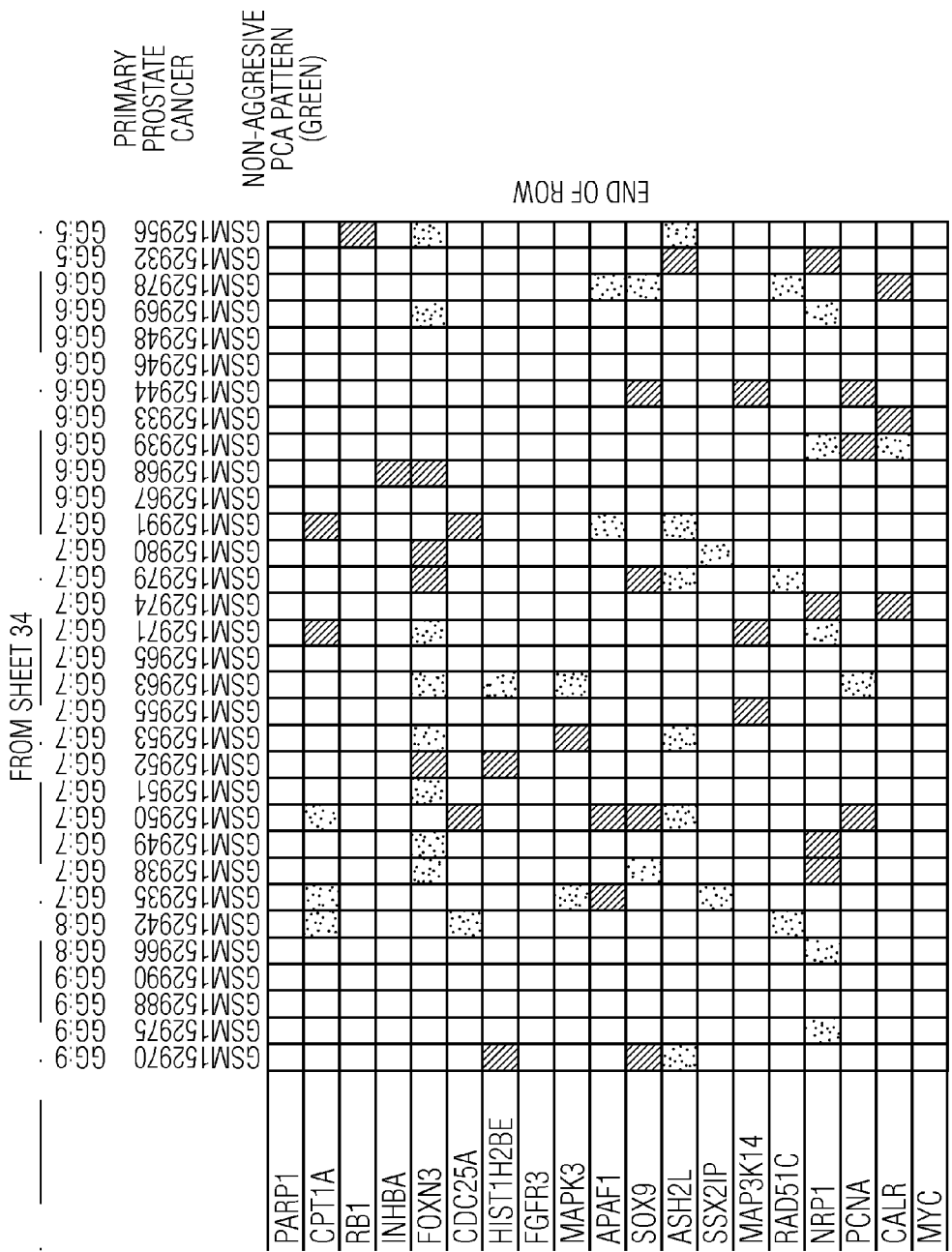

Importantly, the analyses here of thyroid and lung tumors show the frequency of over-expression of E2F-responsive genes that affect the G1/S cell cycle phase transition, and those that affect G2M were preserved in all ERGO tumors, regardless of the site of origin (e.g. breast, lung, or thyroid tissue) (FIG. 17). For example, in ERGO breast cancer tumors and ERGO thyroid cancer tumors, G2M-associated E2F-responsive genes were over-expressed more frequently than E2F-responsive genes associated with the G1/S phases. However, in ERGO lung cancer tumors identified by refined PCA the over-expression of G2M-associated E2F-responsive genes was less common and over-expression of E2F-responsive genes associated with DNA repair, was more common.

Example 3

Analysis of the Role of LINC Multiprotein Gene Transcription Repression Complex Function and FOXM1 Function in ERGO Tumors The analyses above revealed that specific E2F-responsive genes were highly over-expressed in the ERGO tumors identified and that these specific E2F-responsive genes were over-expressed with high frequency among the different ERGO tumors identified. It was observed that many of these E2F responsive genes are targets of a multiprotein gene transcription repressing complex comprising both the Rb and E2F proteins that has been evolutionarily conserved in *Caenorhabditis elegans* as the dRM protein complex, *Drosophila mela-*

*nogaster* as the dREAM protein complex, and in mammals as the LINC protein complex. In *C. elegans* the dRM multiprotein complex represses transcription of genes that are required for DNA synthesis and mitosis, and produces controlled chromosomal aneuploidy to stop cell division and produce aneuploid differentiated cells as part of normal tissue differentiation of the hindgut in this organism.

Figure 5:
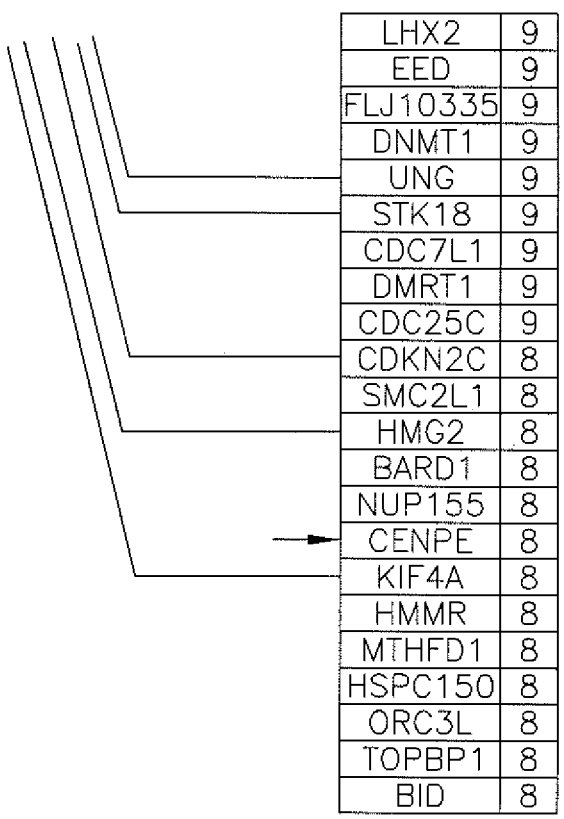
FIG. 5 shows a schematic diagram of genes that are targets of the dRM/dREAM/LINC complex and the downstream consequences of aberrations of the components of this complex (shown at far left).

Aberrations in at least four protein components of the dRM/dREAM/LINC multiprotein gene transcription repressing complex account for the majority of the abnormally over-expressed E2F-responsive genes in the ERGO tumors identified, and the over-expressed genes associated with DNA replication and mitosis. The downstream consequences of aberrations of the four components of this complex are shown in FIG. 5 and would produce a gene expression profile consistent with that observed in the ERGO tumors identified.

When the various components of these multiprotein repressor complexes, such as lin54, are lost these complexes fail to form correctly and, no longer repress G2M-associated genes. Importantly, loss of TESMIN—the human homolog of the *C. Elegans* lin54 protein—results in the up-regulation of a number of known G2M-associated genes (Kittler 2007). Analysis of the complete Dai human breast cancer microarray set (s3) which consists of the entire group of 311 patients in the breast cancer microarray dataset revealed that TESMIN expression is deficient and apparently lost. This loss of TESMIN expression was observed in 25 out of 37 (68%) of ERGO tumors identified by refined PCA in the complete Dai human breast cancer microarray set and 25 out of 41 (61%) non-ERGO basal-like tumors identified. However, this loss of TESMIN expression occurred infrequently in the non-basal-like tumors and only 28 of 231 (12%) of the non-basal-like tumors identified by PCA of this microarray set had an apparent loss of TESMIN expression. Importantly, TESMIN-controlled genes account for 21 of the 107 E2F-responsive genes that are over-expressed in the ERGO tumors identified by refined PCA in the complete Dai human breast cancer microarray set, and almost all of these 21 E2F-responsive genes are associated with mitosis.

The Rb protein is a component of the dRM/dREAM/LINC multiprotein gene transcription repressing complex. Loss of Rb expression in *Mus musculus* results in the over-expression of genes that are responsible for DNA replication and mitotic transit (Black and Nevins). Importantly, the analyses here found that RB1 is under-expressed in 19 of 37 (51%) ERGO tumors identified by refined PCA of the complete Dai human breast cancer microarray set, in 4 of 41 (10%) non-ERGO basal-like tumors identified, and in 23 of 231 (10%) of non-basal-like tumors identified in this microarray set. Twenty-four (24) of the genes that are over-expressed as a result of loss of Rb expression were also among the most highly over-expressed E2F-responsive genes in the ERGO tumors identified. These genes included mitosis-associated genes, and DNA replication-associated genes.

Some components of the dRM/dREAM/LINC multiprotein gene transcription repressing complex are associated with the complex only in quiescent cells. Examples of such proteins are E2F4 and p130 which is a "pocket" protein related to Rb. In proliferating cells the E2F4 and p130 components are shuttled out of the dRM/dREAM/LINC multiprotein gene transcription repressing complex and replaced by p107 which is another Rb-related protein, and B-Myb. When this occurs dRM/dREAM/LINC multiprotein complex becomes a gene transcription activating complex, and induces the transcription of genes that are associated predominantly with the G2M portion of the cell cycle. These induced genes minimally overlap with those induced by Rb loss.

B-myb induces transcription of cyclins A2, B1, and B2 which are also regulated by Rb. The analyses here found that B-myb is constitutively over-expressed in 10 of 37 (27%) ERGO tumors identified by refined PCA of the complete Dia human breast cancer microarray set, 4 of 41 (10%) non-ERGO basal-like tumors identified, and 8 of 231 (3%) of non-basal-like tumors identified. The analyses here also found that A-myb, another closely related member of the vertebrate myb gene family, is over-expressed in 12 of 37 (32%) ERGO tumors identified by refined PCA of the complete Dia human breast cancer microarray set, 2 of 41 (5%) of non-ERGO basal-like tumors identified, and 13 of 231 (6%) of non-basal-like tumors identified. Seven (7) genes that are regulated by B-myb were also over-expressed in the ERGO tumors identified and included cyclins A2, B1 and B2.

Over-expression of E2F1 and E2F2 by transfection of mouse embryo fibroblasts resulted in the identification of specific genes that are directly induced by E2F over-expression (unlike a host of other E2F-responsive genes that might be indirectly induced as a result of downstream E2F-related effects on other genes) (Ishida et al.). The specific genes which are directly induced by E2F over-expression are predominantly genes associated with DNA replication and mitosis. The analyses here found that 15 of 37 (41%) ERGO tumors identified by refined PCA of the complete Dai human breast cancer microarray set over-expressed E2F1 and/or E2F2 (41%), while only 7 of 41 (17%) of non-ERGO basal-like tumors identified, and only 9 of 231 (4%) of non-basal-like tumors identified over-expressed E2F1 and/or E2F2. Twenty-one (21) genes that are governed by E2F are over-expressed in ERGO tumors and included cyclins A2, B1 and B2. This set of 21 genes had substantial overlap with those genes over-expressed as a result of an apparent loss of Rb expression.

Figure 6:
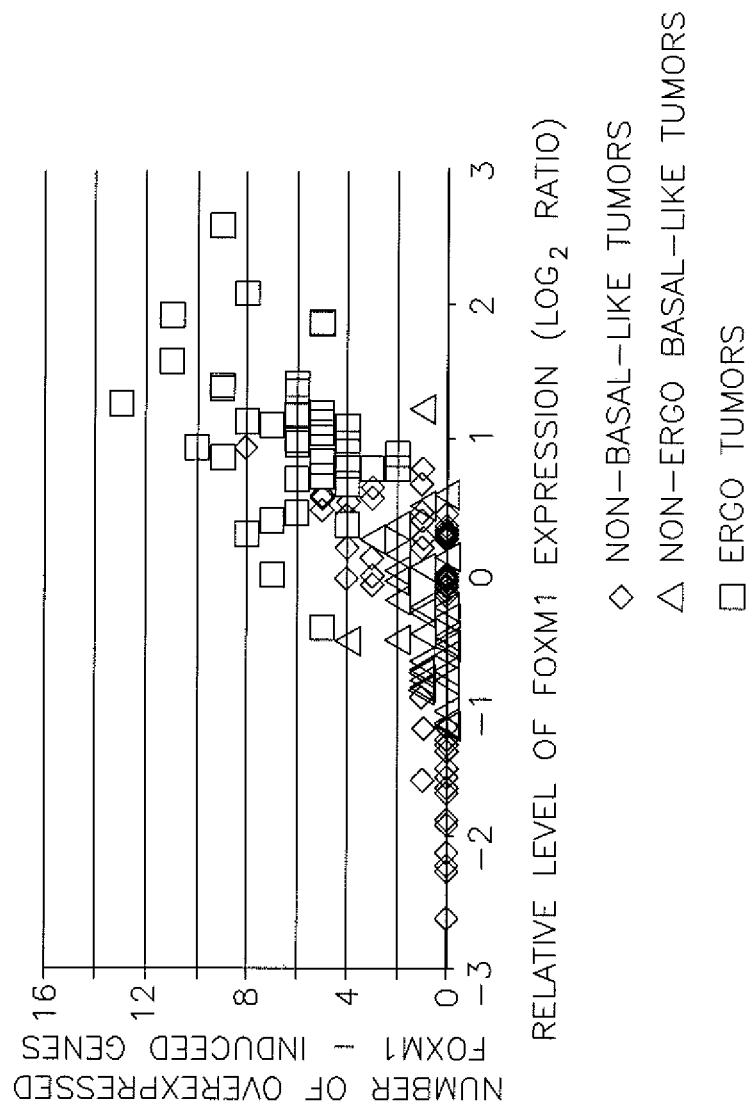
FIG. 6 shows the number of over-expressed FOXM1-associated DNA replication genes and mitotic genes per ERGO tumor as a function of the relative level of FOXM1 over-expression per ERGO tumor.
Figure 7:
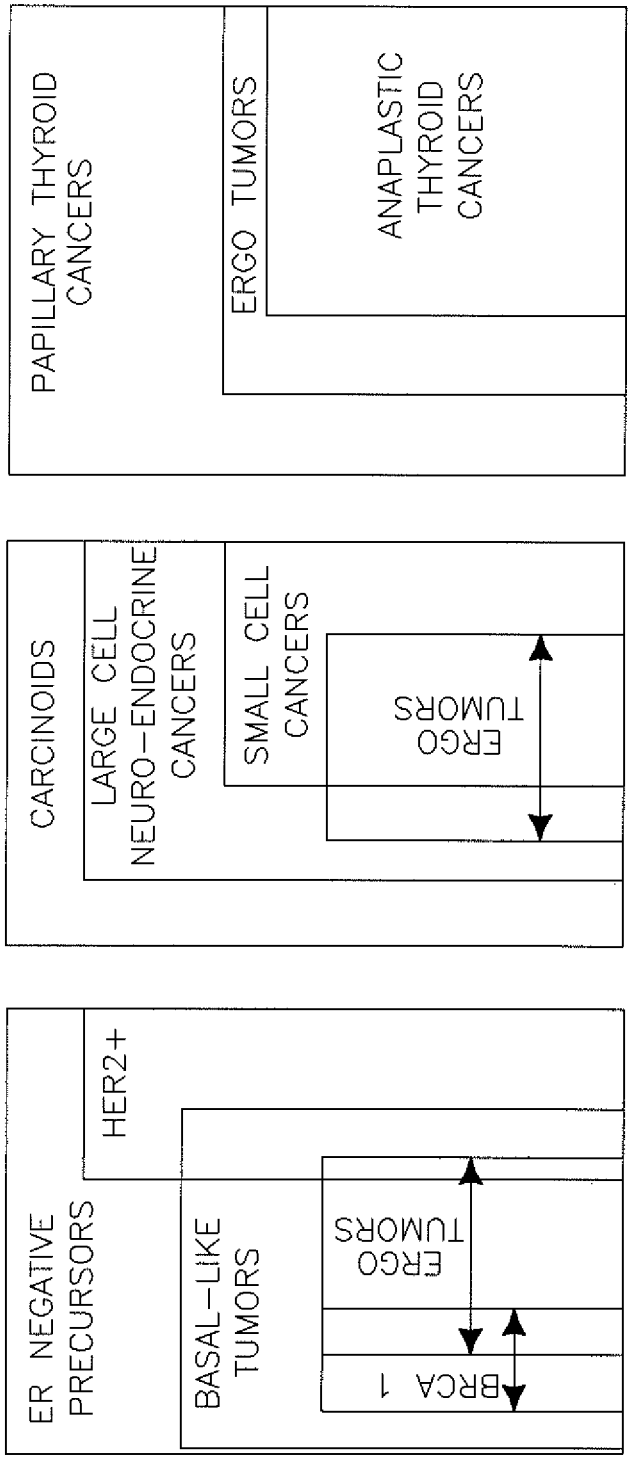
FIG. 7 is a schematic diagram of the phylogenetic origin of ERGO tumors at different organ sites. The schematic is based on results obtained with the weighted rank ordering methods and PCA based methods described in the Examples below.
Figure 8C:
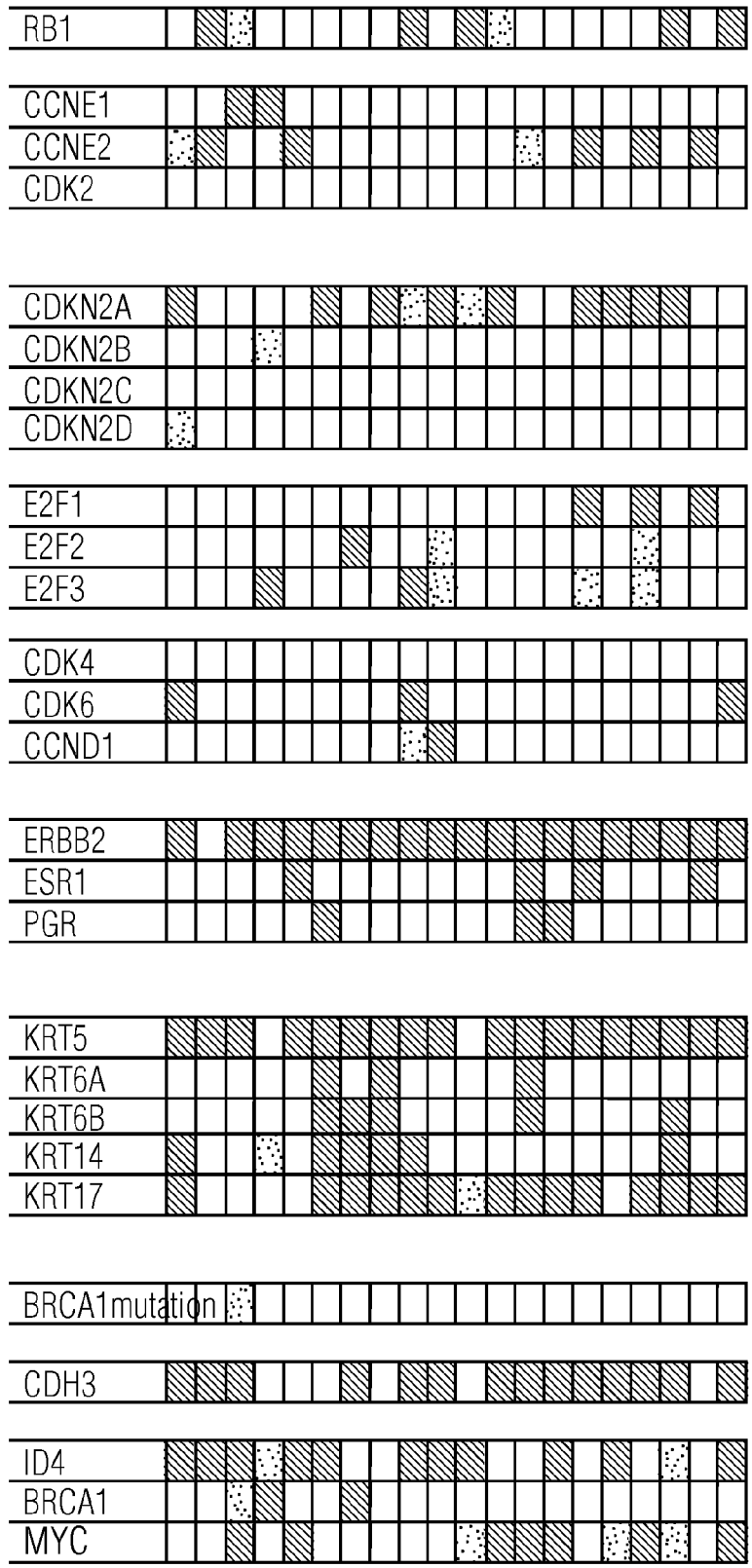
FIGS. 8A to 8FF show partial views intended to form one complete view of the selected gene expression profile for the ERGO, non-ERGO HER2-over-expressing, ER/PR over-expressing non-ERGO, and triple-non-positive non-ERGO tumor subsets of FIG. 1 in greater detail.
Figure 8D:
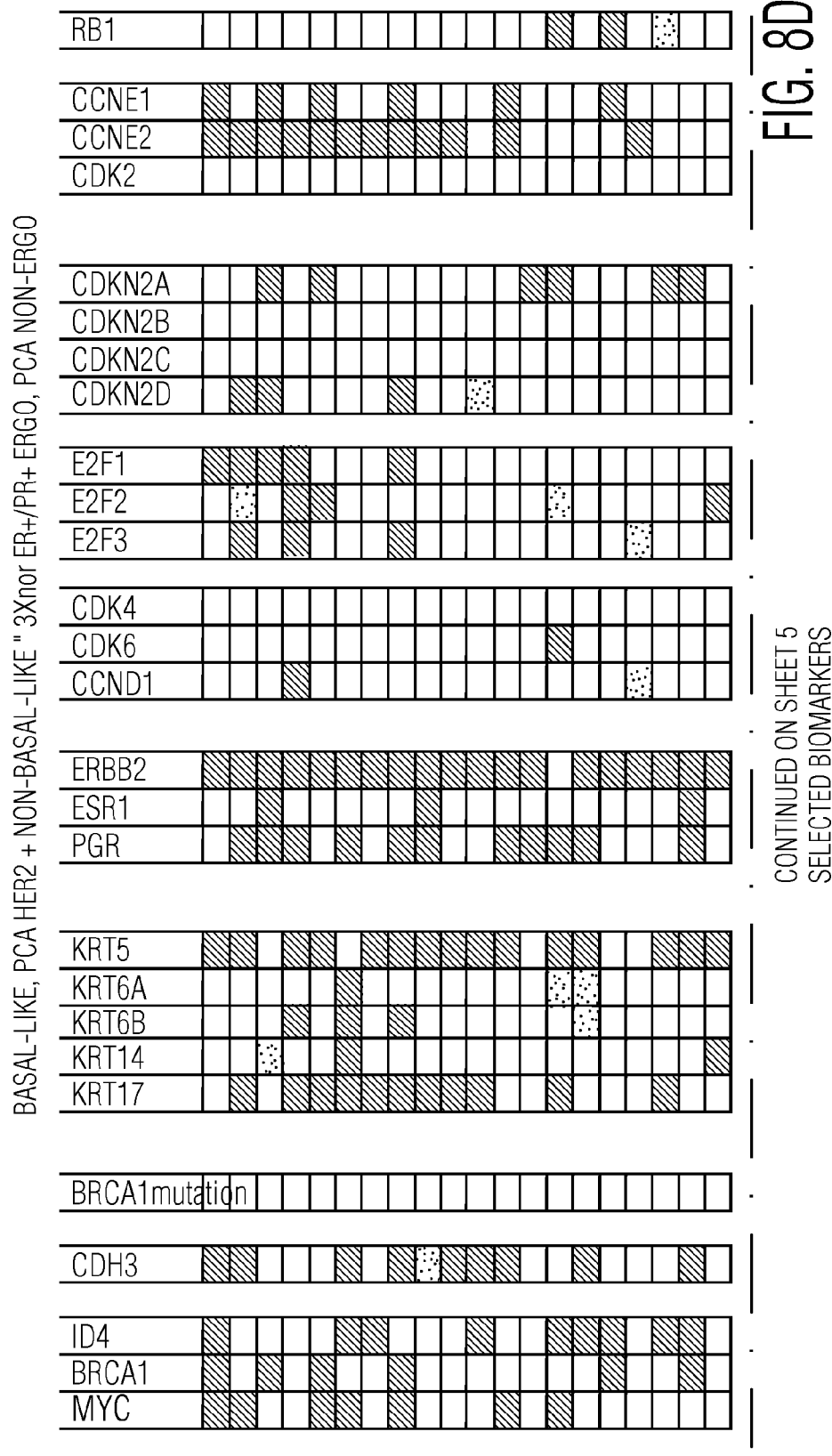
Figure 8K:
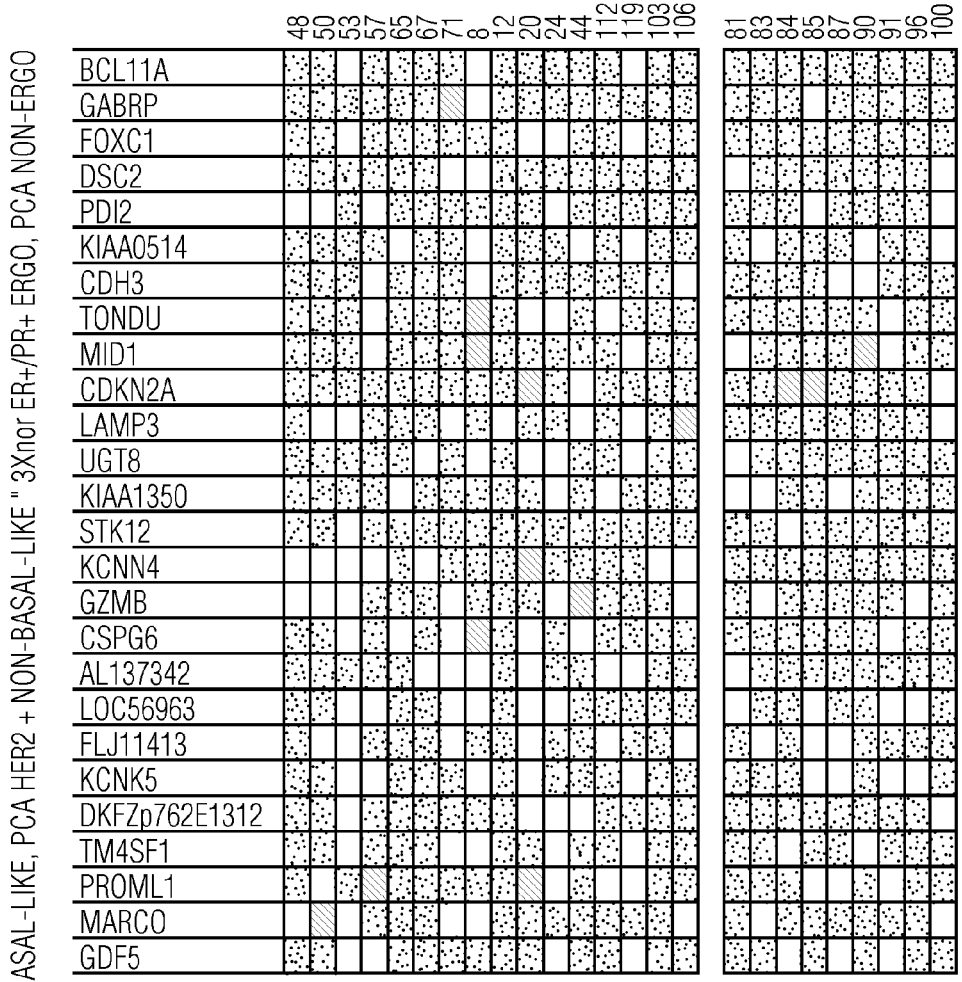
Figure 8Q:
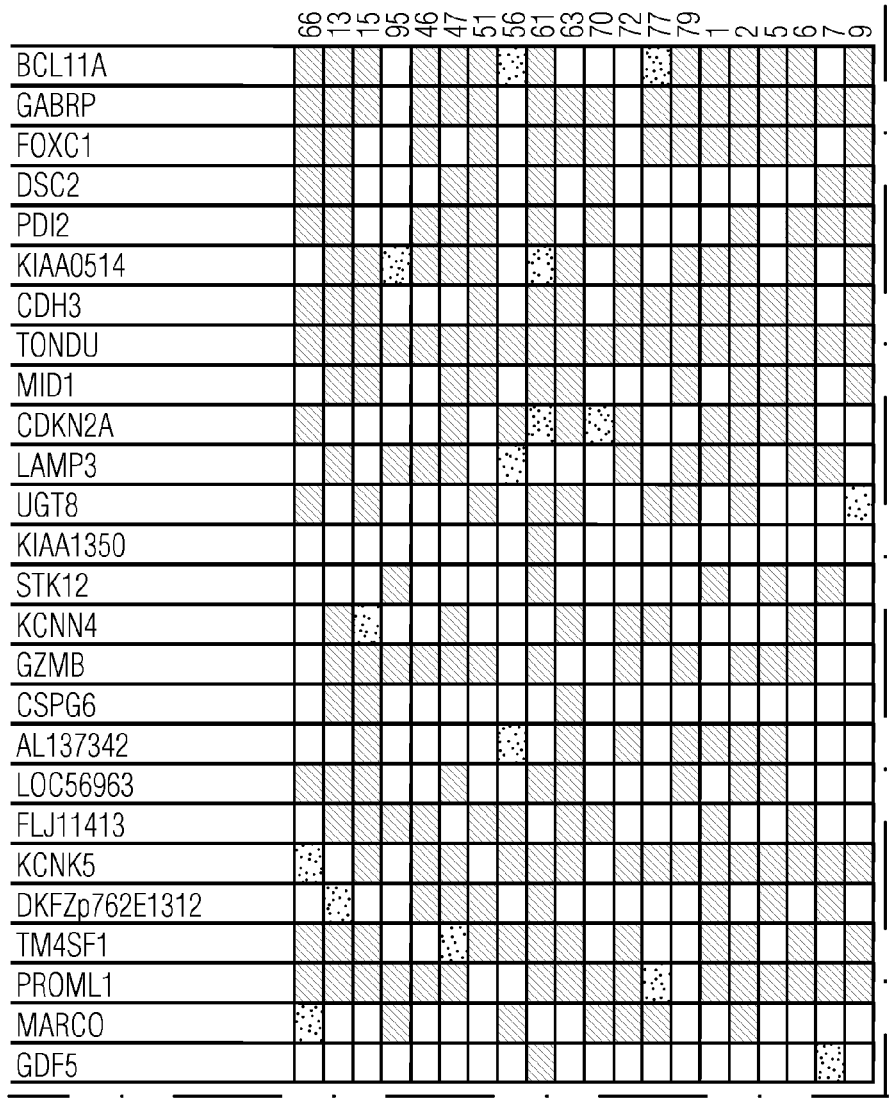
Figure 8V:
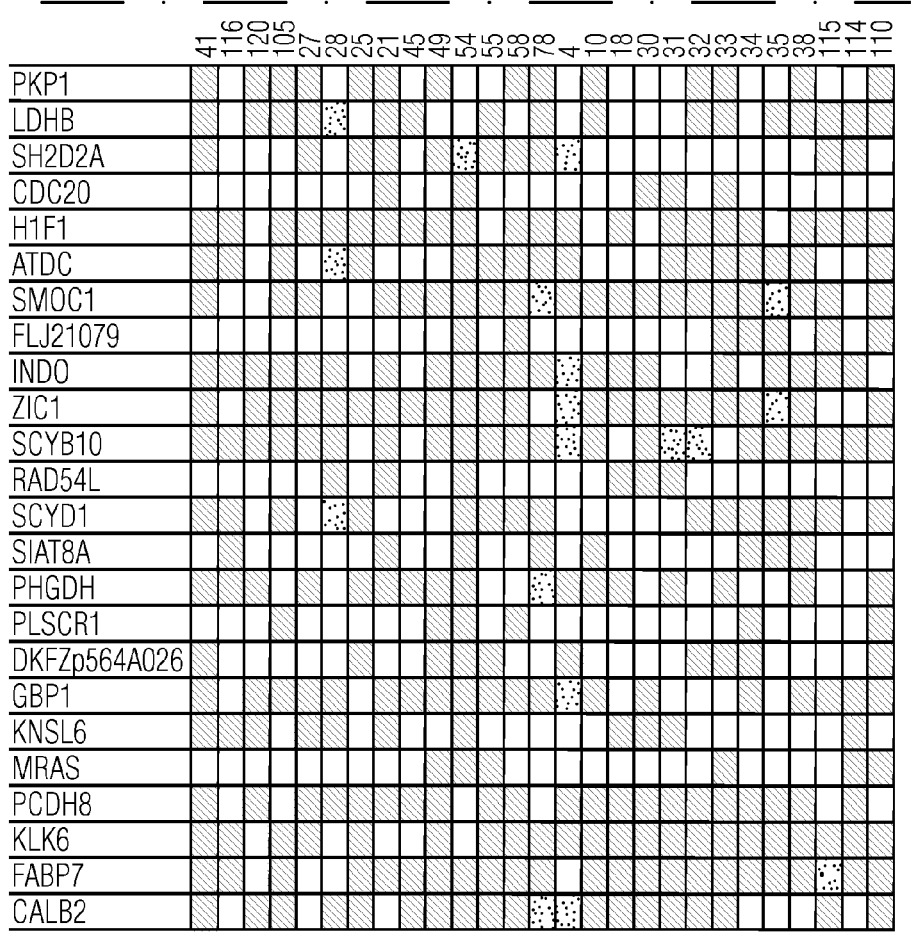
Figure 8B:
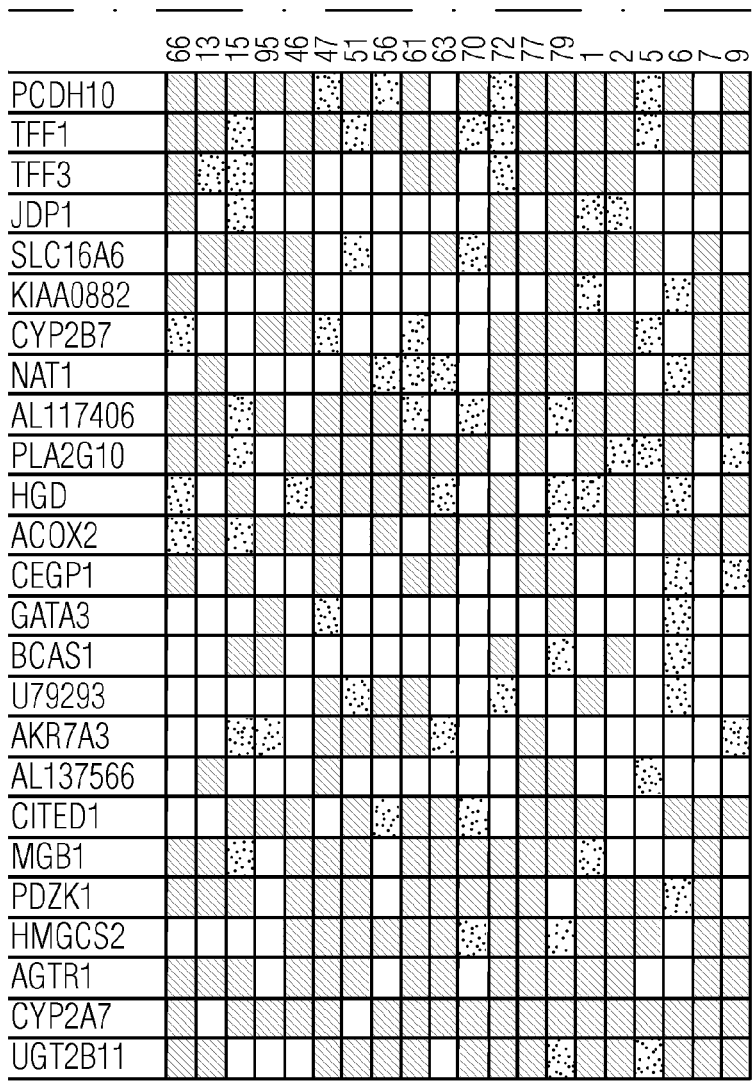

Cyclins A2, B1, and B2 are over-expressed in response to derangement of multiple components of the human LINC multiprotein gene transcription repressing complex. These cyclins phosphorylate and activate the transcription factor FOXM1 (Major ML). FOXM1 is an E2F-responsive gene that is highly over-expressed in ERGO tumors, but is not a component of the LINC multiprotein repressor complex. Importantly, FOXM1 induces several DNA replication-associated and mitotic genes that do not overlap with those induced by derangements in components of the LINC multiprotein complex (FIG. 5). Activated FOXM1 does induce expression of cyclin A2, B1 and B2 which establishes a positive feedback loop between the cyclins and FOXM1. The analyses here found that FOXM1 is over-expressed in 23 of 37 (62%) ERGO tumors identified by refined PCA of the complete Dai human breast cancer microarray set, in 6 of 41 (15%) non-ERGO basal-like tumors identified, and in 2 of 231 (1%) non-basal-like tumors identified in this microarray set. Importantly, there is a direct relationship between the average level of FOXM1 gene expression per tumor and the number of over-expressed FOXM1-associated DNA replication genes and mitotic genes in that tumor (FIG. 6). Furthermore the highest average levels of FOXM1 and the greatest numbers of over-expressed FOXM1-associated genes per tumor are observed in ERGO tumors (FIG. 6).

Several additional over-expressed mitotic and DNA replication-associated genes that are over-expressed by the ERGO tumors identified have also been linked to the derangement of grouped components of LINC multiprotein repressor complex (Georlette). These four genes are identified in FIG. 5 by four short horizontal arrows.

The foregoing clearly indicates that derangements in four of the components of the LINC multiprotein gene transcription repressing complex and/or FOXM1 account for 55 out of 107 (51%) of the over-expressed E2F-responsive genes associated with ERGO tumors identified in the complete Dai human breast cancer microarray set, and 50 of 67 (75%) of the mitotic and DNA replication-associated E2F-responsive genes that are over-expressed in these ERGO tumors. Most of the ERGO tumor-associated E2F-responsive genes that are aberrantly over-expressed in breast cancers, lung cancers, and thyroid cancers are DNA replication and mitosis associated genes that are linked to the Rb/E2F-containing multiprotein repressive complex. Together, these observations indicate that derangements of the human LINC multiprotein gene transcription repressing complex play a central role in the development of aggressive malignancies at multiple organ sites such as human breast, lung, and thyroid.

Example 4

Identification of E2F Responsive Gene Over-Expressing (ERGO) Tumors in a Prostate Cancer Microarray Set Prostate cancer is common among men over 60 years in age, but only about 15% of patients with invasive prostate cancer ultimately die of their disease. "Watchful waiting" is one option for management of prostate cancer, and could be more safely elected if robust markers for distinguishing aggressive prostate cancers from non-aggressive prostate cancers were available for patients with low to intermediate grade tumors (e.g. Gleason score of 4-7). Published studies also indicate that E2F3 over-expression may play some role in the development of prostate and bladder cancers. Here, prostate cancers were analyzed to determine if at least some prostate cancer tumors are ERGO tumors.

The prostate cancer microarray set published by Chandran et al. was used to investigate E2F-responsive gene expression in human prostate cancers and metastatic human prostate cancer samples. Gene expression data from tumor sample probed gene spots this microarray set was normalized to data from normal human prostate tissue sample probed gene spots that were included in the microarray set. The GSE6919 microarray set available from the NCBI GEO site was analyzed.

The Chandran microarray set includes multiple samples from metastatic prostate cancer tumors and androgen ablation-resistant prostate cancer tumors. Metastatic cancer samples in the same patient are known to be heterogeneous in their overall gene expression patterns, and this was confirmed in the Chandran microarray set. However, all metastatic cancer tumor samples in the Chandran microarry set showed fully developed ERGO tumor-associated gene expression patterns, and the homogeneity of ERGO gene expression patterns among different samples in each patient was striking. See FIG. 20. There is substantial overlap between the top 100 over-expressed E2F-responsive genes in metastatic prostate cancer, and the E2F-responsive genes over-expressed in ERGO tumors of the breast, lung, thyroid, and ovary.

Figure 21:
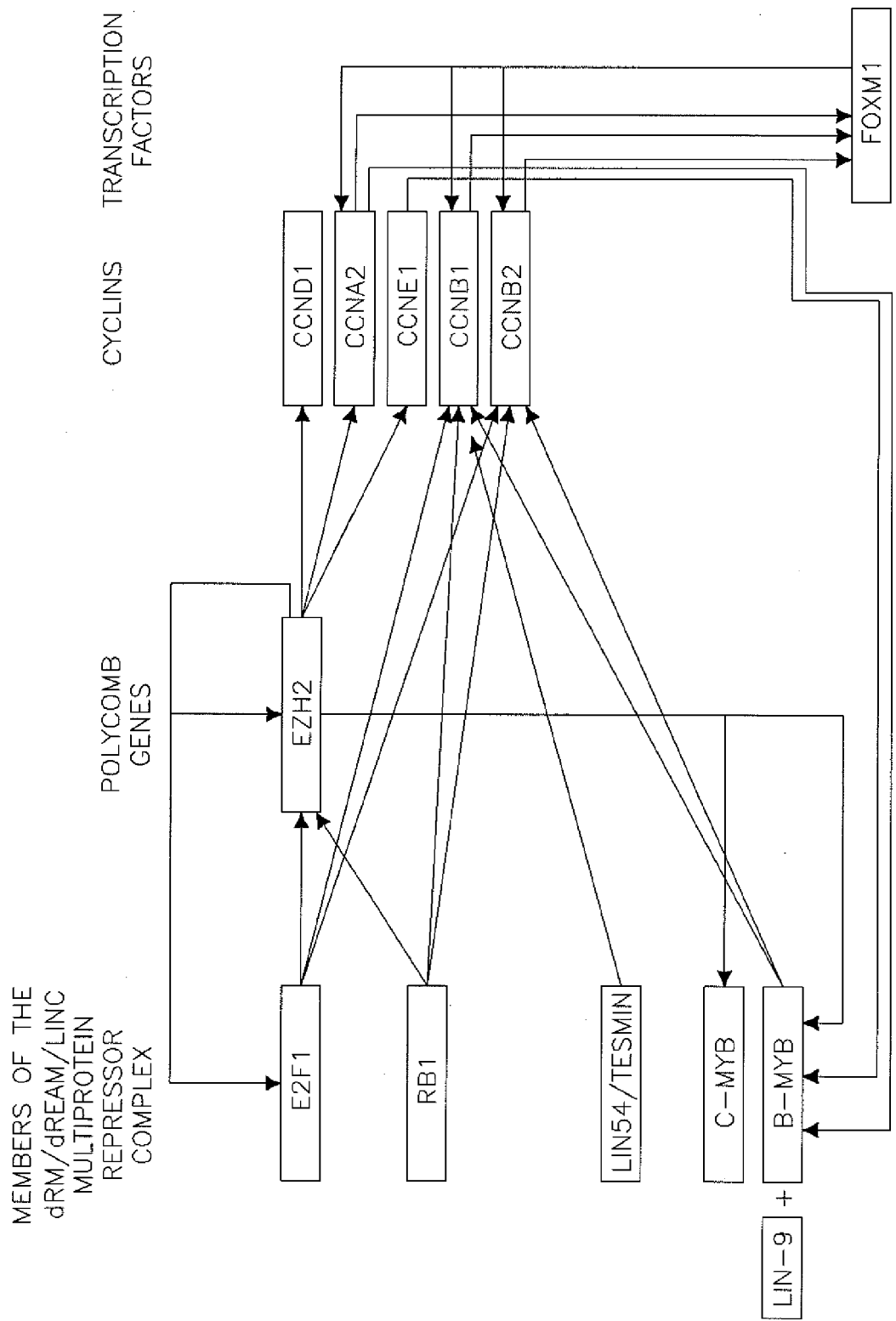
FIG. 21 shows details of the positive feedback loops and regulatory aspects of the cascade of changes associated with dysregulation of the members of the Syn/MULVB/DRM/DREAM/LINC multiprotein repressor/activator complex.

In particular, E2F3 was over-expressed in most metastatic prostate cancer samples, as were cyclin A2, and cyclin E2. Cyclin B2 was was also prominently over-expressed. Many prostate cancer tumor samples also over-expressed EZH2 and FOXM1, as well as MYBL2 (B-MYB). It is noteworthy, that the cyclins FOXM1 and EZH2 are over-expressed, because these genes are members of potential positive feedback loops in the cascade of changes associated with dysregulation of the members of the Syn/MULVB/DRM/DREAM/LINC multiprotein repressor/activator complex. These potential positive feedback loops are shown in a larger context in FIG. 5, and are shown separately with more detail in FIG. 21.

This metastatic prostate cancer derived data indicates that these positive feedback loops are active in dangerous, advanced metastatic cancer, but not in the large subset of patients with non-metastatic primary tumors. Additionally, although the total number of cases included in the Chandran microarray set is relatively small, the fact that every one of these cases of metastatic prostate cancer exhibits over-expression of large numbers of over-expressed ERGO tumor-associated genes shows that E2F3-driven ERGO tumor development is a feature of most dangerous, advanced prostate cancers.

Identification of ERGO Tumors in Prostate by PCA.

Figure 22:
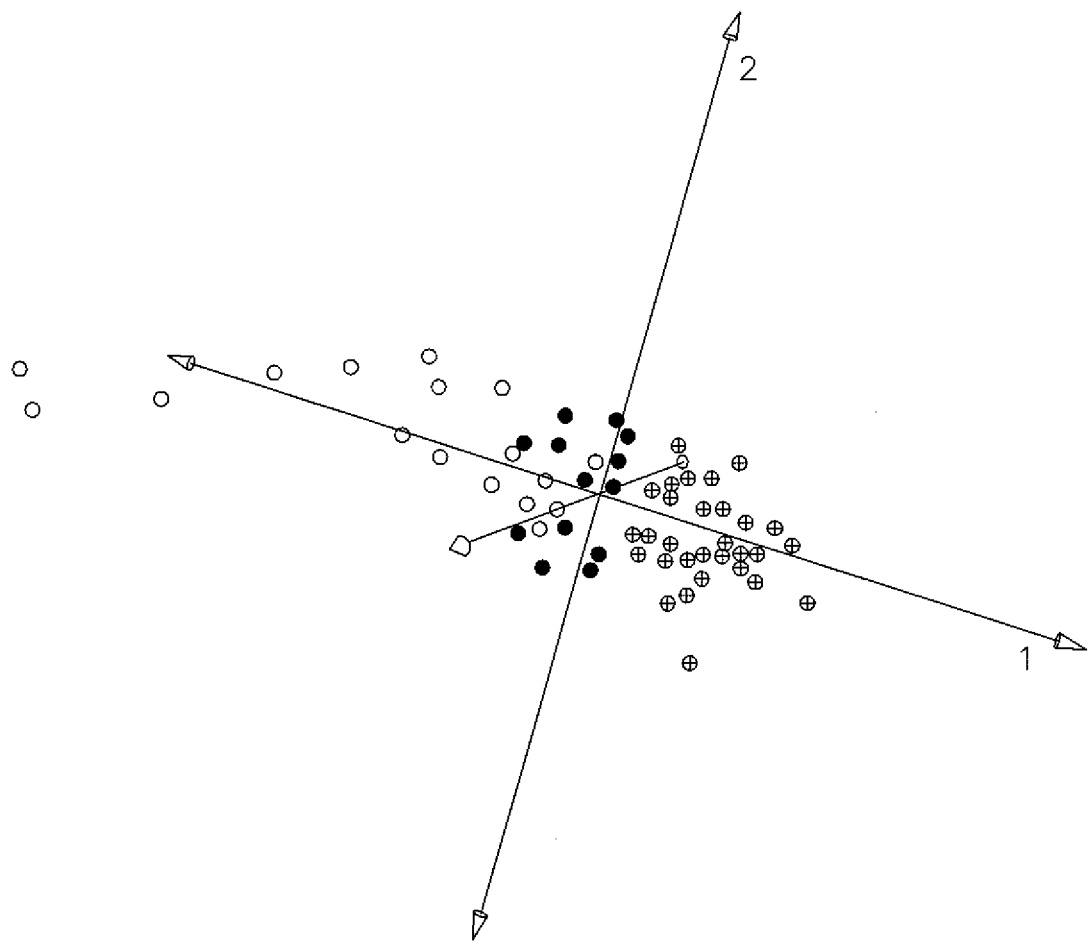
FIG. 22 shows a tumor cluster identified by PCA of primary prostate cancer tumor without metastases in the Chandran microarray set human prostate cancer microarray set.
Figure 23A:
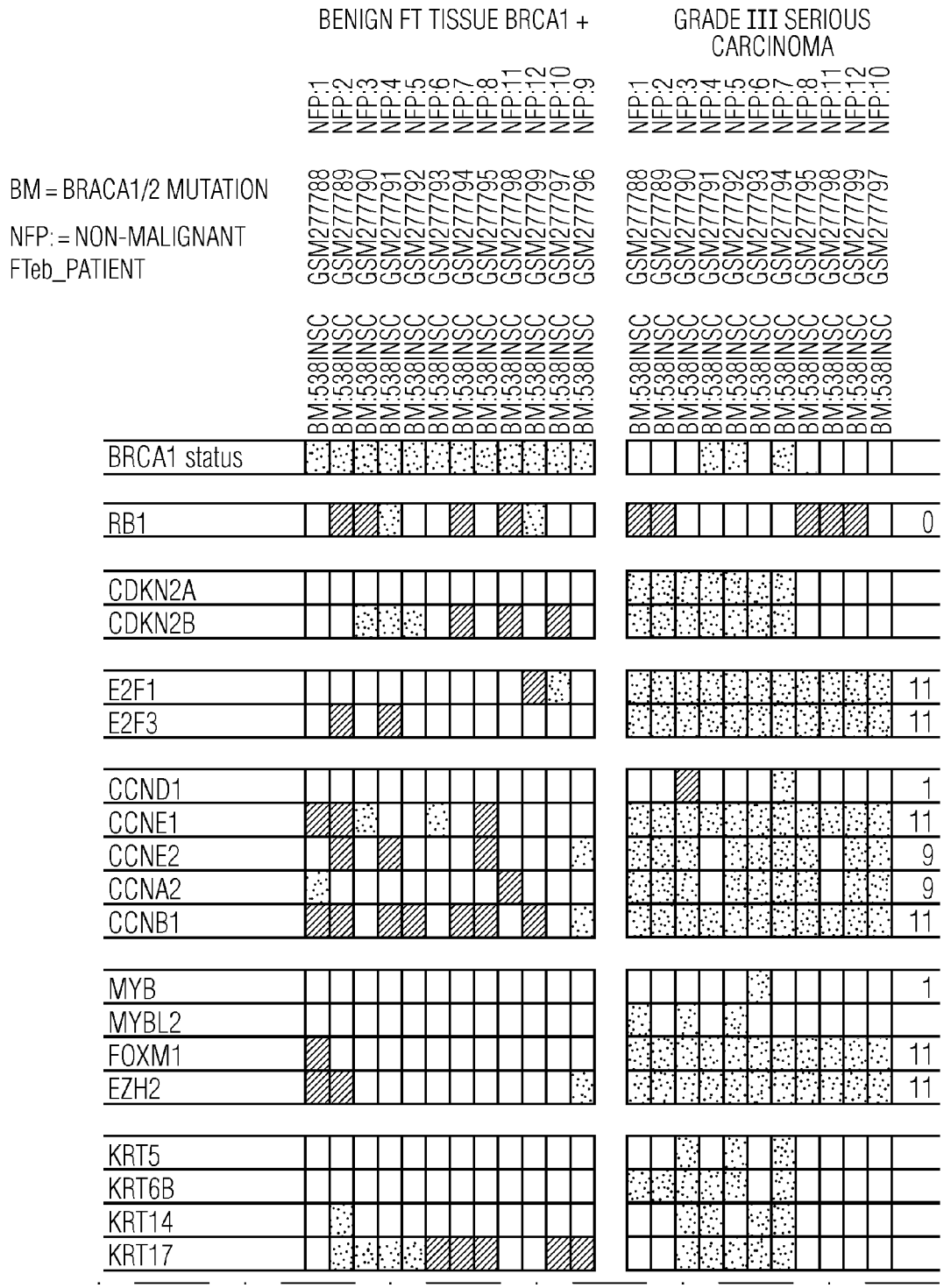
FIGS. 23A to 23N show partial views intended to form one complete view of microarray data from normal fallopian tube epithelium and high grade serous fallopian tube and ovarian carcinomas in both patients carrying BRCA1 gene mutations and patients that do not carry such mutations and the identification of ERGO genes and ERGO tumors in cancers from such patients as indicated.
Figure 23B:
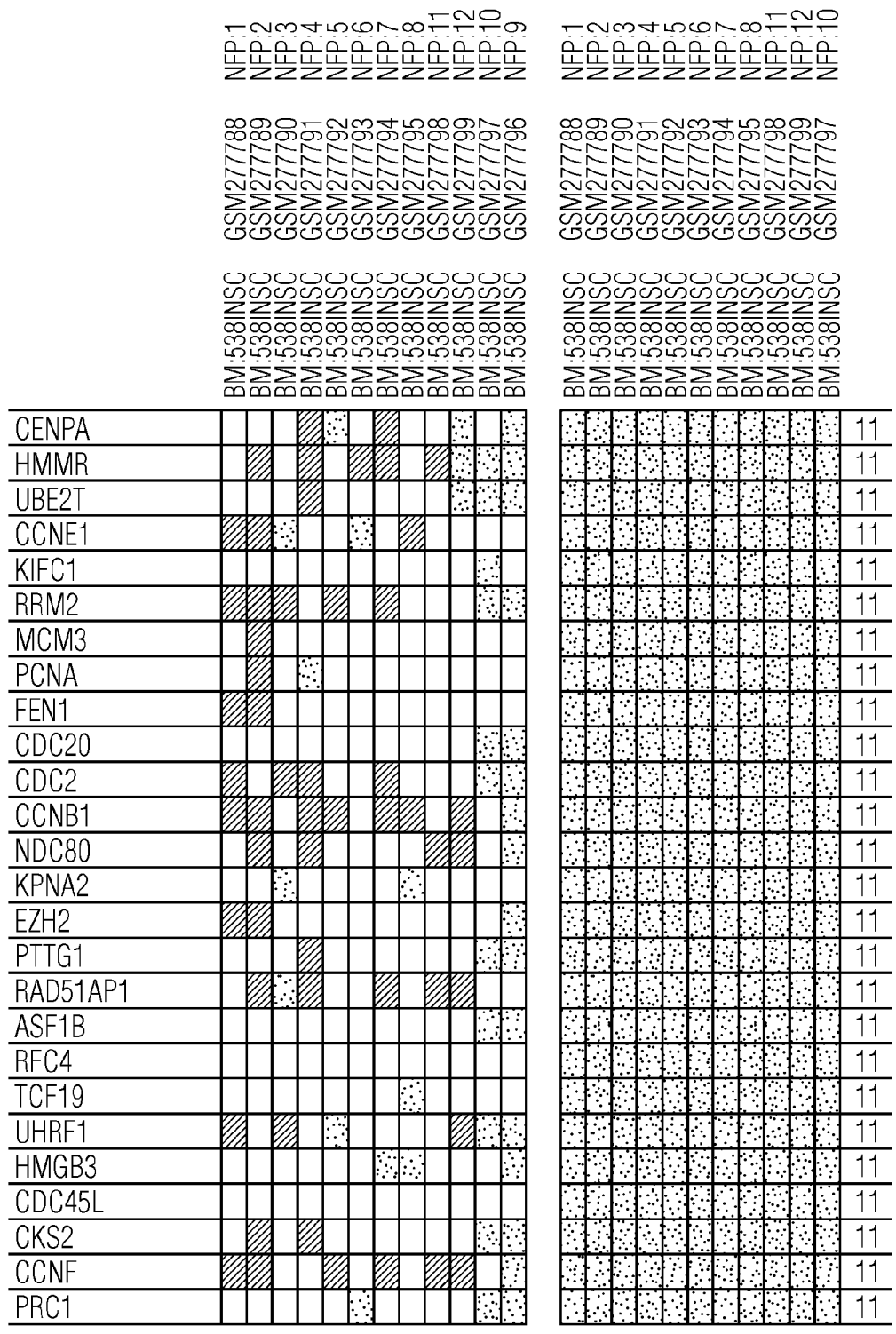
Figure 23C:
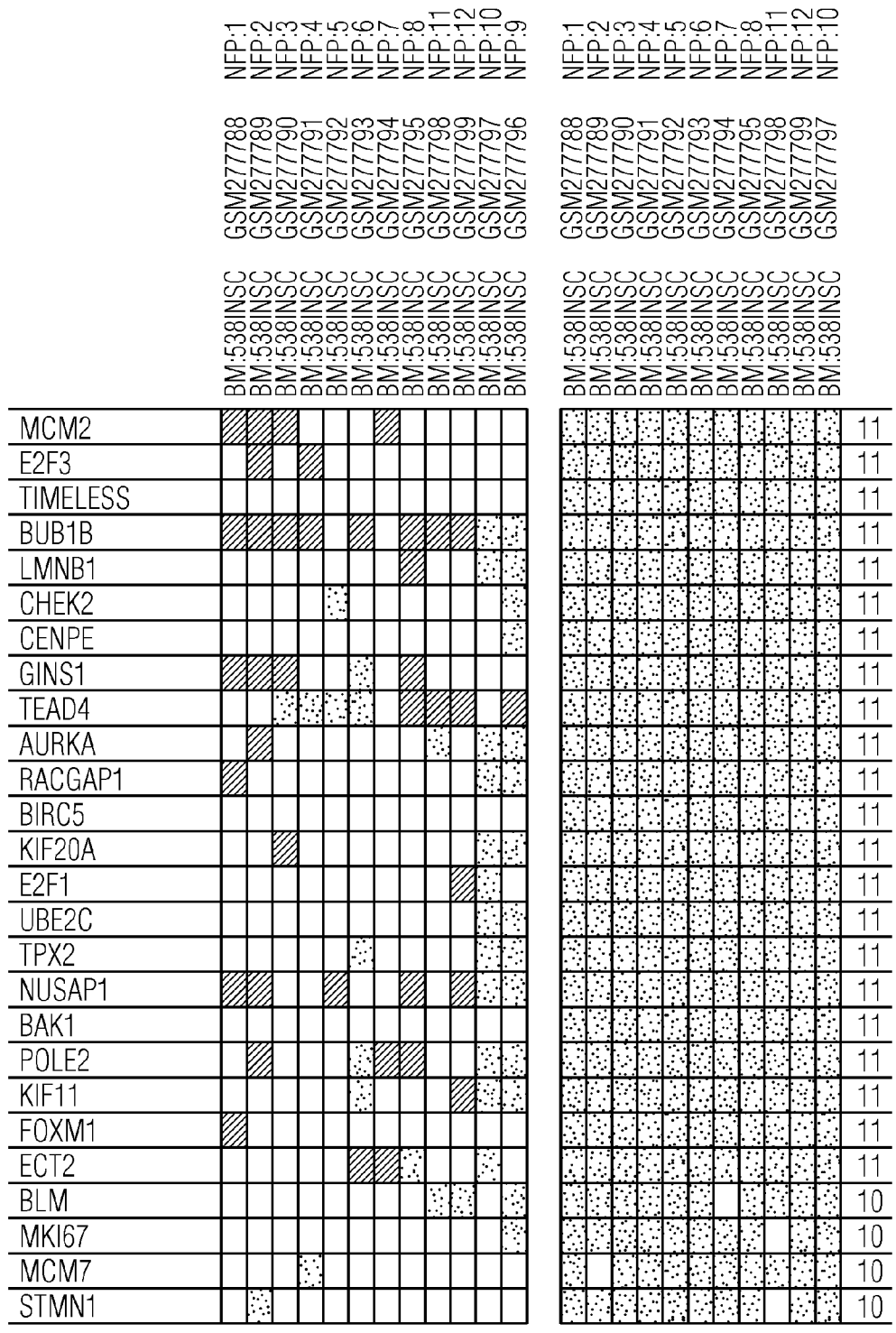
Figure 23D:
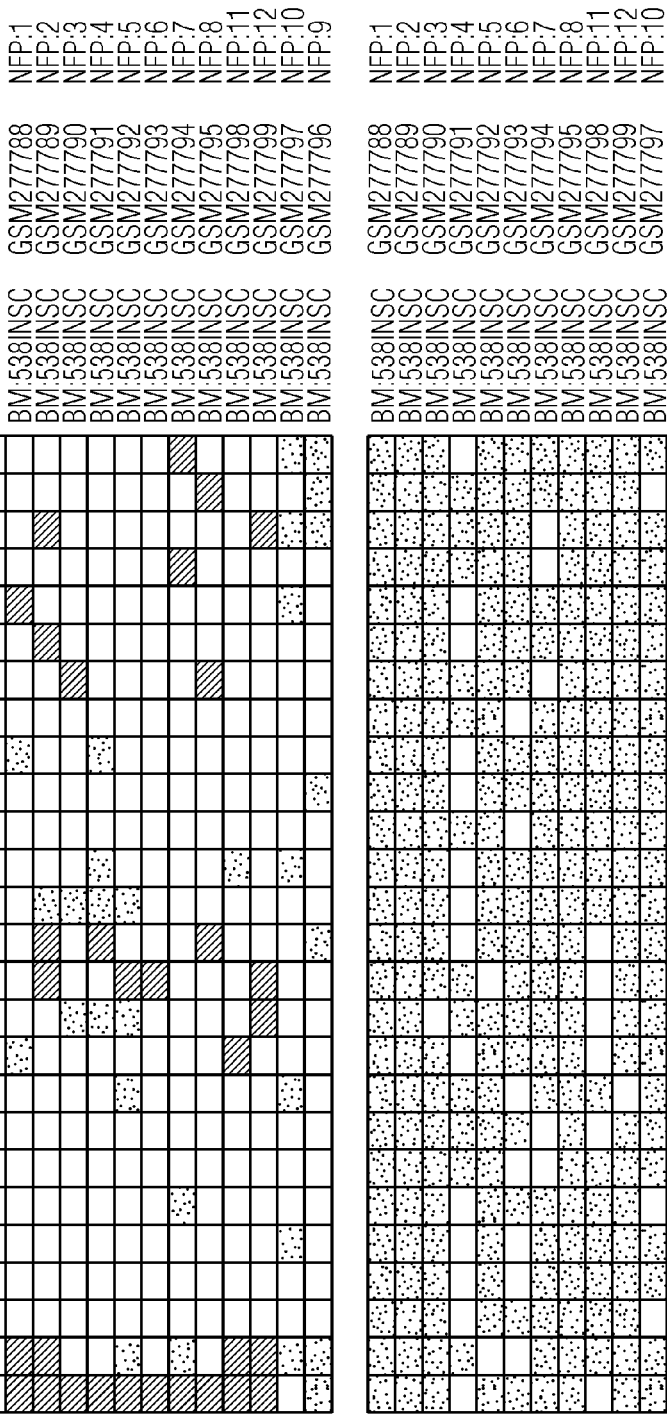
Figure 23F:
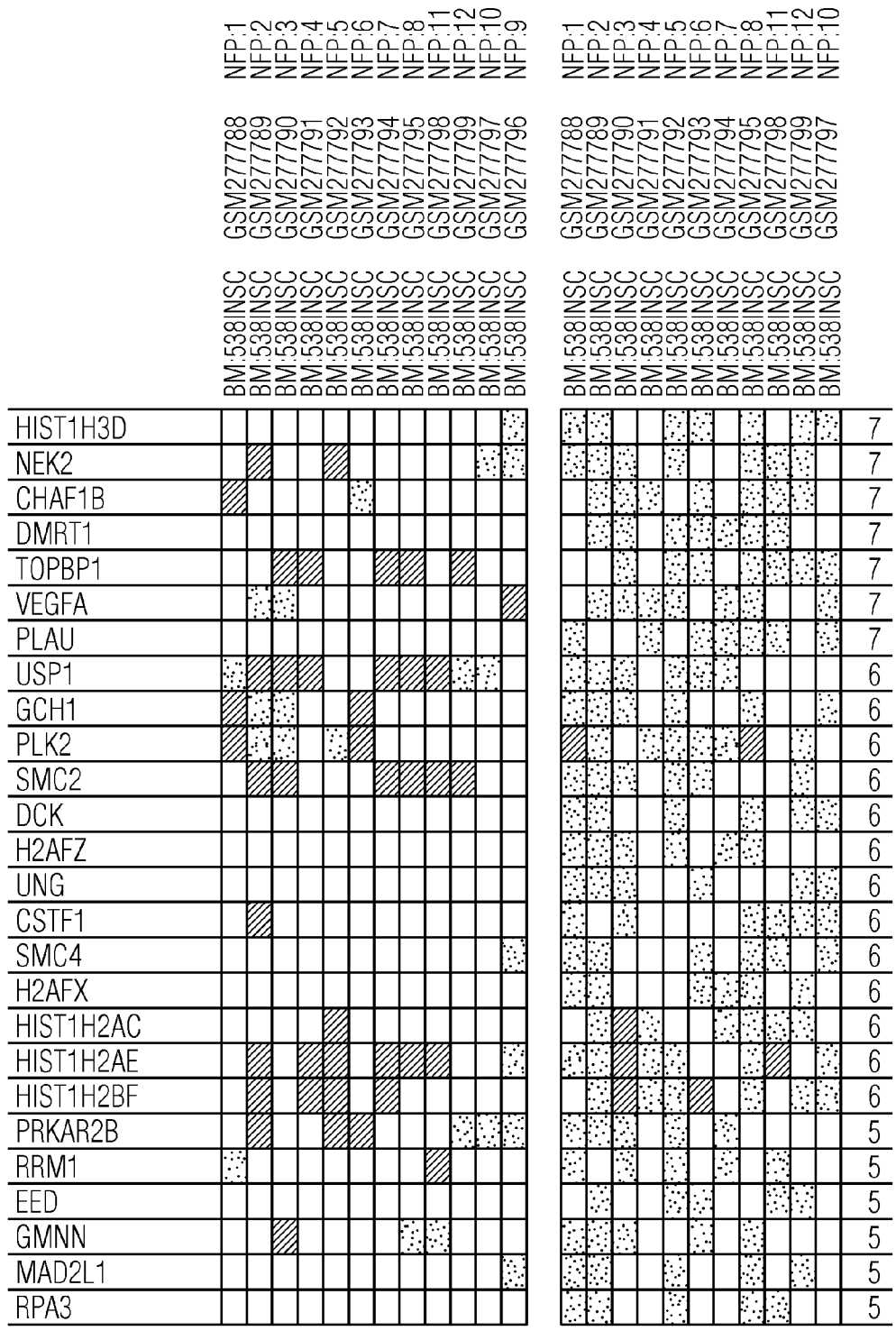
Figure 23G:
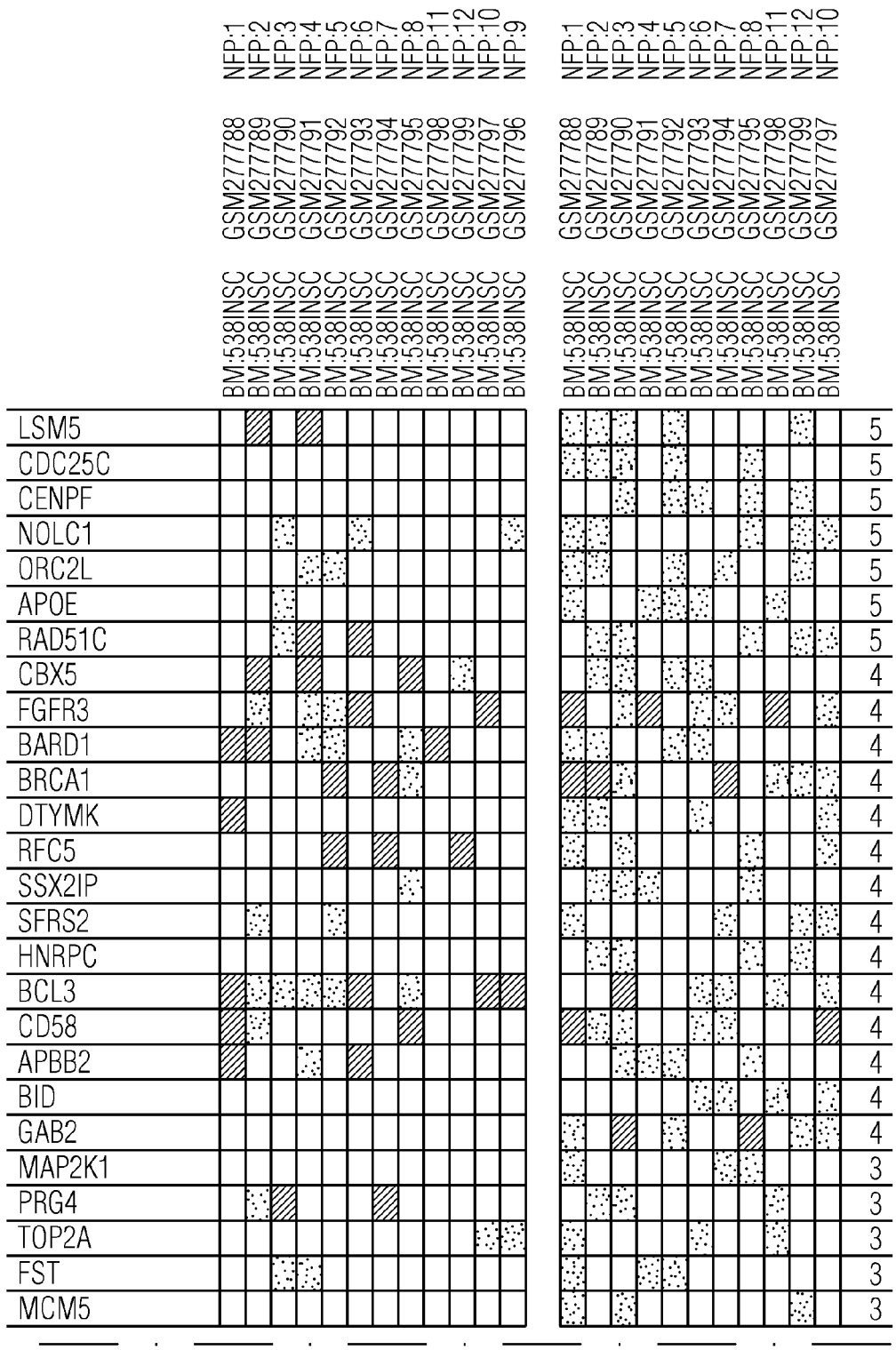
Figure 23H:
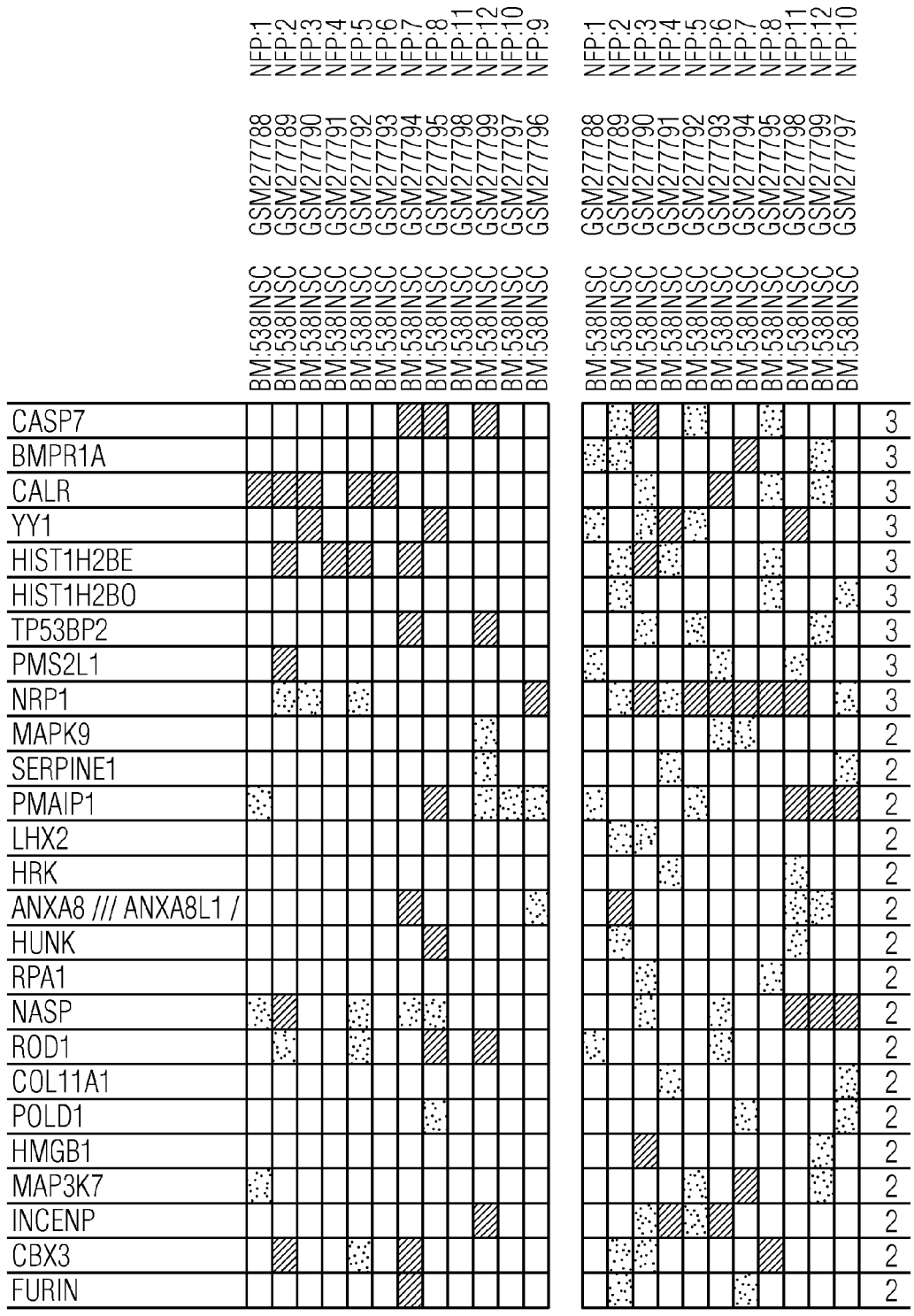
Figure 23I:
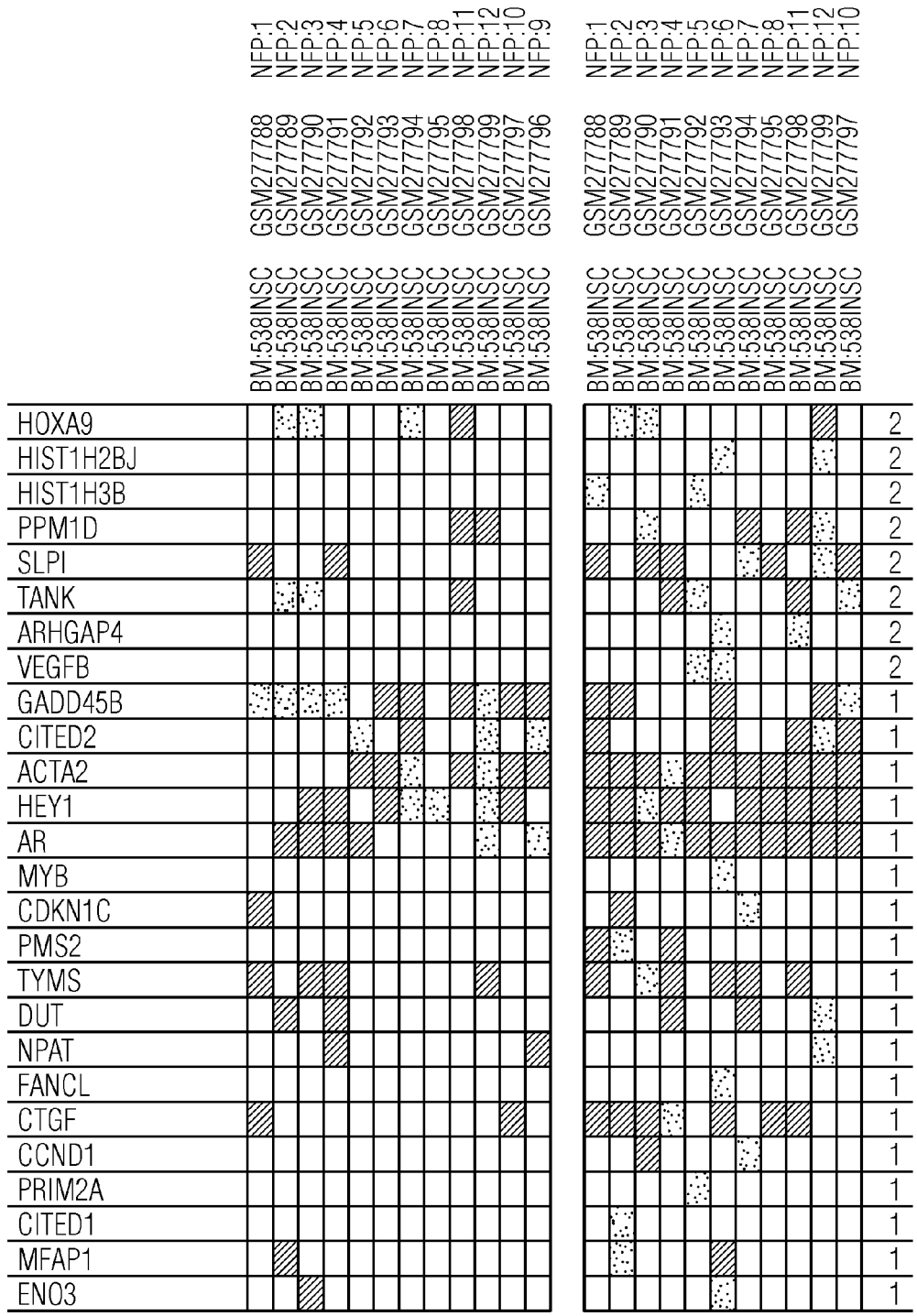
Figure 23J:
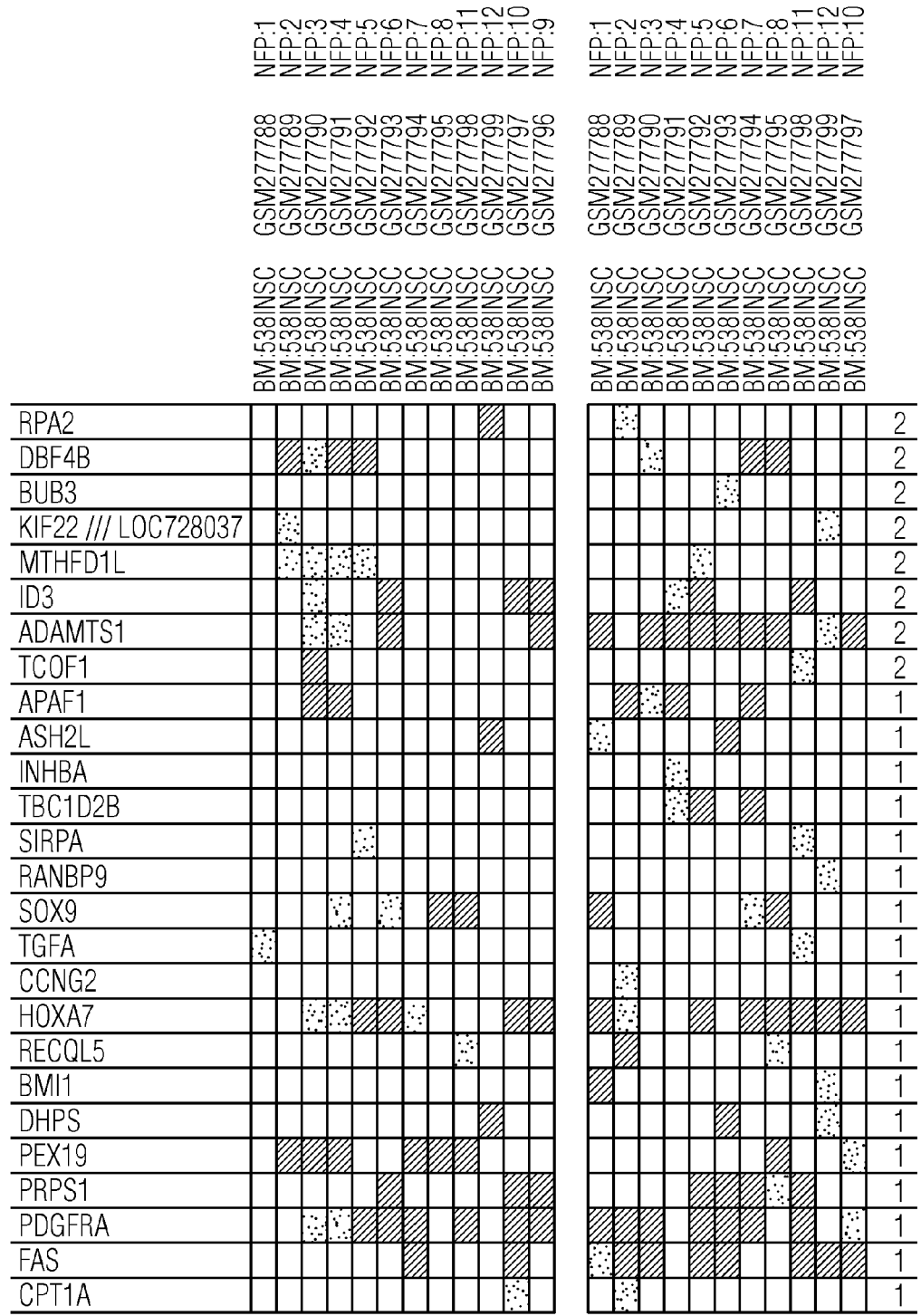
Figure 23L:
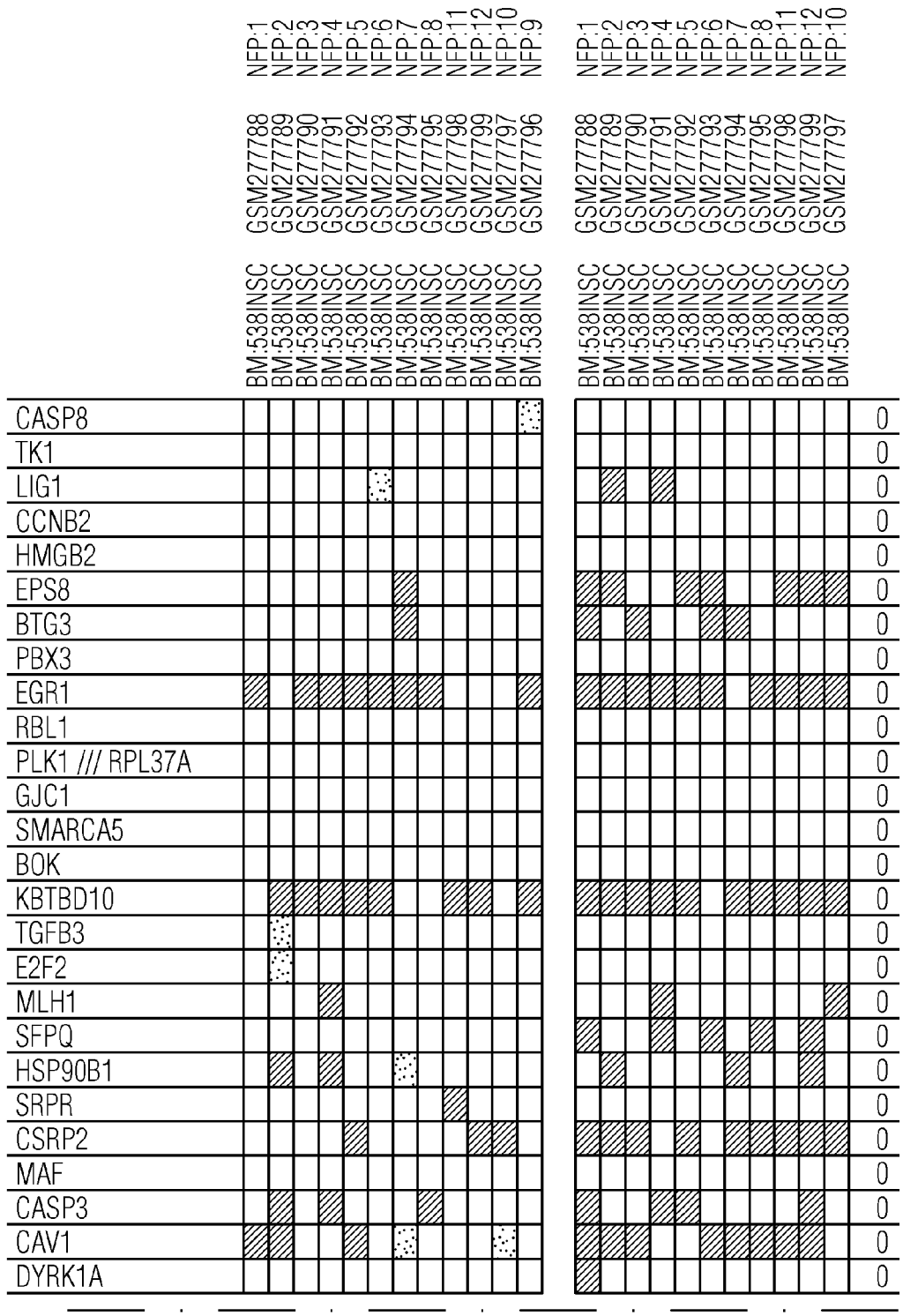
Figure 23M:
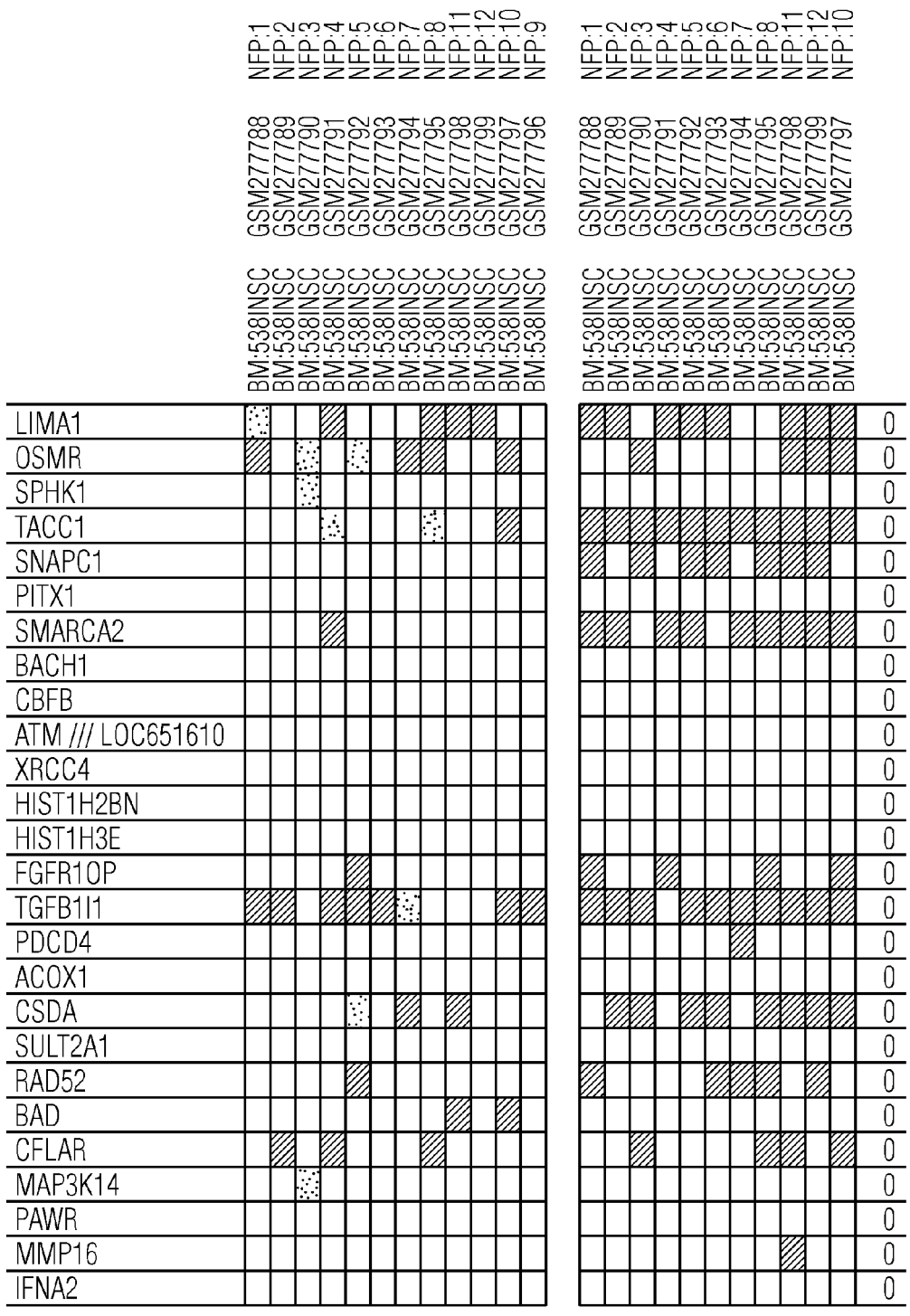
Figure 23N:
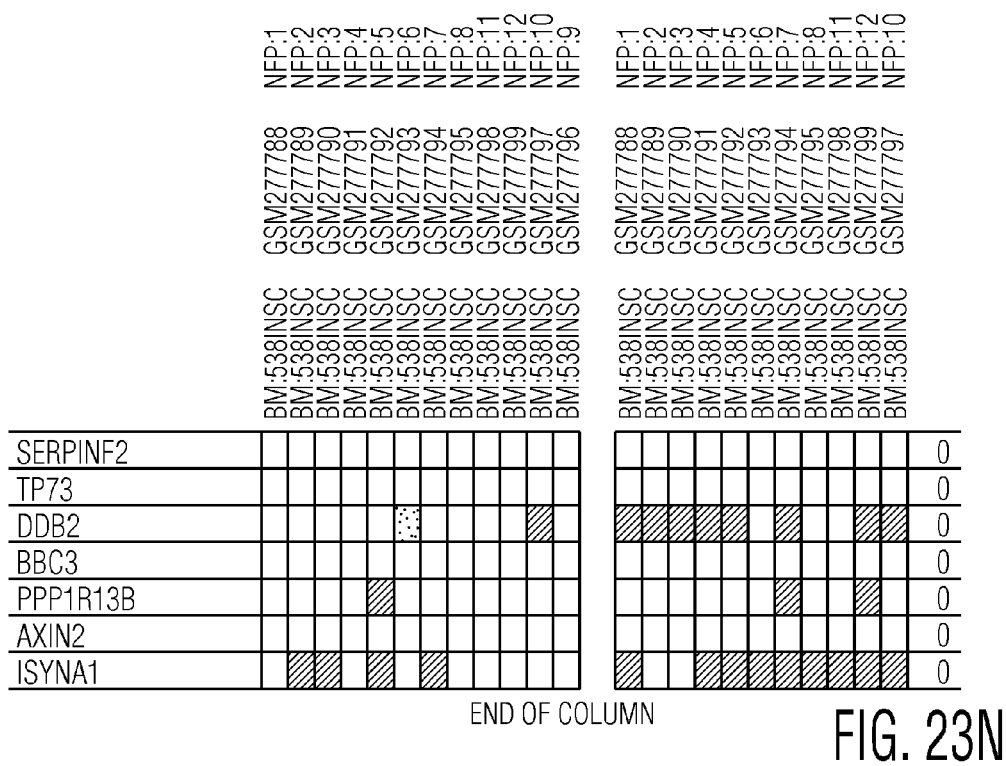
Figure 24A:
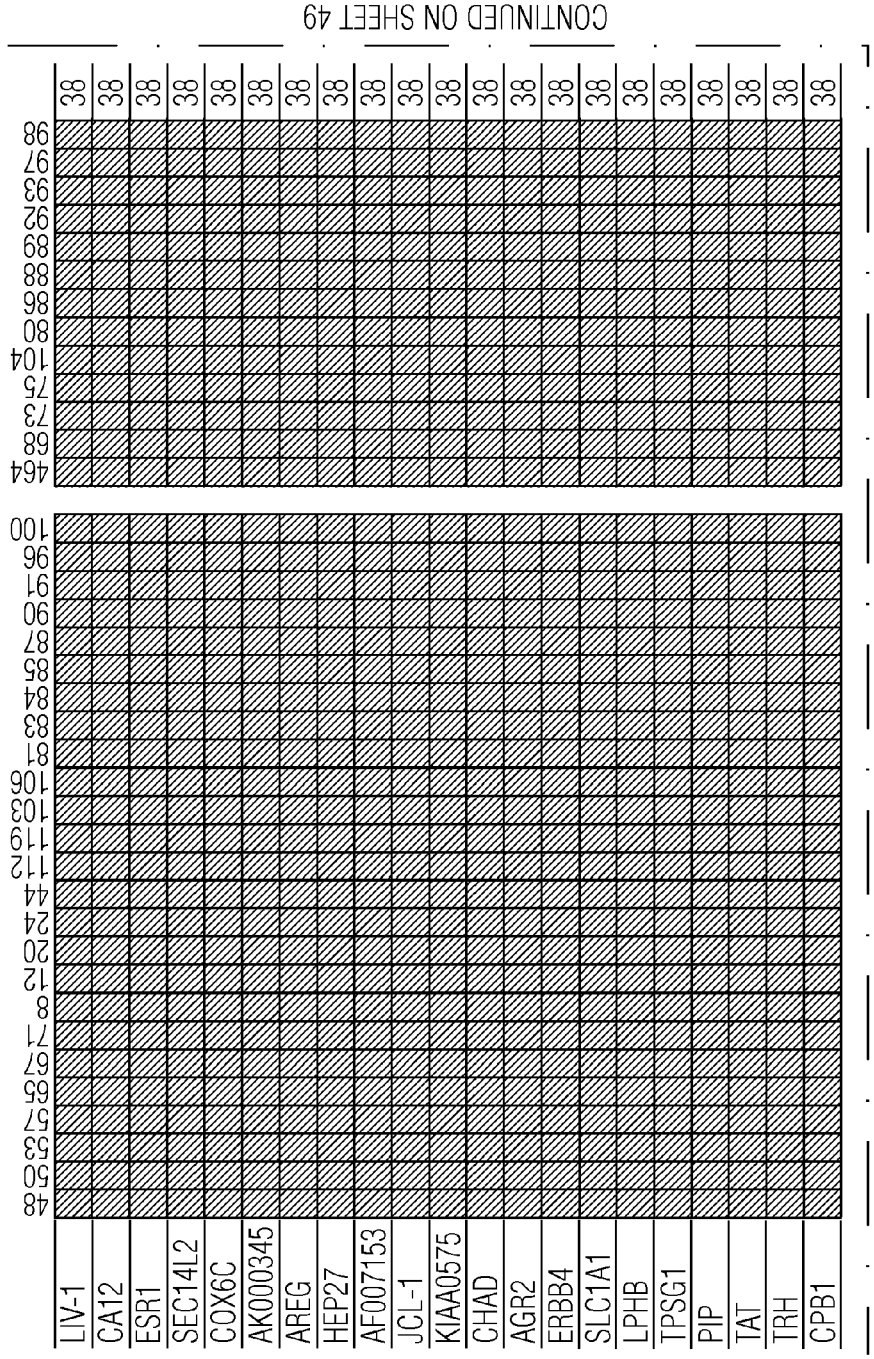
FIGS. 24A to 24NNNNNN show partial views intended to form one complete view of microarray data from the Van't Veer microarray set, showing the non-E2F responsive genes that are statistically significantly differentially under-expressed in basal-like breast cancers relative to non-basal-like breast cancers.
Figure 24B:
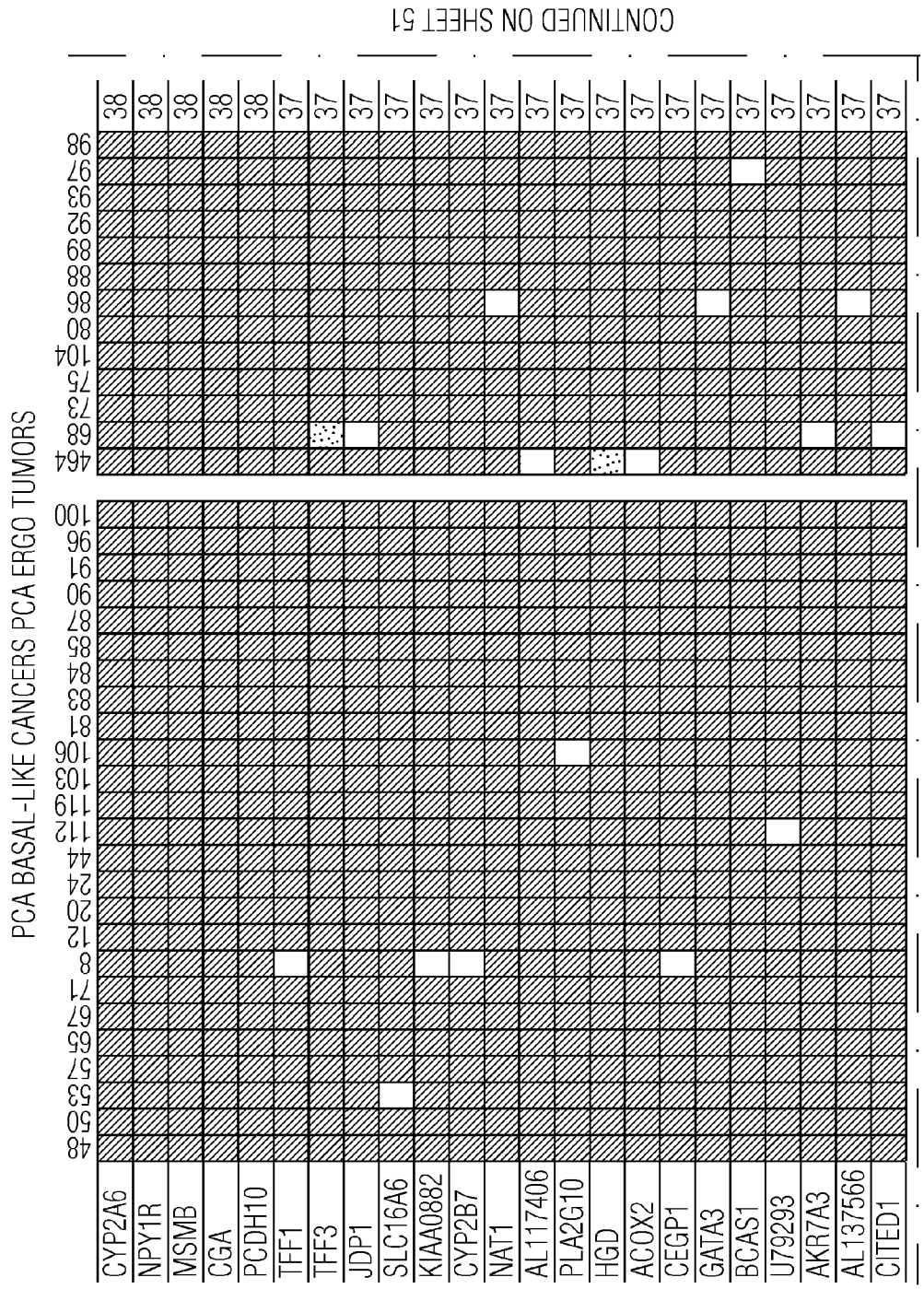
Figure 24C:
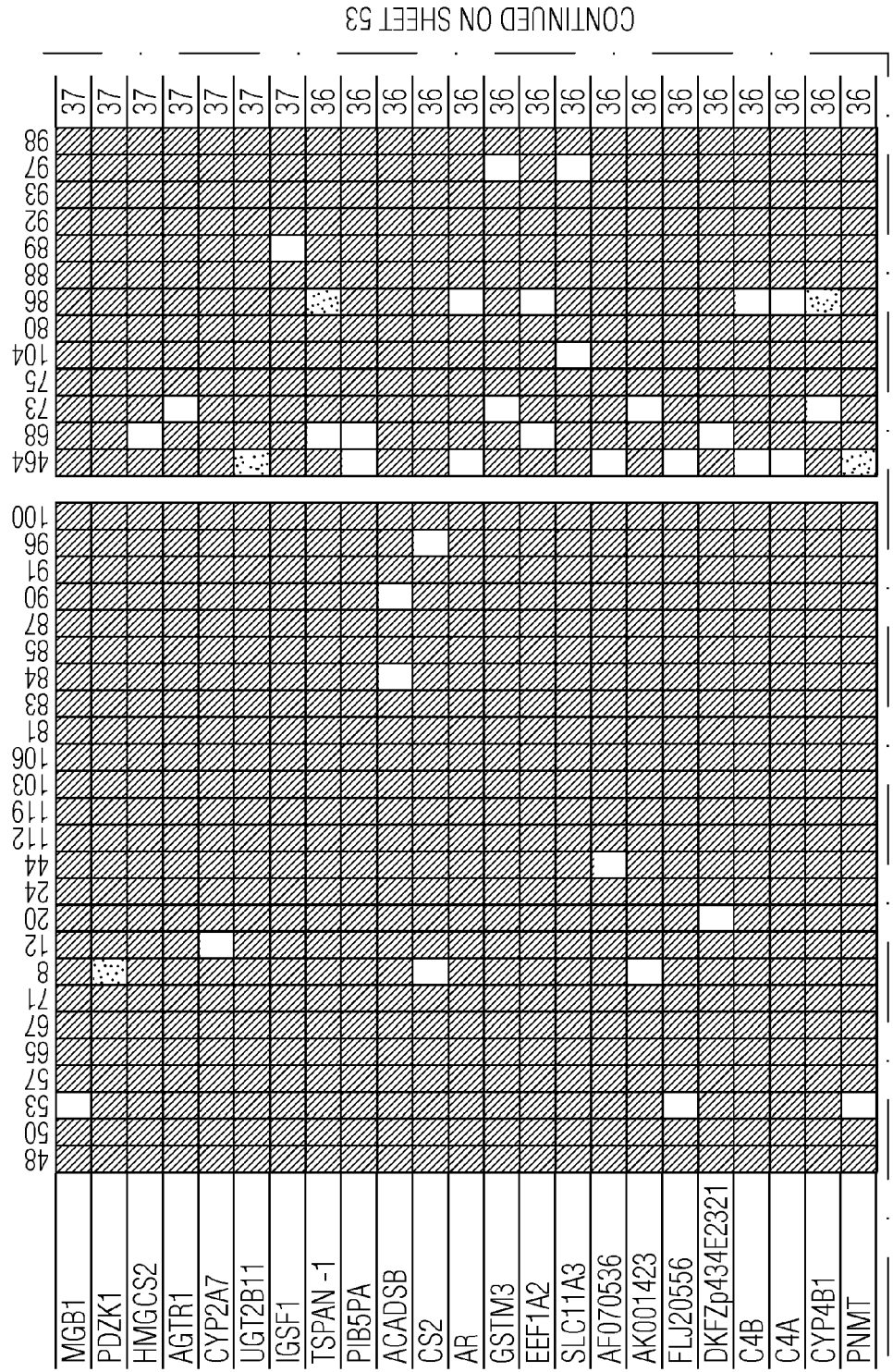
Figure 24D:
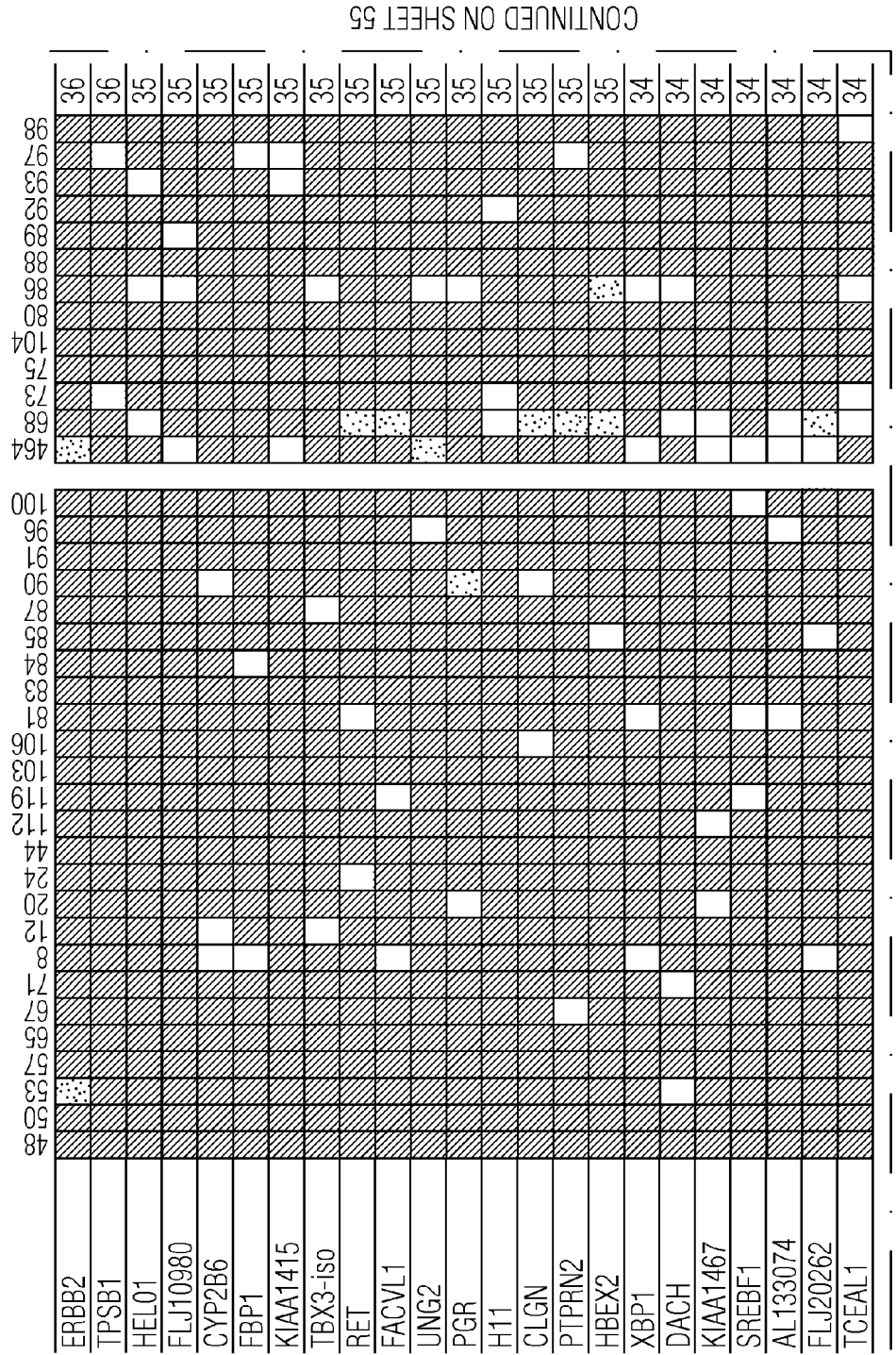
Figure 24E:
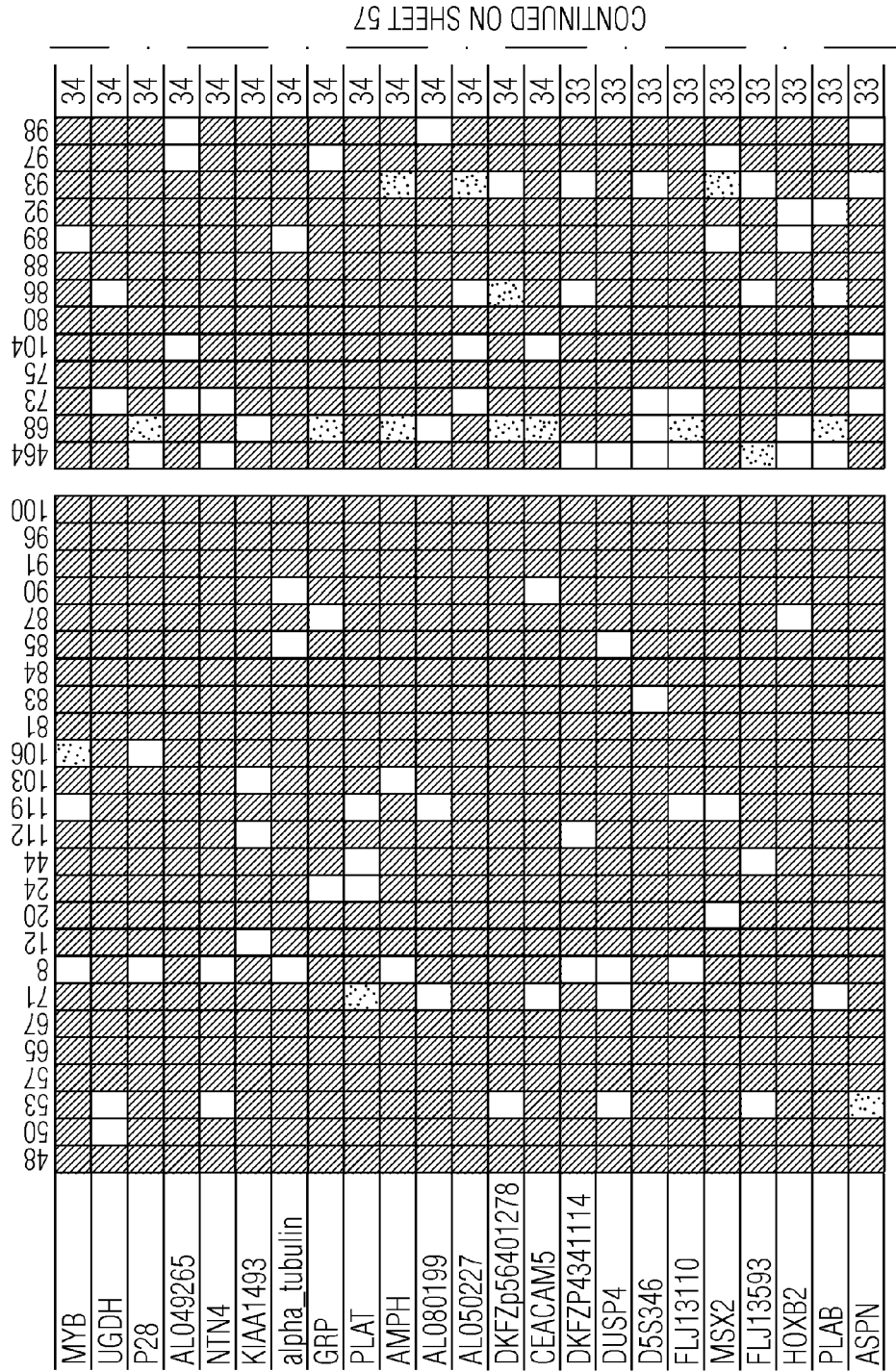
Figure 24F:
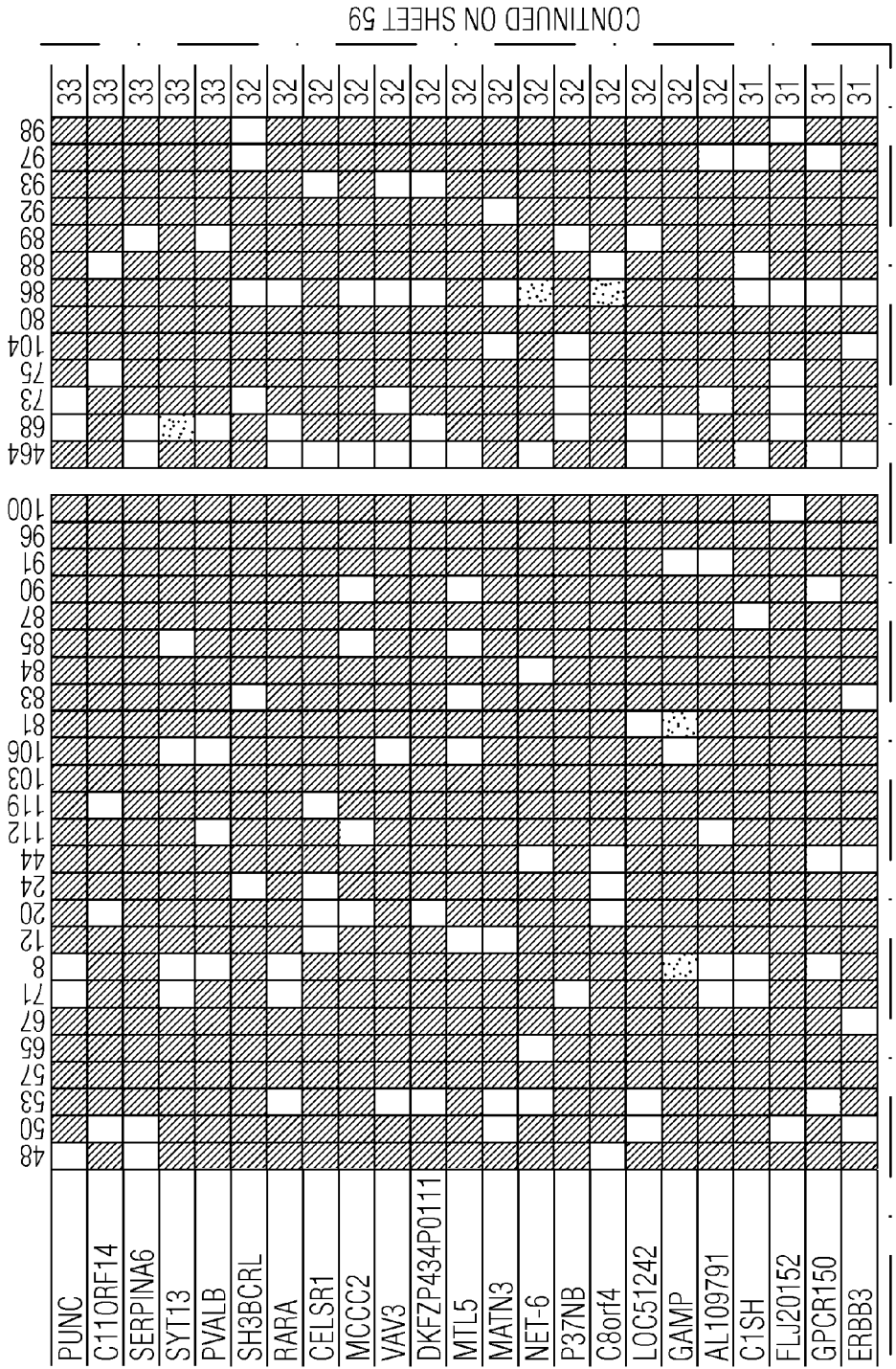
Figure 24G:
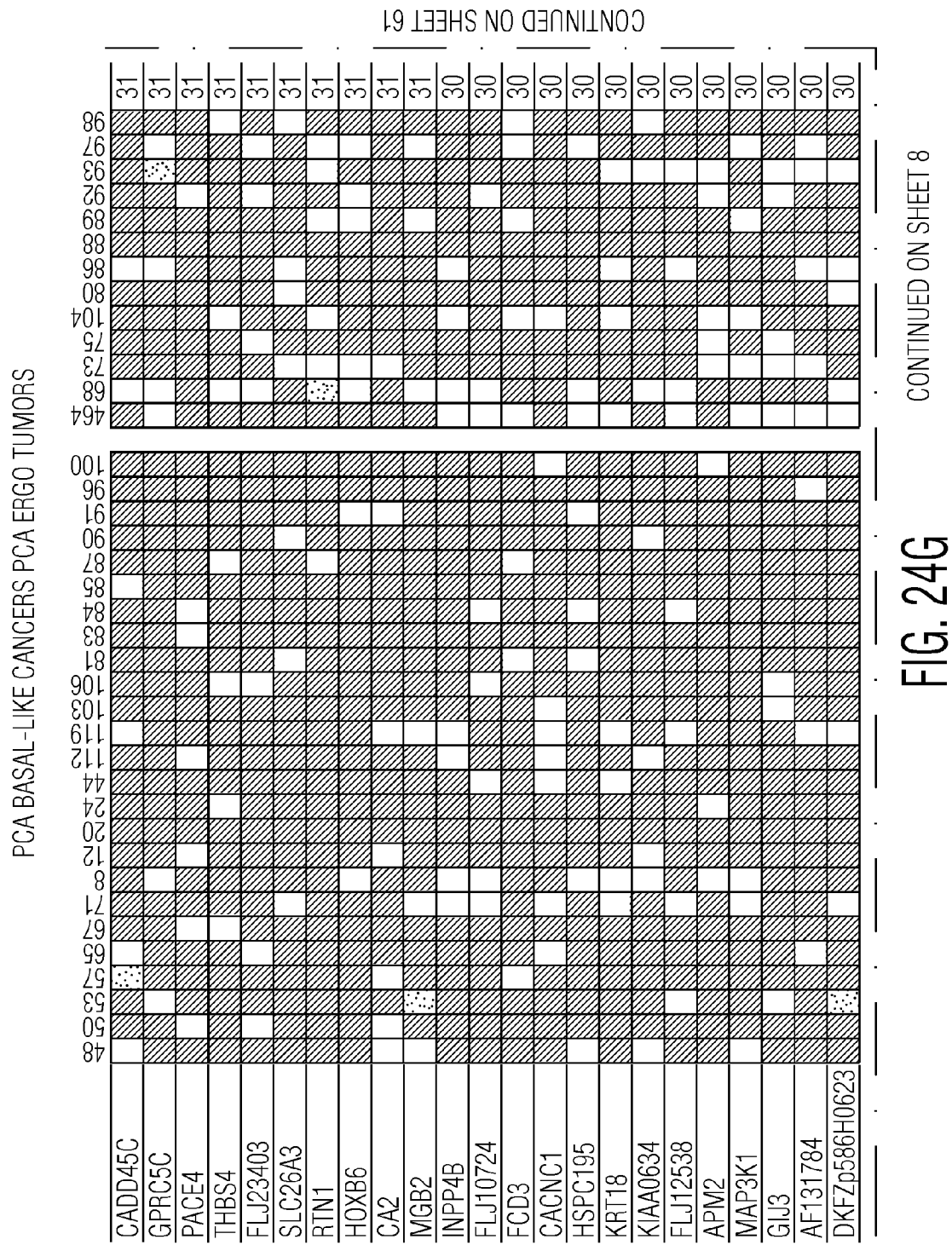
Figure 24H:
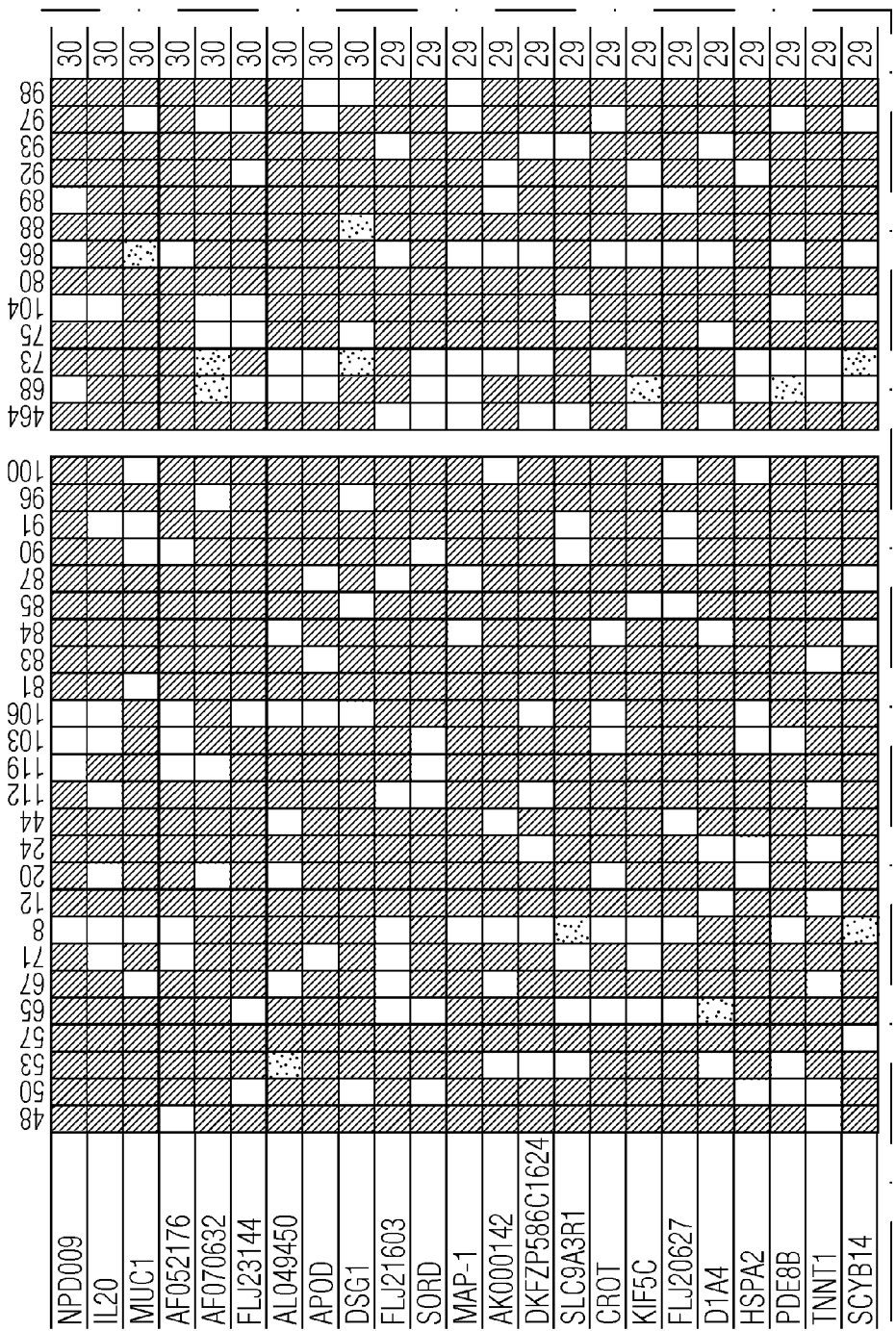
Figure 24I:
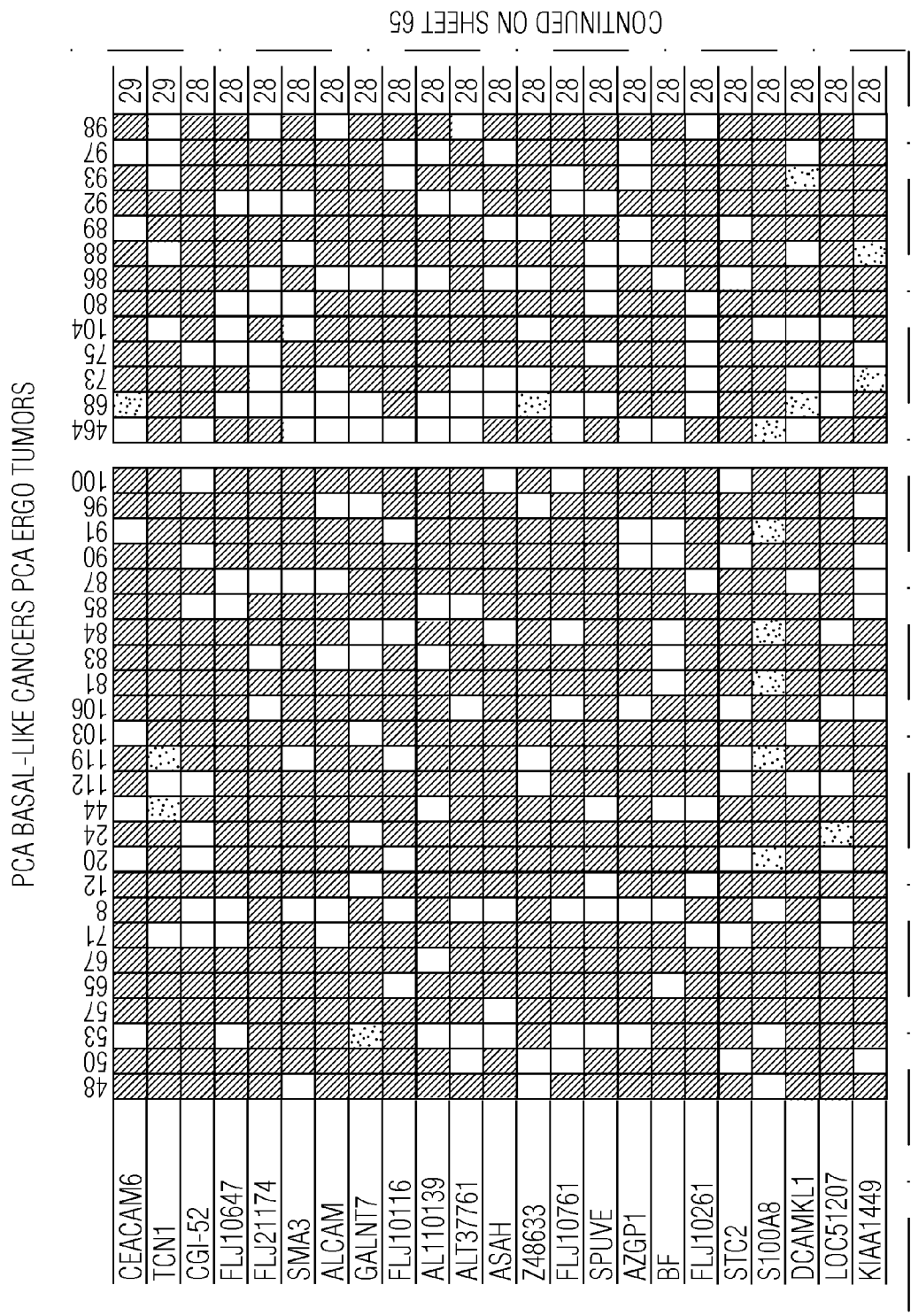
Figure 24J:
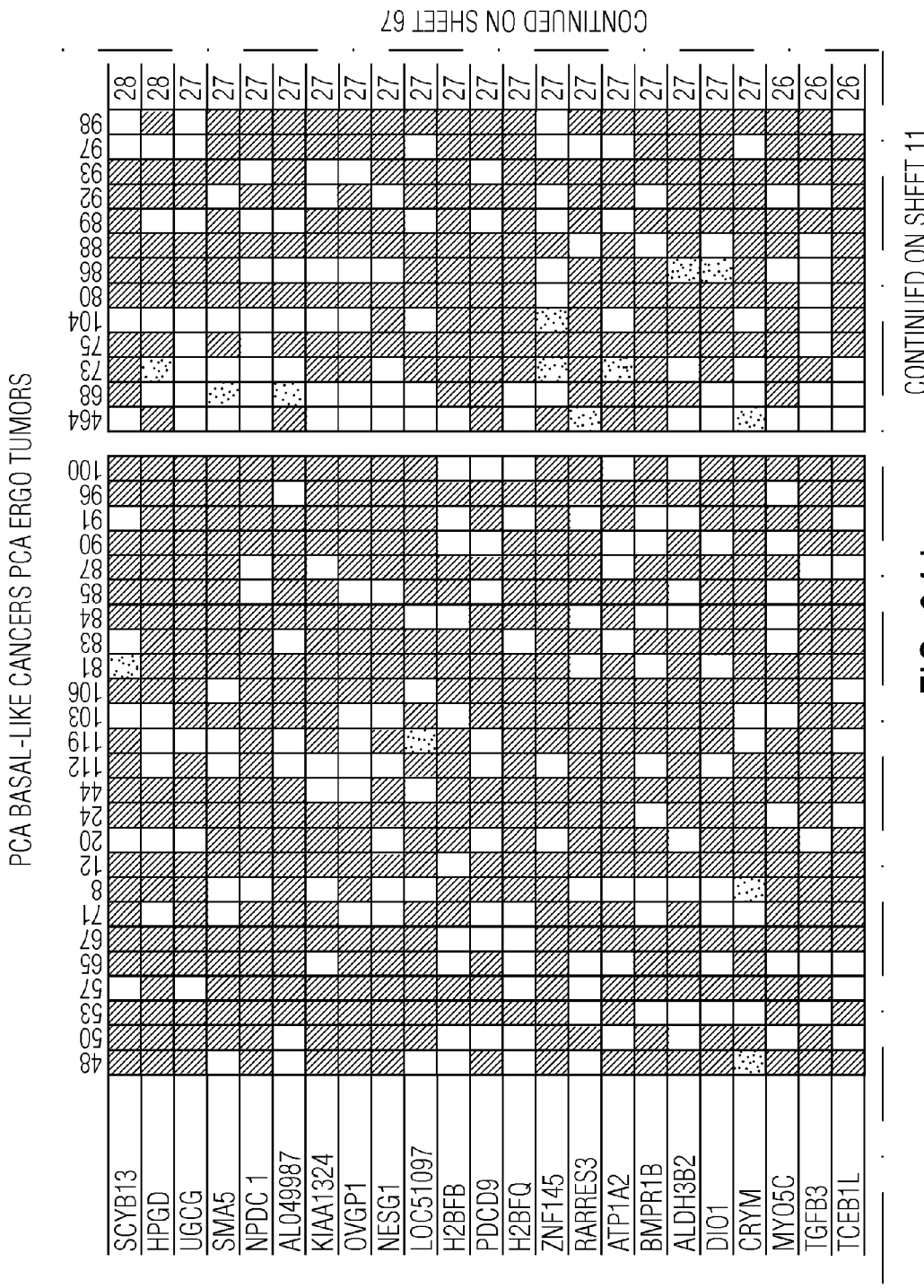
Figure 24K:
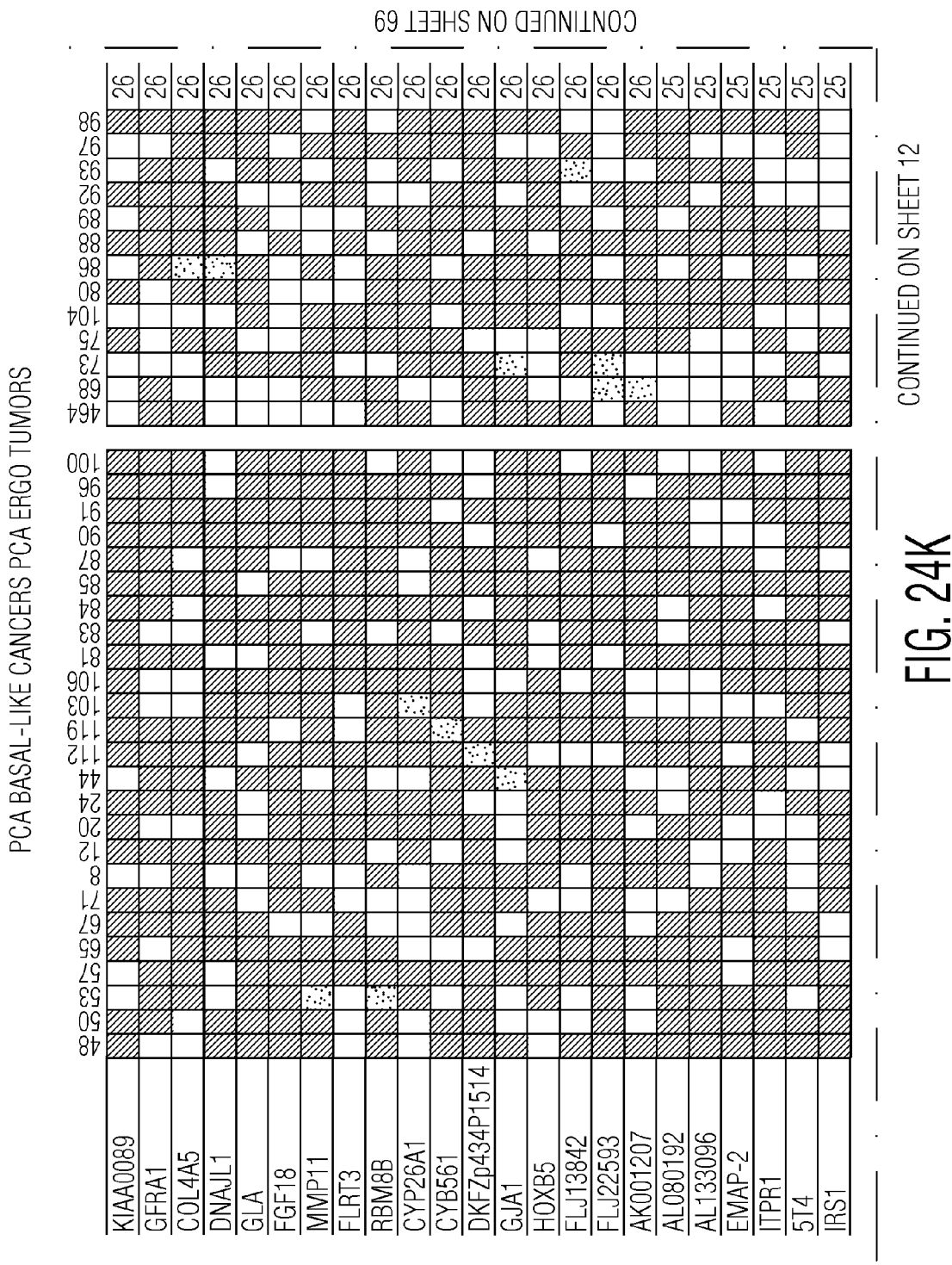
Figure 24L:
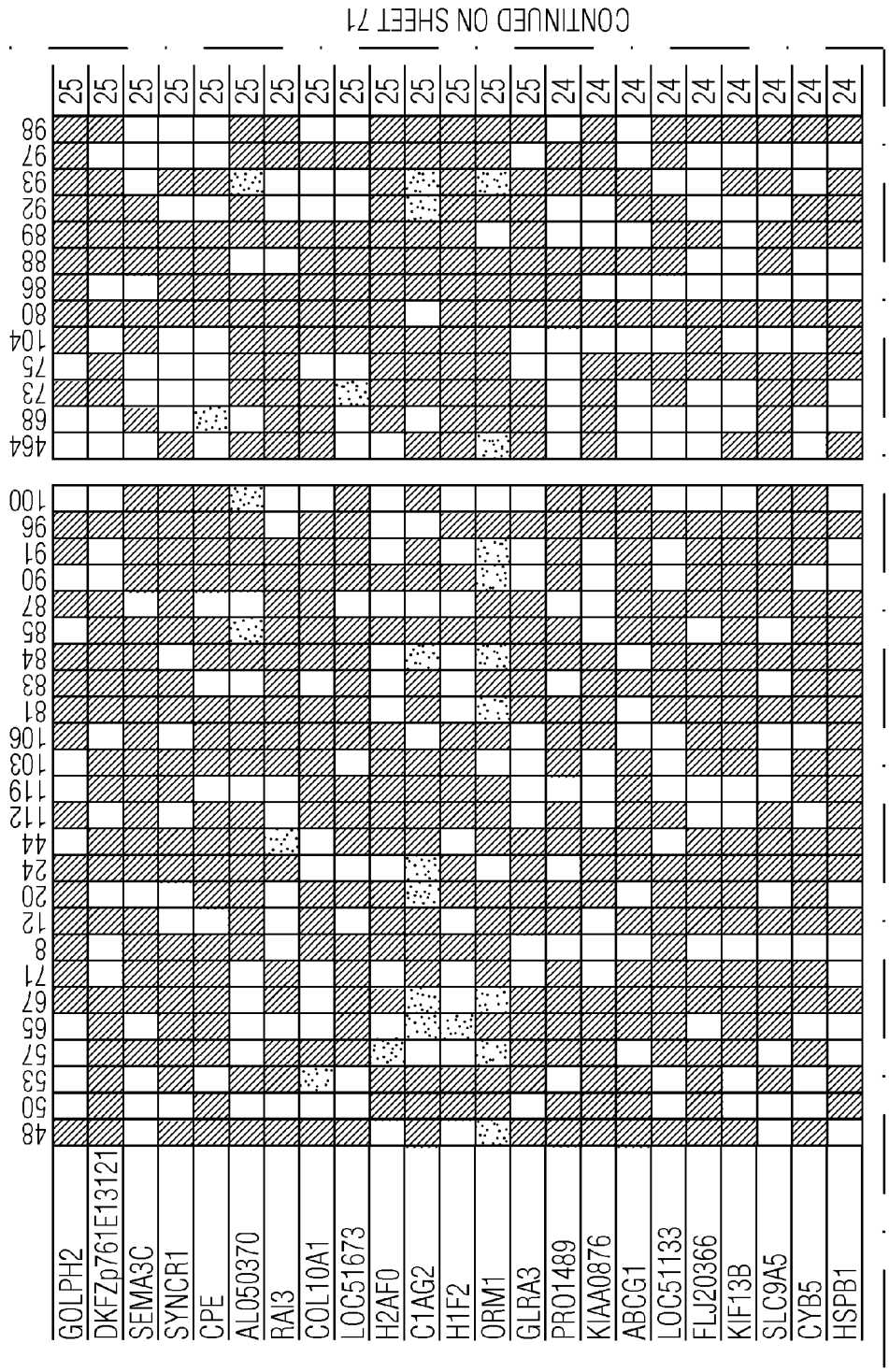
Figure 24M:
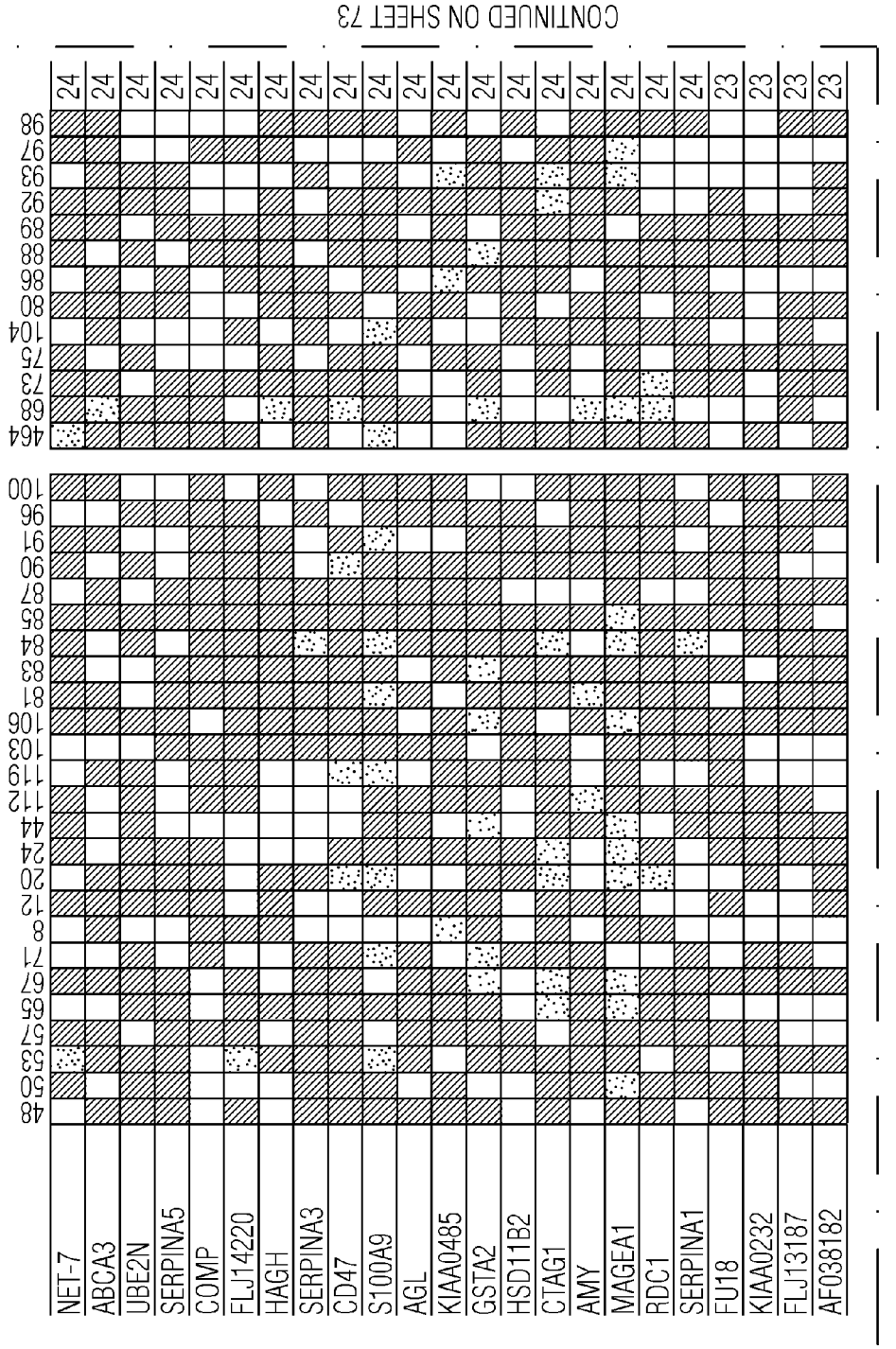
Figure 24N:
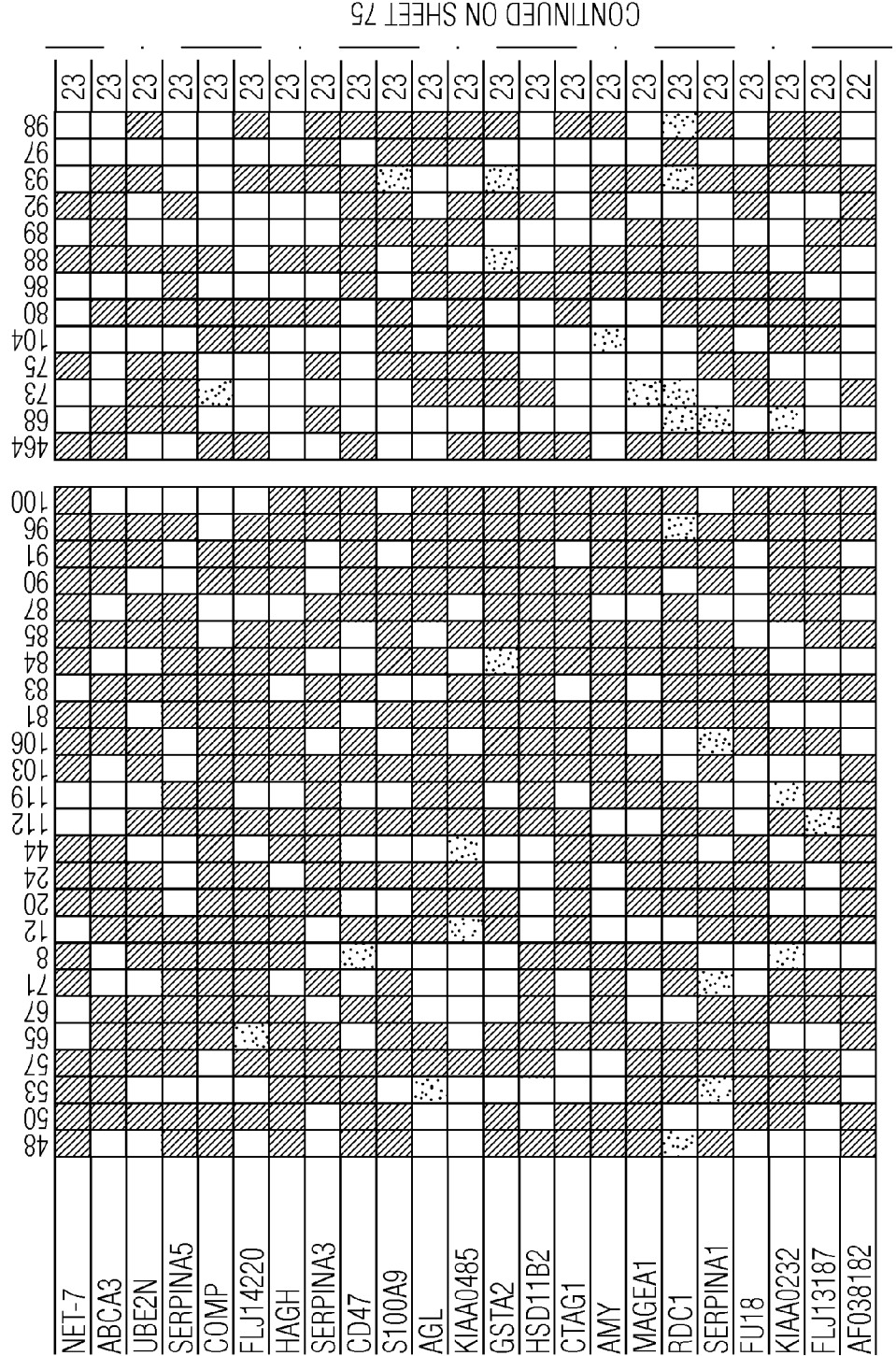
Figure 240:
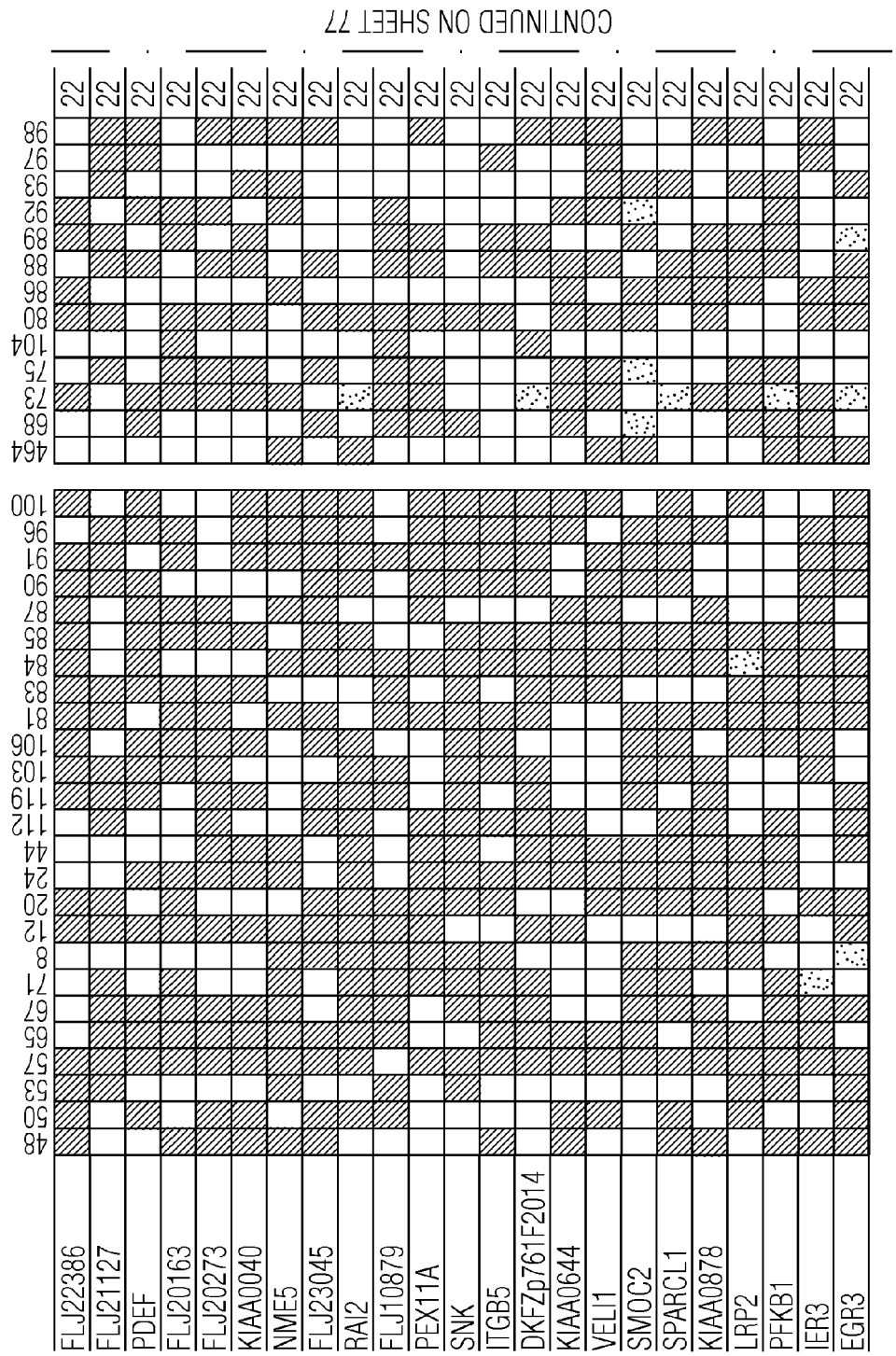
Figure 24P:
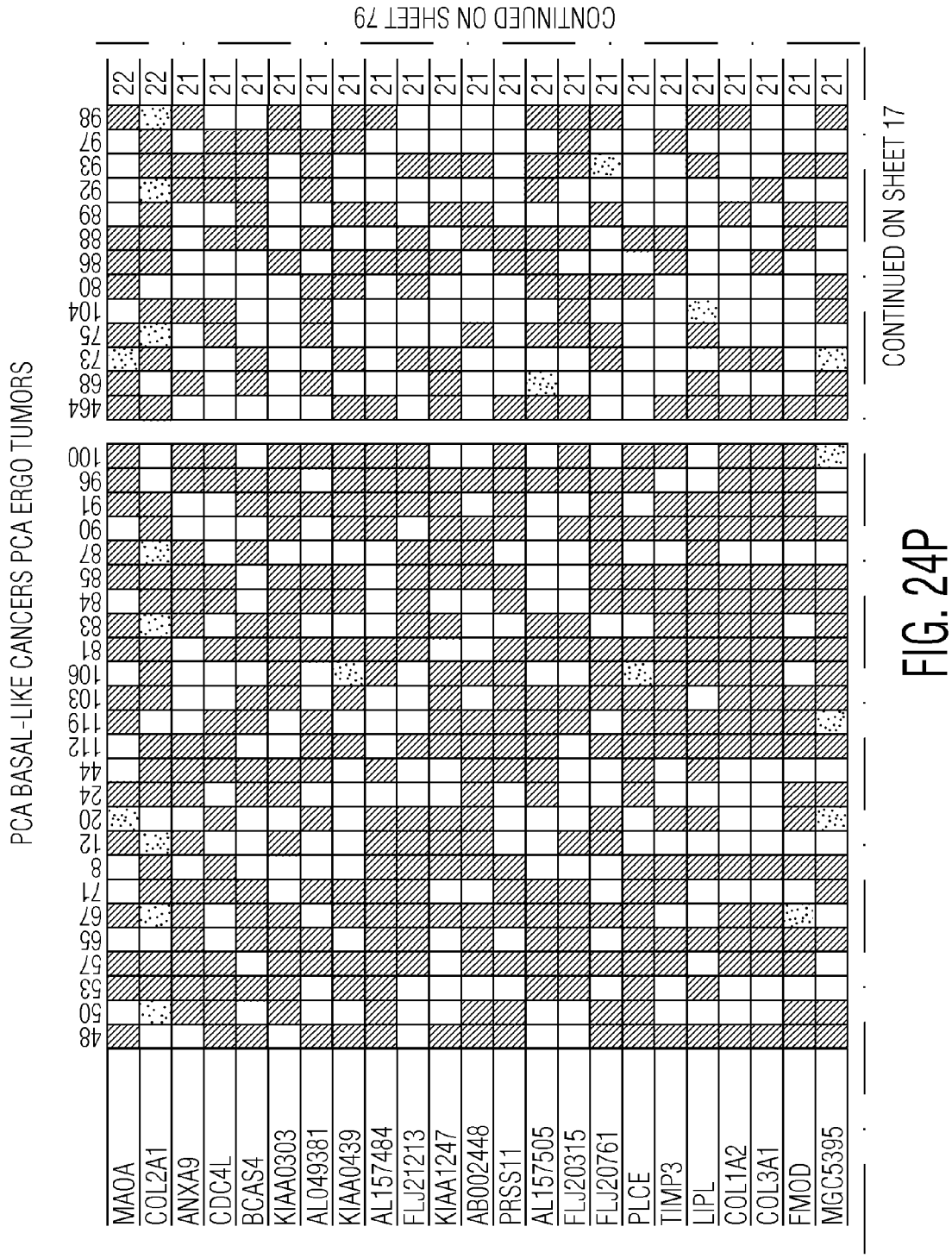
Figure 24Q:
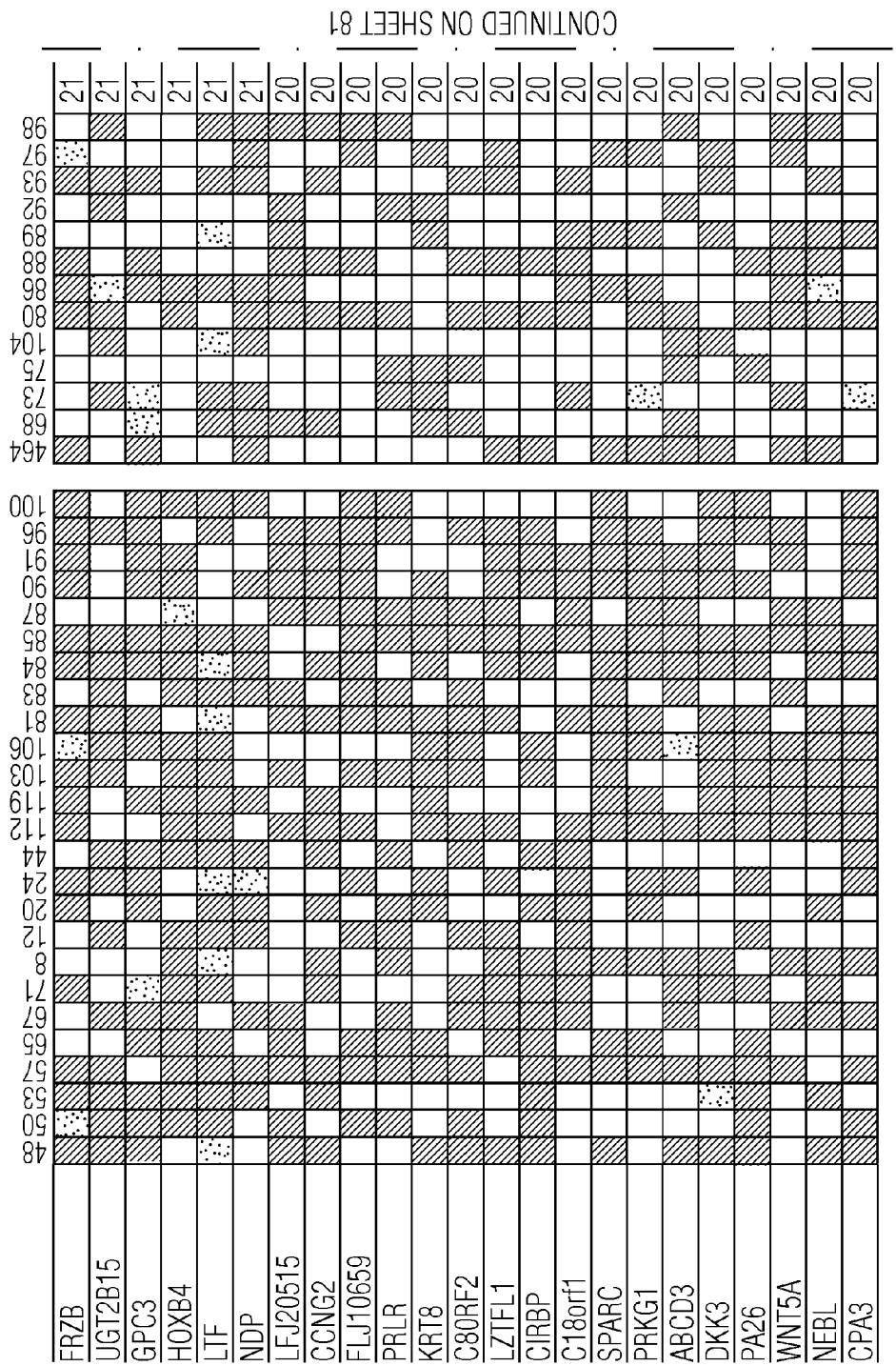
Figure 24R:
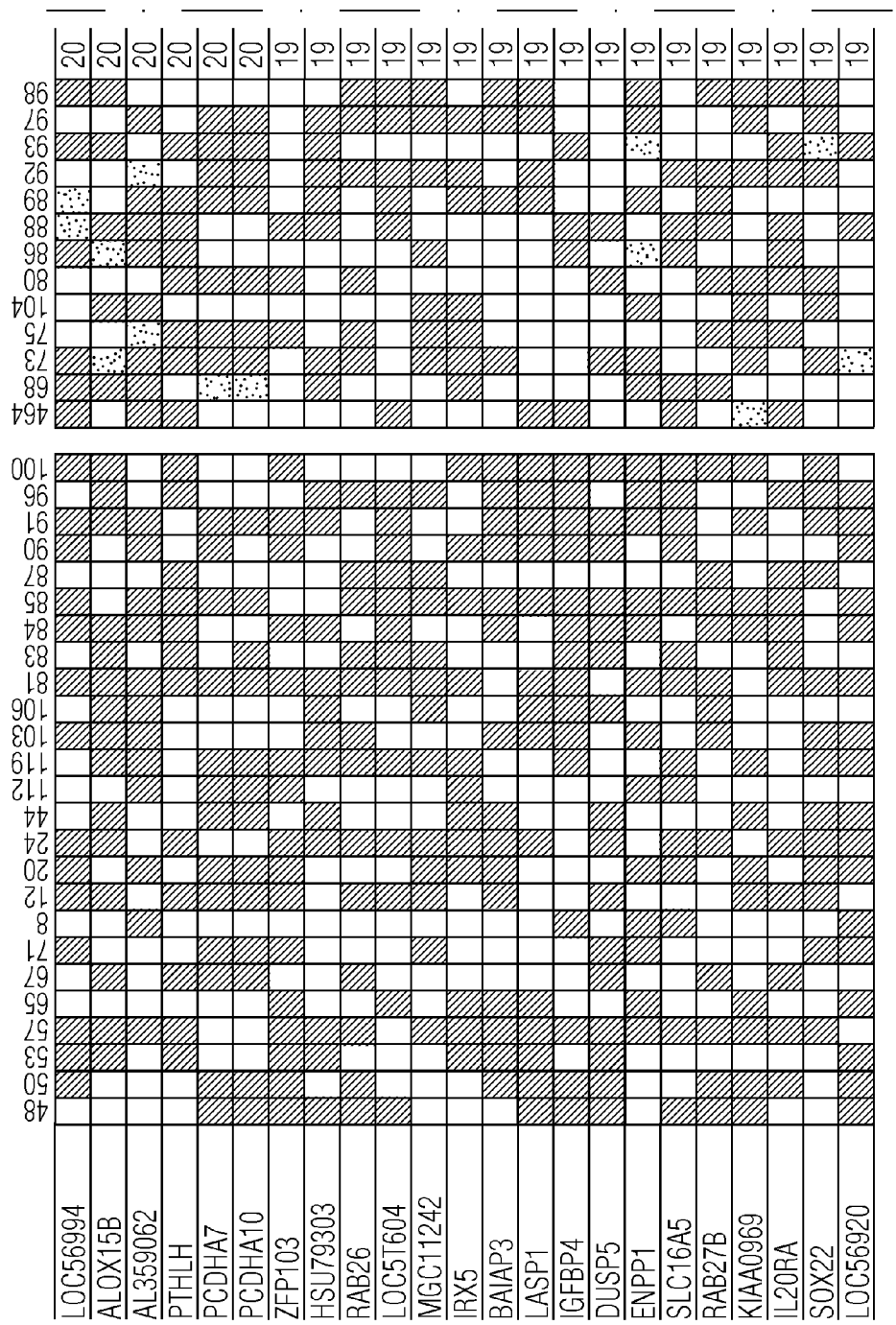
Figure 24S:
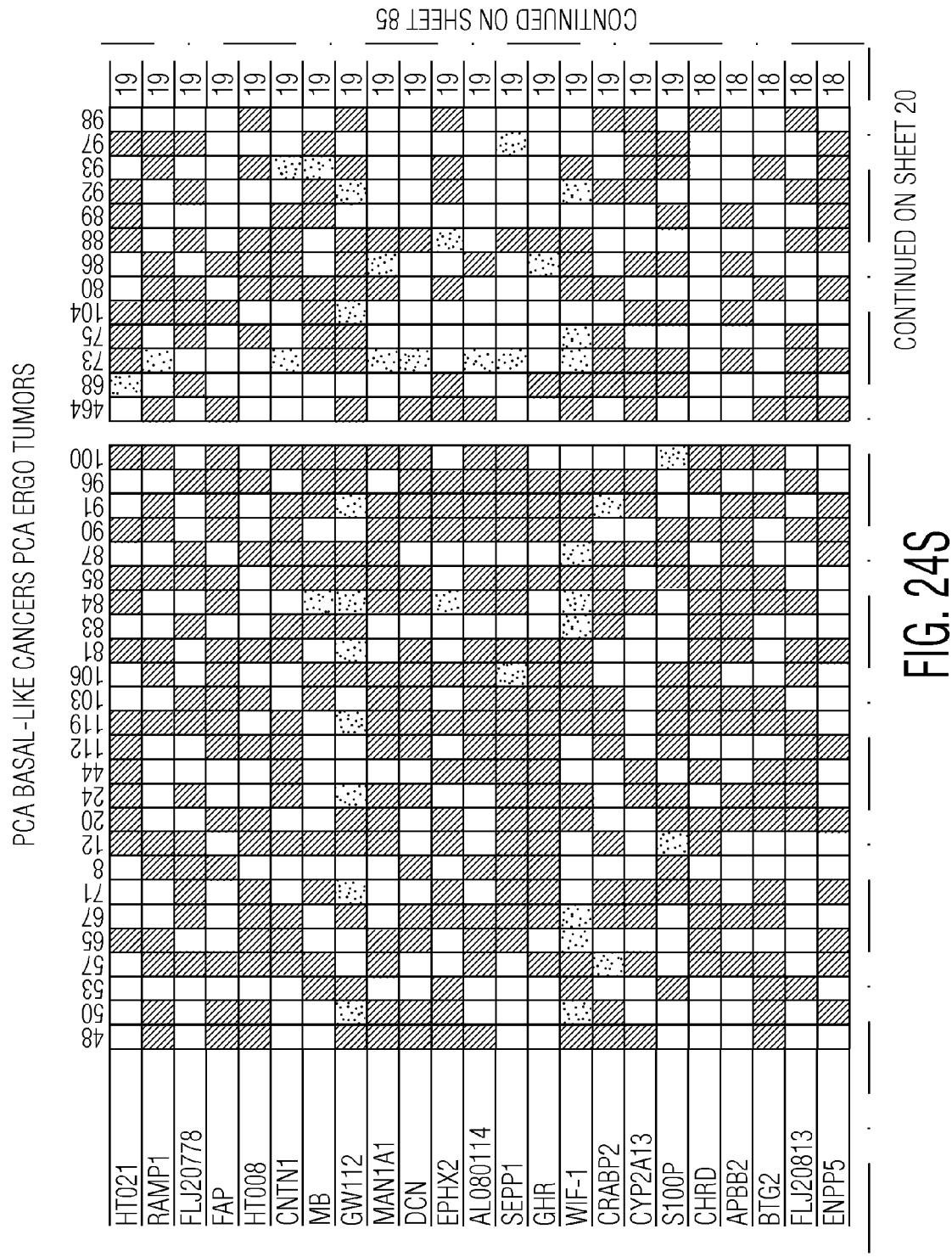
Figure 24T:
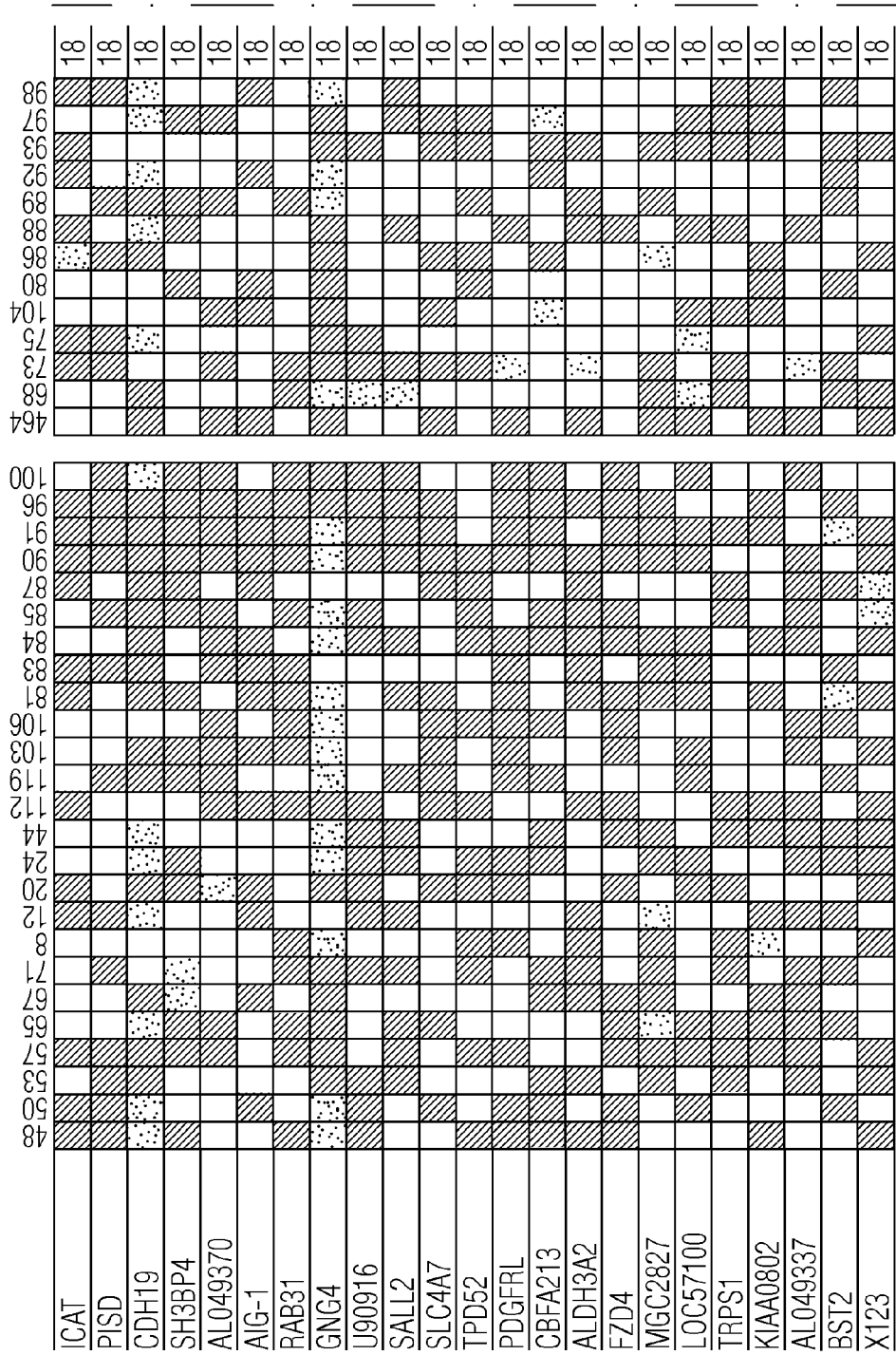
Figure 24U:
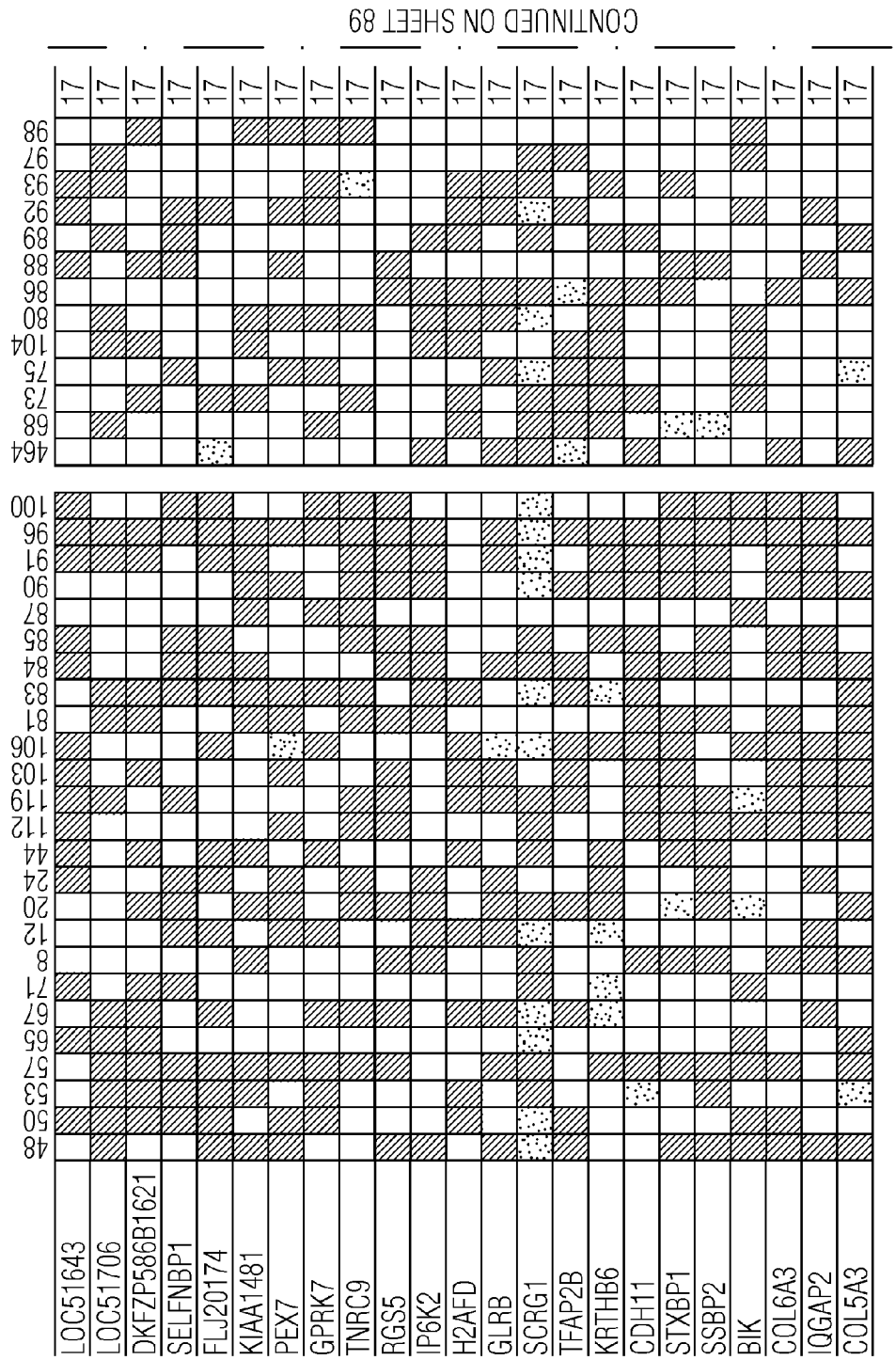
Figure 24V:
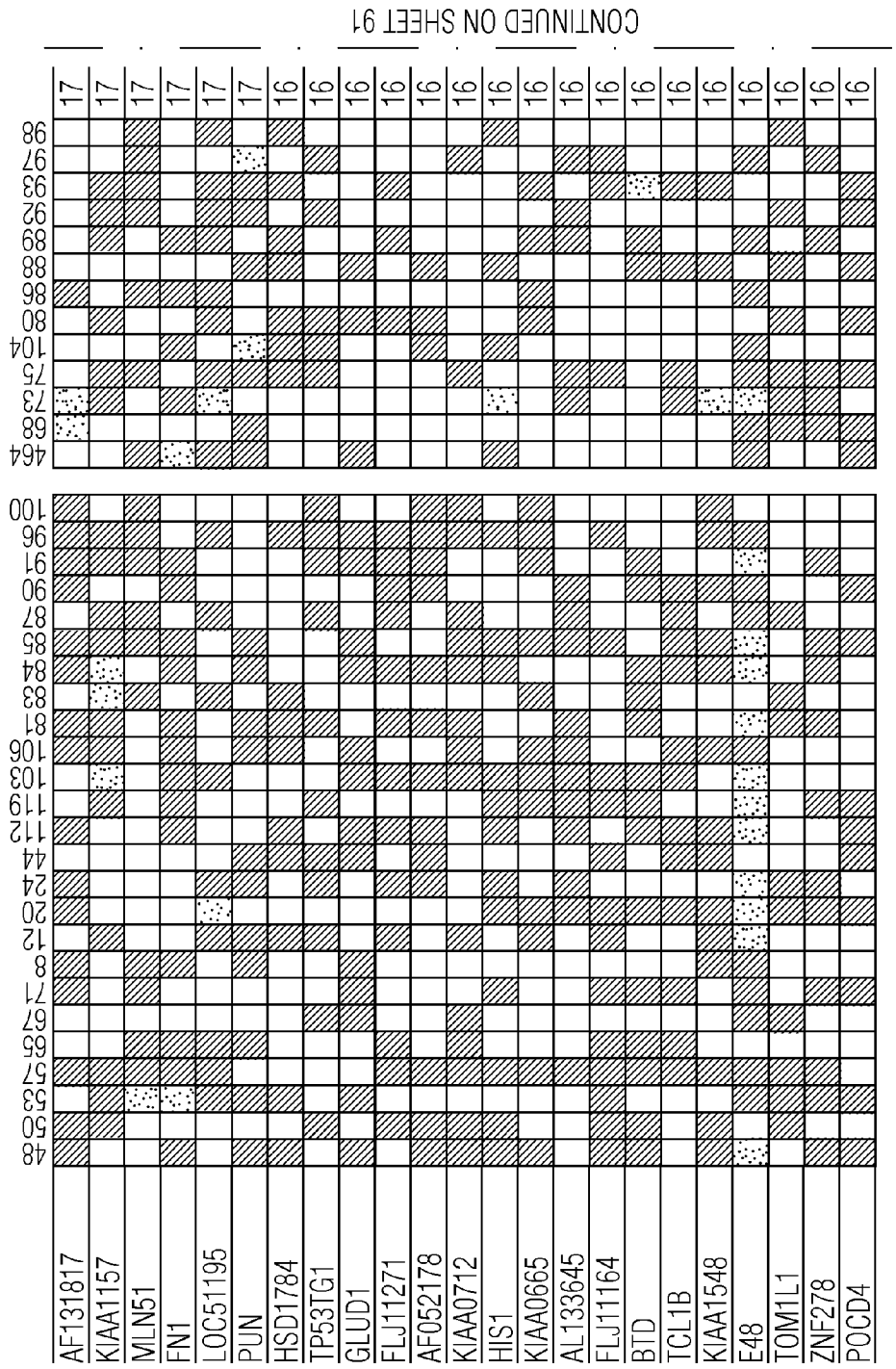
Figure 24W:
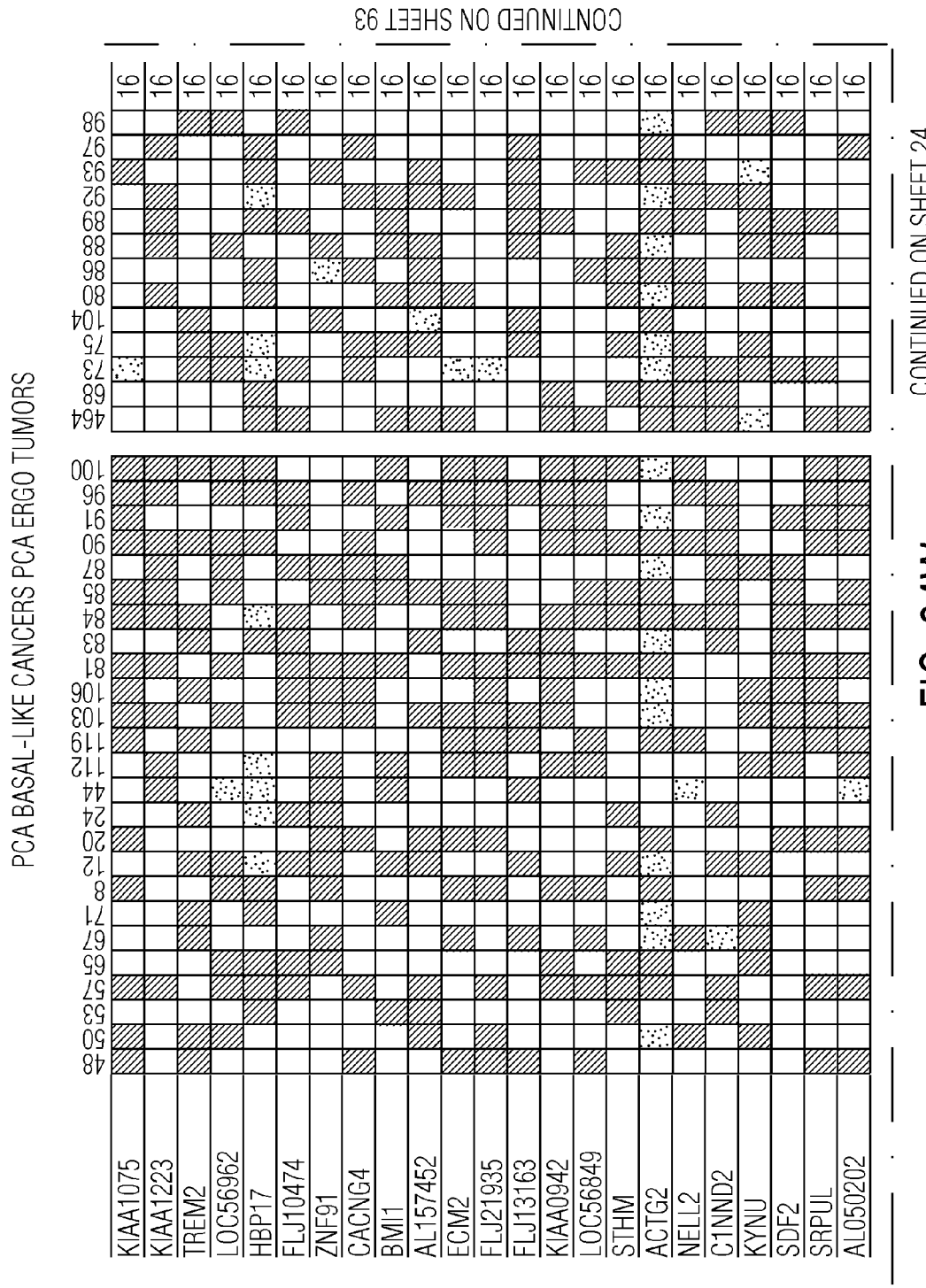
Figure 24X:
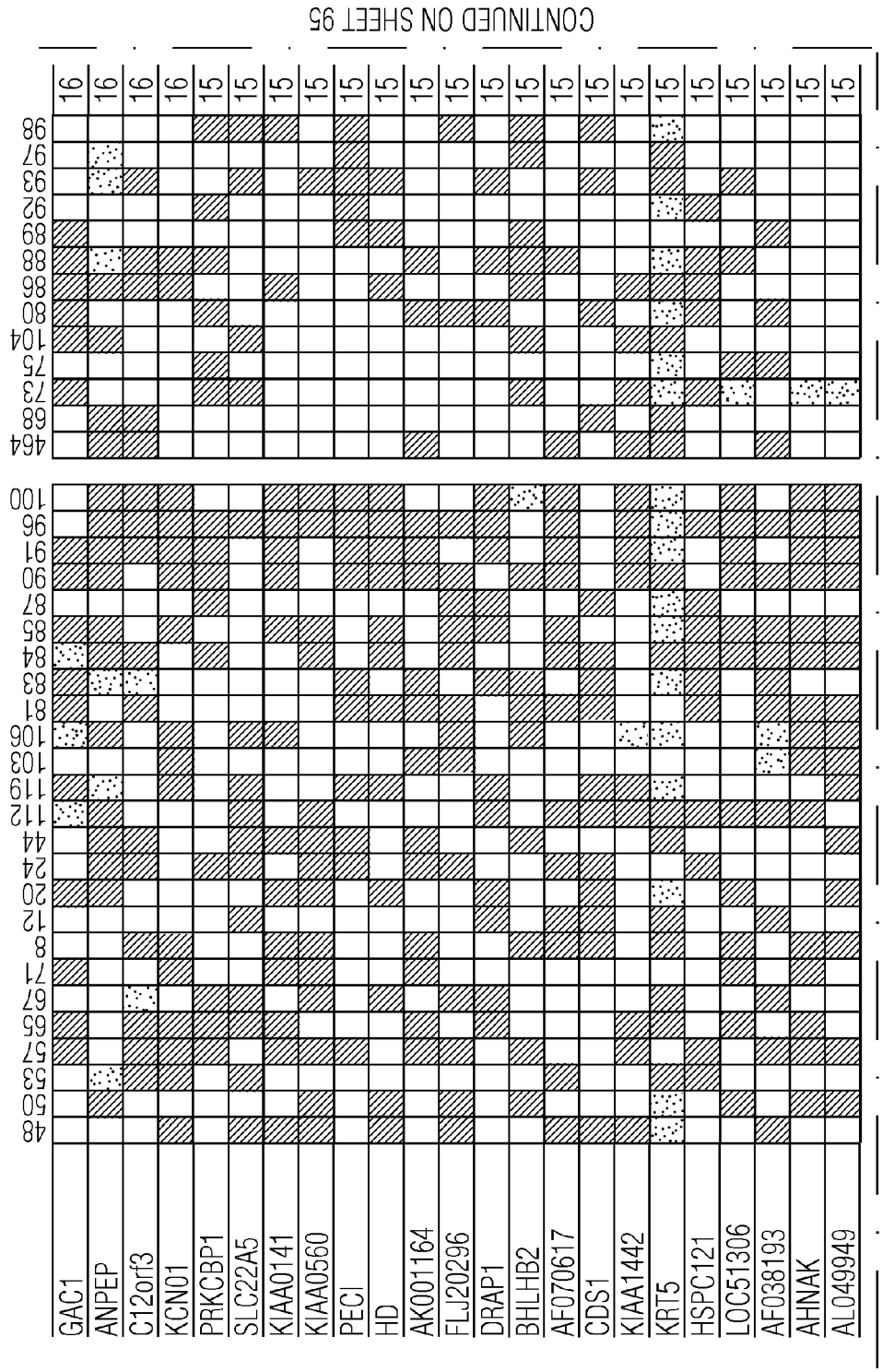
Figure 24Y:
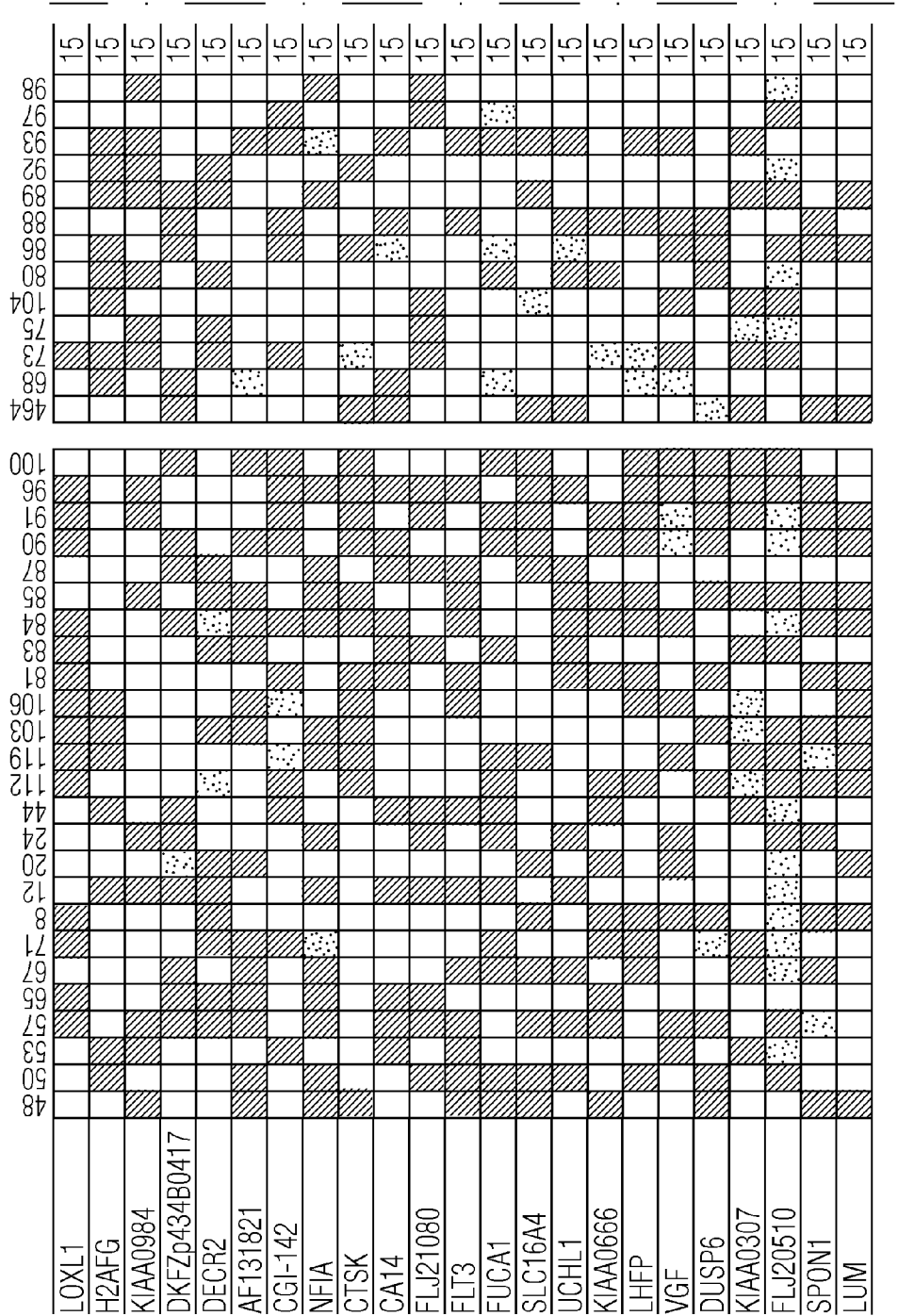
Figure 24Z:
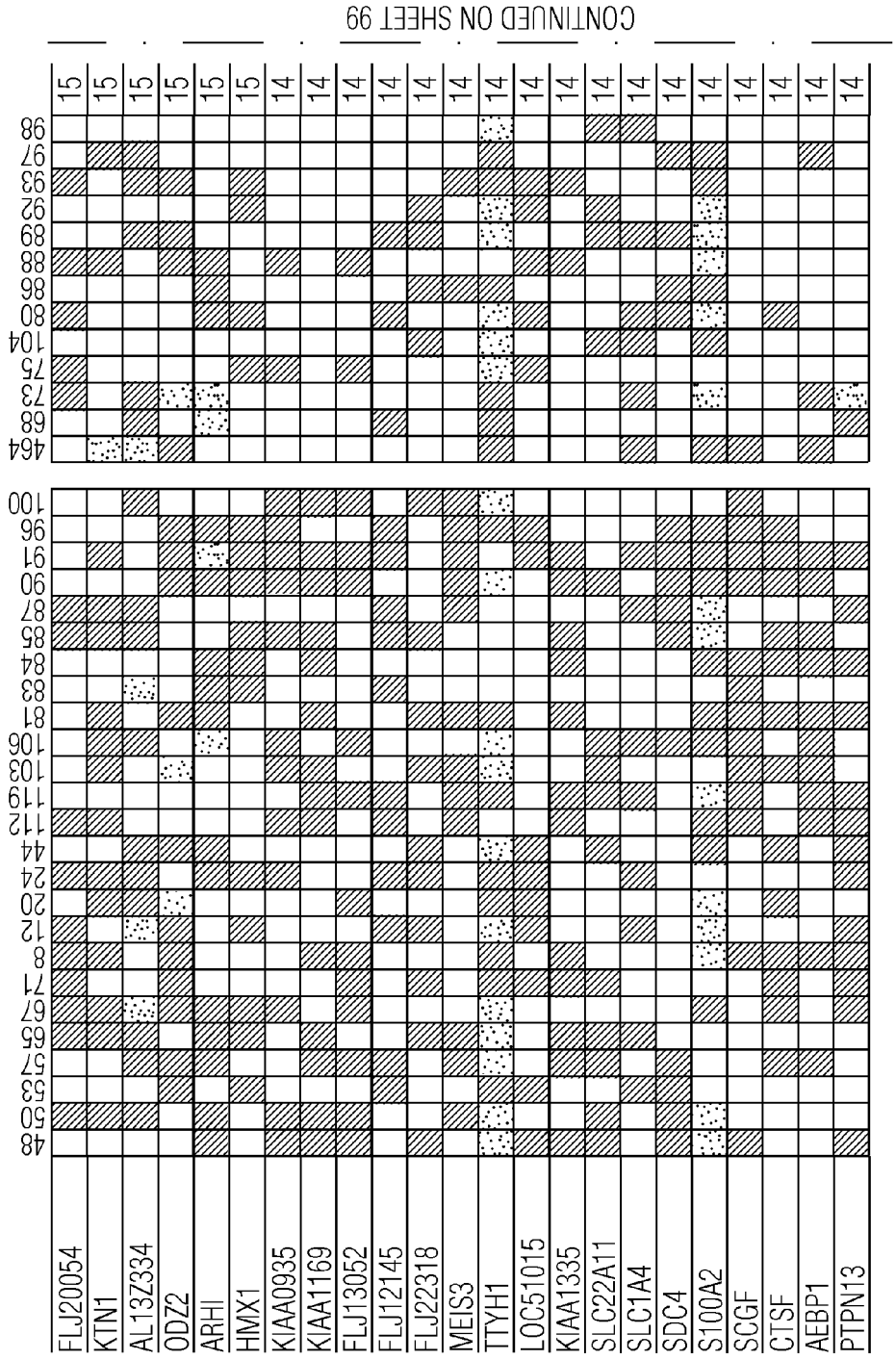
Figure 24A:
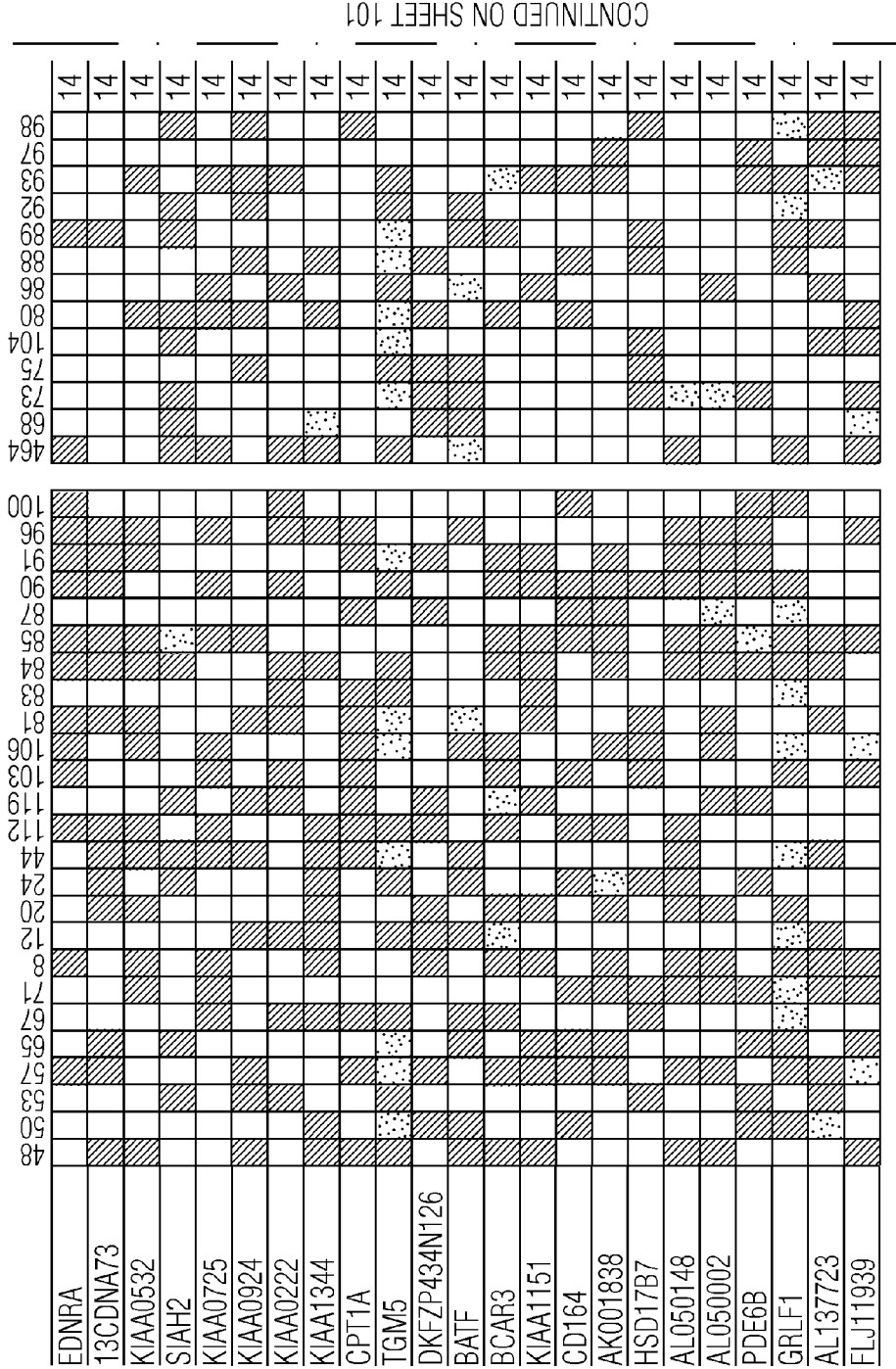
Figure 24B:
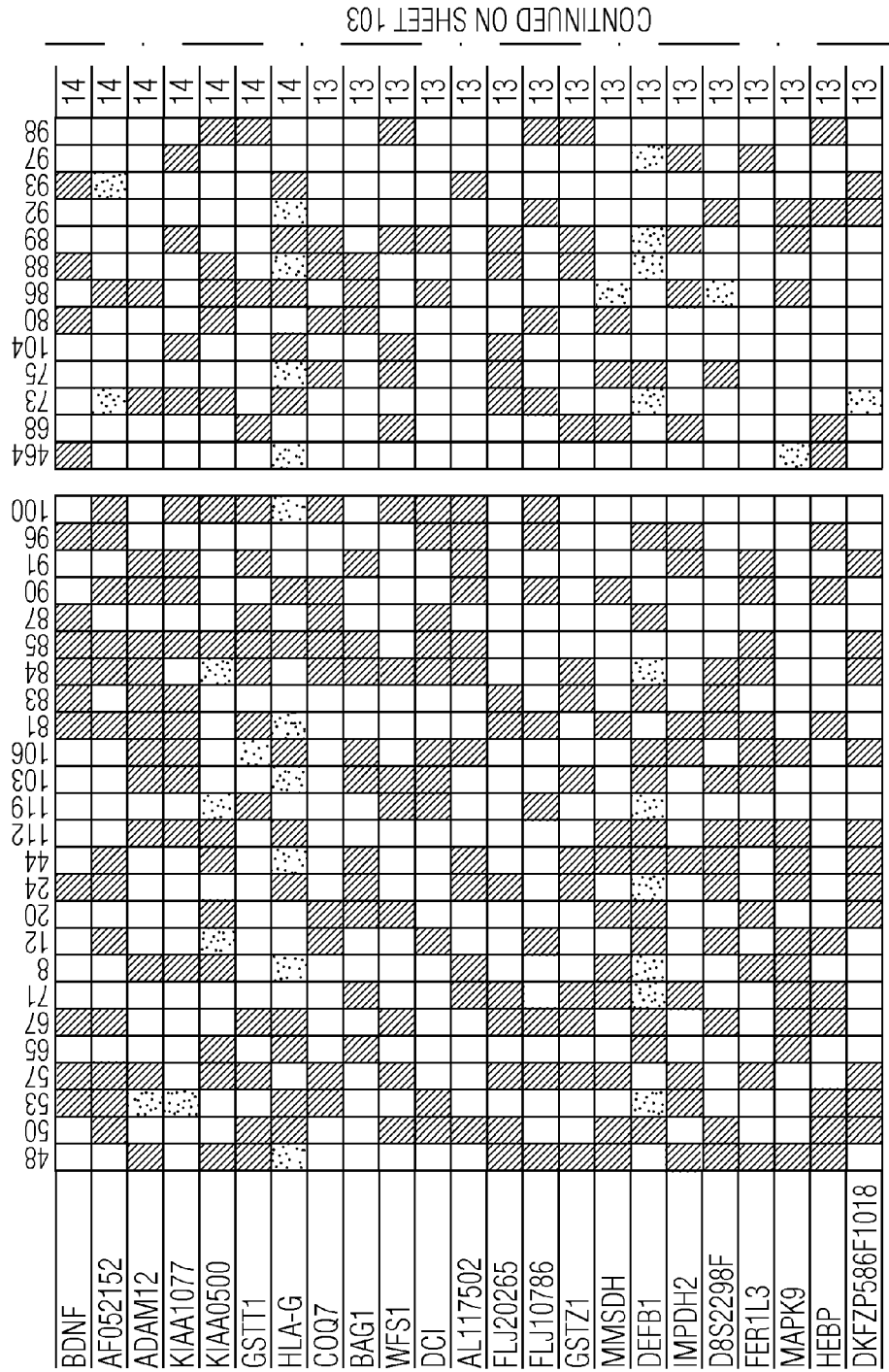
Figure 24C:
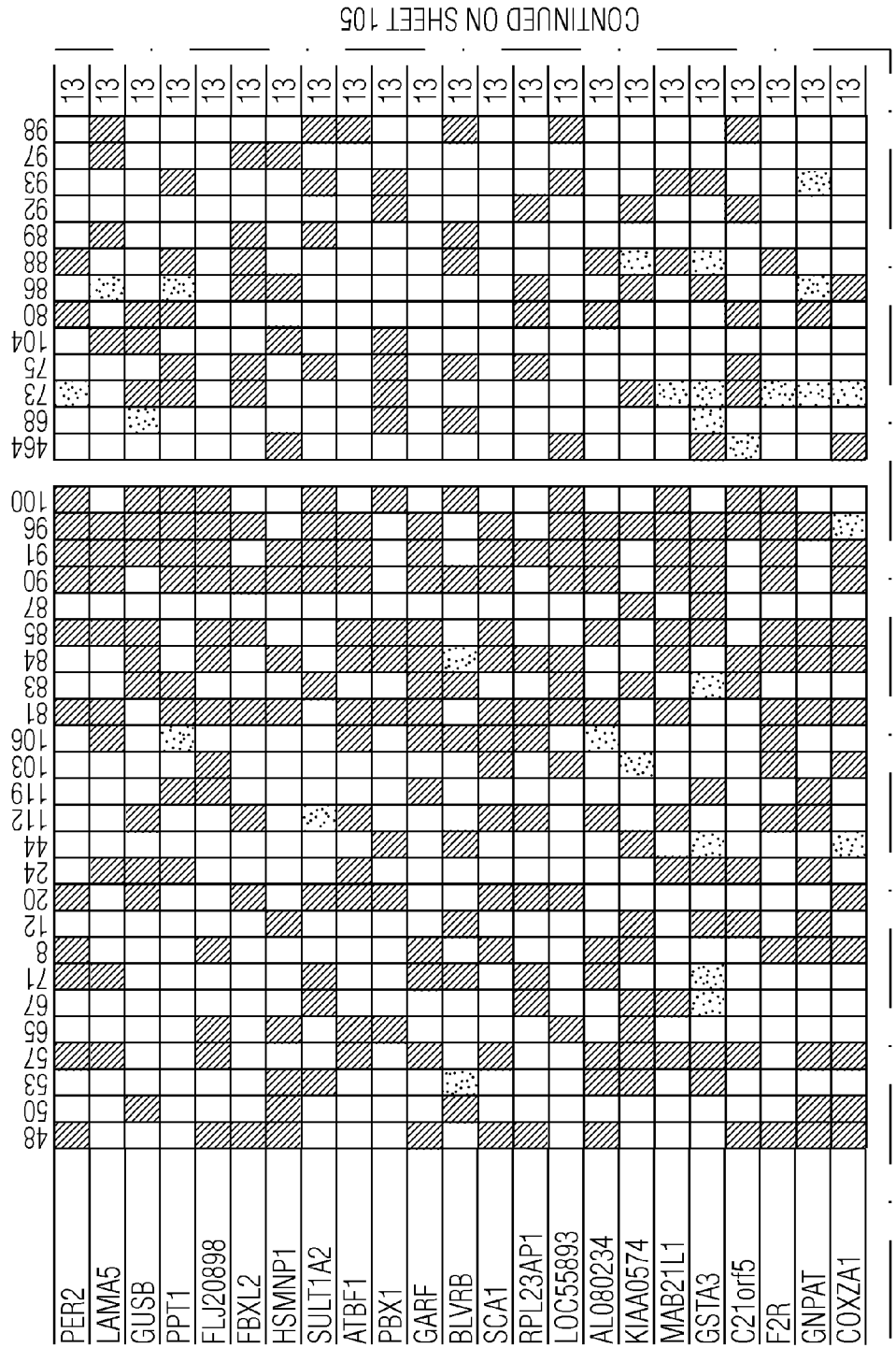
Figure 24D:
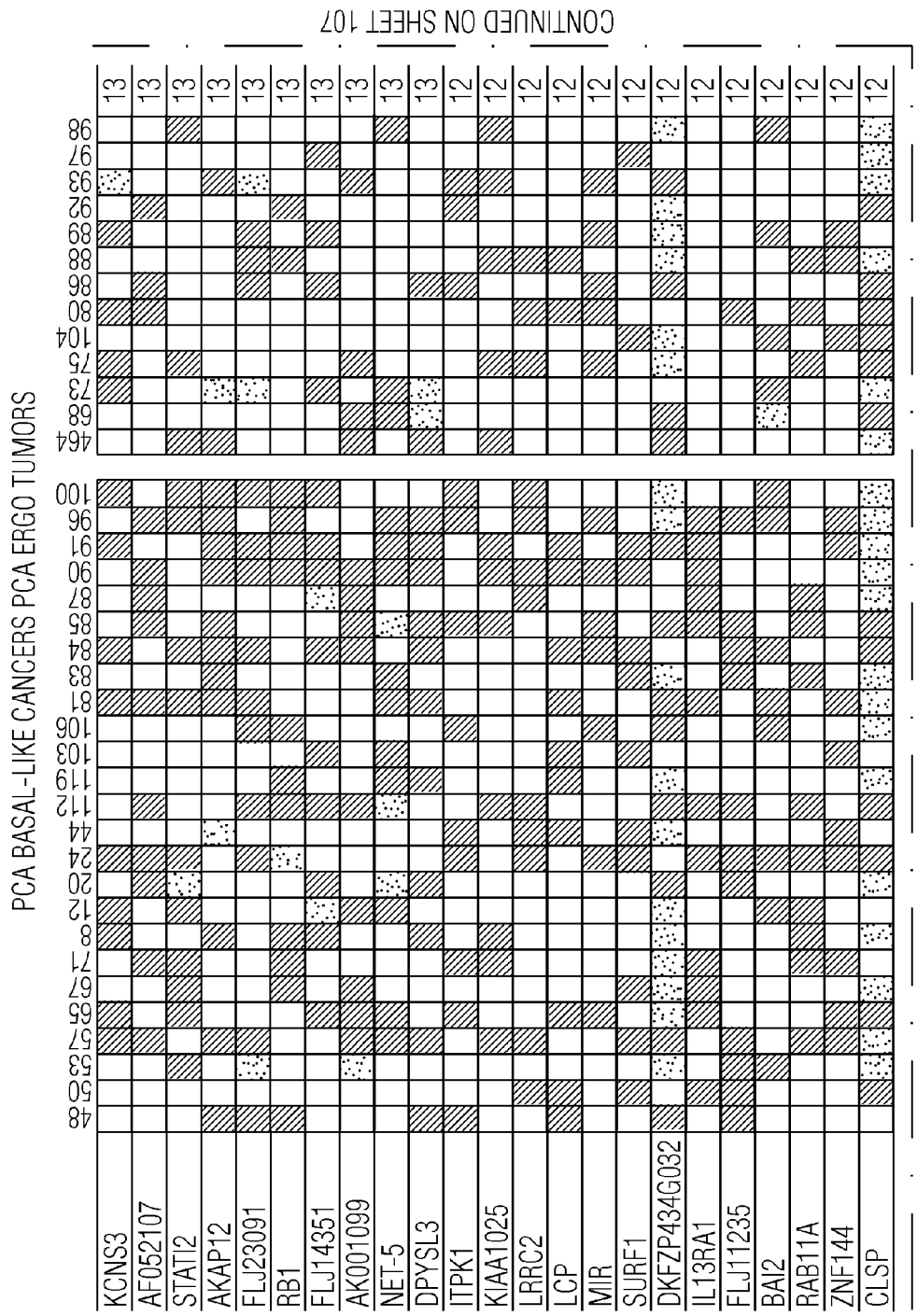
Figure 24E:
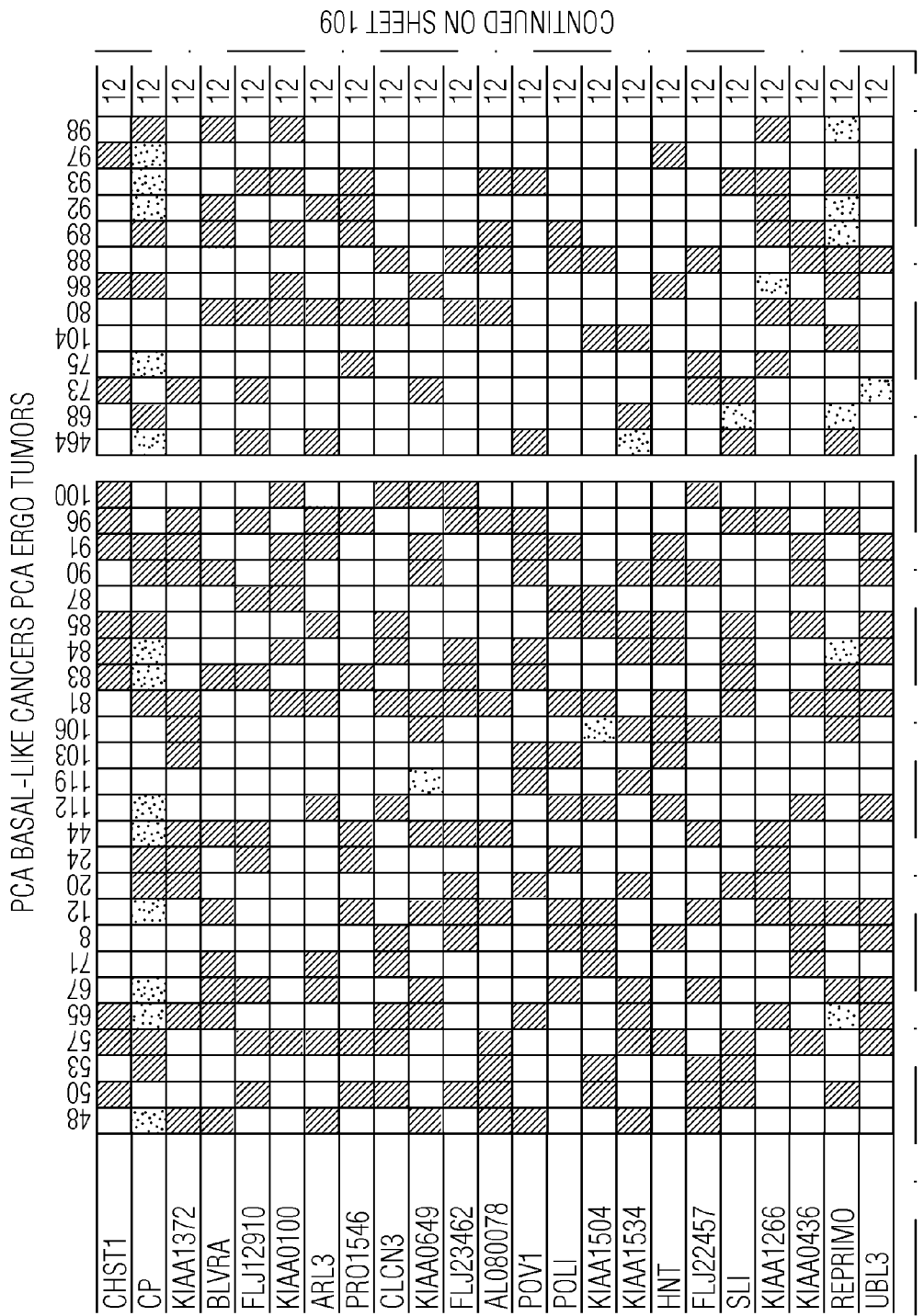
Figure 24F:
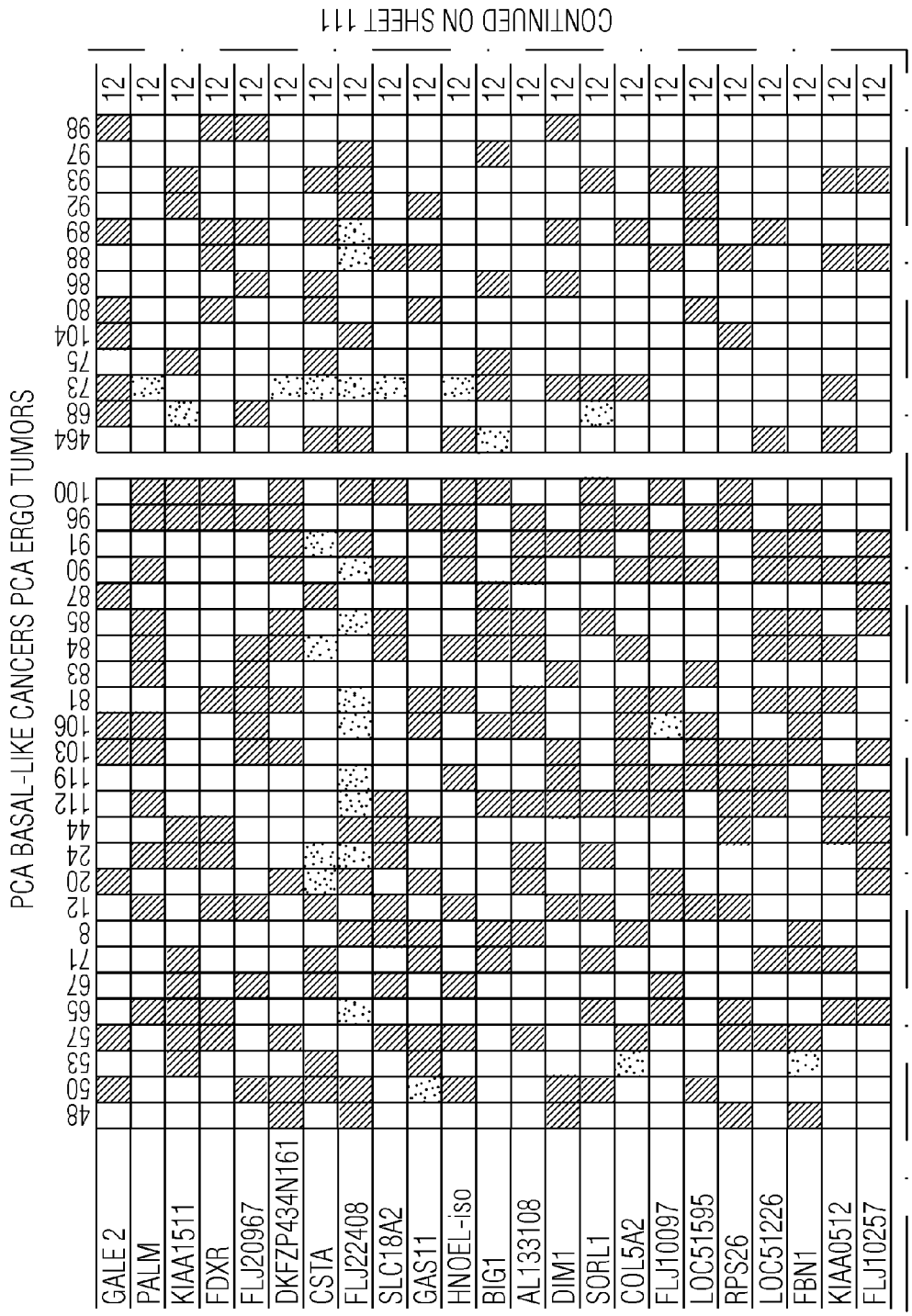
Figure 24G:
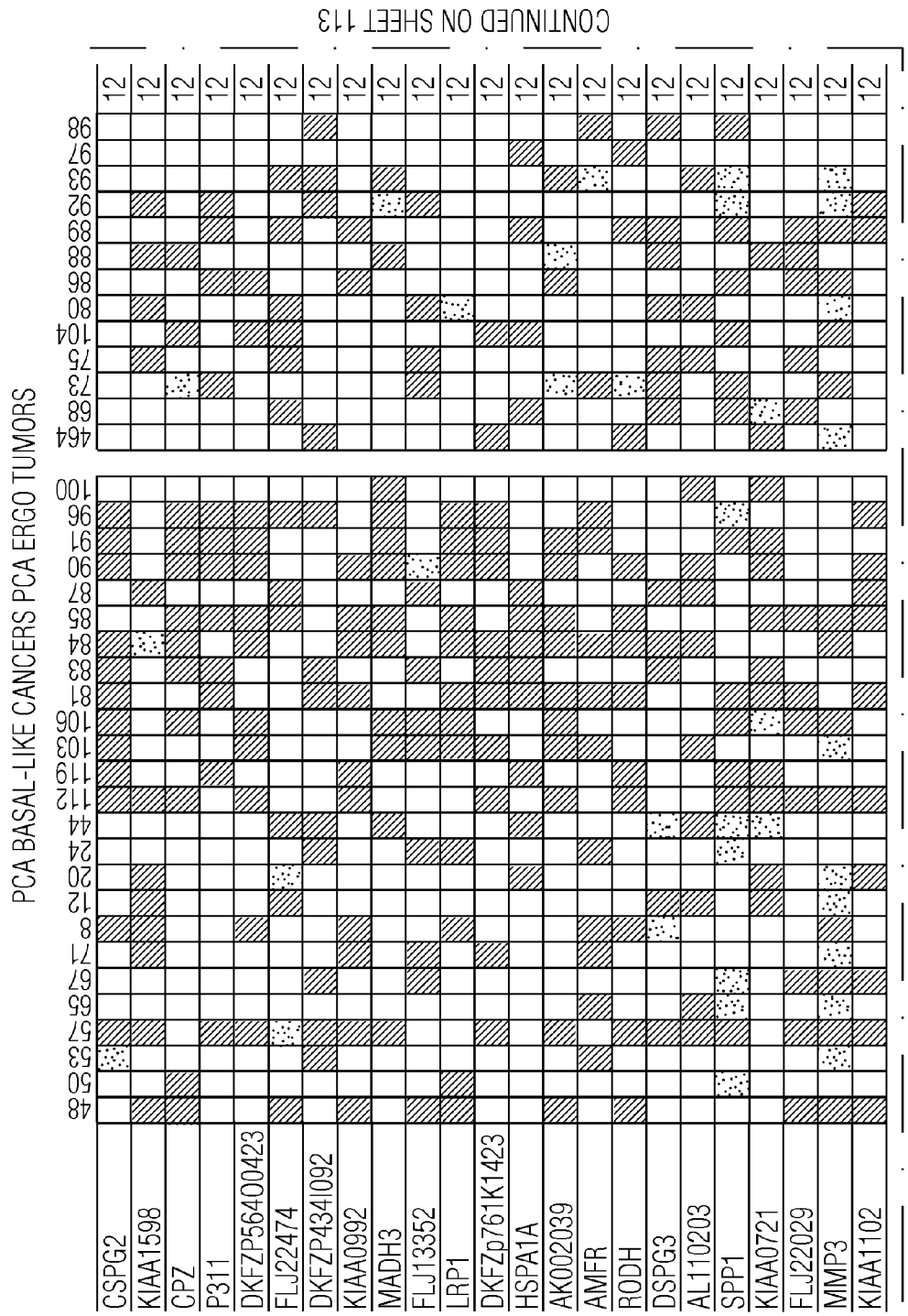
Figure 24H:
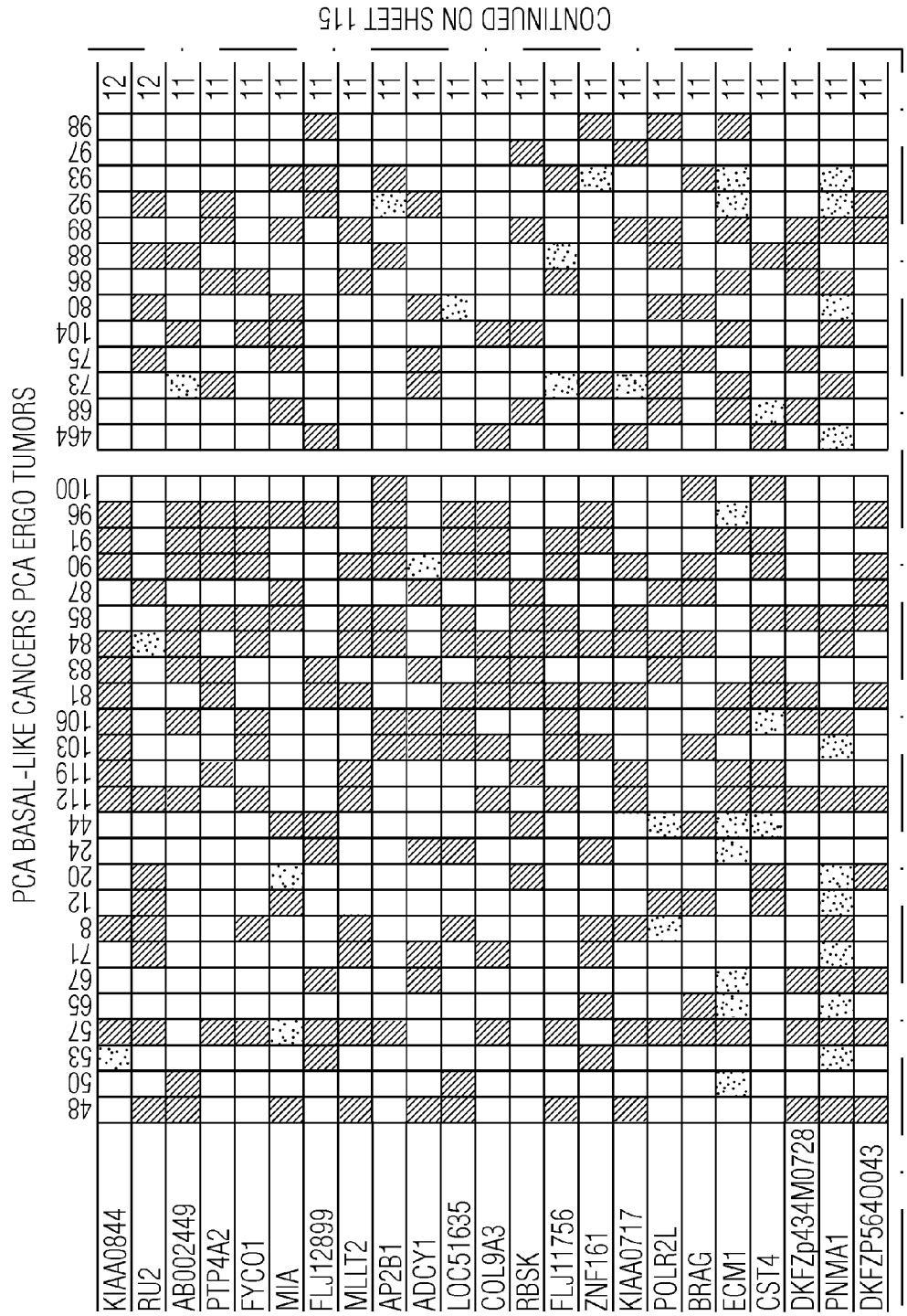
Figure 24I:
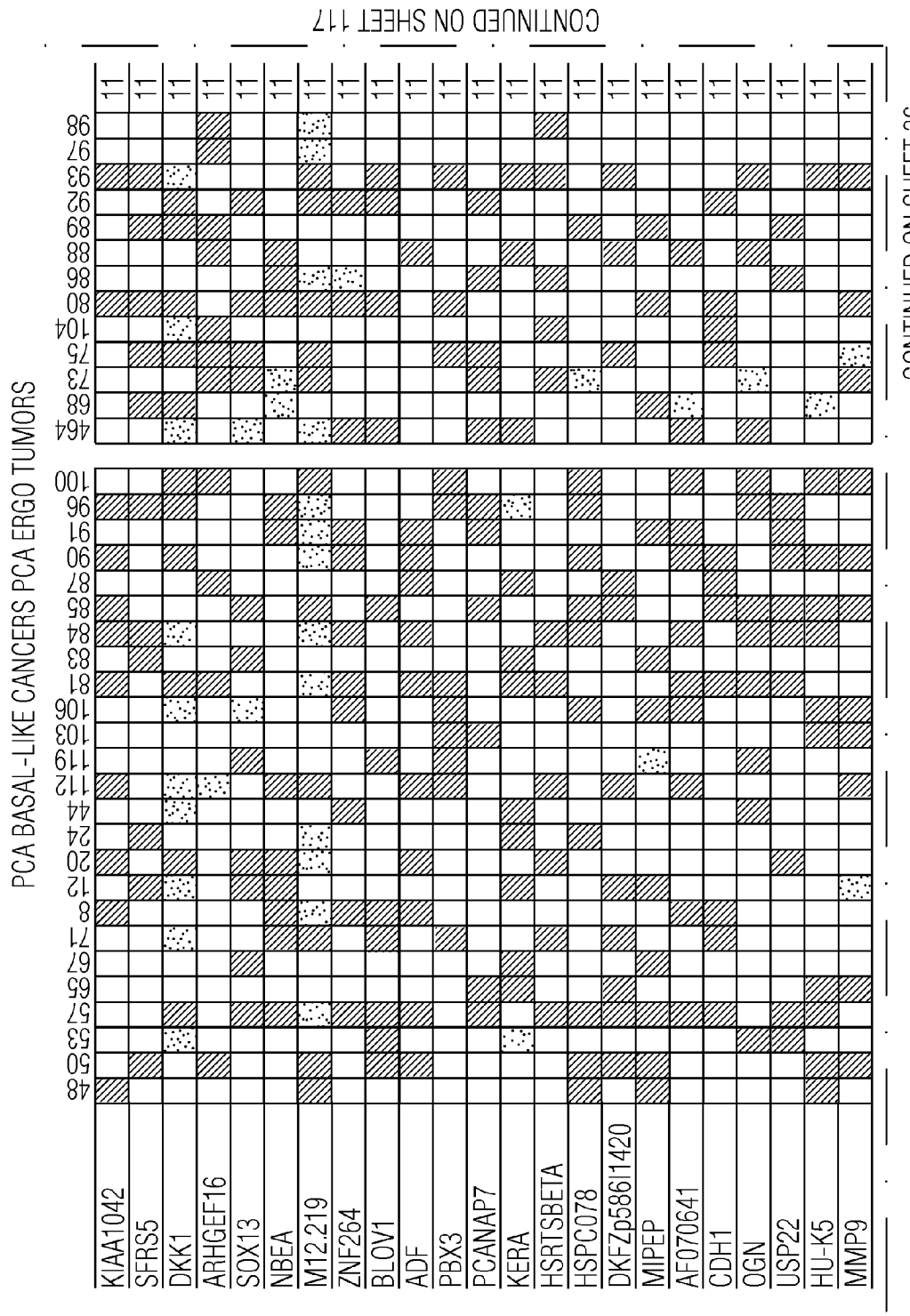
Figure 24J:
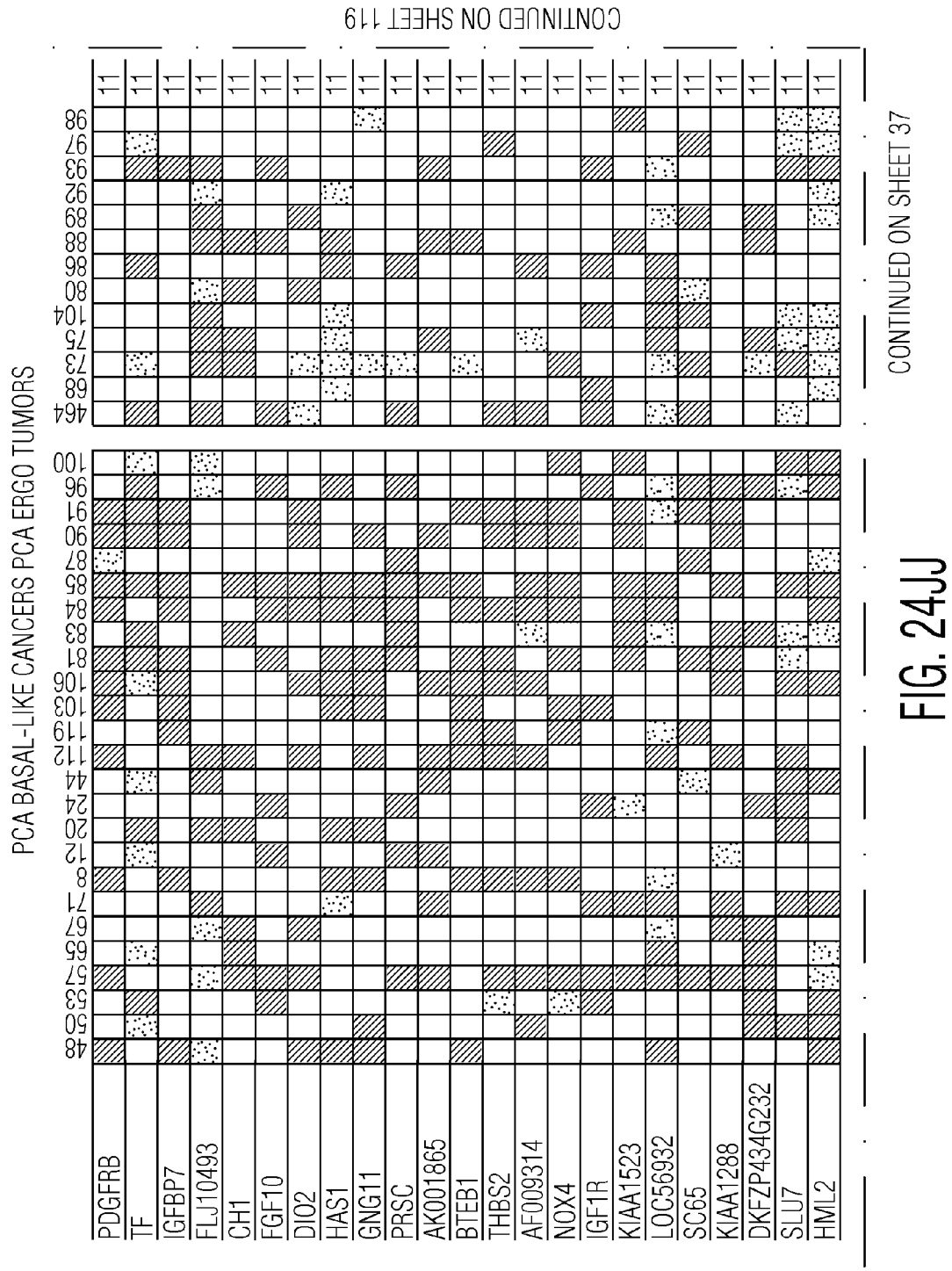
Figure 24K:
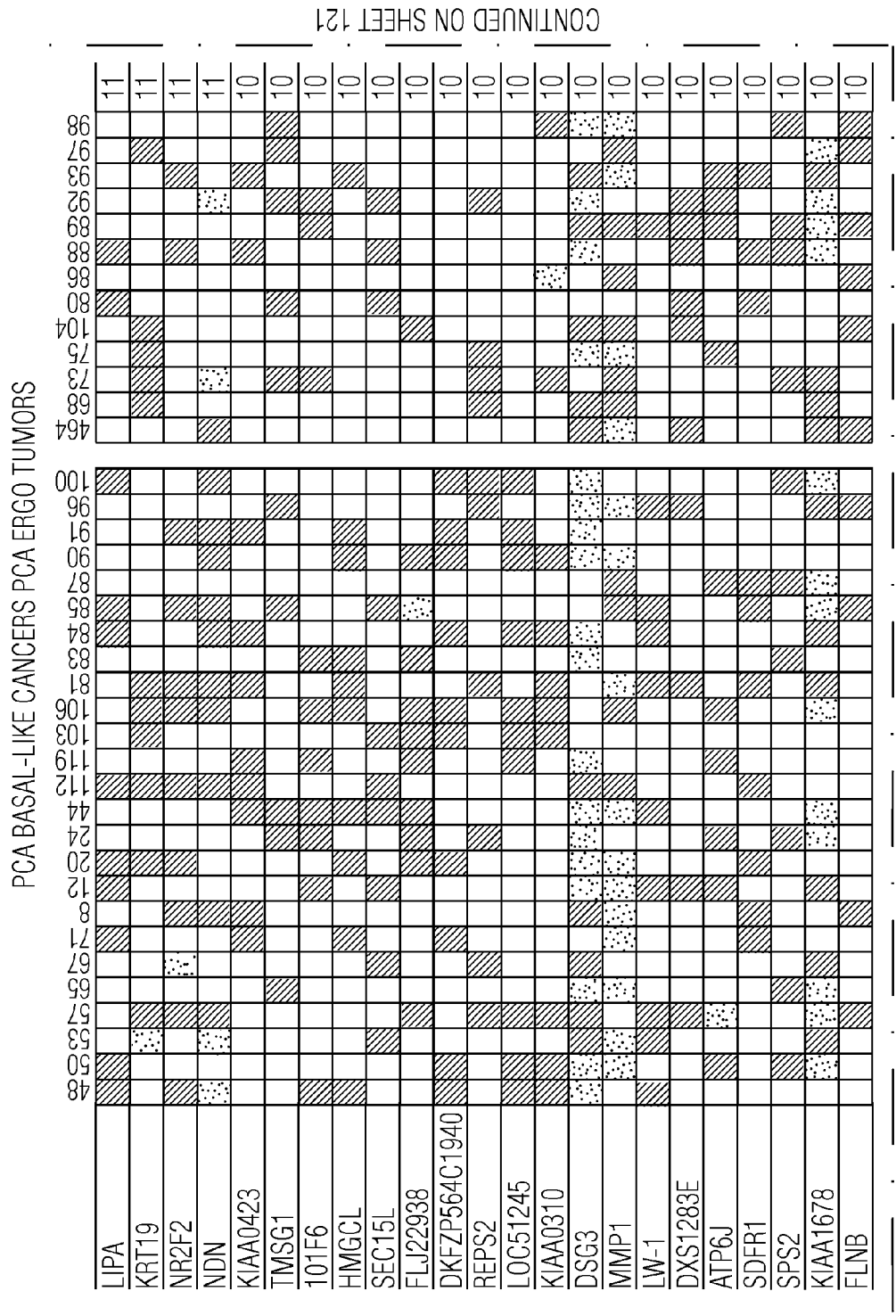
Figure 24L:
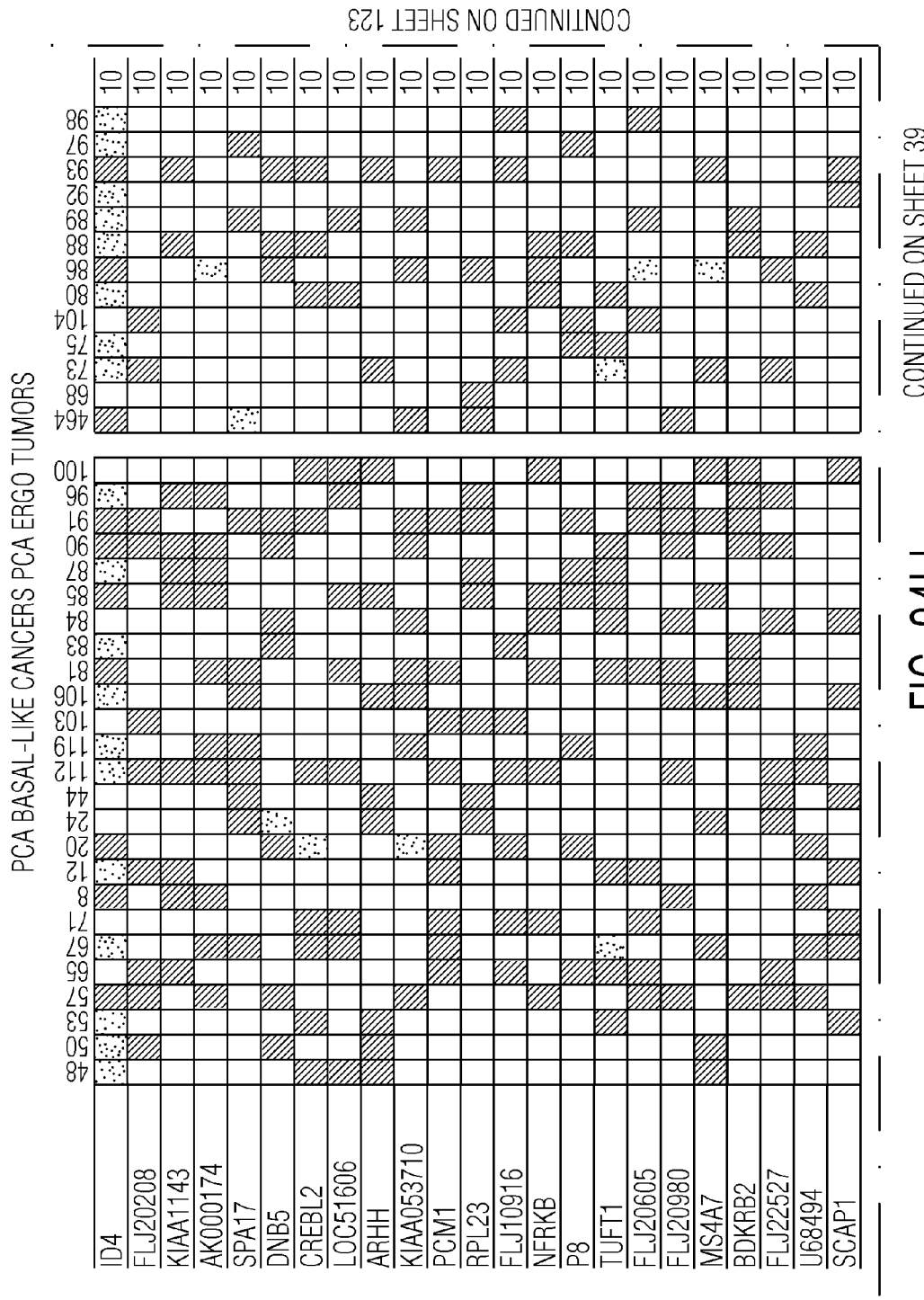
Figure 24M:
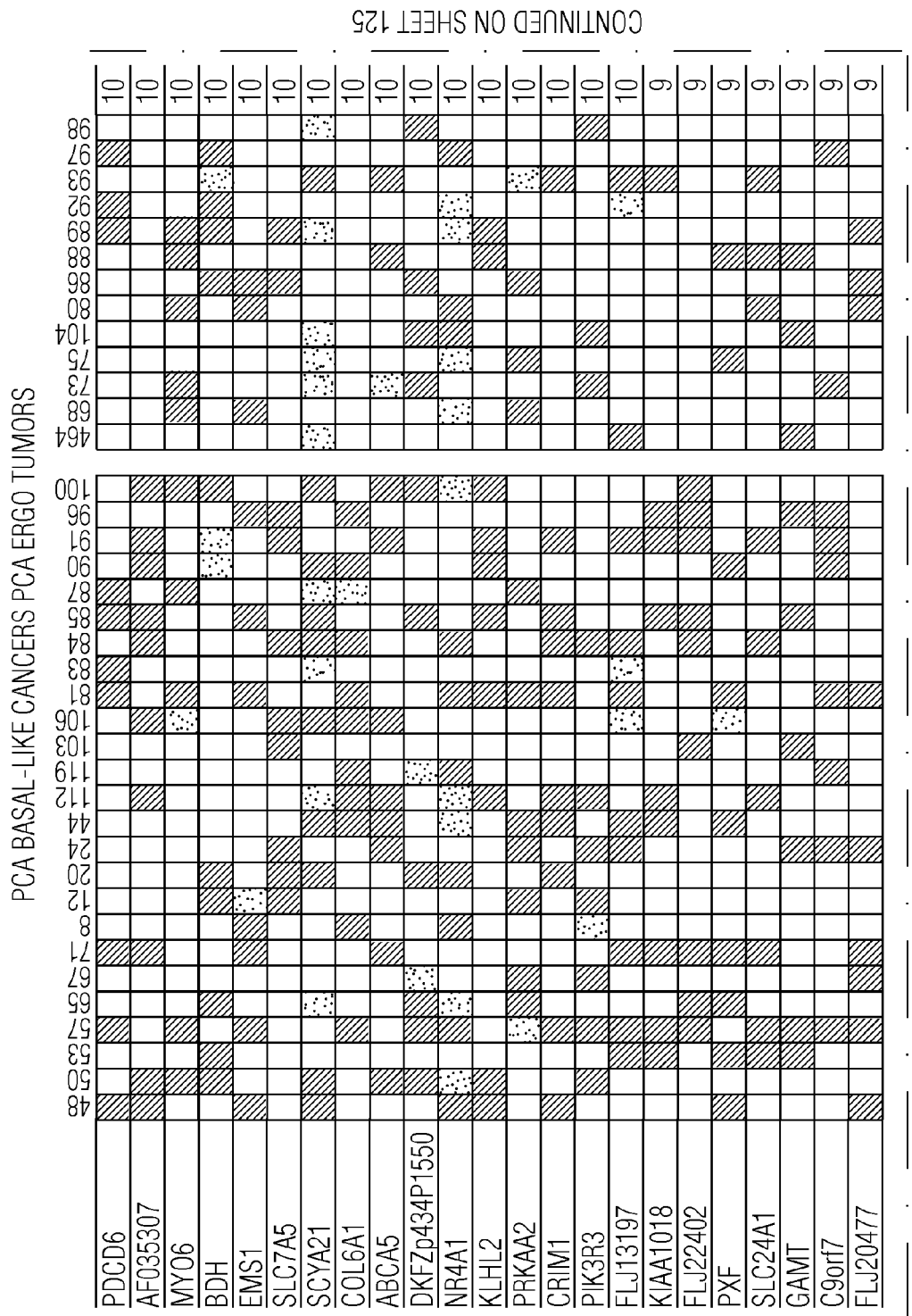
Figure 24N:
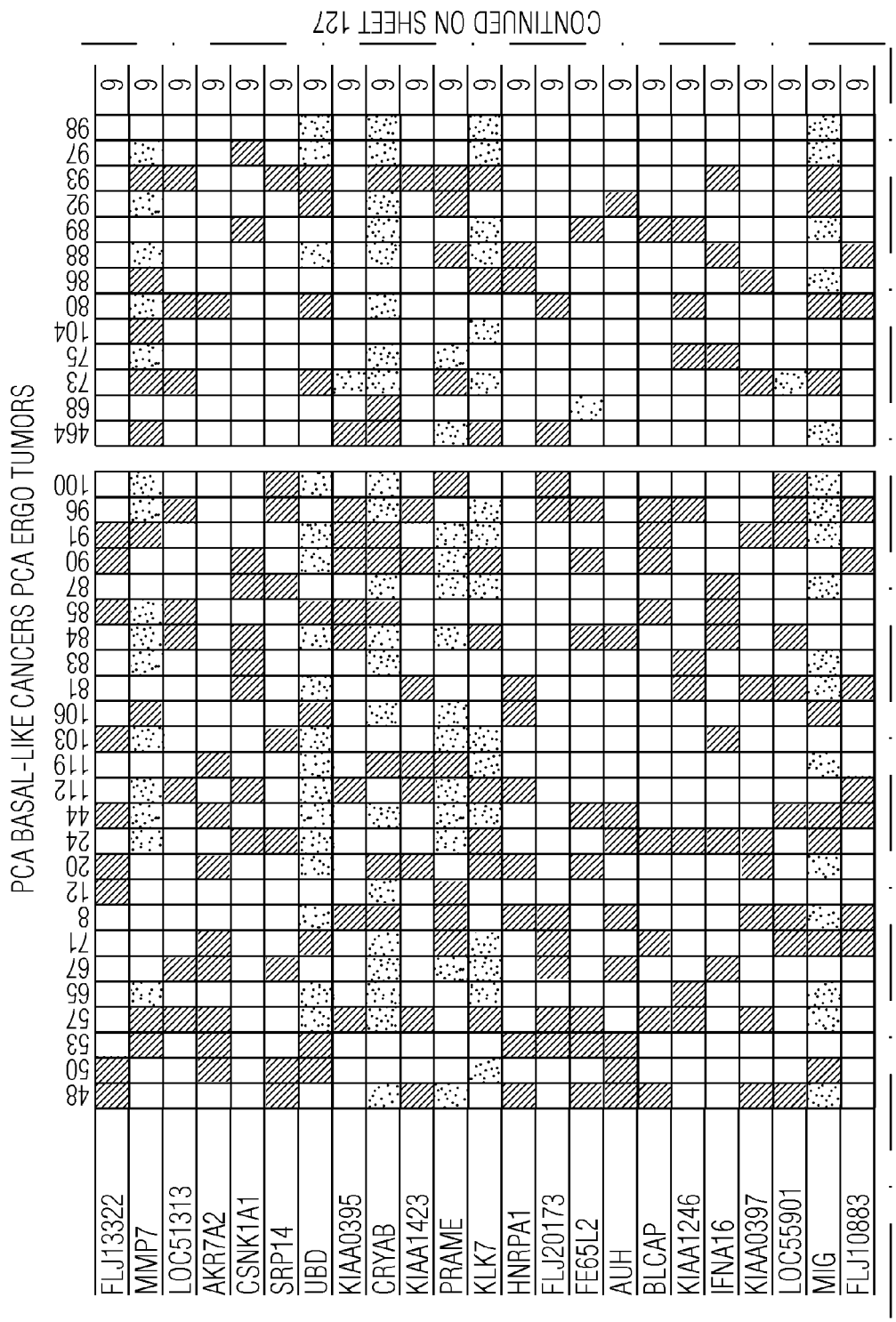
Figure 24P:
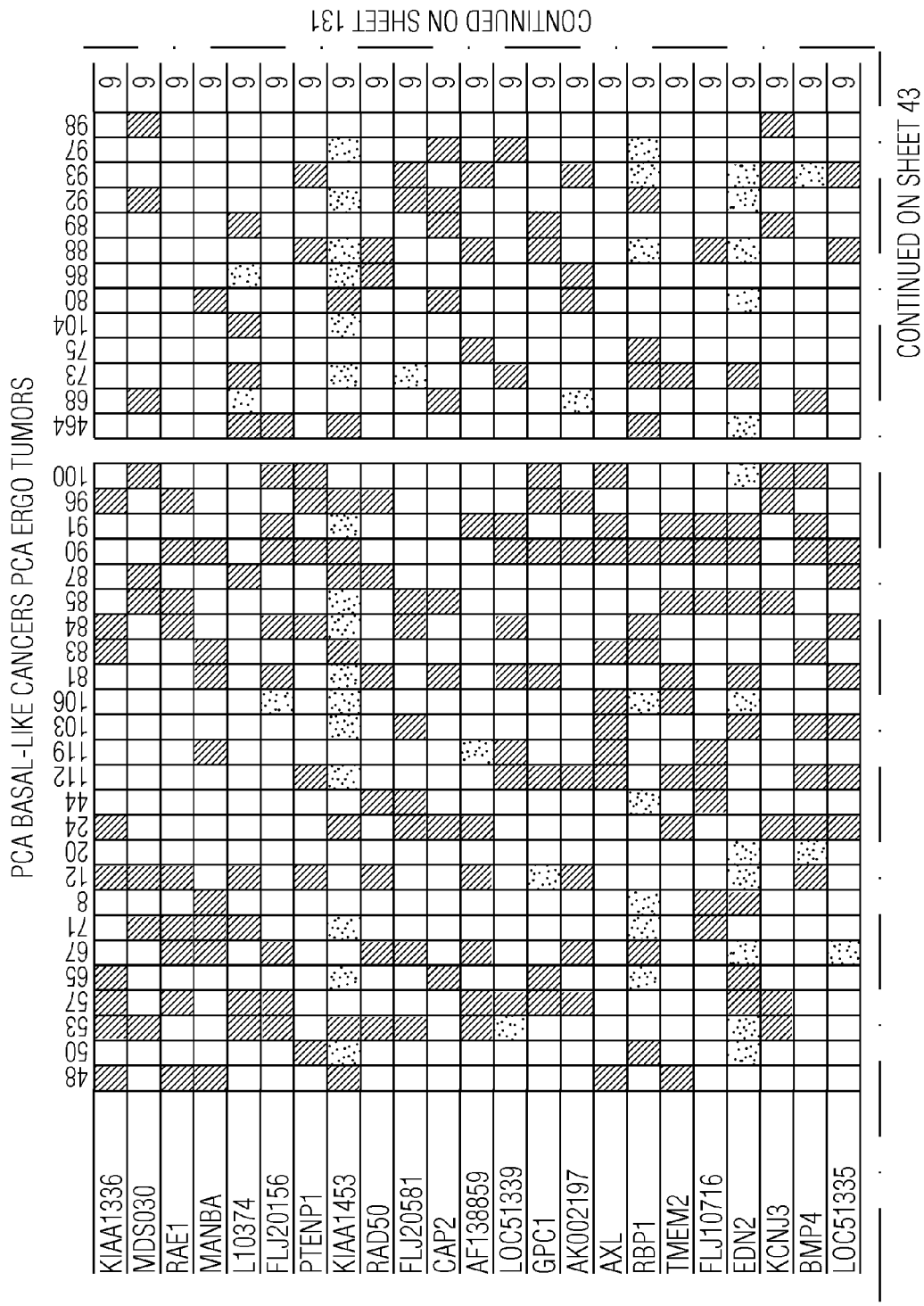
Figure 24Q:
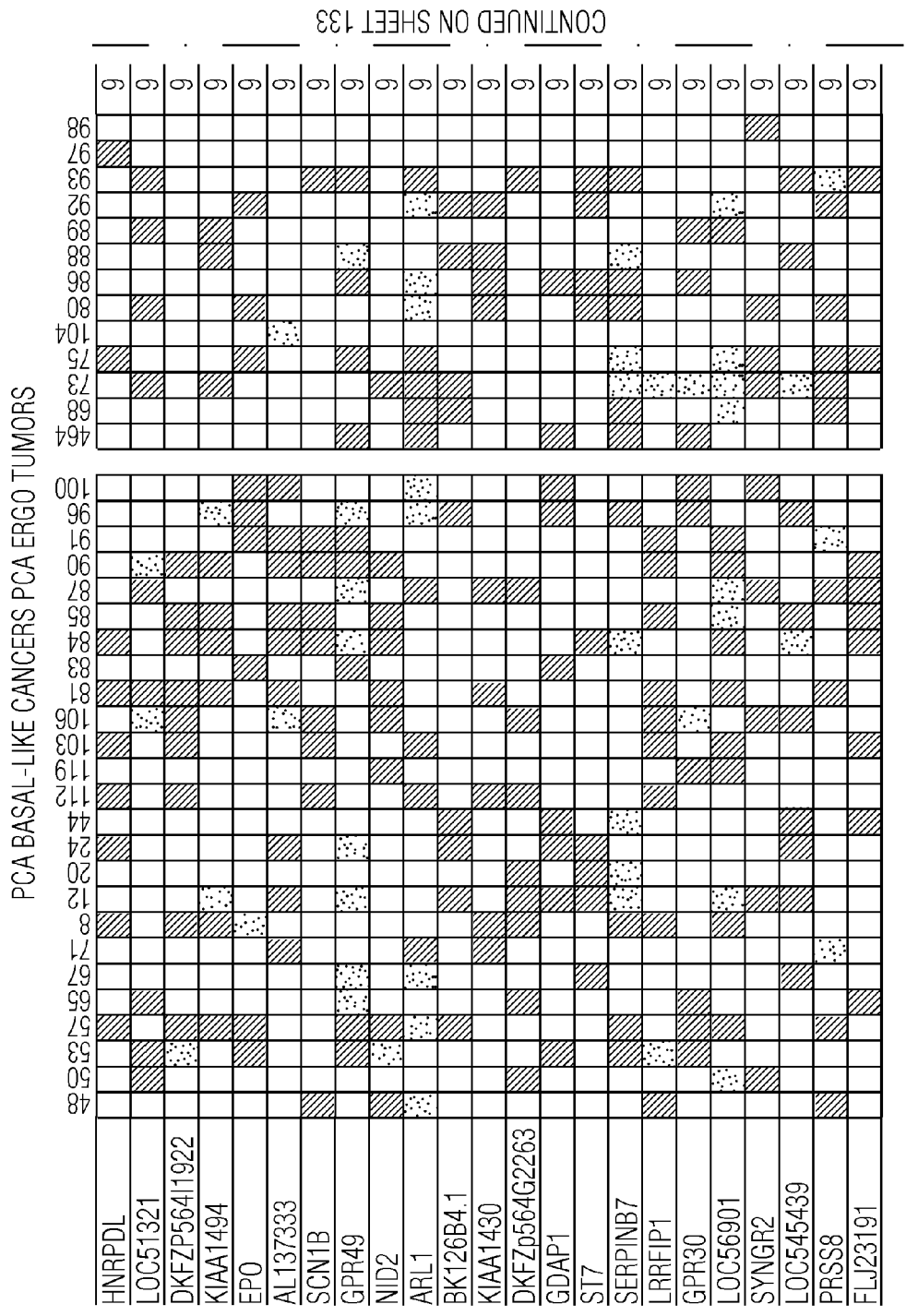
Figure 24R:
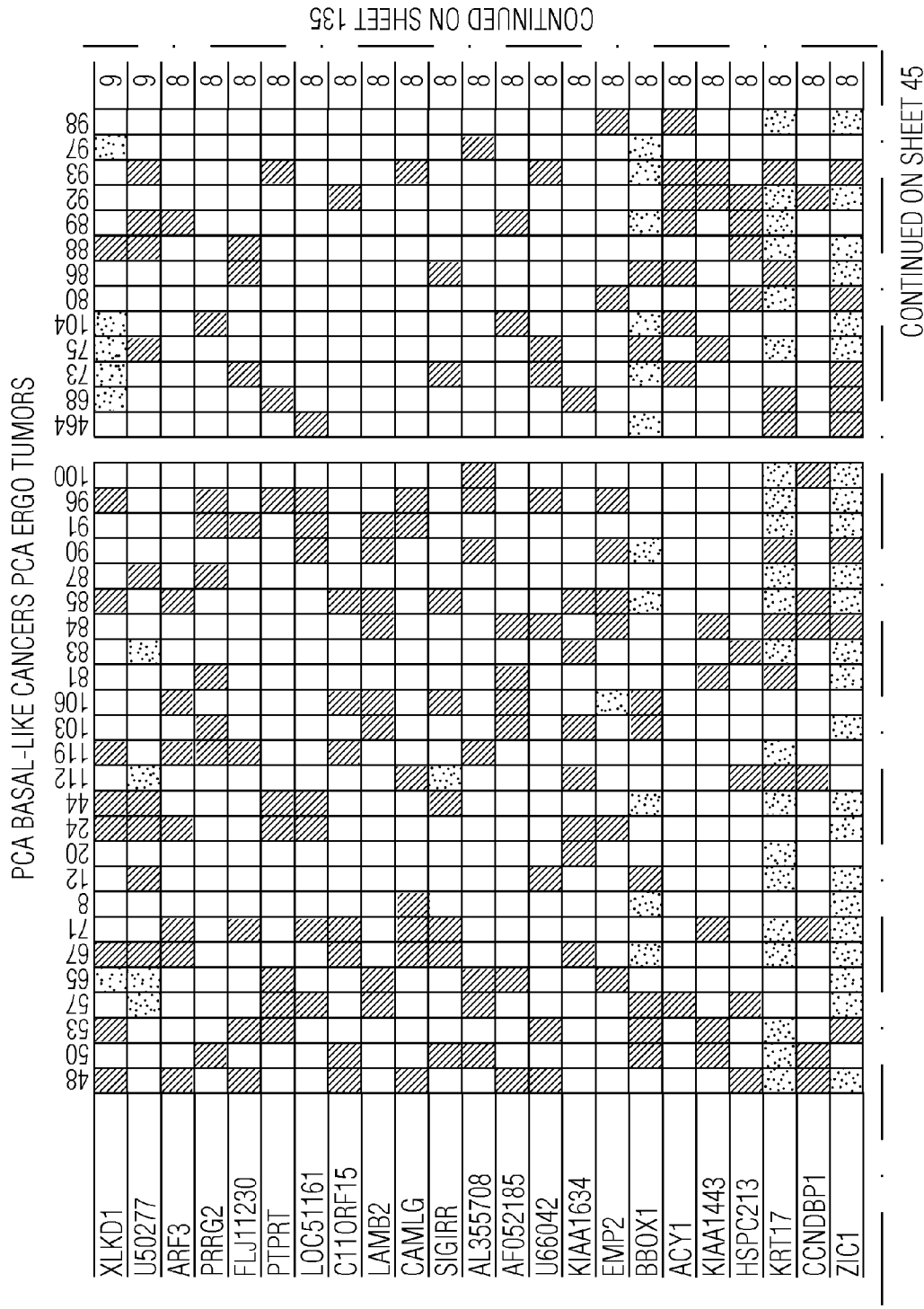
Figure 24S:
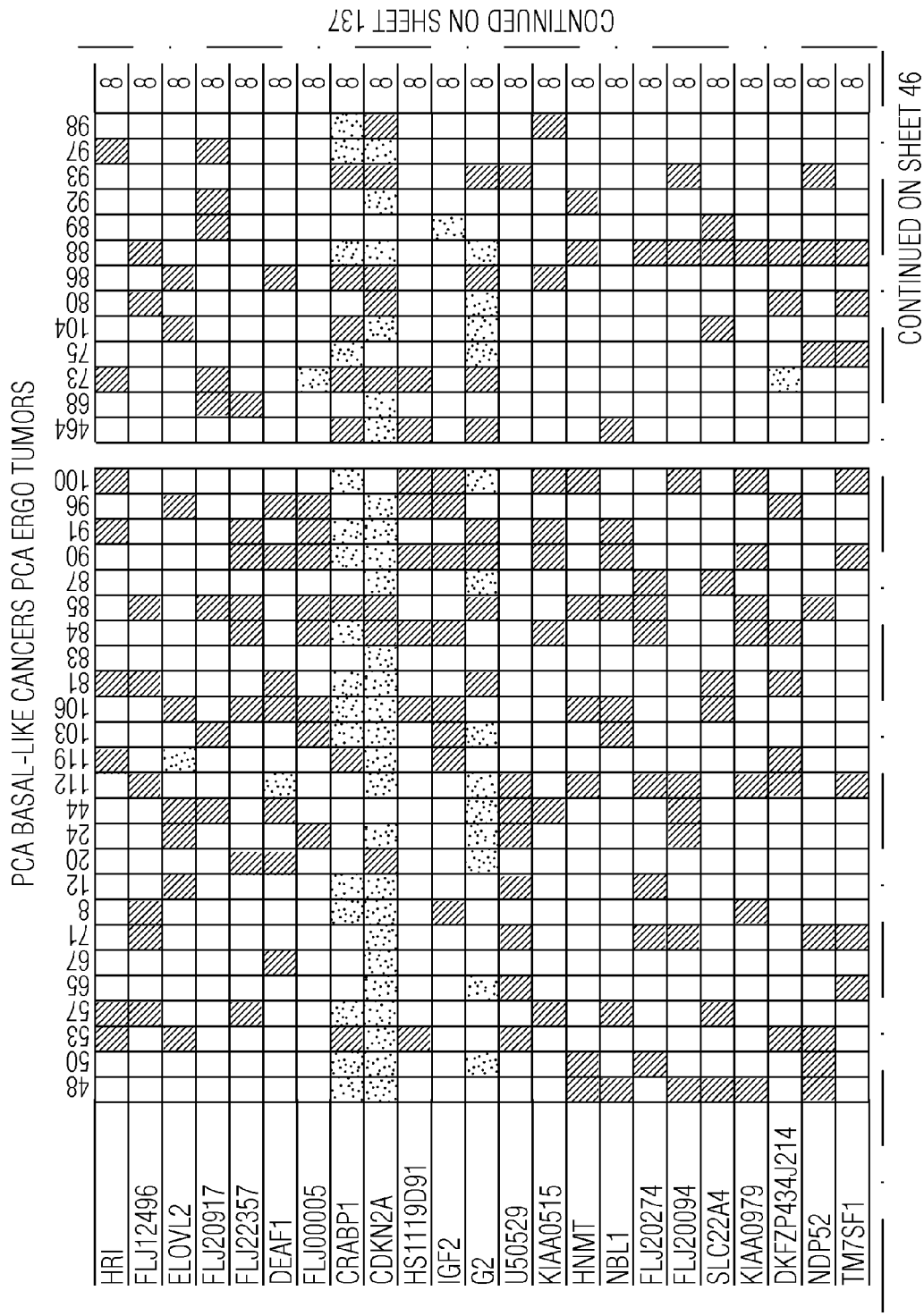
Figure 24T:
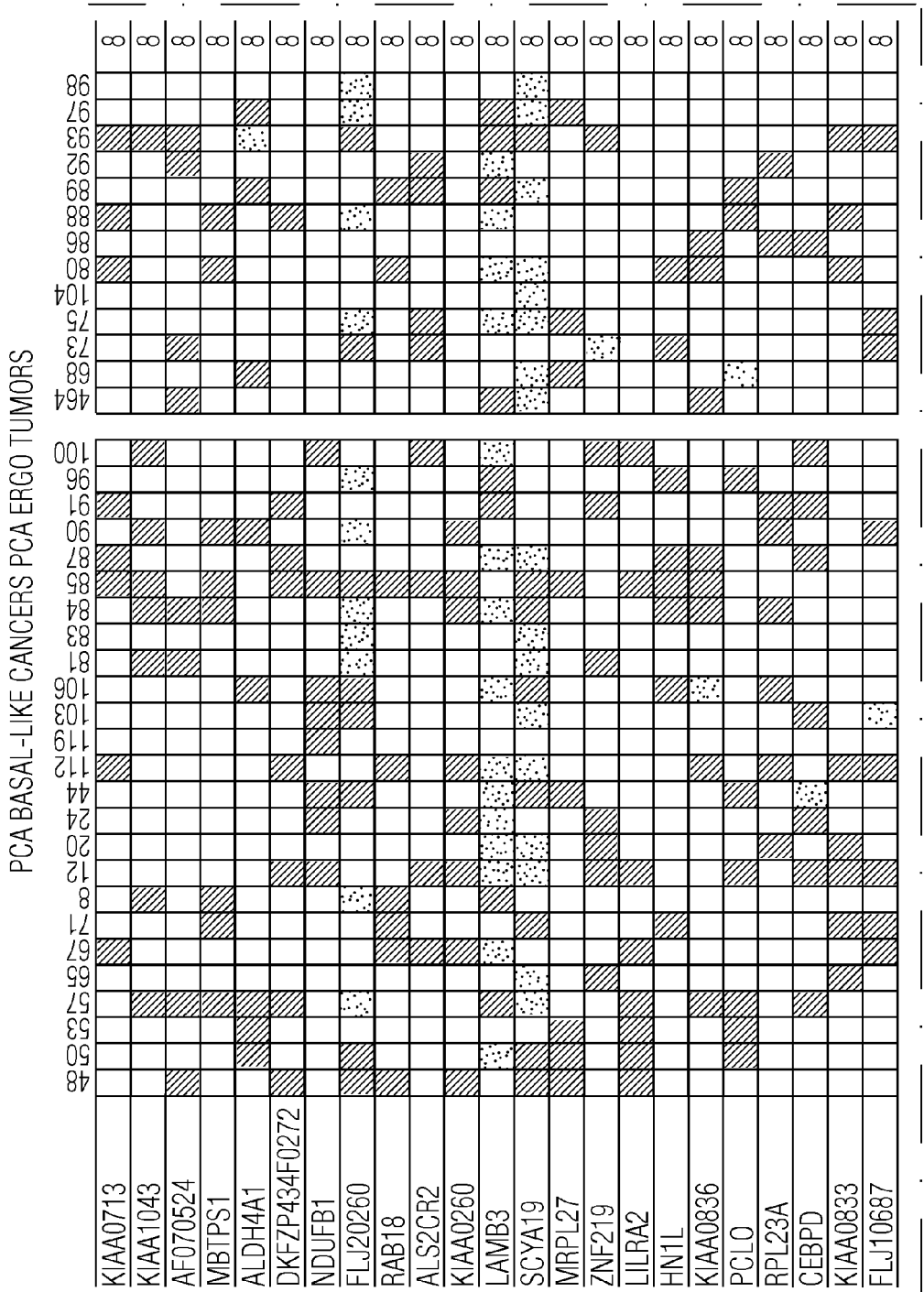
Figure 24U:
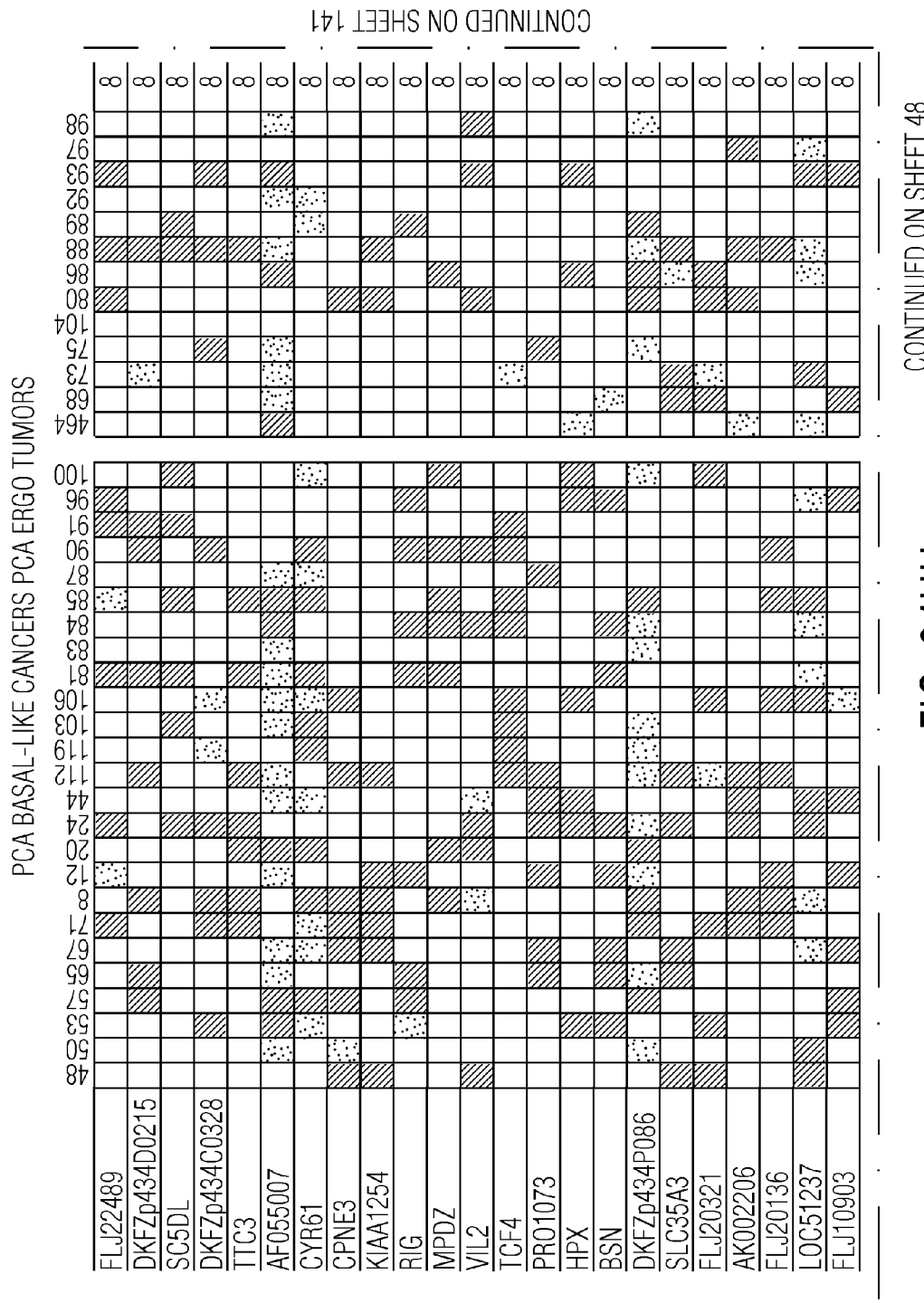
Figure 24V:
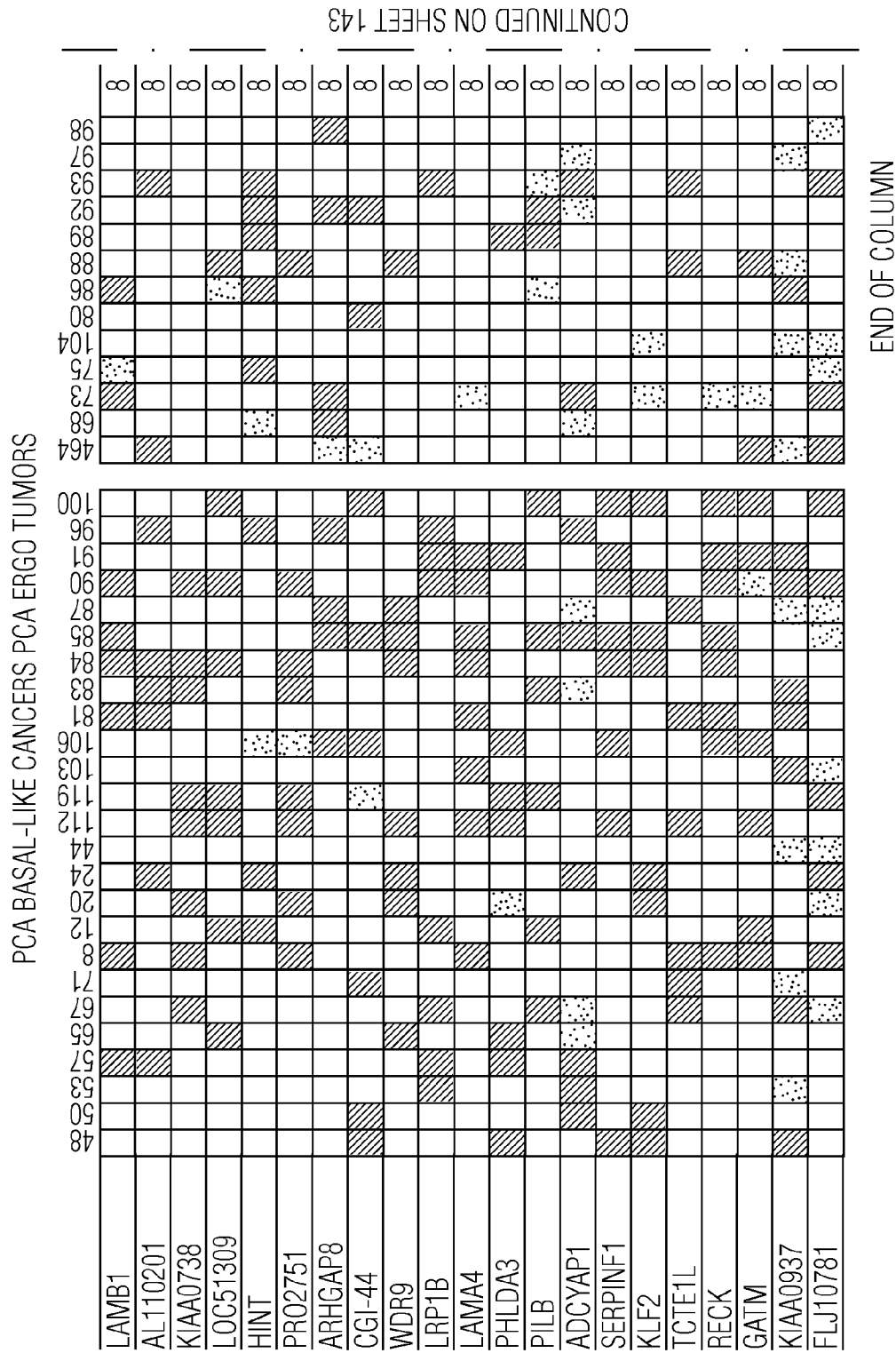
Figure 24W:
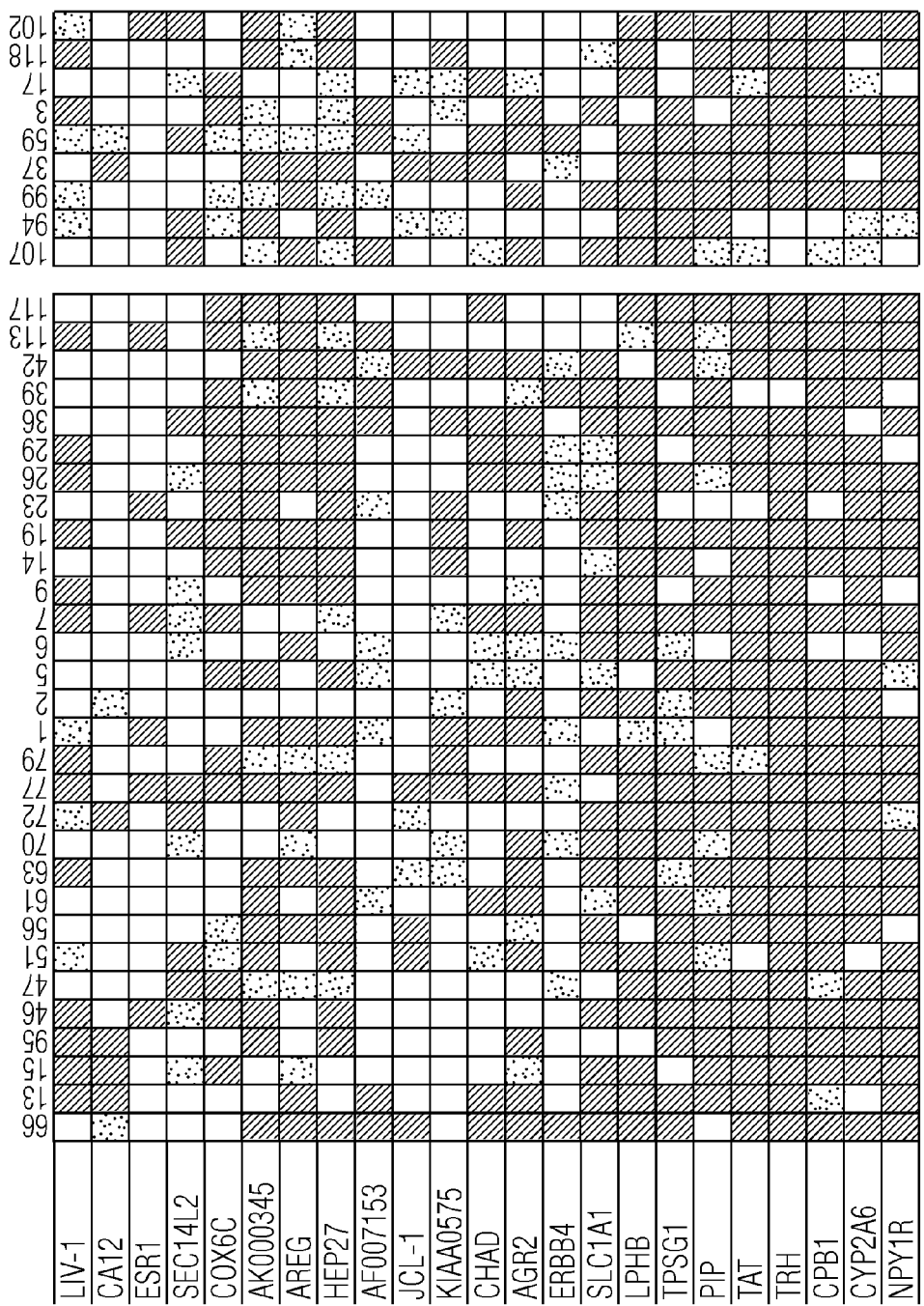
Figure 24Y:
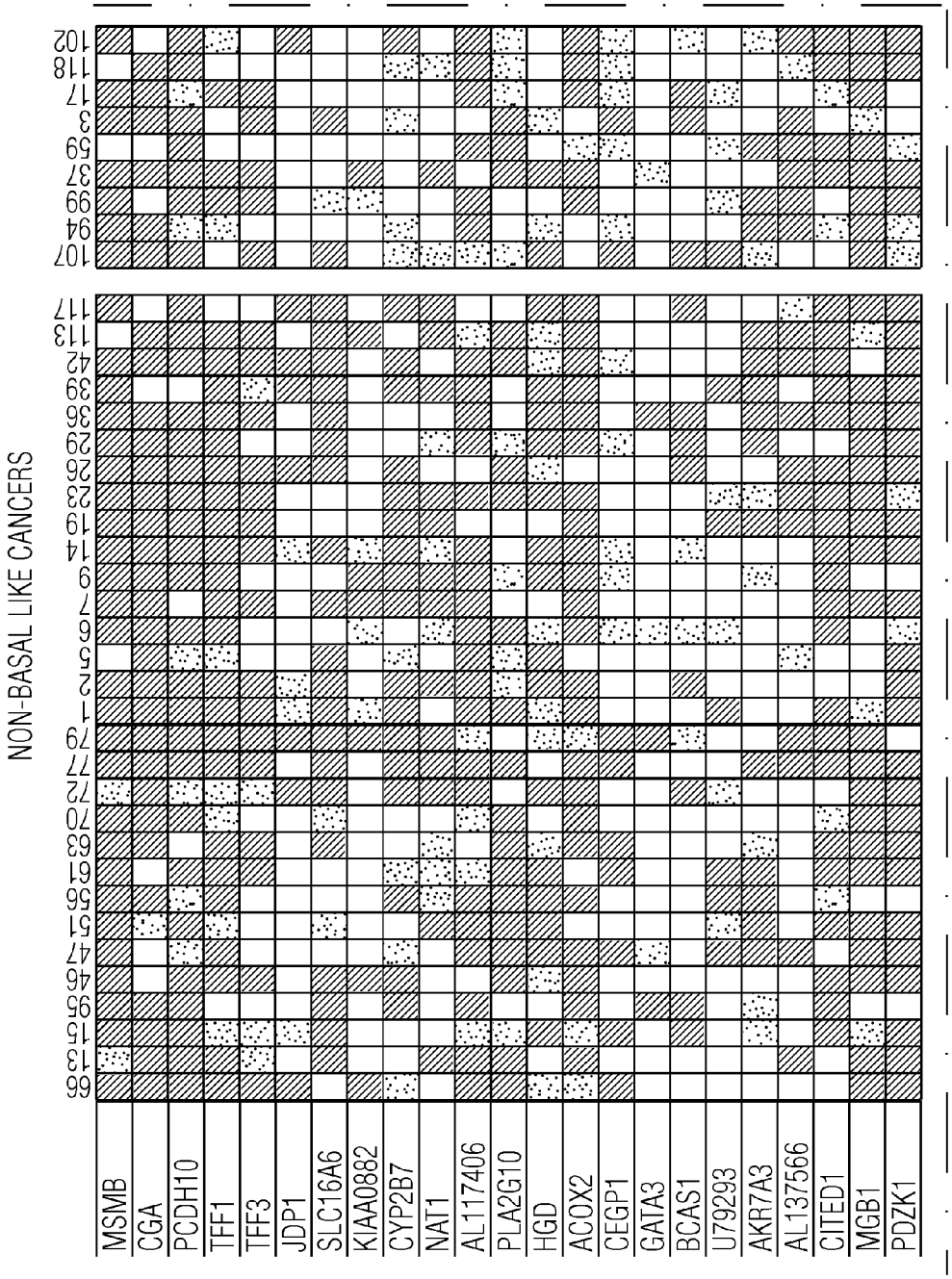
Figure 24Z:
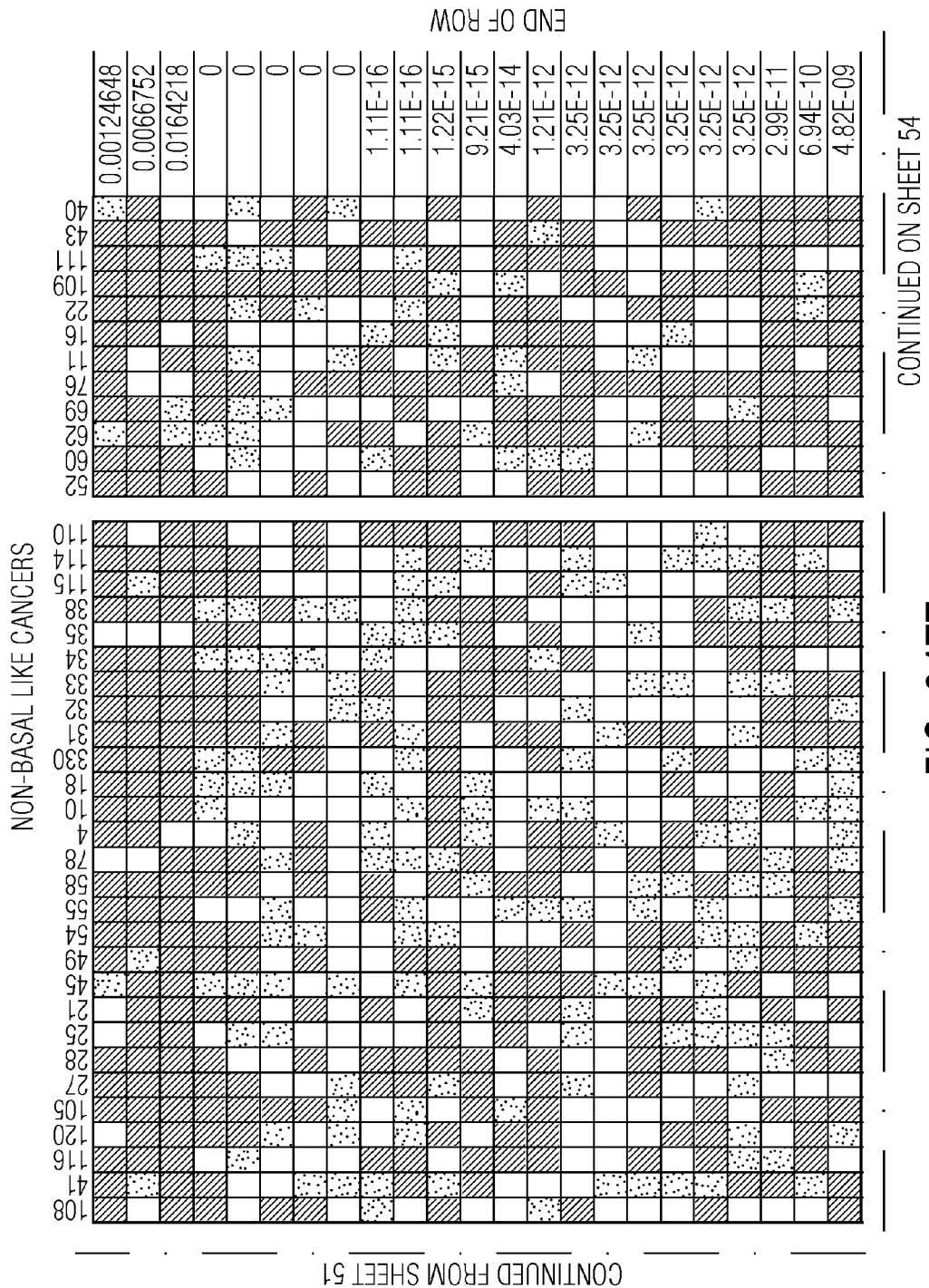
Figure 25A:
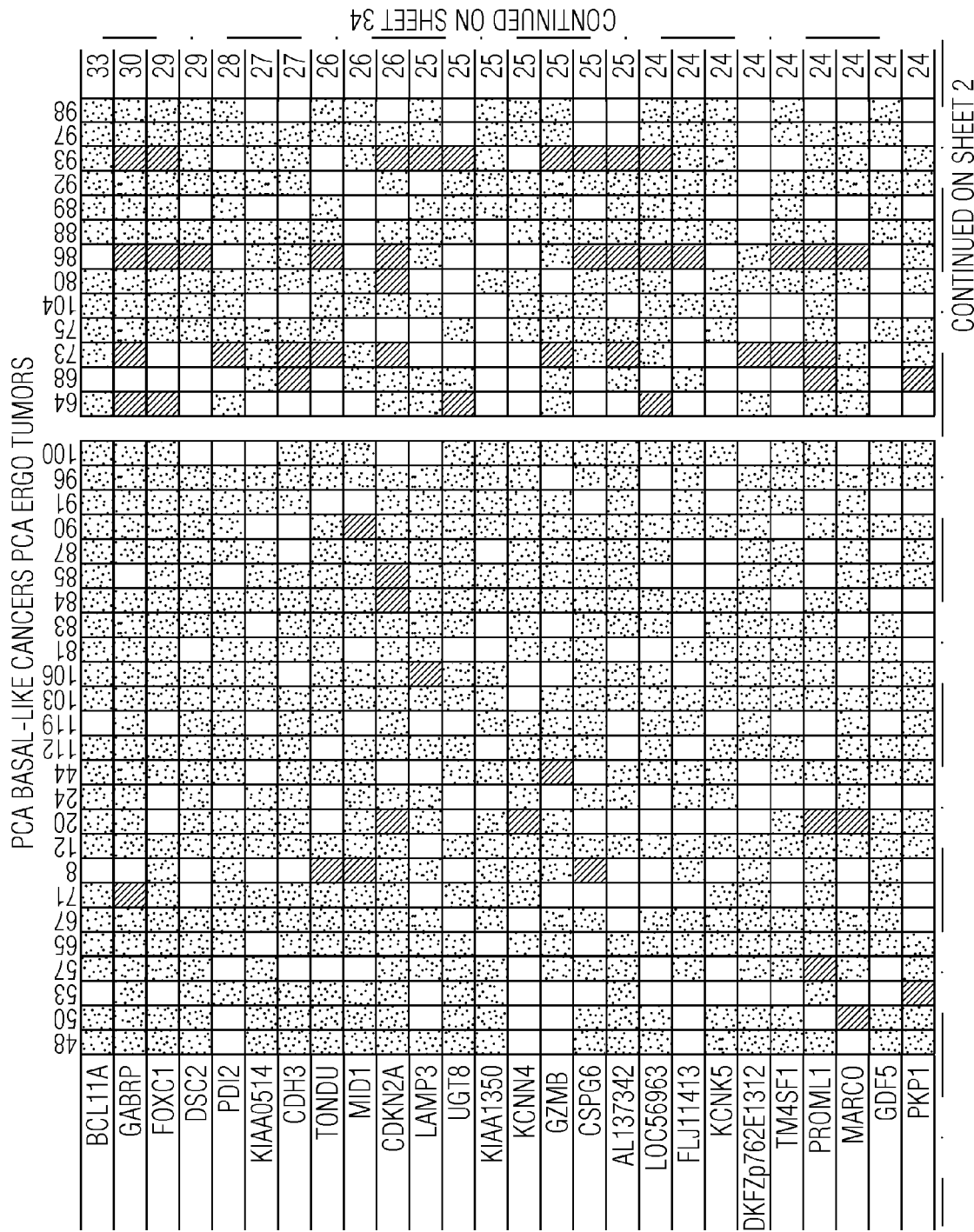
FIGS. 25A to 25UUUU show partial views intended to form one complete view of microarray data from the Van't Veer microarray set, showing the non-E2F responsive genes that are statistically significantly differentially under-expressed in basal-like breast cancers relative to non-basal-like breast cancers.
Figure 25B:
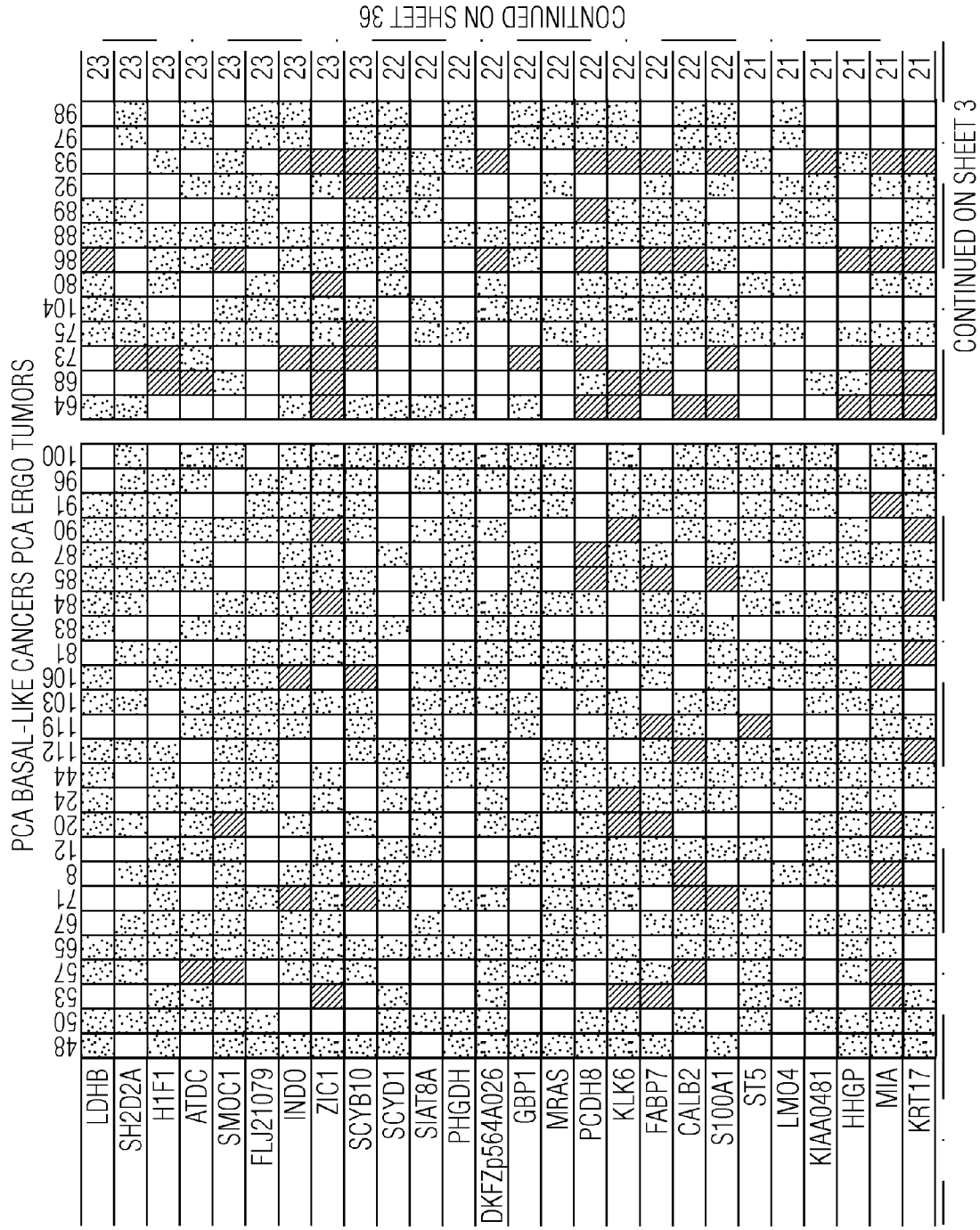
Figure 25C:
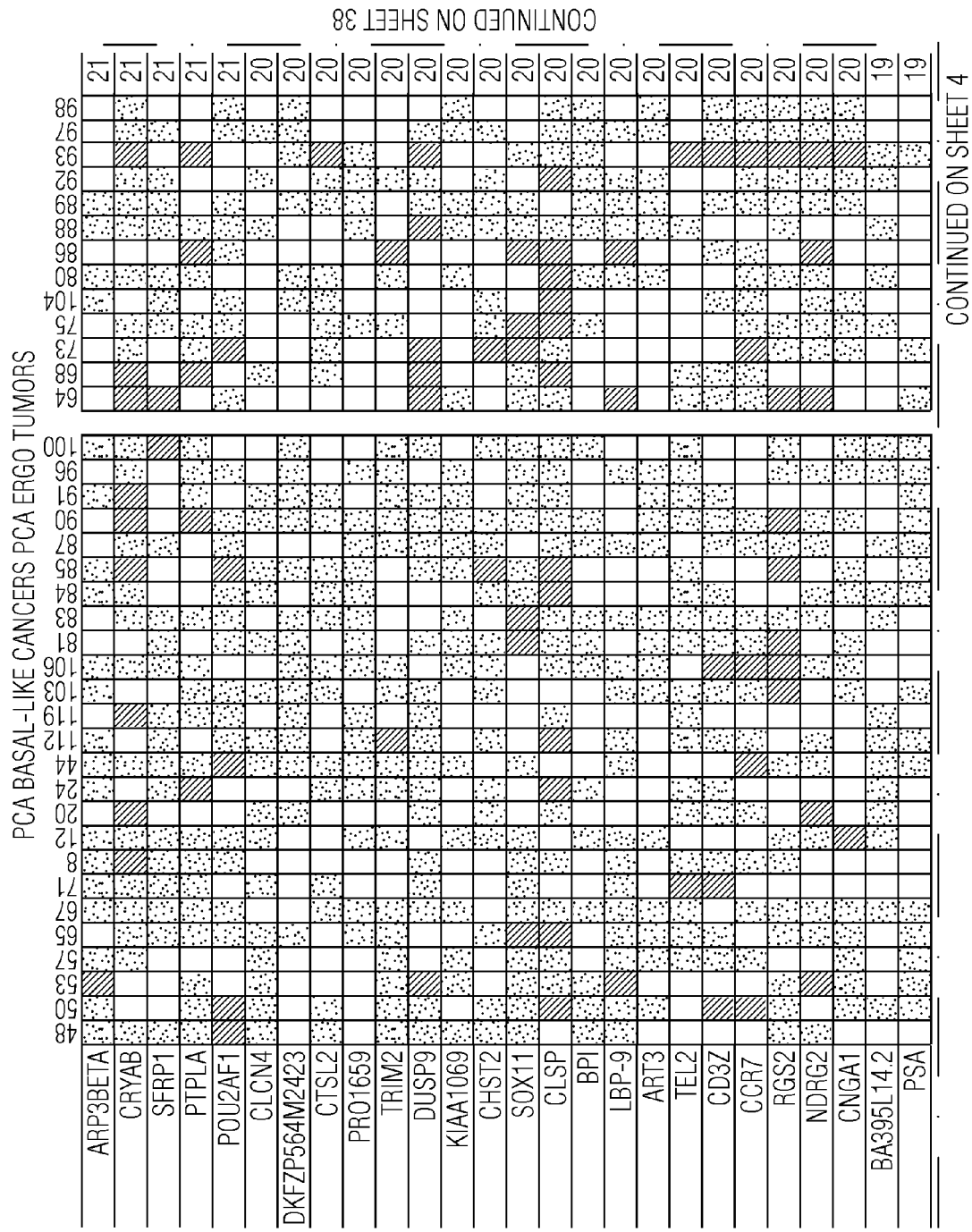
Figure 25D:
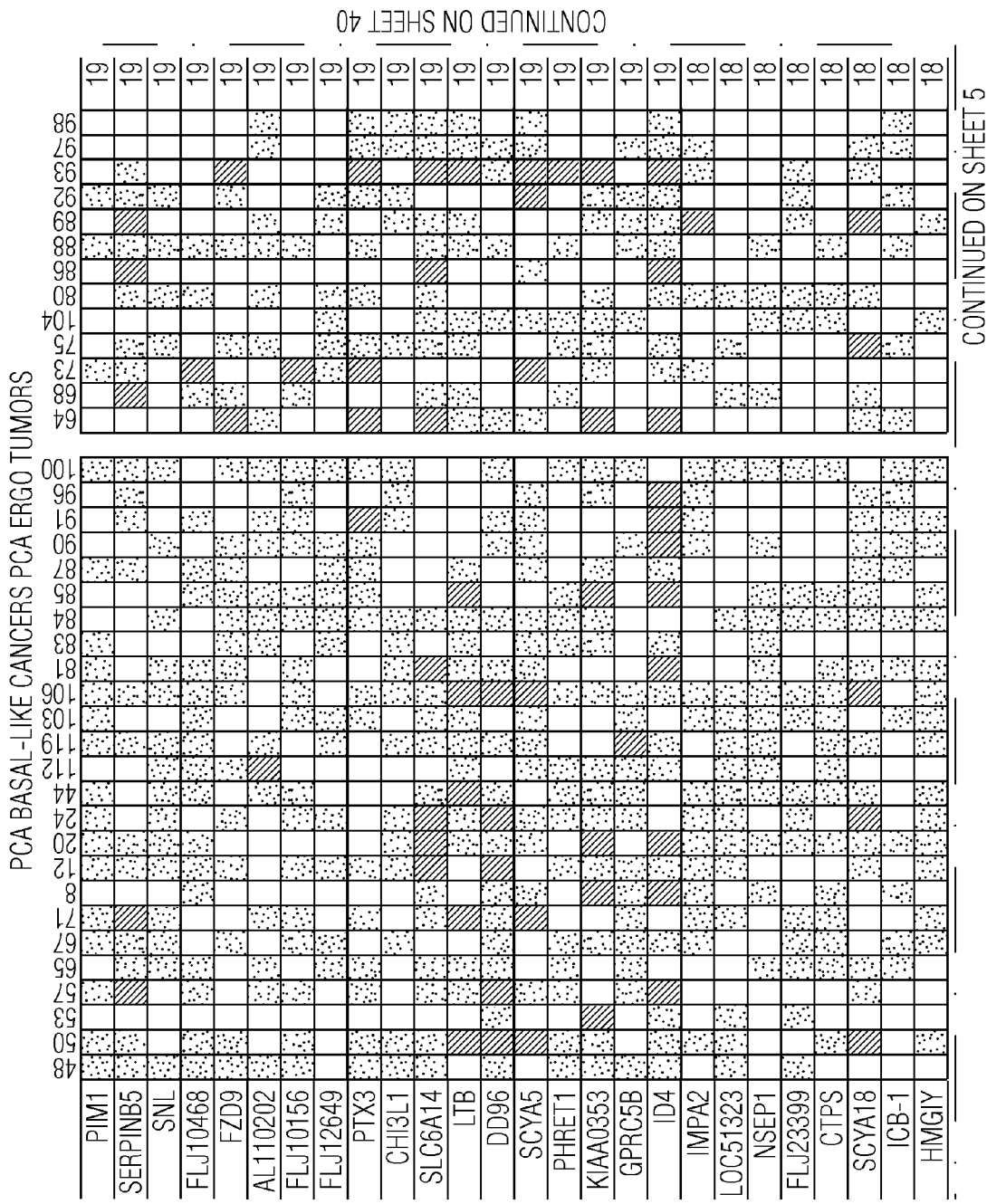
Figure 25E:
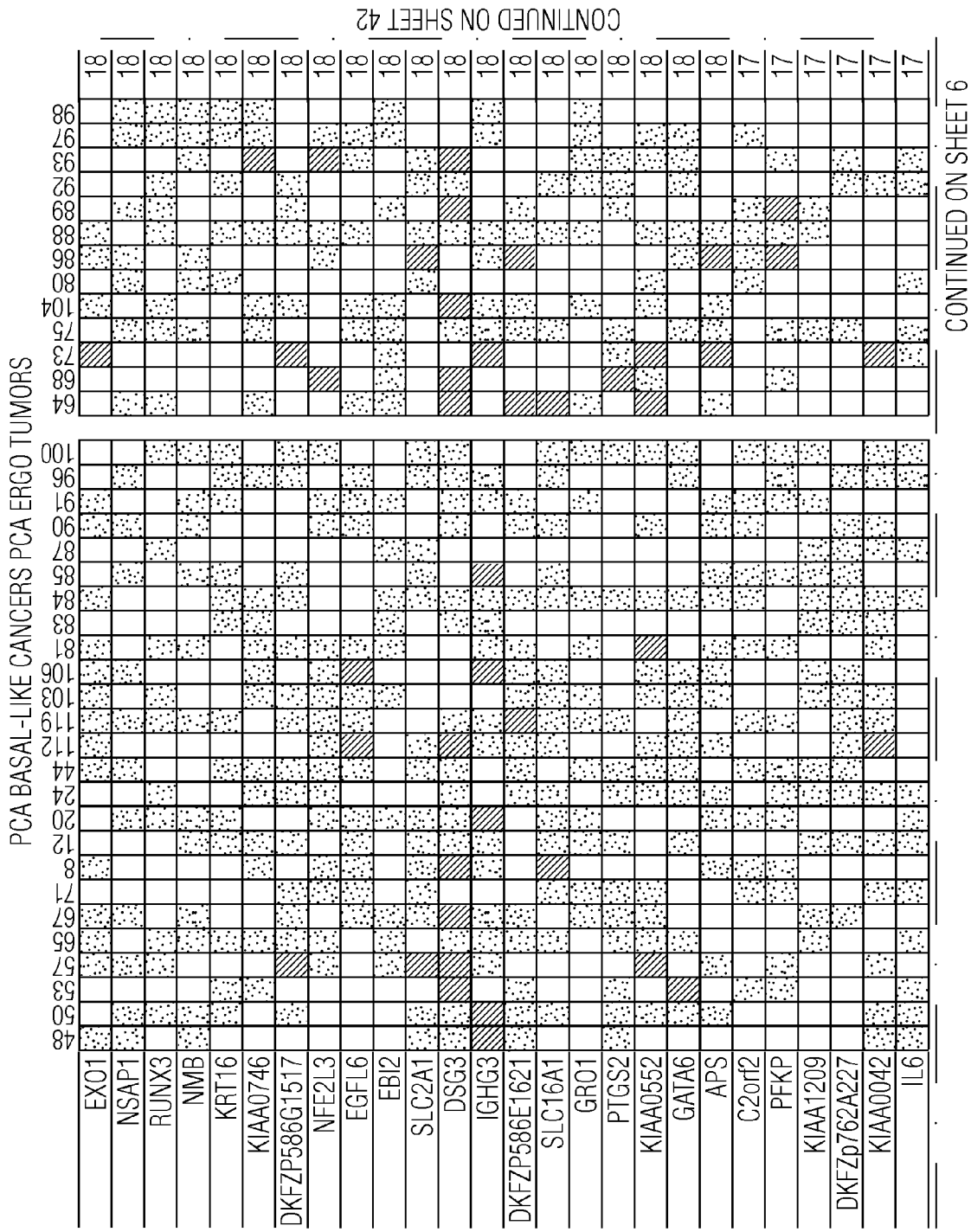
Figure 25F:
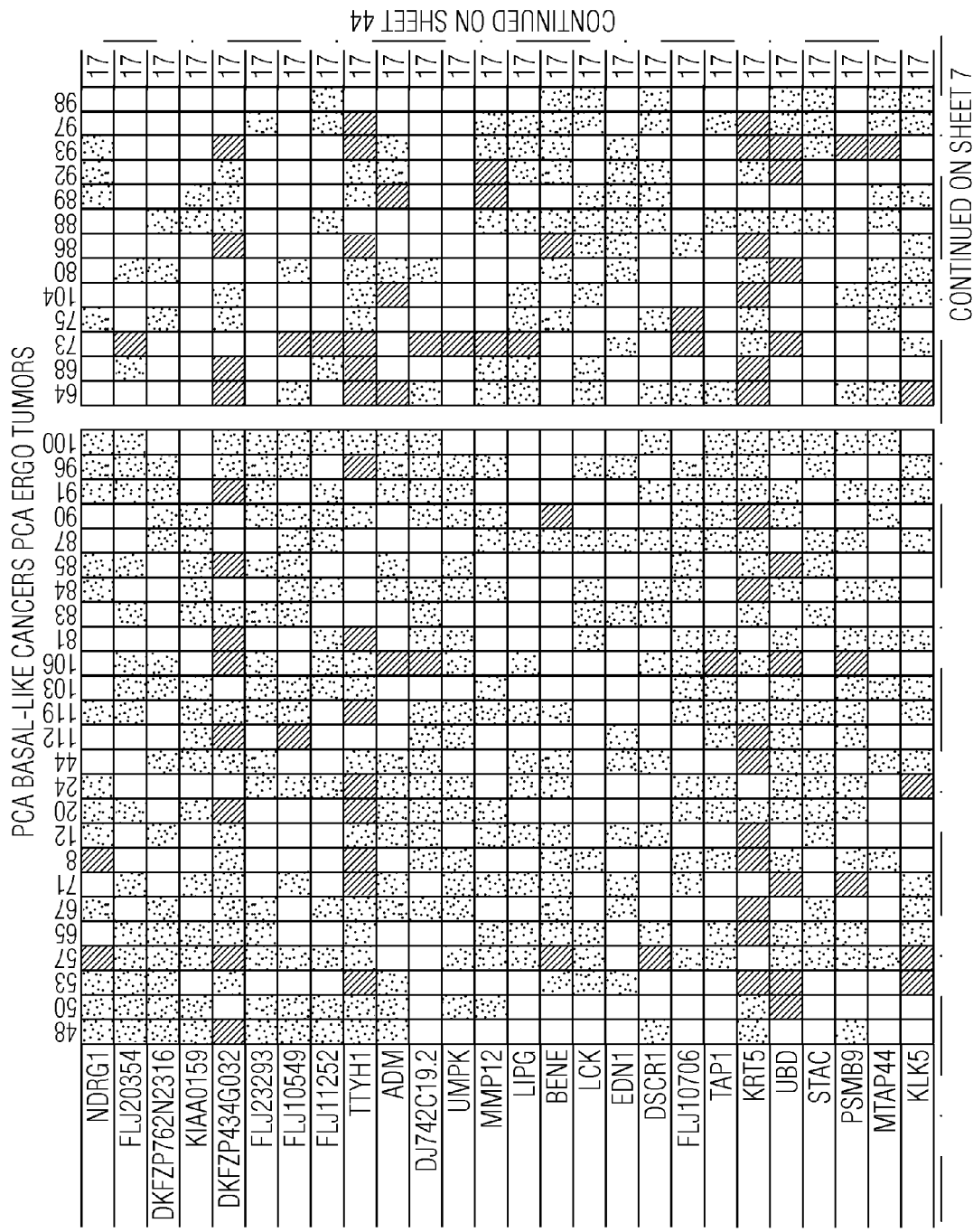
Figure 25G:
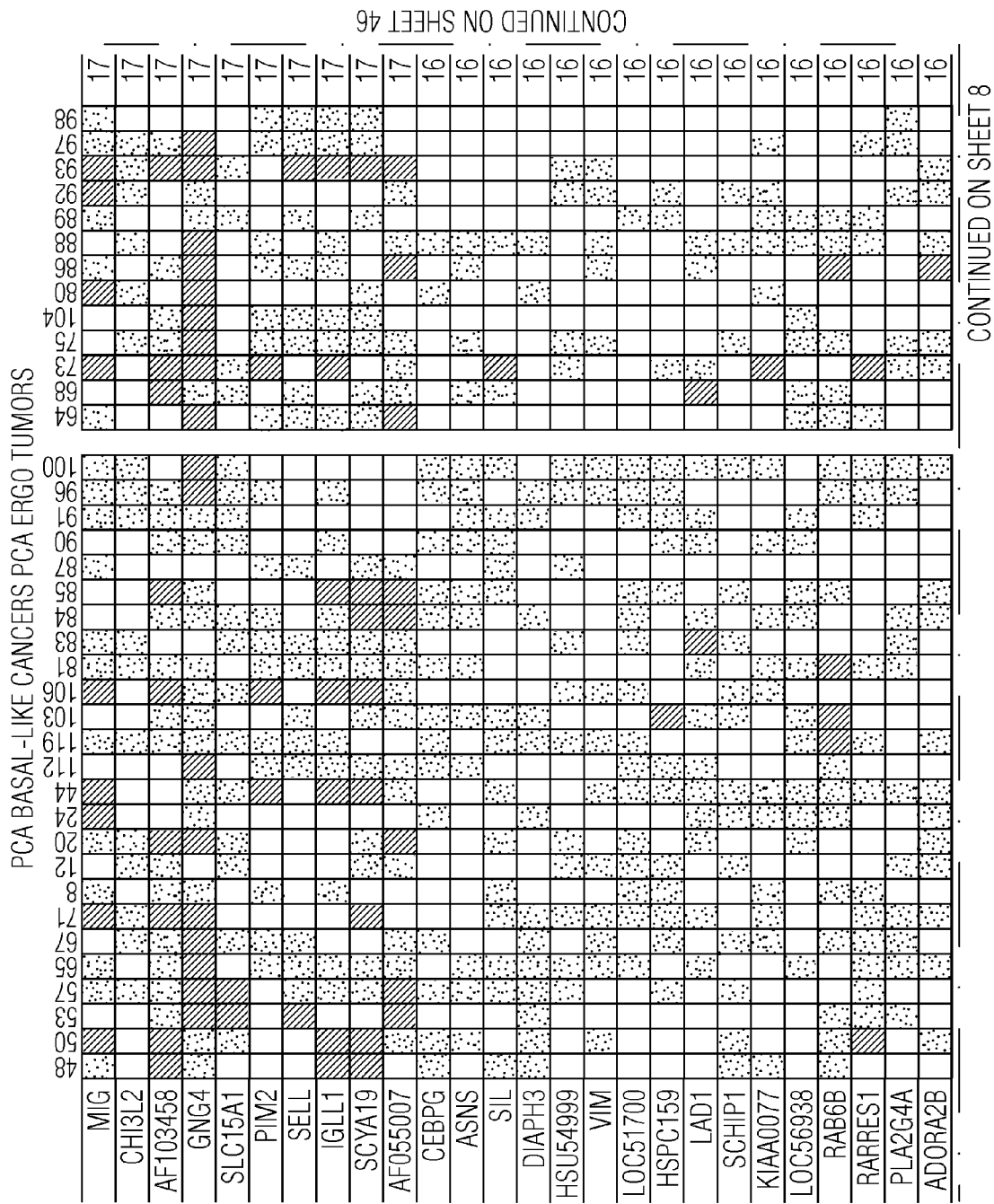
Figure 25H:
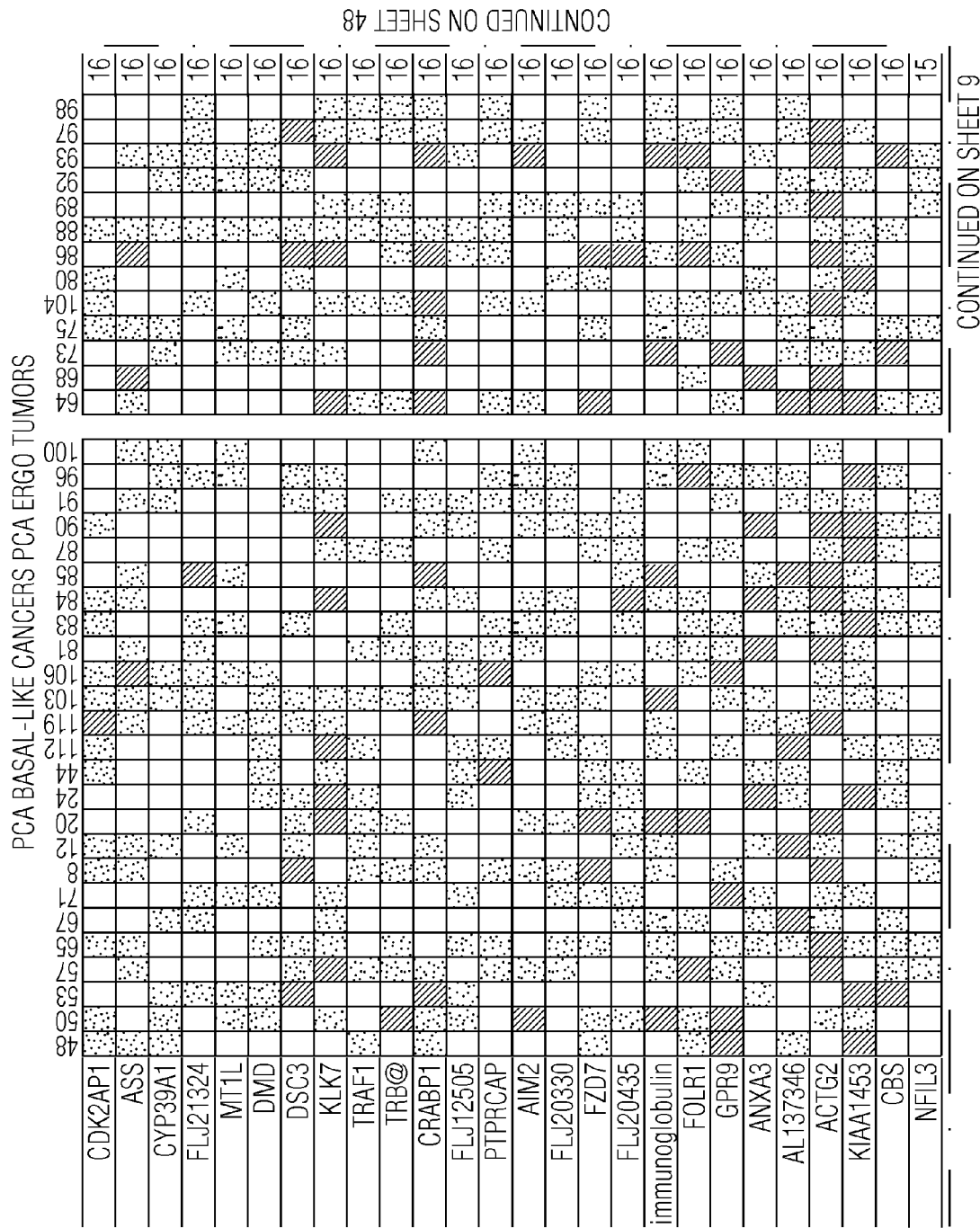
Figure 25I:
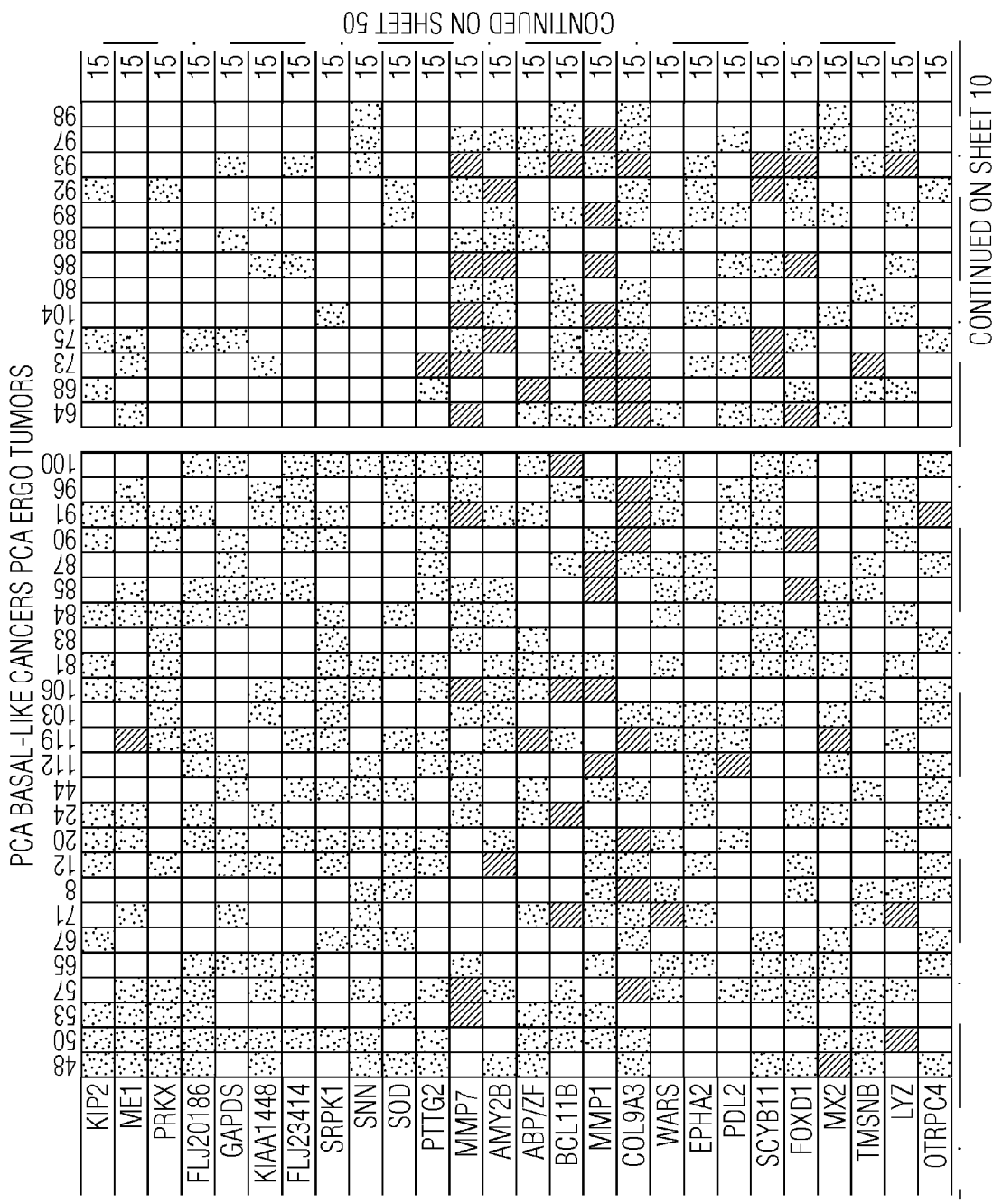
Figure 25J:
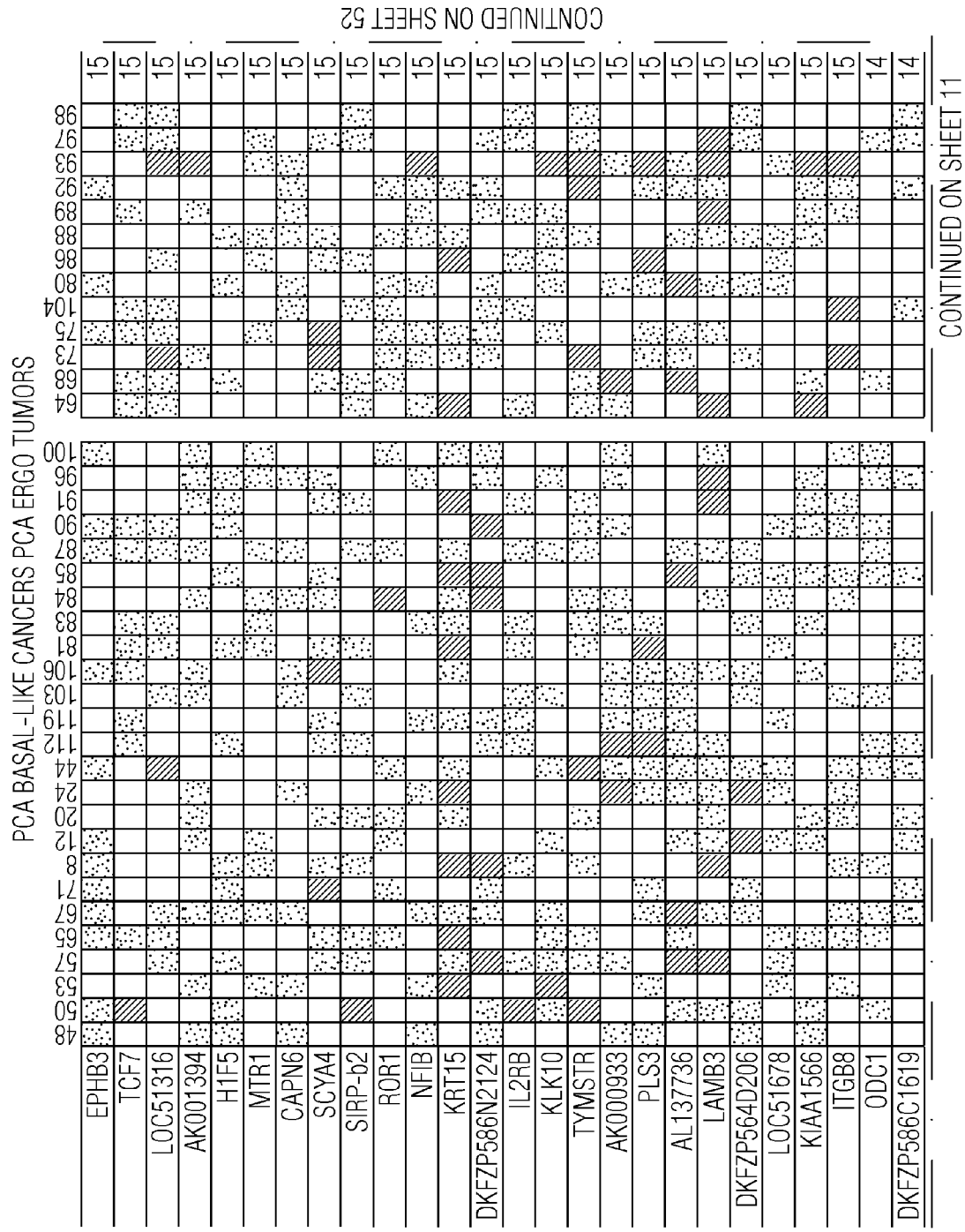
Figure 25K:
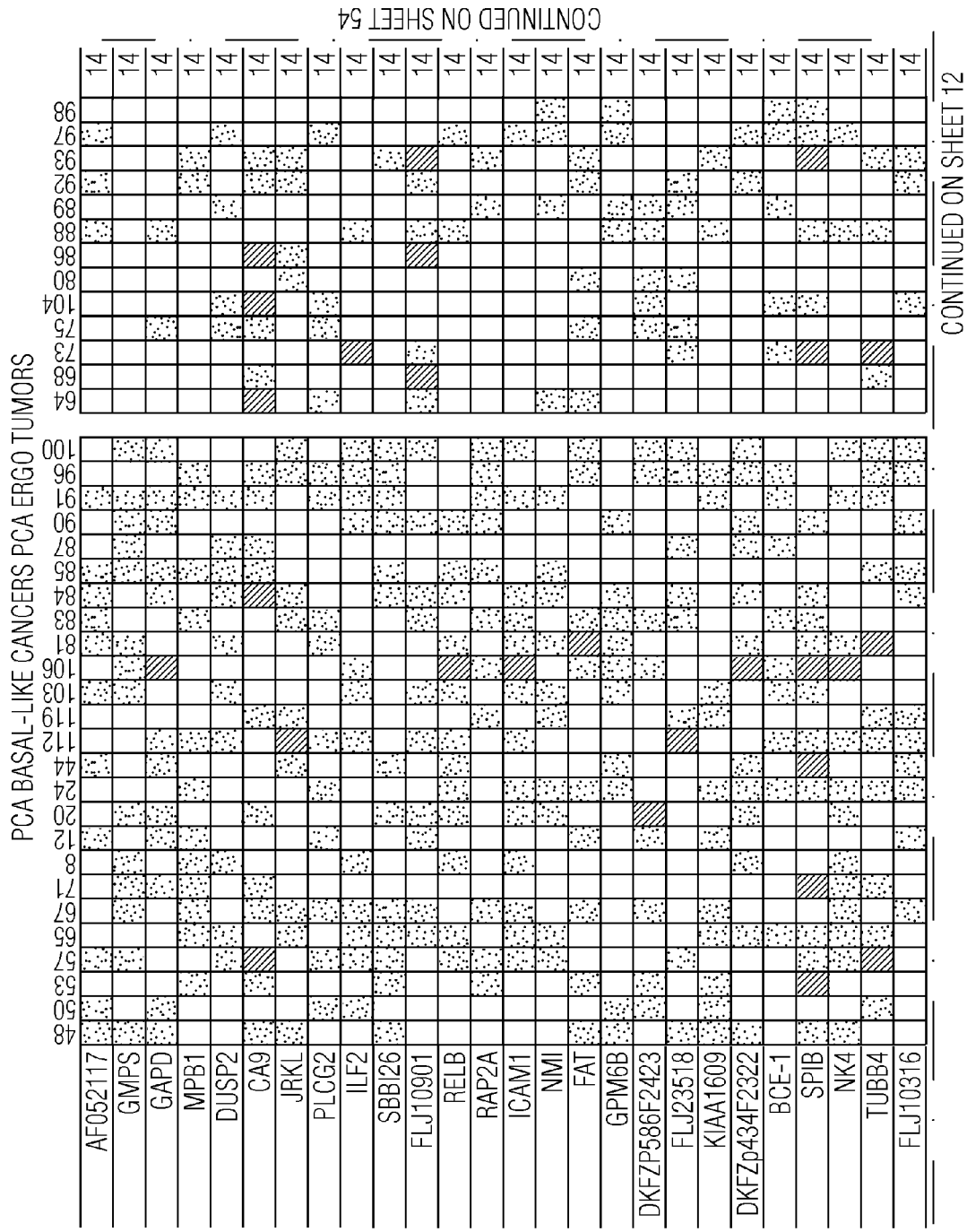
Figure 25L:
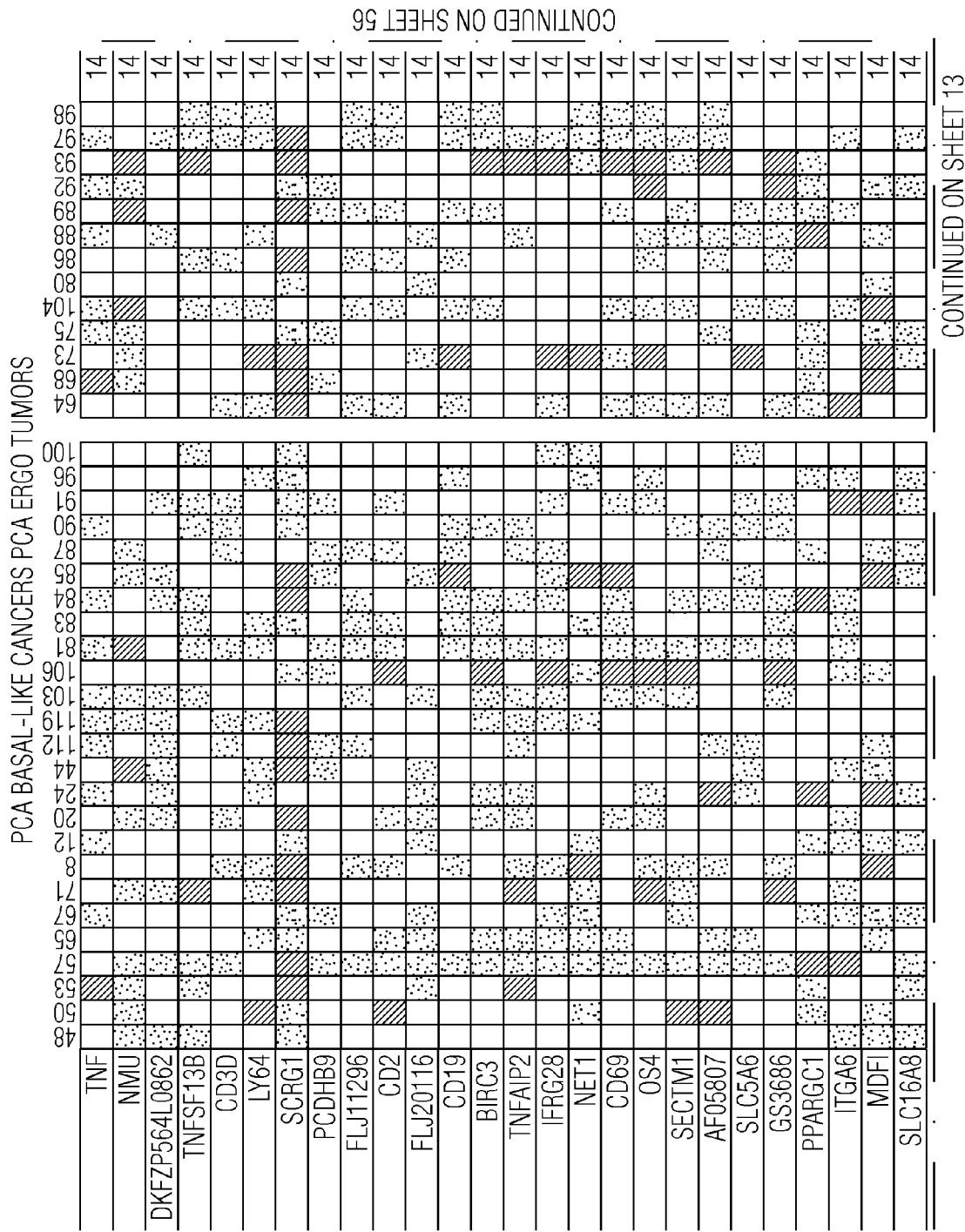
Figure 25M:
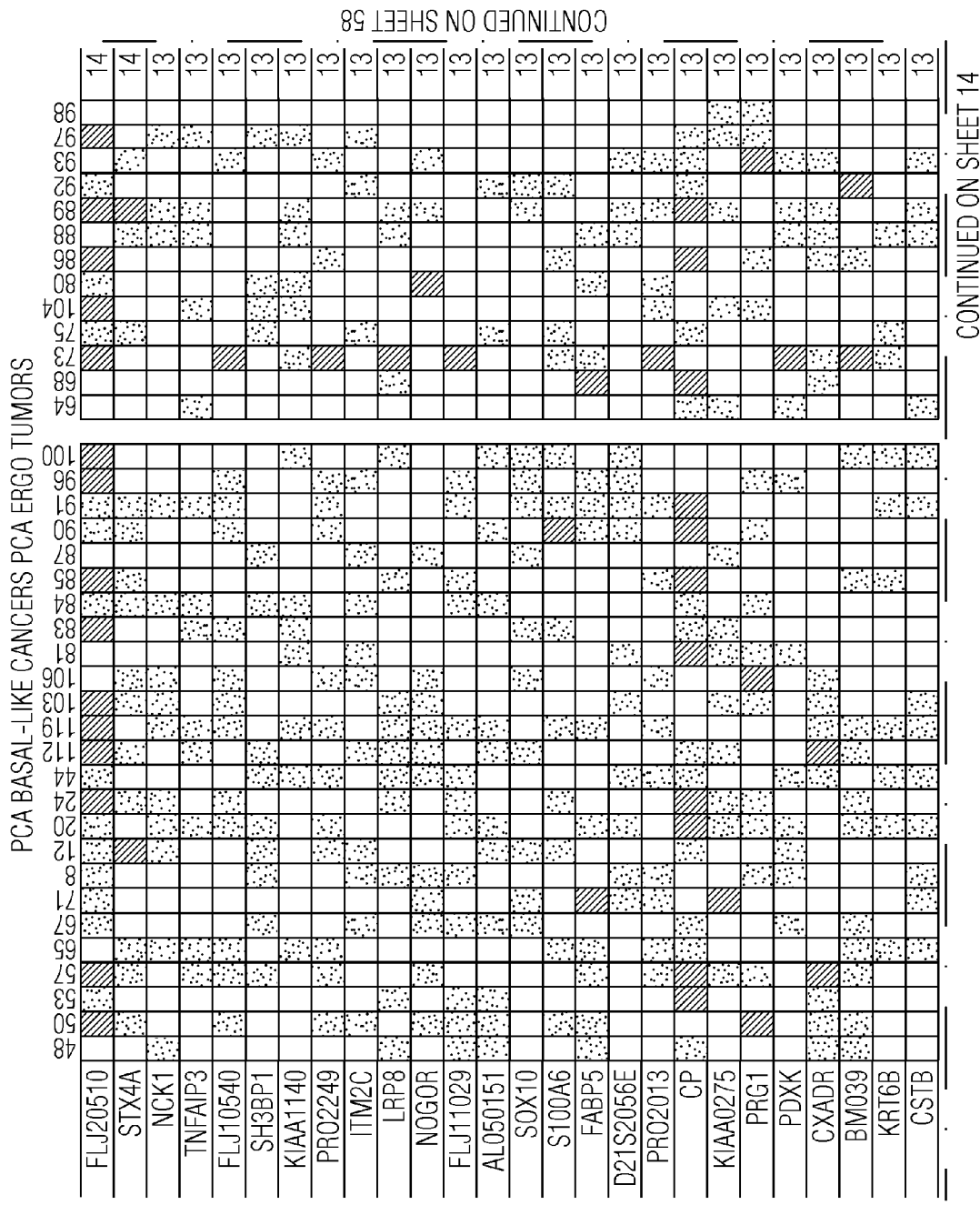
Figure 25N:
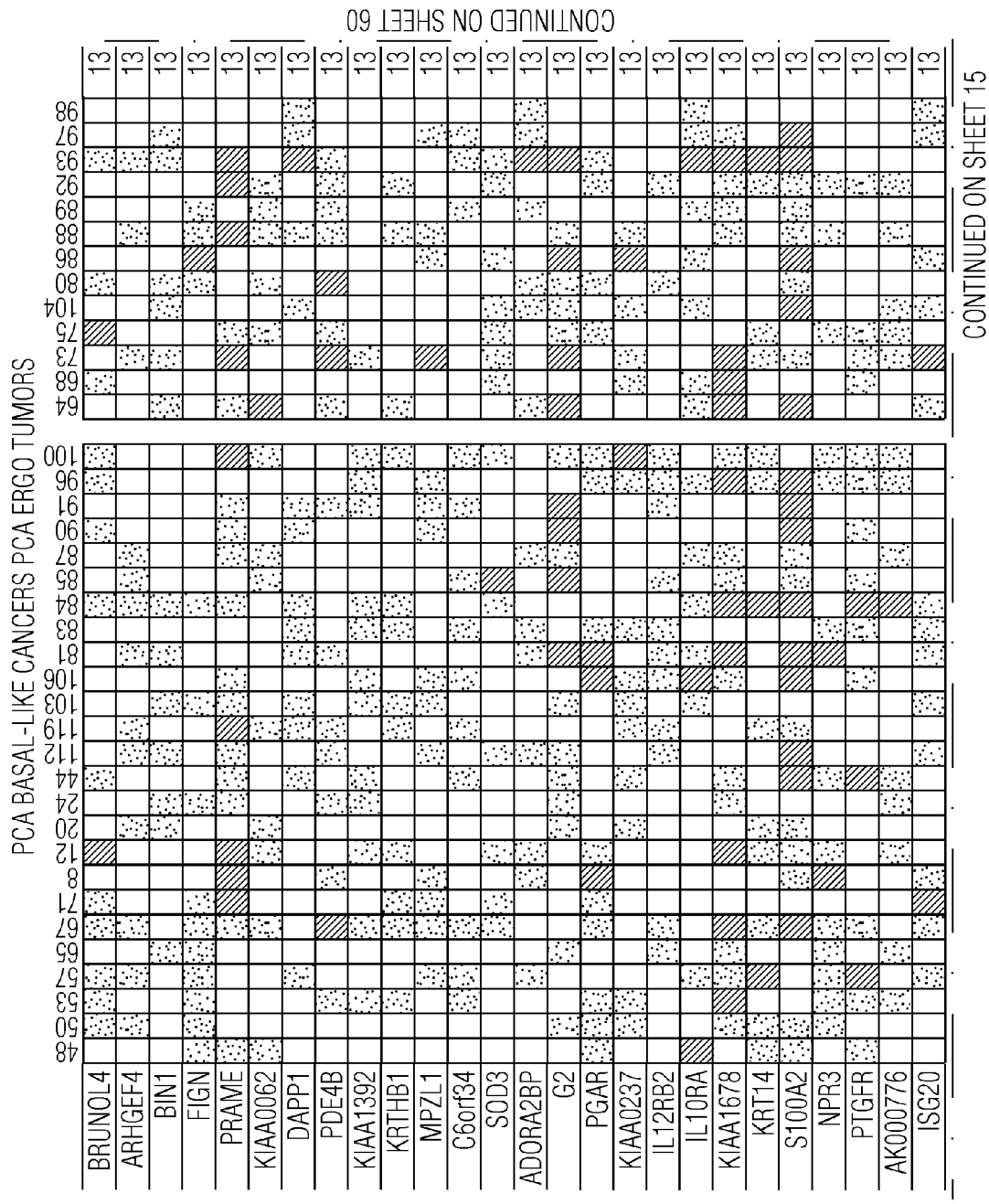
Figure 250:
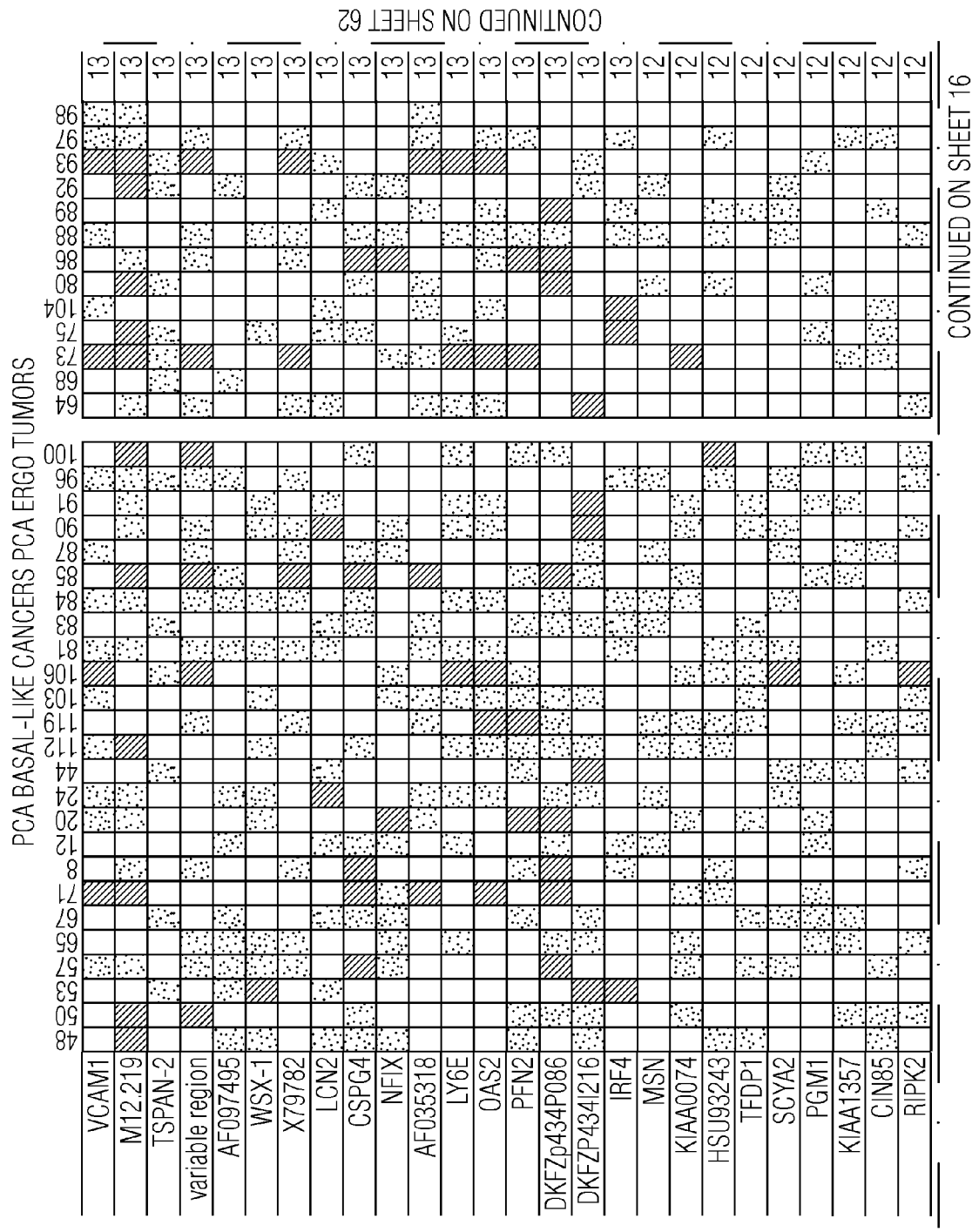
Figure 25P:
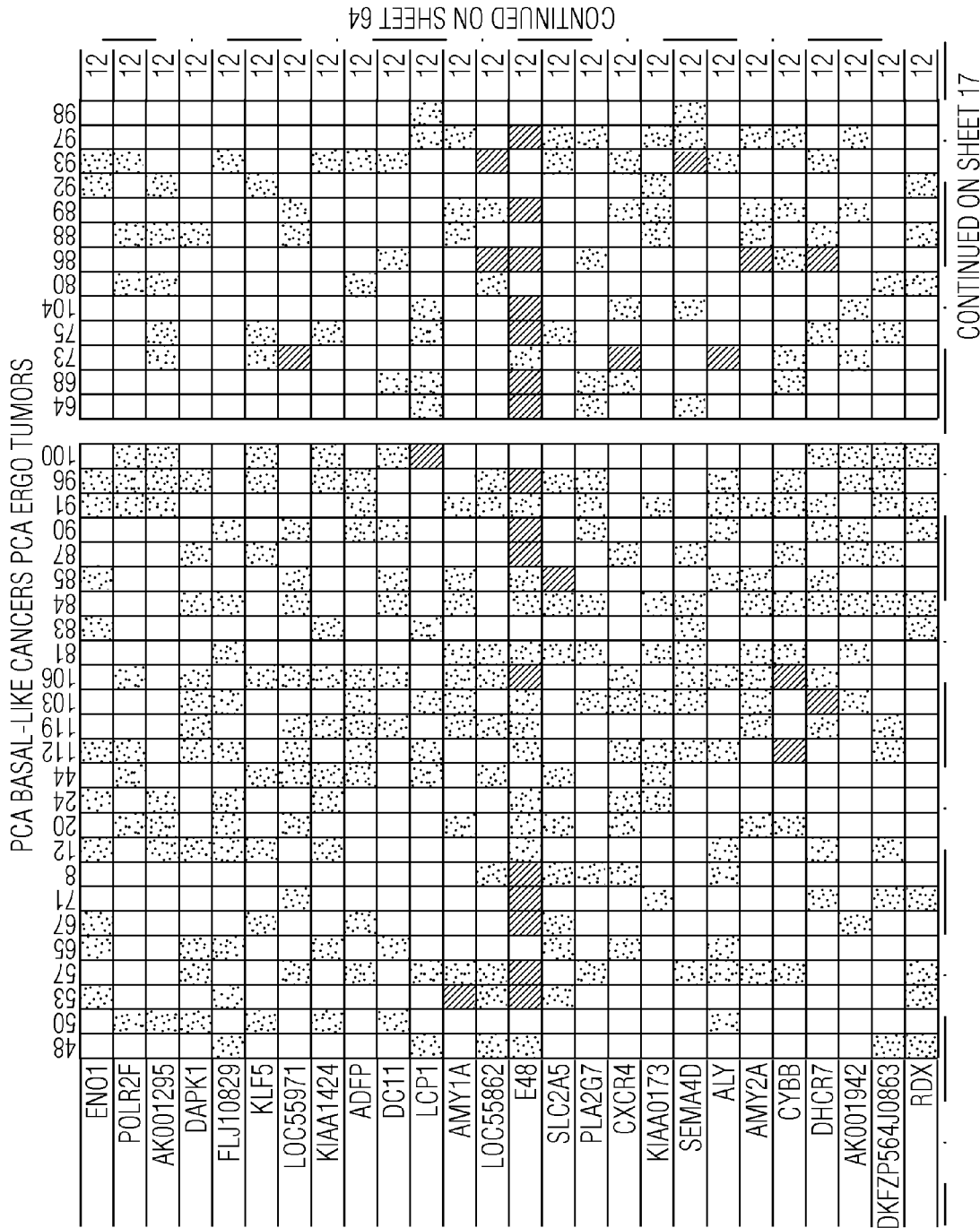
Figure 25Q:
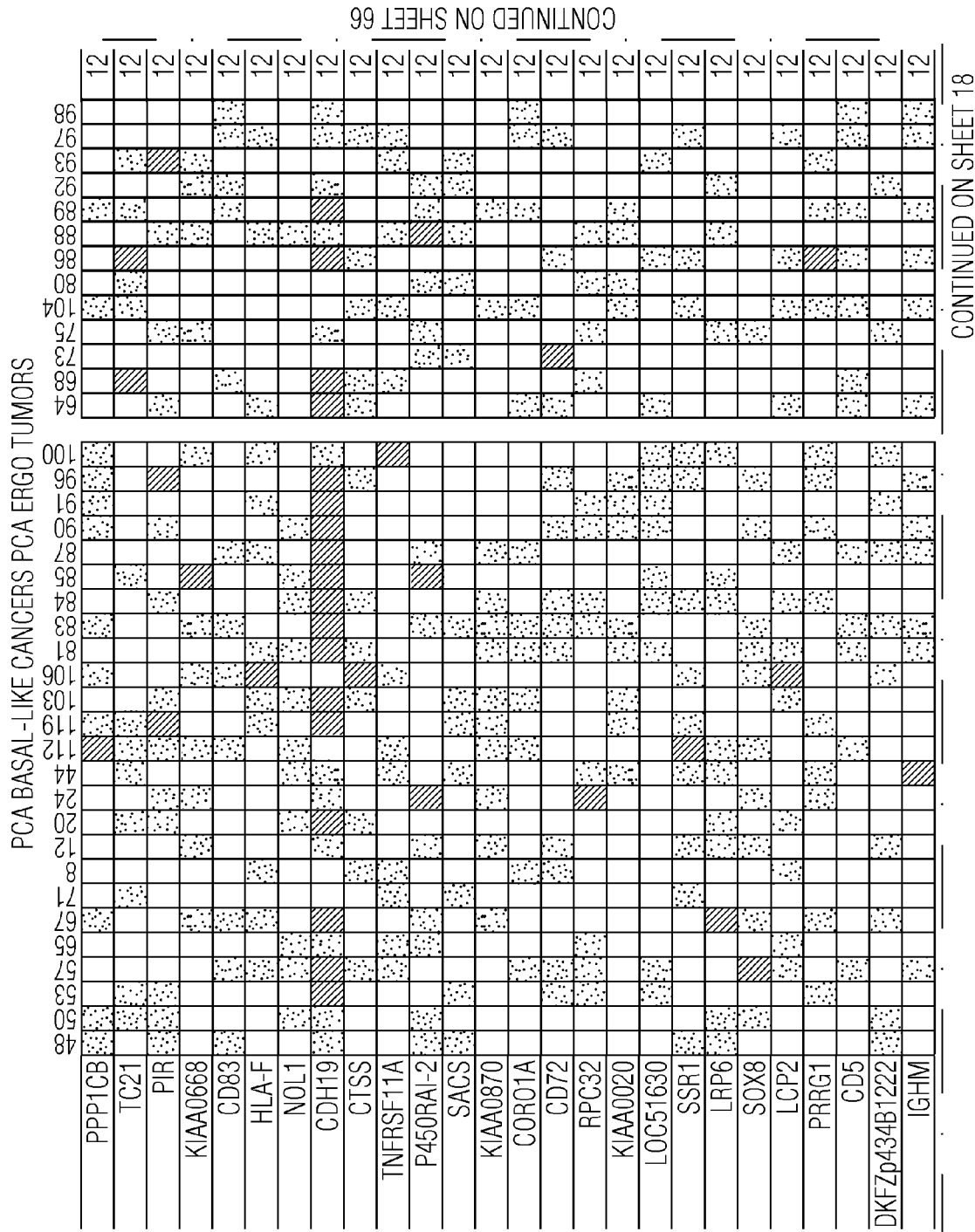
Figure 25R:
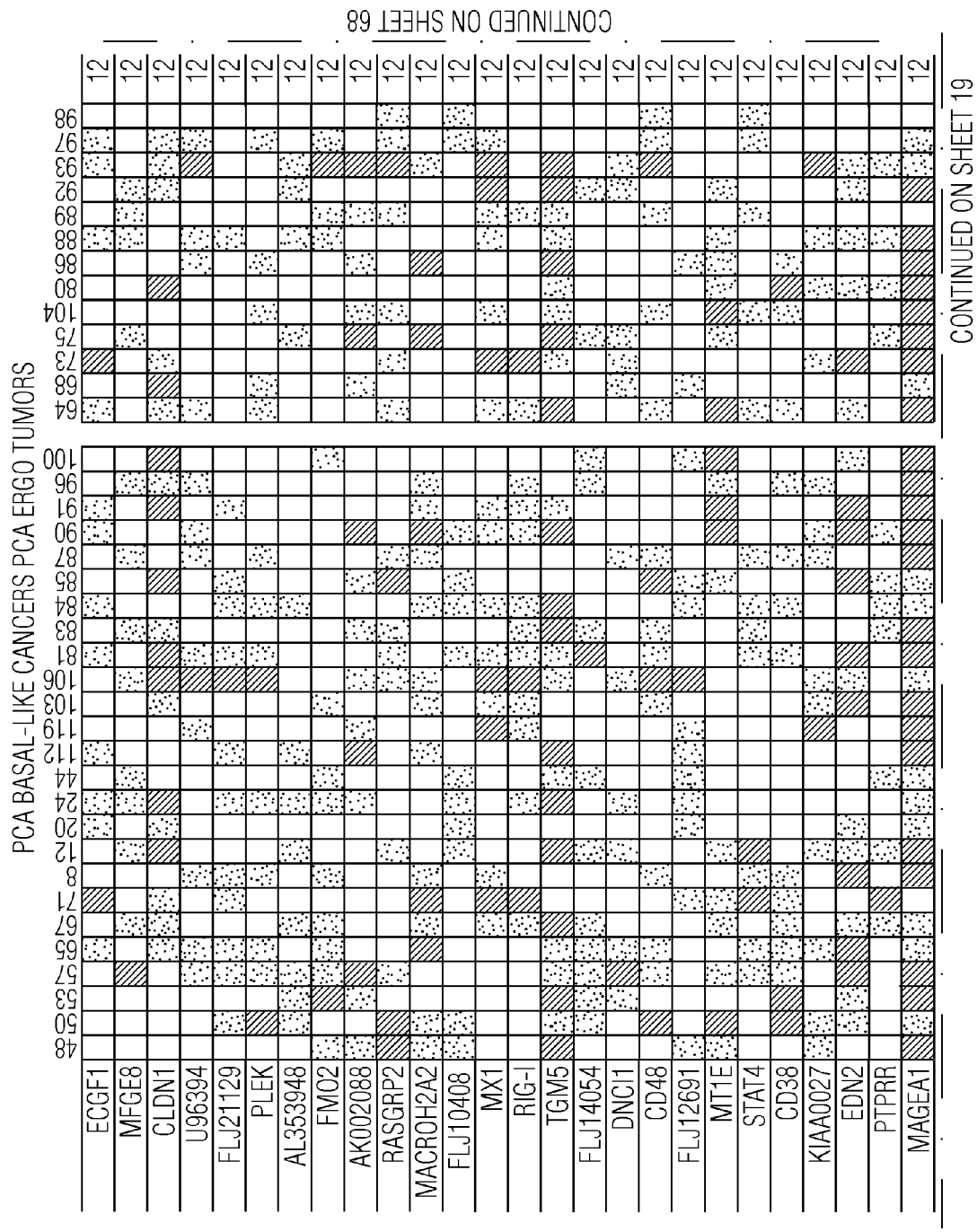
Figure 25T:
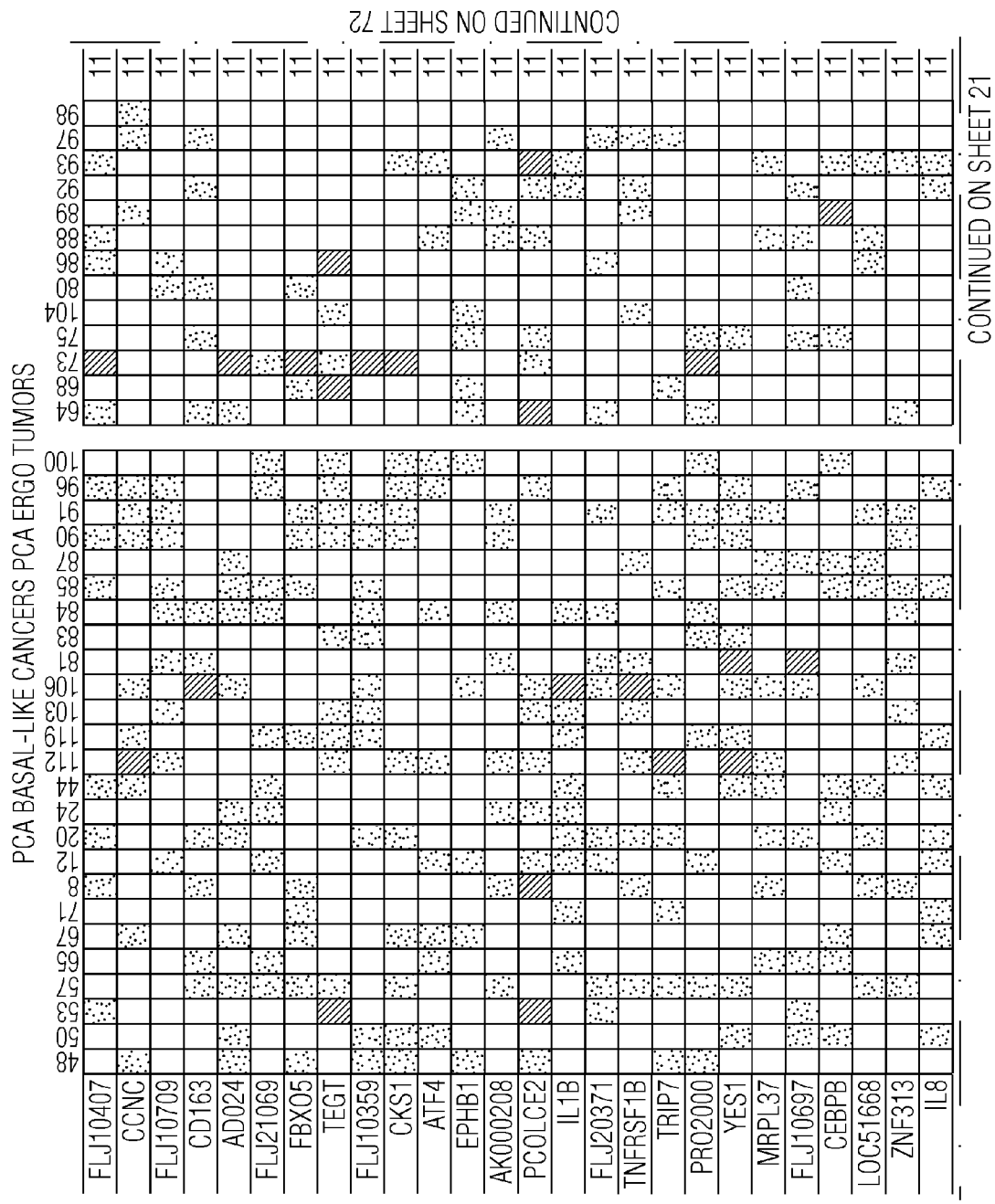
Figure 25U:
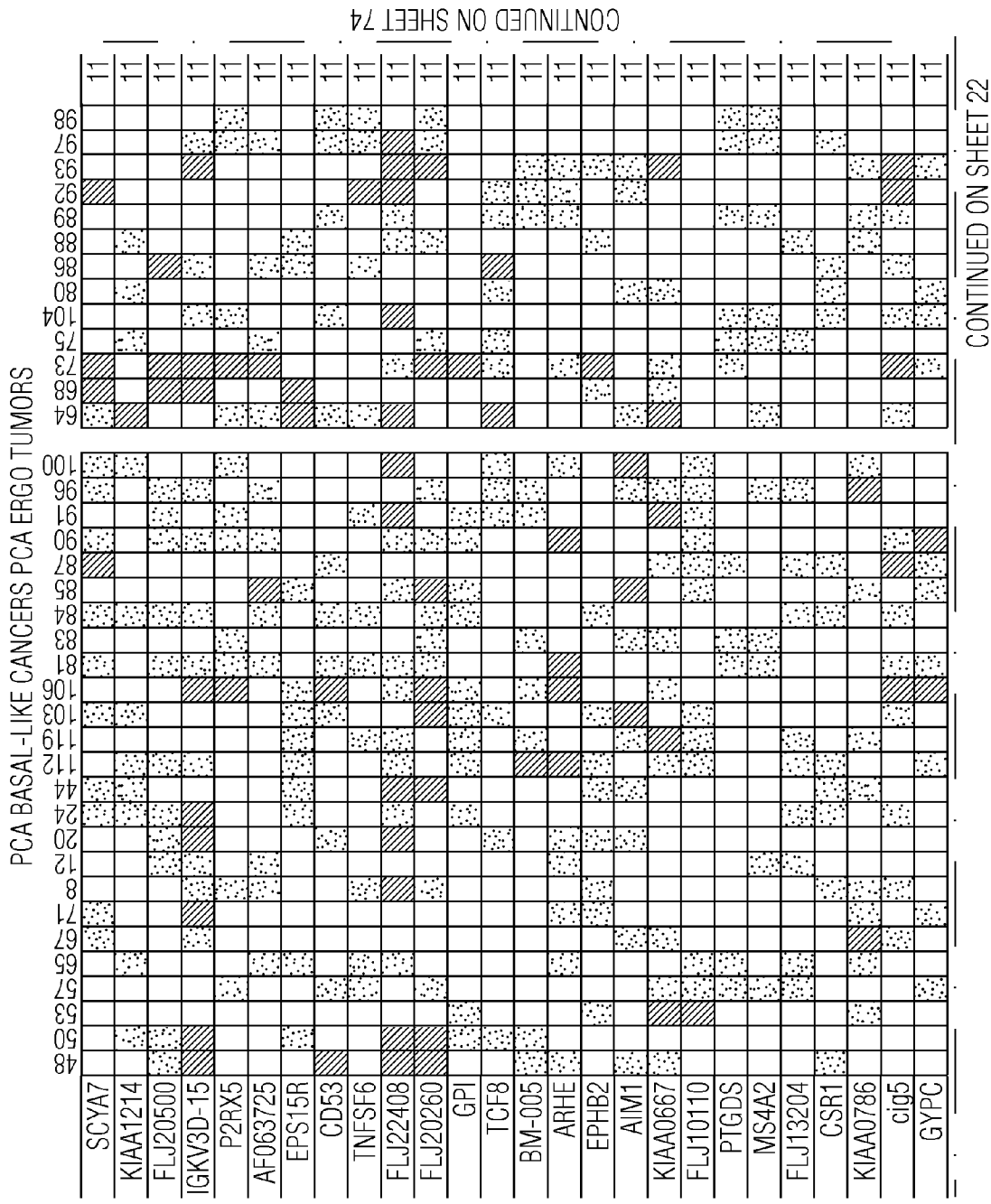
Figure 25V:
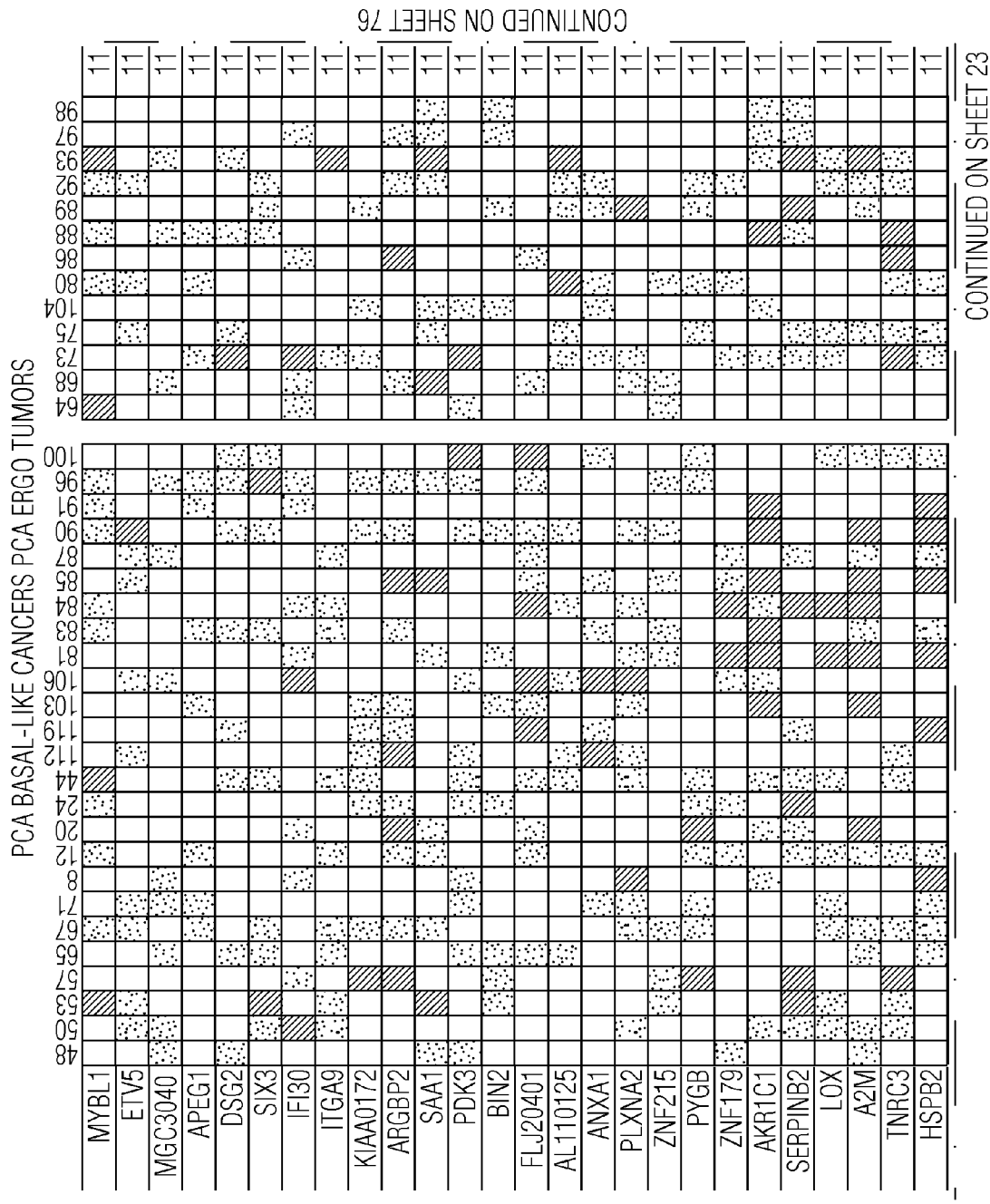
Figure 25W:
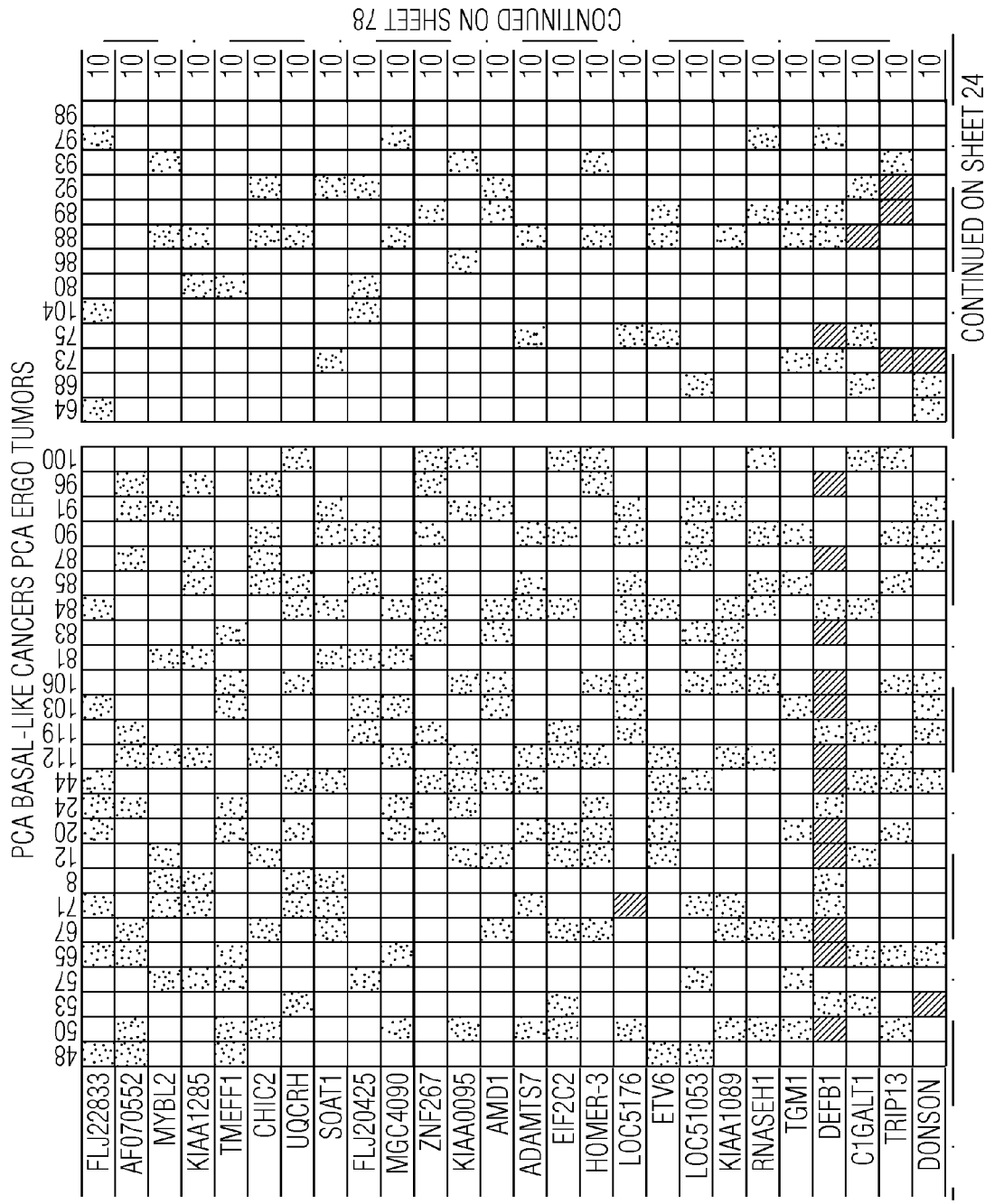
Figure 25X:
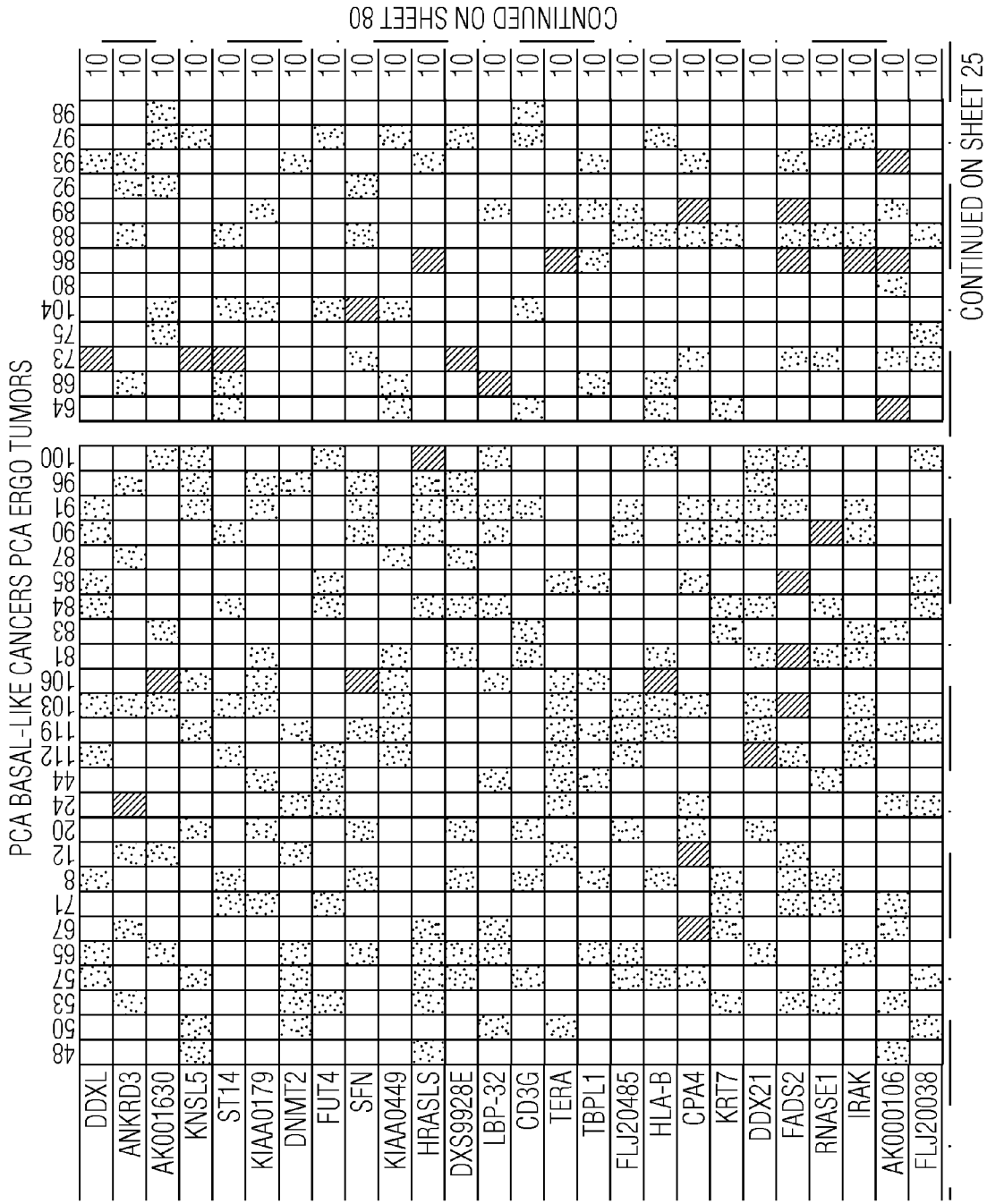
Figure 25Y:
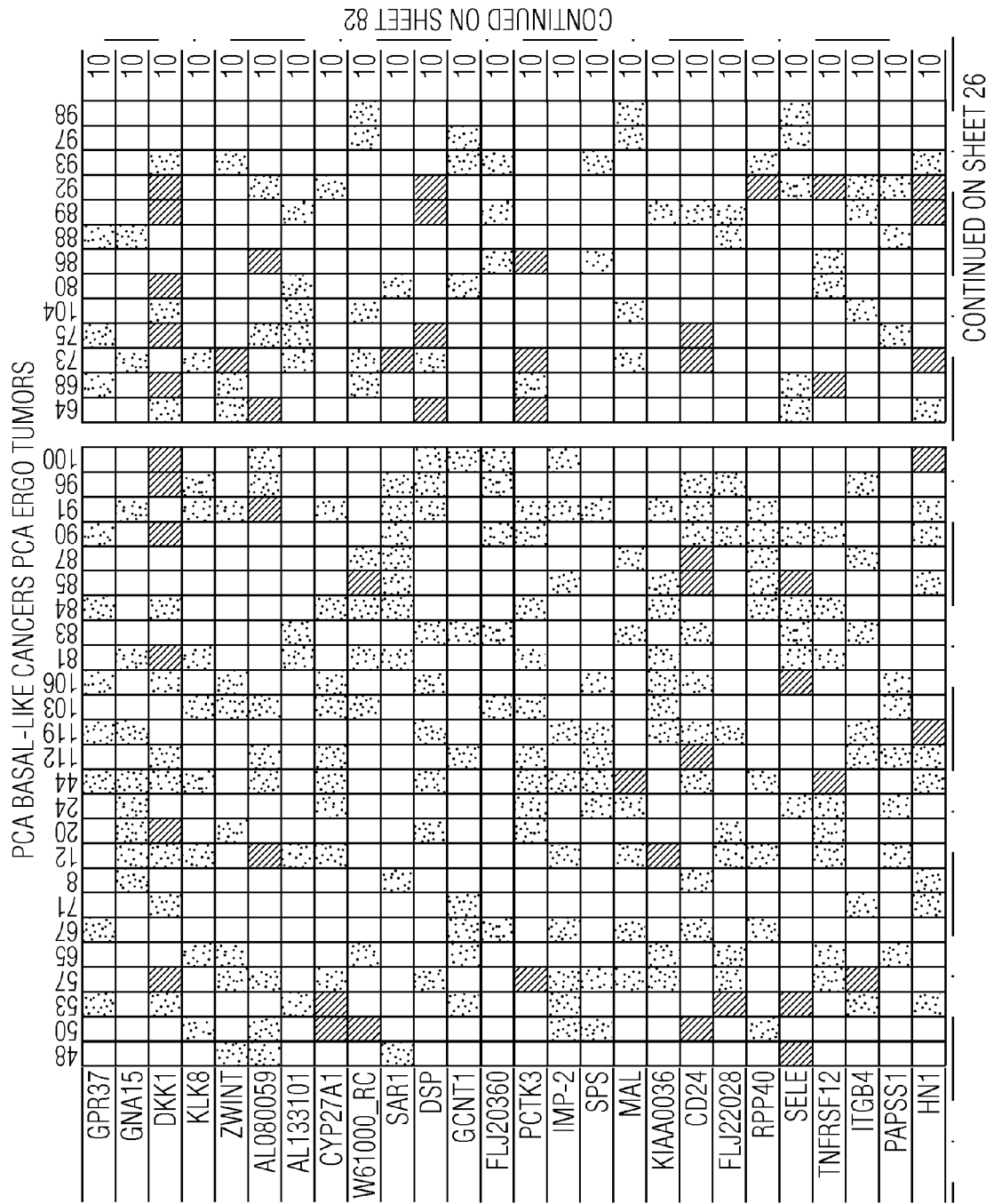
Figure 25Z:
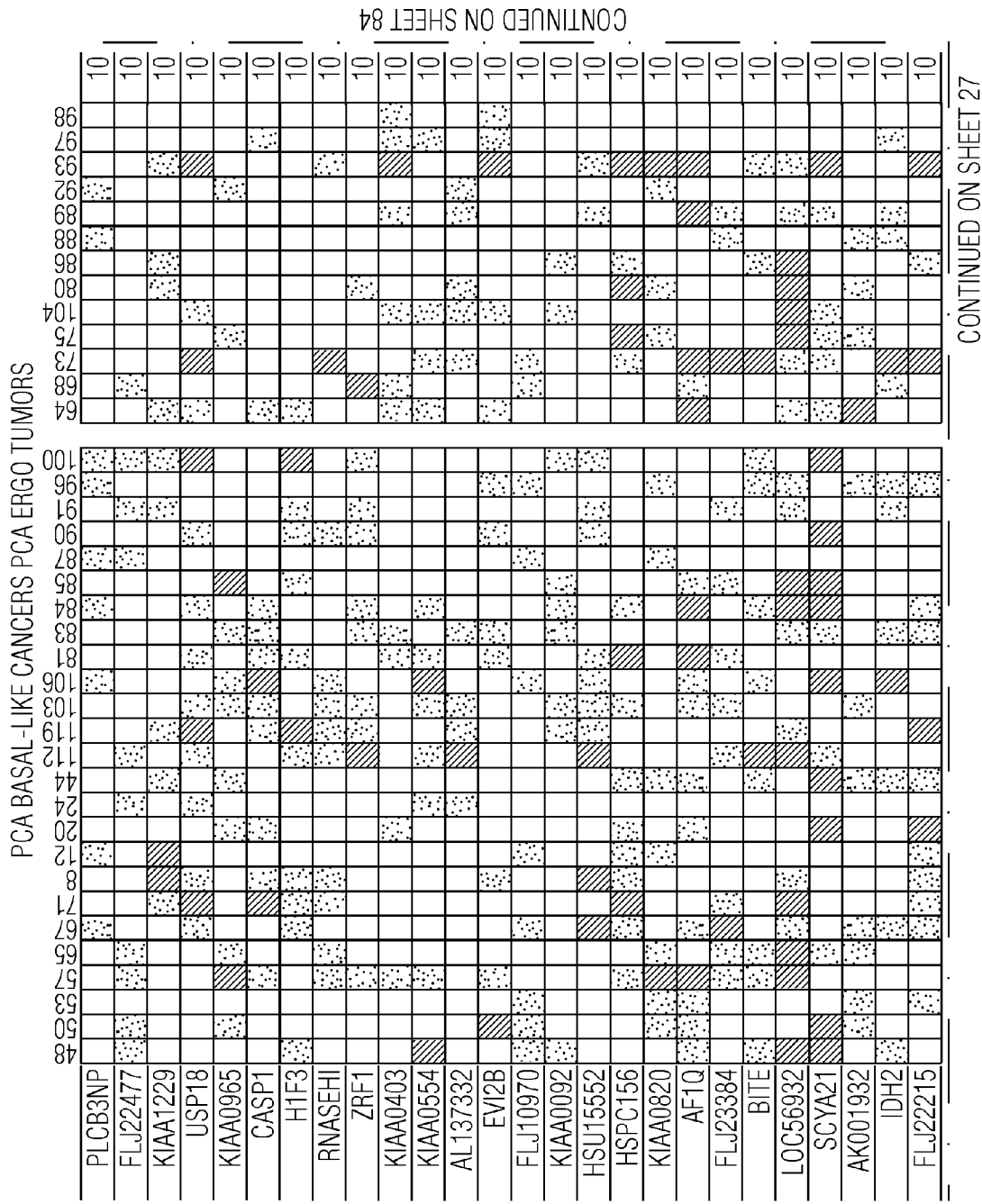
Figure 25A:
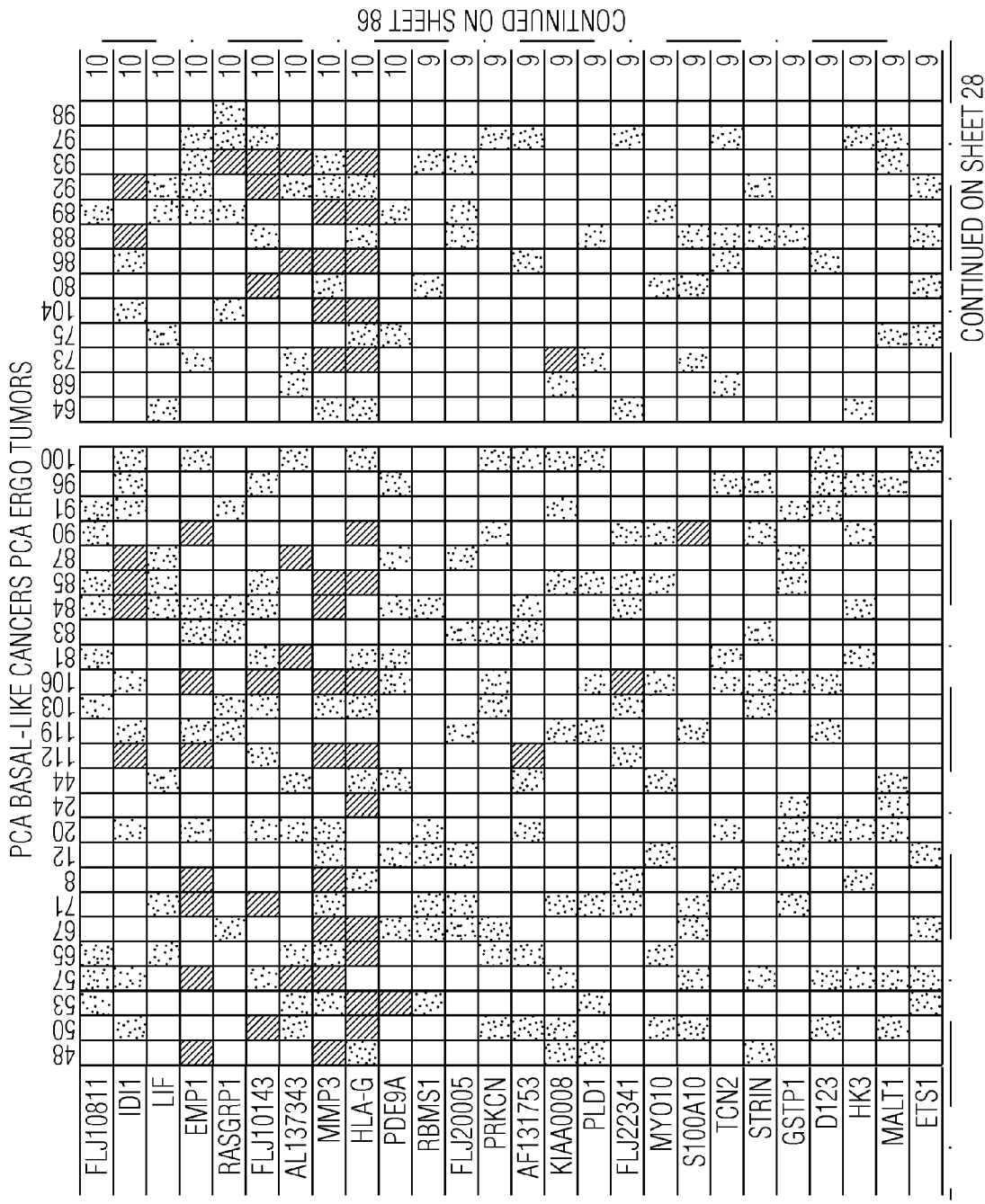
Figure 25B:
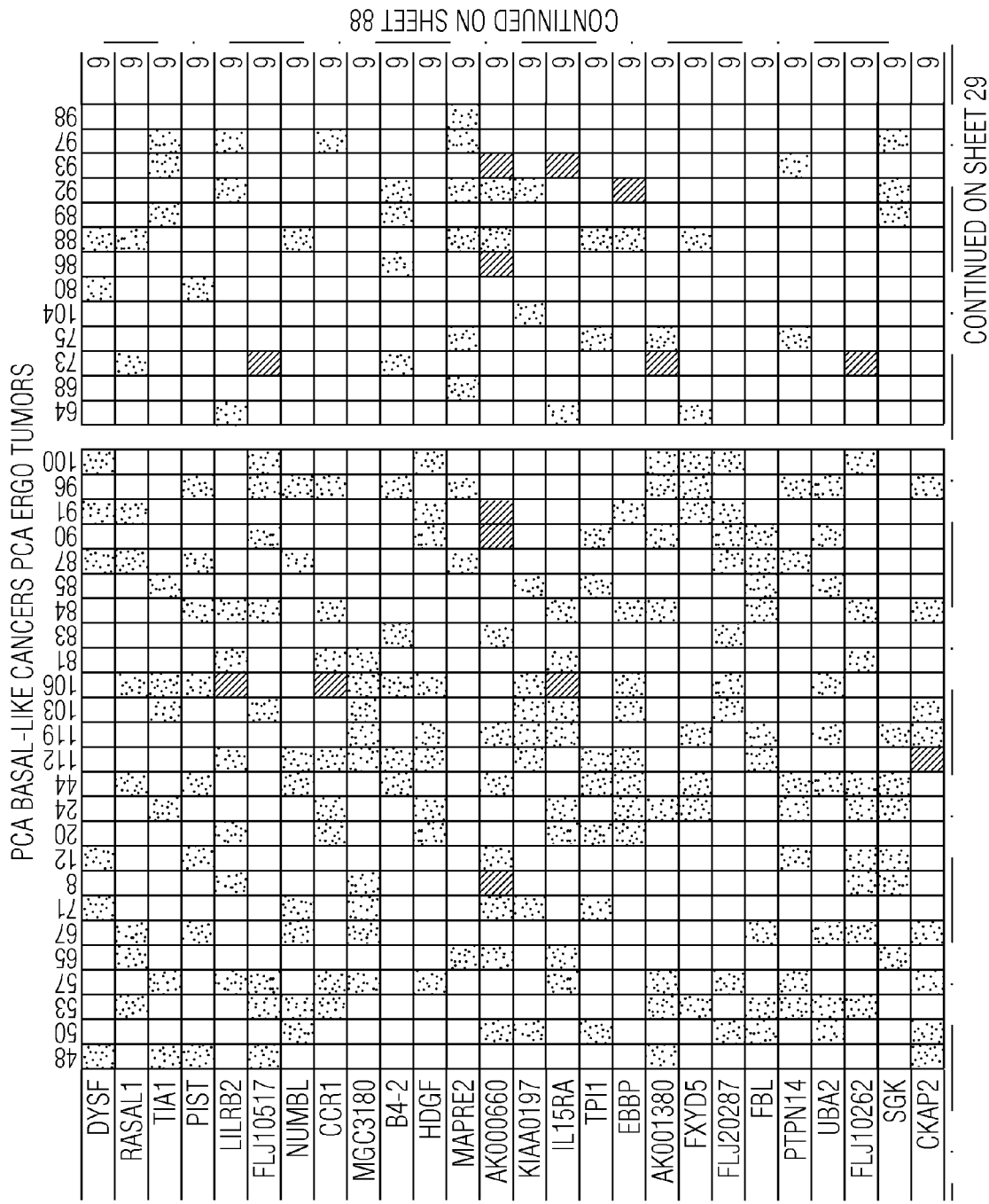
Figure 25C:
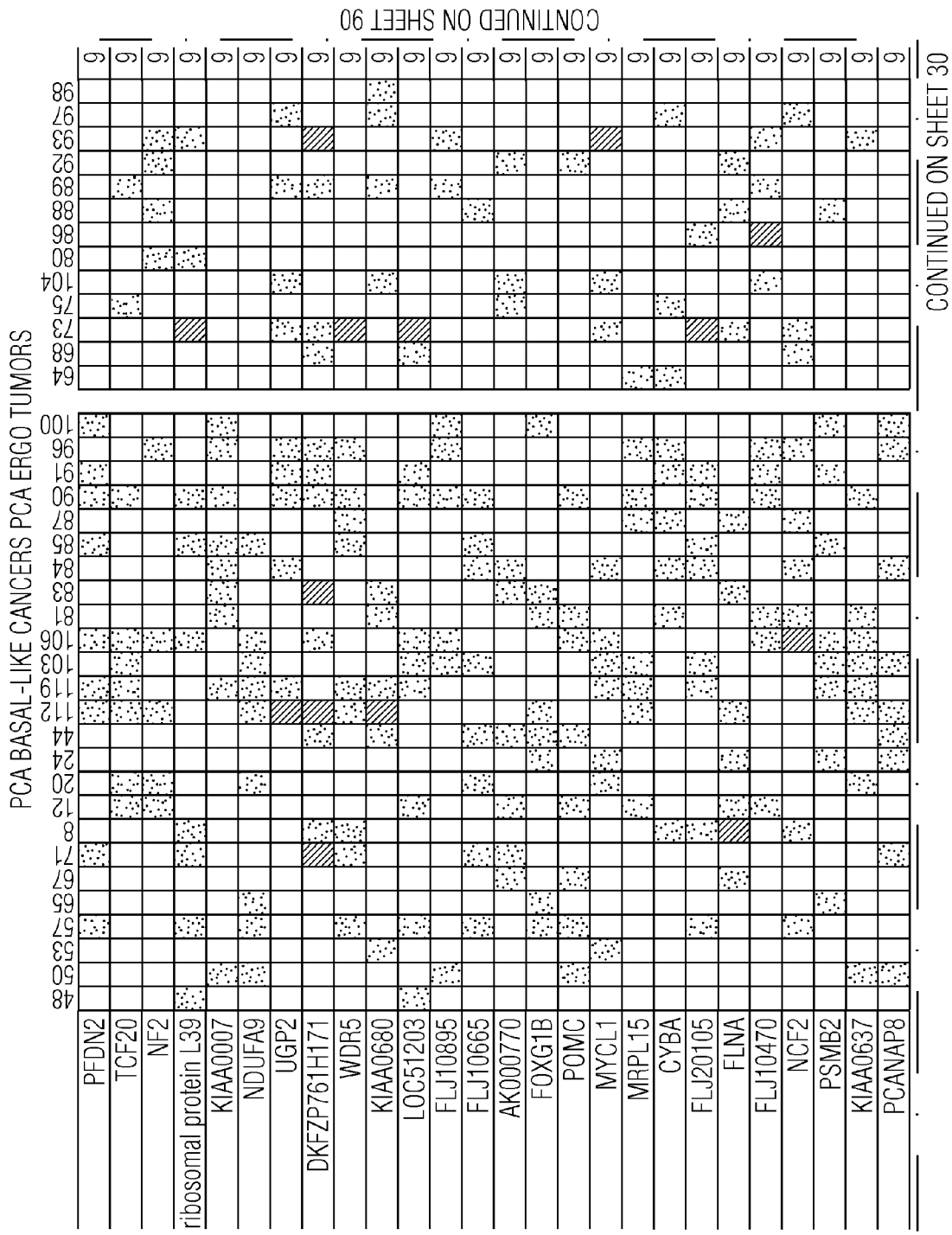
Figure 25D:
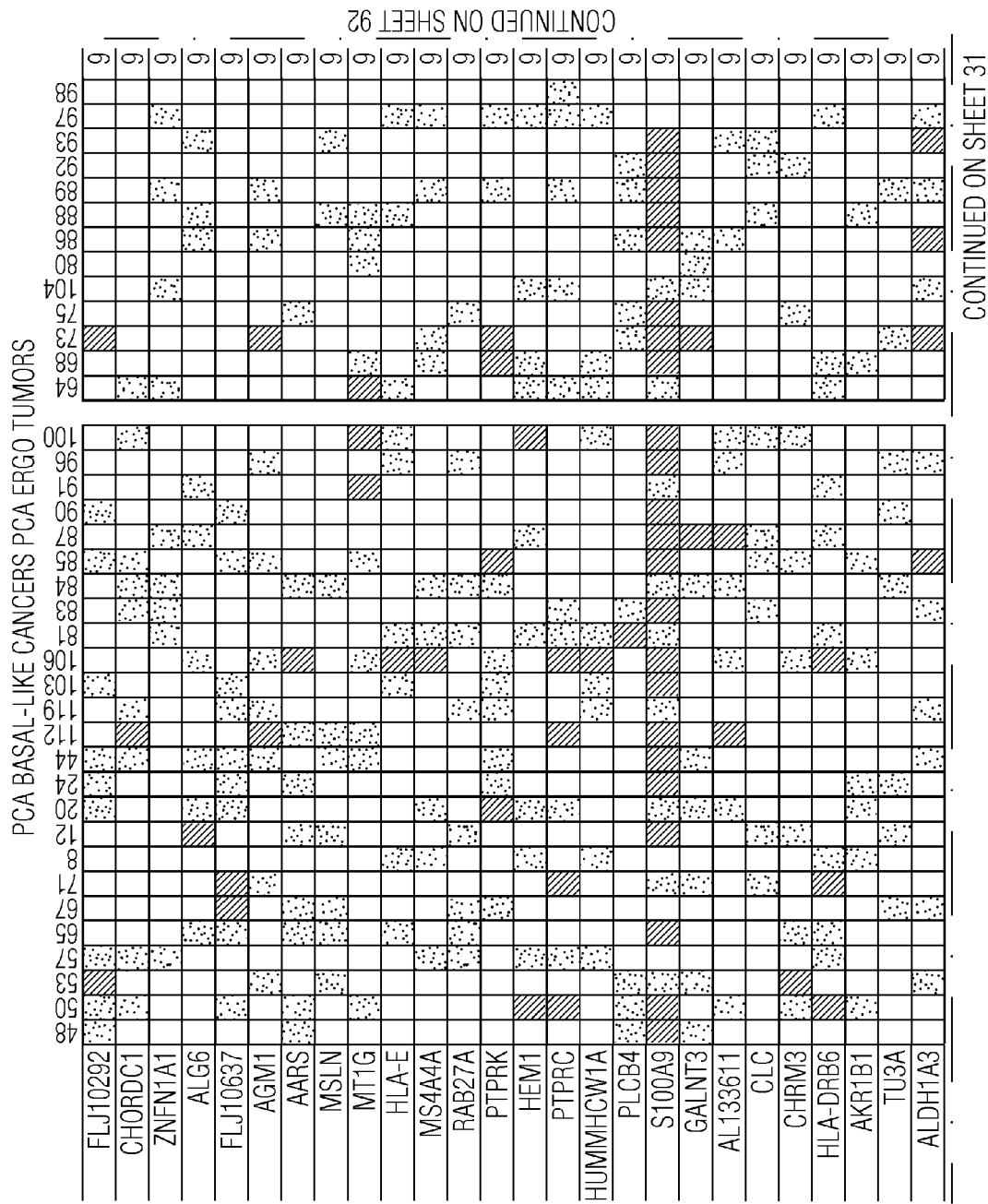
Figure 25E:
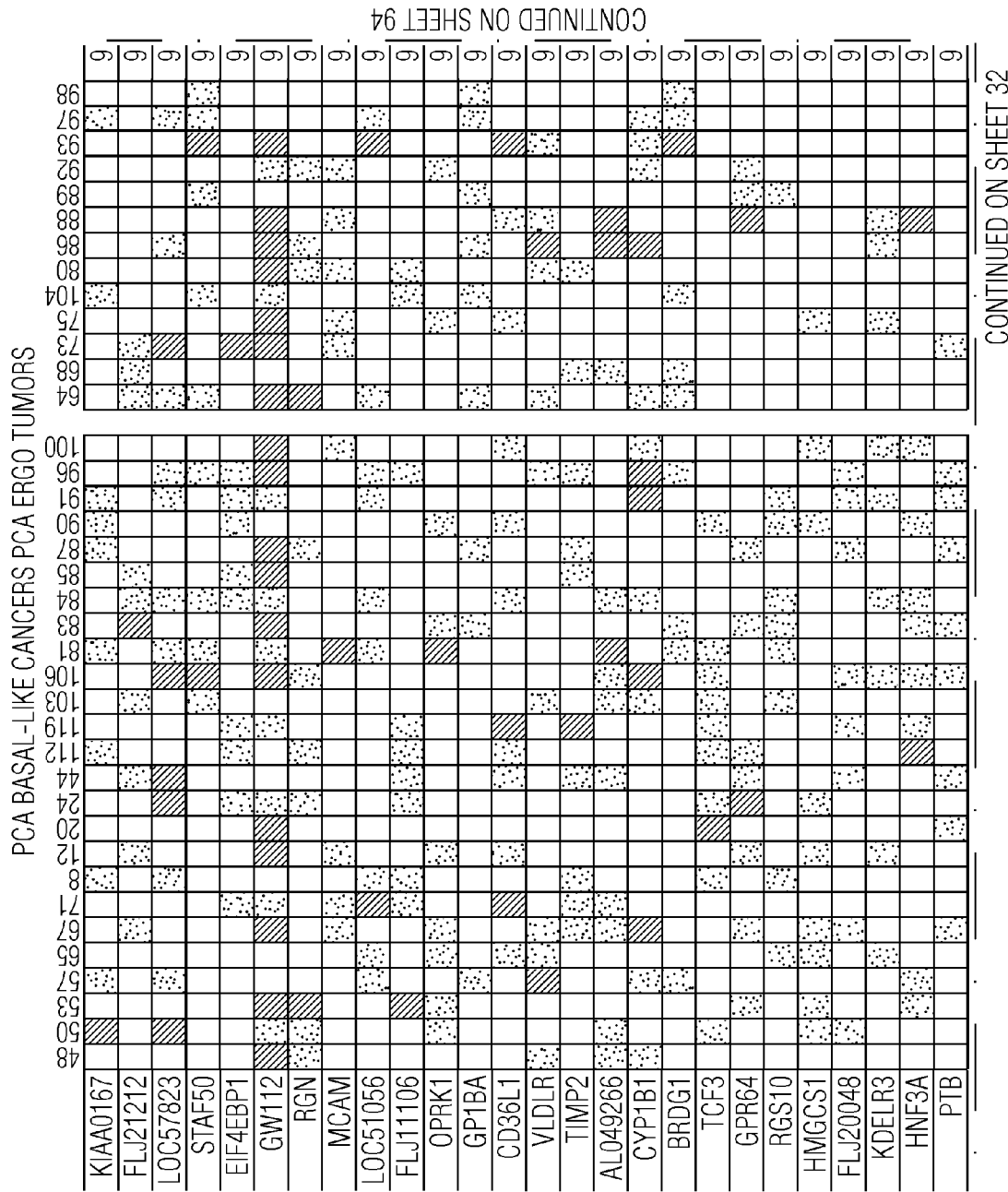
Figure 25F:
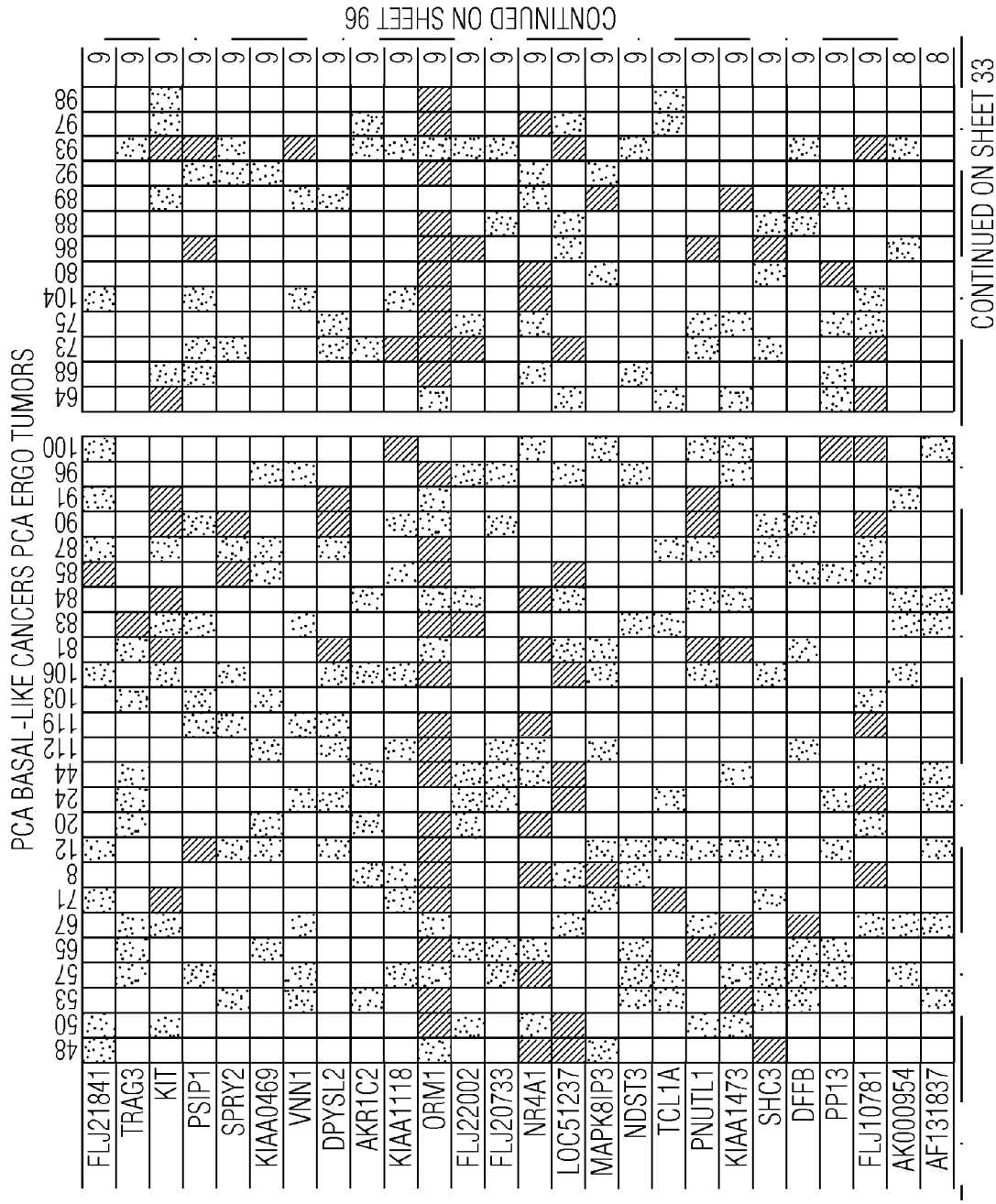
Figure 25G:
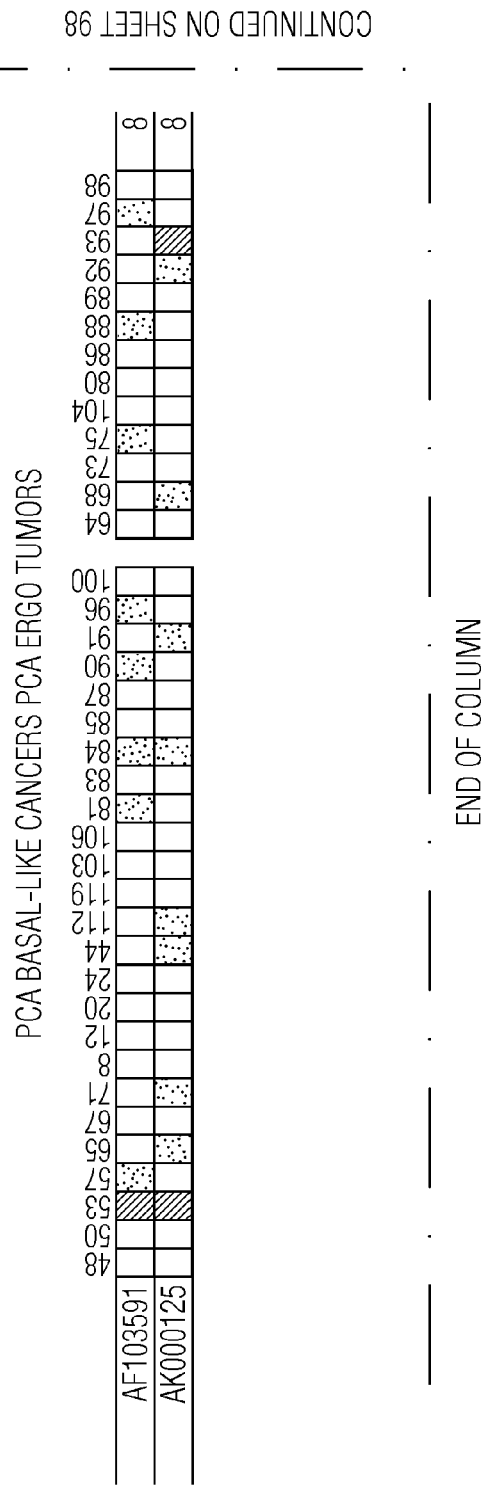
Figure 25H:
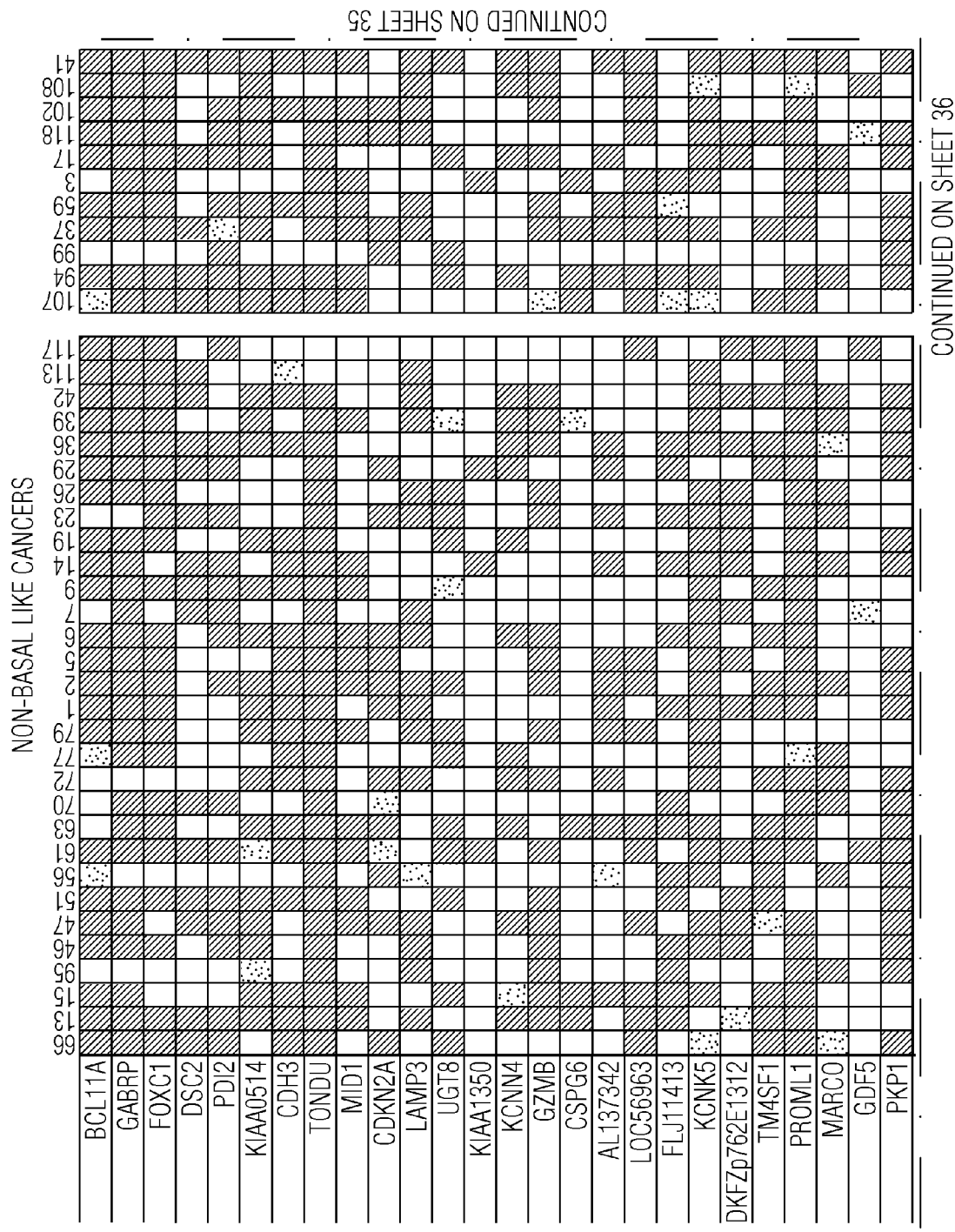
Figure 25I:
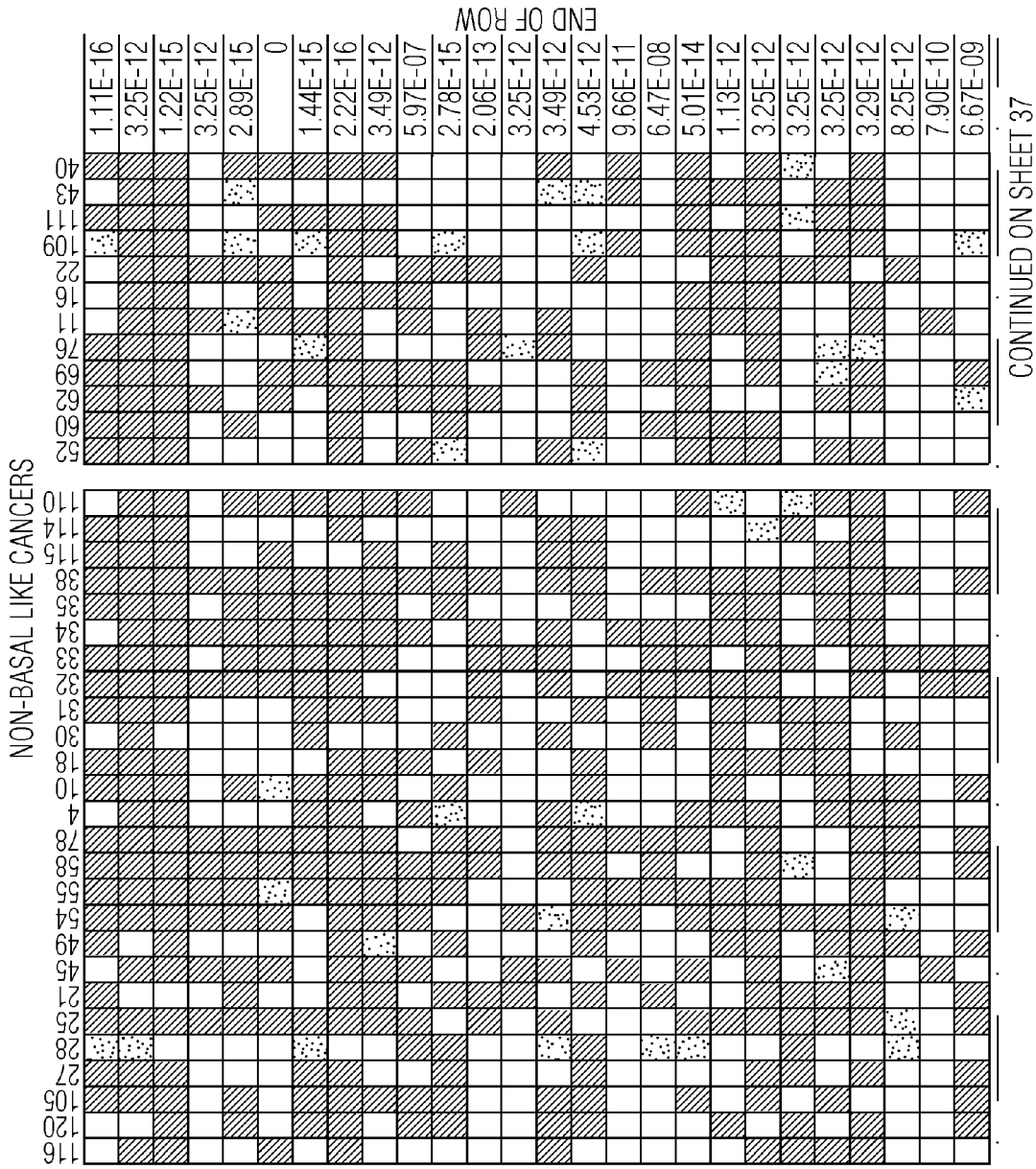
Figure 25J:
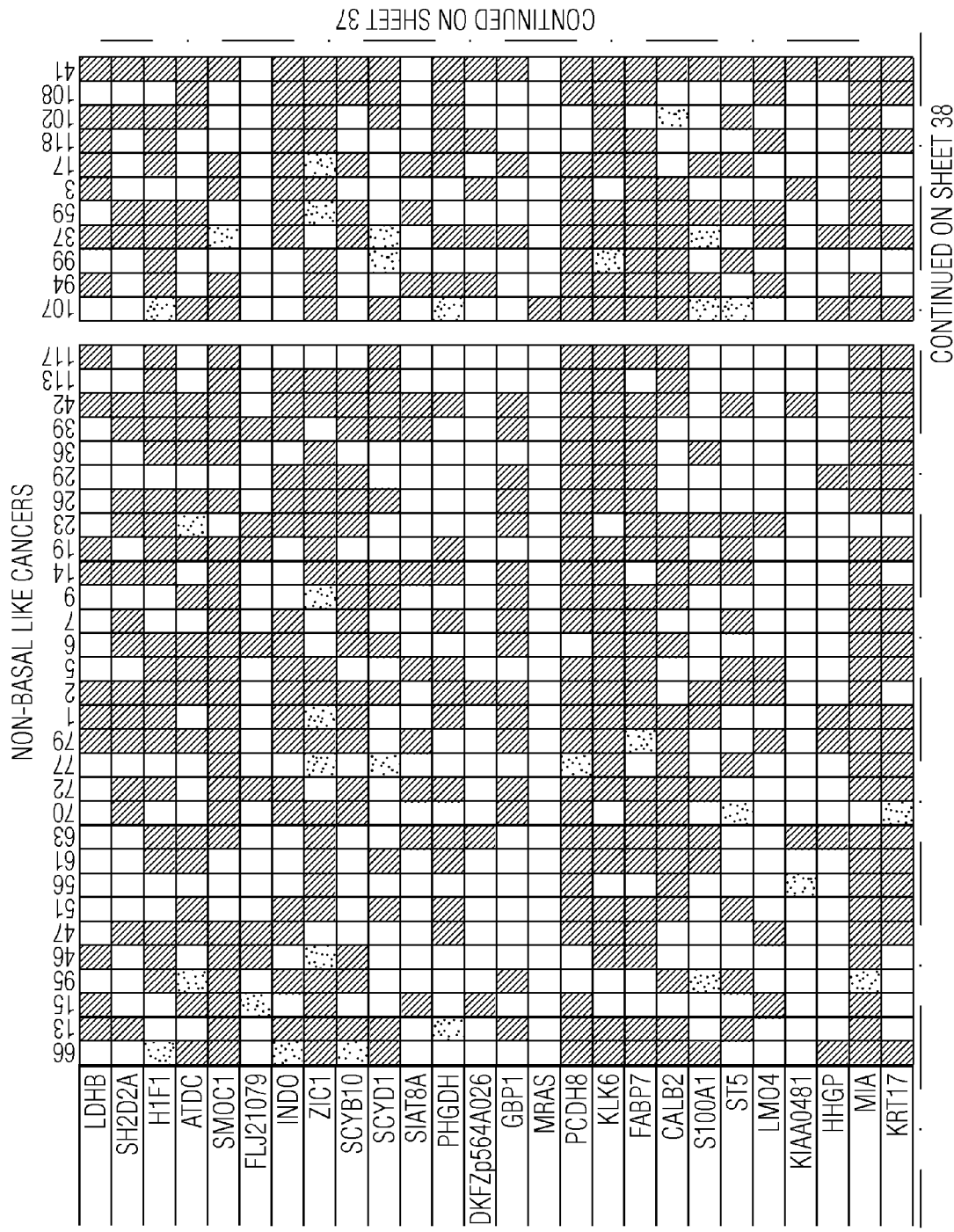
Figure 25K:
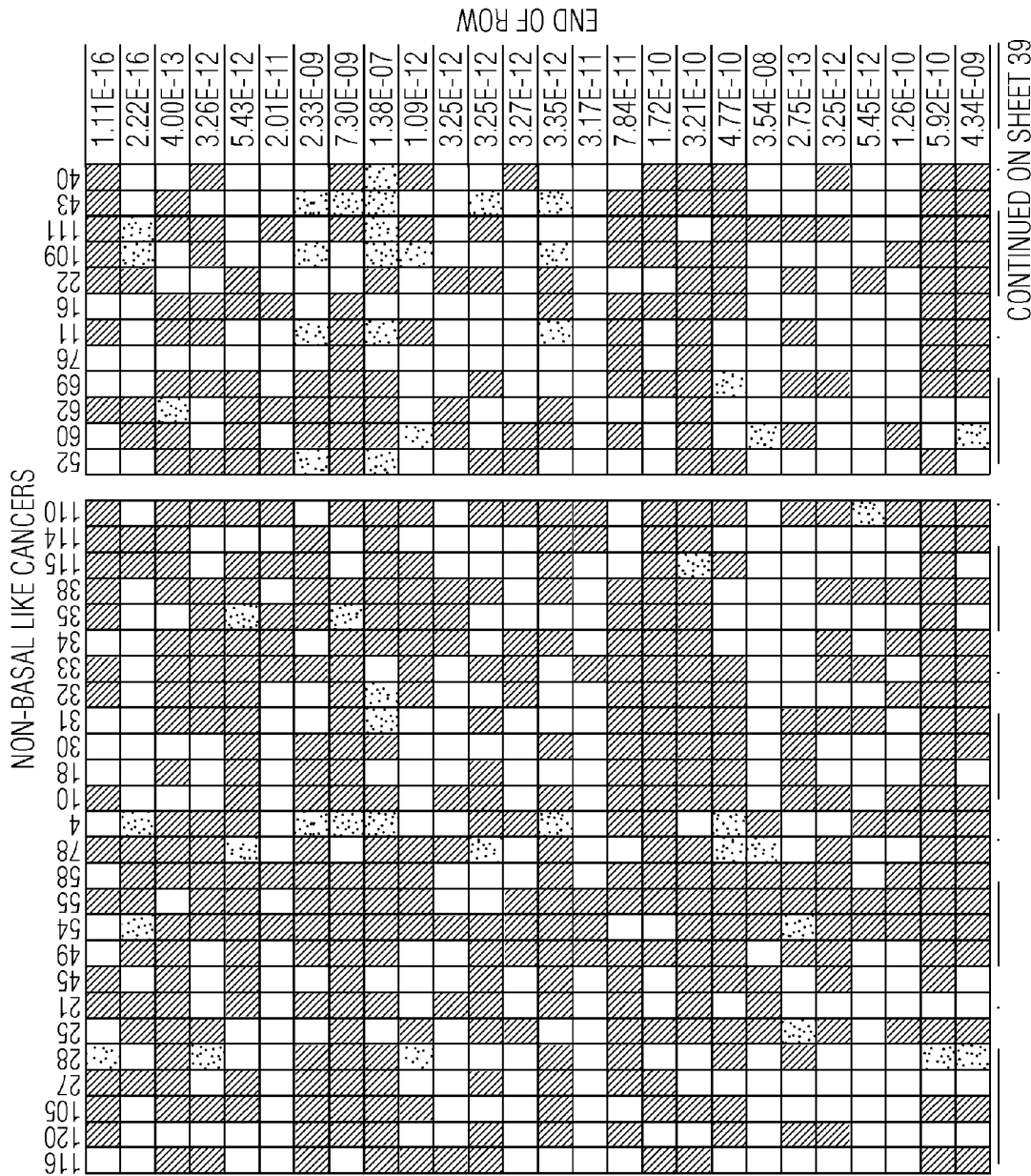
Figure 25L:
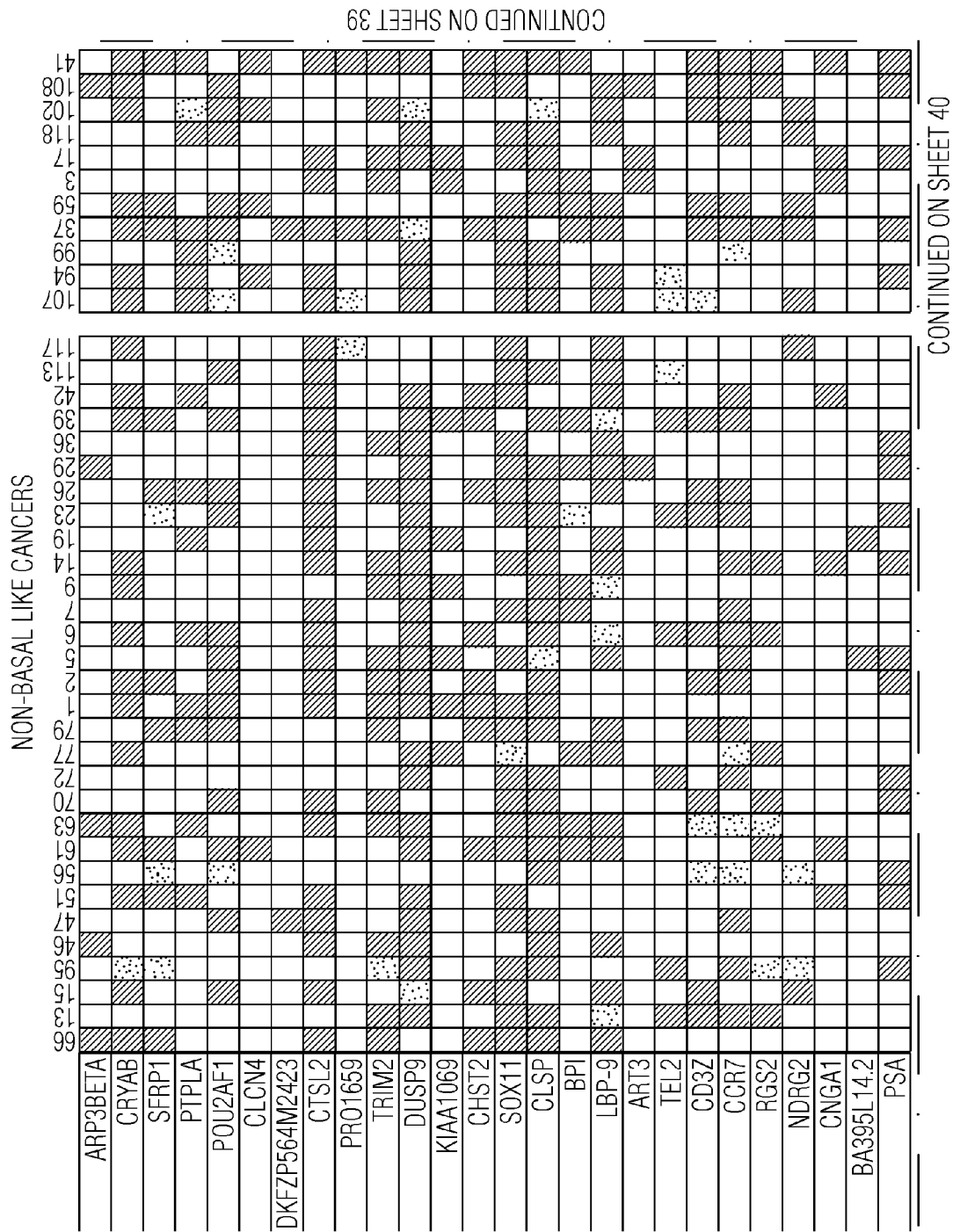
Figure 25M:
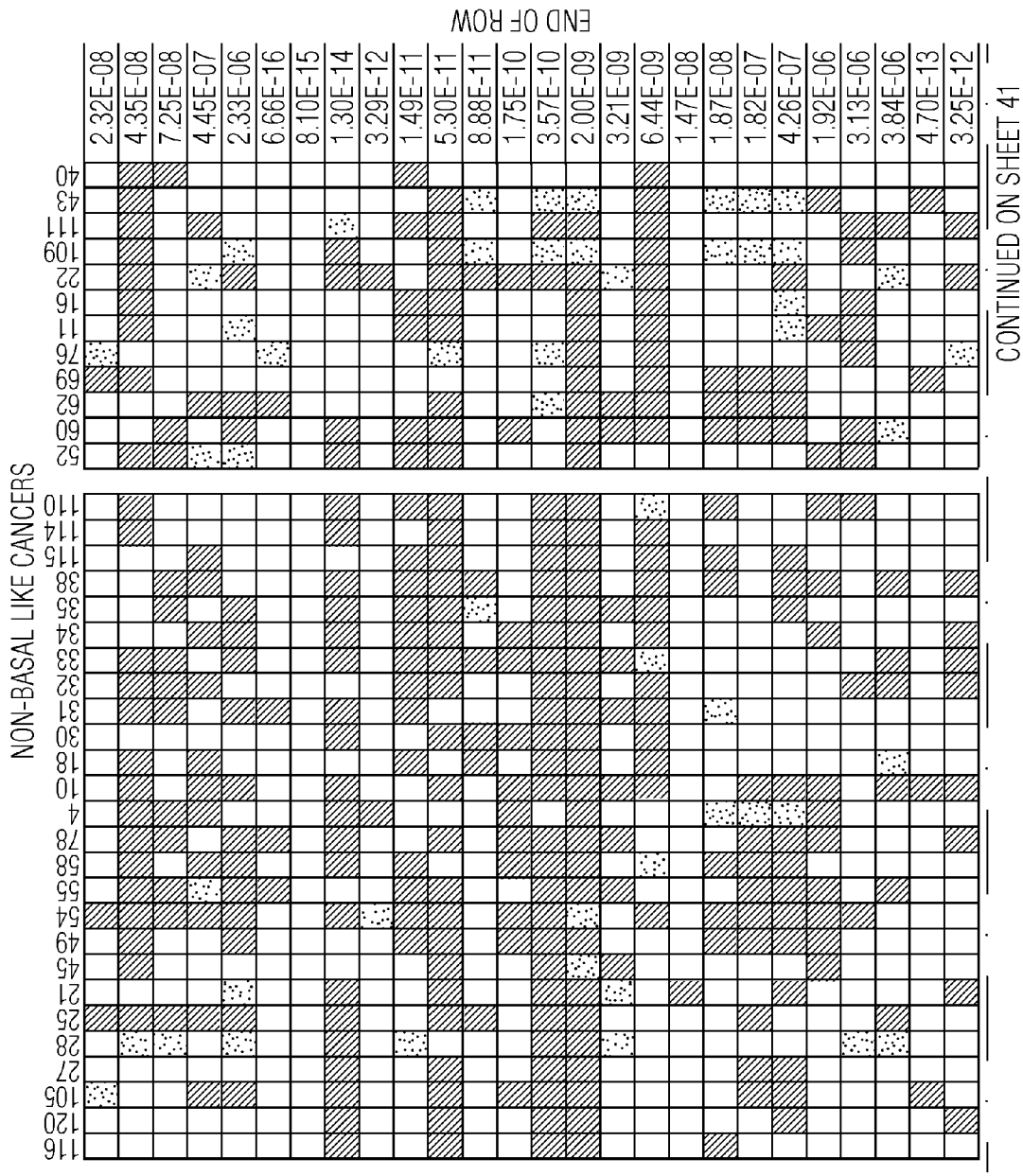
Figure 25N:
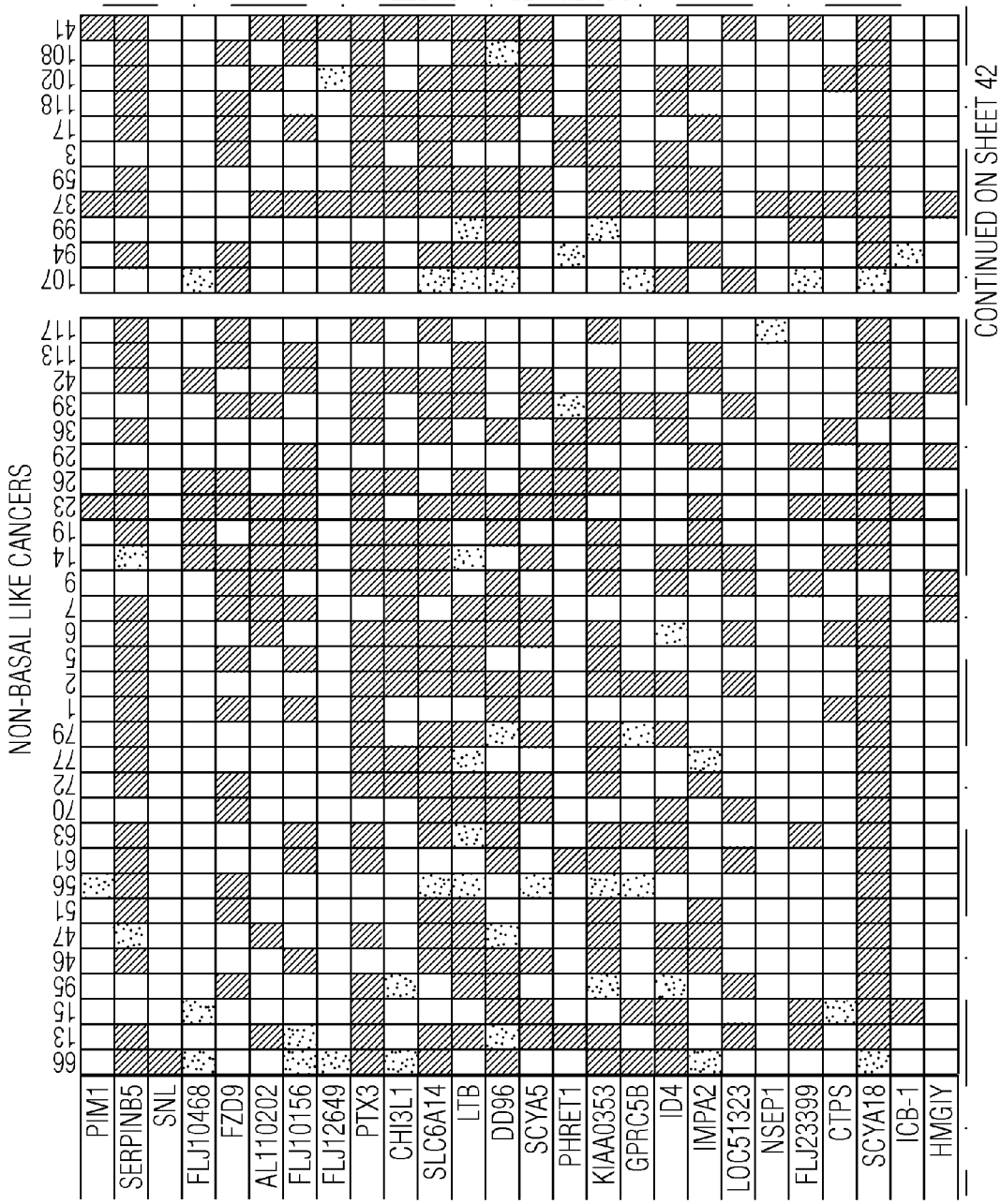
Figure 25P:
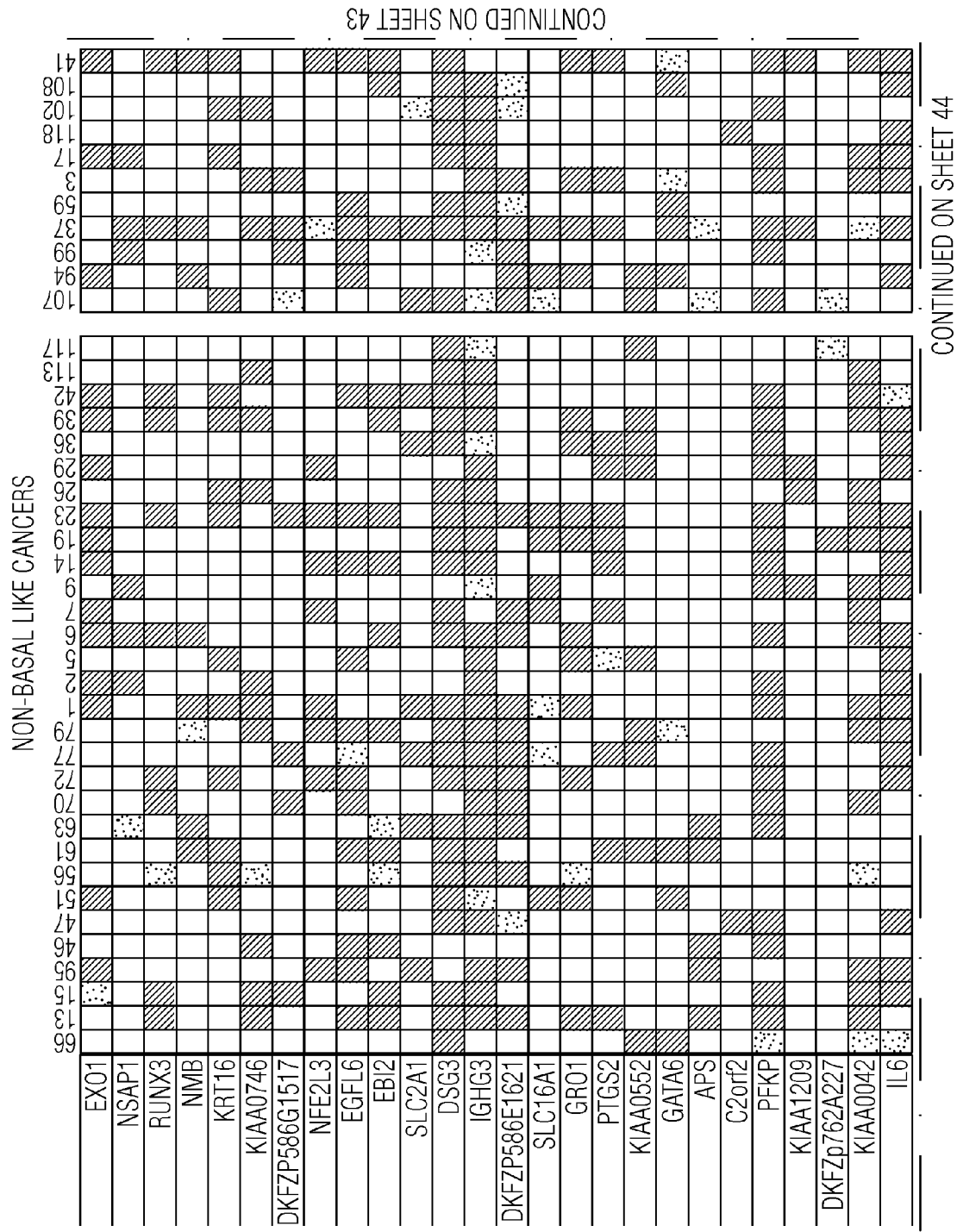
Figure 25Q:
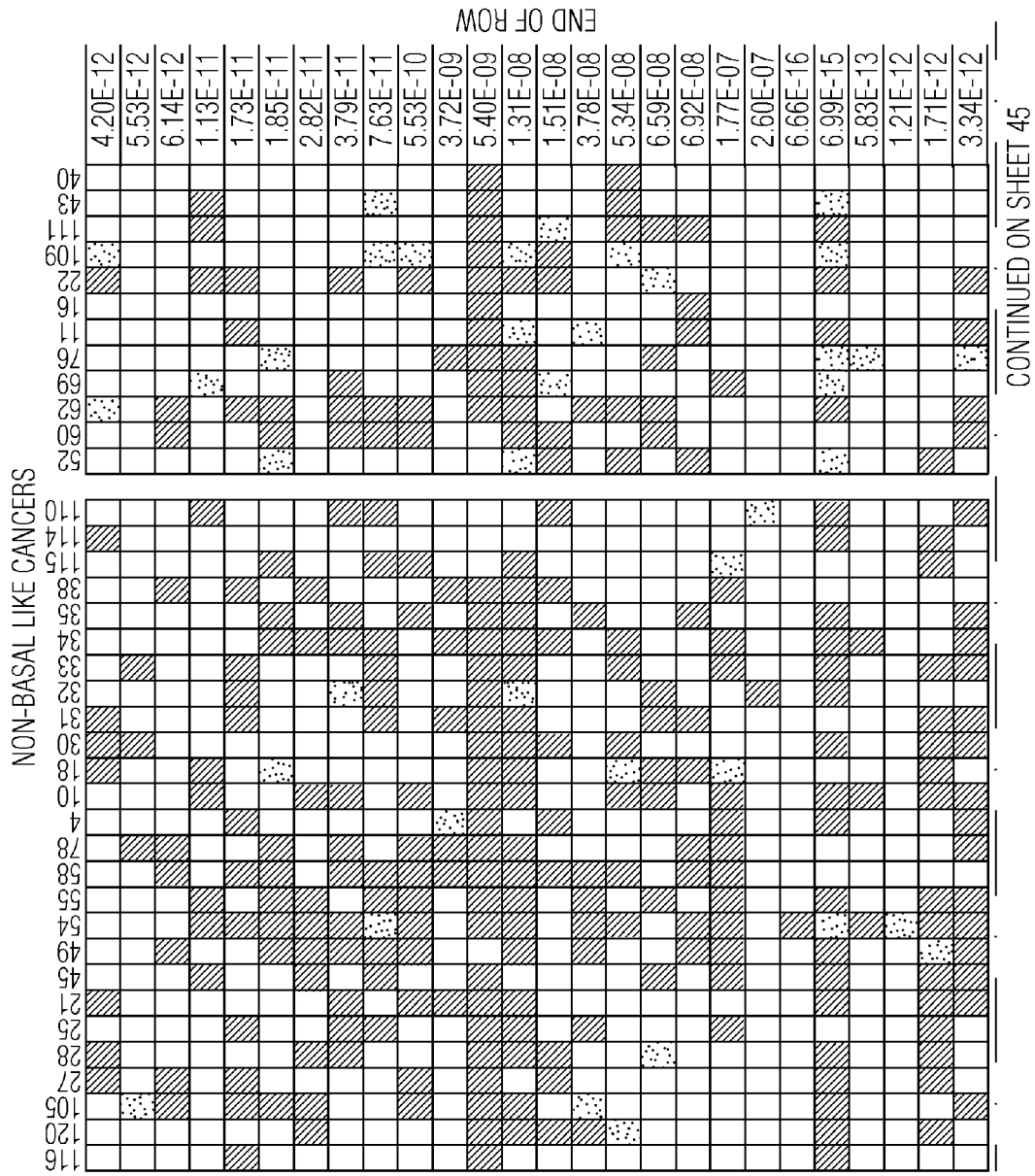
Figure 25S:
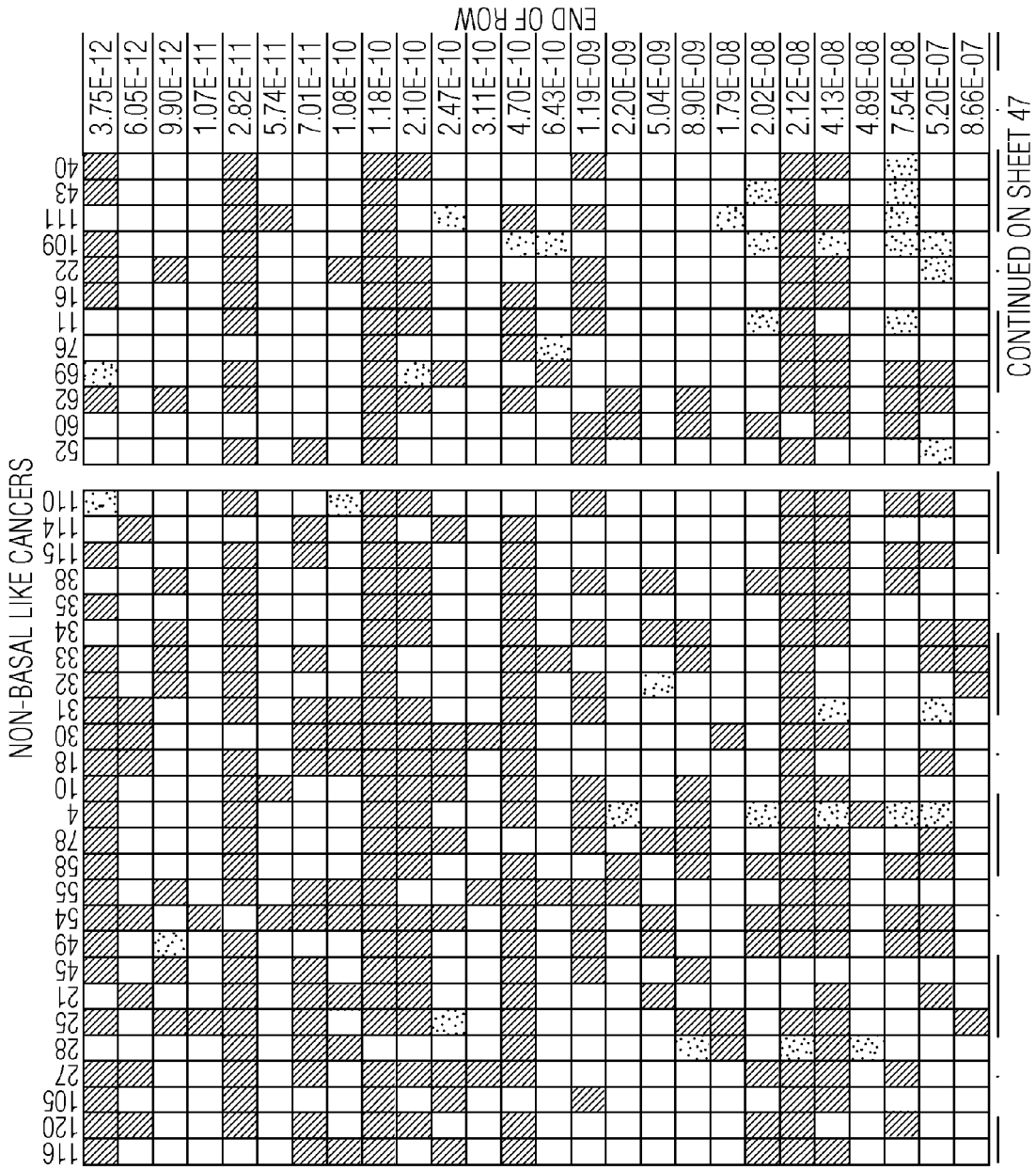
Figure 25T:
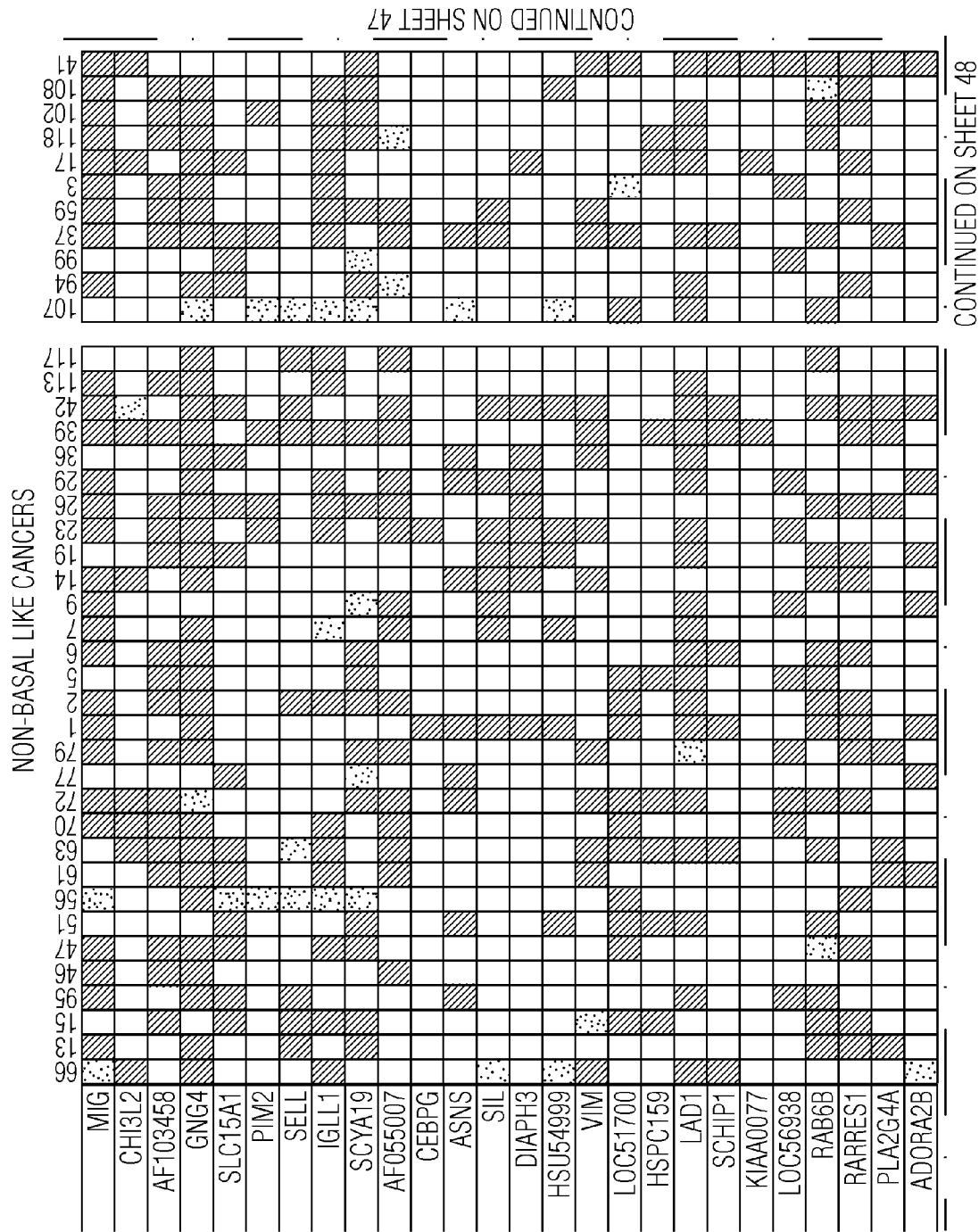
Figure 25U:
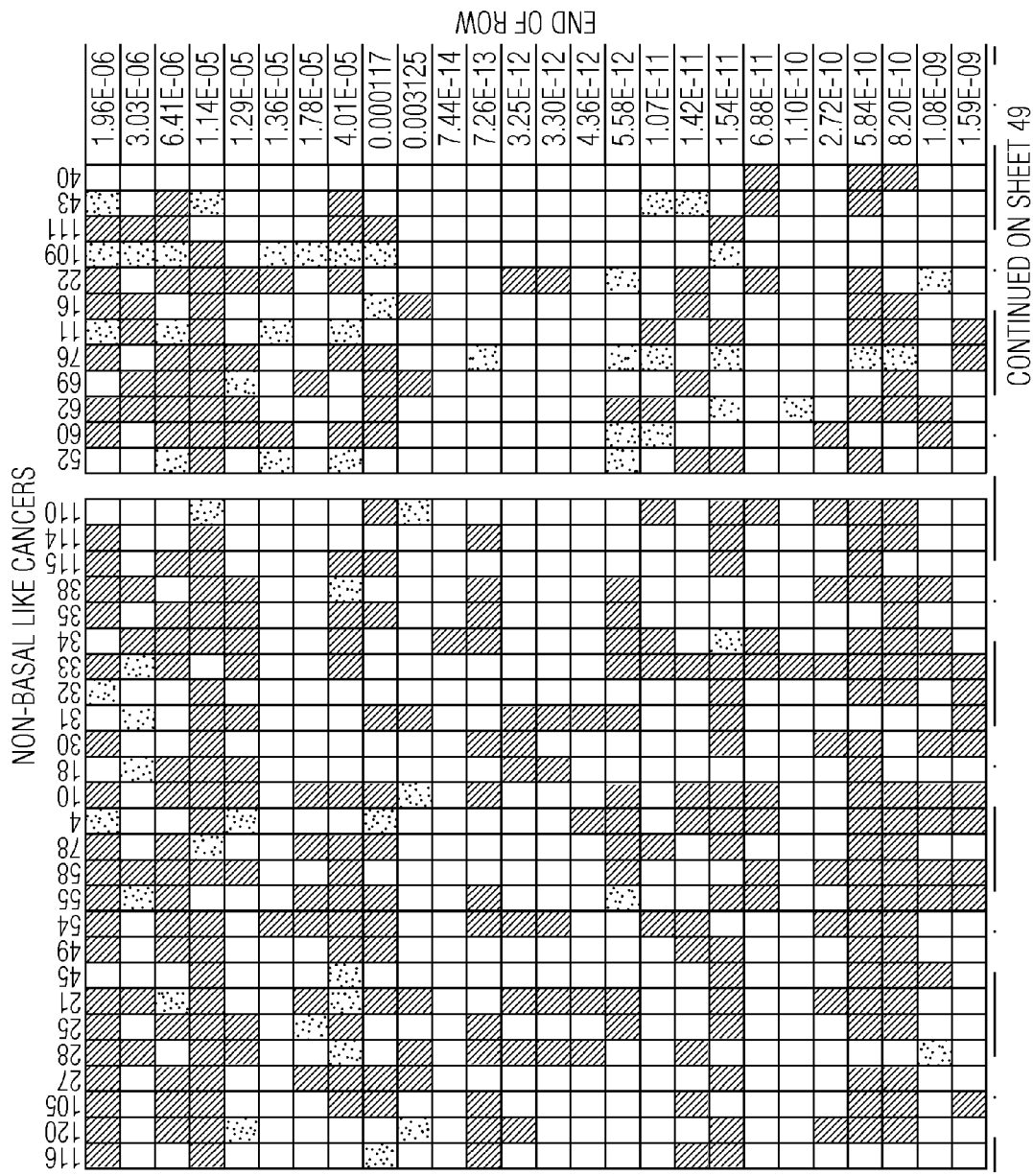
Figure 25V:
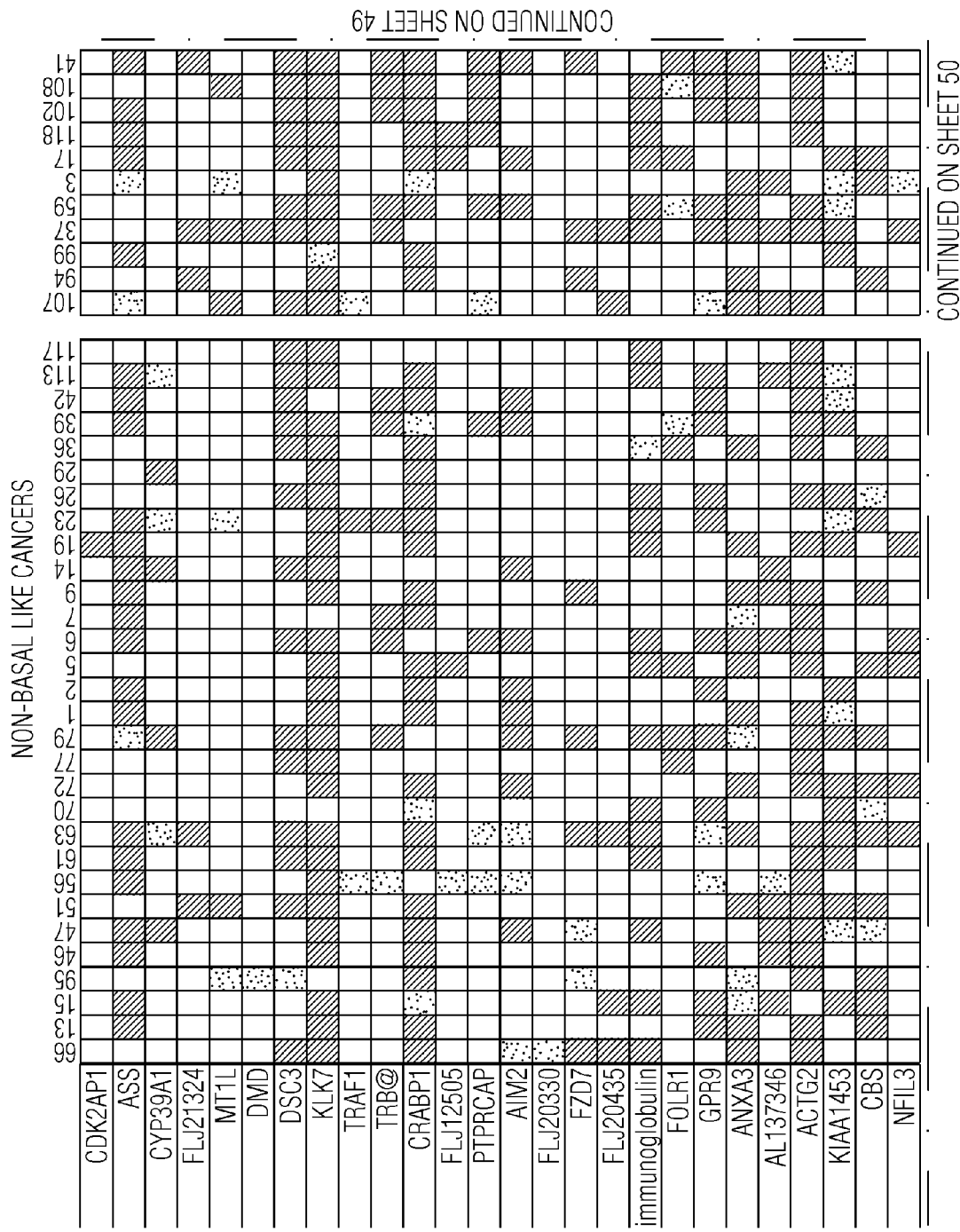
Figure 25W:
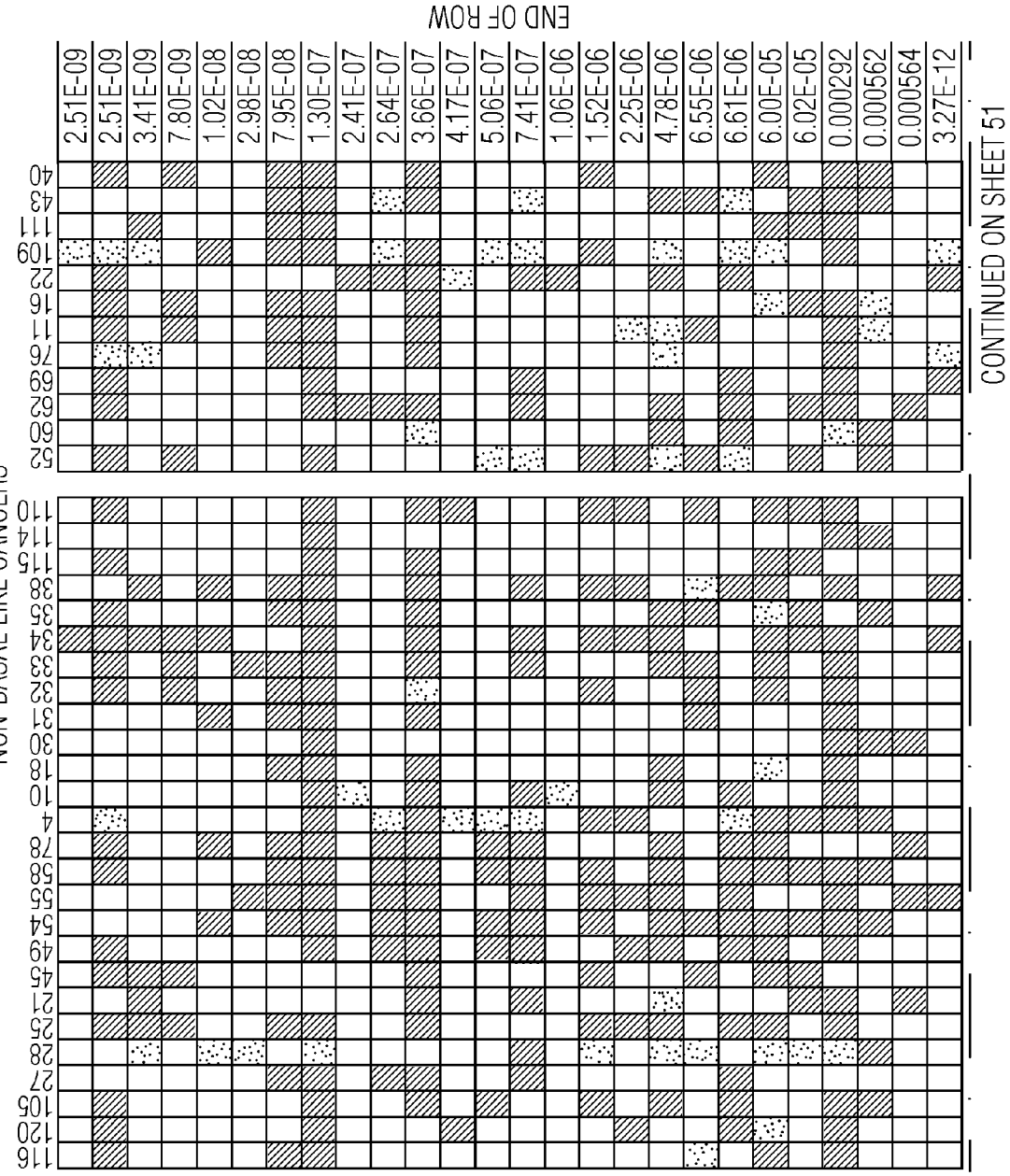
Figure 25X:
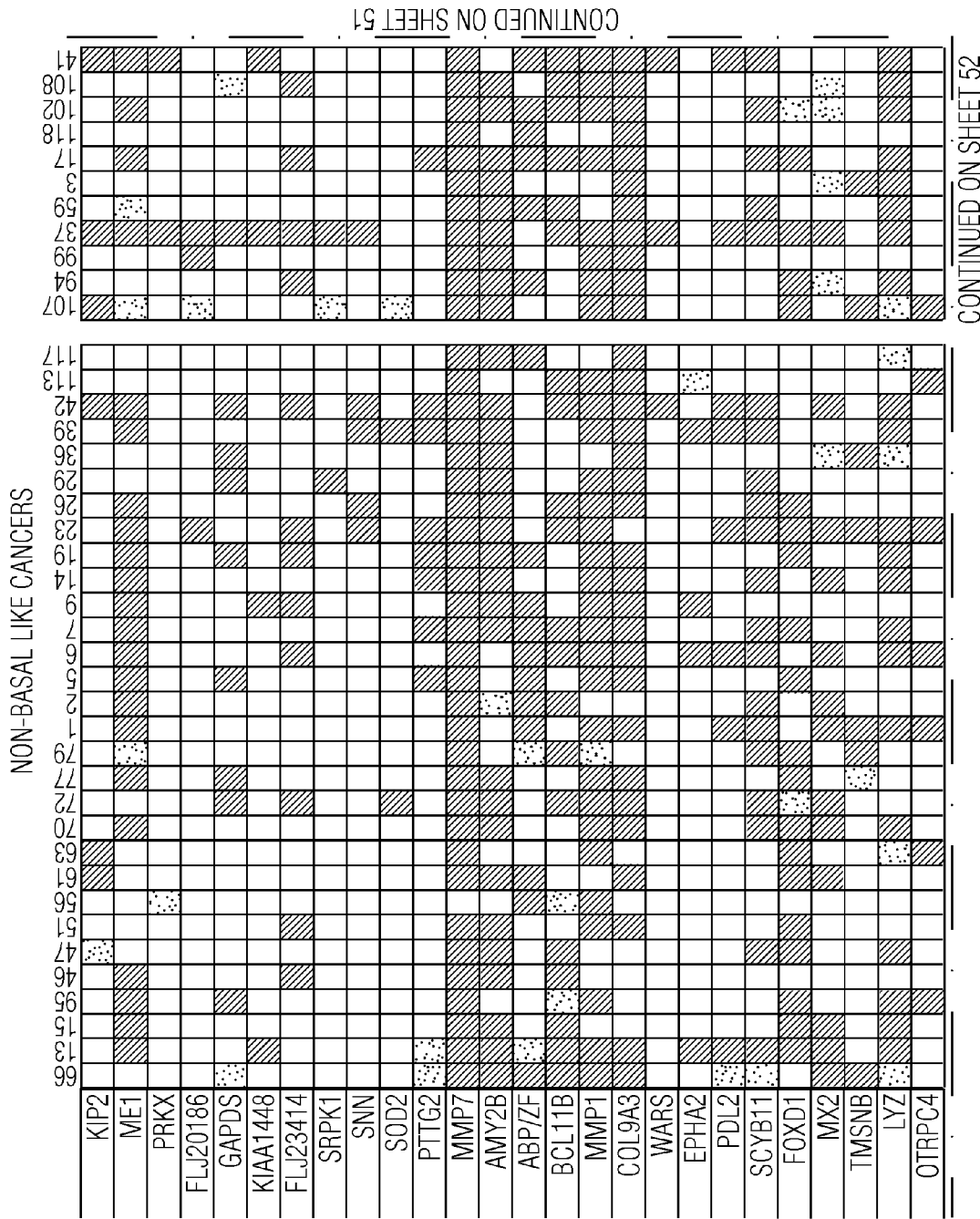
Figure 25Y:
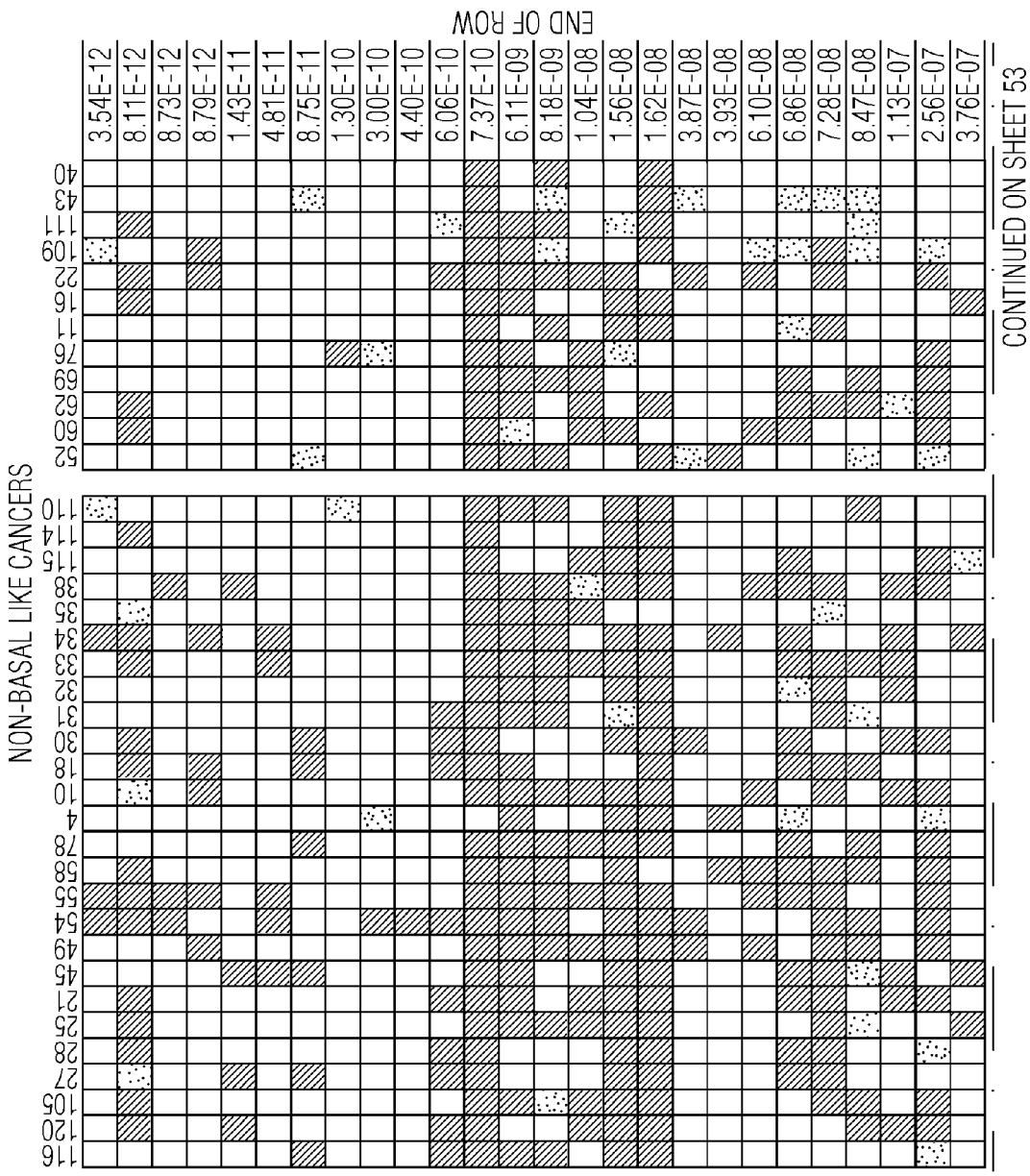
Figure 25Z:
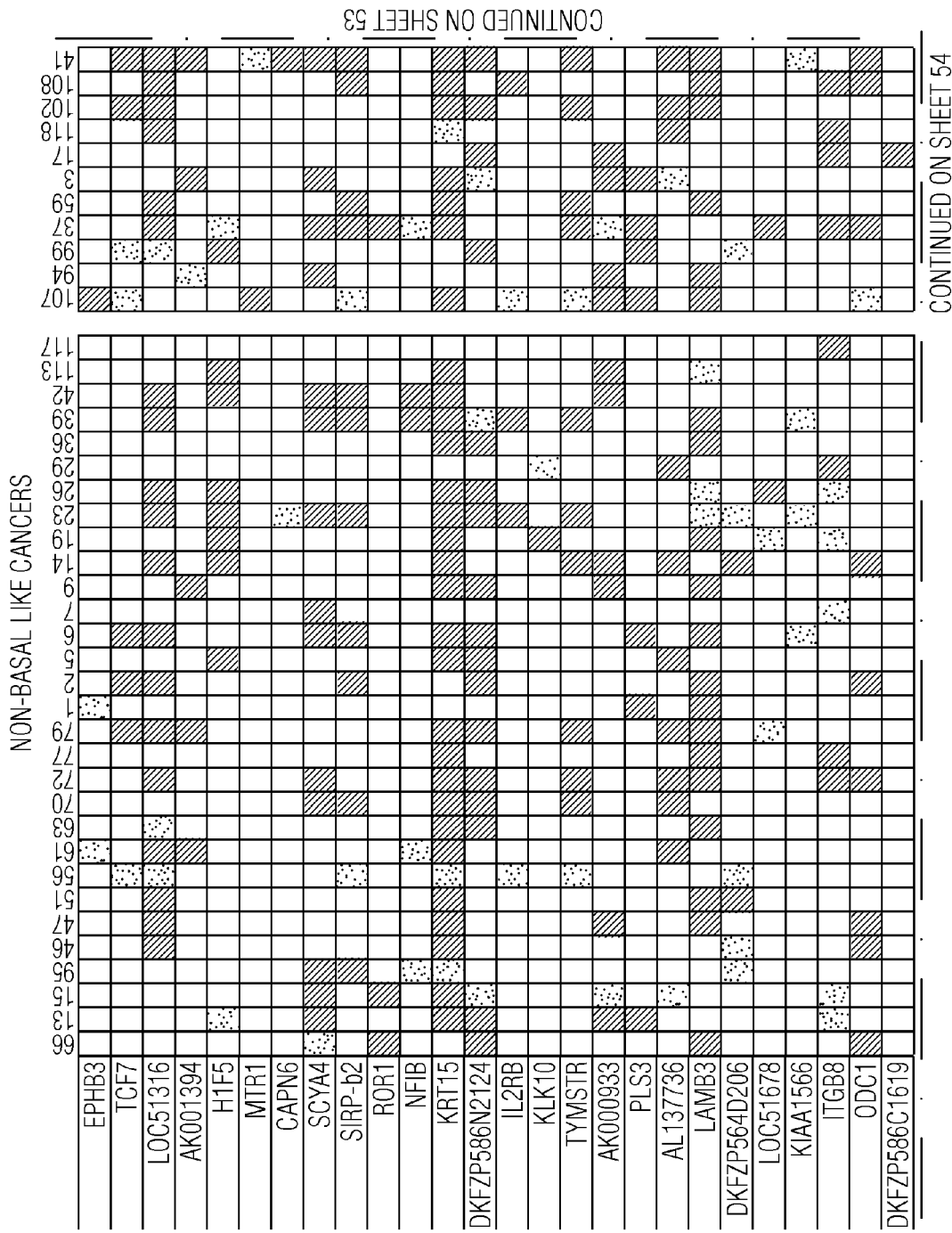
Figure 26B:
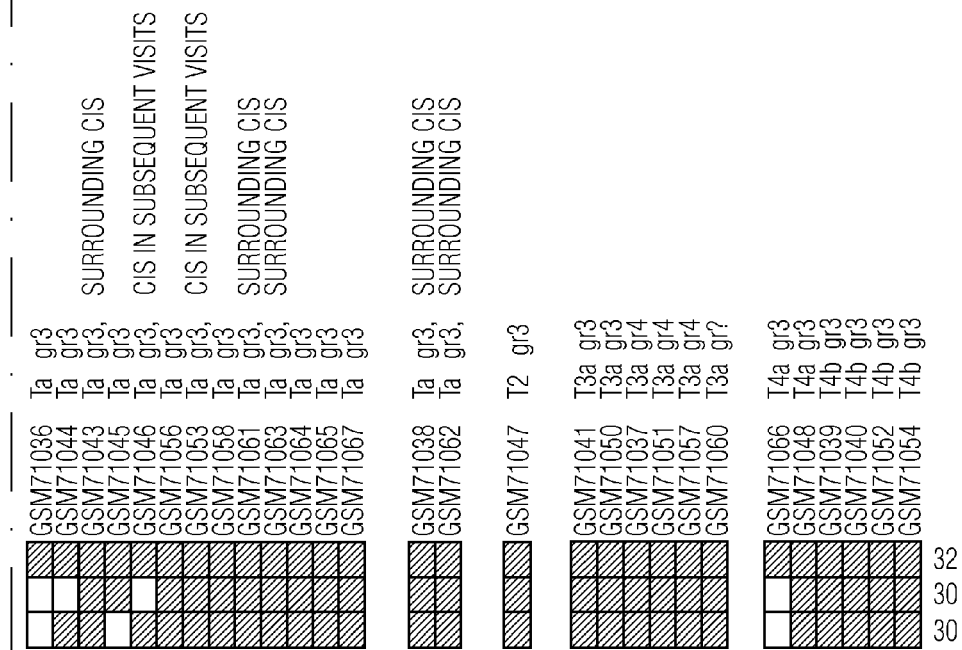
Figure 26C:
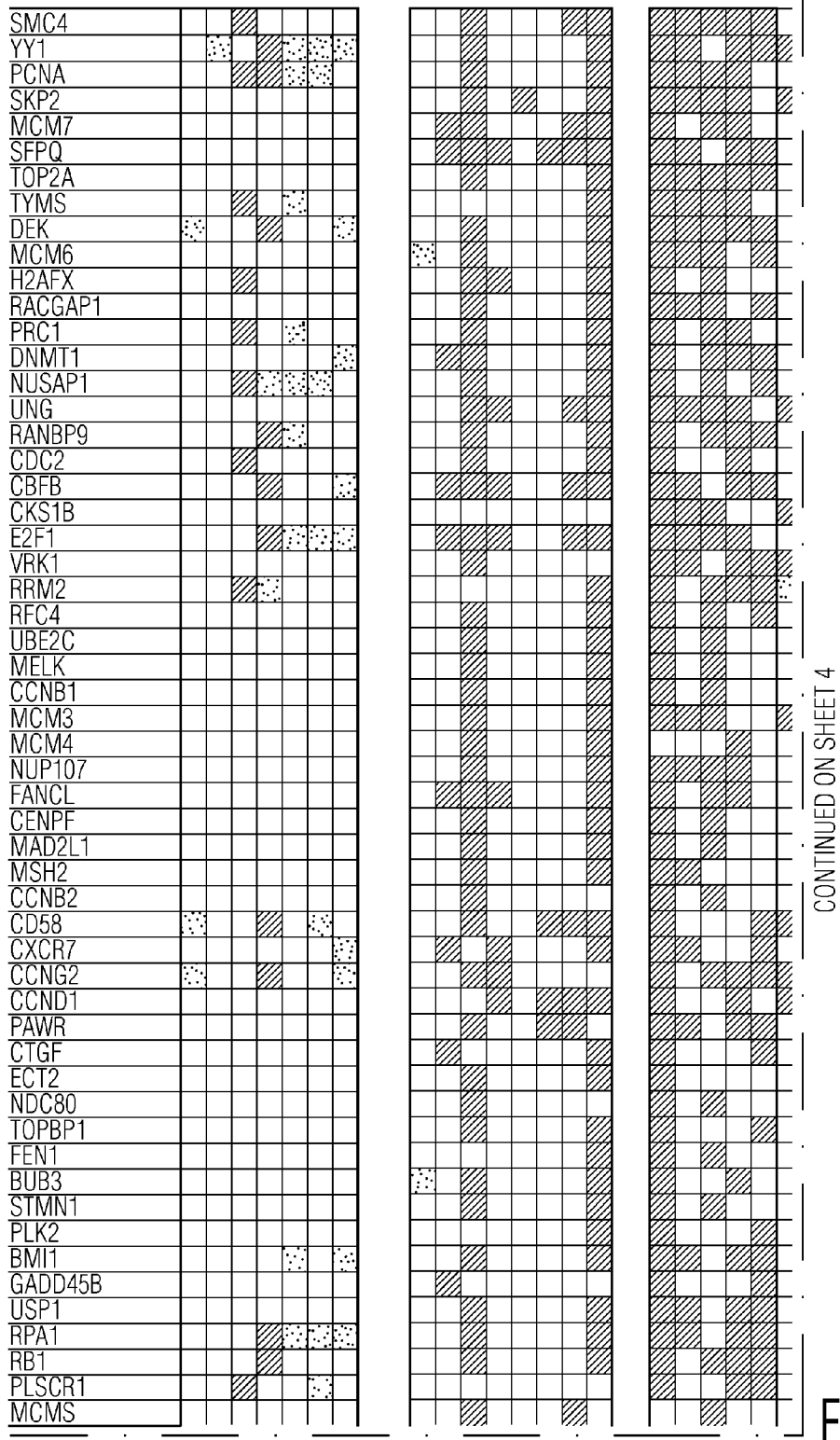
Figure 26D:
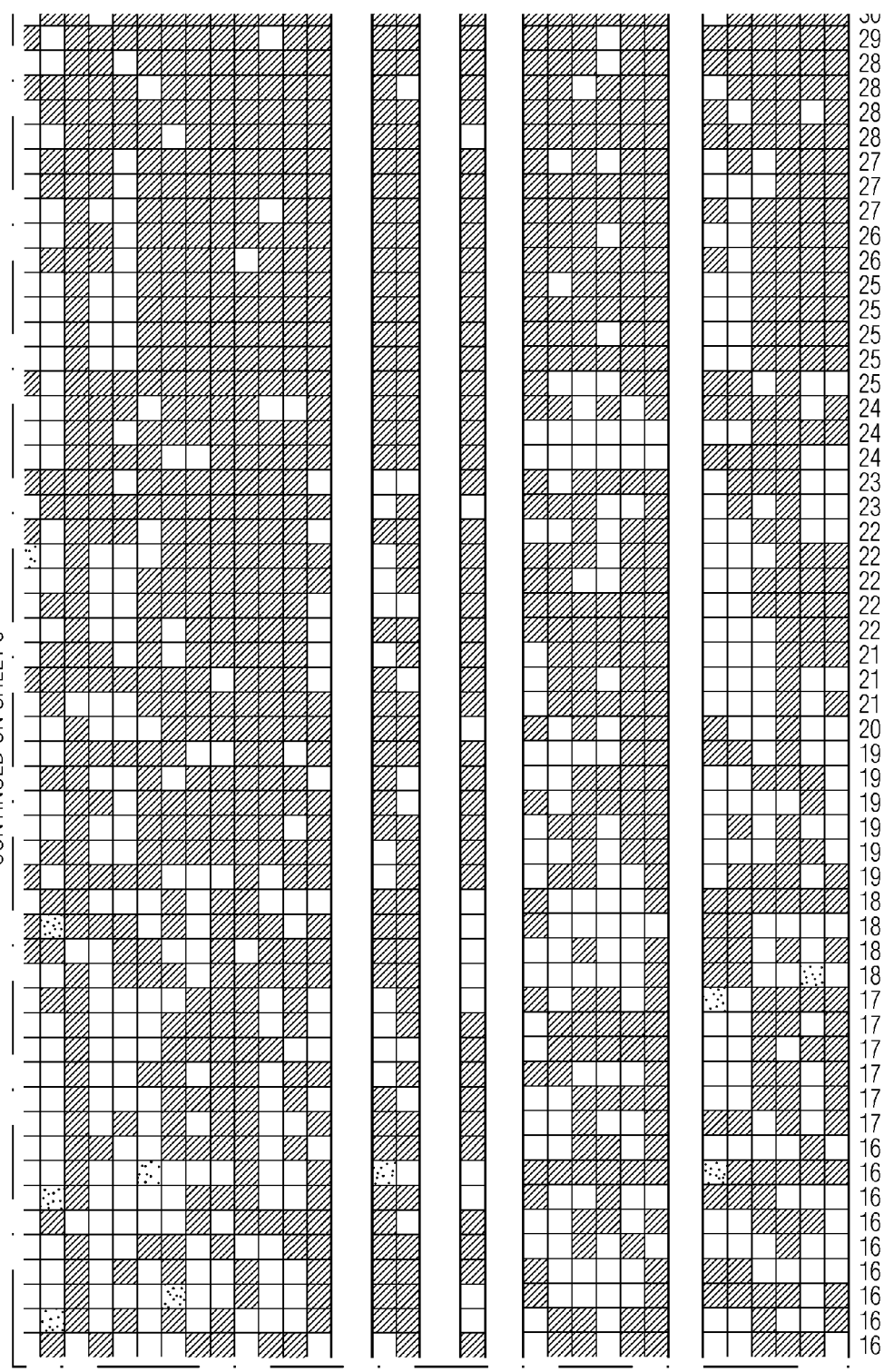
Figure 26F:
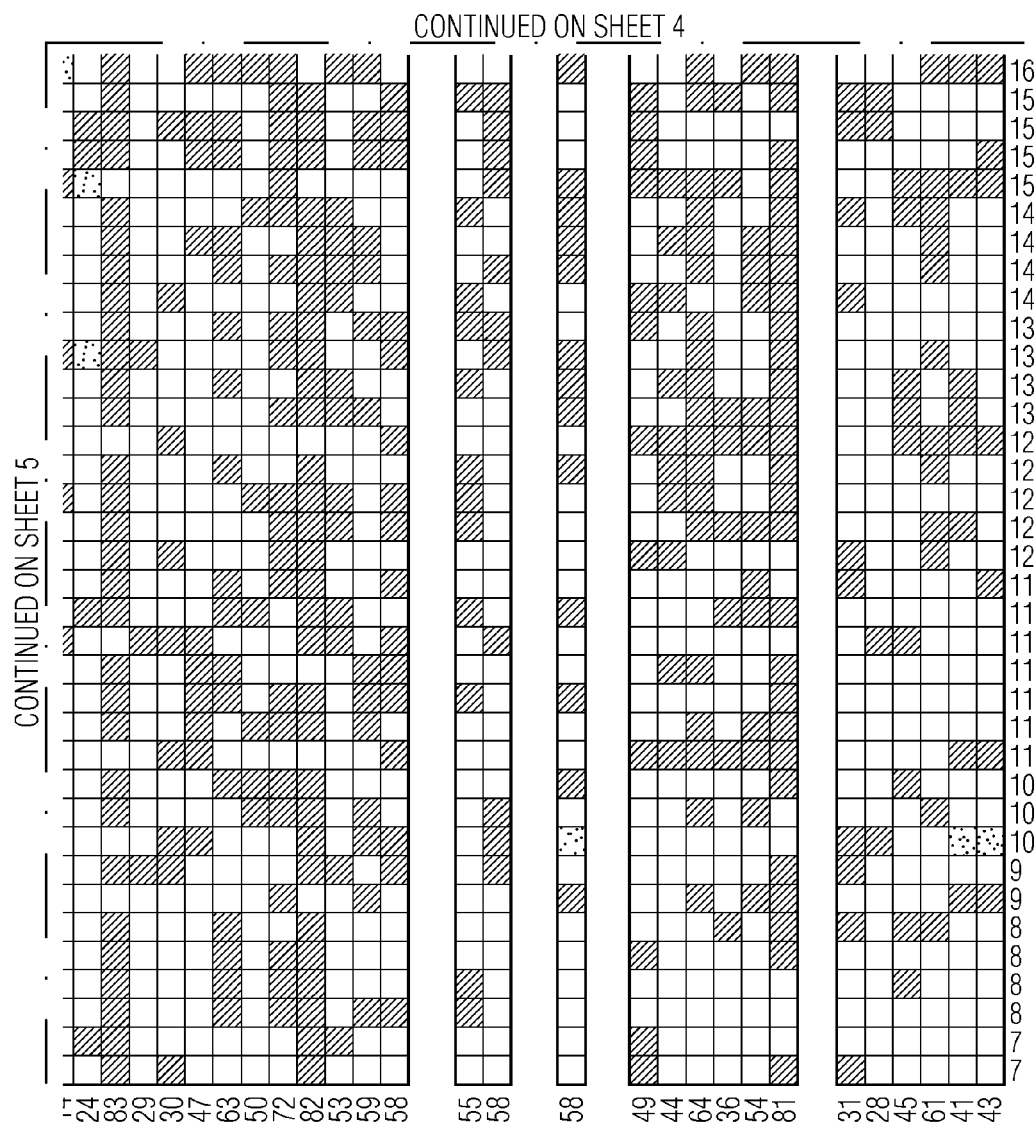

The human prostate cancer microarray set of Chandran was analyzed by PCA. When PCA is applied to the primary prostate cancers without metastases identified in the Chandran microarray set using the limited subset of 325 E2F-responsive genes, a distinctive tumor cluster is apparent in which very few ERGO tumor-associated genes are over-expressed, but in which basal cytokeratin marker over-expression is relatively common. See FIG. 22 (spheres with crosses).

Among the remaining primary prostate cancer without metastases, there is a subset of primary prostate cancer tumors that exhibits many of the same features present in metastatic tumor samples. See FIG. 22 (clear white spheres). The primary prostate cancer tumors in this subset over-express large numbers of ERGO tumor-associated E2F responsive genes and frequently over-express E2F2 and E2F3, cyclin E2, cyclin A2, cyclin B2, EZH2, FOXM1 and MYBL2, suggesting that activation of the same positive feedback loops present in metastatic tumors. See FIG. 20 (tumors listed under "Advanced ERGO PCA Pattern"). Additionally, like the metastatic prostate cancer tumors identified, these tumors express basal cytokeratins only rarely. This subset of primary prostate cancer tumors also exhibits a wide range of Gleason scores, ranging from 4 to 9. Consequently, patients with primary prostate cancer tumors in this subset should not be offered the "watchful waiting" option to manage their prostate cancer, and should instead be treated intensively at the time of diagnosis because the analyses here indicate these subsets of tumors have such extensive similarity with the dangerous metastatic prostate cancer tumors and are also ERGO tumors.

Example 5

Identification of E2F Responsive Gene Over-Expressing (ERGO) Tumors in a Ovarian Cancer Microarray Set Ovarian cancer, like breast cancer, arises in large proportions of patients with hereditary BRCA1 mutation (~50% of cases by age 70). Serous carcinomas is the predominant histological type of ovarian cancer occuring in BRCA1 patients. Patients carrying BRCA1 mutations that undergo prophylactic surgery are also frequently found to have occult serous cancers of the fallopian tube, suggesting that this is a preferred site of tumor formation in patients carrying BRCA1 mutations. Studies of normal fallopian tube epithelium and high grade serous fallopian tube and ovarian carcinomas in both patients carrying BRCA1 gene mutations and patients that do not carry such mutations were performed by microarray, and found that the gene expression profiles of the normal fallopian tube tissue in BRCA1 carriers clustered with the those of serous carcinomas not with normal fallopian tube epithelium from patients who do not carry BRCA1 mutations.

We have analyzed the normal fallopian tube epithelium, high grade serous fallopian tube and ovarian carcinoma microarray sets from these studies. These microarray sets are available as the GSE10971 series in the NCBI GEO data repository.

Theses analyses showed that high grade serous carcinomas from fallopian tube and ovary of both BRCA1 and non-BRCA1 mutation carriers were all advanced ERGO tumors. Results are shown in FIG. 23. The top 50 ERGO tumor-associated E2F-responsive genes were over-expressed in essentially every tumor. Every tumor over-expressed both E2F1 and E2F3, and also over-expressed CDKN2A and indicated a functional Rb defect. Essentially every tumor over-expressed at least one basal cytokeratin, and all but one expressed at least 2 basal cytokeratins, indicating that these cancers started out as basal like tumors, and that they retained their basal-like status in advanced malignancy—unlike the prostate cancers. All tumors over-expressed both EZH2 and FOXM1 plus at least two cyclins, indicating the activation of positive feedback loops involving derangements of these components of the SYNMULVB/DRM/DREAM/LINC multiprotein repressor/activator complex. See FIG. 21.

In contrast, 10 of the 12 fallopian tube samples from the patients carrying BRCA1 mutations showed none of these patterns of gene over-expression. In the remaining two fallopian tube samples, approximately half of the top 50 ERGO tumor associated genes were over-expressed, and one over-expressed EZH2 and two cyclins. The findings in these two samples are interpreted as transitional evolutionary pattern phenotypes indicative of cells on the way toward developing into cells having an aggressive cancer phenotype in BRCA1 carriers.

The results here lead to the conclusion that all high grade serous ovarian and fallopian tube cancers, whether from patients carrying BRCA1 carriers or patients who do not carry such a mutation, are advanced ERGO tumors having patterns of gene over-expression consistent with the activation of positive feedback loops involving over-expression of EZH2, FOXM1, MYB2L (B-MYB), and mitotic cyclins. A Minority of fallopian tube samples (<20%) from patients carrying BRCA1 mutation exhibit gene expression patterns consistent with early ERGO tumor-associated changes.

Example 6

Identification of ERGO Tumor Associated Over-Expressed Genes

A scoring system was developed to compile definitive master lists of ERGO tumor-associated over-expressed genes which took into account both the frequency of over-expression of a particular gene at any given organ site and the number of organ sites at which a particular gene is over-expressed. In this scoring system the "individual gene score" was determined using the following formula:

"Individual Gene Score" =
fraction of ERGO breast cancers over-expressing the gene +
fraction of ERGO lung cancers over-expressing the gene +
fraction of ERGO thyroid cancers over-expressing the gene +
fraction of ERGO ovarian cancers over-expressing the gene +
fraction of metastatic ERGO prostate cancers over-expressing the gene.

A cutoff "individual gene score" of >1.2 was used to assign over-expressed E2F-responsive genes to the ERGO-tumor associated list. Genes with an "individual gene score" of greater than 1.2 were included in the list, and genes with an "individual gene score" of less than 1.2 were not included in the list. This insured that the gene was over-expressed in at least two organ sites, and that a frequency of over-expression of at least 0.6 was present at at least one organ site. Details concerning the frequencies of gene over-expression at each site and the individual gene scores for genes over-expressed in at least 20 percent of tumors at each site is shown in Table 5 below.

TABLE 5

ERGO tumor associated genes based on score cutoff >1.2

| | breast | lung | thyroid | ovary | prostate met | sum |
|---|---|---|---|---|---|---|
| BUB1 | 0.81081081 | 0.5 | 1 | 0.84615385 | 0.68 | 3.83696466 |
| TPX2/C20ORF1 | 0.48648649 | 0.55555556 | 0.71428571 | 0.92307692 | 1 | 3.67940468 |
| AURKA/STK15 | 0.45945946 | 0.5 | 0.71428571 | 1 | 1 | 3.67374517 |
| CENPA | 0.72972973 | 0.44444444 | 0.71428571 | 1 | 0.76 | 3.64845989 |
| CKS2 | 0.32432432 | 0.33333333 | 1 | 1 | 0.92 | 3.57765766 |
| AURKB/STK12 | 0.78378378 | 0.5 | 0.85714286 | 0.84615385 | 0.52 | 3.50708049 |
| UBE2C/UBCH10 | 0.62162162 | 0.38888889 | 0.28571429 | 0.92307692 | 0.96 | 3.17930172 |
| KIF2C/KNSL6 | 0.75675676 | 0.38888889 | 0.71428571 | 0.76923077 | 0.48 | 3.10916213 |
| STMN1 | 0.51351351 | 0.83333333 | 0.71428571 | 0.69230769 | 0.28 | 3.03344025 |
| CDC45L | 0.56756757 | 0.27777778 | 0.85714286 | 0.92307692 | 0.4 | 3.02556513 |
| LMNB1 | 0.40540541 | | 0.85714286 | 1 | 0.76 | 3.02254826 |
| MAD2L1 | 0.48648649 | 0.66666667 | 0.71428571 | 0.53846154 | 0.56 | 2.96590041 |
| KIFC1/KNSL2 | 0.81081081 | | 0.57142857 | 0.92307692 | 0.56 | 2.86531631 |
| HMMR | 0.21621622 | 0.44444444 | 0.71428571 | 0.92307692 | 0.56 | 2.8580233 |
| PTTG1 | 0.37837838 | 0.77777778 | | 0.92307692 | 0.72 | 2.79923308 |
| KIF11/KNSL1 | 0.32432432 | 0.5 | 0.42857143 | 0.92307692 | 0.6 | 2.77597268 |
| CCNA2 | 0.62162162 | | 0.71428571 | 0.76923077 | 0.64 | 2.74513811 |
| UNG | 0.24324324 | 0.72222222 | 0.57142857 | 0.61538462 | 0.52 | 2.67227865 |
| CENPF | 0.56756757 | 0.83333333 | 0.85714286 | 0.38461538 | | 2.64265914 |
| TTK | 0.56756757 | 0.5 | 0.71428571 | 0.84615385 | | 2.62800713 |

TABLE 5-continued

| Gene | C1 | C2 | C3 | C4 | C5 | Total |
|---|---|---|---|---|---|---|
| CCNB2 | 0.62162162 | 0.5 | 0.85714286 | | 0.64 | 2.61876448 |
| CDC2 | 0.37837838 | 0.61111111 | | 0.92307692 | 0.68 | 2.59256641 |
| EZH2 | 0.7027027 | | | 1 | 0.84 | 2.5427027 |
| CDKN3 | | 0.61111111 | 0.42857143 | 0.76923077 | 0.64 | 2.44891331 |
| BUB1B | | | 0.71428571 | 0.92307692 | 0.76 | 2.39736264 |
| ASF1B/FLJ10604 | | 0.44444444 | 1 | 0.92307692 | | 2.36752137 |
| MKI67 | | | 0.71428571 | 0.84615385 | 0.8 | 2.36043956 |
| NDC80/HEC | 0.59459459 | | 0.42857143 | 0.92307692 | 0.4 | 2.34624295 |
| FOXM1 | 0.62162162 | | | 1 | 0.72 | 2.34162162 |
| BIRC5 | 0.54054054 | 0.38888889 | | 0.92307692 | 0.48 | 2.33250635 |
| CDC20/p55CDC | 0.7027027 | | | 0.92307692 | 0.68 | 2.30577963 |
| CDC25B | 0.45945946 | 0.44444444 | 0.42857143 | 0.92307692 | | 2.25555226 |
| BLM | 0.54054054 | | 0.28571429 | 0.84615385 | 0.56 | 2.23240867 |
| TIMELESS | | 0.66666667 | 0.28571429 | 1 | 0.24 | 2.19238095 |
| MCM2 | 0.51351351 | | 0.71428571 | 0.92307692 | | 2.15087615 |
| CENPE | 0.21621622 | | 0.71428571 | 0.92307692 | 0.28 | 2.13357885 |
| KPNA2 | 0.43243243 | 0.33333333 | | 1 | 0.36 | 2.12576577 |
| TMPO | | 0.83333333 | | 0.76923077 | 0.52 | 2.1225641 |
| MCM7 | 0.43243243 | 0.5 | | 0.84615385 | 0.32 | 2.09858628 |
| RAD54L | 0.64864865 | 0.55555556 | | 0.69230769 | 0.2 | 2.0965119 |
| CDC6 | | | 1 | 0.69230769 | 0.4 | 2.09230769 |
| CHEK1 | 0.45945946 | | 0.28571429 | 0.76923077 | 0.56 | 2.07440451 |
| ANLN | 0.43243243 | | 0.85714286 | 0.76923077 | | 2.05880606 |
| CCNB1 | 0.40540541 | | | 0.92307692 | 0.72 | 2.04848233 |
| TK1 | 0.40540541 | | 1 | | 0.64 | 2.04540541 |
| TOP2A | | 0.94444444 | | 0.23076923 | 0.84 | 2.01521368 |
| NUSAP1/BM037 | 0.2972973 | | 0.71428571 | 1 | | 2.01158301 |
| RFC4 | 0.43243243 | 0.72222222 | | 0.84615385 | | 2.0008085 |
| DEK | 0.43243243 | 0.72222222 | | 0.84615385 | | 2.0008085 |
| SMC2/SMC2L1 | 0.21621622 | 0.66666667 | | 0.61538462 | 0.48 | 1.9782675 |
| TYMS | 0.2972973 | 0.55555556 | 0.42857143 | 0.23076923 | 0.44 | 1.95219351 |
| PBK | | | 1 | 0.92307692 | | 1.92307692 |
| CCNE2 | 0.27027027 | | | 0.76923077 | 0.88 | 1.91950104 |
| H2AFX | 0.32432432 | | 0.28571429 | 0.53846154 | 0.76 | 1.90850015 |
| MCM6 | 0.43243243 | 0.27777778 | 0.42857143 | 0.76923077 | | 1.90801241 |
| ECT2 | 0.35135135 | 0.55555556 | | 1 | | 1.90690691 |
| MELK/KIAA0175 | 0.62162162 | | | 0.92307692 | 0.36 | 1.90469854 |
| CDC25C | 0.24324324 | | 0.57142857 | 0.46153846 | 0.6 | 1.87621028 |
| NEK2 | 0.2972973 | 0.66666667 | | 0.61538462 | 0.28 | 1.85934858 |
| TOPBP1 | 0.21621622 | 0.66666667 | | 0.61538462 | 0.36 | 1.8582675 |
| CHAF1A | 0.32432432 | 0.55555556 | | 0.61538462 | 0.36 | 1.8552645 |
| E2F1 | 0.35135135 | 0.57142857 | | 0.92307692 | | 1.84585685 |
| PCNA | 0.27027027 | 0.72222222 | | 0.84615385 | | 1.83864634 |
| PRC1 | 0.40540541 | 0.5 | | 0.92307692 | | 1.82848233 |
| HMGB3/HMG4 | 0.35135135 | 0.33333333 | | 0.61538462 | 0.52 | 1.8200693 |
| MSH2 | 0.27027027 | 0.38888889 | | 0.69230769 | 0.44 | 1.79146685 |
| E2F3 | | | | 1 | 0.76 | 1.76 |
| SRGAP2/KIAA0456 | 0.5 | | 0.28571429 | | 0.96 | 1.74571429 |
| NUP155 | 0.21621622 | 0.27777778 | | 0.76923077 | 0.48 | 1.74322476 |
| RRM2 | | | 0.28571429 | 1 | 0.44 | 1.72571429 |
| CHAF1B | 0.48648649 | 0.61111111 | | 0.61538462 | | 1.71298221 |
| UBE2T/HSPC150 | 0.21621622 | 0.77777778 | | 0.92307692 | | 1.7008547 |
| RFC2 | | 0.44444444 | | 0.76923077 | 0.48 | 1.69367521 |
| CDKN2C | 0.21621622 | 0.72222222 | | 0.30769231 | 0.4 | 1.64613075 |
| SMC4/SMC4L1 | 0.37837838 | 0.33333333 | 0.28571429 | 0.30769231 | 0.30769231 | 1.61281061 |
| UHRF1/ICBP90 | | | 0.57142857 | 1 | | 1.57142857 |
| PLAU | | | 0.85714286 | 0.69230769 | | 1.54945055 |
| KIF20A/RAB6KIFL | 0.62162162 | | | 0.92307692 | | 1.54469854 |
| GCH1 | | 0.38888889 | 0.42857143 | 0.46153846 | 0.24 | 1.51899878 |
| PARP1/ADPRT | | 0.72222222 | | 0.76923077 | | 1.49145299 |
| TCF19 | | 0.55555556 | | 0.92307692 | | 1.47863248 |
| DNMT1 | 0.24324324 | 0.44444444 | | 0.76923077 | | 1.45691846 |
| RACGAP1/ID-GAP | 0.43243243 | | | 1 | | 1.43243243 |
| CCNF | | 0.55555556 | 0.85714286 | | | 1.41269841 |
| DCK | | 0.38888889 | | 0.61538462 | 0.4 | 1.4042735 |
| TEAD4 | 0.45945946 | | | 0.92307692 | | 1.38253638 |
| MCM3 | | 0.44444444 | | 0.92307692 | | 1.36752137 |
| FEN1 | 0.40540541 | | | 0.92307692 | | 1.32848233 |
| GINS1/KIAA0186 | | | | 0.92307692 | 0.4 | 1.32307692 |
| RRM1 | | | 0.28571429 | 0.30769231 | 0.72 | 1.31340659 |
| POLE2 | | 0.38888889 | | 0.92307692 | | 1.31196581 |
| BARD1 | 0.21621622 | 0.5 | | 0.38461538 | 0.2 | 1.3008316 |
| RAD51AP1/PIR51 | 0.2972973 | | | 1 | | 1.2972973 |
| PLK4/STK18 | 0.24324324 | 0.61111111 | | | 0.44 | 1.29435435 |
| SERPINE1 | | | 0.85714286 | 0.23076923 | 0.2 | 1.28791209 |
| POLA2 | 0.27027027 | | | 0.69230769 | 0.32 | 1.28257796 |
| CDCA4/FLJ20764 | | | 0.42857143 | 0.84615385 | | 1.27472527 |
| CCND1 | | | 0.71428571 | | 0.56 | 1.27428571 |
| DTYMK | | | | 0.46153846 | 0.8 | 1.26153846 |
| CCNE1 | 0.24324324 | | | 1 | | 1.24324324 |

TABLE 5-continued

| | | | | | |
|---|---|---|---|---|---|
| MCM4 | 0.27027027 | | | 0.76923077 | 0.2 | 1.23950104 |
| H2AFZ | | 0.5 | | 0.53846154 | 0.2 | 1.23846154 |
| HIST1H2BF/H2BFG | | | 0.57142857 | 0.46153846 | 0.2 | 1.23296703 |
| LHX2 | 0.24324324 | 0.66666667 | | | 0.32 | 1.22990991 |
| CKS1 | 0.37837838 | | | 0.84615385 | | 1.22453222 |

Rejected based on score cutoff of 1.2 or less

| | breast | lung | tyroid | ovary | Prostate met | sum |
|---|---|---|---|---|---|---|
| PMAIP1 | | 0.38888889 | | | 0.8 | 1.18888889 |
| MRE11A | | | | 0.69230769 | 0.48 | 1.17230769 |
| USP1 | 0.35135135 | 0.27777778 | | 0.53846154 | | 1.16759067 |
| SFPQ | | 0.44444444 | | | 0.72 | 1.16444444 |
| ORC6L | 0.37837838 | | | 0.76923077 | | 1.14760915 |
| MYC | 0.56756757 | | 0.57142857 | | | 1.13899614 |
| CDC7L1 | 0.24324324 | | | 0.84615385 | | 1.08939709 |
| UMPS | | | | 0.76923077 | 0.32 | 1.08923077 |
| PRIM2A | 0.45945946 | | | 0.61538462 | | 1.07484407 |
| VRK1 | | 0.33333333 | | 0.53846154 | 0.2 | 1.07179487 |
| DNA2L | 0.37837838 | | | 0.69230769 | | 1.07068607 |
| VEGF | 0.40540541 | | | 0.61538462 | | 1.02079002 |
| SLBP | | | | 0.61538462 | 0.4 | 1.01538462 |
| MCL1 | | | | 0.76923077 | 0.24 | 1.00923077 |
| CDCA7L/ DKFZp762L0311 | 0.2972973 | | | 0.69230769 | | 0.98960499 |
| DUT | | 0.5 | | | 0.48 | 0.98 |
| AR | | | | | 0.96 | 0.96 |
| HMGB2/HMG2 | 0.21621622 | | | | 0.72 | 0.93621622 |
| PRIM1 | | | | 0.69230769 | 0.24 | 0.93230769 |
| RAD51 | | | | 0.69230769 | 0.24 | 0.93230769 |
| FANCL/FLJ10335 | 0.24324324 | | | | 0.68 | 0.92324324 |
| BAK1 | | | | 0.92307692 | | 0.92307692 |
| KIF4A | 0.21621622 | | | 0.69230769 | | 0.90852391 |
| CDK2 | | 0.44444444 | | 0.46153846 | | 0.90598291 |
| RAD51C | | 0.66666667 | | 0.23076923 | | 0.8974359 |
| MPHOSPH1 | | | | 0.69230769 | 0.2 | 0.89230769 |
| FGFR1OP | | | | | 0.88 | 0.88 |
| PRKAR2B | | | | 0.38461538 | 0.48 | 0.86461538 |
| APOE | | | | 0.46153846 | 0.4 | 0.86153846 |
| PBX3 | | 0.5 | | | 0.36 | 0.86 |
| DMRT1 | 0.24324324 | | | 0.61538462 | | 0.85862786 |
| HRK | 0.56756757 | | 0.28571429 | | | 0.85328185 |
| FIGNL1 | | | | 0.84615385 | | 0.84615385 |
| SHCBP1/FLJ22009 | | | | 0.84615385 | | 0.84615385 |
| ORC3L | 0.21621622 | 0.38888889 | | 0.23076923 | | 0.83587434 |
| TP53BP2 | 0.48648649 | | | 0.30769231 | | 0.79417879 |
| ARHGAP4 | | | 0.28571429 | 0.30769231 | 0.2 | 0.79340659 |
| MTHFD1 | 0.21621622 | | 0.57142857 | | | 0.78764479 |
| MAPK1 | | | | 0.76923077 | | 0.76923077 |
| DHFR | | | | 0.76923077 | | 0.76923077 |
| CITED2 | | | | | 0.76 | 0.76 |
| PRG4 | | | | 0.46153846 | 0.28 | 0.74153846 |
| RPA3 | | | | 0.46153846 | 0.28 | 0.74153846 |
| CSTF1 | | | | 0.53846154 | 0.2 | 0.73846154 |
| HOXA7 | | 0.5 | | 0.23076923 | | 0.73076923 |
| BTG3 | 0.48648649 | | | | 0.24 | 0.72648649 |
| MMP16 | | | 0.28571429 | | 0.44 | 0.72571429 |
| PLK1 | | | 0.71428571 | | | 0.71428571 |
| INHBA | | | 0.71428571 | | | 0.71428571 |
| EED | 0.24324324 | | | 0.46153846 | | 0.7047817 |
| SSX2IP/KIAA0923 | | 0.38888889 | | 0.30769231 | | 0.6965812 |
| RFC3 | | | | 0.69230769 | | 0.69230769 |
| FKSG14 | | | | 0.69230769 | | 0.69230769 |
| NUP107 | | | | 0.69230769 | | 0.69230769 |
| CASP8 | | 0.44444444 | | | 0.24 | 0.68444444 |
| ORC2L | | | | 0.46153846 | 0.2 | 0.66153846 |
| FST | | | 0.42857143 | 0.23076923 | | 0.65934066 |
| RPA1 | | | 0.42857143 | 0.23076923 | | 0.65934066 |
| COL11A1 | | | | | 0.64 | 0.64 |
| DBF4/ASK | | | | 0.30769231 | 0.32 | 0.62769231 |
| RDC1 | | | | 0.61538462 | | 0.61538462 |
| BID | 0.21621622 | | | 0.38461538 | | 0.6008316 |
| HIST1H2AE | | | | | 0.6 | 0.6 |
| PLK2/SNK | | | 0.28571429 | 0.30769231 | | 0.59340659 |
| SPHK1 | | | 0.57142857 | | | 0.57142857 |
| MCM5 | 0.56756757 | | | | | 0.56756757 |
| EGR1 | | | 0.28571429 | | 0.28 | 0.56571429 |
| NPAT | | 0.55555556 | | | | 0.55555556 |
| PLSCR1 | 0.54054054 | | | | | 0.54054054 |

TABLE 5-continued

| | | | | | |
|---|---|---|---|---|---|
| CSRP2 | 0.54054054 | | | | 0.54054054 |
| H2AFL | | | | 0.53846154 | 0.53846154 |
| LSM5 | | | | 0.53846154 | 0.53846154 |
| H2AFA | | | | 0.53846154 | 0.53846154 |
| RBL1 | | | | 0.52 | 0.52 |
| CBX5 | | | 0.23076923 | 0.28 | 0.51076923 |
| | | 0.5 | | | 0.5 |
| LIG1 | | | | 0.48 | 0.48 |
| PDGFRA | | | | 0.48 | 0.48 |
| H3FB | | | | 0.46153846 | 0.46153846 |
| H2BFH | | | | 0.46153846 | 0.46153846 |
| APBB2 | | | | 0.46153846 | 0.46153846 |
| SMARCA5 | | 0.44444444 | | | 0.44444444 |
| HIST1H3D | | | | 0.44 | 0.44 |
| SOX9 | 0.43243243 | | | | 0.43243243 |
| NASP | 0.43243243 | | | | 0.43243243 |
| HIST1H2BN/H2BFD | | | 0.42857143 | | 0.42857143 |
| BACH1 | | | 0.42857143 | | 0.42857143 |
| TGFA | 0.40540541 | | | | 0.40540541 |
| ROD1 | | | | 0.4 | 0.4 |
| KIF22 | | | | 0.4 | 0.4 |
| PTPNS1 | 0.37837838 | | | | 0.37837838 |
| CSDA | 0.37837838 | | | | 0.37837838 |
| BMP2 | | | | 0.36 | 0.36 |
| SNAPC1 | | | | 0.36 | 0.36 |
| RAD52 | | | | 0.36 | 0.36 |
| PAWR | | | | 0.36 | 0.36 |
| ANXA8 | 0.35135135 | | | | 0.35135135 |
| PRPS1 | | 0.33333333 | | | 0.33333333 |
| BUB3 | | 0.33333333 | | | 0.33333333 |
| HSP90B1 | | | | 0.32 | 0.32 |
| RECQL5 | | | | 0.32 | 0.32 |
| CFLAR | | | | 0.32 | 0.32 |
| FGFR3 | | | 0.30769231 | | 0.30769231 |
| RFC5 | | | 0.30769231 | | 0.30769231 |
| BMPR1A | | | 0.30769231 | | 0.30769231 |
| HNRPC | | | 0.30769231 | | 0.30769231 |
| CD58 | | | 0.30769231 | | 0.30769231 |
| PEX19/PXF | | | 0.30769231 | | 0.30769231 |
| GAB2 | | | 0.30769231 | | 0.30769231 |
| NRP1 | | | 0.30769231 | | 0.30769231 |
| GMNN/GEM | | 0.28571429 | | | 0.28571429 |
| RECQL | | 0.28571429 | | | 0.28571429 |
| ADAMTS1 | | 0.28571429 | | | 0.28571429 |
| TGFB3 | | 0.28571429 | | | 0.28571429 |
| SERPINF2 | | 0.28571429 | | | 0.28571429 |
| HMGB1 | | | | 0.28 | 0.28 |
| HIST1H2AC | | | | 0.28 | 0.28 |
| CASP3 | | | | 0.28 | 0.28 |
| ACOX1 | | | | 0.28 | 0.28 |
| MAP3K14 | 0.27027027 | | | | 0.27027027 |
| BCL2L11 | | | | 0.24 | 0.24 |
| SKP2 | | | | 0.24 | 0.24 |
| E2F2 | | | | 0.24 | 0.24 |
| SLPI | | | | 0.24 | 0.24 |
| BBC3 | | | | 0.24 | 0.24 |
| PPP1R13B | | | | 0.24 | 0.24 |
| MAP2K1 | | | 0.23076923 | | 0.23076923 |
| CASP7 | | | 0.23076923 | | 0.23076923 |
| ENO3 | | | 0.23076923 | | 0.23076923 |
| CALR | | | 0.23076923 | | 0.23076923 |
| INCENP | | | 0.23076923 | | 0.23076923 |
| YY1 | | | 0.23076923 | | 0.23076923 |
| NOLC1 | | | 0.23076923 | | 0.23076923 |
| H2BFN | | | 0.23076923 | | 0.23076923 |
| H2BFR | | | 0.23076923 | | 0.23076923 |
| PMS2L1 | | | 0.23076923 | | 0.23076923 |
| POLD1 | | | | 0.2 | 0.2 |
| CDC7 | | | | 0.2 | 0.2 |
| ATM | | | | 0.2 | 0.2 |
| SULT2A1 | | | | 0.2 | 0.2 |

The working premise underlying the scoring system is that derangements of one or more of the components of the SYN-MULVB/DRM/DREAM/LINC repressor/activator complex produces a cascade of gene over-expression that can occur at many different organ sites and produce ERGO tumors.

The final list of ERGO tumor associated over-expressed genes identified and their scores are summarized in Table 6 below.

TABLE 6

ERGO Gene List

| gene/protein name | score |
| --- | --- |
| BUB1 | 3.83696466 |
| TPX2/C20ORF1 | 3.67940468 |
| AURKA/STK15 | 3.67374517 |
| CENPA | 3.64845989 |
| CKS2 | 3.57765766 |
| AURKB/STK12 | 3.50708049 |
| UBE2C/UBCH10 | 3.17930172 |
| KIF2C/KNSL6 | 3.10916213 |
| STMN1 | 3.03344025 |
| CDC45L | 3.02556513 |
| LMNB1 | 3.02254826 |
| MAD2L1 | 2.96590041 |
| KIFC1/KNSL2 | 2.86531631 |
| HMMR | 2.8580233 |
| PTTG1 | 2.79923308 |
| KIF11/KNSL1 | 2.77597268 |
| CCNA2 | 2.74513811 |
| UNG | 2.67227865 |
| CENPF | 2.64265914 |
| TTK | 2.62800713 |
| CCNB2 | 2.61876448 |
| CDC2 | 2.59256641 |
| EZH2 | 2.5427027 |
| CDKN3 | 2.44891331 |
| BUB1B | 2.39736264 |
| ASF1B/FLJ10604 | 2.36752137 |
| MKI67 | 2.36043956 |
| NDC80/HEC | 2.34624295 |
| FOXM1 | 2.34162162 |
| BIRC5 | 2.33250635 |
| CDC20/p55CDC | 2.30577963 |
| CDC25B | 2.25555226 |
| BLM | 2.23240867 |
| TIMELESS | 2.19238095 |
| MCM2 | 2.15087615 |
| CENPE | 2.13357885 |
| KPNA2 | 2.12576577 |
| TMPO | 2.1225641 |
| MCM7 | 2.09858628 |
| RAD54L | 2.0965119 |
| CDC6 | 2.09230769 |
| CHEK1 | 2.07440451 |
| ANLN | 2.05880606 |
| CCNB1 | 2.04848233 |
| TK1 | 2.04540541 |
| TOP2A | 2.01521368 |
| NUSAP1/BM037 | 2.01158301 |
| RFC4 | 2.0008085 |
| DEK | 2.0008085 |
| SMC2/SMC2L1 | 1.9782675 |
| TYMS | 1.95219351 |
| PBK | 1.92307692 |
| CCNE2 | 1.91950104 |
| H2AFX | 1.90850015 |
| MCM6 | 1.90801241 |
| ECT2 | 1.90690691 |
| MELK/KIAA0175 | 1.90469854 |
| CDC25C | 1.87621028 |
| NEK2 | 1.85934858 |
| TOPBP1 | 1.8582675 |
| CHAF1A | 1.8552645 |
| E2F1 | 1.84585685 |
| PCNA | 1.83864634 |
| PRC1 | 1.82848233 |
| HMGB3/HMG4 | 1.8200693 |

TABLE 6-continued

ERGO Gene List

| gene/protein name | score |
| --- | --- |
| MSH2 | 1.79146685 |
| E2F3 | 1.76 |
| SRGAP2/KIAA0456 | 1.74571429 |
| NUP155 | 1.74322476 |
| RRM2 | 1.72571429 |
| CHAF1B | 1.71298221 |
| UBE2T/HSPC150 | 1.7008547 |
| RFC2 | 1.69367521 |
| CDKN2C | 1.64613075 |
| SMC4/SMC4L1 | 1.61281061 |
| UHRF1/ICBP90 | 1.57142857 |
| PLAU | 1.54945055 |
| KIF20A/RAB6KIFL | 1.54469854 |
| GCH1 | 1.51899878 |
| PARP1/ADPRT | 1.49145299 |
| TCF19 | 1.47863248 |
| DNMT1 | 1.45691846 |
| RACGAP1/ID-GAP | 1.43243243 |
| CCNF | 1.41269841 |
| DCK | 1.4042735 |
| TEAD4 | 1.38253638 |
| MCM3 | 1.36752137 |
| FEN1 | 1.32848233 |
| GINS1/KIAA0186 | 1.32307692 |
| RRM1 | 1.31340659 |
| POLE2 | 1.31196581 |
| BARD1 | 1.3008316 |
| RAD51AP1/PIR51 | 1.2972973 |
| PLK4/STK18 | 1.29435435 |
| SERPINE1 | 1.28791209 |
| POLA2 | 1.28257796 |
| CDCA4/FLJ20764 | 1.27472527 |
| CCND1 | 1.27428571 |
| DTYMK | 1.26153846 |
| CCNE1 | 1.24324324 |
| MCM4 | 1.23950104 |
| H2AFZ | 1.23846154 |
| HIST1H2BF/H2BFG | 1.23296703 |
| LHX2 | 1.22990991 |
| CKS1 | 1.22453222 |

This list of 105 ERGO tumor associated genes includes the nucleic acid sequences shown in SEQ ID NO:s 12-14, 20-21, 35, 37, 43-44, 46-47, 49-51, 54, 56, 58-67, 69-71, 75, 79-84, 86, 88, 91, 93-95, 103-105, 107-110, 112, 116, 118-120, 122, 125-126, 128-129, 131, 145-146, 148-149, 151, 154, 156-157, 163, 165-166, 171, 173, 176-177, 180, 184, 186, 188, 193, 196, 198, 200-201, 203, 205, 209, 246-247, 249, 254, 267, 269, 274-275, 292-294, 311, 316, 231-323, and 333; and splice variants or nucleic acids encoding different peptide chain isoforms derived from these nucleic acids that are capable of hybridizing to the nucleic acid sequences shown in these SEQ ID NO:s, or the complement thereof, under the hybridization conditions of a microarray experiment. This list accounts for a common list, or basic "mosaic" of over-expressed genes that are observed in ERGO tumors including ERGO tumors occurring at different organ sites. Table 7 below provides a key and identifies the gene or protein name as appropriate, the accession number of each amino acid sequence or nucleic acid sequence as appropriate, the SEQ ID NO:s for the 325 E2F response genes used in the analyses here and the SEQ ID NO:s for the final list of 105 ERGO tumor associated over-expressed genes identified. Astericks ("*") are used in Table 7 to identify the final list of 105 ERGO tumor associated over-expressed genes identified. Daggers ("†") are used in Table 7 to identify a refined list of 125 ERGO tumor associated over-expressed genes that were also identified. Double daggers ("‡") are used in Table 7 to identify housekeeping genes with transcript levels that do not appreciably vary in either normal or malignant tissue, such as normal or cancerous prostate tissue, and are useful for normalization of indicator values and references values. Genes having the sequences shown in SEQ ID NO:s 68 and 335-336 are E2F responsive genes with high sequence identity, or sequence similarity, to other ERGO genes identified. Genes having the sequences shown in SEQ ID NO:s 39, 72, 102, 123, 160, 164, 174, 217, 259, 295, 298, 307, 331 and 337-340 are E2F responsive genes that were identified by analyses of microarray data from prostate tissue samples and have been found to be useful in discriminating aggressive prostate cancers from non-aggressive prostate cancers.

TABLE 7

| gene/protein name | accession number | SEQ ID NO: |
|---|---|---|
| BCL2L11 | NM_006538 | 10 |
| FOXO1//FOXO1A | NM_002015 | 11 |
| CCNE2*† | NM_057749 | 12 |
| CDKN2C*† | NM_001262 | 13 |
| CCNE1*† | NM_001238 | 14 |
| MYC | NM_002467 | 15 |
| FGFR3 | NM_000142 | 16 |
| MAP3K5 | NM_005923 | 17 |
| BMP2 | NM_001200 | 18 |
| MYB | NM_005375 | 19 |
| LHX2*† | NM_004789 | 20 |
| GCH1*† | NM_000161 | 21 |
| MAPK9 | NM_002752 | 22 |
| MAPK8 | NM_002750 | 23 |
| MAPK3 | X60188 | 24 |
| MAPK1 | NM_002745 | 25 |
| MAPK4 | NM_002747 | 26 |
| MAP2K1 | NM_002755 | 27 |
| MAP2K2 | NM_030662 | 28 |
| FOXO3//FOXO3A | NM_001455 | 29 |
| GADD45B | NM_015675 | 30 |
| MCL1 | L08246 | 31 |
| BCL2 | NM_000633 | 32 |
| CCND3 | NM_00176 | 33 |
| FOXN3//CHES1 | NM_005197 | 34 |
| MKI67*† | NM_002417 | 35 |
| CDKN1C | NM_000076 | 36 |
| KIFC1*† | D14678 | 37 |
| PRG4 | NM_005807 | 38 |
| PMS2† | NM_000535 | 39 |
| PLK2//SNK | NM_006622 | 40 |
| HRK | NM_003806 | 41 |
| CASP8 | NM_001228 | 42 |
| TYMS*† | NM_001071 | 43 |
| TK1*† | NM_003258 | 44 |
| DUT | NM_001948 | 45 |
| RRM1*† | NM_001033 | 46 |
| RRM2*† | NM_001034 | 47 |
| CDK2 | NM_001798 | 48 |
| MCM3*† | NM_002388 | 49 |
| MCM7*† | D55716 | 50 |
| PCNA*† | NM_002592 | 51 |
| RFC3 | NM_002915 | 52 |
| PRIM1 | NM_000946 | 53 |
| TOP2A*† | NM_001067 | 54 |
| LIG1 | NM_000234 | 55 |
| FEN1*† | NM_004111 | 56 |
| RAD51 | NM_002875 | 57 |
| CDC20*† | NM_001255 | 58 |
| CDC2*† | NM_001786 | 59 |
| CCNA2*† | NM_001237 | 60 |
| CCNB1*† | NM_031966 | 61 |
| CCNB2*† | NM_004701 | 62 |
| SMC2//SMC2L1*† | NM_006444 | 63 |
| STMN1*† | NM_005563 | 64 |
| NDC80//HEC*† | NM_006101 | 65 |
| BUB1*† | NM_004336 | 66 |
| KPNA2*† | NM_002266 | 67 |
| HMGB2† | NM_001130688 | 68 |
| EZH2*† | NM_004456 | 69 |
| AURKB//STK12*† | NM_004217 | 70 |

TABLE 7-continued

| gene/protein name | accession number | SEQ ID NO: |
|---|---|---|
| PTTG1*† | NM_004219 | 71 |
| SLBP† | NM_006527 | 72 |
| RB1 | NM_000321 | 73 |
| ANXA8 | NM_001040084 | 74 |
| DCK*† | NM_000788 | 75 |
| CDC25A | NM_001789 | 76 |
| EPS8 | NM_004447 | 77 |
| FST | NM_013409 | 78 |
| TMPO*† | NM_003276 | 79 |
| RAD51AP1//PIR51*† | NM_006479 | 80 |
| ASF1B*† | NM_018154 | 81 |
| CDCA4*† | NM_017955 | 82 |
| RFC4*† | NM_002916 | 83 |
| BLM*† | NM_000057 | 84 |
| VRK1 | NM_003384 | 85 |
| BARD1*† | NM_000465 | 86 |
| BTG3 | NM_006806 | 87 |
| CHAF1A*† | NM_005483 | 88 |
| NPAT | NM_002519 | 89 |
| HUNK | NM_014586 | 90 |
| DEK*† | NM_003472 | 91 |
| EED | AF099032 | 92 |
| MCM4*† | X74794 | 93 |
| MELK*† | NM_014791 | 94 |
| TCF19*† | NM_007109 | 95 |
| FANCL | NM_018062 | 96 |
| PBX3 | NM_006195 | 97 |
| EGR1 | NM_001964 | 98 |
| CDCA7L | NM_001127370 | 99 |
| SKP2 | NM_005983 | 100 |
| CTGF | NM_001901 | 101 |
| CITED2† | NM_006079 | 102 |
| SERPINE1*† | M16006 | 103 |
| CCND1*† | NM_053056 | 104 |
| UHRF1//ICBP90*† | NM_013282 | 105 |
| MCM5 | NM_006739 | 106 |
| HMGB3*† | NM_005342 | 107 |
| MCM6*† | NM_005915 | 108 |
| CDC45L*† | NM_003504 | 109 |
| CDC6*† | NM_001254 | 110 |
| ORC6L | NM_014321 | 111 |
| CKS2*† | NM_001827 | 112 |
| GMNN | NM_015895 | 113 |
| PRIM2 | NM_000947 | 114 |
| CENPK//FKSG14 | NM_022145 | 115 |
| NUP155*† | NM_004298 | 116 |
| FIGNL1 | NM_001042762 | 117 |
| MAD2L1*† | NM_002358 | 118 |
| CCNF*† | NM_001761 | 119 |
| DNMT1*† | NM_001379 | 120 |
| RPA1 | NM_002945 | 121 |
| PRC1*† | NM_003981 | 122 |
| RBL1† | NM_002895 | 123 |
| BRCA1 | NM_007294 | 124 |
| H2AFZ*† | NM_002106 | 125 |
| DTYMK*† | NM_012145 | 126 |
| PLK1 | NM_005030 | 127 |
| POLA2*† | NM_002689 | 128 |
| PBK*† | NM_018492 | 129 |
| CASP7 | NM_001227 | 130 |
| MCM2*† | NM_004526 | 131 |
| RPA3 | NM_002947 | 132 |
| GJC1//GJA7 | NM_005497 | 133 |
| USP1 | NM_003368 | 134 |
| DNA2L | D42046 | 135 |
| CITED1 | NM_004143 | 136 |
| NASP | NM_002482 | 137 |
| RFC5† | NM_007370, NM_001130112 | 138, 340 |
| SMARCA5 | NM_003601 | 139 |
| SHCBP1//FLJ22009 | NM_024745 | 140 |
| SSX2IP | NM_014021 | 141 |
| MFAP1 | NM_005926 | 142 |
| ROD1 | NM_005156 | 143 |
| BMPR1A | NM_004329 | 144 |
| E2F3*† | NM_001949 | 145 |
| UNG*† | NM_003362 | 146 |

TABLE 7-continued

| gene/protein name | accession number | SEQ ID NO: |
|---|---|---|
| ENO3 | NM_001976 | 147 |
| MSH2*'† | NM_000251 | 148 |
| PLK4*'† | NM_014264 | 149 |
| ACTA2 | NM_001613 | 150 |
| TIMELESS*'† | NM_003920 | 151 |
| BOK | NM_032515 | 152 |
| KBTBD10//SARCOSIN | NM_006063 | 153 |
| BUB1B*'† | NM_001211 | 154 |
| NUP107 | NM_020401 | 155 |
| KIF2C//KNSL6*'† | NM_006845 | 156 |
| LMNB1*'† | NM_005573 | 157 |
| RPA2 | NM_002946 | 158 |
| CHEK2//CDS1 | NM_007194 | 159 |
| COL11A1† | NM_001854 | 160 |
| TGFB3 | NM_003239 | 161 |
| CALR‡ | NM_004343 | 162 |
| TTK*'† | NM_003318 | 163 |
| E2F2† | NM_004091 | 164 |
| CKS1B//CKS1*'† | NM_001826 | 165 |
| RFC2*'† | NM_002914 | 166 |
| UMPS | NM_000373 | 167 |
| DBF4//ASK | NM_006716 | 168 |
| CHEK1*'† | NM_001274 | 169 |
| BUB3 | NM_004725 | 170 |
| CENPE*'† | NM_001813 | 171 |
| CSTF1 | NM_001324 | 172 |
| RAD54L*'† | NM_003579 | 173 |
| POLD1† | NM_002691 | 174 |
| MLH1 | NM_000249 | 175 |
| CENPA*'† | NM_001809 | 176 |
| SMC4//SMC4L1*'† | NM_005496 | 177 |
| HMGB1//HMG1† | AL110194, NM_002128 | 178, 336 |
| HIST1H3D//H3FB | NM_003530 | 179 |
| H2AFX*'† | NM_002105 | 180 |
| CBX5 | NM_012117 | 181 |
| HIST1H2AC//H2AFL | NM_003512 | 182 |
| KIF22//KNSL4 | NM_007317 | 183 |
| NEK2*'† | NM_002497 | 184 |
| KIF4A | NM_012310 | 185 |
| HMMR*'† | NM_012484 | 186 |
| MTHFD1 | NM_005956 | 187 |
| GINS1*'† | D80008 | 188 |
| SFPQ | NM_005066 | 189 |
| HSP90B1//TRA1 | NM_003299 | 190 |
| MAP3K7 | NM_003188 | 191 |
| PLSCR1 | AB006746 | 192 |
| ANLN*'† | NM_018685 | 193 |
| SFRS2 | NM_003016 | 194 |
| ID3 | X69111 | 195 |
| TEAD4*'† | NM_003213 | 196 |
| SRPR | NM_003139 | 197 |
| UBE2T//HSPC150*'† | NM_014176 | 198 |
| INCENP | NM_020238 | 199 |
| CDC25B*'† | NM_004358 | 200 |
| AURKA//STK15*'† | NM_003600 | 201 |
| DHFR | NM_000791 | 202 |
| CDKN3*'† | NM_005192 | 203 |
| CDC7//CDC7L1 | AF015592 | 204 |
| RACGAP1//ID-GAP*'† | NM_013277 | 205 |
| CSRP2 | NM_001321 | 206 |
| MAF | NM_005360 | 207 |
| CBX3 | NM_007276 | 208 |
| CHAF1B*'† | NM_005541 | 209 |
| ADAMTS1 | NM_006988 | 210 |
| TCOF1 | NM_000356 | 211 |
| LSM5 | NM_012322 | 212 |
| HNRNPC//HNRPC | NM_001077442 | 213 |
| APAF1 | NM_013229 | 214 |
| ASH2L | NM_004674 | 215 |
| BCL3 | NM_005178 | 216 |
| CASP3† | NM_004346 | 217 |
| CAV1 | AF070648 | 218 |
| CD58 | NM_001779 | 219 |
| DMRT1 | AF130728 | 220 |
| DYRK1A | NM_001396 | 221 |
| LIMA1//EPLIN | NM_016357 | 222 |
| FGFR2 | NM_000141 | 223 |
| HEY1 | NM_012258 | 224 |
| INHBA | NM_002192 | 225 |
| TBC1D2B//KIAA1055 | AK000173 | 226 |
| OSMR | NM_003999 | 227 |
| FURIN//PACE | NM_002569 | 228 |
| PRKAR2B | NM_002736 | 229 |
| SIRPA//PTPNS1 | NM_001040022 | 230 |
| RANBP9 | NM_005493 | 231 |
| SOX9 | NM_000346 | 232 |
| SPHK1 | AF238083 | 233 |
| TACC1 | NM_006283 | 234 |
| TGFA | NM_003236 | 235 |
| TGFB2 | NM_003238 | 236 |
| YY1 | NM_003403 | 237 |
| SNAPC1 | NM_003082 | 238 |
| CCNG2 | NM_004354 | 239 |
| HOXA7 | NM_006896 | 240 |
| HOXA9 | NM_152739 | 241 |
| PITX1 | NM_002653 | 242 |
| SMARCA2 | NM_003070 | 243 |
| BACH1 | NM_001186 | 244 |
| CBFB | NM_001755 | 245 |
| BIRC5*'† | NM_001168 | 246 |
| CDC25C*'† | NM_001790 | 247 |
| ORC3L | NM_012381 | 248 |
| TOPBP1*'† | NM_007027 | 249 |
| MRE11A | NM_005590 | 250 |
| ATM | NM_000051 | 251 |
| XRCC4 | NM_003401 | 252 |
| RECQL | NM_002907 | 253 |
| CENPF*'† | NM_016343 | 254 |
| CENPH//PMF1 | NM_022909 | 255 |
| NOLC1 | NM_004741 | 256 |
| KIF20B//MPHOSPH1 | NM_016195 | 257 |
| BMI1 | NM_005180 | 258 |
| HIST1H2AE//H2AFA† | NM_021052 | 259 |
| HIST1H2AD//H2AFG | NM_021065 | 260 |
| HIST1H2BN//H2BFD | NM_003520 | 261 |
| HIST1H2BE//H2BFH | NM_003523 | 262 |
| HIST1H2BO//H2BFN | NM_003527 | 263 |
| HIST1H2BJ//H2BFR | NM_021058 | 264 |
| HIST1H3B//H3FL | NM_003537 | 265 |
| HIST2H4A//H4F2 | NM_003548 | 266 |
| HIST1H2BF//H2BFG*'† | NM_003522 | 267 |
| HIST1H3E//H3FD | NM_003532 | 268 |
| KIF20A//RAB6KIFL*'† | NM_005733 | 269 |
| FGFR1OP//FOP† | AL117608, NM_007045 | 270, 337 |
| DHPS | NM_013406 | 271 |
| PEX19//PXF | NM_002857 | 272 |
| PPM1D | NM_003620 | 273 |
| E2F1*'† | M96577 | 274 |
| PARP1//ADPRT*'† | NM_001618 | 275 |
| ORC2L | NM_006190 | 276 |
| VEGFA//VEGF | NM_003376 | 277 |
| APOE | NM_000041 | 278 |
| PRPS1 | NM_002764 | 279 |
| TGFB1I1 | NM_015927 | 280 |
| CXCR7//RDC1 | U67784 | 281 |
| PDGFRA | X76079 | 282 |
| SLPI | NM_003064 | 283 |
| FAS//TNFRSF6 | NM_000043 | 284 |
| CPT1A | NM_001876 | 285 |
| PDCD4 | NM_014456 | 286 |
| TANK | NM_004180 | 287 |
| APBB2 | NM_173075 | 288 |
| GADD45A | NM_001924 | 289 |
| ACOX1 | NM_007292 | 290 |
| CSDA | NM_003651 | 291 |
| UBE2C//UBCH10*'† | NM_007019 | 292 |
| TPX2//C20orf1*'† | AB024704 | 293 |
| NUSAP1//BM037*'† | NM_016359 | 294 |
| SULT2A1† | NM_003167 | 295 |
| INMT | NM_006774 | 296 |
| ARHGAP4 | X78817 | 297 |
| RAD52† | NM_134424 | 298 |

TABLE 7-continued

| gene/protein name | accession number | SEQ ID NO: |
|---|---|---|
| TNFSF9 | NM_003811 | 299 |
| BAD | U66879 | 300 |
| BAK1 | NM_001188 | 301 |
| BID | NM_001196 | 302 |
| CFLAR | NM_003879 | 303 |
| MAP3K14 | NM_003954 | 304 |
| PAWR | NM_002583 | 305 |
| FGF2 | NM_002006 | 306 |
| MMP16† | NM_005941 | 307 |
| TP53BP2 | NM_005426 | 308 |
| VEGFB | NM_003377 | 309 |
| IFNA2 | M54886 | 310 |
| SRGAP2//KIAA0456*'† | AK000885 | 311 |
| DIP//KIAA0767 | AB018310 | 312 |
| SERPINF2 | D00174 | 313 |
| CCNO//UNG2 | NM_021147 | 314 |
| TP73 | NM_005427 | 315 |
| POLE2*'† | NM_002692 | 316 |
| RAD51C | NM_002876 | 317 |
| PMS2L1 | D38435 | 318 |
| DDB2 | NM_000107 | 319 |
| NFKB2 | NM_002502 | 320 |
| KIF11//KNSL1*'† | NM_004523 | 321 |
| FOXM1*'† | U74612 | 322 |
| PLAU*'† | NM_002658 | 323 |
| BBC3 | U82987 | 324 |
| PMAIP1 | D90070 | 325 |
| GAB2 | NM_012296 | 326 |
| SIVA1//SIVA | NM_006427 | 327 |
| PPP1R13B | AB018314 | 328 |
| AXIN2 | NM_004655 | 329 |
| DIABLO//SMAC | NM_019887 | 330 |
| AR† | NM_000044 | 331 |
| NRP1 | NM_003873 | 332 |
| ECT2*'† | NM_018098 | 333 |
| ISYNA1 | NM_016368 | 334 |
| MYBL1† | NM_001080416 | 335 |
| MYBL2† | NM_002466 | 338 |
| HIST1H2BK† | NM_080593 | 339 |
| CUL4B‡ | NM_001079872 | 341 |
| OAZ2‡ | NM_002537 | 342 |
| TBCC‡ | NM_003192 | 343 |
| NUP214‡ | NM_005085 | 344 |
| FBXW11‡ | NM_012300 | 345 |
| POP4‡ | NM_006627 | 346 |
| LPCAT3‡ | NM_005768 | 347 |
| ARSE‡ | NM_000047 | 348 |
| ARC‡ | NM_015193 | 349 |
| POLR3D‡ | NM_001722 | 350 |
| DLGAP4‡ | NM_001042486 | 351 |
| SLC22A5‡ | NM_003060 | 352 |
| BRMS1‡ | NM_001024957 | 353 |
| ZFAND5‡ | NM_001102420 | 354 |
| THOP1‡ | NM_003249 | 355 |
| DNPEP‡ | NM_012100 | 356 |
| USP20‡ | NM_001008563 | 357 |
| HMGN2‡ | NM_005517 | 358 |
| ARF3‡ | NM_001659 | 359 |
| PSMB1‡ | NM_002793 | 360 |
| CFL1‡ | NM_005507 | 361 |
| RPS25‡ | NM_001028 | 362 |
| MANF‡ | NM_006010 | 363 |
| HADHB‡ | NM_000183 | 364 |
| RPL22‡ | NM_000983 | 365 |

Example 7

Bladder Cancer is an ERGO Tumor

Studies by Olsson et al. (2007) have indicated that E2F3 overexpression may play a role in the development of bladder cancers. We examined dataset GSE3167 (Dyrskjøt et al., (2004)), available from the NCBI GEO site, which contains gene expression microarray data from patient samples of normal bladder tissues which were used for data normalization, patient samples of localized bladder cancers, and patient samples of muscle-invasive bladder cancers. Among 33 tumor samples that were histopathologically grade 3 or 4, 32 of these 33 samples simultaneously overexpressed at least 20 of a list of 93 E2F-responsive genes included in these analyses. See FIG. 26. All of the genes in the list were overexpressed in a least 20 percent of the 33 tumors. Fifty-five of these 93 E2F-responsive genes, or 59% of the 93 E2F-responsive genes, were amoung the 125 genes identified in the generic ERGO gene list shown in Table 8. In contrast, only 2 of 8 grade 2 bladder cancer samples, and none of the 7 normal bladder samples, overexpressed at least 20 of these 93 E2F responsive genes. See FIG. 26. These results demonstrate that bladder cancers are an ERGO tumor and that the overexpression of ERGO tumor genes is correlated to increasing bladder cancer grade.

Example 8

Hepatoma is an ERGO Tumor

Figure 27A:
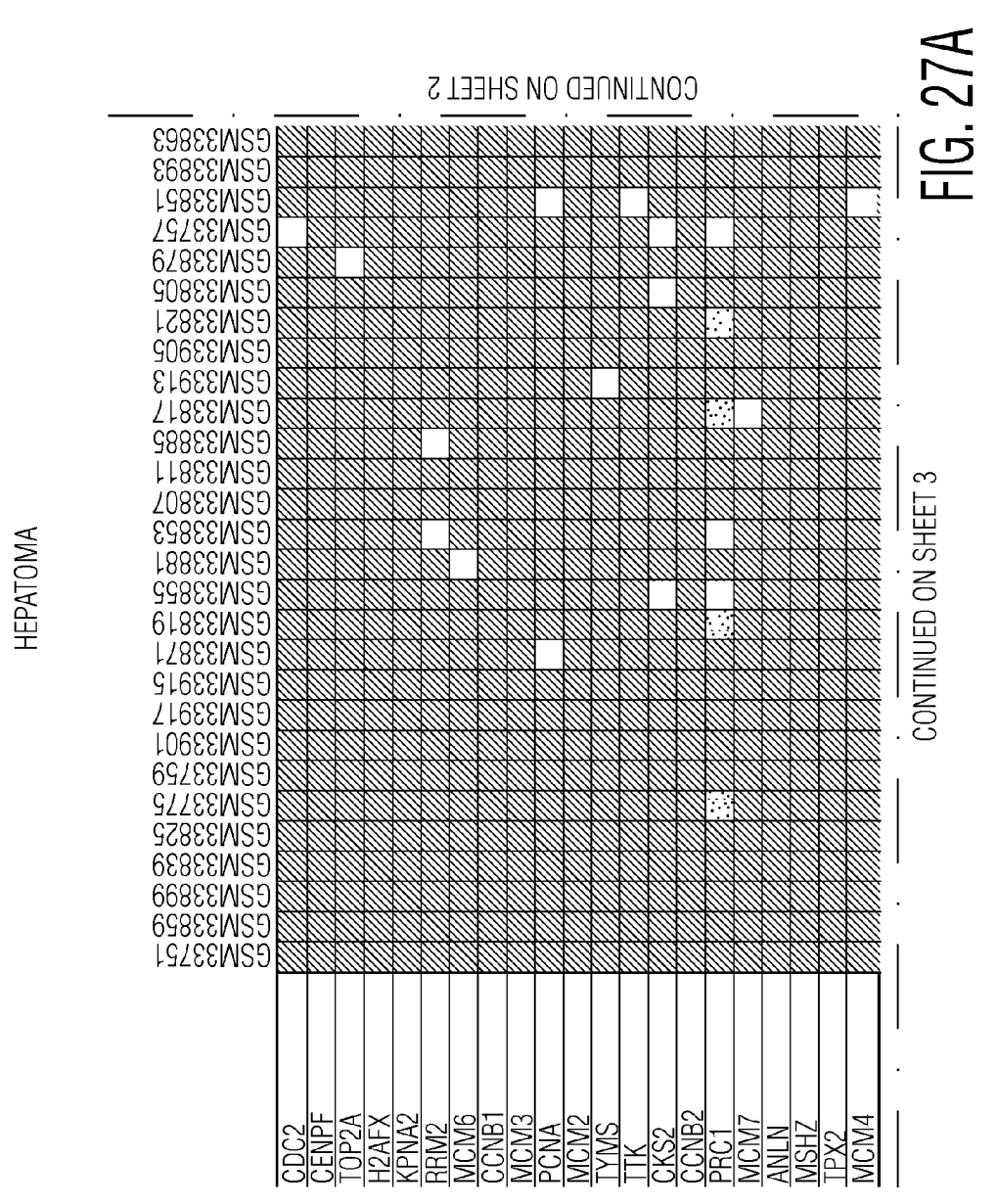
Figure 27C:
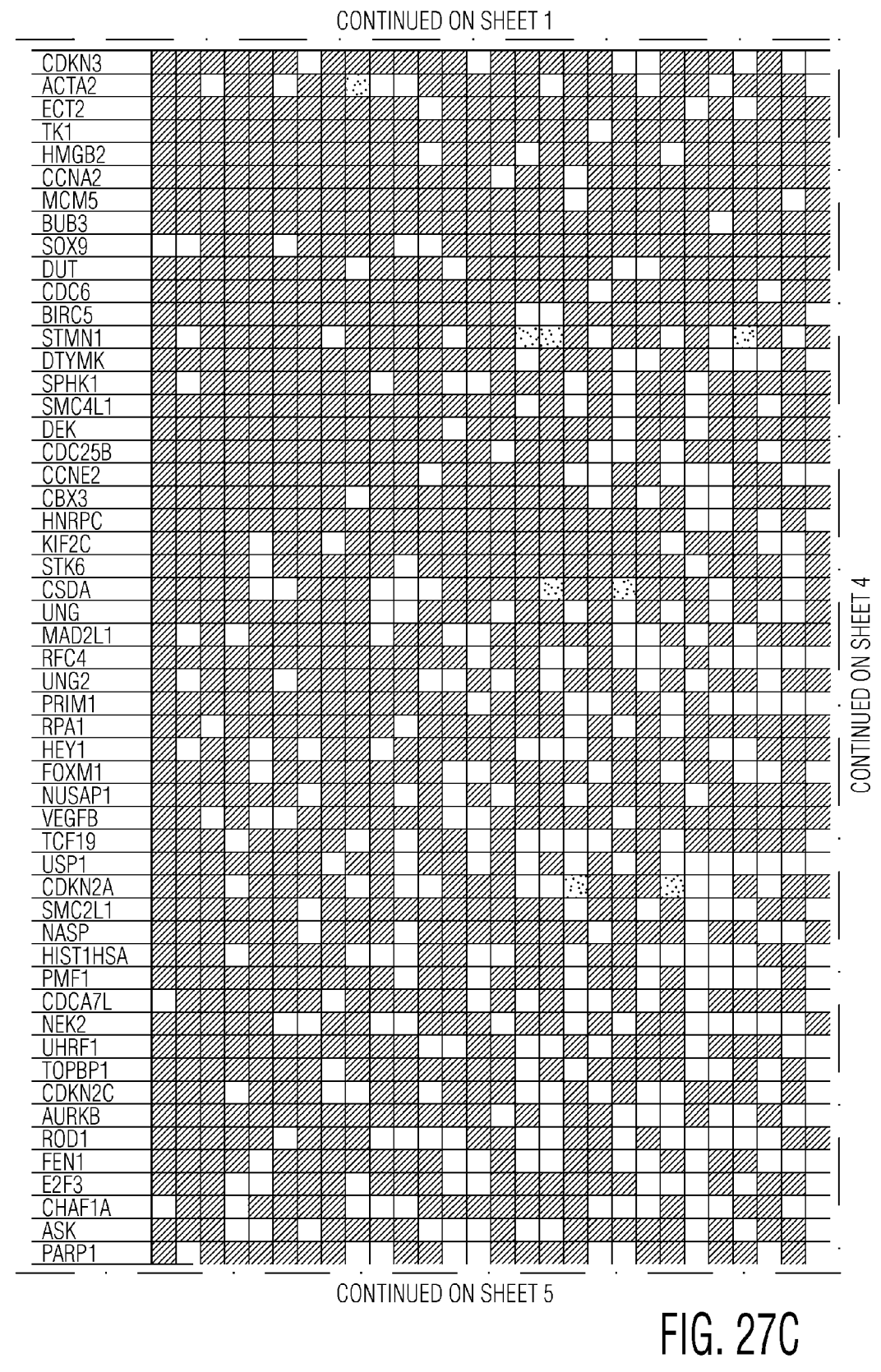
Figure 27D:
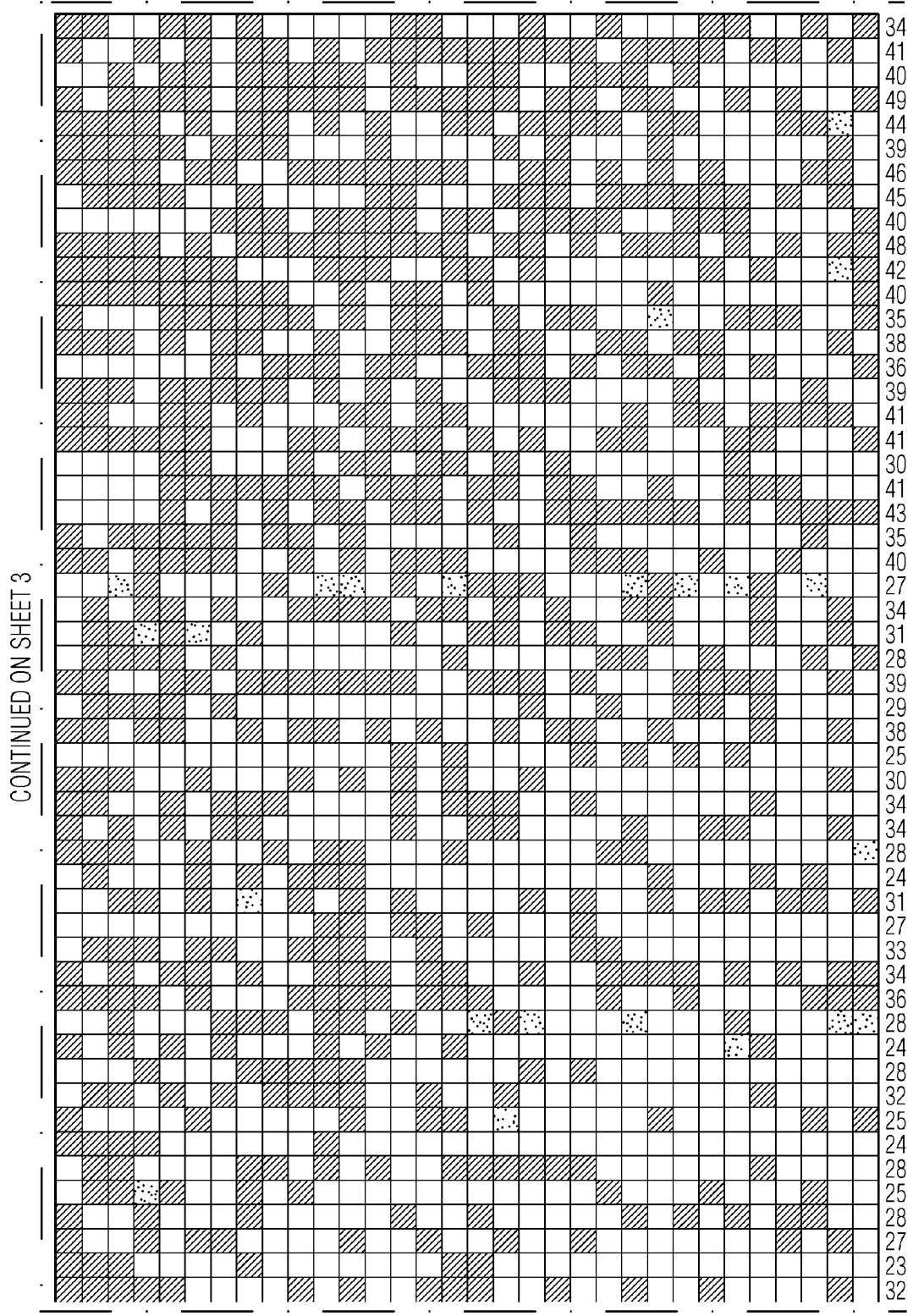
Figure 27E:
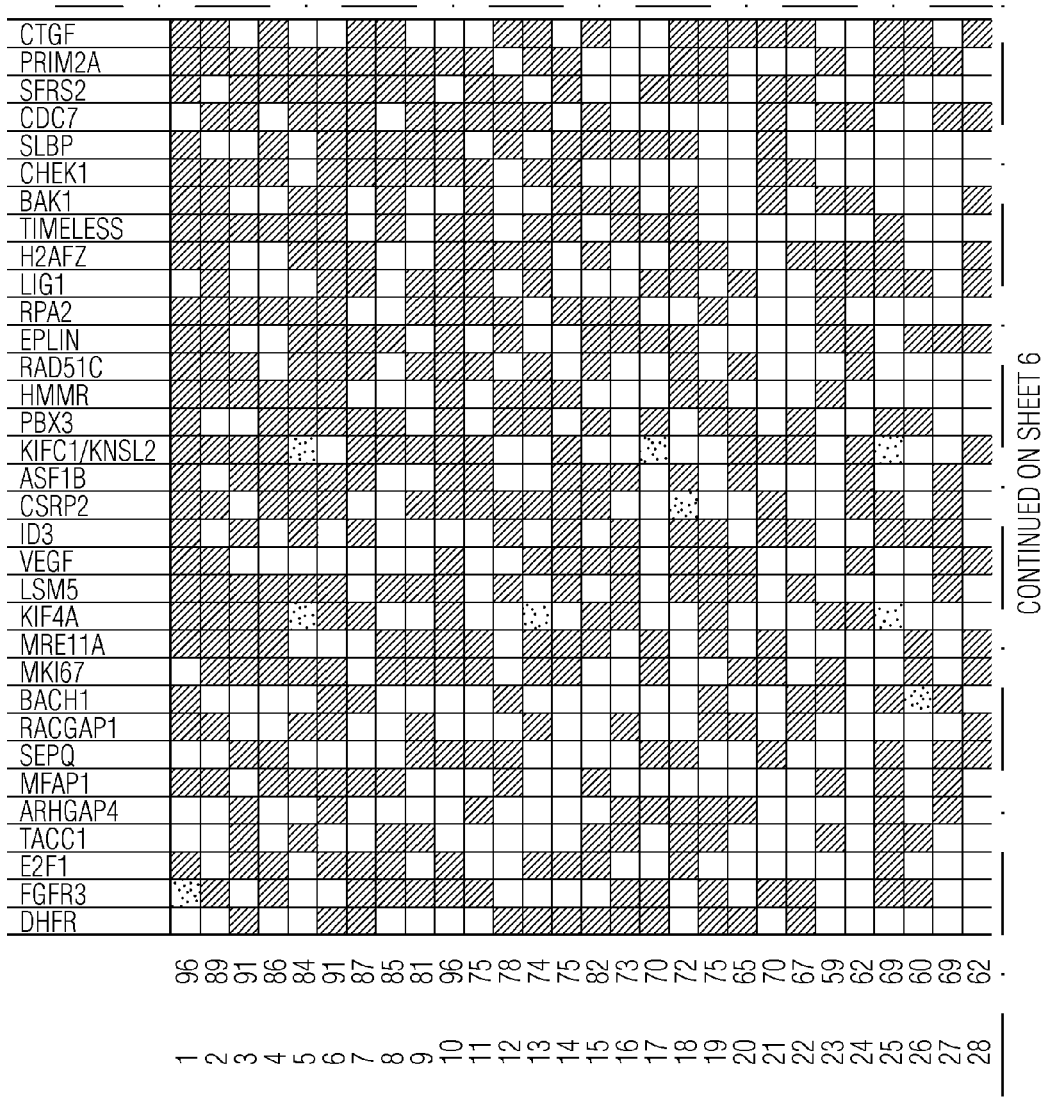
Figure 27F:
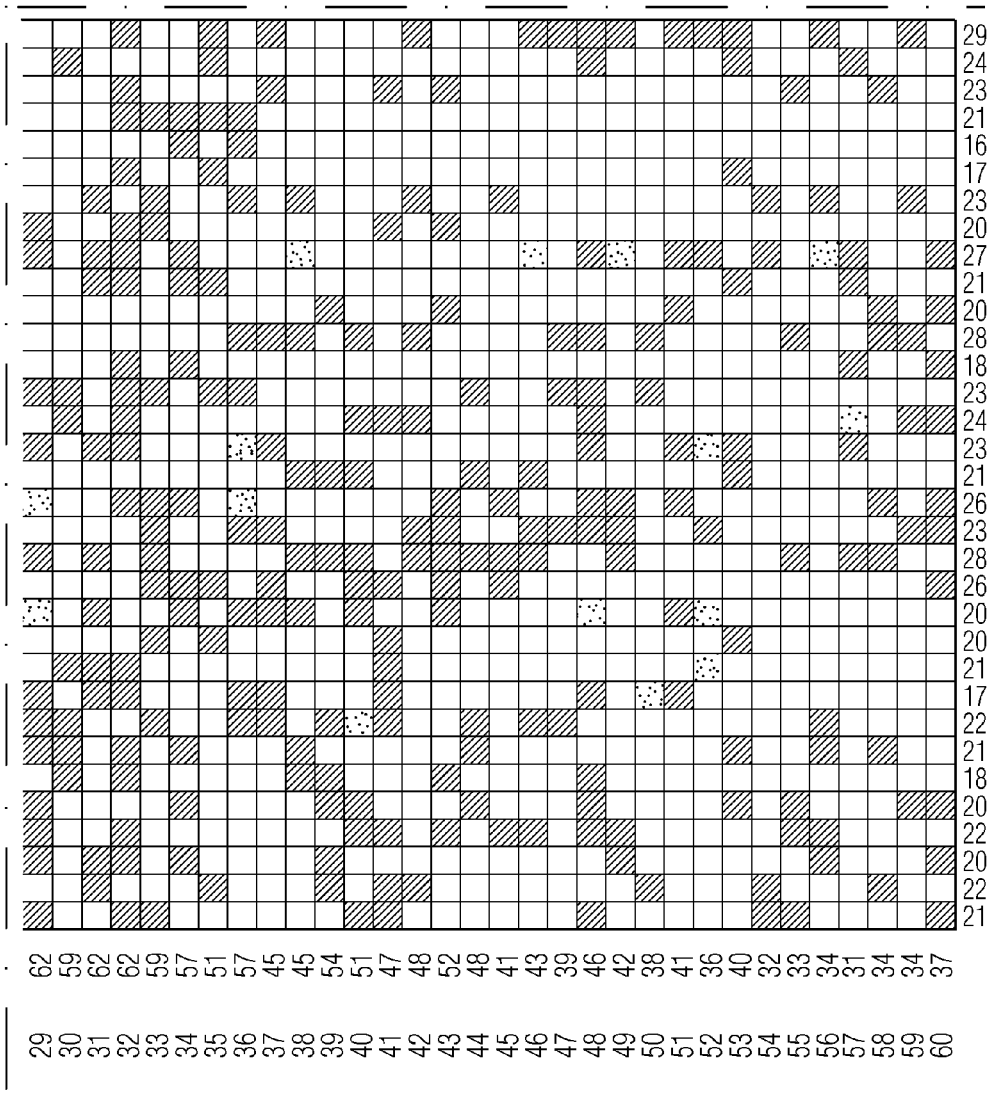

Heptomas have been reported by Kalinichenko et al., (2004) to overexpress FOXM1 which we know to be an ERGO tumor-associated gene. We examined dataset GSE1898, available from the NCBI GEO site, which contained gene expression microarray data from 182 patient samples of hepatoma. Sixty (60) of these samples simultaneously overexpressed at least 20% of the genes in a list of 107 E2F-responsive genes included in these analyses. See FIG. 27. Moreover, each one of the individual E2F-responsive genes in this list of 107 E2F-responsive genes was also overexpressed in at least 20% of the tumors. In fact, 58% of these genes were included in the list of 125 genes identified in the generic ERGO gene list shown in Table 8. These results demonstrate that approximately one third of hepatomas, or 60 out of 182 patient samples of hepatoma, are ERGO tumors.

All references (e.g. journal articles, patent documents, and accession numbers) cited herein are incorporated by reference in their entirety.

REFERENCES

Abstract #1462, 2008 for the SNS-314 aurora kinase inhibitor compound.
Abstract #2203, the aurora kinase inhibitor compounds ZM 447439, American Society of Clinical Oncology 2008 Meeting.
Abstract #2517, PF-03814735, American Society of Clinical Oncology 2008 Meeting.
Abstract #2663, American Association of Cancer Researchers 2008 Meeting.
Abstract #3008, American Society of Clinical Oncology (ASCO) 2008 Annual Meeting.
Abstract #3009, ASCO 2008 Annual Meeting.
Abstract #3237, American Association for Cancer Research (AACR) 2008 Annual Meeting.
Abstract #3280, American Association of Cancer Researchers 2008 Meeting.
Abstract #3507, PHA-739358, American Society of Clinical Oncology 2008 Meeting.
Abstract #3577, MLN8054, American of Clinical Oncology 2008 Meeting.
Abstracts #3536, 5135, and 8538, American Society of Oncologist 2008 Meeting.
Abstract #14130, AS703569, American Society of Clinical Oncology 2008 Meeting.

Abdel-Fatah, T. M., D. G. Powe, et al. (2008). "Morphologic and molecular evolutionary pathways of low nuclear grade invasive breast cancers and their putative precursor lesions: further evidence to support the concept of low nuclear grade breast neoplasia family." *Am J Surg Pathol* 32(4): 513-23.

Agnese, V et al., Annals of Oncology 18: vi47-vi52, 2007.

Arlot-Bonnemains, Y., E. Baldini, et al. (2008). "Effects of the Aurora kinase inhibitor VX-680 on anaplastic thyroid cancer-derived cell lines." *Endocr Relat Cancer* 15(2): 559-68.

Ames, J. B., J. S. Brunet, et al. (2005) "Placental cadherin and the basal epithelial phenotype of BRCA1-related breast cancer." *Clin Cancer Res* 11(11): 4003-11.

Bachmann, I. M., O. J. Halvorsen, et al. (2006). "EZH2 expression is associated with high proliferation rate and aggressive tumor subgroups in cutaneous melanoma and cancers of the endometrium, prostate, and breast." *J Clin Oncol* 24(2): 268-73.

Beardmore, V. A., L. J. Ahonen, et al. (2004). "Survivin dynamics increases at centromeres during G2/M phase transition and is regulated by microtubule-attachment and Aurora B kinase activity." *J Cell Sci* 117(Pt 18): 4033-42.

Beger, C., L. N. Pierce, et al. (2001). "Identification of Id4 as a regulator of BRC1 expression by using a ribozyme-library-based inverse genomics approach." *Proc Natl Acad Sci USA* 98(1): 130-5.

Bettoun, D. J., T. P. Burris, et al. (2003). "Retinoid X receptor is a nonsilent major contributor to vitamin D receptor-mediated transcriptional activation." *Mol Endocrinol* 17(11): 2320-8.

Black, E. P., E. Huang, et al. (2003). "Distinct gene expression phenotypes of cells lacking Rb and Rb family members." *Cancer Res* 63(13): 3716-23.

Buck, M. B., P. Fritz, et al. (2004). "Prognostic significance of transforming growth factor beta receptor II in estrogen receptor-negative breast cancer patients." *Clin Cancer Res* 10(2): 491-8.

Buck, M. B. and C. Knabbe (2006). "TGF-beta signaling in breast cancer." *Ann N Y Acad Sci* 1089: 119-26.

Callagy, G. M., P. D. Pharoah, et al (2006). "Bcl-2 is a prognostic marker in breast cancer independently of the Nottingham Prognostic Index." *Clin Cancer Res* 12(8): 2468-75.

Carter, S. L., A. C. Eklund, et al. (2006). "A signature of chromosomal instability inferred from gene expression profiles predicts clinical outcome in multiple human cancers." *Nat Genet* 38(9): 1043-8.

Chandran, U. R., C. Ma, et al. (2007). "Gene expression profiles of prostate cancer reveal involvement of multiple molecular pathways in the metastatic process." *BMC Cancer* 7: 64.

Charafe-Jauffret, E., C. Ginestier, et al. (2006). "Gene expression profiling of breast cell lines identifies potential new basal markers." *Oncogene* 25(15): 2273-84.

Charafe-Jauffret, E., F. Monville, et al. (2007). "Moesin expression is a marker of basal breast carcinomas." *Int J Cancer* 121(8): 1779-85.

Collett, K., G. E. Eide, et al. (2006). "Expression of enhancer of zeste homologue 2 is significantly associated with increased tumor cell proliferation and is a marker of aggressive breast cancer." *Clin Cancer Res* 12(4): 1168-74.

Dai, H., L. van't Veer, et al. (2005). "A cell proliferation signature is a marker of extremely poor outcome in a subpopulation of breast cancer patients." *Cancer Res* 65(10): 4059-66.

Dankof, A., F. R. Fritzsche, et al. (2007). "KPNA2 protein expression in invasive breast carcinoma and matched peritumoral ductal carcinoma in situ." *Virchows Arch* 451(5): 877-81.

Dolled-Filhart, M., L. Ryden, et al. (2006). "Classification of breast cancer using genetic algorithms and tissue microarrays." *Clin Cancer Res* 12(21): 6459-68.

Dyrskjøt L, Kruhøffer M, Thykjaer T, Marcussen N et al. (2004). "Gene expression in the urinary bladder: a common carcinoma in situ gene expression signature exists disregarding histopathological classification." *Cancer Res* 64(11): 4040-8.

Ekholm-Reed, S., J. Mendez, et al. (2004). "Deregulation of cyclin E in human cells interferes with prereplication complex assembly." *J Cell Biol* 165(6): 789-800.

Esseghir, S., A. Kennedy, et al. (2007). "Identification of NTN4, TRA1, and STC2 as prognostic markers in breast cancer in a screen for signal sequence encoding proteins." *Clin Cancer Res* 13(11): 3164-73.

Foulkes, W. D., J. S. Brunet, et al. (2004). "The prognostic implication of the basal-like (cyclin E high/p27 low/p53+/glomeruloid-microvascular-proliferation+) phenotype of BRCA1-related breast cancer." *Cancer Res* 64(3): 830-5.

Frasor, J., J. M. Danes, et al. (2005). "Estrogen down-regulation of the corepressor N-CoR: mechanism and implications for estrogen derepression of N-CoR-regulated genes." *Proc Natl Acad Sci USA* 102(37): 13153-7.

Frasor, J., J. M. Danes, et al. (2003). "Profiling of estrogen up- and down-regulated gene expression in human breast cancer cells: insights into gene networks and pathways underlying estrogenic control of proliferation and cell phenotype." *Endocrinology* 144(10): 4562-74.

Fritzsche, F. R., E. Dahl, et al. (2006). "Prognostic relevance of AGR2 expression in breast cancer." *Clin Cancer Res* 12(6): 1728-34.

Fulford, L. G., J. S. Reis-Filho, et al. (2007). "Basal-like grade III invasive ductal carcinoma of the breast: patterns of metastasis and long-term survival." *Breast Cancer Res* 9(1): R4.

Garcia, S., J. P. Dales, et al. (2007). "Poor prognosis in breast carcinomas correlates with increased expression of targetable CD146 and c-Met and with proteomic basal-like phenotype." *Hum Pathol* 38(6): 830-41.

Gartel, A. and A. Tyner (1998). "The growth-regulatory role of p21 (WAF1/CIP1)." *Progress in Molecular and Subcellular Biology* 20: 43-71.

Georlette, D., S. Alm, et al. (2007). "Genomic profiling and expression studies reveal both positive and negative activities for the *Drosophila* Myb MuvB/dREAM complex in proliferating cells." *Genes Dev* 21(22): 2880-96.

Ghosh, R., N. Nadiminty, et al. (2005). "Eugenol causes melanoma growth suppression through inhibition of E2F1 transcriptional activity." *J Biol Chem* 280(7): 5812-9.

Goncalves, A., E. Charafe-Jauffret, et al. (2008). "Protein profiling of human breast tumor cells identifies novel biomarkers associated with molecular subtypes." *Mol Cell Proteomics*.

Gonzalez, M. A., S. E. Pinder, et al. (2003). "Minichromosome maintenance protein 2 is a strong independent prognostic marker in breast cancer." *J Clin Oncol* 21(23): 4306-13.

Gray-Bablin, J., J. Zalvide, et al. (1996). "Cyclin E, a redundant cyclin in breast cancer." *Proc Natl Acad Sci USA* 93(26): 15215-20.

Gusarova, et al., J Clin Invest, 117: 99-111, 2007.

Harrington E., et al., Nat. Med. 2004 March; 10(3):262-7.

Harrison, M. M., C. J. Ceol, et al. (2006). "Some *C. elegans* class B synthetic multivulva proteins encode a conserved LIN-35 Rb-containing complex distinct from a NuRD-like complex." *Proc Natl Acad Sci USA* 103(45): 16782-7.

Huang, H., J. Groth, et al. (2005). "Aberrant expression of novel and previously described cell membrane markers in human breast cancer cell lines and tumors." *Clin Cancer Res* 11(12): 4357-64.

Ignatiadis, M., N. Xenidis, et al. (2007). "Different prognostic value of cytokeratin-19 mRNA positive circulating tumor cells according to estrogen receptor and HER2 status in early-stage breast cancer." *J Clin Oncol* 25(33): 5194-202.

Inamura, K., T. Fujiwara, et al. (2005). "Two subclasses of lung squamous cell carcinoma with different gene expression profiles and prognosis identified by hierarchical clustering and non-negative matrix factorization." *Oncogene* 24(47): 7105-13.

Ishida, S., E. Huang, et al. (2001). "Role for E2F in control of both DNA replication and mitotic functions as revealed from DNA microarray analysis." *Mol Cell Biol* 21(14): 4684-99.

Jones, C., A. Mackay, et al. (2004). "Expression profiling of purified normal human luminal and myoepithelial breast cells: identification of novel prognostic markers for breast cancer." *Cancer Res* 64(9): 3037-45.

Jones, M. H., C. Virtanen, et al. (2004). "Two prognostically significant subtypes of high-grade lung neuroendocrine tumours independent of small-cell and large-cell neuroendocrine carcinomas identified by gene expression profiles." *Lancet* 363(9411): 775-81.

Jones, S. F., Cohen, R. B., Dees, E. C., Lee, Y., Papas, J. A., Cooper, M. R., Galvin, K. M., Burris, H. A. 2007. Phase 1 clinical trial of MLN8054, a selective inhibitor of aurora A kinase. *Journal of Clinical Oncology,* 2007 ASCO Annual Meeting Proceedings Part 1. 25(18S): 3577.

Kalin, T. V., I. C. Wang, et al. (2006). "Increased levels of the FoxM1 transcription factor accelerate development and progression of prostate carcinomas in both TRAMP and LADY transgenic mice." *Cancer Res* 66(3): 1712-20.

Kalinichenko et al. (2004). "Foxm1b transcription factor is essential for development of hepatocellular carcinomas and is negatively regulated by the p19ARF tumor suppressor." *Genes Dev.* 18(7): 830-50.

Katzenellenbogen, B. S. and J. Frasor (2004). "Therapeutic targeting in the estrogen receptor hormonal pathway." *Semin Oncol* 31(1 Suppl 3): 28-38.

Kittler, R., L. Pelletier, et al. (2007). "Genome-scale RNAi profiling of cell division in human tissue culture cells." *Nat Cell Biol* 9(12): 1401-12.

Klopocki, E., G. Kristiansen, et al. (2004). "Loss of SFRP1 is associated with breast cancer progression and poor prognosis in early stage tumors." *Int J Oncol* 25(3): 641-9.

Knauer, S. K., W. Mann, et al. (2007). "Survivin's dual role: an export's view." *Cell Cycle* 6(5): 518-21.

Knowlden, J. M., I. R. Hutcheson, et al. (2003). "Elevated levels of epidermal growth factor receptor/c-erbB2 heterodimers mediate an autocrine growth regulatory pathway in tamoxifen-resistant MCF-7 cells." *Endocrinology* 144(3): 1032-44.

Kotake, Y., R. Cao, et al. (2007). "pRB family proteins are required for H3K27 trimethylation and Polycomb repression complexes binding to and silencing p16INK4alpha tumor suppressor gene." *Genes Dev* 21(1): 49-54.

Lee, R. J., C. Albanese, et al. (2000). "Cyclin D1 is required for transformation by activated Neu and is induced through an E2F-dependent signaling pathway." *Mol Cell Biol* 20(2): 672-83.

Lee, R. J., Albanese, C., Fu, M., D'Amico, M., Lin, B., Watanabe, G., Haines, G. K., 3rd, Siegel, P. M., Hung, M. C., Yarden, Y., Horowitz, J. M., Muller, W. J. and Pestell, R. G. 2000. Cyclin D1 is required for transformation by activated Neu and is induced through an E2F-dependent signaling pathway. *Mol Cell Biol* 20(2): 672-683.

Li, X., X. Cao, et al. (2007). "Expression level of insulin-like growth factor binding protein 5 mRNA is a prognostic factor for breast cancer." *Cancer Sci* 98(10): 1592-6.

Livasy, C. A., G. Karaca, et al. (2006). "Phenotypic evaluation of the basal-like subtype of invasive breast carcinoma." *Mod Pathol* 19(2): 264-71.

Lu, S., K. Simin, et al. (2008). "Analysis of integrin beta4 expression in human breast cancer: association with basal-like tumors and prognostic significance." *Clin Cancer Res* 14(4): 1050-8.

Lukas, J., J. Bartkova, et al. (1995). "Cyclin D1 is dispensable for G1 control in retinoblastoma gene-deficient cells independently of cdk4 activity." *Mol Cell Biol* 15(5): 2600-11.

Major, M. L., R. Lepe, et al. (2004). "Forkhead box M1B transcriptional activity requires binding of Cdk-cyclin complexes for phosphorylation-dependent recruitment of p300/CBP coactivators." *Mol Cell Biol* 24(7): 2649-61.

Manfredi, M. G., Ecsedy, J. A., Meetze, K. A., Balani, S. K., Burenkova, O., Chen, W., Galvin, K. M., Hoar, K. M., Huck, J. J., LeRoy, P. J., Ray, E. T., Sells, T. B., Stringer, B., Stroud, S. G., Vos, T. J., Weatherhead, G. S., Wysong, D. R., Zhang, M., Bolen, J. B. and Claiborne, C. F. 2007. Antitumor activity of MLN0854, an orally active small-molecule inhibitor of aurora A kinase. *PNAS* 104(10): 4106-4111.

Matos, I., R. Dufloth, et al. (2005). "p63, cytokeratin 5, and P-cadherin: three molecular markers to distinguish basal phenotype in breast carcinomas." *Virchows Arch* 447(4): 688-94.

McBryan, J., J. Howlin, et al. (2007). "ERalpha-CITED1 co-regulated genes expressed during pubertal mammary gland development: implications for breast cancer prognosis." *Oncogene* 26(44): 6406-19.

McCarthy, M. M., M. Sznol, et al. (2005). "Evaluating the expression and prognostic value of TRAIL-R1 and TRAIL-R2 in breast cancer." *Clin Cancer Res* 11(14): 5188-94.

Mehra, R., S. Varambally, et al. (2005). "Identification of GATA3 as a breast cancer prognostic marker by global gene expression meta-analysis." *Cancer Res* 65(24): 11259-64.

Moyano, J. V., J. R. Evans, et al. (2006). "AlphaB-crystallin is a novel oncoprotein that predicts poor clinical outcome in breast cancer." *J Clin Invest* 116(1): 261-70.

Myatt, S. S. and E. W. Lam (2007). "The emerging roles of forkhead box (Fox) proteins in cancer." *Nat Rev Cancer* 7(11): 847-59.

Nadler, Y., R. L. Camp, et al. (2008). "Expression patterns and prognostic value of Bag-1 and Bcl-2 in breast cancer." *Breast Cancer Res* 10(2): R35.

Nakahara, T., Takeuchi, M., Kinoyama, I., Minematsu, T., Shirasuna, K., Matsuhisa, A., Kita, A., Tominaga, F., Yamanaka, K., Kudoh, M. and Sasamata, M. 2007. YM155, a novel small-molecule survivin suppressant, induces regression of established human hormone-refractory prostate tumor xenografts. *Cancer Research* 67(17): 8014-8021.

Nielsen, N. H., S. O. Emdin, et al. (1997). "Deregulation of cyclin E and D1 in breast cancer is associated with inactivation of the retinoblastoma protein." *Oncogene* 14(3): 295-304.

Nielsen, T. O., F. D. Hsu, et al. (2004). "Immunohistochemical and clinical characterization of the basal-like subtype of invasive breast carcinoma." *Clin Cancer Res* 10(16): 5367-74.

O'Brien, S. L., A. Fagan, et al. (2007). "CENP-F expression is associated with poor prognosis and chromosomal instability in patients with primary breast cancer." *Int J Cancer* 120(7): 1434-43.

O'Connor, J. K., L. J. Hazard, et al. (2006). "Topoisomerase II alpha expression correlates with diminished disease-free survival in invasive breast cancer." *Int J Radiat Oncol Biol Phys* 65(5): 1411-5.

Olsson, A. Y., A. Feber, et al. (2007). "Role of E2F3 expression in modulating cellular proliferation rate in human bladder and prostate cancer cells." *Oncogene* 26(7): 1028-37.

Pan et al, Oral Oncol. 2008 July; 44(7):639-45.

Paredes, J., N. Lopes, et al. (2007). "P-cadherin and cytokeratin 5: useful adjunct markers to distinguish basal-like ductal carcinomas in situ." *Virchows Arch* 450(1): 73-80.

Potemski, P., R. Kusinska, et al. (2005). "Prognostic relevance of basal cytokeratin expression in operable breast cancer." *Oncology* 69(6): 478-85.

Rai, D., A. Frolova, et al. (2005). "Distinctive actions of membrane-targeted versus nuclear localized estrogen receptors in breast cancer cells." *Mol Endocrinol* 19(6): 1606-17.

Rakha, E. A., M. E. El-Sayed, et al. (2007). "Prognostic markers in triple-negative breast cancer." *Cancer* 109(1): 25-32.

Rakha, E. A., J. S. Reis-Filho, et al. (2008). "Basal-like breast cancer: a critical review." *J Clin Oncol* 26(15): 2568-81.

Rodriguez-Pinilla, S. M., D. Sarrio, et al. (2006). "Prognostic significance of basal-like phenotype and fascin expression in node-negative invasive breast carcinomas." *Clin Cancer Res* 12(5): 1533-9.

Rodriguez-Pinilla, S. M., D. Sarrio, et al. (2007). "Vimentin and laminin expression is associated with basal-like phenotype in both sporadic and BRCA1-associated breast carcinomas." *J Clin Pathol* 60(9): 1006-12.

Rodriguez-Pinilla, S. M., D. Sarrio, et al. (2007). "Sox2: a possible driver of the basal-like phenotype in sporadic breast cancer." *Mod Pathol* 20(4): 474-81.

Saeed, A. I., V. Sharov, et al. (2003). "TM4: a free, open-source system for microarray data management and analysis." *Biotechniques* 34(2): 374-8.

Salvatore, G., T. C. Nappi, et al. (2007). "A cell proliferation and chromosomal instability signature in anaplastic thyroid carcinoma." Cancer Res 67(21): 10148-58.

Savage, K., M. B. Lambros, et al. (2007). "Caveolin 1 is overexpressed and amplified in a subset of basal-like and metaplastic breast carcinomas: a morphologic, ultrastructural, immunohistochemical, and in situ hybridization analysis." *Clin Cancer Res* 13(1): 90-101.

Savage, K., S. Leung, et al. (2008). "Distribution and significance of caveolin 2 expression in normal breast and invasive breast cancer: an immunofluorescence and immunohistochemical analysis." *Breast Cancer Res Treat* 110(2): 245-56.

Schmit et al., 6 *Cell Cycle* 1903 (2007).

Shackney, S. E. and J. F. Silverman (2003). "Molecular evolutionary patterns in breast cancer." *Adv Anat Pathol* 10(5): 278-90.

Sherr, C. J. (2000). "The Pezcoller lecture: cancer cell cycles revisited." *Cancer Res* 60(14): 3689-95.

Sitterding, S. M., W. R. Wiseman, et al. (2008). "AlphaB-crystallin: a novel marker of invasive basal-like and metaplastic breast carcinomas." *Ann Diagn Pathol* 12(1): 33-40.

Sorlie, T., C. M. Perou, et al. (2001). "Gene expression patterns of breast carcinomas distinguish tumor subclasses with clinical implications." *Proc Natl Acad Sci USA* 98(19): 10869-74.

Sotiriou, C., S. Y. Neo, et al. (2003). "Breast cancer classification and prognosis based on gene expression profiles from a population-based study." *Proc Natl Acad Sci USA* 100(18): 10393-8.

Stauber, R. H., W. Mann, et al. (2007). "Nuclear and cytoplasmic survivin: molecular mechanism, prognostic, and therapeutic potential." *Cancer Res* 67(13): 5999-6002.

Stein, T., K. N. Price, et al. (2005). "Annexin A8 is up-regulated during mouse mammary gland involution and predicts poor survival in breast cancer." *Clin Cancer Res* 11(19 Pt 1): 6872-9.

Stender, J. D., J. Frasor, et al. (2007). "Estrogen-regulated gene networks in human breast cancer cells: involvement of E2F1 in the regulation of cell proliferation." *Mol Endocrinol* 21(9): 2112-23.

Stossi, F., D. H. Barnett, et al. (2004). "Transcriptional profiling of estrogen-regulated gene expression via estrogen receptor (ER) alpha or ERbeta in human osteosarcoma cells: distinct and common target genes for these receptors." *Endocrinology* 145(7): 3473-86.

Stuelten, C. H., M. B. Buck, et al. (2006). "Smad4-expression is decreased in breast cancer tissues: a retrospective study." *BMC Cancer* 6: 25.

Sun, L., D. Li, et al. (2008). "Small-molecule inhibition of Aurora kinases triggers spindle checkpoint-independent apoptosis in cancer cells." *Biochem Pharmacol* 75(5): 1027-34.

Suzuki, T., T. Urano, et al. (2007). "Nuclear cyclin B1 in human breast carcinoma as a potent prognostic factor." *Cancer Sci* 98(5): 644-51.

Tabach, Y., M. Milyavsky, et al. (2005). "The promoters of human cell cycle genes integrate signals from two tumor suppressive pathways during cellular transformation." *Mol Syst Biol* 1: 2005 0022.

Tan, D. S., C. Marchio, et al. (2007). "Triple negative breast cancer: molecular profiling and prognostic impact in adjuvant anthracycline-treated patients." *Breast Cancer Res Treat*.

Thorat, M. A., C. Marchio, et al. (2008). "Forkhead box A1 expression in breast cancer is associated with luminal subtype and good prognosis." *J Clin Pathol* 61(3): 327-32.

Tone, A. A., H. Begley, et al. (2008). "Gene expression profiles of luteal phase fallopian tube epithelium from BRCA mutation carriers resemble high-grade serous carcinoma." *Clin Cancer Res* 14(13): 4067-78.

Turner, N. C., J. S. Reis-Filho, et al. (2007). "BRCA1 dysfunction in sporadic basal-like breast cancer." *Oncogene* 26(14): 2126-32.

van de Rijn, M., C. M. Perou, et al. (2002). "Expression of cytokeratins 17 and 5 identifies a group of breast carcinomas with poor clinical outcome." *Am J Pathol* 161(6): 1991-6.

van der Vegt, B., J. Peterse, et al. (2007). "The expression pattern of MUC1 (EMA) is related to tumour characteristics and clinical outcome of invasive ductal breast carcinoma." *Histopathology*. 51: 322-35.

van't Veer, L. J., H. Dai, et al. (2002). "Gene expression profiling predicts clinical outcome of breast cancer." *Nature* 415(6871): 530-6.

Veeck, J., C. Geisler, et al. (2008). "Epigenetic inactivation of the Secreted frizzled-related protein-5 (SFRP5) gene in human breast cancer is associated with unfavorable prognosis." *Carcinogenesis*.

Veeck, J., D. Niederacher, et al. (2006). "Aberrant methylation of the Wnt antagonist SFRP1 in breast cancer is associated with unfavourable prognosis." *Oncogene* 25(24): 3479-88.

Vogel, C. L., M. A. Cobleigh, et al. (2002). "Efficacy and safety of trastuzumab as a single agent in first-line treatment of HER2-overexpressing metastatic breast cancer." *J Clin Oncol* 20(3): 719-26.

Wang, I. C., Y. J. Chen, et al. (2005). "Forkhead box M1 regulates the transcriptional network of genes essential for mitotic progression and genes encoding the SCF (Skp2-Cks1) ubiquitin ligase." *Mol Cell Biol* 25(24): 10875-94.

Wang, L. and Z. M. Shao (2006). "Cyclin e expression and prognosis in breast cancer patients: a meta-analysis of published studies." *Cancer Invest* 24(6): 581-7.

Wang, W., L. Dong, et al. (1999). "Transcriptional activation of E2F1 gene expression by 17beta-estradiol in MCF-7 cells is regulated by NF-Y-Sp1/estrogen receptor interactions." *Mol Endocrinol* 13(8): 1373-87.

Watkins, G., A. Douglas-Jones, et al. (2005). "Increased levels of SPARC (osteonectin) in human breast cancer tissues and its association with clinical outcomes." *Prostaglandins Leukot Essent Fatty Acids* 72(4): 267-72.

Wykoff, C. C., N. Beasley, et al. (2001). "Expression of the hypoxia-inducible and tumor-associated carbonic anhydrases in ductal carcinoma in situ of the breast." *Am J Pathol* 158(3): 1011-9.

Yamashita, S., Y. Masuda, et al. (2007). "Survivin expression predicts early recurrence in early-stage breast cancer." *Anticancer Res* 27(4C): 2803-8.

Yao, E. S., H. Zhang, et al. (2007). "Increased beta1 integrin is associated with decreased survival in invasive breast cancer." *Cancer Res* 67(2): 659-64.

Yu, Q., Y. Geng, et al. (2001). "Specific protection against breast cancers by cyclin D1 ablation." *Nature* 411(6841): 1017-21.

Zerkowski, M. P., R. L. Camp, et al. (2007). "Quantitative analysis of breast cancer tissue microarrays shows high cox-2 expression is associated with poor outcome." *Cancer Invest* 25(1): 19-26.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08877445B2). An electronic copy of the "Sequence Listing" will also be available from the USPTO upon request and payment of the fee set forth in 37 CFR 1.19(b)(3).

What is claimed is:

1. A method of identifying a tumor as an ERGO tumor comprising the steps of:
   a) providing a tumor sample;
   b) providing a reference from non-cancerous tissue;
   c) providing a nucleic acid array comprising at least 21 of the nucleic acid sequences shown in SEQ ID NO:s 12-14, 20-21, 35, 37, 39, 43-44, 46-47, 49-51, 54, 56, 58-72, 75, 79-84, 86, 88, 91.93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340 adapted for hybridization to nucleic acids in a tumor sample;
   d) measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340 by hybridizing a nucleic acid obtained from the tumor sample to the nucleic acid array;
   e) measuring the reference to produce a reference value; and
   f) comparing the indicator value to the reference value to determine which of the gene transcripts is over-expressed;
   whereby the tumor is identified as an ERGO tumor if at least 21 of these gene transcripts are over-expressed.

2. The method of claim 1 wherein the tumor sample is from lung tissue.

3. The method of claim 1 wherein the tumor sample is from thyroid tissue.

4. The method of claim 1 wherein the tumor sample is from prostate tissue.

5. The method of claim 1 wherein the tumor sample is from ovarian tissue.

6. A method as in claim 4 further comprising measuring an indicator of gene transcript levels in at least one selected from the group consisting of the tumor sample and the reference to produce a housekeeping value for at least one gene transcript selected from the group consisting of the nucleic acid sequences shown in SEQ ID NO:s 162, 341-364 and 365; and normalizing at least one selected from the group consisting of the indicator value and the reference value to the housekeeping value.

7. The method of claim 1 wherein the indicator value is at least 1.8 times greater than the reference value for each of the gene transcripts.

8. The method of claim 1 wherein the tumor sample is from liver tissue.

9. The method of claim 1 wherein the tumor sample is from bladder tissue.

10. A method of determining the odds that an individual ERGO tumor patient will survive to a future date comprising the steps of:
  a) providing a tumor sample from an individual patient;
  b) providing a reference from non-cancerous tissue;
  c) providing a nucleic acid array comprising at least 21 of the nucleic acid sequences shown in SEQ ID NO:s 12-14, 20-21, 35, 37, 39, 43-44, 46-47, 49-51, 54, 56, 58-72, 75.79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340 adapted for hybridization to nucleic acids in a tumor sample;
  d) measuring an indicator of gene transcript levels in the tumor sample to produce an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340 by hybridizing a nucleic acid obtained from tumor sample to nucleic acid array;
  e) measuring the reference to produce a reference value; and
  f) comparing the indicator value to the reference value to determine which of the gene transcripts is over-expressed, whereby the tumor is identified as an ERGO tumor and the individual patient is diagnosed as an ERGO tumor patient if at least 21 of these gene transcripts are over-expressed;
  g) plotting the fraction of surviving patients in a population of patients diagnosed as ERGO tumor patients as a function of the time since diagnosis of the ERGO tumor to generate a survival plot; and
  h) selecting a future date after the individual patient is diagnosed as an ERGO tumor patient and determining the fraction of surviving patients in the population from the survival plot;
whereby the fraction of surviving patients on the survival plot at the future date predicts the odds that an individual tumor patient will survive to the future date.

11. The method of claim 10 wherein the tumor sample is from lung tissue and the population of patients is diagnosed as ERGO lung tumor patients.

12. The method of claim 10 wherein the tumor sample is from thyroid tissue and the population of patients is diagnosed as ERGO thyroid tumor patients.

13. The method of claim 10 wherein the tumor sample is from ovarian tissue and the population of patients is diagnosed as ERGO ovarian tumor patients.

14. The method of claim 10 wherein the tumor sample is from prostate tissue and the population of patients is diagnosed as ERGO) prostate tumor patients.

15. A method as in claim 14 further comprising measuring an indicator of gene transcript levels in at least one selected from the group consisting of the tumor sample and the reference to produce a housekeeping value for at least one gene transcript selected from the group consisting of the nucleic acid sequences shown in SEQ ID NO:s 162, 341-364 and 365; and normalizing at least one selected from the group consisting of the indicator value and the reference value to the housekeeping value.

16. The method of claim 10 wherein the indicator value is at least 1.8 times greater than the reference value for each of the gene transcripts.

17. The method of claim 10 wherein the tumor sample is from liver tissue and the population of patients is diagnosed as ERGO hepatoma tumor patients.

18. The method of claim 10 wherein the tumor sample is from bladder tissue and the population of patients is diagnosed as ERGO bladder tumor patients.

19. An apparatus comprising:
  a) a specifically programmed computer in communication with a nucleic acid array analyzer and an output display, wherein the specifically programmed computer is adapted to compare indicator values to reference values from non-cancerous tissue and to determine which gene transcripts are over-expressed in a tumor sample;
  b) a nucleic acid array comprising at least 21 of the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174, 176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340 adapted for hybridization to nucleic acids in a tumor sample;
  c) a memory containing an indicator value for each of the following gene transcripts having the nucleic acid sequences shown in SEQ ID NO:s 12-14, 20-21, 35, 37, 39, 43-44, 46-47, 49-51, 54, 56, 58-72, 75, 79-84, 86, 88, 91, 93-95, 102-105, 107-110, 112, 116, 118-120, 122-123, 125-126, 128-129, 131, 145-146, 148-149, 151, 154, 156-157, 160, 163-166, 169, 171, 173-174.176-177, 180, 184, 186, 188, 193, 196, 198, 200-201, 203, 205, 209, 217, 246-247, 249, 254, 259, 267, 269, 274-275, 292-295, 298, 307, 311, 316, 321-323, 331, 333, and 335-340 produced by hybridization of the nucleic acid array to the nucleic acids in the tumor sample, and containing reference values for the gene transcripts from non-cancerous tissue; and
  d) an output display which shows the tumor sample is an ERGO tumor when the specifically programmed computer determines at least 21 of the gene transcripts are over-expressed in a tumor sample.

* * * * *